US010053715B2

(12) United States Patent
Franklin et al.

(10) Patent No.: US 10,053,715 B2
(45) Date of Patent: Aug. 21, 2018

(54) TAILORED OILS

(71) Applicant: Corbion Biotech, Inc., South San Francisco, CA (US)

(72) Inventors: Scott Franklin, Woodside, CA (US); Aravind Somanchi, Redwood City, CA (US); George Rudenko, Mountain View, CA (US); Riyaz Bhat, South San Francisco, CA (US); Xinhua Zhao, Dubllin, CA (US); Jeffrey L. Moseley, Redwood City, CA (US)

(73) Assignee: Corbion Biotech, Inc., South San Francisco, CA (US)

( * ) Notice: Subject to any disclaimer, the term of this patent is extended or adjusted under 35 U.S.C. 154(b) by 684 days.

(21) Appl. No.: 14/506,491

(22) Filed: Oct. 3, 2014

(65) Prior Publication Data

US 2015/0125914 A1 May 7, 2015

Related U.S. Application Data

(60) Provisional application No. 61/887,268, filed on Oct. 4, 2013, provisional application No. 61/892,399, filed on Oct. 17, 2013, provisional application No. 61/895,355, filed on Oct. 24, 2013, provisional application No. 61/923,327, filed on Jan. 3, 2014, provisional application No. 62/023,109, filed on Jul. 10, 2014.

(51) Int. Cl.

*C12P 7/64* (2006.01)
*C11C 1/00* (2006.01)
*C11D 9/00* (2006.01)

(52) U.S. Cl.

CPC ................ *C12P 7/64* (2013.01); *C11C 1/002* (2013.01); *C11D 9/00* (2013.01); *C12P 7/6409* (2013.01); *C12Y 203/01041* (2013.01); *C12Y 301/02014* (2013.01)

(58) Field of Classification Search

None

See application file for complete search history.

(56) References Cited

U.S. PATENT DOCUMENTS 2,235,056 A 3/1941 Walmesley
2,383,602 A 8/1945 Gerald et al.
2,967,700 A 1/1961 Lee et al.
3,142,135 A 7/1964 Kathrein
3,280,502 A 10/1966 Farrow et al.
3,320,693 A 5/1967 Shirota et al.
3,475,274 A 10/1969 Harned
3,957,578 A 5/1976 Narita et al.
3,962,466 A 6/1976 Nakabayashi
3,983,008 A 9/1976 Shinozaki et al.
4,005,062 A 1/1977 Schnell
4,103,039 A 7/1978 Mandai et al.
4,182,777 A 1/1980 Saunders
4,273,790 A 6/1981 Bosco et al.
4,341,038 A 7/1982 Bloch et al.
4,373,434 A 2/1983 Alexander et al.
4,390,561 A 6/1983 Blair et al.
4,519,845 A 5/1985 Ou
4,627,192 A 12/1986 Fick
4,673,490 A 6/1987 Subramanian et al.
4,755,467 A 7/1988 Scopes et al.
4,901,635 A 2/1990 Williams
4,992,605 A 2/1991 Craig et al.
5,001,059 A 3/1991 Skatrud et al.
5,130,242 A 7/1992 Barclay
5,212,087 A 5/1993 Fournier et al.
5,252,198 A 10/1993 Harrison
5,270,175 A 12/1993 Moll et al.
5,270,177 A 12/1993 Ramos Lazcano et al.
5,304,481 A 4/1994 Davies et al.
5,330,913 A 7/1994 Nakayama (Continued)

FOREIGN PATENT DOCUMENTS

CN 1251108 A 4/2000
CN 1852986 A 10/2006

(Continued)

OTHER PUBLICATIONS

"Soybean Oil Innovations, 3rd Edition," United Soybean Board, www.soyconnection.com, 8 pages, (2009). [Available from the Internet on Jan. 15, 2009: <URL: http://www.soyconnection.com/sites/default/files/soy-oil-solutions.pdf>].

"Codex Standard for Named Vegetable Oils," CODEX Alimentarius, CODEX STAN 210-1999, pp. 1-16, (1999).

Abbadi et al., "Knockout of the regulatory site of 3-ketoacyl-ACP synthase III enhances short- and medium-chain acyl-ACP synthesis," The Plant Journal, 24(1):1-9, (2000).

Aggelis et al., "Enhancement of single cell oil production by Yarrowia lipolytica growing in the presence of *Teucrium polium* L. aqueous extract," Biotechnology Letters, 21:747-749, (1999).

Aguirre et al., "Engineering challenges in biodiesel production from microalgae," Critical Reviews in Biotechnology, 33(3): 293-308, (2013).

Altschul et al., "Basic local alignment search tool," J Mol Biol, 215(3):403-410, (1990).

(Continued)

*Primary Examiner* — Paul J Holland

(74) *Attorney, Agent, or Firm* — Weaver Austin Villeneuve & Sampson, LLC.

(57) ABSTRACT

Recombinant DNA techniques are used to produce oleaginous recombinant cells that produce triglyceride oils having desired fatty acid profiles and regiospecific or stereospecific profiles. Genes manipulated include those encoding stearoyl-ACP desaturase, delta 12 fatty acid desaturase, acyl-ACP thioesterase, ketoacyl-ACP synthase, and lysophosphatidic acid acyltransferase. The oil produced can have enhanced oxidative or thermal stability, or can be useful as a frying oil, shortening, roll-in shortening, tempering fat, cocoa butter replacement, as a lubricant, or as a feedstock for various chemical processes. The fatty acid profile can be enriched in midchain profiles or the oil can be enriched in triglycerides of the saturated-unsaturated-saturated type.

7 Claims, 24 Drawing Sheets

(56) References Cited

U.S. PATENT DOCUMENTS 5,338,673 A 8/1994 Thepenier et al.
5,354,878 A 10/1994 Connemann et al.
5,360,730 A 11/1994 Orndorff et al.
5,391,724 A 2/1995 Kindl et al.
5,395,455 A 3/1995 Scott et al.
5,436,394 A 7/1995 Willmitzer et al.
5,455,167 A 10/1995 Voelker et al.
5,460,870 A 10/1995 Arthurs
5,492,938 A 2/1996 Kyle et al.
5,518,918 A 5/1996 Barclay et al.
5,547,699 A 8/1996 Iizuka et al.
5,563,058 A 10/1996 Davies et al.
5,595,965 A 1/1997 Wiggins
5,597,400 A 1/1997 Nonomura et al.
5,680,812 A 10/1997 Linsgeseder
5,685,218 A 11/1997 Kemper
5,693,507 A 12/1997 Daniell et al.
5,711,983 A 1/1998 Kyle et al.
5,723,761 A 3/1998 Voelker et al.
5,756,135 A 5/1998 Seeley
5,826,500 A 10/1998 Kemper
5,888,947 A 3/1999 Lambert et al.
5,900,370 A 5/1999 Running
5,910,630 A 6/1999 Davies et al.
5,945,585 A 8/1999 Hitz et al.
5,968,791 A 10/1999 Davis et al.
6,139,897 A 10/2000 Goto et al.
6,166,231 A 12/2000 Hoeksema
6,255,505 B1 7/2001 Bijl et al.
6,338,866 B1 1/2002 Criggall et al.
6,344,231 B1 2/2002 Nakajo et al.
6,355,861 B1 3/2002 Thomas
6,372,460 B1 4/2002 Gladue et al.
6,410,281 B1 6/2002 Barclay
6,441,208 B2 8/2002 Bijl et al.
6,534,261 B1 3/2003 Cox, III et al.
6,620,427 B2 9/2003 Lasekan et al.
6,680,426 B2 1/2004 Daniell et al.
6,727,373 B2 4/2004 Bijl et al.
6,750,048 B2 6/2004 Ruecker et al.
6,762,345 B1 7/2004 Cahoon et al.
6,763,345 B1 7/2004 Hempleman et al.
6,867,308 B2 3/2005 Bartok et al.
7,053,267 B2 5/2006 Knauf et al.
7,063,957 B2 6/2006 Chen
7,081,567 B2 7/2006 Xue et al.
7,109,392 B1 9/2006 Broglie et al.
7,135,620 B2 11/2006 Daniell et al.
7,214,297 B2 5/2007 Wang et al.
7,268,276 B2 9/2007 Ruezinsky et al.
7,309,602 B2 12/2007 David
7,351,558 B2 4/2008 Ruecker et al.
7,468,267 B2 12/2008 Monod et al.
7,504,259 B2 3/2009 Yadav et al.
7,588,931 B2 9/2009 Damude et al.
7,622,570 B2 11/2009 Oswald et al.
7,652,156 B2 1/2010 Hillion et al.
7,662,598 B2 2/2010 Ruecker et al.
7,678,931 B2 3/2010 Fichtali et al.
7,781,193 B2 8/2010 Ruecker et al.
7,851,199 B2 12/2010 Bailey et al.
7,879,591 B2 2/2011 Damude et al.
7,883,882 B2 2/2011 Franklin et al.
7,914,832 B2 3/2011 Uchino
7,935,515 B2 5/2011 Franklin et al.
7,939,710 B1 5/2011 Apt et al.
8,003,365 B2 8/2011 Yoshikuni et al.
8,029,579 B2 10/2011 Knuth et al.
8,043,496 B1 10/2011 Schuh et al.
8,088,718 B2 1/2012 Bicerano et al.
8,119,583 B2 2/2012 Day et al.
8,163,675 B2 4/2012 Navarrete et al.
8,187,860 B2 5/2012 Franklin et al.
8,222,010 B2 7/2012 Franklin et al.
8,268,610 B2 9/2012 Franklin et al.
8,278,261 B2 10/2012 Day et al.
8,283,483 B2 10/2012 Williams et al.
8,435,767 B2 5/2013 Franklin et al.
8,450,083 B2 5/2013 Day et al.
8,476,059 B2 7/2013 Trimbur et al.
8,497,116 B2 7/2013 Trimbur et al.
8,512,999 B2 8/2013 Trimbur et al.
8,518,689 B2 8/2013 Trimbur et al.
8,530,207 B2 9/2013 Watts et al.
8,592,188 B2 11/2013 Franklin et al.
8,633,012 B2 1/2014 Franklin et al.
8,647,397 B2 2/2014 Trimbur et al.
8,674,180 B2 3/2014 Franklin et al.
8,697,402 B2 4/2014 Trimbur et al.
8,697,427 B2 4/2014 Franklin et al.
8,765,424 B2 7/2014 Franklin et al.
8,772,575 B2 7/2014 Franklin et al.
8,790,914 B2 7/2014 Trimbur et al.
8,802,422 B2 8/2014 Trimbur et al.
8,822,176 B2 9/2014 Day et al.
8,822,177 B2 9/2014 Day et al.
8,846,352 B2 9/2014 Chua et al.
8,846,375 B2 9/2014 Franklin et al.
8,852,885 B2 10/2014 Franklin et al.
8,889,401 B2 11/2014 Trimbur et al.
8,889,402 B2 11/2014 Trimbur et al.
8,945,908 B2 2/2015 Franklin et al.
8,951,777 B2 2/2015 Franklin et al.
9,062,294 B2 6/2015 Franklin et al.
9,066,527 B2 6/2015 Franklin et al.
9,068,213 B2 6/2015 Franklin et al.
9,102,973 B2 8/2015 Franklin et al.
9,109,239 B2 8/2015 Franklin et al.
9,200,307 B2 12/2015 Franklin et al.
9,249,436 B2 2/2016 Franklin et al.
9,249,441 B2 2/2016 Franklin et al.
9,255,282 B2 2/2016 Franklin et al.
9,279,136 B2 3/2016 Franklin et al.
9,353,389 B2 5/2016 Franklin et al.
9,388,435 B2 7/2016 Franklin et al.
9,434,909 B2 9/2016 Trimbur et al.
9,464,304 B2 10/2016 Franklin et al.
9,551,017 B2 1/2017 Franklin et al.
9,593,351 B2 3/2017 Franklin et al.
9,657,299 B2 5/2017 Franklin et al.
9,719,114 B2 8/2017 Franklin et al.
2002/0012979 A1 1/2002 Berry et al.
2002/0059661 A1 5/2002 Dehesh
2002/0122868 A1 9/2002 Floeter et al.
2002/0144455 A1 10/2002 Bertrand et al.
2002/0178467 A1 11/2002 Dehesh
2003/0054524 A1 3/2003 Spener et al.
2003/0079249 A1 4/2003 Shanklin et al.
2003/0082595 A1 5/2003 Jiang et al.
2003/0097686 A1 5/2003 Knauf et al.
2003/0145350 A1 7/2003 Spener et al.
2003/0211594 A1 11/2003 Rosebrook
2003/0229237 A1 12/2003 Haas et al.
2004/0053235 A1 3/2004 Smirnoff et al.
2004/0074760 A1 4/2004 Portnoff et al.
2004/0230085 A1 11/2004 Jakkula et al.
2004/0235123 A1 11/2004 Liao et al.
2004/0033557 A1 12/2004 Scott et al.
2005/0005333 A1 1/2005 Ruezinsky et al.
2005/0102716 A1 5/2005 Venkatramesh et al.
2005/0112735 A1 5/2005 Zappi et al.
2005/0153002 A1 7/2005 Socia Rosales et al.
2005/0170479 A1 8/2005 Weaver et al.
2005/0262588 A1 11/2005 Dehesh et al.
2005/0266537 A1 12/2005 Chen
2005/0272611 A1 12/2005 Lord et al.
2006/0048240 A1 3/2006 Alexandrov et al.
2006/0075522 A1 4/2006 Cleveland et al.
2006/0094088 A1 5/2006 Picataggio et al.
2006/0094089 A1 5/2006 Barclay
2006/0094090 A1 5/2006 Damude et al.
2006/0107346 A1 5/2006 Schneeberger et al.
2006/0122410 A1 6/2006 Fichtali et al.
2006/0130182 A1 6/2006 Heim et al.

(56) References Cited

U.S. PATENT DOCUMENTS

2006/0153826 A1 7/2006 Arnould et al.
2006/0156436 A1 7/2006 Nakamura et al.
2006/0162006 A9 7/2006 Sherman et al.
2006/0199984 A1 9/2006 Kuechler et al.
2006/0225341 A1 10/2006 Rohr et al.
2006/0286205 A1 12/2006 Fichtali et al.
2007/0004016 A1 1/2007 Picataggio et al.
2007/0009988 A1 1/2007 Monod et al.
2007/0048848 A1 3/2007 Sears
2007/0099280 A1 5/2007 Barclay
2007/0118916 A1 5/2007 Puzio et al.
2007/0167396 A1 7/2007 Dillon et al.
2007/0218183 A1 9/2007 Nakhasi et al.
2007/0248531 A1 10/2007 Debryun et al.
2007/0254354 A1 11/2007 Millis et al.
2007/0261138 A1 11/2007 Graham et al.
2007/0275438 A1 11/2007 David
2008/0014620 A1 1/2008 Op Den Camp et al.
2008/0038804 A1 2/2008 Du et al.
2008/0040822 A1 2/2008 Metz et al.
2008/0107776 A1 5/2008 Prakash et al.
2008/0160593 A1 7/2008 Oyler
2008/0194029 A1 8/2008 Hegemann et al.
2008/0206379 A1 8/2008 Fabritius et al.
2008/0229451 A1 9/2008 Cao et al.
2008/0256666 A1 10/2008 Zhu et al.
2008/0283803 A1 11/2008 Rapp et al.
2009/0004715 A1 1/2009 Trimbur et al.
2009/0011480 A1 1/2009 Trimbur et al.
2009/0018300 A1 1/2009 Bloom et al.
2009/0035842 A1 2/2009 Trimbur et al.
2009/0047721 A1 2/2009 Trimbur et al.
2009/0061493 A1 3/2009 Trimbur et al.
2009/0064567 A1 3/2009 Lippmeier et al.
2009/0099260 A1 4/2009 Namal Senanayake et al.
2009/0117253 A1 5/2009 Hong et al.
2009/0142322 A1 6/2009 Ye
2009/0145392 A1 6/2009 Clark et al.
2009/0148918 A1 6/2009 Trimbur et al.
2009/0176272 A1 7/2009 Champagne et al.
2009/0211150 A1 8/2009 Wu et al.
2009/0234146 A1 9/2009 Cooney et al.
2009/0271892 A1 10/2009 Thomasset et al.
2009/0274736 A1 11/2009 Dillon et al.
2009/0298143 A1 12/2009 Roessler et al.
2009/0298159 A1 12/2009 Wu et al.
2009/0305942 A1 12/2009 Day et al.
2009/0317878 A1 12/2009 Champagne et al.
2010/0010088 A1 1/2010 Chilton et al.
2010/0021912 A1 1/2010 Farese et al.
2010/0035320 A1 2/2010 Blanchard et al.
2010/0058651 A1 3/2010 Knuth et al.
2010/0093031 A1 4/2010 Kobayashi et al.
2010/0105955 A1 4/2010 Alibhai et al.
2010/0120643 A1 5/2010 Brown et al.
2010/0137647 A1 6/2010 Bradin
2010/0151112 A1 6/2010 Franklin et al.
2010/0151535 A1 6/2010 Franklin et al.
2010/0151538 A1 6/2010 Franklin et al.
2010/0151539 A1 6/2010 Franklin et al.
2010/0151567 A1 6/2010 Franklin et al.
2010/0154293 A1 6/2010 Hom et al.
2010/0170144 A1 7/2010 Day et al.
2010/0186117 A1 7/2010 Fabijanski et al.
2010/0196575 A1 8/2010 Sanchez et al.
2010/0239712 A1 9/2010 Brooks et al.
2010/0248322 A1 9/2010 Pfeiffer et al.
2010/0249260 A1 9/2010 Casati et al.
2010/0297292 A1 11/2010 Brooks et al.
2010/0297295 A1 11/2010 Brooks et al.
2010/0297296 A1 11/2010 Brooks et al.
2010/0297323 A1 11/2010 Brooks et al.
2010/0297325 A1 11/2010 Brooks et al.
2010/0297331 A1 11/2010 Brooks et al.
2010/0035309 A1 12/2010 Havemen et al.
2010/0303957 A1 12/2010 Brooks et al.
2010/0303961 A1 12/2010 Brooks et al.
2010/0303989 A1 12/2010 Brooks et al.
2010/0303990 A1 12/2010 Brooks et al.
2010/0323413 A1 12/2010 Trimbur et al.
2010/0323414 A1 12/2010 Trimbur et al.
2011/0014665 A1 1/2011 Trimbur et al.
2011/0015417 A1 1/2011 Trimbur et al.
2011/0047863 A1 3/2011 Trimbur et al.
2011/0065821 A1 3/2011 Abraham et al.
2011/0072714 A1 3/2011 Gaertner et al.
2011/0111470 A1 5/2011 Berry et al.
2011/0165634 A1 7/2011 Franklin et al.
2011/0190522 A1 8/2011 Trimbur et al.
2011/0203168 A1 8/2011 Franklin et al.
2011/0250658 A1 10/2011 Franklin et al.
2011/0252696 A1 10/2011 Franklin et al.
2011/0256268 A1 10/2011 Franklin et al.
2011/0256282 A1 10/2011 Piechocki et al.
2011/0284215 A1 11/2011 Pfeiffer et al.
2011/0293785 A1 12/2011 Franklin et al.
2011/0294174 A1 12/2011 Franklin et al.
2012/0009636 A1 1/2012 Berry et al.
2012/0021495 A1 1/2012 Vanzin
2012/0028319 A1 2/2012 Trimbur et al.
2012/0034662 A1 2/2012 Hu et al.
2012/0060242 A1* 3/2012 Senger ................ C12N 9/1029
800/298
2012/0119862 A1 5/2012 Franklin et al.
2012/0122192 A1 5/2012 Trimbur et al.
2012/0128851 A1 5/2012 Brooks et al.
2012/0156717 A1 6/2012 Allnutt et al.
2012/0164701 A1 6/2012 Trimbur et al.
2012/0203018 A1 8/2012 Franklin et al.
2012/0277452 A1 11/2012 Franklin et al.
2012/0277453 A1 11/2012 Franklin et al.
2012/0283460 A1 11/2012 Franklin et al.
2012/0288930 A1 11/2012 Trimbur et al.
2012/0324784 A1 12/2012 Franklin et al.
2012/0329109 A1 12/2012 Chua et al.
2013/0004646 A1 1/2013 Franklin et al.
2013/0006006 A1 1/2013 Day et al.
2013/0031678 A1 1/2013 Zheng et al.
2013/0034887 A1 2/2013 Franklin et al.
2013/0078709 A1 3/2013 Franklin et al.
2013/0089916 A1 4/2013 Franklin et al.
2013/0096211 A1 4/2013 Franklin et al.
2013/0102039 A1 4/2013 Franklin et al.
2013/0116462 A1 5/2013 Durrett et al.
2013/0122180 A1 5/2013 Brooks et al.
2013/0165677 A1 6/2013 Franklin et al.
2013/0197247 A1 8/2013 Franklin et al.
2013/0273621 A1 10/2013 Franklin et al.
2013/0295268 A1 11/2013 Day et al.
2013/0296591 A1 11/2013 Day et al.
2013/0317240 A1 11/2013 Franklin et al.
2013/0323382 A1 12/2013 Franklin et al.
2013/0323823 A1 12/2013 Franklin et al.
2013/0330790 A1 12/2013 Trimbur et al.
2013/0331584 A1 12/2013 Franklin et al.
2013/0338385 A1 12/2013 Franklin et al.
2014/0170716 A1 6/2014 Trimbur et al.
2014/0249342 A1 9/2014 Franklin et al.
2014/0256024 A1 9/2014 Franklin et al.
2014/0256600 A1 9/2014 Dillon et al.
2014/0305031 A1 10/2014 Day et al.
2014/0315267 A1 10/2014 Franklin et al.
2014/0336100 A1 11/2014 Day et al.
2014/0357746 A1 12/2014 Ngantung et al.
2014/0377847 A1 12/2014 Franklin et al.
2015/0073163 A1 3/2015 Chua et al.
2015/0218604 A1 8/2015 Franklin et al.
2015/0275149 A1 10/2015 Dummer et al.
2015/0344917 A1 12/2015 Franklin et al.
2016/0010066 A1 1/2016 Davis et al.
2016/0024538 A1 1/2016 Franklin et al.
2016/0032332 A1 2/2016 Davis et al.
2016/0186191 A1 6/2016 Franklin et al.
2016/0186219 A1 6/2016 Franklin et al.

(56) References Cited

U.S. PATENT DOCUMENTS

| | | | |
|---|---|---|---|
| 2016/0194672 A1 | 7/2016 | Franklin et al. | |
| 2016/0348119 A1 | 12/2016 | Franklin et al. | |
| 2016/0376617 A1 | 12/2016 | Franklin et al. | |
| 2017/0022436 A1 | 1/2017 | Trimbur et al. | |
| 2017/0145450 A1 | 5/2017 | Franklin et al. | |
| 2017/0314048 A1 | 11/2017 | Franklin et al. | |

FOREIGN PATENT DOCUMENTS

| | | | |
|---|---|---|---|
| CN | 101037639 | A | 9/2007 |
| CN | 101092353 | A | 12/2007 |
| CN | 101108997 | A | 1/2008 |
| CN | 101611125 | A | 12/2009 |
| CN | 101765661 | A | 6/2010 |
| CN | 101824440 | A | 9/2010 |
| DE | 2756977 | A1 | 6/1978 |
| EP | 0562504 | B1 | 11/1995 |
| EP | 1 178 118 | A1 | 2/2002 |
| EP | 1 642 959 | A1 | 4/2006 |
| EP | 1 681 337 | A1 | 7/2006 |
| EP | 1 741 767 | A1 | 1/2007 |
| EP | 1 947 189 | A2 | 7/2008 |
| EP | 2 327 776 | A1 | 6/2011 |
| EP | 2 152 849 | B1 | 2/2013 |
| FR | 2924126 | A1 | 5/2009 |
| GB | 824151 | | 11/1959 |
| JP | 57-150379 | | 9/1982 |
| JP | 06-253872 | A | 9/1994 |
| JP | 07-008217 | | 1/1995 |
| JP | 07-075557 | | 3/1995 |
| JP | H09-511650 | A | 11/1997 |
| JP | H10-46181 | A | 2/1998 |
| JP | 2000-136199 | | 5/2000 |
| JP | 2000-175696 | A | 6/2000 |
| JP | 2002-125601 | | 5/2002 |
| JP | 2002-523864 | A | 7/2002 |
| JP | 2003-102467 | A | 4/2003 |
| JP | 2003-325067 | A | 11/2003 |
| JP | 2007-314549 | A | 12/2007 |
| JP | 2008-081559 | | 4/2008 |
| JP | 2008-514221 | | 5/2008 |
| JP | 2008-148663 | | 7/2008 |
| JP | 2008-178871 | | 8/2008 |
| JP | 2010-528627 | | 8/2010 |
| JP | 2015-500009 | A | 1/2015 |
| JP | 6071904 | | 2/2017 |
| KR | 10-2007-00085649 | A | 8/2007 |
| WO | WO 91/018105 | A1 | 11/1991 |
| WO | WO 92/011373 | A1 | 7/1992 |
| WO | WO 93/006712 | A1 | 4/1993 |
| WO | WO 94/010288 | A2 | 5/1994 |
| WO | WO 95/13390 | A2 | 5/1995 |
| WO | WO 95/27791 | A1 | 10/1995 |
| WO | WO 95/031553 | A1 | 11/1995 |
| WO | WO 97/040698 | A1 | 11/1997 |
| WO | WO 98/032770 | A1 | 7/1998 |
| WO | WO 99/037166 | A1 | 7/1999 |
| WO | WO 99/64618 | | 11/1999 |
| WO | WO 00/011682 | A1 | 3/2000 |
| WO | WO 00/61740 | A1 | 10/2000 |
| WO | WO 00/066750 | A2 | 11/2000 |
| WO | WO 00/74471 | A1 | 12/2000 |
| WO | WO 02/008403 | A2 | 1/2002 |
| WO | WO 02/085293 | A2 | 10/2002 |
| WO | WO 2004/016282 | A1 | 2/2004 |
| WO | WO 04/101753 | A2 | 11/2004 |
| WO | WO 05/003310 | A2 | 1/2005 |
| WO | WO 05/035693 | A2 | 4/2005 |
| WO | WO 06/055322 | A2 | 5/2006 |
| WO | WO 2006/052807 | A2 | 5/2006 |
| WO | WO 06/122299 | A2 | 11/2006 |
| WO | WO 07/027669 | A1 | 3/2007 |
| WO | WO 07/38566 | A2 | 4/2007 |
| WO | WO 07/106903 | A2 | 9/2007 |
| WO | WO 07/117511 | A2 | 10/2007 |
| WO | WO 07/121100 | | 10/2007 |
| WO | WO 07/134294 | A2 | 11/2007 |
| WO | WO 07/141257 | A1 | 12/2007 |
| WO | WO 08/002643 | A2 | 1/2008 |
| WO | WO 08/011811 | A1 | 1/2008 |
| WO | WO 08/060571 | A2 | 5/2008 |
| WO | WO 2008/058664 | A1 | 5/2008 |
| WO | WO 08/083352 | A1 | 7/2008 |
| WO | WO 08/130372 | A2 | 10/2008 |
| WO | WO 08/134836 | A2 | 11/2008 |
| WO | WO 08/151149 | A2 | 12/2008 |
| WO | WO 09/076559 | A1 | 6/2009 |
| WO | WO 09/105620 | A1 | 8/2009 |
| WO | WO 09/126843 | A2 | 10/2009 |
| WO | WO 2009/124070 | A1 | 10/2009 |
| WO | WO 10/017346 | A2 | 2/2010 |
| WO | WO 10/019813 | A2 | 2/2010 |
| WO | WO 10/045368 | A2 | 4/2010 |
| WO | WO 2010/037209 | A1 | 4/2010 |
| WO | WO 10/063031 | A2 | 6/2010 |
| WO | WO 10/063032 | A2 | 6/2010 |
| WO | WO 10/111698 | A2 | 9/2010 |
| WO | WO 10/120923 | A1 | 10/2010 |
| WO | WO 10/120939 | A2 | 10/2010 |
| WO | WO 11/026008 | A1 | 3/2011 |
| WO | WO 11/075716 | A1 | 6/2011 |
| WO | WO 11/090730 | A1 | 7/2011 |
| WO | WO 11/130573 | A1 | 10/2011 |
| WO | WO 11/130576 | A1 | 10/2011 |
| WO | WO 11/130578 | A2 | 10/2011 |
| WO | WO 11/150410 | A2 | 12/2011 |
| WO | WO 11/150411 | A1 | 12/2011 |
| WO | WO 12/061647 | A2 | 5/2012 |
| WO | WO 12/106560 | A1 | 8/2012 |
| WO | WO 12/154626 | A1 | 11/2012 |
| WO | WO 13/082186 | A2 | 6/2013 |
| WO | WO 2013/096891 | A1 | 6/2013 |
| WO | WO 13/158938 | | 10/2013 |
| WO | WO 14/176515 | A2 | 10/2014 |
| WO | WO 15/051319 | A2 | 4/2015 |
| WO | WO 2016/007862 | A2 | 1/2016 |
| WO | WO 2016/164495 | A1 | 10/2016 |
| WO | WO 2017/058802 | A1 | 4/2017 |

OTHER PUBLICATIONS

Amaro et al., "Advances and perspectives in using microalgae to produce biodiesel," Applied Energy, 88:3402-3410, (2011).

Andersen, "Biology and Systematics of Heterokont and Haptophyte Algae," American Journal of Botany, 91(10):1508-1522, (2004).

Appel et al., "A multicopy vector system for genetic studies in Mucor circinelloides and other zygomycetes," Molecular Genetics and Genomics, 271(5):595-602, (2004).

Apt et al., "Stable nuclear transformation of the diatom Phaeodactylum tricornutum," Mol Gen Genet, 252(5):572-579, (1996).

Barnes et al., "Contribution of 5'- and 3'-untranslated regions of plastid mRNAs to the expression of Chlamydomonas reinhardtii chloroplast genes," Mol Genet Genomics, 274(6):625-636, (2005).

Beale et al., "Chlorophyll Synthesis in Chlorella: Regulation by Degree of Light Limitation of Growth," Plant Physiol., 47:230-235, (1971).

Bhunia et al., "Algal Biodiesel Production: Challenges and Opportunities," Bioenergy and Biofuel from Biowastes and Biomass, American Society of Civil Engineers, pp. 313-345, (2010).

Bigogno et al., "Biosynthesis of arachidonic acid in the oleaginous microalga Parietochloris incisa(Cholorphyceae): Radiolabeling studies," Lipids 37(2):209-216 (2002); Abstract Only.

Bigogno et al., "Lipid and fatty acid composition of the green oleaginous alga Parietochloris incisa, the richest plant source of arachidonic acid," Pytochemistry, 60:497-503, (2002).

Blowers et al., "Studies on Chlamydomonas chloroplast transformation: foreign DNA can be stably maintained in the chromosome," Plant Cell, 1(1):123-132, (1989).

Bohacenko et al., "Detection of Olive Oils Authenticity by Determination of their Sterol Content using LC/GC," Czech J. Food Sci., 19(3):97-103, (2001).

(56) References Cited

OTHER PUBLICATIONS

Bonaventure et al., "Disruption of the FATB Gene in Arabidopsis Dethonstrates an Essential Role of Saturated Fatty Acids in Plant Growth," The Plant Cell 15:1020-1033, (2003).
Bordes et al., "A new recombinant protein expression system for high-throughput screening in the yeast Yarrowia lipolytica," Journal of Microbiological Methods, 70(3):493-502, (2007).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).
Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book).
Borza et al., "Multiple Metabolic Roles for the Nonphotosynthetic Plastid of the Green Alga Prototheca Wickerhamii," Eukaryotic Cell, 4(2):253-261, (2005).
Boutry et al., "Targeting of bacterial chloramphenicol acetyltransferase to mitochondria in transgenic plants," Nature, 328(6128):340-2, (1987).
Boynton et al., "Chloroplast Transformation in Chlamydomonas with High Velocity Microprojectiles," Science, 240(4858):1534-1538, (1988).
Broun et al., "A bifunctional oleate 12-hydroxylase: desaturase from Lesquerella fendleri," The Plant Journal, 13(2):201-210, (1998).
Broun et al., "Accumulation of Ricinoleic, Lesquerolic, and Densipolic Acids in Seeds of Transgenic Arabidopsis Plants That Express a Fatty Acyl Hydroxylase cDNA from Castor Bean," Plant Physiol., 113:933-942, (1997).
Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Cahoon et al., "A Determinant of Substrate Specificity Predicted from the Acyl-Acyl Carrier Protein Desaturase of Developing Cat's Claw Seed," Plant Physiol., 117:593-598, (1998).
Chang et al., "Deletion of the Δ12-oleic acid desaturase gene of a nonaflatoxigenic Aspergillus parasiticus field isolate affects conidiation and sclerotial development," Journal of Applied Microbiology, 97:1178-1184, (2004).
Chasan, "Engineering Fatty Acids—The Long and Short of It," Plant Cell, 7:235-237, (1995).
Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Highly Effective Expression of Rabbit Neutrophil Peptide-1 Gene in Chlorella Ellipsoidea Cells," Current Genetics, 39:365-370, (2001).
Chen et al., "Structural classification and properties of ketoacyl syntheses," Protein Science, 20(10):1659-1667, (2011).
Chica et al., "Semi-rational approaches to engineering enzyme activity: combining the benefits of directed evolution and rational design," Current Opinion in Biotechnology, 16:378-384, (2005).
Chow et al., "Electrotranformation of Chlorella Vulgaris," Plant Cell Reports, 18:778-780, (1999).
Ciferri, "Thiamine-deficiency of Prototheca, a Yeast-like Achloric Alga," Nature, 178:1475-1476, (1956).
Co et al., "Matching the Functionality of Single-Cell Algal Oils with Different Molecular Compositions," J Am Oil Chem Soc, doi:I0.1007/s11746-013-2405-y, 16 pages, (2014).
Cobley et al., "CpeR is an activator required for expression of the phycoerythrin operon (cpeBA) in the cyanobacterium Fremyella diplosiphon and is encoded in the phycoerythrin linker-polypeptide operon (cpeCDESTR)," Molecular Microbiology, 44(6):1517-1531, (2002).
Cobley et al., Construction of Shuttle Plasmids Which Can Be Efficiently Mobilized From *Escherichia coli* Into the Chromatically Adapting Cyanobacterium, Plasmid, 30:90-105, (1993).
Cohen et al., "The Heterotrophic Connection in a Photoautotrophic Chlorella Vulgaris Dominant in W Astew Ater Oxidation Ponds," War. Sci. Tech., 27(7-8):151-155, (1993).
Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemistry, 263(29);15104-15109 (1988).
Cordy et al., "Chlorellasis in a Lamb," Vet. Path., 10:171-176, (1973).
Courchesne et al., "Enhancement of Lipid Production Using Biochemical, Genetic and Transcription Factor Engineering Approaches," J Biotechnol. Epub, 141(1-2):31-41, (2009).
Covello et al., "Functional Expression of the Extraplastidial Arabidopsis thaliana Oleate Desaturase Gene (FAD2) in *Saccharomyces cerevisiae*'," Plant Physiol., 111:223-226, (1996).
Davies et al.,"Expression of the Arylsulfatase Gene from the Beta 2-Tubulin Promoter in Chlamydomonas reinhardtii," Nucleic Acids Research, 20(12):2959-2965, (1992).
Dawson et al., "Stable Transformation of Chlorella: Rescure of Nitrate Reductase-Deficient Mutants with the Nitrate Reductase Gene," Current Microbiology, 35:356-362, (1997).
Day, Al. et al., "Safety evaluation of a high-lipid algal biomass from Chlorella protorhecoides," Rego!. Toxicol. Pharmacol., doi:10.1016/j.yrtph.2009.06.014, 15 pages, (2009).
De Cock, "Structure development in confectionery products: importance of triacylglycerol composition," Master Thesis, Masters in Bioscience Engineering, Ghent University, 73 pages, (2011).
Debuchy et al., "The argininosuccinate lyase gene of Chlamydomonas reinhardtii: an important tool for nuclear transformation and for correlating the genetic and molecular maps of the ARG7 locus," EMBO J., 8(10):2803-2809, (1989).
Dehesh et al., "KAS IV: a 3-ketoacyl-ACP synthase from *Cuphea* sp. is a medium chain specific condensing enzyme," The Plant Journal, 16:383-390, (1998).
Dehesh et al., "Production of high levels of 8:0 and 10:0 fatty acids in transgenic canola by overexpression of Ch FatB2, a thioesterase cDNA from Cuphea hookeriana," The Plant Journal, 9(2):167-172, (1996).
Demirbas et al., "Importance of algae oil as a source of biodiesel," Energy Conversion and Management, 52:163-170, (2011).
Deshnium et al., "Transformation of Synechococcus with a gene for choline oxidase enhances tolerance to salt stress," Plant Mol Biol, 29(5):897-907, (1995).
Desmond et al., "Phylogenomics of Sterol Synthesis: Insights into the Origin, Evolution, and Diversity of a Key Eukaryotic Feature," Genome. Biol. Evol., 1:364-381, (2009).
Devos et al., "Practical Limits of Function Prediction," Proteins: Structure, Function, and Genetics, 41:98-107, (2000).
Dormann et al., "Cloning and Expression in *Escherichia coli* of a Novel Thioesterase from Arabidopsis thaliana Specific for Long-Chain Acyl-Acyl Carrier Proteins," Archives of Biochemistry and Biophysics, 316(1):612-618, (1995).
Dunahay et al., "Genetic Engineering of Microalgae for Fuel Production," Applied Biochemistry and Biotechnology, 34/35:331-339 (1992).
Dunahay et al., "Manipulation of Microalgal Lipid Production Using Genetic Engineering," Applied Biochemistry and Biotechnology, 57/58:223-231, (1996).
Eccleston et al., "Medium-chain Fatty Acid Biosynthesis and Utilization in *Brassica Mapus* Plants Expressing Lauroyl-Acyl Carrier Protein Thioesterase," Planta 198:46-53, (1996).
El-Fadaly et al., "Single Cell Oil Production by an Oleaginous Yeast Strain in a Low Cost Cultivation Medium," Research Journal of Microbiology, 4(8):301-313, (2009).

(56) References Cited

OTHER PUBLICATIONS

El-Sheekh, MM., "Stable Transformation of the Intact Cells of Chlorella Kessleri With High Velocity Microprojectiles," Biologia Plantarium 42(2): 209-216, (1999).
EPO Supplementary European Search Report and European Search Opinion for application EP 12782478.7 dated Oct. 22, 2014.
EPO Supplementary European Search Report and European Search Opinion for application EP 09829850.8 dated May 16, 2014.
EPO Supplementary European Search Report and European Search Opinion for application EP09729658 dated Jan. 3, 2013.
Erhan, "Vegetable Oils as Lubricants, Hydraulic Fluids, and Inks," Bailey's Industrial Oil and Fat Products, 6:259-278, (2005).
European Search Report and European Search Opinion for application EP08769988 dated Jul. 1, 2011.
European Search Report and European Search Opinion for application EP11158642 dated Jul. 1, 2011.
Evans et al., "A comparison of the oleaginous yeast, Candida curvata, grown on different carbon sources in continuous and batch culture," Lipids, 18(09):623-629, (1983).
Facciotti et al., "Improved stearate phenotype in transgenic canola expressing a modified acyl-acyl carrier protein thioesterase," Nat Biotechnol., 17(6):593-597, (1999).
Falciatore et al., "Transformation of Nonselectable Reporter Genes in Marine Diatoms," Marine Biotechnology; 1:239-251, (1999).
Fall et al., "Bioconversion of Xylan to Triglycerides by Oil-Rich Yeasts," Applied and Environmental Microbiology, 47(5):1130-1134, (1984).
Ferrentino, "Microalgal oil extraction and in situ transesterification," University of New Hampshire, Pub. No. MT 1447885, 93 pages, (2007).
Ferrentino, et al., "Microalgal Oil Extraction and In-situ Transesterification," AlChE Annual Mtg, San Francisco, CA, Nov. 11-13, 2006. Abstract.
Franklin et al., "Prospects for molecular farming in the green alga Chlamydomonas reinhardtii," Current Opinion in Plant Biology, 7:159-165, (2004).
Franzen et al., "Chloroplast transit peptides from the green alga Chlamydomonas reinhardtii share features with both mitochondrial and higher plant chloroplast presequences," FEBS Letters, 260(2)165-168, (1990).
Frenz et al., "Hydrocarbon recovery by extraction with a biocompatible solvent from free and immobilized cultures of Botryococcus braunii," Enzyme Microb Technol, 11(11):717-724, (1989).
Frohns et al., "Potassium ion channels of Chlorella viruses cause rapid depolarization of host cells during infection," J Virol, 80(5):2437-2444, (2006).
Fromm et al., "Expression of Genes Transferred into Monocot and Dicot Plant Cells by Electroporation," Proc Natl Acad Sci, 82:5824-5828, (1985).
Funes et al., "The typically mitochondrial DNA-encoded ATP6 subunit of the F1F0-ATPase is encoded by a nuclear gene in Chlamydomonas reinhardtii," J Biol Chem, 277(8):6051-6058, (2002).
Gabay et al., "Stigmasterol: a phytosterol with potential anti-osteoarthritic properties," Osteoarthritis and Cartilage,18:106-116, (2010).
GenBank: Accession No. AAC49001.1, May 1995. [Retrieved from the Internet Oct. 14, 2014: <URL: http://www.ncbi.nlrrtnih.gov/protein/595955?sat=13&satkey=6522409>].
Gill et al, "Lipid Accumulation in an Oleaginous Yeast (*Candida* 107) Growing on Glucose in Single-Stage Continuous Culture," Applied and Environmental Microbiology, 33(02):231-239, (1977).
Gouveia et al., "Microalgae in Novel Food Products," Food Chemistry Research Developments, Chapter 2, Nova Science Publishers, Inc., ISBN 978-1-60456-262-0, 37 pages, (May 2008).
Graves et al., "Hyaluronan synthesis in virus PBCV-1-infected chlorella-like green algae," Virology, 257(1):15-23, (1999).
Gruber et al., "*Escherichia coli*-Anacystis nidulans plasmid shuttle vectors containing the PL promoter from bacteriophage lambda," Current Microbiology, 22(1):15-19, (1991).
Guiry et al., "How Many Species of Algae are There?," J. Phycol., 48:1057-1063, (2012).
Gul et al., "Sterols and the Phytosterol Content in Oilseed Rape (*Brassica napus* L.)," Journal of Cell and Molecular Biology, 5:71-79 (2006).
Gunstone, "Enzymes as biocatalysts in the modification of natural lipids," Journal of the Science of Food and Agriculture, 79:1535-1549, (1999).
Guo et al., "Increase in nervonic acid content in transformed yeast and transgenic plants by introduction of a *Lunaria annua* L. 3-ketoacyl-CoA synthase (KCS) gene," Plant Mol. Biol., 69:565-575, (2009).
Guo-Zhong et al., "The Actin Gene Promoter-driven Bar as a Dominant Selectable Marker for Nuclear Transformation of Dunaliella Salina," Acta Genetica Sinica, 32(4): 424-433, (2005).
Guschina et al., "Lipids and lipid metabolism in eukaryotic algae," Progress in Lipid Research, 45:160-186, (2006).
Hall et al., "Expression of a foreign gene in Chlamydomonas reinhardtii," Gene, 124(1):75-81, (1993).
Hall et al., "Lipid Accumulation in an Oleaginous Yeast (*Candida* 107) Growing on Glucose Under Various Conditions in a One- and Two-Stage Continuous Culture," Applied and Environmental Microbiology, 33(3):577-584, (1977).
Hallmann et al., "Reporter Genes and Highly Regulated Promoters as Tools for Transformation Experiements in Volvox Carteri," Proc Natl Acad Sci U S A., 91(24):11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, Chlorella," Current Microbiology, 38:335-341, (1999).
Heifetz, "Genetic Engineering of the Chloroplast," Biochimie, 82:655-666, (2000).
Heise et al., "Factors Controlling Medium-Chain Fatty Acid Synthesis in Plastids From Cuphea Embryos," Prog. Lipid Res., 33(1/2):87-95, (1994).
Henderson et al., "Lipid Composition and Biosynthesis in the Marine Dinoflagellate Crypthecodznzum Cohnii," Phytochem. 27(6):1679-1683 (1988).
Henikoff et al., "Amino Acid Substitution Matrices from Protein Blocks," Proc Natl Acad of Sci, 89(22):10915-10919, (1992).
Heredia et al., "Simultaneous utilization of glucose and xylose by Candida curvata D in continuous culture," Biotechnology Letters, 10(01):25-30, (1988).
Heredia-Arroyo et al., "Oil Accumulation via Heterotrophic/Mixotrophic Chlorella protothecoides," Appl Biochem Biotechnol, 162:1978-1995, (2010).
Hillen et al., "Hydrocracking of the Oils of Botryococcus braunii to Transport Fuels," Biotechnology and Bioengineering, 24(1):193-205, (1982).
Hiramatsu et al., "Expression of a chitinase gene and lysis of the host cell wall during Chlorella virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Hortensteiner et al., "Chlorophyll breakdown in Chlorella protothecoides: characterization of degreening and cloning of degreening-related genes," Plant Molecular Biology, 42:439-450, (2000).
Hu et al., "Microalgal Triacylglycerols as Feedstocks for Biofuel Production: Perspectives and Advances," The Plant Journal 54:621-639, (2008).
Huang et al., "Sterols as ecological indicators," Geochimica et Cosmochimica Acta, 43:739-745, (1979).
Huang et al., "Expression of Mercuric Reductase From Bacillus Megaterium MB1 in Eukaryotic Microalga *Chlorella* sp. DT: An Approach for Mercury Phytoremediation," Appl. Microbial. Biotechnol., 72:197-205, (2006).

(56) References Cited

OTHER PUBLICATIONS

Inoue et al., "Analysis of oil derived from liquefaction of Botryococcus Braunii," Biomass and Bioenergy, 6(4):269-274, (1994).
Itoh et al., "Sterol Compositoin of 19 Vegetable Oils," Journal of the American Oil Chmists' Society, 50:122-125, (1973).
Iturriaga et al. "Heterologous transformation of Mucor circinelloides with the Phycomyces blakesleeanus leu1 gene," Current Genetics, 21(3):215-223, (1992).
Jakobiak et al., "The Bacterial Paromomycin Resistance Gene, aphH, as a Dominant Selectable Marker in Volvox carteri," Protist, 55: 381-393, (2004).
Jarvis et al. "Transient Expression of Firefly Luciferase in Protoplasts of the Green Alga Chlorella Ellipsoidea," Current Genet., 19: 317-322, (1991).
Jaworski et al., "Industrial oils from transgenic plants," Current Opinion in Plant Biology, 6:178-184, (2003).
Jha et al., "Cloning and functional expression of an acyl-ACP thioesterase FatB type from Diploknema (Madhuca) butyracea seeds in Escherichia coli," Plant Physiology and Biochemistry, 44:645-655, (2006).
Jiang et al., "The actin gene promoter-driven bar as a dominant selectable marker for nuclear transformation of Dunaliella salina," Yi Chuan Xue Bao, 32(4):424-433, (2005).
Jones et al., "Palmitoyl-Acyl Carrier Protein (ACP) Thioesterase and the Evolutionary Origin of Plant Acyl-ACP Thioesterases," Plant Cell, 7:359-371, (1995).
Kalscheuer et al., "Establishment of a Gene Transfer System for Rhodococcus Opacus PD630 Based on Electraporation and its Application for Recombinant Biosynthesis of Poly(3-hyroxyalkanoic acids)," Applied Microbiology and Biotechnology, 52(4):508-515, (1999).
Kamiya, "Effects of Blue Light and Ammonia on Nitrogen Metabolism in a Colorless Mutant of Chlorella," Plant Celll Physiol., 30(4):513-521, (1989).
Kamurthy et al., "Antinocieptive Activity of Stigmosterol-3-Glyceryl-2-Linoleiate, Campesterol and Daucosterol Isolated From Aerva Lanata Linn. Aerial Parts," Asian J Pharm Clin Res, 6(1):149-152, (2013).
Kang et al., "Genetic diversity in chlorella viruses flanking kcv, a gene that encodes a potassium ion channel protein," Virology, 326(1):150-159, (2004).
Kang et al., "The regulation activity of Chlorella virus gene 5' upstream sequence in Escherichia coli and eucaryotic alage," Institute of Microbiology, Chinese Academy of Sciences, Beijing, 16(4):443-6, (2000). Abstract only.
Karabulut et al., "Determination of changes in some physical and chemical properties of soybean oil during hydrogenation," Food Chemistry, 81:453-456, (2003).
Karlin et al., "Applications and statistics for multiple high-scoring segments in molecular sequences," Proc Natl Acad Sci, 90(12):5873-5877, (1993).
Katayama et al., "Alpha-Linolenate and Photosynethetic Activity in Chlorella Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kim et al. "Stable Integraion and Functional Expression of Flounder Growth Hormone Gene in Tranformed Microalga, Chlorella Ellipsoidea," Mar. Biotechnol. 4:63-73 (2002).
Kimchi-Sarfaty et al., "A 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of Chlamydomonas reinhardtii," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Klosty et al., "Sterols of Algae. The Occurrence of Ergosterol in Chiorelia pyrarwidosa," J. Am. Chem. Soc., Notes, 74(6):1601-1601, (1952).
Knauf, "The application of genetic engineering to oilseed crops," Trends in Biotechnology, 5(2):40-47, (1987).
Knothe, "'Designer' Biodiesel: Optimizing Fatty Ester Composition to Improve Fuel Properties," Energy & Fuels, 22:1358-1364, (2008).
Knothe, "Analyzing Biodiesel: Standards and Other Methods," JAOCS, 83(10):823-833, (2006).
Kohler et al., "The green fluorescent protein as a marker to visualize plant mitochondria in vivo," Plant J, 11(3):613-621, (1997).
Koksharova, "Genetic Tools for Cyanobacteria," Appl Microbial Biotechnol, 58(2)123-37, (2002).
Kong et al., "Microbial production of lipids by cofermentation of glucose and xylose with Lipomyces starkeyi 2#," Chinese Journal of Bioprocess Engineering, 05(02):36, (2007). Abstract.
Krebbers et al., "The maize chloroplast genes for the beta and epsilon subunits of the photosynthetic coupling factor CF1 are fused," Nucleic Acids Res, 10(16): 4986-5002, (1982).
Kuo et al., "Diversity of Oleic Acid, Ricinoleic Acid and Linoleic Acid Conversions Among Pseudomonas aeruginosa Strains," Current Microbiology, 49:261-266, (2004).
La Scala et al., "The effect of fatty acid composition on the acrylation kinetics of epoxidized triacylglycerols," Journal of the American Oil Chemists' Society, 79(1):59-63, (2002).
Lapidot et al., "Stable Chloroplast Transformation of the Unicellular Red Alga Porphyridium Species," Plant Physiol, 129:7-12, (2002).
Lawford et al., "Performance Testing of Zymomonas Mobilis Metabolically Engeineered for Confermation of Glucose, Xylose, and Arabinose," Appl Biochem Biotechnol., 98-100:429-48, (2002).
Larson et al., "Acyl CoA profilesof transgenic plants that accumulate medium-chain fatty acids indicate inefficient storage lipid synthesis in developing oilseeds," The Plant Journal, 32(4):519-527, (2002).
Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).
Leon-Banares et al., "Transgenic microalgae as green cell-factories," Trends in Biotechnology, 22(1):45-52, (2004).
Levitan et al., "Dual targeting of the protein disulfide isomerase RB60 to the chloroplast and the endoplasmic reticulum," Proc Natl Acad Sci, 102(17):6225-6230, (2005).
Li et al., "High-density cultivation of oleaginous yeast Rhodosporidium toriloides Y4 in fed-batch culture," Enzyme and Microbial Technology, 41:312-317, (2007).
Li et al., "Screening of oleaginous yeasts for broad-spectrum carbohydrates assimilating capacity," China Biotechnology, 25(12):39-44 (2005), and machine translation.
Lindley, "The impact of food processing antioxidants in vegetable oils, fruits, and vegetables," Trends in Food Science & Technology. 9:336-340, (1998).
List et al., "Melting properties of some structured lipids native to high stearic acid soybean oil," Grasas y Aceites, 55(Fasc. 2):135-137, (2004).
Lu et al., "Molecular cloning and stress-dependent expression of a gene encoding A12-fatty acid desaturase in the Antarctic microalga Chlorella vulgaris NJ-7," Extremophiles, 13:875-884, (2009).
Lu, "Biosynthesis and Gene Engineering of Plant Fatty Acids," Chinese Bulletin of Botany, 17(6):481-491, (2000). Abstract only.
Lubitz, "The Protein Quality, Digestibility, and Composition of Algae, Chlorella 71105," J. Food Sci. 28(2):229-232 (1963).
Lumbreras et al., "Efficient Foreign Gene Expression in Chlamydomonas Reinhardtii Mediated by an Endogenous Intron," Plant Journal, 14(4):441-447, (1998).

(56) References Cited

OTHER PUBLICATIONS

Madzak et al., "Functional analysis of upstream regulating regions from Yarrowia lipolytica XPR2 promoter," Microbiology, 145:75-87, (1999).
Manuell et al., "Robust expression of a bioactive mammalian protein in Chlamydomonas chloroplast," Plant Biotech J, 5(3):402-412, (2007).
Maruyama et al., "Introduction of Foreign DNA Into Chlorella Saccharophila by Electroporation," Biotechnology Techniques, 8:821-826, (1994).
Matsuka et al., "The Role of Respiration & Photosynthesis in the Chloroplast Regeneration in the Glucose-Bleached Cells of Chlorella Protothecoides," Plant and Cell Physiol., 7:149-162 (1966).
Mayer et al., "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," The Journal of Biological Chemistry, 280(5):3621-3627, (2005).
Mayer et al., "Identification of amino acid residues involved in substrate specificity of plant acyl-ACP thioesterases using a bioinformatics-guided approach," BMC Plant Biology, 7(1):1-11, (2007).
Mayfield et al., "Expression and Assembly of a Fully Active Antibody in Algae," Proc Natl Acad Sci, 100(2):438-442, (2003).
Mayfield et al., "Stable nuclear transformation of Chlamydomonas reinhardtii by using a C. reinhardtii gene as the selectable marker," Proc. Natl. Acad. Sci. USA, Cell Biology, 87:2087-2091, (1990).
Meesters et al., "High-cell-density cultivation of the lipid accumulating yeast Cryptococcus curvatus using glycerol as a carbon source," Applied Microbiology and Biotechnology, 45:575-579, (1996).
Meguro et al., "Original Communication Solubilization of phytosterols in diacylglycerol versus triacylglycerol improves the serum cholesterol-lowering effect," European Journal of Clinical Nutrition, 55:513-517, (2001).
Mekhedov et al., "Toward a Functional Catalog of the Plant Genome. A Survey of Genes for Lipid Biosynthesis," Plant Physiology, 122:389-401, (2000).
Mendes et al., "Supercritical Carbon Dioxide Extraction of Compounds With Pharmaceutical Importance from Microalgae," Inorganica Chimica Acta, 356:328-334, (2003).
Meng et al., "Biodiesel production from oleaginous microorganisms," Renewable Energy, 34:1-5, (2009).
Metzger et al., "Botryococcus braunii: A Rich Source for Hydrocarbons and Related Ether Lipids," Applied Microbiology and Biotechnology, 66(5):486-496, (2005).
Miao et al., "High Yield Bio-Oil Production from Fast Pyrolysis by Metabolic Controlling of Chlorella Protothecoides," J. Biotech., 110:85-93, (2004).
Minowa et al., "Oil Production from Algal Cells of Dunaliella tertiolecta by Direct Thermochemical Liquefaction," Fuel, 74(12)1735-1738, (1995).
Mitra et al., "A Chlorella Virus Gene Promoter Functions as a Strong Promoter Both in Plants and Bacteria," Biochemical and Biophysical Research Communications, 204(1):189-194, (1994).
Mitra et al., "The Chlorella Virus Adenine Methyltransferase Gene Promoter is a Strong Promoter in Plants," Plant Molecular Biology, 26(1):85-93, (1994).
Moreno-Perez et al., "Reduced expression of FatA thioesterases in Arabidopsis affects the oil content and fatty acid composition of the seeds," Planta, 235:629-639, (2012).
Morris, "Effect of Growth Temperature on the Cryopreservation of Prototheca," Journal of General Microbiology, 94:395-399, (1976).
Mullet et al., "Multiple transcripts for higher plantrbcL andatpB genes and localization of the transcription initiation site of therbcL gene," Plant Molecular Biology, 4(1):39-54, (1985).
Murakami et al., "Lipid Composition of Commercial Bakers' Yeasts Having Different Freeze-tolerance in Frozen Dough," Biosci. Biotechnol. Biochem., 60(11)1874-1876, (1996).
Murakami et al., "Lipids and Fatty Acid Custipvsi lions of Chlorella," Nihon Yuka gakkai-shi, 46(4):423-427, (1997).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1, 2007: <URL: http://www.sciencemag.org>].
Nahm, "Quality Characteristics of West African Shea Butter (*Vitellaria paradoxa*) and Approaches to Extend Shelf-Life," Master Thesis, Master of Science in Food Service, Rutgers, The State University of New Jersey, 133 pages, (2011).
Napier et al., "Tailoring plant lipid composition: designer oilseeds come of age," Current Opinion in Plant Biology, 13:330-337, (2010).
Nazaruddin et al., "The Effect of Enzymatic Alcoholysis on the Physicochemical Properties of Commercial Cocoa Butter Substitutes," Pakistan Journal of Nutrition, 10(8):718-723, (2011).
Needleman et al., "A general method applicable to the search for similarities in the amino acid sequence of two proteins," Journal of Molecular Biology, 48(3):443-453, (1970).
Nes et al., "Biosynthesis of Cholesterol and Other Sterols," Chem. Rev., 111:6423-6451, (2011).
Norton et al., "Identification of Ergosta-6(7),8(14),25(27)-trien-3β-ol and Ergosta-5(6),7(8),25(27)-trien-3β-ol, Two New Steroidal Trienes Synthesized by Prototheca wickerhamii," Lipids, 26: 247-249, (1991).
Onai et al., "Natural Tranformation of the Termophillic Cyanbacterium Thermosynechococcus Elongatus BP-1: A Simple and Efficicent Method for Gene Transfer," Mol Genet Genomics, 271(1):50-9, (2004).
Papanikolaou et al., "Single cell oil production by Yarrowia lipolytica growing on an industrial derivative of animal fat in batch cultures," Appl. Microbiol. Biotechnol, 58:308-312, (2002).
Papanikolaou et al., "Lipid production by Yarrowia lipolytica growing on industrial glycerol in a single-stage continuous culture," Bioresource Technology, 82:43-49, (2002).
Park et al., "Isolation and Characterization of Chlorella Virus From Fresh Water in Korea and Application in Chlorella Transformation System," Plant Pathol. J., 21(1):13-20, (2005).
Patil et al., "Fatty acid composition of 12 microalgae for possible use in aquaculture feed," Aquacult Int , 15:1-9, (2007).
Patterson et al., "Sterols of Chlorella. II. The Occurrence of an Unusual Sterol Mixture in Chlorella vulgaris," Plant Physiol., 42:1457-1459, (1967).
Patterson et al., "Sterols of Chlorella-III. Species Containing Ergosterol," Comp. Biochem. Physiol., 31:391-394, (1969).
PCT International Preliminary Report on Patentability (Chapter I) dated May 31, 2011 for application PCT/US09/066142.
PCT International Preliminary Report on Patentability (Chapter I) dated Aug. 13, 2012 for application PCT/US11/38463.
PCT International Preliminary Report on Patentability (Chapter I) dated Oct. 12, 2010 for application PCT/US2009/040123.
PCT International Preliminary Report on Patentability (Chapter I) dated Dec. 7, 2009 for application PCT/US08/65563.
PCT International Preliminary Report on Patentability for application PCT/US10/31088 dated Oct. 27, 2011.
PCT International Preliminary Report on Patentability for application PCT/US2011/059224 dated May 16, 2013.
PCT International Search Report and Written Opinion of the International Searching Authority for application PCT/US2013/037261 dated Aug. 23, 2013.
PCT International Search Report and Written Opinion of the International Searching Authority for application PCT/US2014/035476 dated Feb. 18, 2015.
PCT International Search Report for application PCT/US11/32588 dated Jun. 27, 2011.
PCT International Search Report for application PCT/US09/060692 dated Apr. 22, 2010.
PCT International Search Report for application PCT/US10/31088 dated Jun. 28, 2010.
PCT International Search Report for application PCT/US11/32586 dated Jun. 20, 2011.
PCT International Search Report for application PCT/US2009/040123 dated Oct. 5, 2009.

(56) References Cited

OTHER PUBLICATIONS

PCT International Search Report for application PCT/US2011/032582 dated Aug. 9, 2011.
PCT International Search Report for application PCT/US2011/038463 dated Jan. 18, 2012.
PCT International Search Report for application PCT/US2011/038464 dated Nov. 3, 2011.
PCT International Search Report for application PCT/US2011/059224 dated Jun. 27, 2012.
PCT International Search Report for application PCT/US2012/023696 dated May 23, 2012.
PCT International Search Report for application PCT/US2012/036690 dated Aug. 30, 2012.
PCT International Search Report dated Aug. 20, 2010 for application PCT/US2009/066142.
PCT International Search Report dated Nov. 5, 2010 for application PCT/US2009/066141.
PCT International Search Report dated Nov. 6, 2008 for application PCT/US2008/065563.
PCT Invitation to Pay Additional Fees from the International Searching Authority for application PCT/US2014/035476 dated Dec. 1, 2014.
PCT Invitation to Pay Additional Fees from the International Searching Authority for application PCT/US2014/059161 dated Mar. 9, 2015.
PCT Written Opinion of the International Search Authority dated Aug. 20, 2010 for application PCT/US2009/066142.
PCT Written Opinion of the International Searching Authority for application PCT/US11/32588 dated Jun. 27, 2011.
PCT Written Opinion of the International Searching Authority for application PCT/US09/060692 dated Apr. 22, 2010.
PCT Written Opinion of the International Searching Authority for application PCT/US10/31088 dated Jun. 28, 2010.
PCT Written Opinion of the International Searching Authority for application PCT/US11/32586 dated Jun. 20, 2011.
PCT Written Opinion of the International Searching Authority for application PCT/US2011/032582 dated Aug. 9, 2011.
PCT Written Opinion of the International Searching Authority for application PCT/US2011/038463 dated Jan. 18, 2012.
PCT Written Opinion of the International Searching Authority for application PCT/US2011/038464 dated Nov. 3, 2011.
PCT Written Opinion of the International Searching Authority for application PCT/US2012/023696 dated May 23, 2012.
PCT Written Opinion of the International Searching Authority for application PCT/US2012/036690 dated Aug. 30, 2012.
PCT Written Opinion of the International Searching Authority dated Nov. 5, 2010 for application PCT/US2009/066141.
PCT Written Opinion of the International Searching Authority dated Nov. 6, 2008 for application PCT/US2008/065563.
Pearson et al., "Improved tools for biological sequence comparison," Proc Natl Acad Sci, 85(8):2444-2448, (1988).
Petkov et al., "Which are fatty acids of the green alga Chlorella?," Biochemical Systematics and Ecology, 35:281-285, (2007).
Powell et al., "Algae Feeding in Humans," J. Nutrition, 75:7-12, (1961).
Pratoomyot et al., "Fatty acids composition of 10 microalgal species," Songklanakarin J. Sci. Technol., 27(6):1179-1187, (2005).
Proschold et al., "Portrait of a Species: *Chlamydomonas reinhardtii*," Genetics, 170(4):1601-1610, (2005).
Puglia et al., "In viva spectrophotometric evaluation of skin barrier recovery after topical application of soybean phytosterols," J. Cosmet. Sci., 59:217-224, (2008).
Qingyu et al., "Fine Cell Structure and Biochemical Compositions of Chlorella Protothecoides after Transferring from Autotrophic to Heterotrophic Metabolism," Journal of Nanjing University, Natural Sciences Edition, 29(4):622-630, (1993). Abstract.
Radakovits et al., "Genetic Engineering of Algae for Enhanced Biofuel Production," Eukaryotic Cell, 9(04): 486-501, (2010).
Randolph-Anderson et al., "Further characterization of the respiratory deficient dum-1 mutation of Chlamydomonas reinhardtii and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-100, (2002).
Rehm et al., "Heterologous expression of the acyl-acyl carrier protein thioesterase gene from the plant Umbellularia californica mediates polyhydroxyalkanoate biosynthesis in recombinant *Escherichia coli*," Appl Microbial Biotechnol, 55:205-209, (2001).
Rismani-Yazdi et al., "Transcriptome sequencing and annotation of the microalgae Dunaliella tertiolecta: Pathway description and gene discovery for production of next-generation biofuels," BMC Genomics, 12:148, 17 pages; doi:10.1186/1471-2164-12-148, (2011).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Roscoe et al., "Mutations in the fatty acid elongation 1 gene are associated with a loss of beta-ketoacyl-CoA synthase activity in low erucic acid rapeseed," FEBS Letters, 492:107-111, (2001).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracellular Fat by the Yeast Lipomyces starkeyi," Indian Journal of Experimental Biology, 16(4):511-512, (1978).
Running et al., "Extracellular production of L-ascorbic acid by Chlorella protothecoides, Prototheca species, and mutants of P. moriformis during aerobic culturing at low pH," Journal of Industrial Microbiology & Biotechnology, 29:93-98, (2002).
Saha et al., "Transformation in Aspergillus ochraceus," Current Microbiology, 30(2):83-86, (1995)
Sakuradani, "Studies of Metabolic Engineering of Useful Lipid-producing Microorganisms," NISR Research Grant, (2004).
Sanchez et al., "Mixotrophic culture of Chlorella pyrenoidosa with olive-mill wastewater as the nutrient medium," Journal of Applied Phycology, 13:443-449, (2001).
Sanford, "The biolistic process," Trends in Biotechnology, 6(12):299-302, (1988).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and CO2 mitigation by thermochemical liquefaction of microalgae," Biomass and Bioenergy, 17(1):33-39, (1999).
Schechter et al., "Relations between Structure and Function in Cytoplasmic Membrane Vesicles Isolated from an *Escherichia coli* Fatty-Acid Auxotroph," Eur. J. Biochem, 49 61-76, (1974).
Schomburg et al. (eds.), "Δ12-fatty-acid desaturase," Springer Handbook of Enzymes S8, Class 1 Oxidoreductases: EC 1, DOI 10.1007/978-3-642-36265-1_97, pp. 668-678, (2013).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Schütt et al., "The role of acyl carrier protein isoforms from Cuphea lanceolata seeds in the de-novo biosynthesis of medium-chain fatty acids," Publication, Planta, 205:263-268, (1998).
Schütt et al., "β-Ketoacyl-acyl carrier protein synthase IV: a key enzyme for regulation of medium-chain fatty acid synthesis in Cuphea lanceolata seeds," Planta, 215:847-854, (2002).
Seffernick et al., "Melamine Deaminase and Atrazine Chlorohydrolase: 98 Percent Identical but Functionally Different," Journal of Bacteriology, 183(8):2405-2410, (2001).
Sen et al., "Developments in Directed Evolution for Improving Enzyme Functions," Appl Biochem Biotechnol, 143:212-223, (2007).

(56) References Cited

OTHER PUBLICATIONS

Shao et al., “Cloning and expression of metallothionein mutant α-KKS-α in *Anabaena* sp. PCC 7120,” Marine Pollution Bulletin, 45(1012):163-167, (2002).
Shi et al., “High-Yield Production of Lutein by the Green Microalga Chlorella protothecoides in Heterotrophic Fed-Batch Culture,” Biotechnol. Prog., 18(4):723-727 (2002).
Shi et al., “Production and rapid extraction of lutein and the other lipid-soluble pigments from Chlorella protothecoides grown under heterotrophic and mixotrophic conditions,” Nahrung, 43:109-113, (1999).
Skolnick et al., “From genes to protein structure and function: novel applications of computational approaches in the genomic era,” TIBTECH, 18: 34-39, (2000).
Smallwood et al., “Different Substitutions at Conserved Amino Acids in Domains II and III in the Sendai L RNA Polymerase Protein Inactivate Viral RNA Synthesis,” Virology, 304:135-145, (2002).
Smith et al., “Comparison of Biosequences,” Adv Appl Math, 2(4):482-489, (1981).
Smith et al., “Production of hydroxy fatty acids in the seeds of *Arabidopsis thaliana*,” Biochemical Society Transactions, 28(6):947-950, (2000).
Sorger et al., “Triacylglycerol biosynthesis in yeast,” AppL Microbiol Biotechnol, 61:289-299, (2003).
Spolaore et al., “Commercial Applications of Microalgae,” J. Biosci. Bioeng. 101(2):87-96 (2006).
Stemmer et al., “Single-Step Assembly of a Gene and Entire Plasmid from Large Numbers of Oligodeoxyribonucleotides,” Gene, 164:49-53, (1995).
Sud et al., “Lipid Composition and Sensitivity of Prototheca wickerhamii to Membrane-Active Antimicrobial Agents,” Antimicrobial Agents and Chemotherapy, 16:486-490, (1979).
Suda, et al., “Evidence for a novel Chlorella virus-encoded alginate lyase,” FEMS Microbiology Letters, 180(1):45-53, (1999).
Suh et al., “What limits production of unusual monoenoic fatty acids in transgenic plants?,” Planta, 215:684-595, (2002).
Sun et al., “Characterization of two chitinase genes and one chitosanase gene encoded by Chlorella virus PBCV-1,” Virology, 263(2):376-387, (1999).
Sung et al., “The research on the lipid content and composition of microalgae and their impact factors,” Marine Science, 12(33)122-128, (2009). (English translation of first two pages).
Swern et al. “Fractionation of tallow fatty acids:Preparation of purified oleic acid and an inedible olive oil substitute,” Oil & Soap, 22(11):302-304 (1945).
Szabo et al., “Safety evaluation of a high lipid Whole Algalin Flour (WAF) from Chlorella protothecoides,” Regulatory Toxicology and Pharmacology, 63:165-165, (2012).
Szabo et al., “Safety evaluation of Whole Algalin Protein (WAP) from Chlorella protothecoides,” Food and Chemical Toxicology, 59:34-45, (2013).
Takaku et al., “Isolation of an Antitumor Compound from Agaricus blazei Murill and Its Mechanism of Action,” J. Nutr., 131:1409-1413, (2001). [Retrieved from the Internet May 14, 2013: <URL: http://jn.nutrition.org>].
Takeno et al., “Establishment of an overall transformation system for an oil-producing filamentous fungus, Mortierella alpina 1S-4,” Appl Microbiol Biotechnol, 65:419-425, (2004).
Talbot et al., “Formulation and Production of Confectionery Fats,” OFI Middle East 2007 Conference and Exhibition, 378 pages, (2007).
Talebi et al., “Genetic manipulation, a feasible tool to enhance unique characteristic of Chlarella vulgaris as a feedstock for biodiesel production,” Mol Biol Rep, 40:4421-4428, (2013).
Tan et al., “Establishment of a Micro-Particle Bombardment Transformation System for Dunaliella Salina,” J Microbiol.;43(4):361-365, (2005).
Tang et al., “Insertion mutagenesis of Chlamydomonas reinhardtii by electroporation and heterologous DNA,” Biochem Mol Biol Int, 36(5):1025-1035, (1995).
Tomasinsig et al., “The Cathelicidins—Structure, Function and Evolution,” Current Protein and Peptide Science, 6: 23-34, (2005).
Tornabene et al., “Lipid composition of the nitrogen starved green alga Neochloris oleoabundans,” Enzyme Microb. Technol., 5:435-440, (1983).
U.S. Appl. No. 12/131,766, Advisory Action dated Oct. 13, 2011.
U.S. Appl. No. 12/131,766, Non-Final Office Action dated Aug. 1, 2011.
U.S. Appl. No. 12/131,766, Non-Final Office Action dated Nov. 23, 2010.
U.S. Appl. No. 12/131,766, Non-Final Office Action dated Dec. 10, 2009.
U.S. Appl. No. 12/131,766, Requirement for Restriction/Election dated Aug. 5, 2009.
U.S. Appl. No. 12/131,766, Requirement for Restriction/Election dated Aug. 17, 2010.
U.S. Appl. No. 12/131,773, Advisory Action dated Jan. 27, 2014.
U.S. Appl. No. 12/131,773, Final Office Action dated Mar. 21, 2011.
U.S. Appl. No. 12/131,773, Final Office Action dated Oct. 15, 2013.
U.S. Appl. No. 12/131,773, Non-Final Office Action dated Jun. 5, 2013.
U.S. Appl. No. 12/131,773, Non-Final Office Action dated Jun. 25, 2010.
U.S. Appl. No. 12/131,773, Non-Final Office Action dated Dec. 15, 2009.
U.S. Appl. No. 12/131,773, Notice of Allowance and Examiner Initiated Interview Summary dated Apr. 1, 2014.
U.S. Appl. No. 12/131,773, Requirement for Restriction/Election dated Aug. 6, 2009.
U.S. Appl. No. 12/131,783, Final Office Action dated Jan. 12, 2012.
U.S. Appl. No. 12/131,783, Final Office Action dated Dec. 13, 2013.
U.S. Appl. No. 12/131,783, Non-Final Office Action dated Jun. 6, 2011.
U.S. Appl. No. 12/131,783, Non-Final Office Action dated Jul. 18, 2013.
U.S. Appl. No. 12/131,783, Notice of Allowance and Examiner Initiated Interview Summary dated Mar. 24, 2014.
U.S. Appl. No. 12/131,783, Requirement for Restriction/Election dated Apr. 19, 2011.
U.S. Appl. No. 12/131,793, Final Office Action dated Mar. 30, 2010.
U.S. Appl. No. 12/131,793, Non-Final Office Action dated Jun. 21, 2012.
U.S. Appl. No. 12/131,793, Non-Final Office Action dated Sep. 16, 2009.
U.S. Appl. No. 12/131,793, Non-Final Office Action dated Nov. 13, 2012.
U.S. Appl. No. 12/131,793, Notice of Allowance dated Apr. 3, 2013.
U.S. Appl. No. 12/131,793, Requirement for Restriction/Election dated Aug. 6, 2009.
U.S. Appl. No. 12/131,804, Final Office Action dated Feb. 2, 2011.
U.S. Appl. No. 12/131,804, Non-Final Office Action dated Oct. 26, 2012.
U.S. Appl. No. 12/131,804, Non-Final Office Action dated Mar. 3, 2010.
U.S. Appl. No. 12/131,804, Non-Final Office Action dated Jun. 7, 2012.
U.S. Appl. No. 12/131,804, Requirement for Restriction/Election dated Sep. 17, 2009.
U.S. Appl. No. 12/131,804, Requirement for Restriction/Election dated Nov. 18, 2009.
U.S. Appl. No. 12/194,389, Final Office Action dated Jan. 5, 2011.
U.S. Appl. No. 12/194,389, Non-Final Office Action dated Feb. 4, 2010.
U.S. Appl. No. 12/194,389, Notice of Allowance dated Jan. 15, 2014.
U.S. Appl. No. 12/194,389, Requirement for Restriction/Election dated Oct. 5, 2010.
U.S. Appl. No. 12/194,389, Requirement for Restriction/Election dated Nov. 2, 2009.
U.S. Appl. No. 12/499,033, Final Office Action dated Oct. 19, 2011.

(56) References Cited

OTHER PUBLICATIONS

U.S. Appl. No. 12/499,033, Non-Final Office Action dated Feb. 18, 2011.
U.S. Appl. No. 12/499,033, Requirement for Restriction/Election dated Oct. 15, 2010.
U.S. Appl. No. 12/579,091, Requirement for Restriction/Election dated Oct. 18, 2012.
U.S. Appl. No. 12/628,140, Final Office Action dated Mar. 15, 2013.
U.S. Appl. No. 12/628,140, Final Office Action dated May 22, 2014.
U.S. Appl. No. 12/628,140, Final Office Action dated Sep. 12, 2013.
U.S. Appl. No. 12/628,140, Final Office Action dated Oct. 8, 2014.
U.S. Appl. No. 12/628,140, Non-Final Office Action dated Oct. 30, 2012.
U.S. Appl. No. 12/628,144, Final Office Action dated Nov. 16, 2010.
U.S. Appl. No. 12/628,144, Final Office Action dated Dec. 5, 2011.
U.S. Appl. No. 12/628,144, Final Office Action dated Dec. 12, 2014.
U.S. Appl. No. 12/628,144, Non-Final Office Action dated May 16, 2014.
U.S. Appl. No. 12/628,144, Non-Final Office Action dated Jun. 7, 2011.
U.S. Appl. No. 12/628,144, Non-Final Office Action dated Jul. 8, 2010.
U.S. Appl. No. 12/628,144, Requirement for Restriction/Election and Examiner Initiated Interview Summary dated Oct. 7, 2014.
U.S. Appl. No. 12/628,147, Examiner Interview Summary Record dated Mar. 3, 2011.
U.S. Appl. No. 12/628,147, Final Office Action dated Jul. 12, 2012.
U.S. Appl. No. 12/628,147, Final Office Action dated Oct. 1, 2010.
U.S. Appl. No. 12/628,147, Non-Final Office Action dated May 25, 2010.
U.S. Appl. No. 12/628,147, Non-Final Office Action dated Oct. 25, 2011.
U.S. Appl. No. 12/628,147, Notice of Allowance and Examiner Initiated Interview Summary dated Aug. 7, 2012.
U.S. Appl. No. 12/628,149, Non-Final Office Action dated Jun. 25, 2010.
U.S. Appl. No. 12/628,149, Non-Final Office Action dated Sep. 16, 2010.
U.S. Appl. No. 12/628,149, Notice of Allowance dated Dec. 15, 2010.
U.S. Appl. No. 12/628,150, Non-Final Office Action dated Apr. 29, 2010.
U.S. Appl. No. 12/628,150, Non-Final Office Action dated Oct. 13, 2010.
U.S. Appl. No. 12/628,150, Notice of Allowance dated Mar. 21, 2011.
U.S. Appl. No. 12/684,884, Final Office Action dated Oct. 23, 2013.
U.S. Appl. No. 12/684,884, Non-Final Office Action and Applicant-Initiated Interview Summary dated Aug. 14, 2014.
U.S. Appl. No. 12/684,884, Non-Final Office Action dated Apr. 25, 2013.
U.S. Appl. No. 12/684,884, Requirement for Restriction/Election dated Oct. 23, 2012.
U.S. Appl. No. 12/684,885, Requirement for Restriction/Election dated Oct. 5, 2012.
U.S. Appl. No. 12/684,886, Final Office Action dated Jan. 3, 2014.
U.S. Appl. No. 12/684,886, Final Office Action dated Jan. 16, 2015.
U.S. Appl. No. 12/684,886, Non-Final Office Action dated Jun. 6, 2013.
U.S. Appl. No. 12/684,886, Non-Final Office Action dated Aug. 27, 2014.
U.S. Appl. No. 12/684,886, Requirement for Restriction/Election dated Nov. 2, 2012.
U.S. Appl. No. 12/684,887, Requirement for Restriction/Election dated Oct. 12, 2012.
U.S. Appl. No. 12/684,888, Requirement for Restriction/Election dated Oct. 29, 2012.
U.S. Appl. No. 12/684,889, Requirement for Restriction/Election dated Oct. 23, 2012.
U.S. Appl. No. 12/684,891, Final Office Action dated Jan. 7, 2014.
U.S. Appl. No. 12/684,891, Non-Final Office Action dated Jan. 2, 2015.
U.S. Appl. No. 12/684,891, Non-Final Office Action dated Apr. 2, 2013.
U.S. Appl. No. 12/684,891, Requirement for Restriction/Election dated Oct. 23, 2012.
U.S. Appl. No. 12/684,892, Requirement for Restriction/Election dated Oct. 9, 2012.
U.S. Appl. No. 12/684,893, Requirement for Restriction/Election dated Oct. 10, 2012.
U.S. Appl. No. 12/684,894, Requirement for Restriction/Election dated Oct. 9, 2012.
U.S. Appl. No. 12/772,163, Non-Final Office Action dated May 25, 2012.
U.S. Appl. No. 12/772,163, Non-Final Office Action dated Dec. 12, 2012.
U.S. Appl. No. 12/772,163, Notice of Allowance dated May 28, 2013.
U.S. Appl. No. 12/772,163, Requirement for Restriction/Election dated Jun. 24, 2011.
U.S. Appl. No. 12/772,164, Final Office Action dated May 24, 2012.
U.S. Appl. No. 12/772,164, Non-Final Office Action dated Oct. 12, 2011.
U.S. Appl. No. 12/772,164, Requirement for Restriction/Election dated Jul. 20, 2011.
U.S. Appl. No. 12/772,170, Final Office Action dated Feb. 21, 2012.
U.S. Appl. No. 12/772,170, Non-Final Office Action dated Sep. 13, 2011.
U.S. Appl. No. 12/772,170, Non-Final Office Action dated Dec. 17, 2013.
U.S. Appl. No. 12/772,170, Notice of Allowance and Examiner-Initiated Interview Summary dated Jul. 11, 2014.
U.S. Appl. No. 12/772,170, Requirement for Restriction/Election dated Jul. 13, 2011.
U.S. Appl. No. 12/772,173, Final Office Action dated May 7, 2012.
U.S. Appl. No. 12/772,173, Non-Final Office Action dated Dec. 16, 2011.
U.S. Appl. No. 12/772,173, Notice of Allowance dated Mar. 29, 2013.
U.S. Appl. No. 12/772,173, Notice of Allowance dated Jul. 10, 2013.
U.S. Appl. No. 12/772,173, Requirement for Restriction/Election dated Oct. 26, 2011.
U.S. Appl. No. 12/772,174, Non-Final Office Action dated Nov. 29, 2011.
U.S. Appl. No. 12/772,174, Requirement for Restriction/Election dated Aug. 10, 2011.
U.S. Appl. No. 12/960,388, Notice of Allowance dated May 28, 2013.
U.S. Appl. No. 12/960,388, Requirement for Restriction/Election dated Apr. 1, 2013.
U.S. Appl. No. 12/981,409, Non-Final Office Action dated Jan. 6, 2012.
U.S. Appl. No. 12/981,409, Notice of Allowance dated May 29, 2012.
U.S. Appl. No. 12/981,409, Requirement for Restriction/Election dated Apr. 19, 2012.
U.S. Appl. No. 12/981,409, Requirement for Restriction/Election dated Oct. 28, 2011.
U.S. Appl. No. 13/029,061, Requirement for Restriction/Election dated Nov. 29, 2011.
U.S. Appl. No. 13/045,500, Non-Final Office Action dated Mar. 9, 2012.
U.S. Appl. No. 13/045,500, Non-Final Office Action dated Jun. 5, 2014.
U.S. Appl. No. 13/045,500, Final Office Action dated Sep. 26, 2012.
U.S. Appl. No. 13/073,757, Non-Final Office Action dated Aug. 15, 2011.
U.S. Appl. No. 13/073,757, Non-Final Office Action dated Dec. 29, 2011.
U.S. Appl. No. 13/073,757, Notice of Allowance dated Apr. 17, 2012.
U.S. Appl. No. 13/087,305, Final Office Action dated Mar. 18, 2013.

(56) References Cited

OTHER PUBLICATIONS

U.S. Appl. No. 13/087,305, Non-Final Office Action dated Aug. 15, 2012.
U.S. Appl. No. 13/087,311, Final Office Action dated Dec. 16, 2013.
U.S. Appl. No. 13/087,311, Non-Final Office Action dated Apr. 23, 2013.
U.S. Appl. No. 13/087,311, Non-Final Office Action dated Jun. 24, 2014.
U.S. Appl. No. 13/087,330, Requirement for Restriction/Election dated Dec. 21, 2012.
U.S. Appl. No. 13/118,365, Final Office Action dated Jul. 22, 2013.
U.S. Appl. No. 13/118,365, Non-Final Office Action dated Feb. 11, 2013.
U.S. Appl. No. 13/118,365, Requirement for Restriction/Election dated Oct. 11, 2012.
U.S. Appl. No. 13/118,369, Final Office Action dated Mar. 28, 2014.
U.S. Appl. No. 13/118,369, Non-Final Office Action dated Mar. 28, 2013.
U.S. Appl. No. 13/118,369, Requirement for Restriction/Election dated Dec. 13, 2012.
U.S. Appl. No. 13/263,724, Non-Final Office Action dated Feb. 28, 2013.
U.S. Appl. No. 13/263,724, Non-Final Office Action dated Oct. 23, 2013.
U.S. Appl. No. 13/263,724, Non-Final Office Action dated Nov. 20, 2014.
U.S. Appl. No. 13/273,179, Non-Final Office Action dated Jan. 28, 2014.
U.S. Appl. No. 13/273,179, Notice of Allowance dated Jul. 11, 2014.
U.S. Appl. No. 13/273,179, Requirement for Restriction/Election dated Nov. 14, 2013.
U.S. Appl. No. 13/288,815, Final Office Action dated Oct. 22, 2014.
U.S. Appl. No. 13/288,815, Non-Final Office Action dated Jun. 18, 2014.
U.S. Appl. No. 13/288,815, Notice of Allowance dated Feb. 26, 2015.
U.S. Appl. No. 13/288,815, Requirement for Restriction/Election dated Jan. 30, 2014.
U.S. Appl. No. 13/365,253, Requirement for Restriction/Election dated Dec. 16, 2014.
U.S. Appl. No. 13/366,198, Non-Final Office Action dated Jun. 18, 2012.
U.S. Appl. No. 13/366,198, Notice of Allowance and Applicant Initiated Interview Summary dated Aug. 21, 2012.
U.S. Appl. No. 13/406,417, Non-Final Office Action dated Nov. 5, 2012.
U.S. Appl. No. 13/406,417, Requirement for Restriction/Election dated Apr. 30, 2012.
U.S. Appl. No. 13/464,948, Final Office Action dated Feb. 13, 2014.
U.S. Appl. No. 13/464,948, Non-Final Office Action dated Oct. 9, 2013.
U.S. Appl. No. 13/464,948, Notice of Allowance dated May 25, 2014.
U.S. Appl. No. 13/464,948, Requirement for Restriction/Election dated Aug. 21, 2013.
U.S. Appl. No. 13/479,194, Non-Final Office Action dated Mar. 26, 2014.
U.S. Appl. No. 13/479,200, Non-Final Office Action dated Apr. 10, 2013.
U.S. Appl. No. 13/479,200, Non-Final Office Action dated Sep. 9, 2013.
U.S. Appl. No. 13/479,200, Notice of Allowance dated Nov. 25, 2013.
U.S. Appl. No. 13/479,200,Requirement for Restriction/Election dated Jan. 15, 2013.
U.S. Appl. No. 13/527,480, Final Office Action dated Jan. 16, 2014.
U.S. Appl. No. 13/527,480, Non-Final Office Action dated Jun. 26, 2013.
U.S. Appl. No. 13/527,480, Requirement for Restriction/Election dated May 3, 2013.
U.S. Appl. No. 13/543,666, Non-Final Office Action dated Sep. 5, 2013.
U.S. Appl. No. 13/543,666, Notice of Allowance dated Feb. 10, 2014.
U.S. Appl. No. 13/543,666, Requirement for Restriction/Election dated Jan. 3, 2013.
U.S. Appl. No. 13/547,457, Final Office Action dated Mar. 20, 2014.
U.S. Appl. No. 13/547,457, Non-Final Office Action dated Jul. 8, 2013.
U.S. Appl. No. 13/547,457, Notice of Allowance and Examiner-Initiated Interview Summary dated May 29, 2014.
U.S. Appl. No. 13/550,412, Non-Final Office Action dated Oct. 29, 2012.
U.S. Appl. No. 13/550,412, Notice of Allowance dated Feb. 21, 2013.
U.S. Appl. No. 13/555,009, Non-Final Office Action dated Sep. 16, 2014.
U.S. Appl. No. 13/555,009, Notice of Allowance dated Jan. 9, 2015.
U.S. Appl. No. 13/555,009, Requirement for Restriction/Election dated Jun. 16, 2014.
U.S. Appl. No. 13/558,252, Final Office Action dated Jul. 9, 2013.
U.S. Appl. No. 13/558,252, Non-Final Office Action dated Jan. 18, 2013.
U.S. Appl. No. 13/558,252, Notice of Allowance dated Oct. 23, 2013.
U.S. Appl. No. 13/601,928, Non-Final Office Action dated Jan. 31, 2013.
U.S. Appl. No. 13/601,928, Notice of Allowance dated Feb. 26, 2013.
U.S. Appl. No. 13/601,937, Final Office Action dated Nov. 22, 2013.
U.S. Appl. No. 13/601,937, Non-Final Office Action dated Jun. 10, 2013.
U.S. Appl. No. 13/601,937, Requirement for Restriction/Election dated Feb. 27, 2013.
U.S. Appl. No. 13/621,722, Requirement for Restriction/Election dated Jan. 31, 2013.
U.S. Appl. No. 13/621,722, Final Office Action dated Oct. 25, 2013.
U.S. Appl. No. 13/621,722, Non-Final Office Action dated May 9, 2013.
U.S. Appl. No. 13/621,722, Notice of Allowance and Examiner Initiated Interview Summary dated Jan. 10, 2014.
U.S. Appl. No. 13/628,039, Non-Final Office Action dated Jun. 4, 2013.
U.S. Appl. No. 13/628,039, Notice of Allowance and Examiner-Initiated Interview Summary dated Feb. 20, 2014.
U.S. Appl. No. 13/628,039, Requirement for Restriction/Election dated Mar. 7, 2013.
U.S. Appl. No. 13/630,757, Non-Final Office Action dated Oct. 27, 2014.
U.S. Appl. No. 13/630,757, Requirement for Restriction/Election dated Jun. 12, 2014.
U.S. Appl. No. 13/650,018, Non-Final Office Action dated Dec. 23, 2013.
U.S. Appl. No. 13/650,018, Notice of Allowance dated Aug. 14, 2014.
U.S. Appl. No. 13/650,018, Requirement for Restriction/Election dated Aug. 22, 2013.
U.S. Appl. No. 13/650,024, Non-Final Office Action dated Jul. 2, 2013.
U.S. Appl. No. 13/650,024, Notice of Allowance dated Oct. 17, 2013.
U.S. Appl. No. 13/667,784, Final Office Action dated Dec. 22, 2014.
U.S. Appl. No. 13/667,784, Non-Final Office Action dated Mar. 27, 2014.
U.S. Appl. No. 13/804,185, Requirement for Restriction/Election dated Mar. 16, 2015.
U.S. Appl. No. 13/849,330, Requirement for Restriction/Election dated Jan. 21, 2015.
U.S. Appl. No. 13/852,116, Final Office Action dated Aug. 18, 2014.
U.S. Appl. No. 13/852,116, Non-Final Office Action dated Mar. 26, 2014.

(56) References Cited

OTHER PUBLICATIONS

U.S. Appl. No. 13/852,116, Notice of Allowance dated Nov. 7, 2014.
U.S. Appl. No. 13/865,974, Non-Final Office Action dated May 2, 2014.
U.S. Appl. No. 13/865,974, Notice of Allowance dated Oct. 22, 2014.
U.S. Appl. No. 13/865,974, Requirement for Restriction/Election dated Jan. 29, 2014.
U.S. Appl. No. 13/889,214, Non-Final Office Action dated Sep. 18, 2013.
U.S. Appl. No. 13/889,214, Notice of Allowance dated Apr. 28, 2014.
U.S. Appl. No. 13/889,221, Non-Final Office Action dated Sep. 6, 2013.
U.S. Appl. No. 13/889,221, Notice of Allowance dated Apr. 24, 2014.
U.S. Appl. No. 13/941,346, Final Office Action dated Jun. 26, 2014.
U.S. Appl. No. 13/941,346, Non-Final Office Action dated Jan. 21, 2014.
U.S. Appl. No. 13/941,346, Non-Final Office Action dated Nov. 3, 2014.
U.S. Appl. No. 13/941,346, Notice of Allowance dated Feb. 23, 2015.
U.S. Appl. No. 13/941,353, Requirement for Restriction/Election dated Jan. 16, 2014.
U.S. Appl. No. 13/941,357, Final Office Action dated Nov. 6, 2014.
U.S. Appl. No. 13/941,357, Non-Final Office Action dated Jun. 3, 2014.
U.S. Appl. No. 13/941,357, Requirement for Restriction/Election dated Jan. 7, 2014.
Ueno et al., "Optimization of heterotrophic culture conditions for n-alkane utilization and phylogenetic position based on the 18S rDNA sequence of a thermotolerant Prototheca zopfii strain," J Biosci Bioeng, 94(2):160-165, (2002). Abstract. [Retrieved from the Internet Dec. 1, 2014: <URL: http://www.ncbi.nlm.nih.gov/pubmed/16233286>].
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van De Loo et al., "An oleate 12-hydroxylase from *Ricinus communis* L. is a fatty acyl desaturase homolog," Proc. Natl. Acad. Sci. USA, 92:6743-6747, (1995).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2):155-159, (2003).
Vazquez-Bermudez et al., "Uptake of 2-Oxoglutarate in Synechococcus Strains Transformed with the *Escherichia coli* kgtP Gene," Journal of Bacteriology, 182(1):211-215, (2000).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from Cuphea lanceolata'," Plant Physiol., 106:785-786, (1994).
Volkman et al., "Sterols in microorganisms," Appl Microbial Biotechnol, 60:495-506, (2003).
Walker et al., "Characterization of the Dunaliella tertiolecta RbcS Genes and Their Promoter Activity in Chlamydomonas reinhardtii," Plant Cell Rep, 23(10-11):727-735, (2005).
Wang et al., "Rapid isolation and functional analysis of promoter sequences of the nitrate reductase gene from Chlorella ellipsoidea," J. Appl. Phycol., 16:11-16, (2004).
Warner et al., "Analysis of Tocopherols and Phytosterols in Vegetable Oils by HPLC with Evaporative Light-Scattering Detection," JAOCS, 67(11):827-831 (1990).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).
Whisstock et al., "Prediction of protein function from protein sequence and structure," Quarterly Reviews of Biophysics, 36(3):307-340, (2003).
Whittle et al., "Engineering Δ9-16:0-Acyl Carrier Protein (ACP) Desaturase Specificity Based on Combinatorial Saturation Mutagenesis and Logical Redesign of the Castor Δ9-18:0-ACP Desaturase," The Journal of Biological Chemistry, 276(24):21500-21505, (2001).
Wiberg et al., "The distribution of caprylate, caprate and laurate in lipids from developing and mature seeds of transgenic *Brassica napus* L.," Planta, 212:33-40, (2000).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45):26782-26785, (1995).
Witkowski et al., "Conversion of a β-Ketoacyl Synthase to a Malonyl Decarboxylase by Replacement of the Active-Site Cysteine with Glutamine," Biochemistry, 38:11643-11650, (1999).
Wolk et al., "Construction of Shuttle Vectors Capable of Conjugative Transfer From *Escherichia coli* to Nitrogen-Fixing Filamentous Cyanobacteria," Proc Natl Acad Sci U S A., 81(5):1561-1565, (1984).
Wong et al., "Arabidopsis thaliana small subunit leader and transit peptide enhance the expression of Bacillus thuringiensis proteins in transgenic plants," Plant Mol Biol, 20(1):81-93, (1992).
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae", Science in China, 37(3):326-35, (1994).
Xiong et al., "High-density fermentation of microalga Chlorella protothecoides in bioreactor for microbic-diesel production," Appl. Microbiol. Biotechnol., 78:29-36, (2008).
Yamada et al., "Alternative expression of a chitosanase gene produces two different proteins in cells infected with Chlorella virus CVK2," Virology, 230(2):361-368, (1997).
Yamada et al., "Chlorella viruses," Adv Virus Res, 66:293-336, (2006).
Yu et al., "Modifications of the metabolic pathways of lipid and triacylglycerol production in microalgae," Microbial Cell Factories, 10:91, (2011). [Retrieved from the Internet Jul. 24, 2012: <URL: http://www.microbialcellfactories.com/content/10/1/91>].
Yuan et al., "Modification of the substrate specificity of an acyl-acyl carrier protein thioesterase by protein engineering," Proc. NatL Acad. Sci. USA, Biochemistry, 92:10639-10643, (1995).
Zaidul et al., "Supercritical carbon dioxide (SC-0O2) extraction and fractionation of palm kernel oil from palm kernel as cocoa butter replacers blend," Journal of Food Engineering, 73:210-216, (2006).
Zhang et al., "Malic enzyme: the controlling activity for lipid production? Overexpression of malic enzyme in Mucor circinelloides leads to a 2.5-fold increase in lipid accumulation," Microbiology, 153(7):2013-2025, (2007).
Zhao et al., "Medium optimization for lipid production through co-fermentation of glucose and xylose by the oleaginous yeast Lipomyces starkeyi," Eur. J. Lipid Sci. Technol., 110:405-412, (2008).

(56) References Cited

OTHER PUBLICATIONS

Zurawski et al., "Nucleotide sequence of the gene for the Mr 32,000 thylakoid membrane protein from spinacia oleracea and Nicotiana debneyi predicts a totally conserved primary translation product of Mr 38,950," Proc Natl Acad Sci, 79(24):7699-7703, (1982).
GenBank Accession No. ACQ42234.1 "Tbifunctional oleate 12-hydroxylase:desaturase [*Physaria fendleri*]", May 2009, Salywon et al.
GenBank Accession No. ALM22867.1 "lysophosphatidic acid acyltransferase 2 [*Cuphea viscosissima*]," Nov. 8, 2015, 2pp.
GenBank Accession No. ALM22871.8 "microsomal lysophosphatidic acid acyltransferase 2c [*Cuphea avigera* var. pulcherrima]," Nov. 8, 2015, 2pp.
GenBank Accession No. KT694311.1 "*Cuphea avigera* var. pulcherrima plastid lysophosphatidic acid acyltransferase 1 mRNA, complete cds; nuclear gene for plastid product," Nov. 8, 2015, 2pp.
GenBank Accession No. KT694310.1 "Cuphea viscosissima lysophosphatidic acid acyltransferase 2 mRNA, complete cds," Nov. 8, 2015, 2pp.
GenBank Accession No. KT694314.1 "*Cuphea avigera* var. pulcherrima microsomal lysophosphatidic acid acyltransferase 2c mRNA, complete cds," Nov. 8, 2015, 2pp.
GenBank: Accession No. L42851.1, "Protothaca wickerhamii large subunit ribosomal RNA (rrnL) gene, partial sequence; chloroplast gene for chloroplast product," Nov. 21, 2001. [retrieved from the Internet on Dec. 23, 2009 at http://www.ncbi.nlm.nih.gov/nuccore/17028073].
Geneseq: Database Accession No. AED66345, CN1618976, May 25, 2005, Zhang et al.
GenBank: "Codo Usage Database file for Chlorella vulgaris," Jun. 2007. [Retrieved from the Internet Aug. 26, 2010: ,URL: http://www.kazusa.or.jp/coldo/cgi-bin/showcodon.cgi?species=3077.].
Geneseq: Database Accession No. AXE01814, "Palmitic acid production-related gene, SEQ:20024," XP002750550, Oct. 14, 2010.
Geneseq: Database Accession No. ADJ49365, "Oil-associated gene related protein #865," XP002750551, Jun. 15, 2007.
Uniprot Accession No. P41758. Phosphoglycerate kinase, chloroplastic. Jul. 22, 2008. [Retrieved from the Internet Aug. 25, 2010:<http://http://www.uniprot.org/uniprot/P41758.txt?version=44>]; amino acids 1-60.
Uniprot Accession No. P41758. Phosphoglycerate kinase, chloroplastic. Nov. 25, 2008. [Retrieved from the Internet Aug. 12, 2010:<http://www.uniprot.org/uniprot/P41758.txt?version=46>].
Abate et al., "Production of ethanol by a flocculent *Saccharomyces* sp. In a continuous upflow reactor using sucrose, sugar-can juice, and molasses as the carbon source," *MIRCEN Journal*, 3:401-409 (1987).
Alvarez et al., (2002) "Triacylglycerols in prokaryotic microorganisms," *Appl Microbiol Biotechnol*, 60:367-376.
Angerbauer et al. (2008) "Conversion of sewage sludge into lipids by Lipomyces starkeyl for biodiesel production," *Bioresource Technology*, 99:3051-3056.
Bergh et al., "Expression of the *Saccharomyces cerevisiae* glycoprotein invertase in mouse fibroblasts: Glycosylation, secretion, and enzymatic activity," Proc. Natl. Acad. Sci. USA, 84:3570-3574, (1987).
Blatti, Jillian L. et al. "Manipulating Fatty Acid Biosynthesis in Microalgae for Biofuel through Protein-Protein Interactions." Ed. Elena A. Rozhkova. PLoS ONE, 7.9 (2012): e42949. PMC. Web. Sep. 1, 2017.
Blatti, Jillian L. et al. (Jun. 2013) "Engineering fatty acid biosynthesis in microalgae for sustainable biodiesel," Current Opinion in Chemical Biology, 17(3):496-505.
Bognar, A. (1998) "Comparative study of frying to other cooking techniques influence on the nutritive value," *Grasas y Aceites*, 49(3-4):250-260.
Bouchard et al., "Characterization of Depolymerized Cellulosic Residues," *Wood Sci. Technol.*, 23:343-355 (1989).
Butzen et al., "High Oleic Soybean," *Crop Insights*, 17(17):3 pp [Retrieved on Dec. 3, 2008 from www.McCormickcompany.net].
Campbell et al. (1990) "Codon Usage in Higher Plants, Green Algae, and Cyanobacteria," *Plant Physiol.*, 92:1-11.
Canakci et al. (2001) "Biodiesel production from oils and fats with high free fatty acids," *Transaction of the ASABE*, 44(6): 1429-1436.
Canam, "An Investigation of the Physiological Roles and Enzymatic Properties of Invertases in Tobacco and Hybrid Poplar," Thomas Benjamin Canam, 165 pages, (2008).
Carlson et al., "The Secreted Form of Invertase in *Saccharomyces cerevisiae* Is Synthesized from mRNA Encoding a Signal Sequence," Molecular and Cellular Biology,3(3):439-447, (1983).
Chen et al., "Effect of C/N ratio and aeration on the fatty acid composition of heterotrophic Chlorella sorokiniana," Journal of Applied Phycology, 3:203-209, (1991).
Chen et al., "Heterotrophic Growth of Chlamydomonas reinhardtii on Acetate in Chemostat Culture," Process Biochemistry, 31(6):601-604, (1996).
Chen et al., "High cell density culture of microalgae in heterotrophic growth," Trends in Biotechnology, 14:421-426, (1996).
Cheng et al., "Sugars modulate an unusual mode of control of the cell-wall invertase gene (Incw1) through its 3' untranslated region in a cell suspension culture of maize," Proc. Natl. Acad. Sci. USA, 96:10512-10517, (1999).
Chisti et al., (2007) "Biodiesel from microalgae," *Biotechnology Advances*, 25:294-306.
Cho et al., "Molecular cloning and expression analysis of the cell-wall invertase gene family in rice (*Oryza sativa* L.)," Plant Cell Rep, 24:225-236 , (2005).
Cook et al., "Photo-Assimilation of Acetate by an Obligate Phototrophic Strain of Euglena gracilis," Publication, J. Protozool., 14(3):382-384, (1967).
Curtain, (2000) "Plant Biotechnology—The growth of Australia's algal b-carotene industry," *Australasian Biotech.*, 10(3):19-23. [Retrieved from the Internet Apr. 5, 2010:, <http://www.bioline.org.br/request?au00032>].
Da Silva et al., (2006) "Effect of n-dodecane on Crypthecodinium cohnii fermentations and DHA production," *J Ind Microbiol Biotechnol*, 33(6):408-416 [DOW 10.1007/s10295-006-0081-8], 9pp.
Dai et al., (2007) "Biodiesel generation from oleaginous yeast Rhodotorula glutinis with xylose assimilating capacity," *African Journal of Biotechnology*, 6(18):2130-2134.
Day et al., "An investigation of the heterotrophic culture of the green alga Tetraselmis," Journal of Applied Phycology, 8:73-77, (1996).
De Coninck et al., "Arabidopsis AtcwINV3 and 6 are not invertases but are fructan exohydrolases (FEHs) with different substrate specificities," Plant, Cell and Environment, 28,:432-443, (2005).
Demirbas et al., "Fuel Conversional Aspects of Palm Oil and Sunflower Oil," *Energy Sources*, 457-466, (2003).
Deng et al., "Ionic Liquid as a Green Catalytic Reaction Medium for Esterifications," *J. Mol. Catalysis A: Chemical*, 165:33-36 (2001).
Dimou et al., "Genes coding for a putative cell-wall invertase and two putative monosaccharide/H+ transporters are expressed in roots of etiolated Glycine max seedlings," Plant Science, 169:798-804, (2005).
Ehneb et al., (1997) "Co-ordinated induction of mRNAs for extracellular invertase and a glucose transporter in Chenopodium rubrum by cytokinins," *The Plant Journal*, 11(3):539-548.
Elumalai et al., "Optimizatin of abiotic conditions suitable for the production of biodiesel from Chlorella vulgaris," Indian J. Sci. Technol., 4(2):91-97, (2011).
"Enzymatic Assay of INVERTASE (EC 3.2.1.26)," Sigma-Aldrich Co. LLC., (1999). [Retrieved from the Internet Aug. 21, 2012: <http://www.sigmaaldrich.com/etc/medialib/docs/Sigma/General_Information/invertase_temp_25.Par.0001.File.tmp/invertase_temp_25.pdf>] (Author is not Available).
Fernandez-Reirlz et al., (1989) "Biomass Production and Variation in the Biochemical Profile (Total Protein, Carbohydrates, RNA, Lipids and Fatty Acids) of Seven Species of Marine Microalgae," Aquaculture, 83:17-37.
Forster et al., "Citric acid production from sucrose using a recombinant strain of the yeast Yarrowia lipolyticae," Appl Microbiol Biotechnol, 75:1409-1417, (2007).

(56) References Cited

OTHER PUBLICATIONS

Foyer et al., "Sucrose and Invertase, an Uneasy Alliance," Iger Innovations, pp. 18-21, (1997).
Fukuda et al.,"Biodiesel Fuel Production by Transesterification of Oils," *J Biosci. Bioeng*., 92(5):405-416 (2001).
Gallagher et al., "Isolation and characterization of a cDNA clone from *Lolium temulentum* L. encoding for a sucrose hydrolytic enzyme which shows alkaline/neutral invertase activity'," Journal of Experimental Bota, 49(322.):789-795, (1998).
Garay et al., (2014) "Accumulation of High-Value lipids in Single-Cell Microorganisms: A Mechanistic Approach and Future Perspectives," *J. of Agric. and Food Chem*., 62:2709-2727.
Garrote et al., "Manufacture of Xylose-Based Fermentation Media from Corncobs by Posthydrolysis of Autohydrolysis Liquors," *Appl Biochem Biotechnol*, 95(3):195-207 (2001).
Gascon et al., "Comparative Study of the Properties of the Purified Internal and External Invertases from Yeast," The Journal of Biological Chemistry, 243(7):1573-1577, (1968).
Gimpel et al., (Dec. 15, 2015) "In Metabolic Engineering of Eukaryotic Microalgae: Potential and Challenges Come with Great Diversity," *Metabolic Engineering of Eukaryotic Microalgae, Frontiers in Microbiology*, 6(Article 1376):14pp.
Godt et al., "Regulation and Tissue-Specific Distribution of mRNAs for Three Extracellular Invertase Isoenzymes of Tomato Suggests an Important Function in Establishing and Maintaining Sink Metabolism'," Plant Physiol, 115:273-282, (1997).
Goetz et al., "The different pH optima and substrate specificities of extracellular and vacuolar invertases from plants are determined by a single amino-acid substitution," The Plant Journal, 20(6):707-711, (1999).
Grima et al., "Recovery of microalgal biomass and metabolites: process options and economics," Biotechnology Advances, 20:491-515, (2003).
Grinna et al.,"Size Distribution and General Structual Features of N-Linked Oligosaccharides from the Methylotrophic Yeast, Pichia pastoris," Yeast, 5:107-115, (1989).
Gusakov et al., "Design of Highly Efficenet Cellulase Mixtures for Enzymatic Hydrolysis of Cellulose," *Biotechnol. and Bioengineering*, 97(5):1028-1038 (2007).
Ha et al., "Engineered *Saccharomyces cerevisiae* capable of simultaneous cellobiose and xylose fermentation," *PNAS*, 108(2):504-509 (2011).
Haas et al., (2007) "The General Applicability of in Situ Transesterification for the Production of Fatty Acid Esters from a Variety of Feedstocks," *J. Am Oil. Chem. Soc*., 84:963-970.
Khozin-Goldberg et al. (2011) "Unravelling algal lipid metabolism: Recent advances in gene identification," *BIOCHEMIE*, 93:91-100.
U.S. Appl. No. 15/443,209, filed Feb. 27, 2017, Franklin et al.
U.S. Appl. No. 14/184,288, Requirement for Restriction/Election dated Jun. 9, 2015.
U.S. Appl. No. 14/184,288, Non-Final Office Action dated Sep. 11, 2015.
U.S. Appl. No. 14/184,288, Notice of Allowance dated Feb. 3, 2016.
U.S. Appl. No. 15/173,335, Requirement for Restriction/Election dated Jul. 5, 2017.
U.S. Appl. No. 15/173,335, Non-Final Office Action dated Oct. 12, 2017.
U.S. Appl. No. 12/628,140, Non-Final Office Action dated Jul. 17, 2015.
U.S. Appl. No. 12/628,140, Final Office Action dated Feb. 2, 2016.
U.S. Appl. No. 12/628,140, Non-Final Office Action dated Nov. 21, 2016.
U.S. Appl. No. 12/628,144, Final Office Action dated Mar. 1, 2016.
U.S. Appl. No. 12/628,144, Notice of Allowance dated Jun. 13, 2016.
U.S. Appl. No. 14/285,354, Requirement for Restriction/Election dated Jul. 20, 2015.
U.S. Appl. No. 14/285,354, Notice of Allowance dated Feb. 1, 2016.
U.S. Appl. No. 14/626,505, Requirement for Restriction/Election dated Apr. 26, 2016.
U.S. Appl. No. 14/626,505, Non-Final Office Action dated Jul. 19, 2016.
U.S. Appl. No. 13/118,365, Notice of Allowance dated Sep. 20, 2013.
U.S. Appl. No. 14/276,943, Requirement for Restriction/Election dated Jun. 4, 2015.
U.S. Appl. No. 14/276,943, Notice of Allowance dated Sep. 22, 2015.
U.S. Appl. No. 14/975,016, Notice of Allowance dated Jan. 10, 2017.
U.S. Appl. No. 14/975,016, Notice of Allowance dated Jan. 31, 2017.
U.S. Appl. No. 14/975,016, Notice of Allowance dated Feb. 24, 2017.
U.S. Appl. No. 13/630,757, Non-Final Office Action dated Apr. 23, 2015.
U.S. Appl. No. 13/630,757, Notice of Allowance dated Oct. 23, 2015.
U.S. Appl. No. 13/630,757, Supplemental Notice of Allowance dated Dec. 3, 2015.
U.S. Appl. No. 13/630,757, Miscellaneous Communication dated Dec. 17, 2015.
U.S. Appl. No. 13/630,757, Notice of Allowance (Supplemental Notice of Allowability) dated Jan. 15, 2016.
U.S. Appl. No. 13/650,018, Notice of Allowance dated Apr. 10, 2015.
U.S. Appl. No. 14/819,117, Requirement for Restriction/Election dated Apr. 11, 2016.
U.S. Appl. No. 14/819,117, Non-Final Office Action dated Nov. 2, 2016.
U.S. Appl. No. 14/819,117, Final Office Action dated Mar. 22, 2017.
U.S. Appl. No. 14/819,117, Notice of Allowance dated Sep. 7, 2017.
U.S. Appl. No. 14/819,117, Supplemental Notice of Allowance dated Nov. 13, 2017.
U.S. Appl. No. 13/288,815, Requirement for Restriction/Election dated Feb. 11, 2014.
U.S. Appl. No. 14/730,671, Notice of Allowance dated Mar. 21, 2016.
U.S. Appl. No. 15/179,253, Requirement for Restriction/Election dated Sep. 28, 2017.
U.S. Appl. No. 13/365,253, Non-Final Office Action dated Mar. 25, 2015.
U.S. Appl. No. 13/365,253, Notice of Allowance dated Sep. 24, 2015.
U.S. Appl. No. 13/365,253, Notice of Allowance (Notice of Allowability) dated Nov. 6, 2015.
U.S. Appl. No. 14/974,983, Requirement for Restriction/Election dated Jul. 28, 2016.
U.S. Appl. No. 14/974,983, Non-Final Office Action dated Dec. 5, 2016.
U.S. Appl. No. 14/974,983, Final Office Action dated Jul. 19, 2017.
U.S. Appl. No. 14/974,983, Non-Final Office Action dated Oct. 26, 2017.
U.S. Appl. No. 13/804,185, Non-Final Office Action dated Jun. 1, 2015.
U.S. Appl. No. 13/804,185, Final Office Action dated Dec. 11, 2015.
U.S. Appl. No. 13/804,185, Non-Final Office Action dated Jul. 20, 2016.
U.S. Appl. No. 13/804,185, Notice of Allowance dated Jan. 27, 2017.
U.S. Appl. No. 13/941,342, Requirement for Restriction/Election dated Apr. 13, 2015.
U.S. Appl. No. 13/941,342, Notice of Allowance dated Jul. 24, 2015.
U.S. Appl. No. 13/941,353, Notice of Allowance dated May 21, 2014.
U.S. Appl. No. 13/941,357, Notice of Allowance dated Mar. 30, 2015.
U.S. Appl. No. 14/474,244, Non-Final Office Action dated Apr. 24, 2015.
U.S. Appl. No. 14/474,244, Final Office Action dated Jul. 30, 2015.
U.S. Appl. No. 14/474,244, Notice of Allowance dated Sep. 18, 2015.

(56) References Cited

OTHER PUBLICATIONS

U.S. Appl. No. 14/975,137, Notice of Allowance dated Sep. 6, 2016.
U.S. Appl. No. 15/369,557, Non-Final Office Action dated Jun. 23, 2017.
U.S. Appl. No. 15/369,557, Notice of Allowance dated Oct. 17, 2017.
U.S. Appl. No. 14/796,406, Requirement for Restriction/Election dated Oct. 5, 2016.
U.S. Appl. No. 14/796,406, Non-Final Office Action dated Jan. 25, 2017.
U.S. Appl. No. 14/796,406, Notice of Allowance dated Jun. 15, 2017.
U.S. Appl. No. 14/796,406, Notice of Allowance dated Oct. 3, 2017.
U.S. Appl. No. 15/092,538, Requirement for Restriction/Election dated Oct. 6, 2017.
Australian Patent Examination Report No. 1 dated Jan. 23, 2013 issued in Application No. AU 2008259834.
Australian Patent Examination Report No. 1 dated May 4, 2015 issued in Application No. AU 2013251198.
Canadian Examination Report dated Nov. 30, 2015 issued in Application No. CA 2,689,724.
Chinese First Office Action dated Apr. 23, 2012 issued in Application No. CN 200880100976.9.
Chinese Second Office Action dated Jan. 21, 2013 issued in Application No. CN 200880100976.9.
Chinese Third Office Action dated May 28, 2013 issued in Application No. CN 200880100976.9.
Chinese Fourth Office Action dated Sep. 11, 2013 issued in Application No. CN 200880100976.9.
Chinese Fifth Office Action dated Jan. 23, 2014 issued in Application No. CN 200880100976.9.
Chinese First Office Action dated May 18, 2016 issued in Application No. CN 201410321130.5.
Colombian Opposition dated Sep. 5, 2011 [Brief Communication dated Sep. 5, 2011 re Application No. EP 06 075 479.3, D50-Declaration of Dr. Matthias Staufenbiel; D51-WO-A-2004/016282; D52-Sturchler-Pierrat et al. *Proc Natl. Acad. Sci*. USA, 94:13287-13292 (1997)].
Declaration of Dr. Matthias Staufenbiel, Opposition Document for European Patent No. EP-B-1679080 dated Aug. 2, 2011; Patentee: Janssen Alzheimer Immuno-therapy; Opponent: Dr. Alexander Esslinger, 19 pp.
Colombian Office Action dated Jan. 28, 2013 issued in Application No. CO 09149183.
Colombian Office Action dated Jun. 13, 2013 issued in Application No. CO 09149183.
Colombian Office Action dated Sep. 25, 2013 issued in Application No. CO 09149183.
European Office Action dated Mar. 9, 2012 issued in Application No. EP 08 769 988.0.
Indonesian First Office Action dated Apr. 13, 2016 issued in Application No. W00200903371.
Indonesian Second Office Action dated Aug. 4, 2016 issued in Application No. W00200903371.
Indian Examination Report dated Oct. 4, 2016 issued in Application No. IN 8573/DELNP/2009.
Japanese Notice of Reason for Denial [no translation] dated May 24, 2016 issued in Application No. JP 2016-095504.
Korean Office Action dated Aug. 25, 2014 issued in Application No. KR 10-2009-7027618.
Mexican Office Action dated Oct. 13, 2011 issued in Application No. MX/a/2009/012850.
Mexican First Office Action dated Sep. 30, 2013 issued in Application No. MX/a/2012/000844.
Mexican Second Office Action dated Jan. 22, 2014 issued in Application No. MX/a/2012/000844.
Mexican Third Office Action dated Oct. 13, 2014 issued in Application No. MX/a/2012/000844.
Mexican Fourth Office Action dated Apr. 1, 2015 issued in Application No. MX/a/2012/000844.
Mexican Office Action dated Feb. 23, 2017 issued in Application No. MX/a/2015/008626.
Malaysian Examination and Search Report dated Dec. 31, 2013 issued in Application No. PI20095102.
Malaysian Examination and Adverse Report dated Dec. 31, 2014 issued in Application No. PI20095102.
Malaysian Examination and Clear Report dated Jul. 15, 2015 issued in Application No. PI20095102.
Malaysian Examination and Search Report dated May 15, 2017 issued in Application No. PI2014000965.
New Zealand First Examination Report dated Oct. 19, 2010 issued in Application No. NZ 581700.
New Zealand Examination Report dated Sep. 22, 2011 issued in Application No. NZ 581700.
New Zealand Examination Report dated Sep. 8, 2011 issued in Application No. NZ 595029.
New Zealand Examination Report dated Dec. 19, 2012 issued in Application No. NZ 595029.
Philippines Examination Report dated Apr. 7, 2014 issued in Application No. PH 1-2009-502294.
Philippines Examination Report dated Nov. 18, 2014 issued in Application No. PH 1-2009-502294.
Singapore Written Opinion and Search Report dated Apr. 29, 2011 issued in Application No. SG 200907978-1.
Thailand Office Action dated Feb. 22, 2011 issued in Application No. TH 0901005340.
Thailand Office Action dated Jul. 26, 2017 issued in Application No. TH 0901005340.
Australian Patent Examination Report No. 1 dated Dec. 9, 2014 issued in Application No. AU 2009319722.
Australian Patent Examination Report No. 1 dated Jul. 20, 2017 issued in Application No. AU 2016250460.
Canadian Examination Report dated Aug. 18, 2015 issued in Application No. CA 2,745,129.
Canadian Examination Report dated Oct. 3, 2016 issued in Application No. CA 2,745,129.
Canadian Examination Report dated Nov. 16, 2017 issued in Application No. CA 2,745,129.
Chinese First Office Action dated Apr. 26, 2013 issued in Application No. CN 200980155465.1.
Chinese Second Office Action dated Jan. 16, 2014 issued in Application No. CN 200980155465.1.
Chinese Third Office Action dated Aug. 28, 2014 issued in Application No. CN 200980155465.1.
Chinese Rejection Decision dated Mar. 24, 2015 issued in Application No. CN 200980155465.1.
Chinese Reexamination notification dated Nov. 10, 2016 issued in Application No. CN 200980155465.1.
Chinese Reexamination Decision dated Apr. 27, 2017 issued in Application No. CN 200980155465.1.
Chinese Fourth Office Action dated Sep. 25, 2017 issued in Application No. CN 200980155465.1.
Colombian Office Action dated Feb. 13, 2013 issued in Application No. CO 11.080.882.
Colombian Office Action dated Jun. 18, 2013 issued in Application No. CO 11.080.882.
Colombian Office Action dated Nov. 24, 2014 issued in Application No. CO 11.080.882.
Colombian Office Action dated Mar. 16, 2015 issued in Application No. CO 11.080.882.
Colombian Office Action dated Mar. 1, 2016 issued in Application No. CO 11.080.882.
European Extended Search Report dated Sep. 12, 2014 issued in Application No. EP 09 829 851.6.
European Office Action dated Jun. 25, 2015 issued in Application No. EP 09 829 851.6.
European Partial Search Report dated Sep. 12, 2016 issued in Application No. EP 16 16 6059.2.
European Extended Search Report dated Dec. 14, 2016 issued in Application No. EP 16 16 6059.2.
Indonesia Substantive Examination Report Stage 1 dated Aug. 5, 2015 issued in Application No. ID W-00 2011 02343.

(56) References Cited

OTHER PUBLICATIONS

Israel Office Action dated Sep. 30, 2013 issued in Application No. IL 213157.
First Examination Report, dated Nov. 23, 2017, issued in Inidina Patent Aplication No. 4960-DELNP-2011.
Japanese Office Action dated May 27, 2014 issued in Application No. JP 2011-538719.
Japanese Final Office Action dated Feb. 24, 2015 issued in Application No. JP 2011-538719.
Japanese Pre-Appeal Examination Report dated Aug. 27, 2015 issued in Application No. JP 2011-538719.
Japanese Office Action dated Jul. 1, 2016 issued in Application No. JP 2011-538719.
Japanese Office Action dated Oct. 31, 2016 issued in Application No. JP 2011-538719.
Japanese Office Action [no translation] dated May 9, 2016 issued in Application No. JP 2015-126360.
Japanese Final Office Action [no translation] dated Nov. 24, 2016 issued in Application No. JP 2015-126360.
Japanese Office Action [no translation] dated Oct. 27, 2017 issued in Application No. JP 2017-015080.
Korean Office Action dated Nov. 14, 2015 issued in Application No. KR 10-2011-7014923.
Korean Office Action dated Oct. 5, 2016 issued in Application No. KR 10-2011-7014923.
Korean Office Action dated Nov. 15, 2017 issued in Application No. KR 10-2017-7021034, with English translation.
Malaysian Examination Report dated Mar. 31, 2016 issued in Application No. MY PI2011002435.
Mexican Office Action dated Sep. 14, 2012 issued in Application No. MX/a/2010/011065.
PCT International Search Report dated Nov. 5, 2010 issued in PCT/US2009/066141.
PCT International Preliminary Report on Patentability and Written Opinion dated Oct. 26, 2012 issued in PCT/US2009/066141.
Australian Patent Examination Report No. 1 dated Feb. 25, 2014 issued in Application No. AU 2009319721.
Australian Patent Examination Report No. 2 dated Oct. 29, 2015 issued in Application No. AU 2009319721.
Canadian Office Action dated Dec. 1, 2015 issued in Application No. CA 2,745,040.
Chinese First Office Action dated Dec. 23, 2013 issued in Application No. CN 200980155463.2.
Chinese Second Office Action dated Oct. 20, 2014 issued in Application No. CN 200980155463.2.
Colombian Office Action dated Mar. 21, 2013 issued in Application No. CO 11.080.835.
European Office Action dated Mar. 21, 2016 issued in Application No. EP 09 829 850.8.
European Extended Search Report dated May 16, 2016 issued in Application No. EP 09 829 850.8.
Indonesian Examination Report dated Feb. 22, 2017 issued in Application No. W-00201102342.
Israel Office Action dated Apr. 8, 2014 issued in Application No. IL 213154.
Israel Office Action dated Jun. 30, 2015 issued in Application No. IL 213154.
Israel Office Action dated Sep. 14, 2016 issued in Application No. IL 213154.
Indian Examination Report dated Sep. 1, 2017 issued in Application No. IN 4959/DELNP/2011.
Japanese Office Action dated May 13, 2014 issued in Application No. JP 2011-538718.
Japanese Office Action dated Jun. 1, 2015 issued in Application No. JP 2011-538718.
Japanese Office Action [no translation] dated Oct. 16, 2016 issued in Application No. JP 2014-227718.
Japanese Final Office Action [no translation] dated Jul. 13, 2016 issued in Application No. JP 2014-227718.
Korean Office Action dated Jan. 4, 2016 issued in Application No. KR 10-2011-7014925.
Korean Office Action dated Jul. 18, 2016 issued in Application No. KR 10-2011-7014925.
Korean Office Action dated Feb. 23, 2017 issued in Application No. KR 10-2011-7014925.
Korean Office Action dated Jan. 4, 2018, issued in Application No. KR 10-2017-7026170.
Mexican Office Action [no translation] dated Dec. 6, 2012 issued in Application No. MX/a/2011/005630.
Mexican Office Action [no translation] dated May 14, 2013 issued in Application No. MX/a/2011/005630.
Mexican Office Action [no translation] dated Dec. 9, 2013 issued in Application No. MX/a/2011/005630.
Malaysian Examination Report dated Mar. 15, 2017 issued in Application No. MY PI2011002435.
Australian Patent Examination Report No. 1 dated Jul. 21, 2016 issued in Application No. AU 2011257982.
Canadian Examination Report dated Feb. 23, 2017 issued in Application No. CA 2,801,057.
Chinese First Office Action dated May 29, 2014 issued in Application No. CN 201180036870.9.
Chinese Second Office Action dated Apr. 15, 2015 issued in Application No. CN 201180036870.9.
Chinese Third Office Action dated Nov. 4, 2015 issued in Application No. CN 201180036870.9.
Chinese Rejection Decision dated Apr. 14, 2016 issued in Application No. CN 201180036870.9.
Chinese Notification of Reexamination dated Jan. 26, 2017 issued in Application No. CN 201180036870.9.
European Extended Search Report dated Jun. 9, 2016 issued in Application No. EP 11 787 551.8.
European Office Action dated Jan. 25, 2017 issued in Application No. EP 11 787 551.8.
European Consultation by telephone dated May 29, 2017 issued in Application No. EP 11 787 551.8.
European Office Action dated Aug. 23, 2017 issued in Application No. EP 11 787 551.8.
Indonesian Office Action dated Sep. 21, 2017 issued in Application No. W00201205280.
Japanese Office Action dated Jul. 7, 2015 issued in Application No. JP 2013-512064.
Japanese Office Action dated Dec. 16, 2016 issued in Application No. JP 2016-001030.
Japanese Office Action dated Dec. 19, 2017 issued in Application No. JP 2017-48186, in Japanese Only.
Korean Office Action dated Nov. 29, 2017 issued in Application No. KR 10-2012-7034232.
Mexican Office Action dated Aug. 11, 2015 issued in Application No. MX/a/2012/013777.
Mexican Office Action dated Jan. 15, 2016 issued in Application No. MX/a/2012/013777.
Malaysian Examination Report dated Sep. 15, 2015 issued in Application No. MY PI 2012005117.
PCT International Preliminary Report on Patentability dated Jun. 28, 2012 issued in PCT/US2011/038464.
Australian Patent Examination Report No. 1 dated Feb. 26, 2015 issued in Application No. AU 2011257983.
Australian Examination Report No. 1 dated Feb. 1, 2017 issued in Application No. AU 2016202905.
Australian Examination Report No. 2 dated Aug. 28, 2017 issued in Application No. AU 2016202905.
Canadian Examination Report dated May 17, 2017 issued in Application No. CA 2,801,024.
Chinese First Office Action dated Oct. 29, 2013 issued in Application No. CN 201180036696.8.
Chinese Second Office Action dated Jun. 5, 2014 issued in Application No. CN 201180036696.8.
Chinese Rejection Decision dated Jan. 14, 2015 issued in Application No. CN 201180036696.8.
Chinese Re-examination Decision dated May 26, 2015 issued in Application No. CN 201180036696.8.

(56) References Cited

OTHER PUBLICATIONS

Chinese Third Office Action dated Jul. 31, 2015 issued in Application No. CN 201180036696.8.
Chinese Fourth Office Action dated Dec. 30, 2015 issued in Application No. CN 201180036696.8.
European Extended Search Report dated Feb. 19, 2016 issued in Application No. EP 11 787 552.6.
European Office Action dated Oct. 11, 2016 issued in Application No. EP 11 787 552.6.
Japanese Office Action dated Jul. 7, 2015 issued in Application No. JP 2013-512065.
Japanese Final Office Action dated Feb. 29, 2016 issued in Application No. JP 2013-512065.
Japanese Office Action [no translation] dated Jul. 8, 2016 issued in Application No. JP 2013-512065.
Japanese Office Action [no translation] dated Sep. 6, 2016 issued in Application No. JP 2015-199078.
Korean Office action [no translation] dated Dec. 11, 2017 issued in Application No. KR 10-2012-7034225.
Mexican Office Action dated Sep. 12, 2017 issued in Application No. MX/a/2012/013756.
Malaysian Examination Report dated Sep. 15, 2015 issued in Application No. MY PI 2012005120.
Australian Patent Examination Report No. 1 dated May 20, 2015 issued in Application No. AU 2011323288.
Australian Patent Examination Report No. 2 dated Mar. 23, 2016 issued in Application No. AU 2011323288.
Australian Patent Examination Report No. 1 dated Aug. 21, 2017 issued in Application No. AU 2016202999.
Canadian Office Action dated Aug. 8, 2017 issued in Application No. CA 2,816,125.
Chinese First Office Action dated Apr. 15, 2014 issued in Application No. CN 201180053258.2.
Chinese Second Office Action dated Feb. 2, 2015 issued in Application No. CN 201180053258.2.
Chinese Third Office Action dated Jul. 3, 2015 issued in Application No. CN 201180053258.2.
Chinese Fourth Office Action dated Dec. 16, 2015 issued in Application No. CN 201180053258.2.
Chinese Fifth Office Action dated Jun. 6, 2016 issued in Application No. CN 201180053258.2.
Chinese Sixth Office Action (Rejection Decision) dated Nov. 2, 2016 issued in Application No. CN 201180053258.2.
Chinese Notification of Reexamination dated Aug. 31, 2017 issued in Application No. CN 201180053258.2.
European Office Action dated Aug. 15, 2014 issued in Application No. EP 11 785 851.4.
European Office Action dated Apr. 11, 2017 issued in Application No. EP 11 785 851.4.
Japanese Office Action dated Oct. 21, 2015 issued in Application No. JP 2013-537836.
Japanese Office Action dated Feb. 12, 2016 issued in Application No. JP 2013-537836.
Japanese Office Action dated Apr. 3, 2017 issued in Application No. JP 2016-009933.
Mexican First Office Action dated Jul. 19, 2016 issued in Application No. MX/a/2013/004631.
Mexican Second Office Action dated Jan. 16, 2017 issued in Application No. MX/a/2013/004631.
Mexican Third Office Action dated May 10, 2017 issued in Application No. MX/a/2013/004631.
Mexican Fourth Office Action dated Jul. 18, 2017 issued in Application No. MX/a/2013/004631.
Malaysian Examination Report dated May 31, 2016 issued in Application No. MY PI2013001587.
Australian Patent Examination Report No. 1 dated Jul. 22, 2015 issued in Application No. AU 2012212079.
Australian Patent Examination Report No. 1 dated Oct. 19, 2017, issued in Application No. AU 2016247159.
Australian Patent Examination Report No. 2 dated Feb. 26, 2018, issued in Application No. AU 2016247159.
Canadian Examination Report dated Nov. 22, 2017 issued in Application No. CA 2,825,691.
Chinese First Office Action dated Apr. 7, 2015 issued in Application No. CN 201280007593.3.
Chinese Second Office Action dated Nov. 17, 2015 issued in Application No. CN 201280007593.3.
Chinese Third Office Action dated Apr. 26, 2016 issued in Application No. CN 201280007593.3.
Chinese Fourth Office Action dated Oct. 17, 2016 issued in Application No. CN 201280007593.3.
Chinese Rejection Decision dated May 26, 2017 issued in Application No. CN 201280007593.3.
European Partial Supplementary Search Report dated May 8, 2015 issued in Application No. EP 12 741 997.6.
European Extended Search Report dated Aug. 31, 2015 issued in Application No. EP 12 741 997.6.
European Office Action dated Feb. 6, 2017 issued in Application No. EP 12 741 997.6.
European Examination Report dated Oct. 10, 2017 issued in Application No. EP 12 741 997.6.
Japanese Office Action dated Jan. 25, 2016 issued in Application No. JP 2013-552645.
Japanese Office Action [no translation] dated Apr. 20, 2017 issued in Application No. JP 2016-145348.
Japanese Office Action dated Dec. 1, 2017 issued in Application No. JP 2016-145348.
Mexican First Office Action dated Nov. 6, 2015 issued in Application No. MX/a/2013/008651.
Mexican Second Office Action dated Mar. 23, 2016 issued in Application No. MX/a/2013/008651.
Mexican Third Office Action dated Jul. 15, 2016 issued in Application No. MX/a/2013/008651.
Mexican First Office Action dated Apr. 24, 2017 issued in Application No. MX/a/2016/015902.
Malaysia Office Action dated Sep. 30, 2016 issued in Application No. MY PI2013002880.
PCT International Preliminary Report on Patentability dated Oct. 30, 2014 issued in PCT/US2013/037261.
Australian Patent Examination Report No. 1 dated Apr. 20, 2016 issued in Application No. AU 2013249172.
Australian Examination Report No. 2 dated Jan. 25, 2017 issued in Application No. AU 2013249172.
Chinese First Office Action dated Jul. 7, 2016 issued in Application No. CN 201380031877.0.
Chinese Second Office Action dated Mar. 24, 2017 issued in Application No. CN 201380031877.0.
Chinese Rejection Decision dated Oct. 10, 2017 issued in Application No. CN 201380031877.0.
European Supplementary Search Report dated Jan. 25, 2016 issued in Application No. EP 13 778 920.2.
European Examination Report dated Mar. 6, 2017 issued in Application No. EP 13 778 920.2.
Japanese First Office Action dated Mar. 10, 2017 issued in Application No. JP 2015-507197.
Mexican First Office Action dated Jul. 27, 2017 issued in Application No. MX/a/2014/012552.
Singapore Search Report and Written Opinion dated Mar. 24, 2016 issued in Application No. SG 11201406711T.
PCT International Search Report and Written Opinion of the International Searching Authority dated Jun. 1, 2015 issued in PCT/US2014/059161.
PCT International Report on Patentability and Written Opinion of the International Searching Authority dated Apr. 5, 2016 issued in PCT/US2014/059161.
Singapore Search Report and Written Opinion dated Aug. 7, 2017 issued in Application No. SG 11201602638S.
PCT Invitation to Pay Additional Fees dated Nov. 20, 2015 issued in PCT/US2015/039951.
PCT International Search Report and Written Opinion of the International Searching Authority dated Jan. 29, 2016 issued in Application No. PCT/US2015/039951.

(56) References Cited

OTHER PUBLICATIONS

PCT International Preliminary Report on Patentability and Written Opinion dated Jan. 10, 2017 issued in PCT/US2015/039951.
PCT International Search Report and Written Opinion of the International Searching Authority dated Jan. 3, 2017 issued in PCT/US2016/053979.
PCT International Search Report and Written Opinion of the International Searching Authority dated Jul. 18, 2016 issued in PCT/US2016/026265.
PCT International Preliminary Report on Patentability and Written Opinion of the International Searching Authority dated Oct. 19, 2017 issued in PCT/US2016/026265.
GenBank Accession No. AAC49269.1 "FatB2 [Cuphea hookeriana ]", (Apr. 30, 1996), 2pp.
GenBank Accession No. M94159.1 "California Bay Tree thioesterase mRNA, complete cds", (Apr. 27, 1993), 2pp.
GenBank: U31813 "Cinnamomum camphora acyl-ACP thioesterase mRNA, complete cds," Jan. 31, 1996, 2pp.
Beld et al., (Oct. 23, 2014) "Versatility of acyl-acyl carrier protein synthetases," *Chem. Biol.*, 21(10):1293-1299.
Dehesh et al., (2001) "Overexpression of 3-Ketoacyl-Acyl-Carrier Protein Synthase IIIs in Plants Reduces the Rate of Lipid Synthesis," *Plant Physiology*, 125:1103-1114.
Facciotti et al., (May 1998) "Molecular dissection of the plant acyl-acyl carrier protein thioesterases," *Fett/Lipid, Lipid-Weinheim*, 100(4-5), S.:167-172. [<URL:http://www.researchgate.net/publication/247961590>].
Hsieh et al., (2012) "Accumulation of Lipid Production in *Chlorella minutissima* by Triacylglycerol Biosynthesis-Related Genes Cloned from *Saccharomyces cerevisiae* and *Yarrowia lipolytica,*" *The Journal of Microbiology*, 50(3):526-534.
Iwasaki et al., (2000) "Enzymatic synthesis of structured lipids," *Journal of Molecular Catalysis B: Enzymatic*, 10:129-140.
List et al., (2004) "Melting properties of some structured lipids native to high stearic acid soybean oil," *Grasas y Aceites*, 55(Fasc. 2):135-137.
Liu et al., (2013) "Lipid metabolism in microalgae distinguishes itself," *Current Opinion in Biotechnology*, 24:300-309.
Miao et al., (2006) "Biodiesel Production From Heterotrophic Microalgal Oil," *Biosource Technology*, 97(06): 841-846.
Snyder et al., (2009) "Acyltransferase action in the modification of seed oil biosynthesis," *New Biotechnology*, 26(1/2): 11-16.
Xu et al., (2006) "High quality biodiesel production from a microalga *Chlorella protothecoides* by heterotrophic growth in fermenters," *Journal of Biotechnology*, 126:499-507.
U.S. Appl. No. 15/725,222, filed Oct. 4, 2017, Moseley et al.

* cited by examiner

SAMPLE OIL PROFILES: LOW TO HIGH OLEIC CONTENT

| | capric-rich | lauric-rich | myristic-palmitic | high palmitic | balanced | stearic-palmitic-oleic | mixed palmitic-oleic | mixed palmitic-oleic-2 | high oleic | high-stability oleic |
|---|---|---|---|---|---|---|---|---|---|---|
| *Oil* | *RB Z* | *RBD-1* | *RBD-2* | *RBD-3* | *RBD Y* | *RBD X* | *RBD W* | *RBD-4* | *RDB-5* | *RBD-6* |
| C8:0 | 4.5 | 0.2 | 0.9 | 0.0 | 0.0 | 0.0 | 0.0 | 0.0 | 0.0 | 0.0 |
| C10:0 | 29.3 | 16.8 | 13.2 | 0.0 | 2.4 | 0.0 | 0.0 | 0.0 | 0.0 | 0.0 |
| C12:0 | 4.4 | 47.2 | 2.8 | 0.2 | 0.9 | 0.0 | 0.1 | 0.1 | 0.0 | 0.0 |
| C14:0 | 23.6 | 11.3 | 24.8 | 6.0 | 15.3 | 0.7 | 2.0 | 1.7 | 0.5 | 0.6 |
| C16:0 | 21.5 | 5.1 | 31.6 | 49.1 | 35.9 | 24.0 | 28.7 | 25.0 | 6.9 | 8.2 |
| C16:1 | 0.1 | 0.1 | 0.1 | 0.4 | 0.3 | 0.2 | 0.4 | 1.0 | 0.7 | 0.8 |
| C18:0 | 2.3 | 0.9 | 4.8 | 5.1 | 3.5 | 21.4 | 9.5 | 3.6 | 1.4 | 1.9 |
| **C18:1** | **8.5** | **12.8** | **13.9** | **28.7** | **29.6** | **43.5** | **48.9** | **59.4** | **79.5** | **85.9** |
| C18:2 | 4.6 | 4.2 | 4.8 | 8.3 | 10.3 | 7.8 | 8.0 | 7.4 | 8.9 | 0.05 |
| C18:3 | 0.3 | 0.3 | 0.2 | 0.3 | 0.2 | 0.1 | 0.2 | 0.2 | 0.2 | 0.0 |

Figure 1

| Lot | Name | Features | Benefits |
| --- | --- | --- | --- |
| RBD-6 | High Stability Oleic Rich | Very low levels of polyunsaturates < .1% combined with very high levels of mono unsaturates (oleic) >85% | Unprecedented low levels of polyunsaturates creates perhaps the most stable natural oleic-rich oil available anywhere in the world for use in industrial and food applications. Outstanding stability and low (oxidative) reactivity is ideal for use in snack foods or spray-coating applications in foods. Combination of low pour point and oxidative stability is attractive for industrial uses such as bio-based functional fluids and lubricants. Remarkable stability minimizes need for antioxidants to be added to the oil. |
| RBD-5 | High Oleic Sunflower Oil Mimetic | Low levels of polyunsaturates <10% combined with high levels of mono unsaturates (oleic) ~80% | Sugar-derived alternative to high oleic sunflower with better GHG profile (Brazilian production). Ideal oil for cooking and frying; balances stability with health benefits of polyunsaturates. The higher level of polyunsaturates (than high stability algal oil) lowers the pour point for food and industrial applications e.g. functional fluids. |
| RBD-1 | Lauric Rich Alternative to Palm Kernel Oil, Coconut oil | High levels of mid-chain length saturated fatty acids ($C_{10}$ -$C_{14}$) | Sugar-derived alternative to palm kernel oil and coconut oil with enhanced sustainability and fatty acid profiles for the oleochemical and food industries. Enhanced mid-chain fatty acid (C10 – C14) concentration will create sharper melting fat for confectionary coating application, and efficient foaming properties in soaps. Lauric-rich oil also interesting as food oil catching wave of coconut oil as lauric is neutral-to-heart-healthy; solid sat for baking and/or confectionery. |

Figure 13

| Lot | Name | Features | Benefits |
|---|---|---|---|
| RBD-3 | High Palmitic / Low Oleic | 50% palmitic and 30% oleic; similar profile to a specialty palm mid fraction used to create structure in food products | Very efficient structuring fat for food products maximizes structuring while minimizing saturated fat content. Sharp melting profile minimizes negative impact on sensory properties of food products. Replacement for specialty palm fractions in food products; enhanced sustainability profile compared to palm |
| RBD-2 | Myrisitc / Palmitic Rich | Highest level of myrisitc than any existing oil | Uniquely high concentration of myristic acid combined with capric and palmitic creates sharp melting profiles and higher solid fat content at low temperature than palm oil; enhanced sustainability profile compared to palm. Very unique solid fat content profile |
| RBD-4 | High Oleic Mid Palmitic | 60% oleic and 25% palmitic; higher oleic & lower palmitic than palm oil | High oleic content combined with mid palmitic levels produces very stable oil with solid fat content that makes it an excellent frying oil alternative: food product texture may be positively impacted by reduced liquid oil pick up. 30% saturated fats in range for shortening applications. Potentially good alternative to trans-fat-containing oils. |

Figure 14

| *test* | *RBD oil tested* | *result* | *test protocol* |
|---|---|---|---|
| OSI | RBD 502 | current max: 242 hours at 110 °C | AOCS Method Cd 12b-92 (modified) |
| pour point | RBD 437 | -19.5 °C | D97 |
| cloud point | RBD 437 | 7.5 °C | AOCS Cc 6-25 |
| flash point | RBD 437 | 245 °C | AOCS Cc 9b-55 |
| viscosity | average of RBD 437 and RBD 469 | 41.6 cSt | Viscosity (D445) at 40 °C |
| viscosity index | " | 195.5 | Viscosity Index (D445) |
| color | RBD 437 | 2.0 Red, 18.0 Yellow | Lovibond Color AOCS Cc 13j-97 (5 1/4 inch cell) |
| color (converted) | RBD 437 | 87.3, -8.7, 32.3 | Hunter Transmittance: L, a, b |
| bio-degradeability | | Ultimate Biodegradation* | OECD 301 B |

Figure 16

| TEST | TEST PROTOCOL | HIGH STABILITY ALGAL OIL | HIGH OLEIC ALGAL OIL | COMMENTS ON HIGH STABILITY ALGAL OIL |
|---|---|---|---|---|
| **OSI at 110 °C** | AOCS Method Cd 12b-92 | 41.0 – 56.6 hours (neat)<br>**242** hours (natural antioxidants) | 14.4 hours (neat)<br>-- | *HSAO outperforms natural plant-based oils with same additives* |
| **RPVOT** | ASTM D2272 | 33 min (neat)<br>**500 min** (prelim. formulation) | 30 minutes (neat)<br>-- | *Neat oil outperforms neat PAO; HSAO outperforms natural plant-based oils with same additives* |
| **4-Ball wear** | @ 40kg; unformulated | 0.64 mm | 0.60 mm | |
| **Copper Strip Corrosion** | ASTM D130, 24 hrs | 1A | 1A | |
| **Pour point** | ASTM D6749/D97; unformulated | -19.5 °C (neat)<br>**-29 °C** (w/ pp depressant) | -21 °C (neat)<br>-- | *Low pour point with high oxidative stability* |
| **Cloud point** | ASTM D7683/D2500 | -14 °C | -18 °C | |
| **Flash point** | D92 Cleveland Open Cup | **315 °C** | 330 °C | *Outperforms mineral oils* |
| **Viscosity** | Viscosity (D445) at 40 °C | 41.6 cSt | 38.6 cSt | |
| **Viscosity index** | Viscosity Index (D445) | 196 | 202 | |
| **VOCs** | ASTM E1868-10 | 0.37% (near-zero) | nm | *Outperforms mineral oils* |
| **Biodegradability** | OECD 301 B | **Ultimate Biodegradation:**<br>96% degradation by day 28 | Ultimate Biodegradation:<br>94% degradation by day 28 | *Outperforms mineral oils* |

Figure 19 pSZ1500 (D696): FAD2 5'::CrTUB2-ScSUC2-CvNR:PmAMT3-CpSADtp-CtOTE-CvNR::FAD2 3' pSZ1501 (D697): FAD2 5'::CrTUB2-ScSUC2-CvNR:CrTUB2-CpSADtp-CtOTE-CvNR::FAD2 3' pSZ2276 (D1266): FATA 5'::CpACT-AtTHIC-CvNR:PmAMT3-PmKASII-CvNR::FATA 3' pSZ2441 (D1415): FATA 5'::CpACT-AtTHIC-CvNR:PmUAPA1-PmKASII-CvNR::FATA 3'

SEQUENCE LISTING

<160> NUMBER OF SEQ ID NOS: 171

<210> SEQ ID NO 1
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacc                                                               726
```

<210> SEQ ID NO 2
<211> LENGTH: 749
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gagctccttg ttttccagaa ggagttgctc cttgagcctt tcattctcag cctcgataac     60

ctccaaagcc gctctaattg tggagggggt tcgaatttaa aagcttggaa tgttggttcg    120

tgcgtctgga acaagcccag acttgttgct cactgggaaa aggaccatca gctccaaaaa    180

acttgccgct caaaccgcgt acctctgctt tcgcgcaatc tgccctgttg aaatcgccac    240

cacattcata ttgtgacgct tgagcagtct gtaattgcct cagaatgtgg aatcatctgc    300

cccctgtgcg agcccatgcc aggcatgtcg cgggcgagga cacccgccac tcgtacagca    360

gaccattatg ctacctcaca atagttcata acagtgacca tatttctcga agctccccaa    420

cgagcacctc catgctctga gtggccaccc cccggccctg gtgcttgcgg agggcaggtc    480

aaccggcatg gggctaccga aatccccgac cggatcccac cacccccgcg atgggaagaa    540

tctctccccg ggatgtgggc ccaccaccag cacaacctgc tggcccaggc gagcgtcaaa    600

ccataccaca caaatatcct tggcatcggc cctgaattcc ttctgccgct ctgctacccg    660

gtgcttctgt ccgaagcagg ggttgctagg gatcgctccg agtccgcaaa cccttgtcgc    720

gtggcggggc ttgttcgagc ttgaagagc                                      749
```

<210> SEQ ID NO 3
<211> LENGTH: 532
<212> TYPE: PRT
<213> ORGANISM: Saccharomyces cerevisiae

<400> SEQUENCE: 3

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30
```

Phe Thr Pro Asn Lys Gly Trp Met Asn Asp Pro Asn Gly Leu Trp Tyr
35 40 45

Asp Glu Lys Asp Ala Lys Trp His Leu Tyr Phe Gln Tyr Asn Pro Asn
50 55 60

Asp Thr Val Trp Gly Thr Pro Leu Phe Trp Gly His Ala Thr Ser Asp
65 70 75 80

Asp Leu Thr Asn Trp Glu Asp Gln Pro Ile Ala Ile Ala Pro Lys Arg
85 90 95

Asn Asp Ser Gly Ala Phe Ser Gly Ser Met Val Val Asp Tyr Asn Asn
100 105 110

Thr Ser Gly Phe Phe Asn Asp Thr Ile Asp Pro Arg Gln Arg Cys Val
115 120 125

Ala Ile Trp Thr Tyr Asn Thr Pro Glu Ser Glu Glu Gln Tyr Ile Ser
130 135 140

Tyr Ser Leu Asp Gly Gly Tyr Thr Phe Thr Glu Tyr Gln Lys Asn Pro
145 150 155 160

Val Leu Ala Ala Asn Ser Thr Gln Phe Arg Asp Pro Lys Val Phe Trp
165 170 175

Tyr Glu Pro Ser Gln Lys Trp Ile Met Thr Ala Ala Lys Ser Gln Asp
180 185 190

Tyr Lys Ile Glu Ile Tyr Ser Ser Asp Asp Leu Lys Ser Trp Lys Leu
195 200 205

Glu Ser Ala Phe Ala Asn Glu Gly Phe Leu Gly Tyr Gln Tyr Glu Cys
210 215 220

Pro Gly Leu Ile Glu Val Pro Thr Glu Gln Asp Pro Ser Lys Ser Tyr
225 230 235 240

Trp Val Met Phe Ile Ser Ile Asn Pro Gly Ala Pro Ala Gly Gly Ser
245 250 255

Phe Asn Gln Tyr Phe Val Gly Ser Phe Asn Gly Thr His Phe Glu Ala
260 265 270

Phe Asp Asn Gln Ser Arg Val Val Asp Phe Gly Lys Asp Tyr Tyr Ala
275 280 285

Leu Gln Thr Phe Phe Asn Thr Asp Pro Thr Tyr Gly Ser Ala Leu Gly
290 295 300

Ile Ala Trp Ala Ser Asn Trp Glu Tyr Ser Ala Phe Val Pro Thr Asn
305 310 315 320

Pro Trp Arg Ser Ser Met Ser Leu Val Arg Lys Phe Ser Leu Asn Thr
325 330 335

Glu Tyr Gln Ala Asn Pro Glu Thr Glu Leu Ile Asn Leu Lys Ala Glu
340 345 350

Pro Ile Leu Asn Ile Ser Asn Ala Gly Pro Trp Ser Arg Phe Ala Thr
355 360 365

Asn Thr Thr Leu Thr Lys Ala Asn Ser Tyr Asn Val Asp Leu Ser Asn
370 375 380

Ser Thr Gly Thr Leu Glu Phe Glu Leu Val Tyr Ala Val Asn Thr Thr
385 390 395 400

Gln Thr Ile Ser Lys Ser Val Phe Ala Asp Leu Ser Leu Trp Phe Lys
405 410 415

Gly Leu Glu Asp Pro Glu Glu Tyr Leu Arg Met Gly Phe Glu Val Ser
420 425 430

Ala Ser Ser Phe Phe Leu Asp Arg Gly Asn Ser Lys Val Lys Phe Val
435 440 445

-continued

```
Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530


<210> SEQ ID NO 4
<211> LENGTH: 1599
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

atgctgctgc aggccttcct gttcctgctg gccggcttcg ccgccaagat cagcgcctcc     60

atgacgaacg agacgtccga ccgccccctg gtgcacttca cccccaacaa gggctggatg    120

aacgacccca acggcctgtg gtacgacgag aaggacgcca agtggcacct gtacttccag    180

tacaacccga acgacaccgt ctgggggacg ccccttgttct ggggccacgc cacgtccgac    240

gacctgacca actgggagga ccagcccatc gccatcgccc cgaagcgcaa cgactccggc    300

gccttctccg gctccatggt ggtggactac aacaacacct ccggcttctt caacgacacc    360

atcgacccgc gccagcgctg cgtggccatc tggacctaca acaccccgga gtccgaggag    420

cagtacatct cctacagcct ggacggcggc tacaccttca ccgagtacca gaagaacccc    480

gtgctggccg ccaactccac ccagttccgc gacccgaagg tcttctggta cgagccctcc    540

cagaagtgga tcatgaccgc ggccaagtcc caggactaca agatcgagat ctactcctcc    600

gacgacctga agtcctggaa gctggagtcc gcgttcgcca acgagggctt cctcggctac    660

cagtacgagt gccccggcct gatcgaggtc cccaccgagc aggaccccag caagtcctac    720

tgggtgatgt tcatctccat caaccccggc gccccggccg gcggctcctt caaccagtac    780

ttcgtcggca gcttcaacgg cacccacttc gaggccttcg acaaccagtc ccgcgtggtg    840

gacttcggca aggactacta cgccctgcag accttcttca acaccgaccc gacctacggg    900

agcgccctgg gcatcgcgtg ggcctccaac tgggagtact ccgccttcgt gcccaccaac    960

ccctggcgct cctccatgtc cctcgtgcgc aagttctccc tcaacaccga gtaccaggcc   1020

aacccggaga cggagctgat caacctgaag gccgagccga tcctgaacat cagcaacgcc   1080

ggcccctgga gccggttcgc caccaacacc acgttgacga aggccaacag ctacaacgtc   1140

gacctgtcca acagcaccgg caccctggag ttcgagctgg tgtacgccgt caacaccacc   1200

cagacgatct ccaagtccgt gttcgcggac ctctccctct ggttcaaggg cctggaggac   1260

cccgaggagt acctccgcat gggcttcgag gtgtccgcgt cctccttctt cctggaccgc   1320

gggaacagca aggtgaagtt cgtgaaggag aacccctact tcaccaaccg catgagcgtg   1380

aacaaccagc ccttcaagag cgagaacgac ctgtcctact acaaggtgta cggcttgctg   1440

gaccagaaca tcctggagct gtacttcaac gacggcgacg tcgtgtccac caacacctac   1500
```

-continued ttcatgacca ccgggaacgc cctgggctcc gtgaacatga cgacgggggt ggacaacctg 1560
ttctacatcg acaagttcca ggtgcgcgag gtcaagtga 1599

<210> SEQ ID NO 5
<211> LENGTH: 312
<212> TYPE: DNA
<213> ORGANISM: Chlamydomonas reinhardtii

<400> SEQUENCE: 5
ctttcttgcg ctatgacact tccagcaaaa ggtagggcgg gctgcgagac ggcttcccgg 60
cgctgcatgc aacaccgatg atgcttcgac ccccgaagc tccttcgggg ctgcatgggc 120
gctccgatgc cgctccaggg cgagcgctgt ttaaatagcc aggcccccga ttgcaaagac 180
attatagcga gctaccaaag ccatattcaa acacctagat cactaccact tctacacagg 240
ccactcgagc ttgtgatcgc actccgctaa gggggcgcct cttcctcttc gtttcagtca 300
caacccgcaa ac 312

<210> SEQ ID NO 6
<211> LENGTH: 408
<212> TYPE: DNA
<213> ORGANISM: Chlorella vulgaris

<400> SEQUENCE: 6
gcagcagcag ctcggatagt atcgacacac tctggacgct ggtcgtgtga tggactgttg 60
ccgccacact tgctgccttg acctgtgaat atccctgccg cttttatcaa acagcctcag 120
tgtgtttgat cttgtgtgta cgcgcttttg cgagttgcta gctgcttgtg ctatttgcga 180
ataccacccc cagcatcccc ttccctcgtt tcatatcgct tgcatcccaa ccgcaactta 240
tctacgctgt cctgctatcc ctcagcgctg ctcctgctcc tgctcactgc ccctcgcaca 300
gccttggttt gggctccgcc tgtattctcc tggtactgca acctgtaaac cagcactgca 360
atgctgatgc acgggaagta gtgggatggg aacacaaatg gaaagctt 408

<210> SEQ ID NO 7
<211> LENGTH: 2333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
ctttcttgcg ctatgacact tccagcaaaa ggtagggcgg gctgcgagac ggcttcccgg 60
cgctgcatgc aacaccgatg atgcttcgac ccccgaagc tccttcgggg ctgcatgggc 120
gctccgatgc cgctccaggg cgagcgctgt ttaaatagcc aggcccccga ttgcaaagac 180
attatagcga gctaccaaag ccatattcaa acacctagat cactaccact tctacacagg 240
ccactcgagc ttgtgatcgc actccgctaa gggggcgcct cttcctcttc gtttcagtca 300
caacccgcaa acggcgcgcc atgctgctgc aggccttcct gttcctgctg gccggcttcg 360
ccgccaagat cagcgcctcc atgacgaacg agacgtccga ccgcccctg gtgcacttca 420 cccccaacaa gggctggatg aacgacccca acggcctgtg gtacgacgag aaggacgcca 480
agtggcacct gtacttccag tacaacccga acgacaccgt ctgggggacg cccttgttct 540
ggggccacgc cacgtccgac gacctgacca actgggagga ccagcccatc gccatcgccc 600
cgaagcgcaa cgactccggc gccttctccg gctccatggt ggtggactac aacaacacct 660

```
ccggcttctt caacgacacc atcgacccgc gccagcgctg cgtggccatc tggacctaca    720
acaccccgga gtccgaggag cagtacatct cctacagcct ggacggcggc tacaccttca    780
ccgagtacca gaagaacccc gtgctggccg ccaactccac ccagttccgc gacccgaagg    840
tcttctggta cgagccctcc cagaagtgga tcatgaccgc ggccaagtcc caggactaca    900
agatcgagat ctactcctcc gacgacctga agtcctggaa gctggagtcc gcgttcgcca    960
acgagggctt cctcggctac cagtacgagt gccccggcct gatcgaggtc cccaccgagc   1020
aggaccccag caagtcctac tgggtgatgt tcatctccat caaccccggc gccccggccg   1080
gcggctcctt caaccagtac ttcgtcggca gcttcaacgg cacccacttc gaggccttcg   1140
acaaccagtc ccgcgtggtg gacttcggca aggactacta cgccctgcag accttcttca   1200
acaccgaccc gacctacggg agcgccctgg gcatcgcgtg ggcctccaac tgggagtact   1260
ccgccttcgt gcccaccaac ccctggcgct cctccatgtc cctcgtgcgc aagttctccc   1320
tcaacaccga gtaccaggcc aacccggaga cggagctgat caacctgaag gccgagccga   1380
tcctgaacat cagcaacgcc ggcccctgga gccggttcgc caccaacacc acgttgacga   1440
aggccaacag ctacaacgtc gacctgtcca acagcaccgg caccctggag ttcgagctgg   1500
tgtacgccgt caacaccacc cagacgatct ccaagtccgt gttcgcggac ctctccctct   1560
ggttcaaggg cctggaggac cccgaggagt acctccgcat gggcttcgag gtgtccgcgt   1620
cctccttctt cctggaccgc gggaacagca aggtgaagtt cgtgaaggag aacccctact   1680
tcaccaaccg catgagcgtg aacaaccagc ccttcaagag cgagaacgac ctgtcctact   1740
acaaggtgta cggcttgctg gaccagaaca tcctggagct gtacttcaac gacggcgacg   1800
tcgtgtccac caacacctac ttcatgacca ccgggaacgc cctgggctcc gtgaacatga   1860
cgacgggggt ggacaacctg ttctacatcg acaagttcca ggtgcgcgag gtcaagtgac   1920
aattggcagc agcagctcgg atagtatcga cacactctgg acgctggtcg tgtgatggac   1980
tgttgccgcc acacttgctg ccttgacctg tgaatatccc tgccgctttt atcaaacagc   2040
ctcagtgtgt ttgatcttgt gtgtacgcgc ttttgcgagt tgctagctgc ttgtgctatt   2100
tgcgaatacc acccccagca tccccttccc tcgtttcata tcgcttgcat cccaaccgca   2160
acttatctac gctgtcctgc tatccctcag cgctgctcct gctcctgctc actgcccctc   2220
gcacagcctt ggtttgggct ccgcctgtat tctcctggta ctgcaacctg taaaccagca   2280
ctgcaatgct gatgcacggg aagtagtggg atgggaacac aaatggagga tcc          2333
```

<210> SEQ ID NO 8
<211> LENGTH: 1065
<212> TYPE: DNA
<213> ORGANISM: Prototheca moriformis

<400> SEQUENCE: 8

```
ggccgacagg acgcgcgtca aaggtgctgg tcgtgtatgc cctggccggc aggtcgttgc     60
tgctgctggt tagtgattcc gcaaccctga ttttggcgtc ttattttggc gtggcaaacg    120
ctggcgcccg cgagccgggc cggcggcgat gcggtgcccc acggctgccg gaatccaagg    180
gaggcaagag cgcccgggtc agttgaaggg ctttacgcgc aaggtacagc cgctcctgca    240
aggctgcgtg gtggaattgg acgtgcaggt cctgctgaag ttcctccacc gcctcaccag    300
cggacaaagc accggtgtat caggtccgtg tcatccactc taaagagctc gactacgacc    360
tactgatggc cctagattct tcatcaaaaa cgcctgagac acttgcccag gattgaaact    420
ccctgaaggg accaccaggg gccctgagtt gttccttccc cccgtggcga gctgccagcc    480
```

aggctgtacc tgtgatcgag gctggcggga aaataggctt cgtgtgctca ggtcatggga 540
ggtgcaggac agctcatgaa acgccaacaa tcgcacaatt catgtcaagc taatcagcta 600
tttcctcttc acgagctgta attgtcccaa aattctggtc taccgggggt gatccttcgt 660
gtacgggccc ttccctcaac cctaggtatg cgcgcatgcg gtcgccgcgc aactcgcgcg 720
agggccgagg gtttgggacg ggccgtcccg aaatgcagtt gcacccggat gcgtggcacc 780
ttttttgcga taatttatgc aatggactgc tctgcaaaat tctggctctg tcgccaaccc 840
taggatcagc ggcgtaggat ttcgtaatca ttcgtcctga tggggagcta ccgactaccc 900
taatatcagc ccgactgcct gacgccagcg tccacttttg tgcacacatt ccattcgtgc 960
ccaagacatt tcattgtggt gcgaagcgtc cccagttacg ctcacctgtt tcccgacctc 1020
cttactgttc tgtcgacaga gcgggcccac aggccggtcg cagcc 1065

<210> SEQ ID NO 9
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
actagtatgg ccaccgcatc cactttctcg gcgttcaatg cccgctgcgg cgacctgcgt 60
cgctcggcgg gctccgggcc ccggcgccca gcgaggcccc tccccgtgcg cgggcgcgcc 120

<210> SEQ ID NO 10
<211> LENGTH: 1236
<212> TYPE: DNA
<213> ORGANISM: Cuphea wrightii

<400> SEQUENCE: 10
atggtggtgg ccgccgccgc cagcagcgcc ttcttccccg tgcccgcccc ccgccccacc 60
cccaagcccg gcaagttcgg caactggccc agcagcctga gccagccctt caagcccaag 120
agcaacccca acggccgctt ccaggtgaag gccaacgtga gcccccacgg gcgcgccccc 180
aaggccaacg gcagcgccgt gagcctgaag tccggcagcc tgaacaccct ggaggacccc 240
cccagcagcc cccccccccg caccttcctg aaccagctgc ccgactggag ccgcctgcgc 300
accgccatca ccaccgtgtt cgtggccgcc gagaagcagt tcacccgcct ggaccgcaag 360
agcaagcgcc ccgacatgct ggtggactgg ttcggcagcg agaccatcgt gcaggacggc 420
ctggtgttcc gcgagcgctt cagcatccgc agctacgaga tcggcgccga ccgcaccgcc 480
agcatcgaga ccctgatgaa ccacctgcag gacaccagcc tgaaccactg caagagcgtg 540
ggcctgctga acgacggctt cggccgcacc cccgagatgt gcacccgcga cctgatctgg 600
gtgctgacca agatgcagat cgtggtgaac cgctacccca cctggggcga caccgtggag 660
atcaacagct ggttcagcca gagcggcaag atcggcatgg gccgcgagtg gctgatcagc 720
gactgcaaca ccggcgagat cctggtgcgc gccaccagcg cctgggccat gatgaaccag 780
aagacccgcc gcttcagcaa gctgccctgc gaggtgcgcc aggagatcgc cccccacttc 840
gtggacgccc cccccgtgat cgaggacaac gaccgcaagc tgcacaagtt cgacgtgaag 900
accggcgaca gcatctgcaa gggcctgacc cccggctgga acgacttcga cgtgaaccag 960
cacgtgagca acgtgaagta catcggctgg attctggaga gcatgcccac cgaggtgctg 1020
gagacccagg agctgtgcag cctgaccctg gagtaccgcc gcgagtgcgg ccgcgagagc 1080
gtggtggaga gcgtgaccag catgaacccc agcaaggtgg gcgaccgcag ccagtaccag 1140
cacctgctgc gcctggagga cggcgccgac atcatgaagg gccgcaccga gtggcgcccc 1200
aagaacgccg gcaccaaccg cgccatcagc acctga 1236

<210> SEQ ID NO 11
<211> LENGTH: 408
<212> TYPE: PRT
<213> ORGANISM: Cuphea wrightii

<400> SEQUENCE: 11

Met Val Val Ala Ala Ala Ala Ser Ser Ala Phe Phe Pro Val Pro Ala
1 5 10 15

Pro Arg Pro Thr Pro Lys Pro Gly Lys Phe Gly Asn Trp Pro Ser Ser
20 25 30

Leu Ser Gln Pro Phe Lys Pro Lys Ser Asn Pro Asn Gly Arg Phe Gln
35 40 45

Val Lys Ala Asn Val Ser Pro His Pro Lys Ala Asn Gly Ser Ala Val
50 55 60

Ser Leu Lys Ser Gly Ser Leu Asn Thr Leu Glu Asp Pro Pro Ser Ser
65 70 75 80

Pro Pro Pro Arg Thr Phe Leu Asn Gln Leu Pro Asp Trp Ser Arg Leu
85 90 95

Arg Thr Ala Ile Thr Thr Val Phe Val Ala Ala Glu Lys Gln Phe Thr
100 105 110

Arg Leu Asp Arg Lys Ser Lys Arg Pro Asp Met Leu Val Asp Trp Phe
115 120 125

Gly Ser Glu Thr Ile Val Gln Asp Gly Leu Val Phe Arg Glu Arg Phe
130 135 140

Ser Ile Arg Ser Tyr Glu Ile Gly Ala Asp Arg Thr Ala Ser Ile Glu
145 150 155 160

Thr Leu Met Asn His Leu Gln Asp Thr Ser Leu Asn His Cys Lys Ser
165 170 175

Val Gly Leu Leu Asn Asp Gly Phe Gly Arg Thr Pro Glu Met Cys Thr
180 185 190

Arg Asp Leu Ile Trp Val Leu Thr Lys Met Gln Ile Val Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Glu Trp Leu Ile Ser Asp Cys Asn
225 230 235 240

Thr Gly Glu Ile Leu Val Arg Ala Thr Ser Ala Trp Ala Met Met Asn
245 250 255

Gln Lys Thr Arg Arg Phe Ser Lys Leu Pro Cys Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Cys Lys
290 295 300

Gly Leu Thr Pro Gly Trp Asn Asp Phe Asp Val Asn Gln His Val Ser
305 310 315 320

Asn Val Lys Tyr Ile Gly Trp Ile Leu Glu Ser Met Pro Thr Glu Val
325 330 335

Leu Glu Thr Gln Glu Leu Cys Ser Leu Thr Leu Glu Tyr Arg Arg Glu 340 345 350

Cys Gly Arg Glu Ser Val Val Glu Ser Val Thr Ser Met Asn Pro Ser
355 360 365

Lys Val Gly Asp Arg Ser Gln Tyr Gln His Leu Leu Arg Leu Glu Asp
370 375 380

Gly Ala Asp Ile Met Lys Gly Arg Thr Glu Trp Arg Pro Lys Asn Ala
385 390 395 400

Gly Thr Asn Arg Ala Ile Ser Thr
405

<210> SEQ ID NO 12
<211> LENGTH: 933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
atggacgcct ccggcgcctc ctccttcctg cgcggccgct gcctggagtc ctgcttcaag 60
gcctccttcg gctacgtaat gtcccagccc aaggacgccg ccggccagcc ctcccgccgc 120
cccgccgacg ccgacgactt cgtggacgac gaccgctgga tcaccgtgat cctgtccgtg 180
gtgcgcatcg ccgcctgctt cctgtccatg atggtgacca ccatcgtgtg gaacatgatc 240
atgctgatcc tgctgccctg gccctacgcc cgcatccgcc agggcaacct gtacggccac 300
gtgaccggcc gcatgctgat gtggattctg ggcaacccca tcaccatcga gggctccgag 360
ttctccaaca cccgcgccat ctacatctgc aaccacgcct ccctggtgga catcttcctg 420
atcatgtggc tgatccccaa gggcaccgtg accatcgcca agaaggagat catctggtat 480
cccctgttcg gccagctgta cgtgctggcc aaccaccagc gcatcgaccg ctccaacccc 540
tccgccgcca tcgagtccat caaggaggtg gcccgcgccg tggtgaagaa gaacctgtcc 600
ctgatcatct tccccgaggg cacccgctcc aagaccggcc gcctgctgcc cttcaagaag 660
ggcttcatcc acatcgccct ccagacccgc ctgcccatcg tgccgatggt gctgaccggc 720
acccacctgg cctggcgcaa gaactccctg cgcgtgcgcc ccgcccccat caccgtgaag 780
tacttctccc ccatcaagac cgacgactgg gaggaggaga agatcaacca ctacgtggag 840
atgatccacg ccctgtacgt ggaccacctg cccgagtccc agaagcccct ggtgtccaag 900
ggccgcgacg cctccggccg ctccaactcc tga 933

<210> SEQ ID NO 13
<211> LENGTH: 563
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
gctcttcgct aacggaggtc tgtcaccaaa tggaccccgt ctattgcggg aaaccacggc 60
gatggcacgt ttcaaaactt gatgaaatac aatattcagt atgtcgcggg cggcgacggc 120
ggggagctga tgtcgcgctg ggtattgctt aatcgccagc ttcgcccccg tcttggcgcg 180
aggcgtgaac aagccgaccg atgtgcacga gcaaatcctg acactagaag ggctgactcg 240
cccggcacgg ctgaattaca caggcttgca aaaataccag aatttgcacg caccgtattc 300
gcggtatttt gttggacagt gaatagcgat gcggcaatgg cttgtggcgt tagaaggtgc 360
gacgaaggtg gtgccaccac tgtgccagcc agtcctggcg gctcccaggg ccccgatcaa 420
gagccaggac atccaaacta cccacagcat caacgccccg gcctatactc gaaccccact 480
tgcactctgc aatggtatgg gaaccacggg gcagtcttgt gtgggtcgcg cctatcgcgg 540
tcggcgaaga ccgggaaggt acc 563

<210> SEQ ID NO 14
<211> LENGTH: 465
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
gagctcagcg gcgacggtcc tgctaccgta cgacgttggg cacgcccatg aaagtttgta 60
taccgagctt gttgagcgaa ctgcaagcgc ggctcaagga tacttgaact cctggattga 120
tatcggtcca ataatggatg gaaaatccga acctcgtgca agaactgagc aaacctcgtt 180
acatggatgc acagtcgcca gtccaatgaa cattgaagtg agcgaactgt tcgcttcggt 240
ggcagtacta ctcaaagaat gagctgctgt taaaaatgca ctctcgttct ctcaagtgag 300
tggcagatga gtgctcacgc cttgcacttc gctgcccgtg tcatgccctg cgccccaaaa 360
tttgaaaaaa gggatgagat tattgggcaa tggacgacgt cgtcgctccg ggagtcagga 420
ccggcggaaa ataagaggca acacactccg cttcttagct cttcc 465

<210> SEQ ID NO 15
<211> LENGTH: 1533
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
ctttcttgcg ctatgacact tccagcaaaa ggtagggcgg gctgcgagac ggcttcccgg 60
cgctgcatgc aacaccgatg atgcttcgac cccccgaagc tccttcgggg ctgcatgggc 120
gctccgatgc cgctccaggg cgagcgctgt ttaaatagcc aggcccccga ttgcaaagac 180
attatagcga gctaccaaag ccatattcaa acacctagat cactaccact tctacacagg 240
ccactcgagc ttgtgatcgc actccgctaa gggggcgcct cttcctcttc gtttcagtca 300
caacccgcaa actctagaat atcaatgatc gagcaggacg gcctccacgc cggctccccc 360
gccgcctggg tggagcgcct gttcggctac gactgggccc agcagaccat cggctgctcc 420
gacgccgccg tgttccgcct gtccgcccag ggccgccccg tgctgttcgt gaagaccgac 480
ctgtccggcg ccctgaacga gctgcaggac gaggccgccc gcctgtcctg gctggccacc 540
accggcgtgc cctgcgccgc cgtgctggac gtggtgaccg aggccggccg cgactggctg 600
ctgctgggcg aggtgcccgg ccaggacctg ctgtcctccc acctggcccc cgccgagaag 660
gtgtccatca tggccgacgc catgcgccgc ctgcacaccc tggaccccgc cacctgcccc 720
ttcgaccacc aggccaagca ccgcatcgag cgcgcccgca cccgcatgga ggccggcctg 780
gtggaccagg acgacctgga cgaggagcac cagggcctgg cccccgccga gctgttcgcc 840
cgcctgaagg cccgcatgcc cgacggcgag gacctggtgg tgacccacgg cgacgcctgc 900
ctgcccaaca tcatggtgga gaacggccgc ttctccggct tcatcgactg cggccgcctg 960
ggcgtggccg accgctacca ggacatcgcc ctggccaccc gcgacatcgc cgaggagctg 1020
ggcggcgagt gggccgaccg cttcctggtg ctgtacggca tcgccgcccc cgactcccag 1080
cgcatcgcct tctaccgcct gctggacgag ttcttctgac aattggcagc agcagctcgg 1140
atagtatcga cacactctgg acgctggtcg tgtgatggac tgttgccgcc acacttgctg 1200
ccttgacctg tgaatatccc tgccgctttt atcaaacagc ctcagtgtgt ttgatcttgt 1260
gtgtacgcgc ttttgcgagt tgctagctgc ttgtgctatt tgcgaatacc acccccagca 1320
tccccttccc tcgtttcata tcgcttgcat cccaaccgca acttatctac gctgtcctgc 1380
tatccctcag cgctgctcct gctcctgctc actgcccctc gcacagcctt ggtttgggct 1440
ccgcctgtat tctcctggta ctgcaacctg taaaccagca ctgcaatgct gatgcacggg 1500
aagtagtggg atgggaacac aaatggagga tcc 1533

<210> SEQ ID NO 16
<211> LENGTH: 310
<212> TYPE: PRT
<213> ORGANISM: Cocos nucifera

<400> SEQUENCE: 16

Met Asp Ala Ser Gly Ala Ser Ser Phe Leu Arg Gly Arg Cys Leu Glu
1 5 10 15

Ser Cys Phe Lys Ala Ser Phe Gly Tyr Val Met Ser Gln Pro Lys Asp
20 25 30

Ala Ala Gly Gln Pro Ser Arg Arg Pro Ala Asp Ala Asp Asp Phe Val
35 40 45

Asp Asp Asp Arg Trp Ile Thr Val Ile Leu Ser Val Val Arg Ile Ala
50 55 60

Ala Cys Phe Leu Ser Met Met Val Thr Thr Ile Val Trp Asn Met Ile
65 70 75 80

Met Leu Ile Leu Leu Pro Trp Pro Tyr Ala Arg Ile Arg Gln Gly Asn
85 90 95

Leu Tyr Gly His Val Thr Gly Arg Met Leu Met Trp Ile Leu Gly Asn
100 105 110

Pro Ile Thr Ile Glu Gly Ser Glu Phe Ser Asn Thr Arg Ala Ile Tyr
115 120 125

Ile Cys Asn His Ala Ser Leu Val Asp Ile Phe Leu Ile Met Trp Leu
130 135 140

Ile Pro Lys Gly Thr Val Thr Ile Ala Lys Lys Glu Ile Ile Trp Tyr
145 150 155 160

Pro Leu Phe Gly Gln Leu Tyr Val Leu Ala Asn His Gln Arg Ile Asp
165 170 175

Arg Ser Asn Pro Ser Ala Ala Ile Glu Ser Ile Lys Glu Val Ala Arg
180 185 190

Ala Val Val Lys Lys Asn Leu Ser Leu Ile Ile Phe Pro Glu Gly Thr
195 200 205

Arg Ser Lys Thr Gly Arg Leu Leu Pro Phe Lys Lys Gly Phe Ile His
210 215 220

Ile Ala Leu Gln Thr Arg Leu Pro Ile Val Pro Met Val Leu Thr Gly
225 230 235 240

Thr His Leu Ala Trp Arg Lys Asn Ser Leu Arg Val Arg Pro Ala Pro
245 250 255

Ile Thr Val Lys Tyr Phe Ser Pro Ile Lys Thr Asp Asp Trp Glu Glu
260 265 270

```
Glu Lys Ile Asn His Tyr Val Glu Met Ile His Ala Leu Tyr Val Asp
        275                 280                 285

His Leu Pro Glu Ser Gln Lys Pro Leu Val Ser Lys Gly Arg Asp Ala
    290                 295                 300

Ser Gly Arg Ser Asn Ser
305                 310
```

<210> SEQ ID NO 17
<211> LENGTH: 6676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gggctggtct gaatccttca ggcgggtgtt acccgagaaa gaaagggtgc cgatttcaaa     60

gcagacccat gtgccgggcc ctgtggcctg tgttggcgcc tatgtagtca cccccccctca    120

cccaattgtc gccagtttgc gcactccata aactcaaaac agcagcttct gagctgcgct    180

gttcaagaac acctctgggg tttgctcacc cgcgaggtcg acgcccagca tggctatcaa    240

gacgaacagg cagcctgtgg agaagcctcc gttcacgatc gggacgctgc gcaaggccat    300

ccccgcgcac tgtttcgagc gctcggcgct tcgtagcagc atgtacctgg cctttgacat    360

cgcggtcatg tccctgctct acgtcgcgtc gacgtacatc gaccctgcac cggtgcctac    420

gtgggtcaag tacggcatca tgtggccgct ctactggttc ttccaggtgt gtttgagggt    480

tttggttgcc cgtattgagg tcctggtggc gcgcatggag gagaaggcgc ctgtcccgct    540

gacccccccg gctaccctcc cggcaccttc cagggcgcct tcggcacggg tgtctgggtg    600

tgcgcgcacg agtgcggcca ccaggccttt tcctccagcc aggccatcaa cgacggcgtg    660

ggcctggtgt tccacagcct gctgctggtg ccctactact cctggaagca ctcgcaccgg    720

gtaccctttc ttgcgctatg acacttccag caaaaggtag ggcgggctgc gagacggctt    780

cccggcgctg catgcaacac cgatgatgct tcgacccccc gaagctcctt cggggctgca    840

tgggcgctcc gatgccgctc cagggcgagc gctgtttaaa tagccaggcc cccgattgca    900

aagacattat agcgagctac caaagccata ttcaaacacc tagatcacta ccacttctac    960

acaggccact cgagcttgtg atcgcactcc gctaaggggg cgcctcttcc tcttcgtttc   1020

agtcacaacc cgcaaactct agaatatcaa tgctgctgca ggccttcctg ttcctgctgg   1080

ccggcttcgc cgccaagatc agcgcctcca tgacgaacga gacgtccgac cgccccctgg   1140

tgcacttcac ccccaacaag ggctggatga acgaccccaa cggcctgtgg tacgacgaga   1200

aggacgccaa gtggcacctg tacttccagt acaacccgaa cgacaccgtc tgggggacgc   1260

ccttgttctg ggccacgcc acgtccgacg acctgaccaa ctgggaggac cagcccatcg   1320

ccatcgcccc gaagcgcaac gactccggcg ccttctccgg ctccatggtg gtggactaca   1380

acaacacctc cggcttcttc aacgacacca tcgacccgcg ccagcgctgc gtggccatct   1440

ggacctacaa caccccggag tccgaggagc agtacatctc ctacagcctg gacggcggct   1500

acaccttcac cgagtaccag aagaaccccg tgctggccgc caactccacc cagttccgcg   1560

acccgaaggt cttctggtac gagccctccc agaagtggat catgaccgcg gccaagtccc   1620

aggactacaa gatcgagatc tactcctccg acgacctgaa gtcctggaag ctggagtccg   1680

cgttcgccaa cgagggcttc ctcggctacc agtacgagtg ccccggcctg atcgaggtcc   1740

ccaccgagca ggaccccagc aagtcctact gggtgatgtt catctccatc aaccccggcg   1800
```

-continued

```
ccccggccgg cggctccttc aaccagtact tcgtcggcag cttcaacggc acccacttcg   1860
aggccttcga caaccagtcc cgcgtggtgg acttcggcaa ggactactac gccctgcaga   1920
ccttcttcaa caccgacccg acctacggga gcgccctggg catcgcgtgg gcctccaact   1980
gggagtactc cgccttcgtg cccaccaacc cctggcgctc ctccatgtcc ctcgtgcgca   2040
agttctccct caacaccgag taccaggcca acccggagac ggagctgatc aacctgaagg   2100
ccgagccgat cctgaacatc agcaacgccg gcccctggag ccggttcgcc accaacacca   2160
cgttgacgaa ggccaacagc tacaacgtcg acctgtccaa cagcaccggc accctggagt   2220
tcgagctggt gtacgccgtc aacaccaccc agacgatctc caagtccgtg ttcgcggacc   2280
tctccctctg gttcaagggc ctggaggacc ccgaggagta cctccgcatg ggcttcgagg   2340
tgtccgcgtc ctccttcttc ctggaccgcg ggaacagcaa ggtgaagttc gtgaaggaga   2400
acccctactt caccaaccgc atgagcgtga acaaccagcc cttcaagagc gagaacgacc   2460
tgtcctacta caaggtgtac ggcttgctgg accagaacat cctggagctg tacttcaacg   2520
acggcgacgt cgtgtccacc aacacctact tcatgaccac cgggaacgcc ctgggctccg   2580
tgaacatgac gacgggggtg gacaacctgt tctacatcga caagttccag gtgcgcgagg   2640
tcaagtgaca attggcagca gcagctcgga tagtatcgac acactctgga cgctggtcgt   2700
gtgatggact gttgccgcca cacttgctgc cttgacctgt gaatatccct gccgctttta   2760
tcaaacagcc tcagtgtgtt tgatcttgtg tgtacgcgct tttgcgagtt gctagctgct   2820
tgtgctattt gcgaatacca cccccagcat ccccttccct cgtttcatat cgcttgcatc   2880
ccaaccgcaa cttatctacg ctgtcctgct atccctcagc gctgctcctg ctcctgctca   2940
ctgcccctcg cacagccttg gtttgggctc cgcctgtatt ctcctggtac tgcaacctgt   3000
aaaccagcac tgcaatgctg atgcacggga agtagtggga tgggaacaca aatggaggat   3060
cccgcgtctc gaacagagcg cgcagaggaa cgctgaaggt ctcgcctctg tcgcacctca   3120
gcgcggcata caccacaata accacctgac gaatgcgctt ggttcttcgt ccattagcga   3180
agcgtccggt tcacacacgt gccacgttgg cgaggtggca ggtgacaatg atcggtggag   3240
ctgatggtcg aaacgttcac agcctaggga tatcgaattc ggccgacagg acgcgcgtca   3300
aaggtgctgg tcgtgtatgc cctggccggc aggtcgttgc tgctgctggt tagtgattcc   3360
gcaaccctga ttttggcgtc ttattttggc gtggcaaacg ctggcgcccg cgagccgggc   3420
cggcggcgat gcggtgcccc acggctgccg gaatccaagg gaggcaagag cgcccgggtc   3480
agttgaaggg ctttacgcgc aaggtacagc cgctcctgca aggctgcgtg gtggaattgg   3540
acgtgcaggt cctgctgaag ttcctccacc gcctcaccag cggacaaagc accggtgtat   3600
caggtccgtg tcatccactc taaagaactc gactacgacc tactgatggc cctagattct   3660
tcatcaaaaa cgcctgagac acttgcccag gattgaaact ccctgaaggg accaccaggg   3720
gccctgagtt gttccttccc cccgtggcga gctgccagcc aggctgtacc tgtgatcgag   3780
gctggcggga aaataggctt cgtgtgctca ggtcatggga ggtgcaggac agctcatgaa   3840
acgccaacaa tcgcacaatt catgtcaagc taatcagcta tttcctcttc acgagctgta   3900
attgtcccaa aattctggtc taccgggggt gatccttcgt gtacgggccc ttccctcaac   3960
cctaggtatg cgcgcatgcg gtcgccgcgc aactcgcgcg agggccgagg gtttgggacg   4020
ggccgtcccg aaatgcagtt gcacccggat gcgtggcacc ttttttgcga taatttatgc   4080
aatggactgc tctgcaaaat tctggctctg tcgccaaccc taggatcagc ggcgtaggat   4140
```

ttcgtaatca ttcgtcctga tggggagcta ccgactaccc taatatcagc ccgactgcct 4200
gacgccagcg tccacttttg tgcacacatt ccattcgtgc ccaagacatt tcattgtggt 4260
gcgaagcgtc cccagttacg ctcacctgtt tcccgacctc cttactgttc tgtcgacaga 4320
gcgggcccac aggccggtcg cagccactag tatggccacc gcatccactt tctcggcgtt 4380
caatgcccgc tgcggcgacc tgcgtcgctc ggcgggctcc gggccccggc gcccagcgag 4440
gcccctcccc gtgcgcgggc gcgccgccac cggcgagcag ccctccggcg tggcctccct 4500
gcgcgaggcc gacaaggaga agtccctggg caaccgcctg cgcctgggct ccctgaccga 4560
ggacggcctg tcctacaagg agaagttcgt gatccgctgc tacgaggtgg gcatcaacaa 4620
gaccgccacc atcgagacca tcgccaacct gctgcaggag gtgggcggca accacgccca 4680
gggcgtgggc ttctccaccg acggcttcgc caccaccacc accatgcgca agctgcacct 4740
gatctgggtg accgcccgca tgcacatcga gatctaccgc taccccgcct ggtccgacgt 4800
gatcgagatc gagacctggg tgcagggcga gggcaaggtg ggcacccgcc gcgactggat 4860
cctgaaggac tacgccaacg gcgaggtgat cggccgcgcc acctccaagt gggtgatgat 4920
gaacgaggac acccgccgcc tgcagaaggt gtccgacgac gtgcgcgagg agtacctggt 4980
gttctgcccc cgcaccctgc gcctggcctt ccccgaggag aacaacaact ccatgaagaa 5040
gatccccaag ctggaggacc ccgccgagta ctcccgcctg ggcctggtgc cccgccgctc 5100
cgacctggac atgaacaagc acgtgaacaa cgtgacctac atcggctggg ccctggagtc 5160
catccccccc gagatcatcg acacccacga gctgcaggcc atcaccctgg actaccgccg 5220
cgagtgccag cgcgacgaca tcgtggactc cctgacctcc cgcgagcccc tgggcaacgc 5280
cgccggcgtg aagttcaagg agatcaacgg ctccgtgtcc cccaagaagg acgagcagga 5340
cctgtcccgc ttcatgcacc tgctgcgctc cgccggctcc ggcctggaga tcaaccgctg 5400
ccgcaccgag tggcgcaaga agcccgccaa gcgcatggac tacaaggacc acgacggcga 5460
ctacaaggac cacgacatcg actacaagga cgacgacgac aagtgaatcg atagatctct 5520
taaggcagca gcagctcgga tagtatcgac acactctgga cgctggtcgt gtgatggact 5580
gttgccgcca cacttgctgc cttgacctgt gaatatccct gccgctttta tcaaacagcc 5640
tcagtgtgtt tgatcttgtg tgtacgcgct tttgcgagtt gctagctgct tgtgctattt 5700
gcgaatacca cccccagcat ccccttccct cgtttcatat cgcttgcatc ccaaccgcaa 5760
cttatctacg ctgtcctgct atccctcagc gctgctcctg ctcctgctca ctgcccctcg 5820
cacagccttg gtttgggctc cgcctgtatt ctcctggtac tgcaacctgt aaaccagcac 5880
tgcaatgctg atgcacggga agtagtggga tgggaacaca aatggaaagc ttaattaaga 5940
gctcccgcca ccactccaac acggggtgcc tggacaagga cgaggtgttt gtgccgccgc 6000
accgcgcagt ggcgcacgag ggcctggagt gggaggagtg gctgcccatc cgcatgggca 6060
aggtgctggt caccctgacc ctgggctggc cgctgtacct catgttcaac gtcgcctcgc 6120
ggccgtaccc gcgcttcgcc aaccactttg acccgtggtc gcccatcttc agcaagcgcg 6180
agcgcatcga ggtggtcatc tccgacctgg cgctggtggc ggtgctcagc gggctcagcg 6240
tgctgggccg caccatgggc tgggcctggc tggtcaagac ctacgtggtg ccctacctga 6300
tcgtgaacat gtggctcgtg ctcatcacgc tgctccagca cacgcacccg gcgctgccgc 6360
actacttcga gaaggactgg gactggctgc gcggcgccat ggccaccgtg gaccgctcca 6420
tgggcccgcc cttcatggac aacatcctgc accacatctc cgacacccac gtgctgcacc 6480
acctcttcag caccatcccg cactaccacg ccgaggaggc ctccgccgcc atcaggccca 6540
tcctgggcaa gtactaccag tccgacagcc gctgggtcgg ccgcgccctg tgggaggact 6600
ggcgcgactg ccgctacgtc gtcccggacg cgcccgagga cgactccgcg ctctggttcc 6660
acaagtgagt gagtga 6676

<210> SEQ ID NO 18
<211> LENGTH: 719
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18
gggctggtct gaatccttca ggcgggtgtt acccgagaaa gaaagggtgc cgatttcaaa 60
gcagacccat gtgccgggcc ctgtggcctg tgttggcgcc tatgtagtca cccccccctca 120 cccaattgtc gccagtttgc gcactccata aactcaaaac agcagcttct gagctgcgct 180
gttcaagaac acctctgggg tttgctcacc cgcgaggtcg acgcccagca tggctatcaa 240
gacgaacagg cagcctgtgg agaagcctcc gttcacgatc gggacgctgc gcaaggccat 300
ccccgcgcac tgtttcgagc gctcggcgct tcgtagcagc atgtacctgg cctttgacat 360
cgcggtcatg tccctgctct acgtcgcgtc gacgtacatc gaccctgcac cggtgcctac 420
gtgggtcaag tacggcatca tgtggccgct ctactggttc ttccaggtgt gtttgagggt 480
tttggttgcc cgtattgagg tcctggtggc gcgcatggag gagaaggcgc ctgtcccgct 540
gacccccccg gctaccctcc cggcaccttc cagggcgcct tcggcacggg tgtctgggtg 600
tgcgcgcacg agtgcggcca ccaggccttt tcctccagcc aggccatcaa cgacggcgtg 660
ggcctggtgt tccacagcct gctgctggtg ccctactact cctggaagca ctcgcaccg 719

<210> SEQ ID NO 19
<211> LENGTH: 732
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
ccgccaccac tccaacacgg ggtgcctgga caaggacgag gtgtttgtgc cgccgcaccg 60
cgcagtggcg cacgagggcc tggagtggga ggagtggctg cccatccgca tgggcaaggt 120
gctggtcacc ctgaccctgg gctggccgct gtacctcatg ttcaacgtcg cctcgcggcc 180
gtacccgcgc ttcgccaacc actttgaccc gtggtcgccc atcttcagca agcgcgagcg 240
catcgaggtg gtcatctccg acctggcgct ggtggcggtg ctcagcgggc tcagcgtgct 300
gggccgcacc atgggctggg cctggctggt caagacctac gtggtgccct acctgatcgt 360
gaacatgtgg ctcgtgctca tcacgctgct ccagcacacg cacccggcgc tgccgcacta 420
cttcgagaag gactgggact ggctgcgcgg cgccatggcc accgtggacc gctccatggg 480
cccgcccttc atggacaaca tcctgcacca catctccgac acccacgtgc tgcaccacct 540
cttcagcacc atcccgcact accacgccga ggaggcctcc gccgccatca ggcccatcct 600
gggcaagtac taccagtccg acagccgctg ggtcggccgc gccctgtggg aggactggcg 660
cgactgccgc tacgtcgtcc cggacgcgcc cgaggacgac tccgcgctct ggttccacaa 720
gtgagtgagt ga 732

<210> SEQ ID NO 20
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gctcttcgga gtcactgtgc cactgagttc gactggtagc tgaatggagt cgctgctcca     60

ctaaacgaat tgtcagcacc gccagccggc cgaggacccg agtcatagcg agggtagtag    120

cgcgccatgg caccgaccag cctgcttgcc agtactggcg tctcttccgc ttctctgtgg    180

tcctctgcgc gctccagcgc gtgcgctttt ccggtggatc atgcggtccg tggcgcaccg    240

cagcggccgc tgcccatgca gcgccgctgc ttccgaacag tggcggtcag ggccgcaccc    300

gcggtagccg tccgtccgga acccgcccaa gagttttggg agcagcttga gccctgcaag    360

atggcggagg acaagcgcat cttcctggag gagcaccggt gcgtggaggt ccggggctga    420

ccggccgtcg cattcaacgt aatcaatcgc atgatgatca gaggacacga agtcttggtg    480

gcggtggcca gaaacactgt ccattgcaag ggcataggga tgcgttcctt cacctctcat    540

ttctcatttc tgaatccctc cctgctcact ctttctcctc ctccttcccg ttcacgcagc    600

attcggggta cc                                                        612
```

<210> SEQ ID NO 21
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gacagggtgg ttggctggat ggggaaacgc tggtcgcggg attcgatcct gctgcttata     60

tcctccctgg aagcacaccc acgactctga agaagaaaac gtgcacacac acaacccaac    120

cggccgaata tttgcttcct tatcccgggt ccaagagaga ctgcgatgcc cccctcaatc    180

agcatcctcc tccctgccgc ttcaatcttc cctgcttgcc tgcgcccgcg gtgcgccgtc    240

tgcccgccca gtcagtcact cctgcacagg ccccttgtgc gcagtgctcc tgtacccttt    300

accgctcctt ccattctgcg aggcccccta ttgaatgtat tcgttgcctg tgtggccaag    360

cgggctgctg ggcgcgccgc cgtcgggcag tgctcggcga ctttggcgga agccgattgt    420

tcttctgtaa gccacgcgct tgctgctttg ggaagagaag gggggggta ctgaatggat     480

gaggaggaga aggaggggta ttggtattat ctgagttggg tgaagagc                 528
```

<210> SEQ ID NO 22
<211> LENGTH: 1174
<212> TYPE: DNA
<213> ORGANISM: Chlorella protothecoides

<400> SEQUENCE: 22

```
agtttaggtc cagcgtccgt gggggggac gggctgggag cttgggccgg gaagggcaag      60

acgatgcagt ccctctgggg agtcacagcc gactgtgtgt gttgcactgt gcggcccgca    120

gcactcacac gcaaaatgcc tggccgacag gcaggccctg tccagtgcaa catccacggt    180

ccctctcatc aggctcacct tgctcattga cataacggaa tgcgtaccgc tctttcagat    240

ctgtccatcc agagagggga gcaggctccc caccgacgct gtcaaacttg cttcctgccc    300
```

```
aaccgaaaac attattgttt gaggggggggg ggggggggggc agattgcatg gcgggatatc    360

tcgtgaggaa catcactggg acactgtgga acacagtgag tgcagtatgc agagcatgta    420

tgctaggggt cagcgcagga agggggcctt tcccagtctc ccatgccact gcaccgtatc    480

cacgactcac caggaccagc ttcttgatcg gcttccgctc ccgtggacac cagtgtgtag    540

cctctggact ccaggtatgc gtgcaccgca aaggccagcc gatcgtgccg attcctgggg    600

tggaggatat gagtcagcca acttggggct cagagtgcac actggggcac gatacgaaac    660

aacatctaca ccgtgtcctc catgctgaca caccacagct tcgctccacc tgaatgtggg    720

cgcatgggcc cgaatcacag ccaatgtcgc tgctgccata atgtgatcca gaccctctcc    780

gcccagatgc cgagcggatc gtgggcgctg aatagattcc tgtttcgatc actgtttggg    840

tcctttcctt ttcgtctcgg atgcgcgtct cgaaacaggc tgcgtcgggc tttcggatcc    900

cttttgctcc ctccgtcacc atcctgcgcg cgggcaagtt gcttgaccct gggctgtacc    960

agggttggag ggtattaccg cgtcaggcca ttcccagccc ggattcaatt caaagtctgg   1020

gccaccaccc tccgccgctc tgtctgatca ctccacattc gtgcatacac tacgttcaag   1080

tcctgatcca ggcgtgtctc gggacaaggt gtgcttgagt ttgaatctca aggacccact   1140

ccagcacagc tgctggttga ccccgccctc gcaa                               1174
```

<210> SEQ ID NO 23
<211> LENGTH: 3529
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23

```
agtttaggtc cagcgtccgt gggggggggac gggctgggag cttgggccgg gaagggcaag     60

acgatgcagt ccctctgggg agtcacagcc gactgtgtgt gttgcactgt gcggcccgca    120

gcactcacac gcaaaatgcc tggccgacag gcaggccctg tccagtgcaa catccacggt    180

ccctctcatc aggctcacct tgctcattga cataacggaa tgcgtaccgc tctttcagat    240

ctgtccatcc agagagggga gcaggctccc caccgacgct gtcaaacttg cttcctgccc    300

aaccgaaaac attattgttt gaggggggggg ggggggggggc agattgcatg gcgggatatc    360

tcgtgaggaa catcactggg acactgtgga acacagtgag tgcagtatgc agagcatgta    420

tgctaggggt cagcgcagga agggggcctt tcccagtctc ccatgccact gcaccgtatc    480

cacgactcac caggaccagc ttcttgatcg gcttccgctc ccgtggacac cagtgtgtag    540

cctctggact ccaggtatgc gtgcaccgca aaggccagcc gatcgtgccg attcctgggg    600

tggaggatat gagtcagcca acttggggct cagagtgcac actggggcac gatacgaaac    660

aacatctaca ccgtgtcctc catgctgaca caccacagct tcgctccacc tgaatgtggg    720

cgcatgggcc cgaatcacag ccaatgtcgc tgctgccata atgtgatcca gaccctctcc    780

gcccagatgc cgagcggatc gtgggcgctg aatagattcc tgtttcgatc actgtttggg    840

tcctttcctt ttcgtctcgg atgcgcgtct cgaaacaggc tgcgtcgggc tttcggatcc    900

cttttgctcc ctccgtcacc atcctgcgcg cgggcaagtt gcttgaccct gggctgtacc    960

agggttggag ggtattaccg cgtcaggcca ttcccagccc ggattcaatt caaagtctgg   1020

gccaccaccc tccgccgctc tgtctgatca ctccacattc gtgcatacac tacgttcaag   1080

tcctgatcca ggcgtgtctc gggacaaggt gtgcttgagt ttgaatctca aggacccact   1140
```

-continued

```
ccagcacagc tgctggttga ccccgccctc gcaatctaga atggccgcgt ccgtccactg   1200
caccctgatg tccgtggtct gcaacaacaa gaaccactcc gcccgcccca agctgcccaa   1260
ctcctccctg ctgcccggct tcgacgtggt ggtccaggcc gcggccaccc gcttcaagaa   1320
ggagacgacg accacccgcg ccacgctgac gttcgacccc cccacgacca actccgagcg   1380
cgccaagcag cgcaagcaca ccatcgaccc ctcctccccc gacttccagc ccatcccctc   1440
cttcgaggag tgcttcccca agtccacgaa ggagcacaag gaggtggtgc acgaggagtc   1500
cggccacgtc ctgaaggtgc ccttccgccg cgtgcacctg tccggcggcg agcccgcctt   1560
cgacaactac gacacgtccg gcccccagaa cgtcaacgcc cacatcggcc tggcgaagct   1620
gcgcaaggag tggatcgacc gccgcgagaa gctgggcacg ccccgctaca cgcagatgta   1680
ctacgcgaag cagggcatca tcacggagga gatgctgtac tgcgcgacgc gcgagaagct   1740
ggaccccgag ttcgtccgct ccgaggtcgc gcggggccgc gccatcatcc cctccaacaa   1800
gaagcacctg gagctggagc ccatgatcgt gggccgcaag ttcctggtga aggtgaacgc   1860
gaacatcggc aactccgccg tggcctcctc catcgaggag gaggtctaca aggtgcagtg   1920
ggccaccatg tggggcgccg acaccatcat ggacctgtcc acgggccgcc acatccacga   1980
gacgcgcgag tggatcctgc gcaactccgc ggtccccgtg ggcaccgtcc ccatctacca   2040
ggcgctggag aaggtggacg gcatcgcgga gaacctgaac tgggaggtgt tccgcgagac   2100
gctgatcgag caggccgagc agggcgtgga ctacttcacg atccacgcgg gcgtgctgct   2160
gcgctacatc cccctgaccg ccaagcgcct gacgggcatc gtgtcccgcg gcggctccat   2220
ccacgcgaag tggtgcctgg cctaccacaa ggagaacttc gcctacgagc actgggacga   2280
catcctggac atctgcaacc agtacgacgt cgccctgtcc atcggcgacg gcctgcgccc   2340
cggctccatc tacgacgcca acgacacggc ccagttcgcc gagctgctga cccagggcga   2400
gctgacgcgc cgcgcgtggg agaaggacgt gcaggtgatg aacgagggcc ccggccacgt   2460
gcccatgcac aagatccccg agaacatgca gaagcagctg gagtggtgca acgaggcgcc   2520
cttctacacc ctgggccccc tgacgaccga catcgcgccc ggctacgacc acatcacctc   2580
cgccatcggc gcggccaaca tcggcgccct gggcaccgcc ctgctgtgct acgtgacgcc   2640
caaggagcac ctgggcctgc ccaaccgcga cgacgtgaag gcgggcgtca tcgcctacaa   2700
gatcgccgcc cacgcggccg acctggccaa gcagcacccc cacgcccagg cgtgggacga   2760
cgcgctgtcc aaggcgcgct tcgagttccg ctggatggac cagttcgcgc tgtccctgga   2820
ccccatgacg gcgatgtcct tccacgacga gacgctgccc gcggacggcg cgaaggtcgc   2880
ccacttctgc tccatgtgcg gccccaagtt ctgctccatg aagatcacgg aggacatccg   2940
caagtacgcc gaggagaacg gctacggctc cgccgaggag gccatccgcc agggcatgga   3000
cgccatgtcc gaggagttca acatcgccaa gaagacgatc tccggcgagc agcacggcga   3060
ggtcggcggc gagatctacc tgcccgagtc ctacgtcaag gccgcgcaga agtgacaatt   3120
ggcagcagca gctcggatag tatcgacaca ctctggacgc tggtcgtgtg atggactgtt   3180
gccgccacac ttgctgcctt gacctgtgaa tatccctgcc gcttttatca aacagcctca   3240
gtgtgtttga tcttgtgtgt acgcgctttt gcgagttgct agctgcttgt gctatttgcg   3300
aataccaccc ccagcatccc cttccctcgt ttcatatcgc ttgcatccca accgcaactt   3360
atctacgctg tcctgctatc cctcagcgct gctcctgctc ctgctcactg cccctcgcac   3420
agccttggtt tgggctccgc ctgtattctc ctggtactgc aacctgtaaa ccagcactgc   3480
```

aatgctgatg cacgggaagt agtgggatgg gaacacaaat ggaggatcc 3529

<210> SEQ ID NO 24
<211> LENGTH: 1476
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
atggccaccg catccacttt ctcggcgttc aatgcccgct gcggcgacct gcgtcgctcg 60
gcgggctccg ggccccggcg cccagcgagg cccctccccg tgcgcgggcg cgccgccgcc 120
gccgccgacg ccaaccccgc ccgccccgag cgccgcgtgg tgatcaccgg ccagggcgtg 180
gtgacctccc tgggccagac catcgagcag ttctactcct ccctgctgga gggcgtgtcc 240
ggcatctccc agatccagaa gttcgacacc accggctaca ccaccaccat cgccggcgag 300
atcaagtccc tgcagctgga cccctacgtg cccaagcgct gggccaagcg cgtggacgac 360
gtgatcaagt acgtgtacat cgccggcaag caggccctgg agtccgccgg cctgcccatc 420
gaggccgccg gcctggccgg cgccggcctg gaccccgccc tgtgcggcgt gctgatcggc 480
accgccatgg ccggcatgac ctccttcgcc gccggcgtgg aggccctgac ccgcggcggc 540
gtgcgcaaga tgaacccctt ctgcatcccc ttctccatct ccaacatggg cggcgccatg 600
ctggccatgg acatcggctt catgggcccc aactactcca tctccaccgc ctgcgccacc 660
ggcaactact gcatcctggg cgccgccgac cacatccgcc gcggcgacgc caacgtgatg 720
ctggccggcg gcgccgacgc cgccatcatc ccctccggca tcggcggctt catcgcctgc 780
aaggccctgt ccaagcgcaa cgacgagccc gagcgcgcct cccgcccctg ggacgccgac 840
cgcgacggct tcgtgatggg cgagggcgcc ggcgtgctgg tgctggagga gctggagcac 900
gccaagcgcc gcggcgccac catcctggcc gagctggtgg gcggcgccgc cacctccgac 960
gcccaccaca tgaccgagcc cgacccccag ggccgcggcg tgcgcctgtg cctggagcgc 1020
gccctggagc gcgcccgcct ggcccccgag cgcgtgggct acgtgaacgc ccacggcacc 1080
tccacccccg ccggcgacgt ggccgagtac cgcgccatcc gcgccgtgat cccccaggac 1140
tccctgcgca tcaactccac caagtccatg atcggccacc tgctgggcgg cgccggcgcc 1200
gtggaggccg tggccgccat ccaggccctg cgcaccggct ggctgcaccc caacctgaac 1260
ctggagaacc ccgcccccgg cgtggacccc gtggtgctgg tgggcccccg caaggagcgc 1320
gccgaggacc tggacgtggt gctgtccaac tccttcggct tcggcggcca caactcctgc 1380
gtgatcttcc gcaagtacga cgagatggac tacaaggacc acgacggcga ctacaaggac 1440
cacgacatcg actacaagga cgacgacgac aagtga 1476

<210> SEQ ID NO 25
<211> LENGTH: 491
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

-continued

```
Pro Val Arg Gly Arg Ala Ala Ala Ala Ala Asp Ala Asn Pro Ala Arg
        35                  40                  45

Pro Glu Arg Arg Val Val Ile Thr Gly Gln Gly Val Val Thr Ser Leu
    50                  55                  60

Gly Gln Thr Ile Glu Gln Phe Tyr Ser Ser Leu Leu Glu Gly Val Ser
65                  70                  75                  80

Gly Ile Ser Gln Ile Gln Lys Phe Asp Thr Thr Gly Tyr Thr Thr Thr
                85                  90                  95

Ile Ala Gly Glu Ile Lys Ser Leu Gln Leu Asp Pro Tyr Val Pro Lys
            100                 105                 110

Arg Trp Ala Lys Arg Val Asp Asp Val Ile Lys Tyr Val Tyr Ile Ala
        115                 120                 125

Gly Lys Gln Ala Leu Glu Ser Ala Gly Leu Pro Ile Glu Ala Ala Gly
    130                 135                 140

Leu Ala Gly Ala Gly Leu Asp Pro Ala Leu Cys Gly Val Leu Ile Gly
145                 150                 155                 160

Thr Ala Met Ala Gly Met Thr Ser Phe Ala Ala Gly Val Glu Ala Leu
                165                 170                 175

Thr Arg Gly Gly Val Arg Lys Met Asn Pro Phe Cys Ile Pro Phe Ser
            180                 185                 190

Ile Ser Asn Met Gly Gly Ala Met Leu Ala Met Asp Ile Gly Phe Met
        195                 200                 205

Gly Pro Asn Tyr Ser Ile Ser Thr Ala Cys Ala Thr Gly Asn Tyr Cys
    210                 215                 220

Ile Leu Gly Ala Ala Asp His Ile Arg Arg Gly Asp Ala Asn Val Met
225                 230                 235                 240

Leu Ala Gly Gly Ala Asp Ala Ala Ile Ile Pro Ser Gly Ile Gly Gly
                245                 250                 255

Phe Ile Ala Cys Lys Ala Leu Ser Lys Arg Asn Asp Glu Pro Glu Arg
            260                 265                 270

Ala Ser Arg Pro Trp Asp Ala Asp Arg Asp Gly Phe Val Met Gly Glu
        275                 280                 285

Gly Ala Gly Val Leu Val Leu Glu Glu Leu Glu His Ala Lys Arg Arg
    290                 295                 300

Gly Ala Thr Ile Leu Ala Glu Leu Val Gly Gly Ala Ala Thr Ser Asp
305                 310                 315                 320

Ala His His Met Thr Glu Pro Asp Pro Gln Gly Arg Gly Val Arg Leu
                325                 330                 335

Cys Leu Glu Arg Ala Leu Glu Arg Ala Arg Leu Ala Pro Glu Arg Val
            340                 345                 350

Gly Tyr Val Asn Ala His Gly Thr Ser Thr Pro Ala Gly Asp Val Ala
        355                 360                 365

Glu Tyr Arg Ala Ile Arg Ala Val Ile Pro Gln Asp Ser Leu Arg Ile
    370                 375                 380

Asn Ser Thr Lys Ser Met Ile Gly His Leu Leu Gly Gly Ala Gly Ala
385                 390                 395                 400

Val Glu Ala Val Ala Ala Ile Gln Ala Leu Arg Thr Gly Trp Leu His
                405                 410                 415

Pro Asn Leu Asn Leu Glu Asn Pro Ala Pro Gly Val Asp Pro Val Val
            420                 425                 430

Leu Val Gly Pro Arg Lys Glu Arg Ala Glu Asp Leu Asp Val Val Leu
        435                 440                 445
```

-continued

```
Ser Asn Ser Phe Gly Phe Gly Gly His Asn Ser Cys Val Ile Phe Arg
    450                 455                 460

Lys Tyr Asp Glu Met Asp Tyr Lys Asp His Asp Gly Asp Tyr Lys Asp
465                 470                 475                 480

His Asp Ile Asp Tyr Lys Asp Asp Asp Asp Lys
                485                 490
```

<210> SEQ ID NO 26
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atggccatca agaccaaccg ccagcccgtg gagaagcccc ccttcaccat cggcaccctg     60

cgcaaggcca tccccgccca ctgcttcgag cgctccgccc tgcgctcctc catgtacctg    120

gccttcgaca tcgccgtgat gtccctgctg tacgtggcct ccacctacat cgaccccgcc    180

cccgtgccca cctgggtgaa gtacggcgtg atgtggcccc tgtactggtt cttccagggc    240

gccttcggca ccggcgtgtg ggtgtgcgcc cacgagtgcg gccaccaggc cttctcctcc    300

tcccaggcca tcaacgacgg cgtgggcctg gtgttccact ccctgctgct ggtgccctac    360

tactcctgga agcactccca ccgccgccac cactccaaca ccggctgcct ggacaaggac    420

gaggtgttcg tgccccccca ccgcgccgtg gcccacgagg gcctggagtg ggaggagtgg    480

ctgcccatcc gcatgggcaa ggtgctggtg accctgaccc tgggctggcc cctgtacctg    540

atgttcaacg tggcctcccg cccctacccc cgcttcgcca accacttcga cccctggtcc    600

cccatcttct ccaagcgcga gcgcatcgag gtggtgatct ccgacctggc cctggtggcc    660

gtgctgtccg gcctgtccgt gctgggccgc accatgggct gggcctggct ggtgaagacc    720

tacgtggtgc cctacctgat cgtgaacatg tggctggtgc tgatcaccct gctgcagcac    780

acccaccccg ccctgcccca ctacttcgag aaggactggg actggctgcg cggcgccatg    840

gccaccgtgg accgctccat gggccccccc ttcatggaca acatcctgca ccacatctcc    900

gacacccacg tgctgcacca cctgttctcc accatccccc actaccacgc cgaggaggcc    960

tccgccgcca tccgccccat cctgggcaag tactaccagt ccgactcccg ctgggtgggc   1020

cgcgccctgt gggaggactg gcgcgactgc cgctacgtgg tgcccgacgc ccccgaggac   1080

gactccgccc tgtggttcca caagtag                                       1107
```

<210> SEQ ID NO 27
<211> LENGTH: 368
<212> TYPE: PRT
<213> ORGANISM: Prototheca moriformis

<400> SEQUENCE: 27

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Ser Ser Met Tyr Leu Ala Phe Asp Ile Ala Val Met Ser
        35                  40                  45

Leu Leu Tyr Val Ala Ser Thr Tyr Ile Asp Pro Ala Pro Val Pro Thr
    50                  55                  60

Trp Val Lys Tyr Gly Val Met Trp Pro Leu Tyr Trp Phe Phe Gln Gly
```

65 70 75 80

Ala Phe Gly Thr Gly Val Trp Val Cys Ala His Glu Cys Gly His Gln
85 90 95

Ala Phe Ser Ser Ser Gln Ala Ile Asn Asp Gly Val Gly Leu Val Phe
100 105 110

His Ser Leu Leu Leu Val Pro Tyr Tyr Ser Trp Lys His Ser His Arg
115 120 125

Arg His His Ser Asn Thr Gly Cys Leu Asp Lys Asp Glu Val Phe Val
130 135 140

Pro Pro His Arg Ala Val Ala His Glu Gly Leu Glu Trp Glu Glu Trp
145 150 155 160

Leu Pro Ile Arg Met Gly Lys Val Leu Val Thr Leu Thr Leu Gly Trp
165 170 175

Pro Leu Tyr Leu Met Phe Asn Val Ala Ser Arg Pro Tyr Pro Arg Phe
180 185 190

Ala Asn His Phe Asp Pro Trp Ser Pro Ile Phe Ser Lys Arg Glu Arg
195 200 205

Ile Glu Val Val Ile Ser Asp Leu Ala Leu Val Ala Val Leu Ser Gly
210 215 220

Leu Ser Val Leu Gly Arg Thr Met Gly Trp Ala Trp Leu Val Lys Thr
225 230 235 240

Tyr Val Val Pro Tyr Leu Ile Val Asn Met Trp Leu Val Leu Ile Thr
245 250 255

Leu Leu Gln His Thr His Pro Ala Leu Pro His Tyr Phe Glu Lys Asp
260 265 270

Trp Asp Trp Leu Arg Gly Ala Met Ala Thr Val Asp Arg Ser Met Gly
275 280 285

Pro Pro Phe Met Asp Asn Ile Leu His His Ile Ser Asp Thr His Val
290 295 300

Leu His His Leu Phe Ser Thr Ile Pro His Tyr His Ala Glu Glu Ala
305 310 315 320

Ser Ala Ala Ile Arg Pro Ile Leu Gly Lys Tyr Tyr Gln Ser Asp Ser
325 330 335

Arg Trp Val Gly Arg Ala Leu Trp Glu Asp Trp Arg Asp Cys Arg Tyr
340 345 350

Val Val Pro Asp Ala Pro Glu Asp Asp Ser Ala Leu Trp Phe His Lys
355 360 365

<210> SEQ ID NO 28
<211> LENGTH: 1191
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
actagtatgc tgaagctgtc ctgcaacgtg accaacaacc tgcacacctt ctccttcttc 60
tccgactcct ccctgttcat ccccgtgaac cgccgcacca tcgccgtgtc ctccgggcgc 120
gcctcccagc tgcgcaagcc cgccctggac cccctgcgcg ccgtgatctc cgccgaccag 180
ggctccatct cccccgtgaa ctcctgcacc cccgccgacc gcctgcgcgc cggccgcctg 240
atggaggacg gctactccta caaggagaag ttcatcgtgc gctcctacga ggtgggcatc 300
aacaagaccg ccaccgtgga gaccatcgcc aacctgctgc aggaggtggc ctgcaaccac 360

```
gtgcagaagt gcggcttctc caccgacggc ttcgccacca ccctgaccat gcgcaagctg    420

cacctgatct gggtgaccgc ccgcatgcac atcgagatct acaagtaccc cgcctggtcc    480

gacgtggtgg agatcgagac ctggtgccag tccgagggcc gcatcggcac ccgccgcgac    540

tggatcctgc gcgactccgc caccaacgag gtgatcggcc gcgccacctc caagtgggtg    600

atgatgaacc aggacacccg ccgcctgcag cgcgtgaccg acgaggtgcg cgacgagtac    660

ctggtgttct gccccccgcga gccccgcctg gccttccccg aggagaacaa ctcctccctg    720

aagaagatcc ccaagctgga ggaccccgcc cagtactcca tgctggagct gaagccccgc    780

cgcgccgacc tggacatgaa ccagcacgtg aacaacgtga cctacatcgg ctgggtgctg    840

gagtccatcc cccaggagat catcgacacc cacgagctgc aggtgatcac cctggactac    900

cgccgcgagt gccagcagga cgacatcgtg gactccctga ccacctccga gatccccgac    960

gaccccatct ccaagttcac cggcaccaac ggctccgcca tgtcctccat ccagggccac   1020

aacgagtccc agttcctgca catgctgcgc ctgtccgaga acggccagga gatcaaccgc   1080

ggccgcaccc agtggcgcaa gaagtcctcc cgcatggact acaaggacca cgacggcgac   1140

tacaaggacc acgacatcga ctacaaggac gacgacgaca agtgaatcga t            1191
```

<210> SEQ ID NO 29
<211> LENGTH: 366
<212> TYPE: PRT
<213> ORGANISM: Brassica napus

<400> SEQUENCE: 29

```
Met Leu Lys Leu Ser Cys Asn Val Thr Asn Asn Leu His Thr Phe Ser
1               5                   10                  15

Phe Phe Ser Asp Ser Ser Leu Phe Ile Pro Val Asn Arg Arg Thr Ile
            20                  25                  30

Ala Val Ser Ser Ser Gln Leu Arg Lys Pro Ala Leu Asp Pro Leu Arg
        35                  40                  45

Ala Val Ile Ser Ala Asp Gln Gly Ser Ile Ser Pro Val Asn Ser Cys
    50                  55                  60

Thr Pro Ala Asp Arg Leu Arg Ala Gly Arg Leu Met Glu Asp Gly Tyr
65                  70                  75                  80

Ser Tyr Lys Glu Lys Phe Ile Val Arg Ser Tyr Glu Val Gly Ile Asn
                85                  90                  95

Lys Thr Ala Thr Val Glu Thr Ile Ala Asn Leu Leu Gln Glu Val Ala
            100                 105                 110

Cys Asn His Val Gln Lys Cys Gly Phe Ser Thr Asp Gly Phe Ala Thr
        115                 120                 125

Thr Leu Thr Met Arg Lys Leu His Leu Ile Trp Val Thr Ala Arg Met
    130                 135                 140

His Ile Glu Ile Tyr Lys Tyr Pro Ala Trp Ser Asp Val Val Glu Ile
145                 150                 155                 160

Glu Thr Trp Cys Gln Ser Glu Gly Arg Ile Gly Thr Arg Arg Asp Trp
                165                 170                 175

Ile Leu Arg Asp Ser Ala Thr Asn Glu Val Ile Gly Arg Ala Thr Ser
            180                 185                 190

Lys Trp Val Met Met Asn Gln Asp Thr Arg Arg Leu Gln Arg Val Thr
        195                 200                 205

Asp Glu Val Arg Asp Glu Tyr Leu Val Phe Cys Pro Arg Glu Pro Arg
    210                 215                 220

Leu Ala Phe Pro Glu Glu Asn Asn Ser Ser Leu Lys Lys Ile Pro Lys
```

```
225                 230                 235                 240

Leu Glu Asp Pro Ala Gln Tyr Ser Met Leu Glu Leu Lys Pro Arg Arg
                245                 250                 255

Ala Asp Leu Asp Met Asn Gln His Val Asn Asn Val Thr Tyr Ile Gly
            260                 265                 270

Trp Val Leu Glu Ser Ile Pro Gln Glu Ile Ile Asp Thr His Glu Leu
        275                 280                 285

Gln Val Ile Thr Leu Asp Tyr Arg Arg Glu Cys Gln Gln Asp Asp Ile
    290                 295                 300

Val Asp Ser Leu Thr Thr Ser Glu Ile Pro Asp Asp Pro Ile Ser Lys
305                 310                 315                 320

Phe Thr Gly Thr Asn Gly Ser Ala Met Ser Ser Ile Gln Gly His Asn
                325                 330                 335

Glu Ser Gln Phe Leu His Met Leu Arg Leu Ser Glu Asn Gly Gln Glu
            340                 345                 350

Ile Asn Arg Gly Arg Thr Gln Trp Arg Lys Lys Ser Ser Arg
        355                 360                 365


<210> SEQ ID NO 30
<211> LENGTH: 599
<212> TYPE: DNA
<213> ORGANISM: Prototheca moriformis

<400> SEQUENCE: 30

ggagtcactg tgccactgag ttcgactggt agctgaatgg agtcgctgct ccactaaacg     60

aattgtcagc accgccagcc ggccgaggac ccgagtcata gcgagggtag tagcgcgcca    120

tggcaccgac cagcctgctt gccagtactg gcgtctcttc cgcttctctg tggtcctctg    180

cgcgctccag cgcgtgcgct tttccggtgg atcatgcggt ccgtggcgca ccgcagcggc    240

cgctgcccat gcagcgccgc tgcttccgaa cagtggcggt cagggccgca cccgcggtag    300

ccgtccgtcc ggaacccgcc caagagtttt gggagcagct tgagccctgc aagatggcgg    360

aggacaagcg catcttcctg gaggagcacc ggtgcgtgga ggtccggggc tgaccggccg    420

tcgcattcaa cgtaatcaat cgcatgatga tcagaggaca cgaagtcttg gtggcggtgg    480

ccagaaacac tgtccattgc aagggcatag ggatgcgttc cttcacctct catttctcat    540

ttctgaatcc ctccctgctc actctttctc ctcctccttc ccgttcacgc agcattcgg     599


<210> SEQ ID NO 31
<211> LENGTH: 521
<212> TYPE: DNA
<213> ORGANISM: Prototheca moriformis

<400> SEQUENCE: 31

gacagggtgg ttggctggat ggggaaacgc tggtcgcggg attcgatcct gctgcttata     60

tcctccctgg aagcacaccc acgactctga agaagaaaac gtgcacacac acaacccaac    120

cggccgaata tttgcttcct tatcccgggt ccaagagaga ctgcgatgcc cccctcaatc    180

agcatcctcc tccctgccgc ttcaatcttc cctgcttgcc tgcgcccgcg gtgcgccgtc    240

tgcccgccca gtcagtcact cctgcacagg ccccttgtgc gcagtgctcc tgtacccttt    300

accgctcctt ccattctgcg aggcccccta ttgaatgtat tcgttgcctg tgtggccaag    360

cgggctgctg ggcgcgccgc cgtcgggcag tgctcggcga ctttggcgga agccgattgt    420

tcttctgtaa gccacgcgct tgctgctttg ggaagagaag gggggggta ctgaatggat    480

gaggaggaga aggaggggta ttggtattat ctgagttggg t                        521
```

<210> SEQ ID NO 32
<211> LENGTH: 563
<212> TYPE: DNA
<213> ORGANISM: Prototheca moriformis

<400> SEQUENCE: 32
aatggagtcg ctgctccact aatcgaattg tcagcaccgc cagccggccg aggacccgag 60
tcatagcgag ggtagtagcg cgccatggca ccgaccagcc tgcttgcccg tactggcgtc 120
tcttccgctt ctctgtgctc ctctacgcgc tccggcgcgt gcgcttttcc ggtggatcat 180
gcggtccgtg gcgcaccgca gcggccgctg cccatgcagc gccgctgctt ccgaacagtg 240
gctgtcaggg ccgcacccgc agtagccgtc cgtccggaac ccgcccaaga gttttgggag 300
cagcttgagc cctgcaagat ggcggaggac aagcgcatct tcctggagga gcaccggtgc 360
gcggaggtcc ggggctgacc ggccgtcgca ttcaacgtaa tcaatcgcat gatgatcaca 420
ggacgcgacg tcttggtggc ggtggccagg gacactgccc attgcacagg cataggaatg 480
cgttccttct catttctcag ttttctgagc ccctccctct tcactctttc tcctcctcct 540
cccctctcac gcagcattcg tgg 563

<210> SEQ ID NO 33
<211> LENGTH: 547
<212> TYPE: DNA
<213> ORGANISM: Prototheca moriformis

<400> SEQUENCE: 33
cactagtatc gatttcgaac agaggagagg gtggctggta gttgcgggat ggctggtcgc 60
ccgtcgatcc tgctgctgct attgtctcct cctgcacaag cccacccacg actccgaaga 120
agaagaagaa aacgcgcaca cacacaaccc aaccggccga atatttgctt ccttatcccg 180
ggtccaagag agacggcgat gcccccctca atcagcctcc tcctccctgc cgctccaatc 240
ttccctgctt gcatgcgccc gcgagaggct gtctgcgcgc cccgtcagtc actccccgtg 300
cagacgcctc gtgctcggtg ctcctgtatc ctttaccgct cctttcattc tgcgaggccc 360
cctgttgaat gtattcgttg cctgtgtggc caagcgcgct gctgggcgcg ccgccgtcgg 420
gcggtgctcg gcgactctgg cggaagccgg ttgttcttct gtaagccacg cgcttgctgc 480
ttttggaaaa gagggggggtt tactgaatgg aggaggagca ggataattgg tagtatctga 540
gttgttg 547

<210> SEQ ID NO 34
<211> LENGTH: 615
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34
actagtgcgc tggacgcggc agtgggtggc cgaggagaac cggcacggcg acctgctgaa 60
caagtactgt tggctgacgg ggcgcgtcaa catgcgggcc gtggaggtga ccatcaacaa 120
cctgatcaag agcggcatga acccgcagac ggacaacaac ccttacttgg gcttcgtcta 180
cacctccttc caggagcgcg cgaccaagta cagccacggc aacaccgcgc gccttgcggc 240
cgagcagtgt gtttgagggt tttggttgcc cgtatcgagg tcctggtggc gcgcatgggg 300
gagaaggcgc ctgtcccgct gacccccccg gctaccctcc cggcaccttc cagggcgcgt 360

-continued

```
acgggatcct gctcggccgc aaggcgcgcg gtgttgccgt ggctgtactt ggtcgcgcgc    420

tcctggaagg aggtgtagac gaagcccaag taagggttgt tgtccgtctg cgggttcatg    480

ccgctcttga tcaggttgtt gatggtcacc tccacggccc gcatgttgac gcgccccgtc    540

agccaacagt acttgttcag caggtcgccg tgccggttct cctcggccac ccactgccgc    600

gtccagcgca agctt                                                     615


<210> SEQ ID NO 35
<211> LENGTH: 452
<212> TYPE: PRT
<213> ORGANISM: Prototheca moriformis

<400> SEQUENCE: 35

Met Ser Ile Gln Phe Ala Leu Arg Ala Ala Tyr Ile Lys Gly Thr Cys
1               5                   10                  15

Gln Arg Leu Ser Gly Arg Gly Ala Ala Leu Gly Leu Ser Arg Asp Trp
            20                  25                  30

Thr Pro Gly Trp Thr Leu Pro Arg Cys Trp Pro Ala Ser Ala Ala Ala
        35                  40                  45

Thr Ala Pro Pro Arg Ala Arg His Gln Glu Arg Ala Ile His Leu Thr
    50                  55                  60

Ser Gly Arg Arg Arg His Ser Ala Leu Ala Ser Asp Ala Asp Glu Arg
65                  70                  75                  80

Ala Leu Pro Ser Asn Ala Pro Gly Leu Val Met Ala Ser Gln Ala Asn
                85                  90                  95

Tyr Phe Arg Val Arg Leu Leu Pro Glu Gln Glu Glu Gly Glu Leu Glu
            100                 105                 110

Ser Trp Ser Pro Asn Val Arg His Thr Thr Leu Leu Cys Lys Pro Arg
        115                 120                 125

Ala Met Leu Ser Lys Leu Gln Met Arg Val Met Val Gly Asp Arg Val
    130                 135                 140

Ile Val Thr Ala Ile Asp Pro Val Asn Met Thr Val His Ala Pro Pro
145                 150                 155                 160

Phe Asp Pro Leu Pro Ala Thr Arg Phe Leu Val Ala Gly Glu Ala Ala
                165                 170                 175

Asp Met Asp Ile Thr Val Val Leu Asn Lys Ala Asp Leu Val Pro Glu
            180                 185                 190

Glu Glu Ser Ala Ala Leu Ala Gln Glu Val Ala Ser Trp Gly Pro Val
        195                 200                 205

Val Leu Thr Ser Thr Leu Thr Gly Arg Gly Leu Gln Glu Leu Glu Arg
    210                 215                 220

Gln Leu Gly Ser Thr Thr Ala Val Leu Ala Gly Pro Ser Gly Ala Gly
225                 230                 235                 240

Lys Ser Ser Ile Ile Asn Ala Leu Ala Arg Ala Ala Arg Glu Arg Pro
                245                 250                 255

Ser Asp Ala Ser Val Ser Asn Val Pro Glu Glu Gln Val Val Gly Glu
            260                 265                 270

Asp Gly Arg Ala Leu Ala Asn Pro Pro Pro Phe Thr Leu Ala Asp Ile
        275                 280                 285

Arg Asn Ala Ile Pro Lys Asp Cys Phe Arg Lys Ser Ala Ala Lys Ser
    290                 295                 300

Leu Ala Tyr Leu Gly Asp Leu Ser Ile Thr Gly Met Ala Val Leu Ala
305                 310                 315                 320
```

```
Tyr Lys Ile Asn Ser Pro Trp Leu Trp Pro Leu Tyr Trp Phe Ala Gln
                325                 330                 335

Gly Thr Met Phe Trp Ala Leu Phe Val Val Gly His Asp Cys Gly His
            340                 345                 350

Gln Ser Phe Ser Thr Ser Lys Arg Leu Asn Asp Ala Leu Ala Trp Leu
        355                 360                 365

Gly Ala Leu Ala Ala Gly Thr Trp Thr Trp Ala Leu Gly Val Leu Pro
    370                 375                 380

Met Leu Asn Leu Tyr Leu Ala Pro Tyr Val Trp Leu Leu Val Thr Tyr
385                 390                 395                 400

Leu His His His Gly Pro Ser Asp Pro Arg Glu Glu Met Pro Trp Tyr
                405                 410                 415

Arg Gly Arg Glu Trp Ser Tyr Met Arg Gly Gly Leu Thr Thr Ile Asp
            420                 425                 430

Arg Asp Tyr Gly Leu Phe Asn Lys Val His His Asp Ile Gly Thr His
        435                 440                 445

Val Val His His
    450


<210> SEQ ID NO 36
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Phe Trp Ala Leu Phe Val Val Gly His Asp Cys Gly His Gln Ser
1               5                   10                  15

Phe Ser Thr Ser Lys Arg Leu Asn Asp Ala Val Gly Leu Phe Val His
            20                  25                  30

Ser Ile Ile Gly Val Pro Tyr His Gly Trp Arg Ile Ser His Arg Thr
        35                  40                  45

His His Asn Asn His Gly His Val Glu Asn Asp Glu Ser Trp Tyr Pro
    50                  55                  60

Pro Thr Glu Ser Gly Leu Lys Ala Met Thr Asp Met Gly Arg Gln Gly
65                  70                  75                  80

Arg Phe His Phe Pro Ser Met Leu Phe Val Tyr Pro Phe Tyr Leu Phe
                85                  90                  95

Trp Arg Ser Pro Gly Lys Thr Gly Ser His Phe Ser Pro Ala Thr Asp
            100                 105                 110

Leu Phe Ala Leu Trp Glu Ala Pro Leu Ile Arg Thr Ser Asn Ala Cys
        115                 120                 125

Gln Leu Ala Trp Leu Gly Ala Leu Ala Ala Gly Thr Trp Ala Leu Gly
    130                 135                 140

Val Leu Pro Met Leu Asn Leu Tyr Leu Ala Pro Tyr Val Ile Ser Val
145                 150                 155                 160

Ala Trp Leu Asp Leu Val Thr Tyr Leu His His His Gly Pro Ser Asp
                165                 170                 175

Pro Arg Glu Glu Met Pro Trp Tyr Arg Gly Arg Glu Trp Ser Tyr Met
            180                 185                 190

Arg Gly Gly Leu Thr Thr Ile Asp Arg Asp Tyr Gly Leu Phe Asn Lys
        195                 200                 205

Val His His Asp Ile Gly Thr His Val Val His His Leu Phe Pro Gln
    210                 215                 220
```

```
Ile Pro His Tyr Asn Leu Cys Arg Ala Thr Lys Ala Ala Lys Lys Val
225                 230                 235                 240

Leu Gly Pro Tyr Tyr Arg Glu Pro Glu Arg Cys Pro Leu Gly Leu Leu
                245                 250                 255

Pro Val His Leu Leu Ala Pro Leu Leu Arg Ser Leu Gly Gln Asp His
            260                 265                 270

Phe Val Asp Asp Ala Gly Ser Val Leu Phe Tyr Arg Arg Ala Glu Gly
        275                 280                 285

Ile Asn Pro Trp Ile Gln Lys Leu Leu Pro Trp Leu Gly Gly Ala Arg
    290                 295                 300

Arg Gly Ala Asp Ala Gln Arg Asp Ala Ala Gln
305                 310                 315


<210> SEQ ID NO 37
<211> LENGTH: 448
<212> TYPE: PRT
<213> ORGANISM: Camelina sativa

<400> SEQUENCE: 37

Met Ala Asn Leu Val Leu Ser Glu Cys Gly Ile Arg Pro Leu Pro Arg
1               5                   10                  15

Ile Tyr Thr Thr Pro Arg Ser Asn Phe Val Ser Asn Asn Asn Lys Pro
            20                  25                  30

Ile Phe Lys Phe Arg Pro Phe Thr Ser Tyr Lys Thr Ser Ser Ser Pro
        35                  40                  45

Leu Ala Cys Ser Arg Asp Gly Phe Gly Lys Asn Trp Ser Leu Asn Val
    50                  55                  60

Ser Val Pro Leu Thr Thr Thr Thr Pro Ile Val Asp Glu Ser Pro Leu
65                  70                  75                  80

Lys Glu Glu Glu Glu Glu Lys Gln Arg Phe Asp Pro Gly Ala Pro Pro
                85                  90                  95

Pro Phe Asn Leu Ala Asp Ile Arg Ala Ala Ile Pro Lys His Cys Trp
            100                 105                 110

Val Lys Asn Pro Trp Lys Ser Met Ser Tyr Val Leu Arg Asp Val Ala
        115                 120                 125

Ile Val Phe Ala Leu Ala Ala Gly Ala Ser Tyr Leu Asn Asn Trp Ile
    130                 135                 140

Val Trp Pro Leu Tyr Trp Leu Ala Gln Gly Thr Met Phe Trp Ala Leu
145                 150                 155                 160

Phe Val Leu Gly His Asp Cys Gly His Gly Ser Phe Ser Asn Asn Pro
                165                 170                 175

Arg Leu Asn Asn Val Val Gly His Leu Leu His Ser Ser Ile Leu Val
            180                 185                 190

Pro Tyr His Gly Trp Arg Ile Ser His Arg Thr His His Gln Asn His
        195                 200                 205

Gly His Val Glu Asn Asp Glu Ser Trp His Pro Met Ser Glu Lys Ile
    210                 215                 220

Tyr Gln Ser Leu Asp Lys Pro Thr Arg Phe Phe Arg Phe Thr Leu Pro
225                 230                 235                 240

Leu Val Met Leu Ala Tyr Pro Phe Tyr Leu Trp Ala Arg Ser Pro Gly
                245                 250                 255

Lys Lys Gly Ser His Tyr His Pro Glu Ser Asp Leu Phe Leu Pro Lys
            260                 265                 270

Glu Lys Thr Asp Val Leu Thr Ser Thr Ala Cys Trp Thr Ala Met Ala
```

-continued

```
        275                 280                 285

Ala Leu Leu Ile Cys Leu Asn Phe Val Val Gly Pro Val Gln Met Leu
    290                 295                 300

Lys Leu Tyr Gly Ile Pro Tyr Trp Ile Asn Val Met Trp Leu Asp Phe
305                 310                 315                 320

Val Thr Tyr Leu His His His Gly His Glu Asp Lys Leu Pro Trp Tyr
                325                 330                 335

Arg Gly Lys Glu Trp Ser Tyr Leu Arg Gly Gly Leu Thr Thr Leu Asp
            340                 345                 350

Arg Asp Tyr Gly Val Ile Asn Asn Ile His His Asp Ile Gly Thr His
        355                 360                 365

Val Ile His His Leu Phe Pro Gln Ile Pro His Tyr His Leu Val Glu
    370                 375                 380

Ala Thr Glu Ala Val Lys Pro Val Leu Gly Lys Tyr Tyr Arg Glu Pro
385                 390                 395                 400

Asp Lys Ser Gly Pro Leu Pro Leu His Leu Leu Gly Ile Leu Ala Lys
                405                 410                 415

Ser Ile Lys Glu Asp His Tyr Val Ser Asp Glu Gly Asp Val Val Tyr
            420                 425                 430

Tyr Lys Ala Asp Pro Asn Met Tyr Gly Glu Ile Lys Val Gly Ala Asp
        435                 440                 445


<210> SEQ ID NO 38
<211> LENGTH: 368
<212> TYPE: PRT
<213> ORGANISM: Prototheca moriformis

<400> SEQUENCE: 38

Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Ser Ser Met Tyr Leu Ala Phe Asp Ile Ala Val Met Ser
        35                  40                  45

Leu Leu Tyr Val Ala Ser Thr Tyr Ile Asp Pro Ala Pro Val Pro Thr
    50                  55                  60

Trp Val Lys Tyr Gly Ile Met Trp Pro Leu Tyr Trp Phe Phe Gln Gly
65                  70                  75                  80

Ala Phe Gly Thr Gly Val Trp Val Cys Ala His Glu Cys Gly His Gln
                85                  90                  95

Ala Phe Ser Ser Ser Gln Ala Ile Asn Asp Gly Val Gly Leu Val Phe
            100                 105                 110

His Ser Leu Leu Leu Val Pro Tyr Tyr Ser Trp Lys His Ser His Arg
        115                 120                 125

Arg His His Ser Asn Thr Gly Cys Leu Asp Lys Asp Glu Val Phe Val
    130                 135                 140

Pro Pro His Arg Ala Val Ala His Glu Gly Leu Glu Trp Glu Glu Trp
145                 150                 155                 160

Leu Pro Ile Arg Met Gly Lys Val Leu Val Thr Leu Thr Leu Gly Trp
                165                 170                 175

Pro Leu Tyr Leu Met Phe Asn Val Ala Ser Arg Pro Tyr Pro Arg Phe
            180                 185                 190

Ala Asn His Phe Asp Pro Trp Ser Pro Ile Phe Ser Lys Arg Glu Arg
        195                 200                 205
```

-continued

Ile Glu Val Val Ile Ser Asp Leu Ala Leu Val Ala Val Leu Ser Gly
    210                 215                 220

Leu Ser Val Leu Gly Arg Thr Met Gly Trp Ala Trp Leu Val Lys Thr
225                 230                 235                 240

Tyr Val Val Pro Tyr Met Ile Val Asn Met Trp Leu Val Leu Ile Thr
                245                 250                 255

Leu Leu Gln His Thr His Pro Ala Leu Pro His Tyr Phe Glu Lys Asp
            260                 265                 270

Trp Asp Trp Leu Arg Gly Ala Met Ala Thr Val Asp Arg Ser Met Gly
        275                 280                 285

Pro Pro Phe Met Asp Ser Ile Leu His His Ile Ser Asp Thr His Val
    290                 295                 300

Leu His His Leu Phe Ser Thr Ile Pro His Tyr His Ala Glu Glu Ala
305                 310                 315                 320

Ser Ala Ala Ile Arg Pro Ile Leu Gly Lys Tyr Tyr Gln Ser Asp Ser
                325                 330                 335

Arg Trp Val Gly Arg Ala Leu Trp Glu Asp Trp Arg Asp Cys Arg Tyr
            340                 345                 350

Val Val Pro Asp Ala Pro Glu Asp Asp Ser Ala Leu Trp Phe His Lys
        355                 360                 365

<210> SEQ ID NO 39
<211> LENGTH: 448
<212> TYPE: PRT
<213> ORGANISM: Camelina sativa

<400> SEQUENCE: 39

Met Ala Asn Leu Val Leu Ser Glu Cys Gly Ile Arg Pro Leu Pro Arg
1               5                   10                  15

Ile Tyr Thr Thr Pro Arg Ser Asn Phe Val Ser Asn Asn Asn Lys Pro
            20                  25                  30

Ile Phe Lys Phe Arg Pro Leu Thr Ser Tyr Lys Thr Ser Ser Pro Leu
        35                  40                  45

Phe Cys Ser Arg Asp Gly Phe Gly Arg Asn Trp Ser Leu Asn Val Ser
    50                  55                  60

Val Pro Leu Ala Thr Thr Thr Pro Ile Val Asp Glu Ser Pro Leu Glu
65                  70                  75                  80

Glu Glu Glu Glu Glu Glu Lys Gln Arg Phe Asp Pro Gly Ala Pro Pro
                85                  90                  95

Pro Phe Asn Leu Ala Asp Ile Arg Ala Ala Ile Pro Lys His Cys Trp
            100                 105                 110

Val Lys Asn Pro Trp Lys Ser Met Ser Tyr Val Leu Arg Asp Val Ala
        115                 120                 125

Ile Val Phe Ala Leu Ala Ala Gly Ala Ala Tyr Leu Asn Asn Trp Ile
    130                 135                 140

Val Trp Pro Leu Tyr Trp Leu Ala Gln Gly Thr Met Phe Trp Ala Leu
145                 150                 155                 160

Phe Val Leu Gly His Asp Cys Gly His Gly Ser Phe Ser Asn Asn Pro
                165                 170                 175

Arg Leu Asn Asn Val Val Gly His Leu Leu His Ser Ser Ile Leu Val
            180                 185                 190

Pro Tyr His Gly Trp Arg Ile Ser His Arg Thr His His Gln Asn His
        195                 200                 205

Gly His Val Glu Asn Asp Glu Ser Trp His Pro Met Ser Glu Lys Ile
    210                 215                 220

Tyr Gln Ser Leu Asp Lys Pro Thr Arg Phe Phe Arg Phe Thr Leu Pro
225 230 235 240

Leu Val Met Leu Ala Tyr Pro Phe Tyr Leu Trp Ala Arg Ser Pro Gly
245 250 255

Lys Lys Gly Ser His Tyr His Pro Glu Ser Asp Leu Phe Leu Pro Lys
260 265 270

Glu Lys Thr Asp Val Leu Thr Ser Thr Ala Cys Trp Thr Ala Met Ala
275 280 285

Ala Leu Leu Ile Cys Leu Asn Phe Val Val Gly Pro Val Gln Met Leu
290 295 300

Lys Leu Tyr Gly Ile Pro Tyr Trp Ile Asn Val Met Trp Leu Asp Phe
305 310 315 320

Val Thr Tyr Leu His His His Gly His Glu Asp Lys Leu Pro Trp Tyr
325 330 335

Arg Gly Lys Glu Trp Ser Tyr Leu Arg Gly Gly Leu Thr Thr Leu Asp
340 345 350

Arg Asp Tyr Gly Val Ile Asn Asn Ile His His Asp Ile Gly Thr His
355 360 365

Val Ile His His Leu Phe Pro Gln Ile Pro His Tyr His Leu Val Glu
370 375 380

Ala Thr Glu Ala Val Lys Pro Val Leu Gly Lys Tyr Tyr Arg Glu Pro
385 390 395 400

Asp Lys Ser Gly Pro Leu Pro Leu His Leu Leu Gly Ile Leu Ala Lys
405 410 415

Ser Ile Lys Glu Asp His Tyr Val Ser Asp Glu Gly Asp Val Val Tyr
420 425 430

Tyr Lys Ala Asp Pro Asn Met Tyr Gly Glu Ile Lys Val Gly Ala Asp
435 440 445

<210> SEQ ID NO 40
<211> LENGTH: 353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
actagtcatt cggggcaacg aggtgggccc ctcgcagcgg ctgacgatca cggcggtggc 60
caacatcctg caggaggcgg cgggcaacca cgcggtggcc atgtggggcc ggagcgtgtg 120
tttgagggtt ttggttgccc gtattgaggt cctggtggcg cgcatggggg agaaggcgcc 180
tgtcccgctg acccccccgg ctaccctccc ggcaccttcc agggcgcgta cgggatccgc 240
tccggcccca catggccacc gcgtggttgc ccgccgcctc ctgcaggatg ttggccaccg 300
ccgtgatcgt cagccgctgc gaggggccca cctcgttgcc ccgaatgaag ctt 353

<210> SEQ ID NO 41
<211> LENGTH: 391
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41
actagtggag ggtttcgcga cggacccgga gctgcaggag gcgggtctca tctttgtgat 60
gacgcgcatg cagatccaga tgtaccgcta cccgcgctgg ggcgacctga tgcaggtgga 120
gacctggttc cagagtgtgt ttgagggttt tggttgcccg tattgaggtc ctggtggcgc 180 gcatgggga gaaggcgcct gtcccgctga cccccccggc taccctcccg gcaccttcca 240
gggcgcgtac gggatcctct ggaaccaggt ctccacctgc atcaggtcgc cccagcgcgg 300
gtagcggtac atctggatct gcatgcgcgt catcacaaag atgagacccg cctcctgcag 360
ctccgggtcc gtcgcgaaac cctccaagct t 391

<210> SEQ ID NO 42
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
actagtcggc gggcaagctg ggcgcgcagc gcgagtgggt gctgcgcgac aagctgaccg 60
gcgaggcgct gggcgcggcc acctcgagct gggtcatgat caacatccgc acgcgccggc 120
cgtgccgcat gccgggtgtg tttgagggtt ttggttgccc gtatcgaggt cctggtggcg 180
cgcatggggg agaaggcgcc tgtcccgctg acccccccgg ctaccctccc ggcaccttcc 240
agggcgcgta cgggatcccc ggcatgcggc acggccggcg cgtgcggatg ttgatcatga 300
cccagctcga ggtggccgcg cccagcgcct cgccggtcag cttgtcgcgc agcacccact 360
cgcgctgcgc gcccagcttg cccgccgaag ctt 393

<210> SEQ ID NO 43
<211> LENGTH: 517
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43
actagtgtcc gcgtcaagtc ggccttcttc gcgcgcgagc cgccgcgcct ggcgctgccg 60
cccgcggtca cgcgtgccaa gctgcccaac atcgcgacgc cggcgccgct gcgcgggcac 120
cgccaggtcg cgcgccgcac cgacatggac atgaacgggc acgtgaacaa cgtggcctac 180
ctggcctggt gcctggagtg tgtttgaggg ttttggttgc ccgtattgag gtcctggtgg 240
cgcgcatggg ggagaaggcg cctgtcccgc tgaccccccc ggctaccctc ccggcacctt 300
ccagggcgcg tacgggatcc tccaggcacc aggccaggta ggccacgttg ttcacgtgcc 360
cgttcatgtc catgtcggtg cggcgcgcga cctggcggtg cccgcgcagc ggcgccggcg 420
tcgcgatgtt gggcagcttg gcacgcgtga ccgcgggcgg cagcgccagg cgcggcggct 480
cgcgcgcgaa gaaggccgac ttgacgcgga caagctt 517

<210> SEQ ID NO 44
<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
actagtccgt gcccgagcac gtcttcagcg actaccacct ctaccagatg gagatcgact 60

-continued

```
tcaaggccga gtgccacgcg ggcgacgtca tctcctccca ggccgagcag atcccgcccc    120

aggaggcgct cacgcacaac ggcgccggcc gcaacccctc ctgcttcgtc catagcattc    180

tgcgcgccga gaccgagcgt gtgtttgagg gttttggttg cccgtatcga ggtcctggtg    240

gcgcgcatgg gggagaaggc gcctgtcccg ctgacccccc cggctaccct cccggcacct    300

tccagggcgc gtacgggatc cgctcggtct cggcgcgcag aatgctatgg acgaagcagg    360

aggggttgcg gccggcgccg ttgtgcgtga gcgcctcctg ggcgcgggatc tgctcggcct    420

gggaggagat gacgtcgccc gcgtggcact cggccttgaa gtcgatctcc atctggtaga    480

ggtggtagtc gctgaagacg tgctcgggca cggaagctt                           519
```

<210> SEQ ID NO 45
<211> LENGTH: 415
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
actagttcgt ccgcgcgcga accacatggt cggcccccat cgacgcgccc gccgccaagc     60

cgcccaaggc gagccactga ggacagggtg gttggctgga tggggaaacg ctggtcgcgg    120

gattcgatcc tgctgcttat atcctcgtgt gtttgagggt tttggttgcc cgtattgagg    180

tcctggtggc gcgcatgggg gagaaggcgc ctgtcccgct gacccccccg gctaccctcc    240

cggcaccttc cagggcgcgt acgggatccg aggatataag cagcaggatc gaatcccgcg    300

accagcgttt ccccatccag ccaaccaccc tgtcctcagt ggctcgcctt gggcggcttg    360

gcggcgggcg cgtcgatggg ggccgaccat gtggttcgcg cgcggacgaa agctt         415
```

<210> SEQ ID NO 46
<211> LENGTH: 1629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
atggccgccg ccgccagcat ggtggccagc cccttctgca cctggctggt ggccagctgc     60

atgagcacca gcttcgacaa cgacccccgc agccccagcg tgaagcgctt cccccgccgc    120

aagcgcgtgc tgagccagcg cggcagcacc tacgtattcc agtgcctggt ggccagctgc    180

atcgacccct gcgaccagta ccgcagcagc gccagcctga gcttcctggg cgacaacggc    240

ttcgccagcc tgttcggcag caagcccttc atgagcaacc gcggccaccg ccgcctgcgc    300

cgcgccagcc acagcggcga ggccatggcc gtggccctgc agcccgccca ggaggccggc    360

accaagaaga agcccgtgat caagcagcgc cgcgtggtgg tgaccggcat gggcgtggtg    420

acccccctgg gccacgagcc cgacgtgttc tacaacaacc tgctggacgg cgtgagcggc    480

atcagcgaga tcgagacctt cgactgcacc cagttcccca cccgcatcgc cggcgagatc    540

aagagcttca gcaccgacgg ctgggtggcc cccaagctga gcaagcgcat ggacaagttc    600

atgctgtacc tgctgaccgc cggcaagaag gccctggccg acggcggcat caccgacgag    660

gtgatgaagg agctggacaa gcgcaagtgc ggcgtgctga tcggcagcgg catgggcggc    720

atgaaggtgt tcaacgacgc catcgaggcc ctgcgcgtga gctacaagaa gatgaacccc    780

ttctgcgtgc ccttcgccac caccaacatg ggcagcgcca tgctggccat ggacctgggc    840
```

tggatgggcc ccaactacag catcagcacc gcctgcgcca ccagcaactt ctgcatcctg 900
aacgccgcca accacatcat ccgcggcgag gccgacatga tgctgtgcgg cggcagcgac 960
gccgtgatca tccccatcgg cctgggcggc ttcgtggcct gccgcgccct gagccagcgc 1020
aacagcgacc ccaccaaggc cagccgcccc tgggacagca accgcgacgg cttcgtgatg 1080
ggcgagggcg ccggcgtgct gctgctggag gagctggagc acgccaagaa gcgcggcgcc 1140
accatctacg ccgagttcct gggcggcagc ttcacctgcg acgcctacca catgaccgag 1200
ccccaccccg agggcgccgg cgtgatcctg tgcatcgaga aggccctggc ccaggccggc 1260
gtgagcaagg aggacgtgaa ctacatcaac gcccacgcca ccagcaccag cgccggcgac 1320
atcaaggagt accaggccct ggcccgctgc ttcggccaga acagcgagct gcgcgtgaac 1380
agcaccaaga gcatgatcgg ccacctgctg ggcgccgccg gcggcgtgga ggccgtgacc 1440
gtggtgcagg ccatccgcac cggctggatt caccccaacc tgaacctgga ggaccccgac 1500
aaggccgtgg acgccaagct gctggtgggc cccaagaagg agcgcctgaa cgtgaaggtg 1560
ggcctgagca acagcttcgg cttcggcggc cacaacagca gcatcctgtt cgcccccctgc 1620 aacgtgtga 1629

<210> SEQ ID NO 47
<211> LENGTH: 1552
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
atgggccgcg gtgtctccct tccccggccc agggtcgcgg tgcgcgccca gtcggcgagt 60
caggttttgg agagctgtat tccagtgcct ggtggccagc tgcatcgacc cctgcgacca 120
gtaccgcagc agcgccagcc tgagcttcct gggcgacaac ggcttcgcca gcctgttcgg 180
cagcaagccc ttcatgagca accgcggcca ccgccgcctg cgccgcgcca gccacagcgg 240
cgaggccatg gccgtggccc tgcagcccgc ccaggaggcc ggcaccaaga agaagcccgt 300
gatcaagcag cgccgcgtgg tggtgaccgg catgggcgtg gtgacccccc tgggccacga 360
gcccgacgtg ttctacaaca acctgctgga cggcgtgagc ggcatcagcg agatcgagac 420
cttcgactgc acccagttcc ccacccgcat cgccggcgag atcaagagct tcagcaccga 480
cggctgggtg gcccccaagc tgagcaagcg catggacaag ttcatgctgt acctgctgac 540
cgccggcaag aaggccctgg ccgacggcgg catcaccgac gaggtgatga aggagctgga 600
caagcgcaag tgcggcgtgc tgatcggcag cggcatgggc ggcatgaagg tgttcaacga 660
cgccatcgag gccctgcgcg tgagctacaa gaagatgaac cccttctgcg tgcccttcgc 720
caccaccaac atgggcagcg ccatgctggc catggacctg ggctggatgg gccccaacta 780
cagcatcagc accgcctgcg ccaccagcaa cttctgcatc ctgaacgccg ccaaccacat 840
catccgcggc gaggccgaca tgatgctgtg cggcggcagc gacgccgtga tcatccccat 900
cggcctgggc ggcttcgtgg cctgccgcgc cctgagccag cgcaacagcg accccaccaa 960
ggccagccgc ccctgggaca gcaaccgcga cggcttcgtg atgggcgagg gcgccggcgt 1020
gctgctgctg gaggagctgg agcacgccaa gaagcgcggc gccaccatct acgccgagtt 1080
cctgggcggc agcttcacct gcgacgccta ccacatgacc gagccccacc ccgagggcgc 1140
cggcgtgatc ctgtgcatcg agaaggccct ggcccaggcc ggcgtgagca aggaggacgt 1200
gaactacatc aacgcccacg ccaccagcac cagcgccggc gacatcaagg agtaccaggc 1260
cctggcccgc tgcttcggcc agaacagcga gctgcgcgtg aacagcacca agagcatgat 1320
cggccacctg ctgggcgccg ccggcggcgt ggaggccgtg accgtggtgc aggccatccg 1380
caccggctgg attcacccca acctgaacct ggaggacccc gacaaggccg tggacgccaa 1440
gctgctggtg ggccccaaga aggagcgcct gaacgtgaag gtgggcctga gcaacagctt 1500
cggcttcggc ggccacaaca gcagcatcct gttcgccccc tgcaacgtgt ga 1552

<210> SEQ ID NO 48
<211> LENGTH: 1641
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
atgcccgcgg ccagctcgct gctggcgtcc cccctgtgca cctggctgct ggccgcgtgc 60
atgagcacct cgttccaccc ctccgacccc ctgcccccca gcatctcgtc cccccgccgc 120
cgcctgagcc gccgccgcat cctgtcgcag tgcgcccccc tgccctccgc gagctcggcc 180
ctgcgcggct ccagcttcca caccctggtg acctcgtatc tggcgtgctt cgagccctgc 240
cacgactatt ataccagcgc ctccctgttc ggctcgcgcc ccatccgcac cacccgccgc 300
caccgccgcc tgaaccgcgc gagcccctcg cgcgaggcga tggcggtcgc cctgcagccc 360
gagcaggagg tgaccaccaa gaagaagccc tccatcaagc agcgccgcgt cgtggtcacc 420
ggcatgggcg tggtcacccc cctgggccac gaccccgacg tgttctataa caacctgctg 480
gacggcacca gcggcatctc ggagatcgag accttcgact gcgcgcagtt ccccacccgc 540
atcgccggcg agatcaagtc cttcagcacc gacggctggg tcgcgcccaa gctgtcgaag 600
cgcatggaca agttcatgct gtatatgctg accgccggca agaaggcgct gaccgacggc 660
ggcatcaccg aggacgtgat gaaggagctg gacaagcgca agtgcggcgt cctgatcggc 720
tccgcgatgg gcggcatgaa ggtgttcaac gacgcgatcg aggccctgcg catcagctat 780
aagaagatga acccottctg cgtgcccttc gcgaccacca acatgggctc ggccatgctg 840
gcgatggacc tgggctggat gggccccaac tattccatca gcaccgcctg cgcgacctcg 900
aacttctgca tcatgaacgc ggccaaccac atcatccgcg gcgaggcgga cgtcatgctg 960
tgcggcggct ccgacgccgt gatcatcccc atcggcatgg gcggcttcgt cgcgtgccgc 1020
gccctgagcc agcgcaactc ggaccccacc aaggcgtccc gcccctggga cagcaaccgc 1080
gacggcttcg tgatgggcga gggcgccggc gtcctgctgc tggaggagct ggagcacgcg 1140
aagaagcgcg gcgccaccat ctatgcggag ttcctgggcg gctcgttcac ctgcgacgcc 1200
tatcacatga ccgagcccca ccccgacggc gccggcgtga tcctgtgcat cgagaaggcg 1260
ctggcccagt ccggcgtcag ccgcgaggac gtgaactata tcaacgcgca cgccacctcg 1320
acccccgcgg gcgacatcaa ggagtatcag gccctgatcc actgcttcgg ccagaaccgc 1380
gagctgaagg tcaactccac caagagcatg atcggccacc tgctgggcgc ggcgggcggc 1440
gtggaggcgg tctcggtggt ccaggccatc cgcaccggct ggatccaccc caacatcaac 1500
ctggagaacc ccgacgaggg cgtggacacc aagctgctgg tgggccccaa gaaggagcgc 1560
ctgaacgtca aggtgggcct gtccaacagc ttcggcttcg gcggccacaa ctcgtccatc 1620
ctgttcgcgc cctatatctg a 1641

<210> SEQ ID NO 49
<211> LENGTH: 1251
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
atggtggccg ccgccgcctc cagcgccttc ttccccgtgc ccgcccccgg cgcctccccc 60
aagcccggca agttcggcaa ctggccctcc agcctgagcc cctccttcaa gcccaagtcc 120
atccccaacg gcggcttcca ggtgaaggcc aacgacagcg cccaccccaa ggccaacggc 180
tccgccgtga gcctgaagag cggcagcctg aacacccagg aggacacctc ctccagcccc 240 ccccccgca ccttcctgca ccagctgccc gactggagcc gcctgctgac cgccatcacc 300
accgtgttcg tgaagtccaa gcgccccgac atgcacgacc gcaagtccaa gcgccccgac 360
atgctggtgg acagcttcgg cctggagtcc accgtgcagg acggcctggt gttccgccag 420
tccttctcca tccgctccta cgagatcggc accgaccgca ccgccagcat cgagaccctg 480
atgaaccacc tgcaggagac ctccctgaac cactgcaaga gcaccggcat cctgctggac 540
ggcttcggcc gcaccctgga gatgtgcaag cgcgacctga tctgggtggt gatcaagatg 600
cagatcaagg tgaaccgcta ccccgcctgg ggcgacaccg tggagatcaa cacccgcttc 660
agccgcctgg gcaagatcgg catgggccgc gactggctga tctccgactg caacaccggc 720
gagatcctgg tgcgcgccac cagcgcctac gccatgatga accagaagac ccgccgcctg 780
tccaagctgc cctacgaggt gcaccaggag atcgtgcccc tgttcgtgga cagccccgtg 840
atcgaggact ccgacctgaa ggtgcacaag ttcaaggtga agaccggcga cagcatccag 900
aagggcctga cccccggctg gaacgacctg gacgtgaacc agcacgtgtc caacgtgaag 960
tacatcggct ggatcctgga gagcatgccc accgaggtgc tggagaccca ggagctgtgc 1020
tccctggccc tggagtaccg ccgcgagtgc ggccgcgact ccgtgctgga gagcgtgacc 1080
gccatggacc ccagcaaggt gggcgtgcgc tcccagtacc agcacctgct gcgcctggag 1140
gacggcaccg ccatcgtgaa cggcgccacc gagtggcgcc ccaagaacgc cggcgccaac 1200
ggcgccatct ccaccggcaa gaccagcaac ggcaactccg tgtccatgtg a 1251

<210> SEQ ID NO 50
<211> LENGTH: 659
<212> TYPE: DNA
<213> ORGANISM: Prototheca moriformis

<400> SEQUENCE: 50
gctcttcctc accgcgtgaa ttgctgtccc aaacgtaagc atcatcgtgg ctcggtcacg 60
cgatcctgga tccggggatc ctagaccgct ggtggagagc gctgccgtcg gattggtggc 120
aagtaagatt gcgcaggttg gcgaagggag agaccaaaac cggaggctgg aagcgggcac 180
aacatcgtat tattgcgtat agtagagcag tggcagtcgc atttcgaggt ccgcaacgga 240
tctcgcaagc tcgctacgct cacagtagga gaaaggggac cactgcccct gccagaatgg 300
tcgcgaccct ctccctcgcc ggccccgcct gcaacacgca gtgcgtatcc ggcaagcggg 360
ctgtcgcctt caaccgcccc catgttggcg tccgggctcg atcaggtgcg ctgagggggg 420
tttggtgtgc ccgcgcctct gggcccgtgt cggccgtgcg gacgtggggc cctgggcagt 480
ggatcagcag ggtttgcgtg caaatgccta taccggcgat tgaatagcga tgaacgggat 540
acggttgcgc tcactccatg cccatgcgac cccgtttctg tccgccagcc gtggtcgccc 600
gggctgcgaa gcgggacccc acccagcgca ttgtgatcac cggaatgggc gtgggtacc 659

<210> SEQ ID NO 51
<211> LENGTH: 607
<212> TYPE: DNA
<213> ORGANISM: Prototheca moriformis

<400> SEQUENCE: 51
gagctccacc tgcatccgcc tggcgctcga ggacgccggc gtctcgcccg acgaggtcaa 60
ctacgtcaac gcgcacgcca cctccaccct ggtgggcgac aaggccgagg tgcgcgcggt 120
caagtcggtc tttggcgaca tgaagggcat caagatgaac gccaccaagt ccatgatcgg 180
gcactgcctg ggcgccgccg gcggcatgga ggccgtcgcc acgctcatgg ccatccgcac 240
cggctgggtg caccccacca tcaaccacga caaccccatc gccgaggtcg acggcctgga 300
cgtcgtcgcc aacgccaagg cccagcacaa aatcaacgtc gccatctcca actccttcgg 360
cttcggcggg cacaactccg tcgtcgcctt tgcgcccttc cgcgagtagg cggagcgagc 420
gcgcttggct gaggagggag gcggggtgcg agccctttgg ctgcgcgcga tactctcccc 480
gcacgagcag actccacgcg cctgaatcta cttgtcaacg agcaaccgtg tgttttgtcc 540
gtggccattc ttattatttc tccgactgtg gccgtactct gtttggctgt gcaagcaccg 600
aagagcc 607

<210> SEQ ID NO 52
<211> LENGTH: 636
<212> TYPE: DNA
<213> ORGANISM: Prototheca moriformis

<400> SEQUENCE: 52
gctcttcgcg caagctcgct acgctcacag taggagatag gggaccactg cccctgccag 60
aatggtcgcg accctgtccc tcgccggccc cgcctgcaac acgcagtgcg tatccagcaa 120
gcgggttgtc gccttcaacc gcccccatgt tggcgtccgg gctcgatcag gtgcgctgag 180
gggggtttgg tgggcccgcg cctctgggcc cgtgtcggcc gtgcggacgt ggggcccggg 240
gtagtggatc agcaggggtt gcatgcaaat gcctataccg gcgattgaat agcgatgaac 300
gggatacggt tgcgctcact ccatgcccat gcgaccccgt ttctgtccgc cagccgtggt 360
cgcccgagct gcgaagcggg accccaccca gcgcattgtg atcaccggaa tgggcgtggc 420
ctccgtgttt ggcaacgatg tcgagacctt ttacgacaag cttctggaag gaacgagcgg 480
cgtggacctg atttccaggt gcgtaggtcc ttggatgaat gcgtctaggt tgcgaggtga 540
ctggccagga agcagcaggc ttggggtttg gtgttctgat ttctggtaat ttgaggtttc 600
attataagat tctgtacggt cttgtttcgg ggtacc 636

<210> SEQ ID NO 53
<211> LENGTH: 607
<212> TYPE: DNA
<213> ORGANISM: Prototheca moriformis

<400> SEQUENCE: 53
gagctccacc tgcatccgcc tggcgctcga ggacgccggc gtctcgcccg acgaggtcaa 60
ctacgtcaac gcgcacgcca cctccaccct ggtgggcgac aaggccgagg tgcgcgcggt 120
caagtcggtc tttggcgaca tgaagggcat caagatgaac gccaccaagt ccatgatcgg 180

-continued

```
gcactgcctg ggcgccgccg gcggcatgga ggccgtcgcc acgctcatgg ccatccgcac    240

cggctgggtg caccccacca tcaaccacga caaccccatc gccgaggtcg acggcctgga    300

cgtcgtcgcc aacgccaagg cccagcacaa aatcaacgtc gccatctcca actccttcgg    360

cttcggcggg cacaactccg tcgtcgcctt tgcgcccttc cgcgagtagg cggagcgagc    420

gcgcttggct gaggagggag gcggggtgcg agccctttgg ctgcgcgcga tactctcccc    480

gcacgagcag actccacgcg cctgaatcta cttgtcaacg agcaaccgtg tgttttgtcc    540

gtggccattc ttattatttc tccgactgtg gccgtactct gtttggctgt gcaagcaccg    600

aagagcc                                                              607
```

<210> SEQ ID NO 54
<211> LENGTH: 335
<212> TYPE: DNA
<213> ORGANISM: Prototheca moriformis

<400> SEQUENCE: 54

```
actagtcatg gtcgcccggg ctgcgaagcg ggaccccacc cagcgcattg tgatcaccgg     60

aatgggcgtg gcctccgtgt ttggcaacga tgtcgagacc ttttacagtg tgtttgaggg    120

ttttggttgc ccgtattgag gtcctggtgg cgcgcatgga ggagaaggcg cctgtcccgc    180

tgaccccccc ggctaccctc ccggcacctt ccagggcgcg tacgggatcc tgtaaaaggt    240

ctcgacatcg ttgccaaaca cggaggccac gcccattccg gtgatcacaa tgcgctgggt    300

ggggtcccgc ttcgcagccc gggcgaccaa agctt                               335
```

<210> SEQ ID NO 55
<211> LENGTH: 503
<212> TYPE: DNA
<213> ORGANISM: Prototheca moriformis

<400> SEQUENCE: 55

```
actagtcatt gacatctccg agttcccgac caagtttgcg gcgcagatca ccggcttctc     60

cgtggaggac tgcgtggaca agaagaacgc gcggcggtac gacgacgcgc tgtcgtacgc    120

gatggtggcc tccaagaagg ccctgcgcca ggcgggactg gagaaggaca agtgccccga    180

gggctacgga ggtgtgtttg agggttttgg ttgcccgtat tgaggtcctg gtggcgcgca    240

tggaggagaa ggcgcctgtc ccgctgaccc ccccggctac cctcccggca ccttccaggg    300

cgcgtacggg atccctccgt agccctcggg gcacttgtcc ttctccagtc ccgcctggcg    360

cagggccttc ttggaggcca ccatcgcgta cgacagcgcg tcgtcgtacc gccgcgcgtt    420

cttcttgtcc acgcagtcct ccacggagaa gccggtgatc tgcgccgcaa acttggtcgg    480

gaactcggag atgtcaaaag ctt                                            503
```

<210> SEQ ID NO 56
<211> LENGTH: 457
<212> TYPE: DNA
<213> ORGANISM: Prototheca moriformis

<400> SEQUENCE: 56

```
actagtcatg ggcgtgagca cctgcatccg cctggcgctc gaggacgccg gcgtctcgcc     60

cgacgaggtc aactacgtca acgcgcacgc cacctccacc ctggtgggcg acaaggccga    120

ggtgcgcgcg gtcaagtcgg tctttggcga catgaagggc atcaagatgt gtgtttgagg    180

gttttggttg cccgtattga ggtcctggtg gcgcgcatgg aggagaaggc gcctgtcccg    240

ctgacccccc cggctaccct cccggcacct tccagggcgc gtacgggatc catcttgatg    300
```

cccttcatgt cgccaaagac cgacttgacc gcgcgcacct cggccttgtc gcccaccagg 360
gtggaggtgg cgtgcgcgtt gacgtagttg acctcgtcgg gcgagacgcc ggcgtcctcg 420
agcgccaggc ggatgcaggt gctcacgccc aaagctt 457

<210> SEQ ID NO 57
<211> LENGTH: 345
<212> TYPE: DNA
<213> ORGANISM: Prototheca moriformis

<400> SEQUENCE: 57
actagtcaca accatcaacc acgacaaccc catcgccgag gtcgacggcc tggacgtcgt 60
cgccaacgcc aaggcccagc acaaaatcaa cgtcgccatc tccaactcct tcggtgtgtt 120
tgagggtttt ggttgcccgt attgaggtcc tggtggcgcg catggaggag aaggcgcctg 180
tcccgctgac ccccccggct accctcccgg caccttccag ggcgcgtacg ggatcccgaa 240
ggagttggag atggcgacgt tgattttgtg ctgggccttg gcgttggcga cgacgtccag 300
gccgtcgacc tcggcgatgg ggttgtcgtg gttgatggta agctt 345

<210> SEQ ID NO 58
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atggactccc gcgcccagaa ccgcgacggc ggcgaggacg tgaagcagga gctgctgtcc 60
gccggcgacg acggcaaggt gccctgcccc accgtggcca tcggcatccg ccagcgcctg 120
cccgacttcc tgcagtccgt gaacatgaag tacgtgaagc tgggctacca ctacctgatc 180
acccacgcca tgttcctgct gaccctgccc gccttcttcc tggtggccgc cgagatcggc 240
cgcctgggcc acgagcgcat ctaccgcgag ctgtggaccc acctgcacct gaacctggtg 300
tccatcatgg cctgctcctc cgccctggtg gccggcgcca ccctgtactt catgtcccgc 360
ccccgccccg tgtacctggt ggagttcgcc tgctaccgcc ccgacgagcg cctgaaggtg 420
tccaaggact tcttcctgga catgtcccgc cgcaccggcc tgttctcctc ctcctccatg 480
gacttccaga ccaagatcac ccagcgctcc ggcctgggcg acgagaccta cctgcccccc 540
gccatcctgg cctccccccc caacccctgc atgcgcgagg cccgcgagga ggccgccatg 600
gtgatgttcg gcgccctgga cgagctgttc gagcagaccg gcgtgaagcc caaggagatc 660
ggcgtgctgg tggtgaactg ctccctgttc aaccccaccc cctccatgtc cgccatgatc 720
gtgaaccact accacatgcg cggcaacatc aagtccctga acctgggcgg catgggctgc 780
tccgccggcc tgatctccat cgacctggcc cgcgacctgc tgcaggtgca cggcaacacc 840
tacgccgtgg tggtgtccac cgagaacatc accctgaact ggtacttcgg cgacgaccgc 900
tccaagctga tgtccaactg catcttccgc atgggcggcg ccgccgtgct gctgtccaac 960
aagcgccgcg agcgccgccg cgccaagtac gagctgctgc acaccgtgcg cacccacaag 1020
ggcgccgacg acaagtgctt ccgctgcgtg taccaggagg aggactccac cggctccctg 1080
ggcgtgtccc tgtcccgcga gctgatggcc gtggccggca acgccctgaa ggccaacatc 1140
accaccctgg gcccccctggt gctgcccctg tccgagcaga tcctgttctt cgcctccctg 1200
gtggcccgca agttcctgaa catgaagatg aagccctaca tccccgactt caagctggcc 1260

```
ttcgagcact tctgcatcca cgccggcggc cgcgccgtgc tggacgagct ggagaagaac   1320

ctggacctga ccgagtggca catggagccc tcccgcatga ccctgtaccg cttcggcaac   1380

acctcctcct cctccctgtg gtacgagctg gcctacaccg aggcccaggg ccgcgtgaag   1440

cgcggcgacc gcctgtggca gatcgccttc ggctccggct tcaagtgcaa ctccgccgtg   1500

tggcgcgcgc tgcgcaccgt gaagccccc gtgaacaacg cctggtccga cgtgatcgac    1560

cgcttccccg tgaagctgcc ccagttctga                                      1590
```

<210> SEQ ID NO 59
<211> LENGTH: 529
<212> TYPE: PRT
<213> ORGANISM: Metrosideros polymorpha

<400> SEQUENCE: 59

```
Met Asp Ser Arg Ala Gln Asn Arg Asp Gly Gly Glu Asp Val Lys Gln
1               5                   10                  15

Glu Leu Leu Ser Ala Gly Asp Asp Gly Lys Val Pro Cys Pro Thr Val
            20                  25                  30

Ala Ile Gly Ile Arg Gln Arg Leu Pro Asp Phe Leu Gln Ser Val Asn
        35                  40                  45

Met Lys Tyr Val Lys Leu Gly Tyr His Tyr Leu Ile Thr His Ala Met
    50                  55                  60

Phe Leu Leu Thr Leu Pro Ala Phe Phe Leu Val Ala Ala Glu Ile Gly
65                  70                  75                  80

Arg Leu Gly His Glu Arg Ile Tyr Arg Glu Leu Trp Thr His Leu His
                85                  90                  95

Leu Asn Leu Val Ser Ile Met Ala Cys Ser Ser Ala Leu Val Ala Gly
            100                 105                 110

Ala Thr Leu Tyr Phe Met Ser Arg Pro Arg Pro Val Tyr Leu Val Glu
        115                 120                 125

Phe Ala Cys Tyr Arg Pro Asp Glu Arg Leu Lys Val Ser Lys Asp Phe
    130                 135                 140

Phe Leu Asp Met Ser Arg Arg Thr Gly Leu Phe Ser Ser Ser Ser Met
145                 150                 155                 160

Asp Phe Gln Thr Lys Ile Thr Gln Arg Ser Gly Leu Gly Asp Glu Thr
                165                 170                 175

Tyr Leu Pro Pro Ala Ile Leu Ala Ser Pro Pro Asn Pro Cys Met Arg
            180                 185                 190

Glu Ala Arg Glu Glu Ala Ala Met Val Met Phe Gly Ala Leu Asp Glu
        195                 200                 205

Leu Phe Glu Gln Thr Gly Val Lys Pro Lys Glu Ile Gly Val Leu Val
    210                 215                 220

Val Asn Cys Ser Leu Phe Asn Pro Thr Pro Ser Met Ser Ala Met Ile
225                 230                 235                 240

Val Asn His Tyr His Met Arg Gly Asn Ile Lys Ser Leu Asn Leu Gly
                245                 250                 255

Gly Met Gly Cys Ser Ala Gly Leu Ile Ser Ile Asp Leu Ala Arg Asp
            260                 265                 270

Leu Leu Gln Val His Gly Asn Thr Tyr Ala Val Val Val Ser Thr Glu
        275                 280                 285

Asn Ile Thr Leu Asn Trp Tyr Phe Gly Asp Asp Arg Ser Lys Leu Met
    290                 295                 300

Ser Asn Cys Ile Phe Arg Met Gly Gly Ala Ala Val Leu Leu Ser Asn
```

```
305                 310                 315                 320

Lys Arg Arg Glu Arg Arg Arg Ala Lys Tyr Glu Leu Leu His Thr Val
                325                 330                 335

Arg Thr His Lys Gly Ala Asp Asp Lys Cys Phe Arg Cys Val Tyr Gln
            340                 345                 350

Glu Glu Asp Ser Thr Gly Ser Leu Gly Val Ser Leu Ser Arg Glu Leu
        355                 360                 365

Met Ala Val Ala Gly Asn Ala Leu Lys Ala Asn Ile Thr Thr Leu Gly
    370                 375                 380

Pro Leu Val Leu Pro Leu Ser Glu Gln Ile Leu Phe Phe Ala Ser Leu
385                 390                 395                 400

Val Ala Arg Lys Phe Leu Asn Met Lys Met Lys Pro Tyr Ile Pro Asp
                405                 410                 415

Phe Lys Leu Ala Phe Glu His Phe Cys Ile His Ala Gly Gly Arg Ala
            420                 425                 430

Val Leu Asp Glu Leu Glu Lys Asn Leu Asp Leu Thr Glu Trp His Met
        435                 440                 445

Glu Pro Ser Arg Met Thr Leu Tyr Arg Phe Gly Asn Thr Ser Ser Ser
    450                 455                 460

Ser Leu Trp Tyr Glu Leu Ala Tyr Thr Glu Ala Gln Gly Arg Val Lys
465                 470                 475                 480

Arg Gly Asp Arg Leu Trp Gln Ile Ala Phe Gly Ser Gly Phe Lys Cys
                485                 490                 495

Asn Ser Ala Val Trp Arg Ala Leu Arg Thr Val Lys Pro Pro Val Asn
            500                 505                 510

Asn Ala Trp Ser Asp Val Ile Asp Arg Phe Pro Val Lys Leu Pro Gln
        515                 520                 525

Phe


<210> SEQ ID NO 60
<211> LENGTH: 906
<212> TYPE: DNA
<213> ORGANISM: Trypanosoma brucei

<400> SEQUENCE: 60

atgctgatga acttcggcgg ctcctacgac gcctacatca acaacttcca gggcaccttc     60

ctggccgagt ggatgctgga ccacccctcc gtgccctaca tcgccggcgt gatgtacctg    120

atcctggtgc tgtacgtgcc caagtccatc atggcctccc agcccccccct gaacctgcgc    180

gccgccaaca tcgtgtggaa cctgttcctg accctgttct ccatgtgcgg cgcctactac    240

accgtgccct acctggtgaa ggccttcatg aaccccgaga tcgtgatggc cgcctccggc    300

atcaagctgg acgccaacac ctcccccatc atcacccact ccggcttcta caccaccacc    360

tgcgccctgg ccgactcctt ctacttcaac ggcgacgtgg gcttctgggt ggccctgttc    420

gccctgtcca agatccccga gatgatcgac accgccttcc tggtgttcca gaagaagccc    480

gtgatcttcc tgcactggta ccaccacctg accgtgatgc tgttctgctg gttcgcctac    540

gtgcagaaga tctcctccgg cctgtggttc gcctccatga actactccgt gcactccatc    600

atgtacctgt actacttcgt gtgcgcctgc ggccaccgcc gcctggtgcg cccccttcgcc    660

cccatcatca ccttcgtgca gatcttccag atggtggtgg gcaccatcgt ggtgtgctac    720

acctacaccg tgaagcacgt gctgggccgc tcctgcaccg tgaccgactt ctccctgcac    780

accggcctgg tgatgtacgt gtcctacctg ctgctgttct cccagctgtt ctaccgctcc    840
```

```
tacctgtccc cccgcgacaa ggcctccatc ccccacgtgg ccgccgagat caagaagaag    900

gagtga                                                               906


<210> SEQ ID NO 61
<211> LENGTH: 322
<212> TYPE: PRT
<213> ORGANISM: Trypanosoma brucei

<400> SEQUENCE: 61

Met Tyr Pro Thr His Arg Asp Leu Ile Leu Asn Asn Tyr Ser Asp Ile
1               5                   10                  15

Tyr Arg Ser Pro Thr Cys His Tyr His Thr Trp His Thr Leu Ile His
            20                  25                  30

Thr Pro Ile Asn Glu Leu Leu Phe Pro Asn Leu Pro Arg Glu Cys Asp
        35                  40                  45

Phe Gly Tyr Asp Ile Pro Tyr Phe Arg Gly Gln Ile Asp Val Phe Asp
    50                  55                  60

Gly Trp Ser Met Ile His Phe Thr Ser Ser Asn Trp Cys Ile Pro Ile
65                  70                  75                  80

Thr Val Cys Leu Cys Tyr Ile Met Met Ile Ala Gly Leu Lys Lys Tyr
                85                  90                  95

Met Gly Pro Arg Asp Gly Gly Arg Ala Pro Ile Gln Ala Lys Asn Tyr
            100                 105                 110

Ile Ile Ala Trp Asn Leu Phe Leu Ser Phe Phe Ser Phe Ala Gly Val
        115                 120                 125

Tyr Tyr Thr Val Pro Tyr His Leu Phe Asp Pro Glu Asn Gly Leu Phe
    130                 135                 140

Ala Gln Gly Phe Tyr Ser Thr Val Cys Asn Asn Gly Ala Tyr Tyr Gly
145                 150                 155                 160

Asn Gly Asn Val Gly Phe Phe Val Trp Leu Phe Ile Tyr Ser Lys Ile
                165                 170                 175

Phe Glu Leu Val Asp Thr Phe Phe Leu Leu Ile Arg Lys Asn Pro Val
            180                 185                 190

Ile Phe Leu His Trp Tyr His His Leu Thr Val Leu Leu Tyr Cys Trp
        195                 200                 205

His Ala Tyr Ser Val Arg Ile Gly Thr Gly Ile Trp Phe Ala Thr Met
    210                 215                 220

Asn Tyr Ser Val His Ser Val Met Tyr Leu Tyr Phe Ala Met Thr Gln
225                 230                 235                 240

Tyr Gly Pro Ser Thr Lys Lys Phe Ala Lys Lys Phe Ser Lys Phe Ile
                245                 250                 255

Thr Thr Ile Gln Ile Leu Gln Met Val Val Gly Ile Ile Val Thr Phe
            260                 265                 270

Ala Ala Met Leu Tyr Val Thr Phe Asp Val Pro Cys Tyr Thr Ser Leu
        275                 280                 285

Ala Asn Ser Val Leu Gly Leu Met Met Tyr Ala Ser Tyr Phe Val Leu
    290                 295                 300

Phe Val Gln Leu Tyr Val Ser His Tyr Val Ser Pro Lys His Val Lys
305                 310                 315                 320

Gln Glu


<210> SEQ ID NO 62
<211> LENGTH: 933
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 62

```
atggtgtccg actggaagaa cttctgcctg gagaaggcct cccgcttccg ccccaccatc     60

gaccgcccct tcttcaacat ctacctgtgg gactacttca accgcgccgt gggctgggcc    120

accgccggcc gcttccagcc caaggacttc gagttcaccg tgggcaagca gcccctgtcc    180

gagccccgcc ccgtgctgct gttcatcgcc atgtactacg tggtgatctt cggcggccgc    240

tccctggtga agtcctgcaa gcccctgaag ctgcgcttca tctcccaggt gcacaacctg    300

atgctgacct ccgtgtcctt cctgtggctg atcctgatgg tggagcagat gctgcccatc    360

gtgtaccgcc acggcctgta cttcgccgtg tgcaacgtgg agtcctggac ccagcccatg    420

gagaccctgt actacctgaa ctacatgacc aagttcgtgg agttcgccga caccgtgctg    480

atggtgctga agcaccgcaa gctgaccttc ctgcacacct accaccacgg cgccaccgcc    540

ctgctgtgct acaaccagct ggtgggctac accgccgtga cctgggtgcc cgtgaccctg    600

aacctggccg tgcacgtgct gatgtactgg tactacttcc tgtccgcctc cggcatccgc    660

gtgtggtgga aggcctgggt gacccgcctg cagatcgtgc agttcatgct ggacctgatc    720

gtggtgtact acgtgctgta ccagaagatc gtggccgcct acttcaagaa cgcctgcacc    780

ccccagtgcg aggactgcct gggctccatg accgccatcg ccgccggcgc cgccatcctg    840

acctcctacc tgttcctgtt catctccttc tacatcgagg tgtacaagcg cggctccgcc    900

tccggcaaga agaagatcaa caagaacaac tga                                 933
```

<210> SEQ ID NO 63
<211> LENGTH: 310
<212> TYPE: PRT
<213> ORGANISM: Saccharomyces cerevisiae

<400> SEQUENCE: 63

```
Met Val Ser Asp Trp Lys Asn Phe Cys Leu Glu Lys Ala Ser Arg Phe
1               5                   10                  15

Arg Pro Thr Ile Asp Arg Pro Phe Phe Asn Ile Tyr Leu Trp Asp Tyr
            20                  25                  30

Phe Asn Arg Ala Val Gly Trp Ala Thr Ala Gly Arg Phe Gln Pro Lys
        35                  40                  45

Asp Phe Glu Phe Thr Val Gly Lys Gln Pro Leu Ser Glu Pro Arg Pro
    50                  55                  60

Val Leu Leu Phe Ile Ala Met Tyr Tyr Val Val Ile Phe Gly Gly Arg
65                  70                  75                  80

Ser Leu Val Lys Ser Cys Lys Pro Leu Lys Leu Arg Phe Ile Ser Gln
                85                  90                  95

Val His Asn Leu Met Leu Thr Ser Val Ser Phe Leu Trp Leu Ile Leu
            100                 105                 110

Met Val Glu Gln Met Leu Pro Ile Val Tyr Arg His Gly Leu Tyr Phe
        115                 120                 125

Ala Val Cys Asn Val Glu Ser Trp Thr Gln Pro Met Glu Thr Leu Tyr
    130                 135                 140

Tyr Leu Asn Tyr Met Thr Lys Phe Val Glu Phe Ala Asp Thr Val Leu
145                 150                 155                 160

Met Val Leu Lys His Arg Lys Leu Thr Phe Leu His Thr Tyr His His
                165                 170                 175
```

```
Gly Ala Thr Ala Leu Leu Cys Tyr Asn Gln Leu Val Gly Tyr Thr Ala
            180                 185                 190

Val Thr Trp Val Pro Val Thr Leu Asn Leu Ala Val His Val Leu Met
        195                 200                 205

Tyr Trp Tyr Tyr Phe Leu Ser Ala Ser Gly Ile Arg Val Trp Trp Lys
    210                 215                 220

Ala Trp Val Thr Arg Leu Gln Ile Val Gln Phe Met Leu Asp Leu Ile
225                 230                 235                 240

Val Val Tyr Tyr Val Leu Tyr Gln Lys Ile Val Ala Ala Tyr Phe Lys
                245                 250                 255

Asn Ala Cys Thr Pro Gln Cys Glu Asp Cys Leu Gly Ser Met Thr Ala
            260                 265                 270

Ile Ala Ala Gly Ala Ala Ile Leu Thr Ser Tyr Leu Phe Leu Phe Ile
        275                 280                 285

Ser Phe Tyr Ile Glu Val Tyr Lys Arg Gly Ser Ala Ser Gly Lys Lys
    290                 295                 300

Lys Ile Asn Lys Asn Asn
305                 310
```

<210> SEQ ID NO 64
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atgctgaagc tgtcctgcaa cgtgaccaac aacctgcaca ccttctcctt cttctccgac     60

tcctccctgt tcatccccgt gaaccgccgc accatcgccg tgtcctccgg gcgcgcctcc    120

cagctgcgca agcccgccct ggaccccctg cgcgccgtga tctccgccga ccagggctcc    180

atctccccccg tgaactcctg cacccccgcc gaccgcctgc gcgccggccg cctgatggag    240

gacggctact cctacaagga gaagttcatc gtgcgctcct acgaggtggg catcaacaag    300

accgccaccg tggagaccat cgccaacctg ctgcaggagg tggcctgcaa ccacgtgcag    360

aagtgcggct tctccaccga cggcttcgcc accaccctga ccatgcgcaa gctgcacctg    420

atctgggtga ccgcccgcat gcacatcgag atctacaagt accccgcctg gtccgacgtg    480

gtggagatcg agacctggtg ccagtccgag ggccgcatcg gcacccgccg cgactggatc    540

ctgcgcgact ccgccaccaa cgaggtgatc ggccgcgcca cctccaagtg ggtgatgatg    600

aaccaggaca cccgccgcct gcagcgcgtg accgacgagg tgcgcgacga gtacctggtg    660

ttctgccccc gcgagccccg cctggccttc cccgaggaga acaactcctc cctgaagaag    720

atccccaagc tggaggaccc cgcccagtac tccatgctgg agctgaagcc ccgccgcgcc    780

gacctggaca tgaaccagca cgtgaacaac gtgacctaca tcggctgggt gctggagtcc    840

atcccccagg agatcatcga cacccacgag ctgcaggtga tcaccctgga ctaccgccgc    900

gagtgccagc aggacgacat cgtggactcc ctgaccacct ccgagatccc cgacgacccc    960

atctccaagt tcaccggcac caacggctcc gccatgtcct ccatccaggg ccacaacgag   1020

tcccagttcc tgcacatgct gcgcctgtcc gagaacggcc aggagatcaa ccgcggccgc   1080

acccagtggc gcaagaagtc ctcccgcatg gactacaagg accacgacgg cgactacaag   1140

gaccacgaca tcgactacaa ggacgacgac gacaagtga                          1179
```

<210> SEQ ID NO 65
<211> LENGTH: 392
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Met Leu Lys Leu Ser Cys Asn Val Thr Asn Asn Leu His Thr Phe Ser
1 5 10 15

Phe Phe Ser Asp Ser Ser Leu Phe Ile Pro Val Asn Arg Arg Thr Ile
20 25 30

Ala Val Ser Ser Gly Arg Ala Ser Gln Leu Arg Lys Pro Ala Leu Asp
35 40 45

Pro Leu Arg Ala Val Ile Ser Ala Asp Gln Gly Ser Ile Ser Pro Val
50 55 60

Asn Ser Cys Thr Pro Ala Asp Arg Leu Arg Ala Gly Arg Leu Met Glu
65 70 75 80

Asp Gly Tyr Ser Tyr Lys Glu Lys Phe Ile Val Arg Ser Tyr Glu Val
85 90 95

Gly Ile Asn Lys Thr Ala Thr Val Glu Thr Ile Ala Asn Leu Leu Gln
100 105 110

Glu Val Ala Cys Asn His Val Gln Lys Cys Gly Phe Ser Thr Asp Gly
115 120 125

Phe Ala Thr Thr Leu Thr Met Arg Lys Leu His Leu Ile Trp Val Thr
130 135 140

Ala Arg Met His Ile Glu Ile Tyr Lys Tyr Pro Ala Trp Ser Asp Val
145 150 155 160

Val Glu Ile Glu Thr Trp Cys Gln Ser Glu Gly Arg Ile Gly Thr Arg
165 170 175

Arg Asp Trp Ile Leu Arg Asp Ser Ala Thr Asn Glu Val Ile Gly Arg
180 185 190

Ala Thr Ser Lys Trp Val Met Met Asn Gln Asp Thr Arg Arg Leu Gln
195 200 205

Arg Val Thr Asp Glu Val Arg Asp Glu Tyr Leu Val Phe Cys Pro Arg
210 215 220

Glu Pro Arg Leu Ala Phe Pro Glu Glu Asn Asn Ser Ser Leu Lys Lys
225 230 235 240

Ile Pro Lys Leu Glu Asp Pro Ala Gln Tyr Ser Met Leu Glu Leu Lys
245 250 255

Pro Arg Arg Ala Asp Leu Asp Met Asn Gln His Val Asn Asn Val Thr
260 265 270

Tyr Ile Gly Trp Val Leu Glu Ser Ile Pro Gln Glu Ile Ile Asp Thr
275 280 285

His Glu Leu Gln Val Ile Thr Leu Asp Tyr Arg Arg Glu Cys Gln Gln
290 295 300

Asp Asp Ile Val Asp Ser Leu Thr Thr Ser Glu Ile Pro Asp Asp Pro
305 310 315 320

Ile Ser Lys Phe Thr Gly Thr Asn Gly Ser Ala Met Ser Ser Ile Gln
325 330 335

Gly His Asn Glu Ser Gln Phe Leu His Met Leu Arg Leu Ser Glu Asn
340 345 350

Gly Gln Glu Ile Asn Arg Gly Arg Thr Gln Trp Arg Lys Lys Ser Ser
355 360 365

```
Arg Met Asp Tyr Lys Asp His Asp Gly Asp Tyr Lys Asp His Asp Ile
    370                 375                 380

Asp Tyr Lys Asp Asp Asp Asp Lys
385                 390


<210> SEQ ID NO 66
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

atggccaccg catccacttt ctcggcgttc aatgcccgct gcggcgacct gcgtcgctcg      60

gcgggctccg ggcccggcg cccagcgagg cccctccccg tgcgcgggcg cgcctcccag      120

ctgcgcaagc ccgccctgga ccccctgcgc gccgtgatct ccgccgacca gggctccatc    180

tcccccgtga actcctgcac ccccgccgac cgcctgcgcg ccggccgcct gatggaggac    240

ggctactcct acaaggagaa gttcatcgtg cgctcctacg aggtgggcat caacaagacc    300

gccaccgtgg agaccatcgc caacctgctg caggaggtgg cctgcaacca cgtgcagaag    360

tgcggcttct ccaccgacgg cttcgccacc accctgacca tgcgcaagct gcacctgatc    420

tgggtgaccg cccgcatgca catcgagatc tacaagtacc ccgcctggtc cgacgtggtg    480

gagatcgaga cctggtgcca gtccgagggc cgcatcggca cccgccgcga ctggatcctg    540

cgcgactccg ccaccaacga ggtgatcggc cgcgccacct ccaagtgggt gatgatgaac    600

caggacaccc gccgcctgca gcgcgtgacc gacgaggtgc gcgacgagta cctggtgttc    660

tgcccccgcg agccccgcct ggccttcccc gaggagaaca actcctccct gaagaagatc    720

cccaagctgg aggaccccgc ccagtactcc atgctggagc tgaagccccg ccgcgccgac    780

ctggacatga accagcacgt gaacaacgtg acctacatcg gctgggtgct ggagtccatc    840

ccccaggaga tcatcgacac ccacgagctg caggtgatca ccctggacta ccgccgcgag    900

tgccagcagg acgacatcgt ggactccctg accacctccg agatccccga cgaccccatc    960

tccaagttca ccggcaccaa cggctccgcc atgtcctcca tccagggcca caacgagtcc   1020

cagttcctgc acatgctgcg cctgtccgag aacggccagg agatcaaccg cggccgcacc   1080

cagtggcgca agaagtcctc ccgcatggac tacaaggacc acgacggcga ctacaaggac   1140

cacgacatcg actacaagga cgacgacgac aagtga                             1176


<210> SEQ ID NO 67
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Gln Leu Arg Lys Pro Ala Leu Asp Pro
        35                  40                  45

Leu Arg Ala Val Ile Ser Ala Asp Gln Gly Ser Ile Ser Pro Val Asn
    50                  55                  60
```

Ser Cys Thr Pro Ala Asp Arg Leu Arg Ala Gly Arg Leu Met Glu Asp
65 70 75 80

Gly Tyr Ser Tyr Lys Glu Lys Phe Ile Val Arg Ser Tyr Glu Val Gly
85 90 95

Ile Asn Lys Thr Ala Thr Val Glu Thr Ile Ala Asn Leu Leu Gln Glu
100 105 110

Val Ala Cys Asn His Val Gln Lys Cys Gly Phe Ser Thr Asp Gly Phe
115 120 125

Ala Thr Thr Leu Thr Met Arg Lys Leu His Leu Ile Trp Val Thr Ala
130 135 140

Arg Met His Ile Glu Ile Tyr Lys Tyr Pro Ala Trp Ser Asp Val Val
145 150 155 160

Glu Ile Glu Thr Trp Cys Gln Ser Glu Gly Arg Ile Gly Thr Arg Arg
165 170 175

Asp Trp Ile Leu Arg Asp Ser Ala Thr Asn Glu Val Ile Gly Arg Ala
180 185 190

Thr Ser Lys Trp Val Met Met Asn Gln Asp Thr Arg Arg Leu Gln Arg
195 200 205

Val Thr Asp Glu Val Arg Asp Glu Tyr Leu Val Phe Cys Pro Arg Glu
210 215 220

Pro Arg Leu Ala Phe Pro Glu Glu Asn Asn Ser Ser Leu Lys Lys Ile
225 230 235 240

Pro Lys Leu Glu Asp Pro Ala Gln Tyr Ser Met Leu Glu Leu Lys Pro
245 250 255

Arg Arg Ala Asp Leu Asp Met Asn Gln His Val Asn Asn Val Thr Tyr
260 265 270

Ile Gly Trp Val Leu Glu Ser Ile Pro Gln Glu Ile Ile Asp Thr His
275 280 285

Glu Leu Gln Val Ile Thr Leu Asp Tyr Arg Arg Glu Cys Gln Gln Asp
290 295 300

Asp Ile Val Asp Ser Leu Thr Thr Ser Glu Ile Pro Asp Asp Pro Ile
305 310 315 320

Ser Lys Phe Thr Gly Thr Asn Gly Ser Ala Met Ser Ser Ile Gln Gly
325 330 335

His Asn Glu Ser Gln Phe Leu His Met Leu Arg Leu Ser Glu Asn Gly
340 345 350

Gln Glu Ile Asn Arg Gly Arg Thr Gln Trp Arg Lys Lys Ser Ser Arg
355 360 365

Met Asp Tyr Lys Asp His Asp Gly Asp Tyr Lys Asp His Asp Ile Asp
370 375 380

Tyr Lys Asp Asp Asp Asp Lys
385 390

<210> SEQ ID NO 68
<211> LENGTH: 1155
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
atggccaccg catccacttt ctcggcgttc aatgcccgct gcggcgacct gcgtcgctcg 60
gcgggctccg ggccccggcg cccagcgagg cccctccccg tgcgcgggcg cgccgccacc 120

-continued

```
ggcgagcagc cctccggcgt ggcctccctg cgcgaggccg acaaggagaa gtccctgggc    180

aaccgcctgc gcctgggctc cctgaccgag gacggcctgt cctacaagga gaagttcgtg    240

atccgctgct acgaggtggg catcaacaag accgccacca tcgagaccat cgccaacctg    300

ctgcaggagg tgggcggcaa ccacgcccag ggcgtgggct tctccaccga cggcttcgcc    360

accaccacca ccatgcgcaa gctgcacctg atctgggtga ccgcccgcat gcacatcgag    420

atctaccgct accccgcctg gtccgacgtg atcgagatcg agacctgggt gcagggcgag    480

ggcaaggtgg gcacccgccg cgactggatc ctgaaggact acgccaacgg cgaggtgatc    540

ggccgcgcca cctccaagtg ggtgatgatg aacgaggaca cccgccgcct gcagaaggtg    600

tccgacgacg tgcgcgagga gtacctggtg ttctgccccc gcaccctgcg cctggccttc    660

cccgaggaga acaacaactc catgaagaag atccccaagc tggaggaccc cgccgagtac    720

tcccgcctgg gcctggtgcc ccgccgctcc gacctggaca tgaacaagca cgtgaacaac    780

gtgacctaca tcggctgggc cctggagtcc atcccccccg agatcatcga cacccacgag    840

ctgcaggcca tcaccctgga ctaccgccgc gagtgccagc gcgacgacat cgtggactcc    900

ctgacctccc gcgagcccct gggcaacgcc gccggcgtga agttcaagga gatcaacggc    960

tccgtgtccc ccaagaagga cgagcaggac ctgtcccgct tcatgcacct gctgcgctcc   1020

gccggctccg gcctggagat caaccgctgc cgcaccgagt ggcgcaagaa gcccgccaag   1080

cgcatggact acaaggacca cgacggcgac tacaaggacc acgacatcga ctacaaggac   1140

gacgacgaca agtga                                                     1155
```

<210> SEQ ID NO 69
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ala Thr Gly Glu Gln Pro Ser Gly Val Ala
        35                  40                  45

Ser Leu Arg Glu Ala Asp Lys Glu Lys Ser Leu Gly Asn Arg Leu Arg
    50                  55                  60

Leu Gly Ser Leu Thr Glu Asp Gly Leu Ser Tyr Lys Glu Lys Phe Val
65                  70                  75                  80

Ile Arg Cys Tyr Glu Val Gly Ile Asn Lys Thr Ala Thr Ile Glu Thr
                85                  90                  95

Ile Ala Asn Leu Leu Gln Glu Val Gly Gly Asn His Ala Gln Gly Val
            100                 105                 110

Gly Phe Ser Thr Asp Gly Phe Ala Thr Thr Thr Thr Met Arg Lys Leu
        115                 120                 125

His Leu Ile Trp Val Thr Ala Arg Met His Ile Glu Ile Tyr Arg Tyr
    130                 135                 140

Pro Ala Trp Ser Asp Val Ile Glu Ile Glu Thr Trp Val Gln Gly Glu
145                 150                 155                 160

Gly Lys Val Gly Thr Arg Arg Asp Trp Ile Leu Lys Asp Tyr Ala Asn
                165                 170                 175
```

```
Gly Glu Val Ile Gly Arg Ala Thr Ser Lys Trp Val Met Met Asn Glu
            180                 185                 190

Asp Thr Arg Arg Leu Gln Lys Val Ser Asp Asp Val Arg Glu Glu Tyr
        195                 200                 205

Leu Val Phe Cys Pro Arg Thr Leu Arg Leu Ala Phe Pro Glu Glu Asn
    210                 215                 220

Asn Asn Ser Met Lys Lys Ile Pro Lys Leu Glu Asp Pro Ala Glu Tyr
225                 230                 235                 240

Ser Arg Leu Gly Leu Val Pro Arg Arg Ser Asp Leu Asp Met Asn Lys
                245                 250                 255

His Val Asn Asn Val Thr Tyr Ile Gly Trp Ala Leu Glu Ser Ile Pro
            260                 265                 270

Pro Glu Ile Ile Asp Thr His Glu Leu Gln Ala Ile Thr Leu Asp Tyr
        275                 280                 285

Arg Arg Glu Cys Gln Arg Asp Asp Ile Val Asp Ser Leu Thr Ser Arg
    290                 295                 300

Glu Pro Leu Gly Asn Ala Ala Gly Val Lys Phe Lys Glu Ile Asn Gly
305                 310                 315                 320

Ser Val Ser Pro Lys Lys Asp Glu Gln Asp Leu Ser Arg Phe Met His
                325                 330                 335

Leu Leu Arg Ser Ala Gly Ser Gly Leu Glu Ile Asn Arg Cys Arg Thr
            340                 345                 350

Glu Trp Arg Lys Lys Pro Ala Lys Arg Met Asp Tyr Lys Asp His Asp
        355                 360                 365

Gly Asp Tyr Lys Asp His Asp Ile Asp Tyr Lys Asp Asp Asp Asp Lys
    370                 375                 380
```

<210> SEQ ID NO 70
<211> LENGTH: 1194
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
atgctgaagg tgccctgctg caacgccacc gaccccatcc agtccctgtc ctcccagtgc     60

cgcttcctga cccacttcaa caaccgcccc tacttcaccc gccgcccctc catccccacc    120

ttcttctcct ccaagaactc ctccgcctcc ctgcaggccg tggtgtccga catctcctcc    180

gtggagtccg ccgcctgcga ctccctggcc aaccgcctgc gcctgggcaa gctgaccgag    240

gacggcttct cctacaagga gaagttcatc gtggggcgcg cccgctccta cgaggtgggc    300

atcaacaaga ccgccaccgt ggagaccatc gccaacctgc tgcaggaggt gggctgcaac    360

cacgcccagt ccgtgggctt ctccaccgac ggcttcgcca ccaccacctc catgcgcaag    420

atgcacctga tctgggtgac cgcccgcatg cacatcgaga tctacaagta ccccgcctgg    480

tccgacgtgg tggaggtgga gacctggtgc cagtccgagg gccgcatcgg cacccgccgc    540

gactggatcc tgaccgacta cgccaccggc cagatcatcg gccgcgccac ctccaagtgg    600

gtgatgatga accaggacac ccgccgcctg cagaaggtga ccgacgacgt gcgcgaggag    660

tacctggtgt tctgcccccg cgagctgcgc ctggccttcc ccgaggagaa caaccgctcc    720

tccaagaaga tctccaagct ggaggacccc gcccagtact ccaagctggg cctggtgccc    780

cgccgcgccg acctggacat gaaccagcac gtgaacaacg tgacctacat cggctgggtg    840
```

-continued ctggagtcca tcccccagga gatcatcgac acccacgagc tgcagaccat caccctggac 900
taccgccgcg agtgccagca cgacgacatc gtggactccc tgacctccgt ggagccctcc 960
gagaacctgg aggccgtgtc cgagctgcgc ggcaccaacg gctccgccac caccaccgcc 1020
ggcgacgagg actgccgcaa cttcctgcac ctgctgcgcc tgtccggcga cggcctggag 1080
atcaaccgcg gccgcaccga gtggcgcaag aagtccgccc gcatggacta caaggaccac 1140
gacggcgact acaaggacca cgacatcgac tacaaggacg acgacgacaa gtga 1194

<210> SEQ ID NO 71
<211> LENGTH: 397
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

Met Leu Lys Val Pro Cys Cys Asn Ala Thr Asp Pro Ile Gln Ser Leu
1 5 10 15

Ser Ser Gln Cys Arg Phe Leu Thr His Phe Asn Asn Arg Pro Tyr Phe
20 25 30

Thr Arg Arg Pro Ser Ile Pro Thr Phe Phe Ser Ser Lys Asn Ser Ser
35 40 45

Ala Ser Leu Gln Ala Val Val Ser Asp Ile Ser Ser Val Glu Ser Ala
50 55 60

Ala Cys Asp Ser Leu Ala Asn Arg Leu Arg Leu Gly Lys Leu Thr Glu
65 70 75 80

Asp Gly Phe Ser Tyr Lys Glu Lys Phe Ile Val Gly Arg Ala Arg Ser
85 90 95

Tyr Glu Val Gly Ile Asn Lys Thr Ala Thr Val Glu Thr Ile Ala Asn
100 105 110

Leu Leu Gln Glu Val Gly Cys Asn His Ala Gln Ser Val Gly Phe Ser
115 120 125

Thr Asp Gly Phe Ala Thr Thr Thr Ser Met Arg Lys Met His Leu Ile
130 135 140

Trp Val Thr Ala Arg Met His Ile Glu Ile Tyr Lys Tyr Pro Ala Trp
145 150 155 160

Ser Asp Val Val Glu Val Glu Thr Trp Cys Gln Ser Glu Gly Arg Ile
165 170 175

Gly Thr Arg Arg Asp Trp Ile Leu Thr Asp Tyr Ala Thr Gly Gln Ile
180 185 190

Ile Gly Arg Ala Thr Ser Lys Trp Val Met Met Asn Gln Asp Thr Arg
195 200 205

Arg Leu Gln Lys Val Thr Asp Asp Val Arg Glu Glu Tyr Leu Val Phe
210 215 220

Cys Pro Arg Glu Leu Arg Leu Ala Phe Pro Glu Glu Asn Asn Arg Ser
225 230 235 240

Ser Lys Lys Ile Ser Lys Leu Glu Asp Pro Ala Gln Tyr Ser Lys Leu
245 250 255

Gly Leu Val Pro Arg Arg Ala Asp Leu Asp Met Asn Gln His Val Asn
260 265 270

Asn Val Thr Tyr Ile Gly Trp Val Leu Glu Ser Ile Pro Gln Glu Ile
275 280 285

Ile Asp Thr His Glu Leu Gln Thr Ile Thr Leu Asp Tyr Arg Arg Glu
290 295 300

Cys Gln His Asp Asp Ile Val Asp Ser Leu Thr Ser Val Glu Pro Ser
305 310 315 320

Glu Asn Leu Glu Ala Val Ser Glu Leu Arg Gly Thr Asn Gly Ser Ala
325 330 335

Thr Thr Thr Ala Gly Asp Glu Asp Cys Arg Asn Phe Leu His Leu Leu
340 345 350

Arg Leu Ser Gly Asp Gly Leu Glu Ile Asn Arg Gly Arg Thr Glu Trp
355 360 365

Arg Lys Lys Ser Ala Arg Met Asp Tyr Lys Asp His Asp Gly Asp Tyr
370 375 380

Lys Asp His Asp Ile Asp Tyr Lys Asp Asp Asp Asp Lys
385 390 395

<210> SEQ ID NO 72
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72
atgctgaagc tgtcctcctc ccgctccccc ctggcccgca tccccacccg cccccgcccc 60
aactccatcc ccccccgcat catcgtggtg tcctcctcct cctccaaggt gaaccccctg 120
aagaccgagg ccgtggtgtc ctccggcctg gccgaccgcc tgcgcctggg ctccctgacc 180
gaggacggcc tgtcctacaa ggagaagttc atcgtgcgct gctacgaggt gggcatcaac 240
aagaccgcca ccgtggagac catcgccaac ctgctgcagg aggtgggctg caaccacgcc 300
cagtccgtgg gctactccac cggcggcttc tccaccaccc ccaccatgcg caagctgcgc 360
ctgatctggg tgaccgcccg catgcacatc gagatctaca agtaccccgc ctggtccgac 420
gtggtggaga tcgagtcctg ggccagggc gagggcaaga tcggcacccg ccgcgactgg 480
atcctgcgcg actacgccac cggccaggtg atcggccgcg ccacctccaa gtgggtgatg 540
atgaaccagg acacccgccg cctgcagaag gtggacgtgg acgtgcgcga cgagtacctg 600
gtgcactgcc cccgcgagct gcgcctggcc ttccccgagg agaacaactc ctccctgaag 660
aagatctcca agctggagga cccctcccag tactccaagc tgggcctggt gccccgccgc 720
gccgacctgg acatgaacca gcacgtgaac aacgtgacct acatcggctg ggtgctggag 780
tccatgcccc aggagatcat cgacacccac gagctgcaga ccatcaccct ggactaccgc 840
cgcgagtgcc agcacgacga cgtggtggac tccctgacct cccccgagcc ctccgaggac 900
gccgaggccg tgttcaacca caacggcacc aacggctccg ccaacgtgtc cgccaacgac 960
cacggctgcc gcaacttcct gcacctgctg cgcctgtccg gcaacggcct ggagatcaac 1020
cgcggccgca ccgagtggcg caagaagccc acccgcatgg actacaagga ccacgacggc 1080
gactacaagg accacgacat cgactacaag gacgacgacg acaagtga 1128

<210> SEQ ID NO 73
<211> LENGTH: 375
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

```
Met Leu Lys Leu Ser Ser Ser Arg Ser Pro Leu Ala Arg Ile Pro Thr
1               5                   10                  15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45

Gly Leu Ala Asp Arg Leu Arg Leu Gly Ser Leu Thr Glu Asp Gly Leu
    50                  55                  60

Ser Tyr Lys Glu Lys Phe Ile Val Arg Cys Tyr Glu Val Gly Ile Asn
65                  70                  75                  80

Lys Thr Ala Thr Val Glu Thr Ile Ala Asn Leu Leu Gln Glu Val Gly
                85                  90                  95

Cys Asn His Ala Gln Ser Val Gly Tyr Ser Thr Gly Gly Phe Ser Thr
            100                 105                 110

Thr Pro Thr Met Arg Lys Leu Arg Leu Ile Trp Val Thr Ala Arg Met
        115                 120                 125

His Ile Glu Ile Tyr Lys Tyr Pro Ala Trp Ser Asp Val Val Glu Ile
    130                 135                 140

Glu Ser Trp Gly Gln Gly Glu Gly Lys Ile Gly Thr Arg Arg Asp Trp
145                 150                 155                 160

Ile Leu Arg Asp Tyr Ala Thr Gly Gln Val Ile Gly Arg Ala Thr Ser
                165                 170                 175

Lys Trp Val Met Met Asn Gln Asp Thr Arg Arg Leu Gln Lys Val Asp
            180                 185                 190

Val Asp Val Arg Asp Glu Tyr Leu Val His Cys Pro Arg Glu Leu Arg
        195                 200                 205

Leu Ala Phe Pro Glu Glu Asn Asn Ser Ser Leu Lys Lys Ile Ser Lys
    210                 215                 220

Leu Glu Asp Pro Ser Gln Tyr Ser Lys Leu Gly Leu Val Pro Arg Arg
225                 230                 235                 240

Ala Asp Leu Asp Met Asn Gln His Val Asn Asn Val Thr Tyr Ile Gly
                245                 250                 255

Trp Val Leu Glu Ser Met Pro Gln Glu Ile Ile Asp Thr His Glu Leu
            260                 265                 270

Gln Thr Ile Thr Leu Asp Tyr Arg Arg Glu Cys Gln His Asp Asp Val
        275                 280                 285

Val Asp Ser Leu Thr Ser Pro Glu Pro Ser Glu Asp Ala Glu Ala Val
    290                 295                 300

Phe Asn His Asn Gly Thr Asn Gly Ser Ala Asn Val Ser Ala Asn Asp
305                 310                 315                 320

His Gly Cys Arg Asn Phe Leu His Leu Leu Arg Leu Ser Gly Asn Gly
                325                 330                 335

Leu Glu Ile Asn Arg Gly Arg Thr Glu Trp Arg Lys Lys Pro Thr Arg
            340                 345                 350

Met Asp Tyr Lys Asp His Asp Gly Asp Tyr Lys Asp His Asp Ile Asp
        355                 360                 365

Tyr Lys Asp Asp Asp Asp Lys
    370                 375
```

<210> SEQ ID NO 74
<211> LENGTH: 1197
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74
atgctgaagc tgtcctcctg caacgtgacc gaccagcgcc aggccctggc ccagtgccgc 60
ttcctggccc cccccgcccc cttctccttc cgctggcgca cccccgtggt ggtgtcctgc 120
tccccctcct cccgccccaa cctgtccccc ctgcaggtgg tgctgtccgg ccagcagcag 180
gccggcatgg agctggtgga gtccggctcc ggctccctgg ccgaccgcct gcgcctgggc 240
tccctgaccg aggacggcct gtcctacaag gagaagttca tcgtgcgctg ctacgaggtg 300
ggcatcaaca agaccgccac cgtggagacc atcgccaacc tgctgcagga ggtgggctgc 360
aaccacgccc agtccgtggg ctactccacc gacggcttcg ccaccacccg caccatgcgc 420
aagctgcacc tgatctgggt gaccgcccgc atgcacatcg agatctacaa gtaccccgcc 480
tggtccgacg tgatcgagat cgagacctgg tgccagtccg agggccgcat cggcacccgc 540
cgcgactgga tcctgaagga cttcggcacc ggcgaggtga tcggccgcgc cacctccaag 600
tgggtgatga tgaaccagga cacccgccgc ctgcagaagg tgtccgacga cgtgcgcgag 660
gagtacctgg tgttctgccc ccgcgagctg cgcctggcct tccccgagga gaacaacaac 720
tccctgaaga agatcgccaa gctggacgac tccttccagt actcccgcct gggcctgatg 780
ccccgccgcg ccgacctgga catgaaccag cacgtgaaca acgtgaccta catcggctgg 840
gtgctggagt ccatgcccca ggagatcatc gacacccacg agctgcagac catcaccctg 900
gactaccgcc gcgagtgcca gcaggacgac gtggtggact ccctgacctc ccccgagcag 960
gtggagggca ccgagaaggt gtccgccatc cacggcacca acggctccgc cgccgcccgc 1020
gaggacaagc aggactgccg ccagttcctg cacctgctgc gcctgtcctc cgacggccag 1080
gagatcaacc gcggccgcac cgagtggcgc aagaagcccg cccgcatgga ctacaaggac 1140
cacgacggcg actacaagga ccacgacatc gactacaagg acgacgacga caagtga 1197

<210> SEQ ID NO 75
<211> LENGTH: 398
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

Met Leu Lys Leu Ser Ser Cys Asn Val Thr Asp Gln Arg Gln Ala Leu
1 5 10 15

Ala Gln Cys Arg Phe Leu Ala Pro Pro Ala Pro Phe Ser Phe Arg Trp
20 25 30

Arg Thr Pro Val Val Val Ser Cys Ser Pro Ser Ser Arg Pro Asn Leu
35 40 45

Ser Pro Leu Gln Val Val Leu Ser Gly Gln Gln Gln Ala Gly Met Glu
50 55 60

Leu Val Glu Ser Gly Ser Gly Ser Leu Ala Asp Arg Leu Arg Leu Gly
65 70 75 80

Ser Leu Thr Glu Asp Gly Leu Ser Tyr Lys Glu Lys Phe Ile Val Arg
85 90 95

Cys Tyr Glu Val Gly Ile Asn Lys Thr Ala Thr Val Glu Thr Ile Ala
100 105 110

Asn Leu Leu Gln Glu Val Gly Cys Asn His Ala Gln Ser Val Gly Tyr
115 120 125

```
Ser Thr Asp Gly Phe Ala Thr Thr Arg Thr Met Arg Lys Leu His Leu
    130                 135                 140

Ile Trp Val Thr Ala Arg Met His Ile Glu Ile Tyr Lys Tyr Pro Ala
145                 150                 155                 160

Trp Ser Asp Val Ile Glu Ile Glu Thr Trp Cys Gln Ser Glu Gly Arg
                165                 170                 175

Ile Gly Thr Arg Arg Asp Trp Ile Leu Lys Asp Phe Gly Thr Gly Glu
            180                 185                 190

Val Ile Gly Arg Ala Thr Ser Lys Trp Val Met Met Asn Gln Asp Thr
        195                 200                 205

Arg Arg Leu Gln Lys Val Ser Asp Asp Val Arg Glu Glu Tyr Leu Val
    210                 215                 220

Phe Cys Pro Arg Glu Leu Arg Leu Ala Phe Pro Glu Glu Asn Asn Asn
225                 230                 235                 240

Ser Leu Lys Lys Ile Ala Lys Leu Asp Asp Ser Phe Gln Tyr Ser Arg
                245                 250                 255

Leu Gly Leu Met Pro Arg Arg Ala Asp Leu Asp Met Asn Gln His Val
            260                 265                 270

Asn Asn Val Thr Tyr Ile Gly Trp Val Leu Glu Ser Met Pro Gln Glu
        275                 280                 285

Ile Ile Asp Thr His Glu Leu Gln Thr Ile Thr Leu Asp Tyr Arg Arg
    290                 295                 300

Glu Cys Gln Gln Asp Asp Val Val Asp Ser Leu Thr Ser Pro Glu Gln
305                 310                 315                 320

Val Glu Gly Thr Glu Lys Val Ser Ala Ile His Gly Thr Asn Gly Ser
                325                 330                 335

Ala Ala Ala Arg Glu Asp Lys Gln Asp Cys Arg Gln Phe Leu His Leu
            340                 345                 350

Leu Arg Leu Ser Ser Asp Gly Gln Glu Ile Asn Arg Gly Arg Thr Glu
        355                 360                 365

Trp Arg Lys Lys Pro Ala Arg Met Asp Tyr Lys Asp His Asp Gly Asp
    370                 375                 380

Tyr Lys Asp His Asp Ile Asp Tyr Lys Asp Asp Asp Asp Lys
385                 390                 395
```

<210> SEQ ID NO 76
<211> LENGTH: 573
<212> TYPE: DNA
<213> ORGANISM: Prototheca moriformis

<400> SEQUENCE: 76

```
tgttgaagaa tgagccggcg acttaaaata aatggcaggc taagagaatt aataactcga     60

aacctaagcg aaagcaagtc ttaatagggc gctaatttaa caaaacatta aataaaatct    120

aaagtcattt attttagacc cgaacctgag tgatctaacc atggtcagga tgaaacttgg    180

gtgacaccaa gtggaagtcc gaaccgaccg atgttgaaaa atcggcggat gaactgtggt    240

tagtggtgaa ataccagtcg aactcagagc tagctggttc tccccgaaat gcgttgaggc    300

gcagcaatat atctcgtcta tctaggggta aagcactgtt tcggtgcggg ctatgaaaat    360

ggtaccaaat cgtggcaaac tctgaatact agaaatgacg atatattagt gagactatgg    420

gggataagct ccatagtcga gagggaaaca gcccagacca ccagttaagg ccccaaaatg    480

ataatgaagt ggtaaaggag gtgaaaatgc aaatacaacc aggaggttgg cttagaagca    540

gccatccttt aaagagtgcg taatagctca ctg                                  573
```

<210> SEQ ID NO 77
<211> LENGTH: 384
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Met Ala Ile Ala Ala Ala Ala Val Ile Phe Leu Phe Gly Leu Ile Phe
1               5                   10                  15

Phe Ala Ser Gly Leu Ile Ile Asn Leu Phe Gln Ala Leu Cys Phe Val
            20                  25                  30

Leu Ile Arg Pro Leu Ser Lys Asn Ala Tyr Arg Arg Ile Asn Arg Val
        35                  40                  45

Phe Ala Glu Leu Leu Leu Ser Glu Leu Leu Cys Leu Phe Asp Trp Trp
    50                  55                  60

Ala Gly Ala Lys Leu Lys Leu Phe Thr Asp Pro Glu Thr Phe Arg Leu
65                  70                  75                  80

Met Gly Lys Glu His Ala Leu Val Ile Ile Asn His Met Thr Glu Leu
                85                  90                  95

Asp Trp Met Val Gly Trp Val Met Gly Gln His Phe Gly Cys Leu Gly
            100                 105                 110

Ser Ile Ile Ser Val Ala Lys Lys Ser Thr Lys Phe Leu Pro Val Leu
        115                 120                 125

Gly Trp Ser Met Trp Phe Ser Glu Tyr Leu Tyr Leu Glu Arg Ser Trp
    130                 135                 140

Ala Lys Asp Lys Ser Thr Leu Lys Ser His Ile Glu Arg Leu Ile Asp
145                 150                 155                 160

Tyr Pro Leu Pro Phe Trp Leu Val Ile Phe Val Glu Gly Thr Arg Phe
                165                 170                 175

Thr Arg Thr Lys Leu Leu Ala Ala Gln Gln Tyr Ala Val Ser Ser Gly
            180                 185                 190

Leu Pro Val Pro Arg Asn Val Leu Ile Pro Arg Thr Lys Gly Phe Val
        195                 200                 205

Ser Cys Val Ser His Met Arg Ser Phe Val Pro Ala Val Tyr Asp Val
    210                 215                 220

Thr Val Ala Phe Pro Lys Thr Ser Pro Pro Pro Thr Leu Leu Asn Leu
225                 230                 235                 240

Phe Glu Gly Gln Ser Ile Met Leu His Val His Ile Lys Arg His Ala
                245                 250                 255

Met Lys Asp Leu Pro Glu Ser Asp Asp Ala Val Ala Glu Trp Cys Arg
            260                 265                 270

Asp Lys Phe Val Glu Lys Asp Ala Leu Leu Asp Lys His Asn Ala Glu
        275                 280                 285

Asp Thr Phe Ser Gly Gln Glu Val Cys His Ser Gly Ser Arg Gln Leu
    290                 295                 300

Lys Ser Leu Leu Val Val Ile Ser Trp Val Val Val Thr Thr Phe Gly
305                 310                 315                 320

Ala Leu Lys Phe Leu Gln Trp Ser Ser Trp Lys Gly Lys Ala Phe Ser
                325                 330                 335

Ala Ile Gly Leu Gly Ile Val Thr Leu Leu Met His Val Leu Ile Leu
            340                 345                 350

Ser Ser Gln Ala Glu Arg Ser Asn Pro Ala Glu Val Ala Gln Ala Lys
        355                 360                 365
```

```
Leu Lys Thr Gly Leu Ser Ile Ser Lys Lys Val Thr Asp Lys Glu Asn
    370                 375                 380


<210> SEQ ID NO 78
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Ala Ile Ala Ala Ala Ala Val Ile Val Pro Leu Ser Leu Leu Phe
1               5                   10                  15

Phe Val Ser Gly Leu Ile Val Asn Leu Val Gln Ala Val Cys Phe Val
            20                  25                  30

Leu Ile Arg Pro Leu Ser Lys Asn Thr Tyr Arg Arg Ile Asn Arg Val
        35                  40                  45

Val Ala Glu Leu Leu Trp Leu Glu Leu Val Trp Leu Ile Asp Trp Trp
    50                  55                  60

Ala Gly Val Lys Ile Lys Val Phe Thr Asp His Glu Thr Phe His Leu
65                  70                  75                  80

Met Gly Lys Glu His Ala Leu Val Ile Cys Asn His Lys Ser Asp Ile
                85                  90                  95

Asp Trp Leu Val Gly Trp Val Leu Gly Gln Arg Ser Gly Cys Leu Gly
            100                 105                 110

Ser Thr Leu Ala Val Met Lys Lys Ser Ser Lys Phe Leu Pro Val Leu
        115                 120                 125

Gly Trp Ser Met Trp Phe Ser Glu Tyr Leu Phe Leu Glu Arg Ser Trp
    130                 135                 140

Ala Lys Asp Glu Ile Thr Leu Lys Ser Gly Leu Asn Arg Leu Lys Asp
145                 150                 155                 160

Tyr Pro Leu Pro Phe Trp Leu Ala Leu Phe Val Glu Gly Thr Arg Phe
                165                 170                 175

Thr Arg Ala Lys Leu Leu Ala Ala Gln Gln Tyr Ala Ala Ser Ser Gly
            180                 185                 190

Leu Pro Val Pro Arg Asn Val Leu Ile Pro Arg Thr Lys Gly Phe Val
        195                 200                 205

Ser Ser Val Ser His Met Arg Ser Phe Val Pro Ala Ile Tyr Asp Val
    210                 215                 220

Thr Val Ala Ile Pro Lys Thr Ser Pro Pro Pro Thr Leu Ile Arg Met
225                 230                 235                 240

Phe Lys Gly Gln Ser Ser Val Leu His Val His Leu Lys Arg His Leu
                245                 250                 255

Met Lys Asp Leu Pro Glu Ser Asp Asp Ala Val Ala Gln Trp Cys Arg
            260                 265                 270

Asp Ile Phe Val Glu Lys Asp Ala Leu Leu Asp Lys His Asn Ala Glu
        275                 280                 285

Asp Thr Phe Ser Gly Gln Glu Leu Gln Glu Thr Gly Arg Pro Ile Lys
    290                 295                 300

Ser Leu Leu Val Val Ile Ser Trp Ala Val Leu Glu Val Phe Gly Ala
305                 310                 315                 320

Val Lys Phe Leu Gln Trp Ser Ser Leu Leu Ser Ser Trp Lys Gly Leu
                325                 330                 335

Ala Phe Ser Gly Ile Gly Leu Gly Val Ile Thr Leu Leu Met His Ile
```

```
            340                 345                 350

Leu Ile Leu Phe Ser Gln Ser Glu Arg Ser Thr Pro Ala Lys Val Ala
        355                 360                 365

Pro Ala Lys Pro Lys Asn Glu Gly Glu Ser Ser Lys Thr Glu Met Glu
    370                 375                 380

Lys Glu Lys
385


<210> SEQ ID NO 79
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Glu Ile Pro Pro His Cys Leu Cys Ser Pro Ser Pro Ala Pro Ser
1               5                   10                  15

Gln Leu Tyr Tyr Lys Lys Lys Lys His Ala Ile Leu Gln Thr Gln Thr
            20                  25                  30

Pro Tyr Arg Tyr Arg Val Ser Pro Thr Cys Phe Ala Pro Pro Arg Leu
        35                  40                  45

Arg Lys Gln His Pro Tyr Pro Leu Pro Val Leu Cys Tyr Pro Lys Leu
    50                  55                  60

Leu His Phe Ser Gln Pro Arg Tyr Pro Leu Val Arg Ser His Leu Ala
65                  70                  75                  80

Glu Ala Gly Val Ala Tyr Arg Pro Gly Tyr Glu Leu Leu Gly Lys Ile
                85                  90                  95

Arg Gly Val Cys Phe Tyr Ala Val Thr Ala Ala Val Ala Leu Leu Leu
            100                 105                 110

Phe Gln Cys Met Leu Leu Leu His Pro Phe Val Leu Leu Phe Asp Pro
        115                 120                 125

Phe Pro Arg Lys Ala His His Thr Ile Ala Lys Leu Trp Ser Ile Cys
    130                 135                 140

Ser Val Ser Leu Phe Tyr Lys Ile His Ile Lys Gly Leu Glu Asn Leu
145                 150                 155                 160

Pro Pro Pro His Ser Pro Ala Val Tyr Val Ser Asn His Gln Ser Phe
                165                 170                 175

Leu Asp Ile Tyr Thr Leu Leu Thr Leu Gly Arg Thr Phe Lys Phe Ile
            180                 185                 190

Ser Lys Thr Glu Ile Phe Leu Tyr Pro Ile Ile Gly Trp Ala Met Tyr
        195                 200                 205

Met Leu Gly Thr Ile Pro Leu Lys Arg Leu Asp Ser Arg Ser Gln Leu
    210                 215                 220

Asp Thr Leu Lys Arg Cys Met Asp Leu Ile Lys Lys Gly Ala Ser Val
225                 230                 235                 240

Phe Phe Phe Pro Glu Gly Thr Arg Ser Lys Asp Gly Lys Leu Gly Ala
                245                 250                 255

Phe Lys Lys Gly Ala Phe Ser Ile Ala Ala Lys Ser Lys Val Pro Val
            260                 265                 270

Val Pro Ile Thr Leu Ile Gly Thr Gly Lys Ile Met Pro Pro Gly Ser
        275                 280                 285

Glu Leu Thr Val Asn Pro Gly Thr Val Gln Val Ile Ile His Lys Pro
    290                 295                 300
```

-continued

Ile Glu Gly Ser Asp Ala Glu Ala Met Cys Asn Glu Ala Arg Ala Thr
305 310 315 320

Ile Ser His Ser Leu Asp Asp
325

<210> SEQ ID NO 80
<211> LENGTH: 984
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80
atggagatcc cgcctcactg tctctgttcg ccttcgcctg cgccttcgca attgtattac 60
aagaagaaga agcatgccat tctccaaact caaactccct atagatatag agtttccccg 120
acatgctttg cccccccccg attgaggaag cagcatcctt accctctccc tgtcctctgc 180
tatccaaaac tcctccactt cagccagcct aggtaccctc tggttagatc tcatttggct 240
gaagctggtg ttgcttatcg tccaggatac gaattattag gaaaaataag gggagtgtgt 300
ttctatgctg tcactgctgc cgttgccttg cttctatttc agtgcatgct cctcctccat 360
ccctttgtgc tcctcttcga tccatttcca agaaaggctc accataccat cgccaaactc 420
tggtctatct gctctgtttc tctttttac aagattcaca tcaagggttt ggaaaatctt 480
cccccacccc actctcctgc cgtctatgtc tctaatcatc agagttttct cgacatctat 540
actctcctca ctctcggtag aaccttcaag ttcatcagca agactgagat ctttctctat 600
ccaattatcg gttgggccat gtatatgttg ggtaccattc ctctcaagcg gttggacagc 660
agaagccaat tggacactct taagcgatgt atggatctca tcaagaaggg agcatccgtc 720
tttttcttcc cagagggaac acgaagtaaa gatgggaaac tgggtgcttt caagaaaggt 780
gcattcagca tcgcagcaaa aagcaaggtt cctgttgtgc cgatcaccct tattggaact 840
ggcaagatta tgccacctgg gagcgaactt actgtcaatc caggaactgt gcaagtaatc 900
atacataaac ctatcgaagg aagtgatgca gaagcaatgt gcaatgaagc tagagccacg 960
atttctcact cacttgatga ttaa 984

<210> SEQ ID NO 81
<211> LENGTH: 1155
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
atggcgattg cagcggcagc tgtcatcttc ctcttcggcc ttatcttctt cgcctccggc 60
ctcataatca atctcttcca ggcgctttgc tttgtcctta ttcggcctct ttcgaaaaac 120
gcctacmgga gaataaacag agtttttgca gaattgttgt tgtcggagct tttatgccta 180
ttcgattggt gggctggtgc taagctcaaa ttatttaccg accctgaaac ctttcgcctt 240
atgggcaagg aacatgctct tgtcataatt aatcacatga ctgaacttga ctggatggtt 300
ggatgggtta tgggtcagca ttttggttgc cttgggagca taatatctgt tgcgaagaaa 360
tcaacaaaat ttcttccggt attggggtgg tcaatgtggt tttcagagta cctatatctt 420
gagagaagct gggccaagga taaaagtaca ttaaagtcac atatcgagag gctgatagac 480
taccccctgc ccttctggtt ggtaattttt gtggaaggaa ctcggtttac tcggacaaaa 540
ctcttggcag cccagcagta tgctgtctca tctgggctac cagtgccgag aaatgttttg 600
atcccacgta ctaagggttt tgtttcatgt gtaagtcaca tgcgatcatt tgttccagca 660
gtatatgatg tcacagtggc attccctaag acttcacctc caccaacgtt gctaaatctt 720
ttcgagggtc agtccataat gcttcacgtt cacatcaagc gacatgcaat gaaagattta 780
ccagaatccg atgatgcagt agcagagtgg tgtagagaca aatttgtgga aaaggatgct 840
ttgttggaca agcataatgc tgaggacact ttcagtggtc aagaagtttg tcatagcggc 900
agccgccagt taaagtctct tctggtggta atatcttggg tggttgtaac aacatttggg 960
gctctaaagt tccttcagtg gtcatcatgg aaggggaaag cattttcagc tatcgggctg 1020
ggcatcgtca ctctacttat gcacgtattg attctatcct cacaagcaga gcggtctaac 1080
cctgcggagg tggcacaggc aaagctaaag accgggttgt cgatctcaaa gaaggtaacg 1140
gacaaggaaa actag 1155

<210> SEQ ID NO 82
<211> LENGTH: 1164
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82
atggcgattg ctgcggcagc tgtcatcgtc ccgctcagcc tcctcttctt cgtctccggc 60
ctcatcgtca atctcgtaca ggcagtttgc tttgtactga ttaggcctct gtcgaaaaac 120
acttacagaa gaataaacag agtggttgca gaattgttgt ggttggagtt ggtatggctg 180
attgattggt gggctggtgt caagataaaa gtattcacgg atcatgaaac ctttcacctt 240
atgggcaaag aacatgctct tgtcatttgt aatcacaaga gtgacataga ctggctggtt 300
gggtgggttc tgggacagcg gtcaggttgc cttggaagca cattagctgt tatgaagaaa 360
tcatcaaagt ttctcccggt attagggtgg tcaatgtggt tctcagagta tctattcctt 420
gaaagaagct gggccaagga tgaaattaca ttaaagtcag gtttgaatag gctgaaagac 480
tatcccttac ccttctggtt ggcacttttt gtggaaggaa ctcggttcac tcgagcaaaa 540
ctcttggcag cccagcagta tgctgcctct tcggggctac ctgtgccgag aaatgttctg 600
atcccgcgta ctaagggttt tgtttcttct gtgagtcaca tgcgatcatt tgttccagcc 660
atatatgatg ttacagtggc aatcccaaag acgtcacctc caccaacatt gataagaatg 720
ttcaagggac agtcctcagt gcttcacgtc cacctcaagc gacacctaat gaaagattta 780
cctgaatcag atgatgctgt tgctcagtgg tgcagagata tattcgtcga gaaggatgct 840
ttgttggata agcataatgc tgaggacact ttcagtggcc aagaacttca agaaactggc 900
cgcccaataa agtctcttct ggttgtaatc tcttgggcgg tgttggaggt atttggagct 960
gtgaagtttc ttcaatggtc atcgctgtta tcatcatgga agggacttgc attttcggga 1020
ataggactgg gtgtcatcac gctactcatg cacatactga ttttattctc acaatccgag 1080
cggtctaccc ctgcaaaagt ggcaccagca aagccaaaga atgagggaga gtcctccaag 1140
acggaaatgg aaaaggaaaa gtag 1164

<210> SEQ ID NO 83
<211> LENGTH: 984
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atggagatcc ccccccactg cctgtgctcc ccctccccg cccctccca gctgtactac 60 aagaagaaga agcacgccat cctgcagacc cagacccct accgctaccg cgtgtcccc 120 acctgcttcg cccccccccg cctgcgcaag cagcacccct accccctgcc cgtgctgtgc 180
taccccaagc tgctgcactt ctcccagccc cgctaccccc tggtgcgctc ccacctggcc 240
gaggccggcg tggcctaccg ccccggctac gagctgctgg gcaagatccg cggcgtgtgc 300
ttctacgccg tgaccgccgc cgtggccctg ctgctgttcc agtgcatgct gctgctgcac 360
cccttcgtgc tgctgttcga ccccttcccc cgcaaggccc accacaccat cgccaagctg 420
tggtccatct gctccgtgtc cctgttctac aagatccaca tcaagggcct ggagaacctg 480 ccccccccc actcccccgc cgtgtacgtg tccaaccacc agtccttcct ggacatctac 540
accctgctga ccctgggccg caccttcaag ttcatctcca agaccgagat cttcctgtac 600
cccatcatcg gctgggccat gtacatgctg ggcaccatcc ccctgaagcg cctggactcc 660
cgctcccagc tggacaccct gaagcgctgc atggacctga tcaagaaggg cgcctccgtg 720
ttcttcttcc ccgagggcac ccgctccaag gacggcaagc tgggcgcctt caagaagggc 780
gccttctcca tcgccgccaa gtccaaggtg cccgtggtgc ccatcaccct gatcggcacc 840
ggcaagatca tgccccccgg ctccgagctg accgtgaacc ccggcaccgt gcaggtgatc 900
atccacaagc ccatcgaggg ctccgacgcc gaggccatgt gcaacgaggc ccgcgccacc 960
atctcccact ccctggacga ctga 984

<210> SEQ ID NO 84
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
atggcgatcg cggccgcggc ggtgatcttc ctgttcggcc tgatcttctt cgcctccggc 60
ctgatcatca acctgttcca ggcgctgtgc ttcgtcctga tccgccccct gtccaagaac 120
gcctaccgcc gcatcaaccg cgtgttcgcg gagctgctgc tgtccgagct gctgtgcctg 180
ttcgactggt gggcgggcgc gaagctgaag ctgttcaccg accccgagac gttccgcctg 240
atgggcaagg agcacgccct ggtcatcatc aaccacatga ccgagctgga ctggatggtg 300
ggctgggtga tgggccagca cttcggctgc ctgggctcca tcatctccgt cgccaagaag 360
tccacgaagt tcctgcccgt gctgggctgg tccatgtggt tctccgagta cctgtacctg 420
gagcgctcct gggccaagga caagtccacc ctgaagtccc acatcgagcg cctgatcgac 480
taccccctgc ccttctggct ggtcatcttc gtcgagggca cccgcttcac gcgcacgaag 540
ctgctggcgg cccagcagta cgcggtctcc tccggcctgc ccgtcccccg caacgtcctg 600
atcccccgca cgaagggctt cgtctcctgc gtgtcccaca tgcgctcctt cgtccccgcg 660
gtgtacgacg tcacggtggc gttccccaag acgtcccccc cccccacgct gctgaacctg 720
ttcgagggcc agtccatcat gctgcacgtg cacatcaagc gccacgccat gaaggacctg 780
cccgagtccg acgacgccgt cgcggagtgg tgccgcgaca agttcgtcga gaaggacgcc 840

```
ctgctggaca agcacaacgc ggaggacacg ttctccggcc aggaggtgtg ccactccggc    900

tcccgccagc tgaagtccct gctggtcgtg atctcctggg tcgtggtgac gacgttcggc    960

gccctgaagt tcctgcagtg gtcctcctgg aagggcaagg cgttctccgc catcggcctg   1020

ggcatcgtca ccctgctgat gcacgtgctg atcctgtcct cccaggccga gcgctccaac   1080

cccgccgagg tggcccaggc caagctgaag accggcctgt ccatctccaa gaaggtgacg   1140

gacaaggaga actga                                                    1155
```

<210> SEQ ID NO 85
<211> LENGTH: 1164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
atggccatcg cggcggccgc ggtgatcgtg cccctgtccc tgctgttctt cgtgtccggc     60

ctgatcgtca acctggtgca ggccgtctgc ttcgtcctga tccgccccct gtccaagaac    120

acgtaccgcc gcatcaaccg cgtggtcgcg gagctgctgt ggctggagct ggtgtggctg    180

atcgactggt gggcgggcgt gaagatcaag gtcttcacgg accacgagac gttccacctg    240

atgggcaagg agcacgccct ggtcatctgc aaccacaagt ccgacatcga ctggctggtc    300

ggctgggtcc tgggccagcg ctccggctgc ctgggctcca ccctggcggt catgaagaag    360

tcctccaagt tcctgcccgt cctgggctgg tccatgtggt tctccgagta cctgttcctg    420

gagcgctcct gggccaagga cgagatcacg ctgaagtccg gcctgaaccg cctgaaggac    480

taccccctgc ccttctggct ggcgctgttc gtggagggca cgcgcttcac ccgcgcgaag    540

ctgctggcgg cgcagcagta cgccgcgtcc tccggcctgc ccgtgccccg caacgtgctg    600

atcccccgca cgaagggctt cgtgtcctcc gtgtcccaca tgcgctcctt cgtgcccgcg    660

atctacgacg tcaccgtggc catccccaag acgtcccccc cccccacgct gatccgcatg    720

ttcaagggcc agtcctccgt gctgcacgtg cacctgaagc gccacctgat gaaggacctg    780

cccgagtccg acgacgccgt cgcgcagtgg tgccgcgaca tcttcgtgga gaaggacgcg    840

ctgctggaca agcacaacgc cgaggacacc ttctccggcc aggagctgca ggagaccggc    900

cgccccatca agtccctgct ggtcgtcatc tcctgggccg tcctggaggt gttcggcgcc    960

gtcaagttcc tgcagtggtc ctccctgctg tcctcctgga agggcctggc gttctccggc   1020

atcggcctgg gcgtgatcac cctgctgatg cacatcctga tcctgttctc ccagtccgag   1080

cgctccaccc ccgccaaggt ggcccccgcg aagcccaaga acgagggcga gtcctccaag   1140

accgagatgg agaaggagaa gtga                                          1164
```

<210> SEQ ID NO 86
<211> LENGTH: 1098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
gcgcacccca aggcgaacgg cagcgcggtg tcgctgaagt cgggctccct ggagacccag     60

gaggacaaga cgagcagctc gtcccccccc ccccgcacgt tcatcaacca gctgcccgtg    120

tggagcatgc tgctgtcggc ggtgaccacg gtcttcggcg tggccgagaa gcagtggccc    180
```

```
atgctggacc gcaagtccaa gcgccccgac atgctggtcg agcccctggg cgtggaccgc    240

atcgtctacg acggcgtgag cttccgccag tcgttctcca tccgcagcta cgagatcggc    300

gccgaccgca ccgcctcgat cgagacgctg atgaacatgt tccaggagac ctccctgaac    360

cactgcaaga tcatcggcct gctgaacgac ggcttcggcc gcacgcccga gatgtgcaag    420

cgcgacctga tctgggtcgt gaccaagatg cagatcgagg tgaaccgcta ccccacgtgg    480

ggcgacacca tcgaggtcaa cacgtgggtg agcgcctcgg gcaagcacgg catgggccgc    540

gactggctga tctccgactg ccacaccggc gagatcctga tccgcgcgac gagcgtctgg    600

gcgatgatga accagaagac ccgccgcctg tcgaagatcc cctacgaggt gcgccaggag    660

atcgagcccc agttcgtcga ctccgccccc gtgatcgtgg acgaccgcaa gttccacaag    720

ctggacctga agacgggcga cagcatctgc aacggcctga ccccccgctg gacggacctg    780

gacgtgaacc agcacgtcaa caacgtgaag tacatcggct ggatcctgca gtcggtcccc    840

accgaggtgt tcgagacgca ggagctgtgc ggcctgaccc tggagtaccg ccgcgagtgc    900

ggccgcgact ccgtgctgga gagcgtcacg gccatggacc cctcgaagga gggcgaccgc    960

tccctgtacc agcacctgct gcgcctggag gacggcgcgg acatcgtgaa gggccgcacc   1020

gagtggcgcc ccaagaacgc cggcgccaag ggcgccatcc tgacgggcaa gaccagcaac   1080

ggcaactcga tctcctga                                                 1098
```

```
<210> SEQ ID NO 87
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30

Thr Phe Ile Asn Gln Leu Pro Val Trp Ser Met Leu Leu Ser Ala Val
        35                  40                  45

Thr Thr Val Phe Gly Val Ala Glu Lys Gln Trp Pro Met Leu Asp Arg
    50                  55                  60

Lys Ser Lys Arg Pro Asp Met Leu Val Glu Pro Leu Gly Val Asp Arg
65                  70                  75                  80

Ile Val Tyr Asp Gly Val Ser Phe Arg Gln Ser Phe Ser Ile Arg Ser
                85                  90                  95

Tyr Glu Ile Gly Ala Asp Arg Thr Ala Ser Ile Glu Thr Leu Met Asn
            100                 105                 110

Met Phe Gln Glu Thr Ser Leu Asn His Cys Lys Ile Ile Gly Leu Leu
        115                 120                 125

Asn Asp Gly Phe Gly Arg Thr Pro Glu Met Cys Lys Arg Asp Leu Ile
    130                 135                 140

Trp Val Val Thr Lys Met Gln Ile Glu Val Asn Arg Tyr Pro Thr Trp
145                 150                 155                 160

Gly Asp Thr Ile Glu Val Asn Thr Trp Val Ser Ala Ser Gly Lys His
                165                 170                 175

Gly Met Gly Arg Asp Trp Leu Ile Ser Asp Cys His Thr Gly Glu Ile
            180                 185                 190
```

Leu Ile Arg Ala Thr Ser Val Trp Ala Met Met Asn Gln Lys Thr Arg
        195                 200                 205

Arg Leu Ser Lys Ile Pro Tyr Glu Val Arg Gln Glu Ile Glu Pro Gln
    210                 215                 220

Phe Val Asp Ser Ala Pro Val Ile Val Asp Asp Arg Lys Phe His Lys
225                 230                 235                 240

Leu Asp Leu Lys Thr Gly Asp Ser Ile Cys Asn Gly Leu Thr Pro Arg
                245                 250                 255

Trp Thr Asp Leu Asp Val Asn Gln His Val Asn Asn Val Lys Tyr Ile
            260                 265                 270

Gly Trp Ile Leu Gln Ser Val Pro Thr Glu Val Phe Glu Thr Gln Glu
        275                 280                 285

Leu Cys Gly Leu Thr Leu Glu Tyr Arg Arg Glu Cys Gly Arg Asp Ser
    290                 295                 300

Val Leu Glu Ser Val Thr Ala Met Asp Pro Ser Lys Glu Gly Asp Arg
305                 310                 315                 320

Ser Leu Tyr Gln His Leu Leu Arg Leu Glu Asp Gly Ala Asp Ile Val
                325                 330                 335

Lys Gly Arg Thr Glu Trp Arg Pro Lys Asn Ala Gly Ala Lys Gly Ala
            340                 345                 350

Ile Leu Thr Gly Lys Thr Ser Asn Gly Asn Ser Ile Ser
        355                 360                 365

<210> SEQ ID NO 88
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gcgcacccca aggcgaacgg cagcgcggtg tcgctgaagt cgggctccct ggagacccag 60
gaggacaaga cgagcagctc gtcccccccc ccccgcacgt tcatcaacca gctgcccgtg 120
tggagcatgc tgctgtcggc ggtgaccacg gtcttcggcg tggccgagaa gcagtggccc 180
atgctggacc gcaagtccaa gcgccccgac atgctggtcg agcccctggg cgtggaccgc 240
atcgtctacg acggcgtgag cttccgccag tcgttctcca tccgcagcta cgagatcggc 300
gccgaccgca ccgcctcgat cgagacgctg atgaacatgt tccaggagac ctccctgaac 360
cactgcaaga tcatcggcct gctgaacgac ggcttcggcc gcacgcccga gatgtgcaag 420
cgcgacctga tctgggtcgt gaccaagatg cagatcgagg tgaaccgcta ccccacgtgg 480
ggcgacacca tcgaggtcaa cacgtgggtg agcgcctcgg gcaagcacgg catgggccgc 540
gactggctga tctccgactg ccacaccggc gagatcctga tccgcgcgac gagcgtctgg 600
gcgatgatga accagaagac ccgccgcctg tcgaagatcc cctacgaggt gcgccaggag 660
atcgagcccc agttcgtcga ctccgccccc gtgatcgtgg acgaccgcaa gttccacaag 720
ctggacctga agacgggcga cagcatctgc aacggcctga ccccccgctg gacggacctg 780
gacgtgaacc agcacgtcaa caacgtgaag tacatcggct ggatcctgca gtcggtcccc 840
accgaggtgt tcgagacgca ggagctgtgc ggcctgaccc tggagtaccg ccgcgagtgc 900
ggccgcgact ccgtgctgga gagcgtcacg gccatggacc cctcgaagga gggcgaccgc 960
tccctgtacc agcacctgct gcgcctggag gacggcgcgg acatcgtgaa gggccgcacc 1020
gagtggcgcc ccaagaacgc cggcgccaag ggcgccatcc tgacgggcaa gaccagcaac 1080
ggcaactcga tctccatgga ctacaaggac cacgacggcg actacaagga ccacgacatc 1140
gactacaagg acgacgacga caagtga 1167

<210> SEQ ID NO 89
<211> LENGTH: 388
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Ala His Pro Lys Ala Asn Gly Ser Ala Val Ser Leu Lys Ser Gly Ser
1 5 10 15

Leu Glu Thr Gln Glu Asp Lys Thr Ser Ser Ser Ser Pro Pro Pro Arg
20 25 30

Thr Phe Ile Asn Gln Leu Pro Val Trp Ser Met Leu Leu Ser Ala Val
35 40 45

Thr Thr Val Phe Gly Val Ala Glu Lys Gln Trp Pro Met Leu Asp Arg
50 55 60

Lys Ser Lys Arg Pro Asp Met Leu Val Glu Pro Leu Gly Val Asp Arg
65 70 75 80

Ile Val Tyr Asp Gly Val Ser Phe Arg Gln Ser Phe Ser Ile Arg Ser
85 90 95

Tyr Glu Ile Gly Ala Asp Arg Thr Ala Ser Ile Glu Thr Leu Met Asn
100 105 110

Met Phe Gln Glu Thr Ser Leu Asn His Cys Lys Ile Ile Gly Leu Leu
115 120 125

Asn Asp Gly Phe Gly Arg Thr Pro Glu Met Cys Lys Arg Asp Leu Ile
130 135 140

Trp Val Val Thr Lys Met Gln Ile Glu Val Asn Arg Tyr Pro Thr Trp
145 150 155 160

Gly Asp Thr Ile Glu Val Asn Thr Trp Val Ser Ala Ser Gly Lys His
165 170 175

Gly Met Gly Arg Asp Trp Leu Ile Ser Asp Cys His Thr Gly Glu Ile
180 185 190

Leu Ile Arg Ala Thr Ser Val Trp Ala Met Met Asn Gln Lys Thr Arg
195 200 205

Arg Leu Ser Lys Ile Pro Tyr Glu Val Arg Gln Glu Ile Glu Pro Gln
210 215 220

Phe Val Asp Ser Ala Pro Val Ile Val Asp Asp Arg Lys Phe His Lys
225 230 235 240

Leu Asp Leu Lys Thr Gly Asp Ser Ile Cys Asn Gly Leu Thr Pro Arg
245 250 255

Trp Thr Asp Leu Asp Val Asn Gln His Val Asn Asn Val Lys Tyr Ile
260 265 270

Gly Trp Ile Leu Gln Ser Val Pro Thr Glu Val Phe Glu Thr Gln Glu
275 280 285

Leu Cys Gly Leu Thr Leu Glu Tyr Arg Arg Glu Cys Gly Arg Asp Ser
290 295 300

Val Leu Glu Ser Val Thr Ala Met Asp Pro Ser Lys Glu Gly Asp Arg
305 310 315 320

Ser Leu Tyr Gln His Leu Leu Arg Leu Glu Asp Gly Ala Asp Ile Val
325 330 335

-continued

```
Lys Gly Arg Thr Glu Trp Arg Pro Lys Asn Ala Gly Ala Lys Gly Ala
            340                 345                 350

Ile Leu Thr Gly Lys Thr Ser Asn Gly Asn Ser Ile Ser Met Asp Tyr
        355                 360                 365

Lys Asp His Asp Gly Asp Tyr Lys Asp His Asp Ile Asp Tyr Lys Asp
    370                 375                 380

Asp Asp Asp Lys
385


<210> SEQ ID NO 90
<211> LENGTH: 5428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

gctcttccgc taacggaggt ctgtcaccaa atggaccccg tctattgcgg gaaaccacgg     60

cgatggcacg tttcaaaact tgatgaaata caatattcag tatgtcgcgg gcggcgacgg    120

cggggagctg atgtcgcgct gggtattgct taatcgccag cttcgccccc gtcttggcgc    180

gaggcgtgaa caagccgacc gatgtgcacg agcaaatcct gacactagaa gggctgactc    240

gcccggcacg gctgaattac acaggcttgc aaaaatacca gaatttgcac gcaccgtatt    300

cgcggtattt tgttggacag tgaatagcga tgcggcaatg gcttgtggcg ttagaaggtg    360

cgacgaaggt ggtgccacca ctgtgccagc cagtcctggc ggctcccagg gccccgatca    420

agagccagga catccaaact acccacagca tcaacgcccc ggcctatact cgaaccccac    480

ttgcactctg caatggtatg ggaaccacgg ggcagtcttg tgtgggtcgc gcctatcgcg    540

gtcggcgaag accgggaagg taccctttct tgcgctatga cacttccagc aaaaggtagg    600

gcgggctgcg agacggcttc ccggcgctgc atgcaacacc gatgatgctt cgaccccccg    660

aagctccttc ggggctgcat gggcgctccg atgccgctcc agggcgagcg ctgtttaaat    720

agccaggccc ccgattgcaa agacattata gcgagctacc aaagccatat tcaaacacct    780

agatcactac cacttctaca caggccactc gagcttgtga tcgcactccg ctaagggggc    840

gcctcttcct cttcgtttca gtcacaaccc gcaaactcta gaatatcaat gatcgagcag    900

gacggcctcc acgccggctc cccgccgcc tgggtggagc gcctgttcgg ctacgactgg    960

gcccagcaga ccatcggctg ctccgacgcc gccgtgttcc gcctgtccgc ccagggccgc   1020

cccgtgctgt tcgtgaagac cgacctgtcc ggcgccctga acgagctgca ggacgaggcc   1080

gcccgcctgt cctggctggc caccaccggc gtgccctgcg ccgccgtgct ggacgtggtg   1140

accgaggccg gccgcgactg gctgctgctg ggcgaggtgc ccggccagga cctgctgtcc   1200

tcccacctgg cccccgccga gaaggtgtcc atcatggccg acgccatgcg ccgcctgcac   1260

accctggacc ccgccacctg ccccttcgac caccaggcca agcaccgcat cgagcgcgcc   1320

cgcacccgca tggaggccgg cctggtggac caggacgacc tggacgagga gcaccagggc   1380

ctggcccccg ccgagctgtt cgcccgcctg aaggcccgca tgcccgacgg cgaggacctg   1440

gtggtgaccc acggcgacgc ctgcctgccc aacatcatgg tggagaacgg ccgcttctcc   1500

ggcttcatcg actgcggccg cctgggcgtg gccgaccgct accaggacat cgccctggcc   1560

acccgcgaca tcgccgagga gctgggcggc gagtgggccg accgcttcct ggtgctgtac   1620

ggcatcgccg cccccgactc ccagcgcatc gccttctacc gcctgctgga cgagttcttc   1680
```

```
tgacaattgg cagcagcagc tcggatagta tcgacacact ctggacgctg gtcgtgtgat   1740
ggactgttgc cgccacactt gctgccttga cctgtgaata tccctgccgc ttttatcaaa   1800
cagcctcagt gtgtttgatc ttgtgtgtac gcgcttttgc gagttgctag ctgcttgtgc   1860
tatttgcgaa taccaccccc agcatcccct tccctcgttt catatcgctt gcatcccaac   1920
cgcaacttat ctacgctgtc ctgctatccc tcagcgctgc tcctgctcct gctcactgcc   1980
cctcgcacag ccttggtttg ggctccgcct gtattctcct ggtactgcaa cctgtaaacc   2040
agcactgcaa tgctgatgca cgggaagtag tgggatggga acacaaatgg aggatcccgc   2100
gtctcgaaca gagcgcgcag aggaacgctg aaggtctcgc ctctgtcgca cctcagcgcg   2160
gcatacacca caataaccac ctgacgaatg cgcttggttc ttcgtccatt agcgaagcgt   2220
ccggttcaca cacgtgccac gttggcgagg tggcaggtga caatgatcgg tggagctgat   2280
ggtcgaaacg ttcacagcct agggatatcg aattcggccg acaggacgcg cgtcaaaggt   2340
gctggtcgtg tatgccctgg ccggcaggtc gttgctgctg ctggttagtg attccgcaac   2400
cctgattttg gcgtcttatt ttggcgtggc aaacgctggc gcccgcgagc cgggccggcg   2460
gcgatgcggt gccccacggc tgccggaatc caagggaggc aagagcgccc gggtcagttg   2520
aagggcttta cgcgcaaggt acagccgctc ctgcaaggct gcgtggtgga attggacgtg   2580
caggtcctgc tgaagttcct ccaccgcctc accagcggac aaagcaccgg tgtatcaggt   2640
ccgtgtcatc cactctaaag agctcgacta cgacctactg atggccctag attcttcatc   2700
aaaaacgcct gagacacttg cccaggattg aaactccctg aagggaccac caggggccct   2760
gagttgttcc ttccccccgt ggcgagctgc cagccaggct gtacctgtga tcgaggctgg   2820
cgggaaaata ggcttcgtgt gctcaggtca tgggaggtgc aggacagctc atgaaacgcc   2880
aacaatcgca caattcatgt caagctaatc agctatttcc tcttcacgag ctgtaattgt   2940
cccaaaattc tggtctaccg ggggtgatcc ttcgtgtacg ggcccttccc tcaaccctag   3000
gtatgcgcgc atgcggtcgc cgcgcaactc gcgcgagggc cgagggtttg ggacgggccg   3060
tcccgaaatg cagttgcacc cggatgcgtg gcaccttttt tgcgataatt tatgcaatgg   3120
actgctctgc aaaattctgg ctctgtcgcc aaccctagga tcagcggcgt aggatttcgt   3180
aatcattcgt cctgatgggg agctaccgac taccctaata tcagcccgac tgcctgacgc   3240
cagcgtccac ttttgtgcac acattccatt cgtgcccaag acatttcatt gtggtgcgaa   3300
gcgtccccag ttacgctcac ctgtttcccg acctccttac tgttctgtcg acagagcggg   3360
cccacaggcc ggtcgcagcc actagtatgg cgatcgcggc cgcggcggtg atcttcctgt   3420
tcggcctgat cttcttcgcc tccggcctga tcatcaacct gttccaggcg ctgtgcttcg   3480
tcctgatccg ccccctgtcc aagaacgcct accgccgcat caaccgcgtg ttcgcggagc   3540
tgctgctgtc cgagctgctg tgcctgttcg actggtgggc gggcgcgaag ctgaagctgt   3600
tcaccgaccc cgagacgttc cgcctgatgg gcaaggagca cgccctggtc atcatcaacc   3660
acatgaccga gctggactgg atggtgggct gggtgatggg ccagcacttc ggctgcctgg   3720
gctccatcat ctccgtcgcc aagaagtcca cgaagttcct gcccgtgctg ggctggtcca   3780
tgtggttctc cgagtacctg tacctggagc gctcctgggc caaggacaag tccaccctga   3840
agtcccacat cgagcgcctg atcgactacc ccctgccctt ctggctggtc atcttcgtcg   3900
agggcacccg cttcacgcgc acgaagctgc tggcggccca gcagtacgcg gtctcctccg   3960
gcctgcccgt cccccgcaac gtcctgatcc cccgcacgaa gggcttcgtc tcctgcgtgt   4020
```

cccacatgcg ctccttcgtc cccgcggtgt acgacgtcac ggtggcgttc cccaagacgt 4080
cccccccccc cacgctgctg aacctgttcg agggccagtc catcatgctg cacgtgcaca 4140
tcaagcgcca cgccatgaag gacctgcccg agtccgacga cgccgtcgcg gagtggtgcc 4200
gcgacaagtt cgtcgagaag gacgccctgc tggacaagca caacgcggag gacacgttct 4260
ccggccagga ggtgtgccac tccggctccc gccagctgaa gtccctgctg gtcgtgatct 4320
cctgggtcgt ggtgacgacg ttcggcgccc tgaagttcct gcagtggtcc tcctggaagg 4380
gcaaggcgtt ctccgccatc ggcctgggca tcgtcaccct gctgatgcac gtgctgatcc 4440
tgtcctccca ggccgagcgc tccaaccccg ccgaggtggc ccaggccaag ctgaagaccg 4500
gcctgtccat ctccaagaag gtgacggaca aggagaactg attaattaac tcgaggcagc 4560
agcagctcgg atagtatcga cacactctgg acgctggtcg tgtgatggac tgttgccgcc 4620
acacttgctg ccttgacctg tgaatatccc tgccgctttt atcaaacagc ctcagtgtgt 4680
ttgatcttgt gtgtacgcgc ttttgcgagt tgctagctgc ttgtgctatt tgcgaatacc 4740
acccccagca tccccttccc tcgtttcata tcgcttgcat cccaaccgca acttatctac 4800
gctgtcctgc tatccctcag cgctgctcct gctcctgctc actgcccctc gcacagcctt 4860
ggtttgggct ccgcctgtat tctcctggta ctgcaacctg taaaccagca ctgcaatgct 4920
gatgcacggg aagtagtggg atgggaacac aaatggaaag cttgagctca gcggcgacgg 4980
tcctgctacc gtacgacgtt gggcacgccc atgaaagttt gtataccgag cttgttgagc 5040
gaactgcaag cgcggctcaa ggatacttga actcctggat tgatatcggt ccaataatgg 5100
atggaaaatc cgaacctcgt gcaagaactg agcaaacctc gttacatgga tgcacagtcg 5160
ccagtccaat gaacattgaa gtgagcgaac tgttcgcttc ggtggcagta ctactcaaag 5220
aatgagctgc tgttaaaaat gcactctcgt tctctcaagt gagtggcaga tgagtgctca 5280
cgccttgcac ttcgctgccc gtgtcatgcc ctgcgcccca aaatttgaaa aaagggatga 5340
gattattggg caatggacga cgtcgtcgct ccgggagtca ggaccggcgg aaaataagag 5400
gcaacacact ccgcttctta gctcttcg 5428

<210> SEQ ID NO 91
<211> LENGTH: 5436
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 91
gctcttccgc taacggaggt ctgtcaccaa atggaccccg tctattgcgg gaaaccacgg 60
cgatggcacg tttcaaaact tgatgaaata caatattcag tatgtcgcgg gcggcgacgg 120
cggggagctg atgtcgcgct gggtattgct taatcgccag cttcgccccc gtcttggcgc 180
gaggcgtgaa caagccgacc gatgtgcacg agcaaatcct gacactagaa gggctgactc 240
gcccggcacg gctgaattac acaggcttgc aaaaatacca gaatttgcac gcaccgtatt 300
cgcggtattt tgttggacag tgaatagcga tgcggcaatg gcttgtggcg ttagaaggtg 360
cgacgaaggt ggtgccacca ctgtgccagc cagtcctggc ggctcccagg gccccgatca 420
agagccagga catccaaact acccacagca tcaacgcccc ggcctatact cgaaccccac 480
ttgcactctg caatggtatg ggaaccacgg ggcagtcttg tgtgggtcgc gcctatcgcg 540
gtcggcgaag accgggaagg taccctttct tgcgctatga cacttccagc aaaaggtagg 600

```
gcgggctgcg agacggcttc ccggcgctgc atgcaacacc gatgatgctt cgaccccccg    660
aagctccttc ggggctgcat gggcgctccg atgccgctcc agggcgagcg ctgtttaaat    720
agccaggccc ccgattgcaa agacattata gcgagctacc aaagccatat tcaaacacct    780
agatcactac cacttctaca caggccactc gagcttgtga tcgcactccg ctaagggggc    840
gcctcttcct cttcgtttca gtcacaaccc gcaaactcta gaatatcaat gatcgagcag    900
gacggcctcc acgccggctc ccccgccgcc tgggtggagc gcctgttcgg ctacgactgg    960
gcccagcaga ccatcggctg ctccgacgcc gccgtgttcc gcctgtccgc ccagggccgc   1020
cccgtgctgt tcgtgaagac cgacctgtcc ggcgccctga acgagctgca ggacgaggcc   1080
gcccgcctgt cctggctggc caccaccggc gtgccctgcg ccgccgtgct ggacgtggtg   1140
accgaggccg gccgcgactg gctgctgctg ggcgaggtgc ccggccagga cctgctgtcc   1200
tcccacctgg cccccgccga gaaggtgtcc atcatggccg acgccatgcg ccgcctgcac   1260
accctggacc ccgccacctg cccettcgac caccaggcca agcaccgcat cgagcgcgcc   1320
cgcacccgca tggaggccgg cctggtggac caggacgacc tggacgagga gcaccagggc   1380
ctggcccccg ccgagctgtt cgcccgcctg aaggcccgca tgcccgacgg cgaggacctg   1440
gtggtgaccc acggcgacgc ctgcctgccc aacatcatgg tggagaacgg ccgcttctcc   1500
ggcttcatcg actgcggccg cctgggcgtg gccgaccgct accaggacat cgccctggcc   1560
acccgcgaca tcgccgagga gctgggcggc gagtgggccg accgcttcct ggtgctgtac   1620
ggcatcgccg cccccgactc ccagcgcatc gccttctacc gcctgctgga cgagttcttc   1680
tgacaattgg cagcagcagc tcggatagta tcgacacact ctggacgctg gtcgtgtgat   1740
ggactgttgc cgccacactt gctgccttga cctgtgaata tccctgccgc ttttatcaaa   1800
cagcctcagt gtgtttgatc ttgtgtgtac gcgcttttgc gagttgctag ctgcttgtgc   1860
tatttgcgaa taccaccccc agcatcccct tccctcgttt catatcgctt gcatcccaac   1920
cgcaacttat ctacgctgtc ctgctatccc tcagcgctgc tcctgctcct gctcactgcc   1980
cctcgcacag ccttggtttg ggctccgcct gtattctcct ggtactgcaa cctgtaaacc   2040
agcactgcaa tgctgatgca cgggaagtag tgggatggga acacaaatgg aggatcccgc   2100
gtctcgaaca gagcgcgcag aggaacgctg aaggtctcgc ctctgtcgca cctcagcgcg   2160
gcatacacca caataaccac ctgacgaatg cgcttggttc ttcgtccatt agcgaagcgt   2220
ccggttcaca cacgtgccac gttggcgagg tggcaggtga caatgatcgg tggagctgat   2280
ggtcgaaacg ttcacagcct agggatatcg aattcggccg acaggacgcg cgtcaaaggt   2340
gctggtcgtg tatgccctgg ccggcaggtc gttgctgctg ctggttagtg attccgcaac   2400
cctgattttg gcgtcttatt ttggcgtggc aaacgctggc gcccgcgagc cgggccggcg   2460
gcgatgcggt gccccacggc tgccggaatc caagggaggc aagagcgccc gggtcagttg   2520
aagggcttta cgcgcaaggt acagccgctc ctgcaaggct gcgtggtgga attggacgtg   2580
caggtcctgc tgaagttcct ccaccgcctc accagcggac aaagcaccgg tgtatcaggt   2640
ccgtgtcatc cactctaaag agctcgacta cgacctactg atggccctag attcttcatc   2700
aaaaacgcct gagacacttg cccaggattg aaactccctg aagggaccac caggggccct   2760
gagttgttcc ttcccccegt ggcgagctgc cagccaggct gtacctgtga tcgaggctgg   2820
cgggaaaata ggcttcgtgt gctcaggtca tgggaggtgc aggacagctc atgaaacgcc   2880
aacaatcgca caattcatgt caagctaatc agctatttcc tcttcacgag ctgtaattgt   2940
cccaaaattc tggtctaccg gggtgatcc ttcgtgtacg ggcccttccc tcaaccctag   3000
```

```
gtatgcgcgc atgcggtcgc cgcgcaactc gcgcgagggc cgagggtttg ggacgggccg   3060
tcccgaaatg cagttgcacc cggatgcgtg gcaccttttt tgcgataatt tatgcaatgg   3120
actgctctgc aaaattctgg ctctgtcgcc aaccctagga tcagcggcgt aggatttcgt   3180
aatcattcgt cctgatgggg agctaccgac taccctaata tcagcccgac tgcctgacgc   3240
cagcgtccac ttttgtgcac acattccatt cgtgcccaag acatttcatt gtggtgcgaa   3300
gcgtccccag ttacgctcac ctgtttcccg acctccttac tgttctgtcg acagagcggg   3360
cccacaggcc ggtcgcagcc actagtatgg ccatcgcggc ggccgcggtg atcgtgcccc   3420
tgtccctgct gttcttcgtg tccggcctga tcgtcaacct ggtgcaggcc gtctgcttcg   3480
tcctgatccg cccccctgtcc aagaacacgt accgccgcat caaccgcgtg gtcgcggagc   3540
tgctgtggct ggagctggtg tggctgatcg actggtgggc gggcgtgaag atcaaggtct   3600
tcacggacca cgagacgttc cacctgatgg gcaaggagca cgccctggtc atctgcaacc   3660
acaagtccga catcgactgg ctggtcggct gggtcctggg ccagcgctcc ggctgcctgg   3720
gctccaccct ggcggtcatg aagaagtcct ccaagttcct gcccgtcctg ggctggtcca   3780
tgtggttctc cgagtacctg ttcctggagc gctcctgggc caaggacgag atcacgctga   3840
agtccggcct gaaccgcctg aaggactacc ccctgccctt ctggctggcg ctgttcgtgg   3900
agggcacgcg cttcacccgc gcgaagctgc tggcggcgca gcagtacgcc gcgtcctccg   3960
gcctgcccgt gccccgcaac gtgctgatcc cccgcacgaa gggcttcgtg tcctccgtgt   4020
cccacatgcg ctccttcgtg cccgcgatct acgacgtcac cgtggccatc cccaagacgt   4080
cccccccccc cacgctgatc cgcatgttca agggccagtc ctccgtgctg cacgtgcacc   4140
tgaagcgcca cctgatgaag gacctgcccg agtccgacga cgccgtcgcg cagtggtgcc   4200
gcgacatctt cgtggagaag gacgcgctgc tggacaagca caacgccgag gacaccttct   4260
ccggccagga gctgcaggag accggccgcc ccatcaagtc cctgctggtc gtcatctcct   4320
gggccgtcct ggaggtgttc ggcgccgtca agttcctgca gtggtcctcc ctgctgtcct   4380
cctggaaggg cctggcgttc tccggcatcg gcctgggcgt gatcaccctg ctgatgcaca   4440
tcctgatcct gttctcccag tccgagcgct ccaccccccgc caaggtggcc cccgcgaagc   4500
ccaagaacga gggcgagtcc tccaagaccg agatggagaa ggagaagtga ttaattaact   4560
cgaggcagca gcagctcgga tagtatcgac acactctgga cgctggtcgt gtgatggact   4620
gttgccgcca cacttgctgc cttgacctgt gaatatccct gccgctttta tcaaacagcc   4680
tcagtgtgtt tgatcttgtg tgtacgcgct tttgcgagtt gctagctgct tgtgctattt   4740
gcgaatacca cccccagcat ccccttccct cgtttcatat cgcttgcatc ccaaccgcaa   4800
cttatctacg ctgtcctgct atccctcagc gctgctcctg ctcctgctca ctgcccctcg   4860
cacagccttg gtttgggctc cgcctgtatt ctcctggtac tgcaacctgt aaaccagcac   4920
tgcaatgctg atgcacggga agtagtggga tgggaacaca aatggaaagc ttgagctcag   4980
cggcgacggt cctgctaccg tacgacgttg ggcacgccca tgaaagtttg tataccgagc   5040
ttgttgagcg aactgcaagc gcggctcaag gatacttgaa ctcctggatt gatatcggtc   5100
caataatgga tggaaaatcc gaacctcgtg caagaactga gcaaacctcg ttacatggat   5160
gcacagtcgc cagtccaatg aacattgaag tgagcgaact gttcgcttcg gtggcagtac   5220
tactcaaaga atgagctgct gttaaaaatg cactctcgtt ctctcaagtg agtggcagat   5280
gagtgctcac gcctgcactt cgctgcccgt gtcatgccct gcgccccaaa atttgaaaaa   5340
```

agggatgaga ttattgggca atggacgacg tcgtcgctcc gggagtcagg accggcggaa 5400
aataagaggc aacacactcc gcttcttagc tcttcg 5436

<210> SEQ ID NO 92
<211> LENGTH: 5257
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92
gctcttccgc taacggaggt ctgtcaccaa atggaccccg tctattgcgg gaaaccacgg 60
cgatggcacg tttcaaaact tgatgaaata caatattcag tatgtcgcgg gcggcgacgg 120
cggggagctg atgtcgcgct gggtattgct taatcgccag cttcgccccc gtcttggcgc 180
gaggcgtgaa caagccgacc gatgtgcacg agcaaatcct gacactagaa gggctgactc 240
gcccggcacg gctgaattac acaggcttgc aaaaatacca gaatttgcac gcaccgtatt 300
cgcggtattt tgttggacag tgaatagcga tgcggcaatg gcttgtggcg ttagaaggtg 360
cgacgaaggt ggtgccacca ctgtgccagc cagtcctggc ggctcccagg gccccgatca 420
agagccagga catccaaact acccacagca tcaacgcccc ggcctatact cgaaccccac 480
ttgcactctg caatggtatg ggaaccacgg ggcagtcttg tgtgggtcgc gcctatcgcg 540
gtcggcgaag accgggaagg taccctttct tgcgctatga cacttccagc aaaaggtagg 600
gcgggctgcg agacggcttc ccggcgctgc atgcaacacc gatgatgctt cgacccccccg 660 aagctccttc ggggctgcat gggcgctccg atgccgctcc agggcgagcg ctgtttaaat 720
agccaggccc ccgattgcaa agacattata gcgagctacc aaagccatat tcaaacacct 780
agatcactac cacttctaca caggccactc gagcttgtga tcgcactccg ctaagggggc 840
gcctcttcct cttcgtttca gtcacaaccc gcaaactcta gaatatcaat gatcgagcag 900
gacggcctcc acgccggctc cccgccgcc tgggtggagc gcctgttcgg ctacgactgg 960
gcccagcaga ccatcggctg ctccgacgcc gccgtgttcc gcctgtccgc ccagggccgc 1020
cccgtgctgt tcgtgaagac cgacctgtcc ggcgccctga acgagctgca ggacgaggcc 1080
gcccgcctgt cctggctggc caccaccggc gtgccctgcg ccgccgtgct ggacgtggtg 1140
accgaggccg gccgcgactg gctgctgctg ggcgaggtgc ccggccagga cctgctgtcc 1200
tcccacctgg cccccgccga gaaggtgtcc atcatggccg acgccatgcg ccgcctgcac 1260
accctggacc ccgccacctg ccccttcgac caccaggcca agcaccgcat cgagcgcgcc 1320
cgcacccgca tggaggccgg cctggtggac caggacgacc tggacgagga gcaccagggc 1380
ctggcccccg ccgagctgtt cgcccgcctg aaggcccgca tgcccgacgg cgaggacctg 1440
gtggtgaccc acggcgacgc ctgcctgccc aacatcatgg tggagaacgg ccgcttctcc 1500
ggcttcatcg actgcggccg cctgggcgtg gccgaccgct accaggacat cgccctggcc 1560
acccgcgaca tcgccgagga gctgggcggc gagtgggccg accgcttcct ggtgctgtac 1620
ggcatcgccg cccccgactc ccagcgcatc gccttctacc gcctgctgga cgagttcttc 1680
tgacaattgg cagcagcagc tcggatagta tcgacacact ctggacgctg gtcgtgtgat 1740
ggactgttgc cgccacactt gctgccttga cctgtgaata tccctgccgc ttttatcaaa 1800
cagcctcagt gtgtttgatc ttgtgtgtac gcgcttttgc gagttgctag ctgcttgtgc 1860
tatttgcgaa taccaccccc agcatcccct tccctcgttt catatcgctt gcatcccaac 1920

-continued

```
cgcaacttat ctacgctgtc ctgctatccc tcagcgctgc tcctgctcct gctcactgcc   1980
cctcgcacag ccttggtttg ggctccgcct gtattctcct ggtactgcaa cctgtaaacc   2040
agcactgcaa tgctgatgca cgggaagtag tgggatggga acacaaatgg aggatcccgc   2100
gtctcgaaca gagcgcgcag aggaacgctg aaggtctcgc ctctgtcgca cctcagcgcg   2160
gcatacacca caataaccac ctgacgaatg cgcttggttc ttcgtccatt agcgaagcgt   2220
ccggttcaca cacgtgccac gttggcgagg tggcaggtga caatgatcgg tggagctgat   2280
ggtcgaaacg ttcacagcct agggatatcg aattcggccg acaggacgcg cgtcaaaggt   2340
gctggtcgtg tatgccctgg ccggcaggtc gttgctgctg ctggttagtg attccgcaac   2400
cctgattttg gcgtcttatt ttggcgtggc aaacgctggc gcccgcgagc cgggccggcg   2460
gcgatgcggt gccccacggc tgccggaatc caagggaggc aagagcgccc gggtcagttg   2520
aagggcttta cgcgcaaggt acagccgctc ctgcaaggct gcgtggtgga attggacgtg   2580
caggtcctgc tgaagttcct ccaccgcctc accagcggac aaagcaccgg tgtatcaggt   2640
ccgtgtcatc cactctaaag agctcgacta cgacctactg atggccctag attcttcatc   2700
aaaaacgcct gagacacttg cccaggattg aaactccctg aagggaccac caggggccct   2760
gagttgttcc ttcccccgt ggcgagctgc cagccaggct gtacctgtga tcgaggctgg   2820
cgggaaaata ggcttcgtgt gctcaggtca tgggaggtgc aggacagctc atgaaacgcc   2880
aacaatcgca caattcatgt caagctaatc agctatttcc tcttcacgag ctgtaattgt   2940
cccaaaattc tggtctaccg ggggtgatcc ttcgtgtacg ggcccttccc tcaaccctag   3000
gtatgcgcgc atgcggtcgc cgcgcaactc gcgcgagggc cgagggtttg ggacgggccg   3060
tcccgaaatg cagttgcacc cggatgcgtg gcaccttttt tgcgataatt tatgcaatgg   3120
actgctctgc aaaattctgg ctctgtcgcc aaccctagga tcagcggcgt aggatttcgt   3180
aatcattcgt cctgatgggg agctaccgac taccctaata tcagcccgac tgcctgacgc   3240
cagcgtccac ttttgtgcac acattccatt cgtgcccaag acatttcatt gtggtgcgaa   3300
gcgtccccag ttacgctcac ctgtttcccg acctccttac tgttctgtcg acagagcggg   3360
cccacaggcc ggtcgcagcc actagtatgg agatcccccc ccactgcctg tgctcccccct   3420
cccccgcccc ctcccagctg tactacaaga agaagaagca cgccatcctg cagacccaga   3480
ccccctaccg ctaccgcgtg tcccccacct gcttcgcccc cccccgcctg cgcaagcagc   3540
acccctaccc cctgcccgtg ctgtgctacc ccaagctgct gcacttctcc cagccccgct   3600
accccctggt gcgctcccac ctggccgagg ccggcgtggc ctaccgcccc ggctacgagc   3660
tgctgggcaa gatccgcggc gtgtgcttct acgccgtgac cgccgccgtg gccctgctgc   3720
tgttccagtg catgctgctg ctgcacccct tcgtgctgct gttcgacccc ttcccccgca   3780
aggcccacca caccatcgcc aagctgtggt ccatctgctc cgtgtccctg ttctacaaga   3840
tccacatcaa gggcctggag aacctgcccc ccccccactc ccccgccgtg tacgtgtcca   3900
accaccagtc cttcctggac atctacaccc tgctgaccct gggccgcacc ttcaagttca   3960
tctccaagac cgagatcttc ctgtacccca tcatcggctg ggccatgtac atgctgggca   4020
ccatccccct gaagcgcctg gactcccgct cccagctgga caccctgaag cgctgcatgg   4080
acctgatcaa gaagggcgcc tccgtgttct tcttccccga gggcacccgc tccaaggacg   4140
gcaagctggg cgccttcaag aagggcgcct tctccatcgc cgccaagtcc aaggtgcccg   4200
tggtgcccat caccctgatc ggcaccggca agatcatgcc ccccggctcc gagctgaccg   4260
tgaaccccgg caccgtgcag gtgatcatcc acaagcccat cgagggctcc gacgccgagg   4320
```

```
ccatgtgcaa cgaggcccgc gccaccatct cccactccct ggacgactga ttaattaact   4380

cgaggcagca gcagctcgga tagtatcgac acactctgga cgctggtcgt gtgatggact   4440

gttgccgcca cacttgctgc cttgacctgt gaatatccct gccgctttta tcaaacagcc   4500

tcagtgtgtt tgatcttgtg tgtacgcgct tttgcgagtt gctagctgct tgtgctattt   4560

gcgaatacca cccccagcat ccccttccct cgtttcatat cgcttgcatc ccaaccgcaa   4620

cttatctacg ctgtcctgct atccctcagc gctgctcctg ctcctgctca ctgcccctcg   4680

cacagccttg gtttgggctc cgcctgtatt ctcctggtac tgcaacctgt aaaccagcac   4740

tgcaatgctg atgcacggga agtagtggga tgggaacaca aatggaaagc ttgagctcag   4800

cggcgacggt cctgctaccg tacgacgttg ggcacgccca tgaaagtttg tataccgagc   4860

ttgttgagcg aactgcaagc gcggctcaag gatacttgaa ctcctggatt gatatcggtc   4920

caataatgga tggaaaatcc gaacctcgtg caagaactga gcaaacctcg ttacatggat   4980

gcacagtcgc cagtccaatg aacattgaag tgagcgaact gttcgcttcg gtggcagtac   5040

tactcaaaga atgagctgct gttaaaaatg cactctcgtt ctctcaagtg agtggcagat   5100

gagtgctcac gccttgcact tcgctgcccg tgtcatgccc tgcgccccaa aatttgaaaa   5160

aagggatgag attattgggc aatggacgac gtcgtcgctc cgggagtcag gaccggcgga   5220

aaataagagg caacacactc cgcttcttag ctcttcg                            5257
```

<210> SEQ ID NO 93
<211> LENGTH: 6714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccacccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080
```

gccggcttcg ccgccaagat cagcgcctcc atgacgaacg agacgtccga ccgccccctg 1140
gtgcacttca cccccaacaa gggctggatg aacgacccca acggcctgtg gtacgacgag 1200
aaggacgcca agtggcacct gtacttccag tacaacccga acgacaccgt ctgggggacg 1260
cccttgttct ggggccacgc cacgtccgac gacctgacca actgggagga ccagcccatc 1320
gccatcgccc cgaagcgcaa cgactccggc gccttctccg gctccatggt ggtggactac 1380
aacaacacct ccggcttctt caacgacacc atcgacccgc gccagcgctg cgtggccatc 1440
tggacctaca acaccccgga gtccgaggag cagtacatct cctacagcct ggacggcggc 1500
tacaccttca ccgagtacca gaagaacccc gtgctggccg ccaactccac ccagttccgc 1560
gacccgaagg tcttctggta cgagccctcc cagaagtgga tcatgaccgc ggccaagtcc 1620
caggactaca agatcgagat ctactcctcc gacgacctga agtcctggaa gctggagtcc 1680
gcgttcgcca acgagggctt cctcggctac cagtacgagt gccccggcct gatcgaggtc 1740
cccaccgagc aggaccccag caagtcctac tgggtgatgt tcatctccat caaccccggc 1800
gccccggccg gcggctcctt caaccagtac ttcgtcggca gcttcaacgg cacccacttc 1860
gaggccttcg acaaccagtc ccgcgtggtg gacttcggca aggactacta cgccctgcag 1920
accttcttca acaccgaccc gacctacggg agcgccctgg gcatcgcgtg ggcctccaac 1980
tgggagtact ccgccttcgt gcccaccaac ccctggcgct cctccatgtc cctcgtgcgc 2040
aagttctccc tcaacaccga gtaccaggcc aacccggaga cggagctgat caacctgaag 2100
gccgagccga tcctgaacat cagcaacgcc ggcccctgga gccggttcgc caccaacacc 2160
acgttgacga aggccaacag ctacaacgtc gacctgtcca acagcaccgg caccctggag 2220
ttcgagctgg tgtacgccgt caacaccacc cagacgatct ccaagtccgt gttcgcggac 2280
ctctccctct ggttcaaggg cctggaggac cccgaggagt acctccgcat gggcttcgag 2340
gtgtccgcgt cctccttctt cctggaccgc gggaacagca aggtgaagtt cgtgaaggag 2400
aacccctact tcaccaaccg catgagcgtg aacaaccagc ccttcaagag cgagaacgac 2460
ctgtcctact acaaggtgta cggcttgctg gaccagaaca tcctggagct gtacttcaac 2520
gacggcgacg tcgtgtccac caacacctac ttcatgacca ccgggaacgc cctgggctcc 2580
gtgaacatga cgacgggggt ggacaacctg ttctacatcg acaagttcca ggtgcgcgag 2640
gtcaagtgac aattggcagc agcagctcgg atagtatcga cacactctgg acgctggtcg 2700
tgtgatggac tgttgccgcc acacttgctg ccttgacctg tgaatatccc tgccgctttt 2760
atcaaacagc ctcagtgtgt ttgatcttgt gtgtacgcgc ttttgcgagt tgctagctgc 2820
ttgtgctatt tgcgaatacc acccccagca tccccttccc tcgtttcata tcgcttgcat 2880
cccaaccgca acttatctac gctgtcctgc tatccctcag cgctgctcct gctcctgctc 2940
actgcccctc gcacagcctt ggtttgggct ccgcctgtat tctcctggta ctgcaacctg 3000
taaaccagca ctgcaatgct gatgcacggg aagtagtggg atgggaacac aaatggagga 3060
tcccgcgtct cgaacagagc gcgcagagga acgctgaagg tctcgcctct gtcgcacctc 3120
agcgcggcat acaccacaat aaccacctga cgaatgcgct tggttcttcg tccattagcg 3180
aagcgtccgg ttcacacacg tgccacgttg gcgaggtggc aggtgacaat gatcggtgga 3240
gctgatggtc gaaacgttca cagcctaggg atatcgaatt cggccgacag gacgcgcgtc 3300
aaaggtgctg gtcgtgtatg ccctggccgg caggtcgttg ctgctgctgg ttagtgattc 3360
cgcaaccctg attttggcgt cttattttgg cgtggcaaac gctggcgccc gcgagccggg 3420

```
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac ctttttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
tgcgaagcgt ccccagttac gctcacctgt ttcccgacct ccttactgtt ctgtcgacag   4320
agcgggccca caggccggtc gcagccacta gtatggcccc cacctccctg ctggcctcca   4380
ccggcgtgtc ctccgcctcc ctgtggtcct ccgcccgctc ctccgcctgc gccttccccg   4440
tggaccacgc cgtgcgcggc gccccccagc gcccccctgcc catgcagcgc cgctgcttcc   4500
gcaccgtggc cgtgcgcggg cgcgccgccg cccccgccgt ggccgtgcgc cccgagcccg   4560
cccaggagtt ctgggagcag ctggagccct gcaagatggc cgaggacaag cgcatcttcc   4620
tggaggagca ccgcatccgc ggcaacgagg tgggcccctc ccagcgcctg accatcaccg   4680
ccgtggccaa catcctgcag gaggccgccg gcaaccacgc cgtggccatg tggggccgct   4740
cctccgaggg cttcgccacc gaccccgagc tgcaggaggc cggcctgatc ttcgtgatga   4800
cccgcatgca gatccagatg taccgctacc cccgctgggg cgacctgatg caggtggaga   4860
cctggttcca gaccgccggc aagctgggcg cccagcgcga gtgggtgctg cgcgacaagc   4920
tgaccggcga ggccctgggc gccgccacct cctcctgggt gatgatcaac atccgcaccc   4980
gccgcccctg ccgcatgccc gagctggtgc gcgtgaagtc cgccttcttc gcccgcgagc   5040
ccccccgcct ggccctgccc cccgccgtga cccgcgccaa gctgcccaac atcgccaccc   5100
ccgccccccct gcgcggccac cgccaggtgg cccgccgcac cgacatggac atgaacggcc   5160
acgtgaacaa cgtggcctac ctggcctggt gcctggaggc cgtgcccgag cacgtgttct   5220
ccgactacca cctgtaccag atggagatcg acttcaaggc cgagtgccac gccggcgacg   5280
tgatctcctc ccaggccgag cagatccccc cccaggaggc cctgacccac aacggcgccg   5340
gccgcaaccc ctcctgcttc gtgcactcca tcctgcgcgc cgagaccgag ctggtgcgcg   5400
cccgcaccac ctggtccgcc cccatcgacg cccccgccgc caagcccccc aaggcctccc   5460
acatggacta caaggaccac gacggcgact acaaggacca cgacatcgac tacaaggacg   5520
acgacgacaa gtgaatcgat agatctctta aggcagcagc agctcggata gtatcgacac   5580
actctggacg ctggtcgtgt gatggactgt tgccgccaca cttgctgcct tgacctgtga   5640
atatccctgc cgcttttatc aaacagcctc agtgtgtttg atcttgtgtg tacgcgcttt   5700
tgcgagttgc tagctgcttg tgctatttgc gaataccacc cccagcatcc ccttccctcg   5760
tttcatatcg cttgcatccc aaccgcaact tatctacgct gtcctgctat ccctcagcgc   5820
```

-continued

```
tgctcctgct cctgctcact gcccctcgca cagccttggt ttgggctccg cctgtattct   5880

cctggtactg caacctgtaa accagcactg caatgctgat gcacgggaag tagtgggatg   5940

ggaacacaaa tggaaagctt aattaagagc tcttgttttc cagaaggagt tgctccttga   6000

gcctttcatt ctcagcctcg ataacctcca aagccgctct aattgtggag gggttcgaa    6060

tttaaaagct tggaatgttg gttcgtgcgt ctggaacaag cccagacttg ttgctcactg   6120

ggaaaaggac catcagctcc aaaaaacttg ccgctcaaac cgcgtacctc tgctttcgcg   6180

caatctgccc tgttgaaatc gccaccacat tcatattgtg acgcttgagc agtctgtaat   6240

tgcctcagaa tgtggaatca tctgcccct gtgcgagccc atgccaggca tgtcgcgggc    6300

gaggacaccc gccactcgta cagcagacca ttatgctacc tcacaatagt tcataacagt   6360

gaccatattt ctcgaagctc cccaacgagc acctccatgc tctgagtggc cacccccgg    6420

ccctggtgct tgcggagggc aggtcaaccg gcatggggct accgaaatcc ccgaccggat   6480

cccaccaccc ccgcgatggg aagaatctct ccccgggatg tgggcccacc accagcacaa   6540

cctgctggcc caggcgagcg tcaaaccata ccacacaaat atccttggca tcggccctga   6600

attccttctg ccgctctgct acccggtgct tctgtccgaa gcaggggttg ctagggatcg   6660

ctccgagtcc gcaaaccctt gtcgcgtggc ggggcttgtt cgagcttgaa gagc         6714
```

```
<210> SEQ ID NO 94
<211> LENGTH: 5279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

gctcttcggg tcgccgcgct gcctcgcgtc ccctggtggt gcgcgcggtc gccagcgagg     60

ccccgctggg cgttccgccc tcggtgcagc gcccctcccc cgtggtctac tccaagctgg    120

acaagcagca ccgcctgacg cccgagcgcc tggagctggt gcagagcatg ggcagtttg     180

cggaggagag ggtgctgccc gtgctgcacc ccgtggacaa gctgtggcag ccgcaggact    240

ttttgcccga ccccgagtcg cccgacttcg aggatcaggt ggcggagctg cgcgcgcgcg    300

ccaaggacct gcccgacgag tactttgtgg tgctggtggg ggacatgatc acggaggagg    360

cgctgccgac ctacatggcc atgctcaaca cgctggacgg cgtgcgcgac gacacgggcg    420

cggccgacca cccgtgggcg cgctggacgc ggcagtgggt ggccgaggag aaccggcacg    480

gcgacctgct gaacaagtac tgctggctga cggggcgcgt caacatgcgg gccgtggagg    540

tgaccatcaa caacctgatc aagagcggca tgaacccgca gacggacaac aacccttatt    600

tggggttcgt ctacacctcc ttccaggagc gcgccaccaa gtaggtaccc tttcttgcgc    660

tatgacactt ccagcaaaag gtagggcggg ctgcgagacg gcttcccggc gctgcatgca    720

acaccgatga tgcttcgacc ccccgaagct ccttcggggc tgcatgggcg ctccgatgcc    780

gctccagggc gagcgctgtt taaatagcca ggcccccgat tgcaaagaca ttatagcgag    840

ctaccaaagc catattcaaa cacctagatc actaccactt ctacacaggc cactcgagct    900

tgtgatcgca ctccgctaag gggcgcctc ttcctcttcg tttcagtcac aacccgcaaa     960

cggcgcgcca tgctgctgca ggccttcctg ttcctgctgg ccggcttcgc cgccaagatc   1020

agcgcctcca tgacgaacga gacgtccgac cgcccctgg tgcacttcac ccccaacaag    1080

ggctggatga acgaccccaa cggcctgtgg tacgacgaga aggacgccaa gtggcacctg   1140
```

```
tacttccagt acaacccgaa cgacaccgtc tgggggacgc ccttgttctg gggccacgcc   1200
acgtccgacg acctgaccaa ctgggaggac cagcccatcg ccatcgcccc gaagcgcaac   1260
gactccggcg ccttctccgg ctccatggtg gtggactaca acaacacctc cggcttcttc   1320
aacgacacca tcgacccgcg ccagcgctgc gtggccatct ggacctacaa caccccggag   1380
tccgaggagc agtacatctc ctacagcctg gacggcggct acaccttcac cgagtaccag   1440
aagaaccccg tgctggccgc caactccacc cagttccgcg acccgaaggt cttctggtac   1500
gagccctccc agaagtggat catgaccgcg gccaagtccc aggactacaa gatcgagatc   1560
tactcctccg acgacctgaa gtcctggaag ctggagtccg cgttcgccaa cgagggcttc   1620
ctcggctacc agtacgagtg ccccggcctg atcgaggtcc ccaccgagca ggaccccagc   1680
aagtcctact gggtgatgtt catctccatc aaccccggcg ccccggccgg cggctccttc   1740
aaccagtact tcgtcggcag cttcaacggc acccacttcg aggccttcga caaccagtcc   1800
cgcgtggtgg acttcggcaa ggactactac gccctgcaga ccttcttcaa caccgacccg   1860
acctacggga gcgccctggg catcgcgtgg gcctccaact gggagtactc cgccttcgtg   1920
cccaccaacc cctggcgctc ctccatgtcc ctcgtgcgca agttctccct caacaccgag   1980
taccaggcca acccggagac ggagctgatc aacctgaagg ccgagccgat cctgaacatc   2040
agcaacgccg gcccctggag ccggttcgcc accaacacca cgttgacgaa ggccaacagc   2100
tacaacgtcg acctgtccaa cagcaccggc accctggagt tcgagctggt gtacgccgtc   2160
aacaccaccc agacgatctc caagtccgtg ttcgcggacc tctccctctg gttcaagggc   2220
ctggaggacc ccgaggagta cctccgcatg ggcttcgagg tgtccgcgtc ctccttcttc   2280
ctggaccgcg ggaacagcaa ggtgaagttc gtgaaggaga acccctactt caccaaccgc   2340
atgagcgtga acaaccagcc cttcaagagc gagaacgacc tgtcctacta caaggtgtac   2400
ggcttgctgg accagaacat cctggagctg tacttcaacg acggcgacgt cgtgtccacc   2460
aacacctact tcatgaccac cgggaacgcc ctgggctccg tgaacatgac gacgggggtg   2520
gacaacctgt tctacatcga caagttccag gtgcgcgagg tcaagtgaca attggcagca   2580
gcagctcgga tagtatcgac acactctgga cgctggtcgt gtgatggact gttgccgcca   2640
cacttgctgc cttgacctgt gaatatccct gccgctttta tcaaacagcc tcagtgtgtt   2700
tgatcttgtg tgtacgcgct tttgcgagtt gctagctgct tgtgctattt gcgaatacca   2760
cccccagcat ccccttccct cgtttcatat cgcttgcatc ccaaccgcaa cttatctacg   2820
ctgtcctgct atccctcagc gctgctcctg ctcctgctca ctgcccctcg cacagccttg   2880
gtttgggctc cgcctgtatt ctcctggtac tgcaacctgt aaaccagcac tgcaatgctg   2940
atgcacggga agtagtggga tgggaacaca aatggaggat cccgcgtctc gaacagagcg   3000
cgcagaggaa cgctgaaggt ctcgcctctg tcgcacctca gcgcggcata caccacaata   3060
accacctgac gaatgcgctt ggttcttcgt ccattagcga agcgtccggt tcacacacgt   3120
gccacgttgg cgaggtggca ggtgacaatg atcggtggag ctgatggtcg aaacgttcac   3180
agcctaggga tatcgaattc ctttcttgcg ctatgacact tccagcaaaa ggtagggcgg   3240
gctgcgagac ggcttcccgg cgctgcatgc aacaccgatg atgcttcgac cccccgaagc   3300
tccttcgggg ctgcatgggc gctccgatgc cgctccaggg cgagcgctgt ttaaatagcc   3360
aggcccccga ttgcaaagac attatagcga gctaccaaag ccatattcaa acacctagat   3420
cactaccact tctacacagg ccactcgagc ttgtgatcgc actccgctaa gggggcgcct   3480
```

-continued cttcctcttc gtttcagtca caacccgcaa acactagtgc gctggacgcg gcagtgggtg 3540
gccgaggaga accggcacgg cgacctgctg aacaagtact gttggctgac ggggcgcgtc 3600
aacatgcggg ccgtggaggt gaccatcaac aacctgatca agagcggcat gaacccgcag 3660
acggacaaca acccttactt gggcttcgtc tacacctcct tccaggagcg cgcgaccaag 3720
tacagccacg gcaacaccgc gcgccttgcg gccgagcagt gtgtttgagg gttttggttg 3780
cccgtatcga ggtcctggtg gcgcgcatgg gggagaaggc gcctgtcccg ctgacccccc 3840
cggctaccct cccggcacct tccagggcgc gtacgggatc ctgctcggcc gcaaggcgcg 3900
cggtgttgcc gtggctgtac ttggtcgcgc gctcctggaa ggaggtgtag acgaagccca 3960
agtaagggtt gttgtccgtc tgcgggttca tgccgctctt gatcaggttg ttgatggtca 4020
cctccacggc ccgcatgttg acgcgccccg tcagccaaca gtacttgttc agcaggtcgc 4080
cgtgccggtt ctcctcggcc acccactgcc gcgtccagcg caagcttgca gcagcagctc 4140
ggatagtatc gacacactct ggacgctggt cgtgtgatgg actgttgccg ccacacttgc 4200
tgccttgacc tgtgaatatc cctgccgctt ttatcaaaca gcctcagtgt gtttgatctt 4260
gtgtgtacgc gcttttgcga gttgctagct gcttgtgcta tttgcgaata ccacccccag 4320
catccccttc cctcgtttca tatcgcttgc atcccaaccg caacttatct acgctgtcct 4380
gctatccctc agcgctgctc ctgctcctgc tcactgcccc tcgcacagcc ttggtttggg 4440
ctccgcctgt attctcctgg tactgcaacc tgtaaaccag cactgcaatg ctgatgcacg 4500
ggaagtagtg ggatgggaac acaaatggaa agctggagct ccagccacgg caacaccgcg 4560
cgccttgcgg ccgagcacgg cgacaagaac ctgagcaaga tctgcgggct gatcgccagc 4620
gacgagggcc ggcacgagat cgcctacacg cgcatcgtgg acgagttctt ccgcctcgac 4680
cccgagggcg ccgtcgccgc ctacgccaac atgatgcgca agcagatcac catgcccgcg 4740
cacctcatgg acgacatggg ccacggcgag gccaacccgg gccgcaacct cttcgccgac 4800
ttctccgcgg tcgccgagaa gatcgacgtc tacgacgccg aggactactg ccgcatcctg 4860
gagcacctca acgcgcgctg gaaggtggac gagcgccagg tcagcggcca ggccgccgcg 4920
gaccaggagt acgtcctggg cctgccccag cgcttccgga aactcgccga gaagaccgcc 4980
gccaagcgca agcgcgtcgc gcgcaggccc gtcgccttct cctggatctc cgggcgcgag 5040
atcatggtct agggagcgac gagtgtgcgt gcggggctgg cgggagtggg acgccctcct 5100
cgctcctctc tgttctgaac ggaacaatcg gccaccccgc gctacgcgcc acgcatcgag 5160
caacgaagaa aacccccga tgataggttg cggtggctgc cgggatatag atccggccgc 5220
acatcaaagg gcccctccgc cagagaagaa gctcctttcc cagcagactc ctgaagagc 5279

<210> SEQ ID NO 95
<211> LENGTH: 6580
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240

-continued

```
gcaccgaggc cgcctccaac tggtcctcca gcagccgcag tcgccgccga ccctggcaga    300
ggaagacagg tgaggggtgt atgaattgta cagaacaacc acgagccttg tctaggcaga    360
atccctacca gtcatggctt tacctggatg acggcctgcg aacagctgtc cagcgaccct    420
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccttgcg cgttagtgtt gccatccttt gcagaccggt gagagccgac ttgttgtgcg    600
ccacccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgatcgagc aggacggcct ccacgccggc   1080
tcccccgccg cctgggtgga gcgcctgttc ggctacgact gggcccagca gaccatcggc   1140
tgctccgacg ccgccgtgtt ccgcctgtcc gcccagggcc gccccgtgct gttcgtgaag   1200
accgacctgt ccggcgccct gaacgagctg caggacgagg ccgcccgcct gtcctggctg   1260
gccaccaccg gcgtgccctg cgccgccgtg ctggacgtgg tgaccgaggc cggccgcgac   1320
tggctgctgc tgggcgaggt gcccggccag gacctgctgt cctcccacct ggcccccgcc   1380
gagaaggtgt ccatcatggc cgacgccatg cgccgcctgc acaccctgga ccccgccacc   1440
tgccccttcg accaccaggc caagcaccgc atcgagcgcg cccgcacccg catggaggcc   1500
ggcctggtgg accaggacga cctggacgag gagcaccagg gcctggcccc cgccgagctg   1560
ttcgcccgcc tgaaggcccg catgcccgac ggcgaggacc tggtggtgac ccacggcgac   1620
gcctgcctgc ccaacatcat ggtggagaac ggccgcttct ccggcttcat cgactgcggc   1680
cgcctgggcg tggccgaccg ctaccaggac atcgccctgg ccacccgcga catcgccgag   1740
gagctgggcg gcgagtgggc cgaccgcttc ctggtgctgt acggcatcgc cgcccccgac   1800
tcccagcgca tcgccttcta ccgcctgctg gacgagttct tctgacaatt ggcagcagca   1860
gctcggatag tatcgacaca ctctggacgc tggtcgtgtg atggactgtt gccgccacac   1920
ttgctgcctt gacctgtgaa tatccctgcc gcttttatca aacagcctca gtgtgtttga   1980
tcttgtgtgt acgcgctttt gcgagttgct agctgcttgt gctatttgcg aataccaccc   2040
ccagcatccc cttccctcgt ttcatatcgc ttgcatccca accgcaactt atctacgctg   2100
tcctgctatc cctcagcgct gctcctgctc ctgctcactg cccctcgcac agccttggtt   2160
tgggctccgc ctgtattctc ctggtactgc aacctgtaaa ccagcactgc aatgctgatg   2220
cacgggaagt agtgggatgg gaacacaaat ggaggatccc gcgtctcgaa cagagcgcgc   2280
agaggaacgc tgaaggtctc gcctctgtcg cacctcagcg cggcatacac cacaataacc   2340
acctgacgaa tgcgcttggt tcttcgtcca ttagcgaagc gtccggttca cacacgtgcc   2400
acgttggcga ggtggcaggt gacaatgatc ggtggagctg atggtcgaaa cgttcacagc   2460
ctagggatat cctgaagaat gggaggcagg tgttgttgat tatgagtgtg taaaagaaag   2520
gggtagagag ccgtcctcag atccgactac tatgcaggta gccgctcgcc catgcccgcc   2580
tggctgaata ttgatgcatg cccatcaagg caggcaggca tttctgtgca cgcaccaagc   2640
```

ccacaatctt ccacaacaca cagcatgtac caacgcacgc gtaaaagttg gggtgctgcc 2700
agtgcgtcat gccaggcatg atgtgctcct gcacatccgc catgatctcc tccatcgtct 2760
cgggtgtttc cggcgcctgg tccgggagcc gttccgccag atacccagac gccacctccg 2820
acctcacggg gtacttttcg agcgtctgcc ggtagtcgac gatcgcgtcc accatggagt 2880
agccgaggcg ccggaactgg cgtgacggag ggaggagagg gaggagagag aggggggggg 2940 gggggggga tgattacacg ccagtctcac aacgcatgca agacccgttt gattatgagt 3000
acaatcatgc actactagat ggatgagcgc caggcataag gcacaccgac gttgatggca 3060
tgagcaactc ccgcatcata tttcctattg tcctcacgcc aagccggtca ccatccgcat 3120
gctcatatta cagcgcacgc accgcttcgt gatccaccgg gtgaacgtag tcctcgacgg 3180
aaacatctgg ctcgggcctc gtgctggcac tccctcccat gccgacaacc tttctgctgt 3240
caccacgacc cacgatgcaa cgcgacacga cccggtggga ctgatcggtt cactgcacct 3300
gcatgcaatt gtcacaagcg catactccaa tcgtatccgt ttgatttctg tgaaaactcg 3360
ctcgaccgcc cgcgtcccgc aggcagcgat gacgtgtgcg tgacctgggt gtttcgtcga 3420
aaggccagca accccaaatc gcaggcgatc cggagattgg gatctgatcc gagcttggac 3480
cagatccccc acgatgcggc acgggaactg catcgactcg gcgcggaacc cagctttcgt 3540
aaatgccaga ttggtgtccg ataccttgat ttgccatcag cgaaacaaga cttcagcagc 3600
gagcgtattt ggcgggcgtg ctaccagggt tgcatacatt gcccatttct gtctggaccg 3660
ctttaccggc gcagagggtg agttgatggg gttggcaggc atcgaaacgc gcgtgcatgg 3720
tgtgtgtgtc tgttttcggc tgcacaattt caatagtcgg atgggcgacg gtagaattgg 3780
gtgttgcgct cgcgtgcatg cctcgccccg tcgggtgtca tgaccgggac tggaatcccc 3840
cctcgcgacc ctcctgctaa cgctcccgac tctcccgccc gcgcgcagga tagactctag 3900
ttcaaccaat cgacaactag tatgcagacc gcccaccagc gcccccccac cgagggccac 3960
tgcttcggcg cccgcctgcc caccgcctcc cgccgcgccg tgcgccgcgc ctggtcccgc 4020
atcgcccgcg ggcgcgccgc cgccgccgcc gacgccaacc ccgcccgccc cgagcgccgc 4080
gtggtgatca ccggccaggg cgtggtgacc tccctgggcc agaccatcga gcagttctac 4140
tcctccctgc tggagggcgt gtccggcatc tcccagatcc agaagttcga caccaccggc 4200
tacaccacca ccatcgccgg cgagatcaag tccctgcagc tggaccccta cgtgcccaag 4260
cgctgggcca agcgcgtgga cgacgtgatc aagtacgtgt acatcgccgg caagcaggcc 4320
ctggagtccg ccggcctgcc catcgaggcc gccggcctgg ccggcgccgg cctggacccc 4380
gccctgtgcg gcgtgctgat cggcaccgcc atggccggca tgacctcctt cgccgccggc 4440
gtggaggccc tgacccgcgg cggcgtgcgc aagatgaacc ccttctgcat cccctctcc 4500 atctccaaca tgggcggcgc catgctggcc atggacatcg gcttcatggg ccccaactac 4560
tccatctcca ccgcctgcgc caccggcaac tactgcatcc tgggcgccgc cgaccacatc 4620
cgccgcggcg acgccaacgt gatgctggcc ggcggcgccg acgccgccat catcccctcc 4680
ggcatcggcg gcttcatcgc ctgcaaggcc ctgtccaagc gcaacgacga gcccgagcgc 4740
gcctcccgcc cctgggacgc cgaccgcgac ggcttcgtga tgggcgaggg cgccggcgtg 4800
ctggtgctgg aggagctgga gcacgccaag cgccgcggcg ccaccatcct ggccgagctg 4860
gtgggcggcg ccgccacctc cgacgcccac cacatgaccg agcccgaccc ccagggccgc 4920
ggcgtgcgcc tgtgcctgga gcgcgccctg gagcgcgccc gcctggcccc cgagcgcgtg 4980

```
ggctacgtga acgcccacgg cacctccacc cccgccggcg acgtggccga gtaccgcgcc   5040
atccgcgccg tgatccccca ggactccctg cgcatcaact ccaccaagtc catgatcggc   5100
cacctgctgg gcggcgccgg cgccgtggag gccgtggccg ccatccaggc cctgcgcacc   5160
ggctggctgc accccaacct gaacctggag aaccccgccc ccggcgtgga ccccgtggtg   5220
ctggtgggcc cccgcaagga gcgcgccgag gacctggacg tggtgctgtc caactccttc   5280
ggcttcggcg gccacaactc ctgcgtgatc ttccgcaagt acgacgagat ggactacaag   5340
gaccacgacg gcgactacaa ggaccacgac atcgactaca aggacgacga cgacaagtga   5400
atcgatagat ctcttaaggc agcagcagct cggatagtat cgacacactc tggacgctgg   5460
tcgtgtgatg gactgttgcc gccacacttg ctgccttgac ctgtgaatat ccctgccgct   5520
tttatcaaac agcctcagtg tgtttgatct tgtgtgtacg cgcttttgcg agttgctagc   5580
tgcttgtgct atttgcgaat accaccccca gcatcccctt ccctcgtttc atatcgcttg   5640
catcccaacc gcaacttatc tacgctgtcc tgctatccct cagcgctgct cctgctcctg   5700
ctcactgccc ctcgcacagc cttggtttgg gctccgcctg tattctcctg gtactgcaac   5760
ctgtaaacca gcactgcaat gctgatgcac gggaagtagt gggatgggaa cacaaatgga   5820
aagcttaatt aagagctctt gttttccaga aggagttgct ccttgagcct ttcattctca   5880
gcctcgataa cctccaaagc cgctctaatt gtggaggggg ttcgaattta aaagcttgga   5940
atgttggttc gtgcgtctgg aacaagccca gacttgttgc tcactgggaa aaggaccatc   6000
agctccaaaa aacttgccgc tcaaaccgcg tacctctgct ttcgcgcaat ctgccctgtt   6060
gaaatcgcca ccacattcat attgtgacgc ttgagcagtc tgtaattgcc tcagaatgtg   6120
gaatcatctg ccccctgtgc gagcccatgc caggcatgtc gcgggcgagg acacccgcca   6180
ctcgtacagc agaccattat gctacctcac aatagttcat aacagtgacc atatttctcg   6240
aagctcccca acgagcacct ccatgctctg agtggccacc ccccggccct ggtgcttgcg   6300
gagggcaggt caaccggcat ggggctaccg aaatccccga ccggatccca ccaccccccgc  6360
gatgggaaga atctctcccc gggatgtggg cccaccacca gcacaacctg ctggcccagg   6420
cgagcgtcaa accataccac acaaatatcc ttggcatcgg ccctgaattc cttctgccgc   6480
tctgctaccc ggtgcttctg tccgaagcag gggttgctag ggatcgctcc gagtccgcaa   6540
acccttgtcg cgtggcgggg cttgttcgag cttgaagagc                         6580
```

```
<210> SEQ ID NO 96
<211> LENGTH: 8087
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

gctcttcgga gtcactgtgc cactgagttc gactggtagc tgaatggagt cgctgctcca     60
ctaaacgaat tgtcagcacc gccagccggc cgaggacccg agtcatagcg agggtagtag    120
cgcgccatgg caccgaccag cctgcttgcc agtactggcg tctcttccgc ttctctgtgg    180
tcctctgcgc gctccagcgc gtgcgctttt ccggtggatc atgcggtccg tggcgcaccg    240
cagcggccgc tgcccatgca gcgccgctgc ttccgaacag tggcggtcag ggccgcaccc    300
gcggtagccg tccgtccgga acccgcccaa gagttttggg agcagcttga gccctgcaag    360
atggcggagg acaagcgcat cttcctggag gagcaccggt gcgtggaggt ccggggctga    420
```

-continued

```
ccggccgtcg cattcaacgt aatcaatcgc atgatgatca gaggacacga agtcttggtg    480
gcggtggcca gaaacactgt ccattgcaag ggcataggga tgcgttcctt cacctctcat    540
ttctcatttc tgaatccctc cctgctcact ctttctcctc ctccttcccg ttcacgcagc    600
attcggggta ccctttcttg cgctatgaca cttccagcaa aaggtagggc gggctgcgag    660
acggcttccc ggcgctgcat gcaacaccga tgatgcttcg accccccgaa gctccttcgg    720
ggctgcatgg gcgctccgat gccgctccag ggcgagcgct gtttaaatag ccaggccccc    780
gattgcaaag acattatagc gagctaccaa agccatattc aaacacctag atcactacca    840
cttctacaca ggccactcga gcttgtgatc gcactccgct aagggggcgc ctcttcctct    900
tcgtttcagt cacaacccgc aaacggcgcg ccatgctgct gcaggccttc ctgttcctgc    960
tggccggctt cgccgccaag atcagcgcct ccatgacgaa cgagacgtcc gaccgccccc   1020
tggtgcactt cacccccaac aagggctgga tgaacgaccc caacggcctg tggtacgacg   1080
agaaggacgc caagtggcac ctgtacttcc agtacaaccc gaacgacacc gtctggggga   1140
cgcccttgtt ctggggccac gccacgtccg acgacctgac caactgggag gaccagccca   1200
tcgccatcgc cccgaagcgc aacgactccg gcgccttctc cggctccatg gtggtggact   1260
acaacaacac ctccggcttc ttcaacgaca ccatcgaccc gcgccagcgc tgcgtggcca   1320
tctggaccta caacaccccg gagtccgagg agcagtacat ctcctacagc ctggacggcg   1380
gctacacctt caccgagtac cagaagaacc ccgtgctggc cgccaactcc acccagttcc   1440
gcgacccgaa ggtcttctgg tacgagccct cccagaagtg gatcatgacc gcggccaagt   1500
cccaggacta caagatcgag atctactcct ccgacgacct gaagtcctgg aagctggagt   1560
ccgcgttcgc caacgagggc ttcctcggct accagtacga gtgccccggc ctgatcgagg   1620
tccccaccga gcaggacccc agcaagtcct actgggtgat gttcatctcc atcaaccccg   1680
gcgccccggc cggcggctcc ttcaaccagt acttcgtcgg cagcttcaac ggcacccact   1740
tcgaggcctt cgacaaccag tcccgcgtgg tggacttcgg caaggactac tacgccctgc   1800
agaccttctt caacaccgac ccgacctacg ggagcgccct gggcatcgcg tgggcctcca   1860
actgggagta ctccgccttc gtgcccacca acccctggcg ctcctccatg tccctcgtgc   1920
gcaagttctc cctcaacacc gagtaccagg ccaacccgga gacggagctg atcaacctga   1980
aggccgagcc gatcctgaac atcagcaacg ccggcccctg gagccggttc gccaccaaca   2040
ccacgttgac gaaggccaac agctacaacg tcgacctgtc caacagcacc ggcaccctgg   2100
agttcgagct ggtgtacgcc gtcaacacca cccagacgat ctccaagtcc gtgttcgcgg   2160
acctctccct ctggttcaag ggcctggagg accccgagga gtacctccgc atgggcttcg   2220
aggtgtccgc gtcctccttc ttcctggacc gcgggaacag caaggtgaag ttcgtgaagg   2280
agaacccccta cttcaccaac cgcatgagcg tgaacaacca gcccttcaag agcgagaacg   2340
acctgtccta ctacaaggtg tacggcttgc tggaccagaa catcctggag ctgtacttca   2400
acgacggcga cgtcgtgtcc accaacacct acttcatgac caccgggaac gccctgggct   2460
ccgtgaacat gacgacgggg gtggacaacc tgttctacat cgacaagttc caggtgcgcg   2520
aggtcaagtg acaattggca gcagcagctc ggatagtatc gacacactct ggacgctggt   2580
cgtgtgatgg actgttgccg ccacacttgc tgccttgacc tgtgaatatc cctgccgctt   2640
ttatcaaaca gcctcagtgt gtttgatctt gtgtgtacgc gcttttgcga gttgctagct   2700
gcttgtgcta tttgcgaata ccacccccag catccccttc cctcgtttca tatcgcttgc   2760
atcccaaccg caacttatct acgctgtcct gctatccctc agcgctgctc ctgctcctgc   2820
```

tcactgcccc tcgcacagcc ttggtttggg ctccgcctgt attctcctgg tactgcaacc 2880
tgtaaaccag cactgcaatg ctgatgcacg ggaagtagtg ggatgggaac acaaatggag 2940
gatcccgcgt ctcgaacaga gcgcgcagag gaacgctgaa ggtctcgcct ctgtcgcacc 3000
tcagcgcggc atacaccaca ataaccacct gacgaatgcg cttggttctt cgtccattag 3060
cgaagcgtcc ggttcacaca cgtgccacgt tggcgaggtg gcaggtgaca atgatcggtg 3120
gagctgatgg tcgaaacgtt cacagcctag ggatatcgaa ttcggccgac aggacgcgcg 3180
tcaaaggtgc tggtcgtgta tgccctggcc ggcaggtcgt tgctgctgct ggttagtgat 3240
tccgcaaccc tgattttggc gtcttatttt ggcgtggcaa acgctggcgc ccgcgagccg 3300
ggccggcggc gatgcggtgc cccacggctg ccggaatcca agggaggcaa gagcgcccgg 3360
gtcagttgaa gggctttacg cgcaaggtac agccgctcct gcaaggctgc gtggtggaat 3420
tggacgtgca ggtcctgctg aagttcctcc accgcctcac cagcggacaa agcaccggtg 3480
tatcaggtcc gtgtcatcca ctctaaagaa ctcgactacg acctactgat ggccctagat 3540
tcttcatcaa aaacgcctga gacacttgcc caggattgaa actccctgaa gggaccacca 3600
ggggccctga gttgttcctt ccccccgtgg cgagctgcca gccaggctgt acctgtgatc 3660
gaggctggcg ggaaaatagg cttcgtgtgc tcaggtcatg ggaggtgcag gacagctcat 3720
gaaacgccaa caatcgcaca attcatgtca agctaatcag ctatttcctc ttcacgagct 3780
gtaattgtcc caaaattctg gtctaccggg ggtgatcctt cgtgtacggg cccttccctc 3840
aaccctaggt atgcgcgcat gcggtcgccg cgcaactcgc gcgagggccg agggtttggg 3900
acgggccgtc ccgaaatgca gttgcacccg gatgcgtggc acctttttttg cgataattta 3960
tgcaatggac tgctctgcaa aattctggct ctgtcgccaa ccctaggatc agcggcgtag 4020
gatttcgtaa tcattcgtcc tgatggggag ctaccgacta ccctaatatc agcccgactg 4080
cctgacgcca gcgtccactt ttgtgcacac attccattcg tgcccaagac atttcattgt 4140
ggtgcgaagc gtccccagtt acgctcacct gtttcccgac ctccttactg ttctgtcgac 4200
agagcgggcc cacaggccgg tcgcagccac tagtatggcc accgcatcca ctttctcggc 4260
gttcaatgcc cgctgcggcg acctgcgtcg ctcggcgggc tccgggcccc ggcgcccagc 4320
gaggccccctc cccgtgcgcg ggcgcgccgc cgccgccgcc gacgccaacc ccgcccgccc 4380
cgagcgccgc gtggtgatca ccggccaggg cgtggtgacc tccctgggcc agaccatcga 4440
gcagttctac tcctccctgc tggagggcgt gtccggcatc tcccagatcc agaagttcga 4500
caccaccggc tacaccacca ccatcgccgg cgagatcaag tccctgcagc tggaccccta 4560
cgtgcccaag cgctgggcca agcgcgtgga cgacgtgatc aagtacgtgt acatcgccgg 4620
caagcaggcc ctggagtccg ccggcctgcc catcgaggcc gccggcctgg ccggcgccgg 4680
cctggacccc gccctgtgcg gcgtgctgat cggcaccgcc atggccggca tgacctcctt 4740
cgccgccggc gtggaggccc tgacccgcgg cggcgtgcgc aagatgaacc ccttctgcat 4800
ccccttctcc atctccaaca tgggcggcgc catgctggcc atggacatcg gcttcatggg 4860
ccccaactac tccatctcca ccgcctgcgc caccggcaac tactgcatcc tgggcgccgc 4920
cgaccacatc cgccgcggcg acgccaacgt gatgctggcc ggcggcgccg acgccgccat 4980
catcccctcc ggcatcggcg gcttcatcgc ctgcaaggcc ctgtccaagc gcaacgacga 5040
gcccgagcgc gcctcccgcc cctgggacgc cgaccgcgac ggcttcgtga tgggcgaggg 5100
cgccggcgtg ctggtgctgg aggagctgga gcacgccaag cgccgcggcg ccaccatcct 5160
ggccgagctg gtgggcggcg ccgccacctc cgacgcccac cacatgaccg agcccgaccc 5220
ccagggccgc ggcgtgcgcc tgtgcctgga gcgcgccctg gagcgcgccc gcctggcccc 5280
cgagcgcgtg ggctacgtga acgcccacgg cacctccacc cccgccggcg acgtggccga 5340
gtaccgcgcc atccgcgccg tgatccccca ggactccctg cgcatcaact ccaccaagtc 5400
catgatcggc cacctgctgg gcggcgccgg cgccgtggag gccgtggccg ccatccaggc 5460
cctgcgcacc ggctggctgc accccaacct gaacctggag aaccccgccc ccggcgtgga 5520
ccccgtggtg ctggtgggcc cccgcaagga gcgcgccgag gacctggacg tggtgctgtc 5580
caactccttc ggcttcggcg gccacaactc ctgcgtgatc ttccgcaagt acgacgagat 5640
ggactacaag gaccacgacg gcgactacaa ggaccacgac atcgactaca aggacgacga 5700
cgacaagtga atcgatagat ctcttaaggc agcagcagct cggatagtat cgacacactc 5760
tggacgctgg tcgtgtgatg gactgttgcc gccacacttg ctgccttgac ctgtgaatat 5820
ccctgccgct tttatcaaac agcctcagtg tgtttgatct tgtgtgtacg cgcttttgcg 5880
agttgctagc tgcttgtgct atttgcgaat accaccccca gcatcccctt ccctcgtttc 5940
atatcgcttg catcccaacc gcaacttatc tacgctgtcc tgctatccct cagcgctgct 6000
cctgctcctg ctcactgccc ctcgcacagc cttggtttgg gctccgcctg tattctcctg 6060
gtactgcaac ctgtaaacca gcactgcaat gctgatgcac gggaagtagt gggatgggaa 6120
cacaaatgga aagcttaatt aagagctcct ttcttgcgct atgacacttc cagcaaaagg 6180
tagggcgggc tgcgagacgg cttcccggcg ctgcatgcaa caccgatgat gcttcgaccc 6240
cccgaagctc cttcggggct gcatgggcgc tccgatgccg ctccagggcg agcgctgttt 6300
aaatagccag gcccccgatt gcaaagacat tatagcgagc taccaaagcc atattcaaac 6360
acctagatca ctaccacttc tacacaggcc actcgagctt gtgatcgcac tccgctaagg 6420
gggcgcctct tcctcttcgt ttcagtcaca acccgcaaac actagtatgg ctatcaagac 6480
gaacaggcag cctgtggaga agcctccgtt cacgatcggg acgctgcgca aggccatccc 6540
cgcgcactgt ttcgagcgct cggcgcttcg tagcagcatg tacctggcct ttgacatcgc 6600
ggtcatgtcc ctgctctacg tcgcgtcgac gtacatcgac cctgcaccgg tgcctacgtg 6660
ggtcaagtac ggcatcatgt ggccgctcta ctggttcttc caggtgtgtt tgagggtttt 6720
ggttgcccgt attgaggtcc tggtggcgcg catggaggag aaggcgcctg tcccgctgac 6780
ccccccggct accctcccgg caccttccag ggcgcgtacg ggaagaacca gtagagcggc 6840
cacatgatgc cgtacttgac ccacgtaggc accggtgcag ggtcgatgta cgtcgacgcg 6900
acgtagagca gggacatgac cgcgatgtca aaggccaggt acatgctgct acgaagcgcc 6960
gagcgctcga aacagtgcgc ggggatggcc ttgcgcagcg tcccgatcgt gaacggaggc 7020
ttctccacag gctgcctgtt cgtcttgata gccatctcga ggcagcagca gctcggatag 7080
tatcgacaca ctctggacgc tggtcgtgtg atggactgtt gccgccacac ttgctgcctt 7140
gacctgtgaa tatccctgcc gcttttatca aacagcctca gtgtgtttga tcttgtgtgt 7200
acgcgctttt gcgagttgct agctgcttgt gctatttgcg aataccaccc ccagcatccc 7260
cttccctcgt ttcatatcgc ttgcatccca accgcaactt atctacgctg tcctgctatc 7320
cctcagcgct gctcctgctc ctgctcactg cccctcgcac agccttggtt tgggctccgc 7380
ctgtattctc ctggtactgc aacctgtaaa ccagcactgc aatgctgatg cacgggaagt 7440
agtgggatgg gaacacaaat ggaaagctgt attgttttcc agaaggagtt gctccttgag 7500
cctttcattc tcagcctcga taacctccaa agccgctcta attgtggagg gggttcgaag 7560
acagggtggt tggctggatg gggaaacgct ggtcgcggga ttcgatcctg ctgcttatat 7620
cctccctgga agcacaccca cgactctgaa gaagaaaacg tgcacacaca caacccaacc 7680
ggccgaatat ttgcttcctt atcccgggtc caagagagac tgcgatgccc ccctcaatca 7740
gcatcctcct ccctgccgct tcaatcttcc ctgcttgcct gcgcccgcgg tgcgccgtct 7800
gcccgcccag tcagtcactc ctgcacaggc cccttgtgcg cagtgctcct gtacccttta 7860
ccgctccttc cattctgcga ggccccctat tgaatgtatt cgttgcctgt gtggccaagc 7920
gggctgctgg gcgcgccgcc gtcgggcagt gctcggcgac tttggcggaa gccgattgtt 7980
cttctgtaag ccacgcgctt gctgctttgg gaagagaagg ggggggtac tgaatggatg 8040 aggaggagaa ggaggggtat tggtattatc tgagttgggt gaagagc 8087

<210> SEQ ID NO 97
<211> LENGTH: 4479
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
gctcttcggg tcgccgcgct gcctcgcgtc ccctggtggt gcgcgcggtc gccagcgagg 60
ccccgctggg cgttccgccc tcggtgcagc gcccctcccc cgtggtctac tccaagctgg 120
acaagcagca ccgcctgacg cccgagcgcc tggagctggt gcagagcatg gggcagtttg 180
cggaggagag ggtgctgccc gtgctgcacc ccgtggacaa gctgtggcag ccgcaggact 240
ttttgcccga ccccgagtcg cccgacttcg aggatcaggt ggcggagctg cgcgcgcgcg 300
ccaaggacct gcccgacgag tactttgtgg tgctggtggg ggacatgatc acggaggagg 360
cgctgccgac ctacatggcc atgctcaaca cgctggacgg cgtgcgcgac gacacgggcg 420
cggccgacca cccgtgggcg cgctggacgc ggcagtgggt ggccgaggag aaccggcacg 480
gcgacctgct gaacaagtac tgctggctga cggggcgcgt caacatgcgg gccgtggagg 540
tgaccatcaa caacctgatc aagagcggca tgaacccgca gacggacaac aacccttatt 600
tggggttcgt ctacacctcc ttccaggagc gcgccaccaa gtaggtaccc tttcttgcgc 660
tatgacactt ccagcaaaag gtagggcggg ctgcgagacg gcttcccggc gctgcatgca 720
acaccgatga tgcttcgacc ccccgaagct ccttcggggc tgcatgggcg ctccgatgcc 780
gctccagggc gagcgctgtt taaatagcca ggcccccgat tgcaaagaca ttatagcgag 840
ctaccaaagc catattcaaa cacctagatc actaccactt ctacacaggc cactcgagct 900
tgtgatcgca ctccgctaag gggcgcctc ttcctcttcg tttcagtcac aacccgcaaa 960
ctctagaata tcaatgatcg agcaggacgg cctccacgcc ggctcccccg ccgcctgggt 1020
ggagcgcctg ttcggctacg actgggccca gcagaccatc ggctgctccg acgccgccgt 1080
gttccgcctg tccgcccagg gccgccccgt gctgttcgtg aagaccgacc tgtccggcgc 1140
cctgaacgag ctgcaggacg aggccgcccg cctgtcctgg ctggccacca ccggcgtgcc 1200
ctgcgccgcc gtgctggacg tggtgaccga ggccggccgc gactggctgc tgctgggcga 1260
ggtgcccggc caggacctgc tgtcctccca cctggccccc gccgagaagg tgtccatcat 1320
ggccgacgcc atgcgccgcc tgcacaccct ggaccccgcc acctgcccct tcgaccacca 1380
ggccaagcac cgcatcgagc gcgcccgcac ccgcatggag gccggcctgg tggaccagga 1440
cgacctggac gaggagcacc agggcctggc ccccgccgag ctgttcgccc gcctgaaggc 1500

-continued

```
ccgcatgccc gacggcgagg acctggtggt gacccacggc gacgcctgcc tgcccaacat   1560
catggtggag aacggccgct tctccggctt catcgactgc ggccgcctgg gcgtggccga   1620
ccgctaccag gacatcgccc tggccacccg cgacatcgcc gaggagctgg gcggcgagtg   1680
ggccgaccgc ttcctggtgc tgtacggcat cgccgccccc gactcccagc gcatcgcctt   1740
ctaccgcctg ctggacgagt tcttctgaca attggcagca gcagctcgga tagtatcgac   1800
acactctgga cgctggtcgt gtgatggact gttgccgcca cacttgctgc cttgacctgt   1860
gaatatccct gccgctttta tcaaacagcc tcagtgtgtt tgatcttgtg tgtacgcgct   1920
tttgcgagtt gctagctgct tgtgctattt gcgaatacca cccccagcat ccccttccct   1980
cgtttcatat cgcttgcatc ccaaccgcaa cttatctacg ctgtcctgct atccctcagc   2040
gctgctcctg ctcctgctca ctgcccctcg cacagccttg gtttgggctc cgcctgtatt   2100
ctcctggtac tgcaacctgt aaaccagcac tgcaatgctg atgcacggga agtagtggga   2160
tgggaacaca aatggaggat cccgcgtctc gaacagagcg cgcagaggaa cgctgaaggt   2220
ctcgcctctg tcgcacctca gcgcggcata caccacaata accacctgac gaatgcgctt   2280
ggttcttcgt ccattagcga agcgtccggt tcacacacgt gccacgttgg cgaggtggca   2340
ggtgacaatg atcggtggag ctgatggtcg aaacgttcac agcctaggga tatcgaattc   2400
ctttcttgcg ctatgacact tccagcaaaa ggtagggcgg gctgcgagac ggcttcccgg   2460
cgctgcatgc aacaccgatg atgcttcgac cccccgaagc tccttcgggg ctgcatgggc   2520
gctccgatgc cgctccaggg cgagcgctgt ttaaatagcc aggcccccga ttgcaaagac   2580
attatagcga gctaccaaag ccatattcaa acacctagat cactaccact tctacacagg   2640
ccactcgagc ttgtgatcgc actccgctaa gggggcgcct cttcctcttc gtttcagtca   2700
caacccgcaa acactagtgc gctggacgcg gcagtgggtg gccgaggaga accggcacgg   2760
cgacctgctg aacaagtact gttggctgac ggggcgcgtc aacatgcggg ccgtggaggt   2820
gaccatcaac aacctgatca agagcggcat gaacccgcag acggacaaca acccttactt   2880
gggcttcgtc tacacctcct tccaggagcg cgcgaccaag tacagccacg gcaacaccgc   2940
gcgccttgcg gccgagcagt gtgtttgagg gttttggttg cccgtatcga ggtcctggtg   3000
gcgcgcatgg gggagaaggc gcctgtcccg ctgacccccc cggctaccct cccggcacct   3060
tccagggcgc gtacgggatc ctgctcggcc gcaaggcgcg cggtgttgcc gtggctgtac   3120
ttggtcgcgc gctcctggaa ggaggtgtag acgaagccca agtaagggtt gttgtccgtc   3180
tgcgggttca tgccgctctt gatcaggttg ttgatggtca cctccacggc ccgcatgttg   3240
acgcgccccg tcagccaaca gtacttgttc agcaggtcgc cgtgccggtt ctcctcggcc   3300
acccactgcc gcgtccagcg caagcttgca gcagcagctc ggatagtatc gacacactct   3360
ggacgctggt cgtgtgatgg actgttgccg ccacacttgc tgccttgacc tgtgaatatc   3420
cctgccgctt ttatcaaaca gcctcagtgt gtttgatctt gtgtgtacgc gcttttgcga   3480
gttgctagct gcttgtgcta tttgcgaata ccacccccag catccccttc cctcgtttca   3540
tatcgcttgc atcccaaccg caacttatct acgctgtcct gctatccctc agcgctgctc   3600
ctgctcctgc tcactgcccc tcgcacagcc ttggtttggg ctccgcctgt attctcctgg   3660
tactgcaacc tgtaaaccag cactgcaatg ctgatgcacg ggaagtagtg ggatgggaac   3720
acaaatggaa agctggagct ccagccacgg caacaccgcg cgccttgcgg ccgagcacgg   3780
cgacaagaac ctgagcaaga tctgcgggct gatcgccagc gacgagggcc ggcacgagat   3840
```

```
cgcctacacg cgcatcgtgg acgagttctt ccgcctcgac cccgagggcg ccgtcgccgc   3900

ctacgccaac atgatgcgca agcagatcac catgcccgcg cacctcatgg acgacatggg   3960

ccacggcgag gccaacccgg gccgcaacct cttcgccgac ttctccgcgg tcgccgagaa   4020

gatcgacgtc tacgacgccg aggactactg ccgcatcctg gagcacctca acgcgcgctg   4080

gaaggtggac gagcgccagg tcagcggcca ggccgccgcg gaccaggagt acgtcctggg   4140

cctgccccag cgcttccgga aactcgccga gaagaccgcc gccaagcgca agcgcgtcgc   4200

gcgcaggccc gtcgccttct cctggatctc cgggcgcgag atcatggtct agggagcgac   4260

gagtgtgcgt gcggggctgg cgggagtggg acgccctcct cgctcctctc tgttctgaac   4320

ggaacaatcg gccaccccgc gctacgcgcc acgcatcgag caacgaagaa aaccccccga   4380

tgataggttg cggtggctgc cgggatatag atccggccgc acatcaaagg gcccctccgc   4440

cagagaagaa gctcctttcc cagcagactc ctgaagagc                          4479
```

<210> SEQ ID NO 98
<211> LENGTH: 5243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
atgcatgccg gtcaccaccc gcatgctcgt actacagcgc acgcaccgct tcgtgatcca     60

ccgggtgaac gtagtcctcg acggaaacat ctggttcggg cctcctgctt gcactcccgc    120

ccatgccgac aacctttctg ctgttaccac gacccacaat gcaacgcgac acgaccgtgt    180

gggactgatc ggttcactgc acctgcatgc aattgtcaca agcgcttact ccaattgtat    240

tcgtttgttt tctgggagca gttgctcgac cgcccgcgtc ccgcaggcag cgatgacgtg    300

tgcgtggcct gggtgtttcg tcgaaaggcc agcaacccta aatcgcaggc gatccggaga    360

ttgggatctg atccgagttt ggaccagatc cgccccgatg cggcacggga actgcatcga    420

ctcggcgcgg aacccagctt tcgtaaatgc cagattggtg tccgatacct ggatttgcca    480

tcagcgaaac aagacttcag cagcgagcgt atttggcggg cgtgctacca gggttgcata    540

cattgcccat ttctgtctgg accgctttac tggcgcagag ggtgagttga tggggttggc    600

aggcatcgaa acgcgcgtgc atggtgtgcg tgtctgtttt cggctgcacg aattcaatag    660

tcggatgggc gacggtagaa ttgggtgtgg cgctcgcgtg catgcctcgc cccgtcgggt    720

gtcatgaccg ggactggaat ccccccctcgc gaccatcttg ctaacgctcc cgactctccc    780

gactagtgcg ctggacgcgg cagtgggtgg ccgaggagaa ccggcacggc gacctgctga    840

acaagtactg ttggctgacg gggcgcgtca acatgcgggc cgtggaggtg accatcaaca    900

acctgatcaa gagcggcatg aacccgcaga cggacaacaa cccttacttg ggcttcgtct    960

acacctcctt ccaggagcgc gcgaccaagt acagccacgg caacaccgcg cgccttgcgg   1020

ccgagcagtg tgtttgaggg ttttggttgc ccgtatcgag gtcctggtgg cgcgcatggg   1080

ggagaaggcg cctgtcccgc tgaccccccc ggctaccctc ccggcacctt ccagggcgcg   1140

tacgggatcc tgctcggccg caaggcgcgc ggtgttgccg tggctgtact tggtcgcgcg   1200

ctcctggaag gaggtgtaga cgaagcccaa gtaagggttg ttgtccgtct gcgggttcat   1260

gccgctcttg atcaggttgt tgatggtcac ctccacggcc cgcatgttga cgcgccccgt   1320

cagccaacag tacttgttca gcaggtcgcc gtgccggttc tcctcggcca cccactgccg   1380
```

-continued

```
cgtccagcgc aagcttgcag cagcagctcg gatagtatcg acacactctg gacgctggtc   1440
gtgtgatgga ctgttgccgc cacacttgct gccttgacct gtgaatatcc ctgccgcttt   1500
tatcaaacag cctcagtgtg tttgatcttg tgtgtacgcg cttttgcgag ttgctagctg   1560
cttgtgctat ttgcgaatac cacccccagc atccccttcc ctcgtttcat atcgcttgca   1620
tcccaaccgc aacttatcta cgctgtcctg ctatccctca gcgctgctcc tgctcctgct   1680
cactgcccct cgcacagcct tggtttgggc tccgcctgta ttctcctggt actgcaacct   1740
gtaaaccagc actgcaatgc tgatgcacgg gaagtagtgg gatgggaaca caaatggaaa   1800
gctggagctc aaagatatca acttaattaa ccaaggtacc cgcctgcaac gcaagggcag   1860
ccacagccgc tcccacccgc cgctgaaccg acacgtgctt gggcgcctgc cgcctgcctg   1920
ccgcatgctt gtgctggtga ggctgggcag tgctgccatg ctgattgagg cttggttcat   1980
cgggtggaag cttatgtgtg tgctgggctt gcatgccggg caatgcgcat ggtggcaaga   2040
gggcggcagc acttgctgga gctgccgcgg tgcctccagg tggttcaatc gcggcagcca   2100
gagggatttc agatgatcgc gcgtacaggt tgagcagcag tgtcagcaaa ggtagcagtt   2160
tgccagaatg atcggttcag ctgttaatca atgccagcaa gagaaggggt caagtgcaaa   2220
cacgggcatg ccacagcacg ggcaccgggg agtggaatgg caccaccaag tgtgtgcgag   2280
ccagcatcgc cgcctggctg tttcagctac aacggcagga gtcatccaac gtaaccatga   2340
gctgatcaac actgcaatca tcgggcgggc gtgatgcaag catgcctggc gaagacacat   2400
ggtgtgcgga tgctgccggc tgctgcctgc tgcgcacgcc gttgagttgg cagcaggctc   2460
agccatgcac tggatggcag ctgggctgcc actgcaatgt ggtggatagg atgcaagtgg   2520
agcgaatacc aaaccctctg gctgcttgct gggttgcatg gcatcgcacc atcagcagga   2580
gcgcatgcga agggactggc cccatgcacg ccatgccaaa ccggagcgca ccgagtgtcc   2640
acactgtcac caggcccgca agctttgcag aaccatgctc atggacgcat gtagcgctga   2700
cgtcccttga cggcgctcct ctcgggtgtg ggaaacgcaa tgcagcacag gcagcagagg   2760
cggcggcagc agagcggcgg cagcagcggc gggggccacc cttcttgcgg ggtcgcgccc   2820
cagccagcgg tgatgcgctg atcccaaacg agttcacatt catttgcatg cctggagaag   2880
cgaggctggg gcctttgggc tggtgcagcc cgcaatggaa tgcgggaccg ccaggctagc   2940
agcaaaggcg cctcccctac tccgcatcga tgttccatag tgcattggac tgcatttggg   3000
tggggcggcc ggctgtttct ttcgtgttgc aaaacgcgcc agctcagcaa cctgtcccgt   3060
gggtcccccg tgccgatgaa atcgtgtgca cgccgatcag ctgattgccc ggctcgcgaa   3120
gtaggcgccc tcctttctgc tcgccctctc tccgtcccgc ctctagaata tcaatgatcg   3180
agcaggacgg cctccacgcc ggctcccccg ccgcctgggt ggagcgcctg ttcggctacg   3240
actgggccca gcagaccatc ggctgctccg acgccgccgt gttccgcctg tccgcccagg   3300
gccgccccgt gctgttcgtg aagaccgacc tgtccggcgc cctgaacgag ctgcaggacg   3360
aggccgcccg cctgtcctgg ctggccacca ccggcgtgcc ctgcgccgcc gtgctggacg   3420
tggtgaccga ggccggccgc gactggctgc tgctgggcga ggtgcccggc caggacctgc   3480
tgtcctccca cctggccccc gccgagaagg tgtccatcat ggccgacgcc atgcgccgcc   3540
tgcacaccct ggaccccgcc acctgcccct tcgaccacca ggccaagcac cgcatcgagc   3600
gcgcccgcac ccgcatggag gccggcctgg tggaccagga cgacctggac gaggagcacc   3660
agggcctggc ccccgccgag ctgttcgccc gcctgaaggc ccgcatgccc gacggcgagg   3720
acctggtggt gacccacggc gacgcctgcc tgcccaacat catggtggag aacggccgct   3780
```

tctccggctt catcgactgc ggccgcctgg gcgtggccga ccgctaccag gacatcgccc 3840
tggccacccg cgacatcgcc gaggagctgg gcggcgagtg ggccgaccgc ttcctggtgc 3900
tgtacggcat cgccgccccc gactcccagc gcatcgcctt ctaccgcctg ctggacgagt 3960
tcttctgaca attggcagca gcagctcgga tagtatcgac acactctgga cgctggtcgt 4020
gtgatggact gttgccgcca cacttgctgc cttgacctgt gaatatccct gccgctttta 4080
tcaaacagcc tcagtgtgtt tgatcttgtg tgtacgcgct tttgcgagtt gctagctgct 4140
tgtgctattt gcgaatacca cccccagcat ccccttccct cgtttcatat cgcttgcatc 4200
ccaaccgcaa cttatctacg ctgtcctgct atccctcagc gctgctcctg ctcctgctca 4260
ctgcccctcg cacagccttg gtttgggctc cgcctgtatt ctcctggtac tgcaacctgt 4320
aaaccagcac tgcaatgctg atgcacggga agtagtggga tgggaacaca aatggaggat 4380
cccgcgtctc gaacagagcg cgcagaggaa cgctgaaggt ctcgcctctg tcgcacctca 4440
gcgcggcata caccacaata accacctgac gaatgcgctt ggttcttcgt ccattagcga 4500
agcgtccggt tcacacacgt gccacgttgg cgaggtggca ggtgacaatg atcggtggag 4560
ctgatggtcg aaacgttcac agcctaggga tatcgaattc cgggtcgccg cgctgcctcg 4620
cgtcccctgg tggtgcgcgc ggtcgccagc gaggccccgc tgggcgttcc gccctcggtg 4680
cagcgcccct cccccgtggt ctactccaag ctggacaagc agcaccgcct gacgcccgag 4740
cgcctggagc tggtgcagag catggggcag tttgcggagg agagggtgct gcccgtgctg 4800
caccccgtgg acaagctgtg gcagccgcag gactttttgc ccgaccccga gtcgcccgac 4860
ttcgaggatc aggtggcgga gctgcgcgcg cgcgccaagg acctgcccga cgagtacttt 4920
gtggtgctgg tgggggacat gatcacggag gaggcgctgc cgacctacat ggccatgctc 4980
aacacgctgg acggcgtgcg cgacgacacg ggcgcggccg accacccgtg ggcgcgctgg 5040
acgcggcagt gggtggccga ggagaaccgg cacggcgacc tgctgaacaa gtactgctgg 5100
ctgacggggc gcgtcaacat gcgggccgtg gaggtgacca tcaacaacct gatcaagagc 5160
ggcatgaacc cgcagacgga caacaaccct tatttggggt tcgtctacac ctccttccag 5220
gagcgcgcca ccaagtatct aga 5243

<210> SEQ ID NO 99
<211> LENGTH: 6804
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 99
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgagggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480
gcacgctggc gctgcgcttc gccgatctga ggacagtcgg ggaactctga tcagtctaaa 540

```
ccccccttgcg cgttagtgtt gccatccttt gcagaccggt gagagccgac ttgttgtgcg    600
ccaccccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgcccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
```

-continued

```
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac ctttttgcg ataatttatg    4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
tgcgaagcgt ccccagttac gctcacctgt ttcccgacct ccttactgtt ctgtcgacag   4320
agcgggccca caggccggtc gcagccacta gtatggccac cgcatccact ttctcggcgt   4380
tcaatgcccg ctgcggcgac ctgcgtcgct cggcgggctc cgggccccgg cgcccagcga   4440
ggcccctccc cgtgcgcggg cgcgccgcca ccctgcgctc cggcctgcgc gacgtggaga   4500
ccgtgaagaa gaccttctcc cccgcccgcg aggtgcacgt gcaggtgacc cactccatgg   4560
ccccccagaa gatcgagatc ttcaaggcca tggaggactg ggccgagaac aacatcctgg   4620
tgcacctgaa gaacgtggag aagtgccccc agccccagga cttcctgccc gaccccgcct   4680
ccgacgagtt ccacgaccag atcaaggagc tgcgcgagcg cgccaaggag atccccgacg   4740
actacttcgt ggtgctggtg ggcgacatga tcaccgagga ggccctgccc acctaccaga   4800
ccatgctgaa cacctgggac ggcgtgcgcg acgagaccgg cgcctccccc acctcctggg   4860
ccatctggac ccgcgcctgg accgccgagg agaaccgcca cggcgacccc ctgaacaagt   4920
acctgtacct gtccggccgc gtggacatga agcagatcga gaagaccatc cagtacctga   4980
tcggctccgg catggacccc cgcaccgaga actcccccta cctgggcttc atctacacct   5040
ccttccagga gcgcgccacc ttcatctccc acggcaacac cgcccgcctg gcccgcgacc   5100
acggcgactt caagctggcc cagatctgcg gcaccatcgc ctccgacgag aagcgccacg   5160
agaccgccta caccaagatc gtggagaagc tgttcgagat cgaccccgac ggcaccgtgc   5220
tggccttcgg cgacatgatg aagaagaaga tctccatgcc cgaccacttc atgtacgacg   5280
```

gccgcgacga caacctgttc gaccacttct cctccgtggc ccagcgcctg ggcgtgtaca 5340
ccgccaagga ctacgccgac atcctggagc acctggtggg ccgctggaag gtggagaagc 5400
tgaccggcct gtccgccgag ggccagaagg cccaggacta cgtgtgcggc ctgccccccc 5460
gcatccgccg cctggaggag cgcgcccaga tccgcgccaa gcaggccccc cgcctgccct 5520
tctcctggat ctacgaccgc gaggtgcagc tgatggacta caaggaccac gacggcgact 5580
acaaggacca cgacatcgac tacaaggacg acgacgacaa gtgaatcgat agatctctta 5640
aggcagcagc agctcggata gtatcgacac actctggacg ctggtcgtgt gatggactgt 5700
tgccgccaca cttgctgcct tgacctgtga atatccctgc cgcttttatc aaacagcctc 5760
agtgtgtttg atcttgtgtg tacgcgcttt tgcgagttgc tagctgcttg tgctatttgc 5820
gaataccacc cccagcatcc ccttccctcg tttcatatcg cttgcatccc aaccgcaact 5880
tatctacgct gtcctgctat ccctcagcgc tgctcctgct cctgctcact gcccctcgca 5940
cagccttggt ttgggctccg cctgtattct cctggtactg caacctgtaa accagcactg 6000
caatgctgat gcacgggaag tagtgggatg ggaacacaaa tggaaagctt aattaagagc 6060
tcttgttttc cagaaggagt tgctccttga gcctttcatt ctcagcctcg ataacctcca 6120
aagccgctct aattgtggag gggttcgaa tttaaaagct tggaatgttg gttcgtgcgt 6180
ctggaacaag cccagacttg ttgctcactg ggaaaaggac catcagctcc aaaaaacttg 6240
ccgctcaaac cgcgtacctc tgctttcgcg caatctgccc tgttgaaatc gccaccacat 6300
tcatattgtg acgcttgagc agtctgtaat tgcctcagaa tgtggaatca tctgccccct 6360
gtgcgagccc atgccaggca tgtcgcgggc gaggacaccc gccactcgta cagcagacca 6420
ttatgctacc tcacaatagt tcataacagt gaccatattt ctcgaagctc cccaacgagc 6480
acctccatgc tctgagtggc caccccccgg ccctggtgct tgcggagggc aggtcaaccg 6540
gcatggggct accgaaatcc ccgaccggat cccaccaccc ccgcgatggg aagaatctct 6600
ccccgggatg tgggcccacc accagcacaa cctgctggcc caggcgagcg tcaaaccata 6660
ccacacaaat atccttggca tcggccctga attccttctg ccgctctgct acccggtgct 6720
tctgtccgaa gcaggggttg ctagggatcg ctccgagtcc gcaaaccctt gtcgcgtggc 6780
ggggcttgtt cgagcttgaa gagc 6804

<210> SEQ ID NO 100
<211> LENGTH: 6792
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 100
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480

-continued

```
gcacgctggc gctgcgcttc gccgatctga ggacagtcgg ggaactctga tcagtctaaa    540
ccccccttgcg cgttagtgtt gccatccttt gcagaccggt gagagccgac ttgttgtgcg    600
ccaccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
```

-continued

```
ttgtgctatt tgcgaatacc acccccagca tcccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac ctttttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
tgcgaagcgt ccccagttac gctcacctgt ttcccgacct ccttactgtt ctgtcgacag   4320
agcgggccca caggccggtc gcagccacta gtatggccct gaagctgaac gccatcaact   4380
tccagtcccc caagtgctcc tccttcggcc tgccccccgt ggtgtccctg cgctccccca   4440
agctgtccgt ggccgccacc ctgcgctccg gcctgcgcga cgtggagacc gtgaagaaga   4500
ccttctcccc cgcccgcgag gtgcacgtgc aggtgaccca ctccatggcc ccccagaaga   4560
tcgagatctt caaggccatg gaggactggg ccgagaacaa catcctggtg cacctgaaga   4620
acgtggagaa gtgcccccag ccccaggact tcctgcccga ccccgcctcc gacgagttcc   4680
acgaccagat caaggagctg cgcgagcgcg ccaaggagat ccccgacgac tacttcgtgg   4740
tgctggtggg cgacatgatc accgaggagg ccctgcccac ctaccagacc atgctgaaca   4800
cctgggacgg cgtgcgcgac gagaccggcg cctcccccac ctcctgggcc atctggaccc   4860
gcgcctggac cgccgaggag aaccgccacg gcgacccccct gaacaagtac ctgtacctgt   4920
ccggccgcgt ggacatgaag cagatcgaga agaccatcca gtacctgatc ggctccggca   4980
tggacccccg caccgagaac tccccctacc tgggcttcat ctacacctcc ttccaggagc   5040
gcgccacctt catctcccac ggcaacaccg cccgcctggc ccgcgaccac ggcgacttca   5100
agctggccca gatctgcggc accatcgcct ccgacgagaa gcgccacgag accgcctaca   5160
ccaagatcgt ggagaagctg ttcgagatcg accccgacgg caccgtgctg gccttcggcg   5220
```

acatgatgaa gaagaagatc tccatgcccg accacttcat gtacgacggc cgcgacgaca 5280
acctgttcga ccacttctcc tccgtggccc agcgcctggg cgtgtacacc gccaaggact 5340
acgccgacat cctggagcac ctggtgggcc gctggaaggt ggagaagctg accggcctgt 5400
ccgccgaggg ccagaaggcc caggactacg tgtgcggcct gcccccccgc atccgccgcc 5460
tggaggagcg cgcccagatc cgcgccaagc aggccccccg cctgcccttc tcctggatct 5520
acgaccgcga ggtgcagctg atggactaca aggaccacga cggcgactac aaggaccacg 5580
acatcgacta caaggacgac gacgacaagt gaatcgatag atctcttaag gcagcagcag 5640
ctcggatagt atcgacacac tctggacgct ggtcgtgtga tggactgttg ccgccacact 5700
tgctgccttg acctgtgaat atccctgccg cttttatcaa acagcctcag tgtgtttgat 5760
cttgtgtgta cgcgcttttg cgagttgcta gctgcttgtg ctatttgcga ataccacccc 5820
cagcatcccc ttccctcgtt tcatatcgct tgcatcccaa ccgcaactta tctacgctgt 5880
cctgctatcc ctcagcgctg ctcctgctcc tgctcactgc ccctcgcaca gccttggttt 5940
gggctccgcc tgtattctcc tggtactgca acctgtaaac cagcactgca atgctgatgc 6000
acgggaagta gtgggatggg aacacaaatg gaaagcttaa ttaagagctc ttgttttcca 6060
gaaggagttg ctccttgagc ctttcattct cagcctcgat aacctccaaa gccgctctaa 6120
ttgtggaggg ggttcgaatt taaaagcttg gaatgttggt tcgtgcgtct ggaacaagcc 6180
cagacttgtt gctcactggg aaaaggacca tcagctccaa aaaacttgcc gctcaaaccg 6240
cgtacctctg ctttcgcgca atctgccctg ttgaaatcgc caccacattc atattgtgac 6300
gcttgagcag tctgtaattg cctcagaatg tggaatcatc tgccccctgt gcgagcccat 6360
gccaggcatg tcgcgggcga ggacacccgc cactcgtaca gcagaccatt atgctacctc 6420
acaatagttc ataacagtga ccatatttct cgaagctccc caacgagcac ctccatgctc 6480
tgagtggcca ccccccggcc ctggtgcttg cggagggcag gtcaaccggc atggggctac 6540
cgaaatcccc gaccggatcc caccaccccc gcgatgggaa gaatctctcc ccgggatgtg 6600
ggcccaccac cagcacaacc tgctggccca ggcgagcgtc aaaccatacc acacaaatat 6660
ccttggcatc ggccctgaat tccttctgcc gctctgctac ccggtgcttc tgtccgaagc 6720
aggggttgct agggatcgct ccgagtccgc aaacccttgt cgcgtggcgg ggcttgttcg 6780
agcttgaaga gc 6792

<210> SEQ ID NO 101
<211> LENGTH: 6051
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 101
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360
atccctacca gtcatggctt tacctggatg acggcctgcg aacagctgtc cagcgaccct 420

-continued

```
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccccttgcg cgttagtgtt gccatccttt gcagaccggt gagagccgac ttgttgtgcg    600
ccacccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
```

-continued

```
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cctttcttgc gctatgacac   3300
ttccagcaaa aggtagggcg ggctgcgaga cggcttcccg gcgctgcatg caacaccgat   3360
gatgcttcga ccccccgaag ctccttcggg gctgcatggg cgctccgatg ccgctccagg   3420
gcgagcgctg tttaaatagc caggcccccg attgcaaaga cattatagcg agctaccaaa   3480
gccatattca aacacctaga tcactaccac ttctacacag gccactcgag cttgtgatcg   3540
cactccgcta agggggcgcc tcttcctctt cgtttcagtc acaacccgca aacactagta   3600
tggccaccgc atccactttc tcggcgttca atgcccgctg cggcgacctg cgtcgctcgg   3660
cgggctccgg gccccggcgc ccagcgaggc ccctccccgt gcgcgggcgc gccgccaccc   3720
tgcgctccgg cctgcgcgac gtggagaccg tgaagaagac cttctccccc gcccgcgagg   3780
tgcacgtgca ggtgacccac tccatggccc cccagaagat cgagatcttc aaggccatgg   3840
aggactgggc cgagaacaac atcctggtgc acctgaagaa cgtggagaag tgcccccagc   3900
cccaggactt cctgcccgac cccgcctccg acgagttcca cgaccagatc aaggagctgc   3960
gcgagcgcgc caaggagatc cccgacgact acttcgtggt gctggtgggc gacatgatca   4020
ccgaggaggc cctgcccacc taccagacca tgctgaacac ctgggacggc gtgcgcgacg   4080
agaccggcgc ctcccccacc tcctgggcca tctggacccg cgcctggacc gccgaggaga   4140
accgccacgg cgacccccctg aacaagtacc tgtacctgtc cggccgcgtg gacatgaagc   4200
agatcgagaa gaccatccag tacctgatcg gctccggcat ggacccccgc accgagaact   4260
cccccctacct gggcttcatc tacacctcct tccaggagcg cgccaccttc atctcccacg   4320
gcaacaccgc ccgcctggcc cgcgaccacg gcgacttcaa gctggcccag atctgcggca   4380
ccatcgcctc cgacgagaag cgccacgaga ccgcctacac caagatcgtg gagaagctgt   4440
tcgagatcga ccccgacggc accgtgctgg ccttcggcga catgatgaag aagaagatct   4500
ccatgcccga ccacttcatg tacgacggcc gcgacgacaa cctgttcgac cacttctcct   4560
ccgtggccca gcgcctgggc gtgtacaccg ccaaggacta cgccgacatc ctggagcacc   4620
tggtgggccg ctggaaggtg gagaagctga ccggcctgtc cgccgagggc cagaaggccc   4680
aggactacgt gtgcggcctg ccccccccgca tccgccgcct ggaggagcgc gcccagatcc   4740
gcgccaagca ggcccccccgc ctgcccttct cctggatcta cgaccgcgag gtgcagctga   4800
tggactacaa ggaccacgac ggcgactaca aggaccacga catcgactac aaggacgacg   4860
acgacaagtg aatcgataga tctcttaagg cagcagcagc tcggatagta tcgacacact   4920
ctggacgctg gtcgtgtgat ggactgttgc cgccacactt gctgccttga cctgtgaata   4980
tccctgccgc ttttatcaaa cagcctcagt gtgtttgatc ttgtgtgtac gcgcttttgc   5040
gagttgctag ctgcttgtgc tatttgcgaa taccaccccc agcatcccct tccctcgttt   5100
catatcgctt gcatcccaac cgcaacttat ctacgctgtc ctgctatccc tcagcgctgc   5160
```

```
tcctgctcct gctcactgcc cctcgcacag ccttggtttg ggctccgcct gtattctcct   5220

ggtactgcaa cctgtaaacc agcactgcaa tgctgatgca cgggaagtag tgggatggga   5280

acacaaatgg aaagcttaat taagagctct tgttttccag aaggagttgc tccttgagcc   5340

tttcattctc agcctcgata acctccaaag ccgctctaat tgtggagggg gttcgaattt   5400

aaaagcttgg aatgttggtt cgtgcgtctg gaacaagccc agacttgttg ctcactggga   5460

aaaggaccat cagctccaaa aaacttgccg ctcaaaccgc gtacctctgc tttcgcgcaa   5520

tctgccctgt tgaaatcgcc accacattca tattgtgacg cttgagcagt ctgtaattgc   5580

ctcagaatgt ggaatcatct gccccctgtg cgagcccatg ccaggcatgt cgcgggcgag   5640

gacacccgcc actcgtacag cagaccatta tgctacctca caatagttca taacagtgac   5700

catatttctc gaagctcccc aacgagcacc tccatgctct gagtggccac cccccggccc   5760

tggtgcttgc ggagggcagg tcaaccggca tggggctacc gaaatccccg accggatccc   5820

accacccccg cgatgggaag aatctctccc cgggatgtgg gcccaccacc agcacaacct   5880

gctggcccag gcgagcgtca aaccatacca cacaaatatc cttggcatcg gccctgaatt   5940

ccttctgccg ctctgctacc cggtgcttct gtccgaagca ggggttgcta gggatcgctc   6000

cgagtccgca aacccttgtc gcgtggcggg gcttgttcga gcttgaagag c            6051
```

<210> SEQ ID NO 102
<211> LENGTH: 7041
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgagggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccttgcg cgttagtgtt gccatccttt gcagaccggt gagagccgac ttgttgtgcg    600

ccaccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgcccctg    1140
```

-continued

```
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
```

cagttgaagg gctttacgcg caaggtacag ccgctcctgc aaggctgcgt ggtggaattg 3540
gacgtgcagg tcctgctgaa gttcctccac cgcctcacca gcggacaaag caccggtgta 3600
tcaggtccgt gtcatccact ctaaagaact cgactacgac ctactgatgg ccctagattc 3660
ttcatcaaaa acgcctgaga cacttgccca ggattgaaac tccctgaagg gaccaccagg 3720
ggccctgagt tgttccttcc ccccgtggcg agctgccagc caggctgtac ctgtgatcga 3780
ggctggcggg aaaataggct tcgtgtgctc aggtcatggg aggtgcagga cagctcatga 3840
aacgccaaca atcgcacaat tcatgtcaag ctaatcagct atttcctctt cacgagctgt 3900
aattgtccca aaattctggt ctaccggggg tgatccttcg tgtacgggcc cttccctcaa 3960
ccctaggtat gcgcgcatgc ggtcgccgcg caactcgcgc gagggccgag ggtttgggac 4020
gggccgtccc gaaatgcagt tgcacccgga tgcgtggcac ctttttgcg ataatttatg 4080 caatggactg ctctgcaaaa ttctggctct gtcgccaacc ctaggatcag cggcgtagga 4140
tttcgtaatc attcgtcctg atggggagct accgactacc ctaatatcag cccgactgcc 4200
tgacgccagc gtccactttt gtgcacacat tccattcgtg cccaagacat ttcattgtgg 4260
tgcgaagcgt ccccagttac gctcacctgt ttcccgacct ccttactgtt ctgtcgacag 4320
agcgggccca caggccggtc gcagccacta gtatgacctc catcaacgtg aagctgctgt 4380
accactacgt gatcaccaac ctgttcaacc tgtgcttctt ccccctgacc gccatcgtgg 4440
ccggcaaggc ctcccgcctg accatcgacg acctgcacca cctgtactac tcctacctgc 4500
agcacaacgt gatcaccatc gccccctgt tcgccttcac cgtgttcggc tccatcctgt 4560
acatcgtgac ccgccccaag cccgtgtacc tggtggagta ctcctgctac ctgcccccca 4620
cccagtgccg ctcctccatc tccaaggtga tggacatctt ctaccaggtg cgcaaggccg 4680 acccccttccg caacggcacc tgcgacgact cctcctggct ggacttcctg cgcaagatcc 4740
aggagcgctc cggcctgggc gacgagaccc acggccccga gggcctgctg caggtgcccc 4800
cccgcaagac cttcgccgcc gcccgcgagg agaccgagca ggtgatcgtg ggcgccctga 4860
agaacctgtt cgagaacacc aaggtgaacc ccaaggacat cggcatcctg gtggtgaact 4920
cctccatgtt caaccccacc ccctccctgt ccgccatggt ggtgaacacc ttcaagctgc 4980
gctccaacgt gcgctccttc aacctgggcg gcatgggctg ctccgccggc gtgatcgcca 5040
tcgacctggc caaggacctg ctgcacgtgc acaagaacac ctacgccctg gtggtgtcca 5100
ccgagaacat cacctacaac atctacgccg gcgacaaccg ctccatgatg gtgtccaact 5160
gcctgttccg cgtgggcggc gccgccatcc tgctgtccaa caagccccgc gaccgccgcc 5220
gctccaagta cgagctggtg cacaccgtgc gcacccacac cggcgccgac gacaagtcct 5280
tccgctgcgt gcagcagggc gacgacgaga acggcaagac cggcgtgtcc ctgtccaagg 5340
acatcaccga ggtggccggc cgcaccgtga agaagaacat cgccaccctg ggccccctga 5400
tcctgcccct gtccgagaag ctgctgttct tcgtgacctt catggccaag aagctgttca 5460
aggacaaggt gaagcactac tacgtgcccg acttcaagct ggccatcgac cacttctgca 5520
tccacgccgg cggccgcgcc gtgatcgacg tgctggagaa gaacctgggc ctggccccca 5580
tcgacgtgga ggcctcccgc tccaccctgc accgcttcgg caacacctcc tcctcctcca 5640
tctggtacga gctggcctac atcgaggcca agggccgcat gaagaagggc aacaaggtgt 5700
ggcagatcgc cctgggctcc ggcttcaagt gcaactccgc cgtgtgggtg gccctgtcca 5760
acgtgaaggc ctccaccaac tccccctggg agcactgcat cgaccgctac cccgtgaaga 5820
tcgactccga ctccgccaag tccgagaccc gcgcccagaa cggccgctcc tgacttaagg 5880
cagcagcagc tcggatagta tcgacacact ctggacgctg gtcgtgtgat ggactgttgc 5940
cgccacactt gctgccttga cctgtgaata tccctgccgc ttttatcaaa cagcctcagt 6000
gtgtttgatc ttgtgtgtac gcgcttttgc gagttgctag ctgcttgtgc tatttgcgaa 6060
taccaccccc agcatcccct tccctcgttt catatcgctt gcatcccaac cgcaacttat 6120
ctacgctgtc ctgctatccc tcagcgctgc tcctgctcct gctcactgcc cctcgcacag 6180
ccttggtttg ggctccgcct gtattctcct ggtactgcaa cctgtaaacc agcactgcaa 6240
tgctgatgca cgggaagtag tgggatggga acacaaatgg aaagcttaat taagagctct 6300
tgttttccag aaggagttgc tccttgagcc tttcattctc agcctcgata acctccaaag 6360
ccgctctaat tgtggagggg gttcgaattt aaaagcttgg aatgttggtt cgtgcgtctg 6420
gaacaagccc agacttgttg ctcactggga aaaggaccat cagctccaaa aaacttgccg 6480
ctcaaaccgc gtacctctgc tttcgcgcaa tctgccctgt tgaaatcgcc accacattca 6540
tattgtgacg cttgagcagt ctgtaattgc ctcagaatgt ggaatcatct gccccctgtg 6600
cgagcccatg ccaggcatgt cgcgggcgag gacacccgcc actcgtacag cagaccatta 6660
tgctacctca caatagttca taacagtgac catatttctc gaagctcccc aacgagcacc 6720
tccatgctct gagtggccac cccccggccc tggtgcttgc ggagggcagg tcaaccggca 6780
tggggctacc gaaatccccg accggatccc accacccccg cgatgggaag aatctctccc 6840
cgggatgtgg gcccaccacc agcacaacct gctggcccag gcgagcgtca aaccatacca 6900
cacaaatatc cttggcatcg gccctgaatt ccttctgccg ctctgctacc cggtgcttct 6960
gtccgaagca ggggttgcta gggatcgctc cgagtccgca aacccttgtc gcgtggcggg 7020
gcttgttcga gcttgaagag c 7041

<210> SEQ ID NO 103
<211> LENGTH: 1530
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 103
actagtatga cctccatcaa cgtgaagctg ctgtaccact acgtgatcac caacttcttc 60
aacctgtgct tcttccccct gaccgccatc ctggccggca aggcctcccg cctgaccacc 120
aacgacctgc accacttcta ctcctacctg cagcacaacc tgatcaccct gaccctgctg 180
ttcgccttca ccgtgttcgg ctccgtgctg tacttcgtga cccgccccaa gcccgtgtac 240
ctggtggact actcctgcta cctgcccccc cagcacctgt ccgccggcat ctccaagacc 300
atggagatct tctaccagat ccgcaagtcc gaccccctgc gcaacgtggc cctggacgac 360
tcctcctccc tggacttcct gcgcaagatc caggagcgct ccggcctggg cgacgagacc 420
tacggccccg agggcctgtt cgagatcccc ccccgcaaga acctggcctc cgcccgcgag 480
gagaccgagc aggtgatcaa cggcgccctg aagaacctgt tcgagaacac caaggtgaac 540
cccaaggaga tcggcatcct ggtggtgaac tcctccatgt tcaaccccac cccctccctg 600
tccgccatgg tggtgaacac cttcaagctg cgctccaaca tcaagtcctt caacctgggc 660
ggcatgggct gctccgccgg cgtgatcgcc atcgacctgg ccaaggacct gctgcacgtg 720
cacaagaaca cctacgccct ggtggtgtcc accgagaaca tcacccagaa catctacacc 780
ggcgacaacc gctccatgat ggtgtccaac tgcctgttcc gcgtgggcgg cgccgccatc 840
ctgctgtcca acaagcccgg cgaccgccgc cgctccaagt accgcctggc ccacaccgtg 900
cgcacccaca ccggcgccga cgacaagtcc ttcggctgcg tgcgccagga ggaggacgac 960
tccggcaaga ccggcgtgtc cctgtccaag gacatcaccg gcgtggccgg catcaccgtg 1020
cagaagaaca tcaccaccct gggcccctg gtgctgcccc tgtccgagaa gatcctgttc 1080
gtggtgacct tcgtggccaa gaagctgctg aaggacaaga tcaagcacta ctacgtgccc 1140
gacttcaagc tggccgtgga ccacttctgc atccacgccg gcggccgcgc cgtgatcgac 1200
gtgctggaga agaacctggg cctgtccccc atcgacgtgg aggcctcccg ctccaccctg 1260
caccgcttcg gcaacacctc ctcctcctcc atctggtacg agctggccta catcgaggcc 1320
aagggccgca tgaagaaggg caacaaggcc tggcagatcg ccgtgggctc cggcttcaag 1380
tgcaactccg ccgtgtgggt ggccctgcgc aacgtgaagg cctccgccaa ctcccctgg 1440 gagcactgca tccacaagta ccccgtgcag atgtactccg gctcctccaa gtccgagacc 1500
cgcgcccaga acggccgctc ctgacttaag 1530

<210> SEQ ID NO 104
<211> LENGTH: 1533
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 104
actagtatga cctccatcaa cgtgaagctg ctgtaccact acgtgctgac caacttcttc 60
aacctgtgcc tgttcccct gaccgccttc cccgccggca aggcctccca gctgaccacc 120
aacgacctgc accacctgta ctcctacctg caccacaacc tgatcaccgt gaccctgctg 180
ttcgccttca ccgtgttcgg ctccatcctg tacatcgtga cccgccccaa gcccgtgtac 240
ctggtggact actcctgcta cctgcccccc cgccacctgt cctgcggcat ctcccgcgtg 300
atggagatct tctacgagat ccgcaagtcc gacccctccc gcgaggtgcc cttcgacgac 360
ccctcctccc tggagttcct gcgcaagatc caggagcgct ccggcctggg cgacgagacc 420
tacggccccc agggcctggt gcacgacatg cccctgcgca tgaacttcgc cgccgcccgc 480
gaggagaccg agcaggtgat caacggcgcc ctggagaagc tgttcgagaa caccaaggtg 540
aacccccgcg agatcggcat cctggtggtg aactcctcca tgttcaaccc caccccctcc 600
ctgtccgcca tggtggtgaa caccttcaag ctgcgctcca acatcaagtc cttctccctg 660
ggcggcatgg gctgctccgc cggcatcatc gccatcgacc tggccaagga cctgctgcac 720
gtgcacaaga acacctacgc cctggtggtg tccaccgaga acatcaccca ctccacctac 780
accggcgaca accgctccat gatggtgtcc aactgcctgt tccgcatggg cggcgccgcc 840
atcctgctgt ccaacaaggc cggcgaccgc cgccgctcca agtacaagct ggcccacacc 900
gtgcgcaccc acaccggcgc cgacgaccag tccttccgct gcgtgcgcca ggaggacgac 960
gaccgcggca agatcggcgt gtgcctgtcc aaggacatca ccgccgtggc cggcaagacc 1020
gtgaccaaga acatcgccac cctgggcccc ctggtgctgc ccctgtccga gaagttcctg 1080
tacgtggtgt ccctgatggc caagaagctg ttcaagaaca agatcaagca cacctacgtg 1140
cccgacttca agctggccat cgaccacttc tgcatccacg ccggcggccg cgccgtgatc 1200
gacgtgctgg agaagaacct ggccctgtcc cccgtggacg tggaggcctc ccgctccacc 1260
ctgcaccgct tcggcaacac ctcctcctcc tccatctggt acgagctggc ctacatcgag 1320
gccaagggcc gcatgaagaa gggcaacaag gtgtggcaga tcgccatcgg ctccggcttc 1380
aagtgcaact ccgccgtgtg ggtggccctg tgcaacgtga agccctccgt gaactccccc 1440
tgggagcact gcatcgaccg ctaccccgtg gagatcaact acggctcctc caagtccgag 1500
acccgcgccc agaacggccg ctcctgactt aag 1533

<210> SEQ ID NO 105
<211> LENGTH: 1524
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105
actagtatgt ccggcaccaa ggccacctcc gtgtccgtgc ccctgcccga cttcaagcag 60
tccgtgaacc tgaagtacgt gaagctgggc taccactact ccatcaccca cgccatgtac 120
ctgttcctga cccccctgct gctgatcatg tccgcccaga tctccacctt ctccatccag 180
gacttccacc acctgtacaa ccacctgatc ctgcacaacc tgtcctccct gatcctgtgc 240
atcgccctgc tgctgttcgt gctgaccctg tacttcctga cccgccccac ccccgtgtac 300
ctgctgaact tctcctgcta caagcccgac gccatccaca agtgcgaccg ccgccgcttc 360
atggacacca tccgcggcat gggcacctac accgaggaga acatcgagtt ccagcgcaag 420
gtgctggagc gctccggcat cggcgagtcc tcctacctgc cccccaccgt gttcaagatc 480 ccccccgcg tgtacgacgc cgaggagcgc gccgaggccg agatgctgat gttcggcgcc 540
gtggacggcc tgttcgagaa gatctccgtg aagcccaacc agatcggcgt gctggtggtg 600
aactgcggcc tgttcaaccc catcccctcc ctgtcctcca tgatcgtgaa ccgctacaag 660
atgcgcggca acgtgttctc ctacaacctg ggcggcatgg gctgctccgc cggcgtgatc 720
tccatcgacc tggccaagga cctgctgcag gtgcgcccca actcctacgc cctggtggtg 780
tccctggagt gcatctccaa gaacctgtac ctgggcgagc agcgctccat gctggtgtcc 840
aactgcctgt tccgcatggg cggcgccgcc atcctgctgt ccaacaagat gtccgaccgc 900
tggcgctcca agtaccgcct ggtgcacacc gtgcgcaccc acaagggcac cgaggacaac 960
tgcttctcct gcgtgacccg caaggaggac tccgacggca agatcggcat ctccctgtcc 1020
aagaacctga tggccgtggc cggcgacgcc ctgaagacca acatcaccac cctgggcccc 1080
ctggtgctgc ccatgtccga gcagctgctg ttcttcgcca ccctggtggg caagaaggtg 1140
ttcaagatga agctgcagcc ctacatcccc gacttcaagc tggccttcga gcacttctgc 1200
atccacgccg gcggccgcgc cgtgctggac gagctggaga agaacctgaa gctgtcctcc 1260
tggcacatgg agccctcccg catgtccctg taccgcttcg gcaacacctc ctcctcctcc 1320
ctgtggtacg agctggccta ctccgaggcc aagggccgca tcaagaaggg cgaccgcgtg 1380
tggcagatcg ccttcggctc cggcttcaag tgcaactccg ccgtgtggaa ggccctgcgc 1440
aacgtgaacc ccgccgagga gaagaacccc tggatggacg agatccacct gttccccgtg 1500
gaggtgcccc tgaactgact taag 1524

<210> SEQ ID NO 106
<211> LENGTH: 1530
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106
actagtatga cctccatcaa cgtgaagctg ctgtaccact acgtgatcac caacctgttc 60
aacctgtgct tcttcccccct gaccgccatc gtggccggca aggcctacct gaccatcgac 120
gacctgcacc acctgtacta ctcctacctg cagcacaacc tgatcaccat cgcccccctg 180
ctggccttca ccgtgttcgg ctccgtgctg tacatcgcca cccgccccaa gcccgtgtac 240
ctggtggagt actcctgcta cctgcccccc acccactgcc gctcctccat ctccaaggtg 300
atggacatct tcttccaggt gcgcaaggcc gacccctccc gcaacggcac ctgcgacgac 360
tcctcctggc tggacttcct gcgcaagatc caggagcgct ccggcctggg cgacgagacc 420
cacggccccg agggcctgct gcaggtgccc ccccgcaaga ccttcgcccg cgcccgcgag 480
gagaccgagc aggtgatcat cggcgccctg gagaacctgt tcaagaacac caacgtgaac 540
cccaaggaca tcggcatcct ggtggtgaac tcctccatgt tcaaccccac cccctccctg 600
tccgccatgg tggtgaacac cttcaagctg cgctccaacg tgcgctcctt caacctgggc 660
ggcatgggct gctccgccgg cgtgatcgcc atcgacctgg ccaaggacct gctgcacgtg 720
cacaagaaca cctacgccct ggtggtgtcc accgagaaca tcacctacaa catctacgcc 780
ggcgacaacc gctccatgat ggtgtccaac tgcctgttcc gcgtgggcgg cgccgccatc 840
ctgctgtcca acaagccccg cgaccgccgc cgctccaagt acgagctggt gcacaccgtg 900
cgcacccaca ccggcgccga cgacaagtcc ttccgctgcg tgcagcaggg cgacgacgag 960
aacggccaga ccggcgtgtc cctgtccaag gacatcaccg acgtggccgg ccgcaccgtg 1020
aagaagaaca tcgccaccct gggccccctg atcctgcccc tgtccgagaa gctgctgttc 1080
ttcgtgacct tcatgggcaa gaagctgttc aaggacgaga tcaagcacta ctacgtgccc 1140
gacttcaagc tggccatcga ccacttctgc atccacgccg gcggcaaggc cgtgatcgac 1200
gtgctggaga agaacctggg cctggccccc atcgacgtgg aggcctcccg ctccaccctg 1260
caccgcttcg gcaacacctc ctcctcctcc atctggtacg agctggccta catcgagccc 1320
aagggccgca tgaagaaggg caacaaggtg tggcagatcg ccctgggctc cggcttcaag 1380
tgcaactccg ccgtgtgggt ggccctgaac aacgtgaagg cctccaccaa ctcccccctgg 1440 gagcactgca tcgaccgcta ccccgtgaag atcgactccg actccggcaa gtccgagacc 1500
cgcgtgccca acggccgctc ctgacttaag 1530

<210> SEQ ID NO 107
<211> LENGTH: 1599
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 107
actagtatgg agcgcaccaa ctccatcgag atggaccagg agcgcctgac cgccgagatg 60
gccttcaagg actcctcctc cgccgtgatc cgcatccgcc gccgcctgcc cgacttcctg 120
acctccgtga agctgaagta cgtgaagctg ggcctgcaca actccttcaa cttcaccacc 180
ttcctgttcc tgctgatcat cctgcccctg accggcaccg tgctggtgca gctgaccggc 240
ctgaccttcg agaccttctc cgagctgtgg tacaaccacg ccgcccagct ggacggcgtg 300
acccgcctgg cctgcctggt gtccctgtgc ttcgtgctga tcatctacgt gaccaaccgc 360

-continued

```
tccaagcccg tgtacctggt ggacttctcc tgctacaagc ccgaggacga gcgcaagatg    420

tccgtggact ccttcctgaa gatgaccgag cagaacggcg ccttcaccga cgacaccgtg    480

cagttccagc agcgcatctc caaccgcgcc ggcctgggcg acgagaccta cctgccccgc    540

ggcatcacct ccaccccccc caagctgaac atgtccgagg cccgcgccga ggccgaggcc    600

gtgatgttcg gcgccctgga ctccctgttc gagaagaccg gcatcaagcc cgccgaggtg    660

ggcatcctga tcgtgtcctg ctccctgttc aaccccaccc cctccctgtc cgccatgatc    720

gtgaaccact acaagatgcg cgaggacatc aagtcctaca acctgggcgg catgggctgc    780

tccgccggcc tgatctccat cgacctggcc aacaacctgc tgaaggccaa ccccaactcc    840

tacgccgtgg tggtgtccac cgagaacatc accctgaact ggtacttcgg caacgaccgc    900

tccatgctgc tgtgcaactg catcttccgc atgggcggcg ccgccatcct gctgtccaac    960

cgccgccagg accgctccaa gtccaagtac gagctggtga acgtggtgcg cacccacaag   1020

ggctccgacg acaagaacta caactgcgtg taccagaagg aggacgagcg cggcaccatc   1080

ggcgtgtccc tggcccgcga gctgatgtcc gtggccggcg acgccctgaa gaccaacatc   1140

accaccctgg gccccatggt gctgcccctg tccggccagc tgatgttctc cgtgtccctg   1200

gtgaagcgca agctgctgaa gctgaaggtg aagccctaca tccccgactt caagctggcc   1260

ttcgagcact tctgcatcca cgccggcggc cgcgccgtgc tggacgaggt gcagaagaac   1320

ctggacctgg aggactggca catggagccc tcccgcatga ccctgcaccg cttcggcaac   1380

acctcctcct cctccctgtg gtacgagatg gcctacaccg aggccaaggg ccgcgtgaag   1440

gccggcgacc gcctgtggca gatcgccttc ggctccggct tcaagtgcaa ctccgccgtg   1500

tggaaggccc tgcgcgtggt gtccaccgag gagctgaccg gcaacgcctg ggccggctcc   1560

atcgagaact accccgtgaa gatcgtgcag tgacttaag                          1599
```

<210> SEQ ID NO 108
<211> LENGTH: 5988
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 108

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgagggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccacccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780
```

-continued

```
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
```

```
aagcgtccgg ttcacacacg tgccacgttg gcgaggtggc aggtgacaat gatcggtgga   3240
gctgatggtc gaaacgttca cagcctaggg atatcgaatt cctttcttgc gctatgacac   3300
ttccagcaaa aggtagggcg ggctgcgaga cggcttcccg gcgctgcatg caacaccgat   3360
gatgcttcga ccccccgaag ctccttcggg gctgcatggg cgctccgatg ccgctccagg   3420
gcgagcgctg tttaaatagc caggcccccg attgcaaaga cattatagcg agctaccaaa   3480
gccatattca aacacctaga tcactaccac ttctacacag gccactcgag cttgtgatcg   3540
cactccgcta agggggcgcc tcttcctctt cgtttcagtc acaacccgca aacactagta   3600
tggccaccgc atccactttc tcggcgttca atgcccgctg cggcgacctg cgtcgctcgg   3660
cgggctccgg gccccggcgc ccagcgaggc ccctccccgt gcgcgggcgc gccgaggtgc   3720
acgtgcaggt gacccactcc ctggccccg agaagcgcga gatcttcaac tccctgaaca   3780
actgggccca ggagaacatc ctggtgctgc tgaaggacgt ggacaagtgc tggcagccct   3840
ccgacttcct gcccgactcc gcctccgagg gcttcgacga gcaggtgatg gagctgcgca   3900
agcgctgcaa ggagatcccc gacgactact tcatcgtgct ggtgggcgac atgatcaccg   3960
aggaggccct gcccacctac cagaccatgc tgaacaccct ggacggcgtg cgcgacgaga   4020
ccggcgcctc cctgaccccc tggggccatct ggacccgcgc ctggaccgcc gaggagaacc   4080
gccacggcga cctgctgaac aagtacctgt acctgtccgg ccgcgtggac atgaagcaga   4140
tcgagaagac catccagtac ctgatcggct ccggcatgga cccccgcacc gagaacaacc   4200
cctacctggg cttcatctac acctccttcc aggagcgcgc caccttcatc tcccacggca   4260
acaccgcccg cctggccaag gagcacggcg acctgaagct ggcccagatc tgcggcatca   4320
tcgccgccga cgagaagcgc cacgagaccg cctacaccaa gatcgtggag aagctgttcg   4380
agatcgaccc cgacggcacc gtgctggccc tggccgacat gatgcgcaag aaggtgtcca   4440
tgcccgccca cctgatgtac gacggccagg acgacaacct gttcgagaac ttctcctccg   4500
tggcccagcg cctgggcgtg tacaccgcca aggactacgc cgacatcctg gagttcctgg   4560
tgggccgctg ggacatcgag aagctgaccg gcctgtccgg cgagggccgc aaggcccagg   4620
actacgtgtg caccctgccc ccccgcatcc gccgcctgga ggagcgcgcc cagtcccgcg   4680
tgaagaaggc ctccgccacc cccttctcct ggatcttcgg ccgcgagatc aacctgatgg   4740
actacaagga ccacgacggc gactacaagg accacgacat cgactacaag gacgacgacg   4800
acaagtgaat cgatagatct cttaaggcag cagcagctcg gatagtatcg acacactctg   4860
gacgctggtc gtgtgatgga ctgttgccgc cacacttgct gccttgacct gtgaatatcc   4920
ctgccgcttt tatcaaacag cctcagtgtg tttgatcttg tgtgtacgcg cttttgcgag   4980
ttgctagctg cttgtgctat ttgcgaatac caccccccagc atccccttcc ctcgtttcat   5040
atcgcttgca tcccaaccgc aacttatcta cgctgtcctg ctatccctca gcgctgctcc   5100
tgctcctgct cactgcccct cgcacagcct tggtttgggc tccgcctgta ttctcctggt   5160
actgcaacct gtaaaccagc actgcaatgc tgatgcacgg gaagtagtgg gatgggaaca   5220
caaatggaaa gcttaattaa gagctcttgt tttccagaag gagttgctcc ttgagccttt   5280
cattctcagc ctcgataacc tccaaagccg ctctaattgt ggagggggtt cgaatttaaa   5340
agcttggaat gttggttcgt gcgtctggaa caagcccaga cttgttgctc actgggaaaa   5400
ggaccatcag ctccaaaaaa cttgccgctc aaaccgcgta cctctgcttt cgcgcaatct   5460
gccctgttga aatcgccacc acattcatat tgtgacgctt gagcagtctg taattgcctc   5520
```

-continued

```
agaatgtgga atcatctgcc ccctgtgcga gcccatgcca ggcatgtcgc gggcgaggac   5580

acccgccact cgtacagcag accattatgc tacctcacaa tagttcataa cagtgaccat   5640

atttctcgaa gctccccaac gagcacctcc atgctctgag tggccacccc ccggccctgg   5700

tgcttgcgga gggcaggtca accggcatgg ggctaccgaa atccccgacc ggatcccacc   5760

acccccgcga tgggaagaat ctctccccgg gatgtgggcc caccaccagc acaacctgct   5820

ggcccaggcg agcgtcaaac cataccacac aaatatcctt ggcatcggcc ctgaattcct   5880

tctgccgctc tgctacccgg tgcttctgtc cgaagcaggg gttgctaggg atcgctccga   5940

gtccgcaaac ccttgtcgcg tggcggggct tgttcgagct tgaagagc                5988
```

```
<210> SEQ ID NO 109
<211> LENGTH: 6807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
```

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgccccctg   1140

gtgcacttca cccccaacaa gggctggatg aacgacccca acggcctgtg gtacgacgag   1200

aaggacgcca agtggcacct gtacttccag tacaacccga acgacaccgt ctgggggacg   1260

cccttgttct ggggccacgc cacgtccgac gacctgacca actgggagga ccagcccatc   1320

gccatcgccc cgaagcgcaa cgactccggc gccttctccg gctccatggt ggtggactac   1380

aacaacacct ccggcttctt caacgacacc atcgacccgc gccagcgctg cgtggccatc   1440

tggacctaca acaccccgga gtccgaggag cagtacatct cctacagcct ggacggcggc   1500

tacaccttca ccgagtacca gaagaacccc gtgctggccg ccaactccac ccagttccgc   1560
```

gacccgaagg tcttctggta cgagccctcc cagaagtgga tcatgaccgc ggccaagtcc 1620
caggactaca agatcgagat ctactcctcc gacgacctga agtcctggaa gctggagtcc 1680
gcgttcgcca acgagggctt cctcggctac cagtacgagt gccccggcct gatcgaggtc 1740
cccaccgagc aggaccccag caagtcctac tgggtgatgt tcatctccat caaccccggc 1800
gccccggccg gcggctcctt caaccagtac ttcgtcggca gcttcaacgg cacccacttc 1860
gaggccttcg acaaccagtc ccgcgtggtg gacttcggca aggactacta cgccctgcag 1920
accttcttca acaccgaccc gacctacggg agcgccctgg gcatcgcgtg ggcctccaac 1980
tgggagtact ccgccttcgt gcccaccaac ccctggcgct cctccatgtc cctcgtgcgc 2040
aagttctccc tcaacaccga gtaccaggcc aacccggaga cggagctgat caacctgaag 2100
gccgagccga tcctgaacat cagcaacgcc ggcccctgga gccggttcgc caccaacacc 2160
acgttgacga aggccaacag ctacaacgtc gacctgtcca acagcaccgg caccctggag 2220
ttcgagctgg tgtacgccgt caacaccacc cagacgatct ccaagtccgt gttcgcggac 2280
ctctccctct ggttcaaggg cctggaggac cccgaggagt acctccgcat gggcttcgag 2340
gtgtccgcgt cctccttctt cctggaccgc gggaacagca aggtgaagtt cgtgaaggag 2400
aacccctact tcaccaaccg catgagcgtg aacaaccagc ccttcaagag cgagaacgac 2460
ctgtcctact acaaggtgta cggcttgctg gaccagaaca tcctggagct gtacttcaac 2520
gacggcgacg tcgtgtccac caacacctac ttcatgacca ccgggaacgc cctgggctcc 2580
gtgaacatga cgacgggggt ggacaacctg ttctacatcg acaagttcca ggtgcgcgag 2640
gtcaagtgac aattggcagc agcagctcgg atagtatcga cacactctgg acgctggtcg 2700
tgtgatggac tgttgccgcc acacttgctg ccttgacctg tgaatatccc tgccgctttt 2760
atcaaacagc ctcagtgtgt ttgatcttgt gtgtacgcgc ttttgcgagt tgctagctgc 2820
ttgtgctatt tgcgaatacc acccccagca tccccttccc tcgtttcata tcgcttgcat 2880
cccaaccgca acttatctac gctgtcctgc tatccctcag cgctgctcct gctcctgctc 2940
actgcccctc gcacagcctt ggtttgggct ccgcctgtat tctcctggta ctgcaacctg 3000
taaaccagca ctgcaatgct gatgcacggg aagtagtggg atgggaacac aaatggagga 3060
tcccgcgtct cgaacagagc gcgcagagga acgctgaagg tctcgcctct gtcgcacctc 3120
agcgcggcat acaccacaat aaccacctga cgaatgcgct tggttcttcg tccattagcg 3180
aagcgtccgg ttcacacacg tgccacgttg gcgaggtggc aggtgacaat gatcggtgga 3240
gctgatggtc gaaacgttca cagcctaggg atatcgaatt cggccgacag gacgcgcgtc 3300
aaaggtgctg gtcgtgtatg ccctggccgg caggtcgttg ctgctgctgg ttagtgattc 3360
cgcaaccctg attttggcgt cttattttgg cgtggcaaac gctggcgccc gcgagccggg 3420
ccggcggcga tgcggtgccc cacggctgcc ggaatccaag ggaggcaaga gcgcccgggt 3480
cagttgaagg gctttacgcg caaggtacag ccgctcctgc aaggctgcgt ggtggaattg 3540
gacgtgcagg tcctgctgaa gttcctccac cgcctcacca gcggacaaag caccggtgta 3600
tcaggtccgt gtcatccact ctaaagaact cgactacgac ctactgatgg ccctagattc 3660
ttcatcaaaa acgcctgaga cacttgccca ggattgaaac tccctgaagg gaccaccagg 3720
ggccctgagt tgttccttcc ccccgtggcg agctgccagc caggctgtac ctgtgatcga 3780
ggctggcggg aaaataggct tcgtgtgctc aggtcatggg aggtgcagga cagctcatga 3840
aacgccaaca atcgcacaat tcatgtcaag ctaatcagct atttcctctt cacgagctgt 3900
aattgtccca aaattctggt ctaccggggg tgatccttcg tgtacgggcc cttccctcaa 3960

```
ccctaggtat gcgcgcatgc ggtcgccgcg caactcgcgc gagggccgag ggtttgggac   4020
gggccgtccc gaaatgcagt tgcacccgga tgcgtggcac ctttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
tgcgaagcgt ccccagttac gctcacctgt ttcccgacct ccttactgtt ctgtcgacag   4320
agcgggccca caggccggtc gcagccacta gtatggccac cgcatccact ttctcggcgt   4380
tcaatgcccg ctgcggcgac ctgcgtcgct cggcgggctc cgggccccgg cgcccagcga   4440
ggcccctccc cgtgcgcggg cgcgccgcct ccaccctgaa gtccggctcc aaggaggtgg   4500
agaacctgaa gaagcccttc atgccccccc gcgaggtgca cgtgcaggtg acccactcca   4560
tgcccccca gaagatcgag atcttcaagt ccctggacaa ctgggccgag gagaacatcc   4620
tggtgcacct gaagcccgtg gagaagtgct ggcagcccca ggacttcctg cccgaccccg   4680
cctccgacgg cttcgacgag caggtgcgcg agctgcgcga gcgcgccaag gagatccccg   4740
acgactactt cgtggtgctg gtgggcgaca tgatcaccga ggaggccctg cccacctacc   4800
agaccatgct gaacaccctg gacggcgtgc gcgacgagac cggcgcctcc cccacctcct   4860
gggccatctg gacccgcgcc tggaccgccg aggagaaccg ccacggcgac ctgctgaaca   4920
agtacctgta cctgtccggc cgcgtggaca tgcgccagat cgagaagacc atccagtacc   4980
tgatcggctc cggcatggac ccccgcaccg agaactcccc ctacctgggc ttcatctaca   5040
cctccttcca ggagcgcgcc accttcatct cccacggcaa caccgcccgc caggccaagg   5100
agcacggcga catcaagctg gcccagatct gcggcaccat cgccgccgac gagaagcgcc   5160
acgagaccgc ctacaccaag atcgtggaga agctgttcga gatcgacccc gacggcaccg   5220
tgctggcctt cgccgacatg atgcgcaaga agatctccat gcccgcccac ctgatgtacg   5280
acggccgcga cgacaacctg ttcgaccact tctccgccgt ggcccagcgc ctgggcgtgt   5340
acaccgccaa ggactacgcc gacatcctgg agttcctggt gggccgctgg aaggtggaca   5400
agctgaccgg cctgtccgcc gagggccaga aggcccagga ctacgtgtgc cgcctgcccc   5460
cccgcatccg ccgcctggag gagcgcgccc agggccgcgc caaggaggcc cccaccatgc   5520
ccttctcctg gatcttcgac cgccaggtga agctgatgga ctacaaggac cacgacggcg   5580
actacaagga ccacgacatc gactacaagg acgacgacga caagtgaatc gatagatctc   5640
ttaaggcagc agcagctcgg atagtatcga cacactctgg acgctggtcg tgtgatggac   5700
tgttgccgcc acacttgctg ccttgacctg tgaatatccc tgccgctttt atcaaacagc   5760
ctcagtgtgt ttgatcttgt gtgtacgcgc ttttgcgagt tgctagctgc ttgtgctatt   5820
tgcgaatacc acccccagca tccccttccc tcgtttcata tcgcttgcat cccaaccgca   5880
acttatctac gctgtcctgc tatccctcag cgctgctcct gctcctgctc actgcccctc   5940
gcacagcctt ggtttgggct ccgcctgtat tctcctggta ctgcaacctg taaaccagca   6000
ctgcaatgct gatgcacggg aagtagtggg atgggaacac aaatggaaag cttaattaag   6060
agctcttgtt ttccagaagg agttgctcct tgagcctttc attctcagcc tcgataacct   6120
ccaaagccgc tctaattgtg gagggggttc gaatttaaaa gcttggaatg ttggttcgtg   6180
cgtctggaac aagcccagac ttgttgctca ctgggaaaag gaccatcagc tccaaaaaac   6240
ttgccgctca aaccgcgtac ctctgctttc gcgcaatctg ccctgttgaa atcgccacca   6300
```

-continued

```
cattcatatt gtgacgcttg agcagtctgt aattgcctca gaatgtggaa tcatctgccc   6360

cctgtgcgag cccatgccag gcatgtcgcg ggcgaggaca cccgccactc gtacagcaga   6420

ccattatgct acctcacaat agttcataac agtgaccata tttctcgaag ctccccaacg   6480

agcacctcca tgctctgagt ggccaccccc cggccctggt gcttgcggag ggcaggtcaa   6540

ccggcatggg gctaccgaaa tccccgaccg gatcccacca cccccgcgat gggaagaatc   6600

tctccccggg atgtgggccc accaccagca caacctgctg gcccaggcga gcgtcaaacc   6660

ataccacaca aatatccttg gcatcggccc tgaattcctt ctgccgctct gctacccggt   6720

gcttctgtcc gaagcagggg ttgctaggga tcgctccgag tccgcaaacc cttgtcgcgt   6780

ggcggggctt gttcgagctt gaagagc                                     6807
```

<210> SEQ ID NO 110
<211> LENGTH: 6744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgagggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccttgcg cgttagtgtt gccatccttt gcagaccggt gagagccgac ttgttgtgcg    600

ccacccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgcccctg    1140

gtgcacttca cccccaacaa gggctggatg aacgacccca acggcctgtg gtacgacgag   1200

aaggacgcca agtggcacct gtacttccag tacaacccga acgacaccgt ctgggggacg   1260

cccttgttct ggggccacgc cacgtccgac gacctgacca actgggagga ccagcccatc   1320

gccatcgccc cgaagcgcaa cgactccggc gccttctccg gctccatggt ggtggactac   1380

aacaacacct ccggcttctt caacgacacc atcgacccgc gccagcgctg cgtggccatc   1440

tggacctaca acaccccgga gtccgaggag cagtacatct cctacagcct ggacggcggc   1500
```

-continued

```
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
```

aattgtccca aaattctggt ctaccggggg tgatccttcg tgtacgggcc cttccctcaa 3960
ccctaggtat gcgcgcatgc ggtcgccgcg caactcgcgc gagggccgag ggtttgggac 4020
gggccgtccc gaaatgcagt tgcacccgga tgcgtggcac ctttttgcg ataatttatg 4080
caatggactg ctctgcaaaa ttctggctct gtcgccaacc ctaggatcag cggcgtagga 4140
tttcgtaatc attcgtcctg atggggagct accgactacc ctaatatcag cccgactgcc 4200
tgacgccagc gtccactttt gtgcacacat tccattcgtg cccaagacat ttcattgtgg 4260
tgcgaagcgt ccccagttac gctcacctgt ttcccgacct ccttactgtt ctgtcgacag 4320
agcgggccca caggccggtc gcagccacta gtatggccac cgcctccacc ttctccgcct 4380
tcaacgcccg ctgcggcgac ctgcgccgct ccgccggctc cggcccccgc cgccccgccc 4440
gcccccctgcc cgtgcgcgcc gccatcgcct ccgaggtgcc cgtggccacc acctcccccc 4500
gccccggccc caccgtgtac tccaagctgg acaaggccca caccctgacc cccgagcgca 4560
tggagctgat caacggcatg tccgccttcg ccgaggagcg catcctgccc gtgctgcagc 4620
ccgtggagaa gctgtggcag ccccaggacc tgctgcccga ccccgagtcc cccgacttcc 4680
tggaccaggt ggccgagctg cgcgcccgcg ccgccaacgt gcccgacgac tacttcgtgg 4740
tgctggtggg cgacatgatc accgaggagg ccctgcccac ctacatggcc atgctgaaca 4800
ccctggacgg cgtgcgcgac gagaccggcg ccgccgacca cccctggggc cgctggaccc 4860
gccagtgggt ggccgaggag aaccgccacg gcgacctgct gaacaagtac tgctggctga 4920
ccggccgcgt gaacatgaag gccatcgagg tgaccatcca gaacctgatc ggctccggca 4980
tgaaccccaa gaccgagaac aacccctacc tgggcttcgt gtacacctcc ttccaggagc 5040
gcgccaccaa gtactcccac ggcaacaccg cccgcctggc cgcccagtac ggcgacgcca 5100
ccctgtccaa ggtgtgcggc gtgatcgccg ccgacgaggg ccgccacgag atcgcctaca 5160
cccgcatcgt ggaggagttc ttccgcctgg accccgaggg cgccatgtcc gcctacgccg 5220
acatgatgcg caagcagatc accatgcccg cccacctgat ggacgaccag cagcacggca 5280
cccgcaacac cggccgcaac ctgttcgccg acttctccgc cgtgaccgag aagctggacg 5340
tgtacgacgc cgaggactac tgcaagatcc tggagcacct gaactcccgc tggaagatcg 5400
ccgaccgcac cgtgtccggc gacgccggcg ccgaccagga gtacgtgctg cgcctgccct 5460
cccgcttccg caagctggcc gagaagtccg ccgccaagcg cgccaagacc aagcccaagc 5520
ccgtggcctt ctcctggctg tccggccgcg aggtgatggt gtgaatcgat agatctctta 5580
aggcagcagc agctcggata gtatcgacac actctggacg ctggtcgtgt gatggactgt 5640
tgccgccaca cttgctgcct tgacctgtga atatccctgc cgcttttatc aaacagcctc 5700
agtgtgtttg atcttgtgtg tacgcgcttt tgcgagttgc tagctgcttg tgctatttgc 5760
gaataccacc cccagcatcc ccttccctcg tttcatatcg cttgcatccc aaccgcaact 5820
tatctacgct gtcctgctat ccctcagcgc tgctcctgct cctgctcact gcccctcgca 5880
cagccttggt ttgggctccg cctgtattct cctggtactg caacctgtaa accagcactg 5940
caatgctgat gcacgggaag tagtgggatg ggaacacaaa tggaaagctt aattaagagc 6000
tcttgttttc cagaaggagt tgctccttga gcctttcatt ctcagcctcg ataacctcca 6060
aagccgctct aattgtggag ggggttcgaa tttaaaagct tggaatgttg gttcgtgcgt 6120
ctggaacaag cccagacttg ttgctcactg ggaaaaggac catcagctcc aaaaaacttg 6180
ccgctcaaac cgcgtacctc tgctttcgcg caatctgccc tgttgaaatc gccaccacat 6240

-continued

```
tcatattgtg acgcttgagc agtctgtaat tgcctcagaa tgtggaatca tctgccccct   6300

gtgcgagccc atgccaggca tgtcgcgggc gaggacaccc gccactcgta cagcagacca   6360

ttatgctacc tcacaatagt tcataacagt gaccatattt ctcgaagctc cccaacgagc   6420

acctccatgc tctgagtggc caccccccgg ccctggtgct tgcggagggc aggtcaaccg   6480

gcatggggct accgaaatcc ccgaccggat cccaccaccc ccgcgatggg aagaatctct   6540

ccccgggatg tgggcccacc accagcacaa cctgctggcc caggcgagcg tcaaaccata   6600

ccacacaaat atccttggca tcggccctga attccttctg ccgctctgct acccggtgct   6660

tctgtccgaa gcaggggttg ctagggatcg ctccgagtcc gcaaaccctt gtcgcgtggc   6720

ggggcttgtt cgagcttgaa gagc                                          6744
```

<210> SEQ ID NO 111
<211> LENGTH: 6667
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccttgcg cgttagtgtt gccatccttt gcagaccggt gagagccgac ttgttgtgcg    600

ccaccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaacgg cgcgccatgc tgctgcaggc cttcctgttc ctgctggccg   1080

gcttcgccgc caagatcagc gcctccatga cgaacgagac gtccgaccgc cccctggtgc   1140

acttcacccc caacaagggc tggatgaacg accccaacgg cctgtggtac gacgagaagg   1200

acgccaagtg gcacctgtac ttccagtaca acccgaacga caccgtctgg gggacgccct   1260

tgttctgggg ccacgccacg tccgacgacc tgaccaactg ggaggaccag cccatcgcca   1320

tcgccccgaa gcgcaacgac tccggcgcct tctccggctc catggtggtg gactacaaca   1380

acacctccgg cttcttcaac gacaccatcg acccgcgcca gcgctgcgtg gccatctgga   1440

cctacaacac cccggagtcc gaggagcagt acatctccta cagcctggac ggcggctaca   1500
```

-continued

```
ccttcaccga gtaccagaag aaccccgtgc tggccgccaa ctccacccag ttccgcgacc   1560
cgaaggtctt ctggtacgag ccctcccaga agtggatcat gaccgcggcc aagtcccagg   1620
actacaagat cgagatctac tcctccgacg acctgaagtc ctggaagctg gagtccgcgt   1680
tcgccaacga gggcttcctc ggctaccagt acgagtgccc cggcctgatc gaggtcccca   1740
ccgagcagga ccccagcaag tcctactggg tgatgttcat ctccatcaac cccggcgccc   1800
cggccggcgg ctccttcaac cagtacttcg tcggcagctt caacggcacc cacttcgagg   1860
ccttcgacaa ccagtcccgc gtggtggact tcggcaagga ctactacgcc ctgcagacct   1920
tcttcaacac cgacccgacc tacgggagcg ccctgggcat cgcgtgggcc tccaactggg   1980
agtactccgc cttcgtgccc accaacccct ggcgctcctc catgtccctc gtgcgcaagt   2040
tctccctcaa caccgagtac caggccaacc cggagacgga gctgatcaac ctgaaggccg   2100
agccgatcct gaacatcagc aacgccggcc cctggagccg gttcgccacc aacaccacgt   2160
tgacgaaggc caacagctac aacgtcgacc tgtccaacag caccggcacc ctggagttcg   2220
agctggtgta cgccgtcaac accacccaga cgatctccaa gtccgtgttc gcggacctct   2280
ccctctggtt caagggcctg gaggaccccg aggagtacct ccgcatgggc ttcgaggtgt   2340
ccgcgtcctc cttcttcctg gaccgcggga acagcaaggt gaagttcgtg aaggagaacc   2400
cctacttcac caaccgcatg agcgtgaaca accagccctt caagagcgag aacgacctgt   2460
cctactacaa ggtgtacggc ttgctggacc agaacatcct ggagctgtac ttcaacgacg   2520
gcgacgtcgt gtccaccaac acctacttca tgaccaccgg gaacgccctg ggctccgtga   2580
acatgacgac gggggtggac aacctgttct acatcgacaa gttccaggtg cgcgaggtca   2640
agtgacaatt ggcagcagca gctcggatag tatcgacaca ctctggacgc tggtcgtgtg   2700
atggactgtt gccgccacac ttgctgcctt gacctgtgaa tatccctgcc gcttttatca   2760
aacagcctca gtgtgtttga tcttgtgtgt acgcgctttt gcgagttgct agctgcttgt   2820
gctatttgcg aataccaccc ccagcatccc cttccctcgt ttcatatcgc ttgcatccca   2880
accgcaactt atctacgctg tcctgctatc cctcagcgct gctcctgctc ctgctcactg   2940
cccctcgcac agccttggtt tgggctccgc ctgtattctc ctggtactgc aacctgtaaa   3000
ccagcactgc aatgctgatg cacgggaagt agtgggatgg gaacacaaat ggaggatccc   3060
gcgtctcgaa cagagcgcgc agaggaacgc tgaaggtctc gcctctgtcg cacctcagcg   3120
cggcatacac cacaataacc acctgacgaa tgcgcttggt tcttcgtcca ttagcgaagc   3180
gtccggttca cacacgtgcc acgttggcga ggtggcaggt gacaatgatc ggtggagctg   3240
atggtcgaaa cgttcacagc ctagggatat catagcgact gctacccccc gaccatgtgc   3300
cgaggcagaa attatataca agaagcagat cgcaattagg cacatcgctt tgcattatcc   3360
acacactatt catcgctgct gcggcaaggc tgcagagtgt atttttgtgg cccaggagct   3420
gagtccgaag tcgacgcgac gagcggcgca ggatccgacc cctagacgag ctctgtcatt   3480
ttccaagcac gcagctaaat gcgctgagac cgggtctaaa tcatccgaaa agtgtcaaaa   3540
tggccgattg ggttcgccta ggacaatgcg ctgcggattc gctcgagtcc gctgccggcc   3600
aaaaggcggt ggtacaggaa ggcgcacggg gccaaccctg cgaagccggg ggcccgaacg   3660
ccgaccgccg gccttcgatc tcgggtgtcc ccctcgtcaa tttcctctct cgggtgcagc   3720
cacgaaagtc gtgacgcagg tcacgaaatc cggttacgaa aaacgcaggt cttcgcaaaa   3780
acgtgagggt ttcgcgtctc gccctagcta ttcgtatcgc cgggtcagac ccacgtgcag   3840
aaaagccctt gaataacccg ggaccgtggt taccgcgccg cctgcaccag ggggcttata   3900
```

-continued taagcccaca ccacacctgt ctcaccacgc atttctccaa ctcgcgactt ttcggaagaa 3960
attgttatcc acctagtata gactgccacc tgcaggacct tgtgtcttgc agtttgtatt 4020
ggtcccggcc gtcgagctcg acagatctgg gctagggttg gcctggccgc tcggcactcc 4080
cctttagccg cgcgcatccg cgttccagag gtgcgattcg gtgtgtggag cattgtcatg 4140
cgcttgtggg ggtcgttccg tgcgcggcgg gtccgccatg ggcgccgacc tgggccctag 4200
ggtttgtttt cgggccaagc gagcccctct cacctcgtcg cccccccgca ttccctctct 4260
cttgcagcca ctagtatggc ctccgctgtg accttcgcct gcgctcctcc tcgcaggcgc 4320
gccggtgccg tggccgctcc tggccgacgc gctgcctctc gtcctctggt ggtgcacgcc 4380
gtggcctccg aggctcctct gggcgtgcct ccctccgtgc agcgcccttc tcccgtggtg 4440
tactccaagc tggacaagca gcaccgcctg acgcctgagc gcctggagct ggtgcagtcc 4500
atgggccagt tcgccgagga gcgcgtgctg cccgtgctgc accccgtgga caagctgtgg 4560
cagccccagg acttcctgcc cgaccccgag tcccccgact tcgaggacca ggtggccgag 4620
ctgcgcgccc gcgccaagga cctgcccgac gagtacttcg tggtgctggt gggcgacatg 4680
atcaccgagg aggccctgcc cacctacatg gccatgctga acacctggga cggcgtgcgc 4740
gacgacaccg gcgccgccga ccacccctgg gcccgctgga cccgccagtg ggtggccgag 4800
gagaaccgcc acggcgacct gctgaacaag tactgctggc tgaccggccg cgtgaacatg 4860
cgcgccgtgg aggtgaccat caacaacctg atcaagtccg gcatgaaccc ccagaccgac 4920
aacaacccct acctgggctt cgtgtacacc tccttccagg agcgcgccac caagtactcc 4980
cacggcaaca ccgcccgcct ggccgccgag cacggcgaca agggcctgtc caagatctgc 5040
ggcctgatcg cctccgacga gggccgccac gagatcgcct acacccgcat cgtggacgag 5100
ttcttccgcc tggaccccga gggcgccgtg gccgcctacg ccaacatgat gcgcaagcag 5160
atcaccatgc ccgcccacct gatggacgac atgggccacg gcgaggccaa ccccggccgc 5220
aacctgttcg ccgacttctc cgccgtggcc gagaagatcg acgtgtacga cgccgaggac 5280
tactgccgca tcctggagca cctgaacgcc cgctggaagg tggacgagcg ccaggtgtcc 5340
ggccaggccg ccgccgacca ggagtacgtg ctgggcctgc cccagcgctt ccgcaagctg 5400
gccgagaaga ccgccgccaa gcgcaagcgc gtggcccgcc gccccgtggc cttctcctgg 5460
atctccggcc gcgagatcat ggtgtgaatc gatagatctc ttaaggcagc agcagctcgg 5520
atagtatcga cacactctgg acgctggtcg tgtgatggac tgttgccgcc acacttgctg 5580
ccttgacctg tgaatatccc tgccgctttt atcaaacagc ctcagtgtgt ttgatcttgt 5640
gtgtacgcgc ttttgcgagt tgctagctgc ttgtgctatt tgcgaatacc acccccagca 5700
tccccttccc tcgtttcata tcgcttgcat cccaaccgca acttatctac gctgtcctgc 5760
tatccctcag cgctgctcct gctcctgctc actgcccctc gcacagcctt ggtttgggct 5820
ccgcctgtat tctcctggta ctgcaacctg taaaccagca ctgcaatgct gatgcacggg 5880
aagtagtggg atgggaacac aaatggaaag cttaattaag agctcttgtt ttccagaagg 5940
agttgctcct tgagcctttc attctcagcc tcgataacct ccaaagccgc tctaattgtg 6000
gagggggttc gaatttaaaa gcttggaatg ttggttcgtg cgtctggaac aagcccagac 6060
ttgttgctca ctgggaaaag gaccatcagc tccaaaaaac ttgccgctca aaccgcgtac 6120
ctctgctttc gcgcaatctg ccctgttgaa atcgccacca cattcatatt gtgacgcttg 6180
agcagtctgt aattgcctca gaatgtggaa tcatctgccc cctgtgcgag cccatgccag 6240
gcatgtcgcg ggcgaggaca cccgccactc gtacagcaga ccattatgct acctcacaat 6300
agttcataac agtgaccata tttctcgaag ctccccaacg agcacctcca tgctctgagt 6360
ggccaccccc cggccctggt gcttgcggag ggcaggtcaa ccggcatggg gctaccgaaa 6420
tccccgaccg gatcccacca cccccgcgat gggaagaatc tctccccggg atgtgggccc 6480
accaccagca caacctgctg gcccaggcga gcgtcaaacc ataccacaca aatatccttg 6540
gcatcggccc tgaattcctt ctgccgctct gctacccggt gcttctgtcc gaagcagggg 6600
ttgctaggga tcgctccgag tccgcaaacc cttgtcgcgt ggcggggctt gttcgagctt 6660
gaagagc 6667

<210> SEQ ID NO 112
<211> LENGTH: 5991
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 112
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgagggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480
gcacgctggc gctgcgcttc gccgatctga ggacagtcgg ggaactctga tcagtctaaa 540 ccccttgcg cgttagtgtt gccatccttt gcagaccggt gagagccgac ttgttgtgcg 600 ccaccccca caccacctcc tcccagacca attctgtcac ctttttggcg aaggcatcgg 660
cctcggcctg cagagaggac agcagtgccc agccgctggg ggttggcgga tgcacgctca 720
ggtacccttt cttgcgctat gacacttcca gcaaaaggta gggcgggctg cgagacggct 780
tcccggcgct gcatgcaaca ccgatgatgc ttcgaccccc cgaagctcct tcggggctgc 840
atgggcgctc cgatgccgct ccagggcgag cgctgtttaa atagccaggc ccccgattgc 900
aaagacatta tagcgagcta ccaaagccat attcaaacac ctagatcact accacttcta 960
cacaggccac tcgagcttgt gatcgcactc cgctaagggg gcgcctcttc ctcttcgttt 1020
cagtcacaac ccgcaaactc tagaatatca atgctgctgc aggccttcct gttcctgctg 1080
gccggcttcg ccgccaagat cagcgcctcc atgacgaacg agacgtccga ccgcccctg 1140 gtgcacttca cccccaacaa gggctggatg aacgacccca acggcctgtg gtacgacgag 1200
aaggacgcca agtggcacct gtacttccag tacaacccga acgacaccgt ctgggggacg 1260
cccttgttct ggggccacgc cacgtccgac gacctgacca actgggagga ccagcccatc 1320
gccatcgccc cgaagcgcaa cgactccggc gccttctccg gctccatggt ggtggactac 1380
aacaacacct ccggcttctt caacgacacc atcgacccgc gccagcgctg cgtggccatc 1440
tggacctaca acaccccgga gtccgaggag cagtacatct cctacagcct ggacggcggc 1500
tacaccttca ccgagtacca gaagaacccc gtgctggccg ccaactccac ccagttccgc 1560

-continued

```
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cctttcttgc gctatgacac   3300
ttccagcaaa aggtagggcg ggctgcgaga cggcttcccg gcgctgcatg caacaccgat   3360
gatgcttcga ccccccgaag ctccttcggg gctgcatggg cgctccgatg ccgctccagg   3420
gcgagcgctg tttaaatagc caggcccccg attgcaaaga cattatagcg agctaccaaa   3480
gccatattca aacacctaga tcactaccac ttctacacag gccactcgag cttgtgatcg   3540
cactccgcta agggggcgcc tcttcctctt cgtttcagtc acaacccgca aacactagta   3600
tggcctccgc tgtgaccttc gcctgcgctc ctcctcgcag gcgcgccggt gccgtggccg   3660
ctcctggccg acgcgctgcc tctcgtcctc tggtggtgca cgccgtggcc tccgaggctc   3720
ctctgggcgt gcctccctcc gtgcagcgcc cttctcccgt ggtgtactcc aagctggaca   3780
agcagcaccg cctgacgcct gagcgcctgg agctggtgca gtccatgggc cagttcgccg   3840
aggagcgcgt gctgcccgtg ctgcaccccg tggacaagct gtggcagccc caggacttcc   3900
tgcccgaccc cgagtccccc gacttcgagg accaggtggc cgagctgcgc gcccgcgcca   3960
```

```
aggacctgcc cgacgagtac ttcgtggtgc tggtgggcga catgatcacc gaggaggccc   4020
tgcccaccta catggccatg ctgaacacct gggacggcgt gcgcgacgac accggcgccg   4080
ccgaccaccc ctgggcccgc tggacccgcc agtgggtggc cgaggagaac cgccacggcg   4140
acctgctgaa caagtactgc tggctgaccg gccgcgtgaa catgcgcgcc gtggaggtga   4200
ccatcaacaa cctgatcaag tccggcatga acccccagac cgacaacaac ccctacctgg   4260
gcttcgtgta cacctccttc caggagcgcg ccaccaagta ctcccacggc aacaccgccc   4320
gcctggccgc cgagcacggc gacaagggcc tgtccaagat ctgcggcctg atcgcctccg   4380
acgagggccg ccacgagatc gcctacaccc gcatcgtgga cgagttcttc cgcctggacc   4440
ccgagggcgc cgtggccgcc tacgccaaca tgatgcgcaa gcagatcacc atgcccgccc   4500
acctgatgga cgacatgggc cacggcgagg ccaaccccgg ccgcaacctg ttcgccgact   4560
tctccgccgt ggccgagaag atcgacgtgt acgacgccga ggactactgc cgcatcctgg   4620
agcacctgaa cgcccgctgg aaggtggacg agcgccaggt gtccggccag gccgccgccg   4680
accaggagta cgtgctgggc ctgccccagc gcttccgcaa gctggccgag aagaccgccg   4740
ccaagcgcaa gcgcgtggcc cgccgccccg tggccttctc ctggatctcc ggccgcgaga   4800
tcatggtgtg aatcgataga tctcttaagg cagcagcagc tcggatagta tcgacacact   4860
ctggacgctg gtcgtgtgat ggactgttgc cgccacactt gctgccttga cctgtgaata   4920
tccctgccgc ttttatcaaa cagcctcagt gtgtttgatc ttgtgtgtac gcgcttttgc   4980
gagttgctag ctgcttgtgc tatttgcgaa taccaccccc agcatcccct tccctcgttt   5040
catatcgctt gcatcccaac cgcaacttat ctacgctgtc ctgctatccc tcagcgctgc   5100
tcctgctcct gctcactgcc cctcgcacag ccttggtttg ggctccgcct gtattctcct   5160
ggtactgcaa cctgtaaacc agcactgcaa tgctgatgca cgggaagtag tgggatggga   5220
acacaaatgg aaagcttaat taagagctct tgttttccag aaggagttgc tccttgagcc   5280
tttcattctc agcctcgata acctccaaag ccgctctaat tgtggagggg gttcgaattt   5340
aaaagcttgg aatgttggtt cgtgcgtctg gaacaagccc agacttgttg ctcactggga   5400
aaaggaccat cagctccaaa aaacttgccg ctcaaaccgc gtacctctgc tttcgcgcaa   5460
tctgccctgt tgaaatcgcc accacattca tattgtgacg cttgagcagt ctgtaattgc   5520
ctcagaatgt ggaatcatct gccccctgtg cgagcccatg ccaggcatgt cgcgggcgag   5580
gacacccgcc actcgtacag cagaccatta tgctacctca caatagttca taacagtgac   5640
catatttctc gaagctcccc aacgagcacc tccatgctct gagtggccac cccccggccc   5700
tggtgcttgc ggagggcagg tcaaccggca tggggctacc gaaatccccg accggatccc   5760
accacccccg cgatgggaag aatctctccc cgggatgtgg gcccaccacc agcacaacct   5820
gctggcccag gcgagcgtca aaccatacca cacaaatatc cttggcatcg gccctgaatt   5880
ccttctgccg ctctgctacc cggtgcttct gtccgaagca ggggttgcta gggatcgctc   5940
cgagtccgca aacccttgtc gcgtggcggg gcttgttcga gcttgaagag c            5991
```

<210> SEQ ID NO 113
<211> LENGTH: 5988
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

-continued

```
gctcttcgcc gccgccactc ctgctcgagc gcgcccgcgc gtgcgccgcc agcgccttgg     60
ccttttcgcc gcgctcgtgc gcgtcgctga tgtccatcac caggtccatg aggtctgcct    120
tgcgccggct gagccactgc ttcgtccggg cggccaagag gagcatgagg gaggactcct    180
ggtccagggt cctgacgtgg tcgcggctct gggagcgggc cagcatcatc tggctctgcc    240
gcaccgaggc cgcctccaac tggtcctcca gcagccgcag tcgccgccga ccctggcaga    300
ggaagacagg tgaggggggt atgaattgta cagaacaacc acgagccttg tctaggcaga    360
atccctacca gtcatggctt tacctggatg acggcctgcg aacagctgtc cagcgaccct    420
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccccttgcg cgttagtgtt gccatccttt gcagaccggt gagagccgac ttgttgtgcg    600
ccaccccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgcccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
```

-continued

```
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cctttcttgc gctatgacac   3300
ttccagcaaa aggtagggcg ggctgcgaga cggcttcccg gcgctgcatg caacaccgat   3360
gatgcttcga ccccccgaag ctccttcggg gctgcatggg cgctccgatg ccgctccagg   3420
gcgagcgctg tttaaatagc caggcccccg attgcaaaga cattatagcg agctaccaaa   3480
gccatattca aacacctaga tcactaccac ttctacacag gccactcgag cttgtgatcg   3540
cactccgcta aggggggcgcc tcttcctctt cgtttcagtc acaacccgca aacactagta   3600
tggccaccgc atccactttc tcggcgttca atgcccgctg cggcgacctg cgtcgctcgg   3660
cgggctccgg gccccggcgc ccagcgaggc ccctccccgt gcgcgggcgc gccgaggtgc   3720
acgtgcaggt gacccactcc ctggcccccg agaagcgcga gatcttcaac tccctgaaca   3780
actgggccca ggagaacatc ctggtgctgc tgaaggacgt ggacaagtgc tggcagccct   3840
ccgacttcct gcccgactcc gcctccgagg gcttcgacga gcaggtgatg gagctgcgca   3900
agcgctgcaa ggagatcccc gacgactact tcatcgtgct ggtgggcgac atgatcaccg   3960
aggaggccct gcccacctac cagaccatgc tgaacacctg ggacggcgtg cgcgacgaga   4020
ccggcgcctc cctgaccccc tggggccatct ggacccgcgc ctggaccgcc gaggagaacc   4080
gccacggcga cctgctgaac aagtacctgt acctgtccgg ccgcgtggac atgaagcaga   4140
tcgagaagac catccagtac ctgatcggct ccggcatgga cccccgcacc gagaacaacc   4200
cctacctggg cttcatctac acctccttcc aggagcgcgc caccttcatc tcccacggca   4260
acaccgcccg cctggccaag gagcacggcg acctgaagct ggcccagatc tgcggcatca   4320
tcgccgccga cgagaagcgc cacgagaccg cctacaccaa gatcgtggag aagctgttcg   4380
agatcgaccc cgacggcacc gtgctggccc tggccgacat gatgcgcaag aaggtgtcca   4440
tgcccgccca cctgatgtac gacggccagg acgacaacct gttcgagaac ttctcctccg   4500
tggcccagcg cctgggcgtg tacaccgcca aggactacgc cgacatcctg gagttcctgg   4560
tgggccgctg ggacatcgag aagctgaccg gcctgtccgg cgagggccgc aaggcccagg   4620
actacgtgtg caccctgccc ccccgcatcc gccgcctgga ggagcgcgcc cagtcccgcg   4680
tgaagaaggc ctccgccacc cccttctcct ggatcttcgg ccgcgagatc aacctgatgg   4740
```

actacaagga ccacgacggc gactacaagg accacgacat cgactacaag gacgacgacg 4800
acaagtgaat cgatagatct cttaaggcag cagcagctcg gatagtatcg acacactctg 4860
gacgctggtc gtgtgatgga ctgttgccgc cacacttgct gccttgacct gtgaatatcc 4920
ctgccgcttt tatcaaacag cctcagtgtg tttgatcttg tgtgtacgcg cttttgcgag 4980
ttgctagctg cttgtgctat ttgcgaatac cacccccagc atccccttcc ctcgtttcat 5040
atcgcttgca tcccaaccgc aacttatcta cgctgtcctg ctatccctca gcgctgctcc 5100
tgctcctgct cactgcccct cgcacagcct tggtttgggc tccgcctgta ttctcctggt 5160
actgcaacct gtaaaccagc actgcaatgc tgatgcacgg gaagtagtgg gatgggaaca 5220
caaatggaaa gcttaattaa gagctcttgt tttccagaag gagttgctcc ttgagccttt 5280
cattctcagc ctcgataacc tccaaagccg ctctaattgt ggaggggggtt cgaatttaaa 5340 agcttggaat gttggttcgt gcgtctggaa caagcccaga cttgttgctc actgggaaaa 5400
ggaccatcag ctccaaaaaa cttgccgctc aaaccgcgta cctctgcttt cgcgcaatct 5460
gccctgttga aatcgccacc acattcatat tgtgacgctt gagcagtctg taattgcctc 5520
agaatgtgga atcatctgcc ccctgtgcga gcccatgcca ggcatgtcgc gggcgaggac 5580
acccgccact cgtacagcag accattatgc tacctcacaa tagttcataa cagtgaccat 5640
atttctcgaa gctccccaac gagcacctcc atgctctgag tggccacccc ccggccctgg 5700
tgcttgcgga gggcaggtca accggcatgg ggctaccgaa atccccgacc ggatcccacc 5760
acccccgcga tgggaagaat ctctccccgg gatgtgggcc caccaccagc acaacctgct 5820
ggcccaggcg agcgtcaaac cataccacac aaatatcctt ggcatcggcc ctgaattcct 5880
tctgccgctc tgctacccgg tgcttctgtc cgaagcaggg gttgctaggg atcgctccga 5940
gtccgcaaac ccttgtcgcg tggcggggct tgttcgagct tgaagagc 5988

<210> SEQ ID NO 114
<211> LENGTH: 6696
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 114
gctcttcacc caactcagat aataccaata cccctccttc tcctcctcat ccattcagta 60
ccccccccct tctcttccca aagcagcaag cgcgtggctt acagaagaac aatcggcttc 120
cgccaaagtc gccgagcact gcccgacggc ggcgcgccca gcagcccgct tggccacaca 180
ggcaacgaat acattcaata gggggcctcg cagaatggaa ggagcggtaa agggtacagg 240
agcactgcgc acaaggggcc tgtgcaggag tgactgactg ggcgggcaga cggcgcaccg 300
cgggcgcagg caagcaggga agattgaagc ggcagggagg aggatgctga ttgagggggg 360
catcgcagtc tctcttggac ccgggataag gaagcaaata ttcggccggt tgggttgtgt 420
gtgtgcacgt tttcttcttc agagtcgtgg gtgtgcttcc agggaggata taagcagcag 480
gatcgaatcc cgcgaccagc gtttccccat ccagccaacc accctgtcgg taccctttct 540
tgcgctatga cacttccagc aaaaggtagg gcgggctgcg agacggcttc ccggcgctgc 600
atgcaacacc gatgatgctt cgaccccccg aagctccttc ggggctgcat gggcgctccg 660
atgccgctcc agggcgagcg ctgtttaaat agccaggccc ccgattgcaa agacattata 720
gcgagctacc aaagccatat tcaaacacct agatcactac cacttctaca caggccactc 780

-continued

```
gagcttgtga tcgcactccg ctaagggggc gcctcttcct cttcgtttca gtcacaaccc    840
gcaaacggcg cgccatgctg ctgcaggcct tcctgttcct gctggccggc ttcgccgcca    900
agatcagcgc ctccatgacg aacgagacgt ccgaccgccc cctggtgcac ttcaccccca    960
acaagggctg gatgaacgac cccaacggcc tgtggtacga cgagaaggac gccaagtggc   1020
acctgtactt ccagtacaac ccgaacgaca ccgtctgggg gacgcccttg ttctggggcc   1080
acgccacgtc cgacgacctg accaactggg aggaccagcc catcgccatc gccccgaagc   1140
gcaacgactc cggcgccttc tccggctcca tggtggtgga ctacaacaac acctccggct   1200
tcttcaacga caccatcgac ccgcgccagc gctgcgtggc catctggacc tacaacaccc   1260
cggagtccga ggagcagtac atctcctaca gcctggacgg cggctacacc ttcaccgagt   1320
accagaagaa ccccgtgctg gccgccaact ccacccagtt ccgcgacccg aaggtcttct   1380
ggtacgagcc ctcccagaag tggatcatga ccgcggccaa gtcccaggac tacaagatcg   1440
agatctactc ctccgacgac ctgaagtcct ggaagctgga gtccgcgttc gccaacgagg   1500
gcttcctcgg ctaccagtac gagtgccccg gcctgatcga ggtccccacc gagcaggacc   1560
ccagcaagtc ctactgggtg atgttcatct ccatcaaccc cggcgccccg gccggcggct   1620
ccttcaacca gtacttcgtc ggcagcttca acggcaccca cttcgaggcc ttcgacaacc   1680
agtcccgcgt ggtggacttc ggcaaggact actacgccct gcagaccttc ttcaacaccg   1740
acccgaccta cgggagcgcc ctgggcatcg cgtgggcctc caactgggag tactccgcct   1800
tcgtgcccac caacccctgg cgctcctcca tgtccctcgt gcgcaagttc tccctcaaca   1860
ccgagtacca ggccaacccg gagacggagc tgatcaacct gaaggccgag ccgatcctga   1920
acatcagcaa cgccggcccc tggagccggt tcgccaccaa caccacgttg acgaaggcca   1980
acagctacaa cgtcgacctg tccaacagca ccggcaccct ggagttcgag ctggtgtacg   2040
ccgtcaacac cacccagacg atctccaagt ccgtgttcgc ggacctctcc ctctggttca   2100
agggcctgga ggaccccgag gagtacctcc gcatgggctt cgaggtgtcc gcgtcctcct   2160
tcttcctgga ccgcgggaac agcaaggtga agttcgtgaa ggagaacccc tacttcacca   2220
accgcatgag cgtgaacaac cagcccttca agagcgagaa cgacctgtcc tactacaagg   2280
tgtacggctt gctggaccag aacatcctgg agctgtactt caacgacggc gacgtcgtgt   2340
ccaccaacac ctacttcatg accaccggga acgccctggg ctccgtgaac atgacgacgg   2400
gggtggacaa cctgttctac atcgacaagt tccaggtgcg cgaggtcaag tgacaattgg   2460
cagcagcagc tcggatagta tcgacacact ctggacgctg gtcgtgtgat ggactgttgc   2520
cgccacactt gctgccttga cctgtgaata tccctgccgc ttttatcaaa cagcctcagt   2580
gtgtttgatc ttgtgtgtac gcgcttttgc gagttgctag ctgcttgtgc tatttgcgaa   2640
taccaccccc agcatcccct tccctcgttt catatcgctt gcatcccaac cgcaacttat   2700
ctacgctgtc ctgctatccc tcagcgctgc tcctgctcct gctcactgcc cctcgcacag   2760
ccttggtttg ggctccgcct gtattctcct ggtactgcaa cctgtaaacc agcactgcaa   2820
tgctgatgca cgggaagtag tgggatggga acacaaatgg aggatcccgc gtctcgaaca   2880
gagcgcgcag aggaacgctg aaggtctcgc ctctgtcgca cctcagcgcg gcatacacca   2940
caataaccac ctgacgaatg cgcttggttc ttcgtccatt agcgaagcgt ccggttcaca   3000
cacgtgccac gttggcgagg tggcaggtga caatgatcgg tggagctgat ggtcgaaacg   3060
ttcacagcct agggatatca tagcgactgc taccccccga ccatgtgccg aggcagaaat   3120
```

-continued

```
tatatacaag aagcagatcg caattaggca catcgctttg cattatccac acactattca   3180
tcgctgctgc ggcaaggctg cagagtgtat ttttgtggcc caggagctga gtccgaagtc   3240
gacgcgacga gcggcgcagg atccgacccc tagacgagct ctgtcatttt ccaagcacgc   3300
agctaaatgc gctgagaccg ggtctaaatc atccgaaaag tgtcaaaatg gccgattggg   3360
ttcgcctagg acaatgcgct gcggattcgc tcgagtccgc tgccggccaa aaggcggtgg   3420
tacaggaagg cgcacggggc caaccctgcg aagccggggg cccgaacgcc gaccgccggc   3480
cttcgatctc gggtgtcccc ctcgtcaatt tcctctctcg ggtgcagcca cgaaagtcgt   3540
gacgcaggtc acgaaatccg gttacgaaaa acgcaggtct tcgcaaaaac gtgagggttt   3600
cgcgtctcgc cctagctatt cgtatcgccg ggtcagaccc acgtgcagaa aagcccttga   3660
ataacccggg accgtggtta ccgcgccgcc tgcaccaggg ggcttatata agcccacacc   3720
acacctgtct caccacgcat ttctccaact cgcgactttt cggaagaaat tgttatccac   3780
ctagtataga ctgccacctg caggaccttg tgtcttgcag tttgtattgg tcccggccgt   3840
cgagctcgac agatctgggc tagggttggc ctggccgctc ggcactcccc tttagccgcg   3900
cgcatccgcg ttccagaggt gcgattcggt gtgtggagca ttgtcatgcg cttgtggggg   3960
tcgttccgtg cgcggcgggt ccgccatggg cgccgacctg ggccctaggg tttgttttcg   4020
ggccaagcga gcccctctca cctcgtcgcc cccccgcatt ccctctctct tgcagccttg   4080
ccactagtat ggccaccgca tccactttct cggcgttcaa tgcccgctgc ggcgacctgc   4140
gtcgctcggc gggctccggg ccccggcgcc cagcgaggcc cctccccgtg cgcgggcgcg   4200
ccgccgccgc cgccgacgcc aaccccgccc gccccgagcg ccgcgtggtg atcaccggcc   4260
agggcgtggt gacctccctg ggccagacca tcgagcagtt ctactcctcc ctgctggagg   4320
gcgtgtccgg catctcccag atccagaagt tcgacaccac cggctacacc accaccatcg   4380
ccggcgagat caagtccctg cagctggacc cctacgtgcc caagcgctgg gccaagcgcg   4440
tggacgacgt gatcaagtac gtgtacatcg ccggcaagca ggccctggag tccgccggcc   4500
tgcccatcga ggccgccggc ctggccggcg ccggcctgga ccccgccctg tgcggcgtgc   4560
tgatcggcac cgccatggcc ggcatgacct ccttcgccgc cggcgtggag gccctgaccc   4620
gcggcggcgt gcgcaagatg aaccccttct gcatcccctt ctccatctcc aacatgggcg   4680
gcgccatgct ggccatggac atcggcttca tgggccccaa ctactccatc tccaccgcct   4740
gcgccaccgg caactactgc atcctgggcg ccgccgacca catccgccgc ggcgacgcca   4800
acgtgatgct ggccggcggc gccgacgccg ccatcatccc ctccggcatc ggcggcttca   4860
tcgcctgcaa ggccctgtcc aagcgcaacg acgagcccga gcgcgcctcc cgcccctggg   4920
acgccgaccg cgacggcttc gtgatgggcg agggcgccgg cgtgctggtg ctggaggagc   4980
tggagcacgc caagcgccgc ggcgccacca tcctggccga gctggtgggc ggcgccgcca   5040
cctccgacgc ccaccacatg accgagcccg acccccaggg ccgcggcgtg cgcctgtgcc   5100
tggagcgcgc cctggagcgc gcccgcctgg cccccgagcg cgtgggctac gtgaacgccc   5160
acggcacctc cacccccgcc ggcgacgtgg ccgagtaccg cgccatccgc gccgtgatcc   5220
cccaggactc cctgcgcatc aactccacca agtccatgat cggccacctg ctgggcggcg   5280
ccggcgccgt ggaggccgtg gccgccatcc aggccctgcg caccggctgg ctgcacccca   5340
acctgaacct ggagaacccc gcccccggcg tggaccccgt ggtgctggtg ggccccgca   5400
aggagcgcgc cgaggacctg gacgtggtgc tgtccaactc cttcggcttc ggcggccaca   5460
actcctgcgt gatcttccgc aagtacgacg agatggacta caaggaccac gacggcgact   5520
```

acaaggacca cgacatcgac tacaaggacg acgacgacaa gtgaatcgat agatctctta 5580
aggcagcagc agctcggata gtatcgacac actctggacg ctggtcgtgt gatggactgt 5640
tgccgccaca cttgctgcct tgacctgtga atatccctgc cgcttttatc aaacagcctc 5700
agtgtgtttg atcttgtgtg tacgcgcttt tgcgagttgc tagctgcttg tgctatttgc 5760
gaataccacc cccagcatcc ccttccctcg tttcatatcg cttgcatccc aaccgcaact 5820
tatctacgct gtcctgctat ccctcagcgc tgctcctgct cctgctcact gcccctcgca 5880
cagccttggt ttgggctccg cctgtattct cctggtactg caacctgtaa accagcactg 5940
caatgctgat gcacgggaag tagtgggatg ggaacacaaa tggaaagctt aattaagagc 6000
tcttgttttc cagaaggagt tgctccttga gcctttcatt ctcagcctcg ataacctcca 6060
aagccgctct aattgtggag gggttcgaa ccgaatgctg cgtgaacggg aaggaggagg 6120
agaaagagtg agcagggagg gattcagaaa tgagaaatga gaggtgaagg aacgcatccc 6180
tatgcccttg caatggacag tgtttctggc caccgccacc aagacttcgt gtcctctgat 6240
catcatgcga ttgattacgt tgaatgcgac ggccggtcag ccccggacct ccacgcaccg 6300
gtgctcctcc aggaagatgc gcttgtcctc cgccatcttg cagggctcaa gctgctccca 6360
aaactcttgg gcgggttccg gacggacggc taccgcgggt gcggccctga ccgccactgt 6420
tcggaagcag cggcgctgca tgggcagcgg ccgctgcggt gcgccacgga ccgcatgatc 6480
caccggaaaa gcgcacgcgc tggagcgcgc agaggaccac agagaagcgg aagagacgcc 6540
agtactggca agcaggctgg tcggtgccat ggcgcgctac taccctcgct atgactcggg 6600
tcctcggccg gctggcggtg ctgacaattc gtttagtgga gcagcgactc cattcagcta 6660
ccagtcgaac tcagtggcac agtgactccg ctcttc 6696

<210> SEQ ID NO 115
<211> LENGTH: 993
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 115
gatatctccc tccgtctctg cactctggcg cccctcctcc gtctcgtgga ctgacggacg 60
agagtctggg cgccgctttt ctatccacac cgccctttcc gcatcgaaga caccacccat 120
cgtgccgcca ggtcttcccc aatcacccgc cctgtggtcc tctctcccag ccgtgtttgg 180
tcgctgcgtc cacatttttc cattcgtgcc ccacgatcct cgcccatctt ggcgccttgg 240
ataggcaccc ttttttcagc acgccctggt gtgtagcaca acctgacctc tctctaccgc 300
atcgcctccc tcccacacct cagttgactc cctcgtcgca cgttgcaccc gcaagctccc 360
catttcatcc tattgacaat cgcacactgt acatgtatgc tcattatttt gcaaaaaaac 420
agggggtcgg ttcactcctg gcagacgacg cggtgctgcc gcgcgccgct gaggcggcgt 480
cgcgacggca acacccatcg caccgcacgt cgacgagtca acccaccctg ctcaacggtg 540
atctccccat cgcgacaccc cccgtgaccg tactatgtgc gtccatacgc aacatgaaaa 600
ggaccttggt ccccggaggc ggcgagctcg taatcccgag gttggccccg cttccgctgg 660
acacccatcg catcttccgg ctcgcccgct gtcgagcaag cgccctcgtg cgcgcaaccc 720
ttgtggtgcc tgcccgcaga gccgggcata aaggcgagca ccacacccga accagtccaa 780
tttgctttct gcattcactc accaactttt acatccacac atcgtactac cacacctgcc 840
cagtcgggtt tgatttctat tgcaaaggtg cggggggggtt ggcgcactgc gtgggttgtg 900
cagccggccg ccgcggctgt acccagcgat caggtagctt gggctgtatc ttctcaagca 960
ttaccttgtc ctgggcgtag gtttgccact agt 993

<210> SEQ ID NO 116
<211> LENGTH: 1083
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 116
gatatcgaat tcggccgaca ggacgcgcgt caaaggtgct ggtcgtgtat gccctggccg 60
gcaggtcgtt gctgctgctg gttagtgatt ccgcaaccct gattttggcg tcttattttg 120
gcgtggcaaa cgctggcgcc cgcgagccgg gccggcggcg atgcggtgcc ccacggctgc 180
cggaatccaa gggaggcaag agcgcccggg tcagttgaag ggctttacgc gcaaggtaca 240
gccgctcctg caaggctgcg tggtggaatt ggacgtgcag gtcctgctga agttcctcca 300
ccgcctcacc agcggacaaa gcaccggtgt atcaggtccg tgtcatccac tctaaagaac 360
tcgactacga cctactgatg gccctagatt cttcatcaaa aacgcctgag acacttgccc 420
aggattgaaa ctccctgaag ggaccaccag gggccctgag ttgttccttc cccccgtggc 480
gagctgccag ccaggctgta cctgtgatcg aggctggcgg gaaaataggc ttcgtgtgct 540
caggtcatgg gaggtgcagg acagctcatg aaacgccaac aatcgcacaa ttcatgtcaa 600
gctaatcagc tatttcctct tcacgagctg taattgtccc aaaattctgg tctaccgggg 660
gtgatccttc gtgtacgggc ccttccctca accctaggta tgcgcgcatg cggtcgccgc 720
gcaactcgcg cgagggccga gggtttggga cgggccgtcc cgaaatgcag ttgcacccgg 780
atgcgtggca cctttttgc gataatttat gcaatggact gctctgcaaa attctggctc 840
tgtcgccaac cctaggatca gcggcgtagg atttcgtaat cattcgtcct gatggggagc 900
taccgactac cctaatatca gcccgactgc ctgacgccag cgtccacttt tgtgcacaca 960
ttccattcgt gcccaagaca tttcattgtg gtgcgaagcg tccccagtta cgctcacctg 1020
tttcccgacc tccttactgt tctgtcgaca gagcgggccc acaggccggt cgcagccact 1080
agt 1083

<210> SEQ ID NO 117
<211> LENGTH: 5662
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 117
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360

```
atccctacca gtcatggctt tacctggatg acggcctgcg aacagctgtc cagcgaccct    420
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccccttgcg cgttagtgtt gccatccttt gcagaccggt gagagccgac ttgttgtgcg    600
ccaccccccca caccacctcc tcccagacca attctgtcac ctttttggcg aaggcatcgg    660
cctcggcctg cagagaggac agcagtgccc agccgctggg ggttggcgga tgcacgctca    720
ggtaccgcgg tgagaatcga aaatgcatcg tttctaggtt cggagacggt caattccctg    780
ctccggcgaa tctgtcggtc aagctggcca gtggacaatg ttgctatggc agcccgcgca    840
catgggcctc ccgacgcggc catcaggagc ccaaacagcg tgtcagggta tgtgaaactc    900
aagaggtccc tgctgggcac tccggcccca ctccgggggc gggacgccag gcattcgcgg    960
tcggtcccgc gcgacgagcg aaatgatgat tcggttacga gaccaggacg tcgtcgaggt   1020
cgagaggcag cctcggacac gtctcgctag ggcaacgccc cgagtccccg cgagggccgt   1080
aaacattgtt tctgggtgtc ggagtgggca ttttgggccc gatccaatcg cctcatgccg   1140
ctctcgtctg gtcctcacgt tcgcgtacgg cctggatccc ggaaagggcg gatgcacgtg   1200
gtgttgcccc gccattggcg cccacgtttc aaagtccccg gccagaaatg cacaggaccg   1260
gcccggctcg cacaggccat gctgaacgcc cagatttcga cagcaacacc atctagaata   1320
atcgcaacca tccgcgtttt gaacgaaacg aaacggcgct gtttagcatg tttccgacat   1380
cgtgggggcc gaagcatgct ccgggggggag gaaagcgtgg cacagcggta gcccattctg   1440
tgccacacgc cgacgaggac caatccccgg catcagcctt catcgacggc tgcgccgcac   1500
atataaagcc ggacgcctaa ccggtttcgt ggttatgact agtatgttcg cgttctactt   1560
cctgacggcc tgcatctccc tgaagggcgt gttcggcgtc tccccctcct acaacggcct   1620
gggcctgacg ccccagatgg gctgggacaa ctggaacacg ttcgcctgcg acgtctccga   1680
gcagctgctg ctggacacgg ccgaccgcat ctccgacctg ggcctgaagg acatgggcta   1740
caagtacatc atcctggacg actgctggtc ctccggccgc gactccgacg gcttcctggt   1800
cgccgacgag cagaagttcc ccaacggcat gggccacgtc gccgaccacc tgcacaacaa   1860
ctccttcctg ttcggcatgt actcctccgc gggcgagtac acgtgcgccg gctaccccgg   1920
ctccctgggc cgcgaggagg aggacgccca gttcttcgcg aacaaccgcg tggactacct   1980
gaagtacgac aactgctaca acaagggcca gttcggcacg cccgagatct cctaccaccg   2040
ctacaaggcc atgtccgacg ccctgaacaa gacgggccgc cccatcttct actccctgtg   2100
caactggggc caggacctga ccttctactg ggctccggc atcgcgaact cctggcgcat    2160
gtccggcgac gtcacggcgg agttcacgcg ccccgactcc cgctgcccct gcgacggcga   2220
cgagtacgac tgcaagtacg ccggcttcca ctgctccatc atgaacatcc tgaacaaggc   2280
cgcccccatg ggccagaacg cgggcgtcgg cggctggaac gacctggaca acctggaggt   2340
cggcgtcggc aacctgacgg acgacgagga gaaggcgcac ttctccatgt gggccatggt   2400
gaagtccccc ctgatcatcg gcgcgaacgt gaacaacctg aaggcctcct cctactccat   2460
ctactcccag gcgtccgtca tcgccatcaa ccaggactcc aacggcatcc ccgccacgcg   2520
cgtctggcgc tactacgtgt ccgacacgga cgagtacggc cagggcgaga tccagatgtg   2580
gtccggcccc ctggacaacg gcgaccaggt cgtggcgctg ctgaacggcg gctccgtgtc   2640
ccgccccatg aacacgaccc tggaggagat cttcttcgac tccaacctgg gctccaagaa   2700
gctgacctcc acctgggaca tctacgacct gtgggcgaac cgcgtcgaca actccacggc   2760
```

```
gtccgccatc ctgggccgca acaagaccgc caccggcatc ctgtacaacg ccaccgagca   2820
gtcctacaag gacggcctgt ccaagaacga cacccgcctg ttcggccaga agatcggctc   2880
cctgtccccc aacgcgatcc tgaacacgac cgtccccgcc cacggcatcg cgttctaccg   2940
cctgcgcccc tcctcctgac aattggcagc agcagctcgg atagtatcga cacactctgg   3000
acgctggtcg tgtgatggac tgttgccgcc acacttgctg ccttgacctg tgaatatccc   3060
tgccgctttt atcaaacagc ctcagtgtgt ttgatcttgt gtgtacgcgc ttttgcgagt   3120
tgctagctgc ttgtgctatt tgcgaatacc acccccagca tccccttccc tcgtttcata   3180
tcgcttgcat cccaaccgca acttatctac gctgtcctgc tatccctcag cgctgctcct   3240
gctcctgctc actgcccctc gcacagcctt ggtttgggct ccgcctgtat tctcctggta   3300
ctgcaacctg taaaccagca ctgcaatgct gatgcacggg aagtagtggg atgggaacac   3360
aaatggagga tcccgcgtct cgaacagagc gcgcagagga acgctgaagg tctcgcctct   3420
gtcgcacctc agcgcggcat acaccacaat aaccacctga cgaatgcgct tggttcttcg   3480
tccattagcg aagcgtccgg ttcacacacg tgccacgttg gcgaggtggc aggtgacaat   3540
gatcggtgga gctgatggtc gaaacgttca cagcctaggg atatcgaatt cctttcttgc   3600
gctatgacac ttccagcaaa aggtagggcg ggctgcgaga cggcttcccg gcgctgcatg   3660
caacaccgat gatgcttcga cccccgaag ctccttcggg gctgcatggg cgctccgatg   3720
ccgctccagg gcgagcgctg tttaaatagc caggcccccg attgcaaaga cattatagcg   3780
agctaccaaa gccatattca aacacctaga tcactaccac ttctacacag gccactcgag   3840
cttgtgatcg cactccgcta agggggcgcc tcttcctctt cgtttcagtc acaacccgca   3900
aacactagta tggctatcaa gacgaacagg cagcctgtgg agaagcctcc gttcacgatc   3960
gggacgctgc gcaaggccat ccccgcgcac tgtttcgagc gctcggcgct tcgtagcagc   4020
atgtacctgg cctttgacat cgcggtcatg tccctgctct acgtcgcgtc gacgtacatc   4080
gaccctgcac cggtgcctac gtgggtcaag tacggcatca tgtggccgct ctactggttc   4140
ttccaggtgt gtttgagggt tttggttgcc cgtattgagg tcctggtggc gcgcatggag   4200
gagaaggcgc ctgtcccgct gaccccccg gctaccctcc cggcaccttc cagggcgcgt   4260
acgggaagaa ccagtagagc ggccacatga tgccgtactt gacccacgta ggcaccggtg   4320
cagggtcgat gtacgtcgac gcgacgtaga gcagggacat gaccgcgatg tcaaaggcca   4380
ggtacatgct gctacgaagc gccgagcgct cgaaacagtg cgcggggatg gccttgcgca   4440
gcgtcccgat cgtgaacgga ggcttctcca caggctgcct gttcgtcttg atagccatct   4500
cgaggcagca gcagctcgga tagtatcgac acactctgga cgctggtcgt gtgatggact   4560
gttgccgcca cacttgctgc cttgacctgt gaatatccct gccgctttta tcaaacagcc   4620
tcagtgtgtt tgatcttgtg tgtacgcgct tttgcgagtt gctagctgct tgtgctattt   4680
gcgaatacca cccccagcat ccccttccct cgtttcatat cgcttgcatc ccaaccgcaa   4740
cttatctacg ctgtcctgct atccctcagc gctgctcctg ctcctgctca ctgcccctcg   4800
cacagccttg gtttgggctc cgcctgtatt ctcctggtac tgcaacctgt aaaccagcac   4860
tgcaatgctg atgcacggga agtagtggga tgggaacaca aatggaaagc tgtagagctc   4920
ttgttttcca gaaggagttg ctccttgagc ctttcattct cagcctcgat aacctccaaa   4980
gccgctctaa ttgtggaggg ggttcgaatt taaaagcttg gaatgttggt tcgtgcgtct   5040
ggaacaagcc cagacttgtt gctcactggg aaaaggacca tcagctccaa aaaacttgcc   5100
```

-continued

```
gctcaaaccg cgtacctctg ctttcgcgca atctgccctg ttgaaatcgc caccacattc   5160

atattgtgac gcttgagcag tctgtaattg cctcagaatg tggaatcatc tgccccctgt   5220

gcgagcccat gccaggcatg tcgcgggcga ggacacccgc cactcgtaca gcagaccatt   5280

atgctacctc acaatagttc ataacagtga ccatatttct cgaagctccc caacgagcac   5340

ctccatgctc tgagtggcca ccccccggcc ctggtgcttg cggagggcag gtcaaccggc   5400

atggggctac cgaaatcccc gaccggatcc caccaccccc gcgatgggaa gaatctctcc   5460

ccgggatgtg ggcccaccac cagcacaacc tgctggccca ggcgagcgtc aaaccatacc   5520

acacaaatat ccttggcatc ggccctgaat tccttctgcc gctctgctac ccggtgcttc   5580

tgtccgaagc aggggttgct agggatcgct ccgagtccgc aaacccttgt cgcgtggcgg   5640

ggcttgttcg agcttgaaga gc                                            5662
```

<210> SEQ ID NO 118
<211> LENGTH: 7963
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
gctcttcgga gtcactgtgc cactgagttc gactggtagc tgaatggagt cgctgctcca     60

ctaaacgaat tgtcagcacc gccagccggc cgaggacccg agtcatagcg agggtagtag    120

cgcgccatgg caccgaccag cctgcttgcc agtactggcg tctcttccgc ttctctgtgg    180

tcctctgcgc gctccagcgc gtgcgctttt ccggtggatc atgcggtccg tggcgcaccg    240

cagcggccgc tgcccatgca gcgccgctgc ttccgaacag tggcggtcag ggccgcaccc    300

gcggtagccg tccgtccgga acccgcccaa gagttttggg agcagcttga gccctgcaag    360

atggcggagg acaagcgcat cttcctggag gagcaccggt gcgtggaggt ccggggctga    420

ccggccgtcg cattcaacgt aatcaatcgc atgatgatca gaggacacga agtcttggtg    480

gcggtggcca gaaacactgt ccattgcaag ggcataggga tgcgttcctt cacctctcat    540

ttctcatttc tgaatccctc cctgctcact ctttctcctc ctccttcccg ttcacgcagc    600

attcggggta ccagtttagg tccagcgtcc gtgggggggg acgggctggg agcttgggcc    660

gggaagggca agacgatgca gtccctctgg ggagtcacag ccgactgtgt gtgttgcact    720

gtgcggcccg cagcactcac acgcaaaatg cctggccgac aggcaggccc tgtccagtgc    780

aacatccacg gtccctctca tcaggctcac cttgctcatt gacataacgg aatgcgtacc    840

gctctttcag atctgtccat ccagagaggg gagcaggctc cccaccgacg ctgtcaaact    900

tgcttcctgc ccaaccgaaa acattattgt ttgagggggg gggggggggg gcagattgca    960

tggcgggata tctcgtgagg aacatcactg ggacactgtg gaacacagtg agtgcagtat   1020

gcagagcatg tatgctaggg gtcagcgcag gaagggggcc tttcccagtc tcccatgcca   1080

ctgcaccgta tccacgactc accaggacca gcttcttgat cggcttccgc tcccgtggac   1140

accagtgtgt agcctctgga ctccaggtat gcgtgcaccg caaaggccag ccgatcgtgc   1200

cgattcctgg ggtggaggat atgagtcagc caacttgggg ctcagagtgc acactggggc   1260

acgatacgaa acaacatcta caccgtgtcc tccatgctga cacaccacag cttcgctcca   1320

cctgaatgtg ggcgcatggg cccgaatcac agccaatgtc gctgctgcca taatgtgatc   1380

cagaccctct ccgcccagat gccgagcgga tcgtgggcgc tgaatagatt cctgtttcga   1440
```

```
tcactgtttg ggtcctttcc ttttcgtctc ggatgcgcgt ctcgaaacag gctgcgtcgg   1500
gctttcggat cccttttgct ccctccgtca ccatcctgcg cgcgggcaag ttgcttgacc   1560
ctgggctgta ccagggttgg agggtattac cgcgtcaggc cattcccagc ccggattcaa   1620
ttcaaagtct gggccaccac cctccgccgc tctgtctgat cactccacat tcgtgcatac   1680
actacgttca agtcctgatc caggcgtgtc tcgggacaag gtgtgcttga gtttgaatct   1740
caaggaccca ctccagcaca gctgctggtt gaccccgccc tcgcaatcta gaatggccgc   1800
gtccgtccac tgcaccctga tgtccgtggt ctgcaacaac aagaaccact ccgcccgccc   1860
caagctgccc aactcctccc tgctgcccgg cttcgacgtg gtggtccagg ccgcggccac   1920
ccgcttcaag aaggagacga cgaccacccg cgccacgctg acgttcgacc cccccacgac   1980
caactccgag cgcgccaagc agcgcaagca caccatcgac ccctcctccc ccgacttcca   2040
gcccatcccc tccttcgagg agtgcttccc caagtccacg aaggagcaca aggaggtggt   2100
gcacgaggag tccggccacg tcctgaaggt gcccttccgc cgcgtgcacc tgtccggcgg   2160
cgagcccgcc ttcgacaact acgacacgtc cggcccccag aacgtcaacg cccacatcgg   2220
cctggcgaag ctgcgcaagg agtggatcga ccgccgcgag aagctgggca cgccccgcta   2280
cacgcagatg tactacgcga agcagggcat catcacggag gagatgctgt actgcgcgac   2340
gcgcgagaag ctggaccccg agttcgtccg ctccgaggtc gcgcggggcc gcgccatcat   2400
cccctccaac aagaagcacc tggagctgga gcccatgatc gtgggccgca agttcctggt   2460
gaaggtgaac gcgaacatcg gcaactccgc cgtggcctcc tccatcgagg aggaggtcta   2520
caaggtgcag tgggccacca tgtggggcgc cgacaccatc atggacctgt ccacgggccg   2580
ccacatccac gagacgcgcg agtggatcct gcgcaactcc gcggtccccg tgggcaccgt   2640
ccccatctac caggcgctgg agaaggtgga cggcatcgcg gagaacctga actgggaggt   2700
gttccgcgag acgctgatcg agcaggccga gcagggcgtg gactacttca cgatccacgc   2760
gggcgtgctg ctgcgctaca tccccctgac cgccaagcgc ctgacgggca tcgtgtcccg   2820
cggcggctcc atccacgcga agtggtgcct ggcctaccac aaggagaact tcgcctacga   2880
gcactgggac gacatcctgg acatctgcaa ccagtacgac gtcgccctgt ccatcggcga   2940
cggcctgcgc cccggctcca tctacgacgc caacgacacg gcccagttcg ccgagctgct   3000
gacccagggc gagctgacgc gccgcgcgtg ggagaaggac gtgcaggtga tgaacgaggg   3060
ccccggccac gtgcccatgc acaagatccc cgagaacatg cagaagcagc tggagtggtg   3120
caacgaggcg cccttctaca ccctgggccc cctgacgacc gacatcgcgc ccggctacga   3180
ccacatcacc tccgccatcg gcgcggccaa catcggcgcc ctgggcaccg ccctgctgtg   3240
ctacgtgacg cccaaggagc acctgggcct gcccaaccgc gacgacgtga aggcgggcgt   3300
catcgcctac aagatcgccg cccacgcggc cgacctggcc aagcagcacc cccacgccca   3360
ggcgtgggac gacgcgctgt ccaaggcgcg cttcgagttc cgctggatgg accagttcgc   3420
gctgtccctg gaccccatga cggcgatgtc cttccacgac gagacgctgc ccgcggacgg   3480
cgcgaaggtc gcccacttct gctccatgtg cggccccaag ttctgctcca tgaagatcac   3540
ggaggacatc cgcaagtacg ccgaggagaa cggctacggc tccgccgagg aggccatccg   3600
ccagggcatg gacgccatgt ccgaggagtt caacatcgcc aagaagacga tctccggcga   3660
gcagcacggc gaggtcggcg gcgagatcta cctgcccgag tcctacgtca aggccgcgca   3720
gaagtgacaa ttggcagcag cagctcggat agtatcgaca cactctggac gctggtcgtg   3780
tgatggactg ttgccgccac acttgctgcc ttgacctgtg aatatccctg ccgcttttat   3840
```

```
caaacagcct cagtgtgttt gatcttgtgt gtacgcgctt ttgcgagttg ctagctgctt   3900
gtgctatttg cgaataccac ccccagcatc cccttccctc gtttcatatc gcttgcatcc   3960
caaccgcaac ttatctacgc tgtcctgcta tccctcagcg ctgctcctgc tcctgctcac   4020
tgcccctcgc acagccttgg tttgggctcc gcctgtattc tcctggtact gcaacctgta   4080
aaccagcact gcaatgctga tgcacgggaa gtagtgggat gggaacacaa atggaggatc   4140
ccgcgtctcg aacagagcgc gcagaggaac gctgaaggtc tcgcctctgt cgcacctcag   4200
cgcggcatac accacaataa ccacctgacg aatgcgcttg gttcttcgtc cattagcgaa   4260
gcgtccggtt cacacacgtg ccacgttggc gaggtggcag gtgacaatga tcggtggagc   4320
tgatggtcga aacgttcaca gcctagggat atcgaattcg gccgacagga cgcgcgtcaa   4380
aggtgctggt cgtgtatgcc ctggccggca ggtcgttgct gctgctggtt agtgattccg   4440
caaccctgat tttggcgtct tattttggcg tggcaaacgc tggcgcccgc gagccgggcc   4500
ggcggcgatg cggtgcccca cggctgccgg aatccaaggg aggcaagagc gcccgggtca   4560
gttgaagggc tttacgcgca aggtacagcc gctcctgcaa ggctgcgtgg tggaattgga   4620
cgtgcaggtc ctgctgaagt tcctccaccg cctcaccagc ggacaaagca ccggtgtatc   4680
aggtccgtgt catccactct aaagaactcg actacgacct actgatggcc ctagattctt   4740
catcaaaaac gcctgagaca cttgcccagg attgaaactc cctgaaggga ccaccagggg   4800
ccctgagttg ttccttcccc ccgtggcgag ctgccagcca ggctgtacct gtgatcgagg   4860
ctggcgggaa aataggcttc gtgtgctcag gtcatgggag gtgcaggaca gctcatgaaa   4920
cgccaacaat cgcacaattc atgtcaagct aatcagctat ttcctcttca cgagctgtaa   4980
ttgtcccaaa attctggtct accgggggtg atccttcgtg tacgggccct tccctcaacc   5040
ctaggtatgc gcgcatgcgg tcgccgcgca actcgcgcga gggccgaggg tttgggacgg   5100
gccgtcccga aatgcagttg cacccggatg cgtggcacct tttttgcgat aatttatgca   5160
atggactgct ctgcaaaatt ctggctctgt cgccaaccct aggatcagcg gcgtaggatt   5220
tcgtaatcat tcgtcctgat ggggagctac cgactaccct aatatcagcc cgactgcctg   5280
acgccagcgt ccacttttgt gcacacattc cattcgtgcc caagacattt cattgtggtg   5340
cgaagcgtcc ccagttacgc tcacctgttt cccgacctcc ttactgttct gtcgacagag   5400
cgggcccaca ggccggtcgc agccactagt atgcagaccg cccaccagcg cccccccacc   5460
gagggccact gcttcggcgc ccgcctgccc accgcctccc gccgcgccgt gcgccgcgcc   5520
tggtcccgca tcgcccgcgg gcgcgccgcc gccgccgccg acgccaaccc cgcccgcccc   5580
gagcgccgcg tggtgatcac cggccagggc gtggtgacct ccctgggcca gaccatcgag   5640
cagttctact cctccctgct ggagggcgtg tccggcatct cccagatcca gaagttcgac   5700
accaccggct acaccaccac catcgccggc gagatcaagt ccctgcagct ggacccctac   5760
gtgcccaagc gctgggccaa gcgcgtggac gacgtgatca agtacgtgta catcgccggc   5820
aagcaggccc tggagtccgc cggcctgccc atcgaggccg ccggcctggc cggcgccggc   5880
ctggaccccg ccctgtgcgg cgtgctgatc ggcaccgcca tggccggcat gacctccttc   5940
gccgccggcg tggaggccct gacccgcggc ggcgtgcgca agatgaaccc cttctgcatc   6000
cccttctcca tctccaacat gggcggcgcc atgctggcca tggacatcgg cttcatgggc   6060
cccaactact ccatctccac cgcctgcgcc accggcaact actgcatcct gggcgccgcc   6120
gaccacatcc gccgcggcga cgccaacgtg atgctggccg gcggcgccga cgccgccatc   6180
```

atcccctccg gcatcggcgg cttcatcgcc tgcaaggccc tgtccaagcg caacgacgag 6240
cccgagcgcg cctcccgccc ctgggacgcc gaccgcgacg gcttcgtgat gggcgagggc 6300
gccggcgtgc tggtgctgga ggagctggag cacgccaagc gccgcggcgc caccatcctg 6360
gccgagctgg tgggcggcgc cgccacctcc gacgcccacc acatgaccga gcccgacccc 6420
cagggccgcg gcgtgcgcct gtgcctggag cgcgccctgg agcgcgcccg cctggccccc 6480
gagcgcgtgg gctacgtgaa cgcccacggc acctccaccc ccgccggcga cgtggccgag 6540
taccgcgcca tccgcgccgt gatcccccag gactccctgc gcatcaactc caccaagtcc 6600
atgatcggcc acctgctggg cggcgccggc gccgtggagg ccgtggccgc catccaggcc 6660
ctgcgcaccg gctggctgca ccccaacctg aacctggaga accccgcccc cggcgtggac 6720
cccgtggtgc tggtgggccc ccgcaaggag cgcgccgagg acctggacgt ggtgctgtcc 6780
aactccttcg gcttcggcgg ccacaactcc tgcgtgatct tccgcaagta cgacgagatg 6840
gactacaagg accacgacgg cgactacaag gaccacgaca tcgactacaa ggacgacgac 6900
gacaagtgaa tcgatagatc tcttaaggca gcagcagctc ggatagtatc gacacactct 6960
ggacgctggt cgtgtgatgg actgttgccg ccacacttgc tgccttgacc tgtgaatatc 7020
cctgccgctt ttatcaaaca gcctcagtgt gtttgatctt gtgtgtacgc gcttttgcga 7080
gttgctagct gcttgtgcta tttgcgaata ccacccccag catccccttc cctcgtttca 7140
tatcgcttgc atcccaaccg caacttatct acgctgtcct gctatccctc agcgctgctc 7200
ctgctcctgc tcactgcccc tcgcacagcc ttggtttggg ctccgcctgt attctcctgg 7260
tactgcaacc tgtaaaccag cactgcaatg ctgatgcacg ggaagtagtg ggatgggaac 7320
acaaatggaa agcttaatta agagctcttg ttttccagaa ggagttgctc cttgagcctt 7380
tcattctcag cctcgataac ctccaaagcc gctctaattg tggagggggt tcgaagacag 7440
ggtggttggc tggatgggga aacgctggtc gcgggattcg atcctgctgc ttatatcctc 7500
cctggaagca cacccacgac tctgaagaag aaaacgtgca cacacacaac ccaaccggcc 7560
gaatatttgc ttccttatcc cgggtccaag agagactgcg atgccccct caatcagcat 7620 cctcctccct gccgcttcaa tcttccctgc ttgcctgcgc ccgcggtgcg ccgtctgccc 7680
gcccagtcag tcactcctgc acaggcccct tgtgcgcagt gctcctgtac cctttaccgc 7740
tccttccatt ctgcgaggcc ccctattgaa tgtattcgtt gcctgtgtgg ccaagcgggc 7800
tgctgggcgc gccgccgtcg ggcagtgctc ggcgactttg gcggaagccg attgttcttc 7860
tgtaagccac gcgcttgctg ctttgggaag agaagggggg gggtactgaa tggatgagga 7920
ggagaaggag gggtattggt attatctgag ttgggtgaag agc 7963

<210> SEQ ID NO 119
<211> LENGTH: 7887
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119
gctcttcgga gtcactgtgc cactgagttc gactggtagc tgaatggagt cgctgctcca 60
ctaaacgaat tgtcagcacc gccagccggc cgaggacccg agtcatagcg agggtagtag 120
cgcgccatgg caccgaccag cctgcttgcc agtactggcg tctcttccgc ttctctgtgg 180
tcctctgcgc gctccagcgc gtgcgctttt ccggtggatc atgcggtccg tggcgcaccg 240

-continued

```
cagcggccgc tgcccatgca gcgccgctgc ttccgaacag tggcggtcag ggccgcaccc    300
gcggtagccg tccgtccgga acccgcccaa gagttttggg agcagcttga gccctgcaag    360
atggcggagg acaagcgcat cttcctggag gagcaccggt gcgtggaggt ccggggctga    420
ccggccgtcg cattcaacgt aatcaatcgc atgatgatca gaggacacga agtcttggtg    480
gcggtggcca gaaacactgt ccattgcaag ggcataggga tgcgttcctt cacctctcat    540
ttctcatttc tgaatccctc cctgctcact ctttctcctc ctccttcccg ttcacgcagc    600
attcggggta ccagtttagg tccagcgtcc gtgggggggg acgggctggg agcttgggcc    660
gggaagggca agacgatgca gtccctctgg ggagtcacag ccgactgtgt gtgttgcact    720
gtgcggcccg cagcactcac acgcaaaatg cctggccgac aggcaggccc tgtccagtgc    780
aacatccacg gtccctctca tcaggctcac cttgctcatt gacataacgg aatgcgtacc    840
gctctttcag atctgtccat ccagagaggg gagcaggctc cccaccgacg ctgtcaaact    900
tgcttcctgc ccaaccgaaa acattattgt ttgagggggg gggggggggg gcagattgca    960
tggcgggata tctcgtgagg aacatcactg ggacactgtg gaacacagtg agtgcagtat   1020
gcagagcatg tatgctaggg gtcagcgcag gaagggggcc tttcccagtc tcccatgcca   1080
ctgcaccgta tccacgactc accaggacca gcttcttgat cggcttccgc tcccgtggac   1140
accagtgtgt agcctctgga ctccaggtat gcgtgcaccg caaaggccag ccgatcgtgc   1200
cgattcctgg ggtggaggat atgagtcagc caacttgggg ctcagagtgc acactggggc   1260
acgatacgaa acaacatcta caccgtgtcc tccatgctga cacaccacag cttcgctcca   1320
cctgaatgtg ggcgcatggg cccgaatcac agccaatgtc gctgctgcca taatgtgatc   1380
cagaccctct ccgcccagat gccgagcgga tcgtgggcgc tgaatagatt cctgtttcga   1440
tcactgtttg ggtcctttcc ttttcgtctc ggatgcgcgt ctcgaaacag gctgcgtcgg   1500
gctttcggat cccttttgct ccctccgtca ccatcctgcg cgcgggcaag ttgcttgacc   1560
ctgggctgta ccagggttgg agggtattac cgcgtcaggc cattcccagc ccggattcaa   1620
ttcaaagtct gggccaccac cctccgccgc tctgtctgat cactccacat tcgtgcatac   1680
actacgttca agtcctgatc caggcgtgtc tcgggacaag gtgtgcttga gtttgaatct   1740
caaggaccca ctccagcaca gctgctggtt gaccccgccc tcgcaatcta gaatggccgc   1800
gtccgtccac tgcaccctga tgtccgtggt ctgcaacaac aagaaccact ccgcccgccc   1860
caagctgccc aactcctccc tgctgcccgg cttcgacgtg gtggtccagg ccgcggccac   1920
ccgcttcaag aaggagacga cgaccacccg cgccacgctg acgttcgacc cccccacgac   1980
caactccgag cgcgccaagc agcgcaagca caccatcgac ccctcctccc ccgacttcca   2040
gcccatcccc tccttcgagg agtgcttccc caagtccacg aaggagcaca aggaggtggt   2100
gcacgaggag tccggccacg tcctgaaggt gcccttccgc cgcgtgcacc tgtccggcgg   2160
cgagcccgcc ttcgacaact acgacacgtc cggcccccag aacgtcaacg cccacatcgg   2220
cctggcgaag ctgcgcaagg agtggatcga ccgccgcgag aagctgggca cgccccgcta   2280
cacgcagatg tactacgcga agcagggcat catcacggag gagatgctgt actgcgcgac   2340
gcgcgagaag ctggaccccg agttcgtccg ctccgaggtc gcgcggggcc gcgccatcat   2400
cccctccaac aagaagcacc tggagctgga gcccatgatc gtgggccgca agttcctggt   2460
gaaggtgaac gcgaacatcg gcaactccgc cgtggcctcc tccatcgagg aggaggtcta   2520
caaggtgcag tgggccacca tgtggggcgc cgacaccatc atggacctgt ccacgggccg   2580
ccacatccac gagacgcgcg agtggatcct gcgcaactcc gcggtccccg tgggcaccgt   2640
```

ccccatctac caggcgctgg agaaggtgga cggcatcgcg gagaacctga actgggaggt 2700
gttccgcgag acgctgatcg agcaggccga gcagggcgtg gactacttca cgatccacgc 2760
gggcgtgctg ctgcgctaca tcccccctgac cgccaagcgc ctgacgggca tcgtgtcccg 2820
cggcggctcc atccacgcga agtggtgcct ggcctaccac aaggagaact tcgcctacga 2880
gcactgggac gacatcctgg acatctgcaa ccagtacgac gtcgccctgt ccatcggcga 2940
cggcctgcgc cccggctcca tctacgacgc caacgacacg gcccagttcg ccgagctgct 3000
gacccagggc gagctgacgc gccgcgcgtg ggagaaggac gtgcaggtga tgaacgaggg 3060
ccccggccac gtgcccatgc acaagatccc cgagaacatg cagaagcagc tggagtggtg 3120
caacgaggcg cccttctaca ccctgggccc cctgacgacc gacatcgcgc ccggctacga 3180
ccacatcacc tccgccatcg gcgcggccaa catcggcgcc ctgggcaccg ccctgctgtg 3240
ctacgtgacg cccaaggagc acctgggcct gcccaaccgc gacgacgtga aggcgggcgt 3300
catcgcctac aagatcgccg cccacgcggc cgacctggcc aagcagcacc cccacgccca 3360
ggcgtgggac gacgcgctgt ccaaggcgcg cttcgagttc cgctggatgg accagttcgc 3420
gctgtccctg gaccccatga cggcgatgtc cttccacgac gagacgctgc ccgcggacgg 3480
cgcgaaggtc gcccacttct gctccatgtg cggccccaag ttctgctcca tgaagatcac 3540
ggaggacatc cgcaagtacg ccgaggagaa cggctacggc tccgccgagg aggccatccg 3600
ccagggcatg gacgccatgt ccgaggagtt caacatcgcc aagaagacga tctccggcga 3660
gcagcacggc gaggtcggcg gcgagatcta cctgcccgag tcctacgtca aggccgcgca 3720
gaagtgacaa ttggcagcag cagctcggat agtatcgaca cactctggac gctggtcgtg 3780
tgatggactg ttgccgccac acttgctgcc ttgacctgtg aatatccctg ccgcttttat 3840
caaacagcct cagtgtgttt gatcttgtgt gtacgcgctt ttgcgagttg ctagctgctt 3900
gtgctatttg cgaataccac ccccagcatc cccttccctc gtttcatatc gcttgcatcc 3960
caaccgcaac ttatctacgc tgtcctgcta tccctcagcg ctgctcctgc tcctgctcac 4020
tgcccctcgc acagccttgg tttgggctcc gcctgtattc tcctggtact gcaacctgta 4080
aaccagcact gcaatgctga tgcacgggaa gtagtgggat gggaacacaa atggaggatc 4140
ccgcgtctcg aacagagcgc gcagaggaac gctgaaggtc tcgcctctgt cgcacctcag 4200
cgcggcatac accacaataa ccacctgacg aatgcgcttg gttcttcgtc cattagcgaa 4260
gcgtccggtt cacacacgtg ccacgttggc gaggtggcag gtgacaatga tcggtggagc 4320
tgatggtcga aacgttcaca gcctagggat atcatagcga ctgctacccc ccgaccatgt 4380
gccgaggcag aaattatata caagaagcag atcgcaatta ggcacatcgc tttgcattat 4440
ccacacacta ttcatcgctg ctgcggcaag gctgcagagt gtatttttgt ggcccaggag 4500
ctgagtccga agtcgacgcg acgagcggcg caggatccga cccctagacg agctctgtca 4560
ttttccaagc acgcagctaa atgcgctgag accgggtcta aatcatccga aaagtgtcaa 4620
aatggccgat tgggttcgcc taggacaatg cgctgcggat tcgctcgagt ccgctgccgg 4680
ccaaaaggcg gtggtacagg aaggcgcacg gggccaaccc tgcgaagccg gggggcccgaa 4740
cgccgaccgc cggccttcga tctcgggtgt ccccctcgtc aatttcctct ctcgggtgca 4800
gccacgaaag tcgtgacgca ggtcacgaaa tccggttacg aaaaacgcag gtcttcgcaa 4860
aaacgtgagg gtttcgcgtc tcgccctagc tattcgtatc gccgggtcag acccacgtgc 4920
agaaaagccc ttgaataacc cgggaccgtg gttaccgcgc cgcctgcacc agggggctta 4980

```
tataagccca caccacacct gtctcaccac gcatttctcc aactcgcgac ttttcggaag   5040
aaattgttat ccacctagta tagactgcca cctgcaggac cttgtgtctt gcagtttgta   5100
ttggtcccgg ccgtcgagct cgacagatct gggctagggt tggcctggcc gctcggcact   5160
cccctttagc cgcgcgcatc cgcgttccag aggtgcgatt cggtgtgtgg agcattgtca   5220
tgcgcttgtg gggtcgttc cgtgcgcggc gggtccgcca tgggcgccga cctgggccct    5280
agggtttgtt ttcgggccaa gcgagcccct ctcacctcgt cgcccccccg cattccctct   5340
ctcttgcagc cactagtatg gccaccgcat ccactttctc ggcgttcaat gcccgctgcg   5400
gcgacctgcg tcgctcggcg ggctccgggc cccggcgccc agcgaggccc ctccccgtgc   5460
gcgggcgcgc cgccgccgcc gccgacgcca accccgcccg ccccgagcgc cgcgtggtga   5520
tcaccggcca gggcgtggtg acctccctgg gccagaccat cgagcagttc tactcctccc   5580
tgctggaggg cgtgtccggc atctcccaga tccagaagtt cgacaccacc ggctacacca   5640
ccaccatcgc cggcgagatc aagtccctgc agctggaccc ctacgtgccc aagcgctggg   5700
ccaagcgcgt ggacgacgtg atcaagtacg tgtacatcgc cggcaagcag gccctggagt   5760
ccgccggcct gcccatcgag gccgccggcc tggccggcgc cggcctggac cccgccctgt   5820
gcggcgtgct gatcggcacc gccatggccg gcatgacctc cttcgccgcc ggcgtggagg   5880
ccctgacccg cggcggcgtg cgcaagatga acccctctg catccccttc tccatctcca    5940
acatgggcgg cgccatgctg gccatggaca tcggcttcat gggccccaac tactccatct   6000
ccaccgcctg cgccaccggc aactactgca tcctgggcgc cgccgaccac atccgccgcg   6060
gcgacgccaa cgtgatgctg gccggcggcg ccgacgccgc catcatcccc tccggcatcg   6120
gcggcttcat cgcctgcaag gccctgtcca agcgcaacga cgagcccgag cgcgcctccc   6180
gcccctggga cgccgaccgc gacggcttcg tgatgggcga gggcgccggc gtgctggtgc   6240
tggaggagct ggagcacgcc aagcgccgcg gcgccaccat cctggccgag ctggtgggcg   6300
gcgccgccac ctccgacgcc caccacatga ccgagcccga cccccagggc cgcggcgtgc   6360
gcctgtgcct ggagcgcgcc ctggagcgcg cccgcctggc ccccgagcgc gtgggctacg   6420
tgaacgccca cggcacctcc acccccgccg gcgacgtggc cgagtaccgc gccatccgcg   6480
ccgtgatccc ccaggactcc ctgcgcatca actccaccaa gtccatgatc ggccacctgc   6540
tgggcggcgc cggcgccgtg gaggccgtgg ccgccatcca ggccctgcgc accggctggc   6600
tgcaccccaa cctgaacctg gagaaccccg cccccggcgt ggaccccgtg gtgctggtgg   6660
gcccccgcaa ggagcgcgcc gaggacctgg acgtggtgct gtccaactcc ttcggcttcg   6720
gcggccacaa ctcctgcgtg atcttccgca agtacgacga gatggactac aaggaccacg   6780
acggcgacta caaggaccac gacatcgact acaaggacga cgacgacaag tgaatcgata   6840
gatctcttaa ggcagcagca gctcggatag tatcgacaca ctctggacgc tggtcgtgtg   6900
atggactgtt gccgccacac ttgctgcctt gacctgtgaa tatccctgcc gcttttatca   6960
aacagcctca gtgtgtttga tcttgtgtgt acgcgctttt gcgagttgct agctgcttgt   7020
gctatttgcg aataccaccc ccagcatccc cttccctcgt ttcatatcgc ttgcatccca   7080
accgcaactt atctacgctg tcctgctatc cctcagcgct gctcctgctc ctgctcactg   7140
cccctcgcac agccttggtt tgggctccgc ctgtattctc ctggtactgc aacctgtaaa   7200
ccagcactgc aatgctgatg cacgggaagt agtgggatgg gaacacaaat ggaaagctta   7260
attaagagct cttgttttcc agaaggagtt gctccttgag cctttcattc tcagcctcga   7320
taacctccaa agccgctcta attgtggagg gggttcgaag acagggtggt tggctggatg   7380
```

gggaaacgct ggtcgcggga ttcgatcctg ctgcttatat cctccctgga agcacaccca 7440
cgactctgaa gaagaaaacg tgcacacaca caacccaacc ggccgaatat ttgcttcctt 7500
atcccgggtc caagagagac tgcgatgccc ccctcaatca gcatcctcct ccctgccgct 7560
tcaatcttcc ctgcttgcct gcgcccgcgg tgcgccgtct gcccgcccag tcagtcactc 7620
ctgcacaggc cccttgtgcg cagtgctcct gtacccttta ccgctccttc cattctgcga 7680
ggccccctat tgaatgtatt cgttgcctgt gtggccaagc gggctgctgg gcgcgccgcc 7740
gtcgggcagt gctcggcgac tttggcggaa gccgattgtt cttctgtaag ccacgcgctt 7800
gctgctttgg gaagagaagg gggggggtac tgaatggatg aggaggagaa ggaggggtat 7860
tggtattatc tgagttgggt gaagagc 7887

<210> SEQ ID NO 120
<211> LENGTH: 7072
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
gctcttcgga gtcactgtgc cactgagttc gactggtagc tgaatggagt cgctgctcca 60
ctaaacgaat tgtcagcacc gccagccggc cgaggacccg agtcatagcg agggtagtag 120
cgcgccatgg caccgaccag cctgcttgcc agtactggcg tctcttccgc ttctctgtgg 180
tcctctgcgc gctccagcgc gtgcgctttt ccggtggatc atgcggtccg tggcgcaccg 240
cagcggccgc tgcccatgca gcgccgctgc ttccgaacag tggcggtcag ggccgcaccc 300
gcggtagccg tccgtccgga acccgcccaa gagttttggg agcagcttga gccctgcaag 360
atggcggagg acaagcgcat cttcctggag gagcaccggt gcgtggaggt ccggggctga 420
ccggccgtcg cattcaacgt aatcaatcgc atgatgatca gaggacacga agtcttggtg 480
gcggtggcca gaaacactgt ccattgcaag ggcataggga tgcgttcctt cacctctcat 540
ttctcatttc tgaatccctc cctgctcact ctttctcctc ctccttcccg ttcacgcagc 600
attcggggta ccagtttagg tccagcgtcc gtgggggggg acgggctggg agcttgggcc 660
gggaagggca agacgatgca gtccctctgg ggagtcacag ccgactgtgt gtgttgcact 720
gtgcggcccg cagcactcac acgcaaaatg cctggccgac aggcaggccc tgtccagtgc 780
aacatccacg gtccctctca tcaggctcac cttgctcatt gacataacgg aatgcgtacc 840
gctctttcag atctgtccat ccagagaggg gagcaggctc cccaccgacg ctgtcaaact 900
tgcttcctgc ccaaccgaaa acattattgt ttgagggggg gggggggggg gcagattgca 960
tggcgggata tctcgtgagg aacatcactg ggacactgtg gaacacagtg agtgcagtat 1020
gcagagcatg tatgctaggg gtcagcgcag gaagggggcc tttcccagtc tcccatgcca 1080
ctgcaccgta tccacgactc accaggacca gcttcttgat cggcttccgc tcccgtggac 1140
accagtgtgt agcctctgga ctccaggtat gcgtgcaccg caaaggccag ccgatcgtgc 1200
cgattcctgg ggtggaggat atgagtcagc caacttgggg ctcagagtgc acactggggc 1260
acgatacgaa acaacatcta caccgtgtcc tccatgctga cacaccacag cttcgctcca 1320
cctgaatgtg ggcgcatggg cccgaatcac agccaatgtc gctgctgcca taatgtgatc 1380
cagaccctct ccgcccagat gccgagcgga tcgtgggcgc tgaatagatt cctgtttcga 1440
tcactgtttg ggtcctttcc ttttcgtctc ggatgcgcgt ctcgaaacag gctgcgtcgg 1500
gctttcggat cccttttgct ccctccgtca ccatcctgcg cgcgggcaag ttgcttgacc 1560
ctgggctgta ccagggttgg agggtattac cgcgtcaggc cattcccagc ccggattcaa 1620
ttcaaagtct gggccaccac cctccgccgc tctgtctgat cactccacat tcgtgcatac 1680
actacgttca agtcctgatc caggcgtgtc tcgggacaag gtgtgcttga gtttgaatct 1740
caaggaccca ctccagcaca gctgctggtt gaccccgccc tcgcaatcta gaatgttcgc 1800
gttctacttc ctgacggcct gcatctccct gaagggcgtg ttcggcgtct ccccctccta 1860
caacggcctg ggcctgacgc cccagatggg ctgggacaac tggaacacgt tcgcctgcga 1920
cgtctccgag cagctgctgc tggacacggc cgaccgcatc tccgacctgg gcctgaagga 1980
catgggctac aagtacatca tcctggacga ctgctggtcc tccggccgcg actccgacgg 2040
cttcctggtc gccgacgagc agaagttccc caacggcatg ggccacgtcg ccgaccacct 2100
gcacaacaac tccttcctgt tcggcatgta ctcctccgcg ggcgagtaca cgtgcgccgg 2160
ctaccccggc tccctgggcc gcgaggagga ggacgcccag ttcttcgcga acaaccgcgt 2220
ggactacctg aagtacgaca actgctacaa caagggccag ttcggcacgc ccgagatctc 2280
ctaccaccgc tacaaggcca tgtccgacgc cctgaacaag acgggccgcc ccatcttcta 2340
ctccctgtgc aactggggcc aggacctgac cttctactgg ggctccggca tcgcgaactc 2400
ctggcgcatg tccggcgacg tcacggcgga gttcacgcgc cccgactccc gctgcccctg 2460
cgacggcgac gagtacgact gcaagtacgc cggcttccac tgctccatca tgaacatcct 2520
gaacaaggcc gcccccatgg gccagaacgc gggcgtcggc ggctggaacg acctggacaa 2580
cctggaggtc ggcgtcggca acctgacgga cgacgaggag aaggcgcact tctccatgtg 2640
ggccatggtg aagtcccccc tgatcatcgg cgcgaacgtg aacaacctga aggcctcctc 2700
ctactccatc tactcccagg cgtccgtcat cgccatcaac caggactcca acggcatccc 2760
cgccacgcgc gtctggcgct actacgtgtc cgacacggac gagtacggcc agggcgagat 2820
ccagatgtgg tccggccccc tggacaacgg cgaccaggtc gtggcgctgc tgaacggcgg 2880
ctccgtgtcc cgccccatga acacgaccct ggaggagatc ttcttcgact ccaacctggg 2940
ctccaagaag ctgacctcca cctgggacat ctacgacctg tgggcgaacc gcgtcgacaa 3000
ctccacggcg tccgccatcc tgggccgcaa caagaccgcc accggcatcc tgtacaacgc 3060
caccgagcag tcctacaagg acggcctgtc caagaacgac acccgcctgt tcggccagaa 3120
gatcggctcc ctgtccccca acgcgatcct gaacacgacc gtccccgccc acggcatcgc 3180
gttctaccgc ctgcgcccct cctcctgaca attggcagca gcagctcgga tagtatcgac 3240
acactctgga cgctggtcgt gtgatggact gttgccgcca cacttgctgc cttgacctgt 3300
gaatatccct gccgctttta tcaaacagcc tcagtgtgtt tgatcttgtg tgtacgcgct 3360
tttgcgagtt gctagctgct tgtgctattt gcgaatacca cccccagcat ccccttccct 3420
cgtttcatat cgcttgcatc ccaaccgcaa cttatctacg ctgtcctgct atccctcagc 3480
gctgctcctg ctcctgctca ctgcccctcg cacagccttg gtttgggctc cgcctgtatt 3540
ctcctggtac tgcaacctgt aaaccagcac tgcaatgctg atgcacggga agtagtggga 3600
tgggaacaca aatggaggat cccgcgtctc gaacagagcg cgcagaggaa cgctgaaggt 3660
ctcgcctctg tcgcacctca gcgcggcata caccacaata accacctgac gaatgcgctt 3720
ggttcttcgt ccattagcga agcgtccggt tcacacacgt gccacgttgg cgaggtggca 3780
ggtgacaatg atcggtggag ctgatggtcg aaacgttcac agcctaggga tatcgaattc 3840

-continued ggccgacagg acgcgcgtca aaggtgctgg tcgtgtatgc cctggccggc aggtcgttgc 3900
tgctgctggt tagtgattcc gcaaccctga ttttggcgtc ttattttggc gtggcaaacg 3960
ctggcgcccg cgagccgggc cggcggcgat gcggtgcccc acggctgccg gaatccaagg 4020
gaggcaagag cgcccgggtc agttgaaggg ctttacgcgc aaggtacagc cgctcctgca 4080
aggctgcgtg gtggaattgg acgtgcaggt cctgctgaag ttcctccacc gcctcaccag 4140
cggacaaagc accggtgtat caggtccgtg tcatccactc taaagaactc gactacgacc 4200
tactgatggc cctagattct tcatcaaaaa cgcctgagac acttgcccag gattgaaact 4260
ccctgaaggg accaccaggg gccctgagtt gttccttccc cccgtggcga gctgccagcc 4320
aggctgtacc tgtgatcgag gctggcggga aaataggctt cgtgtgctca ggtcatggga 4380
ggtgcaggac agctcatgaa acgccaacaa tcgcacaatt catgtcaagc taatcagcta 4440
tttcctcttc acgagctgta attgtcccaa aattctggtc taccgggggt gatccttcgt 4500
gtacgggccc ttccctcaac cctaggtatg cgcgcatgcg gtcgccgcgc aactcgcgcg 4560
agggccgagg gtttgggacg ggccgtcccg aaatgcagtt gcacccggat gcgtggcacc 4620
ttttttgcga taatttatgc aatggactgc tctgcaaaat tctggctctg tcgccaaccc 4680
taggatcagc ggcgtaggat ttcgtaatca ttcgtcctga tggggagcta ccgactaccc 4740
taatatcagc ccgactgcct gacgccagcg tccacttttg tgcacacatt ccattcgtgc 4800
ccaagacatt tcattgtggt gcgaagcgtc cccagttacg ctcacctgtt tcccgacctc 4860
cttactgttc tgtcgacaga gcgggcccac aggccggtcg cagccactag tatggccatc 4920
aagaccaacc gccagcccgt ggagaagccc ccttcacca tcggcaccct gcgcaaggcc 4980
atccccgccc actgcttcga gcgctccgcc ctgcgctcct ccatgtacct ggccttcgac 5040
atcgccgtga tgtccctgct gtacgtggcc tccacctaca tcgaccccgc ccccgtgccc 5100
acctgggtga agtacggcgt gatgtggccc ctgtactggt tcttccaggg cgccttcggc 5160
accggcgtgt gggtgtgcgc ccacgagtgc ggccaccagg ccttctcctc ctcccaggcc 5220
atcaacgacg gcgtgggcct ggtgttccac tccctgctgc tggtgcccta ctactcctgg 5280
aagcactccc accgccgcca ccactccaac accggctgcc tggacaagga cgaggtgttc 5340
gtgccccccc accgcgccgt ggcccacgag ggcctggagt gggaggagtg gctgcccatc 5400
cgcatgggca aggtgctggt gaccctgacc ctgggctggc ccctgtacct gatgttcaac 5460
gtggcctccc gcccctaccc ccgcttcgcc aaccacttcg acccctggtc ccccatcttc 5520
tccaagcgcg agcgcatcga ggtggtgatc tccgacctgg ccctggtggc cgtgctgtcc 5580
ggcctgtccg tgctgggccg caccatgggc tgggcctggc tggtgaagac ctacgtggtg 5640
ccctacctga tcgtgaacat gtggctggtg ctgatcaccc tgctgcagca cacccacccc 5700
gccctgcccc actacttcga gaaggactgg gactggctgc gcggcgccat ggccaccgtg 5760
gaccgctcca tgggcccccc cttcatggac aacatcctgc accacatctc cgacacccac 5820
gtgctgcacc acctgttctc caccatcccc cactaccacg ccgaggaggc ctccgccgcc 5880
atccgcccca tcctgggcaa gtactaccag tccgactccc gctgggtggg ccgcgccctg 5940
tgggaggact ggcgcgactg ccgctacgtg gtgcccgacg cccccgagga cgactccgcc 6000
ctgtggttcc acaagtagat cgatagatct cttaaggcag cagcagctcg gatagtatcg 6060
acacactctg gacgctggtc gtgtgatgga ctgttgccgc cacacttgct gccttgacct 6120
gtgaatatcc ctgccgcttt tatcaaacag cctcagtgtg tttgatcttg tgtgtacgcg 6180
cttttgcgag ttgctagctg cttgtgctat ttgcgaatac cacccccagc atccccttcc 6240
ctcgtttcat atcgcttgca tcccaaccgc aacttatcta cgctgtcctg ctatccctca 6300
gcgctgctcc tgctcctgct cactgcccct cgcacagcct tggtttgggc tccgcctgta 6360
ttctcctggt actgcaacct gtaaaccagc actgcaatgc tgatgcacgg gaagtagtgg 6420
gatgggaaca caaatggaaa gcttaattaa gagctcttgt tttccagaag gagttgctcc 6480
ttgagccttt cattctcagc ctcgataacc tccaaagccg ctctaattgt ggaggggggtt 6540 cgaagacagg gtggttggct ggatggggaa acgctggtcg cgggattcga tcctgctgct 6600
tatatcctcc ctggaagcac acccacgact ctgaagaaga aaacgtgcac acacacaacc 6660
caaccggccg aatatttgct tccttatccc gggtccaaga gagactgcga tgccccccctc 6720 aatcagcatc ctcctccctg ccgcttcaat cttccctgct tgcctgcgcc cgcggtgcgc 6780
cgtctgcccg cccagtcagt cactcctgca caggcccctt gtgcgcagtg ctcctgtacc 6840
ctttaccgct ccttccattc tgcgaggccc cctattgaat gtattcgttg cctgtgtggc 6900
caagcgggct gctgggcgcg ccgccgtcgg gcagtgctcg gcgactttgg cggaagccga 6960
ttgttcttct gtaagccacg cgcttgctgc tttgggaaga gaagggggggg ggtactgaat 7020 ggatgaggag gagaaggagg ggtattggta ttatctgagt tgggtgaaga gc 7072

<210> SEQ ID NO 121
<211> LENGTH: 8834
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gtttaaaccc ctcaactgcg acgctgggaa ccttctccgg gcaggcgatg tgcgtgggtt 60
tgcctccttg gcacggctct acaccttcga gtacgccatg aggcggtgat ggctgtggct 120
gtgccccact tcgtccaggg acggcaagtc catcatctgc atgcttggtg cgacgctaca 180
gcagtccctc tgcagcagag gagcacgact ttggccattt cacgcactcg agtgtacaca 240
attcattttt cttaaagtaa atgactgctg attgaccaga tgctgtaacg ctgatttcgc 300
tccagatcgc acagtcacag attgcgacca tgttgctgcg tctgaaaatc tggattccga 360
attcgaccct ggcgctccat ccatgcaaca gatggcgaca cttgttacaa ttcctgtcgc 420
ccatcggcat ggagcaggtc cacttagatc cccgatcacc cacgcgcatc tcgctaatag 480
tcattcattc gtgtcttcga tcaaagtcag gtgagtatgc atggatcttg gttgacgatg 540
cggtatgggt ttgcgccgct gactgcaggg tctgtccaag gcaagccaac ccagctcctc 600
tcctcgacaa tactctcgca gacaaagcca gccacttgcc atccagattg ccaataaact 660
caatcatggc ttctgtcatg ccatccatgg gtctgatgaa tggtcacgct cgtgtcctga 720
ccgttcccca gcctctggcg tcccctgccc cgcccaccag cccacgccgc gcggcagtcg 780
ctgccaaggc tgtctcggag gtaccctttc ttgcgctatg acacttccag caaaaggtag 840
ggcgggctgc gagacggctt cccggcgctg catgcaacac cgatgatgct tcgacccccc 900
gaagctcctt cggggctgca tgggcgctcc gatgccgctc cagggcgagc gctgtttaaa 960
tagccaggcc cccgattgca aagacattat agcgagctac caaagccata ttcaaacacc 1020
tagatcacta ccacttctac acaggccact cgagcttgtg atcgcactcc gctaaggggg 1080
cgcctcttcc tcttcgtttc agtcacaacc cgcaaactct agaatatcaa tgatcgagca 1140
ggacggcctc cacgccggct cccccgccgc ctgggtggag cgcctgttcg gctacgactg 1200

```
ggcccagcag accatcggct gctccgacgc cgccgtgttc cgcctgtccg cccagggccg   1260
ccccgtgctg ttcgtgaaga ccgacctgtc cggcgccctg aacgagctgc aggacgaggc   1320
cgcccgcctg tcctggctgg ccaccaccgg cgtgccctgc gccgccgtgc tggacgtggt   1380
gaccgaggcc ggccgcgact ggctgctgct gggcgaggtg cccggccagg acctgctgtc   1440
ctcccacctg gcccccgccg agaaggtgtc catcatggcc gacgccatgc gccgcctgca   1500
caccctggac cccgccacct gccccttcga ccaccaggcc aagcaccgca tcgagcgcgc   1560
ccgcacccgc atggaggccg gcctggtgga ccaggacgac ctggacgagg agcaccaggg   1620
cctggccccc gccgagctgt tcgcccgcct gaaggcccgc atgcccgacg gcgaggacct   1680
ggtggtgacc cacggcgacg cctgcctgcc caacatcatg gtggagaacg gccgcttctc   1740
cggcttcatc gactgcggcc gcctgggcgt ggccgaccgc taccaggaca tcgccctggc   1800
cacccgcgac atcgccgagg agctgggcgg cgagtgggcc gaccgcttcc tggtgctgta   1860
cggcatcgcc gcccccgact cccagcgcat cgccttctac cgcctgctgg acgagttctt   1920
ctgacaattg gcagcagcag ctcggatagt atcgacacac tctggacgct ggtcgtgtga   1980
tggactgttg ccgccacact tgctgccttg acctgtgaat atccctgccg cttttatcaa   2040
acagcctcag tgtgtttgat cttgtgtgta cgcgcttttg cgagttgcta gctgcttgtg   2100
ctatttgcga ataccacccc cagcatcccc ttccctcgtt tcatatcgct tgcatcccaa   2160
ccgcaactta tctacgctgt cctgctatcc ctcagcgctg ctcctgctcc tgctcactgc   2220
ccctcgcaca gccttggttt gggctccgcc tgtattctcc tggtactgca acctgtaaac   2280
cagcactgca atgctgatgc acgggaagta gtgggatggg aacacaaatg gaaagctgta   2340
tagggataag aattcggccg acaggacgcg cgtcaaaggt gctggtcgtg tatgccctgg   2400
ccggcaggtc gttgctgctg ctggttagtg attccgcaac cctgattttg gcgtcttatt   2460
ttggcgtggc aaacgctggc gcccgcgagc cgggccggcg gcgatgcggt gccccacggc   2520
tgccggaatc caagggaggc aagagcgccc gggtcagttg aagggcttta cgcgcaaggt   2580
acagccgctc ctgcaaggct gcgtggtgga attggacgtg caggtcctgc tgaagttcct   2640
ccaccgcctc accagcggac aaagcaccgg tgtatcaggt ccgtgtcatc cactctaaag   2700
aactcgacta cgacctactg atggccctag attcttcatc aaaaacgcct gagacacttg   2760
cccaggattg aaactccctg aagggaccac caggggccct gagttgttcc ttcccccgt    2820
ggcgagctgc cagccaggct gtacctgtga tcgaggctgg cgggaaaata ggcttcgtgt   2880
gctcaggtca tgggaggtgc aggacagctc atgaaacgcc aacaatcgca caattcatgt   2940
caagctaatc agctatttcc tcttcacgag ctgtaattgt cccaaaattc tggtctaccg   3000
ggggtgatcc ttcgtgtacg ggcccttccc tcaaccctag gtatgcgcgc atgcggtcgc   3060
cgcgcaactc gcgcgagggc cgagggtttg ggacgggccg tcccgaaatg cagttgcacc   3120
cggatgcgtg gcaccttttt tgcgataatt tatgcaatgg actgctctgc aaaattctgg   3180
ctctgtcgcc aaccctagga tcagcggcgt aggatttcgt aatcattcgt cctgatgggg   3240
agctaccgac taccctaata tcagcccgac tgcctgacgc cagcgtccac ttttgtgcac   3300
acattccatt cgtgcccaag acatttcatt gtggtgcgaa gcgtccccag ttacgctcac   3360
ctgtttcccg acctccttac tgttctgtcg acagagcggg cccacaggcc ggtcgcagcc   3420
actagtgcga ccgccagctg catggtggcg tcgcccttct gcacctggct ggtcgccgcg   3480
tgcatgccca cctccagcga caacgacccc cgctcgctgt cccacaagcg cctgcgcctg   3540
```

agccgccgcc gccgcaccct gagctcgcac tgctccctgc gcggcagcac cttccagtgc 3600
ctggacccct gcaaccagca gcgcttcctg ggcgacaacg gcttcgcgtc gctgttcggc 3660
tccaagcccc tgcgcagcaa ccgcggccac ctgcgcctgg gccgcacctc gcactccggc 3720
gaggtgatgg ccgtcgcgat gcagcccgcc caggaggtga gcaccaacaa gaagcccgcg 3780
accaagcagc gccgcgtggt cgtgaccggc atgggcgtcg tgaccccccct gggccacgac 3840 cccgacgtgt attataacaa cctgctggac ggcatctcgg gcatctccga gatcgagaac 3900
ttcgactgca gccagttccc cacccgcatc gccggcgaga tcaagtcgtt ctccaccgac 3960
ggctgggtcg cgcccaagtt cagcgagcgc atggacaagt tcatgctgta tatgctgacc 4020
gccggcaaga aggcgctggc cgacggcggc atcaccgagg acgcgatgaa ggagctgaac 4080
aagcgcaagt gcggcgtgct gatcggctcg ggcctgggcg gcatgaaggt cttctccgac 4140
agcatcgagg ccctgcgcac ctcgtataag aagatctccc ccttctgcgt gcccttcagc 4200
accaccaaca tgggctcggc gatcctggcg atggacctgg gctggatggg ccccaactat 4260
tccatcagca ccgcgtgcgc cacctcgaac ttctgcatcc tgaacgcggc caaccacatc 4320
atcaagggcg aggcggacat gatgctgtgc ggcggctccg acgccgcggt gctgcccgtc 4380
ggcctgggcg gcttcgtggc ctgccgcgcg ctgagccagc gcaacaacga ccccaccaag 4440
gcctcgcgcc cctgggactc caaccgcgac ggcttcgtca tgggcgaggg cgcgggcgtg 4500
ctgctgctgg aggagctgga gcacgccaag aagcgcggcg cgaccatcta tgccgagttc 4560
ctgggcggca gcttcacctg cgacgcgtat cacatgaccg agccccaccc cgagggcgcc 4620
ggcgtcatcc tgtgcatcga gaaggcgctg gcccagtcgg gcgtgtcccg cgaggacgtg 4680
aactatatca acgcgcacgc caccagcacc cccgcgggcg acatcaagga gtatcaggcc 4740
ctggcgcact gcttcggcca gaactcggag ctgcgcgtca actccaccaa gagcatgatc 4800
ggccacctgc tgggcggcgc cggcggcgtg gaggcggtcg ccgtggtcca ggcgatccgc 4860
accggctgga tccaccccaa catcaacctg gaggaccccg acgagggcgt ggacgccaag 4920
ctgctggtcg gccccaagaa ggagaagctg aaggtgaagg tcggcctgtc gaactccttc 4980
ggcttcggcg gccacaacag ctcgatcctg ttcgcgccct gcaactgact cgaggcagca 5040
gcagctcgga tagtatcgac acactctgga cgctggtcgt gtgatggact gttgccgcca 5100
cacttgctgc cttgacctgt gaatatccct gccgctttta tcaaacagcc tcagtgtgtt 5160
tgatcttgtg tgtacgcgct tttgcgagtt gctagctgct tgtgctattt gcgaatacca 5220
cccccagcat ccccttccct cgtttcatat cgcttgcatc ccaaccgcaa cttatctacg 5280
ctgtcctgct atccctcagc gctgctcctg ctcctgctca ctgcccctcg cacagccttg 5340
gtttgggctc cgcctgtatt ctcctggtac tgcaacctgt aaaccagcac tgcaatgctg 5400
atgcacggga agtagtggga tgggaacaca aatggaaagc ttcacatacg taggccgaca 5460
ggacgcgcgt caaaggtgct ggtcgtgtat gccctggccg gcaggtcgtt gctgctgctg 5520
gttagtgatt ccgcaaccct gattttggcg tcttattttg gcgtggcaaa cgctggcgcc 5580
cgcgagccgg gccggcggcg atgcggtgcc ccacggctgc cggaatccaa gggaggcaag 5640
agcgcccggg tcagttgaag ggctttacgc gcaaggtaca gccgctcctg caaggctgcg 5700
tggtggaatt ggacgtgcag gtcctgctga agttcctcca ccgcctcacc agcggacaaa 5760
gcaccggtgt atcaggtccg tgtcatccac tctaaagaac tcgactacga cctactgatg 5820
gccctagatt cttcatcaaa aacgcctgag acacttgccc aggattgaaa ctccctgaag 5880
ggaccaccag gggccctgag ttgttccttc cccccgtggc gagctgccag ccaggctgta 5940
cctgtgatcg aggctggcgg gaaaataggc ttcgtgtgct caggtcatgg gaggtgcagg 6000
acagctcatg aaacgccaac aatcgcacaa ttcatgtcaa gctaatcagc tatttcctct 6060
tcacgagctg taattgtccc aaaattctgg tctaccgggg gtgatccttc gtgtacgggc 6120
ccttccctca accctaggta tgcgcgcatg cggtcgccgc gcaactcgcg cgagggccga 6180
gggtttggga cgggccgtcc cgaaatgcag ttgcacccgg atgcgtggca ccttttttgc 6240
gataatttat gcaatggact gctctgcaaa attctggctc tgtcgccaac cctaggatca 6300
gcggcgtagg atttcgtaat cattcgtcct gatggggagc taccgactac cctaatatca 6360
gcccgactgc ctgacgccag cgtccacttt tgtgcacaca ttccattcgt gcccaagaca 6420
tttcattgtg gtgcgaagcg tccccagtta cgctcacctg tttcccgacc tccttactgt 6480
tctgtcgaca gagcgggccc acaggccggt cgcagccact agtatggcta tcaagacgaa 6540
caggcagcct gtggagaagc ctccgttcac gatcgggacg ctgcgcaagg ccatccccgc 6600
gcactgtttc gagcgctcgg cgcttcgtgg gcgcgcccag ctgcccgact ggagccgcct 6660
gctgaccgcc atcaccaccg tgttcgtgaa gtccaagcgc cccgacatgc acgaccgcaa 6720
gtccaagcgc cccgacatgc tggtggacag cttcggcctg gagtccaccg tgcaggacgg 6780
cctggtgttc cgccagtcct tctccatccg ctcctacgag atcggcaccg accgcaccgc 6840
cagcatcgag accctgatga accacctgca ggagacctcc ctgaaccact gcaagagcac 6900
cggcatcctg ctggacggct tcggccgcac cctggagatg tgcaagcgcg acctgatctg 6960
ggtggtgatt aagatgcaga tcaaggtgaa ccgctacccc gcctggggcg acaccgtgga 7020
gatcaacacc cgcttcagcc gcctgggcaa gatcggcatg ggccgcgact ggctgatctc 7080
cgactgcaac accggcgaga tcctggtgcg cgccaccagc gcctacgcca tgatgaacca 7140
gaagacccgc cgcctgtcca agctgcccta cgaggtgcac caggagatcg tgcccctgtt 7200
cgtggacagc cccgtgatcg aggactccga cctgaaggtg cacaagttca aggtgaagac 7260
cggcgacagc atccagaagg gcctgacccc cggctggaac gacctggacg tgaaccagca 7320
cgtgtccaac gtgaagtaca tcggctggat cctggagagc atgcccaccg aggtgctgga 7380
gacccaggag ctgtgctccc tggccctgga gtaccgccgc gagtgcggcc gcgactccgt 7440
gctggagagc gtgaccgcca tggaccccag caaggtgggc gtgcgctccc agtaccagca 7500
cctgctgcgc ctggaggacg gcaccgccat cgtgaacggc gccaccgagt ggcgccccaa 7560
gaacgccggc gccaacggcg ccatctccac cggcaagacc agcaacggca actccgtgtc 7620
catggactac aaggaccacg acggcgacta caaggaccac gacatcgact acaaggacga 7680
cgacgacaag tgactcgagg cagcagcagc tcggatagta tcgacacact ctggacgctg 7740
gtcgtgtgat ggactgttgc cgccacactt gctgccttga cctgtgaata tccctgccgc 7800
ttttatcaaa cagcctcagt gtgtttgatc ttgtgtgtac gcgcttttgc gagttgctag 7860
ctgcttgtgc tatttgcgaa taccaccccc agcatcccct tccctcgttt catatcgctt 7920
gcatcccaac cgcaacttat ctacgctgtc ctgctatccc tcagcgctgc tcctgctcct 7980
gctcactgcc cctcgcacag ccttggtttg ggctccgcct gtattctcct ggtactgcaa 8040
cctgtaaacc agcactgcaa tgctgatgca cgggaagtag tgggatggga acacaaatgg 8100
aaagctgtag aattctccag agctccagcg ccatgccacg ccttttgatg gcttcaagta 8160
cgataacggt gttggattgt gcgtttgttg cgtagtgtgc atggcttaga ataatgcagt 8220
tggatttctt gctcacggca atgtcggctt gtccgcaggt tcaaccccat ttcggagtct 8280
caggtcagcc gcgcaatgac cagccgctac ttcaaggact tgcacgacaa cgccgaggtg 8340
agctatgttt aggccttgag tgaaaattgt cgtcgaagca tattcgcgct ccgcgatagc 8400
atccaagcaa aatgtcaagt gcgttccgat ttgcgtccgc aggtcgatgt tgtgatcgtc 8460
ggtgccggat ccgccggtct gtcctgcgct tacgagctga ccaagcaccc cgacgtccgg 8520
gtacgcgagc tgagattcga ttggacataa actgaaaatg aaatcttttg gagaaatgta 8580
agggtctcaa gcggtgctcg attgcaagaa attggtcgtc ccccactccg caggtcgcca 8640
tcatcgagca gggcgttgca cctggtggcg gcgcctggct ggggggacag ctgttctcgg 8700
ccatgtgtgt acgtagaagg gtggatttcg gatggtttcg ttgcacagct gtttgtcaat 8760
gatttgtctt agactattgc cgatgtttct aaatgtttta ggagctatga tatgtctgca 8820
ggcgactgaa gagc 8834

<210> SEQ ID NO 122
<211> LENGTH: 8329
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 122
gctcttcgct caccgcgtga attgctgtcc caaacgtaag catcatcgtg gctcggtcac 60
gcgatcctgg atccggggat cctagaccgc tggtggagag cgctgccgtc ggattggtgg 120
caagtaagat tgcgcaggtt ggcgaaggga gagaccaaaa ccggaggctg gaagcgggca 180
caacatcgta ttattgcgta tagtagagca gtggcagtcg catttcgagg tccgcaacgg 240
atctcgcaag ctcgctacgc tcacagtagg agaaagggga ccactgcccc tgccagaatg 300
gtcgcgaccc tctccctcgc cggccccgcc tgcaacacgc agtgcgtatc cggcaagcgg 360
gctgtcgcct tcaaccgccc ccatgttggc gtccgggctc gatcaggtgc gctgaggggg 420
gtttggtgtg cccgcgcctc tgggcccgtg tcggccgtgc ggacgtgggg ccctgggcag 480
tggatcagca gggtttgcgt gcaaatgcct ataccggcga ttgaatagcg atgaacggga 540
tacggttgcg ctcactccat gcccatgcga ccccgtttct gtccgccagc cgtggtcgcc 600
cgggctgcga agcgggaccc cacccagcgc attgtgatca ccggaatggg cgtggggtac 660
cctttcttgc gctatgacac ttccagcaaa aggtagggcg ggctgcgaga cggcttcccg 720
gcgctgcatg caacaccgat gatgcttcga ccccccgaag ctccttcggg gctgcatggg 780
cgctccgatg ccgctccagg gcgagcgctg tttaaatagc caggcccccg attgcaaaga 840
cattatagcg agctaccaaa gccatattca aacacctaga tcactaccac ttctacacag 900
gccactcgag cttgtgatcg cactccgcta agggggcgcc tcttcctctt cgtttcagtc 960
acaacccgca aactctagaa tatcaatgat cgagcaggac ggcctccacg ccggctcccc 1020
cgccgcctgg gtggagcgcc tgttcggcta cgactgggcc cagcagacca tcggctgctc 1080
cgacgccgcc gtgttccgcc tgtccgccca gggccgcccc gtgctgttcg tgaagaccga 1140
cctgtccggc gccctgaacg agctgcagga cgaggccgcc cgcctgtcct ggctggccac 1200
caccggcgtg ccctgcgccg ccgtgctgga cgtggtgacc gaggccggcc gcgactggct 1260
gctgctgggc gaggtgcccg gccaggacct gctgtcctcc cacctggccc ccgccgagaa 1320
ggtgtccatc atggccgacg ccatgcgccg cctgcacacc ctggaccccg ccacctgccc 1380
cttcgaccac caggccaagc accgcatcga gcgcgcccgc acccgcatgg aggccggcct 1440

-continued

```
ggtggaccag gacgacctgg acgaggagca ccagggcctg gcccccgccg agctgttcgc   1500
ccgcctgaag gcccgcatgc ccgacggcga ggacctggtg gtgacccacg gcgacgcctg   1560
cctgcccaac atcatggtgg agaacggccg cttctccggc ttcatcgact gcggccgcct   1620
gggcgtggcc gaccgctacc aggacatcgc cctggccacc cgcgacatcg ccgaggagct   1680
gggcggcgag tgggccgacc gcttcctggt gctgtacggc atcgccgccc ccgactccca   1740
gcgcatcgcc ttctaccgcc tgctggacga gttcttctga caattggcag cagcagctcg   1800
gatagtatcg acacactctg gacgctggtc gtgtgatgga ctgttgccgc cacacttgct   1860
gccttgacct gtgaatatcc ctgccgcttt tatcaaacag cctcagtgtg tttgatcttg   1920
tgtgtacgcg cttttgcgag ttgctagctg cttgtgctat ttgcgaatac caccccccagc   1980
atccccttcc ctcgtttcat atcgcttgca tcccaaccgc aacttatcta cgctgtcctg   2040
ctatccctca gcgctgctcc tgctcctgct cactgcccct cgcacagcct tggtttgggc   2100
tccgcctgta ttctcctggt actgcaacct gtaaaccagc actgcaatgc tgatgcacgg   2160
gaagtagtgg gatgggaaca caaatggaaa gctgtatagg gataaaagct tatagcgact   2220
gctacccccc gaccatgtgc cgaggcagaa attatataca agaagcagat cgcaattagg   2280
cacatcgctt tgcattatcc acacactatt catcgctgct gcggcaaggc tgcagagtgt   2340
atttttgtgg cccaggagct gagtccgaag tcgacgcgac gagcggcgca ggatccgacc   2400
cctagacgag cactgtcatt ttccaagcac gcagctaaat gcgctgagac cgggtctaaa   2460
tcatccgaaa agtgtcaaaa tggccgattg ggttcgccta ggacaatgcg ctgcggattc   2520
gctcgagtcc gctgccggcc aaaaggcggt ggtacaggaa ggcgcacggg gccaaccctg   2580
cgaagccggg ggcccgaacg ccgaccgccg gccttcgatc tcgggtgtcc ccctcgtcaa   2640
tttcctctct cgggtgcagc cacgaaagtc gtgacgcagg tcacgaaatc cggttacgaa   2700
aaacgcaggt cttcgcaaaa acgtgagggt ttcgcgtctc gccctagcta ttcgtatcgc   2760
cgggtcagac ccacgtgcag aaaagccctt gaataacccg ggaccgtggt taccgcgccg   2820
cctgcaccag gggcttata taagcccaca ccacacctgt ctcaccacgc atttctccaa   2880
ctcgcgactt ttcggaagaa attgttatcc acctagtata gactgccacc tgcaggacct   2940
tgtgtcttgc agtttgtatt ggtcccggcc gtcgagcacg acagatctgg gctagggttg   3000
gcctggccgc tcggcactcc cctttagccg cgcgcatccg cgttccagag gtgcgattcg   3060
gtgtgtggag cattgtcatg cgcttgtggg ggtcgttccg tgcgcggcgg gtccgccatg   3120
ggcgccgacc tgggccctag ggtttgtttt cgggccaagc gagcccctct cacctcgtcg   3180
ccccccccgca ttccctctct cttgcagcca ctagtatggc tatcaagacg aacaggcagc   3240
ctgtggagaa gcctccgttc acgatcggga cgctgcgcaa ggccatcccc gcgcactgtt   3300
tcgagcgctc ggcgcttcgt gggcgcgccc agctgcccga ctggagccgc ctgctgaccg   3360
ccatcaccac cgtgttcgtg aagtccaagc gccccgacat gcacgaccgc aagtccaagc   3420
gccccgacat gctggtggac agcttcggcc tggagtccac cgtgcaggac ggcctggtgt   3480
tccgccagtc cttctccatc cgctcctacg agatcggcac cgaccgcacc gccagcatcg   3540
agaccctgat gaaccacctg caggagacct ccctgaacca ctgcaagagc accggcatcc   3600
tgctggacgg cttcggccgc accctggaga tgtgcaagcg cgacctgatc tgggtggtga   3660
ttaagatgca gatcaaggtg aaccgctacc ccgcctgggg cgacaccgtg gagatcaaca   3720
cccgcttcag ccgcctgggc aagatcggca tgggccgcga ctggctgatc tccgactgca   3780
acaccggcga gatcctggtg cgcgccacca gcgcctacgc catgatgaac cagaagaccc   3840
```

gccgcctgtc caagctgccc tacgaggtgc accaggagat cgtgcccctg ttcgtggaca 3900
gccccgtgat cgaggactcc gacctgaagg tgcacaagtt caaggtgaag accggcgaca 3960
gcatccagaa gggcctgacc cccggctgga acgacctgga cgtgaaccag cacgtgtcca 4020
acgtgaagta catcggctgg atcctggaga gcatgcccac cgaggtgctg gagacccagg 4080
agctgtgctc cctggccctg gagtaccgcc gcgagtgcgg ccgcgactcc gtgctggaga 4140
gcgtgaccgc catggacccc agcaaggtgg gcgtgcgctc ccagtaccag cacctgctgc 4200
gcctggagga cggcaccgcc atcgtgaacg gcgccaccga gtggcgcccc aagaacgccg 4260
gcgccaacgg cgccatctcc accggcaaga ccagcaacgg caactccgtg tccatggact 4320
acaaggacca cgacggcgac tacaaggacc acgacatcga ctacaaggac gacgacgaca 4380
agtgactcga gagcgtccag cgtgtgggat gaagggtgcg atggaacggg gctgccgccc 4440
cccctctggg catctagctc tgcaccgcac gccaggaagc ccaagccagg ccccgtcaca 4500
ctccctcgct gaagtgttcc ccccctgccc cacactcatc caggtatcaa cgccatcatg 4560
ttctacgtcc ccgtcatctt caactccctg gggagcgggc gccgcgcgtc gctgctgaac 4620
accatcatca tcaacgccgt caactttgtt aattaagaat tcggccgaca ggacgcgcgt 4680
caaaggtgct ggtcgtgtat gccctggccg gcaggtcgtt gctgctgctg gttagtgatt 4740
ccgcaaccct gattttggcg tcttattttg gcgtggcaaa cgctggcgcc cgcgagccgg 4800
gccggcggcg atgcggtgcc ccacggctgc cggaatccaa gggaggcaag agcgcccggg 4860
tcagttgaag ggctttacgc gcaaggtaca gccgctcctg caaggctgcg tggtggaatt 4920
ggacgtgcag gtcctgctga agttcctcca ccgcctcacc agcggacaaa gcaccggtgt 4980
atcaggtccg tgtcatccac tctaaagaac tcgactacga cctactgatg gccctagatt 5040
cttcatcaaa aacgcctgag acacttgccc aggattgaaa ctccctgaag ggaccaccag 5100
gggccctgag ttgttccttc cccccgtggc gagctgccag ccaggctgta cctgtgatcg 5160
aggctggcgg gaaaataggc ttcgtgtgct caggtcatgg gaggtgcagg acagctcatg 5220
aaacgccaac aatcgcacaa ttcatgtcaa gctaatcagc tatttcctct tcacgagctg 5280
taattgtccc aaaattctgg tctaccgggg gtgatccttc gtgtacgggc ccttccctca 5340
accctaggta tgcgcgcatg cggtcgccgc gcaactcgcg cgagggccga gggtttggga 5400
cgggccgtcc cgaaatgcag ttgcacccgg atgcgtggca cctttttgc gataatttat 5460
gcaatggact gctctgcaaa attctggctc tgtcgccaac cctaggatca gcggcgtagg 5520
atttcgtaat cattcgtcct gatggggagc taccgactac cctaatatca gcccgactgc 5580
ctgacgccag cgtccacttt tgtgcacaca ttccattcgt gcccaagaca tttcattgtg 5640
gtgcgaagcg tccccagtta cgctcacctg tttcccgacc tccttactgt tctgtcgaca 5700
gagcgggccc acaggccggt cgcagcccat atggcttccg cggcattcac catgtcggcg 5760
tgccccgcga tgactggcag ggcccctggg gcacgtcgct ccggacggcc agtcgccacc 5820
cgcctgaggt acgtattcca gtgcctggtg gccagctgca tcgacccctg cgaccagtac 5880
cgcagcagcg ccagcctgag cttcctgggc gacaacggct tcgccagcct gttcggcagc 5940
aagcccttca tgagcaaccg cggccaccgc cgcctgcgcc gcgccagcca cagcggcgag 6000
gccatggccg tggccctgca gcccgcccag gaggccggca ccaagaagaa gcccgtgatc 6060
aagcagcgcc gcgtggtggt gaccggcatg ggcgtggtga cccccctggg ccacgagccc 6120
gacgtgttct acaacaacct gctggacggc gtgagcggca tcagcgagat cgagaccttc 6180

-continued

```
gactgcaccc agttccccac ccgcatcgcc ggcgagatca agagcttcag caccgacggc   6240
tgggtggccc ccaagctgag caagcgcatg gacaagttca tgctgtacct gctgaccgcc   6300
ggcaagaagg ccctggccga cggcggcatc accgacgagg tgatgaagga gctggacaag   6360
cgcaagtgcg gcgtgctgat cggcagcggc atgggcggca tgaaggtgtt caacgacgcc   6420
atcgaggccc tgcgcgtgag ctacaagaag atgaacccct tctgcgtgcc cttcgccacc   6480
accaacatgg gcagcgccat gctggccatg gacctgggct ggatgggccc caactacagc   6540
atcagcaccg cctgcgccac cagcaacttc tgcatcctga acgccgccaa ccacatcatc   6600
cgcggcgagg ccgacatgat gctgtgcggc ggcagcgacg ccgtgatcat ccccatcggc   6660
ctgggcggct tcgtggcctg ccgcgccctg agccagcgca acagcgaccc caccaaggcc   6720
agccgcccct gggacagcaa ccgcgacggc ttcgtgatgg gcgagggcgc cggcgtgctg   6780
ctgctggagg agctggagca cgccaagaag cgcggcgcca ccatctacgc cgagttcctg   6840
ggcggcagct tcacctgcga cgcctaccac atgaccgagc cccaccccga gggcgccggc   6900
gtgatcctgt gcatcgagaa ggccctggcc caggccggcg tgagcaagga ggacgtgaac   6960
tacatcaacg cccacgccac cagcaccagc gccggcgaca tcaaggagta ccaggccctg   7020
gcccgctgct tcggccagaa cagcgagctg cgcgtgaaca gcaccaagag catgatcggc   7080
cacctgctgg gcgccgccgg cggcgtggag gccgtgaccg tggtgcaggc catccgcacc   7140
ggctggattc accccaacct gaacctggag gaccccgaca aggccgtgga cgccaagctg   7200
ctggtgggcc ccaagaagga gcgcctgaac gtgaaggtgg gcctgagcaa cagcttcggc   7260
ttcggcggcc acaacagcag catcctgttc gccccctgca acgtgtgact cgaggcagca   7320
gcagctcgga tagtatcgac acactctgga cgctggtcgt gtgatggact gttgccgcca   7380
cacttgctgc cttgacctgt gaatatccct gccgctttta tcaaacagcc tcagtgtgtt   7440
tgatcttgtg tgtacgcgct tttgcgagtt gctagctgct tgtgctattt gcgaatacca   7500
cccccagcat ccccttccct cgtttcatat cgcttgcatc ccaaccgcaa cttatctacg   7560
ctgtcctgct atccctcagc gctgctcctg ctcctgctca ctgcccctcg cacagccttg   7620
gtttgggctc cgcctgtatt ctcctggtac tgcaacctgt aaaccagcac tgcaatgctg   7680
atgcacggga agtagtggga tgggaacaca aatggaaagc ttgagctcca cctgcatccg   7740
cctggcgctc gaggacgccg gcgtctcgcc cgacgaggtc aactacgtca acgcgcacgc   7800
cacctccacc ctggtgggcg acaaggccga ggtgcgcgcg gtcaagtcgg tctttggcga   7860
catgaagggc atcaagatga acgccaccaa gtccatgatc gggcactgcc tgggcgccgc   7920
cggcggcatg gaggccgtcg ccacgctcat ggccatccgc accggctggg tgcaccccac   7980
catcaaccac gacaacccca tcgccgaggt cgacggcctg gacgtcgtcg ccaacgccaa   8040
ggcccagcac aaaatcaacg tcgccatctc caactccttc ggcttcggcg ggcacaactc   8100
cgtcgtcgcc tttgcgccct tccgcgagta ggcggagcga gcgcgcttgg ctgaggaggg   8160
aggcggggtg cgagcccttt ggctgcgcgc gatactctcc ccgcacgagc agactccacg   8220
cgcctgaatc tacttgtcaa cgagcaaccg tgtgttttgt ccgtggccat tcttattatt   8280
tctccgactg tggccgtact ctgtttggct gtgcaagcac cgaagagcc               8329
```

<210> SEQ ID NO 123
<211> LENGTH: 6750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
gaagagcgcc caatgtttaa acagcccgca ccctcgttga tctgggagcc ctgcgcagcc     60
ccttaaatca tctcagtcag gtttctgtgt tcaactgagc ctaaagggct ttcgtcatgc    120
gcacgagcac acgtatatcg gccacgcagt ttctcaaaag cggtagaaca gttcgcgagc    180
cctcgtaggt cgaaaacttg cgccagtact attaaattaa attaattgat cgaacgagac    240
gcgaaacttt tgcagaatgc caccgagttt gcccagagaa tgggagtggc gccattcacc    300
atccgcctgt gcccggcttg attcgccgag acgatggacg gcgagaccag ggagcggctt    360
gcgagccccg agccggtagc aggaacaatg atcgacaatc ttcctgtcca attactggca    420
accattagaa agagccggag cgcgttgaaa gtctgcaatc gagtaatttt tcgatacgtc    480
gggcctgctg aaccctaagg ctccggactt tgtttaaggc gatccaagat gcacgcggcc    540
ccaggcacgt atctcaagca caaaccccag ccttagtttc gagactttgg gagatagcga    600
ccgatatcta gtttggcatt ttgtatatta attacctcaa gcaatggagc gctctgatgc    660
ggtgcagcgt cggctgcagc acctggcagt ggcgctaggg tcgccctatc gctcggaacc    720
tggtcagctg gctcccgcct cctgctcagc ctcttccggt accgcggtga gaatcgaaaa    780
tgcatcgttt ctaggttcgg agacggtcaa ttccctgctc cggcgaatct gtcggtcaag    840
ctggccagtg gacaatgttg ctatggcagc ccgcgcacat gggcctcccg acgcggccat    900
caggagccca aacagcgtgt cagggtatgt gaaactcaag aggtccctgc tgggcactcc    960
ggccccactc cgggggcggg acgccaggca ttcgcggtcg gtcccgcgcg acgagcgaaa   1020
tgatgattcg gttacgagac caggacgtcg tcgaggtcga gaggcagcct cggacacgtc   1080
tcgctagggc aacgccccga gtccccgcga gggccgtaaa cattgtttct gggtgtcgga   1140
gtgggcattt tgggcccgat ccaatcgcct catgccgctc tcgtctggtc ctcacgttcg   1200
cgtacggcct ggatcccgga aagggcggat gcacgtggtg ttgccccgcc attggcgccc   1260
acgtttcaaa gtccccggcc agaaatgcac aggaccggcc cggctcgcac aggccatgct   1320
gaacgcccag atttcgacag caacaccatc tagaataatc gcaaccatcc gcgttttgaa   1380
cgaaacgaaa cggcgctgtt tagcatgttt ccgacatcgt gggggccgaa gcatgctccg   1440
gggggaggaa agcgtggcac agcggtagcc cattctgtgc cacacgccga cgaggaccaa   1500
tccccggcat cagccttcat cgacggctgc gccgcacata taaagccgga cgcctaaccg   1560
gtttcgtggt tatgactagt atgttcgcgt tctacttcct gacggcctgc atctccctga   1620
agggcgtgtt cggcgtctcc ccctcctaca acggcctggg cctgacgccc cagatgggct   1680
gggacaactg gaacacgttc gcctgcgacg tctccgagca gctgctgctg gacacggccg   1740
accgcatctc cgacctgggc ctgaaggaca tgggctacaa gtacatcatc ctggacgact   1800
gctggtcctc cggccgcgac tccgacggct tcctggtcgc cgacgagcag aagttcccca   1860
acggcatggg ccacgtcgcc gaccacctgc acaacaactc cttcctgttc ggcatgtact   1920
cctccgcggg cgagtacacg tgcgccggct accccggctc cctgggccgc gaggaggagg   1980
acgcccagtt cttcgcgaac aaccgcgtgg actacctgaa gtacgacaac tgctacaaca   2040
agggccagtt cggcacgccc gagatctcct accaccgcta caaggccatg tccgacgccc   2100
tgaacaagac gggccgcccc atcttctact ccctgtgcaa ctggggccag gacctgacct   2160
tctactgggg ctccggcatc gcgaactcct ggcgcatgtc cggcgacgtc acggcggagt   2220
tcacgcgccc cgactcccgc tgcccctgcg acggcgacga gtacgactgc aagtacgccg   2280
```

```
gcttccactg ctccatcatg aacatcctga acaaggccgc ccccatgggc cagaacgcgg   2340
gcgtcggcgg ctggaacgac ctggacaacc tggaggtcgg cgtcggcaac ctgacggacg   2400
acgaggagaa ggcgcacttc tccatgtggg ccatggtgaa gtccccccctg atcatcggcg   2460
cgaacgtgaa caacctgaag gcctcctcct actccatcta ctcccaggcg tccgtcatcg   2520
ccatcaacca ggactccaac ggcatccccg ccacgcgcgt ctggcgctac tacgtgtccg   2580
acacggacga gtacggccag ggcgagatcc agatgtggtc cggcccccctg gacaacggcg   2640
accaggtcgt ggcgctgctg aacggcggct ccgtgtcccg ccccatgaac acgaccctgg   2700
aggagatctt cttcgactcc aacctgggct ccaagaagct gacctccacc tgggacatct   2760
acgacctgtg ggcgaaccgc gtcgacaact ccacggcgtc cgccatcctg ggccgcaaca   2820
agaccgccac cggcatcctg tacaacgcca ccgagcagtc ctacaaggac ggcctgtcca   2880
agaacgacac ccgcctgttc ggccagaaga tcggctccct gtcccccaac gcgatcctga   2940
acacgaccgt ccccgcccac ggcatcgcgt tctaccgcct gcgcccctcc tcctgatacg   3000
tactcgaggc agcagcagct cggatagtat cgacacactc tggacgctgg tcgtgtgatg   3060
gactgttgcc gccacacttg ctgccttgac ctgtgaatat ccctgccgct tttatcaaac   3120
agcctcagtg tgtttgatct tgtgtgtacg cgcttttgcg agttgctagc tgcttgtgct   3180
atttgcgaat accaccccca gcatcccctt ccctcgtttc atatcgcttg catcccaacc   3240
gcaacttatc tacgctgtcc tgctatccct cagcgctgct cctgctcctg ctcactgccc   3300
ctcgcacagc cttggtttgg gctccgcctg tattctcctg gtactgcaac ctgtaaacca   3360
gcactgcaat gctgatgcac gggaagtagt gggatgggaa cacaaatgga aagctgtaga   3420
attcatagcg actgctaccc cccgaccatg tgccgaggca gaaattatat acaagaagca   3480
gatcgcaatt aggcacatcg ctttgcatta tccacacact attcatcgct gctgcggcaa   3540
ggctgcagag tgtatttttg tggcccagga gctgagtccg aagtcgacgc gacgagcggc   3600
gcaggatccg accccctagac gagcactgtc attttccaag cacgcagcta aatgcgctga   3660
gaccgggtct aaatcatccg aaaagtgtca aaatggccga ttgggttcgc ctaggacaat   3720
gcgctgcgga ttcgctcgag tccgctgccg gccaaaaggc ggtggtacag gaaggcgcac   3780
ggggccaacc ctgcgaagcc gggggcccga acgccgaccg ccggccttcg atctcgggtg   3840
tcccccctcgt caatttcctc tctcgggtgc agccacgaaa gtcgtgacgc aggtcacgaa   3900
atccggttac gaaaaacgca ggtcttcgca aaaacgtgag ggtttcgcgt ctcgccctag   3960
ctattcgtat cgccgggtca gacccacgtg cagaaaagcc cttgaataac ccgggaccgt   4020
ggttaccgcg ccgcctgcac caggggggctt atataagccc acaccacacc tgtctcacca   4080
cgcatttctc caactcgcga cttttcggaa gaaattgtta tccacctagt atagactgcc   4140
acctgcagga ccttgtgtct tgcagtttgt attggtcccg gccgtcgagc acgacagatc   4200
tgggctaggg ttggcctggc cgctcggcac tcccctttag ccgcgcgcat ccgcgttcca   4260
gaggtgcgat tcggtgtgtg gagcattgtc atgcgcttgt gggggtcgtt ccgtgcgcgg   4320
cgggtccgcc atgggcgccg acctgggccc tagggtttgt tttcgggcca agcgagcccc   4380
tctcacctcg tcgccccccc gcattccctc tctcttgcag ccactagtaa caatggccac   4440
cgcatccact ttctcggcgt tcaatgcccg ctgcggcgac ctgcgtcgct cggcgggctc   4500
cgggccccgg cgcccagcga ggcccctccc cgtgcgcgct gccatcgcca gcgaggtccc   4560
cgtggccacc acctcccccc gggcgcaccc caaggcgaac ggcagcgcgg tgtcgctgaa   4620
```

-continued

```
gtcgggctcc ctggagaccc aggaggacaa gacgagcagc tcgtcccccc ccccccgcac   4680
gttcatcaac cagctgcccg tgtggagcat gctgctgtcg gcggtgacca cggtcttcgg   4740
cgtggccgag aagcagtggc ccatgctgga ccgcaagtcc aagcgccccg acatgctggt   4800
cgagcccctg ggcgtggacc gcatcgtcta cgacggcgtg agcttccgcc agtcgttctc   4860
catccgcagc tacgagatcg gcgccgaccg caccgcctcg atcgagacgc tgatgaacat   4920
gttccaggag acctccctga accactgcaa gatcatcggc ctgctgaacg acggcttcgg   4980
ccgcacgccc gagatgtgca agcgcgacct gatctgggtc gtgaccaaga tgcagatcga   5040
ggtgaaccgc taccccacgt ggggcgacac catcgaggtc aacacgtggg tgagcgcctc   5100
gggcaagcac ggcatgggcc gcgactggct gatctccgac tgccacaccg gcgagatcct   5160
gatccgcgcg acgagcgtct gggcgatgat gaaccagaag acccgccgcc tgtcgaagat   5220
cccctacgag gtgcgccagg agatcgagcc ccagttcgtc gactccgccc ccgtgatcgt   5280
ggacgaccgc aagttccaca agctggacct gaagacgggc gacagcatct gcaacggcct   5340
gacccccgc tggacggacc tggacgtgaa ccagcacgtc aacaacgtga agtacatcgg   5400
ctggatcctg cagtcggtcc ccaccgaggt gttcgagacg caggagctgt gcggcctgac   5460
cctggagtac cgccgcgagt gcggccgcga ctccgtgctg gagagcgtca cggccatgga   5520
cccctcgaag gagggcgacc gctccctgta ccagcacctg ctgcgcctgg aggacggcgc   5580
ggacatcgtg aagggccgca ccgagtggcg ccccaagaac gccggcgcca agggcgccat   5640
cctgacgggc aagaccagca acggcaactc gatctccatg gactacaagg accacgacgg   5700
cgactacaag gaccacgaca tcgactacaa ggacgacgac gacaagtgaa agcttgcagc   5760
agcagctcgg atagtatcga cacactctgg acgctggtcg tgtgatggac tgttgccgcc   5820
acacttgctg ccttgacctg tgaatatccc tgccgctttt atcaaacagc ctcagtgtgt   5880
ttgatcttgt gtgtacgcgc ttttgcgagt tgctagctgc ttgtgctatt tgcgaatacc   5940
acccccagca tccccttccc tcgtttcata tcgcttgcat cccaaccgca acttatctac   6000
gctgtcctgc tatccctcag cgctgctcct gctcctgctc actgcccctc gcacagcctt   6060
ggtttgggct cccgcctgta ttctcctggt actgcaacct gtaaaccagc actgcaatgc   6120
tgatgcacgg gaagtagtgg gatgggaaca caaatggaaa gctggagctc agcgtctgcg   6180
tgttgggagc tggagtcgtg ggcttgacga cggcgctgca gctgttgcag gatgtgcctg   6240
gcgtgcgcgt tcacgtcgtg gctgagaaat atggcgacga aacgttgacg gctggggccg   6300
gcgggctgtg gatgccatac gcattgggta cgcggccatt ggatgggatt gataggctta   6360
tggagggata atagagtttt tgccggatcc aacgcatgtg gatgcggtat cccggtgggc   6420
tgaaagtgtg gaaggatagt gcattggcta ttcacatgca ctgcccaccc cttttggcag   6480
gaaatgtgcc ggcatcgttg gtgcaccgat ggggaaaatc gacgttcgac cactacatga   6540
agatttatac gtctgaagat gcagcgactg cgggtgcgaa acggatgacg gtttggtcgt   6600
gtatgtcaca gcatgtgctg gatcttgcgg gctaactccc cctgccacgg cccattgcag   6660
gtgtcatgtt gactggaggg tacgaccttt cgtccgtcaa attcccagag gaggacccgc   6720
tctgggccga cattgtgccc actgaagagc                                    6750
```

<210> SEQ ID NO 124
<211> LENGTH: 6838
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124

```
gaagagcgcc caatgtttaa acagcccgca ccctcgttga tctgggagcc ctgcgcagcc     60
ccttaaatca tctcagtcag gtttctgtgt tcaactgagc ctaaagggct ttcgtcatgc    120
gcacgagcac acgtatatcg gccacgcagt ttctcaaaag cggtagaaca gttcgcgagc    180
cctcgtaggt cgaaaacttg cgccagtact attaaattaa attaattgat cgaacgagac    240
gcgaaacttt tgcagaatgc caccgagttt gcccagagaa tgggagtggc gccattcacc    300
atccgcctgt gcccggcttg attcgccgag acgatggacg gcgagaccag ggagcggctt    360
gcgagccccg agccggtagc aggaacaatg atcgacaatc ttcctgtcca attactggca    420
accattagaa agagccggag cgcgttgaaa gtctgcaatc gagtaatttt tcgatacgtc    480
gggcctgctg aaccctaagg ctccggactt tgtttaaggc gatccaagat gcacgcggcc    540
ccaggcacgt atctcaagca caaaccccag ccttagtttc gagactttgg gagatagcga    600
ccgatatcta gtttggcatt ttgtatatta attacctcaa gcaatggagc gctctgatgc    660
ggtgcagcgt cggctgcagc acctggcagt ggcgctaggg tcgccctatc gctcggaacc    720
tggtcagctg gctcccgcct cctgctcagc ctcttccggt accgcggtga gaatcgaaaa    780
tgcatcgttt ctaggttcgg agacggtcaa ttccctgctc cggcgaatct gtcggtcaag    840
ctggccagtg gacaatgttg ctatggcagc ccgcgcacat gggcctcccg acgcggccat    900
caggagccca aacagcgtgt cagggtatgt gaaactcaag aggtccctgc tgggcactcc    960
ggccccactc cgggggcggg acgccaggca ttcgcggtcg gtcccgcgcg acgagcgaaa   1020
tgatgattcg gttacgagac caggacgtcg tcgaggtcga gaggcagcct cggacacgtc   1080
tcgctagggc aacgccccga gtccccgcga gggccgtaaa cattgtttct gggtgtcgga   1140
gtgggcattt tgggcccgat ccaatcgcct catgccgctc tcgtctggtc ctcacgttcg   1200
cgtacggcct ggatcccgga aagggcggat gcacgtggtg ttgccccgcc attggcgccc   1260
acgtttcaaa gtccccggcc agaaatgcac aggaccggcc cggctcgcac aggccatgct   1320
gaacgcccag atttcgacag caacaccatc tagaataatc gcaaccatcc gcgttttgaa   1380
cgaaacgaaa cggcgctgtt tagcatgttt ccgacatcgt gggggccgaa gcatgctccg   1440
gggggaggaa agcgtggcac agcggtagcc cattctgtgc cacacgccga cgaggaccaa   1500
tccccggcat cagccttcat cgacggctgc gccgcacata taaagccgga cgcctaaccg   1560
gtttcgtggt tatgactagt atgttcgcgt tctacttcct gacggcctgc atctccctga   1620
agggcgtgtt cggcgtctcc ccctcctaca acggcctggg cctgacgccc cagatgggct   1680
gggacaactg gaacacgttc gcctgcgacg tctccgagca gctgctgctg gacacggccg   1740
accgcatctc cgacctgggc ctgaaggaca tgggctacaa gtacatcatc ctggacgact   1800
gctggtcctc cggccgcgac tccgacggct tcctggtcgc cgacgagcag aagttcccca   1860
acggcatggg ccacgtcgcc gaccacctgc acaacaactc cttcctgttc ggcatgtact   1920
cctccgcggg cgagtacacg tgcgccggct accccggctc cctgggccgc gaggaggagg   1980
acgcccagtt cttcgcgaac aaccgcgtgg actacctgaa gtacgacaac tgctacaaca   2040
agggccagtt cggcacgccc gagatctcct accaccgcta caaggccatg tccgacgccc   2100
tgaacaagac gggccgcccc atcttctact ccctgtgcaa ctggggccag gacctgacct   2160
tctactgggg ctccggcatc gcgaactcct ggcgcatgtc cggcgacgtc acggcggagt   2220
tcacgcgccc cgactcccgc tgcccctgcg acggcgacga gtacgactgc aagtacgccg   2280
```

-continued

```
gcttccactg ctccatcatg aacatcctga acaaggccgc ccccatgggc cagaacgcgg   2340
gcgtcggcgg ctggaacgac ctggacaacc tggaggtcgg cgtcggcaac ctgacggacg   2400
acgaggagaa ggcgcacttc tccatgtggg ccatggtgaa gtcccccctg atcatcggcg   2460
cgaacgtgaa caacctgaag gcctcctcct actccatcta ctcccaggcg tccgtcatcg   2520
ccatcaacca ggactccaac ggcatccccg ccacgcgcgt ctggcgctac tacgtgtccg   2580
acacggacga gtacggccag ggcgagatcc agatgtggtc cggcccccctg gacaacggcg   2640
accaggtcgt ggcgctgctg aacggcggct ccgtgtcccg ccccatgaac acgaccctgg   2700
aggagatctt cttcgactcc aacctgggct ccaagaagct gacctccacc tgggacatct   2760
acgacctgtg ggcgaaccgc gtcgacaact ccacggcgtc cgccatcctg ggccgcaaca   2820
agaccgccac cggcatcctg tacaacgcca ccgagcagtc ctacaaggac ggcctgtcca   2880
agaacgacac ccgcctgttc ggccagaaga tcggctccct gtcccccaac gcgatcctga   2940
acacgaccgt ccccgcccac ggcatcgcgt tctaccgcct gcgcccctcc tcctgatacg   3000
tactcgaggc agcagcagct cggatagtat cgacacactc tggacgctgg tcgtgtgatg   3060
gactgttgcc gccacacttg ctgccttgac ctgtgaatat ccctgccgct tttatcaaac   3120
agcctcagtg tgtttgatct tgtgtgtacg cgcttttgcg agttgctagc tgcttgtgct   3180
atttgcgaat accaccccca gcatcccctt ccctcgtttc atatcgcttg catcccaacc   3240
gcaacttatc tacgctgtcc tgctatccct cagcgctgct cctgctcctg ctcactgccc   3300
ctcgcacagc cttggtttgg gctccgcctg tattctcctg gtactgcaac ctgtaaacca   3360
gcactgcaat gctgatgcac gggaagtagt gggatgggaa cacaaatgga aagctgtaga   3420
attcggccga caggacgcgc gtcaaaggtg ctggtcgtgt atgccctggc cggcaggtcg   3480
ttgctgctgc tggttagtga ttccgcaacc ctgattttgg cgtcttattt tggcgtggca   3540
aacgctggcg cccgcgagcc gggccggcgg cgatgcggtg ccccacggct gccggaatcc   3600
aagggaggca agagcgcccg ggtcagttga agggctttac gcgcaaggta cagccgctcc   3660
tgcaaggctg cgtggtggaa ttggacgtgc aggtcctgct gaagttcctc caccgcctca   3720
ccagcggaca aagcaccggt gtatcaggtc cgtgtcatcc actctaaaga actcgactac   3780
gacctactga tggccctaga ttcttcatca aaaacgcctg agacacttgc ccaggattga   3840
aactccctga agggaccacc aggggccctg agttgttcct tccccccgtg gcgagctgcc   3900
agccaggctg tacctgtgat cgaggctggc gggaaaatag gcttcgtgtg ctcaggtcat   3960
gggaggtgca ggacagctca tgaaacgcca acaatcgcac aattcatgtc aagctaatca   4020
gctatttcct cttcacgagc tgtaattgtc ccaaaattct ggtctaccgg gggtgatcct   4080
tcgtgtacgg gcccttccct caaccctagg tatgcgcgca tgcggtcgcc gcgcaactcg   4140
cgcgagggcc gagggtttgg gacgggccgt cccgaaatgc agttgcaccc ggatgcgtgg   4200
cacctttttt gcgataattt atgcaatgga ctgctctgca aaattctggc tctgtcgcca   4260
accctaggat cagcggcgta ggatttcgta atcattcgtc ctgatgggga gctaccgact   4320
accctaatat cagcccgact gcctgacgcc agcgtccact tttgtgcaca cattccattc   4380
gtgcccaaga catttcattg tggtgcgaag cgtccccagt tacgctcacc tgtttcccga   4440
cctccttact gttctgtcga cagagcgggc ccacaggccg gtcgcagcca ctagtatggt   4500
ggccgccgag gcctcctccg ccctgttctc cgtgcgcacc cccggcacct cccccaagcc   4560
cggcaagttc ggcaactggc ccacctccct gtccgtgccc ttcaagtcca agtccaacca   4620
```

caacggcggc ttccaggtga aggccaacgc ctccgcccgc cccaaggcca acggctccgc 4680
cgtgtccctg aagtccggct ccctggacac ccaggaggac acctcctcct cctcctcccc 4740
cccccgcacc ttcatcaacc agctgcccga ctggtccatg ctgctgtccg ccatcaccac 4800
cgtgttcgtg gccgccgaga agcagtggac catgctggac cgcaagtcca agcgccccga 4860
catgctgatg gaccccttcg gcgtggaccg cgtggtgcag gacggcgccg tgttccgcca 4920
gtccttctcc atccgctcct acgagatcgg cgccgaccgc accgcctcca tcgagaccct 4980
gatgaacatc ttccaggaga cctccctgaa ccactgcaag tccatcggcc tgctgaacga 5040
cggcttcggc cgcacccccg agatgtgcaa gcgcgacctg atctgggtgg tgaccaagat 5100
gcacgtggag gtgaaccgct accccacctg gggcgacacc atcgaggtga acacctgggt 5160
gtccgagtcc ggcaagaccg gcatgggccg cgactggctg atctccgact gccacaccgg 5220
cgagatcctg atccgcgcca cctccatgtg cgccatgatg aaccagaaga cccgccgctt 5280
ctccaagttc ccctacgagg tgcgccagga gctggccccc cacttcgtgg actccgcccc 5340
cgtgatcgag gactaccaga agctgcacaa gctggacgtg aagaccggcg actccatctg 5400
caacggcctg acccccgct ggaacgacct ggacgtgaac cagcacgtga acaacgtgaa 5460
gtacatcggc tggatcctgg agtccgtgcc caccgaggtg ttcgagaccc aggagctgtg 5520
cggcctgacc ctggagtacc gccgcgagtg cggccgcgac tccgtgctgg agtccgtgac 5580
cgccatggac ccctccaagg agggcgaccg ctccctgtac cagcacctgc tgcgcctgga 5640
ggacggcgcc gacatcgcca agggccgcac caagtggcgc cccaagaacg ccggcaccaa 5700
cggcgccatc tccaccggca agacctccaa cggcaactcc atctccatgg actacaagga 5760
ccacgacggc gactacaagg accacgacat cgactacaag gacgacgacg acaagtgact 5820
cgaggcagca gcagctcgga tagtatcgac acactctgga cgctggtcgt gtgatggact 5880
gttgccgcca cacttgctgc cttgacctgt gaatatccct gccgctttta tcaaacagcc 5940
tcagtgtgtt tgatcttgtg tgtacgcgct tttgcgagtt gctagctgct tgtgctattt 6000
gcgaatacca cccccagcat ccccttccct cgtttcatat cgcttgcatc ccaaccgcaa 6060
cttatctacg ctgtcctgct atccctcagc gctgctcctg ctcctgctca ctgcccctcg 6120
cacagccttg gtttgggctc cgcctgtatt ctcctggtac tgcaacctgt aaaccagcac 6180
tgcaatgctg atgcacggga agtagtggga tgggaacaca aatggaaagc tgtataggga 6240
taacagggta atgagctcag cgtctgcgtg ttgggagctg gagtcgtggg cttgacgacg 6300
gcgctgcagc tgttgcagga tgtgcctggc gtgcgcgttc acgtcgtggc tgagaaatat 6360
ggcgacgaaa cgttgacggc tggggccggc gggctgtgga tgccatacgc attgggtacg 6420
cggccattgg atgggattga taggcttatg gagggataat agagtttttg ccggatccaa 6480
cgcatgtgga tgcggtatcc cggtgggctg aaagtgtgga aggatagtgc attggctatt 6540
cacatgcact gcccacccct tttggcagga aatgtgccgg catcgttggt gcaccgatgg 6600
ggaaaatcga cgttcgacca ctacatgaag atttatacgt ctgaagatgc agcgactgcg 6660
ggtgcgaaac ggatgacggt ttggtcgtgt atgtcacagc atgtgctgga tcttgcgggc 6720
taactccccc tgccacggcc cattgcaggt gtcatgttga ctggagggta cgacctttcg 6780
tccgtcaaat tcccagagga ggacccgctc tgggccgaca ttgtgcccac tgaagagc 6838

<210> SEQ ID NO 125
<211> LENGTH: 1303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
actagtaaca atggccaccg cctccacctt ctccgccttc aacgcccgct gcggcgacct 60
gcgccgctcc gccggctccg gcccccgccg ccccgcccgc cccctgcccg tgcgcgccgc 120
catcaacgcc tccgcccgcc ccaaggccaa cggctccgcc gtgtccctga agtccggctc 180
cctggacacc caggaggaca cctcctcctc ctcctccccc ccccgcacct tcatcaacca 240
gctgcccgac tggtccatgc tgctgtccgc catcaccacc gtgttcgtgg ccgccgagaa 300
gcagtggacc atgctggacc gcaagtccaa gcgccccgac atgctgatgg accccttcgg 360
cgtggaccgc gtggtgcagg acggcgccgt gttccgccag tccttctcca tccgctccta 420
cgagatcggc gccgaccgca ccgcctccat cgagaccctg atgaacatct tccaggagac 480
ctccctgaac cactgcaagt ccatcggcct gctgaacgac ggcttcggcc gcacccccga 540
gatgtgcaag cgcgacctga tctgggtggt gaccaagatg cacgtggagg tgaaccgcta 600
ccccacctgg ggcgacacca tcgaggtgaa cacctgggtg tccgagtccg gcaagaccgg 660
catgggccgc gactggctga tctccgactg ccacaccggc gagatcctga tccgcgccac 720
ctccatgtgc gccatgatga accagaagac ccgccgcttc tccaagttcc cctacgaggt 780
gcgccaggag ctggcccccc acttcgtgga ctccgccccc gtgatcgagg actaccagaa 840
gctgcacaag ctggacgtga agaccggcga ctccatctgc aacggcctga ccccccgctg 900
gaacgacctg gacgtgaacc agcacgtgaa caacgtgaag tacatcggct ggatcctgga 960
gtccgtgccc accgaggtgt tcgagaccca ggagctgtgc ggcctgaccc tggagtaccg 1020
ccgcgagtgc ggccgcgact ccgtgctgga gtccgtgacc gccatggacc cctccaagga 1080
gggcgaccgc tccctgtacc agcacctgct gcgcctggag gacggcgccg acatcgccaa 1140
gggccgcacc aagtggcgcc ccaagaacgc cggcaccaac ggcgccatct ccaccggcaa 1200
gacctccaac ggcaactcca tctccatgga ctacaaggac cacgacggcg actacaagga 1260
ccacgacatc gactacaagg acgacgacga caagtgactc gag 1303

<210> SEQ ID NO 126
<211> LENGTH: 1282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
actagtaaca atggccaccg cctccacctt ctccgccttc aacgcccgct gcggcgacct 60
gcgccgctcc gccggctccg gcccccgccg ccccgcccgc cccctgcccg tgcgcgccgc 120
catcaacgcc tccgcccacc ccaaggccaa cggctccgcc gtgaacctga agtccggctc 180
cctggagacc caggaggaca cctcctcctc ctcccccccc ccccgcacct tcatcaagca 240
gctgcccgac tggggcatgc tgctgtccaa gatcaccacc gtgttcggcg ccgccgagcg 300
ccagtggaag cgccccggca tgctggtgga gcccttcggc gtggaccgca tcttccagga 360
cggcgtgttc ttccgccagt ccttctccat ccgctcctac gagatcggcg ccgaccgcac 420
cgcctccatc gagaccctga tgaacatctt ccaggagacc tccctgaacc actgcaagtc 480
catcggcctg ctgaacgacg gcttcggccg cacccccgag atgtgcaagc gcgacctgat 540
ctgggtggtg accaagatcc aggtggaggt gaaccgctac cccacctggg gcgacaccat 600
cgaggtgaac acctgggtgt ccgagtccgg caagaacggc atgggccgcg actggctgat 660
ctccgactgc cgcaccggcg agatcctgat ccgcgccacc tccgtgtggg ccatgatgaa 720
ccgcaagacc cgccgcctgt ccaagttccc ctacgaggtg cgccaggaga tcgcccccca 780
cttcgtggac tccgcccccg tgatcgagga cgacaagaag ctgcacaagc tggacgtgaa 840
gaccggcgac tccatccgca agggcctgac cccccgctgg aacgacctgg acgtgaacca 900
gcacgtgaac aacgtgaagt acatcggctg gatcctgaag tccgtgcccg ccgaggtgtt 960
cgagacccag gagctgtgcg gcgtgaccct ggagtaccgc cgcgagtgcg gccgcgactc 1020
cgtgctggag tccgtgaccg ccatggacac cgccaaggag ggcgaccgct ccctgtacca 1080
gcacctgctg cgcctggagg acggcgccga catcaccatc ggccgcaccg agtggcgccc 1140
caagaacgcc ggcgccaacg gcgccatctc caccggcaag acctccaacg agaactccgt 1200
gtccatggac tacaaggacc acgacggcga ctacaaggac cacgacatcg actacaagga 1260
cgacgacgac aagtgactcg ag 1282

<210> SEQ ID NO 127
<211> LENGTH: 6696
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 127
gaagagcgcc caatgtttaa acccctcaac tgcgacgctg ggaaccttct ccgggcaggc 60
gatgtgcgtg ggtttgcctc cttggcacgg ctctacaccg tcgagtacgc catgaggcgg 120
tgatggctgt gtcggttgcc acttcgtcca gagacggcaa gtcgtccatc ctctgcgtgt 180
gtggcgcgac gctgcagcag tccctctgca gcagatgagc gtgactttgg ccatttcacg 240
cactcgagtg tacacaatcc atttttctta aagcaaatga ctgctgattg accagatact 300
gtaacgctga tttcgctcca gatcgcacag atagcgacca tgttgctgcg tctgaaaatc 360
tggattccga attcgaccct ggcgctccat ccatgcaaca gatggcgaca cttgttacaa 420
ttcctgtcac ccatcggcat ggagcaggtc cacttagatt cccgatcacc cacgcacatc 480
tcgctaatag tcattcgttc gtgtcttcga tcaatctcaa gtgagtgtgc atggatcttg 540
gttgacgatg cggtatgggt ttgcgccgct ggctgcaggg tctgcccaag gcaagctaac 600
ccagctcctc tccccgacaa tactctcgca ggcaaagccg gtcacttgcc ttccagattg 660
ccaataaact caattatggc ctctgtcatg ccatccatgg gtctgatgaa tggtcacgct 720
cgtgtcctga ccgttcccca gcctctggcg tcccctgccc cgcccaccag cccacgccgc 780
gcggcagtcg ctgccaaggc tgtctcggag gtaccgcggt gagaatcgaa aatgcatcgt 840
ttctaggttc ggagacggtc aattccctgc tccggcgaat ctgtcggtca agctggccag 900
tggacaatgt tgctatggca gcccgcgcac atgggcctcc cgacgcggcc atcaggagcc 960
caaacagcgt gtcagggtat gtgaaactca agaggtccct gctgggcact ccggccccac 1020
tccgggggcg ggacgccagg cattcgcggt cggtcccgcg cgacgagcga aatgatgatt 1080
cggttacgag accaggacgt cgtcgaggtc gagaggcagc ctcggacacg tctcgctagg 1140
gcaacgcccc gagtccccgc gagggccgta aacattgttt ctgggtgtcg gagtgggcat 1200
tttgggcccg atccaatcgc ctcatgccgc tctcgtctgg tcctcacgtt cgcgtacggc 1260

-continued

```
ctggatcccg gaaagggcgg atgcacgtgg tgttgccccg ccattggcgc ccacgtttca   1320
aagtccccgg ccagaaatgc acaggaccgg cccggctcgc acaggccatg ctgaacgccc   1380
agatttcgac agcaacacca tctagaataa tcgcaaccat ccgcgttttg aacgaaacga   1440
aacggcgctg tttagcatgt ttccgacatc gtgggggccg aagcatgctc cggggggagg   1500
aaagcgtggc acagcggtag cccattctgt gccacacgcc gacgaggacc aatccccggc   1560
atcagccttc atcgacggct gcgccgcaca tataaagccg gacgcctaac cggtttcgtg   1620
gttatgacta gtatgttcgc gttctacttc ctgacggcct gcatctccct gaagggcgtg   1680
ttcggcgtct ccccctccta caacggcctg ggcctgacgc cccagatggg ctgggacaac   1740
tggaacacgt tcgcctgcga cgtctccgag cagctgctgc tggacacggc cgaccgcatc   1800
tccgacctgg gcctgaagga catgggctac aagtacatca tcctggacga ctgctggtcc   1860
tccggccgcg actccgacgg cttcctggtc gccgacgagc agaagttccc caacggcatg   1920
ggccacgtcg ccgaccacct gcacaacaac tccttcctgt tcggcatgta ctcctccgcg   1980
ggcgagtaca cgtgcgccgg ctaccccggc tccctgggcc gcgaggagga ggacgcccag   2040
ttcttcgcga acaaccgcgt ggactacctg aagtacgaca actgctacaa caagggccag   2100
ttcggcacgc ccgagatctc ctaccaccgc tacaaggcca tgtccgacgc cctgaacaag   2160
acgggccgcc ccatcttcta ctccctgtgc aactggggcc aggacctgac cttctactgg   2220
ggctccggca tcgcgaactc ctggcgcatg tccggcgacg tcacggcgga gttcacgcgc   2280
cccgactccc gctgcccctg cgacggcgac gagtacgact gcaagtacgc cggcttccac   2340
tgctccatca tgaacatcct gaacaaggcc gcccccatgg gccagaacgc gggcgtcggc   2400
ggctggaacg acctggacaa cctggaggtc ggcgtcggca acctgacgga cgacgaggag   2460
aaggcgcact tctccatgtg ggccatggtg aagtcccccc tgatcatcgg cgcgaacgtg   2520
aacaacctga aggcctcctc ctactccatc tactcccagg cgtccgtcat cgccatcaac   2580
caggactcca acggcatccc cgccacgcgc gtctggcgct actacgtgtc cgacacggac   2640
gagtacggcc agggcgagat ccagatgtgg tccggccccc tggacaacgg cgaccaggtc   2700
gtggcgctgc tgaacggcgg ctccgtgtcc cgcccccatga acacgaccct ggaggagatc   2760
ttcttcgact ccaacctggg ctccaagaag ctgacctcca cctgggacat ctacgacctg   2820
tgggcgaacc gcgtcgacaa ctccacggcg tccgccatcc tgggccgcaa caagaccgcc   2880
accggcatcc tgtacaacgc caccgagcag tcctacaagg acggcctgtc caagaacgac   2940
acccgcctgt tcggccagaa gatcggctcc ctgtccccca acgcgatcct gaacacgacc   3000
gtccccgccc acggcatcgc gttctaccgc ctgcgcccct cctcctgata caacttatta   3060
cgtaacggag cgtcgtgcgg gagggagtgt gccgagcggg gagtcccggt ctgtgcgagg   3120
cccggcagct gacgctggcg agccgtacgc cccgagggtc cccctcccct gcaccctctt   3180
ccccttccct ctgacggccg cgcctgttct tgcatgttca gcgacgagga tatcgaattc   3240
atagcgactg ctaccccccg accatgtgcc gaggcagaaa ttatatacaa gaagcagatc   3300
gcaattaggc acatcgcttt gcattatcca cacactattc atcgctgctg cggcaaggct   3360
gcagagtgta tttttgtggc ccaggagctg agtccgaagt cgacgcgacg agcggcgcag   3420
gatccgaccc ctagacgagc actgtcattt tccaagcacg cagctaaatg cgctgagacc   3480
gggtctaaat catccgaaaa gtgtcaaaat ggccgattgg gttcgcctag gacaatgcgc   3540
tgcggattcg ctcgagtccg ctgccggcca aaaggcggtg gtacaggaag gcgcacgggg   3600
ccaaccctgc gaagccgggg gcccgaacgc cgaccgccgg ccttcgatct cgggtgtccc   3660
```

-continued

```
cctcgtcaat ttcctctctc gggtgcagcc acgaaagtcg tgacgcaggt cacgaaatcc   3720
ggttacgaaa aacgcaggtc ttcgcaaaaa cgtgagggtt tcgcgtctcg ccctagctat   3780
tcgtatcgcc gggtcagacc cacgtgcaga aaagcccttg aataacccgg gaccgtggtt   3840
accgcgccgc ctgcaccagg gggcttatat aagcccacac cacacctgtc tcaccacgca   3900
tttctccaac tcgcgacttt tcggaagaaa ttgttatcca cctagtatag actgccacct   3960
gcaggacctt gtgtcttgca gtttgtattg gtcccggccg tcgagcacga cagatctggg   4020
ctagggttgg cctggccgct cggcactccc ctttagccgc gcgcatccgc gttccagagg   4080
tgcgattcgg tgtgtggagc attgtcatgc gcttgtgggg gtcgttccgt gcgcggcggg   4140
tccgccatgg gcgccgacct gggccctagg gtttgttttc gggccaagcg agcccctctc   4200
acctcgtcgc ccccccgcat tccctctctc ttgcagccac tagtaacaat ggccaccgca   4260
tccactttct cggcgttcaa tgcccgctgc ggcgacctgc gtcgctcggc gggctccggg   4320
ccccggcgcc cagcgaggcc cctccccgtg cgcgctgcca tcgccagcga ggtccccgtg   4380
gccaccacct ccccccgggc gcaccccaag gcgaacggca gcgcggtgtc gctgaagtcg   4440
ggctccctgg agacccagga ggacaagacg agcagctcgt cccccccccc ccgcacgttc   4500
atcaaccagc tgcccgtgtg gagcatgctg ctgtcggcgg tgaccacggt cttcggcgtg   4560
gccgagaagc agtggcccat gctggaccgc aagtccaagc gccccgacat gctggtcgag   4620
cccctgggcg tggaccgcat cgtctacgac ggcgtgagct tccgccagtc gttctccatc   4680
cgcagctacg agatcggcgc cgaccgcacc gcctcgatcg agacgctgat gaacatgttc   4740
caggagacct ccctgaacca ctgcaagatc atcggcctgc tgaacgacgg cttcggccgc   4800
acgcccgaga tgtgcaagcg cgacctgatc tgggtcgtga ccaagatgca gatcgaggtg   4860
aaccgctacc ccacgtgggg cgacaccatc gaggtcaaca cgtgggtgag cgcctcgggc   4920
aagcacggca tgggccgcga ctggctgatc tccgactgcc acaccggcga gatcctgatc   4980
cgcgcgacga gcgtctgggc gatgatgaac cagaagaccc gccgcctgtc gaagatcccc   5040
tacgaggtgc gccaggagat cgagccccag ttcgtcgact ccgcccccgt gatcgtggac   5100
gaccgcaagt tccacaagct ggacctgaag acgggcgaca gcatctgcaa cggcctgacc   5160
ccccgctgga cggacctgga cgtgaaccag cacgtcaaca acgtgaagta catcggctgg   5220
atcctgcagt cggtccccac cgaggtgttc gagacgcagg agctgtgcgg cctgaccctg   5280
gagtaccgcc gcgagtgcgg ccgcgactcc gtgctggaga gcgtcacggc catggacccc   5340
tcgaaggagg gcgaccgctc cctgtaccag cacctgctgc gcctggagga cggcgcggac   5400
atcgtgaagg gccgcaccga gtggcgcccc aagaacgccg gcgccaaggg cgccatcctg   5460
acgggcaaga ccagcaacgg caactcgatc tccatggact acaaggacca cgacggcgac   5520
tacaaggacc acgacatcga ctacaaggac gacgacgaca agtgaaagct tgcagcagca   5580
gctcggatag tatcgacaca ctctggacgc tggtcgtgtg atggactgtt gccgccacac   5640
ttgctgcctt gacctgtgaa tatccctgcc gcttttatca aacagcctca gtgtgtttga   5700
tcttgtgtgt acgcgctttt gcgagttgct agctgcttgt gctatttgcg aataccaccc   5760
ccagcatccc cttccctcgt ttcatatcgc ttgcatccca accgcaactt atctacgctg   5820
tcctgctatc cctcagcgct gctcctgctc ctgctcactg cccctcgcac agccttggtt   5880
tgggctcccg cctgtattct cctggtactg caacctgtaa accagcactg caatgctgat   5940
gcacgggaag tagtgggatg ggaacacaaa tggaaagctg gagctccagc gccatgccac   6000
```

gccctttgat ggcttcaagt acgattacgg tgttggattg tgtgtttgtt gcgtagtgtg 6060
catggtttag aataatacac ttgatttctt gctcacggca atctcggctt gtccgcaggt 6120
tcaaccccat ttcggagtct caggtcagcc gcgcaatgac cagccgctac ttcaaggact 6180
tgcacgacaa cgccgaggtg agctatgttt aggacttgat tggaaattgt cgtcgacgca 6240
tattcgcgct ccgcgacagc acccaagcaa aatgtcaagt gcgttccgat ttgcgtccgc 6300
aggtcgatgt tgtgatcgtc ggcgccggat ccgccggtct gtcctgcgct tacgagctga 6360
ccaagcaccc tgacgtccgg gtacgcgagc tgagattcga ttagacataa attgaagatt 6420
aaacccgtag aaaaatttga tggtcgcgaa actgtgctcg attgcaagaa attgatcgtc 6480
ctccactccg caggtcgcca tcatcgagca gggcgttgct cccggcggcg gcgcctggct 6540
ggggggacag ctgttctcgg ccatgtgtgt acgtagaagg atgaatttca gctggttttc 6600
gttgcacagc tgtttgtgca tgatttgttt cagactattg ttgaatgttt ttagatttct 6660
taggatgcat gatttgtctg catgcgactg aagagc 6696

<210> SEQ ID NO 128
<211> LENGTH: 5851
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 128
gctcttcgga gtcactgtgc cactgagttc gactggtagc tgaatggagt cgctgctcca 60
ctaaacgaat tgtcagcacc gccagccggc cgaggacccg agtcatagcg agggtagtag 120
cgcgccatgg caccgaccag cctgcttgcc agtactggcg tctcttccgc ttctctgtgg 180
tcctctgcgc gctccagcgc gtgcgctttt ccggtggatc atgcggtccg tggcgcaccg 240
cagcggccgc tgcccatgca gcgccgctgc ttccgaacag tggcggtcag ggccgcaccc 300
gcggtagccg tccgtccgga acccgcccaa gagttttggg agcagcttga gccctgcaag 360
atggcggagg acaagcgcat cttcctggag gagcaccggt gcgtggaggt ccggggctga 420
ccggccgtcg cattcaacgt aatcaatcgc atgatgatca gaggacacga agtcttggtg 480
gcggtggcca gaaacactgt ccattgcaag ggcataggga tgcgttcctt cacctctcat 540
ttctcatttc tgaatccctc cctgctcact ctttctcctc ctccttcccg ttcacgcagc 600
attcggggta ccgcggtgag aatcgaaaat gcatcgtttc taggttcgga gacggtcaat 660
tccctgctcc ggcgaatctg tcggtcaagc tggccagtgg acaatgttgc tatggcagcc 720
cgcgcacatg ggcctcccga cgcggccatc aggagcccaa acagcgtgtc agggtatgtg 780
aaactcaaga ggtccctgct gggcactccg gccccactcc gggggcggga cgccaggcat 840
tcgcggtcgg tcccgcgcga cgagcgaaat gatgattcgg ttacgagacc aggacgtcgt 900
cgaggtcgag aggcagcctc ggacacgtct cgctagggca acgccccgag tccccgcgag 960
ggccgtaaac attgtttctg ggtgtcggag tgggcatttt gggcccgatc caatcgcctc 1020
atgccgctct cgtctggtcc tcacgttcgc gtacggcctg gatcccggaa agggcggatg 1080
cacgtggtgt tgccccgcca ttggcgccca cgtttcaaag tccccggcca gaaatgcaca 1140
ggaccggccc ggctcgcaca ggccatgctg aacgcccaga tttcgacagc aacaccatct 1200
agaataatcg caaccatccg cgttttgaac gaaacgaaac ggcgctgttt agcatgtttc 1260
cgacatcgtg gggccgaag catgctccgg ggggaggaaa gcgtggcaca gcggtagccc 1320

-continued

```
attctgtgcc acacgccgac gaggaccaat ccccggcatc agccttcatc gacggctgcg   1380
ccgcacatat aaagccggac gcctaaccgg tttcgtggtt atgactagta tgttcgcgtt   1440
ctacttcctg acggcctgca tctccctgaa gggcgtgttc ggcgtctccc cctcctacaa   1500
cggcctgggc ctgacgcccc agatgggctg ggacaactgg aacacgttcg cctgcgacgt   1560
ctccgagcag ctgctgctgg acacggccga ccgcatctcc gacctgggcc tgaaggacat   1620
gggctacaag tacatcatcc tggacgactg ctggtcctcc ggccgcgact ccgacggctt   1680
cctggtcgcc gacgagcaga agttccccaa cggcatgggc cacgtcgccg accacctgca   1740
caacaactcc ttcctgttcg gcatgtactc ctccgcgggc gagtacacgt gcgccggcta   1800
ccccggctcc ctgggccgcg aggaggagga cgcccagttc ttcgcgaaca accgcgtgga   1860
ctacctgaag tacgacaact gctacaacaa gggccagttc ggcacgcccg agatctccta   1920
ccaccgctac aaggccatgt ccgacgccct gaacaagacg ggccgcccca tcttctactc   1980
cctgtgcaac tggggccagg acctgacctt ctactggggc tccggcatcg cgaactcctg   2040
gcgcatgtcc ggcgacgtca cggcggagtt cacgcgcccc gactcccgct gcccctgcga   2100
cggcgacgag tacgactgca agtacgccgg cttccactgc tccatcatga acatcctgaa   2160
caaggccgcc cccatgggcc agaacgcggg cgtcggcggc tggaacgacc tggacaacct   2220
ggaggtcggc gtcggcaacc tgacggacga cgaggagaag gcgcacttct ccatgtgggc   2280
catggtgaag tccccccctga tcatcggcgc gaacgtgaac aacctgaagg cctcctccta   2340
ctccatctac tcccaggcgt ccgtcatcgc catcaaccag gactccaacg gcatccccgc   2400
cacgcgcgtc tggcgctact acgtgtccga cacggacgag tacggccagg gcgagatcca   2460
gatgtggtcc ggcccccctgg acaacggcga ccaggtcgtg gcgctgctga acggcggctc   2520
cgtgtcccgc cccatgaaca cgaccctgga ggagatcttc ttcgactcca acctgggctc   2580
caagaagctg acctccacct gggacatcta cgacctgtgg gcgaaccgcg tcgacaactc   2640
cacggcgtcc gccatcctgg gccgcaacaa gaccgccacc ggcatcctgt acaacgccac   2700
cgagcagtcc tacaaggacg gcctgtccaa gaacgacacc cgcctgttcg gccagaagat   2760
cggctccctg tcccccaacg cgatcctgaa cacgaccgtc cccgcccacg gcatcgcgtt   2820
ctaccgcctg cgcccctcct cctgatacgt agcagcagca gctcggatag tatcgacaca   2880
ctctggacgc tggtcgtgtg atggactgtt gccgccacac ttgctgcctt gacctgtgaa   2940
tatccctgcc gcttttatca aacagcctca gtgtgtttga tcttgtgtgt acgcgctttt   3000
gcgagttgct agctgcttgt gctatttgcg aataccaccc ccagcatccc cttccctcgt   3060
ttcatatcgc ttgcatccca accgcaactt atctacgctg tcctgctatc cctcagcgct   3120
gctcctgctc ctgctcactg cccctcgcac agccttggtt tgggctccgc ctgtattctc   3180
ctggtactgc aacctgtaaa ccagcactgc aatgctgatg cacgggaagt agtgggatgg   3240
gaacacaaat ggagatatcg cgaggggtct gcctgggcca gccgctccct ctaaacacgg   3300
gacgcgtggt ccaattcggg cttcgggacc ctttggcggt ttgaacgcca gggatggggc   3360
gcccgcgagc ctggggaccc cggcaacggc ttccccagag cctgccttgc aatctcgcgc   3420
gtcctctccc tcagcacgtg gcggttccac gtgtggtcgg gcttcccgga ctagctcgcg   3480
tcgtgaccta gcttaatgaa cccagccggg cctgtagcac cgcctaagag gttttgatta   3540
tttcattata ccaatctatt cgccactagt atggccatca agaccaaccg ccagcccgtg   3600
gagaagcccc ccttcaccat cggcaccctg cgcaaggcca tccccgccca ctgcttcgag   3660
cgctccgccc tgcgctcctc catgtacctg gccttcgaca tcgccgtgat gtccctgctg   3720
```

```
tacgtggcct ccacctacat cgaccccgcc cccgtgccca cctgggtgaa gtacggcgtg   3780

atgtggcccc tgtactggtt cttccagggc gccttcggca ccggcgtgtg ggtgtgcgcc   3840

cacgagtgcg gccaccaggc cttctcctcc tcccaggcca tcaacgacgg cgtgggcctg   3900

gtgttccact ccctgctgct ggtgccctac tactcctgga agcactccca ccgccgccac   3960

cactccaaca ccggctgcct ggacaaggac gaggtgttcg tgccccccca ccgcgccgtg   4020

gcccacgagg gcctggagtg ggaggagtgg ctgcccatcc gcatgggcaa ggtgctggtg   4080

accctgaccc tgggctggcc cctgtacctg atgttcaacg tggcctcccg cccctacccc   4140

cgcttcgcca accacttcga cccctggtcc cccatcttct ccaagcgcga gcgcatcgag   4200

gtggtgatct ccgacctggc cctggtggcc gtgctgtccg gcctgtccgt gctgggccgc   4260

accatgggct gggcctggct ggtgaagacc tacgtggtgc cctacctgat cgtgaacatg   4320

tggctggtgc tgatcaccct gctgcagcac acccaccccg ccctgcccca ctacttcgag   4380

aaggactggg actggctgcg cggcgccatg gccaccgtgg accgctccat gggccccccc   4440

ttcatggaca acatcctgca ccacatctcc gacacccacg tgctgcacca cctgttctcc   4500

accatccccc actaccacgc cgaggaggcc tccgccgcca tccgccccat cctgggcaag   4560

tactaccagt ccgactcccg ctgggtgggc cgcgccctgt gggaggactg gcgcgactgc   4620

cgctacgtgg tgcccgacgc ccccgaggac gactccgccc tgtggttcca caagtagatc   4680

gatcttaagg cagcagcagc tcggatagta tcgacacact ctggacgctg gtcgtgtgat   4740

ggactgttgc cgccacactt gctgccttga cctgtgaata tccctgccgc ttttatcaaa   4800

cagcctcagt gtgtttgatc ttgtgtgtac gcgcttttgc gagttgctag ctgcttgtgc   4860

tatttgcgaa taccaccccc agcatcccct tccctcgttt catatcgctt gcatcccaac   4920

cgcaacttat ctacgctgtc ctgctatccc tcagcgctgc tcctgctcct gctcactgcc   4980

cctcgcacag ccttggtttg ggctccgcct gtattctcct ggtactgcaa cctgtaaacc   5040

agcactgcaa tgctgatgca cgggaagtag tgggatggga acacaaatgg aaagcttaat   5100

taagagctct tgttttccag aaggagttgc tccttgagcc tttcattctc agcctcgata   5160

acctccaaag ccgctctaat tgtggagggg gttcgaattt aaaagcttgg aatgttggtt   5220

cgtgcgtctg gaacaagccc agacttgttg ctcactggga aaaggaccat cagctccaaa   5280

aaacttgccg ctcaaaccgc gtacctctgc tttcgcgcaa tctgccctgt tgaaatcgcc   5340

accacattca tattgtgacg cttgagcagt ctgtaattgc ctcagaatgt ggaatcatct   5400

gccccctgtg cgagcccatg ccaggcatgt cgcgggcgag gacacccgcc actcgtacag   5460

cagaccatta tgctacctca caatagttca taacagtgac catatttctc gaagctcccc   5520

aacgagcacc tccatgctct gagtggccac cccccggccc tggtgcttgc ggagggcagg   5580

tcaaccggca tggggctacc gaaatccccg accggatccc accacccccg cgatgggaag   5640

aatctctccc cgggatgtgg gcccaccacc agcacaacct gctggcccag gcgagcgtca   5700

aaccatacca cacaaatatc cttggcatcg gccctgaatt ccttctgccg ctctgctacc   5760

cggtgcttct gtccgaagca ggggttgcta gggatcgctc cgagtccgca aacccttgtc   5820

gcgtggcggg gcttgttcga gcttgaagag c                                  5851
```

<210> SEQ ID NO 129
<211> LENGTH: 186
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 129
tacaacttat tacgtaacgg agcgtcgtgc gggagggagt gtgccgagcg gggagtcccg     60
gtctgtgcga ggcccggcag ctgacgctgg cgagccgtac gccccgaggg tccccctccc    120
ctgcaccctc ttccccttcc ctctgacggc cgcgcctgtt cttgcatgtt cagcgacgag    180
gatatc                                                               186

<210> SEQ ID NO 130
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gcgaggggtc tgcctgggcc agccgctccc tctgaacacg ggacgcgtgg tccaattcgg     60
gcttcgggac cctttggcgg tttgaacgcc tgggagaggg cgcccgcgag cctggggacc    120
ccggcaacgg cttccccaga gcctgccttg caatctcgcg cgtcctctcc ctcagcacgt    180
ggcggttcca cgtgtggtcg ggcgtcccgg actagctcac gtcgtgacct agcttaatga    240
acccagccgg gcctgcagca ccaccttaga ggttttgatt atttgattag accaatctat    300
tcacc                                                                305

<210> SEQ ID NO 131
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
ggcgaataga ttggtataat gaaataatca aaacctctta ggcggtgcta caggcccggc     60
tgggttcatt aagctaggtc acgacgcgag ctagtccggg aagcccgacc acacgtggaa    120
ccgccacgtg ctgagggaga ggacgcgcga gattgcaagg caggctctgg ggaagccgtt    180
gccggggtcc ccaggctcgc gggcgcccca tccctggcgt tcaaaccgcc aaagggtccc    240
gaagcccgaa ttggaccacg cgtcccgtgt ttagagggag cggctggccc aggcagaccc    300
ctcgc                                                                305

<210> SEQ ID NO 132
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
ggtgaataga ttggtctaat caaataatca aaacctctaa ggtggtgctg caggcccggc     60
tgggttcatt aagctaggtc acgacgtgag ctagtccggg acgcccgacc acacgtggaa    120
ccgccacgtg ctgagggaga ggacgcgcga gattgcaagg caggctctgg ggaagccgtt    180
gccggggtcc ccaggctcgc gggcgccctc tcccaggcgt tcaaaccgcc aaagggtccc    240
gaagcccgaa ttggaccacg cgtcccgtgt tcagagggag cggctggccc aggcagaccc    300
ctcgc 305

<210> SEQ ID NO 133
<211> LENGTH: 1322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133
gtgatgggtt ctttagacga tccagcccag gatcatgtgt tgcccacatg gagcctatcc 60
acgctggcct agaaggcaag cacatttcaa ggtgaaccca cgtccatgga gcgatggcgc 120
caatatctcg cctctagacc aagcggttct caccccaact gcgtcatttg tatgtatggc 180
tgcaaagttg tcggtacgat agaggccgcc aacctggcgg cgagggcgag gagctggttg 240
ccgatctgtg cccaagcatg tgtcggagct cggctgtctc ggcagcgagc tcctgtgcaa 300
ggggcttgca tcgagaatgt caggcgatag acactgcacg ttggggacac ggaggtgccc 360
ctgtggcgtg tcctggatgc cctcgggtcc gtcgcgagaa gctctggcga ccagcacccg 420
gccacaaccg cagcaggcgt tcacccacaa gaatcttcca gatcgtgatg cgcatgtatc 480
gtgacacgat tggcgaggtc cgcaggacgc acacggactc gtccactcat cagaactggt 540
cagggcaccc atctgcgtcc cttttcagga accacccacc gctgccaggc accttcgcca 600
gcggcggact ccacacagag aatgccttgc tgtgagagac catggccggc aagtgctgtc 660
ggatctgccc gcatacggtc agtccccagc acaaggaagc caagagtaca ggctgttggt 720
gtcgatggag gagtggccgt tcccacaagt agtgagcggc agctgctcaa cggcttcccc 780
ctgttcatct tggcaaagcc agtgacttcc tacaagtatg tgatgcagat cggcactgca 840
atctgtcggc atgcgtacag aacatcggct cgccagggca gcgttgctcg ctctggatga 900
gctgcttggg aggaatcatc ggcacacgcc cgtgccgtgc ccgcgccccg cgcccgtcgg 960
gaaaggcccc cggttaggac actgccgcgt cagccagtcg tgggatcgat cggacgtggc 1020
gaatcctcgc ccggacaccc tcatcacacc ccacatttcc ctgcaagcaa tcttgccgac 1080
aaaatagtca agatccattg ggtttaggga acacgtgcga gactgggcag ctgtatctgt 1140
ccttgccccg cgtcaaattc ctgggcgtga cgcagtcaca ggagaatcta ttagaccctg 1200
gacttgcagc tcagtcatgg gcgtgagtgg ctaaagcacc taggtcaggc gagtaccgcc 1260
ccttccccag gattcactct tctgcgattg acgttgagcc tgcatcgggc tgcttcgtca 1320
cc 1322

<210> SEQ ID NO 134
<211> LENGTH: 841
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134
tcggagctaa agcagagact ggacaagact tgcgttcgca tactggtgac acagaatagc 60
tcccatctat tcatacgcct ttgggaaaag gaacgagcct tgtggcctct gcattgctgc 120
ctgctttgag gccgaggacg gtgcgggacg ctcagatcca tcagcgatcg ccccaccctc 180
agagcacctc cgatccaagg caatactatc aggcaaagtt tccaaattca aacattccaa 240

```
aatcacgcca gggactggat cacacacgca gatcagcgcc gttttgctct ttgcctacgg    300

gcgactgtgc cacttgtcga cccctggtga cgggagggac cacgcctgcg gttggcatcc    360

acttcgacgg acccagggac ggtttctcat gccaaacctg agatttgagc acccagatga    420

gcacattatg cgttttagga tgcctgagca gcgggcgtgc aggaatctgg tctcgccaga    480

ttcaccgaag atgcgcccat cggagcgagg cgagggcttt gtgaccacgc aaggcagtgt    540

gaggcaaaca catagggaca cctgcgtctt tcaatgcaca gacatctatg gtgcccatgt    600

atataaaatg ggctacttct gagtcaaacc aacgcaaact gcgctatggc aaggccggcc    660

aaggttggaa tcccggtctg tctggatttg agtttgtggg ggctatcacg tgacaatccc    720

tgggattggg cggcagcagc gcacggcctg ggtggcaatg gcgcactaat actgctgaaa    780

gcacggctct gcatcccttt ctcttgacct gcgattggtc cttttcgcaa gcgtgatcat    840

c                                                                   841
```

<210> SEQ ID NO 135
<211> LENGTH: 841
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
tcggagctaa agcagaaact gaacaagact tgcgttcgca tacttgtgac actgaatagg     60

ttcaatctat tcatacgcct ttgggaaact gaacgagcct tgtggcctct gcattgctgc    120

ctgctttgag gccgaggacg gcgcggaacg cacagatcca tcagcgatcg ccccaccctc    180

agagtacatc cgatccaagg caatactatc aggcaaagtt tccaaattca aacattccaa    240

aattacgtca gggactggat cacacacgca gatcagcgcc gttttgctct ttgcctacgg    300

gcgactgtgc cacttgtcga cgcctggtga cgggagggac cacgcctgcg gttggcatcc    360

acttcgacgg acccagggac ggtctcacat gccaaacctg agatttgagc accaagatga    420

gcacattatg cgtttttgga tgcctgagca gcgggcgtgc aggaatctgg tctcgccaga    480

ttcaccgaag atgcggccat cggagcgagg cgagggctgt gtggccacgc caggcagtgt    540

gaggcaaaca cacagggaca tctgcttctt tcgatgcaca gacatctatg ttgcccgtgc    600

atataaaatg ggctacttct gaatcaaacc aacgcaaact tcgctatggc aaggccggcc    660

aaggttggaa tcccggtctg tctggatttg agtttgtggg ggctatcacg tgacaatccc    720

tgggattggg cggcagcagc gcacggcctg gatggcaatg gcgcactaat actgctgaaa    780

gcacggctct gcatcccttt ctcttgacct gcgattggtc cttttcgcaa gcgtgatcat    840

c                                                                   841
```

<210> SEQ ID NO 136
<211> LENGTH: 512
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
caccgatcac tccgtcgccg cccaagagaa atcaacctcg atggagggcg aggtggatca     60

gaggtattgg ttatcgttcg ttcttagtct caatcaatcg tacaccttgc agttgcccga    120

gtttctccac acatacagca cctcccgctc ccagcccatt cgagcgaccc aatccgggcg    180
```

atcccagcga tcgtcgtcgc ttcagtgctg accggtggaa agcaggagat ctcgggcgag 240
caggaccaca tccagcccag gatcttcgac tggctcagag ctgaccctca cgcggcacag 300
caaaagtagc acgcacgcgt tatgcaaact ggttacaacc tgtccaacag tgttgcgacg 360
ttgactggct acattgtctg tctgtcgcga gtgcgcctgg gcccttacgg tgggacactg 420
gaactccgcc ccgagtcgaa cacctagggc gacgcccgca gcttggcatg acagctctcc 480
ttgtgttcta aataccttgc gcgtgtggga ga 512

<210> SEQ ID NO 137
<211> LENGTH: 516
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 137
atccaccgat cactccgtcg ccgcccaaga gaattcaacc tcgatggagg gcaaggtgga 60
tcagaggtat tggttatcgt tcgctattag tctcaatcaa tcgtgcacct tgcagttgct 120
cgagtttctc cacacataca gcacctcccg ctcccagccc attcgagcga cccaatccgg 180
gcgatcccag cgatcgtcgt cgcttcagtg ctgaccggtg gaaagcagga gatctcgggc 240
gagcaggacc acatccagca caggatcttc gactggctca gagctgaccc tcacgcggca 300
cagcaaaagt agcccgcacg cgttatgcaa acaggttaca acctgtccaa cactgttgcg 360
acgttgactg gctacattgt ctgtctgtcg cgagtacgcc tggaccctta cggtgggaca 420
ctggaactcc gccccgagtc gaacacctag ggcgacgccc gcagcttggc atgacagctc 480
tccttgtatt ctaaatacct cgcgcgtgtg ggagaa 516

<210> SEQ ID NO 138
<211> LENGTH: 335
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
atgatgcgcg tgtacgacta tcaaggaaga aagaggactt aatttcttac cttctaacca 60
ccatattctt tttgctggat gcttgctcgt ctcgatgaca attgtgaacc tcttgtgtga 120
ccctgaccct gctgcaaggc tctccgaccg cacgcaaggc gcagccggcg cgtccggagg 180
cgatcggatc caatccagtc gtcctcccgc agcccgggca cgtttgccca tgcaggccct 240
tccacaccgc tcaagagact cccgaacacc gcccactcgg cactcgcttc ggctgccgag 300
tgcgcgtttg agtttgccct gccacagaag acacc 335

<210> SEQ ID NO 139
<211> LENGTH: 335
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
atgatgcgcg tgtacgacta tcaaggaaga aagaggactt aatttcttac cttctaacca 60
ccatattctt tttgctggat gcttgctcgt ctcgatgaca attgtgaacc tcttgtgtga 120

```
ccctgaccct gctgcaaggc tctccgaccg cacgcaaggc gcagccggcg cgtccggagg    180

cgatcggatc caatccagtc gtcctcccgc agcccgggca cgtttgccca tgcaggccct    240

tccacaccgc tcaagagact cccgaacacc gcccactcgg cactcgcttc ggctgccgag    300

tgcgcgtttg agtttgccct gccacaggag acatc                               335
```

<210> SEQ ID NO 140
<211> LENGTH: 1097
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
cccgggcgag ctgtacgcct acggagcgag gcctggtgtg accgttgcga tctcgccagc     60

agacgtcgcg gagcctcgtc ccaaaggccc tttctgatcg agcttgtcgt ccactggacg    120

ctttaagttg cgcgcgcgat gggataaccg agctgatctg cactcagatt ttggtttgtt    180

ttcgcgcatg gtgcagcgag gggaggtact acgctggggt acgagatcct ccggattccc    240

agaccgtgtt gccggcattt acccggtcat cgccagcgat tcgggacgac aaggccttat    300

cctgtgctga gacgctcgag cacgtttata aaattgtggg taccgcggta tgcacagcgt    360

tcaacacgcg ccacgccgaa attggttggt gggggagcac gtatgggact gacgtatggc    420

cagcagcgaa cactcaccga acaagtgcca atgtatacct tgcatcaatg atgctccggc    480

agcttcgatt gactgtctcg aaaaagtgtg agcaagcaga tcatgtggcc gctctgtcgc    540

gcagcacctg acgcattcga cacccacggc aatgcccagg ccagggaata gagagtaaga    600

caactcccat tgttcagcaa aacattgcac tgcagtgcct tcacaactat acaatgaatg    660

ggagggaata tgggctctgc atgggacagc ttagctggga cattcggcta ctgaacaaga    720

aaaccccacg agaaccaatt ggcgaaacct gccgggagga ggtgatcgtt tctgtaaatg    780

gcttacgcat tcccccccgg cggctcacga ggggtgtggt gaaccctgcc agctgatcaa    840

gtgcttgctg acgtcggcca gggaggtgta tgtgattggg ccgtggggcg tgagttatcc    900

taccgccgga cccgcgaagt cacatgacga atggccgtgc gggatgacga gagcacgact    960

cgctctttct tcgccggccc ggcttcatgg aggacaataa taaagggtgg ccaccggcaa   1020

cagccctcca tacctgaacc gattccagac ccaaacctct tgaattttga gggatccagt   1080

tcaccggtat agtcacg                                                  1097
```

<210> SEQ ID NO 141
<211> LENGTH: 1105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

```
atccccgggc gagctgtacg cctacggagc gaggcctggt gtgaccgttg cgatctcgcc     60

agcagacgtc gcggagcctc gtcccaaagg ccctttctga tcgagcttgt cgtccactgg    120

acgctttaag ttgcgcgcgc gatgggataa ccgagctgat ctgcactcag attttggttt    180

gttttcgcgc atggtgcagc gaggggaggt actacgctgg ggtacgagat cctccggatt    240

cccagaccgt gttgccggca tttacccggt catcgccagc gattcgggac gacaaggcct    300
```

-continued tatcctgtgc tgagacgctc gagcacgttt ataaaattgt ggtcaccgtg gtacgcacag 360
cgtccaacac gcgccacgcc gaaattcgtt ggtgggggag cacgtatcgg actgacgtat 420
ggccagcagc gaacactcac caaacaggtg ccaatgtata gcttgcatca atgatgctct 480
ggcagcttcg attgactgtc tcgaaaaagt gtgtgcaaac agattatgtg gccgctctgt 540
ggccgcgcag cacctgacgc actcgacacc cacggcaatg cccaggccaa ggaacagaga 600
gtaagacaac tcccattgtt cagtaaaaca ttgcactgca gtgccttcac aaacatacaa 660
cgaatgggag ggaatatggg cttcgaatgg gacagcttag ctgggacatt cggttactga 720
acaagaaaac cccacgagaa ccaactggcg aaacctgccg ggaggaggtg atcgtttttg 780
taaatggctt acgcattccc cccccggcgg ctcacggggg gtgtggtgaa ccctgccagc 840
tgatcaagtg cttgctgacg tcggccaggg aggtgtatgt gatttggccg tggggcgtga 900
gttatcctac cgccggaccc gcgaagtcac atgacgaatg gccgtgcggg atgacgagag 960
cagggctcgc tctttcttcg ccggcccggc ttcatggagg acaataataa agggtggcca 1020
ccggcaacag ccctccatac ctgaaccgat tccagaccca aacctcttga attttgaggg 1080
atccagttca ccggtatagt cacga 1105

<210> SEQ ID NO 142
<211> LENGTH: 754
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 142
gcgagtggtt ttgctgccgg gaagggagtg gggagcgtcg agcgagggac gcggcgctcg 60
aggcgcacgt cgtctgtcaa cgcgcgcggc cctcgcggcc cgcggcccca cccagctcta 120
atcatcgaaa actaagaggc tccacacgcc tgtcgtagaa tgcatgggat tcgccagtag 180
accacgatct gcgccgaaga agctggtcta cccgacgttt tttgttgctc ctttattctg 240
aatgatatga agatagtgtg cgcagtgcca cgcataggca tcaggagcaa gggaggacgg 300
gtcaacttga aagaaccaaa ccatccatcc gagaaatgcg catcatcttt gtagtaccat 360
caaacgcctt ggccaatgtc ttctgcatgg acaacacaac ctgctcctgg ccacacggtc 420
gacttggagc gccccatgcg cccaggtcgc cacgacccgc ggcccagcgc gcggcgattc 480
gcctcacgag atcccggcgg acccggcacg cccgcgggcc gacggtgcgc ttggcgatgc 540
tgctcattaa cccacggccg tcacccgatc cacatgctct ttttcaacac atccacattg 600
gaatagagct ctaccagggt gagtactgca ttctttgggg ctgggaggac cccactcgac 660
acctggtcct tcatcggccg aaagcccgaa cctgagcgct tccccgcccc gttcctcatc 720
cccgactttc cgatggccca ttgcagtttc aaac 754

<210> SEQ ID NO 143
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 143
atctgggtgg aggactggga gtaagatgta aggatattaa ttaaacattc tagtttgttg 60
atggcacaac agtcaatgca tttcagtcgt cttgctcctt ataacctatg cgtgtgccat 120

```
cgccggccat gcacctgtgg cgtggtaccg accatcgggg agaggcccga gattcggagg    180

tacctcccgc cctgggcgag cccttcacgt gacggcacaa gtcccttgca tcggcccgcg    240

agcacggaat acagagcccc gtgcccccca cgggccctca catcatccac tccattgttc    300

ttgccacacc gatcagca                                                 318
```

<210> SEQ ID NO 144
<211> LENGTH: 316
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
tgggtggagg actgggaaga agatgtaagg atatcaattt aacattctag tttgttgatg     60

gcacaacagt cactgaatac cgggcgtctg gctgctaaaa tagccggagc gtgtgccatc    120

gccggccatg catctgtggc gtggtaccga ccatcaggga gaggcccgag attcggaggt    180

acctcccgcc ctgggcgagc ccttcacgtg acggcacaag tcccttgcat cggcccgcga    240

gcacggaata cagagccccg tgctccccac gggccctcac atcatccact ccattgttct    300

tgccacaccg atcagc                                                   316
```

<210> SEQ ID NO 145
<211> LENGTH: 350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

```
ataacgaggc acaatgatcg atatttctat cgaacaactg tatttagccc tgtacgtacc     60

ccgctcttgg gccagcccgt ccgtgcttgc cttcggaaaa ttgcatggcg cctcatgcaa    120

actcgcgctc tcacagcaga tctcgcccag ctcccgggag agcaatcgcg ggtggggccc    180

ggggcgaatc caggacgcgc cccgcggggc cgctccactc gccagggcca atgggcggct    240

tatagtcctg gcatgggctc tgcatgcaca gtatcgcagt ttgggcgagg tgttgccccc    300

gcgatttcga atacgcgacg cccggtactc gtgcgagaac agggttcttg               350
```

<210> SEQ ID NO 146
<211> LENGTH: 818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146

```
atcgcgatgg tgcgcactcg tgcgcaatga atatggggtc acgcggtgga cgaacgcgga     60

gggggcctgg ccgaatctag gcttgcattc ctcagatcac tttctgccgg cggtccgggg    120

tttgcgcgtc gcgcaacgct ccgtctccct agccgctgcg caccgcgcgt gcgacgcgaa    180

ggtcattttc cagaacaacg accatggctt gtcttagcga tcgctcgaat gactgctagt    240

gagtcgtacg ctcgacccag tcgctcgcag gagaacgcgg caactgccga gcttcggctt    300

gccagtcgtg actcgtatgt gatcaggaat cattggcatt ggtagcatta taattcggct    360

tccgcgctgt ttatgggcat ggcaatgtct catgcagtcg accttagtca accaattctg    420
```

ggtggccagc tccgggcgac cgggctccgt gtcgccgggc accacctcct gccatgagta 480
acagggccgc cctctcctcc cgacgttggc ccactgaata ccgtgtcttg gggccctaca 540
tgatgggctg cctagtcggg cgggacgcgc aactgcccgc gcaatctggg acgtggtctg 600
aatcctccag gcgggtttcc ccgagaaaga aagggtgccg atttcaaagc agagccatgt 660
gccgggccct gtggcctgtg ttggcgccta tgtagtcacc ccccctcacc caattgtcgc 720
cagtttgcgc aatccataaa ctcaaaactg cagcttctga gctgcgctgt tcaagaacac 780
ctctggggtt tgctcacccg cgaggtcgac gcccagca 818

<210> SEQ ID NO 147
<211> LENGTH: 819
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147
atcacgatgg tgcgcattcg tgcaaagtga atatggggtc acgcggtgga cgaacgcgga 60
gggggcatga ccgaatctag gctcgcattc ctcagatcac ttcatgccgg cggtccgggg 120
tttgcgcgtc gcgcaaggct acgtctccct agccgctgcg caccacgcgt gcgacgcgga 180
ggccatcttc cggagcaacg accatggatt gtcttagcga tcgcacgaat gagtgctagt 240
gagtcgtacg ctcgacccag tcgctcgcag gagaaggcgg cagctgccga gcttcggctt 300
accagtcgtg actcgtatgt gatcaggaat cattggcatt ggtagcatta taattcggct 360
tccgcgctgc gtatgggcat ggcaatgtct catgcagtcg atcttagtca accaattttg 420
ggtggccagg tccgggcgac cgggctccgt gtcgccgggc accacctcct gccaggagta 480
gcagggccgc cctctcgtcc cgacgttggc ccactgaata ccgtggcttc gagccctaca 540
tgatgggctg cctagtcggg cgggacgcgc aactgcccgc gcgatctggg ggctggtctg 600
aatccttcag gcgggtgtta cccgagaaag aaagggtgcc gatttcaaag cagacccatg 660
tgccgggccc tgtggcctgt gttggcgcct atgtagtcac ccccccctcac ccaattgtcg 720 ccagtttgcg cactccataa actcaaaaca gcagcttctg agctgcgctg ttcaagaaca 780
cctctggggt ttgctcaccc gcgaggtcga cgcccagca 819

<210> SEQ ID NO 148
<211> LENGTH: 5104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148
gaagagcgcc caatgtttaa acgccggtca ccacccgcat gctcgtacta cagcgcacgc 60
accgcttcgt gatccaccgg gtgaacgtag tcctcgacgg aaacatctgg ttcgggcctc 120
ctgcttgcac tcccgcccat gccgacaacc tttctgctgt taccacgacc cacaatgcaa 180
cgcgacacga ccgtgtggga ctgatcggtt cactgcacct gcatgcaatt gtcacaagcg 240
cttactccaa ttgtattcgt ttgttttctg ggagcagttg ctcgaccgcc cgcgtcccgc 300
aggcagcgat gacgtgtgcg tggcctgggt gtttcgtcga aaggccagca accctaaatc 360
gcaggcgatc cggagattgg gatctgatcc gagtttggac cagatccgcc ccgatgcggc 420

-continued

```
acgggaactg catcgactcg gcgcggaacc cagctttcgt aaatgccaga ttggtgtccg    480
atacctggat ttgccatcag cgaaacaaga cttcagcagc gagcgtattt ggcgggcgtg    540
ctaccagggt tgcatacatt gcccatttct gtctggaccg ctttactggc gcagagggtg    600
agttgatggg gttggcaggc atcgaaacgc gcgtgcatgg tgtgcgtgtc tgttttcggc    660
tgcacgaatt caatagtcgg atgggcgacg gtagaattgg gtgtggcgct cgcgtgcatg    720
cctcgccccg tcgggtgtca tgaccgggac tggaatcccc cctcgcgacc atcttgctaa    780
cgctcccgac tctcccgacc gcgcgcagga tagactcttg ttcaaccaat cgacaggtac    840
cagtttaggt ccagcgtccg tggggggga cgggctggga gcttgggccg ggaagggcaa    900
gacgatgcag tccctctggg gagtcacagc cgactgtgtg tgttgcactg tgcggcccgc    960
agcactcaca cgcaaaatgc ctggccgaca ggcaggccct gtccagtgca acatccacgg   1020
tccctctcat caggctcacc ttgctcattg acataacgga atgcgtaccg ctctttcaga   1080
tctgtccatc cagagagggg agcaggctcc ccaccgacgc tgtcaaactt gcttcctgcc   1140
caaccgaaaa cattattgtt tgaggggggg gggggggggg cagattgcat ggcgggatat   1200
ctcgtgagga acatcactgg gacactgtgg aacacagtga gtgcagtatg cagagcatgt   1260
atgctagggg tcagcgcagg aagggggcct ttcccagtct cccatgccac tgcaccgtat   1320
ccacgactca ccaggaccag cttcttgatc ggcttccgct cccgtggaca ccagtgtgta   1380
gcctctggac tccaggtatg cgtgcaccgc aaaggccagc cgatcgtgcc gattcctggg   1440
tggaggatat gagtcagcca acttggggct cagagtgcac actggggcac gatacgaaac   1500
aacatctaca ccgtgtcctc catgctgaca caccacagct tcgctccacc tgaatgtggg   1560
cgcatgggcc cgaatcacag ccaatgtcgc tgctgccata atgtgatcca gaccctctcc   1620
gcccagatgc cgagcggatc gtgggcgctg aatagattcc tgtttcgatc actgtttggg   1680
tcctttcctt ttcgtctcgg atgcgcgtct cgaaacaggc tgcgtcgggc tttcggatcc   1740
cttttgctcc ctccgtcacc atcctgcgcg cgggcaagtt gcttgaccct gggctgatac   1800
cagggttgga gggtattacc gcgtcaggcc attcccagcc cggattcaat tcaaagtctg   1860
ggccaccacc ctccgccgct ctgtctgatc actccacatt cgtgcataca ctacgttcaa   1920
gtcctgatcc aggcgtgtct cgggacaagg tgtgcttgag tttgaatctc aaggacccac   1980
tccagcacag ctgctggttg accccgccct cgcaatctag aatggccgcg tccgtccact   2040
gcaccctgat gtccgtggtc tgcaacaaca agaaccactc cgcccgcccc aagctgccca   2100
actcctccct gctgcccggc ttcgacgtgg tggtccaggc cgcggccacc cgcttcaaga   2160
aggagacgac gaccacccgc gccacgctga cgttcgaccc ccccacgacc aactccgagc   2220
gcgccaagca gcgcaagcac accatcgacc cctcctcccc cgacttccag cccatcccct   2280
ccttcgagga gtgcttcccc aagtccacga aggagcacaa ggaggtggtg cacgaggagt   2340
ccggccacgt cctgaaggtg cccttccgcc gcgtgcacct gtccggcggc gagcccgcct   2400
tcgacaacta cgacacgtcc ggcccccaga acgtcaacgc ccacatcggc ctggcgaagc   2460
tgcgcaagga gtggatcgac cgccgcgaga agctgggcac gccccgctac acgcagatgt   2520
actacgcgaa gcagggcatc atcacggagg agatgctgta ctgcgcgacg cgcgagaagc   2580
tggaccccga gttcgtccgc tccgaggtcg cgcggggccg cgccatcatc ccctccaaca   2640
agaagcacct ggagctggag cccatgatcg tgggccgcaa gttcctggtg aaggtgaacg   2700
cgaacatcgg caactccgcc gtggcctcct ccatcgagga ggaggtctac aaggtgcagt   2760
gggccaccat gtggggcgcc gacaccatca tggacctgtc cacgggccgc cacatccacg   2820
```

```
agacgcgcga gtggatcctg cgcaactccg cggtccccgt gggcaccgtc cccatctacc   2880
aggcgctgga gaaggtggac ggcatcgcgg agaacctgaa ctgggaggtg ttccgcgaga   2940
cgctgatcga gcaggccgag cagggcgtgg actacttcac gatccacgcg ggcgtgctgc   3000
tgcgctacat ccccctgacc gccaagcgcc tgacgggcat cgtgtcccgc ggcggctcca   3060
tccacgcgaa gtggtgcctg gcctaccaca aggagaactt cgcctacgag cactgggacg   3120
acatcctgga catctgcaac cagtacgacg tcgccctgtc catcggcgac ggcctgcgcc   3180
ccggctccat ctacgacgcc aacgacacgg cccagttcgc cgagctgctg acccagggcg   3240
agctgacgcg ccgcgcgtgg gagaaggacg tgcaggtgat gaacgagggc cccggccacg   3300
tgcccatgca caagatcccc gagaacatgc agaagcagct ggagtggtgc aacgaggcgc   3360
ccttctacac cctgggcccc ctgacgaccg acatcgcgcc cggctacgac cacatcacct   3420
ccgccatcgg cgcggccaac atcggcgccc tgggcaccgc cctgctgtgc tacgtgacgc   3480
ccaaggagca cctgggcctg cccaaccgcg acgacgtgaa ggcgggcgtc atcgcctaca   3540
agatcgccgc ccacgcggcc gacctggcca agcagcaccc ccacgcccag gcgtgggacg   3600
acgcgctgtc caaggcgcgc ttcgagttcc gctggatgga ccagttcgcg ctgtccctgg   3660
accccatgac ggcgatgtcc ttccacgacg agacgctgcc cgcggacggc gcgaaggtcg   3720
cccacttctg ctccatgtgc ggccccaagt tctgctccat gaagatcacg gaggacatcc   3780
gcaagtacgc cgaggagaac ggctacggct ccgccgagga ggccatccgc cagggcatgg   3840
acgccatgtc cgaggagttc aacatcgcca agaagacgat ctccggcgag cagcacggcg   3900
aggtcggcgg cgagatctac ctgcccgagt cctacgtcaa ggccgcgcag aagtgacaat   3960
tggcagcagc agctcggata gtatcgacac actctggacg ctggtcgtgt gatggactgt   4020
tgccgccaca cttgctgcct tgacctgtga atatccctgc cgcttttatc aaacagcctc   4080
agtgtgtttg atcttgtgtg tacgcgcttt tgcgagttgc tagctgcttg tgctatttgc   4140
gaataccacc cccagcatcc ccttccctcg tttcatatcg cttgcatccc aaccgcaact   4200
tatctacgct gtcctgctat ccctcagcgc tgctcctgct cctgctcact gcccctcgca   4260
cagccttggt ttgggctccg cctgtattct cctggtactg caacctgtaa accagcactg   4320
caatgctgat gcacgggaag tagtgggatg ggaacacaaa tggaggatcg tagagctcta   4380
gggagcgacg agtgtgcgtg cggggctggc gggagtggga cgccctcctc gctcctctct   4440
gttctgaacg gaacaatcgg ccaccccgcg ctacgcgcca cgcatcgagc aacgaagaaa   4500
accccccgat gataggttgc ggtggctgcc gggatataga tccggccgca catcaaaggg   4560
cccctccgcc agagaagaag ctcctttccc agcagactcc ttctgctgcc aaaacacttc   4620
tctgtccaca gcaacaccaa aggatgaaca gatcaacttg cgtctccgcg tagcttcctc   4680
ggctagcgtg cttgcaacag gtccctgcac tattatcttc ctgctttcct ctgaattatg   4740
cggcaggcga gcgctcgctc tggcgagcgc tccttcgcgc cgccctcgct gatcgagtgt   4800
acagtcaatg aatggtcctg ggcgaagaac gagggaattt gtgggtaaaa caagcatcgt   4860
ctctcaggcc ccggcgcagt ggccgttaaa gtccaagacc gtgaccaggc agcgcagcgc   4920
gtccgtgtgc gggccctgcc tggcggctcg gcgtgccagg ctcgagagca gctccctcag   4980
gtcgccttgg acggcctctg cgaggccggt gagggcctgc aggagcgcct cgagcgtggc   5040
agtggcggtc gtatccgggt cgccggtcac cgcctgcgac tcgccatccg aagagcgttt   5100
aaac                                                                5104
```

<210> SEQ ID NO 149
<211> LENGTH: 5110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 149
gtttaaacgc cggtcaccac ccgcatgctc gtactacagc gcacgcaccg cttcgtgatc 60
caccgggtga acgtagtcct cgacggaaac atctggttcg ggcctcctgc ttgcactccc 120
gcccatgccg acaacctttc tgctgttacc acgacccaca atgcaacgcg acacgaccgt 180
gtgggactga tcggttcact gcacctgcat gcaattgtca caagcgctta ctccaattgt 240
attcgtttgt tttctgggag cagttgctcg accgcccgcg tcccgcaggc agcgatgacg 300
tgtgcgtggc ctgggtgttt cgtcgaaagg ccagcaaccc taaatcgcag gcgatccgga 360
gattgggatc tgatccgagt ttggaccaga tccgccccga tgcggcacgg gaactgcatc 420
gactcggcgc ggaacccagc tttcgtaaat gccagattgg tgtccgatac ctggatttgc 480
catcagcgaa acaagacttc agcagcgagc gtatttggcg ggcgtgctac cagggttgca 540
tacattgccc atttctgtct ggaccgcttt actggcgcag agggtgagtt gatggggttg 600
gcaggcatcg aaacgcgcgt gcatggtgtg cgtgtctgtt ttcggctgca cgaattcaat 660
agtcggatgg gcgacggtag aattgggtgt ggcgctcgcg tgcatgcctc gccccgtcgg 720
gtgtcatgac cgggactgga atccccccctc gcgaccatct tgctaacgct cccgactctc 780
ccgaccgcgc gcaggataga ctcttgttca accaatcgac aggtaccagt ttaggtccag 840
cgtccgtggg gggggacggg ctgggagctt gggccgggaa gggcaagacg atgcagtccc 900
tctggggagt cacagccgac tgtgtgtgtt gcactgtgcg gcccgcagca ctcacacgca 960
aaatgcctgg ccgacaggca ggccctgtcc agtgcaacat ccacggtccc tctcatcagg 1020
ctcaccttgc tcattgacat aacggaatgc gtaccgctct ttcagatctg tccatccaga 1080
gaggggagca ggctccccac cgacgctgtc aaacttgctt cctgcccaac cgaaaacatt 1140
attgtttgag gggggggggg ggggggcaga ttgcatggcg ggatatctcg tgaggaacat 1200
cactgggaca ctgtggaaca cagtgagtgc agtatgcaga gcatgtatgc taggggtcag 1260
cgcaggaagg gggcctttcc cagtctccca tgccactgca ccgtatccac gactcaccag 1320
gaccagcttc ttgatcggct tccgctcccg tggacaccag tgtgtagcct ctggactcca 1380
ggtatgcgtg caccgcaaag gccagccgat cgtgccgatt cctgggtgga ggatatgagt 1440
cagccaactt ggggctcaga gtgcacactg gggcacgata cgaaacaaca tctacaccgt 1500
gtcctccatg ctgacacacc acagcttcgc tccacctgaa tgtgggcgca tgggcccgaa 1560
tcacagccaa tgtcgctgct gccataatgt gatccagacc ctctccgccc agatgccgag 1620
cggatcgtgg gcgctgaata gattcctgtt tcgatcactg tttgggtcct ttccttttcg 1680
tctcggatgc gcgtctcgaa acaggctgcg tcgggctttc ggatcccttt tgctccctcc 1740
gtcaccatcc tgcgcgcggg caagttgctt gaccctgggc tgataccagg gttggagggt 1800
attaccgcgt caggccattc ccagcccgga ttcaattcaa agtctgggcc accaccctcc 1860
gccgctctgt ctgatcactc cacattcgtg catacactac gttcaagtcc tgatccaggc 1920
gtgtctcggg acaaggtgtg cttgagtttg aatctcaagg acccactcca gcacagctgc 1980
tggttgaccc cgccctcgca atctagaatg gccgcgtccg tccactgcac cctgatgtcc 2040

-continued

```
gtggtctgca acaacaagaa ccactccgcc cgccccaagc tgcccaactc ctccctgctg   2100
cccggcttcg acgtggtggt ccaggccgcg gccacccgct tcaagaagga gacgacgacc   2160
acccgcgcca cgctgacgtt cgaccccccc acgaccaact ccgagcgcgc caagcagcgc   2220
aagcacacca tcgacccctc ctcccccgac ttccagccca tcccctcctt cgaggagtgc   2280
ttccccaagt ccacgaagga gcacaaggag gtggtgcacg aggagtccgg ccacgtcctg   2340
aaggtgccct tccgccgcgt gcacctgtcc ggcggcgagc ccgccttcga caactacgac   2400
acgtccggcc cccagaacgt caacgcccac atcggcctgg cgaagctgcg caaggagtgg   2460
atcgaccgcc gcgagaagct gggcacgccc cgctacacgc agatgtacta cgcgaagcag   2520
ggcatcatca cggaggagat gctgtactgc gcgacgcgcg agaagctgga ccccgagttc   2580
gtccgctccg aggtcgcgcg gggccgcgcc atcatcccct ccaacaagaa gcacctggag   2640
ctggagccca tgatcgtggg ccgcaagttc ctggtgaagg tgaacgcgaa catcggcaac   2700
tccgccgtgg cctcctccat cgaggaggag gtctacaagg tgcagtgggc caccatgtgg   2760
ggcgccgaca ccatcatgga cctgtccacg ggccgccaca tccacgagac gcgcgagtgg   2820
atcctgcgca actccgcggt ccccgtgggc accgtcccca tctaccaggc gctggagaag   2880
gtggacggca tcgcggagaa cctgaactgg gaggtgttcc gcgagacgct gatcgagcag   2940
gccgagcagg gcgtggacta cttcacgatc cacgcgggcg tgctgctgcg ctacatcccc   3000
ctgaccgcca agcgcctgac gggcatcgtg tcccgcggcg gctccatcca cgcgaagtgg   3060
tgcctggcct accacaagga gaacttcgcc tacgagcact gggacgacat cctggacatc   3120
tgcaaccagt acgacgtcgc cctgtccatc ggcgacggcc tgcgccccgg ctccatctac   3180
gacgccaacg acacggccca gttcgccgag ctgctgaccc agggcgagct gacgcgccgc   3240
gcgtgggaga aggacgtgca ggtgatgaac gagggccccg gccacgtgcc catgcacaag   3300
atccccgaga acatgcagaa gcagctggag tggtgcaacg aggcgccctt ctacaccctg   3360
ggcccccctga cgaccgacat cgcgcccggc tacgaccaca tcacctccgc catcggcgcg   3420
gccaacatcg gcgccctggg caccgccctg ctgtgctacg tgacgcccaa ggagcacctg   3480
ggcctgccca accgcgacga cgtgaaggcg ggcgtcatcg cctacaagat cgccgcccac   3540
gcggccgacc tggccaagca gcacccccac gcccaggcgt gggacgacgc gctgtccaag   3600
gcgcgcttcg agttccgctg gatggaccag ttcgcgctgt ccctggaccc catgacggcg   3660
atgtccttcc acgacgagac gctgcccgcg gacggcgcga aggtcgccca cttctgctcc   3720
atgtgcggcc ccaagttctg ctccatgaag atcacggagg acatccgcaa gtacgccgag   3780
gagaacggct acggctccgc cgaggaggcc atccgccagg gcatggacgc catgtccgag   3840
gagttcaaca tcgccaagaa gacgatctcc ggcgagcagc acggcgaggt cggcggcgag   3900
atctacctgc ccgagtccta cgtcaaggcc gcgcagaagt gacaattggc agcagcagct   3960
cggatagtat cgacacactc tggacgctgg tcgtgtgatg gactgttgcc gccacacttg   4020
ctgccttgac ctgtgaatat ccctgccgct tttatcaaac agcctcagtg tgtttgatct   4080
tgtgtgtacg cgcttttgcg agttgctagc tgcttgtgct atttgcgaat accaccccca   4140
gcatcccctt ccctcgtttc atatcgcttg catcccaacc gcaacttatc tacgctgtcc   4200
tgctatccct cagcgctgct cctgctcctg ctcactgccc ctcgcacagc cttggtttgg   4260
gctccgcctg tattctcctg gtactgcaac ctgtaaacca gcactgcaat gctgatgcac   4320
gggaagtagt gggatgggaa cacaaatgga ggatcgtaga gctccagcca cggcaacacc   4380
gcgcgccttg cggccgagca cggcgacaag aacctgagca agatctgcgg gctgatcgcc   4440
```

agcgacgagg gccggcacga gatcgcctac acgcgcatcg tggacgagtt cttccgcctc 4500
gaccccgagg gcgccgtcgc cgcctacgcc aacatgatgc gcaagcagat caccatgccc 4560
gcgcacctca tggacgacat gggccacggc gaggccaacc cgggccgcaa cctcttcgcc 4620
gacttctccg cggtcgccga gaagatcgac gtctacgacg ccgaggacta ctgccgcatc 4680
ctggagcacc tcaacgcgcg ctggaaggtg gacgagcgcc aggtcagcgg ccaggccgcc 4740
gcggaccagg agtacgtcct gggcctgccc cagcgcttcc ggaaactcgc cgagaagacc 4800
gccgccaagc gcaagcgcgt cgcgcgcagg cccgtcgcct tctcctggat ctccgggcgc 4860
gagatcatgg tctagggagc gacgagtgtg cgtgcggggc tggcgggagt gggacgccct 4920
cctcgctcct ctctgttctg aacggaacaa tcggccaccc cgcgctacgc gccacgcatc 4980
gagcaacgaa gaaaaccccc cgatgatagg ttgcggtggc tgccgggata tagatccggc 5040
cgcacatcaa agggcccctc cgccagagaa gaagctcctt tcccagcaga ctcctgaaga 5100
gcgtttaaac 5110

<210> SEQ ID NO 150
<211> LENGTH: 5129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 150
gaagagcgcc caatgtttaa acgccggtca ccatccgcat gctcatatta cagcgcacgc 60
accgcttcgt gatccaccgg gtgaacgtag tcctcgacgg aaacatctgg ctcgggcctc 120
gtgctggcac tccctcccat gccgacaacc tttctgctgt caccacgacc cacgatgcaa 180
cgcgacacga cccggtggga ctgatcggtt cactgcacct gcatgcaatt gtcacaagcg 240
catactccaa tcgtatccgt ttgatttctg tgaaaactcg ctcgaccgcc cgcgtcccgc 300
aggcagcgat gacgtgtgcg tgacctgggt gtttcgtcga aaggccagca accccaaatc 360
gcaggcgatc cggagattgg gatctgatcc gagcttggac cagatccccc acgatgcggc 420
acgggaactg catcgactcg gcgcggaacc cagctttcgt aaatgccaga ttggtgtccg 480
ataccttgat ttgccatcag cgaaacaaga cttcagcagc gagcgtattt ggcgggcgtg 540
ctaccagggt tgcatacatt gcccatttct gtctggaccg ctttaccggc gcagagggtg 600
agttgatggg gttggcaggc atcgaaacgc gcgtgcatgg tgtgtgtgtc tgttttcggc 660
tgcacaattt caatagtcgg atgggcgacg gtagaattgg gtgttgcgct cgcgtgcatg 720
cctcgccccg tcgggtgtca tgaccgggac tggaatcccc cctcgcgacc ctcctgctaa 780
cgctcccgac tctcccgccc gcgcgcagga tagactctag ttcaaccaat cgacaggtac 840
cagtttaggt ccagcgtccg tgggggggga cgggctggga gcttgggccg ggaagggcaa 900
gacgatgcag tccctctggg gagtcacagc cgactgtgtg tgttgcactg tgcggcccgc 960
agcactcaca cgcaaaatgc ctggccgaca ggcaggccct gtccagtgca acatccacgg 1020
tccctctcat caggctcacc ttgctcattg acataacgga atgcgtaccg ctctttcaga 1080
tctgtccatc cagagagggg agcaggctcc ccaccgacgc tgtcaaactt gcttcctgcc 1140
caaccgaaaa cattattgtt tgaggggggg gggggggggg cagattgcat ggcgggatat 1200
ctcgtgagga acatcactgg gacactgtgg aacacagtga gtgcagtatg cagagcatgt 1260
atgctagggg tcagcgcagg aagggggcct ttcccagtct cccatgccac tgcaccgtat 1320

-continued

```
ccacgactca ccaggaccag cttcttgatc ggcttccgct cccgtggaca ccagtgtgta   1380
gcctctggac tccaggtatg cgtgcaccgc aaaggccagc cgatcgtgcc gattcctggg   1440
tggaggatat gagtcagcca acttggggct cagagtgcac actggggcac gatacgaaac   1500
aacatctaca ccgtgtcctc catgctgaca caccacagct tcgctccacc tgaatgtggg   1560
cgcatgggcc cgaatcacag ccaatgtcgc tgctgccata atgtgatcca gaccctctcc   1620
gcccagatgc cgagcggatc gtgggcgctg aatagattcc tgtttcgatc actgtttggg   1680
tcctttcctt ttcgtctcgg atgcgcgtct cgaaacaggc tgcgtcgggc tttcggatcc   1740
cttttgctcc ctccgtcacc atcctgcgcg cgggcaagtt gcttgaccct gggctgatac   1800
cagggttgga gggtattacc gcgtcaggcc attcccagcc cggattcaat tcaaagtctg   1860
ggccaccacc ctccgccgct ctgtctgatc actccacatt cgtgcataca ctacgttcaa   1920
gtcctgatcc aggcgtgtct cgggacaagg tgtgcttgag tttgaatctc aaggacccac   1980
tccagcacag ctgctggttg accccgccct cgcaatctag aatggccgcg tccgtccact   2040
gcaccctgat gtccgtggtc tgcaacaaca agaaccactc cgcccgcccc aagctgccca   2100
actcctccct gctgcccggc ttcgacgtgg tggtccaggc cgcggccacc cgcttcaaga   2160
aggagacgac gaccacccgc gccacgctga cgttcgaccc ccccacgacc aactccgagc   2220
gcgccaagca gcgcaagcac accatcgacc cctcctcccc cgacttccag cccatcccct   2280
ccttcgagga gtgcttcccc aagtccacga aggagcacaa ggaggtggtg cacgaggagt   2340
ccggccacgt cctgaaggtg cccttccgcc gcgtgcacct gtccggcggc gagcccgcct   2400
tcgacaacta cgacacgtcc ggcccccaga acgtcaacgc ccacatcggc ctggcgaagc   2460
tgcgcaagga gtggatcgac cgccgcgaga agctgggcac gccccgctac acgcagatgt   2520
actacgcgaa gcagggcatc atcacggagg agatgctgta ctgcgcgacg cgcgagaagc   2580
tggaccccga gttcgtccgc tccgaggtcg cgcggggccg cgccatcatc ccctccaaca   2640
agaagcacct ggagctggag cccatgatcg tgggccgcaa gttcctggtg aaggtgaacg   2700
cgaacatcgg caactccgcc gtggcctcct ccatcgagga ggaggtctac aaggtgcagt   2760
gggccaccat gtggggcgcc gacaccatca tggacctgtc cacgggccgc cacatccacg   2820
agacgcgcga gtggatcctg cgcaactccg cggtccccgt gggcaccgtc cccatctacc   2880
aggcgctgga gaaggtggac ggcatcgcgg agaacctgaa ctgggaggtg ttccgcgaga   2940
cgctgatcga gcaggccgag cagggcgtgg actacttcac gatccacgcg ggcgtgctgc   3000
tgcgctacat ccccctgacc gccaagcgcc tgacgggcat cgtgtcccgc ggcggctcca   3060
tccacgcgaa gtggtgcctg gcctaccaca aggagaactt cgcctacgag cactgggacg   3120
acatcctgga catctgcaac cagtacgacg tcgccctgtc catcggcgac ggcctgcgcc   3180
ccggctccat ctacgacgcc aacgacacgg cccagttcgc cgagctgctg acccagggcg   3240
agctgacgcg ccgcgcgtgg gagaaggacg tgcaggtgat gaacgagggc cccggccacg   3300
tgcccatgca caagatcccc gagaacatgc agaagcagct ggagtggtgc aacgaggcgc   3360
ccttctacac cctgggcccc ctgacgaccg acatcgcgcc cggctacgac cacatcacct   3420
ccgccatcgg cgcggccaac atcggcgccc tgggcaccgc cctgctgtgc tacgtgacgc   3480
ccaaggagca cctgggcctg cccaaccgcg acgacgtgaa ggcgggcgtc atcgcctaca   3540
agatcgccgc ccacgcggcc gacctggcca agcagcaccc ccacgcccag gcgtgggacg   3600
acgcgctgtc caaggcgcgc ttcgagttcc gctggatgga ccagttcgcg ctgtccctgg   3660
```

```
accccatgac ggcgatgtcc ttccacgacg agacgctgcc cgcggacggc gcgaaggtcg   3720
cccacttctg ctccatgtgc ggccccaagt tctgctccat gaagatcacg gaggacatcc   3780
gcaagtacgc cgaggagaac ggctacggct ccgccgagga ggccatccgc cagggcatgg   3840
acgccatgtc cgaggagttc aacatcgcca agaagacgat ctccggcgag cagcacggcg   3900
aggtcggcgg cgagatctac ctgcccgagt cctacgtcaa ggccgcgcag aagtgacaat   3960
tggcagcagc agctcggata gtatcgacac actctggacg ctggtcgtgt gatggactgt   4020
tgccgccaca cttgctgcct tgacctgtga atatccctgc cgcttttatc aaacagcctc   4080
agtgtgtttg atcttgtgtg tacgcgcttt tgcgagttgc tagctgcttg tgctatttgc   4140
gaataccacc cccagcatcc ccttccctcg tttcatatcg cttgcatccc aaccgcaact   4200
tatctacgct gtcctgctat ccctcagcgc tgctcctgct cctgctcact gcccctcgca   4260
cagccttggt ttgggctccg cctgtattct cctggtactg caacctgtaa accagcactg   4320
caatgctgat gcacgggaag tagtgggatg ggaacacaaa tggaggatcg tagagctcca   4380
gccacggcaa caccgcgcgc ctggcggccg agcacggcga caagggcctg agcaagatct   4440
gcgggctgat cgccagcgac gagggccggc acgagatcgc ctacacgcgc atcgtggacg   4500
agttcttccg cctcgacccc gagggcgccg tcgccgccta cgccaacatg atgcgcaagc   4560
agatcaccat gcccgcgcac ctcatggacg acatgggcca cggcgaggcc aacccgggcc   4620
gcaacctctt cgccgacttc tccgccgtcg ccgagaagat cgacgtctac gacgccgagg   4680
actactgccg catcctggag cacctcaacg cgcgctggaa ggtggacgag cgccaggtca   4740
gcggccaggc cgccgcggac caggagtacg ttctgggcct gccccagcgc ttccggaaac   4800
tcgccgagaa gaccgccgcc aagcgcaagc gcgtcgcgcg caggcccgtc gccttctcct   4860
ggatctccgg acgcgagatt atggtctagg gaggtacgag cgcgcgcgag ggattggtgg   4920
gagtgggacg cgctcgtcgc tcctttctat tctgaaggga agattggcca ccccgctcca   4980
cgcgccacgc atcgagcaac gaagaaaacc ccccgatgat aggttgcagt ggctgccgag   5040
atatagatcc ggctgcacgt caaagggccc ctcggccaga gaagaagctc ttttcccagc   5100
gaccgcagac tcctgaagag cgtttaaac                                     5129
```

<210> SEQ ID NO 151
<211> LENGTH: 7194
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 151

```
gtttaaacgc cggtcaccac ccgcatgctc gtactacagc gcacgcaccg cttcgtgatc     60
caccgggtga acgtagtcct cgacggaaac atctggttcg ggcctcctgc ttgcactccc    120
gcccatgccg acaacctttc tgctgttacc acgacccaca atgcaacgcg acacgaccgt    180
gtgggactga tcggttcact gcacctgcat gcaattgtca caagcgctta ctccaattgt    240
attcgtttgt tttctgggag cagttgctcg accgcccgcg tcccgcaggc agcgatgacg    300
tgtgcgtggc ctgggtgttt cgtcgaaagg ccagcaaccc taaatcgcag gcgatccgga    360
gattgggatc tgatccgagt ttggaccaga tccgccccga tgcggcacgg gaactgcatc    420
gactcggcgc ggaacccagc tttcgtaaat gccagattgg tgtccgatac ctggatttgc    480
catcagcgaa acaagacttc agcagcgagc gtatttggcg ggcgtgctac cagggttgca    540
```

-continued

```
tacattgccc atttctgtct ggaccgcttt actggcgcag agggtgagtt gatggggttg    600
gcaggcatcg aaacgcgcgt gcatggtgtg cgtgtctgtt ttcggctgca cgaattcaat    660
agtcggatgg gcgacggtag aattgggtgt ggcgctcgcg tgcatgcctc gccccgtcgg    720
gtgtcatgac cgggactgga atccccccctc gcgaccatct tgctaacgct cccgactctc    780
ccgaccgcgc gcaggataga ctcttgttca accaatcgac aactagtatg cagaccgccc    840
accagcgccc ccccaccgag ggccactgct tcggcgcccg cctgcccacc gcctcccgcc    900
gcgccgtgcg ccgcgcctgg tcccgcatcg cccgcgggcg cgccgccgcc gccgccgacg    960
ccaaccccgc ccgccccgag cgccgcgtgg tgatcaccgg ccagggcgtg gtgacctccc   1020
tgggccagac catcgagcag ttctactcct ccctgctgga gggcgtgtcc ggcatctccc   1080
agatccagaa gttcgacacc accggctaca ccaccaccat cgccggcgag atcaagtccc   1140
tgcagctgga cccctacgtg cccaagcgct gggccaagcg cgtggacgac gtgatcaagt   1200
acgtgtacat cgccggcaag caggccctgg agtccgccgg cctgcccatc gaggccgccg   1260
gcctggccgg cgccggcctg gaccccgccc tgtgcggcgt gctgatcggc accgccatgg   1320
ccggcatgac ctccttcgcc gccggcgtgg aggccctgac ccgcggcggc gtgcgcaaga   1380
tgaacccctt ctgcatcccc ttctccatct ccaacatggg cggcgccatg ctggccatgg   1440
acatcggctt catgggcccc aactactcca tctccaccgc ctgcgccacc ggcaactact   1500
gcatcctggg cgccgccgac cacatccgcc gcggcgacgc caacgtgatg ctggccggcg   1560
gcgccgacgc cgccatcatc ccctccggca tcggcggctt catcgcctgc aaggccctgt   1620
ccaagcgcaa cgacgagccc gagcgcgcct cccgcccctg ggacgccgac cgcgacggct   1680
tcgtgatggg cgagggcgcc ggcgtgctgg tgctggagga gctggagcac gccaagcgcc   1740
gcggcgccac catcctggcc gagctggtgg gcggcgccgc cacctccgac gcccaccaca   1800
tgaccgagcc cgacccccag ggccgcggcg tgcgcctgtg cctggagcgc gccctggagc   1860
gcgcccgcct ggcccccgag cgcgtgggct acgtgaacgc ccacggcacc tccaccccccg   1920
ccggcgacgt ggccgagtac cgcgccatcc gcgccgtgat cccccaggac tccctgcgca   1980
tcaactccac caagtccatg atcggccacc tgctgggcgg cgccggcgcc gtggaggccg   2040
tggccgccat ccaggccctg cgcaccggct ggctgcaccc caacctgaac ctggagaacc   2100
ccgcccccgg cgtggacccc gtggtgctgg tgggcccccg caaggagcgc gccgaggacc   2160
tggacgtggt gctgtccaac tccttcggct tcggcggcca caactcctgc gtgatcttcc   2220
gcaagtacga cgagatggac tacaaggacc acgacggcga ctacaaggac cacgacatcg   2280
actacaagga cgacgacgac aagtgaatcg atagatctct taaggcagca gcagctcgga   2340
tagtatcgac acactctgga cgctggtcgt gtgatggact gttgccgcca cacttgctgc   2400
cttgacctgt gaatatccct gccgctttta tcaaacagcc tcagtgtgtt tgatcttgtg   2460
tgtacgcgct tttgcgagtt gctagctgct tgtgctattt gcgaatacca cccccagcat   2520
ccccttccct cgtttcatat cgcttgcatc ccaaccgcaa cttatctacg ctgtcctgct   2580
atccctcagc gctgctcctg ctcctgctca ctgcccctcg cacagccttg gtttgggctc   2640
cgcctgtatt ctcctggtac tgcaacctgt aaaccagcac tgcaatgctg atgcacggga   2700
agtagtggga tgggaacaca aatggaaagc ttaattaaga gctccgcgtc tcgaacagag   2760
cgcgcagagg aacgctgaag gtctcgcctc tgtcgcacct cagcgcggca tacaccacaa   2820
taaccacctg acgaatgcgc ttggttcttc gtccattagc gaagcgtccg gttcacacac   2880
gtgccacgtt ggcgaggtgg caggtgacaa tgatcggtgg agctgatggt cgaaacgttc   2940
```

-continued

```
acagcctagg tgatatccat cttaaggatc taagtaagat tcgaagcgct cgaccgtgcc   3000
ggacggactg cagccccatg tcgtagtgac cgccaatgta agtgggctgg cgtttccctg   3060
tacgtgagtc aacgtcactg cacgcgcacc accctctcga ccggcaggac caggcatcgc   3120
gagatacagc gcgagccaga cacggagtgc cgagctatgc gcacgctcca actaggtacc   3180
agtttaggtc cagcgtccgt gggggggac gggctgggag cttgggccgg gaagggcaag   3240
acgatgcagt ccctctgggg agtcacagcc gactgtgtgt gttgcactgt gcggcccgca   3300
gcactcacac gcaaaatgcc tggccgacag gcaggccctg tccagtgcaa catccacggt   3360
ccctctcatc aggctcacct tgctcattga cataacggaa tgcgtaccgc tctttcagat   3420
ctgtccatcc agagagggga gcaggctccc caccgacgct gtcaaacttg cttcctgccc   3480
aaccgaaaac attattgttt gagggggggg gggggggggc agattgcatg gcgggatatc   3540
tcgtgaggaa catcactggg acactgtgga acacagtgag tgcagtatgc agagcatgta   3600
tgctaggggt cagcgcagga agggggcctt tcccagtctc ccatgccact gcaccgtatc   3660
cacgactcac caggaccagc ttcttgatcg gcttccgctc ccgtggacac cagtgtgtag   3720
cctctggact ccaggtatgc gtgcaccgca aaggccagcc gatcgtgccg attcctgggt   3780
ggaggatatg agtcagccaa cttggggctc agagtgcaca ctggggcacg atacgaaaca   3840
acatctacac cgtgtcctcc atgctgacac accacagctt cgctccacct gaatgtgggc   3900
gcatgggccc gaatcacagc caatgtcgct gctgccataa tgtgatccag accctctccg   3960
cccagatgcc gagcggatcg tgggcgctga atagattcct gtttcgatca ctgtttgggt   4020
cctttccttt tcgtctcgga tgcgcgtctc gaaacaggct gcgtcgggct ttcggatccc   4080
ttttgctccc tccgtcacca tcctgcgcgc gggcaagttg cttgaccctg ggctgatacc   4140
agggttggag ggtattaccg cgtcaggcca ttcccagccc ggattcaatt caaagtctgg   4200
gccaccaccc tccgccgctc tgtctgatca ctccacattc gtgcatacac tacgttcaag   4260
tcctgatcca ggcgtgtctc gggacaaggt gtgcttgagt ttgaatctca aggacccact   4320
ccagcacagc tgctggttga ccccgccctc gcaatctaga atggccgcgt ccgtccactg   4380
caccctgatg tccgtggtct gcaacaacaa gaaccactcc gcccgcccca agctgcccaa   4440
ctcctccctg ctgcccggct tcgacgtggt ggtccaggcc gcggccaccc gcttcaagaa   4500
ggagacgacg accacccgcg ccacgctgac gttcgacccc cccacgacca actccgagcg   4560
cgccaagcag cgcaagcaca ccatcgaccc ctcctccccc gacttccagc ccatcccctc   4620
cttcgaggag tgcttcccca agtccacgaa ggagcacaag gaggtggtgc acgaggagtc   4680
cggccacgtc ctgaaggtgc ccttccgccg cgtgcacctg tccggcggcg agcccgcctt   4740
cgacaactac gacacgtccg gcccccagaa cgtcaacgcc cacatcggcc tggcgaagct   4800
gcgcaaggag tggatcgacc gccgcgagaa gctgggcacg ccccgctaca cgcagatgta   4860
ctacgcgaag cagggcatca tcacggagga gatgctgtac tgcgcgacgc gcgagaagct   4920
ggaccccgag ttcgtccgct ccgaggtcgc gcggggccgc gccatcatcc cctccaacaa   4980
gaagcacctg gagctggagc ccatgatcgt gggccgcaag ttcctggtga aggtgaacgc   5040
gaacatcggc aactccgccg tggcctcctc catcgaggag gaggtctaca aggtgcagtg   5100
ggccaccatg tggggcgccg acaccatcat ggacctgtcc acgggccgcc acatccacga   5160
gacgcgcgag tggatcctgc gcaactccgc ggtccccgtg ggcaccgtcc ccatctacca   5220
ggcgctggag aaggtggacg gcatcgcgga gaacctgaac tgggaggtgt tccgcgagac   5280
```

-continued

```
gctgatcgag caggccgagc agggcgtgga ctacttcacg atccacgcgg gcgtgctgct   5340

gcgctacatc cccctgaccg ccaagcgcct gacgggcatc gtgtcccgcg gcggctccat   5400

ccacgcgaag tggtgcctgg cctaccacaa ggagaacttc gcctacgagc actgggacga   5460

catcctggac atctgcaacc agtacgacgt cgccctgtcc atcggcgacg gcctgcgccc   5520

cggctccatc tacgacgcca acgacacggc ccagttcgcc gagctgctga cccagggcga   5580

gctgacgcgc cgcgcgtggg agaaggacgt gcaggtgatg aacgagggcc ccggccacgt   5640

gcccatgcac aagatccccg agaacatgca gaagcagctg gagtggtgca acgaggcgcc   5700

cttctacacc ctgggccccc tgacgaccga catcgcgccc ggctacgacc acatcacctc   5760

cgccatcggc gcggccaaca tcggcgccct gggcaccgcc ctgctgtgct acgtgacgcc   5820

caaggagcac ctgggcctgc ccaaccgcga cgacgtgaag gcgggcgtca tcgcctacaa   5880

gatcgccgcc cacgcggccg acctggccaa gcagcacccc cacgcccagg cgtgggacga   5940

cgcgctgtcc aaggcgcgct tcgagttccg ctggatggac cagttcgcgc tgtccctgga   6000

ccccatgacg gcgatgtcct tccacgacga gacgctgccc gcggacggcg cgaaggtcgc   6060

ccacttctgc tccatgtgcg gccccaagtt ctgctccatg aagatcacgg aggacatccg   6120

caagtacgcc gaggagaacg gctacggctc cgccgaggag gccatccgcc agggcatgga   6180

cgccatgtcc gaggagttca acatcgccaa gaagacgatc tccggcgagc agcacggcga   6240

ggtcggcggc gagatctacc tgcccgagtc ctacgtcaag gccgcgcaga agtgacaatt   6300

gacggagcgt cgtgcgggag ggagtgtgcc gagcggggag tcccggtctg tgcgaggccc   6360

ggcagctgac gctggcgagc cgtacgcccc gagggtcccc ctcccctgca ccctcttccc   6420

cttccctctg acggccgcgc ctgttcttgc atgttcagcg acggatccta gggagcgacg   6480

agtgtgcgtg cggggctggc gggagtggga cgccctcctc gctcctctct gttctgaacg   6540

gaacaatcgg ccaccccgcg ctacgcgcca cgcatcgagc aacgaagaaa acccccgat    6600

gataggttgc ggtggctgcc gggatataga tccggccgca catcaaaggg cccctccgcc   6660

agagaagaag ctcctttccc agcagactcc ttctgctgcc aaaacacttc tctgtccaca   6720

gcaacaccaa aggatgaaca gatcaacttg cgtctccgcg tagcttcctc ggctagcgtg   6780

cttgcaacag gtccctgcac tattatcttc ctgctttcct ctgaattatg cggcaggcga   6840

gcgctcgctc tggcgagcgc tccttcgcgc cgccctcgct gatcgagtgt acagtcaatg   6900

aatggtcctg ggcgaagaac gagggaattt gtgggtaaaa caagcatcgt ctctcaggcc   6960

ccggcgcagt ggccgttaaa gtccaagacc gtgaccaggc agcgcagcgc gtccgtgtgc   7020

gggccctgcc tggcggctcg gcgtgccagg ctcgagagca gctccctcag gtcgccttgg   7080

acggcctctg cgaggccggt gagggcctgc aggagcgcct cgagcgtggc agtggcggtc   7140

gtatccgggt cgccggtcac cgcctgcgac tcgccatccg aagagcgttt aaac         7194
```

<210> SEQ ID NO 152
<211> LENGTH: 7081
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 152

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120
```

-continued

```
tgcgccggct gagccactgc ttcgtccggg cggccaagag gagcatgagg gaggactcct    180
ggtccagggt cctgacgtgg tcgcggctct gggagcgggc cagcatcatc tggctctgcc    240
gcaccgaggc cgcctccaac tggtcctcca gcagccgcag tcgccgccga ccctggcaga    300
ggaagacagg tgaggggggt atgaattgta cagaacaacc acgagccttg tctaggcaga    360
atccctacca gtcatggctt tacctggatg acggcctgcg aacagctgtc cagcgaccct    420
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccccttgcg cgttagtgtt gccatccttt gcagaccggt gagagccgac ttgttgtgcg    600
ccaccccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgccccctg   1140
gtgcacttca cccccaacaa gggctggatg aacgacccca acggcctgtg gtacgacgag   1200
aaggacgcca agtggcacct gtacttccag tacaacccga acgacaccgt ctggggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
```

```
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcctgaa gaatgggagg caggtgttgt   3300
tgattatgag tgtgtaaaag aaaggggtag agagccgtcc tcagatccga ctactatgca   3360
ggtagccgct cgcccatgcc cgcctggctg aatattgatg catgcccatc aaggcaggca   3420
ggcatttctg tgcacgcacc aagcccacaa tcttccacaa cacacagcat gtaccaacgc   3480
acgcgtaaaa gttggggtgc tgccagtgcg tcatgccagg catgatgtgc tcctgcacat   3540
ccgccatgat ctcctccatc gtctcgggtg tttccggcgc ctggtccggg agccgttccg   3600
ccagataccc agacgccacc tccgacctca cggggtactt ttcgagcgtc tgccggtagt   3660
cgacgatcgc gtccaccatg gagtagccga ggcgccggaa ctggcgtgac ggagggagga   3720
gagggaggag agagaggggg gggggggggg gggatgatta cacgccagtc tcacaacgca   3780
tgcaagaccc gtttgattat gagtacaatc atgcactact agatggatga gcgccaggca   3840
taaggcacac cgacgttgat ggcatgagca actcccgcat catatttcct attgtcctca   3900
cgccaagccg gtcaccatcc gcatgctcat attacagcgc acgcaccgct tcgtgatcca   3960
ccgggtgaac gtagtcctcg acggaaacat ctggctcggg cctcgtgctg gcactccctc   4020
ccatgccgac aacctttctg ctgtcaccac gacccacgat gcaacgcgac acgacccggt   4080
gggactgatc ggttcactgc acctgcatgc aattgtcaca agcgcatact ccaatcgtat   4140
ccgtttgatt tctgtgaaaa ctcgctcgac cgcccgcgtc ccgcaggcag cgatgacgtg   4200
tgcgtgacct gggtgtttcg tcgaaaggcc agcaacccca aatcgcaggc gatccggaga   4260
ttgggatctg atccgagctt ggaccagatc ccccacgatg cggcacggga actgcatcga   4320
ctcggcgcgg aacccagctt tcgtaaatgc cagattggtg tccgatacct tgatttgcca   4380
tcagcgaaac aagacttcag cagcgagcgt atttggcggg cgtgctacca gggttgcata   4440
cattgcccat ttctgtctgg accgctttac cggcgcagag ggtgagttga tggggttggc   4500
aggcatcgaa acgcgcgtgc atggtgtgtg tgtctgtttt cggctgcaca atttcaatag   4560
tcggatgggc gacggtagaa ttgggtgttg cgctcgcgtg catgcctcgc cccgtcgggt   4620
gtcatgaccg ggactggaat cccccctcgc gaccctcctg ctaacgctcc cgactctccc   4680
gcccgcgcgc aggatagact ctagttcaac caatcgacaa ctagtatggc caccgcatcc   4740
actttctcgg cgttcaatgc ccgctgcggc gacctgcgtc gctcggcggg ctccgggccc   4800
cggcgcccag cgaggcccct ccccgtgcgc gggcgcgcca tcccccccg catcatcgtg    4860
```

-continued

```
gtgtcctcct cctcctccaa ggtgaacccc ctgaagaccg aggccgtggt gtcctccggc   4920

ctggccgacc gcctgcgcct gggctccctg accgaggacg gcctgtccta caaggagaag   4980

ttcatcgtgc gctgctacga ggtgggcatc aacaagaccg ccaccgtgga gaccatcgcc   5040

aacctgctgc aggaggtggg ctgcaaccac gcccagtccg tgggctactc caccggcggc   5100

ttctccacca cccccaccat gcgcaagctg cgcctgatct gggtgaccgc ccgcatgcac   5160

atcgagatct acaagtaccc cgcctggtcc gacgtggtgg agatcgagtc ctggggccag   5220

ggcgagggca agatcggcac ccgccgcgac tggatcctgc gcgactacgc caccggccag   5280

gtgatcggcc gcgccacctc caagtgggtg atgatgaacc aggacacccg ccgcctgcag   5340

aaggtggacg tggacgtgcg cgacgagtac ctggtgcact gcccccgcga gctgcgcctg   5400

gccttccccg aggagaacaa ctcctccctg aagaagatct ccaagctgga ggacccctcc   5460

cagtactcca agctgggcct ggtgccccgc cgcgccgacc tggacatgaa ccagcacgtg   5520

aacaacgtga cctacatcgg ctgggtgctg gagtccatgc cccaggagat catcgacacc   5580

cacgagctgc agaccatcac cctggactac cgccgcgagt gccagcacga cgacgtggtg   5640

gactccctga cctcccccga gccctccgag gacgccgagg ccgtgttcaa ccacaacggc   5700

accaacggct ccgccaacgt gtccgccaac gaccacggct gccgcaactt cctgcacctg   5760

ctgcgcctgt ccggcaacgg cctggagatc aaccgcggcc gcaccgagtg gcgcaagaag   5820

cccacccgca tggactacaa ggaccacgac ggcgactaca aggaccacga catcgactac   5880

aaggacgacg acgacaagtg aatcgataga tctcttaagg cagcagcagc tcggatagta   5940

tcgacacact ctggacgctg gtcgtgtgat ggactgttgc cgccacactt gctgccttga   6000

cctgtgaata tccctgccgc ttttatcaaa cagcctcagt gtgtttgatc ttgtgtgtac   6060

gcgcttttgc gagttgctag ctgcttgtgc tatttgcgaa taccaccccc agcatcccct   6120

tccctcgttt catatcgctt gcatcccaac cgcaacttat ctacgctgtc ctgctatccc   6180

tcagcgctgc tcctgctcct gctcactgcc cctcgcacag ccttggtttg ggctccgcct   6240

gtattctcct ggtactgcaa cctgtaaacc agcactgcaa tgctgatgca cgggaagtag   6300

tgggatggga acacaaatgg aaagcttaat taagagctct tgttttccag aaggagttgc   6360

tccttgagcc tttcattctc agcctcgata acctccaaag ccgctctaat tgtggagggg   6420

gttcgaattt aaaagcttgg aatgttggtt cgtgcgtctg gaacaagccc agacttgttg   6480

ctcactggga aaaggaccat cagctccaaa aaacttgccg ctcaaaccgc gtacctctgc   6540

tttcgcgcaa tctgccctgt tgaaatcgcc accacattca tattgtgacg cttgagcagt   6600

ctgtaattgc ctcagaatgt ggaatcatct gccccctgtg cgagcccatg ccaggcatgt   6660

cgcgggcgag gacacccgcc actcgtacag cagaccatta tgctacctca caatagttca   6720

taacagtgac catatttctc gaagctcccc aacgagcacc tccatgctct gagtggccac   6780

cccccggccc tggtgcttgc ggagggcagg tcaaccggca tggggctacc gaaatccccg   6840

accggatccc accacccccg cgatgggaag aatctctccc cgggatgtgg gcccaccacc   6900

agcacaacct gctggcccag gcgagcgtca aaccatacca cacaaatatc cttggcatcg   6960

gccctgaatt ccttctgccg ctctgctacc cggtgcttct gtccgaagca ggggttgcta   7020

gggatcgctc cgagtccgca aacccttgtc gcgtggcggg gcttgttcga gcttgaagag   7080

c                                                                   7081
```

<210> SEQ ID NO 153
<211> LENGTH: 8286

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 153
gctcttccca actcagataa taccaatacc cctccttctc ctcctcatcc attcagtacc 60
cccccccttc tcttcccaaa gcagcaagcg cgtggcttac agaagaacaa tcggcttccg 120
ccaaagtcgc cgagcactgc ccgacggcgg cgcgcccagc agcccgcttg gccacacagg 180
caacgaatac attcaatagg gggcctcgca gaatggaagg agcggtaaag ggtacaggag 240
cactgcgcac aaggggcctg tgcaggagtg actgactggg cgggcagacg gcgcaccgcg 300
ggcgcaggca agcagggaag attgaagcgg cagggaggag gatgctgatt gagggggggca 360 tcgcagtctc tcttggaccc gggataagga agcaaatatt cggccggttg ggttgtgtgt 420
gtgcacgttt tcttcttcag agtcgtgggt gtgcttccag ggaggatata agcagcagga 480
tcgaatcccg cgaccagcgt ttccccatcc agccaaccac cctgtcggta ccgcggtgag 540
aatcgaaaat gcatcgtttc taggttcgga gacggtcaat tccctgctcc ggcgaatctg 600
tcggtcaagc tggccagtgg acaatgttgc tatggcagcc cgcgcacatg ggcctcccga 660
cgcggccatc aggagcccaa acagcgtgtc agggtatgtg aaactcaaga ggtccctgct 720
gggcactccg gccccactcc gggggcggga cgccaggcat tcgcggtcgg tcccgcgcga 780
cgagcgaaat gatgattcgg ttacgagacc aggacgtcgt cgaggtcgag aggcagcctc 840
ggacacgtct cgctagggca acgccccgag tccccgcgag ggccgtaaac attgtttctg 900
ggtgtcggag tgggcatttt gggcccgatc caatcgcctc atgccgctct cgtctggtcc 960
tcacgttcgc gtacggcctg gatcccggaa agggcggatg cacgtggtgt tgccccgcca 1020
ttggcgccca cgtttcaaag tccccggcca gaaatgcaca ggaccggccc ggctcgcaca 1080
ggccatgctg aacgcccaga tttcgacagc aacaccatct agaataatcg caaccatccg 1140
cgttttgaac gaaacgaaac ggcgctgttt agcatgtttc cgacatcgtg ggggccgaag 1200
catgctccgg ggggaggaaa gcgtggcaca gcggtagccc attctgtgcc acacgccgac 1260
gaggaccaat ccccggcatc agccttcatc gacggctgcg ccgcacatat aaagccggac 1320
gcctaaccgg tttcgtggtt atgactagta tgttcgcgtt ctacttcctg acggcctgca 1380
tctccctgaa gggcgtgttc ggcgtctccc cctcctacaa cggcctgggc ctgacgcccc 1440
agatgggctg ggacaactgg aacacgttcg cctgcgacgt ctccgagcag ctgctgctgg 1500
acacggccga ccgcatctcc gacctgggcc tgaaggacat gggctacaag tacatcatcc 1560
tggacgactg ctggtcctcc ggccgcgact ccgacggctt cctggtcgcc gacgagcaga 1620
agttccccaa cggcatgggc cacgtcgccg accacctgca caacaactcc ttcctgttcg 1680
gcatgtactc ctccgcgggc gagtacacgt gcgccggcta ccccggctcc ctgggccgcg 1740
aggaggagga cgcccagttc ttcgcgaaca accgcgtgga ctacctgaag tacgacaact 1800
gctacaacaa gggccagttc ggcacgcccg agatctccta ccaccgctac aaggccatgt 1860
ccgacgccct gaacaagacg ggccgcccca tcttctactc cctgtgcaac tggggccagg 1920
acctgacctt ctactggggc tccggcatcg cgaactcctg gcgcatgtcc ggcgacgtca 1980
cggcggagtt cacgcgcccc gactcccgct gcccctgcga cggcgacgag tacgactgca 2040
agtacgccgg cttccactgc tccatcatga acatcctgaa caaggccgcc cccatgggcc 2100
agaacgcggg cgtcggcggc tggaacgacc tggacaacct ggaggtcggc gtcggcaacc 2160

-continued

```
tgacggacga cgaggagaag gcgcacttct ccatgtgggc catggtgaag tccccccctga   2220
tcatcggcgc gaacgtgaac aacctgaagg cctcctccta ctccatctac tcccaggcgt   2280
ccgtcatcgc catcaaccag gactccaacg gcatccccgc cacgcgcgtc tggcgctact   2340
acgtgtccga cacggacgag tacggccagg gcgagatcca gatgtggtcc ggcccccctgg   2400
acaacggcga ccaggtcgtg gcgctgctga acggcggctc cgtgtcccgc cccatgaaca   2460
cgaccctgga ggagatcttc ttcgactcca acctgggctc caagaagctg acctccacct   2520
gggacatcta cgacctgtgg gcgaaccgcg tcgacaactc cacggcgtcc gccatcctgg   2580
gccgcaacaa gaccgccacc ggcatcctgt acaacgccac cgagcagtcc tacaaggacg   2640
gcctgtccaa gaacgacacc cgcctgttcg gccagaagat cggctccctg tcccccaacg   2700
cgatcctgaa cacgaccgtc cccgcccacg gcatcgcgtt ctaccgcctg cgcccctcct   2760
cctgatacaa cttattacgt attctgaccg gcgctgatgt ggcgcggacg ccgtcgtact   2820
ctttcagact ttactcttga ggaattgaac ctttctcgct tgctggcatg taaacattgg   2880
cgcaattaat tgtgtgatga agaaagggtg gcacaagatg gatcgcgaat gtacgagatc   2940
gacaacgatg gtgattgtta tgaggggcca aacctggctc aatcttgtcg catgtccggc   3000
gcaatgtgat ccagcggcgt gactctcgca acctggtagt gtgtgcgcac cgggtcgctt   3060
tgattaaaac tgatcgcatt gccatcccgt caactcacaa gcctactcta gctcccattg   3120
cgcactcggg cgcccggctc gatcaatgtt ctgagcggag ggcgaagcgt caggaaatcg   3180
tctcggcagc tggaagcgca tggaatgcgg agcggagatc gaatcaggat cccgcgtctc   3240
gaacagagcg cgcagaggaa cgctgaaggt ctcgcctctg tcgcacctca gcgcggcata   3300
caccacaata accacctgac gaatgcgctt ggttcttcgt ccattagcga agcgtccggt   3360
tcacacacgt gccacgttgg cgaggtggca ggtgacaatg atcggtggag ctgatggtcg   3420
aaacgttcac agcctagcat agcgactgct accccccgac catgtgccga ggcagaaatt   3480
atatacaaga agcagatcgc aattaggcac atcgctttgc attatccaca cactattcat   3540
cgctgctgcg gcaaggctgc agagtgtatt tttgtggccc aggagctgag tccgaagtcg   3600
acgcgacgag cggcgcagga tccgacccct agacgagctc tgtcattttc caagcacgca   3660
gctaaatgcg ctgagaccgg gtctaaatca tccgaaaagt gtcaaaatgg ccgattgggt   3720
tcgcctagga caatgcgctg cggattcgct cgagtccgct gccggccaaa aggcggtggt   3780
acaggaaggc gcacggggcc aaccctgcga agccgggggc ccgaacgccg accgccggcc   3840
ttcgatctcg ggtgtccccc tcgtcaattt cctctctcgg gtgcagccac gaaagtcgtg   3900
acgcaggtca cgaaatccgg ttacgaaaaa cgcaggtctt cgcaaaaacg tgagggtttc   3960
gcgtctcgcc ctagctattc gtatcgccgg gtcagaccca cgtgcagaaa agcccttgaa   4020
taacccggga ccgtggttac cgcgccgcct gcaccagggg gcttatataa gcccacacca   4080
cacctgtctc accacgcatt tctccaactc gcgacttttc ggaagaaatt gttatccacc   4140
tagtatagac tgccacctgc aggaccttgt gtcttgcagt ttgtattggt cccggccgtc   4200
gagctcgaca gatctgggct agggttggcc tggccgctcg gcactcccct ttagccgcgc   4260
gcatccgcgt tccagaggtg cgattcggtg tgtggagcat tgtcatgcgc ttgtgggggt   4320
cgttccgtgc gcggcgggtc cgccatgggc gccgacctgg gccctagggt ttgttttcgg   4380
gccaagcgag cccctctcac ctcgtcgccc ccccgcattc cctctctctt gcagcccata   4440
tggccatggc cgccgccgtg atcgtgcccc tgggcatcct gttcttcatc tccggcctgg   4500
```

-continued

```
tggtgaacct gctgcaggcc atctgctacg tgctgatccg cccccctgtcc aagaacacct   4560

accgcaagat caaccgcgtg gtggccgaga ccctgtggct ggagctggtg tggatcgtgg   4620

actggtgggc cggcgtgaag atccaggtgt tcgccgacaa cgagaccttc aaccgcatgg   4680

gcaaggagca cgccctggtg gtgtgcaacc accgctccga catcgactgg ctggtgggct   4740

ggatcctggc ccagcgctcc ggctgcctgg gctccgccct ggccgtgatg aagaagtcct   4800

ccaagttcct gcccgtgatc ggctggtcca tgtggttctc cgagtacctg ttcctggagc   4860

gcaactgggc caaggacgag tccaccctga agtccggcct gcagcgcctg aacgacttcc   4920

cccgcccctt ctggctggcc ctgttcgtgg agggcacccg cttcaccgag gccaagctga   4980

aggccgccca ggagtacgcc gcctcctccg agctgcccgt gccccgcaac gtgctgatcc   5040

cccgcaccaa gggcttcgtg tccgccgtgt ccaacatgcg ctccttcgtg cccgccatct   5100

acgacatgac cgtggccatc cccaagacct cccccccccc caccatgctg cgcctgttca   5160

agggccagcc ctccgtggtg cacgtgcaca tcaagtgcca ctccatgaag gacctgcccg   5220

agtccgacga cgccatcgcc cagtggtgcc gcgaccagtt cgtggccaag gacgccctgc   5280

tggacaagca catcgccgcc gacaccttcc ccggccagca ggagcagaac atcggccgcc   5340

ccatcaagtc cctggccgtg gtgctgtcct ggtcctgcct gctgatcctg ggcgccatga   5400

agttcctgca ctggtccaac ctgttctcct cctggaaggg catcgccttc tccgccctgg   5460

gcctgggcat catcaccctg tgcatgcaga tcctgatccg ctcctcccag tccgagcgct   5520

ccacccccgc caaggtggtg cccgccaagc ccaaggacaa ccacaacgac tccggctcct   5580

cctcccagac cgaggtggag aagcagaagt gaatgcatgc agcagcagct cggatagtat   5640

cgacacactc tggacgctgg tcgtgtgatg gactgttgcc gccacacttg ctgccttgac   5700

ctgtgaatat ccctgccgct tttatcaaac agcctcagtg tgtttgatct tgtgtgtacg   5760

cgcttttgcg agttgctagc tgcttgtgct atttgcgaat accaccccca gcatcccctt   5820

ccctcgtttc atatcgcttg catcccaacc gcaacttatc tacgctgtcc tgctatccct   5880

cagcgctgct cctgctcctg ctcactgccc ctcgcacagc cttggtttgg gctccgcctg   5940

tattctcctg gtactgcaac ctgtaaacca gcactgcaat gctgatgcac gggaagtagt   6000

gggatgggaa cacaaatgga cttaaggatc taagtaagat tcgaagcgct cgaccgtgcc   6060

ggacggactg cagccccatg tcgtagtgac cgccaatgta agtgggctgg cgtttccctg   6120

tacgtgagtc aacgtcactg cacgcgcacc accctctcga ccggcaggac caggcatcgc   6180

gagatacagc gcgagccaga cacggagtgc cgagctatgc gcacgctcca actagatatc   6240

atgtggatga tgagcatgaa ttcctttctt gcgctatgac acttccagca aaaggtaggg   6300

cgggctgcga gacggcttcc cggcgctgca tgcaacaccg atgatgcttc gacccccccga   6360

agctccttcg gggctgcatg ggcgctccga tgccgctcca gggcgagcgc tgtttaaata   6420

gccaggcccc cgattgcaaa gacattatag cgagctacca aagccatatt caaacaccta   6480

gatcactacc acttctacac aggccactcg agcttgtgat cgcactccgc taagggggcg   6540

cctcttcctc ttcgtttcag tcacaacccg caaacactag tatggctatc aagacgaaca   6600

ggcagcctgt ggagaagcct ccgttcacga tcgggacgct gcgcaaggcc atccccgcgc   6660

actgtttcga gcgctcggcg cttcgtagca gcatgtacct ggcctttgac atcgcggtca   6720

tgtccctgct ctacgtcgcg tcgacgtaca tcgaccctgc accggtgcct acgtgggtca   6780

agtacggcat catgtggccg ctctactggt tcttccaggt gtgtttgagg gttttggttg   6840

cccgtattga ggtcctggtg gcgcgcatgg aggagaaggc gcctgtcccg ctgacccccc   6900
```

cggctaccct cccggcacct tccagggcgc gtacgggaag aaccagtaga gcggccacat 6960
gatgccgtac ttgacccacg taggcaccgg tgcagggtcg atgtacgtcg acgcgacgta 7020
gagcagggac atgaccgcga tgtcaaaggc caggtacatg ctgctacgaa gcgccgagcg 7080
ctcgaaacag tgcgcgggga tggccttgcg cagcgtcccg atcgtgaacg gaggcttctc 7140
cacaggctgc ctgttcgtct tgatagccat ctcgaggcag cagcagctcg gatagtatcg 7200
acacactctg gacgctggtc gtgtgatgga ctgttgccgc cacacttgct gccttgacct 7260
gtgaatatcc ctgccgcttt tatcaaacag cctcagtgtg tttgatcttg tgtgtacgcg 7320
cttttgcgag ttgctagctg cttgtgctat ttgcgaatac cacccccagc atccccttcc 7380
ctcgtttcat atcgcttgca tcccaaccgc aacttatcta cgctgtcctg ctatccctca 7440
gcgctgctcc tgctcctgct cactgcccct cgcacagcct tggtttgggc tccgcctgta 7500
ttctcctggt actgcaacct gtaaaccagc actgcaatgc tgatgcacgg gaagtagtgg 7560
gatgggaaca caaatggaaa gctgtagagc tcttgttttc cagaaggagt tgctccttga 7620
gcctttcatt ctcagcctcg ataacctcca aagccgctct aattgtggag gggttcgaa 7680 ccgaatgctg cgtgaacggg aaggaggagg agaaagagtg agcagggagg gattcagaaa 7740
tgagaaatga gaggtgaagg aacgcatccc tatgcccttg caatggacag tgtttctggc 7800
caccgccacc aagacttcgt gtcctctgat catcatgcga ttgattacgt tgaatgcgac 7860
ggccggtcag ccccggacct ccacgcaccg gtgctcctcc aggaagatgc gcttgtcctc 7920
cgccatcttg cagggctcaa gctgctccca aaactcttgg gcgggttccg gacggacggc 7980
taccgcgggt gcggccctga ccgccactgt tcggaagcag cggcgctgca tgggcagcgg 8040
ccgctgcggt gcgccacgga ccgcatgatc caccggaaaa gcgcacgcgc tggagcgcgc 8100
agaggaccac agagaagcgg aagagacgcc agtactggca agcaggctgg tcggtgccat 8160
ggcgcgctac taccctcgct atgactcggg tcctcggccg gctggcggtg ctgacaattc 8220
gtttagtgga gcagcgactc cattcagcta ccagtcgaac tcagtggcac agtgactccg 8280
ctcttc 8286

<210> SEQ ID NO 154
<211> LENGTH: 1317
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 154
gtggccgccg aggcctcctc cgccctgttc tccgtgcgca cccccggcac ctcccccaag 60
cccggcaagt tcggcaactg gcccacctcc ctgtccgtgc ccttcaagtc caagtccaac 120
cacaacggcg gcttccaggt gaaggccaac gcctccgccc gccccaaggc caacggctcc 180
gccgtgtccc tgaagtccgg ctccctggac acccaggagg acacctcctc ctcctcctcc 240
cccccccgca ccttcatcaa ccagctgccc gactggtcca tgctgctgtc cgccatcacc 300
accgtgttcg tggccgccga gaagcagtgg accatgctgg accgcaagtc caagcgcccc 360
gacatgctga tggacccctt cggcgtggac cgcgtggtgc aggacggcgc cgtgttccgc 420
cagtccttct ccatccgctc ctacgagatc ggcgccgacc gcaccgcctc catcgagacc 480
ctgatgaaca tcttccagga gacctccctg aaccactgca agtccatcgg cctgctgaac 540
gacggcttcg gccgcacccc cgagatgtgc aagcgcgacc tgatctgggt ggtgaccaag 600
atgcacgtgg aggtgaaccg ctaccccacc tggggcgaca ccatcgaggt gaacacctgg 660
gtgtccgagt ccggcaagac cggcatgggc cgcgactggc tgatctccga ctgccacacc 720
ggcgagatcc tgatccgcgc cacctccatg tgcgccatga tgaaccagaa gacccgccgc 780
ttctccaagt tcccctacga ggtgcgccag gagctggccc cccacttcgt ggactccgcc 840
cccgtgatcg aggactacca gaagctgcac aagctggacg tgaagaccgg cgactccatc 900
tgcaacggcc tgaccccccg ctggaacgac ctggacgtga accagcacgt gaacaacgtg 960
aagtacatcg gctggatcct ggagtccgtg cccaccgagg tgttcgagac ccaggagctg 1020
tgcggcctga ccctggagta ccgccgcgag tgcggccgcg actccgtgct ggagtccgtg 1080
accgccatgg accccctccaa ggagggcgac cgctccctgt accagcacct gctgcgcctg 1140
gaggacggcg ccgacatcgc caagggccgc accaagtggc gccccaagaa cgccggcacc 1200
aacggcgcca tctccaccgg caagacctcc aacggcaact ccatctccat ggactacaag 1260
gaccacgacg gcgactacaa ggaccacgac atcgactaca aggacgacga cgacaag 1317

<210> SEQ ID NO 155
<211> LENGTH: 1260
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 155
gccaccgcct ccaccttctc cgccttcaac gcccgctgcg gcgacctgcg ccgctccgcc 60
ggctccggcc cccgccgccc cgcccgcccc ctgcccgtgc gcgccgccat caacgcctcc 120
gcccacccca aggccaacgg ctccgccgtg aacctgaagt ccggctccct ggagacccag 180
gaggacacct cctcctcctc cccccccccc cgcaccttca tcaagcagct gcccgactgg 240
ggcatgctgc tgtccaagat caccaccgtg ttcggcgccg ccgagcgcca gtggaagcgc 300
cccggcatgc tggtggagcc cttcggcgtg gaccgcatct tccaggacgg cgtgttcttc 360
cgccagtcct tctccatccg ctcctacgag atcggcgccg accgcaccgc ctccatcgag 420
accctgatga acatcttcca ggagacctcc ctgaaccact gcaagtccat cggcctgctg 480
aacgacggct tcggccgcac ccccgagatg tgcaagcgcg acctgatctg ggtggtgacc 540
aagatccagg tggaggtgaa ccgctacccc acctggggcg acaccatcga ggtgaacacc 600
tgggtgtccg agtccggcaa gaacggcatg ggccgcgact ggctgatctc cgactgccgc 660
accggcgaga tcctgatccg cgccacctcc gtgtgggcca tgatgaaccg caagacccgc 720
cgcctgtcca agttccccta cgaggtgcgc caggagatcg ccccccactt cgtggactcc 780
gcccccgtga tcgaggacga caagaagctg cacaagctgg acgtgaagac cggcgactcc 840
atccgcaagg gcctgacccc ccgctggaac gacctggacg tgaaccagca cgtgaacaac 900
gtgaagtaca tcggctggat cctgaagtcc gtgcccgccg aggtgttcga gacccaggag 960
ctgtgcggcg tgaccctgga gtaccgccgc gagtgcggcc gcgactccgt gctggagtcc 1020
gtgaccgcca tggacaccgc caaggagggc gaccgctccc tgtaccagca cctgctgcgc 1080
ctggaggacg gcgccgacat caccatcggc cgcaccgagt ggcgccccaa gaacgccggc 1140
gccaacggcg ccatctccac cggcaagacc tccaacgaga actccgtgtc catggactac 1200
aaggaccacg acggcgacta caaggaccac gacatcgact acaaggacga cgacgacaag 1260

<210> SEQ ID NO 156
<211> LENGTH: 352
<212> TYPE: PRT
<213> ORGANISM: Garcinia mangostana

<400> SEQUENCE: 156

```
Met Leu Lys Leu Ser Ser Ser Arg Ser Pro Leu Ala Arg Ile Pro Thr
1               5                   10                  15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45

Gly Leu Ala Asp Arg Leu Arg Leu Gly Ser Leu Thr Glu Asp Gly Leu
    50                  55                  60

Ser Tyr Lys Glu Lys Phe Ile Val Arg Cys Tyr Glu Val Gly Ile Asn
65                  70                  75                  80

Lys Thr Ala Thr Val Glu Thr Ile Ala Asn Leu Leu Gln Glu Val Gly
                85                  90                  95

Cys Asn His Ala Gln Ser Val Gly Tyr Ser Thr Gly Gly Phe Ser Thr
            100                 105                 110

Thr Pro Thr Met Arg Lys Leu Arg Leu Ile Trp Val Thr Ala Arg Met
        115                 120                 125

His Ile Glu Ile Tyr Lys Tyr Pro Ala Trp Ser Asp Val Val Glu Ile
    130                 135                 140

Glu Ser Trp Gly Gln Gly Glu Gly Lys Ile Gly Thr Arg Arg Asp Trp
145                 150                 155                 160

Ile Leu Arg Asp Tyr Ala Thr Gly Gln Val Ile Gly Arg Ala Thr Ser
                165                 170                 175

Lys Trp Val Met Met Asn Gln Asp Thr Arg Arg Leu Gln Lys Val Asp
            180                 185                 190

Val Asp Val Arg Asp Glu Tyr Leu Val His Cys Pro Arg Glu Leu Arg
        195                 200                 205

Leu Ala Phe Pro Glu Glu Asn Asn Ser Ser Leu Lys Lys Ile Ser Lys
    210                 215                 220

Leu Glu Asp Pro Ser Gln Tyr Ser Lys Leu Gly Leu Val Pro Arg Arg
225                 230                 235                 240

Ala Asp Leu Asp Met Asn Gln His Val Asn Asn Val Thr Tyr Ile Gly
                245                 250                 255

Trp Val Leu Glu Ser Met Pro Gln Glu Ile Ile Asp Thr His Glu Leu
            260                 265                 270

Gln Thr Ile Thr Leu Asp Tyr Arg Arg Glu Cys Gln His Asp Asp Val
        275                 280                 285

Val Asp Ser Leu Thr Ser Pro Glu Pro Ser Glu Asp Ala Glu Ala Val
    290                 295                 300

Phe Asn His Asn Gly Thr Asn Gly Ser Ala Asn Val Ser Ala Asn Asp
305                 310                 315                 320

His Gly Cys Arg Asn Phe Leu His Leu Leu Arg Leu Ser Gly Asn Gly
                325                 330                 335

Leu Glu Ile Asn Arg Gly Arg Thr Glu Trp Arg Lys Lys Pro Thr Arg
            340                 345                 350
```

<210> SEQ ID NO 157
<211> LENGTH: 390
<212> TYPE: PRT
<213> ORGANISM: Brassic napus

<400> SEQUENCE: 157

```
Met Ala Met Ala Ala Ala Val Ile Val Pro Leu Gly Ile Leu Phe Phe
1               5                   10                  15

Ile Ser Gly Leu Val Val Asn Leu Leu Gln Ala Val Cys Tyr Val Leu
            20                  25                  30

Val Arg Pro Met Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asp Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Gln Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Ala Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Pro Glu Asp Glu Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Lys Glu Gln Asn Ile Gly Arg Pro Ile Lys Ser
    290                 295                 300

Leu Ala Val Val Val Ser Trp Ala Cys Leu Leu Thr Leu Gly Ala Met
305                 310                 315                 320

Lys Phe Leu His Trp Ser Asn Leu Phe Ser Ser Trp Lys Gly Ile Ala
                325                 330                 335

Leu Ser Ala Phe Gly Leu Gly Ile Ile Thr Leu Cys Met Gln Ile Leu
            340                 345                 350

Ile Arg Ser Ser Gln Ser Glu Arg Ser Thr Pro Ala Lys Val Ala Pro
        355                 360                 365

Ala Lys Pro Lys Asp Asn His Gln Ser Gly Pro Ser Ser Gln Thr Glu
    370                 375                 380

Val Glu Glu Lys Gln Lys
385                 390
```

<210> SEQ ID NO 158

<211> LENGTH: 415
<212> TYPE: PRT
<213> ORGANISM: Cuphea hookeriana

<400> SEQUENCE: 158

```
Met Val Ala Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125

Glu Ser Thr Val Gln Asp Gly Leu Val Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
        195                 200                 205

Ala Trp Gly Asp Thr Val Glu Ile Asn Thr Arg Phe Ser Arg Leu Gly
    210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
```

```
385                 390                 395                 400

Gly Ala Ile Ser Thr Gly Lys Thr Ser Asn Gly Asn Ser Val Ser
                405                 410                 415


<210> SEQ ID NO 159
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Tyr Val Phe Gln Cys Leu Val Ala Ser Cys Ile Asp Pro Cys Asp
        35                  40                  45

Gln Tyr Arg Ser Ser Ala Ser Leu Ser Phe Leu Gly Asp Asn Gly Phe
    50                  55                  60

Ala Ser Leu Phe Gly Ser Lys Pro Phe Met Ser Asn Arg Gly His Arg
65                  70                  75                  80

Arg Leu Arg Arg Ala Ser His Ser Gly Glu Ala Met Ala Val Ala Leu
                85                  90                  95

Gln Pro Ala Gln Glu Ala Gly Thr Lys Lys Lys Pro Val Ile Lys Gln
            100                 105                 110

Arg Arg Val Val Val Thr Gly Met Gly Val Val Thr Pro Leu Gly His
        115                 120                 125

Glu Pro Asp Val Phe Tyr Asn Asn Leu Leu Asp Gly Val Ser Gly Ile
    130                 135                 140

Ser Glu Ile Glu Thr Phe Asp Cys Thr Gln Phe Pro Thr Arg Ile Ala
145                 150                 155                 160

Gly Glu Ile Lys Ser Phe Ser Thr Asp Gly Trp Val Ala Pro Lys Leu
                165                 170                 175

Ser Lys Arg Met Asp Lys Phe Met Leu Tyr Leu Leu Thr Ala Gly Lys
            180                 185                 190

Lys Ala Leu Ala Asp Gly Gly Ile Thr Asp Glu Val Met Lys Glu Leu
        195                 200                 205

Asp Lys Arg Lys Cys Gly Val Leu Ile Gly Ser Gly Met Gly Gly Met
    210                 215                 220

Lys Val Phe Asn Asp Ala Ile Glu Ala Leu Arg Val Ser Tyr Lys Lys
225                 230                 235                 240

Met Asn Pro Phe Cys Val Pro Phe Ala Thr Thr Asn Met Gly Ser Ala
                245                 250                 255

Met Leu Ala Met Asp Leu Gly Trp Met Gly Pro Asn Tyr Ser Ile Ser
            260                 265                 270

Thr Ala Cys Ala Thr Ser Asn Phe Cys Ile Leu Asn Ala Ala Asn His
        275                 280                 285

Ile Ile Arg Gly Glu Ala Asp Met Met Leu Cys Gly Gly Ser Asp Ala
    290                 295                 300

Val Ile Ile Pro Ile Gly Leu Gly Gly Phe Val Ala Cys Arg Ala Leu
305                 310                 315                 320

Ser Gln Arg Asn Ser Asp Pro Thr Lys Ala Ser Arg Pro Trp Asp Ser
                325                 330                 335
```

```
Asn Arg Asp Gly Phe Val Met Gly Glu Gly Ala Gly Val Leu Leu Leu
            340                 345                 350

Glu Glu Leu Glu His Ala Lys Lys Arg Gly Ala Thr Ile Tyr Ala Glu
        355                 360                 365

Phe Leu Gly Gly Ser Phe Thr Cys Asp Ala Tyr His Met Thr Glu Pro
    370                 375                 380

His Pro Glu Gly Ala Gly Val Ile Leu Cys Ile Glu Lys Ala Leu Ala
385                 390                 395                 400

Gln Ala Gly Val Ser Lys Glu Asp Val Asn Tyr Ile Asn Ala His Ala
                405                 410                 415

Thr Ser Thr Ser Ala Gly Asp Ile Lys Glu Tyr Gln Ala Leu Ala Arg
            420                 425                 430

Cys Phe Gly Gln Asn Ser Glu Leu Arg Val Asn Ser Thr Lys Ser Met
        435                 440                 445

Ile Gly His Leu Leu Gly Ala Ala Gly Gly Val Glu Ala Val Thr Val
    450                 455                 460

Val Gln Ala Ile Arg Thr Gly Trp Ile His Pro Asn Leu Asn Leu Glu
465                 470                 475                 480

Asp Pro Asp Lys Ala Val Asp Ala Lys Leu Leu Val Gly Pro Lys Lys
                485                 490                 495

Glu Arg Leu Asn Val Lys Val Gly Leu Ser Asn Ser Phe Gly Phe Gly
            500                 505                 510

Gly His Asn Ser Ser Ile Leu Phe Ala Pro Cys Asn Val
        515                 520                 525


<210> SEQ ID NO 160
<211> LENGTH: 467
<212> TYPE: PRT
<213> ORGANISM: Prototheca moriformis

<400> SEQUENCE: 160

Met Gln Thr Ala His Gln Arg Pro Pro Thr Glu Gly His Cys Phe Gly
1               5                   10                  15

Ala Arg Leu Pro Thr Ala Ser Arg Arg Ala Val Arg Arg Ala Trp Ser
            20                  25                  30

Arg Ile Ala Arg Ala Ala Ala Ala Ala Asp Ala Asn Pro Ala Arg Pro
        35                  40                  45

Glu Arg Arg Val Val Ile Thr Gly Gln Gly Val Val Thr Ser Leu Gly
    50                  55                  60

Gln Thr Ile Glu Gln Phe Tyr Ser Ser Leu Leu Glu Gly Val Ser Gly
65                  70                  75                  80

Ile Ser Gln Ile Gln Lys Phe Asp Thr Thr Gly Tyr Thr Thr Thr Ile
                85                  90                  95

Ala Gly Glu Ile Lys Ser Leu Gln Leu Asp Pro Tyr Val Pro Lys Arg
            100                 105                 110

Trp Ala Lys Arg Val Asp Asp Val Ile Lys Tyr Val Tyr Ile Ala Gly
        115                 120                 125

Lys Gln Ala Leu Glu Ser Ala Gly Leu Pro Ile Glu Ala Ala Gly Leu
    130                 135                 140

Ala Gly Ala Gly Leu Asp Pro Ala Leu Cys Gly Val Leu Ile Gly Thr
145                 150                 155                 160

Ala Met Ala Gly Met Thr Ser Phe Ala Ala Gly Val Glu Ala Leu Thr
                165                 170                 175

Arg Gly Gly Val Arg Lys Met Asn Pro Phe Cys Ile Pro Phe Ser Ile
            180                 185                 190
```

```
Ser Asn Met Gly Gly Ala Met Leu Ala Met Asp Ile Gly Phe Met Gly
        195                 200                 205

Pro Asn Tyr Ser Ile Ser Thr Ala Cys Ala Thr Gly Asn Tyr Cys Ile
    210                 215                 220

Leu Gly Ala Ala Asp His Ile Arg Arg Gly Asp Ala Asn Val Met Leu
225                 230                 235                 240

Ala Gly Gly Ala Asp Ala Ala Ile Ile Pro Ser Gly Ile Gly Gly Phe
                245                 250                 255

Ile Ala Cys Lys Ala Leu Ser Lys Arg Asn Asp Glu Pro Glu Arg Ala
            260                 265                 270

Ser Arg Pro Trp Asp Ala Asp Arg Asp Gly Phe Val Met Gly Glu Gly
        275                 280                 285

Ala Gly Val Leu Val Leu Glu Glu Leu Glu His Ala Lys Arg Arg Gly
    290                 295                 300

Ala Thr Ile Leu Ala Glu Leu Val Gly Gly Ala Ala Thr Ser Asp Ala
305                 310                 315                 320

His His Met Thr Glu Pro Asp Pro Gln Gly Arg Gly Val Arg Leu Cys
                325                 330                 335

Leu Glu Arg Ala Leu Glu Arg Ala Arg Leu Ala Pro Glu Arg Val Gly
            340                 345                 350

Tyr Val Asn Ala His Gly Thr Ser Thr Pro Ala Gly Asp Val Ala Glu
        355                 360                 365

Tyr Arg Ala Ile Arg Ala Val Ile Pro Gln Asp Ser Leu Arg Ile Asn
    370                 375                 380

Ser Thr Lys Ser Met Ile Gly His Leu Leu Gly Gly Ala Gly Ala Val
385                 390                 395                 400

Glu Ala Val Ala Ala Ile Gln Ala Leu Arg Thr Gly Trp Leu His Pro
                405                 410                 415

Asn Leu Asn Leu Glu Asn Pro Ala Pro Gly Val Asp Pro Val Val Leu
            420                 425                 430

Val Gly Pro Arg Lys Glu Arg Ala Glu Asp Leu Asp Val Val Leu Ser
        435                 440                 445

Asn Ser Phe Gly Phe Gly Gly His Asn Ser Cys Val Ile Phe Arg Lys
    450                 455                 460

Tyr Asp Glu
465


<210> SEQ ID NO 161
<211> LENGTH: 431
<212> TYPE: PRT
<213> ORGANISM: Prototheca moriformis

<400> SEQUENCE: 161

Ala Ala Ala Ala Ala Asp Ala Asn Pro Ala Arg Pro Glu Arg Arg Val
1               5                   10                  15

Val Ile Thr Gly Gln Gly Val Val Thr Ser Leu Gly Gln Thr Ile Glu
            20                  25                  30

Gln Phe Tyr Ser Ser Leu Leu Glu Gly Val Ser Gly Ile Ser Gln Ile
        35                  40                  45

Gln Lys Phe Asp Thr Thr Gly Tyr Thr Thr Thr Ile Ala Gly Glu Ile
    50                  55                  60

Lys Ser Leu Gln Leu Asp Pro Tyr Val Pro Lys Arg Trp Ala Lys Arg
65                  70                  75                  80

Val Asp Asp Val Ile Lys Tyr Val Tyr Ile Ala Gly Lys Gln Ala Leu
```

```
                85                  90                  95

Glu Ser Ala Gly Leu Pro Ile Glu Ala Ala Gly Leu Ala Gly Ala Gly
            100                 105                 110

Leu Asp Pro Ala Leu Cys Gly Val Leu Ile Gly Thr Ala Met Ala Gly
        115                 120                 125

Met Thr Ser Phe Ala Ala Gly Val Glu Ala Leu Thr Arg Gly Gly Val
    130                 135                 140

Arg Lys Met Asn Pro Phe Cys Ile Pro Phe Ser Ile Ser Asn Met Gly
145                 150                 155                 160

Gly Ala Met Leu Ala Met Asp Ile Gly Phe Met Gly Pro Asn Tyr Ser
                165                 170                 175

Ile Ser Thr Ala Cys Ala Thr Gly Asn Tyr Cys Ile Leu Gly Ala Ala
            180                 185                 190

Asp His Ile Arg Arg Gly Asp Ala Asn Val Met Leu Ala Gly Gly Ala
        195                 200                 205

Asp Ala Ala Ile Ile Pro Ser Gly Ile Gly Gly Phe Ile Ala Cys Lys
    210                 215                 220

Ala Leu Ser Lys Arg Asn Asp Glu Pro Glu Arg Ala Ser Arg Pro Trp
225                 230                 235                 240

Asp Ala Asp Arg Asp Gly Phe Val Met Gly Glu Gly Ala Gly Val Leu
                245                 250                 255

Val Leu Glu Glu Leu Glu His Ala Lys Arg Arg Gly Ala Thr Ile Leu
            260                 265                 270

Ala Glu Leu Val Gly Gly Ala Ala Thr Ser Asp Ala His His Met Thr
        275                 280                 285

Glu Pro Asp Pro Gln Gly Arg Gly Val Arg Leu Cys Leu Glu Arg Ala
    290                 295                 300

Leu Glu Arg Ala Arg Leu Ala Pro Glu Arg Val Gly Tyr Val Asn Ala
305                 310                 315                 320

His Gly Thr Ser Thr Pro Ala Gly Asp Val Ala Glu Tyr Arg Ala Ile
                325                 330                 335

Arg Ala Val Ile Pro Gln Asp Ser Leu Arg Ile Asn Ser Thr Lys Ser
            340                 345                 350

Met Ile Gly His Leu Leu Gly Gly Ala Gly Ala Val Glu Ala Val Ala
        355                 360                 365

Ala Ile Gln Ala Leu Arg Thr Gly Trp Leu His Pro Asn Leu Asn Leu
    370                 375                 380

Glu Asn Pro Ala Pro Gly Val Asp Pro Val Val Leu Val Gly Pro Arg
385                 390                 395                 400

Lys Glu Arg Ala Glu Asp Leu Asp Val Val Leu Ser Asn Ser Phe Gly
                405                 410                 415

Phe Gly Gly His Asn Ser Cys Val Ile Phe Arg Lys Tyr Asp Glu
            420                 425                 430


<210> SEQ ID NO 162
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Pro Asp Trp Ser Met Leu Phe Ala Val Ile Thr Thr Ile Phe Ser Ala
1               5                   10                  15
```

```
Ala Glu Lys Gln Trp Thr Asn Leu Glu Trp Lys Pro Lys Pro Asn Pro
            20                  25                  30

Pro Gln Leu Leu Asp Asp His Phe Gly Pro His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Val Ala Val Met Asn His Leu Gln Glu Ala Ala Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Ile Trp Val Val Arg Arg Thr His Val Ala
            100                 105                 110

Val Glu Arg Tyr Pro Thr Trp Gly Asp Thr Val Glu Val Glu Cys Trp
        115                 120                 125

Ile Gly Ala Ser Gly Asn Asn Gly Met Arg Arg Asp Phe Leu Val Arg
    130                 135                 140

Asp Cys Lys Thr Gly Glu Ile Leu Thr Arg Cys Thr Ser Leu Ser Val
145                 150                 155                 160

Leu Met Asn Thr Arg Thr Arg Arg Leu Ser Thr Ile Pro Asp Glu Val
                165                 170                 175

Arg Gly Glu Ile Gly Pro Ala Phe Ile Asp Asn Val Ala Val Lys Asp
            180                 185                 190

Asp Glu Ile Lys Lys Leu Gln Lys Leu Asn Asp Ser Thr Ala Asp Tyr
        195                 200                 205

Ile Gln Gly Gly Leu Thr Pro Arg Trp Asn Asp Leu Asp Val Asn Gln
    210                 215                 220

His Val Asn Asn Leu Lys Tyr Val Ala Trp Val Phe Glu Thr Val Pro
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val


<210> SEQ ID NO 163
<211> LENGTH: 361
<212> TYPE: PRT
<213> ORGANISM: Cuphea hyssopifolia

<400> SEQUENCE: 163

Met Val Ala Thr Asn Ala Ala Ala Phe Ser Ala Tyr Thr Phe Phe Leu
1               5                   10                  15

Thr Ser Pro Thr His Gly Tyr Ser Ser Lys Arg Leu Ala Asp Thr Gln
            20                  25                  30

Asn Gly Tyr Pro Gly Thr Ser Leu Lys Ser Lys Ser Thr Pro Pro Pro
        35                  40                  45

Ala Ala Ala Ala Ala Arg Asn Gly Ala Leu Pro Leu Leu Ala Ser Ile
    50                  55                  60
```

```
Cys Lys Cys Pro Lys Lys Ala Asp Gly Ser Met Gln Leu Asp Ser Ser
65                  70                  75                  80

Leu Val Phe Gly Phe Gln Phe Tyr Ile Arg Ser Tyr Glu Val Gly Ala
                85                  90                  95

Asp Gln Thr Val Ser Ile Gln Thr Val Leu Asn Tyr Leu Gln Glu Ala
            100                 105                 110

Ala Ile Asn His Val Gln Ser Ala Gly Tyr Phe Gly Asp Ser Phe Gly
        115                 120                 125

Ala Thr Pro Glu Met Thr Lys Arg Asn Leu Ile Trp Val Ile Thr Lys
    130                 135                 140

Met Gln Val Leu Val Asp Arg Tyr Pro Ala Trp Gly Asp Val Val Gln
145                 150                 155                 160

Val Asp Thr Trp Thr Cys Ser Ser Gly Lys Asn Ser Met Gln Arg Asp
                165                 170                 175

Trp Phe Val Arg Asp Leu Lys Thr Gly Asp Ile Ile Thr Arg Ala Ser
            180                 185                 190

Ser Val Trp Val Leu Met Asn Arg Leu Thr Arg Lys Leu Ser Lys Ile
        195                 200                 205

Pro Glu Ala Val Leu Glu Glu Ala Lys Leu Phe Val Met Asn Thr Ala
    210                 215                 220

Pro Thr Val Asp Asp Asn Arg Lys Leu Pro Lys Leu Asp Gly Ser Ser
225                 230                 235                 240

Ala Asp Tyr Val Leu Ser Gly Leu Thr Pro Arg Trp Ser Asp Leu Asp
                245                 250                 255

Met Asn Gln His Val Asn Asn Val Lys Tyr Ile Ala Trp Ile Leu Glu
            260                 265                 270

Ser Val Pro Gln Ser Ile Pro Glu Thr His Lys Leu Ser Ala Ile Thr
        275                 280                 285

Val Glu Tyr Arg Arg Glu Cys Gly Lys Asn Ser Val Leu Gln Ser Leu
    290                 295                 300

Thr Asn Val Ser Gly Asp Gly Ile Thr Cys Gly Asn Ser Ile Ile Glu
305                 310                 315                 320

Cys His His Leu Leu Gln Leu Glu Thr Gly Pro Glu Ile Leu Leu Ala
                325                 330                 335

Arg Thr Glu Trp Ile Ser Lys Glu Pro Gly Phe Arg Gly Ala Pro Ile
            340                 345                 350

Gln Ala Glu Lys Val Tyr Asn Asn Lys
        355                 360


<210> SEQ ID NO 164
<211> LENGTH: 417
<212> TYPE: PRT
<213> ORGANISM: Cuphea hyssopifolia

<400> SEQUENCE: 164

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80
```

```
Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser
```

<210> SEQ ID NO 165
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Any amino acid
<220> FEATURE:

<221> NAME/KEY: MOD_RES
<222> LOCATION: (24)..(33)
<223> OTHER INFORMATION: Any amino acid
<220> FEATURE:
<221> NAME/KEY: MOD_RES
<222> LOCATION: (92)..(92)
<223> OTHER INFORMATION: Ile or Leu
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (128)..(130)
<223> OTHER INFORMATION: Any amino acid
<220> FEATURE:
<221> NAME/KEY: MOD_RES
<222> LOCATION: (142)..(142)
<223> OTHER INFORMATION: Any amino acid
<220> FEATURE:
<221> NAME/KEY: MOD_RES
<222> LOCATION: (145)..(145)
<223> OTHER INFORMATION: Any amino acid
<220> FEATURE:
<221> NAME/KEY: MOD_RES
<222> LOCATION: (148)..(148)
<223> OTHER INFORMATION: Any amino acid
<220> FEATURE:
<221> NAME/KEY: MOD_RES
<222> LOCATION: (153)..(153)
<223> OTHER INFORMATION: Any amino acid
<220> FEATURE:
<221> NAME/KEY: MOD_RES
<222> LOCATION: (158)..(158)
<223> OTHER INFORMATION: Any amino acid
<220> FEATURE:
<221> NAME/KEY: MOD_RES
<222> LOCATION: (182)..(182)
<223> OTHER INFORMATION: Any amino acid
<220> FEATURE:
<221> NAME/KEY: MOD_RES
<222> LOCATION: (184)..(184)
<223> OTHER INFORMATION: Any amino acid
<220> FEATURE:
<221> NAME/KEY: MOD_RES
<222> LOCATION: (192)..(192)
<223> OTHER INFORMATION: Any amino acid
<220> FEATURE:
<221> NAME/KEY: MOD_RES
<222> LOCATION: (202)..(202)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (249)..(249)
<223> OTHER INFORMATION: Any amino acid
<220> FEATURE:
<221> NAME/KEY: MOD_RES
<222> LOCATION: (295)..(295)
<223> OTHER INFORMATION: Any amino acid
<220> FEATURE:
<221> NAME/KEY: MOD_RES
<222> LOCATION: (310)..(310)
<223> OTHER INFORMATION: Any amino acid
<220> FEATURE:
<221> NAME/KEY: MOD_RES
<222> LOCATION: (322)..(322)
<223> OTHER INFORMATION: Any amino acid
<220> FEATURE:
<221> NAME/KEY: MOD_RES
<222> LOCATION: (350)..(350)
<223> OTHER INFORMATION: Any amino acid
<220> FEATURE:
<221> NAME/KEY: MOD_RES
<222> LOCATION: (352)..(353)
<223> OTHER INFORMATION: Any amino acid

```
<220> FEATURE:
<221> NAME/KEY: MOD_RES
<222> LOCATION: (356)..(356)
<223> OTHER INFORMATION: Any amino acid
<220> FEATURE:
<221> NAME/KEY: MOD_RES
<222> LOCATION: (359)..(359)
<223> OTHER INFORMATION: Any amino acid
<220> FEATURE:
<221> NAME/KEY: MOD_RES
<222> LOCATION: (373)..(373)
<223> OTHER INFORMATION: Any amino acid
<220> FEATURE:
<221> NAME/KEY: MOD_RES
<222> LOCATION: (380)..(380)
<223> OTHER INFORMATION: Any amino acid
<220> FEATURE:
<221> NAME/KEY: MOD_RES
<222> LOCATION: (399)..(400)
<223> OTHER INFORMATION: Any amino acid
<220> FEATURE:
<221> NAME/KEY: MOD_RES
<222> LOCATION: (490)..(490)
<223> OTHER INFORMATION: Any amino acid
<220> FEATURE:
<221> NAME/KEY: MOD_RES
<222> LOCATION: (529)..(529)
<223> OTHER INFORMATION: Any amino acid

<400> SEQUENCE: 165

Met Glu Arg Thr Asn Ser Ile Glu Met Asp Gln Glu Arg Leu Thr Ala
1               5                   10                  15

Glu Met Ala Phe Lys Xaa Ser Xaa Xaa Xaa Xaa Xaa Xaa Xaa Xaa Xaa
            20                  25                  30

Xaa Leu Pro Asp Phe Met Thr Ser Ile Asn Val Lys Leu Leu Tyr His
        35                  40                  45

Tyr Val Ile Thr Asn Leu Phe Asn Leu Cys Phe Phe Pro Leu Thr Ala
    50                  55                  60

Ile Val Ala Gly Lys Ala Ser Arg Leu Thr Ile Asx Asp Leu His His
65                  70                  75                  80

Leu Tyr Ser Tyr Leu Gln His Asn Leu Ile Thr Xaa Xaa Leu Leu Phe
                85                  90                  95

Ala Phe Thr Val Phe Gly Ser Ile Leu Tyr Ile Val Thr Arg Pro Lys
            100                 105                 110

Pro Val Tyr Leu Val Asp Tyr Ser Cys Tyr Leu Pro Pro Thr His Xaa
        115                 120                 125

Xaa Xaa Ser Ile Ser Lys Val Met Asp Ile Phe Tyr Gln Xaa Arg Lys
    130                 135                 140

Xaa Asp Pro Xaa Arg Asn Gly Thr Xaa Asp Asp Ser Ser Xaa Leu Asp
145                 150                 155                 160

Phe Leu Arg Lys Ile Gln Glu Arg Ser Gly Leu Gly Asp Glu Thr Tyr
                165                 170                 175

Gly Pro Glu Gly Leu Xaa Gln Xaa Pro Pro Arg Lys Asn Phe Ala Xaa
            180                 185                 190

Ala Arg Glu Glu Thr Glu Gln Val Ile Xaa Gly Ala Leu Xaa Asn Leu
        195                 200                 205

Phe Glu Asn Thr Lys Val Asn Pro Lys Glu Ile Gly Ile Leu Val Val
    210                 215                 220

Asn Ser Ser Met Phe Asn Pro Thr Pro Ser Leu Ser Ala Met Val Val
225                 230                 235                 240

Asn Thr Phe Lys Leu Arg Ser Asn Xaa Lys Ser Phe Asn Leu Gly Gly
                245                 250                 255
```

-continued

```
Met Gly Cys Ser Ala Gly Val Ile Ala Ile Asp Leu Ala Lys Asp Leu
            260                 265                 270

Leu His Val His Lys Asn Thr Tyr Ala Leu Val Val Ser Thr Glu Asn
        275                 280                 285

Ile Thr Tyr Asn Ile Tyr Xaa Gly Asp Asn Arg Ser Met Met Val Ser
    290                 295                 300

Asn Cys Leu Phe Arg Xaa Gly Gly Ala Ala Ile Leu Leu Ser Asn Lys
305                 310                 315                 320

Pro Xaa Asp Arg Arg Arg Ser Lys Tyr Glu Leu Val His Thr Val Arg
                325                 330                 335

Thr His Thr Gly Ala Asp Asp Lys Ser Phe Arg Cys Val Xaa Gln Xaa
            340                 345                 350

Xaa Asp Glu Xaa Gly Lys Xaa Gly Val Ser Leu Ser Lys Asp Ile Thr
        355                 360                 365

Ala Val Ala Gly Xaa Thr Val Lys Lys Asn Ile Xaa Thr Leu Gly Pro
    370                 375                 380

Leu Val Leu Pro Leu Ser Glu Lys Leu Leu Phe Phe Val Thr Xaa Xaa
385                 390                 395                 400

Ala Lys Lys Leu Phe Lys Asp Lys Ile Lys His Tyr Tyr Val Pro Asp
                405                 410                 415

Phe Lys Leu Ala Ile Asp His Phe Cys Ile His Ala Gly Gly Arg Ala
            420                 425                 430

Val Ile Asp Val Leu Glu Lys Asn Leu Gly Leu Ser Pro Ile Asp Val
        435                 440                 445

Glu Ala Ser Arg Ser Thr Leu His Arg Phe Gly Asn Thr Ser Ser Ser
    450                 455                 460

Ser Ile Trp Tyr Glu Leu Ala Tyr Ile Glu Ala Lys Gly Arg Met Lys
465                 470                 475                 480

Lys Gly Asn Lys Val Trp Gln Ile Ala Xaa Gly Ser Gly Phe Lys Cys
                485                 490                 495

Asn Ser Ala Val Trp Val Ala Leu Arg Asn Val Lys Ala Ser Thr Asn
            500                 505                 510

Ser Pro Trp Glu His Cys Ile Asp Arg Tyr Pro Val Lys Ile Asp Ser
        515                 520                 525

Xaa Ser Ser Lys Ser Glu Thr Arg Ala Gln Asn Gly Arg Ser
    530                 535                 540


<210> SEQ ID NO 166
<211> LENGTH: 505
<212> TYPE: PRT
<213> ORGANISM: Brassica napus

<400> SEQUENCE: 166

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
            20                  25                  30

Ala Tyr Leu Thr Ile Asp Asp Leu His His Leu Tyr Tyr Ser Tyr Leu
        35                  40                  45

Gln His Asn Leu Ile Thr Ile Ala Pro Leu Leu Ala Phe Thr Val Phe
    50                  55                  60

Gly Ser Val Leu Tyr Ile Ala Thr Arg Pro Lys Pro Val Tyr Leu Val
65                  70                  75                  80

Glu Tyr Ser Cys Tyr Leu Pro Pro Thr His Cys Arg Ser Ser Ile Ser
                85                  90                  95
```

```
Lys Val Met Asp Ile Phe Phe Gln Val Arg Lys Ala Asp Pro Ser Arg
            100                 105                 110

Asn Gly Thr Cys Asp Asp Ser Ser Trp Leu Asp Phe Leu Arg Lys Ile
        115                 120                 125

Gln Glu Arg Ser Gly Leu Gly Asp Glu Thr His Gly Pro Glu Gly Leu
    130                 135                 140

Leu Gln Val Pro Pro Arg Lys Thr Phe Ala Arg Ala Arg Glu Glu Thr
145                 150                 155                 160

Glu Gln Val Ile Ile Gly Ala Leu Glu Asn Leu Phe Lys Asn Thr Asn
                165                 170                 175

Val Asn Pro Lys Asp Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Val Arg Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Tyr Asn Ile
                245                 250                 255

Tyr Ala Gly Asp Asn Arg Ser Met Met Val Ser Asn Cys Leu Phe Arg
            260                 265                 270

Val Gly Gly Ala Ala Ile Leu Leu Ser Asn Lys Pro Arg Asp Arg Arg
        275                 280                 285

Arg Ser Lys Tyr Glu Leu Val His Thr Val Arg Thr His Thr Gly Ala
    290                 295                 300

Asp Asp Lys Ser Phe Arg Cys Val Gln Gln Gly Asp Asp Glu Asn Gly
305                 310                 315                 320

Gln Thr Gly Val Ser Leu Ser Lys Asp Ile Thr Asp Val Ala Gly Arg
                325                 330                 335

Thr Val Lys Lys Asn Ile Ala Thr Leu Gly Pro Leu Ile Leu Pro Leu
            340                 345                 350

Ser Glu Lys Leu Leu Phe Phe Val Thr Phe Met Gly Lys Lys Leu Phe
        355                 360                 365

Lys Asp Glu Ile Lys His Tyr Tyr Val Pro Asp Phe Lys Leu Ala Ile
    370                 375                 380

Asp His Phe Cys Ile His Ala Gly Gly Lys Ala Val Ile Asp Val Leu
385                 390                 395                 400

Glu Lys Asn Leu Gly Leu Ala Pro Ile Asp Val Glu Ala Ser Arg Ser
                405                 410                 415

Thr Leu His Arg Phe Gly Asn Thr Ser Ser Ser Ser Ile Trp Tyr Glu
            420                 425                 430

Leu Ala Tyr Ile Glu Pro Lys Gly Arg Met Lys Lys Gly Asn Lys Val
        435                 440                 445

Trp Gln Ile Ala Leu Gly Ser Gly Phe Lys Cys Asn Ser Ala Val Trp
    450                 455                 460

Val Ala Leu Asn Asn Val Lys Ala Ser Thr Asn Ser Pro Trp Glu His
465                 470                 475                 480

Cys Ile Asp Arg Tyr Pro Val Lys Ile Asp Ser Asp Ser Gly Lys Ser
                485                 490                 495

Glu Thr Arg Val Pro Asn Gly Arg Ser
            500                 505
```

<210> SEQ ID NO 167
<211> LENGTH: 528
<212> TYPE: PRT
<213> ORGANISM: Brassica napus

<400> SEQUENCE: 167

Met Glu Arg Thr Asn Ser Ile Glu Met Asp Gln Glu Arg Leu Thr Ala
1 5 10 15

Glu Met Ala Phe Lys Asp Ser Ser Ser Ala Val Ile Arg Ile Arg Arg
20 25 30

Arg Leu Pro Asp Phe Leu Thr Ser Val Lys Leu Lys Tyr Val Lys Leu
35 40 45

Gly Leu His Asn Ser Phe Asn Phe Thr Thr Phe Leu Phe Leu Leu Ile
50 55 60

Ile Leu Pro Leu Thr Gly Thr Val Leu Val Gln Leu Thr Gly Leu Thr
65 70 75 80

Phe Glu Thr Phe Ser Glu Leu Trp Tyr Asn His Ala Ala Gln Leu Asp
85 90 95

Gly Val Thr Arg Leu Ala Cys Leu Val Ser Leu Cys Phe Val Leu Ile
100 105 110

Ile Tyr Val Thr Asn Arg Ser Lys Pro Val Tyr Leu Val Asp Phe Ser
115 120 125

Cys Tyr Lys Pro Glu Asp Glu Arg Lys Met Ser Val Asp Ser Phe Leu
130 135 140

Lys Met Thr Glu Gln Asn Gly Ala Phe Thr Asp Asp Thr Val Gln Phe
145 150 155 160

Gln Gln Arg Ile Ser Asn Arg Ala Gly Leu Gly Asp Glu Thr Tyr Leu
165 170 175

Pro Arg Gly Ile Thr Ser Thr Pro Pro Lys Leu Asn Met Ser Glu Ala
180 185 190

Arg Ala Glu Ala Glu Ala Val Met Phe Gly Ala Leu Asp Ser Leu Phe
195 200 205

Glu Lys Thr Gly Ile Lys Pro Ala Glu Val Gly Ile Leu Ile Val Ser
210 215 220

Cys Ser Leu Phe Asn Pro Thr Pro Ser Leu Ser Ala Met Ile Val Asn
225 230 235 240

His Tyr Lys Met Arg Glu Asp Ile Lys Ser Tyr Asn Leu Gly Gly Met
245 250 255

Gly Cys Ser Ala Gly Leu Ile Ser Ile Asp Leu Ala Asn Asn Leu Leu
260 265 270

Lys Ala Asn Pro Asn Ser Tyr Ala Val Val Val Ser Thr Glu Asn Ile
275 280 285

Thr Leu Asn Trp Tyr Phe Gly Asn Asp Arg Ser Met Leu Leu Cys Asn
290 295 300

Cys Ile Phe Arg Met Gly Gly Ala Ala Ile Leu Leu Ser Asn Arg Arg
305 310 315 320

Gln Asp Arg Ser Lys Ser Lys Tyr Glu Leu Val Asn Val Val Arg Thr
325 330 335

His Lys Gly Ser Asp Asp Lys Asn Tyr Asn Cys Val Tyr Gln Lys Glu
340 345 350

Asp Glu Arg Gly Thr Ile Gly Val Ser Leu Ala Arg Glu Leu Met Ser
355 360 365

Val Ala Gly Asp Ala Leu Lys Thr Asn Ile Thr Thr Leu Gly Pro Met
370 375 380

```
Val Leu Pro Leu Ser Gly Gln Leu Met Phe Ser Val Ser Leu Val Lys
385                 390                 395                 400

Arg Lys Leu Leu Lys Leu Lys Val Lys Pro Tyr Ile Pro Asp Phe Lys
                405                 410                 415

Leu Ala Phe Glu His Phe Cys Ile His Ala Gly Gly Arg Ala Val Leu
            420                 425                 430

Asp Glu Val Gln Lys Asn Leu Asp Leu Glu Asp Trp His Met Glu Pro
        435                 440                 445

Ser Arg Met Thr Leu His Arg Phe Gly Asn Thr Ser Ser Ser Ser Leu
    450                 455                 460

Trp Tyr Glu Met Ala Tyr Thr Glu Ala Lys Gly Arg Val Lys Ala Gly
465                 470                 475                 480

Asp Arg Leu Trp Gln Ile Ala Phe Gly Ser Gly Phe Lys Cys Asn Ser
                485                 490                 495

Ala Val Trp Lys Ala Leu Arg Val Val Ser Thr Glu Glu Leu Thr Gly
            500                 505                 510

Asn Ala Trp Ala Gly Ser Ile Glu Asn Tyr Pro Val Lys Ile Val Gln
        515                 520                 525


<210> SEQ ID NO 168
<211> LENGTH: 506
<212> TYPE: PRT
<213> ORGANISM: Crambe abyssinica

<400> SEQUENCE: 168

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
            20                  25                  30

Ala Ser Arg Leu Thr Ile Asp Asp Leu His His Leu Tyr Tyr Ser Tyr
        35                  40                  45

Leu Gln His Asn Val Ile Thr Ile Ala Pro Leu Phe Ala Phe Thr Val
    50                  55                  60

Phe Gly Ser Ile Leu Tyr Ile Val Thr Arg Pro Lys Pro Val Tyr Leu
65                  70                  75                  80

Val Glu Tyr Ser Cys Tyr Leu Pro Pro Thr Gln Cys Arg Ser Ser Ile
                85                  90                  95

Ser Lys Val Met Asp Ile Phe Tyr Gln Val Arg Lys Ala Asp Pro Phe
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Ala Arg Glu Glu
145                 150                 155                 160

Thr Glu Gln Val Ile Val Gly Ala Leu Lys Asn Leu Phe Glu Asn Thr
                165                 170                 175

Lys Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
```

```
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320

Gly Lys Thr Gly Val Ser Leu Ser Lys Asp Ile Thr Glu Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Ala Lys Lys Leu
        355                 360                 365

Phe Lys Asp Lys Val Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Gly Leu Ala Pro Ile Asp Val Glu Ala Ser Arg
                405                 410                 415

Ser Thr Leu His Arg Phe Gly Asn Thr Ser Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Ser Asn Val Lys Ala Ser Thr Asn Ser Pro Trp Glu
465                 470                 475                 480

His Cys Ile Asp Arg Tyr Pro Val Lys Ile Asp Ser Asp Ser Ala Lys
                485                 490                 495

Ser Glu Thr Arg Ala Gln Asn Gly Arg Ser
            500                 505


<210> SEQ ID NO 169
<211> LENGTH: 506
<212> TYPE: PRT
<213> ORGANISM: Cardamine graeca

<400> SEQUENCE: 169

Met Thr Ser Ile Asn Val Lys Leu Leu Tyr His Tyr Val Leu Thr Asn
1               5                   10                  15

Phe Phe Asn Leu Cys Leu Phe Pro Leu Thr Ala Phe Pro Ala Gly Lys
            20                  25                  30

Ala Ser Gln Leu Thr Thr Asn Asp Leu His His Leu Tyr Ser Tyr Leu
        35                  40                  45

His His Asn Leu Ile Thr Val Thr Leu Leu Phe Ala Phe Thr Val Phe
    50                  55                  60

Gly Ser Ile Leu Tyr Ile Val Thr Arg Pro Lys Pro Val Tyr Leu Val
65                  70                  75                  80

Asp Tyr Ser Cys Tyr Leu Pro Pro Arg His Leu Ser Cys Gly Ile Ser
                85                  90                  95
```

-continued

```
Arg Val Met Glu Ile Phe Tyr Glu Ile Arg Lys Ser Asp Pro Ser Arg
            100                 105                 110

Glu Val Pro Phe Asp Asp Pro Ser Ser Leu Glu Phe Leu Arg Lys Ile
        115                 120                 125

Gln Glu Arg Ser Gly Leu Gly Asp Glu Thr Tyr Gly Pro Gln Gly Leu
    130                 135                 140

Val His Asp Met Pro Leu Arg Met Asn Phe Ala Ala Ala Arg Glu Glu
145                 150                 155                 160

Thr Glu Gln Val Ile Asn Gly Ala Leu Glu Lys Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Ser Leu Gly Gly Met Gly Cys Ser
    210                 215                 220

Ala Gly Ile Ile Ala Ile Asp Leu Ala Lys Asp Leu Leu His Val His
225                 230                 235                 240

Lys Asn Thr Tyr Ala Leu Val Val Ser Thr Glu Asn Ile Thr His Ser
                245                 250                 255

Thr Tyr Thr Gly Asp Asn Arg Ser Met Met Val Ser Asn Cys Leu Phe
            260                 265                 270

Arg Met Gly Gly Ala Ala Ile Leu Leu Ser Asn Lys Ala Gly Asp Arg
        275                 280                 285

Arg Arg Ser Lys Tyr Lys Leu Ala His Thr Val Arg Thr His Thr Gly
    290                 295                 300

Ala Asp Asp Gln Ser Phe Arg Cys Val Arg Gln Glu Asp Asp Asp Arg
305                 310                 315                 320

Gly Lys Ile Gly Val Cys Leu Ser Lys Asp Ile Thr Ala Val Ala Gly
                325                 330                 335

Lys Thr Val Thr Lys Asn Ile Ala Thr Leu Gly Pro Leu Val Leu Pro
            340                 345                 350

Leu Ser Glu Lys Phe Leu Tyr Val Val Ser Leu Met Ala Lys Lys Leu
        355                 360                 365

Phe Lys Asn Lys Ile Lys His Thr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ser Pro Val Asp Val Glu Ala Ser Arg
                405                 410                 415

Ser Thr Leu His Arg Phe Gly Asn Thr Ser Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Ile Gly Ser Gly Phe Lys Cys Asn Ser Ala Val
    450                 455                 460

Trp Val Ala Leu Cys Asn Val Lys Pro Ser Val Asn Ser Pro Trp Glu
465                 470                 475                 480

His Cys Ile Asp Arg Tyr Pro Val Glu Ile Asn Tyr Gly Ser Ser Lys
                485                 490                 495

Ser Glu Thr Arg Ala Gln Asn Gly Arg Ser
            500                 505
```

<210> SEQ ID NO 170
<211> LENGTH: 505
<212> TYPE: PRT
<213> ORGANISM: Lunaria annua

<400> SEQUENCE: 170

```
Met Thr Ser Ile Asn Val Lys Leu Leu Tyr His Tyr Val Ile Thr Asn
1               5                   10                  15

Phe Phe Asn Leu Cys Phe Phe Pro Leu Thr Ala Ile Leu Ala Gly Lys
            20                  25                  30

Ala Ser Arg Leu Thr Thr Asn Asp Leu His His Phe Tyr Ser Tyr Leu
        35                  40                  45

Gln His Asn Leu Ile Thr Leu Thr Leu Leu Phe Ala Phe Thr Val Phe
    50                  55                  60

Gly Ser Val Leu Tyr Phe Val Thr Arg Pro Lys Pro Val Tyr Leu Val
65                  70                  75                  80

Asp Tyr Ser Cys Tyr Leu Pro Pro Gln His Leu Ser Ala Gly Ile Ser
                85                  90                  95

Lys Thr Met Glu Ile Phe Tyr Gln Ile Arg Lys Ser Asp Pro Leu Arg
            100                 105                 110

Asn Val Ala Leu Asp Asp Ser Ser Ser Leu Asp Phe Leu Arg Lys Ile
        115                 120                 125

Gln Glu Arg Ser Gly Leu Gly Asp Glu Thr Tyr Gly Pro Glu Gly Leu
    130                 135                 140

Phe Glu Ile Pro Pro Arg Lys Asn Leu Ala Ser Ala Arg Glu Glu Thr
145                 150                 155                 160

Glu Gln Val Ile Asn Gly Ala Leu Lys Asn Leu Phe Glu Asn Thr Lys
                165                 170                 175

Val Asn Pro Lys Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Ile Lys Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Asn Ile
                245                 250                 255

Tyr Thr Gly Asp Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Arg Leu Ala His Thr Val Arg Thr His Thr Gly Ala
    290                 295                 300

Asp Asp Lys Ser Phe Gly Cys Val Arg Gln Glu Glu Asp Asp Ser Gly
305                 310                 315                 320

Lys Thr Gly Val Ser Leu Ser Lys Asp Ile Thr Gly Val Ala Gly Ile
                325                 330                 335

Thr Val Gln Lys Asn Ile Thr Thr Leu Gly Pro Leu Val Leu Pro Leu
            340                 345                 350

Ser Glu Lys Ile Leu Phe Val Val Thr Phe Val Ala Lys Lys Leu Leu
        355                 360                 365

Lys Asp Lys Ile Lys His Tyr Tyr Val Pro Asp Phe Lys Leu Ala Val
    370                 375                 380
```

```
Asp His Phe Cys Ile His Ala Gly Gly Arg Ala Val Ile Asp Val Leu
385                 390                 395                 400

Glu Lys Asn Leu Gly Leu Ser Pro Ile Asp Val Glu Ala Ser Arg Ser
                405                 410                 415

Thr Leu His Arg Phe Gly Asn Thr Ser Ser Ser Ser Ile Trp Tyr Glu
            420                 425                 430

Leu Ala Tyr Ile Glu Ala Lys Gly Arg Met Lys Lys Gly Asn Lys Ala
        435                 440                 445

Trp Gln Ile Ala Val Gly Ser Gly Phe Lys Cys Asn Ser Ala Val Trp
    450                 455                 460

Val Ala Leu Arg Asn Val Lys Ala Ser Ala Asn Ser Pro Trp Glu His
465                 470                 475                 480

Cys Ile His Lys Tyr Pro Val Gln Met Tyr Ser Gly Ser Ser Lys Ser
                485                 490                 495

Glu Thr Arg Ala Gln Asn Gly Arg Ser
            500                 505


<210> SEQ ID NO 171
<211> LENGTH: 503
<212> TYPE: PRT
<213> ORGANISM: Tropaeolum majus

<400> SEQUENCE: 171

Met Ser Gly Thr Lys Ala Thr Ser Val Ser Val Pro Leu Pro Asp Phe
1               5                   10                  15

Lys Gln Ser Val Asn Leu Lys Tyr Val Lys Leu Gly Tyr His Tyr Ser
            20                  25                  30

Ile Thr His Ala Met Tyr Leu Phe Leu Thr Pro Leu Leu Leu Ile Met
        35                  40                  45

Ser Ala Gln Ile Ser Thr Phe Ser Ile Gln Asp Phe His His Leu Tyr
    50                  55                  60

Asn His Leu Ile Leu His Asn Leu Ser Ser Leu Ile Leu Cys Ile Ala
65                  70                  75                  80

Leu Leu Leu Phe Val Leu Thr Leu Tyr Phe Leu Thr Arg Pro Thr Pro
                85                  90                  95

Val Tyr Leu Leu Asn Phe Ser Cys Tyr Lys Pro Asp Ala Ile His Lys
            100                 105                 110

Cys Asp Arg Arg Arg Phe Met Asp Thr Ile Arg Gly Met Gly Thr Tyr
        115                 120                 125

Thr Glu Glu Asn Ile Glu Phe Gln Arg Lys Val Leu Glu Arg Ser Gly
    130                 135                 140

Ile Gly Glu Ser Ser Tyr Leu Pro Pro Thr Val Phe Lys Ile Pro Pro
145                 150                 155                 160

Arg Val Tyr Asp Ala Glu Glu Arg Ala Glu Ala Glu Met Leu Met Phe
                165                 170                 175

Gly Ala Val Asp Gly Leu Phe Glu Lys Ile Ser Val Lys Pro Asn Gln
            180                 185                 190

Ile Gly Val Leu Val Val Asn Cys Gly Leu Phe Asn Pro Ile Pro Ser
        195                 200                 205

Leu Ser Ser Met Ile Val Asn Arg Tyr Lys Met Arg Gly Asn Val Phe
    210                 215                 220

Ser Tyr Asn Leu Gly Gly Met Gly Cys Ser Ala Gly Val Ile Ser Ile
225                 230                 235                 240

Asp Leu Ala Lys Asp Leu Leu Gln Val Arg Pro Asn Ser Tyr Ala Leu
                245                 250                 255
```

-continued

```
Val Val Ser Leu Glu Cys Ile Ser Lys Asn Leu Tyr Leu Gly Glu Gln
            260                 265                 270

Arg Ser Met Leu Val Ser Asn Cys Leu Phe Arg Met Gly Gly Ala Ala
        275                 280                 285

Ile Leu Leu Ser Asn Lys Met Ser Asp Arg Trp Arg Ser Lys Tyr Arg
    290                 295                 300

Leu Val His Thr Val Arg Thr His Lys Gly Thr Glu Asp Asn Cys Phe
305                 310                 315                 320

Ser Cys Val Thr Arg Lys Glu Asp Ser Asp Gly Lys Ile Gly Ile Ser
                325                 330                 335

Leu Ser Lys Asn Leu Met Ala Val Ala Gly Asp Ala Leu Lys Thr Asn
            340                 345                 350

Ile Thr Thr Leu Gly Pro Leu Val Leu Pro Met Ser Glu Gln Leu Leu
        355                 360                 365

Phe Phe Ala Thr Leu Val Gly Lys Lys Val Phe Lys Met Lys Leu Gln
    370                 375                 380

Pro Tyr Ile Pro Asp Phe Lys Leu Ala Phe Glu His Phe Cys Ile His
385                 390                 395                 400

Ala Gly Gly Arg Ala Val Leu Asp Glu Leu Glu Lys Asn Leu Lys Leu
                405                 410                 415

Ser Ser Trp His Met Glu Pro Ser Arg Met Ser Leu Tyr Arg Phe Gly
            420                 425                 430

Asn Thr Ser Ser Ser Ser Leu Trp Tyr Glu Leu Ala Tyr Ser Glu Ala
        435                 440                 445

Lys Gly Arg Ile Lys Lys Gly Asp Arg Val Trp Gln Ile Ala Phe Gly
    450                 455                 460

Ser Gly Phe Lys Cys Asn Ser Ala Val Trp Lys Ala Leu Arg Asn Val
465                 470                 475                 480

Asn Pro Ala Glu Glu Lys Asn Pro Trp Met Asp Glu Ile His Leu Phe
                485                 490                 495

Pro Val Glu Val Pro Leu Asn
            500
```

TAILORED OILS

CROSS REFERENCE TO RELATED APPLICATIONS

This application claims the benefit under 35 U.S.C. 119(e) of U.S. Provisional Patent Application Nos. 61/887,268, filed Oct. 4, 2013; 61/892,399, filed Oct. 17, 2013; 61/895,355, filed Oct. 24, 2013; 61/923,327, filed Jan. 3, 2014; and 62/023,109, filed Jul. 10, 2014. Each of these applications is incorporated herein by reference in its entirety for all purposes. This application includes subject matter related to that disclosed in U.S. Provisional Patent Application No. 62/023,112, entitled "Novel Ketoacyl ACP Synthase Genes and Uses Thereof," filed Jul. 10, 2014, which is also hereby incorporated by reference in its entirety for all purposes. In particular, Tables 1, 7 and 8 of 62/023,112, and the corresponding sequences identified therein, are hereby incorporated by reference.

SEQUENCE LISTING

The instant application contains a Sequence Listing which has been submitted electronically in ASCII format and is hereby incorporated by reference in its entirety. Said ASCII copy, created on Aug. 28, 2017, is named SOLAP059US_SL.txt and is 599,266 bytes in size.

FIELD OF THE INVENTION

Embodiments of the present invention relate to oils/fats, fuels, foods, and oleochemicals and their production from cultures of genetically engineered cells. Specific embodiments relate to oils with a high content of triglycerides bearing fatty acyl groups upon the glycerol backbone in particular regiospecific patterns, highly stable oils, oils with high levels of oleic or mid-chain fatty acids, and products produced from such oils.

BACKGROUND OF THE INVENTION

PCT Publications WO2008/151149, WO2010/06032, WO2011/150410, WO2011/150411, WO2012/061647, and WO2012/106560 disclose oils and methods for producing those oils in microbes, including microalgae. These publications also describe the use of such oils to make oleochemicals and fuels.

Tempering is a process of converting a fat into a desired polymorphic form by manipulation of the temperature of the fat or fat-containing substance, commonly used in chocolate making.

Certain enzymes of the fatty acyl-CoA elongation pathway function to extend the length of fatty acyl-CoA molecules. Elongase-complex enzymes extend fatty acyl-CoA molecules in 2 carbon additions, for example myristoyl-CoA to palmitoyl-CoA, stearoyl-CoA to arachidyl-CoA, or oleoyl-CoA to eicosanoyl-CoA, eicosanoyl-CoA to erucyl-CoA. In addition, elongase enzymes also extend acyl chain length in 2 carbon increments. KCS enzymes condense acyl-CoA molecules with two carbons from malonyl-CoA to form beta-ketoacyl-CoA. KCS and elongases may show specificity for condensing acyl substrates of particular carbon length, modification (such as hydroxylation), or degree of saturation. For example, the jojoba (*Simmondsia chinensis*) beta-ketoacyl-CoA synthase has been demonstrated to prefer monounsaturated and saturated C18- and C20-CoA substrates to elevate production of erucic acid in transgenic plants (Lassner et al., *Plant Cell,* 1996, Vol 8(2), pp. 281-292), whereas specific elongase enzymes of *Trypanosoma brucei* show preference for elongating short and midchain saturated CoA substrates (Lee et al., *Cell,* 2006, Vol 126(4), pp. 691-9).

The type II fatty acid biosynthetic pathway employs a series of reactions catalyzed by soluble proteins with intermediates shuttled between enzymes as thioesters of acyl carrier protein (ACP). By contrast, the type I fatty acid biosynthetic pathway uses a single, large multifunctional polypeptide.

The oleaginous, non-photosynthetic alga, *Prototheca moriformis*, stores copious amounts of triacylglyceride oil under conditions when the nutritional carbon supply is in excess, but cell division is inhibited due to limitation of other essential nutrients. Bulk biosynthesis of fatty acids with carbon chain lengths up to C18 occurs in the plastids; fatty acids are then exported to the endoplasmic reticulum where (if it occurs) elongation past C18 and incorporation into triacylglycerides (TAGs) is believed to occur. Lipids are stored in large cytoplasmic organelles called lipid bodies until environmental conditions change to favor growth, whereupon they are mobilized to provide energy and carbon molecules for anabolic metabolism.

SUMMARY OF THE INVENTION

In accordance with an embodiment, a method includes cultivating a recombinant cell, the cell (i) expressing an exogenous KASI or KASIV gene, optionally encoding a protein having at least 60, 65, 70, 75, 80, 85, 90, or 95% amino acid sequence identity to an enzyme encoded by any of SEQ ID NOs: 46-49, and at least one FATB acyl-ACP thioesterase gene optionally encoding a protein having at least 60, 65, 70, 75, 80, 85, 90, or 95% nucleic acid sequence identity to SEQ ID NOs: 11, 87, 89, 159, 162 or 163;

(ii) expressing a gene encoding a FATA, FATB, KASI, KASII, LPAAT, SAD, or FAD2 under the control of a nitrogen-sensitive promoter having at least 60, 65, 70, 75, 80, 85, 90, or 95% sequence identity to any of SEQ ID NOs: 129 to 147; or (iii) having a knockout or knockdown of a SAD gene, a FAD2 gene, and a FATA gene, an overexpressing an exogenous C18-preferring FATA gene, an oleoyl-preferring LPAAT gene, and a KASII gene; and extracting oil from the cell.

In a related embodiment, the cell is of type (ii) and comprises at least a second acyl-ACP thioesterase, optionally encoding a protein having at least 60, 65, 70, 75, 80, 85, 90, or 95% nucleic acid sequence identity to any of SEQ ID NOS: δ 11, 87, 89, 159, 162 or 163. The oil can have at least 30% C10:0 and at least 30% C12:0. The oil can have a viscosity of less than 30 cS and optionally of 25 cS±20% at 40° C. as measured by ASTM D445. The C10:0 and C12:0 fatty acids can be balanced to within 20%, 10% or 5%.

In a related embodiment, the cell is of type (iii) and the cell oil comprises at least 60% stearate-oleate-stearate (SOS). Optionally, the C18-preferring FATA gene encodes a protein with at least 60, 65, 70, 75, 80, 85, 90, or 95% amino acid identity to SEQ ID NO: 156, the LPAAT gene encodes a protein with at least 60, 65, 70, 75, 80, 85, 90, or 95% amino acid identity to SEQ ID NO: 157 and/or the KASII gene encodes a protein with at least 60, 65, 70, 75, 80, 85, 90, or 95% amino acid identity to SEQ ID NO 160 or 161.

Optionally, the cell is a microalga, optionally of Trebouxiophyceae, and optionally of the genus *Prototheca.*

In a related embodiment, there is an oil, soap, oleochemical, foodstuff, or other oil-derived product produced according to one of the aforementioned methods.

In accordance with an embodiment of the present invention, a method comprises cultivating an oleaginous recombinant cell. The cell comprises an exogenous gene encoding a palmitate ACP-desaturase enzyme active to produce an oil having a fatty acid profile characterized by a ratio of palmitoleic acid to palmitic acid of at least 0.1 and/or palmitoleic acid levels of 0.5% or more, as determined by FAME GC/FID analysis. Optionally, the cell is of an oleaginous recombinant eukaryotic microalga.

In related embodiments, the exogenous gene encodes a palmitoyl-ACP desaturase (PAD) having desaturating activity toward ACP-palmitate. Optionally, the exogenous PAD gene encodes a stearoyl-ACP desaturase variant having increased activity toward ACP-palmitate. The variant can be a L118W mutant. The gene can be in operable linkage with a promoter, plastid-targeting transit peptide, and 5'UTR active to express the gene product in a eukaryotic oleaginous microalga. The microalga can be of Trebouxiophyceae, and optionally of the genus *Chlorella* or *Prototheca*. Alternately, the microalga has 23S rRNA with at least 65, 70, 75, 80, 85, 90 or 95% nucleotide sequence identity to SEQ ID NO: 76.

Optionally, the fatty acid profile is further characterized by less than 3.5% saturated fatty acids. Optionally, the cell is cultivated to at least 40% oil by dry cell weight. Optionally, the microalga further comprises a knockout or knockdown of an endogenous acyl-ACP thioesterase and/or an exogenous KASII gene. This may reduce the levels of saturated fatty acids in the oil. For example, the exogenous KASII gene can be inserted into the coding region of the endogenous acyl-ACP thioesterase. Optionally, the inserted KASII gene is inverted in orientation relative to the endogenous acyl-ACP thioesterase.

In any of these embodiments, the oil can be produced by heterotrophically cultivating the microalga on sucrose and the microalga comprises an exogenous invertase gene that allows it to metabolize the sucrose.

The oil may be recovered. The recovered oil may be used for frying or as an ingredient in a prepared food. The oil may have a microalgal sterol profile. In a specific embodiment, the microalgal sterol profile is characterized by an excess of ergosterol over β-sitosterol and/or the presence of 22,23-dihydrobrassicasterol, poriferasterol or clionasterol.

In another embodiment, a method comprises cultivating an oleaginous cell, optionally a microalga, so that the cell produces an oil with less than 10% palmitic acid, greater than Optionally the cell is a microalga with FAD and FATA knockouts and expresses an exogenous KASII gene.

In a related embodiment, a method comprises cultivating an oleaginous cell, optionally a microalga, so that the cell produces an oil with a fatty acid profile in which: the sum of lauric and myristic acids is at least 50%; total saturated fatty acids are at least 50% and levels of capric and lauric fatty acids are balanced to within 20%; or capric acid is at least 45% and lauric acid is at least 45%. In specific related embodiments the sum of lauric and myristic acids is at least 60%, 70% or 7%%. Optionally, the cell comprises an exogenous plant FATB gene.

Optionally, the cell comprises an exogenous KASI or KASIV gene.

The oil may be recovered. The recovered oil may be used for frying or as an ingredient in a prepared food. The oil may have a microalgal sterol profile. In a specific embodiment, the microalgal sterol profile is characterized by an excess of ergosterol over β-sitosterol and/or the presence of 22,23-dihydrobrassicasterol, poriferasterol or clionasterol. The oil can be used to make a foodstuff or chemical.

In another embodiment, a method comprises cultivating an oleaginous cell, optionally a microalga, so that the cell produces an oil with a fatty acid profile characterized by 10% or less linolenic acid and 20% or more linoleic acid. The cell can comprise an overexpressed KASII gene and a FAD gene replacement. Optionally, the cell comprises an exogenous gene encoding an oleate-specific acyl-ACP thioesterase or a knockout of one or more FATA alleles, together with an exogenous gene encoding an oleate-specific acyl-ACP thioesterase. The overexpression of the FAD gene can be by environmental control of a regulatable promoter. The oil can be recovered and used to produce a foodstuff or chemicals. The oil may comprise a microalgal sterol profile.

In another aspect, the present invention provides a method for producing a triglyceride oil, in which the method comprises: (a) cultivating an oleaginous cell under nitrogen-replete conditions, thereby increasing the number of cells, then; (b) cultivating the cells under nitrogen-poor conditions thereby causing the cells to accumulate triglycerides to at least 20% by dry cell weight; comprising a FADc (FAD2) allele, optionally a sole allele, under control of a promoter that is active under the nitrogen replete conditions and inactive under the nitrogen-starved conditions, the promoter retaining at least half of its activity at pH 5.0 as compared to pH 7.0; and (c) obtaining the oil, wherein the oil comprises reduced linoleic acid due to the downregulation of the FADc gene under the nitrogen-starved conditions.

In some embodiments, the cell is cultivated at a pH of less than 6.5 using sucrose in the presence of invertase. In some cases, the invertase is produced by the cell. In some cases, the invertase is produced from an exogenous gene expressed by the cell.

In some embodiments, the oil obtained has a fatty acid profile with less than 3%, 2%, 1%, or 0.5% linoleic acid.

In some embodiments, the cell further comprises a FADc knockout so as to amplify the change in linoleic acid. In some cases, the transcript level of FADc decreases by a factor of 10 or more between the nitrogen-replete and nitrogen-starved conditions.

In another aspect, the present invention provides a method for producing a triglyceride cell oil comprising cultivating a recombinant cell comprising an exogenous FATB gene and an exogenous KASI gene, wherein the expression of the KASI gene causes the oil to have a shorter chain distribution relative to a control cell with the FATB gene but without the KASI gene.

In another aspect, the present invention provides a recombinant cell comprising a FATB acyl-ACP thioesterase gene having at least 75, 80, 85, 90, 91, 92, 93, 94, 95, 96, 97, 98, or 88% nucleotide identity to SEQ ID NOs: 90 or 91 or equivalent sequence due to the degeneracy of the genetic code, or encoding an enzyme having at least 75, 80, 85, 90, 91, 92, 93, 94, 95, 96, 97, 98, or 88% amino acid identity to SEQ ID NOs: 90 or 91. In some embodiments, the cell produces triglycerides that are shifted in fatty acid profile due to expression of the FATB gene.

In an embodiment of the invention, there is a process for producing an oil. The process includes obtaining a cell oil from a genetically engineered microbe, optionally a microalga, and fractionating the cell oil to produce a stearin fraction. The stearin fraction can be characterized by a TAG profile having at least 70% SOS with no more than 4% trisaturates and an sn-2 profile characterized by least 90% oleate at the sn-2 position. Optionally, the microbe is a microalga comprising one or more of an overexpressed KASII gene, a SAD knockout or knockdown, or an exogenous C18-preferring FATA gene, an exogenous LPAAT, and a FAD2 knockout or knockdown. Optionally, the stearin fraction has a maximum heat-flow temperatures or DSC-derived SFC curve that is an essentially identical to the equivalent curve of Kokum butter. The fractionation can be a two step fractionation performed at a first temperature that removes OOS, optionally about 24° C., and a second temperature that removes trisaturates, optionally about 29° C.

In accordance with an embodiment of the invention a method produces a triglyceride oil characterized by a TAG profile. The method includes providing an oleaginous plastidic host cell overexpressing a KASII gene, an exogenous FATA gene and an exogenous LPAAT gene, cultivating the cell so as to produce the oil, and isolating the oil; the TAG profile has greater than 50% SOS an less than 10% trisaturates.

In related embodiments, the cell includes a knockdown or knockout of an endogenous SAD2 gene and/or knockdown or knockout of an endogenous FATA gene. The exogenous FATA gene can encode a functional FATA acyl-ACP thioesterase protein with at least 90, 91, 92, 93, 94, 95, 96, 97, 98, or 99% sequence identity to SEQ ID NO: 92. The exogenous LPAAT gene can encode a functional Lysophosphatidic acid acyltransferase protein with at least 90, 91, 92, 93, 94, 95, 96, 97, 98, or 99% sequence identity to SEQ ID NO: 93. Optionally, the host cell can be a microalga, optionally of Trebouxiophyceae, and optionally of the genus *Chlorella* or *Prototheca*, and optionally having 23S rRNA with at least 65, 70, 75, 80, 85, 90 or 95% nucleotide sequence identity to SEQ ID NO: 76.

In an embodiment, a recombinant microlagal host cell optionally of Trebouxiophyceae, and optionally of the genus *Chlorella* or *Prototheca*, and optionally having 23S rRNA with at least 65, 70, 75, 80, 85, 90 or 95% nucleotide sequence identity to SEQ ID NO: 76, expresses an exogenous FATA gene encodes a functional FATA acyl-ACP thioesterase protein with at least 90, 91, 92, 93, 94, 95, 96, 97, 98, or 99% sequence identity to SEQ ID NO: 92.

In an embodiment, a recombinant microlagal host cell optionally of Trebouxiophyceae, and optionally of the genus *Chlorella* or *Prototheca*, and optionally having 23S rRNA with at least 65, 70, 75, 80, 85, 90 or 95% nucleotide sequence identity to SEQ ID NO: 76, expresses an exogenous LPAAT gene encodes a functional Lysophosphatidic acid acyltransferase protein with at least 90, 91, 92, 93, 94, 95, 96, 97, 98, or 99% sequence identity to SEQ ID NO: 93.

These and other aspects and embodiments of the invention are described and/or exemplified in the accompanying drawings, a brief description of which immediately follows, the detailed description of the invention, and in the examples. Any or all of the features discussed above and throughout the application can be combined in various embodiments of the present invention.

BRIEF DESCRIPTION OF THE DRAWINGS

FIGS. 1-14 show fatty acid profiles and melting curves of refined, bleached and deodorized oils from genetically engineered *Prototheca moriformis* strains, as discussed in Example 4;

FIG. 16 shows various properties of cell oils with very low levels of polyunsaturated fatty acids in accordance with an embodiment of the invention.

FIG. 19 shows various properties of high-oleic and high-stability high-oleic algal oils.

DETAILED DESCRIPTION OF THE INVENTION

I. Definitions

Figure 2:
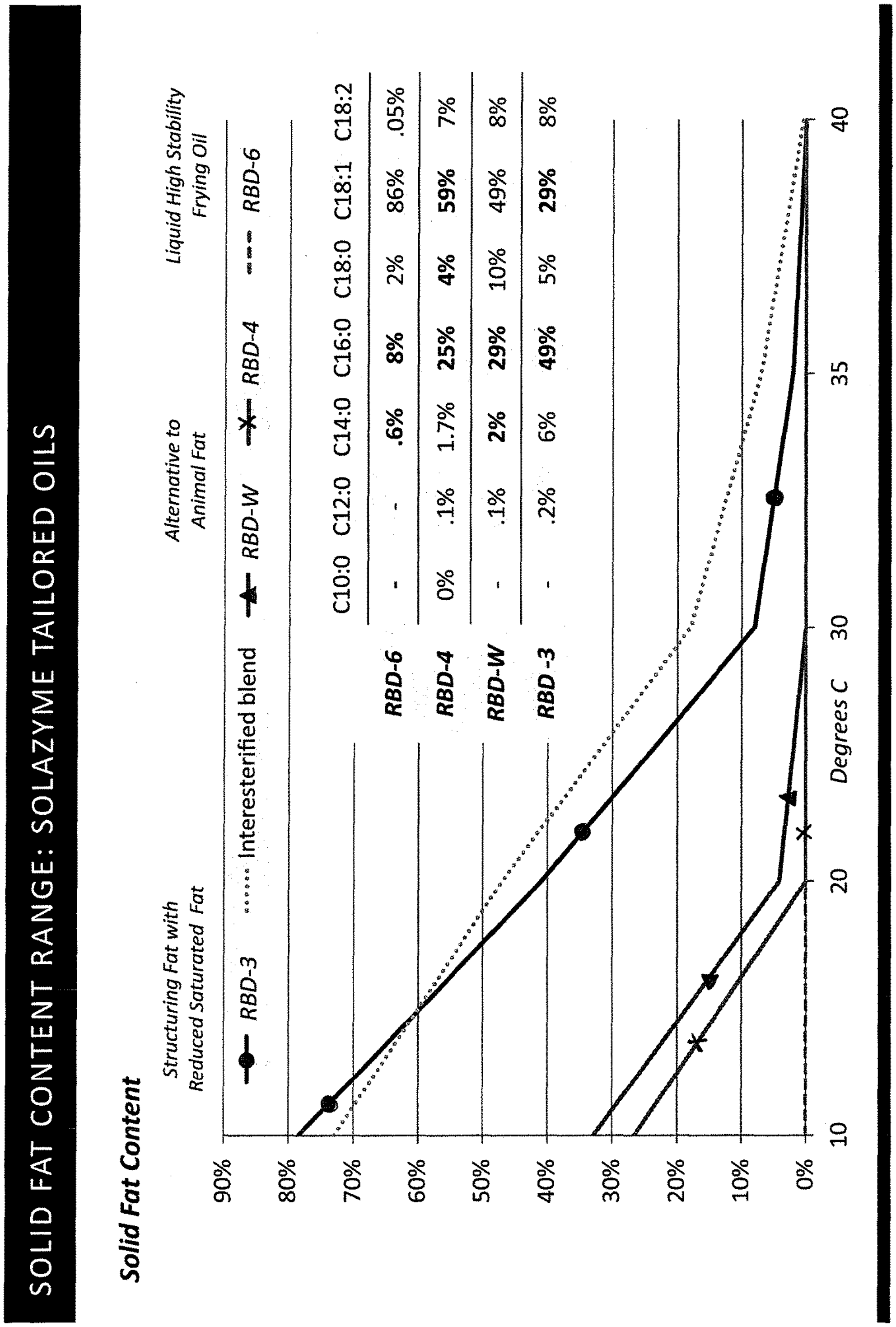
Figure 3:
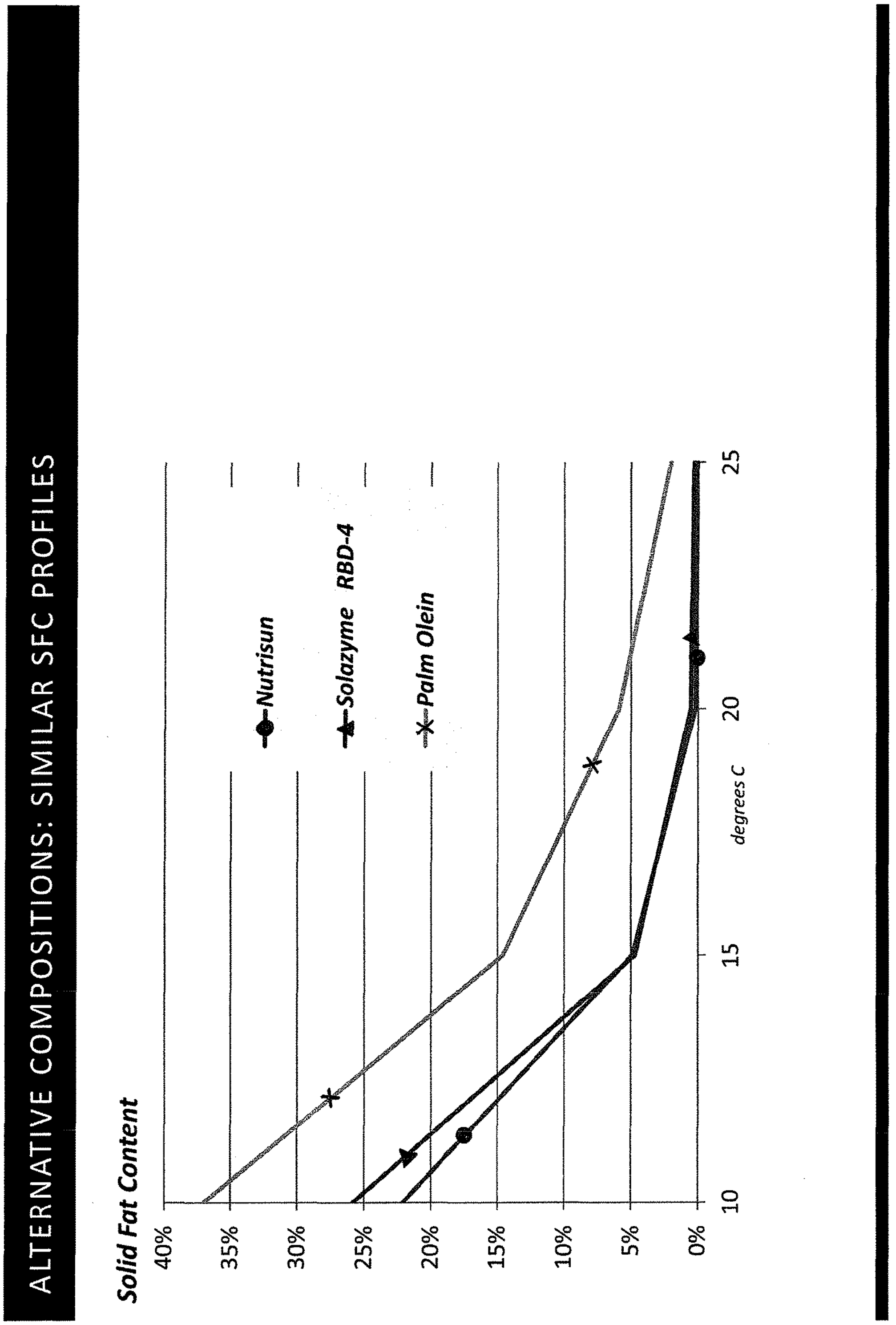
Figure 4:
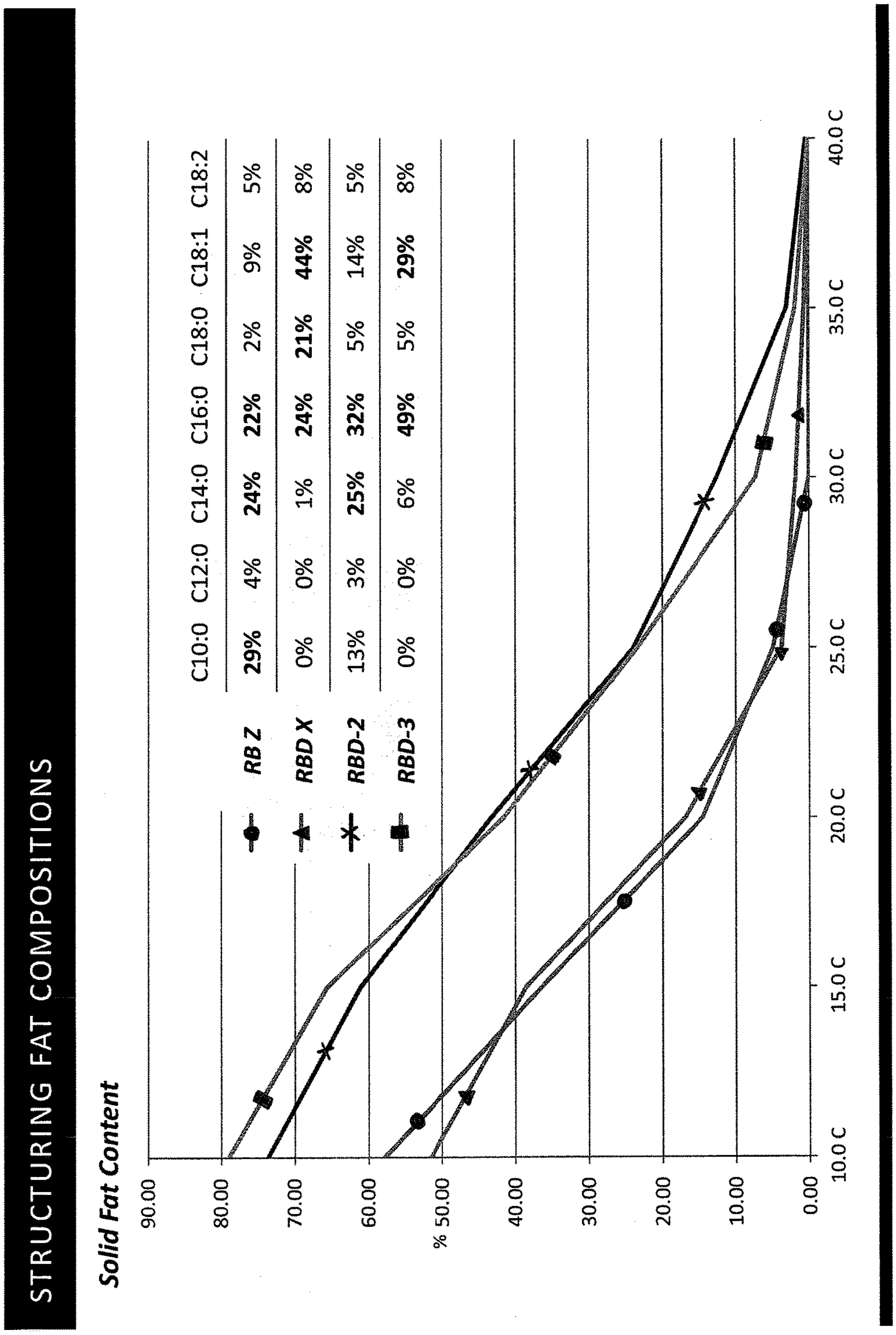
Figure 5:
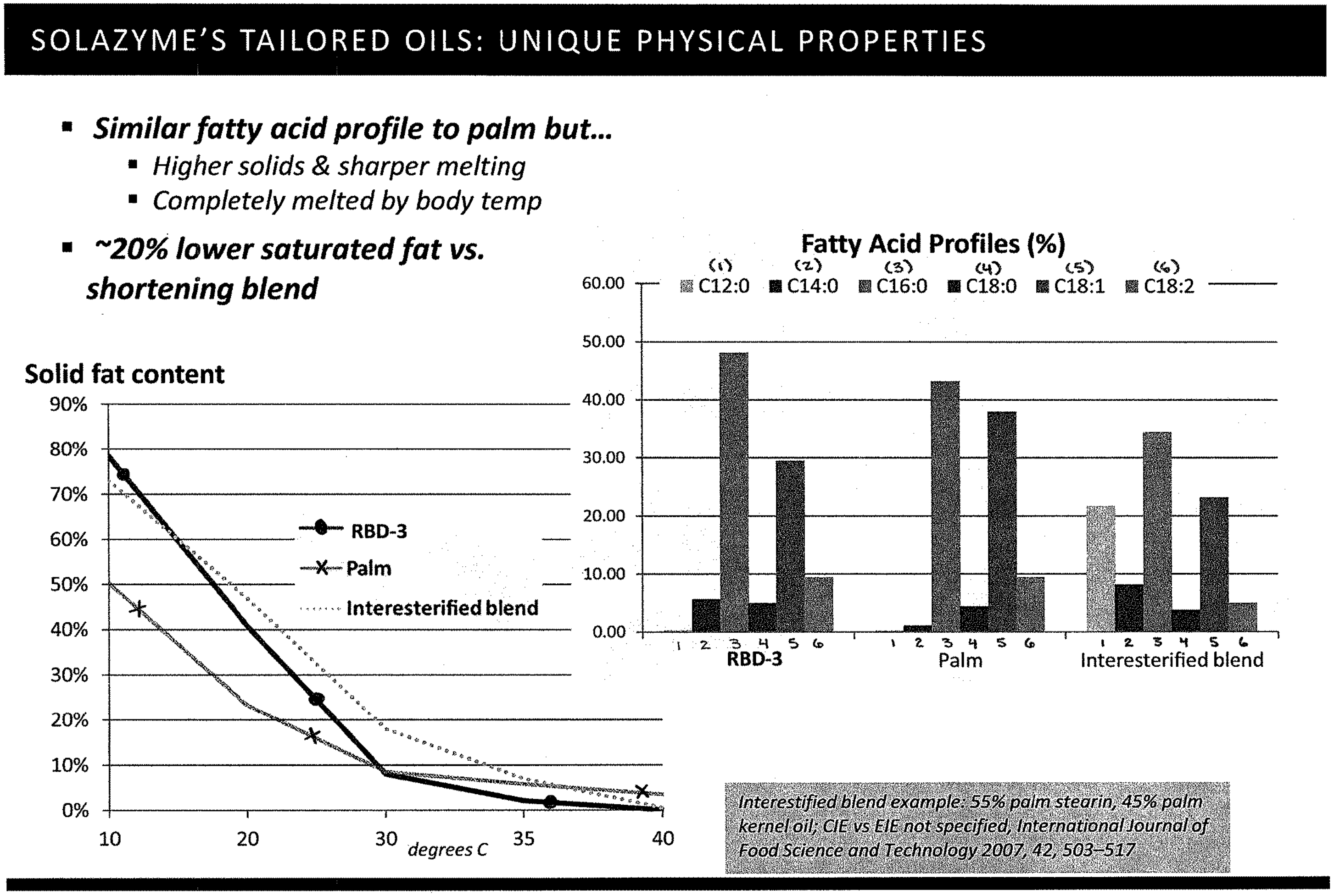
Figure 6:
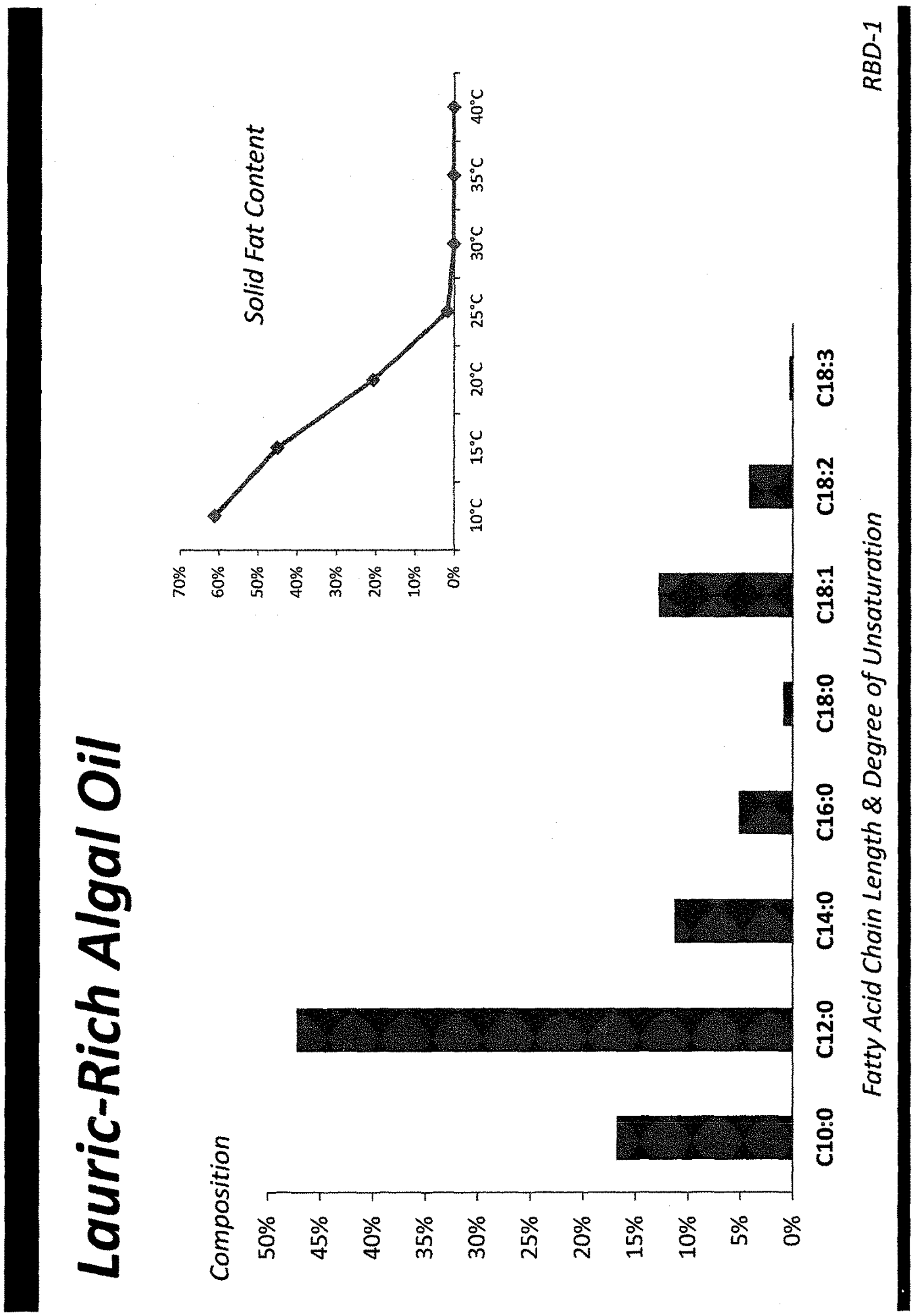
Figure 7:
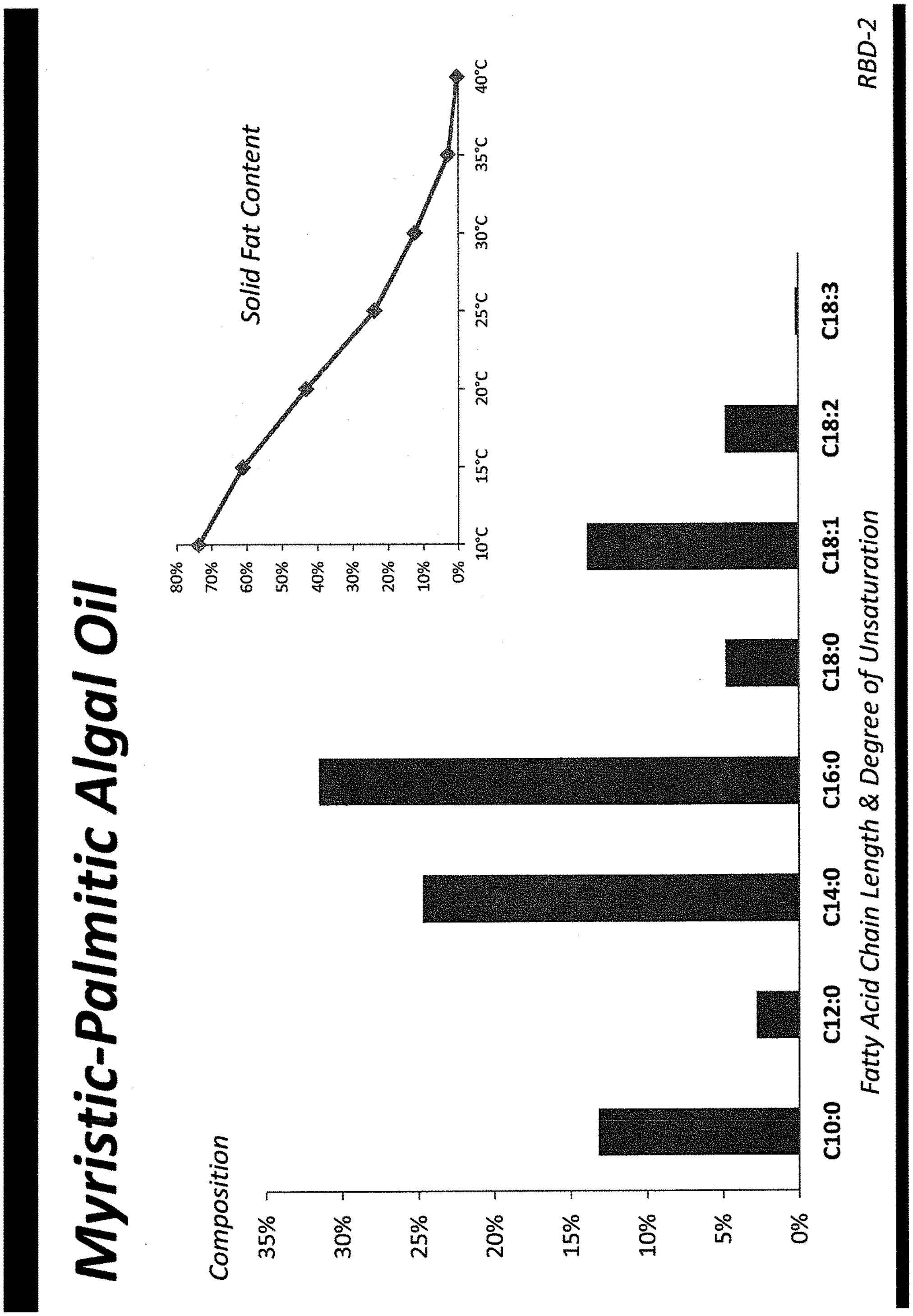
Figure 8:
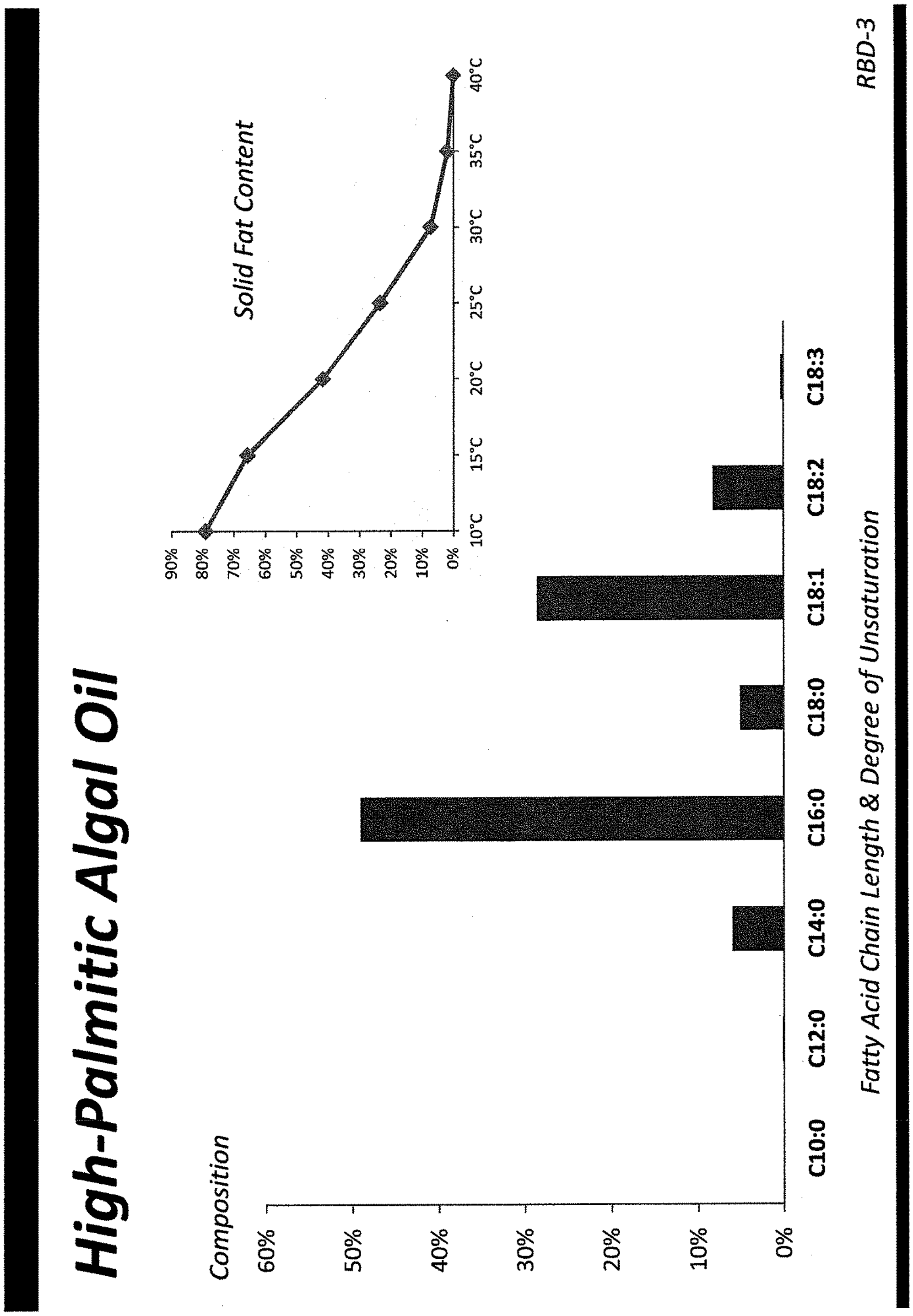
Figure 9:
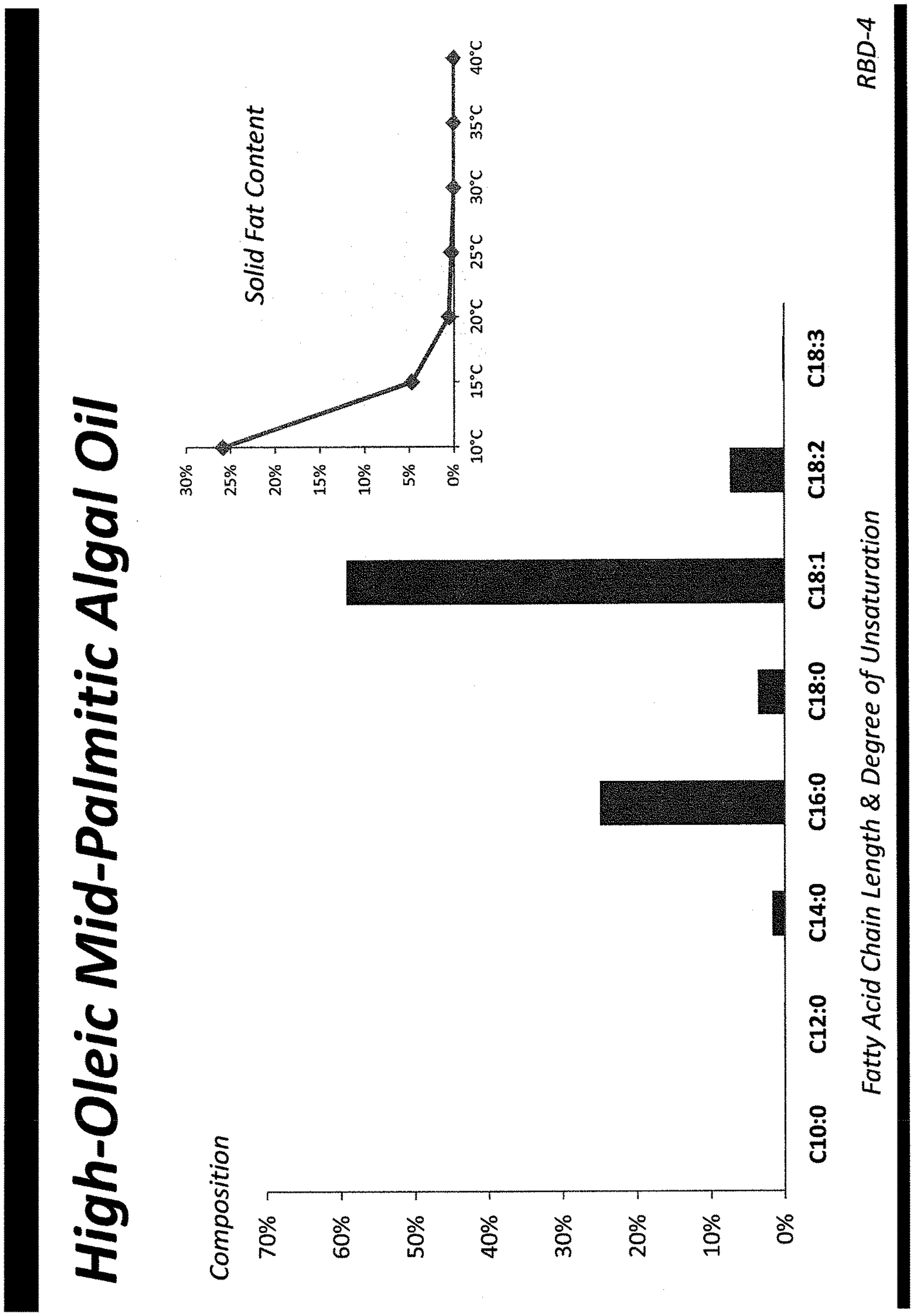

An "allele" refers to a copy of a gene where an organism has multiple similar or identical gene copies, even if on the same chromosome. An allele may encode the same or similar protein.

In connection with two fatty acids in a fatty acid profile, "balanced" shall mean that the two fatty acids are within a specified percentage of their mean area percent. Thus, for fatty acid a in x % abundance and fatty acid b in y % abundance, the fatty acids are "balanced to within z %" if $|x-((x+y)/2)|$ and $|y-((x+y)/2)|$ are $\leq 100(z)$.

A "cell oil" or "cell fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the cell oil or cell fat has not been subjected to interesterification or other synthetic process to obtain that regiospecific triglyceride profile, rather the regiospecificity is produced naturally, by a cell or population of cells. For a cell oil produced by a cell, the sterol profile of oil is generally determined by the sterols produced by the cell, not by artificial reconstitution of the oil by adding sterols in order to mimic the cell oil. In connection with a cell oil or cell fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "cell fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"FADc", also referred to as "FAD2" is a gene encoding a delta-12 fatty acid desaturase.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Fixed carbon source" is a molecule(s) containing carbon, typically an organic molecule that is present at ambient temperature and pressure in solid or liquid form in a culture media that can be utilized by a microorganism cultured therein. Accordingly, carbon dioxide is not a fixed carbon source.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Microalgae" are eukaryotic microbial organisms that contain a chloroplast or other plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca.*

In connection with fatty acid length, "mid-chain" shall mean C8 to C16 fatty acids.

In connection with a recombinant cell, the term "knockdown" refers to a gene that has been partially suppressed (e.g., by about 1-95%) in terms of the production or activity of a protein encoded by the gene.

Also, in connection with a recombinant cell, the term "knockout" refers to a gene that has been completely or nearly completely (e.g., >95%) suppressed in terms of the production or activity of a protein encoded by the gene. Knockouts can be prepared by homologous recombination of a noncoding sequence into a coding sequence, gene deletion, mutation or other method.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous (especially eukaryotic microalgae that store lipid). An oleaginous cell also encompasses a cell that has had some or all of its lipid or other content removed, and both live and dead cells.

An "ordered oil" or "ordered fat" is one that forms crystals that are primarily of a given polymorphic structure. For example, an ordered oil or ordered fat can have crystals that are greater than 50%, 60%, 70%, 80%, or 90% of the β or β' polymorphic form.

In connection with a cell oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID), as in Example 1. The fatty acid profile can be expressed as one or more percent of a fatty acid in the total fatty acid signal determined from the area under the curve for that fatty acid. FAME-GC-FID measurement approximate weight percentages of the fatty acids. A "sn-2 profile" is the distribution of fatty acids found at the sn-2 position of the triacylglycerides in the oil. A "regiospecific profile" is the distribution of triglycerides with reference to the positioning of acyl group attachment to the glycerol backbone without reference to stereospecificity. In other words, a regiospecific profile describes acyl group attachment at sn-1/3 vs. sn-2. Thus, in a regiospecific profile, POS (palmitate-oleate-stearate) and SOP (stearate-oleate-palmitate) are treated identically. A "stereospecific profile" describes the attachment of acyl groups at sn-1, sn-2 and sn-3. Unless otherwise indicated, triglycerides such as SOP and POS are to be considered equivalent. A "TAG profile" is the distribution of fatty acids found in the triglycerides with reference to connection to the glycerol backbone, but without reference to the regiospecific nature of the connections. Thus, in a TAG profile, the percent of SSO in the oil is the sum of SSO and SOS, while in a regiospecific profile, the percent of SSO is calculated without inclusion of SOS species in the oil. In contrast to the weight percentages of the FAME-GC-FID analysis, triglyceride percentages are typically given as mole percentages; that is the percent of a given TAG molecule in a TAG mixture.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap x drop-off 50; Expect: 10; Word Size: 3; Filter: on.

"Recombinant" is a cell, nucleic acid, protein or vector that has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The terms "triglyceride", "triacylglyceride" and "TAG" are used interchangeably as is known in the art.

II. General

Illustrative embodiments of the present invention feature oleaginous cells that produce altered fatty acid profiles and/or altered regiospecific distribution of fatty acids in glycerolipids, and products produced from the cells. Examples of oleaginous cells include microbial cells having a type II fatty acid biosynthetic pathway, including plastidic oleaginous cells such as those of oleaginous algae and, where applicable, oil producing cells of higher plants including but not limited to commercial oilseed crops such as soy, corn, rapeseed/canola, cotton, flax, sunflower, safflower and peanut. Other specific examples of cells include heterotrophic or obligate heterotrophic microalgae of the phylum Chlorophtya, the class Trebouxiophytae, the order Chlorellales, or the family Chlorellacae. Examples of oleaginous microalgae and method of cultivation are also provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in highly unsaturated fatty acids such as DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose) In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012, including disclosure of genetically engineered *Prototheca* strains that utilize xylose.

The oleaginous cells may, optionally, be cultivated in a bioreactor/fermenter. For example, heterotrophic oleaginous microalgal cells can be cultivated on a sugar-containing nutrient broth. Optionally, cultivation can proceed in two stages: a seed stage and a lipid-production stage. In the seed stage, the number of cells is increased from s starter culture. Thus, the seeds stage typically includes a nutrient rich, nitrogen replete, media designed to encourage rapid cell division. After the seeds stage, the cells may be fed sugar under nutrient-limiting (e.g. nitrogen sparse) conditions so that the sugar will be converted into triglycerides. For example, the rate of cell division in the lipid-production stage can be decreased by 50%, 80% or more relative to the seed stage. Additionally, variation in the media between the seed stage and the lipid-production stage can induce the recombinant cell to express different lipid-synthesis genes and thereby alter the triglycerides being produced. For example, as discussed below, nitrogen and/or pH sensitive promoters can be placed in front of endogenous or exogenous genes. This is especially useful when an oil is to be produced in the lipid-production phase that does not support optimal growth of the cells in the seed stage. In an example below, a cell has a fatty acid desaturase with a pH sensitive promoter so than an oil that is low in linoleic acid is produced in the lipid production stage while an oil that has adequate linoleic acid for cell division is produced during the seed stage. The resulting low linoleic oil has exceptional oxidative stability.

The oleaginous cells express one or more exogenous genes encoding fatty acid biosynthesis enzymes. As a result, some embodiments feature cell oils that were not obtainable from a non-plant or non-seed oil, or not obtainable at all.

The oleaginous cells (optionally microalgal cells) can be improved via classical strain improvement techniques such as UV and/or chemical mutagenesis followed by screening or selection under environmental conditions, including selection on a chemical or biochemical toxin. For example the cells can be selected on a fatty acid synthesis inhibitor, a sugar metabolism inhibitor, or an herbicide. As a result of the selection, strains can be obtained with increased yield on sugar, increased oil production (e.g., as a percent of cell volume, dry weight, or liter of cell culture), or improved fatty acid or TAG profile.

For example, the cells can be selected on one or more of 1,2-Cyclohexanedione; 19-Norethindone acetate; 2,2-dichloropropionic acid; 2,4,5-trichlorophenoxyacetic acid; 2,4,5-trichlorophenoxyacetic acid, methyl ester; 2,4-dichlorophenoxyacetic acid; 2,4-dichlorophenoxyacetic acid, butyl ester; 2,4-dichlorophenoxyacetic acid, isooctyl ester; 2,4-dichlorophenoxyacetic acid, methyl ester; 2,4-dichlorophenoxybutyric acid; 2,4-dichlorophenoxybutyric acid, methyl ester; 2,6-dichlorobenzonitrile; 2-deoxyglucose; 5-Tetradecyloxy-w-furoic acid; A-922500; acetochlor; alachlor; ametryn; amphotericin; atrazine; benfluralin; bensulide; bentazon; bromacil; bromoxynil; Cafenstrole; carbonyl cyanide m-chlorophenyl hydrazone (CCCP); carbonyl cyanide-p-trifluoromethoxyphenylhydrazone (FCCP); cerulenin; chlorpropham; chlorsulfuron; clofibric acid; clopyralid; colchicine; cycloate; cyclohexamide; C75; DACTHAL (dimethyl tetrachloroterephthalate); dicamba; dichloroprop ((R)-2-(2,4-dichlorophenoxy)propanoic acid); Diflufenican; dihyrojasmonic acid, methyl ester; diquat; diuron; dimethylsulfoxide; Epigallocatechin gallate (EGCG); endothall; ethalfluralin; ethanol; ethofumesate; Fenoxaprop-p-ethyl; Fluazifop-p-Butyl; fluometuron; fomasefen; foramsulfuron; gibberellic acid; glufosinate ammonium; glyphosate; haloxyfop; hexazinone; imazaquin; isoxaben; Lipase inhibitor THL ((−)-Tetrahydrolipstatin); malonic acid; MCPA (2-methyl-4-chlorophenoxyacetic acid); MCPB (4-(4-chloro-o-tolyloxy)butyric acid); mesotrione; methyl dihydrojasmonate; metolachlor; metribuzin; Mildronate; molinate; naptalam; norharman; orlistat; oxadiazon; oxyfluorfen; paraquat; pendimethalin; pentachlorophenol; PF-04620110; phenethyl alcohol; phenmedipham; picloram; Platencin; Platensimycin; prometon; prometryn; pronamide; propachlor; propanil; propazine; pyrazon; Quizalofop-p-ethyl; s-ethyl dipropylthiocarbamate (EPTC); s,s,s-tributylphosphorotrithioate; salicylhydroxamic acid; sesamol; siduron; sodium methane arsenate; simazine; T-863 (DGAT inhibitor); tebuthiuron; terbacil; thiobencarb; tralkoxydim; triallate; triclopyr; triclosan; trifluralin; and vulpinic acid.

The oleaginous cells produce a storage oil, which is primarily triacylglyceride and may be stored in storage bodies of the cell. A raw oil may be obtained from the cells by disrupting the cells and isolating the oil. The raw oil may comprise sterols produced by the cells. WO2008/151149, WO2010/06032, WO2011/150410, and WO2011/1504 disclose heterotrophic cultivation and oil isolation techniques for oleaginous microalgae. For example, oil may be obtained by providing or cultivating, drying and pressing the cells. The oils produced may be refined, bleached and deodorized (RBD) as known in the art or as described in WO2010/120939. The raw or RBD oils may be used in a variety of food, chemical, and industrial products or processes. Even after such processing, the oil may retain a sterol profile characteristic of the source. Microalgal sterol profiles are disclosed below. See especially Section XII of this patent application. After recovery of the oil, a valuable residual biomass remains. Uses for the residual biomass include the production of paper, plastics, absorbents, adsorbents, drilling fluids, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell. Examples 1, 2, and 8 below give analytical methods for determining TAG fatty acid composition and regiospecific structure.

Broadly categorized, certain embodiments of the invention include (i) auxotrophs of particular fatty acids; (ii) cells that produce oils having low concentrations of polyunsaturated fatty acids, including cells that are auxotrophic for unsaturated fatty acids; (iii) cells producing oils having high concentrations of particular fatty acids due to expression of one or more exogenous genes encoding enzymes that transfer fatty acids to glycerol or a glycerol ester; (iv) cells producing regiospecific oils, (v) genetic constructs or cells encoding a newly discovered gene encoding an LPAAT enzyme from *Cuphea* PSR23 (see Example 43), (vi) cells producing low levels of saturated fatty acids and/or high levels of palmitoleic acid, (vii) cells producing erucic acid, and (viii) other inventions related to producing cell oils with altered profiles. The embodiments also encompass the oils made by such cells, the residual biomass from such cells after oil extraction, oleochemicals, fuels and food products made from the oils and methods of cultivating the cells.

In any of the embodiments below, the cells used are optionally cells having a type II fatty acid biosynthetic pathway such as microalgal cells including heterotrophic or obligate heterotrophic microalgal cells, including cells classified as Chlorophyta, Trebouxiophyceae, Chlorellales, Chlorellaceae, or Chlorophyceae, or cells engineered to have a type II fatty acid biosynthetic pathway using the tools of synthetic biology (i.e., transplanting the genetic machinery for a type II fatty acid biosynthesis into an organism lacking such a pathway). Use of a host cell with a type II pathway avoids the potential for non-interaction between an exogenous acyl-ACP thioesterase or other ACP-binding enzyme and the multienzyme complex of type I cellular machinery. In specific embodiments, the cell is of the species *Prototheca moriformis, Prototheca krugani, Prototheca stagnora* or *Prototheca zopfii* or has a 23S rRNA sequence with at least 65, 70, 75, 80, 85, 90 or 95% nucleotide identity SEQ ID NO: 76. By cultivating in the dark or using an obligate heterotroph, the cell oil produced can be low in chlorophyll or other colorants. For example, the cell oil can have less than 100, 50, 10, 5, 1, 0.0.5 ppm of chlorophyll without substantial purification.

The stable carbon isotope value δ13C is an expression of the ratio of $^{13}C/^{12}C$ relative to a standard (e.g. PDB, carbonite of fossil skeleton of *Belemnite americana* from Peedee formation of South Carolina). The stable carbon isotope value δ13C (‰) of the oils can be related to the δ13C value of the feedstock used. In some embodiments the oils are derived from oleaginous organisms heterotrophically grown on sugar derived from a C4 plant such as corn or sugarcane. In some embodiments the δ13C (‰) of the oil is from −10 to −17‰ or from −13 to −16‰.

In specific embodiments and examples discussed below, one or more fatty acid synthesis genes (e.g., encoding an acyl-ACP thioesterase, a keto-acyl ACP synthase, an LPAAT, a stearoyl ACP desaturase, or others described herein) is incorporated into a microalga. It has been found that for certain microalga, a plant fatty acid synthesis gene product is functional in the absence of the corresponding plant acyl carrier protein (ACP), even when the gene product is an enzyme, such as an acyl-ACP thioesterase, that requires binding of ACP to function. Thus, optionally, the microalgal cells can utilize such genes to make a desired oil without co-expression of the plant ACP gene.

For the various embodiments of recombinant cells comprising exogenous genes or combinations of genes, it is contemplated that substitution of those genes with genes having 60, 70, 80, 85, 90, 91, 92, 93, 94, 95, 96, 97, 98, or 99% nucleic acid sequence identity can give similar results, as can substitution of genes encoding proteins having 60, 70, 80, 85, 90, 91, 92, 93, 94, 95, 95.5, 96, 96.5, 97, 97.5, 98, 98.5, 99 or 99.5% amino acid sequence identity. Likewise, for novel regulatory elements, it is contemplated that substitution of those nucleic acids with nucleic acids having 60, 70, 80, 85, 90, 91, 92, 93, 94, 95, 96, 97, 98, or 99% nucleic acid can be efficacious. In the various embodiments, it will be understood that sequences that are not necessary for function (e.g. FLAG® tags or inserted restriction sites) can often be omitted in use or ignored in comparing genes, proteins and variants.

Although discovered using or exemplified with microalgae, the novel genes and gene combinations reported here can be used in higher plants using techniques that are well known in the art. For example, the use of exogenous lipid metabolism genes in higher plants is described in U.S. Pat. Nos. 6,028,247, 5,850,022, 5,639,790, 5,455,167, 5,512,482, and 5,298,421 disclose higher plants with exogenous acyl-ACP thioesterases. WO2009129582 and WO1995027791 disclose cloning of LPAAT in plants. FAD2 suppression in higher plants is taught in WO 2013112578, and WO 2008006171.

As described in Example 63, transcript profiling was used to discover promoters that modulate expression in response to low nitrogen conditions. The promoters are useful to selectively express various genes and to alter the fatty acid composition of microbial oils. In accordance with an embodiment, there are non-natural constructs comprising a heterologous promoter and a gene, wherein the promoter comprises at least 60, 65, 70, 75, 80, 85, 90, or 95% sequence identity to any of the promoters of Example 63 (e.g., SEQ ID NOs: 130-147) and the gene is differentially expressed under low vs. high nitrogen conditions. Optionally, the expression is less pH sensitive than for the AMT03 promoter. For example, the promoters can be placed in front of a FAD2 gene in a linoleic acid auxotroph to produce an oil with less than 5, 4, 3, 2, or 1% linoleic acid after culturing under high, then low nitrogen conditions.

III. Fatty Acid Auxotrophs/Reducing Fatty Acid Levels to Growth Inhibitory Conditions During an Oil Production Phase In an embodiment, the cell is genetically engineered so that all alleles of a lipid pathway gene are knocked out. Alternately, the amount or activity of the gene products of the alleles is knocked down so as to require supplementation with fatty acids. A first transformation construct can be generated bearing donor sequences homologous to one or more of the alleles of the gene. This first transformation construct may be introduced and selection methods followed to obtain an isolated strain characterized by one or more allelic disruptions. Alternatively, a first strain may be created that is engineered to express a selectable marker from an insertion into a first allele, thereby inactivating the first allele. This strain may be used as the host for still further genetic engineering to knockout or knockdown the remaining allele(s) of the lipid pathway gene (e.g., using a second selectable marker to disrupt a second allele). Complementation of the endogenous gene can be achieved through engineered expression of an additional transformation construct bearing the endogenous gene whose activity was originally ablated, or through the expression of a suitable heterologous gene. The expression of the complementing gene can either be regulated constitutively or through regulatable control, thereby allowing for tuning of expression to the desired level so as to permit growth or create an auxotrophic condition at will. In an embodiment, a population of the fatty acid auxotroph cells are used to screen or select for complementing genes; e.g., by transformation with particular gene candidates for exogenous fatty acid synthesis enzymes, or a nucleic acid library believed to contain such candidates.

Knockout of all alleles of the desired gene and complementation of the knocked-out gene need not be carried out sequentially. The disruption of an endogenous gene of interest and its complementation either by constitutive or inducible expression of a suitable complementing gene can be carried out in several ways. In one method, this can be achieved by co-transformation of suitable constructs, one disrupting the gene of interest and the second providing complementation at a suitable, alternative locus. In another method, ablation of the target gene can be effected through the direct replacement of the target gene by a suitable gene under control of an inducible promoter ("promoter hijacking"). In this way, expression of the targeted gene is now put under the control of a regulatable promoter. An additional approach is to replace the endogenous regulatory elements of a gene with an exogenous, inducible gene expression system. Under such a regime, the gene of interest can now be turned on or off depending upon the particular needs. A still further method is to create a first strain to express an exogenous gene capable of complementing the gene of interest, then to knockout out or knockdown all alleles of the gene of interest in this first strain. The approach of multiple allelic knockdown or knockout and complementation with exogenous genes may be used to alter the fatty acid profile, regiospecific profile, sn-2 profile, or the TAG profile of the engineered cell.

Where a regulatable promoter is used, the promoter can be pH-sensitive (e.g., amt03), nitrogen and pH sensitive (e.g., amt03), or nitrogen sensitive but pH-insensitive (e.g., newly discovered promoters of Example 63) or variants thereof comprising at least 60, 65, 70, 75, 80, 85, 90, 95, 96, 97, 98 or 99% sequence identity to any of the aforementioned promoters. In connection with a promoter, pH-insensitive means that the promoter is less sensitive than the amt03 promoter when environmental conditions are shifter from pH 6.8 to 5.0 (e.g., at least 5, 10, 15, or 20% less relative change in activity upon the pH-shift as compared to an equivalent cell with amt03 as the promoter).

In a specific embodiment, the recombinant cell comprises nucleic acids operable to reduce the activity of an endogenous acyl-ACP thioesterase; for example a FatA or FatB acyl-ACP thioesterase having a preference for hydrolyzing fatty acyl-ACP chains of length C18 (e.g., stearate (C18:0) or oleate (C18:1), or C8:0-C16:0 fatty acids. The activity of an endogenous acyl-ACP thioesterase may be reduced by knockout or knockdown approaches. Knockdown may be achieved, for example, through the use of one or more RNA hairpin constructs, by promoter hijacking (substitution of a lower activity or inducible promoter for the native promoter of an endogenous gene), or by a gene knockout combined with introduction of a similar or identical gene under the control of an inducible promoter. Example 34 describes the engineering of a *Prototheca* strain in which two alleles of the endogenous fatty acyl-ACP thioesterase (FATA1) have been knocked out. The activity of the *Prototheca moriformis* FATA1 was complemented by the expression of an exogenous FatA or FatB acyl-ACP thioesterase. Example 36 details the use of RNA hairpin constructs to reduce the expression of FATA in *Prototheca*, which resulted in an altered fatty acid profile having less palmitic acid and more oleic acid.

Accordingly, oleaginous cells, including those of organisms with a type II fatty acid biosynthetic pathway can have knockouts or knockdowns of acyl-ACP thioesterase-encoding alleles to such a degree as to eliminate or severely limit viability of the cells in the absence of fatty acid supplementation or genetic complementations. These strains can be used to select for transformants expressing acyl-ACP-thioesterase transgenes. Alternately, or in addition, the strains can be used to completely transplant exogenous acyl-ACP-thioesterases to give dramatically different fatty acid profiles of cell oils produced by such cells. For example, FATA expression can be completely or nearly completely eliminated and replaced with FATB genes that produce mid-chain fatty acids. Alternately, an organism with an endogenous FatA gene having specificity for palmitic acid (C16) relative to stearic or oleic acid (C18) can be replaced with an exogenous FatA gene having a greater relative specificity for stearic acid (C18:0) or replaced with an exogenous FatA gene having a greater relative specificity for oleic acid (C18:1). In certain specific embodiments, these transformants with double knockouts of an endogenous acyl-ACP thioesterase produce cell oils with more than 50, 60, 70, 80, or 90% caprylic, capric, lauric, myristic, or palmitic acid, or total fatty acids of chain length less than 18 carbons. Such cells may require supplementation with longer chain fatty acids such as stearic or oleic acid or switching of environmental conditions between growth permissive and restrictive states in the case of an inducible promoter regulating a FatA gene.

In an embodiment the oleaginous cells are cultured (e.g., in a bioreactor). The cells are fully auxotrophic or partially auxotrophic (i.e., lethality or synthetic sickness) with respect to one or more types of fatty acid. The cells are cultured with supplementation of the fatty acid(s) so as to increase the cell number, then allowing the cells to accumulate oil (e.g. to at least 40% by dry cell weight). Alternatively, the cells comprise a regulatable fatty acid synthesis gene that can be switched in activity based on environmental conditions and the environmental conditions during a first, cell division, phase favor production of the fatty acid and the environmental conditions during a second, oil accumulation, phase disfavor production of the fatty acid. In the case of an inducible gene, the regulation of the inducible gene can be mediated, without limitation, via environmental pH (for example, by using the AMT3 promoter as described in the Examples).

As a result of applying either of these supplementation or regulation methods, a cell oil may be obtained from the cell that has low amounts of one or more fatty acids essential for optimal cell propagation. Specific examples of oils that can be obtained include those low in stearic, linoleic and/or linolenic acids.

These cells and methods are illustrated in connection with low polyunsaturated oils in the section immediately below and in Example 6 (fatty acid desaturase auxotroph) in connection with oils low in polyunsaturated fatty acids and in Example 34 (acyl-ACP thioesterase auxotroph).

Likewise, fatty acid auxotrophs can be made in other fatty acid synthesis genes including those encoding a SAD, FAD, KASIII, KASI, KASII, KCS, elongase, GPAT, LPAAT, DGAT or AGPAT or PAP. These auxotrophs can also be used to select for complement genes or to eliminate native expression of these genes in favor of desired exogenous genes in order to alter the fatty acid profile, regiospecific profile, or TAG profile of cell oils produced by oleaginous cells.

Accordingly, in an embodiment of the invention, there is a method for producing an oil/fat. The method comprises cultivating a recombinant oleaginous cell in a growth phase under a first set of conditions that is permissive to cell division so as to increase the number of cells due to the presence of a fatty acid, cultivating the cell in an oil production phase under a second set of conditions that is restrictive to cell division but permissive to production of an oil that is depleted in the fatty acid, and extracting the oil from the cell, wherein the cell has a mutation or exogenous nucleic acids operable to suppress the activity of a fatty acid synthesis enzyme, the enzyme optionally being a stearoyl-ACP desaturase, delta 12 fatty acid desaturase, or a ketoacyl-ACP synthase. The oil produced by the cell can be depleted in the fatty acid by at least 50, 60, 70, 80, or 90%. The cell can be cultivated heterotrophically. The cell can be a microalgal cell cultivated heterotrophically or autotrophically and may produce at least 40, 50, 60, 70, 80, or 90% oil by dry cell weight.

IV. (A) Low Polyunsaturated Cell Oils

In an embodiment of the present invention, the cell oil produced by the cell has very low levels of polyunsaturated fatty acids. As a result, the cell oil can have improved stability, including oxidative stability. The cell oil can be a liquid or solid at room temperature, or a blend of liquid and solid oils, including the regiospecific or stereospecific oils, high stearate oils, or high mid-chain oils described infra. Oxidative stability can be measured by the Rancimat method using the AOCS Cd 12b-92 standard test at a defined temperature. For example, the OSI (oxidative stability index) test may be run at temperatures between 110° C. and 140° C. The oil is produced by cultivating cells (e.g., any of the plastidic microbial cells mentioned above or elsewhere herein) that are genetically engineered to reduce the activity of one or more fatty acid desaturase. For example, the cells may be genetically engineered to reduce the activity of one or more fatty acyl Δ12 desaturase(s) responsible for converting oleic acid (18:1) into linoleic acid (18:2) and/or one or more fatty acyl 415 desaturase(s) responsible for converting linoleic acid (18:2) into linolenic acid (18:3). Various methods may be used to inhibit the desaturase including knockout or mutation of one or more alleles of the gene encoding the desaturase in the coding or regulatory regions, inhibition of RNA transcription, or translation of the enzyme, including RNAi, siRNA, miRNA, dsRNA, antisense, and hairpin RNA techniques. Other techniques known in the art can also be used including introducing an exogenous gene that produces an inhibitory protein or other substance that is specific for the desaturase. In specific examples, a knockout of one fatty acyl Δ12 desaturase allele is combined with RNA-level inhibition of a second allele.

In a specific embodiment, fatty acid desaturase (e.g., Δ12 fatty acid desaturase) activity in the cell is reduced to such a degree that the cell is unable to be cultivated or is difficult to cultivate (e.g., the cell division rate is decreased more than 10, 20, 30, 40, 50, 60, 70, 80, 90, 95, 97 or 99%). Achieving such conditions may involve knockout, or effective suppression of the activity of multiple gene copies (e.g. 2, 3, 4 or more) of the desaturase or their gene products. A specific embodiment includes the cultivation in cell culture of a full or partial fatty acid auxotroph with supplementation of the fatty acid or a mixture of fatty acids so as to increase the cell number, then allowing the cells to accumulate oil (e.g. to at least 40% by cell weight). Alternatively, the cells comprise a regulatable fatty acid synthesis gene that can be switched in activity. For example, the regulation can be based on environmental conditions and the environmental conditions during a first, cell division, phase favor production of the fatty acid and the environmental conditions during a second, oil accumulation, phase disfavor production of the oil. For example, culture media pH and/or nitrogen levels can be used as an environmental control to switch expression of a lipid pathway gene to produce a state of high or low synthetic enzyme activity. Examples of such cells are described in Example 7.

In a specific embodiment, a cell is cultivated using a modulation of linoleic acid levels within the cell. In particular, the cell oil is produced by cultivating the cells under a first condition that is permissive to an increase in cell number due to the presence of linoleic acid and then cultivating the cells under a second condition that is characterized by linoleic acid starvation and thus is inhibitory to cell division, yet permissive of oil accumulation. For example, a seed culture of the cells may be produced in the presence of linoleic acid added to the culture medium. For example, the addition of linoleic acid to 0.25 g/L in the seed culture of a *Prototheca* strain deficient in linoleic acid production due to ablation of two alleles of a fatty acyl Δ12 desaturase (i.e., a linoleic auxotroph) was sufficient to support cell division to a level comparable to that of wild type cells. Optionally, the linoleic acid can then be consumed by the cells, or otherwise removed or diluted. The cells are then switched into an oil producing phase (e.g., supplying sugar under nitrogen limiting conditions such as described in WO2010/063032). Surprisingly, oil production has been found to occur even in the absence of linoleic acid production or supplementation, as demonstrated in the obligate heterotroph oleaginous microalgae *Prototheca* but generally applicable to other oleaginous microalgae, microorganisms, or even multicellular organisms (e.g., cultured plant cells). Under these conditions, the oil content of the cell can increase to about 10, 20, 30, 40, 50, 60, 70, 80, 90%, or more by dry cell weight, while the oil produced can have polyunsaturated fatty acid (e.g.; linoleic+linolenic) profile with 5%, 4%, 3%, 2%, 1%, 0.5%, 0.3%, 0.2%, 0.1%, 0.05% or less, as a percent of total triacylglycerol fatty acids in the oil. For example, the oil content of the cell can be 50% or more by dry cell weight and the triglyceride of the oil produced less than 3% polyunsaturated fatty acids.

These oils can also be produced without the need (or reduced need) to supplement the culture with linoleic acid by using cell machinery to produce the linoleic acid during the cell division phase, but less or no linoleic acid in the lipid production phase. The linoleic-producing cell machinery may be regulatable so as to produce substantially less linoleic acid during the oil producing phase. The regulation may be via modulation of transcription of the desaturase gene(s) or modulation or modulation of production of an inhibitor substance (e.g., regulated production of hairpin RNA/RNAi). For example, the majority, and preferably all, of the fatty acid Δ12 desaturase activity can be placed under a regulatable promoter regulated to express the desaturase in the cell division phase, but to be reduced or turned off during the oil accumulation phase. The regulation can be linked to a cell culture condition such as pH, and/or nitrogen level, as described in the examples herein, or other environmental condition. In practice, the condition may be manipulated by adding or removing a substance (e.g., protons via addition of acid or base) or by allowing the cells to consume a substance (e.g., nitrogen-supplying nutrients) to effect the desired switch in regulation of the desaturase activity.

Other genetic or non-genetic methods for regulating the desaturase activity can also be used. For example, an inhibitor of the desaturase can be added to the culture medium in a manner that is effective to inhibit polyunsaturated fatty acids from being produced during the oil production phase.

Accordingly, in a specific embodiment of the invention, there is a method comprising providing a recombinant cell having a regulatable delta 12 fatty acid desaturase gene, under control of a recombinant regulatory element via an environmental condition. The cell is cultivated under conditions that favor cell multiplication. Upon reaching a given cell density, the cell media is altered to switch the cells to lipid production mode by nutrient limitation (e.g. reduction of available nitrogen). During the lipid production phase, the environmental condition is such that the activity of the delta 12 fatty acid desaturase is downregulated. The cells are then harvested and, optionally, the oil extracted. Due to the low level of delta 12 fatty acid desaturase during the lipid production phase, the oil has less polyunsaturated fatty acids and has improved oxidative stability. Optionally the cells are cultivated heterotrophically and optionally microalgal cells.

Using one or more of these desaturase regulation methods, it is possible to obtain a cell oil that it is believed has been previously unobtainable, especially in large scale cultivation in a bioreactor (e.g., more than 1000 L). The oil can have polyunsaturated fatty acid levels that are 5%, 4%, 3%, 2%, 1%, 0.5%, 0.3%, 0.2%, or less, as an area percent of total triacylglycerol fatty acids in the oil.

One consequence of having such low levels of polyunsaturates is that oils are exceptionally stable to oxidation. Indeed, in some cases the oils may be more stable than any previously known cell oil. In specific embodiments, the oil is stable, without added antioxidants, at 110° C. so that the inflection point in conductance is not yet reached by 10 hours, 15 hours, 20 hours, 30 hours, 40, hours, 50 hours, 60 hours, or 70 hours under conditions of the AOCS Cd 12b-92. Rancimat test, noting that for very stable oils, replenishment of water may be required in such a test due to evaporation that occurs with such long testing periods (see Example 5). For example the oil can have and OSI value of 40-50 hours or 41-46 hours at 110° C. without added antioxidants. When antioxidants (suitable for foods or otherwise) are added, the OSI value measured may be further increased. For example, with added tocopherol (100 ppm) and ascorbyl palmitate (500 ppm) or PANA and ascorbyl palmitate, such an oil can have an oxidative stability index (OSI value) at 110° C. in excess 100 or 200 hours, as measured by the Rancimat test. In another example, 1050 ppm of mixed tocopherols and 500 pm of ascorbyl palmitate are added to an oil comprising less than 1% linoleic acid or less than 1% linoleic+linolenic acids; as a result, the oil is stable at 110° C. for 1, 2, 3, 4, 5, 6, 7, 8, or 9, 10, 11, 12, 13, 14, 15, or 16, 20, 30, 40 or 50 days, 5 to 15 days, 6 to 14 days, 7 to 13 days, 8 to 12 days, 9 to 11 days, about 10 days, or about 20 days. The oil can also be stable at 130° C. for 1, 2, 3, 4, 5, 6, 7, 8, or 9, 10, 11, 12, 13, 14, 15, or 16, 20, 30, 40 or 50 days, 5 to 15 days, 6 to 14 days, 7 to 13 days, 8 to 12 days, 9 to 11 days, about 10 days, or about 20 days. In a specific example, such an oil was found to be stable for greater than 100 hours (about 128 hours as observed). In a further embodiment, the OSI value of the cell oil without added antioxidants at 120° C. is greater than 15 hours or 20 hours or is in the range of 10-15, 15-20, 20-25, or 25-50 hours, or 50-100 hours.

In an example, using these methods, the oil content of a microalgal cell is between 40 and about 85% by dry cell weight and the polyunsaturated fatty acids in the fatty acid profile of the oil is between 0.001% and 3% in the fatty acid profile of the oil and optionally yields a cell oil having an OSI induction time of at least 20 hours at 110° C. without the addition of antioxidants. In yet another example, there is a cell oil produced by RBD treatment of a cell oil from an oleaginous cell, the oil comprises between 0.001% and 2% polyunsaturated fatty acids and has an OSI induction time exceeding 30 hours at 110 C without the addition of antioxidants. In yet another example, there is a cell oil produced by RBD treatment of a cell oil from an oleaginous cell, the oil comprises between 0.001% and 1% polyunsaturated fatty acids and has an OSI induction time exceeding 30 hours at 110 C without the addition of antioxidants.

In another specific embodiment there is an oil with reduced polyunsaturate levels produced by the above-described methods. The oil is combined with antioxidants such as PANA and ascorbyl palmitate. For example, it was found that when such an oil was combined with 0.5% PANA and 500 ppm of ascorbyl palmitate the oil had an OSI value of about 5 days at 130° C. or 21 days at 110° C. These remarkable results suggest that not only is the oil exceptionally stable, but these two antioxidants are exceptionally potent stabilizers of triglyceride oils and the combination of these antioxidants may have general applicability including in producing stable biodegradable lubricants (e.g., jet engine lubricants). In specific embodiments, the genetic manipulation of fatty acyl Δ12 desaturase results in a 2 to 30, or 5 to 25, or 10 to 20 fold increase in OSI (e.g., at 110° C.) relative to a strain without the manipulation. The oil can be produced by suppressing desaturase activity in a cell, including as described above.

Antioxidants suitable for use with the oils of the present invention include alpha, delta, and gamma tocopherol (vitamin E), tocotrienol, ascorbic acid (vitamin C), glutathione, lipoic acid, uric acid, β-carotene, lycopene, lutein, retinol (vitamin A), ubiquinol (coenzyme Q), melatonin, resveratrol, flavonoids, rosemary extract, propyl gallate (PG), tertiary butylhydroquinone (TBHQ), butylated hydroxyanisole (BHA), and butylated hydroxytoluene (BHT), N,N'-di-2-butyl-1,4-phenylenediamine, 2,6-di-tert-butyl-4-methylphenol, 2,4-dimethyl-6-tert-butylphenol, 2,4-dimethyl-6-tert-butylphenol, 2,4-dimethyl-6-tert-butylphenol, 2,6-di-tert-butyl-4-methylphenol, 2,6-di-tert-butylphenol, and phenyl-alpha-naphthylamine (PANA).

In addition to the desaturase modifications, in a related embodiment other genetic modifications may be made to further tailor the properties of the oil, as described throughout, including introduction or substitution of acyl-ACP thioesterases having altered chain length specificity and/or overexpression of an endogenous or exogenous gene encoding a KAS, SAD, LPAAT, or DGAT gene. For example, a strain that produces elevated oleic levels may also produce low levels of polyunsaturates. Such genetic modifications can include increasing the activity of stearoyl-ACP desaturase (SAD) by introducing an exogenous SAD gene, increasing elongase activity by introducing an exogenous KASII gene, and/or knocking down or knocking out a FATA gene.

In a specific embodiment, a high oleic cell oil with low polyunsaturates may be produced. For example, the oil may have a fatty acid profile with greater than 60, 70, 80, 90, or 95% oleic acid and less than 5, 4, 3, 2, or 1% polyunsaturates. In related embodiments, a cell oil is produced by a cell having recombinant nucleic acids operable to decrease fatty acid Δ12 desaturase activity and optionally fatty acid 415 desaturase so as to produce an oil having less than or equal to 3% polyunsaturated fatty acids with greater than 60% oleic acid, less than 2% polyunsaturated fatty acids and greater than 70% oleic acid, less than 1% polyunsaturated fatty acids and greater than 80% oleic acid, or less than 0.5% polyunsaturated fatty acids and greater than 90% oleic acid. It has been found that one way to increase oleic acid is to use recombinant nucleic acids operable to decrease expression of a FATA acyl-ACP thioesterase and optionally overexpress a KAS II gene; such a cell can produce an oil with greater than or equal to 75% oleic acid. Alternately, overexpression of KASII can be used without the FATA knockout or knockdown. Oleic acid levels can be further increased by reduction of delta 12 fatty acid desaturase activity using the methods above, thereby decreasing the amount of oleic acid the is converted into the unsaturates linoleic acid and linolenic acid. Thus, the oil produced can have a fatty acid profile with at least 75% oleic and at most 3%, 2%, 1%, or 0.5% linoleic acid. In a related example, the oil has between 80 to 95% oleic acid and about 0.001 to 2% linoleic acid, 0.01 to 2% linoleic acid, or 0.1 to 2% linoleic acid. In another related embodiment, an oil is produced by cultivating an oleaginous cell (e.g., a microalga) so that the microbe produces a cell oil with less than 10% palmitic acid, greater than 85% oleic acid, 1% or less polyunsaturated fatty acids, and less than 7% saturated fatty acids. See Example 58 in which such an oil is produced in a microalga with FAD and FATA knockouts plus expression of an exogenous KASII gene. Such oils will have a low freezing point, with excellent stability and are useful in foods, for frying, fuels, or in chemical applications. Further, these oils may exhibit a reduced propensity to change color over time. In an illustrative chemical application, the high oleic oil is used to produce a chemical. The oleic acid double bonds of the oleic acid groups of the triglycerides in the oil can be epoxidized or hydroxylated to make a polyol. The epoxidized or hydroxylated oil can be used in a variety of applications. One such application is the production of polyurethane (including polyurethane foam) via condensation of the hydroxylated triglyceride with an isocyanate, as has been practiced with hydroxylated soybean oil or castor oil. See, e.g. US2005/0239915, US2009/0176904, US2005/0176839, US2009/0270520, and U.S. Pat. No. 4,264,743 and Zlatanic, et al, Biomacromolecules 2002, 3, 1048-1056 (2002) for examples of hydroxylation and polyurethane condensation chemistries. Suitable hydroxyl forming reactions include epoxidation of one or more double bonds of a fatty acid followed by acid catalyzed epoxide ring opening with water (to form a diol), alcohol (to form a hydroxylether), or an acid (to form a hydroxyl ester). There are multiple advantages of using the high-oleic/low polyunsaturated oil in producing a bio-based polyurethane: (1) the shelf-life, color or odor, of polyurethane foams may be improved; (2) the reproducibility of the product may be improved due to lack of unwanted side reactions resulting from polyunsaturates; (3) a greater degree of hydroxylation reaction may occur due to lack of polyunsaturates and the structural characteristics of the polyurethane product can be improved accordingly.

The low-polyunsaturated or high-oleic/low-polyunsaturated oils described here may be advantageously used in chemical applications where yellowing is undesirable. For example, yellowing can be undesirable in paints or coatings made from the triglycerides fatty acids derived from the triglycerides. Yellowing may be caused by reactions involving polyunsaturated fatty acids and tocotrienols and/or tocopherols. Thus, producing the high-stability oil in an oleaginous microbe with low levels of tocotrienols can be advantageous in elevating high color stability a chemical composition made using the oil. In contrast to commonly used plant oils, through appropriate choice of oleaginous microbe, the cell oils of these embodiments can have tocopherols and tocotrienols levels of 1 g/L or less. In a specific embodiment, a cell oil has a fatty acid profile with less than 2% with polyunsaturated fatty acids and less than 1 g/L for tocopherols, tocotrienols or the sum of tocopherols and tocotrienols. In another specific embodiment, the cell oil has a fatty acid profile with less than 1% with polyunsaturated fatty acids and less than 0.5 g/L for tocopherols, tocotrienols or the sum of tocopherols and tocotrienols Any of the high-stability (low-polyunsaturate) cell oils or derivatives thereof can be used to formulate foods, drugs, vitamins, nutraceuticals, personal care or other products, and are especially useful for oxidatively sensitive products. For example, the high-stability cell oil (e.g., less than or equal to 3%, 2% or 1% polyunsaturates) can be used to formulate a sunscreen (e.g. a composition having one or more of avobenzone, homosalate, octisalate, octocrylene or oxybenzone) or retinoid face cream with an increased shelf life due to the absence of free-radical reactions associated with polyunsaturated fatty acids. For example, the shelf-life can be increased in terms of color, odor, organoleptic properties or % active compound remaining after accelerated degradation for 4 weeks at 54° C. The high stability oil can also be used as a lubricant with excellent high-temperature stability. In addition to stability, the oils can be biodegradable, which is a rare combination of properties.

In another related embodiment, the fatty acid profile of a cell oil is elevated in C8 to C16 fatty acids through additional genetic modification, e.g. through overexpression of a short-chain to mid chain preferring acyl-ACP thioesterase or other modifications described here. A low polyunsaturated oil in accordance with these embodiments can be used for various industrial, food, or consumer products, including those requiring improved oxidative stability. In food applications, the oils may be used for frying with extended life at high temperature, or extended shelf life.

Where the oil is used for frying, the high stability of the oil may allow for frying without the addition of antioxidant and/or defoamers (e.g. silicone). As a result of omitting defoamers, fried foods may absorb less oil. Where used in fuel applications, either as a triglyceride or processed into biodiesel or renewable diesel (see, e.g., WO2008/151149 WO2010/063032, and WO2011/150410), the high stability can promote storage for long periods, or allow use at elevated temperatures. For example, the fuel made from the high stability oil can be stored for use in a backup generator for more than a year or more than 5 years. The frying oil can have a smoke point of greater than 200° C., and free fatty acids of less than 0.1% (either as a cell oil or after refining).

The low polyunsaturated oils may be blended with food oils, including structuring fats such as those that form beta or beta prime crystals, including those produced as described below. These oils can also be blended with liquid oils. If mixed with an oil having linoleic acid, such as corn oil, the linoleic acid level of the blend may approximate that of high oleic plant oils such as high oleic sunflower oils (e.g., about 80% oleic and 8% linoleic).

Blends of the low polyunsaturated cell oil can be interesterified with other oils. For example, the oil can be chemically or enzymatically interesterified. In a specific embodiment, a low polyunsaturated oil according to an embodiment of the invention has at least 10% oleic acid in its fatty acid profile and less than 5% polyunsaturates and is enzymatically interesterified with a high saturate oil (e.g. hydrogenated soybean oil or other oil with high stearate levels) using an enzyme that is specific for sn-1 and sn-2 triacylglycerol positions. The result is an oil that includes a stearate-oleate-stearate (SOS). Methods for interesterification are known in the art; see for example, "Enzymes in Lipid Modification," Uwe T. Bomschuer, ed., Wiley_VCH, 2000, ISBN 3-527-30176-3.

High stability oils can be used as spray oils. For example, dried fruits such as raisins can be sprayed with a high stability oil having less than 5, 4, 3, 2, or 1% polyunsaturates. As a result, the spray nozzle used will become clogged less frequently due to polymerization or oxidation product buildup in the nozzle that might otherwise result from the presence of polyunsaturates.

In a further embodiment, an oil that is high is SOS, such as those described below can be improved in stability by knockdown or regulation of delta 12 fatty acid desaturase.

Optionally, where the FADc promoter is regulated, it can be regulated with a promoter that is operable at low pH (e.g., one for which the level of transcription of FADc is reduced by less than half upon switching from cultivation at pH 7.0 to cultivation at pH 5.0). The promoter can be sensitive to cultivation under low nitrogen conditions such that the promoter is active under nitrogen replete conditions and inactive under nitrogen starved conditions. For example, the promoter may cause a reduction in FADc transcript levels of 5, 10, 15-fold or more upon nitrogen starvation. Because the promoter is operable at pH 5.0, more optimal invertase activity can be obtained. For example, the cell can be cultivated in the presence of invertase at a pH of less than 6.5, 6.0 or 5.5. The cell may have a FADc knockout to increase the relative gene-dosage of the regulated FADc. Optionally, the invertase is produced by the cell (natively or due to an exogenous invertase gene). Because the promoter is less active under nitrogen starved conditions, fatty acid production can proceed during the lipid production phase that would not allow for optimal cell proliferation in the cell proliferation stage. In particular, a low linoleic oil may be produced. The cell can be cultivated to an oil content of at least 20% lipid by dry cell weight. The oil may have a fatty acid profile having less than 5, 4, 3, 2, 1, or 0.5, 0.2, or 0.1% linoleic acid. Example 62 describes the discovery of such promoters.

IV. (B) High 18:2/LOW 18:3 Oils Obtained Using FAD Gene Replacement

Surprisingly, while researching the production of low polyunsaturate oils as described above, an oil with high polyunsaturates but having a unique fatty acid profile was discovered. The discovery of this oil is described in Example 59. Thus, it is possible to use an oleaginous plastidic cell (e.g., microalgal) culture to produce an oil with a fatty acid profile characterized by 10% or less linolenic acid (C18:3) and 20% or more linoleic acid (C18:2). Such oils can be produced in an oleaginous microalga or other oleaginous plastidic cell by overexpression of a (endogenous or exogenous) KASII and gene replacement of FADc (also referred to as FAD2) and, if necessary based on the host cell, replacing native acyl-ACP thioesterase activity. In Example 58-59, an endogenous KASII was overexpressed and an endogenous FADc gene was placed under control of a pH-inducible promoter, although constitutive expression would also work. Interestingly, the oils were much higher in linoleic acid when the FADc was overexpressed in a linoleic acid auxotroph (e.g., a FADc double knockout). It is believed that this is due to the presence of a previously unrecognized gene-level regulatory system in microalgae that must be disabled in order to efficiently accumulate linoleic acid. In addition, two copies of the endogenous acyl-ACP thioesterase were knocked out and replaced with an oleate-specific plant acyl-ACP thioesterase. Under permissive pH conditions, an oil with 10% or less linolenic acid (C18:3) and 20% or more linoleic acid (C18:2). The oil can be extracted and used for various uses included in foodstuffs or chemicals. If the host cell is a microalga, the oil can comprise microalgal sterols. As with other embodiments, the host cell can be a microalga transformed to express an exogenous invertase, thus enable conversion of sucrose into the oil under conditions of heterotrophic cultivation.

In a specific embodiment, a host cell comprises a FADc knockdown, knockout, or FADc with a down-regulatable promoter combined with an exogenous KASII gene that expresses a protein having at least 80, 85, 90, 91, 92, 93, 94, 95, 96, 97, 98 or 99% amino acid identity to the protein encoded by the *Prototheca moriformis* KASII gene disclose in Example 58, and optionally expresses an acyl-ACP thioesterase gene producing an oleate-specific acyl-ACP thioesterase enzyme. Optionally, the cell can be an a plant cell, a microbial cell, or a microalgal cell.

V. Cells with Exogenous Acyltransferases

In various embodiments of the present invention, one or more genes encoding an acyltransferase (an enzyme responsible for the condensation of a fatty acid with glycerol or a glycerol derivative to form an acylglyceride) can be introduced into an oleaginous cell (e.g., a plastidic microalgal cell) so as to alter the fatty acid composition of a cell oil produced by the cell. The genes may encode one or more of a glycerol-3-phosphate acyltransferase (GPAT), lysophosphatidic acid acyltransferase (LPAAT), also known as 1-acylglycerol-3-phosphate acyltransferase (AGPAT), phosphatidic acid phosphatase (PAP), or diacylglycerol acyltransferase (DGAT) that transfers an acyl group to the sn-3 position of DAG, thereby producing a TAG.

Recombinant nucleic acids may be integrated into a plasmid or chromosome of the cell. Alternately, the gene encodes an enzyme of a lipid pathway that generates TAG precursor molecules through fatty acyl-CoA-independent routes separate from that above. Acyl-ACPs may be substrates for plastidial GPAT and LPAAT enzymes and/or mitochondrial GPAT and LPAAT enzymes. Among further enzymes capable of incorporating acyl groups (e.g., from membrane phospholipids) to produce TAGs is phospholipid diacylglycerol acyltransferase (PDAT). Still further acyltransferases, including lysophosphosphatidylcholine acyltransferase (LPCAT), lysophosphosphatidylserine acyltransferase (LPSAT), lysophosphosphatidylethanolamine acyltransferase (LPEAT), and lysophosphosphatidylinositol acyltransferase (LPIAT), are involved in phospholipid synthesis and remodeling that may impact triglyceride composition.

The exogenous gene can encode an acyltransferase enzyme having preferential specificity for transferring an acyl substrate comprising a specific number of carbon atoms and/or a specific degree of saturation is introduced into a oleaginous cell so as to produce an oil enriched in a given regiospecific triglyceride. For example, the coconut (*Cocos nucifera*) lysophosphatidic acid acyltransferase has been demonstrated to prefer C12:0-CoA substrates over other acyl-CoA substrates (Knutzon et al., *Plant Physiology*, Vol. 120, 1999, pp. 739-746), whereas the 1-acyl-sn-3-glycerol-3-phosphate acyltransferase of maturing safflower seeds shows preference for linoleoyl-CoA and oleoyl-CoA substrates over other acyl-CoA substrates, including stearoyl-CoA (Ichihara et al., *European Journal of Biochemistry*, Vol. 167, 1989, pp. 339-347). Furthermore, acyltransferase proteins may demonstrate preferential specificity for one or more short-chain, medium-chain, or long-chain acyl-CoA or acyl-ACP substrates, but the preference may only be encountered where a particular, e.g. medium-chain, acyl group is present in the sn-1 or sn-3 position of the lysophosphatidic acid donor substrate. As a result of the exogenous gene, a TAG oil can be produced by the cell in which a particular fatty acid is found at the sn-2 position in greater than 20, 30, 40, 50, 60, 70, 90, or 90% of the TAG molecules.

In some embodiments of the invention, the cell makes an oil rich in saturated-unsaturated-saturated (sat-unsat-sat) TAGs. Sat-unsat-sat TAGS include 1,3-dihexadecanoyl-2-(9Z-octadecenoyl)-glycerol (referred to as 1-palmitoyl-2-oleyl-glycero-3-palmitoyl), 1,3-dioctadecanoyl-2-(9Z-octadecenoyl)-glycerol (referred to as 1-stearoyl-2-oleyl-glycero-3-stearoyl), and 1-hexadecanoyl-2-(9Z-octadecenoyl)-3-octadecanoy-glycerol (referred to as 1-palmitoyl-2-oleyl-glycero-3-stearoyl). These molecules are more commonly referred to as POP, SOS, and POS, respectively, where 'P' represents palmitic acid, 'S' represents stearic acid, and 'O' represents oleic acid. Further examples of saturated-unsaturated-saturated TAGs include MOM, LOL, MOL, COC and COL, where 'M' represents myristic acid, 'L' represents lauric acid, and 'C' represents capric acid (C8:0). Trisaturates, triglycerides with three saturated fatty acyl groups, are commonly sought for use in food applications for their greater rate of crystallization than other types of triglycerides. Examples of trisaturates include PPM, PPP, LLL, SSS, CCC, PPS, PPL, PPM, LLP, and LLS. In addition, the regiospecific distribution of fatty acids in a TAG is an important determinant of the metabolic fate of dietary fat during digestion and absorption.

According to certain embodiments of the present invention, oleaginous cells are transformed with recombinant nucleic acids so as to produce cell oils that comprise an elevated amount of a specified regiospecific triglyceride, for example 1-acyl-2-oleyl-glycero-3-acyl, or 1-acyl-2-lauric-glycero-3-acyl where oleic or lauric acid respectively is at the sn-2 position, as a result of introduced recombinant nucleic acids. Alternately, caprylic, capric, myristic, or palmitic acid may be at the sn-2 position. The amount of the specified regiospecific triglyceride present in the cell oil may be increased by greater than 5%, greater than 10%, greater than 15%, greater than 20%, greater than 25%, greater than 30%, greater than 35%, greater than 40%, greater than 50%, greater than 60%, greater than 70%, greater than 80%, greater than 90%, greater than 100-500%, or greater than 500% than in the cell oil produced by the microorganism without the recombinant nucleic acids. As a result, the sn-2 profile of the cell triglyceride may have greater than 10, 20, 30, 40, 50, 60, 70, 80, or 90% of the particular fatty acid.

The identity of the acyl chains located at the distinct stereospecific or regiospecific positions in a glycerolipid can be evaluated through one or more analytical methods known in the art (see Luddy et al., *J. Am. Oil Chem. Soc.,* 41, 693-696 (1964), Brockerhoff, *J. Lipid Res.,* 6, 10-15 (1965), Angers and Aryl, *J. Am. Oil Chem. Soc.*, Vol. 76:4, (1999), Buchgraber et al., *Eur. J. Lipid Sci. Technol.,* 106, 621-648 (2004)), or in accordance with Examples 1, 2, and 8 given below.

The positional distribution of fatty acids in a triglyceride molecule can be influenced by the substrate specificity of acyltransferases and by the concentration and type of available acyl moieties substrate pool. Nonlimiting examples of enzymes suitable for altering the regiospecificity of a triglyceride produced in a recombinant microorganism are listed in Tables 1-4. One of skill in the art may identify additional suitable proteins.

TABLE 1

Glycerol-3-phosphate acyltransferases and GenBank accession numbers.

| | | |
|---|---|---|
| glycerol-3-phosphate acyltransferase | *Arabidopsis thaliana* | BAA00575 |
| glycerol-3-phosphate acyltransferase | *Chlamydomonas reinhardtii* | EDP02129 |
| glycerol-3-phosphate acyltransferase | *Chlamydomonas reinhardtii* | Q886Q7 |
| acyl-(acyl-carrier-protein): glycerol-3-phosphate acyltransferase | *Cucurbita moschata* | BAB39688 |
| glycerol-3-phosphate acyltransferase | *Elaeis guineensis* | AAF64066 |
| glycerol-3-phosphate acyltransferase | *Garcina mangostana* | ABS86942 |
| glycerol-3-phosphate acyltransferase | *Gossypium hirsutum* | ADK23938 |
| glycerol-3-phosphate acyltransferase | *Jatropha curcas* | ADV77219 |
| plastid glycerol-3-phosphate acyltransferase | *Jatropha curcas* | ACR61638 |
| plastidial glycerol-phosphate acyltransferase | *Ricinus communis* | EEF43526 |
| glycerol-3-phosphate acyltransferase | *Vica faba* | AAD05164 |
| glycerol-3-phosphate acyltransferase | *Zea mays* | ACG45812 |

Lysophosphatidic acid acyltransferases suitable for use with the microbes and methods of the invention include, without limitation, those listed in Table 2.

TABLE 2

Lysophosphatidic acid acyltransferases and GenBank accession numbers.

| | | |
|---|---|---|
| 1-acyl-sn-glycerol-3-phosphate acyltransferase | *Arabidopsis thaliana* | AEE85783 |
| 1-acyl-sn-glycerol-3-phosphate acyltransferase | *Brassica juncea* | ABQ42862 |
| 1-acyl-sn-glycerol-3-phosphate acyltransferase | *Brassica juncea* | ABM92334 |
| 1-acyl-sn-glycerol-3-phosphate acyltransferase | *Brassica napus* | CAB09138 |
| lysophosphatidic acid acyltransferase | *Chlamydomonas reinhardtii* | EDP02300 |
| lysophosphatidic acid acyltransferase | *Limnanthes alba* | AAC49185 |
| 1-acyl-sn-glycerol-3-phosphate acyltransferase (putative) | *Limnanthes douglasii* | CAA88620 |
| acyl-CoA: sn-1-acylglycerol-3-phosphate acyltransferase | *Limnanthes douglasii* | ABD62751 |
| 1-acylglycerol-3-phosphate O-acyltransferase | *Limnanthes douglasii* | CAA58239 |
| 1-acyl-sn-glycerol-3-phosphate acyltransferase | *Ricinus communis* | EEF39377 |

Diacylglycerol acyltransferases suitable for use with the microbes and methods of the invention include, without limitation, those listed in Table 3.

TABLE 3

Diacylglycerol acyltransferases and GenBank accession numbers.

| | | |
|---|---|---|
| diacylglycerol acyltransferase | *Arabidopsis thaliana* | CAB45373 |
| diacylglycerol acyltransferase | *Brassica juncea* | AAY40784 |
| putative diacylglycerol acyltransferase | *Elaeis guineensis* | AEQ94187 |
| putative diacylglycerol acyltransferase | *Elaeis guineensis* | AEQ94186 |
| acyl CoA: diacylglycerol acyltransferase | *Glycine max* | AAT73629 |
| diacylglycerol acyltransferase | *Helianthus annus* | ABX61081 |
| acyl-CoA: diacylglycerol acyltransferase 1 | *Olea europaea* | AAS01606 |
| diacylglycerol acyltransferase | *Ricinus communis* | AAR11479 |

Phospholipid diacylglycerol acyltransferases suitable for use with the microbes and methods of the invention include, without limitation, those listed in Table 4.

TABLE 4

Phospholipid diacylglycerol acyltransferases and GenBank accession numbers.

| | | |
|---|---|---|
| phospholipid: diacylglycerol acyltransferase | *Arabidopsis thaliana* | AED91921 |
| Putative phospholipid: diacylglycerol acyltransferase | *Elaeis guineensis* | AEQ94116 |
| phospholipid: diacylglycerol acyltransferase 1-like | *Glycine max* | XP_003541296 |
| phospholipid: diacylglycerol acyltransferase | *Jatropha curcas* | AEZ56255 |

TABLE 4-continued

| Phospholipid diacylglycerol acyltransferases and GenBank accession numbers. | | |
|---|---|---|
| phospholipid: diacylglycerol acyltransferase | *Ricinus communis* | ADK92410 |
| phospholipid: diacylglycerol acyltransferase | *Ricinus communis* | AEW99982 |

In an embodiment of the invention, known or novel LPAAT genes are transformed into the oleaginous cells so as to alter the fatty acid profile of triglycerides produced by those cells, most notably by altering the sn-2 profile of the triglycerides. For example, by virtue of expressing an exogenous active LPAAT in an oleaginous cell, the percent of unsaturated fatty acid at the sn-2 position is increased by 10, 20, 30, 40, 50, 60, 70, 80, 90% or more. For example, a cell may produce triglycerides with 30% unsaturates (which may be primarily 18:1 and 18:2 and 18:3 fatty acids) at the sn-2 position. In this example, introduction of the LPAAT activity increases the unsaturates at the sn-2 position by 20% so that 36% of the triglycerides comprise unsaturates at the sn-2 position. Alternately, an exogenous LPAAT can be used to increase mid-chain fatty acids including saturated mid-chains such as C8:0, C10:0, C12:0, C14:0 or C16:0 moieties at the sn-2 position. As a result, mid-chain levels in the overall fatty acid profile may be increased. Examples 43 and 44 describe altering the sn-2 and fatty acid profiles in an oleaginous microbe. As can be seen from those examples, the choice of LPAAT gene is important in that different LPAATs can cause a shift in the sn-2 and fatty acid profiles toward different acyl group chain-lengths or saturation levels. For example, the LPAAT of Example 43 increases C10-C14 fatty acids and the LPAAT of Example 44 causes an increase in C16 and C18 fatty acids. As in these examples, introduction of an exogenous LPAAT can be combined with introduction of exogenous acyl-ACP thioesterase. Combining a mid-chain preferring LPAAT and a mid-chain preferring FatB was found to give an additive effect; the fatty acid profile was shifted more toward the mid-chain fatty acids when both an exogenous LPAAT and FatB gene was present than when only an exogenous FatB gene was present. In a specific embodiment, the oil produced by a cell comprising an exogenous mid-chain specific LPAAT and (optionally) an exogenous FatB acyl-ACP thioesterase gene can have a fatty acid profile with 40, 50, 60, 70, 80% or more of C8:0, C10:0, C12:0, C14:0, or C16:0 fatty acids (separately or in sum).

Specific embodiments of the invention are a nucleic acid construct, a cell comprising the nucleic acid construct, a method of cultivating the cell to produce a triglyceride, and the triglyceride oil produced where the nucleic acid construct has a promoter operably linked to a novel LPAAT coding sequence. The coding sequence can have an initiation codon upstream and a termination codon downstream followed by a 3 UTR sequence. In a specific embodiment, the LPAAT gene has LPAAT activity and a coding sequence have at least 75, 80, 85, 90, 95, 96, 97, 98, or 99% sequence identity to any of the cDNAs of SEQ ID NOs: 80 to 85 or a functional fragment thereof including equivalent sequences by virtue of degeneracy of the genetic code. Introns can be inserted into the sequence as well. Alternately, the LPAAT gene codes for the amino acid sequence of SEQ ID NOs 77-79 or functional fragments thereof, or a protein having at least 75, 80, 85, 90, 95, 96, 97, 98, or 99% amino acid sequence identity. In addition to microalgae and other oleaginous cells, plants expressing the novel LPAAT as transgenes are expressly included in the embodiments and can be produced using known genetic engineering techniques.

VI. Cells with Exogenous Elongases or Elongase Complex Enzymes

In various embodiments of the present invention, one or more genes encoding elongases or components of the fatty acyl-CoA elongation complex can be introduced into an oleaginous cell (e.g., a plastidic microalgal cell) so as to alter the fatty acid composition of the cell or of a cell oil produced by the cell. The genes may encode a beta-ketoacyl-CoA synthase (also referred to as 3-ketoacyl synthase, beta-ketoacyl synthase or KCS), a ketoacyl-CoA reductase, a hydroxyacyl-CoA dehydratase, enoyl-CoA reductase, or elongase. The enzymes encoded by these genes are active in the elongation of acyl-coA molecules liberated by acyl-ACP thioesterases. Recombinant nucleic acids may be integrated into a plasmid or chromosome of the cell. In a specific embodiment, the cell is of Chlorophyta, including heterotrophic cells such as those of the genus *Prototheca.*

Beta-Ketoacyl-CoA synthase and elongase enzymes suitable for use with the microbes and methods of the invention include, without limitation, those listed in Table 5.

TABLE 5

| Beta-Ketoacyl-CoA synthases and elongases listed with GenBank accession numbers. |
|---|
| *Trypanosoma brucei* elongase 3 (GenBank Accession No. AAX70673), *Marchanita polymorpha* (GenBank Accession No. AAP74370), *Trypanosoma cruzi* fatty acid elongase, putative (GenBank Accession No. EFZ33366), *Nannochloropsis oculata* fatty acid elongase (GenBank Accession No. ACV21066.1), *Leishmania donovani* fatty acid elongase, putative (GenBank Accession No. CBZ32733.1), *Glycine max* 3-ketoacyl-CoA synthase 11-like (GenBank Accession No. XP_003524525.1), *Medicago truncatula* beta-ketoacyl-CoA synthase (GenBank Accession No. XP_003609222), *Zea mays* fatty acid elongase (GenBank Accession No. ACG36525), *Gossypium hirsutum* beta-ketoacyl-CoA synthase (GenBank Accession No. ABV60087), *Helianthus annuus* beta-ketoacyl-CoA synthase (GenBank; Accession No. ACC60973.1), *Saccharomyces cerevisiae* ELO1 (GenBank Accession No. P39540), *Simmondsia chinensis* beta-ketoacyl-CoA synthase (GenBank Accession No. AAC49186), *Tropaeolum majus* putative fatty acid elongase (GenBank Accession No. AAL99199, *Brassica napus* fatty acid elongase (GenBank Accession No. AAA96054) |

In an embodiment of the invention, an exogenous gene encoding a beta-ketoacyl-CoA synthase or elongase enzyme having preferential specificity for elongating an acyl substrate comprising a specific number of carbon atoms and/or a specific degree of acyl chain saturation is introduced into a oleaginous cell so as to produce a cell or an oil enriched in fatty acids of specified chain length and/or saturation. Example 40 describes engineering of *Prototheca* strains in which exogenous fatty acid elongases with preferences for extending midchain fatty acyl-CoAs have been overexpressed to increase the concentration of stearate. Examples 42 and 54 describe engineering of *Prototheca* in which exogenous elongases or beta-ketoacyl-CoA synthases with preferences for extending monounsaturated and saturated C18- and C20-CoA substrates are overexpressed to increase the concentration of erucic acid.

In specific embodiments, the oleaginous cell produces an oil comprising greater than 0.5, 1, 2, 5, 10, 20, 30, 40, 50, 60 70, or 80% erucic and/or eicosenoic acid. Alternately, the cell produces an oil comprising 0.5-5, 5-10, 10-15, 15-20, 20-30, 30-40, 40-50, 50-60, 60-70, 70-80, 80-90, or 90-99% erucic or eicosenoic acid. The cell may comprise recombinant acids described above in connection with high-oleic oils with a further introduction of an exogenous beta-ketoacyl-CoA synthase that is active in elongating oleoyl-CoA. As a result of the expression of the exogenous beta-ketoacyl-CoA synthase, the natural production of erucic or eicosenoic acid by the cell can be increased by more than 2, 3, 4, 5, 10, 20, 30, 40, 50, 70, 100, 130, 170 or 200 fold. The high erucic and/or eicosenoic oil can also be a high stability oil; e.g., one comprising less than 5, 4, 3, 2, or 1% polyunsaturates and/or having the OSI values described in Section IV or this application and accompanying Examples. In a specific embodiment, the cell is a microalgal cell, optionally cultivated heterotrophically. As in the other embodiments, the oil/fat can be produced by genetic engineering of a plastidic cell, including heterotrophic microalgae of the phylum Chlorophyta, the class Trebouxiophytae, the order Chlorellales, or the family Chlorellacae. Preferably, the cell is oleaginous and capable of accumulating at least 40% oil by dry cell weight. The cell can be an obligate heterotroph, such as a species of *Prototheca*, including *Prototheca moriformis* or *Prototheca zopfii.*

In specific embodiments, an oleaginous microbial cell, optionally an oleaginous microalgal cell, optionally of the phylum Chlorophyta, the class Trebouxiophytae, the order Chlorellales, or the family Chlorellacae expresses an enzyme having 80, 85, 90, 95, 96, 97, 98, or 99% amino acid sequence identity to an enzyme of Table 5.

VII. Regiospecific and Stereospecific Oils/Fats

In an embodiment, a recombinant cell produces a cell fat or oil having a given regiospecific makeup. As a result, the cell can produce triglyceride fats having a tendency to form crystals of a given polymorphic form; e.g., when heated to above melting temperature and then cooled to below melting temperature of the fat. For example, the fat may tend to form crystal polymorphs of the β or β' form (e.g., as determined by X-ray diffraction analysis), either with or without tempering. The fats may be ordered fats. In specific embodiments, the fat may directly from either β or β' crystals upon cooling; alternatively, the fat can proceed through a β form to a β' form. Such fats can be used as structuring, laminating or coating fats for food applications. The cell fats can be incorporated into candy, dark or white chocolate, chocolate flavored confections, ice cream, margarines or other spreads, cream fillings, pastries, or other food products. Optionally, the fats can be semi-solid (at room temperature) yet free of artificially produced trans-fatty acids. Such fats can also be useful in skin care and other consumer or industrial products.

As in the other embodiments, the fat can be produced by genetic engineering of a plastidic cell, including heterotrophic eukaryotic microalgae of the phylum Chlorophyta, the class Trebouxiophytae, the order Chlorellales, or the family Chlorellacae. Preferably, the cell is oleaginous and capable of accumulating at least 40% oil by dry cell weight. The cell can be an obligate heterotroph, such as a species of *Prototheca*, including *Prototheca moriformis* or *Prototheca* zopfii. The fats can also be produced in autotrophic algae or plants. Optionally, the cell is capable of using sucrose to produce oil and a recombinant invertase gene may be introduced to allow metabolism of sucrose, as described in PCT Publications WO2008/151149, WO2010/06032, WO2011/150410, WO2011/150411, and international patent application PCT/US12/23696. The invertase may be codon optimized and integrated into a chromosome of the cell, as may all of the genes mentioned here. It has been found that cultivated recombinant microalgae can produce hardstock fats at temperatures below the melting point of the hardstock fat. For example, *Prototheca moriformis* can be altered to heterotrophically produce triglyceride oil with greater than 50% stearic acid at temperatures in the range of 15 to 30° C., wherein the oil freezes when held at 30° C.

In an embodiment, the cell fat has at least 30, 40, 50, 60, 70, 80, or 90% fat of the general structure [saturated fatty acid (sn-1)-unsaturated fatty acid (sn-2)-saturated fatty acid sn-3)]. This is denoted below as Sat-Unsat-Sat fat. In a specific embodiment, the saturated fatty acid in this structure is preferably stearate or palmitate and the unsaturated fatty acid is preferably oleate. As a result, the fat can form primarily β or β' polymorphic crystals, or a mixture of these, and have corresponding physical properties, including those desirable for use in foods or personal care products. For example, the fat can melt at mouth temperature for a food product or skin temperature for a cream, lotion or other personal care product (e.g., a melting temperature of 30 to 40, or 32 to 35° C.). Optionally, the fats can have a 2 L or 3 L lamellar structure (e.g., as determined by X-ray diffraction analysis). Optionally, the fat can form this polymorphic form without tempering.

In a specific related embodiment, a cell fat triglyceride has a high concentration of SOS (i.e. triglyceride with stearate at the terminal sn-1 and sn-3 positions, with oleate at the sn-2 position of the glycerol backbone). For example, the fat can have triglycerides comprising at least 50, 60, 70, 80 or 90% SOS. In an embodiment, the fat has triglyceride of at least 80% SOS. Optionally, at least 50, 60, 70, 80 or 90% of the sn-2 linked fatty acids are unsaturated fatty acids. In a specific embodiment, at least 95% of the sn-2 linked fatty acids are unsaturated fatty acids. In addition, the SSS (tri-stearate) level can be less than 20, 10 or 5% and/or the C20:0 fatty acid (arachidic acid) level may be less than 6%, and optionally greater than 1% (e.g., from 1 to 5%). For example, in a specific embodiment, a cell fat produced by a recombinant cell has at least 70% SOS triglyceride with at least 80% sn-2 unsaturated fatty acyl moieties. In another specific embodiment, a cell fat produced by a recombinant cell has TAGs with at least 80% SOS triglyceride and with at least 95% sn-2 unsaturated fatty acyl moieties. In yet another specific embodiment, a cell fat produced by a recombinant cell has TAGs with at least 80% SOS, with at least 95% sn-2 unsaturated fatty acyl moieties, and between 1 to 6% C20 fatty acids.

In yet another specific embodiment, the sum of the percent stearate and palmitate in the fatty acid profile of the cell fat is twice the percentage of oleate, ±10, 20, 30 or 40% [e.g., (% P+% S)/% O=2.0±20%]. Optionally, the sn-2 profile of this fat is at least 40%, and preferably at least 50, 60, 70, or 80% oleate (at the sn-2 position). Also optionally, this fat may be at least 40, 50, 60, 70, 80, or 90% SOS. Optionally, the fat comprises between 1 to 6% C20 fatty acids.

In any of these embodiments, the high SatUnsatSat fat may tend to form β' polymorphic crystals. Unlike previously available plant fats like cocoa butter, the SatUnsatSat fat produced by the cell may form β' polymorphic crystals without tempering. In an embodiment, the polymorph forms upon heating to above melting temperature and cooling to less that the melting temperature for 3, 2, 1, or 0.5 hours. In a related embodiment, the polymorph forms upon heating to above 60° C. and cooling to 10° C. for 3, 2, 1, or 0.5 hours.

In various embodiments the fat forms polymorphs of the β form, β' form, or both, when heated above melting temperature and the cooled to below melting temperature, and optionally proceeding to at least 50% of polymorphic equilibrium within 5, 4, 3, 2, 1, 0.5 hours or less when heated to above melting temperature and then cooled at 10° C. The fat may form β' crystals at a rate faster than that of cocoa butter.

Optionally, any of these fats can have less than 2 mole % diacylglycerol, or less than 2 mole % mono and diacylglycerols, in sum.

In an embodiment, the fat may have a melting temperature of between 30-60° C., 30-40° C., 32 to 37° C., 40 to 60° C. or 45 to 55° C. In another embodiment, the fat can have a solid fat content (SFC) of 40 to 50%, 15 to 25%, or less than 15% at 20° C. and/or have an SFC of less than 15% at 35° C.

The cell used to make the fat may include recombinant nucleic acids operable to modify the saturate to unsaturate ratio of the fatty acids in the cell triglyceride in order to favor the formation of SatUnsatSat fat. For example, a knock-out or knock-down of stearoyl-ACP desaturase (SAD) gene can be used to favor the formation of stearate over oleate or expression of an exogenous mid-chain-preferring acyl-ACP thioesterase gene can increase the levels mid-chain saturates. Alternately a gene encoding a SAD enzyme can be overexpressed to increase unsaturates.

In a specific embodiment, the cell has recombinant nucleic acids operable to elevate the level of stearate in the cell. As a result, the concentration of SOS may be increased. Example 9 demonstrates that the regiospecific profile of the recombinant microbe is enriched for the SatUnsatSat triglycerides POP, POS, and SOS as a result of overexpressing a *Brassica napus* C18:0-preferring thioesterase. An additional way to increase the stearate of a cell is to decrease oleate levels. For cells having high oleate levels (e.g., in excess of one half the stearate levels) one can also employ recombinant nucleic acids or classical genetic mutations operable to decrease oleate levels. For example, the cell can have a knockout, knockdown, or mutation in one or more FATA alleles, which encode an oleate liberating acyl-ACP thioesterase, and/or one or more alleles encoding a stearoyl ACP desaturase (SAD). Example 35 describes the inhibition of SAD2 gene product expression using hairpin RNA to produce a fatty acid profile of 37% stearate in *Prototheca moriformis* (UTEX 1435), whereas the wildtype strain produced less than 4% stearate, a more than 9-fold improvement. Moreover, while the strains of Example 35 are engineered to reduce SAD activity, sufficient SAD activity remains to produce enough oleate to make SOS, POP, and POS. See the TAG profiles of Example 47. In specific examples, one of multiple SAD encoding alleles may be knocked out and/or one or more alleles are downregulated using inhibition techniques such as antisense, RNAi, or siRNA, hairpin RNA or a combination thereof. In various embodiments, the cell can produce TAGs that have 20-30, 30-40, 40-50, 50-60, 60-70, 70-80, 80-90, or 90 to about 100% stearate. In other embodiments, the cells can produce TAGs that are 20-30, 30-40, 40-50, 50-60, 60-70, 70-80, 80-90, or 90 to about 100% SOS. Optionally, or in addition to genetic modification, stearoyl ACP desaturase can be inhibited chemically; e.g., by addition of sterculic acid to the cell culture during oil production.

Surprisingly, knockout of a single FATA allele has been found to increase the presence of C18 fatty acids produced in microalgae. By knocking out one allele, or otherwise suppressing the activity of the FATA gene product (e.g., using hairpin RNA), while also suppressing the activity of stearoyl-ACP desaturase (using techniques disclosed herein), stearate levels in the cell can be increased.

Another genetic modification to increase stearate levels includes increasing a ketoacyl ACP synthase (KAS) activity in the cell so as to increase the rate of stearate production. It has been found that in microalgae, increasing KASII activity is effective in increasing C18 synthesis and particularly effective in elevating stearate levels in cell triglyceride in combination with recombinant DNA effective in decreasing SAD activity. Recombinant nucleic acids operable to increase KASII (e.g., an exogenous KasII gene) can be also be combined with a knockout or knockdown of a FatA gene, or with knockouts or knockdowns of both a FatA gene and a SAD gene). Optionally, the KASII gene encodes a protein having at least 75, 80, 85, 90, 95, 96, 97, 98, or 99% amino acid identity to the KASII *Prototheca moriformis* (mature protein given in SEQ ID NO: 161), or any plant KASII gene disclosed herein (e.g., in Example 60) or known in the art including a microalgal KASII.

Optionally, the cell can include an exogenous stearate-liberating acyl-ACP thioesterase, either as a sole modification or in combination with one or more other stearate-increasing genetic modifications. For example the cell may be engineered to overexpress an acyl-ACP thioesterase with preference for cleaving C18:0-ACPs. Example 9 describes the expression of exogenous C18:0-preferring acyl-ACP thioesterases to increase stearate in the fatty acid profile of the microalgae, *Prototheca moriformis* (UTEX 1435), from about 3.7% to about 30.4% (over 8-fold). Example 41 provides additional examples of C18:0-preferring acyl-ACP thioesterases function to elevate C18:0 levels in *Prototheca*. Optionally, the stearate-preferring acyl-ACP thioesterase gene encodes an enzyme having at least 80, 85, 90, 91, 92, 93, 94, 95, 96, 97, 98 or 9% amino acid identity to the gene products of Example 9 or 41 (Seq ID NOS. 28, 65, 67, 69, 71, 73, or 75 omitting FLAG tags when present). Introduction of the acyl-ACP-thioesterase can be combined with a knockout or knockdown of one or more endogenous acyl-ACP thioesterase alleles. Introduction of the thioesterase can also be combined with overexpression of an elongase (KCS) or beta-ketoacyl-CoA synthase. In addition, one or more exogenous genes (e.g., encoding SAD or KASII) can be regulated via an environmental condition (e.g., by placement in operable linkage with a regulatable promoter). In a specific example, pH and/or nitrogen level is used to regulate an amt03 promoter. The environmental condition may then be modulated to tune the cell to produce the desired amount of stearate appearing in cell triglycerides (e.g., to twice the oleate concentration). As a result of these manipulations, the cell may exhibit an increase in stearate of at least 5, 10, 15, or 20 fold.

As a further modification, alone or in combination with the other stearate increasing modifications, the cell can comprise recombinant nucleic acids operable to express an elongase or a beta-ketoacyl-CoA synthase. For example, overexpression of a C18:0-preferring acyl-ACP thioesterases may be combined with overexpression of a mid-chain-extending elongase or KCS to increase the production of stearate in the recombinant cell. One or more of the exogenous genes (e.g., encoding a thioesterase, elongase, or KCS) can be regulated via an environmental condition (e.g., by placement in operable linkage with a regulatable promoter). In a specific example, pH and/or nitrogen level is used to regulate an amt03 promoter or any of the promoters of example 63 including those that are less pH-sensitive than amt03. The environmental condition may then be modulated to tune the cell to produce the desired amount of stearate appearing in cell triglycerides (e.g., to twice the oleate concentration). As a result of these manipulations, the cell may exhibit an increase in stearate of at least 5, 10, 15, or 20 fold. In addition to stearate, arachidic, behenic, lignoceric, and cerotic acids may also be produced.

In specific embodiments, due to the genetic manipulations of the cell to increase stearate levels, the ratio of stearate to oleate in the oil produced by the cell is 2:1±30% (i.e., in the range of 1.4:1 to 2.6:1), 2:1±20% or 2:1±10%.

Alternately, the cell can be engineered to favor formation of SatUnsatSat where Sat is palmitate or a mixture of palmitate and stearate. In this case introduction of an exogenous palmitate liberating acyl-ACP thioesterase can promote palmitate formation. In this embodiment, the cell can produce triglycerides, that are at least 30, 40, 50, 60, 70, or 80% POP, or triglycerides in which the sum of POP, SOS, and POS is at least 30, 40, 50, 60, 70, 80, or 90% of cell triglycerides. In other related embodiments, the POS level is at least 30, 40, 50, 60, 70, 80, or 90% of the triglycerides produced by the cell.

In a specific embodiment, the melting temperature of the oil is similar to that of cocoa butter (about 30-32° C.). The POP, POS and SOS levels can approximate cocoa butter at about 16, 38, and 23% respectively. For example, POP can be 16%±20%, POS can be 38%±20%, and SOS can be 23%±20%. Or, POP can be 16%±15%, POS can be 38%±15%, an SOS can be 23%±15%. Or, POP can be 16%±10%, POS can be 38%±10%, an SOS can be 23%±10%.

As a result of the recombinant nucleic acids that increase stearate, a proportion of the fatty acid profile may be arachidic acid. For example, the fatty acid profile can be 0.01% to 5%, 0.1 to 4%, or 1 to 3% arachidic acid. Furthermore, the regiospecific profile may have 0.01% to 4%, 0.05% to 3%, or 0.07% to 2% AOS, or may have 0.01% to 4%, 0.05% to 3%, or 0.07% to 2% AOA. It is believed that AOS and AOA may reduce blooming and fat migration in confection comprising the fats of the present invention, among other potential benefits.

In addition to the manipulations designed to increase stearate and/or palmitate, and to modify the SatUnsatSat levels, the levels of polyunsaturates may be suppressed, including as described above by reducing delta 12 fatty acid desaturase activity (e.g., as encoded by a Fad gene) and optionally supplementing the growth medium or regulating FAD expression. It has been discovered that, in microalgae (as evidenced by work in *Prototheca* strains), polyunsaturates are preferentially added to the sn-2 position. Thus, to elevate the percent of triglycerides with oleate at the sn-2 position, production of linoleic acid by the cell may be suppressed. The techniques described herein, in connection with highly oxidatively stable oils, for inhibiting or ablating fatty acid desaturase (FAD) genes or gene products may be applied with good effect toward producing SatUnsatSat oils by reducing polyunsaturates at the sn-2 position. As an added benefit, such oils can have improved oxidatively stability. As also described herein, the fats may be produced in two stages with polyunsaturates supplied or produced by the cell in the first stage with a deficit of polyunsaturates during the fat producing stage. The fat produced may have a fatty acid profile having less than or equal to 15, 10, 7, 5, 4, 3, 2, 1, or 0.5% polyunsaturates. In a specific embodiment, the oil/fat produced by the cell has greater than 50% SatUnsatSat, and optionally greater than 50% SOS, yet has less than 3% polyunsaturates. Optionally, polyunsaturates can be approximated by the sum of linoleic and linolenic acid area % in the fatty acid profile.

In an embodiment, the cell fat is a Shea stearin substitute having 65% to 95% SOS and optionally 0.001 to 5% SSS. In a related embodiment, the fat has 65% to 95% SOS, 0.001 to 5% SSS, and optionally 0.1 to 8% arachidic acid containing triglycerides. In another related embodiment, the fat has 65% to 95% SOS and the sum of SSS and SSO is less than 10% or less than 5%.

The cell's regiospecific preference can be learned using the analytical method described below (Examples 1-2, 8). Despite balancing the saturates and unsaturates as describe above, it is possible that the cell enzymes do not place the unsaturated fatty acid at the sn-2 position. In this case, genetic manipulations can confer the desired regiospecificity by (i) reducing the activity of endogenous sn-2 specific acyl transferases (e.g., LPAAT) and/or (ii) introducing an exogenous LPAAT with the desired specificity (i.e., introduction of oleate at sn-2). Where an exogenous LPAAT is introduced, preferably the gene encoding the LPAAT is integrated into a host chromosome and is targeted to the endoplasmic reticulum. In some cases, the host cell may have both specific and non-specific LPAAT alleles and suppressing the activity of one of these alleles (e.g., with a gene knockout) will confer the desired specificity. For example, genes encoding the LPAATs of SEQ ID NO: 78 and SEQ ID NO: 79 or an LPAAT comprising at least 90, 95, 98, or 99% amino acid identity to either of these sequences, or a functional fragment thereof, can be used to add oleate to the sn-2 position in order to boost the levels of SatUnsatSat TAGs. The genes can have at least 80, 85, 90, 95, 96, 97, 98, or 99% nucleotide identity to any of SEQ ID NOs: 80 to 85 or equivalent sequences by virtue of the degeneracy of the genetic code. Alternatively, the proteins encoded by the genes can have at least 80, 85, 90, 95, 96, 97, 98, or 99% nucleotide identity to the gene products of any of SEQ ID NOs: 80 to 85. These genes can be manifest as recombinant nucleic acid constructs, vectors, chromosomes or host cells comprising these sequences or functional fragments thereof, which can be found by systematic deletion of nucleic acid from the sequences using known techniques. As a result of expression of the genes, the amount of sat-unsat-sat TAGs such as SOS, POS, POP, or triglycerides with C8 to C16 fatty acids at the sn-2 position can be increased in a host cell.

Among other discoveries, the above discussion and Examples below highlight certain pathways to obtain high Sat-Unsat-Sat oils in general and SOS oils in particular in microorganisms or in plants. Thus, it is possible that the use of genetic engineering techniques, optionally combined with classical mutagenesis and breeding, a microalga or higher plant can be produced with an increase in the amount of SatUnsatSat or SOS produced of at least 1.5-fold, 2-fold, 3-fold, 4-fold, 5-fold, or more relative to the starting strain. In another aspect, the SatUnsatSat or SOS concentration of a species for which the wild-type produces less than 20%, 30%, 40% or 50% SatUnsatSat or SOS can be increased so that the SatUnsatSat or SOS is increased to at least 30%, 40%, 50% or 60%, respectively. The key changes, relative to the starting or wild-type organism, are to increase the amount of stearate (e.g., by reducing the amount of oleate formed from stearate, e.g., by reducing SAD activity, and/or increasing the amount of palmitate that is converted to stearate by reducing the activity of FATA and/or increasing the activity of KASII) and by decreasing the amount of linoleate by reducing FAD2/FADc activity.

Optionally, the starting organism can have triacylglycerol (TAG) biosynthetic machineries which are predisposed toward the synthesis of TAG species in which oleate or unsaturated fatty acids, predominate at the sn-2 position. Many oilseed crops have this characteristic. It has been demonstrated that lysophosphatidic acyltransferases (LPAATs) play a critical role in determining the species of fatty acids which will ultimately be inserted at the sn-2 position. Indeed, manipulation, through heterologous gene expression, of LPAATs in higher plant seeds, can alter the species of fatty acid occupying the sn-2 position.

One approach to generating oils with significant levels of so-called structuring fats (typically comprised of the species SOS-stearate-oleate-stearate, POS-palmitate-oleate-stearate, or POP-palmitate-oleate-palmitate) in agriculturally important oilseeds and in algae, is through the manipulation of endogenous as well as heterologous LPAAT expression. Expression of LPAATs from seeds containing high levels of structuring fats, for example, would be one strategy to increase the level of structuring fats in an oil seed or oleaginous algae that normally contains only limited quantities of such fats.

An alternative or supplementary strategy, however, is to take advantage of the innate propensity of LPAATs in agriculturally important oilseeds (eg, safflower-*Carthamus* sp., sunflower-*Helianthus* sp., canola-*Brassica* sp., peanut-*Arachis* sp., soybean-*Glycine* sp., corn-*Zea* sp., olive-*Olea* sp., flax-*Linum* sp., palm-*Elaeis* sp. and cotton-*Gossypium* sp., see representative profiles in Table 5a below) and through either genetic engineering alone or a combination of genetic engineering and classical strain improvement (i.e. mutagenesis) selectively manipulate the species of fatty acids present in order to increase the levels of structuring fats. In the case of SOS, these manipulations are comprised of a series of discrete steps, which can be carried out independently. These include:

Increasing the level of stearate. This can be achieved, as we have demonstrated in microalgae here and others have shown in higher plants, through the expression of stearate specific FATA activities or down regulation of the endogenous SAD activity; e.g., through direct gene knockout, RNA silencing, or mutation, including classical strain improvement. Simply elevating stearate levels alone, by the above approaches, however, will not be optimal. For example, in the case of palm oil, the already high levels of palmitate, coupled with increased stearate levels, will likely overwhelm the existing LPAAT activity, leading to significant amounts of stearate and palmitate incorporation into tri-saturated fatty acids (SSS, PPP, SSP, PPS ect). Hence, steps must be taken to control palmitate levels as well.

Palmitate levels must be minimized in order to create high SOS containing fats because palmitate, even with a high-functioning LPAAT, will occupy sn-1 or sn-3 positions that could be taken up by stearate, and, as outlined above, too many saturates will result in significant levels of tri-saturated TAG species. Palmitate levels can be lowered. for example, through down-regulation of endogenous FATA activity through mutation/classical strain improvement, gene knockouts or RNAi-mediated strategies, in instances wherein the endogenous FATA activity has significant palmitate activity. Alternatively, or in concert with the above, palmitate levels can be lowered through over expression of endogenous KASII activity or classical strain improvement efforts which manifest in the same effect, such that elongation from palmitate to stearate is enhanced. Simply lowering palmitate levels via the above methods may not be sufficient, however. Take again the example of palm oil. Reduction of palmitate and elevation of stearate via the previous methods would still leave significant levels of linoleic acid. The endogenous LPAAT activity in most higher plants species while they will preferentially insert oleate in the sn-2 position, will insert linoleic as the next most preferred species. As oleate levels decrease, linoleic will come to occupy the sn-2 position with increased frequency. TAG species with linoleic at the sn-2 position have poor structuring properties as the TAGs will tend to display much higher melting temperatures than what is desired in a structuring fat. Hence, increases in stearate and reductions in palmitate must in turn be balanced by reductions in levels of linoleic fatty acids.

In turn, levels of linoleic fatty acids must be minimized in order to create high SOS-containing fats because linoleate, even with a high functioning LPAAT will occupy sn-2 positions to the exclusion of oleate, creating liquid oils as opposed to the desired solid fat (at room temperature). Linoleate levels can be lowered, as we have demonstrated in microalgae and others have shown in plant oilseeds, through down regulation of endogenous FAD2 desaturases; e.g., through mutation/classical strain improvement, FAD2 knockouts or RNAi mediated down regulation of endogenous FAD2 activity. Accordingly, the linoleic acid level in the fatty acid profile can be reduced by at least 10, 20, 30, 40, 50, 100, 200, or 300%. For example, an RNAi construct with at least 70, 75, 80, 85, 90, 95, 96, 97, 98, or 99% identity to those disclosed herein can be used to downregulate FAD2.

Although one can choose a starting strain with such an sn-2 preference one can also introduce an exogenous LPAAT gene having a greater oleate preference, to further boost oleate at the sn-2 position and to further boost Sat-Unsat-Sat in the TAG profile. Optionally, one can replace one or more endogenous LPAAT alleles with the exogenous, more specific LPAAT.

The cell oils resulting from the SatUnsatSat/SOS producing organisms can be distinguished from conventional sources of SOS/POP/POS in that the sterol profile will be indicative of the host organism as distinguishable from the conventional source. Conventional sources of SOS/POP/POS include cocoa, shea, mango, sal, illipe, kokum, and allanblackia. See section XII of this disclosure for a discussion of microalgal sterols.

TABLE 5a

The fatty acid profiles of some commercial oilseed strains.

| Common Food Oils* | C12:0 | C14:0 | C16:0 | C16:1 | C18:0 | C18:1 | C18:2 | C18:3 |
|---|---|---|---|---|---|---|---|---|
| Corn oil (*Zea mays*) | | <1.0 | 8.0-19.0 | <0.5 | 0.5-4.0 | 19-50 | 38-65 | <2.0 |
| Cottonseed oil (*Gossypium barbadense*) | <0.1 | 0.5-2.0 | 17-29 | <1.5 | 1.0-4.0 | 13-44 | 40-63 | 0.1-2.1 |
| Canola (*Brassica rapa*, *B. napus*, *B. juncea*) | <0.1 | <0.2 | <6.0 | <1.0 | <2.5 | >50 | <40 | <14 |
| Olive (*Olea europea*) | | <0.1 | 6.5-20.0 | ≤3.5 | 0.5-5.0 | 56-85 | 3.5-20.0 | ≤1.2 |
| Peanut (*Arachis hypogaea*) | <0.1 | <0.2 | 7.0-16.0 | <1.0 | 1.3-6.5 | 35-72 | 13.0-43 | <0.6 |
| Palm (*Elaeis guineensis*) | | 0.5-5.9 | 32.0-47.0 | | 2.0-8.0 | 34-44 | 7.2-12.0 | |

TABLE 5a-continued

The fatty acid profiles of some commercial oilseed strains.

| Common Food Oils* | C12:0 | C14:0 | C16:0 | C16:1 | C18:0 | C18:1 | C18:2 | C18:3 |
|---|---|---|---|---|---|---|---|---|
| Safflower (*Carthamus tinctorus*) | <0.1 | <1.0 | 2.0-10.0 | <0.5 | 1.0-10.0 | 7.0-16.0 | 72-81 | <1.5 |
| Sunflower (*Helianthus annus*) | <0.1 | <0.5 | 3.0-10.0 | <1.0 | 1.0-10.0 | 14-65 | 20-75 | <0.5 |
| Soybean (*Glycine max*) | <0.1 | <0.5 | 7.0-12.0 | <0.5 | 2.0-5.5 | 19-30 | 48-65 | 5.0-10.0 |
| Solin-Flax (*Linum usitatissimum*) | <0.1 | <0.5 | 2.0-9.0 | <0.5 | 2.0-5.0 | 8.0-60 | 40-80 | <5.0 |

*Unless otherwise indicated, data taken from the U.S. Pharacopeia's Food and Chemicals Codex, 7th Ed. 2010-2011**

Accordingly, in an embodiment of the present invention, there is a method for increasing the amount of SOS in an oil (i.e. oil or fat) produced by a cell. The method comprises providing a cell and using classical and/or genetic engineering techniques (e.g., mutation, selection, strain-improvement, introduction of an exogenous gene and/or regulator element, or RNA-level modulation such as RNAi) to (i) increase the stearate in the oil, (ii) decrease the linoleate in the oil, and optionally (iii) increase the stereospecificity of the addition of oleate in the sn-2 position. The step of increasing the stearate can comprise decreasing desaturation by SAD (e.g., knockout, knockdown or use of regulatory elements) and increasing the conversion of palmitate to stearate (including overexpression of an endogenous or exogenous KASII and/or knockout or knockdown of FATA). Optionally, an exogenous FATA with greater stearate specificity then an endogenous FATA is expressed in the cell to increase stearate levels. Here, stearate-specificity of a FATA gene is a measure of the gene product's rate of cleavage of stearate over palmitate. The stearate-specific FATA gene insertion can be combined with a knockdown or knockout of the less-specific endogenous FATA gene. In this way, the ratio of stearate to palmitate can be increased, by 10%, 20%, 30%, 40%, 50%, 100% or more. The step of decreasing the linoleate can be via reduction of FADc/FAD2 activity including knockout and/or knockdown. The step of increasing the oleate at the sn-2 position can comprise expressing an exogenous oleate-preferring LPAAT such as an LPAAT having at least 75, 80, 85, 90, 85, 96, 97, 98, or 99% amino acid identity to an LPAAT disclosed herein.

In a specific embodiment, the cell (e.g, an oleaginous microalgal or other plastidic cell) produces an oil enriched in SOS (e.g., at least 50% SOS and in some cases 60% SOS). The cell is modified in at least four genes: (i) a β-ketoacyl-ACP synthase II (KASII) is overexpressed, (ii) activity of an endogenous FATA acyl-ACP thioesterase is reduced (iii) a stearate-specific FATA acyl-ACP thioesterase is overexpressed, (iii) endogenous SAD activity is decreased, and (iv) endogenous FAD activity is decreased. Example 65 demonstrates this embodiment in a *Prototheca moriformis* microalga by disrupting the coding region of endogenous FATA and SAD2 through homologous recombination, overexpressing a β-ketoacyl-ACP synthase II (KASII) gene, and activating FAD2 RNAi to decrease polyunsaturates.

In another specific embodiment, the cell (e.g, an oleaginous microalgal or other plastidic cell) produces an oil enriched in SOS (e.g., at least 50% SOS and in some cases 60% SOS). The cell is modified in at least four genes: (i) a β-ketoacyl-ACP synthase II (KASII) is overexpressed, (ii) activity of an endogenous FATA acyl-ACP thioesterase is reduced (iii) a stearate-specific FATA acyl-ACP thioesterase is overexpressed, (iv) endogenous SAD activity is decreased, (v) endogenous FAD activity is decreased and (vi) an exogenous oleate-preferring LPAAT is expressed. See Examples 65 and 66. Optionally, these genes or regulatory elements have at least 75, 80, 85, 90, 85, 96, 97, 98, or 99% nucleic acid or amino acid identity to a gene or gene-product or regulatory element disclosed herein. Optionally, one or more of these genes is under control of a pH-sensitive or nitrogen-sensitive (pH-sensitive or pH-insensitive) promoter such as one having at least 75, 80, 85, 90, 85, 96, 97, 98, or 99% nucleic acid identity to one of those disclosed herein. Optionally, the cell oil is fractionated (see Example 64).

In an embodiment, fats produced by cells according to the invention are used to produce a confection, candy coating, or other food product. As a result, a food product like a chocolate or candy bar may have the "snap" (e.g., when broken) of a similar product produced using cocoa butter. The fat used may be in a beta polymorphic form or tend to a beta polymorphic form. In an embodiment, a method includes adding such a fat to a confection. Optionally, the fat can be a cocoa butter equivalent per EEC regulations, having greater than 65% SOS, less than 45% unsaturated fatty acid, less than 5% polyunsaturated fatty acids, less than 1% lauric acid, and less than 2% trans fatty acid. The fats can also be used as cocoa butter extenders, improvers, replacers, or anti-blooming agents, or as Shea butter replacers, including in food and personal care products. High SOS fats produced using the cells and methods disclosed here can be used in any application or formulation that calls for Shea butter or Shea fraction. However, unlike Shea butter, fats produced by the embodiments of the invention can have low amounts of unsaponifiables; e.g. less than 7, 5, 3, or 2% unsaponifiables. In addition, Shea butter tends to degrade quickly due to the presence of diacylglycerides whereas fats produced by the embodiments of the invention can have low amounts of diacylglycerides; e.g., less than 5, 4, 3, 2, 1, or 0.5% diacylglycerides.

In an embodiment of the invention there is a cell fat suitable as a shortening, and in particular, as a roll-in shortening. Thus, the shortening may be used to make pastries or other multi-laminate foods. The shortening can be produced using methods disclosed herein for producing engineered organisms and especially heterotrophic microalgae. In an embodiment, the shortening has a melting temperature of between 40 to 60° C. and preferably between 45-55° C. and can have a triglyceride profile with 15 to 20% medium chain fatty acids (C8 to C14), 45-50% long chain saturated fatty acids (C16 and higher), and 30-35% unsaturated fatty acids (preferably with more oleic than linoleic). The shortening may form β' polymorphic crystals, optionally without passing through the β polymorphic form. The shortening may be thixotropic. The shortening may have a solid fat content of less than 15% at 35° C. In a specific embodiment, there is a cell oil suitable as a roll-in shortening produced by a recombinant microalga, where the oil has a yield stress between 400 and 700 or 500 and 600 Pa and a storage modulus of greater than $1\times10^5$ Pa or $1\times10^6$ Pa. (see Example 46)

A structured solid-liquid fat system can be produced using the structuring oils by blending them with an oil that is a liquid at room temperature (e.g., an oil high in tristearin or triolein). The blended system may be suitable for use in a food spread, mayonnaise, dressing, shortening; i.e. by forming an oil-water-oil emulsion. The structuring fats according to the embodiments described here, and especially those high in SOS, can be blended with other oils/fats to make a cocoa butter equivalent, replacer, or extender. For example, a cell fat having greater than 65% SOS can be blended with palm mid-fraction to make a cocoa butter equivalent.

In general, such high Sat-Unsat-Sat fats or fat systems can be used in a variety of other products including whipped toppings, margarines, spreads, salad dressings, baked goods (e.g. breads, cookies, crackers muffins, and pastries), cheeses, cream cheese, mayonnaise, etc.

In a specific embodiment, a Sat-Unsat-Sat fat described above is used to produce a margarine, spread, or the like. For example, a margarine can be made from the fat using any of the recipes or methods found in U.S. Pat. Nos. 7,118,773, 6,171,636, 4,447,462, 5,690,985, 5,888,575, 5,972,412, 6,171,636, or international patent publications WO9108677A1.

In an embodiment, a fat comprises a cell (e.g., from microalgal cells) fat optionally blended with another fat and is useful for producing a spread or margarine or other food product is produced by the genetically engineered cell and has glycerides derived from fatty acids which comprises:

(a) at least 10 weight % of $C_{18}$ to $C_{24}$ saturated fatty acids,
(b) which comprise stearic and/or arachidic and/or behenic and/or lignoceric acid and
(c) oleic and/or linoleic acid, while
(d) the ratio of saturated C18 acid/saturated (C20+C22+C24)-acids≥1, preferably ≥5, more preferably ≥10, which glycerides contain:
(e) ≤5 weight % of linolenic acid calculated on total fatty acid weight
(f) ≤5 weight % of trans fatty acids calculated on total fatty acid weight
(g) ≤75 weight %, preferably ≤60 weight % of oleic acid at the sn-2 position: which glycerides contain calculated on total glycerides weight
(h) ≥8 weight % HOH+HHO triglycerides
(i) ≤5 weight % of trisaturated triglycerides, and optionally one or more of the following properties:
(j) a solid fat content of >10% at 10° C.
(k) a solid fat content≤15% at 35° C.,
(l) a solid fat content of >15% at 10° C. and a solid fat content≤25% at 35° C.,
(m) the ratio of (HOH+HHO) and (HLH+HHL) triglycerides is >1, and preferably >2,
where H stands for C18-C24 saturated fatty acid, O for oleic acid, and L for linoleic acid.

Optionally, the solid content of the fat (% SFC) is 11 to 30 at 10° C., 4 to 15 at 20° C., 0.5 to 8 at 30° C., and 0 to 4 at 35° C. Alternately, the % SFC of the fat is 20 to 45 at 10° C., 14 to 25 at 20° C., 2 to 12 at 30° C., and 0 to 5 at 35° C. In related embodiment, the % SFC of the fat is 30 to 60 at 10° C., 20 to 55 at 20° C., 5 to 35 at 30° C., and 0 to 15 at 35° C. The C12-C16 fatty acid content can be ≤15 weight %. The fat can have ≤5 weight % disaturated diglycerides.

In related embodiments there is a spread, margarine or other food product made with the cell oil or cell oil blend. For example, the cell fat can be used to make an edible W/O (water/oil) emulsion spread comprising 70-20 wt. % of an aqueous phase dispersed in 30-80 wt. % of a fat phase which fat phase is a mixture of 50-99 wt. % of a vegetable triglyceride oil A and 1-50 wt. % of a structuring triglyceride fat B, which fat consists of 5-100 wt. % of a hardstock fat C and up to 95 wt. % of a fat D, where at least 45 wt. % of the hardstock fat C triglycerides consist of SatOSat triglycerides and where Sat denotes a fatty acid residue with a saturated C18-C24 carbon chain and O denotes an oleic acid residue and with the proviso that any hardstock fat C which has been obtained by fractionation, hydrogenation, esterification or interesterification of the fat is excluded. The hardstock fat can be a cell fat produced by a cell according to the methods disclosed herein. Accordingly, the hardstock fat can be a fat having a regiospecific profile having at least 50, 60, 70, 80, or 90% SOS. The W/O emulsion can be prepared to methods known in the art including in U.S. Pat. No. 7,118,773.

In related embodiment, the cell also expresses an endogenous hydrolyase enzyme that produces ricinoleic acid. As a result, the oil (e.g., a liquid oil or structured fat) produced may be more easily emulsified into a margarine, spread, or other food product or non-food product. For example, the oil produced may be emulsified using no added emulsifiers or using lower amounts of such emulsifiers. The U.S. patent application Ser. No. 13/365,253 discloses methods for expressing such hydroxylases in microalgae and other cells. In specific embodiments, a cell oil comprises at least 1, 2, or 5% SRS, where S is stearate and R is ricinoleic acid.

In an alternate embodiment, a cell oil that is a cocoa butter mimetic as described above (or other high sat-unsat-sat oil such as a Shea or Kolum mimetic) can be fractionated to remove trisaturates (e.g., tristearin and tripalmitin, SSP, and PPS). For example, it has been found that microalgae engineered to decrease SAD activity to increase SOS concentration make an oil that can be fractionated to remove trisaturated. See Example 47 and example 64. In specific embodiments, the melting temperature of the fractionated cell oil is similar to that of cocoa butter (about 30-32° C.). The POP, POS and SOS levels can approximate cocoa butter at about 16, 38, and 23% respectively. For example, POP can be 16%±20%, POS can be 38%±20%, an SOS can be 23%±20%. Or, POP can be 16%±15%, POS can be 38%±15%, an SOS can be 23%±15%. Or, POP can be 16%±10%, POS can be 38%±10%, an SOS can be 23%±10%. In addition, the tristearin levels can be less than 5% of the triacylglycerides.

In an embodiment, a method comprises obtaining a cell oil obtained from a genetically engineered (e.g., microalga or other microbe) cell that produces a starting oil with a TAG profile having at least 40, 50, or 60% SOS. Optionally, the cell comprises one or more of an overexpressed KASII gene, a SAD knockout or knockdown, or an exogenous C18-preferring FATA gene, an exogenous LPAAT, and a FAD2 knockout or knockdown. The oil is fractionated by dry fractionation or solvent fractionation to give an enriched oil (stearin fraction) that is increased in SOS and decreased in trisaturates relative to the starting oil. The enriched oil can have at least 60%, 70% or 80% SOS with no more than 5%, 4%, 3%, 2% or 1% trisaturates. The enriched oil can have a sn-2 profile having 85, 90, 95% or more oleate at the sn-2 position. For example, the fractionated oil can comprise at least 60% SOS, no more than 5% trisaturates and at least 85% oleate at the sn-2 position. Alternatively, the oil can comprise at least 70% SOS, no more than 4% trisaturates and at least 90% oleate at the sn-2 position or 80% SOS, no more than 4% trisaturates and at least 95% oleate at the sn-2 position. Optionally, the oil has essentially identical maximum heat-flow temperatures and/or the DSC-derived SFC curves to Kokum butter. The stearin fraction can be obtained by dry fractionation, solvent fractionation, or a combination of these. Optionally, the process includes a 2-step dry fractionation at a first temperature and a second temperature. The first temperature can be higher or lower than the second temperature. In a specific embodiment, the first temperature is effective at removing OOS and the second temperature is effective in removing trisaturates. Optionally, the stearin fraction is washed with a solvent (e.g. acetone) to remove the OOS after treatment at the first temperature. Optionally, the first temperature is about 24° C. and the second temperature is about 29° C.

VIII. High Mid-Chain Oils

In an embodiment of the present invention, the cell has recombinant nucleic acids operable to elevate the level of midchain fatty acids (e.g., C8:0, C10:0, C12:0, C14:0, or C16:0 fatty acids) in the cell or in the oil of the cell. One way to increase the levels of midchain fatty acids in the cell or in the oil of the cell is to engineer a cell to express an exogenous acyl-ACP thioesterase that has activity towards midchain fatty acyl-ACP substrates (e.g., one encoded by a FatB gene), either as a sole modification or in combination with one or more other genetic modifications. An additional genetic modification to increase the level of midchain fatty acids in the cell or oil of the cell is the expression of an exogenous lysophosphatidic acid acyltransferase gene encoding an active lysophosphatidic acid acyltransferase (LPAAT) that catalyzes the transfer of a mid-chain fatty-acyl group to the sn-2 position of a substituted acylglyceroester. For example, the LPAAT gene can have 75, 80, 85, 90, 91, 92, 93, 94, 95, 96, 97, 98 or 99% amino acid sequence identity or have 75, 80, 85 90, 91, 92, 93, 94, 95, 96, 97, 98 or 99% nucleic acid sequence identity (or equivalent sequence to degeneracy of the genetic code) to the mid-chain preferring LPAATs disclosed in Examples 43-44 (SEQ ID NOs 77, 78, 79, 81, 82, 84, and 85). In a specific related embodiment, both an exogenous acyl-ACP thioesterase and LPAAT are stably expressed in the cell. In an embodiment, recombinant nucleic acids are introduced into an oleaginous cell (and especially into a plastidic microbial cell) that cause expression of an exogenous mid-chain-specific thioesterase and an exogenous LPAAT that catalyzes the transfer of a mid-chain fatty-acyl group to the sn-2 position of a substituted acylglyceroester. As a result, the cell can be made to increase the percent of a midchain fatty acid in the TAGs that it produces by 10, 20 30, 40, 50, 60, 70, 80, 90-fold, or more. Introduction of the exogenous LPAAT can increase mid-chain fatty acids at the sn-2 position by 1.2, 1.5, 1.7, 2, 3, 4 fold or more compared to introducing an exogenous mid-chain preferring acyl-ACP thioesterase alone. In an embodiment, the mid-chain fatty acid is greater than 30, 40, 50 60, 70, 80, or 90% of the TAG fatty acids produced by the cell. In various embodiments, the mid-chain fatty acid is lauric, myristic, or palmitic. Examples 3, 43, and 44 describe expression of plant LPAATs in microalgal cells with resulting alterations in fatty acid profiles. As in the examples, the cells can also express an exogenous acyl-ACP thioesterase (which can also be from a plant) with a preference for a given fatty acyl-ACP chain length. For example, a microalgal cell can comprise exogenous genes encoding a LPAAT and an acyl-ACP thioesterase that preferentially cleave C8, C10, C12, C14, C8-C12, or C8-C10 fatty acids. In a specific embodiment, such a cell is capable of producing a cell oil with a fatty acid profile comprising 10-20, 20-30, 30-40, 40-50, 50-60, 60-70, 70-80, 80-90, or 90-99%, >20%, >30%, >40%, >50%, >60%, >70%, >80% or >90% C8, C10, C12, C14, C8-C12, or C8-C10 fatty acids. Other LPAATs can preferentially cleave C16 or C18 fatty acids (see Example 44). Further genetic manipulation of the fatty acid desaturase pathway (e.g., as described infra) can increase the stability of the oils.

Any of these cell oils can be interesterified. Interesterification can, for example, be used to lower the melting temperature or pour-point of the oil. In a specific embodiment, the cell oil comprises at least 50% of the sum of caprylic and capric acids and may be interesterified to reduce the pour point and/or kinematic viscosity. Such an oil (cell or interesterified) can optionally be a high stability oil comprising, for example, less than 2% polyunsaturated fatty acids.

Alternately, or in addition to expression of an exogenous LPAAT, the cell may comprise recombinant nucleic acids that are operable to express an exogenous KASI or KASIV enzyme and optionally to decrease or eliminate the activity of a KASII, which is particularly advantageous when a mid-chain-preferring acyl-ACP thioesterase is expressed. Example 37 describes the engineering of *Prototheca* cells to overexpress KASI or KASIV enzymes in conjunction with a mid-chain preferring acyl-ACP thioesterase to generate strains in which production of C10-C12 fatty acids is about 59% of total fatty acids. Mid-chain production can also be increased by suppressing the activity of KASI and/or KASII (e.g., using a knockout or knockdown). Example 38 details the chromosomal knockout of different alleles of *Prototheca moriformis* (UTEX 1435) KASI in conjunction with overexpression of a mid-chain preferring acyl-ACP thioesterase to achieve fatty acid profiles that are about 76% or 84% C10-C14 fatty acids. Example 39 provides recombinant cells and oils characterized by elevated midchain fatty acids as a result of expression of KASI RNA hairpin polynucleotides. In addition to any of these modifications, unsaturated or polyunsaturated fatty acid production can be suppressed (e.g., by knockout or knockdown) of a SAD or FAD enzyme.

In a particular embodiment, a recombinant cell produces TAG having 40% lauric acid or more. In another related embodiment, a recombinant cell produces TAG having a fatty acid profile of 40% or more of myristic, caprylic, capric, or palmitic acid. For example, an oleaginous recombinant clorophyte cell can produce 40% lauric or myristic acid in an oil that makes up 40, 50, or 60% or more of the cell's dry weight.

In a specific embodiment, a recombinant cell comprises nucleic acids operable to express a product of an exogenous gene encoding a lysophosphatidic acid acyltransferase that catalyzes the transfer of a mid-chain fatty-acyl group to the sn-2 position of a substituted acylglyceroester and nucleic acids operable to express a product of an acyl-ACP thioesterase exogenous gene encoding an active acyl-ACP thioesterase that catalyzes the cleavage of mid-chain fatty acids from ACP. As a result, in one embodiment, the oil produced can be characterized by a fatty acid profile elevated in C10 and C12 fatty acids and reduced in C16, C18, and C18:1 fatty acids as a result of the recombinant nucleic acids. See Example 3, in which overexpression of a *Cuphea wrightii* acyl-ACP thioesterase and a *Cocos nucifera* LPAAT gene increased the percentage of C12 fatty acids from about 0.04% in the untransformed cells to about 46% and increased the percentage of C10 fatty acids from about 0.01% in the untransformed cells to about 11%. For example, the FATB gene can have 75, 80, 85, 90, 91, 92, 93, 94, 95, 96, 97, 98 or 99% amino acid sequence identity or have 75, 80, 85 90, 91, 92, 93, 94, 95, 96, 97, 98 or 99% nucleic acid sequence identity (or equivalent sequence to degeneracy of the genetic code) to SEQ ID NOs 10 or 11. In related embodiments, the increase in midchain fatty acid production is greater than 70%, from 75-85%, from 70-90%, from 90-200%, from 200-300%, from 300-400%, from 400-500%, or greater than 500%.

Average chain length can also be reduced by overexpression of a C18-specific acyl-ACP thioesterase. Recombinant nucleic acids operable to overexpress a C18 or other acyl-ACP thioesterase may be used alone or in combination with the other constructs described here to further reduce average chain length. Among other uses, the oils produced can be used as cocoa-butter/milk fat substitute. See Example 45 and the discussion of FIG. 17. In an embodiment, one of the above described high mid-chain producing cells is further engineered to produce a low polyunsaturated oil by knocking out or knocking down one or more fatty acyl desaturases, as described above in section IV. Accordingly, the oil produced can have the high stability characteristic mentioned in that section or in corresponding Examples. In a specific embodiment, the cell produces an oil comprising greater than 30% midchain fatty acids and 5% or less polyunsaturates. In a related embodiment, the cell produces an oil comprising greater than 40% midchain fatty acids and 4% or less polyunsaturates. In a further related embodiment, the cell produces an oil comprising greater than 50% midchain fatty acids and 3% or less polyunsaturates.

In a specific embodiment, the cell produces an oil characterized by a fatty acid profile in which the sum of lauric and myristic acids is at least 50%, 60%, 70%, or 75%. This can be accomplished using the techniques of Examples 37-39, 43-44, 52, and 60-61. For example, Example 52 describes a method for producing an oil that has a fatty acid profile in which the sum of lauric and myristic acids is about 79% using a recombinant cell with an exogenous plant FATB acyl-ACP thioesterase.

In another specific embodiment, the cell produces a cell oil characterized by a fatty acid profile in which capric acid (C10:0) is at least 30% and lauric acid (C12:0) is at least 30%. For example, the absolute level of capric acid and lauric acid in the cell oil can be balanced to within 5, 10, 15, 20 or 30%. This can be accomplished using the techniques of Examples 37-39, 43-44, 52, and 60-61. As in Example 60, exogenous plant FATB and KASI (or KASIV) genes can be combined to give balanced levels of capric and lauric. Optionally, an endogenous KASI gene can be knocked out and replaced with an exogenous KASI. In addition, two or more exogenous FATB genes can be used do reach a desired fatty acid profile. In a specific embodiment, a microalgal cell expresses at least one and optionally at least two exogenous FATB genes and an exogenous KASI/KASIV gene and produces an extractable cell oil with at least 30% C10 and at least 30% C12 fatty acids. For example, the cell can express a FATB acyl-ACP thioesterase having at least 70, 75, 80, 85, 90 or 95% amino acid sequence identity to the *Cuphea hookeriana* FATB2 (SEQ ID NO: 158) and a beta-ketoacyl ACP synthase having at least 70, 75, 80, 85, 90 or 95% amino acid sequence identity to the *Cuphea wrightii* KASA1 (SEQ ID NO: 159, with alternate transit peptide). Further, a second exogenous FATB gene/enzyme can be expressed. The second FATB can have at least 70, 75, 80, 85, 90 or 95% amino acid sequence identity to the *Cuphea wrightii* FATB2 acyl-ACP thioesterase (SEQ ID NO: 11.) For these purposes, plastid targeted peptides can be aligned with or with out the plastid targeting transit peptides, which are less conserved and more easily replaceable than the remaining enzyme domain sequence.

In an embodiment, the cell produces an oil comprising greater than 75% saturated fatty acids. Optionally, the cell produces an oil comprising greater than 75% saturated fatty acids with less than 25% capric acid, less than 50% lauric acid, and less than 5% palmitic acid. In related embodiments, the oil comprises at least 80%, 95% or 90% saturated fatty acids. Example 60 describes the production of such oil by microalgae comprising multiple exogenous FATB genes and replacement of an endogenous KASI gene with exogenous KASI or KASIV genes from plants.

Examples 60 and 62 also shows that selection of FATB and KAS genes can give rise to an oil with at least 50% total saturates with capric and lauric acids balanced to within 20% (or even to within 15%, or 10%).

High-mid chain oils in general, and those produced by strains similar to those of Example 60 and 62 can possess low kinematic viscosity. For example, the oil can have a kinematic viscosity as measured using ASTM D445 at 40° C. of 25 cS±20%, 25 cS±10%, or 25 cS±5%. Likewise, the oil can have a kinematic viscosity according to ASTM D445 at 100° C. of 5.4 cS±20%, 5.4 cS±10%, or 5.4 cS±5%. The oil can have a viscosity index as measured using ASTM 2280 of 160±20%, 160±10%, or 160±5%.

In a specific example, an oil prepared using a strain similar to those reported in Example 60, produced an oil with greater than 30% C10:0 and greater than 30% C12:0 fatty acids. The oil had a kinematic viscosity by ASTM 445 of 24.61 cSt at 40° C. and 5.36 cSt at 100° C. with a viscosity index (ASTM 2270) of 159. To make this oil, a *Cuphea hookeriana* FATB2 acyl-ACP thioesterase was expressed with a *Cuphea wrightii* KASA1 gene (with a *P. moriformis* SAD transit peptide) in *Prototheca moriformis* under control of the UAPA1 and AMT03 promoters, respectively. Neomycin resistance was used at the selection marker and the construct with incorporated in the KAS1-1 site. Accordingly, in an embodiment, a host cell comprises an exogenous gene that expresses a protein having at least 70, 75, 80, 85, 90, or 95% amino acid sequence identity to SEQ ID NO: 158 and also expresses a protein having at least 70, 75, 80, 85, 90, or 95% amino acid sequence identity to SEQ ID NO: 159. The cell produces an oil comprising at least 30% C10:0 and/or at least 30% C12:0 fatty acids. Optionally, a cell oil can be extracted from the cell that has a kinematic viscosity as measured using ASTM D445 at 40° C. of less than 30 cSt.

The high mid-chain oils or fatty acids derived from hydrolysis of these oils may be particularly useful in food, fuel and oleochemical applications including the production of lubricants and surfactants. For example, fatty acids derived from the cells can be esterified, cracked, reduced to an aldehyde or alcohol, aminated, sulfated, sulfonated, or subjected to other chemical process known in the art.

In some embodiments, the cell oil is interesterified and the kinematic viscosity of the interesterified cell oil is less than 30, 20, 15, 10, 9, 8, 7, 6, 5, 4, 3, 2, or 1 centiStokes at 40° C. In some embodiments, the kinematic viscosity is less than 3 centiStokes at 40° C. In some embodiments, the pour point of an interesterified cell oil is less than, 5° C., 0° C., −10° C., −12° C., −15° C., −20° C., −25° C., −30° C., −35° C., −40° C., −45° C., or −50° C. In some embodiments, the pour point is less than −10° C. In some embodiments, the pour point is less than −20° C.

Example 53 describes the use of a plant FatB gene in algae to produce oils in microalgae with greater than 60% myristate. In an embodiment, a gene encoding a protein having at least 90, 95, 96, 97, 98, or 99% amino acid identity to SEQ ID NO:87 or SEQ ID NO:89 is used, optionally in combination with a mid-chain preferred LPAAT as described above.

As described in Example 62, we surprisingly discovered that the combination of a KASI gene with a FATB gene can shift the fatty acid profile of an oil produced by the cell in ways that neither gene can do on its own. Specifically, recombinant cells with exogenous plant myristate-preferring acyl-ACP thioesterases were discovered to shift their fatty acid profile to a greater percentage of laurate when a KASI gene was co-expressed. This is unexpected because KASI has an elongase activity yet the fatty acid profile was shifted to shorter chains. In other words, a cell expressing both the exogenous FATB and KASI gene produced an oil having a fatty acid profile that is shifted toward shorter fatty acid chains than a control cell with the FATB gene but without the KASI gene. Accordingly, an embodiment of the invention comprises constructing a recombinant cell or using the cell to make an oil, where the cell comprises an exogenous FATB with a given chain-length preference and a KASI gene, wherein the cell makes an oil with a shift in distribution toward shorter chains than is obtained without the KASI gene. Optionally, the FATB gene has a nucleic acid sequence that is at least 80, 85, 90, 91, 92, 93, 94, 95, 96, 97, 98, or 99% identical (or an equivalent sequence by virtue of degenerecy of the genetic code) or has an amino acid sequence that is least 80, 85, 90, 91, 92, 93, 94, 95, 96, 97, 98, or 99% identical to the CcFATB2-UcFATB2 FATB of Example 62 (SEQ ID NO: 162), the *Cuphea wrightii* FATB2 (SEQ ID NO: 11), *Cuphea palustris* FATB2 (SEQ ID NO: 87; SEQ ID NO: 89), *Cuphea hyssopifolia* FATB1 (SEQ ID NO: 163), *Cuphea hyssopifolia* FATB3 (SEQ ID NO: 164), or *Cuphea hookeriana* FATB2 (SEQ ID NO: 158). Optionally, the KASI or KASIV gene has a nucleic acid sequence that is at least 80, 85, 90, 91, 92, 93, 94, 95, 96, 97, 98, or 99% identical (or an equivalent sequence by virtue of degenerecy of the genetic code) or has an amino acid sequence that is least 80, 85, 90, 91, 92, 93, 94, 95, 96, 97, 98, or 99% identical to the *Cuphea wrightii* KASAI of Example 62 (SEQ ID NO: 159), the *Cuphea hookeriana* KASIV encoded by the sequence of SEQ ID NO:49, or the *Cuphea pulch*. KASIV encoded by SEQ ID NO: 48.

IX. High Oleic/Palmitic Oil

In another embodiment, there is a high oleic oil with about 60% oleic acid, 25% palmitic acid and optionally 5% polyunsaturates or less. The high oleic oil can be produced using the methods disclosed in U.S. patent application Ser. No. 13/365,253, which is incorporated by reference in relevant part. For example, the cell can have nucleic acids operable to suppress an acyl-ACP thioesterase (e.g., knockout or knockdown of a gene encoding FATA) while also expressing a gene that increases KASII activity. The cell can have further modifications to inhibit expression of delta 12 fatty acid desaturase, including regulation of gene expression as described above. As a result, the polyunsaturates can be less than or equal to 5, 4, 3, 2, or 1 area %.

X. Low Saturate Oil

In an embodiment, a cell oil is produced from a recombinant cell. The oil produced has a fatty acid profile that has less that 4%, 3%, 2%, or 1% (area %), saturated fatty acids. In a specific embodiment, the oil has 0.1 to 3.5% saturated fatty acids. Certain of such oils can be used to produce a food with negligible amounts of saturated fatty acids. Optionally, these oils can have fatty acid profiles comprising at least 90% oleic acid or at least 90% oleic acid with at least 3% polyunsaturated fatty acids. In an embodiment, a cell oil produced by a recombinant cell comprises at least 90% oleic acid, at least 3% of the sum of linoleic and linolenic acid and has less than 3.5% saturated fatty acids. In a related embodiment, a cell oil produced by a recombinant cell comprises at least 90% oleic acid, at least 3% of the sum of linoleic and linolenic acid and has less than 3.5% saturated fatty acids, the majority of the saturated fatty acids being comprised of chain length 10 to 16. These oils may be produced by recombinant oleaginous cells including but not limited to those described here and in U.S. patent application Ser. No. 13/365,253. For example, overexpression of a KASII enzyme in a cell with a highly active SAD can produce a high oleic oil with less than or equal to 3.5% saturates. Optionally, an oleate-specific acyl-ACP thioesterase is also overexpressed and/or an endogenous thioesterase having a propensity to hydrolyze acyl chains of less than C18 knocked out or suppressed. The oleate-specific acyl-ACP thioesterase may be a transgene with low activity toward ACP-palmitate and ACP-stearate so that the ratio of oleic acid relative to the sum of palmitic acid and stearic acid in the fatty acid profile of the oil produced is greater than 3, 5, 7, or 10. Alternately, or in addition, a FATA gene may be knocked out or knocked down, as in Example 36 below. A FATA gene may be knocked out or knocked down and an exogenous KASII overexpressed. Another optional modification is to increase KASI and/or KASIII activity, which can further suppress the formation of shorter chain saturates. Optionally, one or more acyltransferases (e.g., an LPAAT) having specificity for transferring unsaturated fatty acyl moieties to a substituted glycerol is also overexpressed and/or an endogenous acyltransferase is knocked out or attenuated. An additional optional modification is to increase the activity of KCS enzymes having specificity for elongating unsaturated fatty acids and/or an endogenous KCS having specificity for elongating saturated fatty acids is knocked out or attenuated. Optionally, oleate is increased at the expense of linoleate production by knockout or knockdown of a delta 12 fatty acid desaturase; e.g., using the techniques of Section IV of this patent application. Optionally, the exogenous genes used can be plant genes; e.g., obtained from cDNA derived from mRNA found in oil seeds.

As described in Example 51, levels of saturated fats may also be reduced by introduction of an exogenous gene (e.g., a plant gene) that desaturates palmitic acid to palmitoleic acid. Examples of suitable genes for use in the oleaginous cells are found in the plants, including *Macfadyena unguis* (Cat's claw), *Macadamia integrifolia* (*Macadamia* nut) and *Hippophae rhamnoides* (sea buckthorn). Variant exogenous or endogenous SADs that desaturate palmitoyl-ACP can also be used and are further discussed in Example 51. Optionally, the PAD or SAD gene has at least 95% amino acid sequence identity to the gene product described in Example 51. This modification can be used alone, or in combination with oleate-increasing modifications such as those described immediately above, in section 1× and in the Examples, including knockout or knockdown of one or more endogenous FATA alleles and/or overexpression of KASII. In one embodiment, an oleaginous cell such as an oleaginous microalgae has a combination of (i) a FATA knockout or knockdown with (ii) expression of an exogenous PAD gene (this could also be a variant SAD with PAD activity such as a L118W mutant or equivalent, see Examples 55-56) and/or a mutation in an endogenous SAD gene to give PAD activity.

Such as cell may further comprise an overexpressed endogenous or exogenous KASII gene. In accordance with any of these embodiments of the invention, the oleaginous cell produces an oil having a fatty acid profile with 1-2, 2-3, 3-4, 5-6, 7-8, 9-10, 10-15, 15-20, 20-30, 30-40, 40-60, 60-70, 70-80, 80-90, or 90-100 area percent palmitoleic acid. In a specific embodiment, the cell produces greater than 50% oleic acid, greater than 1% palmitoleic acid, and 3.5 area % or less of saturated fatty acids. In another specific embodiment, a eukaryotic microalgal cell comprises an exogenous gene that desaturates palmitic acid to palmitoleic acid in operable linkage with regulatory elements operable in the microalgal cell. Due to expression and activity of the exogenous gene product, the cell produces a cell oil having a fatty acid profile in which the ratio of palmitoleic acid (C16:1) to palmitic acid (C16:0) is at least 0.05, 0.1 or 0.15, or 0.18. See Example 55 for examples of cells that produce such oils. Optionally, palmitoleic acid comprises 0.5% or more of the profile. Optionally, the cell oil comprises less than 3.5% saturated fatty acids.

In addition to the above genetic modifications, the low saturate oil can be a high-stability oil by virtue of low amounts of polyunsaturated fatty acids. Methods and characterizations of high-stability, low-polyunsaturated oils are described in the section above entitled Low Polyunsaturated Oils, including method to reduce the activity of endogenous Δ12 fatty acid desaturase. In a specific embodiment, an oil is produced by a oleaginous microbial cell having a type II fatty acid synthetic pathway and has no more than 3.5% saturated fatty acids and also has no more than 3% polyunsaturated fatty acids. In another specific embodiment, the oil has no more than 3% saturated fatty acids and also has no more than 2% polyunsaturated fatty acids. In another specific embodiment, the oil has no more than 3% saturated fatty acids and also has no more than 1% polyunsaturated fatty acids. In another specific embodiment, a eukaryotic microalgal cell comprises an exogenous gene that desaturates palmitic acid to palmitoleic acid in operable linkage with regulatory elements operable in the microalgal cell. The cell further comprises a knockout or knockdown of a FAD gene. Due to the genetic modifications, the cell produces a cell oil having a fatty acid profile in which the ratio of palmitoleic acid (C16:1) to palmitic acid (C16:0) is greater than 0.1, with no more than 3% polyunsaturated fatty acids. Optionally, palmitoleic acid comprises 0.5% or more of the profile. Optionally, the cell oil comprises less than 3.5% saturated fatty acids.

The low saturate and low saturate/high stability oil can be blended with less expensive oils to reach a targeted saturated fatty acid level at less expense. For example, an oil with 1% saturated fat can be blended with an oil having 7% saturated fat (e.g. high-oleic sunflower oil) to give an oil having 3.5% or less saturated fat.

Oils produced according to embodiments of the present invention can be used in the transportation fuel, oleochemical, and/or food and cosmetic industries, among other applications. For example, transesterification of lipids can yield long-chain fatty acid esters useful as biodiesel. Other enzymatic and chemical processes can be tailored to yield fatty acids, aldehydes, alcohols, alkanes, and alkenes. In some applications, renewable diesel, jet fuel, or other hydrocarbon compounds are produced. The present disclosure also provides methods of cultivating microalgae for increased productivity and increased lipid yield, and/or for more cost-effective production of the compositions described herein. The methods described here allow for the production of oils from plastidic cell cultures at large scale; e.g., 1000, 10,000, 100,000 liters or more.

In an embodiment, an oil extracted from the cell has 3.5%, 3%, 2.5%, or 2% saturated fat or less and is incorporated into a food product. The finished food product has 3.5, 3, 2.5, or 2% saturated fat or less. For example, oils recovered from such recombinant microalgae can be used for frying oils or as an ingredient in a prepared food that is low in saturated fats. The oils can be used neat or blended with other oils so that the food has less than 0.5 g of saturated fat per serving, thus allowing a label stating zero saturated fat (per US regulation). In a specific embodiment, the oil has a fatty acid profile with at least 90% oleic acid, less than 3% saturated fat, and more oleic acid than linoleic acid.

As with the other oils disclosed in this patent application, the low-saturate oils described in this section, including those with increased levels palmitoleic acid, can have a microalgal sterol profile as described in Section XII of this application. For example, via expression of an exogenous PAD gene, an oil can be produced with a fatty acid profile characterized by a ratio of palmitoleic acid to palmitic acid of at least 0.1 and/or palmitoleic acid levels of 0.5% or more, as determined by FAME GC/FID analysis and a sterol profile characterized by an excess of ergosterol over β-sitosterol and/or the presence of 22,23-dihydrobrassicasterol, poriferasterol or clionasterol.

XI. Cocoa Butter/Milk-Fat Blend Mimetics

Figure 17:
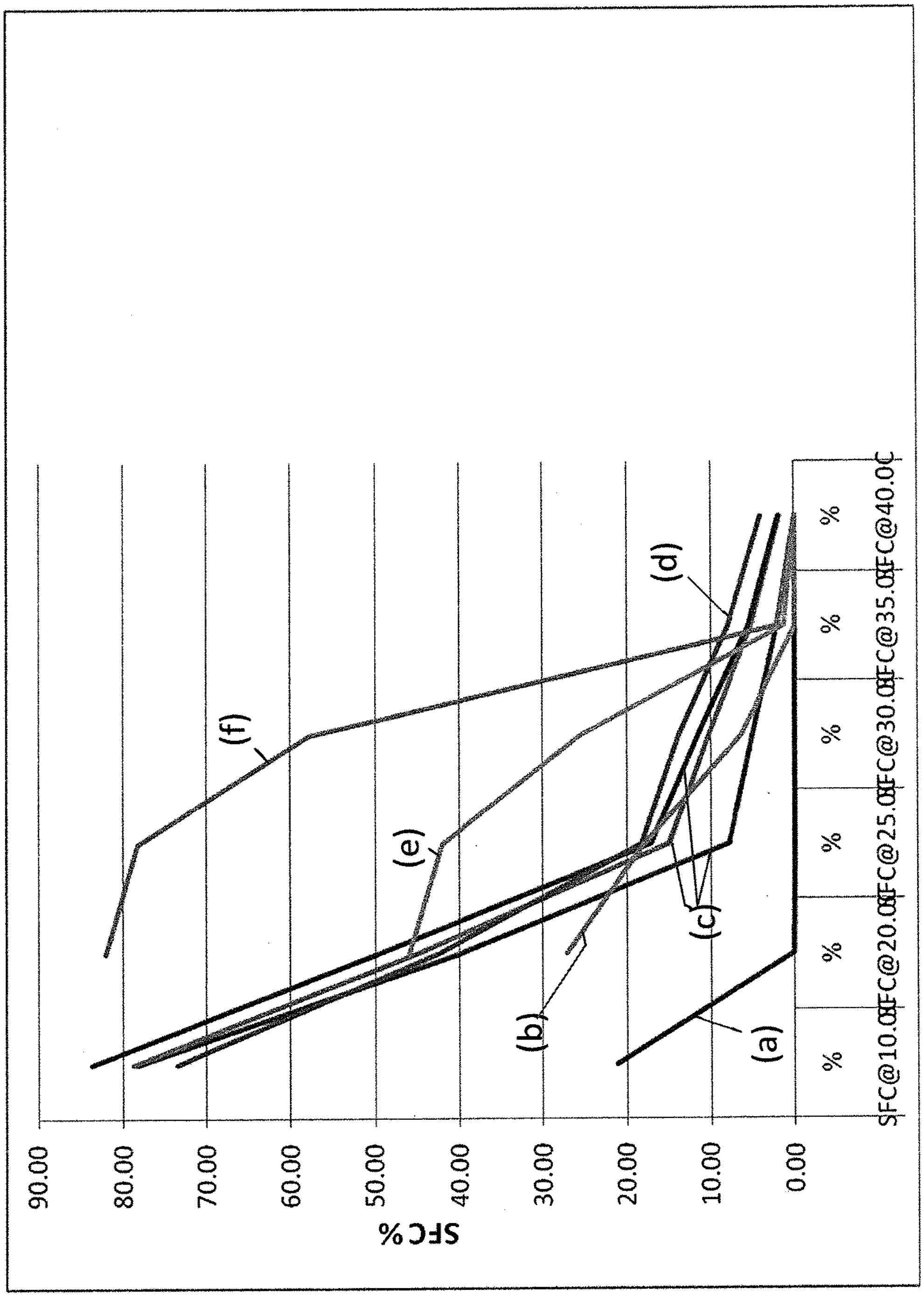
FIG. 17 shows a plot of percent solid fat content for various oils as follows: (a) *P. moriformis* RBD oil without lipid pathway engineering; (b) Brazilian cocoa butter+25% milk fat; (c) three replicates of *P. moriformis* RBD oil from a strain expressing hairpin nucleic acids that reduce levels of a SAD allele thus reducing oleic acid and increasing stearic acid in the TAG profile; (d) *P. moriformis* RBD oil from a strain overexpressing an endogenous OTE (oleoyl acyl-ACP thioesterase, see Example 45); (e) Malaysian cocoa butter+25% milk fat; and (f) Malaysian cocoa butter. The cocoa butter and cocoa butter milk fat values are literature values (Bailey's Industrial Oils and Fat Products, 6th ed.).

In certain embodiments, the cell produces a cell oil that has a temperature-dependent solid fat content ("SFC-curve") that approximates a blend of cocoa butter and milk fat. Such oils may be used where the cocoa butter/milk fat blend could be used; for example, in chocolates other confections, ice cream or other frozen desserts, pastries, or dough, including for quickbreads, or other baked goods. The oils may inhibit blooming, enhance flavor, enhance texture, or reduce costs. In a specific example, the cell oil approximates. Accordingly, an embodiment of the invention is using a cell oil from a recombinant microalgal cell to replace a cocoa butter/milk fat blend in a recipe. In a related embodiment, FIG. 17 shows a plot of % solid fat content for various oils as follows (a) *P. moriformis* RBD oil without lipid pathway engineering, (b) Brazilian cocoa butter+25% milk fat, (c) three replicates of *P. moriformis* RBD oil from a strain expressing hairpin nucleic acids that reduce levels of a SAD allele thus reducing oleic acid and increasing stearic acid in the TAG profile, (d) *P. moriformis* RBD oil from a strain overexpressing an endogenous OTE (oleoyl acyl-ACP thioesterase, see Example 45), (e) Malaysian cocoa butter+25% milk fat, and (f) Malaysian cocoa butter. The cocoa butter and cocoa butter milk fat values are literature values (Bailey's Industrial Oils and Fat Products, $6^{th}$ ed.)

In an embodiment of the present invention, a cell oil that is similar in thermal properties to a 75% cocoa butter/25% milk fat blend is produced by a microalgal or other cell described above. The cell comprises recombinant nucleic acids operable to alter the fatty acid profile of triglycerides produced by the cell so as that the oil has a solid fat content (e.g., as determined by NMR) of 38%±30% at 20° C., 32%±30% at 25° C., 17%±30% at 30° C., and less than 5%±30% at 35° C. For the sake of clarity, ±10% refers to percent of the percent SFC (e.g., 30% of 5% SFC is 1.5% SFC so the range is 3.5 to 6.5% SFC at 35° C.). In related embodiments, the oil has a solid fat content (e.g., as determined by NMR) of 38%±20% at 20° C., 32%±20% at 25° C., 17%±20% at 30° C., and less than 5%±20% at 35° C. or the oil has a solid fat content (e.g., as determined by NMR) of 38%±10% at 20° C., 32%±10% at 25° C., 17%±10% at 30° C., and less than 5%±10% at 35° C.

In a another embodiment a cell high oleic oil produced according to the methods of section 1× or corresponding Examples, is converted into a structuring fat such as a cocoa butter equivalent, substitute, extender by enzymatic interesterification or transesterification with a source of saturated fatty acids (e.g. a hardstock fat or saturated fatty acid esters). For example, a 1,3-specific lipase can be used to add stearate, palmitate or both to a high oleic oil having greater than 80% oleic acid.

XII. Minor Oil Components

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, poriferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, b-sitosterol, and stigmasterol are common plant sterols, with b-sitosterol being a principle plant sterol. For example, b-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g) in Table 5b.

TABLE 5b

Sterol profiles of oils from UTEX 1435.

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campesterol or 22,23-dihydro-brassicasterol) | 10.7 (1.6%) | 11.9 (1.6%) | 10.9 (1.8%) | 10.8 (1.8%) |
| 4 | 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigmasterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol. For any of the oils or cell-oils disclosed in this application, the oil can have the sterol profile of any column of Table 5b, above, with a sterol-by-sterol variation of 30%, 20%, 10% or less.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22,23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5,22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols b-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than b-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

XIII. Fuels and Chemicals

The oils discussed above alone or in combination are useful in the production of foods, fuels and chemicals (including plastics, foams, films, etc.). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

The oils can be converted to alkanes (e.g., renewable diesel) or esters (e.g., methyl or ethyl esters for biodisesel produced by transesterification). The alkanes or esters may be used as fuel, as solvents or lubricants, or as a chemical feedstock. Methods for production of renewable diesel and biodiesel are well established in the art. See, for example, WO2011/150411.

In a specific embodiment of the present invention, a high-oleic or high-oleic-high stability oil described above is esterified. For example, the oils can be transesterified with methanol to an oil that is rich in methyl oleate. As described in Example 49, such formulations have been found to compare favorably with methyl oleate from soybean oil.

In another specific example, the oil is converted to C36 diacids or products of C36 diacids. Fatty acids produced from the oil can be polymerized to give a composition rich in C36 dimer acids. In a specific example, high-oleic oil is split to give a high-oleic fatty acid material which is polymerized to give a composition rich in C36-dimer acids. Optionally, the oil is high oleic high stability oil (e.g., greater than 60% oleic acid with less than 3% polyunsaturates, greater than 70% oleic acid with less than 2% polyunsaturates, or greater than 80% oleic acid with less than 1% polyunsaturates). It is believed that using a high oleic, high stability, starting material will give lower amounts of cyclic products, which may be desirable in some cases. After hydrolyzing the oil, one obtains a high concentration of oleic acid. In the process of making dimer acids, a high oleic acid stream will convert to a "cleaner" C36 dimer acid and not produce trimers acids (C54) and other more complex cyclic by-products which are obtained due to presence of C18:2 and C18:3 acids. For example, the oil can be hydrolyzed to fatty acids and the fatty acids purified and dimerized at 250° C. in the presence of montmorillonite clay. See SRI Natural Fatty Acid, March 2009. A product rich in C36 dimers of oleic acid is recovered.

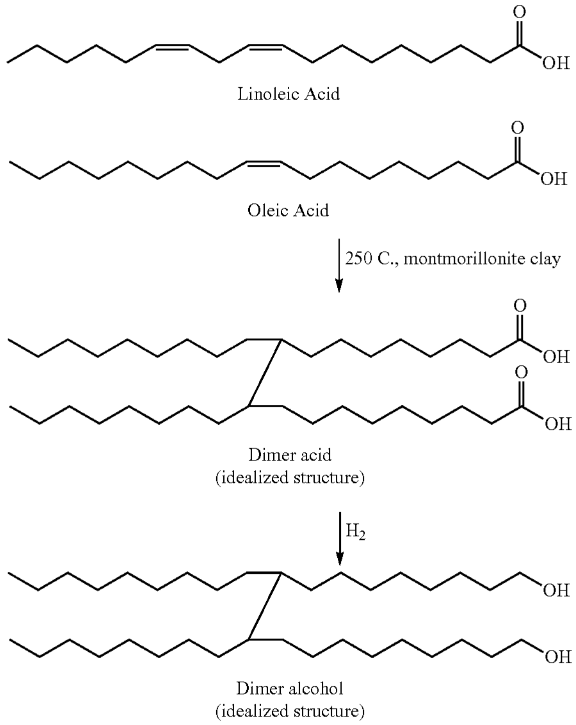

Linoleic Acid

Oleic Acid

Dimer acid
(idealized structure)

Dimer alcohol
(idealized structure)

Further, the C36 dimer acids can be esterified and hydrogenated to give diols. The diols can be polymerized by catalytic dehydration. Polymers can also be produced by transesterification of dimerdiols with dimethyl carbonate.

For the production of fuel in accordance with the methods of the invention lipids produced by cells of the invention are harvested, or otherwise collected, by any convenient means. Lipids can be isolated by whole cell extraction. The cells are first disrupted, and then intracellular and cell membrane/cell wall-associated lipids as well as extracellular hydrocarbons can be separated from the cell mass, such as by use of centrifugation. Intracellular lipids produced in oleaginous cells are, in some embodiments, extracted after lysing the cells. Once extracted, the lipids are further refined to produce oils, fuels, or oleochemicals.

Various methods are available for separating lipids from cellular lysates. For example, lipids and lipid derivatives such as fatty aldehydes, fatty alcohols, and hydrocarbons such as alkanes can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334). Miao and Wu describe a protocol of the recovery of microalgal lipid from a culture of *Chlorella protothecoides* in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Lipids and lipid derivatives can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Lipids produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process is used as described below in this Section.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

Increasing interest is directed to the use of hydrocarbon components of biological origin in fuels, such as biodiesel, renewable diesel, and jet fuel, since renewable biological starting materials that may replace starting materials derived from fossil fuels are available, and the use thereof is desirable. There is an urgent need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel if it is a fatty acid methyl ester (ASTM D6751).

After extraction, lipid and/or hydrocarbon components recovered from the microbial biomass described herein can be subjected to chemical treatment to manufacture a fuel for use in diesel vehicles and jet engines.

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced. Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel. The lipid profile of the biodiesel is usually highly similar to the lipid profile of the feedstock oil.

Lipid compositions can be subjected to transesterification to yield long-chain fatty acid esters useful as biodiesel. Preferred transesterification reactions are outlined below and include base catalyzed transesterification and transesterification using recombinant lipases. In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

Transesterification has also been carried out, as discussed above, using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1. Lipases suitable for use in transesterification include, but are not limited to, those listed in Table 9. Other examples of lipases useful for transesterification are found in, e.g., U.S. Pat. Nos. 4,798,793; 4,940,845 5,156,963; 5,342,768; 5,776,741 and WO89/01032. Such lipases include, but are not limited to, lipases produced by microorganisms of *Rhizopus, Aspergillus, Candida, Mucor, Pseudomonas, Rhizomucor, Candida*, and *Humicola* and pancreas lipase.

Subsequent processes may also be used if the biodiesel will be used in particularly cold temperatures. Such processes include winterization and fractionation. Both processes are designed to improve the cold flow and winter performance of the fuel by lowering the cloud point (the temperature at which the biodiesel starts to crystallize). There are several approaches to winterizing biodiesel. One approach is to blend the biodiesel with petroleum diesel. Another approach is to use additives that can lower the cloud point of biodiesel. Another approach is to remove saturated methyl esters indiscriminately by mixing in additives and allowing for the crystallization of saturates and then filtering out the crystals. Fractionation selectively separates methyl esters into individual components or fractions, allowing for the removal or inclusion of specific methyl esters. Fractionation methods include urea fractionation, solvent fractionation and thermal distillation.

Another valuable fuel provided by the methods of the present invention is renewable diesel, which comprises alkanes, such as C10:0, C12:0, C14:0, C16:0 and C18:0 and thus, are distinguishable from biodiesel. High quality renewable diesel conforms to the ASTM D975 standard. The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In one embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696. Some suitable methods may include mechanical pressing and centrifuging.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet an ASTM D975 standard while leaving components that are heavier than desired for meeting the D975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

In one embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

One suitable method for the hydrogenation of triglycerides includes preparing an aqueous solution of copper, zinc, magnesium and lanthanum salts and another solution of alkali metal or preferably, ammonium carbonate. The two solutions may be heated to a temperature of about 20° C. to about 85° C. and metered together into a precipitation container at rates such that the pH in the precipitation container is maintained between 5.5 and 7.5 in order to form a catalyst. Additional water may be used either initially in the precipitation container or added concurrently with the salt solution and precipitation solution. The resulting precipitate may then be thoroughly washed, dried, calcined at about 300° C. and activated in hydrogen at temperatures ranging from about 100° C. to about 400° C. One or more triglycerides may then be contacted and reacted with hydrogen in the presence of the above-described catalyst in a reactor. The reactor may be a trickle bed reactor, fixed bed gas-solid reactor, packed bubble column reactor, continuously stirred tank reactor, a slurry phase reactor, or any other suitable reactor type known in the art. The process may be carried out either batchwise or in continuous fashion. Reaction temperatures are typically in the range of from about 170° C. to about 250° C. while reaction pressures are typically in the range of from about 300 psig to about 2000 psig. Moreover, the molar ratio of hydrogen to triglyceride in the process of the present invention is typically in the range of from about 20:1 to about 700:1. The process is typically carried out at a weight hourly space velocity (WHSV) in the range of from about 0.1 $hr^{-1}$ to about 5 $hr^{-1}$. One skilled in the art will recognize that the time period required for reaction will vary according to the temperature used, the molar ratio of hydrogen to triglyceride, and the partial pressure of hydrogen. The products produced by the such hydrogenation processes include fatty alcohols, glycerol, traces of paraffins and unreacted triglycerides. These products are typically separated by conventional means such as, for example, distillation, extraction, filtration, crystallization, and the like.

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes. Solid catalysts are employed to increase certain reaction rates, improve selectivity for certain products, and optimize hydrogen consumption.

Suitable methods for the deoxygenation of an oil includes heating an oil to a temperature in the range of from about 350° F. to about 550° F. and continuously contacting the heated oil with nitrogen under at least pressure ranging from about atmospheric to above for at least about 5 minutes.

Suitable methods for isomerization include using alkali isomerization and other oil isomerization known in the art.

Hydrotreating and hydroprocessing ultimately lead to a reduction in the molecular weight of the triglyceride feed. The triglyceride molecule is reduced to four hydrocarbon molecules under hydroprocessing conditions: a propane molecule and three heavier hydrocarbon molecules, typically in the C8 to C18 range.

Thus, in one embodiment, the product of one or more chemical reaction(s) performed on lipid compositions of the invention is an alkane mixture that comprises ASTM D975 renewable diesel. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

The distillation properties of a diesel fuel is described in terms of T10-T90 (temperature at 10% and 90%, respectively, volume distilled). The T10-T90 of the material produced in Example 13 was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

Methods of hydrotreating, isomerization, and other covalent modification of oils disclosed herein, as well as methods of distillation and fractionation (such as cold filtration) disclosed herein can be employed to generate renewable diesel compositions with certain T90 values, such as T90 between 280 and 380, between 290 and 360, between 300 and 350, between 310 and 340, and at least 290.

The FBP of the material produced in Example 13 was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 1%-5%, preferably at least 4%, C8-C14; (b) at least 0.25%-1%, preferably at least 0.3%, C8; (c) at least 1%-5%, preferably at least 2%, C10; (d) at least 1%-5%, preferably at least 2%, C12; and (3) at least 20%-40%, preferably at least 30% C8-C14.

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosene-type Aeroplane fuel (including Jet A and Jet A-1) has a carbon number distribution between about 8 and 16 carbon numbers. Wide-cut or naphtha-type Aeroplane fuel (including Jet B) typically has a carbon number distribution between about 5 and 15 carbons.

In one embodiment of the invention, a jet fuel is produced by blending algal fuels with existing jet fuel. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking (FCC) is one method which is used to produce olefins, especially propylene from heavy crude fractions. The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In one embodiment, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced. In one embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method, it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

Suitable FCC catalysts generally comprise at least two components that may or may not be on the same matrix. In some embodiments, both two components may be circulated throughout the entire reaction vessel. The first component generally includes any of the well-known catalysts that are used in the art of fluidized catalytic cracking, such as an active amorphous clay-type catalyst and/or a high activity, crystalline molecular sieve. Molecular sieve catalysts may be preferred over amorphous catalysts because of their much-improved selectivity to desired products. In some preferred embodiments, zeolites may be used as the molecular sieve in the FCC processes. Preferably, the first catalyst component comprises a large pore zeolite, such as a Y-type zeolite, an active alumina material, a binder material, comprising either silica or alumina and an inert filler such as kaolin.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

In another embodiment of the method for producing a jet fuel using the lipid composition or the lipids produced as described herein, the structure of the lipid composition or the lipids is broken by a process referred to as hydrodeoxygenation (HDO). HDO means removal of oxygen by means of hydrogen, that is, oxygen is removed while breaking the structure of the material. Olefinic double bonds are hydrogenated and any sulfur and nitrogen compounds are removed. Sulfur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerization reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulfur compounds, and light hydrocarbons as gas are removed, and the olefinic bonds are hydrogenated. In the second step of the process, i.e. in the so-called isomerization step, isomerization is carried out for branching the hydrocarbon chain and improving the performance of the paraffin at low temperatures.

In the first step, i.e. HDO step, of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle. In the HDO step, the pressure varies between 20 and 150 bar, preferably between 50 and 100 bar, and the temperature varies between 200 and 500° C., preferably in the range of 300-400° C. In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, $NiMo/Al_2O_3$ and $CoMo/Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50-400° C. and at hydrogen pressures of 1-200 bar, preferably at a temperature between 150 and 250° C. and at a hydrogen pressure between 10 and 100 bar. The catalyst may contain metals from Group VIII and/or VIB of the Periodic System.

Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulfur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapor or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner. In the isomerization step, the pressure varies in the range of 20-150 bar, preferably in the range of 20-100 bar, the temperature being between 200 and 500° C., preferably between 300 and 400° C. In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. The isomerization step and the HDO step may be carried out in the same pressure vessel or in separate pressure vessels. Optional prehydrogenation may be carried out in a separate pressure vessel or in the same pressure vessel as the HDO and isomerization steps.

Thus, in one embodiment, the product of one or more chemical reactions is an alkane mixture that comprises HRJ-5. In another embodiment, the product of the one or more chemical reactions is an alkane mixture that comprises ASTM D1655 jet fuel. In some embodiments, the composition conforming to the specification of ASTM 1655 jet fuel has a sulfur content that is less than 10 ppm. In other embodiments, the composition conforming to the specification of ASTM 1655 jet fuel has a T10 value of the distillation curve of less than 205° C. In another embodiment, the composition conforming to the specification of ASTM 1655 jet fuel has a final boiling point (FBP) of less than 300° C. In another embodiment, the composition conforming to the specification of ASTM 1655 jet fuel has a flash point of at least 38° C. In another embodiment, the composition conforming to the specification of ASTM 1655 jet fuel has a density between 775K/M$^3$ and 840K/M$^3$. In yet another embodiment, the composition conforming to the specification of ASTM 1655 jet fuel has a freezing point that is below −47° C. In another embodiment, the composition conforming to the specification of ASTM 1655 jet fuel has a net Heat of Combustion that is at least 42.8 MJ/K. In another embodiment, the composition conforming to the specification of ASTM 1655 jet fuel has a hydrogen content that is at least 13.4 mass %. In another embodiment, the composition conforming to the specification of ASTM 1655 jet fuel has a thermal stability, as tested by quantitative gravimetric JFTOT at 260° C., which is below 3 mm of Hg. In another embodiment, the composition conforming to the specification of ASTM 1655 jet fuel has an existent gum that is below 7 mg/dl.

Thus, the present invention discloses a variety of methods in which chemical modification of microalgal lipid is undertaken to yield products useful in a variety of industrial and other applications. Examples of processes for modifying oil produced by the methods disclosed herein include, but are not limited to, hydrolysis of the oil, hydroprocessing of the oil, and esterification of the oil. Other chemical modification of microalgal lipid include, without limitation, epoxidation, oxidation, hydrolysis, sulfations, sulfonation, ethoxylation, propoxylation, amidation, and saponification. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein. Examples of basic oleochemicals include, but are not limited to, soaps, fatty acids, fatty esters, fatty alcohols, fatty nitrogen compounds including fatty amides, fatty acid methyl esters, and glycerol. Examples of derivative oleochemicals include, but are not limited to, fatty nitriles, esters, dimer acids, quats (including betaines), surfactants, fatty alkanolamides, fatty alcohol sulfates, resins, emulsifiers, fatty alcohols, olefins, drilling muds, polyols, polyurethanes, polyacrylates, rubber, candles, cosmetics, metallic soaps, soaps, alpha-sulphonated methyl esters, fatty alcohol sulfates, fatty alcohol ethoxylates, fatty alcohol ether sulfates, imidazolines, surfactants, detergents, esters, quats (including betaines), ozonolysis products, fatty amines, fatty alkanolamides, ethoxysulfates, monoglycerides, diglycerides, triglycerides (including medium chain triglycerides), lubricants, hydraulic fluids, greases, dielectric fluids, mold release agents, metal working fluids, heat transfer fluids, other functional fluids, industrial chemicals (e.g., cleaners, textile processing aids, plasticizers, stabilizers, additives), surface coatings, paints and lacquers, electrical wiring insulation, and higher alkanes. Other derivatives include fatty amidoamines, amidoamine carboxylates, amidoamine oxides, amidoamine oxide carboxylates, amidoamine esters, ethanolamine amides, sulfonates, amidoamine sulfonates, diamidoamine dioxides, sulfonated alkyl ester alkoxylates, betaines, quarternized diamidoamine betaines, and sulfobetaines.

Hydrolysis of the fatty acid constituents from the glycerolipids produced by the methods of the invention yields free fatty acids that can be derivatized to produce other useful chemicals. Hydrolysis occurs in the presence of water and a catalyst which may be either an acid or a base. The liberated free fatty acids can be derivatized to yield a variety of products, as reported in the following: U.S. Pat. No. 5,304,664 (Highly sulfated fatty acids); U.S. Pat. No. 7,262,158 (Cleansing compositions); U.S. Pat. No. 7,115,173

(Fabric softener compositions); U.S. Pat. No. 6,342,208 (Emulsions for treating skin); U.S. Pat. No. 7,264,886 (Water repellant compositions); U.S. Pat. No. 6,924,333 (Paint additives); U.S. Pat. No. 6,596,768 (Lipid-enriched ruminant feedstock); and U.S. Pat. No. 6,380,410 (Surfactants for detergents and cleaners).

In some methods, the first step of chemical modification may be hydroprocessing to saturate double bonds, followed by deoxygenation at elevated temperature in the presence of hydrogen and a catalyst. In other methods, hydrogenation and deoxygenation may occur in the same reaction. In still other methods deoxygenation occurs before hydrogenation. Isomerization may then be optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

In some embodiments of the invention, the triglyceride oils are partially or completely deoxygenated. The deoxygenation reactions form desired products, including, but not limited to, fatty acids, fatty alcohols, polyols, ketones, and aldehydes. In general, without being limited by any particular theory, the deoxygenation reactions involve a combination of various different reaction pathways, including without limitation: hydrogenolysis, hydrogenation, consecutive hydrogenation-hydrogenolysis, consecutive hydrogenolysis-hydrogenation, and combined hydrogenation-hydrogenolysis reactions, resulting in at least the partial removal of oxygen from the fatty acid or fatty acid ester to produce reaction products, such as fatty alcohols, that can be easily converted to the desired chemicals by further processing. For example, in one embodiment, a fatty alcohol may be converted to olefins through FCC reaction or to higher alkanes through a condensation reaction.

One such chemical modification is hydrogenation, which is the addition of hydrogen to double bonds in the fatty acid constituents of glycerolipids or of free fatty acids. The hydrogenation process permits the transformation of liquid oils into semi-solid or solid fats, which may be more suitable for specific applications.

Hydrogenation of oil produced by the methods described herein can be performed in conjunction with one or more of the methods and/or materials provided herein, as reported in the following: U.S. Pat. No. 7,288,278 (Food additives or medicaments); U.S. Pat. No. 5,346,724 (Lubrication products); U.S. Pat. No. 5,475,160 (Fatty alcohols); U.S. Pat. No. 5,091,116 (Edible oils); U.S. Pat. No. 6,808,737 (Structural fats for margarine and spreads); U.S. Pat. No. 5,298,637 (Reduced-calorie fat substitutes); U.S. Pat. No. 6,391,815 (Hydrogenation catalyst and sulfur adsorbent); U.S. Pat. No. 5,233,099 and U.S. Pat. No. 5,233,100 (Fatty alcohols); U.S. Pat. No. 4,584,139 (Hydrogenation catalysts); U.S. Pat. No. 6,057,375 (Foam suppressing agents); and U.S. Pat. No. 7,118,773 (Edible emulsion spreads).

One skilled in the art will recognize that various processes may be used to hydrogenate carbohydrates. One suitable method includes contacting the carbohydrate with hydrogen or hydrogen mixed with a suitable gas and a catalyst under conditions sufficient in a hydrogenation reactor to form a hydrogenated product. The hydrogenation catalyst generally can include Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports, depending on the desired functionality of the catalyst. The hydrogenation catalysts may be prepared by methods known to those of ordinary skill in the art.

In some embodiments the hydrogenation catalyst includes a supported Group VIII metal catalyst and a metal sponge material (e.g., a sponge nickel catalyst). Raney nickel provides an example of an activated sponge nickel catalyst suitable for use in this invention. In other embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (i.e., molybdenum or chromium) in the amount such that about 1 to 2 weight % remains in the formed sponge nickel catalyst. In another embodiment, the hydrogenation catalyst is prepared using a solution of ruthenium (III) nitrosylnitrate, ruthenium (III) chloride in water to impregnate a suitable support material. The solution is then dried to form a solid having a water content of less than about 1% by weight. The solid may then be reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 80° C. to 250° C., and preferably at 90° C. to 200° C., and most preferably at 100° C. to 150° C. In some embodiments, the hydrogenation reaction is conducted at pressures from 500 KPa to 14000 KPa.

The hydrogen used in the hydrogenolysis reaction of the current invention may include external hydrogen, recycled hydrogen, in situ generated hydrogen, and any combination thereof. As used herein, the term "external hydrogen" refers to hydrogen that does not originate from the biomass reaction itself, but rather is added to the system from another source.

In some embodiments of the invention, it is desirable to convert the starting carbohydrate to a smaller molecule that will be more readily converted to desired higher hydrocarbons. One suitable method for this conversion is through a hydrogenolysis reaction. Various processes are known for performing hydrogenolysis of carbohydrates. One suitable method includes contacting a carbohydrate with hydrogen or hydrogen mixed with a suitable gas and a hydrogenolysis catalyst in a hydrogenolysis reactor under conditions sufficient to form a reaction product comprising smaller molecules or polyols. As used herein, the term "smaller molecules or polyols" includes any molecule that has a smaller molecular weight, which can include a smaller number of carbon atoms or oxygen atoms than the starting carbohydrate. In an embodiment, the reaction products include smaller molecules that include polyols and alcohols. Someone of ordinary skill in the art would be able to choose the appropriate method by which to carry out the hydrogenolysis reaction.

In some embodiments, a 5 and/or 6 carbon sugar or sugar alcohol may be converted to propylene glycol, ethylene glycol, and glycerol using a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The hydrogenolysis catalyst may also include a carbonaceous pyropolymer catalyst containing transition metals (e.g., chromium, molybdenum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst may include any of the above metals combined with an alkaline earth metal oxide or adhered to a catalytically active support. In certain embodiments, the catalyst described in the hydrogenolysis reaction may include a catalyst support as described above for the hydrogenation reaction.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, they hydrogenolysis reaction is conducted at temperatures of 110° C. to 300° C., and preferably at 170° C. to 220° C., and most preferably at 200° C. to 225° C. In some embodiments, the hydrogenolysis reaction is conducted under basic conditions, preferably at a pH of 8 to 13, and even more preferably at a pH of 10 to 12. In some embodiments, the hydrogenolysis reaction is conducted at pressures in a range between 60 KPa and 16500 KPa, and preferably in a range between 1700 KPa and 14000 KPa, and even more preferably between 4800 KPa and 11000 KPa.

The hydrogen used in the hydrogenolysis reaction of the current invention can include external hydrogen, recycled hydrogen, in situ generated hydrogen, and any combination thereof.

In some embodiments, the reaction products discussed above may be converted into higher hydrocarbons through a condensation reaction in a condensation reactor. In such embodiments, condensation of the reaction products occurs in the presence of a catalyst capable of forming higher hydrocarbons. While not intending to be limited by theory, it is believed that the production of higher hydrocarbons proceeds through a stepwise addition reaction including the formation of carbon-carbon, or carbon-oxygen bond. The resulting reaction products include any number of compounds containing these moieties, as described in more detail below.

In certain embodiments, suitable condensation catalysts include an acid catalyst, a base catalyst, or an acid/base catalyst. As used herein, the term "acid/base catalyst" refers to a catalyst that has both an acid and a base functionality. In some embodiments the condensation catalyst can include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the condensation catalyst can also include a modifier. Suitable modifiers include La, Y, Sc, P, B, Bi, Li, Na, K, Rb, Cs, Mg, Ca, Sr, Ba, and any combination thereof. In some embodiments, the condensation catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof.

In certain embodiments, the catalyst described in the condensation reaction may include a catalyst support as described above for the hydrogenation reaction. In certain embodiments, the condensation catalyst is self-supporting. As used herein, the term "self-supporting" means that the catalyst does not need another material to serve as support. In other embodiments, the condensation catalyst in used in conjunction with a separate support suitable for suspending the catalyst. In an embodiment, the condensation catalyst support is silica.

The conditions under which the condensation reaction occurs will vary based on the type of starting material and the desired products. One of ordinary skill in the art, with the benefit of this disclosure, will recognize the appropriate conditions to use to carry out the reaction. In some embodiments, the condensation reaction is carried out at a temperature at which the thermodynamics for the proposed reaction are favorable. The temperature for the condensation reaction will vary depending on the specific starting polyol or alcohol. In some embodiments, the temperature for the condensation reaction is in a range from 80° C. to 500° C., and preferably from 125° C. to 450° C., and most preferably from 125° C. to 250° C. In some embodiments, the condensation reaction is conducted at pressures in a range between 0 Kpa to 9000 KPa, and preferably in a range between 0 KPa and 7000 KPa, and even more preferably between 0 KPa and 5000 KPa.

The higher alkanes formed by the invention include, but are not limited to, branched or straight chain alkanes that have from 4 to 30 carbon atoms, branched or straight chain alkenes that have from 4 to 30 carbon atoms, cycloalkanes that have from 5 to 30 carbon atoms, cycloalkenes that have from 5 to 30 carbon atoms, aryls, fused aryls, alcohols, and ketones. Suitable alkanes include, but are not limited to, butane, pentane, pentene, 2-methylbutane, hexane, hexene, 2-methylpentane, 3-methylpentane, 2,2,-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, nonyldecane, nonyldecene, eicosane, eicosene, uneicosane, uneicosene, doeicosane, doeicosene, trieicosane, trieicosene, tetraeicosane, tetraeicosene, and isomers thereof. Some of these products may be suitable for use as fuels.

In some embodiments, the cycloalkanes and the cycloalkenes are unsubstituted. In other embodiments, the cycloalkanes and cycloalkenes are mono-substituted. In still other embodiments, the cycloalkanes and cycloalkenes are multi-substituted. In the embodiments comprising the substituted cycloalkanes and cycloalkenes, the substituted group includes, without limitation, a branched or straight chain alkyl having 1 to 12 carbon atoms, a branched or straight chain alkylene having 1 to 12 carbon atoms, a phenyl, and any combination thereof. Suitable cycloalkanes and cycloalkenes include, but are not limited to, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, isomers and any combination thereof.

In some embodiments, the aryls formed are unsubstituted. In another embodiment, the aryls formed are mono-substituted. In the embodiments comprising the substituted aryls, the substituted group includes, without limitation, a branched or straight chain alkyl having 1 to 12 carbon atoms, a branched or straight chain alkylene having 1 to 12 carbon atoms, a phenyl, and any combination thereof. Suitable aryls for the invention include, but are not limited to, benzene, toluene, xylene, ethyl benzene, para xylene, meta xylene, and any combination thereof.

The alcohols produced in the invention have from 4 to 30 carbon atoms. In some embodiments, the alcohols are cyclic. In other embodiments, the alcohols are branched. In another embodiment, the alcohols are straight chained. Suitable alcohols for the invention include, but are not limited to, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The ketones produced in the invention have from 4 to 30 carbon atoms. In an embodiment, the ketones are cyclic. In another embodiment, the ketones are branched. In another embodiment, the ketones are straight chained. Suitable ketones for the invention include, but are not limited to, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Another such chemical modification is interesterification. Naturally produced glycerolipids do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g., 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a percentage of dry cell weight as lipid at least 20%.

Directed interesterification, in which a specific distribution pattern of fatty acids is sought, can be performed by maintaining the oil mixture at a temperature below the melting point of some TAGs which might occur. This results in selective crystallization of these TAGs, which effectively removes them from the reaction mixture as they crystallize. The process can be continued until most of the fatty acids in the oil have precipitated, for example. A directed interesterification process can be used, for example, to produce a product with a lower calorie content via the substitution of longer-chain fatty acids with shorter-chain counterparts. Directed interesterification can also be used to produce a product with a mixture of fats that can provide desired melting characteristics and structural features sought in food additives or products (e.g., margarine) without resorting to hydrogenation, which can produce unwanted trans isomers.

Interesterification of oils produced by the methods described herein can be performed in conjunction with one or more of the methods and/or materials, or to produce products, as reported in the following: U.S. Pat. No. 6,080,853 (Nondigestible fat substitutes); U.S. Pat. No. 4,288,378 (Peanut butter stabilizer); U.S. Pat. No. 5,391,383 (Edible spray oil); U.S. Pat. No. 6,022,577 (Edible fats for food products); U.S. Pat. No. 5,434,278 (Edible fats for food products); U.S. Pat. No. 5,268,192 (Low calorie nut products); U.S. Pat. No. 5,258,197 (Reduce calorie edible compositions); U.S. Pat. No. 4,335,156 (Edible fat product); U.S. Pat. No. 7,288,278 (Food additives or medicaments); U.S. Pat. No. 7,115,760 (Fractionation process); U.S. Pat. No. 6,808,737 (Structural fats); U.S. Pat. No. 5,888,947 (Engine lubricants); U.S. Pat. No. 5,686,131 (Edible oil mixtures); and U.S. Pat. No. 4,603,188 (Curable urethane compositions).

In one embodiment in accordance with the invention, transesterification of the oil, as described above, is followed by reaction of the transesterified product with polyol, as reported in U.S. Pat. No. 6,465,642, to produce polyol fatty acid polyesters. Such an esterification and separation process may comprise the steps as follows: reacting a lower alkyl ester with polyol in the presence of soap; removing residual soap from the product mixture; water-washing and drying the product mixture to remove impurities; bleaching the product mixture for refinement; separating at least a portion of the unreacted lower alkyl ester from the polyol fatty acid polyester in the product mixture; and recycling the separated unreacted lower alkyl ester.

Transesterification can also be performed on microbial biomass with short chain fatty acid esters, as reported in U.S. Pat. No. 6,278,006. In general, transesterification may be performed by adding a short chain fatty acid ester to an oil in the presence of a suitable catalyst and heating the mixture. In some embodiments, the oil comprises about 5% to about 90% of the reaction mixture by weight. In some embodiments, the short chain fatty acid esters can be about 10% to about 50% of the reaction mixture by weight. Non-limiting examples of catalysts include base catalysts, sodium methoxide, acid catalysts including inorganic acids such as sulfuric acid and acidified clays, organic acids such as methane sulfonic acid, benzenesulfonic acid, and toluenesulfonic acid, and acidic resins such as Amberlyst 15. Metals such as sodium and magnesium, and metal hydrides also are useful catalysts.

Another such chemical modification is hydroxylation, which involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027. Hydroxylated fatty acids, including castor oil and its derivatives, are useful as components in several industrial applications, including food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants. One example of how the hydroxylation of a glyceride may be performed is as follows: fat may be heated, preferably to about 30-50° C. combined with heptane and maintained at temperature for thirty minutes or more; acetic acid may then be added to the mixture followed by an aqueous solution of sulfuric acid followed by an aqueous hydrogen peroxide solution which is added in small increments to the mixture over one hour; after the aqueous hydrogen peroxide, the temperature may then be increased to at least about 60° C. and stirred for at least six hours; after the stirring, the mixture is allowed to settle and a lower aqueous layer formed by the reaction may be removed while the upper heptane layer formed by the reaction may be washed with hot water having a temperature of about 60° C.; the washed heptane layer may then be neutralized with an aqueous potassium hydroxide solution to a pH of about 5 to 7 and then removed by distillation under vacuum; the reaction product may then be dried under vacuum at 100° C. and the dried product steam-deodorized under vacuum conditions and filtered at about 50° to 60° C. using diatomaceous earth.

Hydroxylation of microbial oils produced by the methods described herein can be performed in conjunction with one or more of the methods and/or materials, or to produce products, as reported in the following: U.S. Pat. No. 6,590,113 (Oil-based coatings and ink); U.S. Pat. No. 4,049,724 (Hydroxylation process); U.S. Pat. No. 6,113,971 (Olive oil butter); U.S. Pat. No. 4,992,189 (Lubricants and lube additives); U.S. Pat. No. 5,576,027 (Hydroxylated milk); and U.S. Pat. No. 6,869,597 (Cosmetics).

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., *JAOCS* 71(2): 169-174 (1994). Estolides are useful in a variety of applications, including without limitation those reported in the following: U.S. Pat. No. 7,196,124 (Elastomeric materials and floor coverings); U.S. Pat. No. 5,458,795 (Thickened oils for high-temperature applications); U.S. Pat. No. 5,451,332 (Fluids for industrial applications); U.S. Pat. No. 5,427,704 (Fuel additives); and U.S. Pat. No. 5,380,894 (Lubricants, greases, plasticizers, and printing inks).

Another such chemical modification is olefin metathesis. In olefin metathesis, a catalyst severs the alkylidene carbons in an alkene (olefin) and forms new alkenes by pairing each of them with different alkylidine carbons. The olefin metathesis reaction provides a mechanism for processes such as truncating unsaturated fatty acid alkyl chains at alkenes by ethenolysis, cross-linking fatty acids through alkene linkages by self-metathesis, and incorporating new functional groups on fatty acids by cross-metathesis with derivatized alkenes.

In conjunction with other reactions, such as transesterification and hydrogenation, olefin metathesis can transform unsaturated glycerolipids into diverse end products. These products include glycerolipid oligomers for waxes; short-chain glycerolipids for lubricants; homo- and hetero-bifunctional alkyl chains for chemicals and polymers; short-chain esters for biofuel; and short-chain hydrocarbons for jet fuel. Olefin metathesis can be performed on triacylglycerols and fatty acid derivatives, for example, using the catalysts and methods reported in U.S. Pat. No. 7,119,216, US Patent Pub. No. 2010/0160506, and U.S. Patent Pub. No. 2010/0145086.

Olefin metathesis of bio-oils generally comprises adding a solution of Ru catalyst at a loading of about 10 to 250 ppm under inert conditions to unsaturated fatty acid esters in the presence (cross-metathesis) or absence (self-metathesis) of other alkenes. The reactions are typically allowed to proceed from hours to days and ultimately yield a distribution of alkene products. One example of how olefin metathesis may be performed on a fatty acid derivative is as follows: A solution of the first generation Grubbs Catalyst (dichloro[2(1-methylethoxy-α-O)phenyl]methylene-α-C] (tricyclohexyl-phosphine) in toluene at a catalyst loading of 222 ppm may be added to a vessel containing degassed and dried methyl oleate. Then the vessel may be pressurized with about 60 psig of ethylene gas and maintained at or below about 30° C. for 3 hours, whereby approximately a 50% yield of methyl 9-decenoate may be produced.

Olefin metathesis of oils produced by the methods described herein can be performed in conjunction with one or more of the methods and/or materials, or to produce products, as reported in the following: Patent App. PCT/US07/081,427 (α-olefin fatty acids) and U.S. patent application Ser. No. 12/281,938 (petroleum creams), Ser. No. 12/281,931 (paintball gun capsules), Ser. No. 12/653,742 (plasticizers and lubricants), Ser. No. 12/422,096 (bifunctional organic compounds), and Ser. No. 11/795,052 (candle wax).

Other chemical reactions that can be performed on microbial oils include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No. 6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004).

The generation of oil-bearing microbial biomass for fuel and chemical products as described above results in the production of delipidated biomass meal. Delipidated meal is a byproduct of preparing algal oil and is useful as animal feed for farm animals, e.g., ruminants, poultry, swine and aquaculture. The resulting meal, although of reduced oil content, still contains high quality proteins, carbohydrates, fiber, ash, residual oil and other nutrients appropriate for an animal feed. Because the cells are predominantly lysed by the oil separation process, the delipidated meal is easily digestible by such animals. Delipidated meal can optionally be combined with other ingredients, such as grain, in an animal feed. Because delipidated meal has a powdery consistency, it can be pressed into pellets using an extruder or expander or another type of machine, which are commercially available.

The invention, having been described in detail above, is exemplified in the following examples, which are offered to illustrate, but not to limit, the claimed invention.

XIV. Examples

Example 1: Fatty Acid Analysis by Fatty Acid Methyl Ester Detection

Lipid samples were prepared from dried biomass. 20-40 mg of dried biomass was resuspended in 2 mL of 5% $H_2SO_4$ in MeOH, and 200 ul of toluene containing an appropriate amount of a suitable internal standard (C19:0) was added. The mixture was sonicated briefly to disperse the biomass, then heated at 70-75° C. for 3.5 hours. 2 mL of heptane was added to extract the fatty acid methyl esters, followed by addition of 2 mL of 6% $K_2CO_3$ (aq) to neutralize the acid. The mixture was agitated vigorously, and a portion of the upper layer was transferred to a vial containing $Na_2SO_4$ (anhydrous) for gas chromatography analysis using standard FAME GC/FID (fatty acid methyl ester gas chromatography flame ionization detection) methods. Fatty acid profiles reported below were determined by this method.

Example 2: Triacylglyceride Purification from Oil and Methods for Triacylglyceride Lipase Digestion The triacylglyceride (TAG) fraction of each oil sample was isolated by dissolving ~10 mg of oil in dichloromethane and loading it onto a Bond-Elut aminopropyl solid-phase extraction cartridge (500 mg) preconditioned with heptane. TAGs were eluted with dicholoromethane-MeOH (1:1) into a collection tube, while polar lipids were retained on the column. The solvent was removed with a stream of nitrogen gas. Tris buffer and 2 mg porcine pancreatic lipase (Type II, Sigma, 100-400 units/mg) were added to the TAG fraction, followed by addition of bile salt and calcium chloride solutions. The porcine pancreatic lipase cleaves sn-1 and sn-3 fatty acids, thereby generating 2-monoacylglycerides and free fatty acids. This mixture was heated with agitation at 40° C. for three minutes, cooled briefly, then quenched with 6 N HCl. The mixture was then extracted with diethyl ether and the ether layer was washed with water then dried over sodium sulfate. The solvent was removed with a stream of nitrogen. To isolate the monoacylglyceride (MAG) fraction, the residue was dissolved in heptane and loaded onto a second aminopropyl solid phase extraction cartridge pretreated with heptane. Residual TAGs were eluted with diethyl ether-dichloromethane-heptane (1:9:40), diacylglycerides (DAGs) were eluted with ethyl acetate-heptane (1:4), and MAGs were eluted from the cartridge with dichloromethane-methanol (2:1). The resulting MAG, DAG, and TAG fractions were then concentrated to dryness with a stream of nitrogen and subjected to routine direct transesterification method of GC/FID analysis as described in Example 1.

Example 3: Engineering Microorganisms for Fatty Acid and Sn-2 Profiles Increased in Lauric Acid Through Exogenous LPAAT Expression This example describes the use of recombinant polynucleotides that encode a *C. nucifera* 1-acyl-sn-glycerol-3-phosphate acyltransferase (Cn LPAAT) enzyme to engineer a microorganism in which the fatty acid profile and the sn-2 profile of the transformed microorganism has been enriched in lauric acid.

A classically mutagenized strain of *Prototheca moriformis* (UTEX 1435), Strain A, was initially transformed with the plasmid construct pSZ1283 according to biolistic transformation methods as described in PCT/US2009/066141, PCT/US2009/066142, PCT/US2011/038463, PCT/US2011/038464, and PCT/US2012/023696. pSZ1283, described in PCT/US2011/038463, PCT/US2011/038464, and PCT/US2012/023696 hereby incorporated by reference, comprised the coding sequence of the *Cuphea wrightii* FATB2 (CwTE2) thioesterase (SEQ ID NO: 10), 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4), to express the protein sequence given in SEQ ID NO: 3, under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. The CwTE2 protein coding sequence to express the protein sequence given in SEQ ID NO: 11, was under the control of the *P. moriformis* Amt03 promoter/5'UTR (SEQ ID NO: 8) and *C. vulgaris* nitrate reductase 3'UTR. The protein coding regions of CwTE2 and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Upon transformation of pSZ1283 into Strain A, positive clones were selected on agar plates with sucrose as the sole carbon source. Primary transformants were then clonally purified and a single transformant, Strain B, was selected for further genetic modification. This genetically engineered strain was transformed with plasmid construct pSZ2046 to interrupt the pLoop genomic locus of Strain B. Construct pSZ2046 comprised the coding sequence of the *C. nucifera* 1-acyl-sn-glycerol-3-phosphate acyltransferase (Cn LPAAT) enzyme (SEQ ID NO: 12), 5' (SEQ ID NO: 13) and 3' (SEQ ID NO: 14) homologous recombination targeting sequences (flanking the construct) to the pLoop genomic region for integration into the nuclear genome, and a neomycin resistance protein-coding sequence under the control of *C. reinhardtii* β-tubulin promoter/5'UTR (SEQ ID NO: 5), and *Chlorella vulgaris* nitrate reductase 3' UTR (SEQ ID NO: 6). This NeoR expression cassette is listed as SEQ ID NO: 15 and served as a selectable marker. The Cn LPAAT protein coding sequence was under the control of the *P. moriformis* Amt03 promoter/5'UTR (SEQ ID NO: 8) and *C. vulgaris* nitrate reductase 3'UTR. The protein coding regions of Cn LPAAT and NeoR were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696. The amino acid sequence of Cn LPAAT is provided as SEQ ID NO: 16.

Upon transformation of pSZ2046 into Strain B, thereby generating Strain C, positive clones were selected on agar plates comprising G418 (Geneticin). Individual transformants were clonally purified and grown at pH 7.0 under conditions suitable for lipid production as detailed in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The fatty acid profiles (expressed as Area % of total fatty acids) of *P. moriformis* UTEX 1435 (U1) grown on glucose as a sole carbon source, untransformed Strain B and five pSZ2046 positive transformants (Strain C, 1-5) are presented in Table 6.

TABLE 6

Effect of LPAAT expression on fatty acid profiles of transformed *Prototheca moriformis* (UTEX 1435) comprising a mid-chain preferring thioesterase.

| Area % Fatty acid | U1 | Strain B | Strain C-1 | Strain C-2 | Strain C-3 | Strain C-4 | Strain C-5 |
|---|---|---|---|---|---|---|---|
| C10:0 | 0.01 | 5.53 | 11.37 | 11.47 | 10.84 | 11.13 | 11.12 |
| C12:0 | 0.04 | 31.04 | 46.63 | 46.47 | 45.84 | 45.80 | 45.67 |
| C14:0 | 1.27 | 15.99 | 15.14 | 15.12 | 15.20 | 15.19 | 15.07 |
| C16:0 | 27.20 | 12.49 | 7.05 | 7.03 | 7.30 | 7.20 | 7.19 |
| C18:0 | 3.85 | 1.30 | 0.71 | 0.72 | 0.74 | 0.74 | 0.74 |
| C18:1 | 58.70 | 24.39 | 10.26 | 10.41 | 10.95 | 11.31 | 11.45 |
| C18:2 | 7.18 | 7.79 | 7.05 | 6.93 | 7.30 | 6.88 | 7.01 |
| C10-C12 | 0.50 | 36.57 | 58.00 | 57.94 | 56.68 | 56.93 | 56.79 |

As shown in Table 6, the fatty acid profile of Strain B expressing CwTE2 showed increased composition of C10:0, C12:0, and C14:0 fatty acids and a decrease in C16:0, C18:0, and C18:1 fatty acids relative to the fatty acid profile of the untransformed UTEX 1435 strain. The impact of additional genetic modification on the fatty acid profile of the transformed strains, namely the expression of CnLPAAT in Strain B, is a still further increase in the composition of C10:0 and C12:0 fatty acids, a still further decrease in C16:0, C18:0, and C18:1 fatty acids, but no significant effect on the C14:0 fatty acid composition. These data indicate that the CnLPAAT shows substrate preference in the context of a microbial host organism.

The untransformed *P. moriformis* Strain A is characterized by a fatty acid profile comprising less than 0.5% C12 fatty acids and less than 1% C10-C12 fatty acids. In contrast, the fatty acid profile of Strain B expressing a *C. wrightii* thioesterase comprised 31% C12:0 fatty acids, with C10-C12 fatty acids comprising greater than 36% of the total fatty acids. Further, fatty acid profiles of Strain C, expressing a higher plant thioesterase and a CnLPAAT enzyme, comprised between 45.67% and 46.63% C12:0 fatty acids, with C10-C12% fatty acids comprising between 71 and 73% of total fatty acids. The result of expressing an exogenous thioesterase was a 62-fold increase in the percentage of C12 fatty acid present in the engineered microbe. The result of expressing an exogenous thioesterase and exogenous LPAAT was a 92-fold increase in the percentage of C12 fatty acids present in the engineered microbe.

The TAG fraction of oil samples extracted from Strains A, B, and C were analyzed for the sn-2 profile of their triacylglycerides. The TAGs were extracted and processed as described in Example 2 and analyzed as in Examples 1 and 2. The fatty acid composition and the sn-2 profiles of the TAG fraction of oil extracted from Strains A, B, and C (expressed as Area % of total fatty acids) are presented in Table 7. Values not reported are indicated as "n.r."

TABLE 7

Effect of LPAAT expression on the fatty acid composition and the sn-2 profile of TAGs produced from transformed *Prototheca moriformis* (UTEX 1435) comprising a mid-chain preferring thioesterase.

| | Strain | | | | | |
|---|---|---|---|---|---|---|
| Area % fatty | Strain A (untransformed) | | Strain B (pSZ1500) | | Strain C (pSZ1500 + pSZ2046) | |
| acid | FA | sn-2 profile | FA | sn-2 profile | FA | sn-2 profile |
| C10:0 | n.r. | n.r. | 11.9 | 14.2 | 12.4 | 7.1 |
| C12:0 | n.r. | n.r. | 42.4 | 25 | 47.9 | 52.8 |
| C14:0 | 1.0 | 0.6 | 12 | 10.4 | 13.9 | 9.1 |
| C16:0 | 23.9 | 1.6 | 7.2 | 1.3 | 6.1 | 0.9 |
| C18:0 | 3.7 | 0.3 | n.r | n.r. | 0.8 | 0.3 |
| C18:1 | 64.3 | 90.5 | 18.3 | 36.6 | 9.9 | 17.5 |
| C18:2 | 4.5 | 5.8 | 5.8 | 10.8 | 6.5 | 10 |
| C18:3 | n.r. | n.r. | n.r. | n.r. | 1.1 | 1.6 |

As shown in Table 7, the fatty acid composition of triglycerides (TAGs) isolated from Strain B expressing CwTE2 was increased for C10:0, C12:0, and C14:0 fatty acids and decrease in C16:0 and C18:1 fatty acids relative to the fatty acid profile of TAGs isolated from untransformed Strain A. The impact of additional genetic modification on the fatty acid profile of the transformed strains, namely the expression of CnLPAAT, was a still further increase in the composition of C10:0 and C12:0 fatty acids, a still further decrease in C16:0, C18:0, and C18:1 fatty acids, but no significant effect on the C14:0 fatty acid composition. These data indicate that expression of the exogenous CnLPAAT improves the midchain fatty acid profile of transformed microbes.

The untransformed *P. moriformis* Strain A is characterized by an sn-2 profile of about 0.6% C14, about 1.6% C16:0, about 0.3% C18:0, about 90% C18:1, and about 5.8% C18:2. In contrast to Strain A, Strain B, expressing a *C. wrightii* thioesterase is characterized by an sn-2 profile that is higher in midchain fatty acids and lower in long chain fatty acids. C12 fatty acids comprised 25% of the sn-2 profile of Strain B. The impact of additional genetic modification on the sn-2 profile of the transformed strains, namely the expression of CnLPAAT, was still a further increase in C12 fatty acids (from 25% to 52.8%), a decrease in C18:1 fatty acids (from 36.6% to 17.5%), and a decrease in C10:0 fatty acids. (The sn-2 profile composition of C14:0 and C16:0 fatty acids was relatively similar for Strains B and C.)

These data demonstrate the utility and effectiveness of polynucleotides permitting exogenous LPAAT expression to alter the fatty acid profile of engineered microorganisms, and in particular in increasing the concentration of C10:0 and C12:0 fatty acids in microbial cells. These data further demonstrate the utility and effectiveness of polynucleotides permitting exogenous thioesterase and exogenous LPAAT expression to alter the sn-2 profile of TAGs produced by microbial cells, in particular in increasing the C12 composition of sn-2 profiles and decreasing the C18:1 composition of sn-2 profiles.

Example 4: Thermal Behavior of Oils Produced from Recombinant Microalgae

FIGS. 1-14 include fatty acid profiles and melting curves of refined, bleached and deodorized oils from genetically engineered *Prototheca moriformis* strains. In some cases, modifications of the melting curves are obtained via genetic engineering. For example, some of the oils produced have shallower or sharper melting transitions relative to control microalgal oils (i.e., those produced from strains lacking a given genetic modification) or relative to widely available plant oils. In addition, FIG. 12 shows scanning calorimetry for a high palmitic oil when tempered by holding at room temperature for several days (lower trace) and for the same oil after performing the first scan (upper trace). The scans ranged from −60° C. to +50° C. with a heating rate of 10° C./minute. The differences between the two traces suggests that tempering of the oil caused a change in crystal structure within the oil.

Figure 10:
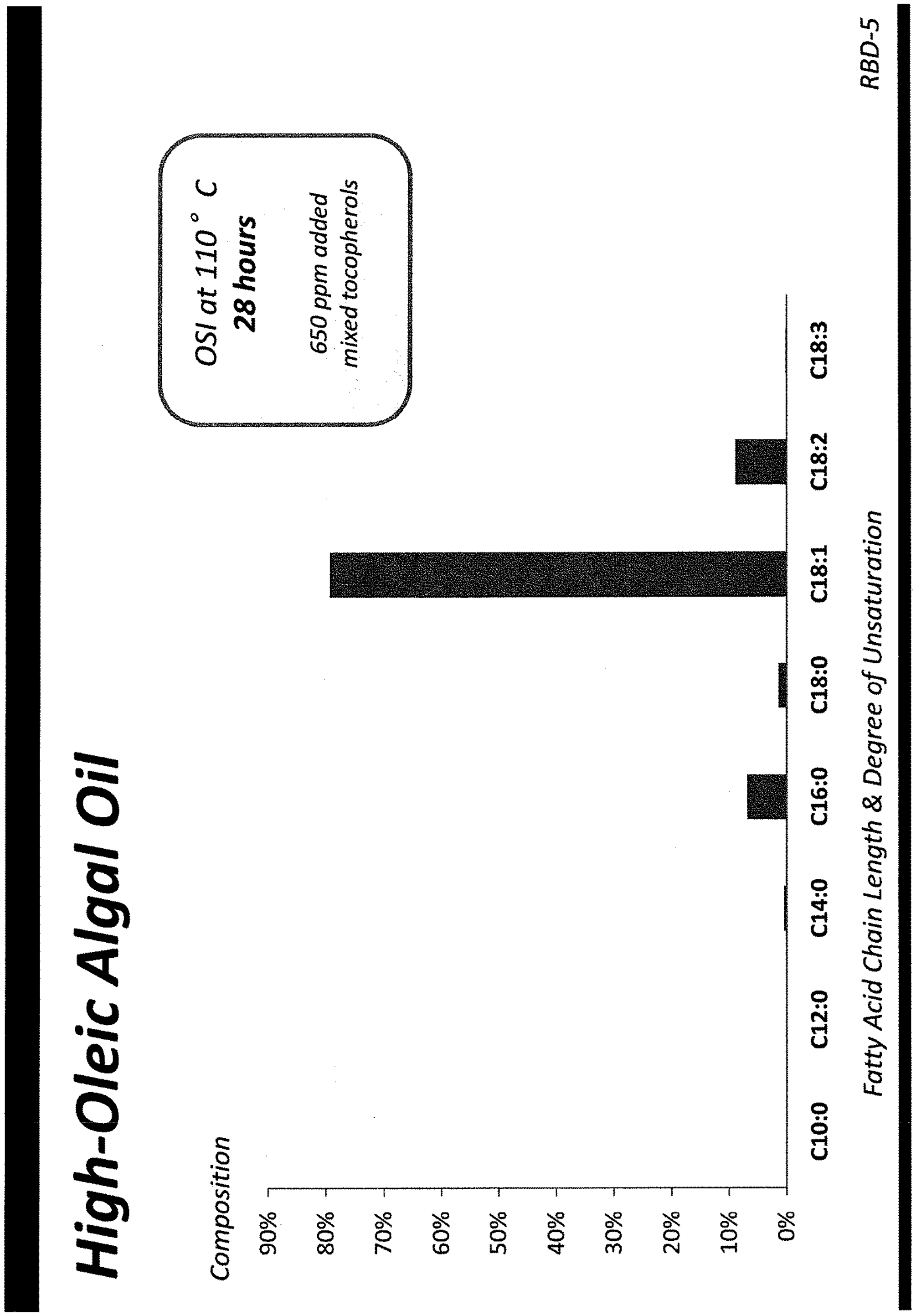
Figure 11:
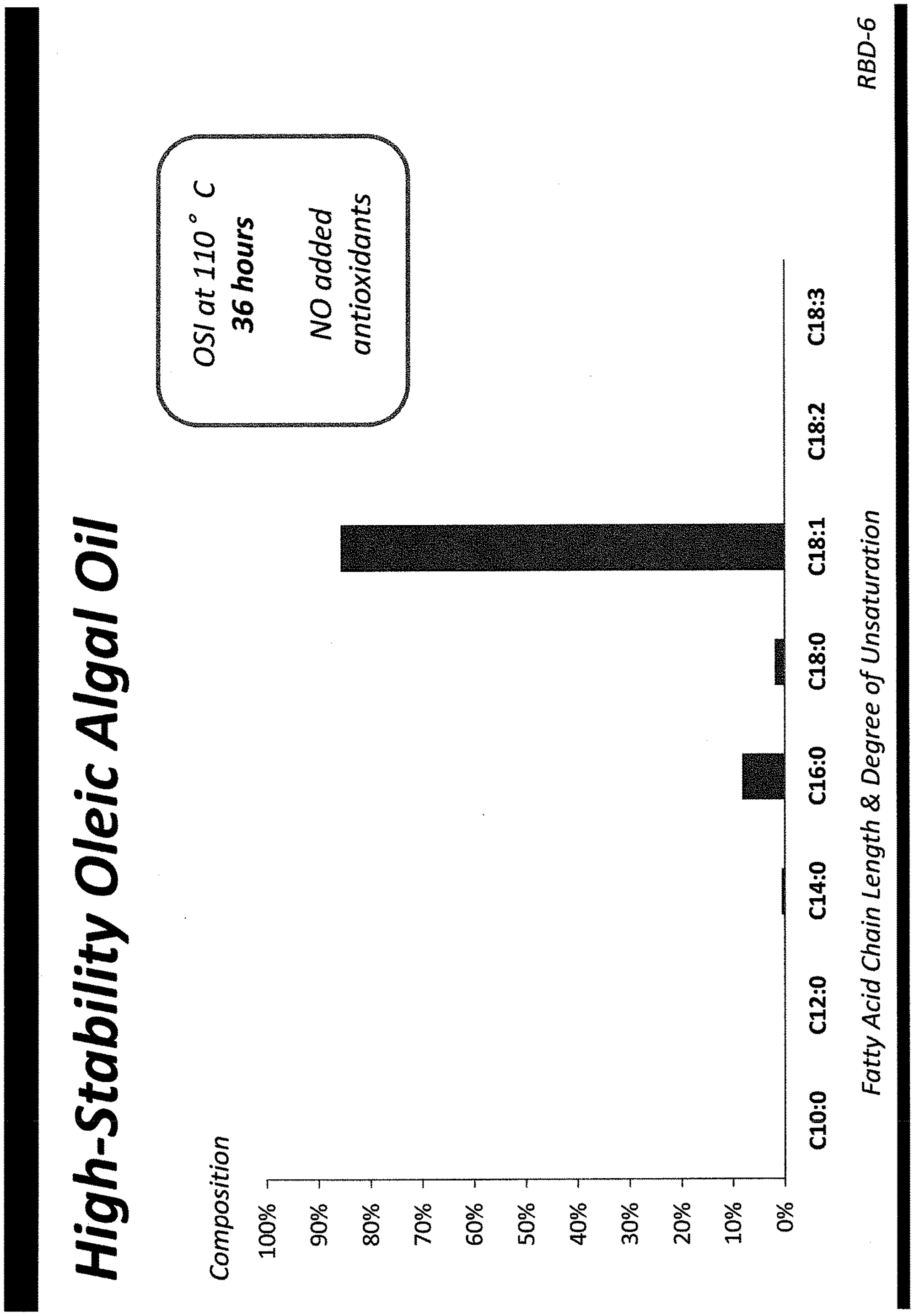
Figure 12:
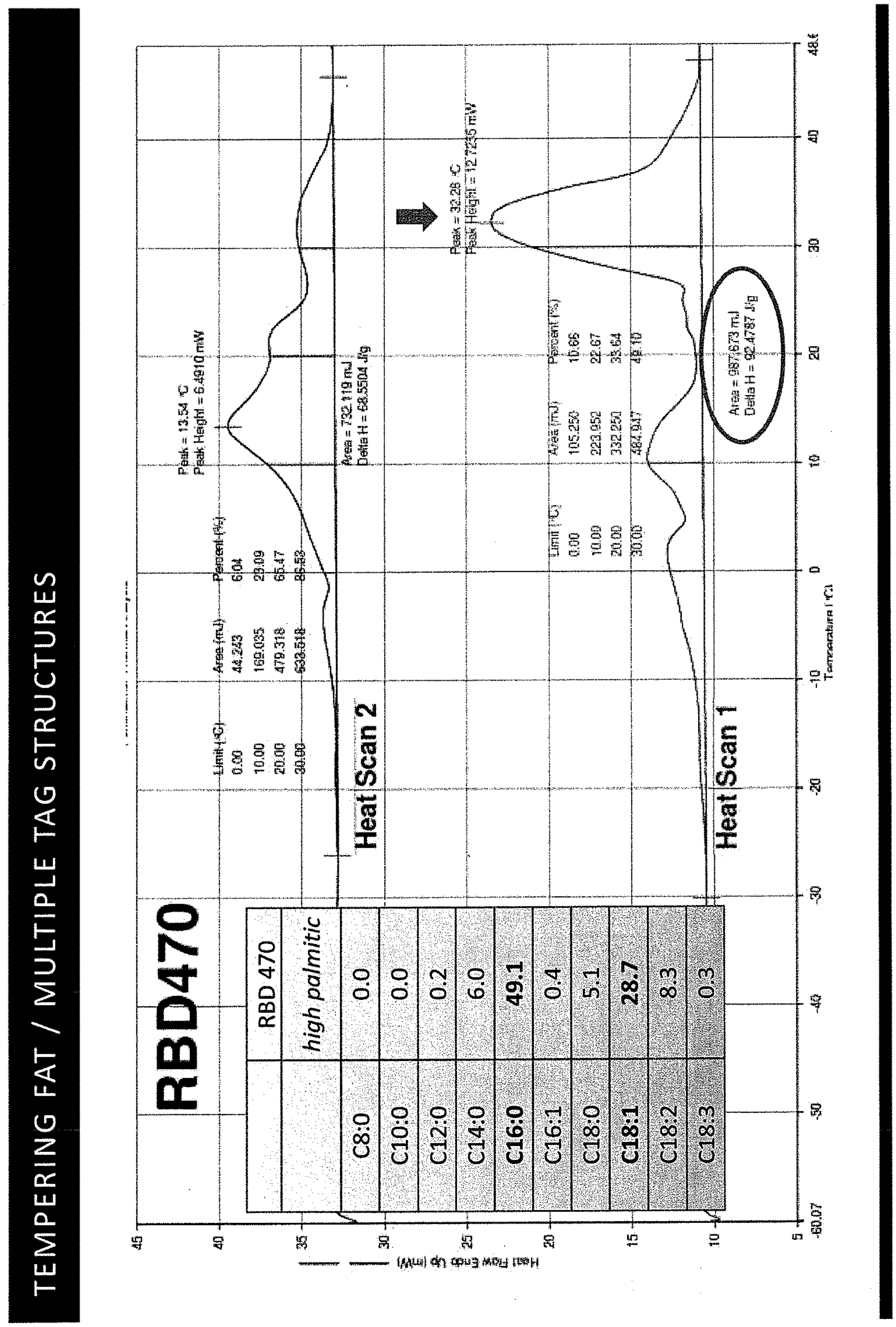
Figure 15:
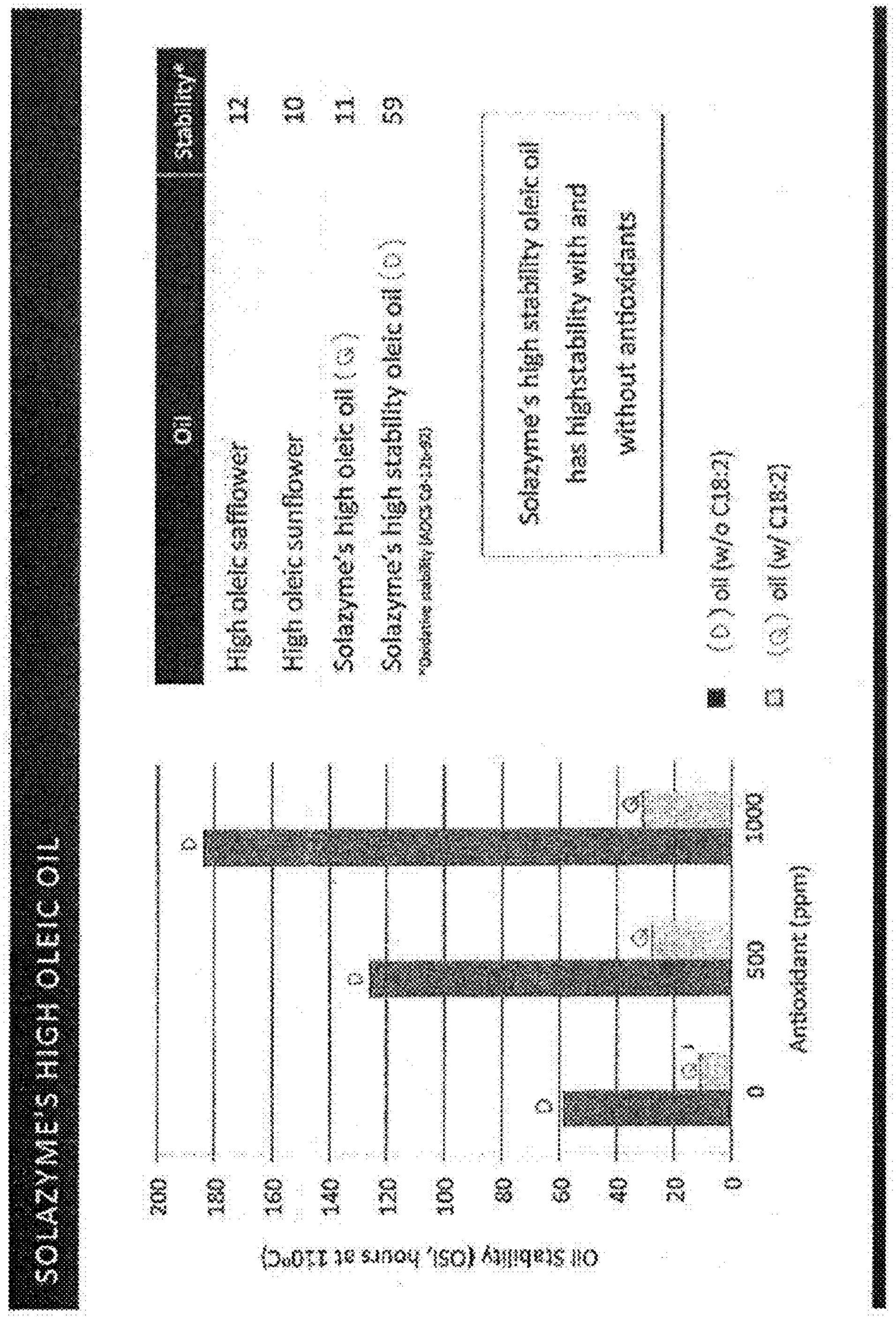
FIG. 15 shows the stability of different oils as a function of antioxidant concentration, as discussed in Example 5.

Also of note, FIGS. 10 and 11 show stability testing of RBD-5 and RBD 6. Remarkably, RBD-6, an oil with less than 0.1% 18:2 and 18:3 fatty acids was substantially stable as measured by the oxidative stability index (AOCS Method Cd 12b-92) even after 36 hours of heating at 110° C.

Table 8, below, gives details of the genetic engineering of the strains identified in FIGS. 1-13.

TABLE 8

Genetically engineered strains.

| | |
|---|---|
| RB Z | *Ulmus Americana* thioesterase |
| RBD-1 | *Cuphea wrightii* FATB2 thioesterase driven by amt03 |
| RBD-2 | *Ulmus americana* thioesterase |
| RBD-3 | Native *C. hookeriana* C16:0-specific thioesterase with amt03 promoter |
| RBD Y | *Ulmus Americana* thioesterase with Btub promoter |
| RBD X | SAD2B knockout with native *C wrightii* FAT2B thioesterase, amt03 promoter |
| RBD W | SAD2B KO with Native *C. wrightii* FATB2 driven by amt03 at insertion site |
| RBD-4 | control strain |
| RBD-5 | FATA-1 knockout with *Carthamus oleate* sp. TE driven by amt03 promoter at insertion site |
| RBD-6 | FADc knockout with *Carthamus tinctorius* oleoyl thioesterase |

Example 5: Characteristics of Processed Oil Produced from Engineered Microorganisms Methods and effects of transforming *Prototheca moriformis* (UTEX 1435) with transformation vector pSZ1500 (SEQ ID NO: 17) have been previously described in PCT Application Nos. PCT/US2011/038463, PCT/US2011/038464, and PCT/US2012/023696.

A classically mutagenized (for higher oil production) derivative of *Prototheca moriformis* (UTEX 1435), Strain A, was transformed with pSZ1500 according to biolistic transformation methods as described in PCT/US2009/066141, PCT/US2009/066142, PCT/US2011/038463, PCT/US2011/038464, and PCT/US2012/023696. pSZ1500 comprised nucleotide sequence of the *Carthamus tinctorius* oleyl-thioesterase (CtOTE) gene, codon-optimized for expression in *P. moriformis* UTEX 1435. The pSZ1500 expression construct included 5' (SEQ ID NO: 18) and 3' (SEQ ID NO: 19) homologous recombination targeting sequences (flanking the construct) to the FADc genomic region for integration into the nuclear genome and a *S. cerevisiae* suc2 sucrose invertase coding region under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selection marker. The CtOTE coding region was under the control of the *P. moriformis* Amt03 promoter/5'UTR (SEQ ID NO: 8) and *C. vulgaris* nitrate reductase 3'UTR, and the native transit peptide was replaced with the *C. protothecoides* stearoyl-ACP desaturase transit peptide (SEQ ID NO: 9). The protein coding regions of CtOTE and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ1500 transformants of Strain A were selected on agar plates containing sucrose as a sole carbon source, clonally purified, and a single engineered line, Strain D was selected for analysis. Strain D was grown as described in PCT/US2009/066141, PCT/US2009/066142, PCT/US2011/038463, PCT/US2011/038464, and PCT/US2012/023696. Hexane extraction of the oil from the generated biomass was then performed using standard methods, and the resulting triglyceride oil was determined to be free of residual hexane. Other methods of extraction of oil from microalgae using an expeller press are described in PCT Application No. PCT/US2010/031108 and are hereby incorporated by reference.

Different lots of oil extracted from biomass of Strain D were refined, bleached, and deodorized using standard vegetable oil processing methods. These procedures generated oil samples RBD437, RBD469, RBD501, RBD 502, RBD503, and RBD529, which were subjected to analytical testing protocols according to methods defined through the American Oil Chemists' Society, the American Society for Testing and Materials, and the International Organization for Standardization. The results of these analyses are summarized below in Tables 9-14.

TABLE 9

Analytical results for oil sample RBD469.

| Method Number | Test Description | Results | Units |
|---|---|---|---|
| AOCS Ca 3a-46 | Insoluble impurities | <0.01 | % |
| AOCS Ca 5a-40 | Free Fatty Acids (Oleic) | 0.02 | % |
| AOCS Ca 5a-40 | Acid Value | 0.04 | mg KOH/g |
| AOCS CA 9f-57 | Neutral oil | 98.9 | % |
| D97 | Cloud Point | −15 | deg C. |
| D97 | Pour Point | −18 | deg C. |
| | Karl Fischer Moisture | 0.01 | % |
| AOCS Cc 13d-55 (modified) | Chlorophyll | <0.01 | ppm |
| | Iodine Value | 78.3 | g $I_2$/100 g |
| AOCS Cd 8b-90 | Peroxide Value | 0.31 | meq/kg |

TABLE 9-continued

Analytical results for oil sample RBD469.

| Method Number | Test Description | Results | Units |
|---|---|---|---|
| ISO 6885 | p-Anisidine Value | 0.65 | |
| AOCS Cc 18-80 | Dropping Melting point (Mettler) | 6.2 | deg C. |
| AOCS Cd 11d-96 | Tricylglicerides | 98.6 | % |
| AOCS Cd 11d-96 | Monoglyceride | <0.01 | % |
| AOCS Cd 11d-96 | Diglicerides | 0.68 | % |
| AOCS Cd 20-91 | Total Polar Compounds | 2.62 | % |
| IUPAC, 2.507 and 2.508 | Oxidized & Polymerized Tricylglicerides | 17.62 | % |
| AOCS Cc 9b-55 | Flash Point | 244 | deg C. |
| AOCS Cc 9a-48 | Smoke Point | 232 | deg C. |
| AOCS Cd 12b-92 | Oxidataive Stability Index Rancimat (110° C.) | 31.6 | hours |
| AOCS Ca 6a-40 | Unsaponified Matter | 2.28 | % |

RBD469 oil was analyzed for trace element content, solid fat content, and Lovibond color according to AOCS methods. Results of these analyses are presented below in Table 10, Table 10, and Table 11.

TABLE 10

ICP Elemental Analysis of RBD469 oil.

| Method Number | Test Description | Results in ppm |
|---|---|---|
| AOCS Ca 20-99 and | Phosphorus | 1.09 |
| AOCS Ca 17-01 | Calcium | 0.1 |
| (modified) | Magnesium | 0.04 |
| | Iron | <0.02 |
| | Sulfur | 28.8 |
| | Copper | <0.05 |
| | Potassium | <0.50 |
| | Sodium | <0.50 |
| | Silicon | 0.51 |
| | Boron | 0.06 |
| | Aluminum | <0.20 |
| | Lead | <0.20 |
| | Lithium | <0.02 |
| | Nickel | <0.20 |
| | Vanadium | <0.05 |
| | Zinc | <0.02 |
| | Arsenic | <0.20 |
| | Mercury | <0.20 |
| | Cadmium | <0.03 |
| | Chromium | <0.02 |
| | Manganese | <0.05 |
| | Silver | <0.05 |
| | Titanium | <0.05 |
| | Selenium | <0.50 |
| UOP779 | Chloride organic | <1 |
| UOP779 | Chloride inorganic | 7.24 |
| AOCS Ba 4e-93 | Nitrogen | 6.7 |

TABLE 11

Solid Fat Content of RBD469 Oil

| Method Number | Solid Fat Content | Result |
|---|---|---|
| AOCS Cd 12b-93 | Solid Fat Content 10° C. | 0.13% |
| AOCS Cd 12b-93 | Solid Fat Content 15° C. | 0.13% |
| AOCS Cd 12b-93 | Solid Fat Content 20° C. | 0.28% |
| AOCS Cd 12b-93 | Solid Fat Content 25° C. | 0.14% |
| AOCS Cd 12b-93 | Solid Fat Content 30° C. | 0.08% |
| AOCS Cd 12b-93 | Solid Fat Content 35° C. | 0.25% |

TABLE 12

Lovibond Color of RBD469 Oil

| Method Number | Color | Result | Unit |
|---|---|---|---|
| AOCS Cc 13j-97 | red | 2 | Unit |
| AOCS Cc 13j-97 | yellow | 27 | Unit |

RBD469 oil was subjected to transesterification to produce fatty acid methyl esters (FAMEs). The resulting FAME profile of RBD469 is shown in Table 12.

TABLE 13

FAME Profile of RBD469 Oil

| Fatty Acid | Area % |
|---|---|
| C10 | 0.01 |
| C12:0 | 0.04 |
| C14:0 | 0.64 |
| C15:0 | 0.08 |
| C16:0 | 8.17 |
| C16:1 iso | 0.39 |
| C16:1 | 0.77 |
| C17:0 | 0.08 |
| C18:0 | 1.93 |
| C18:1 | 85.88 |
| C18:1 iso | 0.05 |
| C18:2 | 0.05 |
| C20:0 | 0.3 |
| C20:1 | 0.06 |
| C20:1 | 0.44 |
| C22:0 | 0.11 |
| C23:0 | 0.03 |
| C24:0 | 0.1 |
| Total FAMEs Identified | 99.13 |

The oil stability indexes (OSI) of 6 RBD oil samples without supplemented antioxidants and 3 RBD oil samples supplemented with antioxidants were analyzed according to the Oil Stability Index AOCS Method Cd 12b-92. Shown in Table 14 are the results of OSI AOCS Cd 12b-92 tests, conducted at 110° C., performed using a Metrohm 873 Biodiesel Rancimat. Results, except where indicated with an asterisks (*), are the average of multiple OSI runs. Those samples not analyzed are indicated (NA).

TABLE 14

Oil Stability Index at 110° C. of RBD oil samples with and without antioxidants.

| Antioxidant | Antioxidant | OSI (hours) for each RBD Sample | | | | | |
|---|---|---|---|---|---|---|---|
| added | Concentration | RBD437 | RBD469 | RBD502 | RBD501 | RBD503 | RBD529 |
| None | 0 | 65.41 | 38.33 | 72.10 | 50.32 | 63.04 | 26.68 |
| Tocopherol & Ascorbyl Palmitate | 35 ppm/16.7 ppm | 77.72 | 48.60 | 82.67 | NA | NA | NA |

TABLE 14-continued

Oil Stability Index at 110° C. of RBD oil samples with and without antioxidants.

| Antioxidant added | Antioxidant Concentration | OSI (hours) for each RBD Sample RBD437 | RBD469 | RBD502 | RBD501 | RBD503 | RBD529 |
|---|---|---|---|---|---|---|---|
| Tocopherol & Ascorbyl Palmitate | 140 ppm/66.7 ppm | 130.27 | 81.54* | 211.49* | NA | NA | NA |
| Tocopherol & Ascorbyl Palmitate | 1050 ppm/500 ppm | >157* | >144 | 242.5* | NA | NA | NA |
| Tocopherol | 50 ppm | NA | 46.97 | NA | NA | NA | NA |
| TBHQ | 20 ppm | 63.37 | 37.4 | NA | NA | NA | NA |

The untransformed *P. moriformis* (UTEX 1435) acid profile comprises less than 60% C18:1 fatty acids and greater than 7% C18:2 fatty acids. In contrast, Strain D (comprising pSZ1500) exhibited fatty acid profiles with an increased composition of C18:1 fatty acids (to above 85%) and a decrease in C18:2 fatty acids (to less than 0.06%). Upon refining, bleaching, and degumming, RBD oils samples prepared from the oil made from strain E exhibited OSI values>26 hrs. With addition of antioxidants, the OSI of RBD oils prepared from oils of Strain D increased from 48.60 hours to greater than 242 hours. In other experiments, OSI values of over 400 hours were achieved. Additional properties of a low polyunsaturated oil according to embodiments of the invention are given in FIG. 16.

Example 6: Improving the Levels of Oleic Acid of Engineered Microbes Through Allelic Disruption of a Fatty Acid Desaturase and an Acyl-ACP Thioesterase This example describes the use of a transformation vector to disrupt a FATA locus of a *Prototheca moriformis* strain previously engineered for high oleic acid and low linoleic acid production. The transformation cassette used in this example comprised a selectable marker and nucleotide sequences encoding a *P. moriformis* KASII enzyme to engineer microorganisms in which the fatty acid profile of the transformed microorganism has been altered for further increased oleic acid and lowered palmitic acid levels.

Strain D, described in Example 5 and in PCT/US2012/023696, is a classically mutagenized (for higher oil production) derivative of *P. moriformis* (UTEX 1435) subsequently transformed with the transformation construct pSZ1500 (SEQ ID NO: 17) according to biolistic transformation methods as described in PCT/US2009/066141, PCT/US2009/066142, PCT/US2011/038463, PCT/US2011/038464, and PCT/US2012/023696. This strain was used as the host for transformation with construct pSZ2276 to increase expression of a KASII enzyme while concomitantly ablating an endogenous acyl-ACP thioesterase genetic locus to generate Strain E. The pSZ2276 transformation construct included 5' (SEQ ID NO: 20) and 3' (SEQ ID NO: 21) homologous recombination targeting sequences (flanking the construct) to the FATA1 genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selection marker. The *P. moriformis* KASII protein coding region was under the control of the *P. moriformis* Amt03 promoter/5'UTR (SEQ ID NO: 8) and *C. vulgaris* nitrate reductase 3'UTR, and the native transit peptide of the KASII enzyme was replaced with the *C. protothecoides* stearoyl-ACP desaturase transit peptide (SEQ ID NO: 9). The codon-optimized sequence of PmKASII (*Prototheca moriformis* KASII) comprising a *C. protothecoides* S106 stearoyl-ACP desaturase transit peptide is provided the sequence listings as SEQ ID NO: 24. SEQ ID NO: 25 provides the protein translation of SEQ ID NO: 24. The protein coding regions of PmKASII and suc2 were codon optimized to reflect the codon bias inherent in *P. moriformis* UTEX 1435 nuclear genes as described in PCT/U52009/066141, PCT/US2009/066142, PCT/US2011/038463, PCT/US2011/038464, and PCT/US2012/023696.

Primary pSZ2276 transformants of Strain D were selected on agar plates lacking thiamine, clonally purified, and a single engineered line, strain E was selected for analysis. Strain E was cultivated under heterotrophic lipid production conditions at pH5.0 and pH7.0 as described in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The fatty acid profiles (expressed as Area % of total fatty acids) from the transgenic line arising from transformation with pSZ2276 into Strain D are shown in Table 15.

TABLE 15

Fatty acid profiles of *Prototheca moriformis* (UTEX 1435) Strains A, D, and E engineered for increased oleic acid and lowered linoleic acid levels.

| Strain | Transformation Construct(s) | pH | Area % Fatty Acid C16:0 | C18:0 | C18:1 | C18:2 | C20:1 |
|---|---|---|---|---|---|---|---|
| Strain A | None | pH 5 | 26.6 | 3.3 | 60.5 | 6.7 | 0.07 |
| Strain A | None | pH 7 | 28.3 | 4.1 | 58 | 6.5 | 0.06 |
| Strain D | pSZ1500 | pH 5 | 17 | 3.6 | 77.1 | 0.01 | 0.14 |

TABLE 15-continued

Fatty acid profiles of *Prototheca moriformis* (UTEX 1435) Strains A, D, and E engineered for increased oleic acid and lowered linoleic acid levels.

| Strain | Transformation Construct(s) | pH | Area % Fatty Acid C16:0 | C18:0 | C18:1 | C18:2 | C20:1 |
|---|---|---|---|---|---|---|---|
| Strain D | pSZ1500 | pH 7 | 19.5 | 5.3 | 72.6 | 0.01 | 0.09 |
| Strain E | pSZ1500 + pSZ2276 | pH 5 | 4.1 | 2.36 | 88.5 | 0.04 | 3.1 |
| Strain E | pSZ1500 + pSZ2276 | pH 7 | 2.1 | 7.8 | 87.9 | 0.01 | 0.5 |

As shown in Table 15, targeted interruption of FADc alleles with a CtOTE expression cassette impacted the fatty acid profiles of transformed microorganisms. Fatty acid profiles of Strain D (comprising the pSZ1500 transformation vector) showed increased composition of C18:1 fatty acids with a concomitant decrease in C16:0 and C18:2 fatty acids relative to Strain A. Subsequent transformation of Strain D with pSZ2276 to overexpress a *P. moriformis* (UTEX 1435) KASII protein while concomitantly ablating a FATA genetic locus (thereby generating Strain E) resulted in still further impact on the fatty acid profiles of the transformed microorganisms. Fatty acid profiles of Strain E showed increased composition of C18:1 fatty acids, with a further decrease in C16:0 fatty acids relative to Strains A and D. Propagation of Strain E in culture conditions at pH 7, to induce expression from the Amt03 promoter, resulted in a fatty acid profile that was higher in C18:0 and C18:1 fatty acids and lower in C16:0 fatty acids, relative to the same strain cultured at pH 5.

These data demonstrate the utility of multiple genetic modifications to impact the fatty acid profile of a host organism for increased levels of oleic acid with concomitant decreased levels of linoleic acid and palmitic acid. Further, this example illustrates the use of recombinant polynucleotides to target gene interruption of an endogenous FATA allele with a cassette comprising a pH-regulatable promoter to control expression of an exogenous KASII protein-coding region in order to alter the fatty acid profile of a host microbe.

Example 7: Conditional Expression of a Fatty Acid Desaturase

This example describes the use of a transformation vector to conditionally express a delta 12 fatty acid desaturase (FADs) in a *Prototheca moriformis* strain previously engineered for high oleic acid and very low linoleic acid production in both seed and lipid productivity stages of propagation. Very low linoleic acid levels in cell oils are sought for use in certain applications. However, absence of linoleic acid during cell division phase ("seed stage") of a host microbe is disadvantageous. Linoleic acid may be supplemented to the seed medium to hasten cell division and not added during lipid production, but this addition imposes unwanted costs. To overcome this challenge, a transformation cassette was constructed for regulated expression of a FAD2 enzyme such that levels of linoleic acids sufficient for cell division could be achieved and oil with very low levels of linoleic acids could be produced during the oil production phase of culture of a microorganism. The transformation cassette used in this example comprised a selectable marker, a pH-regulatable promoter, and nucleotide sequences encoding a *P. moriformis* FAD2 enzyme to engineer microorganisms in which the fatty acid profile of the transformed microorganism has been altered for increased oleic acid production and regulatable linoleic acid production.

Strain D, described in Examples 5, 6, and in PCT/US2012/023696, is a classically mutagenized (for higher oil production) derivative of *P. moriformis* (UTEX 1435) subsequently transformed with the transformation construct pSZ1500 (SEQ ID NO: 17) according to biolistic transformation methods as described in PCT/US2009/066141, PCT/US2009/066142, PCT/US2011/038463, PCT/US2011/038464, and PCT/US2012/023696. This strain was used as the host for transformation with construct pSZ2413 to introduce a pH-driven promoter for regulation of a *P. moriformis* FAD2 enzyme. The pSZ2413 transformation construct included 5' (SEQ ID NO: 1) and 3' (SEQ ID NO: 2) homologous recombination targeting sequences (flanking the construct) to the 6S genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selection marker. The *P. moriformis* FAD2 protein coding region was under the control of the *P. moriformis* Amt03 promoter/5'UTR (SEQ ID NO: 8) and *C. vulgaris* nitrate reductase 3'UTR. The codon-optimized sequence of PmFAD2 is provided the sequence listings as SEQ ID NO: 26. SEQ ID NO: 27 provides the protein translation of SEQ ID NO: 26. The protein coding regions of PmFAD2 and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ2413 transformants of Strain D were selected on agar plates lacking thiamine, clonally purified, and isolates of the engineered line, Strain F were selected for analysis. These isolates were cultivated under heterotrophic lipid production conditions at pH7.0 (to activate expression of FAD2 from the PmAmt03 promoter) and at pH5.0, as described in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The resulting profile of C18:2 fatty acids (expressed in Area %) from nine representative isolates of transgenic Strain F (F-1 through F-9) arising from transformation with pSZ2413 into Strain D are shown in Table 16.

TABLE 16

C18:2 fatty acid profiles of *Prototheca moriformis* (UTEX 1435) Strains A, D, and F.

| Strain | Transformation Construct (s) | Area % C18:2 pH 5.0 | pH 7.0 |
|---|---|---|---|
| A | None | 6.07 | 7.26 |
| D | pSZ1500 | 0.01 | 0.01 |
| F-1 | pSZ1500 + pSZ2413 | 0.37 | 5.29 |
| F-2 | pSZ1500 + pSZ2413 | 0.45 | 6.87 |
| F-3 | pSZ1500 + pSZ2413 | 0.50 | 6.79 |
| F-4 | pSZ1500 + pSZ2413 | 0.57 | 5.06 |
| F-5 | pSZ1500 + pSZ2413 | 0.57 | 7.58 |
| F-6 | pSZ1500 + pSZ2413 | 0.60 | 6.88 |
| F-7 | pSZ1500 + pSZ2413 | 0.62 | 6.52 |
| F-8 | pSZ1500 + pSZ2413 | 0.63 | 5.79 |
| F-9 | pSZ1500 + pSZ2413 | 0.77 | 4.53 |

As shown in Table 16 the impact of regulated expression of the PmFAD2 enzyme, effected though strain culture at different pH levels, is a clear increase in the composition of C18:2 fatty acids in the transformed microorganism. Linoleic acid comprises about 6% to about 7.3% of fatty acids of Strain A. In contrast, Strain D (comprising the pSZ1500 transformation vector to ablate both FAD2 alleles) is characterized by a fatty acid profile of 0.01% linoleic acid. Transformation of Strain D with pSZ2413 to generate Strain F results in a recombinant microbe in which the production of linoleic acid is regulated by the Amt03 promoter. Propagation of Strain F isolates in culture conditions at pH 7, to induce FAD2 expression from the Amt03 promoter, resulted in a fatty acid profile characterized by about 4.5% to about 7.5% linoleic acid. In contrast, propagation of Strain F isolates in culture conditions at pH 5 resulted in a fatty acid profile characterized by about 0.33 to about 0.77% linoleic acid.

These data demonstrate the utility of and effectiveness of recombinant polynucleotides permitting conditional expression of a FAD2 enzyme to alter the fatty acid profile of engineered microorganisms, and in particular in regulating the production of C18:2 fatty acids in microbial cells.

Example 8: Analysis of Regiospecific Profile

LC/MS TAG distribution analyses were carried out using a Shimadzu Nexera ultra high performance liquid chromatography system that included a SIL-30AC autosampler, two LC-30AD pumps, a DGU-20A5 in-line degasser, and a CTO-20A column oven, coupled to a Shimadzu LCMS 8030 triple quadrupole mass spectrometer equipped with an APCI source. Data was acquired using a Q3 scan of m/z 350-1050 at a scan speed of 1428 u/sec in positive ion mode with the CID gas (argon) pressure set to 230 kPa. The APCI, desolvation line, and heat block temperatures were set to 300, 250, and 200° C., respectively, the flow rates of the nebulizing and drying gases were 3.0 L/min and 5.0 L/min, respectively, and the interface voltage was 4500 V. Oil samples were dissolved in dichloromethane-methanol (1:1) to a concentration of 5 mg/mL, and 0.8 μL of sample was injected onto Shimadzu Shim-pack XR-ODS III (2.2 μm, 2.0×200 mm) maintained at 30° C. A linear gradient from 30% dichloromethane-2-propanol (1:1)/acetonitrile to 51% dichloromethane-2-propanol (1:1)/acetonitrile over 27 minutes at 0.48 mL/min was used for chromatographic separations.

Example 9: Engineering Microbes for Increased Production of SOS, POP, and POS Triacylglycerides This example describes the use of recombinant polynucleotides that encode a C18:0-preferring *Brassica napus* thioesterase (BnOTE) enzyme to engineer a microorganism in which the triacylglyceride distribution of the transformed microorganism has been enriched in SOS, POS, and POP triacylglycerides.

A classically mutagenized strain of *Prototheca moriformis* (UTEX 1435), Strain A, was initially transformed with the plasmid construct pSZ1358 according to biolistic transformation methods as described in PCT/US2009/066141, PCT/US2009/066142, PCT/US2011/038463, PCT/US2011/038464, and PCT/US2012/023696. pSZ1358, described in PCT/US2012/023696, hereby incorporated by reference, comprised the coding sequence of the *Brassica napus* thioesterase (BnOTE) thioesterase (SEQ ID NO: 28), 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4), to express the protein sequence given in SEQ ID NO: 3, under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. The BnOTE protein coding sequence to express the protein sequence given in SEQ ID NO: 29, was under the control of the *P. moriformis* Amt03 promoter/5'UTR (SEQ ID NO: 8) and *C. vulgaris* nitrate reductase 3'UTR. The protein coding regions of BnOTE and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ1358 transformants of Strain A were selected on agar plates containing sucrose as a sole carbon source, clonally purified, and single engineered line, Strain G was selected for analysis. Strain G was cultivated under heterotrophic lipid production conditions at pH7.0 (to activate expression of BnOTE from the PmAmt03 promoter) as described in PCT/U52009/066141, PCT/US2009/066142, PCT/US2011/038463, PCT/US2011/038464, and PCT/US2012/023696. Oil samples obtained from Strain A and Strain G were analyzed for fatty acid composition using methods described in Examples 1 and 2, and, using the methods described in Example 8, for the regiospecificity of triacylglycerides in the oil. Fatty acid profiles of TAGs isolated from Strain A and G are shown in Table 17. Table 18 presents the regiospecificity profile of POP, POS, and SOS TAGs present in oil samples from Strain A and G.

TABLE 17

Effect of BnOTE expression on the fatty acid composition and the sn-2 profile of TAGs produced from transformed *Prototheca moriformis*.

| Area % Fatty acid | Strain A FA profile | Strain G (pSZ1358) FA profile |
|---|---|---|
| C10:0 | n.r. | 0.5 |
| C12:0 | n.r. | 0.5 |
| C14:0 | 1.0 | 1.3 |
| C16:0 | 23.9 | 25.8 |

TABLE 17-continued

Effect of BnOTE expression on the fatty acid composition and the sn-2 profile of TAGs produced from transformed *Prototheca moriformis*.

| Area % Fatty acid | Strain A FA profile | Strain G (pSZ1358) FA profile |
|---|---|---|
| C18:0 | 3.7 | 30.4 |
| C18:1 | 64.3 | 30.2 |
| C18:2 | 4.5 | 8.8 |
| C18:3 α | n.r. | 0.4 |

TABLE 18

Effect of BnOTE expression on the regiospecific profile of POP, POS, and SOS TAGs produced from transformed *Prototheca moriformis*.

| | Strain A (untransformed) | | Strain G (pSZ1358) | | Cocoa Butter | |
|---|---|---|---|---|---|---|
| TAG | Area % | Normalized Area % | Area % | Normalized Area % | Area % | Normalized Area % |
| POP | 13.09 | 76.8 | 10.6 | 23.5 | 17.9 | 22.1 |
| POS | 3.51 | 20.5 | 21.0 | 46.6 | 39.2 | 48.4 |
| SOS | 0.45 | 2.6 | 13.5 | 29.9 | 23.9 | 29.5 |
| total | 17.05 | 100 | 45.0 | 100 | 81.1 | 100 |

As shown in Table 17, the fatty acid composition of TAGs isolated from Strain G expressing BnOTE was markedly increased for C18:0 fatty acids (from 3.7% to 30.4%) and decreased in C18:1 fatty acids (from 64.3% to 30.2%) relative to the fatty acid profile of TAGs isolated from untransformed Strain A. The fatty acid composition of TAGs isolated from Strain A was characterized by about 23.9% palmitic acid, 3.7% stearic acid, and 64.3% oleic acid, a ratio for P:S:O of about 6.5:1:17.4. In contrast, the fatty acid composition of TAGs isolated from Strain G was characterized by about 25.8% palmitic acid, 30.4% stearic acid, and 30.2% oleic acid, a ratio for P:O:S of about 1:1.18:1.17.

The impact of expression of a C18:0 preferring thioesterase on the regiospecific profile of POP, POS, and SOS TAGs of oils produced from the transformed microorganism was an increase in all three TAGs as a proportion of the total TAGs present in the oil. As shown in Table 18, the sum of POP+POS+SOS TAGs accounted for 45% of the TAGs produced by Strain G, whereas POP, POS, and SOS TAGs summed to only about 17% of TAGs produced in Strain A. The percentages of POP, POS and SOS of strain G are compared to Cocoa butter in Table 18. As can be seen, ratios of POP, POS and SOS of Strain G are very similar to the ratios observed in cocoa butter.

These data demonstrate the utility and effectiveness of polynucleotides permitting exogenous thioesterase expression to alter the fatty acid and regiospecific profiles of TAGs of engineered microorganisms, in particular to increase the distribution of POP, POS, and SOS TAGs.

Examples 10-33: Engineering of Microorganisms

Examples 10-33 below describe the engineering of various microorganisms in accordance with the present invention. To alter the fatty acid profile of a microorganism, microorganisms can be genetically modified wherein endogenous or exogenous lipid biosynthesis pathway enzymes are expressed, overexpressed, or attenuated. Steps to genetically engineer a microbe to alter its fatty acid profile as to the degree of fatty acid unsaturation and to decrease or increase fatty acid chain length comprise the design and construction of a transformation vector (e.g., a plasmid), transformation of the microbe with one or more vectors, selection of transformed microbes (transformants), growth of the transformed microbe, and analysis of the fatty acid profile of the lipids produced by the engineered microbe.

Transgenes that alter the fatty acid profiles of host organisms can be expressed in numerous eukaryotic microbes. Examples of expression of transgenes in eukaryotic microbes including *Chlamydomonas reinhardtii, Chlorella ellipsoidea, Chlorella saccarophila, Chlorella vulgaris, Chlorella kessleri, Chlorella sorokiniana, Haematococcus pluvialis, Gonium pectorale, Volvox carteri, Dunaliella tertiolecta, Dunaliella viridis, Dunaliella salina, Closterium peracerosum-strigosum-littorale* complex, *Nannochloropsis* sp., *Thalassiosira pseudonana, Phaeodactylum tricornutum, Navicula saprophila, Cylindrotheca fusiformis, Cyclotella cryptica, Symbiodinium microadriacticum, Amphidinium* sp., *Chaetoceros* sp., *Mortierella alpina*, and *Yarrowia lipolytica* can be found in the scientific literature. These expression techniques can be combined with the teachings of the present invention to produce engineered microorganisms with altered fatty acid profiles.

Transgenes that alter the fatty acid profiles of host organisms or alter the regiospecific distribution of glycerolipids produced by host organisms can also be expressed in numerous prokaryotic microbes. Examples of expression of transgenes in oleaginous microbes including *Rhodococcus opacus* can be found in the literature. These expression techniques can be combined with the teachings of the present invention to produce engineered microorganisms with altered fatty acid profiles.

TABLES 19A-D

Codon preference listing.

| Amino Acid | Codon | *Chlorella sorokiniana* | *Chlorella vulgaris* | *Chlorella ellipsoidea* | *Chlorella kessleri* | *Dunaliella tertiolecta* | *Volvox carteri* | *Haematococcus pluvialis* |
|---|---|---|---|---|---|---|---|---|
| Ala | GCG | 0.20 | 0.25 | 0.15 | 0.14 | 0.09 | 0.25 | 0.21 |
| Ala | GCA | 0.05 | 0.24 | 0.32 | 0.10 | 0.17 | 0.13 | 0.27 |
| Ala | GCT | 0.12 | 0.16 | 0.26 | 0.18 | 0.31 | 0.26 | 0.17 |
| Ala | GCC | 0.63 | 0.35 | 0.27 | 0.58 | 0.43 | 0.36 | 0.35 |
| Arg | AGG | 0.03 | 0.09 | 0.10 | 0.09 | 0.26 | 0.08 | 0.14 |
| Arg | AGA | 0.04 | 0.05 | 0.14 | 0.01 | 0.09 | 0.03 | 0.05 |
| Arg | CGG | 0.06 | 0.19 | 0.09 | 0.06 | 0.06 | 0.17 | 0.15 |
| Arg | CGA | 0.00 | 0.10 | 0.08 | 0.00 | 0.08 | 0.08 | 0.10 |
| Arg | CGT | 0.06 | 0.09 | 0.37 | 0.14 | 0.12 | 0.22 | 0.13 |
| Arg | CGC | 0.81 | 0.48 | 0.22 | 0.71 | 0.40 | 0.43 | 0.42 |
| Asn | AAT | 0.04 | 0.16 | 0.43 | 0.06 | 0.27 | 0.23 | 0.21 |

TABLES 19A-D-continued

Codon preference listing.

| | | | | | | | | |
|---|---|---|---|---|---|---|---|---|
| Asn | AAC | 0.96 | 0.84 | 0.57 | 0.94 | 0.73 | 0.77 | 0.79 |
| Asp | GAT | 0.13 | 0.25 | 0.47 | 0.12 | 0.40 | 0.35 | 0.27 |
| Asp | GAC | 0.87 | 0.75 | 0.53 | 0.88 | 0.60 | 0.65 | 0.73 |
| Cys | TGT | 0.06 | 0.13 | 0.43 | 0.09 | 0.20 | 0.17 | 0.27 |
| Cys | TGC | 0.94 | 0.87 | 0.57 | 0.91 | 0.80 | 0.83 | 0.64 |
| End | TGA | 0.00 | 0.72 | 0.14 | 0.14 | 0.36 | 0.24 | 0.70 |
| End | TAG | 0.33 | 0.11 | 0.29 | 0.00 | 0.00 | 0.18 | 0.22 |
| End | TAA | 0.67 | 0.17 | 4.00 | 0.86 | 0.64 | 0.59 | 0.09 |
| Gln | CAG | 0.42 | 0.40 | 0.15 | 0.40 | 0.27 | 0.29 | 0.33 |
| Gln | CAA | 0.04 | 0.04 | 0.21 | 0.40 | 0.27 | 0.07 | 0.10 |
| Glu | GAG | 0.53 | 0.50 | 0.33 | 0.40 | 0.27 | 0.53 | 0.49 |
| Glu | GAA | 0.02 | 0.06 | 0.31 | 0.40 | 0.27 | 0.11 | 0.07 |
| Gly | GGG | 0.04 | 0.16 | 0.19 | 0.08 | 0.10 | 0.12 | 0.22 |
| Gly | GGA | 0.02 | 0.11 | 0.13 | 0.07 | 0.13 | 0.12 | 0.11 |
| Gly | GGT | 0.03 | 0.12 | 0.39 | 0.24 | 0.25 | 0.23 | 0.15 |
| Gly | GGC | 0.91 | 0.61 | 0.29 | 0.96 | 0.51 | 0.53 | 0.52 |
| His | CAT | 0.14 | 0.16 | 0.30 | 0.08 | 0.25 | 0.35 | 0.27 |
| His | CAC | 0.86 | 0.84 | 0.70 | 0.93 | 0.75 | 0.65 | 0.73 |
| Ile | ATA | 0.00 | 0.04 | 0.07 | 0.01 | 0.04 | 0.08 | 0.09 |
| Ile | ATT | 0.15 | 0.30 | 0.63 | 0.29 | 0.31 | 0.35 | 0.29 |
| Ile | ATC | 0.85 | 0.66 | 0.65 | 0.69 | 0.65 | 0.57 | 0.62 |
| Leu | TTG | 0.03 | 0.07 | 0.03 | 0.05 | 0.14 | 0.14 | 0.16 |
| Leu | TTA | 0.00 | 0.01 | 0.32 | 0.00 | 0.02 | 0.03 | 0.02 |
| Leu | CTG | 0.72 | 0.61 | 0.34 | 0.61 | 0.60 | 0.45 | 0.53 |
| Leu | CTA | 0.01 | 0.03 | 0.03 | 0.04 | 0.04 | 0.07 | 0.07 |
| Leu | CTT | 0.04 | 0.08 | 0.16 | 0.06 | 0.06 | 0.14 | 0.09 |
| Leu | CTC | 0.20 | 0.20 | 0.12 | 0.24 | 0.14 | 0.17 | 0.13 |
| Lys | AAG | 0.98 | 0.94 | 0.54 | 0.98 | 0.90 | 0.90 | 0.84 |
| Lys | AAA | 0.02 | 0.06 | 0.46 | 0.02 | 0.10 | 0.10 | 0.16 |
| Met | ATG | 1.00 | 1.00 | 1.00 | 1.00 | 1.00 | 1.00 | 1.00 |
| Phe | TTT | 0.28 | 0.32 | 0.42 | 0.31 | 0.24 | 0.27 | 0.35 |
| Phe | TTC | 0.72 | 0.68 | 0.58 | 0.69 | 0.76 | 0.73 | 0.65 |
| Pro | CCG | 0.18 | 0.31 | 0.09 | 0.07 | 0.04 | 0.34 | 0.15 |
| Pro | CCA | 0.06 | 0.17 | 0.36 | 0.07 | 0.04 | 0.20 | 0.24 |
| Pro | CCT | 0.10 | 0.14 | 0.25 | 0.17 | 0.04 | 0.19 | 0.29 |
| Pro | CCC | 0.66 | 0.38 | 0.29 | 0.69 | 0.04 | 0.27 | 0.32 |
| Ser | AGT | 0.03 | 0.04 | 0.14 | 0.02 | 0.08 | 0.08 | 0.07 |
| Ser | AGC | 0.27 | 0.38 | 0.18 | 0.18 | 0.31 | 0.27 | 0.31 |
| Ser | TCG | 0.12 | 0.14 | 0.08 | 0.10 | 0.02 | 0.19 | 0.10 |
| Ser | TCA | 0.03 | 0.08 | 0.14 | 0.08 | 0.09 | 0.09 | 0.14 |
| Ser | TCT | 0.09 | 0.11 | 0.26 | 0.18 | 0.19 | 0.14 | 0.13 |
| Ser | TCC | 0.47 | 0.24 | 0.20 | 0.44 | 0.30 | 0.24 | 0.24 |
| Thr | ACG | 0.11 | 0.20 | 0.13 | 0.05 | 0.12 | 0.27 | 0.19 |
| Thr | ACA | 0.01 | 0.20 | 0.32 | 0.07 | 0.20 | 0.12 | 0.23 |
| Thr | ACT | 0.12 | 0.13 | 0.29 | 0.12 | 0.24 | 0.20 | 0.18 |
| Thr | ACC | 0.76 | 0.47 | 0.26 | 0.76 | 0.44 | 0.41 | 0.40 |
| Trp | TGG | 1.00 | 1.00 | 1.00 | 1.00 | 1.00 | 1.00 | 1.00 |
| Tyr | TAT | 0.07 | 0.15 | 0.43 | 0.27 | 0.28 | 0.24 | 0.19 |
| Tyr | TAC | 0.93 | 0.85 | 0.57 | 0.73 | 0.72 | 0.76 | 0.81 |
| Val | GTG | 0.71 | 0.54 | 0.37 | 0.60 | 0.54 | 0.46 | 0.62 |
| Val | GTA | 0.00 | 0.05 | 0.25 | 0.03 | 0.09 | 0.07 | 0.09 |
| Val | GTT | 0.11 | 0.14 | 0.24 | 0.09 | 0.14 | 0.17 | 0.09 |
| Val | GTC | 0.18 | 0.27 | 0.14 | 0.28 | 0.23 | 0.30 | 0.21 |

| Amino Acid | Codon | *Closterium peracerosum-strigosum-littorale* complex | *Dunaliella viridis* | *Dunaliella salina* | *Gonium pectorale* | *Phaeodactylum tricornutum* | *Chaetoceros compressum* |
|---|---|---|---|---|---|---|---|
| Ala | GCG | 0.48 | 0.13 | 0.15 | 0.43 | 0.15 | 0.08 |
| Ala | GCA | 0.10 | 0.27 | 0.20 | 0.09 | 0.10 | 0.37 |
| Ala | GCT | 0.15 | 0.25 | 0.27 | 0.08 | 0.23 | 0.36 |
| Ala | GCC | 0.26 | 0.35 | 0.39 | 0.41 | 0.52 | 0.18 |
| Arg | AGG | 0.04 | 0.25 | 0.22 | 0.13 | 0.02 | 0.14 |
| Arg | AGA | 0.00 | 0.06 | 0.05 | 0.00 | 0.04 | 0.29 |
| Arg | CGG | 0.18 | 0.08 | 0.12 | 0.40 | 0.10 | 0.00 |
| Arg | CGA | 0.00 | 0.06 | 0.06 | 0.05 | 0.12 | 0.19 |
| Arg | CGT | 0.13 | 0.15 | 0.13 | 0.08 | 0.41 | 0.38 |
| Arg | CGC | 0.64 | 0.39 | 0.43 | 0.35 | 0.31 | 0.00 |
| Asn | AAT | 0.04 | 0.17 | 0.23 | 0.07 | 0.30 | 0.58 |
| Asn | AAC | 0.96 | 0.83 | 0.77 | 0.93 | 0.65 | 0.42 |
| Asp | GAT | 0.30 | 0.38 | 0.40 | 0.11 | 0.41 | 0.53 |
| Asp | GAC | 0.70 | 0.62 | 0.60 | 0.89 | 0.59 | 0.47 |
| Cys | TGT | 0.06 | 0.24 | 0.17 | 0.20 | 0.39 | 0.44 |
| Cys | TGC | 0.94 | 0.76 | 0.83 | 0.90 | 0.61 | 0.56 |
| End | TGA | 0.75 | 0.31 | 0.37 | 0.50 | 0.06 | 0.50 |
| End | TAG | 0.00 | 0.15 | 0.14 | 0.00 | 0.13 | 0.00 |

TABLES 19A-D-continued

Codon preference listing.

| | | | | | | | |
|---|---|---|---|---|---|---|---|
| End | TAA | 0.25 | 0.54 | 0.49 | 0.50 | 0.81 | 0.50 |
| Gln | CAG | 0.53 | 0.36 | 0.32 | 0.31 | 0.23 | 0.16 |
| Gln | CAA | 0.09 | 0.12 | 0.08 | 0.07 | 0.14 | 0.19 |
| Glu | GAG | 0.31 | 0.44 | 0.51 | 0.56 | 0.21 | 0.28 |
| Glu | GAA | 0.06 | 0.09 | 0.09 | 0.07 | 0.42 | 0.37 |
| Gly | GGG | 0.31 | 0.14 | 0.10 | 0.18 | 0.08 | 0.12 |
| Gly | GGA | 0.06 | 0.11 | 0.12 | 0.09 | 0.34 | 0.33 |
| Gly | GGT | 0.09 | 0.22 | 0.22 | 0.07 | 0.30 | 0.39 |
| Gly | GGC | 0.53 | 0.54 | 0.56 | 0.65 | 0.28 | 0.16 |
| His | CAT | 0.33 | 0.25 | 0.25 | 0.43 | 0.28 | 0.84 |
| His | CAC | 0.67 | 0.75 | 0.75 | 0.57 | 0.72 | 0.16 |
| Ile | ATA | 0.03 | 0.03 | 0.03 | 0.07 | 0.03 | 0.12 |
| Ile | ATT | 0.23 | 0.25 | 0.31 | 0.33 | 0.51 | 0.65 |
| Ile | ATC | 0.74 | 0.72 | 0.66 | 0.59 | 0.46 | 0.23 |
| Leu | TTG | 0.04 | 0.11 | 0.12 | 0.04 | 0.26 | 0.11 |
| Leu | TTA | 0.00 | 0.01 | 0.01 | 0.00 | 0.02 | 0.14 |
| Leu | CTG | 0.31 | 0.60 | 0.61 | 0.64 | 0.15 | 0.05 |
| Leu | CTA | 0.01 | 0.05 | 0.04 | 0.01 | 0.05 | 0.08 |
| Leu | CTT | 0.04 | 0.07 | 0.08 | 0.05 | 0.18 | 0.51 |
| Leu | CTC | 0.60 | 0.16 | 0.14 | 0.26 | 0.34 | 0.11 |
| Lys | AAG | 0.86 | 0.87 | 0.89 | 0.93 | 0.75 | 0.52 |
| Lys | AAA | 0.14 | 0.13 | 0.11 | 0.07 | 0.25 | 0.48 |
| Met | ATG | 1.00 | 1.00 | 1.00 | 1.00 | 1.00 | 1.00 |
| Phe | TTT | 0.09 | 0.25 | 0.29 | 0.10 | 0.44 | 0.65 |
| Phe | TTC | 0.91 | 0.75 | 0.71 | 0.90 | 0.56 | 0.35 |
| Pro | CCG | 0.28 | 0.10 | 0.08 | 0.53 | 0.29 | 0.05 |
| Pro | CCA | 0.15 | 0.10 | 0.17 | 0.09 | 0.12 | 0.45 |
| Pro | CCT | 0.12 | 0.10 | 0.30 | 0.04 | 0.20 | 0.33 |
| Pro | CCC | 0.44 | 0.10 | 0.45 | 0.34 | 0.40 | 0.17 |
| Ser | AGT | 0.04 | 0.09 | 0.06 | 0.02 | 0.12 | 0.14 |
| Ser | AGC | 0.05 | 0.31 | 0.32 | 0.20 | 0.12 | 0.07 |
| Ser | TCG | 0.22 | 0.04 | 0.06 | 0.42 | 0.19 | 0.08 |
| Ser | TCA | 0.16 | 0.08 | 0.10 | 0.09 | 0.06 | 0.31 |
| Ser | TCT | 0.05 | 0.17 | 0.15 | 0.07 | 0.15 | 0.23 |
| Ser | TCC | 0.47 | 0.31 | 0.30 | 0.20 | 0.35 | 0.18 |
| Thr | ACG | 0.30 | 0.16 | 0.13 | 0.42 | 0.23 | 0.10 |
| Thr | ACA | 0.06 | 0.21 | 0.18 | 0.03 | 0.13 | 0.38 |
| Thr | ACT | 0.22 | 0.18 | 0.23 | 0.08 | 0.19 | 0.27 |
| Thr | ACC | 0.42 | 0.46 | 0.46 | 0.47 | 0.45 | 0.25 |
| Trp | TGG | 1.00 | 1.00 | 1.00 | 1.00 | 1.00 | 1.00 |
| Tyr | TAT | 0.07 | 0.16 | 0.21 | 0.12 | 0.18 | 0.67 |
| Tyr | TAC | 0.93 | 0.84 | 0.79 | 0.88 | 0.82 | 0.33 |
| Val | GTG | 0.50 | 0.64 | 0.62 | 0.57 | 0.22 | 0.30 |
| Val | GTA | 0.02 | 0.03 | 0.05 | 0.04 | 0.09 | 0.27 |
| Val | GTT | 0.06 | 0.11 | 0.11 | 0.04 | 0.22 | 0.10 |
| Val | GTC | 0.42 | 0.22 | 0.23 | 0.35 | 0.47 | 0.33 |

| Amino Acid | Codon | *Cylindrotheca fusiformis* | *Amphidinium carterae* | *Symbiodinium micro-adriacticum* | *Nanno-chloropsis* sp | *Cyclotella cryptica* | *Navicula pelliculosa* | *Thalassiosira pseudonana* | *C. reinhardtii* |
|---|---|---|---|---|---|---|---|---|---|
| Ala | GCG | 0.07 | 0.17 | 0.22 | 0.24 | 0.11 | 0.00 | 0.11 | 0.35 |
| Ala | GCA | 0.14 | 0.33 | 0.26 | 0.10 | 0.16 | 0.13 | 0.25 | 0.08 |
| Ala | GCT | 0.35 | 0.29 | 0.20 | 0.17 | 0.45 | 0.44 | 0.33 | 0.13 |
| Ala | GCC | 0.43 | 0.20 | 0.32 | 0.48 | 0.27 | 0.44 | 0.30 | 0.43 |
| Arg | AGG | 0.09 | 0.15 | 0.27 | 0.00 | 0.09 | 0.05 | 0.18 | 0.05 |
| Arg | AGA | 0.14 | 0.03 | 0.27 | 0.00 | 0.05 | 0.10 | 0.17 | 0.01 |
| Arg | CGG | 0.06 | 0.08 | 0.09 | 0.00 | 0.04 | 0.05 | 0.06 | 0.20 |
| Arg | CGA | 0.16 | 0.18 | 0.09 | 0.29 | 0.08 | 0.35 | 0.11 | 0.04 |
| Arg | CGT | 0.34 | 0.18 | 0.09 | 0.14 | 0.47 | 0.20 | 0.34 | 0.09 |
| Arg | CGC | 0.22 | 0.40 | 0.18 | 0.57 | 0.28 | 0.25 | 0.15 | 0.62 |
| Asn | AAT | 0.42 | 0.37 | 0.21 | 0.00 | 0.25 | 0.47 | 0.43 | 0.09 |
| Asn | AAC | 0.58 | 0.63 | 0.79 | 1.00 | 0.75 | 0.53 | 0.57 | 0.91 |
| Asp | GAT | 0.54 | 0.54 | 0.50 | 0.20 | 0.52 | 0.20 | 0.56 | 0.14 |
| Asp | GAC | 0.46 | 0.46 | 0.50 | 0.80 | 0.48 | 0.80 | 0.44 | 0.86 |
| Cys | TGT | 0.44 | 0.75 | 0.50 | 0.00 | 0.29 | 0.10 | 0.54 | 0.10 |
| Cys | TGC | 0.56 | 0.25 | 0.50 | 1.00 | 0.71 | 0.90 | 0.46 | 0.90 |
| End | TGA | 0.13 | 0.50 | 1.00 | 0.00 | 0.10 | 0.00 | 0.31 | 0.27 |
| End | TAG | 0.10 | 0.00 | 0.00 | 0.00 | 0.00 | 0.00 | 0.38 | 0.22 |
| End | TAA | 0.77 | 0.50 | 0.00 | 1.00 | 0.90 | 1.00 | 0.31 | 0.52 |
| Gln | CAG | 0.12 | 0.33 | 0.28 | 0.41 | 0.19 | 0.21 | 0.16 | 0.38 |
| Gln | CAA | 0.25 | 0.15 | 0.17 | 0.00 | 0.17 | 0.28 | 0.19 | 0.04 |
| Glu | GAG | 0.23 | 0.41 | 0.50 | 0.59 | 0.38 | 0.17 | 0.40 | 0.55 |
| Glu | GAA | 0.39 | 0.10 | 0.06 | 0.00 | 0.26 | 0.34 | 0.26 | 0.03 |
| Gly | GGG | 0.06 | 0.19 | 0.32 | 0.10 | 0.10 | 0.03 | 0.12 | 0.11 |
| Gly | GGA | 0.47 | 0.10 | 0.12 | 0.05 | 0.45 | 0.28 | 0.51 | 0.06 |
| Gly | GGT | 0.35 | 0.34 | 0.16 | 0.25 | 0.22 | 0.13 | 0.23 | 0.11 |
| Gly | GGC | 0.12 | 0.37 | 0.40 | 0.60 | 0.24 | 0.56 | 0.14 | 0.72 |

TABLES 19A-D-continued

Codon preference listing.

| | | | | | | | | | |
|---|---|---|---|---|---|---|---|---|---|
| His | CAT | 0.39 | 0.12 | 0.40 | 0.00 | 0.42 | 1.00 | 0.50 | 0.11 |
| His | CAC | 0.61 | 0.88 | 0.60 | 1.00 | 0.58 | 0.00 | 0.50 | 0.89 |
| Ile | ATA | 0.06 | 0.05 | 0.00 | 0.00 | 0.04 | 0.00 | 0.08 | 0.03 |
| Ile | ATT | 0.42 | 0.53 | 0.38 | 0.14 | 0.53 | 0.73 | 0.38 | 0.22 |
| Ile | ATC | 0.52 | 0.42 | 0.63 | 0.86 | 0.42 | 0.27 | 0.54 | 0.75 |
| Leu | TTG | 0.26 | 0.35 | 0.39 | 0.22 | 0.20 | 0.16 | 0.29 | 0.04 |
| Leu | TTA | 0.09 | 0.01 | 0.00 | 0.00 | 0.03 | 0.00 | 0.05 | 0.01 |
| Leu | CTG | 0.09 | 0.22 | 0.39 | 0.09 | 0.06 | 0.12 | 0.08 | 0.73 |
| Leu | CTA | 0.05 | 0.00 | 0.04 | 0.00 | 0.03 | 0.04 | 0.06 | 0.03 |
| Leu | CTT | 0.37 | 0.31 | 0.13 | 0.04 | 0.39 | 0.36 | 0.20 | 0.05 |
| Leu | CTC | 0.13 | 0.12 | 0.04 | 0.65 | 0.29 | 0.32 | 0.32 | 0.15 |
| Lys | AAG | 0.60 | 0.93 | 0.85 | 1.00 | 0.70 | 0.83 | 0.76 | 0.95 |
| Lys | AAA | 0.40 | 0.07 | 0.15 | 0.00 | 0.30 | 0.17 | 0.24 | 0.05 |
| Met | ATG | 1.00 | 1.00 | 1.00 | 1.00 | 1.00 | 1.00 | 1.00 | 1.00 |
| Phe | TTT | 0.37 | 0.21 | 0.25 | 0.20 | 0.31 | 0.78 | 0.38 | 0.16 |
| Phe | TTC | 0.63 | 0.79 | 0.75 | 0.80 | 0.69 | 0.22 | 0.62 | 0.84 |
| Pro | CCG | 0.11 | 0.14 | 0.18 | 0.08 | 0.10 | 0.21 | 0.16 | 0.33 |
| Pro | CCA | 0.33 | 0.42 | 0.09 | 0.08 | 0.16 | 0.29 | 0.31 | 0.08 |
| Pro | CCT | 0.32 | 0.22 | 0.41 | 0.25 | 0.35 | 0.21 | 0.31 | 0.13 |
| Pro | CCC | 0.24 | 0.22 | 0.32 | 0.58 | 0.39 | 0.29 | 0.23 | 0.47 |
| Ser | AGT | 0.12 | 0.13 | 0.09 | 0.00 | 0.09 | 0.13 | 0.18 | 0.04 |
| Ser | AGC | 0.09 | 0.24 | 0.14 | 0.13 | 0.08 | 0.28 | 0.11 | 0.35 |
| Ser | TCG | 0.13 | 0.03 | 0.05 | 0.00 | 0.15 | 0.25 | 0.17 | 0.25 |
| Ser | TCA | 0.12 | 0.25 | 0.05 | 0.00 | 0.12 | 0.08 | 0.12 | 0.05 |
| Ser | TCT | 0.30 | 0.16 | 0.23 | 0.13 | 0.39 | 0.25 | 0.23 | 0.07 |
| Ser | TCC | 0.24 | 0.19 | 0.45 | 0.75 | 0.18 | 0.03 | 0.19 | 0.25 |
| Thr | ACG | 0.09 | 0.14 | 0.10 | 0.28 | 0.10 | 0.18 | 0.21 | 0.30 |
| Thr | ACA | 0.15 | 0.28 | 0.10 | 0.00 | 0.15 | 0.09 | 0.19 | 0.08 |
| Thr | ACT | 0.39 | 0.12 | 0.10 | 0.17 | 0.33 | 0.41 | 0.28 | 0.10 |
| Thr | ACC | 0.37 | 0.47 | 0.70 | 0.56 | 0.43 | 0.32 | 0.32 | 0.52 |
| Trp | TGG | 1.00 | 1.00 | 1.00 | 1.00 | 1.00 | 1.00 | 1.00 | 1.00 |
| Tyr | TAT | 0.38 | 0.32 | 0.20 | 0.00 | 0.38 | 0.20 | 0.39 | 0.10 |
| Tyr | TAC | 0.62 | 0.68 | 0.80 | 1.00 | 0.62 | 0.80 | 0.61 | 0.90 |
| Val | GTG | 0.11 | 0.65 | 0.67 | 0.31 | 0.16 | 0.18 | 0.29 | 0.67 |
| Val | GTA | 0.06 | 0.05 | 0.00 | 0.00 | 0.09 | 0.09 | 0.16 | 0.03 |
| Val | GTT | 0.38 | 0.08 | 0.11 | 0.15 | 0.42 | 0.09 | 0.28 | 0.07 |
| Val | GTC | 0.46 | 0.21 | 0.22 | 0.54 | 0.33 | 0.64 | 0.27 | 0.22 |

| Amino Acid | Codon | *Yarrowia lipolytica* | *Mortierella alpina* | *Rhodococcus opacus* |
|---|---|---|---|---|
| Ala | GCG | 0.08 | 0.14 | 0.35 |
| Ala | GCA | 0.11 | 0.12 | 0.14 |
| Ala | GCT | 0.35 | 0.29 | 0.09 |
| Ala | GCC | 0.46 | 0.45 | 0.43 |
| Arg | AGG | 0.05 | 0.05 | 0.05 |
| Arg | AGA | 0.13 | 0.06 | 0.02 |
| Arg | CGG | 0.12 | 0.06 | 0.26 |
| Arg | CGA | 0.52 | 0.09 | 0.12 |
| Arg | CGT | 0.11 | 0.32 | 0.11 |
| Arg | CGC | 0.07 | 0.42 | 0.44 |
| Asn | AAT | 0.17 | 0.15 | 0.21 |
| Asn | AAC | 0.83 | 0.85 | 0.79 |
| Asp | GAT | 0.35 | 0.42 | 0.24 |
| Asp | GAC | 0.65 | 0.58 | 0.76 |
| Cys | TGT | 0.46 | 0.13 | 0.26 |
| Cys | TGC | 0.54 | 0.87 | 0.74 |
| End | TGA | 0.16 | 0.05 | 0.72 |
| End | TAG | 0.38 | 0.25 | 0.17 |
| End | TAA | 0.46 | 0.70 | 0.11 |
| Gln | CAG | 0.33 | 0.36 | 0.28 |
| Gln | CAA | 0.08 | 0.06 | 0.06 |
| Glu | GAG | 0.44 | 0.49 | 0.45 |
| Glu | GAA | 0.14 | 0.09 | 0.22 |
| Gly | GGG | 0.05 | 0.03 | 0.18 |
| Gly | GGA | 0.28 | 0.29 | 0.15 |
| Gly | GGT | 0.32 | 0.32 | 0.20 |
| Gly | GGC | 0.34 | 0.36 | 0.48 |
| His | CAT | 0.34 | 0.27 | 0.20 |
| His | CAC | 0.66 | 0.73 | 0.80 |
| Ile | ATA | 0.03 | 0.01 | 0.05 |
| Ile | ATT | 0.44 | 0.33 | 0.14 |
| Ile | ATC | 0.53 | 0.66 | 0.81 |
| Leu | TTG | 0.09 | 0.27 | 0.09 |
| Leu | TTA | 0.02 | 0.00 | 0.01 |
| Leu | CTG | 0.37 | 0.26 | 0.41 |
| Leu | CTA | 0.05 | 0.02 | 0.03 |
| Leu | CTT | 0.18 | 0.12 | 0.06 |
| Leu | CTC | 0.29 | 0.32 | 0.40 |

TABLES 19A-D-continued

| Codon preference listing. | | | | |
|---|---|---|---|---|
| Lys | AAG | 0.84 | 0.91 | 0.80 |
| Lys | AAA | 0.16 | 0.09 | 0.20 |
| Met | ATG | 1.00 | 1.00 | 1.00 |
| Phe | TTT | 0.38 | 0.39 | 0.09 |
| Phe | TTC | 0.62 | 0.61 | 0.91 |
| Pro | CCG | 0.10 | 0.07 | 0.52 |
| Pro | CCA | 0.10 | 0.08 | 0.09 |
| Pro | CCT | 0.32 | 0.36 | 0.07 |
| Pro | CCC | 0.47 | 0.49 | 0.32 |
| Ser | AGT | 0.07 | 0.05 | 0.08 |
| Ser | AGC | 0.11 | 0.14 | 0.23 |
| Ser | TCG | 0.16 | 0.32 | 0.33 |
| Ser | TCA | 0.08 | 0.08 | 0.07 |
| Ser | TCT | 0.28 | 0.12 | 0.05 |
| Ser | TCC | 0.30 | 0.29 | 0.24 |
| Thr | ACG | 0.11 | 0.17 | 0.28 |
| Thr | ACA | 0.14 | 0.10 | 0.11 |
| Thr | ACT | 0.26 | 0.23 | 0.07 |
| Thr | ACC | 0.49 | 0.49 | 0.53 |
| Trp | TGG | 1.00 | 1.00 | 1.00 |
| Tyr | TAT | 0.18 | 0.20 | 0.18 |
| Tyr | TAC | 0.82 | 0.80 | 0.82 |
| Val | GTG | 0.33 | 0.22 | 0.37 |
| Val | GTA | 0.05 | 0.02 | 0.05 |
| Val | GTT | 0.26 | 0.27 | 0.10 |
| Val | GTC | 0.36 | 0.49 | 0.49 |

TABLE 20

| Lipid biosynthesis pathway proteins. |
|---|
| 3-Ketoacyl ACP synthase |
| *Cuphea hookeriana* 3-ketoacyl-ACP synthase (GenBank Acc. No. AAC68861.1), *Cuphea wrightii* beta-ketoacyl-ACP synthase II (GenBank Acc. No. AAB37271.1), *Cuphea lanceolata* beta-ketoacyl-ACP synthase IV (GenBank Acc. No. CAC59946.1), *Cuphea wrightii* beta-ketoacyl-ACP synthase II (GenBank Acc. No. AAB37270.1), *Ricinus communis* ketoacyl-ACP synthase (GenBank Acc. No. XP_002516228), *Gossypium hirsutum* ketoacyl-ACP synthase (GenBank Acc. No. ADK23940.1), *Glycine max* plastid 3-keto-acyl-ACP synthase II-A (GenBank Acc No. AAW88763.1), *Elaeis guineensis* beta-ketoacyl-ACP synthase II (GenBank Acc. No. AAF26738.2), *Helianthus annuus* plastid 3-keto-acyl-ACP synthase I (GenkBank Acc. No. ABM53471.1), *Glycine max*3-keto-acyl-ACP synthase I (GenkBank Acc. No. NP_001238610.1), *Helianthus annuus* plastid 3-keto-acyl-ACP synthase II (GenBank Acc ABI18155.1), *Brassica napus* beta-ketoacyl-ACP synthetase 2 (GenBank Acc. No. AAF61739.1), *Perilla frutescens* beta-ketoacyl-ACP synthase II (GenBank Acc. No. AAC04692.1), *Helianthus annus* beta-ketoacyl-ACP synthase II (GenBank Accession No. ABI18155), *Ricinus communis* beta-ketoacyl-ACP synthase II (GenBank Accession No. AAA33872), *Haematococcus pluvialis* beta-ketoacyl acyl carrier protein synthase (GenBank Accession No. HM560033.1), *Jatropha curcasbeta* ketoacyl-ACP synthase I (GenBank Accession No. ABJ90468.1), *Populus trichocarpa* beta-ketoacyl-ACP synthase I (GenBank Accession No. XP_002303661.1), *Coriandrum sativum* beta-ketoacyl-ACP synthetase I (GenBank Accession No. AAK58535.1), *Arabidopsis thaliana* 3-oxoacyl-[acyl-carrier-protein] synthase I (GenBank Accession No. NP_001190479.1), *Vitis vinifera* 3-oxoacyl-[acyl-carrier-protein] synthase I (GenBank Accession No. XP_002272874.2) |
| Fatty acyl-ACP Thioesterases |
| *Umbellularia californica* fatty acyl-ACP thioesterase (GenBank Acc. No. AAC49001), *Cinnamomum camphora* fatty acyl-ACP thioesterase (GenBank Acc. No. Q39473), *Umbellularia californica* fatty acyl-ACP thioesterase (GenBank Acc. No. Q41635), *Myristica fragrans* fatty acyl-ACP thioesterase (GenBank Acc. No. AAB71729), *Myristica fragrans* fatty acyl-ACP thioesterase (GenBank Acc. No. AAB71730), *Elaeis guineensis* fatty acyl-ACP thioesterase (GenBank Acc. No. ABD83939), *Elaeis guineensis* fatty acyl-ACP thioesterase (GenBank Acc. No. AAD42220), *Populus tomentosa* fatty acyl-ACP thioesterase (GenBank Acc. No. ABC47311), *Arabidopsis thaliana* fatty acyl-ACP thioesterase (GenBank Acc. No. NP_172327), *Arabidopsis thaliana* fatty acyl-ACP thioesterase (GenBank Acc. No. CAA85387), *Arabidopsis thaliana* fatty acyl-ACP thioesterase (GenBank Acc. No. CAA85388), *Gossypium hirsutum* fatty acyl-ACP thioesterase (GenBank Acc. No. Q9SQI3), *Cuphea lanceolata* fatty acyl-ACP thioesterase (GenBank Acc. No. CAA54060), *Cuphea hookeriana* fatty acyl-ACP thioesterase (GenBank Acc. No. AAC72882), *Cuphea calophylla* subsp. *mesostemon* fatty acyl-ACP thioesterase (GenBank Acc. No. ABB71581), *Cuphea lanceolata* fatty acyl-ACP thioesterase (GenBank Acc. No. CAC19933), *Elaeis guineensis* fatty acyl-ACP thioesterase (GenBank Acc. No. AAL15645), *Cuphea hookeriana* fatty acyl-ACP thioesterase (GenBank Acc. No. Q39513), *Gossypium hirsutum* fatty acyl-ACP thioesterase (GenBank Acc. No. AAD01982), *Vitis vinifera* fatty acyl-ACP thioesterase (GenBank Acc. No. CAN81819), *Garcinia mangostana* fatty acyl-ACP thioesterase |

TABLE 20-continued

| Lipid biosynthesis pathway proteins. |
| --- |
| (GenBank Acc. No. AAB51525), *Brassica juncea* fatty acyl-ACP thioesterase (GenBank Acc. No. ABI18986), *Madhuca longifolia* fatty acyl-ACP thioesterase (GenBank Acc. No. AAX51637), *Brassica napus* fatty acyl-ACP thioesterase (GenBank Acc. No. ABH11710), *Brassica napus* fatty acyl-ACP thioesterase (GenBank Acc. No. CAA52070.1), *Oryza sativa* (indica cultivar-group) fatty acyl-ACP thioesterase (GenBank Acc. No. EAY86877), *Oryza sativa* (japonica cultivar-group) fatty acyl-ACP thioesterase (GenBank Acc. No. NP_001068400), *Oryza sativa* (indica cultivar-group) fatty acyl-ACP thioesterase (GenBank Acc. No. EAY99617), *Cuphea hookeriana* fatty acyl-ACP thioesterase (GenBank Acc. No. AAC49269), *Ulmus Americana* fatty acyl-ACP thioesterase (GenBank Acc. No. AAB71731), *Cuphea lanceolata* fatty acyl-ACP thioesterase (GenBank Acc. No. CAB60830), *Cuphea palustris* fatty acyl-ACP thioesterase (GenBank Acc. No. AAC49180), *Iris germanica* fatty acyl-ACP thioesterase (GenBank Acc. No. AAG43858, *Iris germanica* fatty acyl-ACP thioesterase (GenBank Acc. No. AAG43858.1), *Cuphea palustris* fatty acyl-ACP thioesterase (GenBank Acc. No. AAC49179), *Myristica fragrans* fatty acyl-ACP thioesterase (GenBank Acc. No. AAB71729), *Myristica fragrans* fatty acyl-ACP thioesterase (GenBank Acc. No. AAB717291.1), *Cuphea hookeriana* fatty acyl-ACP thioesterase GenBank Acc. No. U39834), *Umbelluaria californica* fatty acyl-ACP thioesterase (GenBank Acc. No. M94159), *Cinnamomum camphora* fatty acyl-ACP thioesterase (GenBank Acc. No. U31813), *Ricinus communis* fatty acyl-ACP thioesterase (GenBank Acc. No. ABS30422.1), *Helianthus annuus* acyl-ACP thioesterase (GenBank Accession No. AAL79361.1), *Jatropha curcas* acyl-ACP thioesterase (GenBank Accession No. ABX82799.3), *Zea mays* oleoyl-acyl carrier protein thioesterase, (GenBank Accession No. ACG40089.1), *Haematococcus pluvialis* fatty acyl-ACP thioesterase (GenBank Accession No. HM560034.1) |
| Desaturase Enzymes |
| *Linum usitatissimum* fatty acid desaturase 3C, (GenBank Acc. No. ADV92272.1), *Ricinus communis* omega-3 fatty acid desaturase, endoplasmic reticulum, putative, (GenBank Acc. No. EEF36775.1), *Vernicia fordii* omega-3 fatty acid desaturase, (GenBank Acc. No. AAF12821), *Glycine max* chloroplast omega 3 fatty acid desaturase isoform 2, (GenBank Acc. No. ACF19424.1), *Prototheca moriformis* FAD-D omega 3 desaturase (SEQ ID NO: 221), *Prototheca moriformis* linoleate desaturase (SEQ ID NO: 220), *Carthamus tinctorius* delta 12 desaturase, (GenBank Accession No. ADM48790.1), *Gossypium hirsutum* omega-6 desaturase, (GenBank Accession No. CAA71199.1), *Glycine max* microsomal desaturase (GenBank Accession No. BAD89862.1), *Zea mays* fatty acid desaturase (GenBank Accession No. ABF50053.1), *Brassica napa* linoleic acid desaturase (GenBank Accession No. AAA32994.1), *Camelina sativa* omega-3 desaturase (SEQ ID NO: 214), *Prototheca moriformis* delta 12 desaturase allele 2 (SEQ ID NO: 212), *Camelina sativa* omega-3 FAD7-1 (SEQ ID NO: 215), *Helianthus annuus* stearoyl-ACP desaturase, (GenBank Accession No. AAB65145.1), *Ricinus communis* stearoyl-ACP desaturase, (GenBank Accession No. AACG59946.1), *Brassica juncea* plastidic delta-9-stearoyl-ACP desaturase (GenBank Accession No. AAD40245.1), *Glycine max* stearoyl-ACP desaturase (GenBank Accession No. ACJ39209.1), *Olea europaea* stearoyl-ACP desaturase (GenBank Accession No. AAB67840.1), *Vernicia fordii* stearoyl-acyl-carrier protein desaturase, (GenBank Accession No. ADC32803.1), *Descurainia sophia* delta-12 fatty acid desaturase (GenBank Accession No. ABS86964.2), *Euphorbia lagascae* delta12-oleic acid desaturase (GenBank Acc. No. AAS57577.1), *Chlorella vulgaris* delta 12 fatty acid desaturease (GenBank Accession No. ACF98528), *Chlorella vulgaris* omega-3 fatty acid desaturease (GenBank Accession No. BAB78717), *Haematococcus pluvialis* omega-3 fatty acid desaturase (GenBank Accession No. HM560035.1), *Haematococcus pluvialis* stearoyl-ACP-desaturase GenBank Accession No. EF586860.1, *Haematococcus pluvialis* stearoyl-ACP-desaturase GenBank Accession No. EF523479.1 |
| Oleate 12-hydroxylase Enzymes |
| *Ricinus communis* oleate 12-hydroxylase (GenBank Acc. No. AAC49010.1), *Physaria lindheimeri* oleate 12-hydroxylase (GenBank Acc. No. ABQ01458.1), *Physaria lindheimeri* mutant bifunctional oleate 12-hydroxylase: desaturase (GenBank Acc. No. ACF17571.1), *Physaria lindheimeri* bifunctional oleate 12-hydroxylase: desaturase (GenBank Accession No. ACQ42234.1), *Physaria lindheimeri* bifunctional oleate 12-hydroxylase: desaturase (GenBank Acc. No. AAC32755.1), *Arabidopsis lyrata* subsp. *Lyrata* (GenBank Acc. No. XP_002884883.1) |
| Glycerol-3-phosphate Enzymes |
| *Arabidopsis thaliana* glycerol-3-phosphate acyltransferase BAA00575, *Chlamydomonas reinhardtii* glycerol-3-phosphate acyltransferase (GenBank Acc. No. EDP02129), *Chlamydomonas reinhardtii* glycerol-3-phosphate acyltransferase (GenBank Acc. No. Q886Q7), *Cucurbita moschata* acyl-(acyl-carrier-protein): glycerol-3-phosphate acyltransferase (GenBank Acc. No. BAB39688), *Elaeis guineensis* glycerol-3-phosphate acyltransferase, ((GenBank Acc. No. AAF64066), *Garcina mangostana* glycerol-3-phosphate acyltransferase (GenBank Acc. No. ABS86942), *Gossypium hirsutum* glycerol-3-phosphate acyltransferase (GenBank Acc. No. ADK23938), *Jatropha curcas* glycerol-3-phosphate acyltransferase (GenBank Acc. No. ADV77219), *Jatropha curcas* plastid glycerol-3-phosphate acyltransferase (GenBank Acc. No. ACR61638), *Ricinus communis* plastidial glycerol-phosphate acyltransferase (GenBank Acc. No. EEF43526), *Vica faba* glycerol-3-phosphate acyltransferase (GenBank Accession No. AAD05164), *Zea mays* glycerol-3-phosphate acyltransferase (GenBank Acc. No. ACG45812) |

TABLE 20-continued

| Lipid biosynthesis pathway proteins. |
|---|
| Lysophosphatidic acid acyltransferase Enzymes |
| *Arabidopsis thaliana* 1-acyl-sn-glycerol-3-phosphate acyltransferase (GenBank Accession No. AEE85783), *Brassica juncea* 1-acyl-sn-glycerol-3-phosphate acyltransferase (GenBank Accession No. ABQ42862), *Brassica juncea* 1-acyl-sn-glycerol-3-phosphate acyltransferase (GenBank Accession No. ABM92334), *Brassica napus* 1-acyl-sn-glycerol-3-phosphate acyltransferase (GenBank Accession No. CAB09138), *Chlamydomonas reinhardtii* lysophosphatidic acid acyltransferase (GenBank Accession No. EDP02300), *Cocos nucifera* lysophosphatidic acid acyltransferase (GenBank Acc. No. AAC49119), *Limnanthes alba* lysophosphatidic acid acyltransferase (GenBank Accession No. EDP02300), *Limnanthes douglasii* 1-acyl-sn-glycerol-3-phosphate acyltransferase (putative) (GenBank Accession No. CAA88620), *Limnanthes douglasii* acyl-CoA: sn-1-acylglycerol-3-phosphate acyltransferase (GenBank Accession No. ABD62751), *Limnanthes douglasii* 1-acylglycerol-3-phosphate O-acyltransferase (GenBank Accession No. CAA58239), *Ricinus communis* 1-acyl-sn-glycerol-3-phosphate acyltransferase (GenBank Accession No. EEF39377) |
| Diacylglycerol acyltransferase Enzymes |
| *Arabidopsis thaliana* diacylglycerol acyltransferase (GenBank Acc. No. CAB45373), *Brassica juncea* diacylglycerol acyltransferase (GenBank Acc. No. AAY40784), *Elaeis guineensis* putative diacylglycerol acyltransferase (GenBank Acc. No. AEQ94187), *Elaeis guineensis* putative diacylglycerol acyltransferase (GenBank Acc. No. AEQ94186), *Glycine max* acyl CoA: diacylglycerol acyltransferase (GenBank Acc. No. AAT73629), *Helianthus annus* diacylglycerol acyltransferase (GenBank Acc. No. ABX61081), *Olea europaea* acyl-CoA: diacylglycerol acyltransferase 1 (GenBank Acc. No. AAS01606), *Ricinus communis* diacylglycerol acyltransferase (GenBank Acc. No. AAR11479) |
| Phospholipid diacylglycerol acyltransferase Enzymes |
| *Arabidopsis thaliana* phospholipid: diacylglycerol acyltransferase (GenBank Acc. No. AED91921), *Elaeis guineensis* putative phospholipid: diacylglycerol acyltransferase (GenBank Acc. No. AEQ94116), *Glycine max* phospholipid: diacylglycerol acyltransferase 1-like (GenBank Acc. No. XP_003541296), *Jatropha curcas* phospholipid: diacylglycerol acyltransferase (GenBank Acc. No. AEZ56255), *Ricinus communis* phospholipid: diacylglycerol acyltransferase (GenBank Acc. No. ADK92410), *Ricinus communis* phospholipid: diacylglycerol acyltransferase (GenBank Acc. No. AEW99982) |

Example 10: Engineering *Chlorella sorokiniana*

Expression of recombinant genes in accordance with the present invention in *Chlorella sorokiniana* can be accomplished by modifying the methods and vectors taught by Dawson et al. as discussed herein. Briefly, Dawson et al., *Current Microbiology Vol.* 35 (1997) pp. 356-362, reported the stable nuclear transformation of *Chlorella sorokiniana* with plasmid DNA. Using the transformation method of microprojectile bombardment, Dawson introduced the plasmid pSV72-NR9, encoding the full *Chlorella vulgaris* nitrate reductase gene (NR, GenBank Accession No. U39931), into mutant *Chlorella sorokiniana* (NR-mutants). The NR-mutants are incapable of growth without the use of nitrate as a source of nitrogen. Nitrate reductase catalyzes the conversion of nitrate to nitrite. Prior to transformation, *Chlorella sorokiniana* NR-mutants were unable to grow beyond the microcolony stage on culture medium comprising nitrate ($NO_3^-$) as the sole nitrogen source. The expression of the *Chlorella vulgaris* NR gene product in NR-mutant *Chlorella* sorokiniana was used as a selectable marker to rescue the nitrate metabolism deficiency. Upon transformation with the pSV72-NR9 plasmid, NR-mutant *Chlorella sorokiniana* stably expressing the *Chlorella vulgaris* NR gene product were obtained that were able to grow beyond the microcolony stage on agar plates comprising nitrate as the sole carbon source. Evaluation of the DNA of the stable transformants was performed by Southern analysis and evaluation of the RNA of the stable transformants was performed by RNase protection. Selection and maintenance of the transformed *Chlorella sorokiniana* (NR mutant) was performed on agar plates (pH 7.4) comprising 0.2 g/L $MgSO_4$, 0.67 g/L $KH_2PO_4$, 3.5 g/L $K_2HPO_4$, 1.0 g/L $Na_3C_6H_5O_7.H_2O$ and 16.0 g/L agar, an appropriate nitrogen source (e.g., $NO_3$), micronutrients, and a carbon source. Dawson also reported the propagation of *Chlorella sorokiniana* and *Chlorella sorokiniana* NR mutants in liquid culture medium. Dawson reported that the plasmid pSV72-NR9 and the promoter and 3' UTR/terminator of the *Chlorella vulgaris* nitrate reductase gene were suitable to enable heterologous gene expression in *Chlorella sorokiniana* NR-mutants. Dawson also reported that expression of the *Chlorella vulgaris* nitrate reductase gene product was suitable for use as a selectable marker in *Chlorella sorokiniana* NR-mutants.

In an embodiment of the present invention, vector pSV72-NR9, comprising nucleotide sequence encoding the *Chlorella vulgaris* nitrate reductase (CvNR) gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella sorokiniana* to reflect the codon bias inherent in nuclear genes of *Chlorella sorokiniana* in accordance with Tables 19A-D. For each lipid biosynthesis pathway protein of Table 20, the codon-optimized gene sequence can individually be operably linked to the CvNR promoter upstream of the protein-coding sequence and operably linked to the CvNR 3'UTR/terminator at the 3' region, or downstream, of the protein-coding sequence. The transformation construct may additionally comprise homology regions to the *Chlorella sorokiniana* genome for targeted genomic integration of the transformation vector. Homology regions may be selected to disrupt one or more genomic sites of endogenous lipid biosynthesis pathway genes. Stable transformation of *Chlorella sorokiniana* with the transformation vector is achieved through well-known transformation techniques including microprojectile bombardment or other known methods. Activity of the CvNR gene product can be used as a selectable marker to rescue the nitrogen assimilation deficiency of *Chlorella* sorokiniana NR mutant strains and to select for *Chlorella sorokiniana* NR-mutants stably expressing the transformation vector. Growth media suitable for *Chlorella sorokiniana* lipid production include, but are not limited to 0.5 g/L $KH_2PO_4$, 0.5 g/L $K_2HPO_4$, 0.25 g/L $MgSO_4$-$7H_2O$, with supplemental micronutrients and the appropriate nitrogen and carbon sources (Patterson, *Lipids* Vol. 5:7 (1970), pp. 597-600). Evaluation of fatty acid profiles of *Chlorella sorokiniana* lipids can be assessed through standard lipid extraction and analytical methods described herein.

Example 11: Engineering *Chlorella vulgaris*

Expression of recombinant genes in accordance with the present invention in *Chlorella vulgaris* can be accomplished by modifying the methods and vectors taught by Chow and Tung et al. as discussed herein. Briefly, Chow and Tung et al., *Plant Cell Reports*, Volume 18 (1999), pp. 778-780, reported the stable nuclear transformation of *Chlorella vulgaris* with plasmid DNA. Using the transformation method of electroporation, Chow and Tung introduced the plasmid pIG121-Hm (GenBank Accession No. AB489142) into *Chlorella vulgaris*. The nucleotide sequence of pIG121-Hm comprised sequence encoding a beta-glucuronidase (GUS) reporter gene product operably-linked to a CaMV 35S promoter upstream of the GUS protein-coding sequence and further operably linked to the 3' UTR/terminator of the nopaline synthase (nos) gene downstream of the GUS protein-coding sequence. The sequence of plasmid pIG121-Hm further comprised a hygromycin B antibiotic resistance cassette. This hygromycin B antibiotic resistance cassette comprised a CaMV 35S promoter operably linked to sequence encoding the hygromycin phosphotransferase (hpt, GenBank Accession No. BAH24259) gene product. Prior to transformation, *Chlorella vulgaris* was unable to be propagated in culture medium comprising 50 ug/ml hygromycin B. Upon transformation with the pIG121-Hm plasmid, transformants of *Chlorella vulgaris* were obtained that were propagated in culture medium comprising 50 ug/ml hygromycin B. The expression of the hpt gene product in *Chlorella vulgaris* enabled propagation of transformed *Chlorella vulgaris* in the presence of 50 ug/mL hygromycin B, thereby establishing the utility of the a hygromycin B resistance cassette as a selectable marker for use in *Chlorella vulgaris*. Detectable activity of the GUS reporter gene indicated that CaMV 35S promoter and nos 3'UTR are suitable for enabling heterologous gene expression in *Chlorella vulgaris*. Evaluation of the genomic DNA of the stable transformants was performed by Southern analysis. Selection and maintenance of transformed *Chlorella vulgaris* was performed on agar plates comprising YA medium (agar and 4 g/L yeast extract). The propagation of *Chlorella vulgaris* in liquid culture medium was conducted as discussed by Chow and Tung. Propagation of *Chlorella vulgaris* in media other than YA medium has been described (for examples, see Chader et al., *Revue des Energies Renouvelabes*, Volume 14 (2011), pp. 21-26 and Illman et al., *Enzyme and Microbial Technology*, Vol. 27 (2000), pp. 631-635). Chow and Tung reported that the plasmid pIG121-Hm, the CaMV 35S promoter, and the *Agrobacterium tumefaciens* nopaline synthase gene 3'UTR/terminator are suitable to enable heterologous gene expression in *Chlorella vulgaris*. In addition, Chow and Tung reported the hygromycin B resistance cassette was suitable for use as a selectable marker in *Chlorella vulgaris*. Additional plasmids, promoters, 3'UTR/terminators, and selectable markers suitable for enabling heterologous gene expression in *Chlorella vulgaris* have been discussed in Chader et al., *Revue des Energies Renouvelabes*, Volume 14 (2011), pp. 21-26.

In an embodiment of the present invention, pIG121-Hm, comprising the nucleotide sequence encoding the hygromycin B gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella vulgaris* to reflect the codon bias inherent in nuclear genes of *Chlorella vulgaris* in accordance with Tables 19A-D. For each lipid biosynthesis pathway protein of Table 20, the codon-optimized gene sequence can individually be operably linked to the CaMV 35S promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Chlorella vulgaris* genome for targeted genomic integration of the transformation vector. Homology regions may be selected to disrupt one or more genomic sites of endogenous lipid biosynthesis pathway genes. Stable transformation of *Chlorella vulgaris* with the transformation vector is achieved through well-known transformation techniques including electroporation or other known methods. Activity of the hygromycin B resistance gene product can be used as a marker to select for *Chlorella vulgaris* transformed with the transformation vector on, but not limited to, agar medium comprising hygromycin. Growth media suitable for *Chlorella vulgaris* lipid production include, but are not limited to BG11 medium (0.04 g/L $KH_2PO_4$, 0.075 g/L $CaCl_2$, 0.036 g/L citric acid, 0.006 g/L Ammonium Ferric Citrate, 1 mg/L EDTA, and 0.02 g/L $Na_2CO_3$) supplemented with trace metals, and optionally 1.5 g/L NaNO3. Additional media suitable for culturing *Chlorella vulgaris* for lipid production include, for example, Watanabe medium (comprising 1.5 g/L $KNO_3$, 1.25 g/L $KH_2PO_4$, 1.25 $l^{-1}$ $MgSO_4.7H_2O$, 20 mg $l^{-1}$ $FeSO_4.7H_2O$ with micronutrients and low-nitrogen medium (comprising 203 mg/l $(NH_4)_2HPO_4$, 2.236 g/l KCl, 2.465 g/l $MgSO_4$, 1.361 g/l $KH_2PO_4$ and 10 mg/l $FeSO_4$) as reported by Illman et al., *Enzyme and Microbial Technology*, Vol. 27 (2000), pp. 631-635. Evaluation of fatty acid profiles of *Chlorella vulgaris* lipids can be assessed through standard lipid extraction and analytical methods described herein.

Example 12: Engineering *Chlorella ellipsoidea*

Expression of recombinant genes in accordance with the present invention in *Chlorella ellipsoidea* can be accomplished by modifying the methods and vectors taught by Chen et al. as discussed herein. Briefly, Chen et al., *Current Genetics*, Vol. 39:5 (2001), pp. 365-370, reported the stable transformation of *Chlorella ellipsoidea* with plasmid DNA. Using the transformation method of electroporation, Chen introduced the plasmid pBinUΩNP-1 into *Chlorella ellipsoidea*. The nucleotide sequence of pBinUΩNP-1 comprised sequence encoding the neutrophil peptide-1 (NP-1) rabbit gene product operably linked to a *Zea mays* Ubiquitin (ubi1) gene promoter upstream of the NP-1 protein-coding region and operably linked to the 3' UTR/terminator of the nopaline synthase (nos) gene downstream of the NP-1 protein-coding region. The sequence of plasmid pBinUSΩNP-1 further comprised a G418 antibiotic resistance cassette. This G418 antibiotic resistance cassette comprised sequence encoding the aminoglycoside 3'-phosphotransferase (aph 3') gene product. The aph 3' gene product confers resistance to the antibiotic G418. Prior to transformation, *Chlorella ellipsoidea* was unable to be propagated in culture medium comprising 30 ug/mL G418. Upon transformation with the pBinUΩNP-1 plasmid, transformants of *Chlorella ellipsoidea* were obtained that were propagated in selective culture medium comprising 30 ug/mL G418. The expression of the aph 3' gene product in *Chlorella ellipsoidea* enabled propagation of transformed *Chlorella ellipsoidea* in the presence of 30 ug/mL G418, thereby establishing the utility of the G418 antibiotic resistance cassette as selectable marker for use in *Chlorella* ellipsoidea. Detectable activity of the NP-1 gene product indicated that the ubi1 promoter and nos 3' UTR are suitable for enabling heterologous gene expression in *Chlorella ellipsoidea*. Evaluation of the genomic DNA of the stable transformants was performed by Southern analysis. Selection and maintenance of the transformed *Chlorella ellipsoidea* was performed on Knop medium (comprising 0.2 g/L $K_2HPO_4$, 0.2 g/L $MgSO_4.7H_2O$, 0.12 g/L KCl, and 10 mg/L FeCl3, pH 6.0-8.0 supplemented with 0.1% yeast extract and 0.2% glucose) with 15 ug/mL G418 (for liquid cultures) or with 30 ug/mL G418 (for solid cultures comprising 1.8% agar). Propagation of *Chlorella ellipsoidea* in media other than Knop medium has been reported (see Cho et al., Fisheries Science, Vol. 73:5 (2007), pp. 1050-1056, Jarvis and Brown, *Current Genetics*, Vol. 19 (1991), pp. 317-321 and Kim et al., *Marine Biotechnology*, Vol. 4 (2002), pp. 63-73). Additional plasmids, promoters, 3'UTR/terminators, and selectable markers suitable for enabling heterologous gene expression in *Chlorella ellipsoidea* have been reported (see Jarvis and Brown and Kim et al., *Marine Biotechnology*, Vol. 4 (2002), pp. 63-73). Chen reported that the plasmid pBinUΩNP-1, the ubi1 promoter, and the *Agrobacterium tumefaciens* nopaline synthase gene 3'UTR/terminator are suitable to enable exogenous gene expression in *Chlorella ellipsoidea*. In addition, Chen reported that the G418 resistance cassette encoded on pBinUΩNP-1 was suitable for use as a selectable marker in *Chlorella* ellipsoidea.

In an embodiment of the present invention, vector pBinUΩNP-1, comprising the nucleotide sequence encoding the aph 3' gene product, conferring resistance to G418, for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella ellipsoidea* to reflect the codon bias inherent in nuclear genes of *Chlorella ellipsoidea* in accordance with Tables 19A-D. For each lipid biosynthesis pathway protein of Table 20, the codon-optimized gene sequence can individually be operably linked to the *Zea mays* ubi1 promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Chlorella ellipsoidea* genome for targeted genomic integration of the transformation vector. Homology regions may be selected to disrupt one or more genomic sites of endogenous lipid biosynthesis pathway genes. Stable transformation of *Chlorella ellipsoidea* with the transformation vector is achieved through well-known transformation techniques including electroporation or other known methods. Activity of the aph 3' gene product can be used as a marker to select for *Chlorella ellipsoidea* transformed with the transformation vector on, but not limited to, Knop agar medium comprising G418. Growth media suitable for *Chlorella ellipsoidea* lipid production include, but are not limited to, Knop medium and those culture medium reported by Jarvis and Brown and Kim et al. Evaluation of fatty acid profiles of *Chlorella ellipsoidea* lipids can be assessed through standard lipid extraction and analytical methods described herein.

Example 13: Engineering *Chlorella kessleri*

Expression of recombinant genes in accordance with the present invention in *Chlorella kessleri* can be accomplished by modifying the methods and vectors taught by El-Sheekh et al. as discussed herein. Briefly, El-Sheekh et al., *Biologia Plantarium*, Vol. 42:2 (1999), pp. 209-216, reported the stable transformation of *Chlorella kessleri* with plasmid DNA. Using the transformation method of microprojectile bombardment, El-Sheekh introduced the plasmid pBI121 (GenBank Accession No. AF485783) into *Chlorella* kessleri. Plasmid pBI121 comprised a kanamycin/neomycin antibiotic resistance cassette. This kanamycin/neomycin antibiotic resistance cassette comprised the *Agrobacterium tumefaciens* nopaline synthase (nos) gene promoter, sequence encoding the neomycin phosphotransferase II (nptII) gene product (GenBank Accession No. AAL92039) for resistance to kanamycin and G418, and the 3' UTR/terminator of the *Agrobacterium tumefaciens* nopaline synthase (nos) gene. pBI121 further comprised sequence encoding a beta-glucuronidase (GUS) reporter gene product operably linked to a CaMV 35S promoter and operably linked to a 3' UTR/terminator of the nos gene. Prior to transformation, *Chlorella kessleri* was unable to be propagated in culture medium comprising 15 ug/L kanamycin. Upon transformation with the pBI121plasmid, transformants of *Chlorella kessleri* were obtained that were propagated in selective culture medium comprising 15 mg/L kanamycin. The express ion of the nptII gene product in *Chlorella kessleri* enabled propagation in the presence of 15 mg/L kanamycin, thereby establishing the utility of the kanamycin/neomycin antibiotic resistance cassette as selectable marker for use in *Chlorella kessleri*. Detectable activity of the GUS gene product indicated that the CaMV 35S promoter and nos 3' UTR are suitable for enabling heterologous gene expression in *Chlorella kessleri*. Evaluation of the genomic DNA of the stable transformants was performed by Southern analysis. As reported by El-Sheekh, selection and maintenance of transformed *Chlorella kessleri* was conducted on semisolid agar plates comprising YEG medium (1% yeast extract, 1% glucose) and 15 mg/L kanamycin. El-Sheekh also reported the propagation of *Chlorella kessleri* in YEG liquid culture media. Additional media suitable for culturing *Chlorella kessleri* for lipid production are disclosed in Sato et al., *BBA Molecular and Cell Biology of Lipids*, Vol. 1633 (2003), pp. 27-34). El-Sheekh reported that the plasmid pBI121, the CaMV promoter, and the nopaline synthase gene 3'UTR/terminator are suitable to enable heterologous gene expression in *Chlorella*

*kessleri*. In addition, El-Sheekh reported that the kanamycin/neomycin resistance cassette encoded on pBI121 was suitable for use as a selectable marker in *Chlorella kessleri*.

In an embodiment of the present invention, vector pBI121, comprising the nucleotide sequence encoding the kanamycin/neomycin resistance gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella kessleri* to reflect the codon bias inherent in nuclear genes of *Chlorella kessleri* in accordance with Tables 19A-D. For each lipid biosynthesis pathway protein of Table 20, the codon-optimized gene sequence can individually be operably linked to the CaMV 35S promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Chlorella kessleri* genome for targeted genomic integration of the transformation vector. Homology regions may be selected to disrupt one or more genomic sites of endogenous lipid biosynthesis pathway genes. Stable transformation of *Chlorella kessleri* with the transformation vector is achieved through well-known transformation techniques including microprojectile bombardment or other known methods. Activity of the nptII gene product can be used as a marker to select for *Chlorella kessleri* transformed with the transformation vector on, but not limited to, YEG agar medium comprising kanamycin or neomycin. Growth media suitable for *Chlorella kessleri* lipid production include, but are not limited to, YEG medium, and those culture media reported by Sato et al. Evaluation of fatty acid profiles of *Chlorella kessleri* lipids can be assessed through standard lipid extraction and analytical methods described herein.

Example 14: Engineering *Dunaliella tertiolecta*

Expression of recombinant genes in accordance with the present invention in *Dunaliella tertiolecta* can be accomplished by modifying the methods and vectors taught by Walker et al. as discussed herein. Briefly, Walker et al., *Journal of Applied Phycology*, Vol. 17 (2005), pp. 363-368, reported stable nuclear transformation of *Dunaliella tertiolecta* with plasmid DNA. Using the transformation method of electroporation, Walker introduced the plasmid pDbleFLAG1.2 into *Dunaliella tertiolecta*. pDbleFLAG1.2 comprised sequence encoding a bleomycin antibiotic resistance cassette, comprising sequence encoding the *Streptoalloteichus hindustanus* Bleomycin binding protein (ble), for resistance to the antibiotic phleomycin, operably linked to the promoter and 3' UTR of the *Dunaliella tertiolecta* ribulose-1,5-bisphosphate carboxylase/oxygenase small subunit gene (rbcS1, GenBank Accession No. AY530155). Prior to transformation, *Dunaliella tertiolecta* was unable to be propagated in culture medium comprising 1 mg/L phleomycin. Upon transformation with the pDbleFLAG1.2 plasmid, transformants of *Dunaliella tertiolecta* were obtained that were propagated in selective culture medium comprising 1 mg/L phleomycin. The expression of the ble gene product in *Dunaliella tertiolecta* enabled propagation in the presence of 1 mg/L phleomycin, thereby establishing the utility of the bleomycin antibiotic resistance cassette as selectable marker for use in *Dunaliella tertiolecta*. Evaluation of the genomic DNA of the stable transformants was performed by Southern analysis. As reported by Walker, selection and maintenance of transformed *Dunaliella tertiolecta* was conducted in *Dunaliella* medium (DM, as described by Provasoli et al., *Archiv fur Mikrobiologie*, Vol. 25 (1957), pp. 392-428) further comprising 4.5 g/L NaCl and 1 mg/L pheomycin. Additional media suitable for culturing *Dunaliella tertiolecta* for lipid production are discussed in Takagi et al., *Journal of Bioscience and Bioengineering*, Vol. 101:3 (2006), pp. 223-226 and in Massart and Hanston, Proceedings Venice 2010, *Third International Symposium on Energy from Biomass and Waste*. Walker reported that the plasmid pDbleFLAG1.2 and the promoter and 3' UTR of the *Dunaliella tertiolecta* ribulose-1,5-bisphosphate carboxylase/oxygenase small subunit gene are suitable to enable heterologous expression in *Dunaliella tertiolecta*. In addition, Walker reported that the bleomycin resistance cassette encoded on pDbleFLAG1.2 was suitable for use as a selectable marker in *Dunaliella tertiolecta*.

In an embodiment of the present invention, vector pDbleFLAG1.2, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Dunaliella tertiolecta* to reflect the codon bias inherent in nuclear genes of *Dunaliella tertiolecta* in accordance with Tables 19A-D. For each lipid biosynthesis pathway protein of Table 20, the codon-optimized gene sequence can individually be operably linked to the rbcS1 promoter upstream of the protein-coding sequence and operably linked to the rbcS1 3'UTR/terminator at the 3' region, or downstream, of the protein-coding sequence. The transformation construct may additionally comprise homology regions to the *Dunaliella tertiolecta* genome for targeted genomic integration of the transformation vector. Homology regions may be selected to disrupt one or more genomic sites of endogenous lipid biosynthesis pathway genes. Stable transformation of *Dunaliella tertiolecta* with the transformation vector is achieved through well-known transformation techniques including electroporation or other known methods. Activity of the ble gene product can be used as a marker to select for *Dunaliella tertiolecta* transformed with the transformation vector on, but not limited to, DM medium comprising pheomycin. Growth medium suitable for *Dunaliella tertiolecta* lipid production include, but are not limited to DM medium and those culture media described by Takagi et al. and Massart and Hanston. Evaluation of fatty acid profiles of *Dunaliella tertiolecta* lipids can be assessed through standard lipid extraction and analytical methods described herein.

Example 15: Engineering *Volvox carteri*

Expression of recombinant genes in accordance with the present invention in *Volvox carteri* can be accomplished by modifying the methods and vectors taught by Hallman and Rappel et al. as discussed herein. Briefly, Hallman and Rappel et al., *The Plant Journal*, Volume 17 (1999), pp. 99-109, reported the stable nuclear transformation of *Volvox carteri* with plasmid DNA. Using the transformation method of microprojectile bombardment, Hallman and Rappel introduced the pzeoE plasmid into *Volvox carteri*. The pzeoE plasmid comprised sequence encoding a bleomycin antibiotic resistance cassette, comprising sequence encoding the *Streptoalloteichus hindustanus* Bleomycin binding protein (ble), for resistance to the antibiotic zeocin, operably linked to and the promoter and 3' UTR of the *Volvox carteri* beta-tubulin gene (GenBank Accession No. L24547). Prior to transformation, *Volvox carteri* was unable to be propagated in culture medium comprising 1.5 ug/ml zeocin. Upon transformation with the pzeoE plasmid, transformants of *Volvox carteri* were obtained that were propagated in selective culture medium comprising greater than 20 ug/ml zeocin. The expression of the ble gene product in *Volvox carteri* enabled propagation in the presence of 20 ug/ml zeocin, thereby establishing the utility of the bleomycin antibiotic resistance cassette as selectable marker for use in *Volvox carteri*. Evaluation of the genomic DNA of the stable transformants was performed by Southern analysis. As reported by Hallman and Rappel, selection and maintenance of transformed *Volvox carteri* was conducted in *Volvox* medium (VM, as described by Provasoli and Pintner, The Ecology of Algae, Special Publication No. 2 (1959), Tyron, C. A. and Hartman, R. T., eds., Pittsburgh: University of Pittsburgh, pp. 88-96) with 1 mg/L pheomycin. Media suitable for culturing *Volvox carteri* for lipid production are also discussed by Starr in Starr R, C. *Dev Biol Suppl*., Vol. 4 (1970), pp. 59-100). Hallman and Rappel reported that the plasmid pzeoE and the promoter and 3' UTR of the *Volvox carteri* beta-tubulin gene are suitable to enable heterologous expression in *Volvox carteri*. In addition, Hallman and Rappel reported that the bleomycin resistance cassette encoded on pzeoE was suitable for use as a selectable marker in *Volvox carteri*. Additional plasmids, promoters, 3'UTR/terminators, and selectable markers suitable for enabling heterologous gene expression in *Volvox carteri* and suitable for use as selective markers *Volvox carteri* in have been reported (for instance see Hallamann and Sumper, *Proceedings of the National Academy of Sciences*, Vol. 91 (1994), pp 11562-11566 and Hallman and Wodniok, *Plant Cell Reports*, Volume 25 (2006), pp. 582-581).

In an embodiment of the present invention, vector pzeoE, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 19, each protein-coding sequence codon-optimized for expression in *Volvox carteri* to reflect the codon bias inherent in nuclear genes of *Volvox carteri* in accordance with Tables 19A-D. For each lipid biosynthesis pathway protein of Table 20, the codon-optimized gene sequence can individually be operably linked to the *Volvox carteri* beta-tubulin promoter upstream of the protein-coding sequence and operably linked to the *Volvox carteri* beta-tubulin 3'UTR/terminator at the 3' region, or downstream, of the protein-coding sequence. The transformation construct may additionally comprise homology regions to the *Volvox carteri* genome for targeted genomic integration of the transformation vector. Homology regions may be selected to disrupt one or more genomic sites of endogenous lipid biosynthesis pathway genes. One skilled in the art can identify such homology regions within the sequence of the *Volvox carteri* genome (referenced in the publication by Prochnik et al., *Science*, Vol. 329:5988 (2010), pp 223-226). Stable transformation of *Volvox carteri* with the transformation vector is achieved through well-known transformation techniques including microprojectile bombardment or other known methods. Activity of the ble gene product can be used as a marker to select for *Volvox carteri* transformed with the transformation vector on, but not limited to, VM medium comprising zeocin. Growth medium suitable for *Volvox carteri* lipid production include, but are not limited to VM medium and those culture media discussed by Starr. Evaluation of fatty acid profiles of *Volvox carteri* lipids can be assessed through standard lipid extraction and analytical methods described herein.

Example 16: Engineering *Haematococcus pluvialis*

Expression of recombinant genes in accordance with the present invention in *Haematococcus pluvialis* can be accomplished by modifying the methods and vectors taught by Steinbrenner and Sandmann et al. as discussed herein. Briefly, Steinbrenner and Sandmann et al., *Applied and Environmental Microbiology*, Vol. 72:12 (2006), pp. 7477-7484, reported the stable nuclear transformation of *Haematococcus pluvialis* with plasmid DNA. Using the transformation method of microprojectile bombardment, Steinbrenner introduced the plasmid pPlat-pds-L504R into *Haematococcus pluvialis*. The plasmid pPlat-pds-L504R comprised a norflurazon resistance cassette, which comprised the promoter, protein-coding sequence, and 3'UTR of the *Haematococcus pluvialis* phytoene desaturase gene (Pds, GenBank Accession No. AY781170), wherein the protein-coding sequence of Pds was modified at position 504 (thereby changing a leucine to an arginine) to encode a gene product (Pds-L504R) that confers resistance to the herbicide norflurazon. Prior to transformation with pPlat-pds-L504R, *Haematococcus pluvialis* was unable to propagate on medium comprising 5 uM norflurazon. Upon transformation with the pPlat-pds-L504R plasmid, transformants of *Haematococcus pluvialis* were obtained that were propagated in selective culture medium comprising 5 uM norflurazon. The expression of the Pds-L504R gene product in *Haematococcus pluvialis* enabled propagation in the presence of 5 uM norflurazon, thereby establishing the utility of the norflurazon herbicide resistance cassette as selectable marker for use in *Haematococcus pluvialis*. Evaluation of the genomic DNA of the stable transformants was performed by Southern analysis. As reported by Steinbrenner, selection and maintenance of transformed *Haematococcus pluvialis* was conducted on agar plates comprising OHA medium (OHM (0.41 g/L $KNO_3$, 0.03 g/L $Na_2HPO_4$, 0.246 g/L $MgSO_4.7H_2O$, 0.11 g/L $CaCl_2.2H_2O$, 2.62 mg/L $Fe_{(III)}$citrate x $H_2O$, 0.011 mg/L $CoCl_2.6H_2O$, 0.012 mg/L $CuSO_4.5H_2O$, 0.075 mg/L $Cr_2O_3$, 0.98 mg/L $MnCl_2.4H_2O$, 0.12 mg/L $Na_2MoO_4 \times 2H_2O$, 0.005 mg/L $SeO_2$ and 25 mg/L biotin, 17.5 mg/L thiamine, and 15 mg/L vitamin B12), supplemented with 2.42 g/L Tris-acetate, and 5 mM norflurazon. Propagation of *Haematococcus pluvialis* in liquid culture was performed by Steinbrenner and Sandmann using basal medium (basal medium as described by Kobayashi et al., *Applied and Environmental Microbiology*, Vol. 59 (1993), pp. 867-873). Steinbrenner and Sandmann reported that the pPlat-pds-L504R plasmid and promoter and 3' UTR of the *Haematococcus pluvialis* phytoene desaturase gene are suitable to enable heterologous expression in *Haematococcus pluvialis*. In addition, Steinbrenner and Sandmann reported that the norflurazon resistance cassette encoded on pPlat-pds-L504R was suitable for use as a selectable marker in *Haematococcus pluvialis*. Additional plasmids, promoters, 3'UTR/terminators, and selectable markers suitable for enabling heterologous gene expression in *Haematococcus pluvialis* have been reported (see Kathiresan et al., *Journal of Phycology*, Vol. 45 (2009), pp 642-649).

In an embodiment of the present invention, vector pPlat-pds-L504R, comprising the nucleotide sequence encoding the Pds-L504R gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Haematococcus pluvialis* to reflect the codon bias inherent in nuclear genes of *Haematococcus pluvialis* in accordance with Tables 19 A-D. For each lipid biosynthesis pathway protein of Table 20, the codon-optimized gene sequence can individually be operably linked to the *Haematococcus pluvialis* pds gene promoter upstream of the protein-coding sequence and operably linked to the *Haematococcus pluvialis* pds gene 3'UTR/terminator at the 3' region, or downstream, of the protein-coding sequence. The transformation construct may additionally comprise homology regions to the *Haematococcus pluvialis* genome for targeted genomic integration of the transformation vector. Homology regions may be selected to disrupt one or more genomic sites of endogenous lipid biosynthesis pathway genes. Stable transformation of *Haematococcus pluvialis* with the transformation vector is achieved through well-known transformation techniques including microprojectile bombardment or other known methods. Activity of the Pds-L504R gene product can be used as a marker to select for *Haematococcus pluvialis* transformed with the transformation vector on, but not limited to, OHA medium comprising norflurazon. Growth media suitable for *Haematococcus pluvialis* lipid production include, but are not limited to basal medium and those culture media described by Kobayashi et al., Kathiresan et al, and Gong and Chen, *Journal of Applied Phycology*, Vol. 9:5 (1997), pp. 437-444). Evaluation of fatty acid profiles of *Haematococcus pluvialis* lipids can be assessed through standard lipid extraction and analytical methods described herein.

Example 17: Engineering *Closterium peracerosum-strigosum-littorale* complex Expression of recombinant genes in accordance with the present invention in *Closterium peracerosum-strigosum-littorale* complex can be accomplished by modifying the methods and vectors taught by Abe et al. as discussed herein. Briefly, Abe et al., *Plant Cell Physiology*, Vol. 52:9 (2011), pp. 1676-1685, reported the stable nuclear transformation of *Closterium peracerosum-strigosum-littorale* complex with plasmid DNA. Using the transformation methods of microprojectile bombardment, Abe introduced the plasmid pSA106 into *Closterium peracerosum-strigosum-littorale* complex. Plasmid pSA106 comprised a bleomycin resistance cassette, comprising sequence encoding the *Streptoalloteichus hindustanus* Bleomycin binding protein gene (ble, GenBank Accession No. CAA37050) operably linked to the promoter and 3' UTR of the *Closterium peracerosum-strigosum-littorale* complex Chlorophyll a/b-binding protein gene (CAB, GenBank Accession No. AB363403). Prior to transformation with pSA106, *Closterium peracerosum-strigosum-littorale* complex was unable to propagate on medium comprising 3 ug/ml phleomycin. Upon transformation with pSA106, transformants of *Closterium peracerosum-strigosum-littorale* complex were obtained that were propagated in selective culture medium comprising 3 ug/ml phleomycin. The expression of the ble gene product in *Closterium peracerosum-strigosum-littorale* complex enabled propagation in the presence of 3 ug/ml phleomycin, thereby establishing the utility of the bleomycin antibiotic resistance cassette as selectable marker for use in *Closterium peracerosum-strigosum-littorale* complex. Evaluation of the genomic DNA of the stable transformants was performed by Southern analysis. As reported by Abe, selection and maintenance of transformed *Closterium peracerosum-strigosum-littorale* complex was conducted first in top agar with C medium (0.1 g/L $KNO_3$, 0.015 g/L $Ca(NO_3)_2.4H_2O$, 0.05 g/L glycerophosphate-Na2, 0.04 g/L $MgSO_4.7H_2O$, 0.5 g/L Tris(hydroxylmethyl)aminomethane, trace minerals, biotin, vitamins $B_1$ and $B_{12}$) and then subsequently isolated to agar plates comprising C medium supplemented with phleomycin. As reported by Abe, propagation of *Closterium peracerosum-strigosum-littorale* complex in liquid culture was performed in C medium. Additional liquid culture medium suitable for propagation of *Closterium peracerosum-strigosum-littorale* complex are discussed by Sekimoto et al., *DNA Research,* 10:4 (2003), pp. 147-153. Abe reported that the pSA106 plasmid and promoter and 3' UTR of the *Closterium peracerosum-strigosum-littorale* complex CAB gene are suitable to enable heterologous gene expression in *Closterium peracerosum-strigosum-littorale* complex. In addition, Abe reported that the bleomycin resistance cassette encoded on pSA106 was suitable for use as a selectable marker in *Closterium peracerosum-strigosum-littorale* complex. Additional plasmids, promoters, 3'UTR/terminators, and selectable markers suitable for enabling heterologous gene expression in *Closterium peracerosum-strigosum-littorale* complex have been reported (see Abe et al., *Plant Cell Physiology, Vol.* 49 (2008), pp. 625-632).

In an embodiment of the present invention, vector pSA106, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Closterium peracerosum-strigosum-littorale* complex to reflect the codon bias inherent in nuclear genes of *Closterium peracerosum-strigosum-littorale* complex in accordance with Tables 19A-D. For each lipid biosynthesis pathway protein of Table 20, the codon-optimized gene sequence can individually be operably linked to the *Closterium peracerosum-strigosum-littorale* complex CAB gene promoter upstream of the protein-coding sequence and operably linked to the *Closterium peracerosum-strigosum-littorale* complex CAB gene 3'UTR/terminator at the 3' region, or downstream, of the protein-coding sequence. The transformation construct may additionally comprise homology regions to the *Closterium peracerosum-strigosum-littorale* complex genome for targeted genomic integration of the transformation vector. Homology regions may be selected to disrupt one or more genomic sites of endogenous lipid biosynthesis pathway genes. Stable transformation of *Closterium peracerosum-strigosum-littorale* complex with the transformation vector is achieved through well-known transformation techniques including microprojectile bombardment or other known methods. Activity of the ble gene product can be used as a marker to select for *Closterium peracerosum-strigosum-littorale* complex transformed with the transformation vector on, but not limited to, C medium comprising phleomycin. Growth media suitable for *Closterium peracerosum-strigosum-littorale* complex lipid production include, but are not limited to C medium and those culture media reported by Abe et al. and Sekimoto et al. Evaluation of fatty acid profiles of *Closterium peracerosum-strigosum-littorale* complex lipids can be assessed through standard lipid extraction and analytical methods described herein.

Example 18: Engineering *Dunaliella viridis*

Expression of recombinant genes in accordance with the present invention in *Dunaliella viridis* can be accomplished by modifying the methods and vectors taught by Sun et al. as discussed herein. Briefly, Sun et al., *Gene*, Vol. 377 (2006), pp. 140-149, reported the stable transformation of *Dunaliella viridis* with plasmid DNA. Using the transformation method of electroporation, Sun introduced the plasmid pDVNR, encoding the full *Dunaliella viridis* nitrate reductase gene into mutant *Dunaliella viridis* (*Dunaliella viridis* NR-mutants.) The NR-mutants are incapable of growth without the use of nitrate as a source of nitrogen. Nitrate reductase catalyzes the conversion of nitrate to nitrite. Prior to transformation, *Dunaliella viridis* NR-mutants were unable to propagate in culture medium comprising nitrate ($NO_3^-$) as the sole nitrogen source. The expression of the *Dunaliella viridis* NR gene product in NR-mutant *Dunaliella viridis* was used as a selectable marker to rescue the nitrate metabolism deficiency. Upon transformation with the pDVNR plasmid, NR-mutant *Dunaliella viridis* stably expressing the *Dunaliella viridis* NR gene product were obtained that were able to grow on agar plates comprising nitrate as the sole carbon source. Evaluation of the DNA of the stable transformants was performed by Southern analysis. Selection and maintenance of the transformed *Dunaliella viridis* (NR mutant) was performed on agar plates comprising 5 mM $KNO_3$. Sun also reported the propagation of *Dunaliella viridis* and *Dunaliella viridis* NR mutants in liquid culture medium. Additional media suitable for propagation of *Dunaliella viridis* are reported by Gordillo et al., *Journal of Applied Phycology*, Vol. 10:2 (1998), pp. 135-144 and by Moulton and Burford, *Hydrobiologia*, Vols. 204-205:1 (1990), pp. 401-408. Sun reported that the plasmid pDVNR and the promoter and 3' UTR/terminator of the *Dunaliella viridis* nitrate reductase gene were suitable to enable heterologous expression in *Dunaliella viridis* NR-mutants. Sun also reported that expression of the *Dunaliella viridis* nitrate reductase gene product was suitable for use as a selectable marker in *Dunaliella viridis* NR-mutants.

In an embodiment of the present invention, vector pDVNR, comprising the nucleotide sequence encoding the *Dunaliella viridis* nitrate reductase (DvNR) gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Dunaliella viridis* to reflect the codon bias inherent in nuclear genes of *Dunaliella viridis* in accordance with Tables 19A-D. For each lipid biosynthesis pathway protein of Table 20, the codon-optimized gene sequence can individually be operably linked to the DvNR promoter upstream of the protein-coding sequence and operably linked to the DvNR3'UTR/terminator at the 3' region, or downstream, of the protein-coding sequence. The transformation construct may additionally comprise homology regions to the *Dunaliella viridis* genome for targeted genomic integration of the transformation vector. Homology regions may be selected to disrupt one or more genomic sites of endogenous lipid biosynthesis pathway genes. Stable transformation of *Dunaliella viridis* NR mutants with the transformation vector is achieved through well-known transformation techniques including electroporation or other known methods. Activity of the DvNR gene product can be used as a selectable marker to rescue the nitrogen assimilation deficiency of *Dunaliella viridis* NR mutant strains and to select for *Dunaliella viridis* NR-mutants stably expressing the transformation vector. Growth media suitable for *Dunaliella viridis* lipid production include, but are not limited to those discussed by Sun et al., Moulton and Burford, and Gordillo et al. Evaluation of fatty acid profiles of *Dunaliella viridis* lipids can be assessed through standard lipid extraction and analytical methods described herein.

Example 19: Engineering *Dunaliella salina*

Expression of recombinant genes in accordance with the present invention in *Dunaliella salina* can be accomplished by modifying the methods and vectors taught by Geng et al. as discussed herein. Briefly, Geng et al., *Journal of Applied Phycology*, Vol. 15 (2003), pp. 451-456, reported the stable transformation of *Dunaliella salina* with plasmid DNA. Using the transformation method of electroporation, Geng introduced the pUΩHBsAg-CAT plasmid into *Dunaliella salina*. pUΩHBsAg-CAT comprises a hepatitis B surface antigen (HBsAG) expression cassette comprising sequence encoding the hepatitis B surface antigen operably linked to a *Zea mays* ubi1 promoter upstream of the HBsAG protein-coding region and operably linked to the 3' UTR/terminator of the *Agrobacterium tumefaciens* nopaline synthase gene (nos) downstream of the HBsAG protein-coding region. pUΩHBsAg-CAT further comprised a chloramphenicol resistance cassette, comprising sequence encoding the chloramphenicol acetyltransferase (CAT) gene product, conferring resistance to the antibiotic chloramphenicol, operably linked to the simian virus 40 promoter and enhancer. Prior to transformation with pUΩHBsAg-CAT, *Dunaliella salina* was unable to propagate on medium comprising 60 mg/L chloramphenicol. Upon transformation with the pUΩHBsAg-CAT plasmid, transformants of *Dunaliella salina* were obtained that were propagated in selective culture medium comprising 60 mg/L chloramphenicol. The expression of the CAT gene product in *Dunaliella salina* enabled propagation in the presence of 60 mg/L chloramphenicol, thereby establishing the utility of the chloramphenicol resistance cassette as selectable marker for use in *Dunaliella salina*. Detectable activity of the HBsAg gene product indicated that ubi1 promoter and nos 3'UTR/terminator are suitable for enabling gene expression in *Dunaliella salina*. Evaluation of the genomic DNA of the stable transformants was performed by Southern analysis. Geng reported that selection and maintenance of the transformed *Dunaliella salina* was performed on agar plates comprising Johnson's medium (J1, described by Borowitzka and Borowitzka (eds), Micro-algal Biotechnology. Cambridge University Press, Cambridge, pp. 460-461) with 60 mg/L chloramphenicol. Liquid propagation of *Dunaliella salina* was performed by Geng in J1 medium with 60 mg/L chloramphenicol. Propagation of *Dunaliella salina* in media other than J1 medium has been discussed (see Feng et al., *Mol. Bio. Reports*, Vol. 36 (2009), pp. 1433-1439 and Borowitzka et al., *Hydrobiologia, Vols.* 116-117:1 (1984), pp. 115-121). Additional plasmids, promoters, 3'UTR/terminators, and selectable markers suitable for enabling heterologous gene expression in *Dunaliella salina* have been reported by Feng et al. Geng reported that the plasmid pUΩHBsAg-CAT, the ubi1 promoter, and the *Agrobacte-*

*rium tumefaciens* nopaline synthase gene 3'UTR/terminator are suitable to enable exogenous gene expression in *Dunaliella salina*. In addition, Geng reported that the CAT resistance cassette encoded on pUΩHBsAg-CAT was suitable for use as a selectable marker in *Dunaliella salina*.

In an embodiment of the present invention, vector pUΩHBsAg-CAT, comprising the nucleotide sequence encoding the CAT gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Dunaliella salina* to reflect the codon bias inherent in nuclear genes of *Dunaliella salina* in accordance with Tables 19A-D. For each lipid biosynthesis pathway protein of Table 20, the codon-optimized gene sequence can individually be operably linked to the ubi1 promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Dunaliella salina* genome for targeted genomic integration of the transformation vector. Homology regions may be selected to disrupt one or more genomic sites of endogenous lipid biosynthesis pathway genes. Stable transformation of *Dunaliella salina* with the transformation vector is achieved through well-known transformation techniques including electroporation or other known methods. Activity of the CAT gene product can be used as a selectable marker to select for *Dunaliella salina* transformed with the transformation vector in, but not limited to, J1 medium comprising chloramphenicol. Growth medium suitable for *Dunaliella salina* lipid production include, but are not limited to J1 medium and those culture media described by Feng et al. and Borowitzka et al. Evaluation of fatty acid profiles of *Dunaliella salina* lipids can be assessed through standard lipid extraction and analytical methods described herein.

Example 20: Engineering *Gonium pectoral*

Expression of recombinant genes in accordance with the present invention in *Gonium pectoral* can be accomplished by modifying the methods and vectors taught by Lerche and Hallman et al. as discussed herein. Briefly, Lerche and Hallman et al., *BMC Biotechnology*, Volume 9:64, 2009, reported the stable nuclear transformation of *Gonium pectorale* with plasmid DNA. Using the transformation method of microprojectile bombardment, Lerche introduced the plasmid pPmr3 into *Gonium pectorale*. Plasmid pPmr3 comprised a paromomycin resistance cassette, comprising a sequence encoding the aminoglycoside 3'-phosphotransferase (aphVIII) gene product (GenBank Accession No. AAB03856) of *Streptomyces rimosus* for resistance to the antibiotic paromomycin, operably linked to the *Volvox carteri* hsp70A-rbcS3 hybrid promoter upstream of the aphVIII protein-coding region and operably linked to the 3' UTR/terminator of the *Volvox carteri* rbcS3 gene downstream of the aphVIII protein-coding region. Prior to transformation with pPmr3, *Gonium pectorale* was unable to propagate on medium comprising 0.06 ug/ml paromomycin. Upon transformation with pPmr3, transformants of *Gonium pectorale* were obtained that were propagated in selective culture medium comprising 0.75 and greater ug/ml paromomycin. The expression of the aphVIII gene product in *Gonium pectorale* enabled propagation in the presence of 0.75 and greater ug/ml paromomycin, thereby establishing the utility of the paromomycin antibiotic resistance cassette as selectable marker for use in *Gonium pectorale*. Evaluation of the genomic DNA of the stable transformants was performed by Southern analysis. Lerche and Hallman reported that selection and maintenance of the transformed *Gonium pectorale* was performed in liquid Jaworski's medium (20 mg/L $Ca(NO_3)_2.4H_2O$, 12.4 mg/L $KH_2PO_4$, 50 mg/L $MgSO_4.7H_2O$, 15.9 mg/L $NaHCO_3$, 2.25 mg/L EDTA-FeNa, 2.25 mg/L EDTA $Na_e$, 2.48 g/L $H_3BO_3$, 1.39 g/L $MnCl_2.4H_2O$, 1 mg/L $(NH_4)_6MO_7O_24.4H_2O$, 0.04 mg/L vitamin B12, 0.04 mg/L Thiamine-HCl, 0.04 mg/L biotin, 80 mg/L $NaNO_3$, 36 mg/L $Na_4HPO_4.12H_2O$) with 1.0 ug/ml paromomycin. Additional plasmids, promoters, 3'UTR/terminators, and selectable markers suitable for enabling heterologous gene expression in *Gonium pectorale* are further discussed by Lerche and Hallman. Lerche and Hallman reported that the plasmid pPmr3, *Volvox carteri* hsp70A-rbcS3 hybrid promoter, and the 3' UTR/terminator of the *Volvox carteri* rbcS3 gene are suitable to enable exogenous gene expression in *Gonium pectorale*. In addition, Lerche and Hallman reported that the paromomycin resistance cassette encoded pPmr3 was suitable for use as a selectable marker in *Gonium pectorale*.

In an embodiment of the present invention, vector pPmr3, comprising the nucleotide sequence encoding the aphVIII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Gonium pectorale* to reflect the codon bias inherent in nuclear genes of *Gonium pectorale* in accordance with Tables 19A-D. For each lipid biosynthesis pathway protein of Table 20, the codon-optimized gene sequence can individually be operably linked to the *Volvox carteri* hsp70A-rbcS3 hybrid promoter upstream of the protein-coding sequence and operably linked to the *Volvox carteri* rbcS3 gene 3'UTR/terminator at the 3' region, or downstream, of the protein-coding sequence. The transformation construct may additionally comprise homology regions to the *Gonium pectorale* genome for targeted genomic integration of the transformation vector. Homology regions may be selected to disrupt one or more genomic sites of endogenous lipid biosynthesis pathway genes. Stable transformation of *Gonium pectorale* with the transformation vector can be achieved through well-known transformation techniques including microprojectile bombardment or other known methods. Activity of the aphVIII gene product can be used as a selectable marker to select for *Gonium pectorale* transformed with the transformation vector in, but not limited to, Jaworski's medium comprising paromomycin. Growth media suitable for *Gonium pectorale* lipid production include Jaworski's medium and media reported by Stein, American Journal of Botany, Vol. 45:9 (1958), pp. 664-672. Evaluation of fatty acid profiles of *Gonium pectorale* lipids can be assessed through standard lipid extraction and analytical methods described herein.

Example 21: Engineering *Phaeodactylum tricornutum*

Expression of recombinant genes in accordance with the present invention in *Phaeodactylum tricornutum* can be accomplished by modifying the methods and vectors taught by Apt et al. as discussed herein. Briefly, Apt et al., *Molecular and General Genetics*, Vol. 252 (1996), pp. 572-579, reported the stable nuclear transformation of *Phaeodactylum tricornutum* with vector DNA. Using the transformation technique of microprojectile bombardment, Apt introduced the plasmid pfcpA into *Phaeodactylum tricornutum*. Plasmid pfcpA comprised a bleomycin resistance cassette, comprising sequence encoding the *Streptoalloteichus hindustanus* Bleomycin binding protein (ble), for resistance to the antibiotics phleomycin and zeocin, operably linked to the promoter of the *Phaeodactylum tricornutum* fucoxanthin chlorophyll a binding protein gene (fcpA) upstream of the ble protein-coding region and operably linked to the 3' UTR/terminator of the *Phaeodactylum tricornutum* fcpA gene at the 3' region, or downstream of the ble protein-coding region. Prior to transformation with pfcpA, *Phaeodactylum tricornutum* was unable to propagate on medium comprising 50 ug/ml zeocin. Upon transformation with pfcpA, transformants of *Phaeodactylum tricornutum* were obtained that were propagated in selective culture medium comprising 50 ug/ml zeocin. The expression of the ble gene product in *Phaeodactylum tricornutum* enabled propagation in the presence of 50 ug/ml zeocin, thereby establishing the utility of the bleomycin antibiotic resistance cassette as selectable marker for use in *Phaeodactylum tricornutum*. Evaluation of the genomic DNA of the stable transformants was performed by Southern analysis. Apt reported that selection and maintenance of the transformed *Phaeodactylum tricornutum* was performed on agar plates comprising LDM medium (as reported by Starr and Zeikus, *Journal of Phycology*, Vol. 29, Supplement, (1993)) with 50 mg/L zeocin. Apt reported liquid propagation of *Phaeodactylum tricornutum* transformants in LDM medium with 50 mg/L zeocin. Propagation of *Phaeodactylum tricornutum* in medium other than LDM medium has been discussed (by Zaslayskaia et al., *Science, Vol.* 292 (2001), pp. 2073-2075, and by Radokovits et al., *Metabolic Engineering*, Vol. 13 (2011), pp. 89-95). Additional plasmids, promoters, 3'UTR/terminators, and selectable markers suitable for enabling heterologous gene expression in *Phaeodactylum tricornutum* have been reported in the same report by Apt et al., by Zaslayskaia et al., and by Radokovits et al.). Apt reported that the plasmid pfcpA, and the *Phaeodactylum tricornutum* fcpA promoter and 3' UTR/terminator are suitable to enable exogenous gene expression in *Phaeodactylum tricornutum*. In addition, Apt reported that the bleomycin resistance cassette encoded on pfcpA was suitable for use as a selectable marker in *Phaeodactylum tricornutum*.

In an embodiment of the present invention, vector pfcpA, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Phaeodactylum tricornutum* to reflect the codon bias inherent in nuclear genes of *Phaeodactylum tricornutum* in accordance with Tables 19A-D. For each lipid biosynthesis pathway protein of Table 20, the codon-optimized gene sequence can individually be operably linked to the *Phaeodactylum tricornutum* fcpA gene promoter upstream of the protein-coding sequence and operably linked to the *Phaeodactylum tricornutum* fcpA gene 3'UTR/terminator at the 3' region, or downstream, of the protein-coding sequence. The transformation construct may additionally comprise homology regions to the *Phaeodactylum tricornutum* genome for targeted genomic integration of the transformation vector. Homology regions may be selected to disrupt one or more genomic sites of endogenous lipid biosynthesis pathway genes. One skilled in the art can identify such homology regions within the sequence of the *Phaeodactylum tricornutum* genome (referenced in the publication by Bowler et al., *Nature*, Vol. 456 (2008), pp. 239-244). Stable transformation of *Phaeodactylum tricornutum* with the transformation vector is achieved through well-known transformation techniques including microprojectile bombardment or other known methods. Activity of the ble gene product can be used as a marker to select for *Phaeodactylum tricornutum* transformed with the transformation vector in, but not limited to, LDM medium comprising paromomycin. Growth medium suitable for *Phaeodactylum tricornutum* lipid production include, but are not limited to f/2 medium as reported by Radokovits et al. Evaluation of fatty acid profiles of *Phaeodactylum tricornutum* lipids can be assessed through standard lipid extraction and analytical methods described herein.

Example 22: Engineering *Chaetoceros* sp.

Expression of recombinant genes in accordance with the present invention in *Chaetoceros* sp. can be accomplished by modifying the methods and vectors taught by Yamaguchi et al. as discussed herein. Briefly, Yamaguchi et al., Phycological Research, Vol. 59:2 (2011), pp. 113-119, reported the stable nuclear transformation of *Chaetoceros* sp. with plasmid DNA. Using the transformation method of microprojectile bombardment, Yamaguchi introduced the plasmid pTpfcp/nat into *Chaetoceros* sp. pTpfcp/nat comprised a nourseothricin resistance cassette, comprising sequence encoding the nourseothricin acetyltransferase (nat) gene product (GenBank Accession No. AAC60439) operably linked to the *Thalassiosira pseudonana* fucoxanthin chlorophyll a/c binding protein gene (fcp) promoter upstream of the nat protein-coding region and operably linked to the *Thalassiosira pseudonana* fcp gene 3' UTR/terminator at the 3' region (downstream of the nat protein coding-sequence). The nat gene product confers resistance to the antibiotic nourseothricin. Prior to transformation with pTpfcp/nat, *Chaetoceros* sp. was unable to propagate on medium comprising 500 ug/ml nourseothricin. Upon transformation with pTpfcp/nat, transformants of *Chaetoceros* sp. were obtained that were propagated in selective culture medium comprising 500 ug/ml nourseothricin. The expression of the nat gene product in *Chaetoceros* sp. enabled propagation in the presence of 500 ug/ml nourseothricin, thereby establishing the utility of the nourseothricin antibiotic resistance cassette as selectable marker for use in *Chaetoceros* sp. Evaluation of the genomic DNA of the stable transformants was performed by Southern analysis. Yamaguchi reported that selection and maintenance of the transformed *Chaetoceros* sp. was performed on agar plates comprising f/2 medium (as reported by Guilard, R. R., Culture of Phytoplankton for feeding marine invertebrates, In Culture of Marine Invertebrate Animals, Smith and Chantey (eds) 1975, Plenum Press, New York, pp. 26-60) with 500 ug/ml nourseothricin. Liquid propagation of *Chaetoceros* sp. transformants, as performed by Yamaguchi, was carried out in f/2 medium with 500 mg/L nourseothricin. Propagation of *Chaetoceros* sp. in additional culture medium has been reported (for example in Napolitano et al., *Journal of the World Aquaculture Society*, Vol. 21:2 (1990), pp. 122-130, and by Volkman et al., *Journal of Experimental Marine Biology and Ecology*, Vol. 128:3 (1989), pp. 219-240). Additional plasmids, promoters, 3'UTR/terminators, and selectable markers suitable for enabling heterologous gene expression in *Chaetoceros* sp. have been reported in the same report by Yamaguchi et al. Yamaguchi reported that the plasmid pTpfcp/nat, and the *Thalassiosira pseudonana* fcp promoter and 3' UTR/terminator are suitable to enable exogenous gene expression in *Chaetoceros* sp. In addition, Yamaguchi reported that the nourseothricin resistance cassette encoded on pTpfcp/nat was suitable for use as a selectable marker in *Chaetoceros* sp.

In an embodiment of the present invention, vector pTpfcp/nat, comprising the nucleotide sequence encoding the nat gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in the closely-related *Chaetoceros compressum* to reflect the codon bias inherent in nuclear genes of *Chaetoceros compressum* in accordance with Tables 19A-D. For each lipid biosynthesis pathway protein of Table 20, the codon-optimized gene sequence can individually be operably linked to the *Thalassiosira pseudonana* fcp gene promoter upstream of the protein-coding sequence and operably linked to the *Thalassiosira pseudonana* fcp gene 3'UTR/terminator at the 3' region, or downstream, of the protein-coding sequence. The transformation construct may additionally comprise homology regions to the *Chaetoceros* sp. genome for targeted genomic integration of the transformation vector. Homology regions may be selected to disrupt one or more genomic sites of endogenous lipid biosynthesis pathway genes. Stable transformation of *Chaetoceros* sp. with the transformation vector is achieved through well-known transformation including microprojectile bombardment or other known methods. Activity of the nat gene product can be used as a selectable marker to select for *Chaetoceros* sp. transformed with the transformation vector in, but not limited to, f/2 agar medium comprising nourseothricin. Growth medium suitable for *Chaetoceros* sp. lipid production include, but are not limited to, f/2 medium, and those culture media discussed by Napolitano et al. and Volkman et al. Evaluation of fatty acid profiles of *Chaetoceros* sp lipids can be assessed through standard lipid extraction and analytical methods described herein.

Example 23: Engineering *Cylindrotheca fusiformis*

Expression of recombinant genes in accordance with the present invention in *Cylindrotheca fusiformis* can be accomplished by modifying the methods and vectors taught by Poulsen and Kroger et al. as discussed herein. Briefly, Poulsen and Kroger et al., *FEBS Journal*, Vol. 272 (2005), pp. 3413-3423, reported the transformation of *Cylindrotheca fusiformis* with plasmid DNA. Using the transformation method of microprojectile bombardment, Poulsen and Kroger introduced the pCF-ble plasmid into *Cylindrotheca fusiformis*. Plasmid pCF-ble comprised a bleomycin resistance cassette, comprising sequence encoding the *Streptoalloteichus hindustanus* Bleomycin binding protein (ble), for resistance to the antibiotics zeocin and phleomycin, operably linked to the *Cylindrotheca fusiformis* fucozanthin chlorophyll a/c binding protein gene (fcpA, GenBank Accession No. AY125580) promoter upstream of the ble protein-coding region and operably linked to the *Cylindrotheca fusiformis* fcpA gene 3'UTR/terminator at the 3' region (down-stream of the ble protein-coding region). Prior to transformation with pCF-ble, *Cylindrotheca fusiformis* was unable to propagate on medium comprising 1 mg/ml zeocin. Upon transformation with pCF-ble, transformants of *Cylindrotheca fusiformis* were obtained that were propagated in selective culture medium comprising 1 mg/ml zeocin. The expression of the ble gene product in *Cylindrotheca fusiformis* enabled propagation in the presence of 1 mg/ml zeocin, thereby establishing the utility of the bleomycin antibiotic resistance cassette as selectable marker for use in *Cylindrotheca fusiformis*. Poulsen and Kroger reported that selection and maintenance of the transformed *Cylindrotheca fusiformis* was performed on agar plates comprising artificial seawater medium with 1 mg/ml zeocin. Poulsen and Kroger reported liquid propagation of *Cylindrotheca fusiformis* transformants in artificial seawater medium with 1 mg/ml zeocin. Propagation of *Cylindrotheca fusiformis* in additional culture medium has been discussed (for example in Liang et al., *Journal of Applied Phycology*, Vol. 17:1 (2005), pp. 61-65, and by Orcutt and Patterson, *Lipids, Vol.* 9:12 (1974), pp. 1000-1003). Additional plasmids, promoters, and 3'UTR/terminators for enabling heterologous gene expression in *Chaetoceros* sp. have been reported in the same report by Poulsen and Kroger. Poulsen and Kroger reported that the plasmid pCF-ble and the *Cylindrotheca fusiformis* fcp promoter and 3' UTR/terminator are suitable to enable exogenous gene expression in *Cylindrotheca fusiformis*. In addition, Poulsen and Kroger reported that the bleomycin resistance cassette encoded on pCF-ble was suitable for use as a selectable marker in *Cylindrotheca fusiformis*.

In an embodiment of the present invention, vector pCF-ble, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Cylindrotheca fusiformis* to reflect the codon bias inherent in nuclear genes of *Cylindrotheca fusiformis* in accordance with Tables 19A-D. For each lipid biosynthesis pathway protein of Table 20, the codon-optimized gene sequence can individually be operably linked to the *Cylindrotheca fusiformis* fcp gene promoter upstream of the protein-coding sequence and operably linked to the *Cylindrotheca fusiformis* fcp gene 3'UTR/terminator at the 3' region, or downstream, of the protein-coding sequence. The transformation construct may additionally comprise homology regions to the *Cylindrotheca fusiformis* genome for targeted genomic integration of the transformation vector. Homology regions may be selected to disrupt one or more genomic sites of endogenous lipid biosynthesis pathway genes. Stable transformation of *Cylindrotheca fusiformis* with the transformation vector is achieved through well-known transformation techniques including microprojectile bombardment or other known methods. Activity of the ble gene product can be used as a selectable marker to select for *Cylindrotheca fusiformis* transformed with the transformation vector in, but not limited to, artificial seawater agar medium comprising zeocin. Growth media suitable for *Cylindrotheca fusiformis* lipid production include, but are not limited to, artificial seawater and those media reported by Liang et al. and Orcutt and Patterson. Evaluation of fatty acid profiles of *Cylindrotheca fusiformis* lipids can be assessed through standard lipid extraction and analytical methods described herein.

Example 24: Engineering *Amphidinium* sp.

Expression of recombinant genes in accordance with the present invention in *Amphidinium* sp. can be accomplished by modifying the methods and vectors taught by ten Lohuis and Miller et al. as discussed herein. Briefly, ten Lohuis and Miller et al., *The Plant Journal*, Vol. 13:3 (1998), pp. 427-435, reported the stable transformation of *Amphidinium* sp. with plasmid DNA. Using the transformation technique of agitation in the presence of silicon carbide whiskers, ten Lohuis introduced the plasmid pMT NPT/GUS into *Amphidinium* sp. pMT NPT/GUS comprised a neomycin resistance cassette, comprising sequence encoding the neomycin phosphotransferase II (nptII) gene product (GenBank Accession No. AAL92039) operably linked to the *Agrobacterium tumefaciens* nopaline synthase (nos) gene promoter upstream, or 5' of the nptII protein-coding region and operably linked to the 3' UTR/terminator of the nos gene at the 3' region (down-stream of the nptII protein-coding region). The nptII gene product confers resistance to the antibiotic G418. The pMT NPT/GUS plasmid further comprised sequence encoding a beta-glucuronidase (GUS) reporter gene product operably-linked to a CaMV 35S promoter and further operably linked to the CaMV 35S 3' UTR/terminator. Prior to transformation with pMT NPT/GUS, *Amphidinium* sp. was unable to be propagated on medium comprising 3 mg/ml G418. Upon transformation with pMT NPT/GUS, transformants of *Amphidinium* sp. were obtained that were propagated in selective culture medium comprising 3 mg/ml G418. The expression of the nptII gene product in *Amphidinium* sp. enabled propagation in the presence of 3 mg/ml G418, thereby establishing the utility of the neomycin antibiotic resistance cassette as selectable marker for use in *Amphidinium* sp. Detectable activity of the GUS reporter gene indicated that CaMV 35S promoter and 3'UTR are suitable for enabling gene expression in *Amphidinium* sp. Evaluation of the genomic DNA of the stable transformants was performed by Southern analysis. ten Lohuis and Miller reported liquid propagation of *Amphidinium* sp transformants in medium comprising seawater supplemented with F/2 enrichment solution (provided by the supplier Sigma) and 3 mg/ml G418 as well as selection and maintenance of *Amphidinium* sp. transformants on agar medium comprising seawater supplemented with F/2 enrichment solution and 3 mg/ml G418. Propagation of *Amphidinium* sp. in additional culture medium has been reported (for example in Mansour et al., *Journal of Applied Phycology*, Vol. 17:4 (2005) pp. 287-v300). An additional plasmid, comprising additional promoters, 3'UTR/terminators, and a selectable marker for enabling heterologous gene expression in *Amphidinium* sp. have been reported in the same report by ten Lohuis and Miller. ten Lohuis and Miller reported that the plasmid pMT NPT/GUS and the promoter and 3' UTR/terminator of the nos and CaMV 35S genes are suitable to enable exogenous gene expression in *Amphidinium* sp. In addition, ten Lohuis and Miller reported that the neomycin resistance cassette encoded on pMT NPT/GUS was suitable for use as a selectable marker in *Amphidinium* sp.

In an embodiment of the present invention, vector pMT NPT/GUS, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Amphidinium* sp. to reflect the codon bias inherent in nuclear genes of the closely-related species, *Amphidinium carterae* in accordance with Tables 19A-D. For each lipid biosynthesis pathway protein of Table 20, the codon-optimized gene sequence can individually be operably linked to the *Agrobacterium tumefaciens* nopaline synthase (nos) gene promoter upstream of the protein-coding sequence and operably linked to the nos 3'UTR/terminator at the 3' region, or downstream, of the protein-coding sequence. The transformation construct may additionally comprise homology regions to the *Amphidinium* sp. genome for targeted genomic integration of the transformation vector. Homology regions may be selected to disrupt one or more genomic sites of endogenous lipid biosynthesis pathway genes. Stable transformation of *Amphidinium* sp. with the transformation vector is achieved through well-known transformation techniques including silicon fibre-mediated microinjection or other known methods. Activity of the nptII gene product can be used as a selectable marker to select for *Amphidinium* sp. transformed with the transformation vector in, but not limited to, seawater agar medium comprising G418. Growth media suitable for *Amphidinium* sp. lipid production include, but are not limited to, artificial seawater and those media reported by Mansour et al. and ten Lohuis and Miller. Evaluation of fatty acid profiles of *Amphidinium* sp. lipids can be assessed through standard lipid extraction and analytical methods described herein.

Example 25: Engineering *Symbiodinium microadriacticum*

Expression of recombinant genes in accordance with the present invention in *Symbiodinium microadriacticum* can be accomplished by modifying the methods and vectors taught by ten Lohuis and Miller et al. as discussed herein. Briefly, ten Lohuis and Miller et al., *The Plant Journal*, Vol. 13:3 (1998), pp. 427-435, reported the stable transformation of *Symbiodinium microadriacticum* with plasmid DNA. Using the transformation technique of silicon fibre-mediated microinjection, ten Lohuis introduced the plasmid pMT NPT/GUS into *Symbiodinium microadriacticum*. pMT NPT/GUS comprised a neomycin resistance cassette, comprising sequence encoding the neomycin phosphotransferase II (nptII) gene product (GenBank Accession No. AAL92039) operably linked to the *Agrobacterium tumefaciens* nopaline synthase (nos) gene promoter upstream, or 5' of the nptII protein-coding region and operably linked to the 3' UTR/terminator of the nos gene at the 3' region (down-stream of the nptII protein-coding region). The nptII gene product confers resistance to the antibiotic G418. The pMT NPT/GUS plasmid further comprised sequence encoding a beta-glucuronidase (GUS) reporter gene product operably-linked to a CaMV 35S promoter and further operably linked to the CaMV 35S 3' UTR/terminator. Prior to transformation with pMT NPT/GUS, *Symbiodinium microadriacticum* was unable to be propagated on medium comprising 3 mg/ml G418. Upon transformation with pMT NPT/GUS, transformants of *Symbiodinium microadriacticum* were obtained that were propagated in selective culture medium comprising 3 mg/ml G418. The expression of the nptII gene product in *Symbiodinium microadriacticum* enabled propagation in the presence of 3 mg/ml G418, thereby establishing the utility of the neomycin antibiotic resistance cassette as selectable marker for use in *Symbiodinium microadriacticum*. Detectable activity of the GUS reporter gene indicated that CaMV 35S promoter and 3'UTR are suitable for enabling gene expression in *Symbiodinium microadriacti-*

*cum*. Evaluation of the genomic DNA of the stable transformants was performed by Southern analysis. ten Lohuis and Miller reported liquid propagation of *Symbiodinium microadriacticum* transformants in medium comprising seawater supplemented with F/2 enrichment solution (provided by the supplier Sigma) and 3 mg/ml G418 as well as selection and maintenance of *Symbiodinium microadriacticum* transformants on agar medium comprising seawater supplemented with F/2 enrichment solution and 3 mg/ml G418. Propagation of *Symbiodinium microadriacticum* in additional culture medium has been discussed (for example in Iglesias-Prieto et al., *Proceedings of the National Academy of Sciences*, Vol. 89:21 (1992) pp. 10302-10305). An additional plasmid, comprising additional promoters, 3'UTR/terminators, and a selectable marker for enabling heterologous gene expression in *Symbiodinium microadriacticum* have been discussed in the same report by ten Lohuis and Miller. ten Lohuis and Miller reported that the plasmid pMT NPT/GUS and the promoter and 3' UTR/terminator of the nos and CaMV 35S genes are suitable to enable exogenous gene expression in *Symbiodinium microadriacticum*. In addition, ten Lohuis and Miller reported that the neomycin resistance cassette encoded on pMT NPT/GUS was suitable for use as a selectable marker in *Symbiodinium microadriacticum.*

In an embodiment of the present invention, vector pMT NPT/GUS, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Symbiodinium microadriacticum* to reflect the codon bias inherent in nuclear genes of *Symbiodinium microadriacticum* in accordance with Tables 19A-D. For each lipid biosynthesis pathway protein of Table 20, the codon-optimized gene sequence can individually be operably linked to the *Agrobacterium tumefaciens* nopaline synthase (nos) gene promoter upstream of the protein-coding sequence and operably linked to the nos 3' UTR/terminator at the 3' region, or downstream, of the protein-coding sequence. The transformation construct may additionally comprise homology regions to the *Symbiodinium microadriacticum* genome for targeted genomic integration of the transformation vector. Homology regions may be selected to disrupt one or more genomic sites of endogenous lipid biosynthesis pathway genes. Stable transformation of *Symbiodinium microadriacticum* with the transformation vector is achieved through well-known transformation techniques including silicon fibre-mediated microinjection or other known methods. Activity of the nptII gene product can be used as a selectable marker to select for *Symbiodinium microadriacticum* transformed with the transformation vector in, but not limited to, seawater agar medium comprising G418. Growth media suitable for *Symbiodinium microadriacticum* lipid production include, but are not limited to, artificial seawater and those media reported by Iglesias-Prieto et al. and ten Lohuis and Miller. Evaluation of fatty acid profiles of *Symbiodinium microadriacticum* lipids can be assessed through standard lipid extraction and analytical methods described herein.

Example 26: Engineering *Nannochloropsis* sp.

Expression of recombinant genes in accordance with the present invention in *Nannochloropsis* sp. W2J3B can be accomplished by modifying the methods and vectors taught by Kilian et al. as discussed herein. Briefly, Kilian et al., *Proceedings of the National Academy of Sciences*, Vol. 108:52 (2011) pp. 21265-21269, reported the stable nuclear transformation of *Nannochloropsis* with a transformation construct. Using the transformation method of electroporation, Kilian introduced the transformation construct C2 into *Nannochloropsis* sp. W2J3B. The C2 transformation construct comprised a bleomycin resistance cassette, comprising the coding sequence for the *Streptoalloteichus hindustanus* Bleomycin binding protein (ble), for resistance to the antibiotics phleomycin and zeocin, operably linked to and the promoter of the *Nannochloropsis* sp. W2J3B violaxanthin/chlorophyll a-binding protein gene VCP2 upstream of the ble protein-coding region and operably linked to the 3'UTR/terminator of the *Nannochloropsis* sp. W2J3B violaxanthin/chlorophyll a-binding gene VCP1 downstream of the ble protein-coding region. Prior to transformation with C2, *Nannochloropsis* sp. W2J3B was unable to propagate on medium comprising 2 ug/ml zeocin. Upon transformation with C2, transformants of *Nannochloropsis* sp. W2J3B were obtained that were propagated in selective culture medium comprising 2 ug/ml zeocin. The expression of the ble gene product in *Nannochloropsis* sp. W2J3B enabled propagation in the presence of 2 ug/ml zeocin, thereby establishing the utility of the bleomycin antibiotic resistance cassette as selectable marker for use in *Nannochloropsis*. Evaluation of the genomic DNA of the stable transformants was performed by PCR. Kilian reported liquid propagation of *Nannochloropsis* sp. W2J3B transformants in F/2 medium (reported by Guilard and Ryther, *Canadian Journal of Microbiology*, Vol. 8 (1962), pp. 229-239) comprising fivefold levels of trace metals, vitamins, and phosphate solution, and further comprising 2 ug/ml zeocin. Kilian also reported selection and maintenance of *Nannochloropsis* sp. W2J3B transformants on agar F/2 medium comprising artificial seawater 2 mg/ml zeocin. Propagation of *Nannochloropsis* in additional culture medium has been discussed (for example in Chiu et al., *Bioresour Technol.*, Vol. 100:2 (2009), pp. 833-838 and Pal et al., *Applied Microbiology and Biotechnology*, Vol. 90:4 (2011), pp. 1429-1441.). Additional transformation constructs, comprising additional promoters and 3'UTR/terminators for enabling heterologous gene expression in *Nannochloropsis* sp. W2J3B and selectable markers for selection of transformants have been described in the same report by Kilian. Kilian reported that the transformation construct C2 and the promoter of the *Nannochloropsis* sp. W2J3B violaxanthin/chlorophyll a-binding protein gene VCP2 and 3' UTR/terminator of the *Nannochloropsis* sp. W2J3B violaxanthin/chlorophyll a-binding protein gene VCP1 are suitable to enable exogenous gene expression in *Nannochloropsis* sp. W2J3B. In addition, Kilian reported that the bleomycin resistance cassette encoded on C2 was suitable for use as a selectable marker in *Nannochloropsis* sp. W2J3B.

In an embodiment of the present invention, transformation construct C2, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Nannochloropsis* sp. W2J3B to reflect the codon bias inherent in nuclear genes of *Nannochloropsis* sp. in accordance with Tables 19A-D. For each lipid biosynthesis pathway protein of Table 20, the codon-optimized gene sequence can individually be operably linked to the *Nannochloropsis* sp. W2J3B VCP2 gene promoter upstream of the protein-coding sequence and operably linked to the *Nannochloropsis* sp. W2J3B VCP1 gene 3'UTR/terminator at the 3' region, or downstream, of the protein-coding sequence. The transformation construct may additionally comprise homology regions to the *Nannochloropsis* sp. W2J3B genome for targeted genomic integration of the transformation vector. Homology regions may be selected to disrupt one or more genomic sites of endogenous lipid biosynthesis pathway genes. Stable transformation of *Nannochloropsis* sp. W2J3B with the transformation vector is achieved through well-known transformation techniques including electroporation or other known methods. Activity of the ble gene product can be used as a selectable marker to select for *Nannochloropsis* sp. W2J3B transformed with the transformation vector in, but not limited to, F/2 medium comprising zeocin. Growth media suitable for *Nannochloropsis* sp. W2J3B lipid production include, but are not limited to, F/2 medium and those media reported by Chiu et al. and Pal et al. Evaluation of fatty acid profiles of *Nannochloropsis* sp. W2J3B lipids can be assessed through standard lipid extraction and analytical methods described herein.

Example 27: Engineering *Cyclotella cryptica*

Expression of recombinant genes in accordance with the present invention in *Cyclotella cryptica* can be accomplished by modifying the methods and vectors taught by Dunahay et al. as discussed herein. Briefly, Dunahay et al., *Journal of Phycology*, Vol. 31 (1995), pp. 1004-1012, reported the stable transformation of *Cyclotella cryptica* with plasmid DNA. Using the transformation method of microprojectile bombardment, Dunahay introduced the plasmid pACCNPT5.1 into *Cyclotella cryptica*. Plasmid pACCNPT5.1 comprised a neomycin resistance cassette, comprising the coding sequence of the neomycin phosphotransferase II (nptII) gene product operably linked to the promoter of the *Cyclotella cryptica* acetyl-CoA carboxylase (ACCase) gene (GenBank Accession No. L20784) upstream of the nptII coding-region and operably linked to the 3'UTR/terminator of the *Cyclotella cryptica* ACCase gene at the 3' region (downstream of the nptII coding-region). The nptII gene product confers resistance to the antibiotic G418. Prior to transformation with pACCNPT5.1, *Cyclotella cryptica* was unable to propagate on 50% artificial seawater medium comprising 100 ug/ml G418. Upon transformation with pACCNPT5.1, transformants of *Cyclotella cryptica* were obtained that were propagated in selective 50% artificial seawater medium comprising 100 ug/ml G418. The expression of the nptII gene product in *Cyclotella cryptica* enabled propagation in the presence of 100 ug/ml G418, thereby establishing the utility of the neomycin antibiotic resistance cassette as selectable marker for use in *Cyclotella cryptica*. Evaluation of the genomic DNA of the stable transformants was performed by Southern analysis. Dunahay reported liquid propagation of *Cyclotella cryptica* in artificial seawater medium (ASW, as discussed by Brown, L., *Phycologia*, Vol. 21 (1982), pp. 408-410) supplemented with 1.07 mM sodium silicate and with 100 ug/ml G418. Dunahay also reported selection and maintenance of *Cyclotella cryptica* transformants on agar plates comprising ASW medium with 100 ug/ml G418. Propagation of *Cyclotella cryptica* in additional culture medium has been discussed (for example in Sriharan et al., *Applied Biochemistry and Biotechnology*, Vol. 28-29:1 (1991), pp. 317-326 and Pahl et al., *Journal of Bioscience and Bioengineering*, Vol. 109:3 (2010), pp. 235-239). Dunahay reported that the plasmid pACCNPT5.1 and the promoter of the *Cyclotella cryptica* acetyl-CoA carboxylase (ACCase) gene are suitable to enable exogenous gene expression in *Cyclotella cryptica*. In addition, Dunahay reported that the neomycin resistance cassette encoded on pACCNPT5.1 was suitable for use as a selectable marker in *Cyclotella cryptica*.

In an embodiment of the present invention, vector pACCNPT5.1, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Cyclotella cryptica* to reflect the codon bias inherent in nuclear genes of *Cyclotella cryptica* in accordance with Tables 19A-D. For each lipid biosynthesis pathway protein of Table 20, the codon-optimized gene sequence can individually be operably linked to the *Cyclotella cryptica* ACCase promoter upstream of the protein-coding sequence and operably linked to the *Cyclotella cryptica* ACCase 3'UTR/terminator at the 3' region, or downstream, of the protein-coding sequence. The transformation construct may additionally comprise homology regions to the *Cyclotella cryptica* genome for targeted genomic integration of the transformation vector. Homology regions may be selected to disrupt one or more genomic sites of endogenous lipid biosynthesis pathway genes. Stable transformation of *Cyclotella cryptica* with the transformation vector is achieved through well-known transformation techniques including microprojectile bombardment or other known methods. Activity of the nptII gene product can be used as a marker to select for *Cyclotella cryptica* transformed with the transformation vector in, but not limited to, agar ASW medium comprising G418. Growth media suitable for *Cyclotella cryptica* lipid production include, but are not limited to, ASW medium and those media reported by Sriharan et al., 1991 and Pahl et al. Evaluation of fatty acid profiles of *Cyclotella cryptica* lipids can be assessed through standard lipid extraction and analytical methods described herein.

Example 28: Engineering *Navicula saprophila*

Expression of recombinant genes in accordance with the present invention in *Navicula saprophila* can be accomplished by modifying the methods and vectors taught by Dunahay et al. as discussed herein. Briefly, Dunahay et al., *Journal of Phycology*, Vol. 31 (1995), pp. 1004-1012, reported the stable transformation of *Navicula saprophila* with plasmid DNA. Using the transformation method of microprojectile bombardment, Dunahay introduced the plasmid pACCNPT5.1 into *Navicula saprophila*. Plasmid pACCNPT5.1 comprised a neomycin resistance cassette, comprising the coding sequence of the neomycin phosphotransferase II (nptII) gene product operably linked to the promoter of the *Cyclotella cryptica* acetyl-CoA carboxylase (ACCase) gene (GenBank Accession No. L20784) upstream of the nptII coding-region and operably linked to the 3'UTR/terminator of the *Cyclotella cryptica* ACCase gene at the 3' region (downstream of the nptII coding-region). The nptII gene product confers resistance to the antibiotic G418. Prior to transformation with pACCNPT5.1, *Navicula saprophila* was unable to propagate on artificial seawater medium comprising 100 ug/ml G418. Upon transformation with pACCNPT5.1, transformants of *Navicula*

*saprophila* were obtained that were propagated in selective artificial seawater medium comprising 100 ug/ml G418. The expression of the nptII gene product in *Navicula saprophila* enabled propagation in the presence of G418, thereby establishing the utility of the neomycin antibiotic resistance cassette as selectable marker for use in *Navicula saprophila*. Evaluation of the genomic DNA of the stable transformants was performed by Southern analysis. Dunahay reported liquid propagation of *Navicula saprophila* in artificial seawater medium (ASW, as discussed by Brown, L., *Phycologia*, Vol. 21 (1982), pp. 408-410) supplemented with 1.07 mM sodium silicate and with 100 ug/ml G418. Dunahay also reported selection and maintenance of *Navicula saprophila* transformants on agar plates comprising ASW medium with 100 ug/ml G418. Propagation of *Navicula saprophila* in additional culture medium has been discussed (for example in Tadros and Johansen, *Journal of Phycology*, Vol. 24:4 (1988), pp. 445-452 and Sriharan et al., *Applied Biochemistry and Biotechnology*, Vol. 20-21:1 (1989), pp. 281-291). Dunahay reported that the plasmid pACCNPT5.1 and the promoter of the *Cyclotella cryptica* acetyl-CoA carboxylase (ACCase) gene are suitable to enable exogenous gene expression in *Navicula saprophila*. In addition, Dunahay reported that the neomycin resistance cassette encoded on pACCNPT5.1 was suitable for use as a selectable marker in *Navicula saprophila*.

In an embodiment of the present invention, vector pACCNPT5.1, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Navicula saprophila* to reflect the codon bias inherent in nuclear genes of the closely-related *Navicula pelliculosa* in accordance with Tables 19A-D. For each lipid biosynthesis pathway protein of Table 20, the codon-optimized gene sequence can individually be operably linked to the *Cyclotella cryptica* ACCase gene promoter upstream of the protein-coding sequence and operably linked to the *Cyclotella cryptica* ACCase gene 3'UTR/terminator at the 3' region, or downstream, of the protein-coding sequence. The transformation construct may additionally comprise homology regions to the *Navicula saprophila* genome for targeted genomic integration of the transformation vector. Homology regions may be selected to disrupt one or more genomic sites of endogenous lipid biosynthesis pathway genes. Stable transformation of *Navicula saprophila* with the transformation vector is achieved through well-known transformation techniques including microprojectile bombardment or other known methods. Activity of the nptII gene product can be used as a selectable marker to select for *Navicula saprophila* transformed with the transformation vector in, but not limited to, agar ASW medium comprising G418. Growth media suitable for *Navicula saprophila* lipid production include, but are not limited to, ASW medium and those media reported by Sriharan et al. 1989 and Tadros and Johansen. Evaluation of fatty acid profiles of *Navicula saprophila* lipids can be assessed through standard lipid extraction and analytical methods described herein.

Example 29: Engineering *Thalassiosira pseudonana*

Expression of recombinant genes in accordance with the present invention in *Thalassiosira pseudonana* can be accomplished by modifying the methods and vectors taught by Poulsen et al. as discussed herein. Briefly, Poulsen et al., *Journal of Phycology*, Vol. 42 (2006), pp. 1059-1065, reported the stable transformation of *Thalassiosira pseudonana* with plasmid DNA. Using the transformation method of microprojectile bombardment, Poulsen introduced the plasmid pTpfcp/nat in to *Thalassiosira pseudonana*. pTpfcp/nat comprised a nourseothricin resistance cassette, comprising sequence encoding the nourseothricin acetyltransferase (nat) gene product (GenBank Accession No. AAC60439) operably linked to the *Thalassiosira pseudonana* fucoxanthin chlorophyll a/c binding protein gene (fcp) promoter upstream of the nat protein-coding region and operably linked to the *Thalassiosira pseudonana* fcp gene 3' UTR/terminator at the 3' region (downstream of the nat protein coding-sequence). The nat gene product confers resistance to the antibiotic nourseothricin. Prior to transformation with pTpfcp/nat, *Thalassiosira pseudonana* was unable to propagate on medium comprising 10 ug/ml nourseothricin. Upon transformation with pTpfcp/nat, transformants of *Thalassiosira pseudonana* were obtained that were propagated in selective culture medium comprising 100 ug/ml nourseothricin. The expression of the nat gene product in *Thalassiosira pseudonana* enabled propagation in the presence of 100 ug/ml nourseothricin, thereby establishing the utility of the nourseothricin antibiotic resistance cassette as selectable marker for use in *Thalassiosira pseudonana*. Evaluation of the genomic DNA of the stable transformants was performed by Southern analysis. Poulsen reported that selection and maintenance of the transformed *Thalassiosira pseudonana* was performed in liquid culture comprising modified ESAW medium (as discussed by Harrison et al., *Journal of Phycology*, Vol. 16 (1980), pp. 28-35) with 100 ug/ml nourseothricin. Propagation of *Thalassiosira pseudonana* in additional culture medium has been discussed (for example in Volkman et al., *Journal of Experimental Marine Biology and Ecology*, Vol. 128:3 (1989), pp. 219-240). An additional plasmid, comprising additional selectable markers suitable for use in *Thalassiosira pseudonana* has been discussed in the same report by Poulsen. Poulsen reported that the plasmid pTpfcp/nat, and the *Thalassiosira pseudonana* fcp promoter and 3' UTR/terminator are suitable to enable exogenous gene expression in *Thalassiosira pseudonana*. In addition, Poulsen reported that the nourseothricin resistance cassette encoded on pTpfcp/nat was suitable for use as a selectable marker in *Thalassiosira pseudonana*.

In an embodiment of the present invention, vector pTpfcp/nat, comprising the nucleotide sequence encoding the nat gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Thalassiosira pseudonana* to reflect the codon bias inherent in nuclear genes of *Thalassiosira pseudonana* in accordance with Tables 19A-D. For each lipid biosynthesis pathway protein of Table 20, the codon-optimized gene sequence can individually be operably linked to the *Thalassiosira pseudonana* fcp gene promoter upstream of the protein-coding sequence and operably linked to the *Thalassiosira pseudonana* fcp gene 3'UTR/terminator at the 3' region, or downstream, of the protein-coding sequence. The transformation construct may additionally comprise homology regions to the *Thalassiosira pseudonana* genome for targeted genomic integration of the transformation vector. Homology regions may be selected to disrupt one or more genomic sites of endogenous lipid biosynthesis pathway genes. One skilled in the art can identify such homology regions within the sequence of the *Thalassiosira pseudonana* genome (referenced in the publication by Armbrust et al., *Science, Vol.* 306: 5693 (2004): pp. 79-86). Stable transformation of *Thalassiosira pseudonana* with the transformation vector is achieved through well-known transformation techniques including microprojectile bombardment or other known methods. Activity of the nat gene product can be used as a marker to select for *Thalassiosira pseudonana* transformed with the transformation vector in but not limited to, ESAW agar medium comprising nourseothricin. Growth media suitable for *Thalassiosira pseudonana* lipid production include, but are not limited to, ESAW medium, and those culture media discussed by Volkman et al. and Harrison et al. Evaluation of fatty acid profiles of *Thalassiosira pseudonana* lipids can be assessed through standard lipid extraction and analytical methods described herein.

Example 30: Engineering *Chlamydomonas reinhardtii*

Expression of recombinant genes in accordance with the present invention in *Chlamydomonas reinhardtii* can be accomplished by modifying the methods and vectors taught by Cerutti et al. as discussed herein. Briefly, Cerutti et al., *Genetics*, Vol. 145:1 (1997), pp. 97-110, reported the stable nuclear transformation of *Chlamydomonas reinhardtii* with a transformation vector. Using the transformation method of microprojectile bombardment, Cerutti introduced transformation construct P[1030] into *Chlamydomonas reinhardtii*. Construct P[1030] comprised a spectinomycin resistance cassette, comprising sequence encoding the aminoglucoside 3"-adenyltransferase (aadA) gene product operably linked to the *Chlamydomonas reinhardtii* ribulose-1,5-bisphosphate carboxylase/oxygenase small subunit gene (RbcS2, GenBank Accession No. X04472) promoter upstream of the aadA protein-coding region and operably linked to the *Chlamydomonas reinhardtii* RbcS2 gene 3' UTR/terminator at the 3' region (downstream of the aadA protein coding-sequence). The aadA gene product confers resistance to the antibiotic spectinomycin. Prior to transformation with P[1030], *Chlamydomonas reinhardtii* was unable to propagate on medium comprising 90 ug/ml spectinomycin. Upon transformation with P[1030], transformants of *Chlamydomonas reinhardtii* were obtained that were propagated in selective culture medium comprising 90 ug/ml spectinomycin, thereby establishing the utility of the spectinomycin antibiotic resistance cassette as a selectable marker for use in *Chlamydomonas reinhardtii*. Evaluation of the genomic DNA of the stable transformants was performed by Southern analysis. Cerutti reported that selection and maintenance of the transformed *Chlamydomonas reinhardtii* was performed on agar plates comprising Tris-acetate-phosphate medium (TAP, as described by Harris, The *Chlamydomonas* Sourcebook, Academic Press, San Diego, 1989) with 90 ug/ml spectinomycin. Cerutti additionally reported propagation of *Chlamydomonas reinhardtii* in TAP liquid culture with 90 ug/ml spectinomycin. Propagation of *Chlamydomonas reinhardtii* in alternative culture medium has been discussed (for example in Dent et al., *African Journal of Microbiology Research*, Vol. 5:3 (2011), pp. 260-270 and Yantao et al., *Biotechnology and Bioengineering*, Vol. 107:2 (2010), pp. 258-268). Additional constructs, comprising additional selectable markers suitable for use in *Chlamydomonas reinhardtii* as well as numerous regulatory sequences, including promoters and 3' UTRs suitable for promoting heterologous gene expression in *Chlamydomonas* reinhardtii are known in the art and have been discussed (for a review, see Radakovits et al., *Eukaryotic Cell, Vol.* 9:4 (2010), pp. 486-501). Cerutti reported that the transformation vector P[1030] and the *Chlamydomonas reinhardtii* promoter and 3' UTR/terminator are suitable to enable exogenous gene expression in *Chlamydomonas reinhardtii*. In addition, Cerutti reported that the spectinomycin resistance cassette encoded on P[1030] was suitable for use as a selectable marker in *Chlamydomonas reinhardtii.*

In an embodiment of the present invention, vector P[1030], comprising the nucleotide sequence encoding the aadA gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlamydomonas reinhardtii* to reflect the codon bias inherent in nuclear genes of *Chlamydomonas reinhardtii* in accordance with Tables 19A-D. For each lipid biosynthesis pathway protein of Table 20, the codon-optimized gene sequence can individually be operably linked to the *Chlamydomonas reinhardtii* RbcS2 promoter upstream of the protein-coding sequence and operably linked to the *Chlamydomonas reinhardtii* RbcS2 3'UTR/terminator at the 3' region, or downstream, of the protein-coding sequence. The transformation construct may additionally comprise homology regions to the *Chlamydomonas reinhardtii* genome for targeted genomic integration of the transformation vector. Homology regions may be selected to disrupt one or more genomic site of an endogenous lipid biosynthesis pathway gene. One skilled in the art can identify such homology regions within the sequence of the *Chlamydomonas reinhardtii* genome (referenced in the publication by Merchant et al., *Science*, Vol. 318:5848 (2007), pp. 245-250). Stable transformation of *Chlamydomonas reinhardtii* with the transformation vector is achieved through well-known transformation techniques including microprojectile bombardment or other known methods. Activity of the aadA gene product can be used as a marker to select for *Chlamydomonas reinhardtii* transformed with the transformation vector on, but not limited to, TAP agar medium comprising spectinomycin. Growth media suitable for *Chlamydomonas reinhardtii* lipid production include, but are not limited to, ESAW medium, and those culture media discussed by Yantao et al. and Dent et al. Evaluation of fatty acid profiles of *Chlamydomonas reinhardtii* lipids can be assessed through standard lipid extraction and analytical methods described herein.

Example 31: Engineering *Yarrowia lipolytica*

Expression of recombinant genes in accordance with the present invention in *Yarrowia lipolytica* can be accomplished by modifying the methods and vectors taught by Fickers et al. as discussed herein. Briefly, Fickers et al., *Journal of Microbiological Methods*, Vol. 55 (2003), pp. 727-737, reported the stable nuclear transformation of *Yarrowia lipolytica* with plasmid DNA. Using a lithium acetate transformation method, Fickers introduced the plasmid JMP123 into *Yarrowia lipolytica*. Plasmid JMP123 comprised a hygromycin B resistance cassette, comprising sequence encoding the hygromycin B phosphotransferase gene product (hph), operably-linked to the *Yarrowia lipolytica* LIP2 gene promoter (GenBank Accession No.

AJ012632) upstream of the hph protein-coding region and operably linked to the *Yarrowia lipolytica* LIP2 gene 3'UTR/terminator downstream of the hph protein-coding region. Prior to transformation with JMP123, *Yarrowia lipolytica* were unable to propagate on medium comprising 100 ug/ml hygromycin. Upon transformation with JMP123, transformed *Yarrowia lipolytica* were obtained that were able to propagate on medium comprising 100 ug/ml hygromycin, thereby establishing the hygromycin B antibiotic resistance cassette as a selectable marker for use in *Yarrowia lipolytica*. The nucleotide sequence provided on JMP123 of the promoter and 3'UTR/terminator of the *Yarrowia lipolytica* LIP2 gene served as donor sequences for homologous recombination of the hph coding sequence into the LIP2 locus. Evaluation of the genomic DNA of the stable transformants was performed by Southern. Fickers reported that selection and maintenance of the transformed *Yarrowia lipolytica* was performed on agar plates comprising standard YPD medium (Yeast Extract Peptone Dextrose) with 100 ug/ml hygromycin. Liquid culturing of transformed *Yarrowia lipolytica* was performed in YPD medium with hygromycin. Other media and techniques used for culturing *Yarrowia lipolytica* have been reported and numerous other plasmids, promoters, 3' UTRs, and selectable markers for use in *Yarrowia lipolytica* have been reported (for example see Pignede et al., *Applied and Environmental Biology*, Vol. 66:8 (2000), pp. 3283-3289, Chuang et al., *New Biotechnology*, Vol. 27:4 (2010), pp. 277-282, and Barth and Gaillardin, (1996), In: K,W. (Ed.), Nonconventional Yeasts in Biotechnology. Sprinter-Verlag, Berlin-Heidelber, pp. 313-388). Fickers reported that the transformation vector JMP123 and the *Yarrowia lipolytica* LIP2 gene promoter and 3' UTR/terminator are suitable to enable heterologous gene expression in *Yarrowia lipolytica*. In addition, Fickers reported that the hygromycin resistance cassette encoded on JMP123 was suitable for use as a selectable marker in *Yarrowia lipolytica*.

In an embodiment of the present invention, vector JMP123, comprising the nucleotide sequence encoding the hph gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Yarrowia lipolytica* to reflect the codon bias inherent in nuclear genes of *Yarrowia lipolytica* in accordance with Tables 19A-D. For each lipid biosynthesis pathway protein of Table 20, the codon-optimized gene sequence can individually be operably linked to the *Yarrowia lipolytica* LIP2 gene promoter upstream of the protein-coding sequence and operably linked to the *Yarrowia lipolytica* LIP2 gene 3'UTR/terminator at the 3' region, or downstream, of the protein-coding sequence. The transformation construct may additionally comprise homology regions to the *Yarrowia lipolytica* genome for targeted genomic integration of the transformation vector. Homology regions may be selected to disrupt one or more genomic sites of endogenous lipid biosynthesis pathway genes. One skilled in the art can identify such homology regions within the sequence of the *Yarrowia lipolytica* genome (referenced in the publication by Dujun et al., *Nature*, Vol. 430 (2004), pp. 35-44). Stable transformation of *Yarrowia lipolytica* with the transformation vector is achieved through well-known transformation techniques including lithium acetate transformation or other known methods. Activity of the hph gene product can be used as a marker to select for *Yarrowia lipolytica* transformed with the transformation vector on, but not limited to, YPD medium comprising hygromycin. Growth media suitable for *Yarrowia lipolytica* lipid production include, but are not limited to, YPD medium, and those culture media described by Chuang et al. Evaluation of fatty acid profiles of *Yarrowia lipolytica* lipids can be assessed through standard lipid extraction and analytical methods described herein.

Example 32: Engineering *Mortierella alpine*

Expression of recombinant genes in accordance with the present invention in *Mortierella alpine* can be accomplished by modifying the methods and vectors taught by Mackenzie et al. as discussed herein. Briefly, Mackenzie et al., *Applied and Environmental Microbiology*, Vol. 66 (2000), pp. 4655-4661, reported the stable nuclear transformation of *Mortierella alpina* with plasmid DNA. Using a protoplast transformation method, MacKenzie introduced the plasmid pD4 into *Mortierella alpina*. Plasmid pD4 comprised a hygromycin B resistance cassette, comprising sequence encoding the hygromycin B phosphotransferase gene product (hpt), operably-linked to the *Mortierella alpina* histone H4.1 gene promoter (GenBank Accession No. AJ249812) upstream of the hpt protein-coding region and operably linked to the *Aspergillus nidulans* N-(5'-phosphoribosyl)anthranilate isomerase (trpC) gene 3'UTR/terminator downstream of the hpt protein-coding region. Prior to transformation with pD4, *Mortierella alpina* were unable to propagate on medium comprising 300 ug/ml hygromycin. Upon transformation with pD4, transformed *Mortierella alpina* were obtained that were propagated on medium comprising 300 ug/ml hygromycin, thereby establishing the hygromycin B antibiotic resistance cassette as a selectable marker for use in *Mortierella alpina*. Evaluation of the genomic DNA of the stable transformants was performed by Southern. Mackenzie reported that selection and maintenance of the transformed *Mortierella alpina* was performed on PDA (potato dextrose agar) medium comprising hygromycin. Liquid culturing of transformed *Mortierella alpina* by Mackenzie was performed in PDA medium or in S2GYE medium (comprising 5% glucose, 0.5% yeast extract, 0.18% $NH_4SO_4$, 0.02% $MgSO_4$-$7H_2O$, 0.0001% $FeCl_3$-$6H_2O$, 0.1%, trace elements, 10 mM $K_2HPO_4$—$NaH_2PO_4$), with hygromycin. Other media and techniques used for culturing *Mortierella alpina* have been reported and other plasmids, promoters, 3' UTRs, and selectable markers for use in *Mortierella alpina* have been reported (for example see Ando et al., *Applied and Environmental Biology*, Vol. 75:17 (2009) pp. 5529-35 and Lu et al., *Applied Biochemistry and Biotechnology*, Vol. 164:7 (2001), pp. 979-90). Mackenzie reported that the transformation vector pD4 and the *Mortierella alpina* histone H4.1 promoter and *A. nidulans* trpC gene 3' UTR/terminator are suitable to enable heterologous gene expression in *Mortierella alpina*. In addition, Mackenzie reported that the hygromycin resistance cassette encoded on pD4 was suitable for use as a selectable marker in *Mortierella alpina*.

In an embodiment of the present invention, vector pD4, comprising the nucleotide sequence encoding the hpt gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Mortierella alpina* to reflect the codon bias inherent in nuclear genes of *Mortierella alpina* in accordance with Tables 19A-D. For each lipid biosynthesis pathway protein of Table 20, the codon-optimized gene sequence can individually be operably linked to the *Mortierella alpina* histone H4.1 gene promoter upstream of the protein-coding sequence and operably linked to the *A. nidulans* trpC 3'UTR/terminator at the 3' region, or downstream, of the protein-coding sequence. The transformation construct may additionally comprise homology regions to the *Mortierella alpina* genome for targeted genomic integration of the transformation vector. Homology regions may be selected to disrupt one or more genomic sites of endogenous lipid biosynthesis pathway genes. One skilled in the art can identify such homology regions within the sequence of the *Mortierella alpina* genome (referenced in the publication by Wang et al., *PLOS One*, Vol. 6:12 (2011)). Stable transformation of *Mortierella alpina* with the transformation vector is achieved through well-known transformation techniques including protoplast transformation or other known methods. Activity of the hpt gene product can be used as a marker to select for *Mortierella alpina* transformed with the transformation vector on, but not limited to, PDA medium comprising hygromycin. Growth media suitable for *Mortierella alpina* lipid production include, but are not limited to, S2GYE medium, and those culture media described by Lu et al. and Ando et al. Evaluation of fatty acid profiles of *Mortierella alpina* lipids can be assessed through standard lipid extraction and analytical methods described herein.

Example 33: Engineering *Rhodococcus opacus* PD630

Expression of recombinant genes in accordance with the present invention in *Rhodococcus opacus* PD630 can be accomplished by modifying the methods and vectors taught by Kalscheuer et al. as discussed herein. Briefly, Kalscheuer et al., *Applied and Environmental Microbiology*, Vol. 52 (1999), pp. 508-515, reported the stable transformation of *Rhodococcus opacus* with plasmid DNA. Using the transformation method of electroporation, Kalscheuer introduced the plasmid pNC9501 into *Rhodococcus opacus* PD630. Plasmid pNC9501 comprised a thiostrepton resistance ($thio^r$) cassette, comprising the full nucleotide sequence of the *Streptomyces azureus* 23S rRNA A1067 methyltransferase gene, including the gene's promoter and 3' terminator sequence. Prior to transformation with pNC9501, *Rhodococcus opacus* was unable to propagate on medium comprising 1 mg/ml thiostrepton. Upon transformation of *Rhodococcus opacus* PD630 with pNC9501, transformants were obtained that propagated on culture medium comprising 1 mg/ml thiostrepton, thereby establishing the use of the thiostrepton resistance cassette as a selectable marker in *Rhodococcus opacus* PD630. A second plasmid described by Kalscheuer, pAK68, comprised the resistance $thio^r$ cassette as well as the gene sequences of the *Ralstonia eutropha* beta-ketothiolase (phaB), acetoacetyl-CoA reductase (phaA), and poly3-hydroxyalkanoic acid synthase (phaC) genes for polyhydroxyalkanoate biosynthesis, driven by the lacZ promoter. Upon pAK68 transformation of a *Rhodococcus opacus* PD630 strain deficient in polyhydroxyalkanoate biosynthesis, transformed *Rhodococcus opacus* PD630 were obtained that produced higher amounts of polyhydroxyalkanoates than the untransformed strain. Detectable activity of the introduced *Ralstonia eutropha* phaB, phaA, and phaC enzymes indicted that the regulatory elements encoded on the pAK68 plasmid were suitable for heterologous gene expression in *Rhodococcus opacus* PD630. Kalscheuer reported that selection and maintenance of the transformed *Rhodococcus opacus* PD630 was performed on standard Luria Broth (LB) medium, nutrient broth (NB), or mineral salts medium (MSM) comprising thiostrepton. Other media and techniques used for culturing *Rhodococcus opacus* PD630 have been described (for example see Kurosawa et al., *Journal of Biotechnology*, Vol. 147:3-4 (2010), pp. 212-218 and Alverez et al., *Applied Microbial and Biotechnology*, Vol. 54:2 (2000), pp. 218-223). Kalscheuer reported that the transformation vectors pNC9501 and pAK68, the promoters of the *Streptomyces azureus* 23S rRNA A1067 methyltransferase gene and lacZ gene are suitable to enable heterologous gene expression in *Rhodococcus opacus* PD630. In addition, Kalscheuer reported that the $thio^r$ cassette encoded on pNC9501 and pAK68 was suitable for use as a selectable marker in *Rhodococcus opacus* PD630.

In an embodiment of the present invention, vector pNC9501, comprising the nucleotide sequence encoding the $thio^r$ gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Rhodococcus opacus* PD630 to reflect the codon bias inherent in nuclear genes of *Rhodococcus opacus* in accordance with Tables 19A-D. For each lipid biosynthesis pathway protein of Table 20, the codon-optimized gene sequence can individually be operably linked to the lacZ gene promoter upstream of the protein-coding sequence. The transformation construct may additionally comprise homology regions to the *Rhodococcus opacus* PD630 genome for targeted genomic integration of the transformation vector. Homology regions may be selected to disrupt one or more genomic sites of endogenous lipid biosynthesis pathway genes. One skilled in the art can identify such homology regions within the sequence of the *Rhodococcus opacus* PD630 genome (referenced in the publication by Holder et al., *PLOS Genetics*, Vol. 7:9 (2011). Transformation of *Rhodococcus opacus* PD630 with the transformation vector is achieved through well-known transformation techniques including electroporation or other known methods. Activity of the *Streptomyces azureus* 23S rRNA A1067 methyltransferase gene product can be used as a marker to select for *Rhodococcus opacus* PD630 transformed with the transformation vector on, but not limited to, LB medium comprising thiostrepton. Growth media suitable *Rhodococcus opacus* PD630 lipid production include, but are not limited to those culture media discussed by Kurosawa et al. and Alvarez et al. Evaluation of fatty acid profiles of *Rhodococcus opacus* PD630 lipids can be assessed through standard lipid extraction and analytical methods described herein.

Example 34: Engineering Microalgae for Fatty Acid Auxotrophy

Strain B of Example 3, *Prototheca moriformis* (UTEX 1435) engineered to express a *Cuphea wrightii* thioesterase (CwTE2), was used as the host organism for further genetic modification to knockout both endogenous thioesterase alleles, FATA1-1 and FATA1-2. Here, a first transformation construct was generated to integrate a neomycin expression cassette into Strain B at the FATA1-1 locus. This construct, pSZ2226, included 5' (SEQ ID NO: 30) and 3' (SEQ ID NO: 31) homologous recombination targeting sequences (flanking the construct) to the FATA1-1 locus of the nuclear genome and a neomycin resistance protein-coding sequence under the control of the *C. reinhardtii* β-tubulin promoter/5'UTR (SEQ ID NO: 5) and the *Chlorella vulgaris* nitrate reductase 3' UTR (SEQ ID NO: 6). This NeoR expression cassette is listed as SEQ ID NO: 15 and served as a selectable marker.

Upon transformation of pSZ2226 into Strain B, individual transformants were selected on agar plates comprising sucrose and G418. A single isolate, Strain H, was selected for further genetic modification. A second transformation construct, pSZ2236, was generated to integrate polynucleotides enabling expression of a thiamine selectable marker into Strain H at the FATA1-2 locus. pSZ2236 included 5' (SEQ ID NO: 32) and 3' (SEQ ID NO: 33) homologous recombination targeting sequences (flanking the construct) to the FATA1-2 genomic region for integration into the *P. moriformis* (UTEX 1435) nuclear genome and an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selectable marker. Upon transformation of Strain H with pSZ2236 to generate Strain I, individual transformants, were selected on agar plates comprising free fatty acids. Strain I was able to propagate on agar plates and in medium lacking thiamine and supplemented with free fatty acids.

Example 35: Engineering Microorganisms for Increased Production of Stearic Acid A classically mutagenized strain of *Prototheca moriformis* (UTEX 1435), Strain J, was transformed with the plasmid construct pSZ2281 according to biolistic transformation methods as described in PCT/US2009/066141, PCT/US2009/066142, PCT/US2011/038463, PCT/US2011/038464, and PCT/US2012/023696. pSZ2281 included polynucleotides encoding RNA hairpins (SAD2hpC, SEQ ID NO: 34) to down-regulate the expression of stearoyl-ACP desaturase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4), to express the protein sequence given in SEQ ID NO: 3, under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. The polynucleotide sequence encoding the SAD2hpC RNA hairpin was under the control of the *C. protothecoides* actin promoter/5'UTR (SEQ ID NO: 22) and *C. vulgaris* nitrate reductase 3' UTR (SEQ ID NO: 6).

Upon transformation of Strain J with construct pSZ2281, thereby generating Strain K, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using standard fatty acid methyl ester gas chromatography flame ionization detection methods as described in Example 1 (also see PCT/US2012/023696). The fatty acid profiles (expressed as Area % of total fatty acids) of *P. moriformis* UTEX Strain J propagated on glucose as a sole carbon source and three representative isolates of Strain K, propagated on sucrose as a sole carbon source, are presented in Table 21.

TABLE 21

Fatty acid profiles of *Prototheca moriformis* (UTEX 1435) cells engineered to express a hairpin RNA construct targeting stearoyl ACP desaturase gene/gene products.

| Area % Fatty acid | Strain J | Strain K-1 | Strain K-2 | Strain K-3 | Strain K-4 |
|---|---|---|---|---|---|
| C8:0 | | | | | 0.02 |
| C10:0 | 0.01 | 0.00 | 0.02 | 0.02 | 0.04 |
| C12:0 | 0.03 | 0.05 | 0.05 | 0.05 | 0.08 |
| C14:0 | 1.22 | 0.89 | 0.87 | 0.77 | 1.2 |
| C16:0 | 26.75 | 29.23 | 28.96 | 27.55 | 28.06 |
| C18:0 | 3.06 | 37.39 | 36.76 | 36.41 | 40.82 |
| C18:1 | 59.62 | 23.90 | 24.76 | 26.92 | 22.02 |
| C18:2 | 7.33 | 5.44 | 5.54 | 5.54 | 4.53 |
| C18:3 | | | | | 0.14 |
| C20:0 | | | | | 1.43 |

The data presented in Table 21 show a clear impact of the expression of SAD2 hairpin RNA construct on the C18:0 and C18:1 fatty acid profiles of the transformed organism. The fatty acid profiles of Strain K transformants comprising a SAD2 hairpin RNA construct demonstrated an increase in the percentage of saturated C18:0 fatty acids with a concomitant diminution of unsaturated C18:1 fatty acids. Fatty acid profiles of the untransformed strain comprise about 3% C18:0. Fatty acid profiles of the transformed strains comprise about 37% C18:0. These data illustrate the successful expression and use of polynucleotides enabling expression of a SAD RNA hairpin construct in *Prototheca moriformis* to alter the percentage of saturated fatty acids in the engineered host microbes, and in particular in increasing the concentration of C18:0 fatty acids and decreasing C18:1 fatty acids in microbial cells.

Also shown in Table 21, strain K-4 had a yet further elevated level of stearate. Strain K4 was created by inserting the construct of strains K1-K3 into the SAD2B locus. Thus, by knocking out one copy of the SAD gene and inhibiting the remaining copies at the RNA level, a further reduction in oleic acid and corresponding increase in stearate was obtained. Triglyceride analysis of RBD oil obtained from strain $K_4$ showed about 12% POP, 27% POS and 18% SOS.

Example 36: Engineering Microorganisms for Increased Production of Oleic Acid Through Knockdown of an Endogenous Acyl-ACP Thioesterase A classically mutagenized strain of *Prototheca moriformis* (UTEX 1435), Strain J, was transformed independently with each of the constructs pSZ2402-pSZ2407 according to biolistic transformation methods as described in PCT/US2009/066141, PCT/US2009/066142, PCT/US2011/038463, PCT/US2011/038464, and PCT/US2012/023696. Each of the constructs pSZ2402-pSZ2407 included different polynucleotides encoding a hairpin RNA targeted against *Prototheca moriformis* FATA1 mRNA transcripts to down-regulate the expression of fatty acyl-ACP thioesterase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii*

β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each hairpin are listed in Table 22. The polynucleotide sequence encoding each RNA hairpin was under the control of the *C. reinhardtii* β-tubulin promoter/5'UTR (SEQ ID NO: 5) and *C. vulgaris* nitrate reductase 3' UTR (SEQ ID NO: 6).

TABLE 22

Plasmid constructs used to transform *Prototheca moriformis* (UTEX 1435) Strain J.

| Plasmid construct | Hairpin designation | SEQ ID NO: |
|---|---|---|
| pSZ2402 | PmFATA-hpB | SEQ ID NO: 40 |
| pSZ2403 | PmFATA-hpC | SEQ ID NO: 41 |
| pSZ2404 | PmFATA-hpD | SEQ ID NO: 42 |
| pSZ2405 | PmFATA-hpE | SEQ ID NO: 43 |
| pSZ2406 | PmFATA-hpF | SEQ ID NO: 44 |
| pSZ2407 | PmFATA-hpG | SEQ ID NO: 45 |

Upon independent transformation of Strain J with each of the constructs listed in Table 22, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using standard fatty acid methyl ester gas chromatography flame ionization detection methods as described in Example 1 (also see PCT/US2012/023696). The fatty acid profiles (expressed as Area % of total fatty acids) of *P. moriformis* (UTEX 1435) Strain J propagated on glucose as a sole carbon source and representative isolates of each transformation of Strain J, propagated on sucrose as a sole carbon source, are presented in Table 23.

TABLE 23

Fatty acid profiles of *Prototheca moriformis* (UTEX 1435) cells engineered to express hairpin RNA constructs targeting fatty acyl-ACP thioesterase gene/gene products.

| | Area % Fatty Acid | | | | | | |
|---|---|---|---|---|---|---|---|
| Construct | C10:0 | C12:0 | C14:0 | C16:0 | C18:0 | C18:1 | C18:2 |
| Strain J untransformed | 0 | 0.05 | 1.32 | 26.66 | 3.1 | 59.07 | 7.39 |
| PmFATA-hpB | 0.04 | 0.07 | 1.36 | 24.88 | 2.24 | 61.92 | 6.84 |
| | 0 | 0.08 | 1.33 | 25.34 | 2.39 | 61.72 | 6.5 |
| | 0 | 0.07 | 1.29 | 25.44 | 2.26 | 61.7 | 6.69 |
| | 0 | 0.06 | 1.33 | 25.1 | 2.37 | 61.56 | 6.87 |
| PmFATA-hpC | 0 | 0.08 | 1.18 | 22.03 | 1.71 | 63.8 | 8.63 |
| | 0 | 0.07 | 1.21 | 24.5 | 2.23 | 62.32 | 7.19 |
| | 0 | 0.08 | 1.29 | 24.93 | 2.24 | 62.02 | 7.01 |
| | 0.05 | 0.06 | 1.29 | 25.45 | 2.26 | 61.81 | 6.76 |
| PmFATA-hpD | 0 | 0.02 | 0.68 | 15.8 | 1.88 | 72.64 | 6.96 |
| | 0 | 0.03 | 0.78 | 17.56 | 1.7 | 71.8 | 6.03 |
| | 0 | 0.03 | 0.92 | 19.04 | 2.03 | 68.82 | 7.05 |
| | 0 | 0.04 | 1.27 | 23.14 | 2.25 | 65.27 | 6.07 |
| PmFATA-hpE | 0 | 0.03 | 0.79 | 18.55 | 2.13 | 69.66 | 6.77 |
| | 0 | 0.04 | 1.11 | 21.01 | 1.74 | 65.18 | 8.55 |
| | 0 | 0.03 | 1.08 | 21.11 | 1.54 | 64.76 | 8.87 |
| | 0 | 0.03 | 1.17 | 21.93 | 1.71 | 63.89 | 8.77 |
| PmFATA-hpF | 0.03 | 0.04 | 0.34 | 8.6 | 1.69 | 78.08 | 8.87 |
| | 0 | 0.03 | 0.49 | 10.2 | 1.52 | 76.97 | 8.78 |
| | 0 | 0.03 | 1 | 20.47 | 2.22 | 66.34 | 7.45 |
| | 0 | 0.03 | 1.03 | 21.61 | 1.88 | 65.39 | 7.76 |
| PmFATA-hpG | 0 | 0.03 | 1.03 | 20.57 | 2.36 | 64.73 | 8.75 |
| | 0 | 0.03 | 1.2 | 24.39 | 2.47 | 61.9 | 7.49 |
| | 0 | 0.04 | 1.29 | 24.14 | 2.29 | 61.41 | 8.22 |

The data presented in Table 23 show a clear impact of the expression of FATA hairpin RNA constructs on the C18:0 and C18:1 fatty acid profiles of the transformed organism. The fatty acid profiles of Strain J transformants comprising a FATA hairpin RNA construct demonstrated an increase in the percentage of C18:1 fatty acids with a concomitant diminution of C16:0 and C18:0 fatty acids. Fatty acid profiles of the untransformed Strain J are about 26.66% C16:0, 3% C18:0, and about 59% C18:1 fatty acids. In contrast, the fatty acid profiles of the transformed strains comprise as low as 8.6% C16:0 and 1.54% C18:0 and greater than 78% C18:1 fatty acids.

These data illustrate the utility and successful use of polynucleotide FATA RNA hairpin constructs in *Prototheca moriformis* to alter the fatty acids profile of engineered microbes, and in particular in increasing the concentration of C18:1 fatty acids and decreasing C18:0 and C16:0 fatty acids in microbial cells.

Example 37: Engineering Microorganisms for Increased Production of Mid-Chain Fatty Acids Through KASI or KASIV Overexpression This example describes the use of recombinant polynucleotides that encode KASI or KASIV enzymes to engineer microorganisms in which the fatty acid profiles of the transformed microorganisms have been enriched in lauric acid, C10:0, and total saturated fatty acids.

Each of the constructs pSZD1132, pSZD1133, pSZD1134, or pSZD1201 was used independently to transform Strain B of Example 3, *Prototheca moriformis* (UTEX 1435) engineered to express a *Cuphea wrightii* thioesterase (CwTE2), according to biolistic transformation methods as described in PCT/US2009/066141, PCT/US2009/066142, PCT/US2011/038463, PCT/US2011/038464, and PCT/US2012/023696. Each of the above constructs included different polynucleotides encoding a KASI or KASIV enzyme, 5' (SEQ ID NO: 13) and 3' (SEQ ID NO: 14) homologous recombination targeting sequences (flanking the construct) to the pLoop genomic region for integration into the nuclear genome, and a neomycin resistance protein-coding sequence under the control of the *C. reinhardtii* β-tubulin promoter/5'UTR (SEQ ID NO: 5) and the *Chlorella vulgaris* nitrate reductase 3' UTR (SEQ ID NO: 6). This NeoR expression cassette is listed as SEQ ID NO: 15 and served as a selectable marker. Sequence listing identities for the polynucleotides corresponding to each construct are listed in Table 20. The polynucleotide sequence encoding each KAS enzyme was under the control of the *P. moriformis* UTEX 1435 Amt03 promoter/5'UTR (SEQ ID NO: 8) and *C. vulgaris* nitrate reductase 3' UTR (SEQ ID NO: 6). The protein coding regions of the KAS enzymes and neomycin resistance gene were codon optimized to reflect the codon bias inherent in *P. moriformis* UTEX 1435 nuclear genes as described in PCT/U52009/066141, PCT/US2009/066142, PCT/US2011/038463, PCT/US2011/038464, and PCT/US2012/023696.

Upon transformation of individual plasmids into Strain B, positive clones were selected on agar plates comprising G418. Individual transformants were clonally purified and grown on sucrose as a sole carbon source at pH 7.0 under conditions suitable for lipid production as detailed in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The fatty acid profiles (expressed as Area % of total fatty acids) of Strain B and four positive transformants of each of pSZ2046 (Strains M-P, 1-4) are presented in Table 24.

TABLE 24

Plasmid constructs used to transform *Prototheca moriformis* (UTEX 1435) Strain B.

| Plasmid construct | KASI/KASIV source | Transit peptide | SEQ ID NO: |
|---|---|---|---|
| pSZD1134 | *Cuphea wrightii* GenBank Accession No. U67317 | Native | SEQ ID NO: 46 |
| pSZD1201 | *Cuphea wrightii* | PmSAD | SEQ ID NO: 47 |
| pSZD1132 | *Cuphea pulcherrima* GenBank Accession No. AAC68860 | Native | SEQ ID NO: 48 |
| pSZD1133 | *Cuphea hookeriana* | Native | SEQ ID NO: 49 |

TABLE 25

Fatty acid profiles of *Prototheca moriformis* (UTEX 1435) Strain B engineered for increased C10, lauric acid, and total saturated fatty acids.

| | | Fatty Acid (Area %) | | | | | | | | |
|---|---|---|---|---|---|---|---|---|---|---|
| Plasmid construct(s) | No. | C10 | C12 | C14 | C16 | C18:0 | C18:1 | C18:2 | C10-C12 | % Saturates/ Total |
| pSZ1283 | | 7.89 | 35.49 | 16.58 | 11.5 | 1.09 | 19.64 | 6.49 | 43.38 | 72.55 |
| pSZ1283, pSZD1134 | 1 | 14.94 | 43.97 | 12.19 | 7.56 | 0.72 | 14.11 | 5.31 | 58.91 | 79.38 |
| pSZ1283, pSZD1134 | 2 | 10.27 | 39.61 | 15.35 | 9.61 | 0.94 | 17.1 | 5.88 | 49.88 | 75.78 |
| pSZ1283, pSZD1134 | 3 | 11.69 | 41.83 | 15.21 | 8.77 | 0.83 | 15.04 | 5.40 | 53.52 | 78.33 |
| D1134-20 | 4 | 10.76 | 40.77 | 15.32 | 9.19 | 0.88 | 16.06 | 5.76 | 51.53 | 76.92 |
| pSZ1283, pSZD1132 | 1 | 10.77 | 40.31 | 15.21 | 9.43 | 0.88 | 16.18 | 5.97 | 51.08 | 76.6 |
| pSZ1283, pSZD1132 | 2 | 9.19 | 37.03 | 15.02 | 10.52 | 1.00 | 19.63 | 6.29 | 46.22 | 72.76 |
| pSZ1283, pSZD1132 | 3 | 8.97 | 36.09 | 15.01 | 10.77 | 1.05 | 20.38 | 6.39 | 45.06 | 71.89 |
| pSZ1283, pSZD1132 | 4 | 9.51 | 38.12 | 14.96 | 9.96 | 0.94 | 18.93 | 6.32 | 47.63 | 73.49 |
| pSZ1283, pSZD1201 | 1 | 13.06 | 46.21 | 9.84 | 7.12 | 0.75 | 16.7 | 5.22 | 59.27 | 76.98 |
| pSZ1283, pSZD1201 | 2 | 11.02 | 43.91 | 13.01 | 7.78 | 0.86 | 16.53 | 5.77 | 54.93 | 76.58 |
| pSZ1283, pSZD1201 | 3 | 11.59 | 45.14 | 12.41 | 7.61 | 0.82 | 15.72 | 5.65 | 56.73 | 77.57 |
| pSZ1283, pSZD1201 | 4 | 10.66 | 41.32 | 13.74 | 8.75 | 0.68 | 18.64 | 5.21 | 51.98 | 75.15 |
| pSZ1283, pSZD1133 | 1 | 6.90 | 36.08 | 15.15 | 11.02 | 1.00 | 21.74 | 6.77 | 42.98 | 70.15 |
| pSZ1283, pSZD1133 | 2 | 7.01 | 35.88 | 15.01 | 10.75 | 1.07 | 22.02 | 6.93 | 42.89 | 69.72 |
| pSZ1283, pSZD1133 | 3 | 10.65 | 41.94 | 12.38 | 8.48 | 0.85 | 18.28 | 6.15 | 52.59 | 74.3 |
| pSZ1283, pSZD1133 | 4 | 10.23 | 41.88 | 12.58 | 8.52 | 0.82 | 18.48 | 6.22 | 52.11 | 74.03 |

The data presented in Table 25 show a clear impact of the exogenous expression of KASI and KASIV enzymes on the C10:0 and C12 fatty acid profiles of the transformed organism. The fatty acid profiles of Strain B, expressing the *Cuphea wrightii* thioesterase alone, comprised about 8% C10:0 and about 35.5% C12:0, with saturated fatty acids accounting for 72.55% of total fatty acids. In contrast, transformants of Strain B engineered to additionally express a *Cuphea wrightii* KASI with a *P. moriformis* stearoyl ACP desaturase transit peptide were characterized by a fatty acid profile of about 13% C10:0 and about 46% C12:0. Saturated fatty acids accounted for as high as 77% in transformants of Strain B co-expressing the *C. wrightii* KASI fusion protein. Similarly, transformants of Strain B engineered to express the *C. wrightii* KASI with the enzyme's native transit peptide were characterized by a fatty acid profile of about 15% C10, about 44% C12, and about 79% saturated fatty acids. The fatty acid profiles or many transformants of Strain B expressing either *Cuphea pulcherrima* KASIV or *Cuphea hookeriana* KASIV also displayed elevated C10% and C12% levels, compared to the fatty acid profile of Strain B itself.

These data demonstrate the utility and effectiveness of polynucleotides enabling expression of KASI and KASIV constructs in *Prototheca moriformis* (UTEX 1435) to alter the percentage of saturated fatty acids in the engineered host microbes, and in particular in increasing the concentration of C10:0 and C12:0 fatty acids in microbial cells.

Example 38: Engineering Microorganisms for Increased Production of Mid-Chain Fatty Acids Through KASI Knockout This example describes the use of recombinant polynucleotides that disrupt different KASI alleles to engineer microorganisms in which the fatty acid profiles of the transformed microorganisms have been enriched in C10:0 and midchain fatty acids.

Constructs pSZ2302 and pSZ2304 were used to independently transform Strain B of Example 3, *Prototheca moriformis* (UTEX 1435) engineered to express a *Cuphea wrightii* thioesterase (CwTE2), according to biolistic transformation methods as described in PCT/U52009/066141, PCT/US2009/066142, PCT/US2011/038463, PCT/US2011/038464, and PCT/US2012/023696. pSZ2302 included 5' (SEQ ID NO: 50) and 3' (SEQ ID NO: 51) homologous recombination targeting sequences (flanking the construct) to the KAS1 allele 1 genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). pSZ2304 included 5' (SEQ ID NO: 52) and 3' (SEQ ID NO: 53) homologous recombination targeting sequences (flanking the construct) to the KAS1 allele 2 genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selection marker. The protein coding region of AtTHIC was codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Upon independent transformation pSZ2302 and pSZ2304 into Strain B, thereby generating Strain Q and R, positive clones were selected on agar plates comprising thiamine. Individual transformants were clonally purified and cultivated on sucrose as a sole carbon source at pH 5.0 or pH 7.0 under heterotrophic conditions suitable for lipid production as detailed in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using fatty acid methyl ester gas chromatography flame ionization (FAME GC/FID) detection methods as described in Example 1. The fatty acid profiles (expressed as Area % of total fatty acids) of Strain B and positive pSZ2302 (Strain Q, 1-5) and pSZ2304 (Strain R, 1-5) transformants are presented in Tables 26 and 27.

TABLE 26

Fatty acid profiles of *Prototheca moriformis* (UTEX 1435) Strains B, Q, and R engineered for increased midchain fatty acids, cultured at pH 5.0.

| | Transformation | Fatty Acid (Area %) | | | | | | | |
|---|---|---|---|---|---|---|---|---|---|
| Strain | plasmid(s) | C10:0 | C12:0 | C14:0 | C16:0 | C18:0 | C18:1 | C18:2 | C10-C14 |
| UTEX 1435 | None | 0.00 | 0.04 | 1.28 | 26.67 | 3.05 | 59.96 | 7.19 | 1.32 |
| Strain B | pSZ1283 | 0.01 | 0.09 | 1.09 | 21.60 | 2.21 | 65.15 | 7.94 | 1.19 |
| Strain Q-1 | pSZ1283, pSZ2302 | 0.08 | 1.21 | 7.52 | 38.71 | 1.38 | 38.32 | 8.75 | 8.81 |
| Strain Q-2 | pSZ1283, pSZ2302 | 0.15 | 1.36 | 7.51 | 38.23 | 1.33 | 38.27 | 8.94 | 9.02 |
| Strain Q-3 | pSZ1283, pSZ2302 | 0.16 | 1.43 | 7.49 | 38.88 | 1.30 | 37.58 | 8.73 | 9.08 |
| Strain Q-4 | pSZ1283, pSZ2302 | 0.00 | 1.71 | 7.42 | 37.67 | 1.43 | 37.26 | 10.38 | 9.13 |
| Strain Q-5 | pSZ1283, pSZ2302 | 0.13 | 1.21 | 7.36 | 38.81 | 1.31 | 38.07 | 8.71 | 8.7 |
| Strain R-1 | pSZ1283, pSZ2304 | 0.19 | 1.78 | 8.47 | 40.11 | 1.34 | 33.46 | 9.98 | 10.44 |
| Strain R-2 | pSZ1283, pSZ2304 | 0.90 | 8.00 | 7.78 | 28.96 | 1.15 | 30.26 | 17.14 | 16.68 |
| Strain R-3 | pSZ1283, pSZ2304 | 0.26 | 3.58 | 7.77 | 34.98 | 1.56 | 32.86 | 14.60 | 11.61 |

TABLE 26-continued

Fatty acid profiles of *Prototheca moriformis* (UTEX 1435) Strains B, Q, and R engineered for increased midchain fatty acids, cultured at pH 5.0.

| Strain | Transformation plasmid(s) | Fatty Acid (Area %) C10:0 | C12:0 | C14:0 | C16:0 | C18:0 | C18:1 | C18:2 | C10-C14 |
|---|---|---|---|---|---|---|---|---|---|
| Strain R-4 | pSZ1283, pSZ2304 | 1.64 | 13.50 | 7.61 | 21.38 | 0.90 | 36.13 | 14.73 | 22.75 |
| Strain R-5 | pSZ1283, pSZ2304 | 1.03 | 9.63 | 7.56 | 25.61 | 1.00 | 31.70 | 18.23 | 18.22 |

TABLE 27

Fatty acid profiles of *Prototheca moriformis* (UTEX 1435), Strains B, Q, and R engineered for increased midchain fatty acids, cultured at pH 7.0.

| Strain | Transformation plasmid(s) | Fatty Acid (Area %) C10:0 | C12:0 | C14:0 | C16:0 | C18:0 | C18:1 | C18:2 | C10-C14 |
|---|---|---|---|---|---|---|---|---|---|
| UTEX 1435 | None | 0.01 | 0.04 | 1.34 | 27.94 | 3.24 | 57.46 | 7.88 | 1.39 |
| Strain B | pSZ1283 | 4.72 | 29.57 | 15.56 | 12.63 | 1.20 | 27.65 | 7.39 | 49.85 |
| Strain Q-1 | pSZ1283, pSZ2302 | 16.00 | 50.61 | 9.52 | 5.33 | 0.54 | 11.79 | 5.28 | 76.13 |
| Strain Q-2 | pSZ1283, pSZ2302 | 16.32 | 49.79 | 9.82 | 5.52 | 0.54 | 12.28 | 4.87 | 75.93 |
| Strain Q-3 | pSZ1283, pSZ2302 | 15.08 | 47.58 | 10.23 | 5.93 | 0.56 | 15.12 | 4.50 | 72.89 |
| Strain Q-4 | pSZ1283, pSZ2302 | 14.27 | 47.30 | 10.44 | 6.17 | 0.56 | 15.50 | 4.59 | 72.01 |
| Strain Q-5 | pSZ1283, pSZ2302 | 14.75 | 47.28 | 10.32 | 6.04 | 0.59 | 15.50 | 4.65 | 72.35 |
| Strain R-1 | pSZ1283, pSZ2304 | 21.25 | 55.42 | 7.97 | 3.65 | 0.00 | 5.46 | 5.66 | 84.64 |
| Strain R-2 | pSZ1283, pSZ2304 | 13.00 | 55.05 | 10.88 | 5.78 | 0.28 | 7.90 | 6.29 | 78.93 |
| Strain R-3 | pSZ1283, pSZ2304 | 12.89 | 53.15 | 11.11 | 6.13 | 0.00 | 9.87 | 6.13 | 77.15 |
| Strain R-4 | pSZ1283, pSZ2304 | 12.80 | 51.64 | 13.86 | 6.69 | 0.00 | 7.51 | 6.70 | 78.3 |
| Strain R-5 | pSZ1283, pSZ2304 | 16.61 | 51.42 | 9.84 | 5.27 | 0.33 | 11.15 | 4.79 | 77.87 |

The data presented in Tables 26 and 27 show a clear impact of disruption of different KASI alleles on the fatty acid profiles of the transformed organisms. When cultivated at pH 5.0, the fatty acid profiles of *Prototheca moriformis* (UTEX 1435) and *Prototheca moriformis* (UTEX 1435) Strain B, expressing a *Cuphea wrightii* FATB2 thioesterase under control of a pH regulatable promoter were very similar. These profiles were characterized by about 1% C14:0, about 21-26% C16:0, about 2-3% C18:0, about 60-65% C18:1, about 7% C18:2, with C10-C14 fatty acids comprising about 1.19-1.3% of total fatty acids. In contrast, when cultivated at pH 5.0, Strain B further engineered to disrupt KASI allele 1 (Strain Q) or KASI allele 2 (Strain R) demonstrated altered fatty acid profiles that were characterized by increased levels of C12, increased levels of C14, decreased levels of C18, and decreased levels of C18:1 fatty acids compared to Strain B or UTEX 1435. The fatty acid profiles of isolates of Strains Q and R differed in that Strain R (allele 2 knockout) isolates had generally greater C12s and lower C16s and C18:1s than Strain Q (allele 1 knockout).

When cultivated at pH 7.0, the fatty acid profile of *Prototheca moriformis* (UTEX 1435) is distinct from that *Prototheca moriformis* (UTEX 1435) Strain B expressing a *Cuphea wrightii* FATB2 thioesterase under control of a pH regulatable promoter. When cultured at pH 7.0, Strain B was characterized by a fatty acid profile elevated in C10, C12, and C14 fatty acids (these comprised about 50% of the total fatty acids). When cultured at pH 7.0, Strain Q and Strain R demonstrated fatty acid profiles with still further increases in C10, C12, and C14 fatty acids and still further decreases in C18:0 and C18:1 fatty acids relative to that of Strain B. Again, differences in fatty acid profiles between Strain Q and R were observed with the profile of Strain R comprising greater percentage levels of C12 and lower levels of C18:1 than that of Strain Q.

These data illustrate the successful expression and use of polynucleotides enabling expression of KASI and KASIV constructs in *Prototheca moriformis* to alter the percentage of saturated fatty acids in the engineered host microbes, and in particular in increasing the concentration of C10:0 and C12:0 fatty acids and decreasing the concentration of C18:0 and C18:1 fatty acids in microbial cells. In addition, the data here indicate the different KASI alleles can be disrupted to result in altered fatty acid profiles of the transformed organisms.

Example 39: Engineering Microorganisms for Increased Production of Mid-Chain Fatty Acids Through KASI Knockdown This example describes the use of recombinant polynucleotides that encode RNA hairpins to attenuate a KASI enzyme to engineer a microorganism in which the fatty acid profile of the transformed microorganism has been enriched in midchain fatty acids.

A classically mutagenized strain of *Prototheca moriformis* (UTEX 1435), Strain S, was transformed independently with each of the constructs pSZ2482-pSZ2485 according to biolistic transformation methods as described in PCT/US2009/066141, PCT/US2009/066142, PCT/US2011/038463, PCT/US2011/038464, and PCT/US2012/023696. Each of the constructs pSZ2482-pSZ2485 included different polynucleotides encoding hairpin RNAs targeted against *Prototheca moriformis* (UTEX 1435) KASI mRNA transcripts to down-regulate the expression of fatty acyl-ACP thioesterase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each KASI hairpin are listed in Table 28. The polynucleotide sequence encoding each RNA hairpin was under the control of the *P. moriformis* Amt03 promoter/5'UTR (SEQ ID NO: 8) and *C. vulgaris* nitrate reductase 3' UTR (SEQ ID NO: 6). The protein coding region of the suc2 expression cassette was codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

TABLE 28

Plasmid constructs used to transform *Prototheca moriformis* (UTEX 1435) Strain S.

| Transformation construct | Hairpin | SEQ ID NO: |
|---|---|---|
| pSZ2482 | KASI hairpin B | SEQ ID NO: 54 |
| pSZ2483 | KASI hairpin C | SEQ ID NO: 55 |
| pSZ2484 | KASI hairpin D | SEQ ID NO: 56 |
| pSZ2485 | KASI hairpin E | SEQ ID NO: 57 |

Upon independent transformation of Strain S with each of the constructs listed in Table 28, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using fatty acid methyl ester gas chromatography flame ionization detection methods as described in Example 1 (also see PCT/US2012/023696). The fatty acid profiles (expressed as Area % of total fatty acids) of *P. moriformis* UTEX 1435 propagated on glucose as a sole carbon source and four representative isolates of each transformation of Strain S, propagated on sucrose as a sole carbon source, are presented in Table 29.

TABLE 29

Fatty acid profiles of *Prototheca moriformis* (UTEX 1435) cells engineered to express hairpin RNA constructs targeting KASI gene/gene products.

| | | | Fatty Acid (Area %) | | | | | | | |
|---|---|---|---|---|---|---|---|---|---|---|
| Strain | Plasmid | Number | C10:0 | C12:0 | C14:0 | C16:0 | C18:0 | C18:1 | C18:2 | C18:3 |
| UTEX 1435 | none | 1 | 0.00 | 0.04 | 1.45 | 27.97 | 3.18 | 58.35 | 6.78 | 0.60 |
| Strain S | pSZ2482 | 1 | 0.19 | 0.74 | 8.47 | 38.30 | 2.15 | 36.24 | 9.45 | 1.42 |
| | | 2 | 0.07 | 0.25 | 4.16 | 32.46 | 2.62 | 49.57 | 7.73 | 0.82 |
| | | 3 | 0.03 | 0.10 | 2.68 | 27.48 | 2.65 | 56.40 | 8.14 | 0.55 |
| | | 4 | 0.03 | 0.10 | 2.60 | 27.44 | 2.01 | 55.54 | 9.15 | 0.78 |
| | pSZ2483 | 1 | 0.00 | 0.06 | 1.94 | 30.58 | 1.55 | 53.26 | 9.31 | 0.76 |
| | | 2 | 0.20 | 0.05 | 1.76 | 28.01 | 2.31 | 56.61 | 8.70 | 0.60 |
| | | 3 | 0.00 | 0.06 | 1.60 | 24.38 | 2.65 | 58.25 | 9.93 | 1.15 |
| | | 4 | 0.00 | 0.04 | 1.56 | 26.65 | 2.96 | 60.06 | 6.92 | 0.52 |
| | pSZ2484 | 1 | 0.72 | 3.71 | 19.15 | 38.03 | 1.68 | 14.22 | 15.00 | 4.21 |
| | | 2 | 0.66 | 2.76 | 16.34 | 38.19 | 1.78 | 18.52 | 14.91 | 3.38 |
| | | 3 | 0.69 | 2.96 | 16.20 | 37.28 | 1.77 | 19.05 | 15.26 | 3.48 |
| | | 4 | 0.18 | 0.70 | 8.61 | 36.80 | 2.35 | 36.22 | 10.89 | 1.10 |
| | pSZ2485 | 1 | 0.00 | 0.04 | 1.41 | 25.34 | 3.16 | 60.12 | 7.78 | 0.48 |
| | | 2 | 0.03 | 0.04 | 1.41 | 23.85 | 2.19 | 61.23 | 8.75 | 0.67 |
| | | 3 | 0.00 | 0.04 | 1.41 | 24.41 | 2.23 | 60.64 | 8.69 | 0.67 |
| | | 4 | 0.00 | 0.04 | 1.41 | 24.51 | 2.16 | 60.85 | 8.91 | 0.66 |

The data presented in Table 29 show a clear impact of the expression of KAS hairpin RNA constructs on the fatty acid profiles of the transformed organisms. The fatty acid profiles of Strain S transformants comprising either pSZ2482 or pSZ2484 KASI hairpin RNA construct demonstrated an increase in the percentage of C10, C12, C14, and C16 fatty acids with a concomitant diminution of C18:0 and C18:1 fatty acids relative to the fatty acid profile of UTEX 1435.

These data illustrate the utility and successful use of polynucleotide KASI RNA hairpin constructs in *Prototheca moriformis* (UTEX 1435) to alter the fatty acids profile of engineered microbes, and in particular in increasing the concentration of midchain fatty acids and decreasing C18:0 and C18:1 fatty acids in microbial cells.

Example 40: Engineering Microorganisms for Increased Production of Stearic Acid Through Fatty Acid Elongase Overexpression This example describes the use of recombinant polynucleotides that encode fatty acid elongases to engineer a microorganism in which the fatty acid profile of the transformed microorganism has been enriched in stearic acid, arachidic acid, and docosadienoic acid.

A classically mutagenized strain of *Prototheca moriformis* (UTEX 1435), Strain J, was transformed independently with each of the constructs pSZ2323, pSZ2324, or pSZ2328 according to biolistic transformation methods as described in PCT/US2009/066141, PCT/US2009/066142, PCT/US2011/038463, PCT/US2011/038464, and PCT/US2012/023696. Each of the constructs included a protein coding region to overexpress an elongase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each elongase are listed in Table 30. The polynucleotide sequence encoding each elongase was under control of the *P. moriformis* Amt03 promoter/5'UTR (SEQ ID NO: 8) and *C. vulgaris* nitrate reductase 3' UTR (SEQ ID NO: 6). The protein coding regions of the exogenous elongases and the suc2 expression cassette were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

TABLE 30

Plasmid constructs used to transform *Prototheca moriformis* (UTEX 1435) Strain J.

| Plasmid construct | Elongase source | GenBank Accession No. | SEQ ID NO: |
|---|---|---|---|
| pSZ2328 | *Marchantia polymorpha* | AAP74370 | 58, 59 |
| pSZ2324 | *Trypanosoma brucei* | AAX70673 | 60, 61 |
| pSZ2323 | *Saccharomyces cerevisiae* | P39540 | 62, 63 |

Upon independent transformation of Strain J with the constructs listed in Table 30, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using fatty acid methyl ester gas chromatography flame ionization detection methods as described in Example 1 (also see PCT/US2012/023696). The fatty acid profiles (expressed as Area % of total fatty acids) of *P. moriformis* UTEX 1435 Strain J propagated on glucose as a sole carbon source and three representative isolates of each transformation of Strain J, propagated on sucrose as a sole carbon source are presented in Table 31.

TABLE 31

Fatty acid profiles of *Prototheca moriformis* (UTEX 1435) Strain J cells engineered to overexpress elongases.

| Plasmid | | Fatty Acid Area % | | | | | | | | |
|---|---|---|---|---|---|---|---|---|---|---|
| construct | No. | C14:0 | C16:0 | C16:1 | C18:0 | C18:1 | C18:2 | C18:3α | C20:0 | C22:2n6 |
| None | 1 | 1.39 | 27.42 | 0.77 | 3.33 | 57.46 | 8.05 | 0.61 | 0.30 | 0.03 |
| pSZ2328 | 1 | 1.25 | 19.23 | 0.85 | 8.26 | 57.54 | 9.34 | 0.79 | 0.73 | 0.94 |
| pSZ2328 | 2 | 1.22 | 17.76 | 0.69 | 7.86 | 60.56 | 9.38 | 0.59 | 0.6 | 0.47 |
| pSZ2328 | 3 | 1.26 | 18.37 | 0.92 | 7.83 | 58.77 | 10.01 | 0.72 | 0.64 | 0.52 |
| pSZ2324 | 1 | 1.51 | 22.97 | 1.09 | 8.71 | 53.01 | 9.63 | 0.65 | 0.68 | 0.55 |
| pSZ2324 | 2 | 1.29 | 20.6 | 0.92 | 7.53 | 56.97 | 9.92 | 0.73 | 0.64 | 0.43 |
| pSZ2324 | 3 | 1.28 | 20.59 | 0.93 | 7.33 | 57.52 | 9.68 | 0.65 | 0.58 | 0.42 |
| pSZ2323 | 1 | 1.65 | 27.27 | 0.67 | 3.56 | 56.68 | 8.72 | 0.33 | 0.36 | 0.00 |
| pSZ2323 | 2 | 1.56 | 28.44 | 0.74 | 3.36 | 55.22 | 9.07 | 0.46 | 0.39 | 0.03 |
| pSZ2323 | 3 | 1.64 | 28.7 | 0.75 | 3.34 | 55.29 | 8.59 | 0.49 | 0.36 | 0.02 |

The data presented in Table 31 show a clear impact of the expression of *Marchantia polymorpha* and *Trypanosoma* brucei enzymes on the C14, C16, C18:0, C20:0, and C22:2n6 fatty acid profiles of the transformed organisms. The fatty acid profile of untransformed Strain J was about 27.42% C16:0, about 3% C18:0, about 57.5% C18:1, about 0.3% C20:0 and about 0.03% C22:2n6 fatty acids. In contrast to that of Strain J, the fatty acid profiles of Strain J transformed with different plasmid constructs to express elongases comprised lower percentage levels of C16 and higher percentage levels of C18:0, C20:0, and C22:2n6 fatty acids. The result of overexpression of *Marchantia polymorpha* elongase was about a 2.5 fold increase in percentage levels of C18:0 fatty acids, a 2 fold increase in percentage levels of C20:0 fatty acids, and about a 15 to 30 fold increase in percentage levels of C22:2n6 fatty acids relative to the fatty acid profile of Strain J.

These data illustrate the successful use of polynucleotides encoding elongases for expression in *Prototheca moriformis* (UTEX 1435) to alter the fatty acid profile of engineered microbes, and in particular in increasing the concentration of C18:0, C20:0, and C22:2n6 fatty acids and decreasing C16:0 fatty acids in recombinant microbial cells.

Example 41: Engineering Microorganisms for Increased Production of Stearic Acid Through Acyl-ACP Thioesterase Overexpression This example describes the use of recombinant polynucleotides that encode different C18:0-preferring acyl-ACP thioesterases to engineer microorganisms in which the fatty acid profiles of the transformed microorganisms have been enriched in stearic acid.

Classically mutagenized strains of *Prototheca moriformis* (UTEX 1435), Strain J or Strain A, were transformed independently with the constructs listed in Table 32 according to biolistic transformation methods as described in PCT/US2009/066141, PCT/US2009/066142, PCT/US2011/038463, PCT/US2011/038464, and PCT/US2012/023696. Each of the constructs included a protein coding region to overexpress a fatty acyl-ACP thioesterase with a C-terminal 3× FLAG® epitope tag, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each thioesterase are listed in Table 32. The polynucleotide sequence encoding each thioesterase was under control of the *P. moriformis* Amt03 promoter/5'UTR (SEQ ID NO: 8) and *C. vulgaris* nitrate reductase 3' UTR (SEQ ID NO: 6). The protein coding regions of the exogenous thioesterases and the suc2 expression cassette were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

TABLE 32

Plasmid constructs used to transform *Prototheca moriformis* (UTEX 1435) Strain A or Strain J.

| Plasmid construct | Acyl-ACP Thioesterase, GenBank Accession No. | Acyl-ACP Thioesterase source | Transit Peptide source | SEQ ID NO: |
|---|---|---|---|---|
| pSZD581 | FATA, CAA52070 | *Brassica napus* | native | 64, 65 |
| pSZD643 | FATA, CAA52070 | *Brassica napus* | UTEX 250 SAD | 66, 67 |
| pSZD645 | FATA, AAA33019 | *C. tinctorius* | UTEX 250 SAD | 68, 69 |
| pSZD644 | FATA, ABS30422 | *Ricinis communis* | native | 70, 71 |
| pSZD1323 | FATA, AAB51523 | *G. mangostana* | native | 72, 73 |
| pSZD1320 | FATA | *Theobroma cacao* | native | 74, 75 |

Upon independent transformation of Strain A or J with the constructs listed in Table 32, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using fatty acid methyl ester gas chromatography flame ionization detection methods as described in Example 1 (also see PCT/US2012/023696). The fatty acid profiles (expressed as Area % of total fatty acids) of *P. moriformis* UTEX 1435 Strain J propagated on glucose as a sole carbon source and representative isolates of each transformation of Strain J, propagated on sucrose as a sole carbon source are presented in Table 33.

TABLE 33

Fatty acid profiles of *Prototheca moriformis* (UTEX 1435) Strain J cells engineered to overexpress exogenous acyl-ACP thioesterase enzymes.

| | Plasmid | | Fatty Acid Area % | | | | | |
|---|---|---|---|---|---|---|---|---|
| Strain | construct | No. | C14:0 | C16:0 | C18:0 | C18:1 | C18:2 | C18:3α |
| A | None | 1 | 1.08 | 25.48 | 3.23 | 59.70 | 8.25 | 0.70 |
| J | None | 1 | 1.41 | 27.33 | 3.38 | 57.07 | 8.15 | 0.64 |
| A | pSZD581 | 1 | 1.02 | 26.60 | 14.47 | 44.80 | 10.05 | 0.65 |
| | | 2 | 1.08 | 28.24 | 13.57 | 43.89 | 10.07 | 0.68 |
| | | 3 | 0.97 | 24.70 | 9.13 | 50.85 | 11.27 | 0.82 |
| A | pSZD643 | 1 | 1.39 | 26.97 | 16.21 | 44.10 | 8.43 | 0.83 |
| | | 2 | 1.37 | 27.91 | 11.15 | 48.31 | 8.40 | 0.78 |
| A | pSZD645 | 1 | 0.90 | 23.39 | 8.35 | 50.69 | 13.34 | 0.96 |
| A | pSZD644 | 1 | 1.67 | 19.70 | 4.40 | 59.15 | 12.32 | 1.01 |
| J | pSZD1323 | 1 | 1.33 | 23.26 | 9.28 | 53.42 | 10.35 | 0.69 |
| | | 2 | 1.47 | 26.84 | 7.36 | 52.78 | 9.29 | 0.64 |
| | | 3 | 1.43 | 26.31 | 6.05 | 54.45 | 9.37 | 0.66 |
| J | pSZD1320 | 1 | 1.30 | 24.76 | 3.84 | 60.90 | 6.96 | 0.55 |
| | | 2 | 1.36 | 26.30 | 3.27 | 58.19 | 8.66 | 0.48 |
| | | 3 | 1.39 | 25.51 | 3.18 | 58.78 | 8.85 | 0.45 |

The data presented in Table 33 show a clear impact of the expression of exogenous acyl-ACP enzymes on the fatty acid profiles of the transformed microorganisms. The fatty acid profiles of untransformed Strain A and J were about 25% C16:0, about 3.3% C18:0, about 57 to 60% C18:1. In contrast, the fatty acid profiles of Strain A transformed with different plasmid constructs to express acyl-ACP enzymes comprised greater percentage levels of C18:0 and lower percentage levels of C18:1 fatty acids than that of Strain A. Expression of FATA enzymes from *B. napus, C. tinctorius, R. communis* and *G. mangostana* in Strain A or J enabled the accumulation of stearate levels in the transformed organisms. The result of overexpression of a *Brassica napus* acyl-ACP thioesterase was about a 2 to 5 fold increase in the percentage levels of C18:0 fatty acids of the fatty acid profile of the transformed organisms relative to the fatty acid profile of Strain A. Fatty acid profiles of cells engineered to overexpress a *G. mangostana* acyl-ACP FATA thioesterase with a *C. protothecoides* SAD1 transit peptide were characterized by about a 2 to 3 fold increase in the percentage levels of C18:0 fatty acids of the fatty acid profile of the transformed organism relative to the fatty acid profile of Strain J.

These data illustrate the utility and effective use of polynucleotides encoding fatty acyl-ACP thioesterases for expression in *Prototheca moriformis* (UTEX 1435) to alter the fatty acid profile of engineered microbes, and in particular in increasing the concentration of C18:0 and decreasing C18:1 fatty acids in recombinant microbial cells.

Example 42: Engineering Microorganisms for Increased Production of Erucic Acid Through Elongase or Beta-Ketoacyl-COA Synthase Overexpression In an embodiment of the present invention, a recombinant polynucleotide transformation vector operable to express an exogenous elongase or beta-ketoacyl-CoA synthase in an optionally plastidic oleaginous microbe is constructed and employed to transform *Prototheca moriformis* (UTEX 1435) according to the biolistic transformation methods as described in PCT/US2009/066141, PCT/US2009/066142, PCT/US2011/038463, PCT/US2011/038464, and PCT/US2012/023696 to obtain a cell increased for production of erucic acid. The transformation vector includes a protein coding region to overexpress an elongase or beta-ketoacyl-CoA synthase such as those listed in Table 5, promoter and 3'UTR control sequences to regulate expression of the exogenous gene, 5' and 3' homologous recombination targeting sequences targeting the recombinant polynucleotides for integration into the *P. moriformis* (UTEX 1435) nuclear genome, and nucleotides operable to express a selectable marker. The protein-coding sequences of the transformation vector are codon-optimized for expression in *P. moriformis* (UTEX 1435) as described in PCT/US2009/066141, PCT/US2009/066142, PCT/US2011/038463, PCT/US2011/038464, and PCT/US2012/023696. Recombinant polynucleotides encoding promoters, 3' UTRs, and selectable markers operable for expression in *P. moriformis* (UTEX 1435) are disclosed herein and in PCT/US2009/066141, PCT/US2009/066142, PCT/US2011/038463, PCT/US2011/038464, and PCT/US2012/023696.

Upon transformation of the transformation vector into *P. moriformis* (UTEX 1435) or a classically-mutagenized strain of *P. moriformis* (UTEX 1435), positive clones are selected on agar plates. Individual transformants are clonally purified and cultivated under heterotrophic conditions suitable for lipid production as detailed in PCT/US2009/066141, PCT/US2009/066142, PCT/US2011/038463, PCT/US2011/038464, and PCT/US2012/023696. Lipid samples are prepared from dried biomass from each transformant and fatty acid profiles from these samples are analyzed using fatty acid methyl ester gas chromatography flame ionization (FAME GC/FID) detection methods as described in Example 1. As a result of these manipulations, the cell may exhibit an increase in erucic acid of at least 5, 10, 15, or 20 fold.

Example 43: Generation of Capric, Lauric, and Myristic Acid Rich Oils in Strain UTEX1435 by the Expression of *Cuphea* PSR23 LPAATs We tested the effect of expression of two 1-acyl-sn-glycerol-3-phosphate acyltransferases (LPAATs) in a previously described *P. moriformis* (UTEX 1435) transgenic strain, expressing the acyl ACP thioesterase (FATB2) from *Cuphea wrightii*. The LPAAT2 and LPAAT3 genes from *Cuphea* PSR23 (CuPSR23) were identified by analysis of a combination of CuPSR23 genomic sequences and transcriptomic sequences derived from seed RNAs. The two LPAATs have not been previously described. The genes were codon optimized to reflect UTEX 1435 codon usage. Transformations, cell culture, lipid production and fatty acid analysis were all carried out as previously described.

Increased Capric, Lauric, and Myristic Accumulation in Strain B by the Expression of the *Cuphea* PSR231-Acyl-Sn-Glycerol-3-Phosphate Acyltransferases (LPAAT2 and LPAAT3) [pSZ2299 and pSZ2300, Respectively]:

In this example, transgenic strains were generated via transformation of strain B with the constructs pSZ2299 or pSZ2300, encoding CuPSR23 LPAAT2 and LPAAT3, respectively. The transgenic strains were selected for resistance to the antibiotic G418. Construct pSZ2299 can be written as pLOOP5'::CrTUB2:NeoR:CvNR::PmAMT3:CuPSR23 LPAAT2-1:CvNR::pLOOP3'. Construct pSZ2300 can be written as pLOOP5'::CrTUB2:NeoR:CvNR::PmAMT3:CuPSR23 LPAAT3-1:CvNR::pLOOP3'. The sequence of the transforming DNA (pSZ2299 and pSZ2300) is provided below. The relevant restriction sites in the construct from 5'-3', BspQI, KpnI, XbaI, Mfe I, BamHI, EcoRI, SpeI, XhoI, SacI, BspQI, respectively, are indicated in lowercase, bold, and underlined. BspQI sites delimit the 5' and 3' ends of the transforming DNA. Bold, lowercase sequences at the 5' and 3' end of the construct represent genomic DNA from UTEX 1435 that target integration to the pLoop locus via homologous recombination. Proceeding in the 5' to 3' direction, the selection cassette has the *C. reinhardtii* β-tubulin promoter driving expression of the NeoR gene (conferring resistance to G418) and the *Chlorella vulgaris* Nitrate Reductase (NR) gene 3' UTR. The promoter is indicated by lowercase, boxed text. The initiator ATG and terminator TGA for NeoR are indicated by uppercase italics, while the coding region is indicated with lowercase italics. The 3' UTR is indicated by lowercase underlined text. The spacer region between the two cassettes is indicated by upper case text. The second cassette containing the codon optimized LPAAT2 gene (pSZ2299) or LPAAT3 gene (pSZ2300) from *Cuphea* PSR23 is driven by the *Prototheca moriformis* endogenous AMT3 promoter, and has the same *Chlorella vulgaris* Nitrate Reductase (NR) gene 3' UTR. In this cassette, the AMT3 promoter in indicated by lowercase, boxed text. The initiator ATG and terminator TGA for the CuPSR23 LPAAT2 and LPAAT3 genes are indicated in uppercase italics, while the coding regions are indicated by lowercase italics. The 3' UTR is indicated by lowercase underlined text. The final constructs were sequenced to ensure correct reading frames and targeting sequences.

pSZ2299 Transforming Construct:

(SEQ ID NO: 90)

```
gctcttccgctaacggaggtctgtcaccaaatggaccccgtctattgcgggaaaccacggcgatggcacgtttcaaaacttgatg
aaatacaatattcagtatgtcgcgggcggcgacggcggggagctgatgtcgcgctgggtattgcttaatcgccagcttcgcccc
gtcttggcgcgaggcgtgaacaagccgaccgatgtgcacgagcaaatcctgacactagaagggctgactcgcccggcacggctga
attacacaggcttgcaaaaataccagaatttgcacgcaccgtattcgcggtattttgttggacagtgaatagcgatgcggcaatg
gcttgtggcgttagaaggtgcgacgaaggtggtgccaccactgtgccagccagtcctggcggctcccagggccccgatcaagagc
caggacatccaaactacccacagcatcaacgccccggcctatactcgaaccccacttgcactctgcaatggtatgggaaccacgg
ggcagtcttgtgtgggtcgcgcctatcgcggtcggcgaagaccgggaaggtaccctttcttgcgctatgacacttccagcaaaag
gtagggcgggctgcgagacggcttcccggcgctgcatgcaacaccgatgatgcttcgacccccccgaagctccttcggggctgcat
gggcgctccgatgccgctccagggcgagcgctgtttaaatagccaggcccccgattgcaaagacattatagcgagctaccaaagc
catattcaaacacctagatcactaccacttctacacaggccactcgagcttgtgatcgcactccgctaagggggcgcctcttcct
```

-continued cttcgtttcagtcacaacccgcaaactctagaatatcaATGatcgagcaggacggcctccacgccggctcccccgccgcctgggtg gagcgcctgttcggctacgactgggcccagcagaccatcggctgctccgacgccgccgtgttccgcctgtccgcccagggccgcc ccgtgctgttcgtgaagaccgacctgtccggcgccctgaacgagctgcaggacgaggccgcccgcctgtcctggctggccaccac cggcgtgccctgcgccgccgtgctggacgtggtgaccgaggccggccgcgactggctgctgctgggcgaggtgcccggccaggac ctgctgtcctcccacctggcccccgccgagaaggtgtccatcatggccgacgccatgcgccgcctgcacaccctggaccccgcca cctgccccttcgaccaccaggccaagcaccgcatcgagcgcgcccgcacccgcatggaggccggcctggtggaccaggacgacct ggacgaggagcaccagggcctggcccccgccgagctgttcgcccgcctgaaggcccgcatgcccgacggcgaggacctggtggtg acccacggcgacgcctgcctgcccaacatcatggtggagaacggccgcttctccggcttcatcgactgcggccgcctgggcgtgg ccgaccgctaccaggacatcgccctggccacccgcgacatcgccgaggagctgggcggcgagtgggccgaccgcttcctggtgct gtacggcatcgccgcccccgactcccagcgcatcgccttctaccgcctgctggacgagttcttcTGAcaattggcagcagcagct cggatagtatcgacacactctggacgctggtcgtgtgatggactgttgccgccacacttgctgccttgacctgtgaatatccctg ccgcttttatcaaacagcctcagtgtgtttgatcttgtgtgtacgcgcttttgcgagttgctagctgcttgtgctatttgcgaat accacccccagcatccccttccctcgtttcatatcgcttgcatcccaaccgcaacttatctacgctgtcctgctatccctcagcg ctgctcctgctcctgctcactgcccctcgcacagccttggtttgggctccgcctgtattctcctggtactgcaacctgtaaacca gcactgcaatgctgatgcacgggaagtagtgggatgggaacacaaatggaggatccCGCGTCTCGAACAGAGCGCGCAGAGGAAC GCTGAAGGTCTCGCCTCTGTCGCACCTCAGCGCGGCATACACCACAATAACCACCTGACGAATGCGCTTGGTTCTTCGTCCATTA GCGAAGCGTCCGGTTCACACACGTGCCACGTTGGCGAGGTGGCAGGTGACAATGATCGGTGGAGCTGATGGTCGAAACGTTCACA GCCTAGGGATATCgaattcggccgacaggacgcgcgtcaaaggtgctggtcgtgtatgccctggccggcaggtcgttgctgctgctg gttagtgattccgcaaccctgattttggcgtcttattttggcgtggcaaacgctggcgcccgcgagccgggccggcggcgatgcg gtgccccacggctgccggaatccaagggaggcaagagcgcccgggtcagttgaagggctttacgcgcaaggtacagccgctcctg caaggctgcgtggtggaattggacgtgcaggtcctgctgaagttcctccaccgcctcaccagcggacaaagcaccggtgtatcag gtccgtgtcatccactctaaagagctcgactacgacctactgatggccctagattcttcatcaaaaacgcctgagacacttgccc aggattgaaactccctgaagggaccaccaggggccctgagttgttccttcccccgtggcgagctgccagccaggctgtacctgt gatcgaggctggcgggaaaataggcttcgtgtgctcaggtcatgggaggtgcaggacagctcatgaaacgccaacaatcgcacaa ttcatgtcaagctaatcagctatttcctcttcacgagctgtaattgtcccaaaattctggtctaccgggggtgatccttcgtgta cgggcccttccctcaaccctaggtatgcgcgcatgcggtcgccgcgcaactcgcgcgagggccgagggtttgggacgggccgtcc cgaaatgcagttgcacccggatgcgtggcacctttttttgcgataatttatgcaatggactgctctgcaaaattctggctctgtcg ccaaccctaggatcagcggcgtaggatttcgtaatcattcgtcctgatggggagctaccgactaccctaatatcagcccgactgc ctgacgccagcgtccacttttgtgcacacattccattcgtgcccaagacatttcattgtggtgcgaagcgtccccagttacgctc acctgtttcccgacctccttactgttctgtcgacagagcgggcccacaggccggtcgcagccactagtATGgcgatcgcggccgc ggcggtgatcttcctgttcggcctgatcttcttcgcctccggcctgatcatcaacctgttccaggcgctgtgcttcgtcctgatc cgcccccctgtccaagaacgcctaccgccgcatcaaccgcgtgttcgcggagctgctgctgtccgagctgctgtgcctgttcgact ggtgggcgggcgcgaagctgaagctgttcaccgaccccgagacgttccgcctgatgggcaaggagcacgccctggtcatcatcaa ccacatgaccgagctggactggatggtgggctgggtgatgggccagcacttcggctgcctgggctccatcatctccgtcgccaag aagtccacgaagttcctgcccgtgctgggctggtccatgtggttctccgagtacctgtacctggagcgctcctgggccaaggaca agtccaccctgaagtcccacatcgagcgcctgatcgactacccccctgcccttctggctggtcatcttcgtcgagggcacccgctt cacgcgcacgaagctgctggcggcccagcagtacgcggtctcctccggcctgcccgtcccccgcaacgtcctgatcccccgcacg -continued

*aagggcttcgtctcctgcgtgtcccacatgcgctccttcgtccccgcggtgtacgacgtcacggtggcgttccccaagacgtccc*

*cccccccacgctgctgaacctgttcgagggccagtccatcatgctgcacgtgcacatcaagcgccacgccatgaaggacctgcc*

*cgagtccgacgacgccgtcgcggagtggtgccgcgacaagttcgtcgagaaggacgccctgctggacaagcacaacgcggaggac*

*acgttctccggccaggaggtgtgccactccggctcccgccagctgaagtccctgctggtcgtgatctcctgggtcgtggtgacga*

*cgttcggcgccctgaagttcctgcagtggtcctcctggaagggcaaggcgttctccgccatcggcctgggcatcgtcaccctgct*

*gatgcacgtgctgatcctgtcctcccaggccgagcgctccaaccccgccgaggtggcccaggccaagctgaagaccggcctgtcc*

*atctccaagaaggtgacggacaaggagaacTGAttaattaa*__ctcgag__gcagcagcagctcggatagtatcgacacactctggacg ctggtcgtgtgatggactgttgccgccacacttgctgccttgacctgtgaatatccctgccgcttttatcaaacagcctcagtgt gtttgatcttgtgtgtacgcgcttttgcgagttgctagctgcttgtgctatttgcgaataccacccccagcatccccttccctc gtttcatatcgcttgcatcccaaccgcaacttatctacgctgtcctgctatccctcagcgctgctcctgctcctgctcactgccc ctcgcacagccttggtttgggctccgcctgtattctcctggtactgcaacctgtaaaccagcactgcaatgctgatgcacgggaa gtagtgggatgggaacacaaatggaaagcttgagctcagcggcgacggtcctgctaccgtacgacgttgggcacgcccatgaaag tttgtataccgagcttgttgagcgaactgcaagcgcggctcaaggatacttgaactcctggattgatatcggtccaataatggat ggaaaatccgaacctcgtgcaagaactgagcaaacctcgttacatggatgcacagtcgccagtccaatgaacattgaagtgagcg aactgttcgcttcggtggcagtactactcaaagaatgagctgctgttaaaaatgcactctcgttctctcaagtgagtggcagatg agtgctcacgccttgcacttcgctgcccgtgtcatgccctgcgccccaaaatttgaaaaaagggatgagattattgggcaatgga cgacgtcgtcgctccgggagtcaggaccggcggaaaataagaggcaacacactccgcttcttagctcttcg pSZ2300 Transforming Construct:

(SEQ ID NO:91)

gctcttccgctaacggaggtctgtcaccaaatggaccccgtctattgcgggaaaccacggcgatggcacgtttcaaaacttgat gaaatacaatattcagtatgtcgcgggcggcgacggcggggagctgatgtcgcgctgggtattgcttaatcgccagcttcgcc cccgtcttggcgcgaggcgtgaacaagccgaccgatgtgcacgagcaaatcctgacactagaagggctgactcgcccggca cggctgaattacacaggcttgcaaaaataccagaatttgcacgcaccgtattcgcggtattttgttggacagtgaatagcgatg cggcaatggcttgtggcgttagaaggtgcgacgaaggtggtgccaccactgtgccagccagtcctggeggctcccagggccc cgatcaagagccaggacatccaaactacccacagcatcaacgccccggcctatactegaaccccacttgcactetgcaatggt atgggaaccacggggcagtcttgtgtgggtcgcgcctatcgcggtcggcgaagaccgggaaggtaccctttcttgcgctatgac acttccagcaaaaggtagggcgggctgcgagacggcttcccggcgctgcatgcaacaccgatgatgcttcgacccccccgaagctcc ttcggggctgcatgggcgctccgatgccgctccagggcgagcgctgtttaaatagccaggcccccgattgcaaagacattatagcga gctaccaaagccatattcaaacacctagatcactaccacttctacacaggccactcgagcttgtgatcgcactccgctaagggggcgc ctcttcctcttcgtttcagtcacaacccgcaaactctagaatatca*ATGatcgagcaggacggcctccacgccggctcccccgccg*

*cctgggtggagcgcctgttcggctacgactgggcccagcagaccatcggctgctccgacgccgccgtgttccgcctgtccgccca*

*gggccgccccgtgctgacgtgaagaccgacctgtccggcgccctgaacgagctgcaggacgaggccgcccgcctgtcctggct*

*ggccaccaccggcgtgccctgcgccgccgtgctggacgtggtgaccgaggccggccgcgactggctgctgctgggcgaggtgc*

*ccggccaggacctgctgtcctcccacctggcccccgccgagaaggtgtccatcatggccgacgccatgcgccgcctgcacaccc*

*tggaccccgccacctgccccacgaccaccaggccaagcaccgcatcgagcgcgcccgcacccgcatggaggccggcctggtg*

*gaccaggacgacctggacgaggagcaccagggcctggcccccgccgagctgacgcccgcctgaaggcccgcatgcccgacg*

*gcgaggacctggtggtgacccacggcgacgcctgcctgcccaacatcatggtggagaacggccgcactccggcttcatcgactg*

*cggccgcctgggcgtggccgaccgctaccaggacatcgccctggccacccgcgacatcgccgaggagctgggcggcgagtgg*

*gccgaccgcacctggtgctgtacggcatcgccgcccccgactcccagcgcatcgccactaccgcctgctggacgagacacTG*

-continued

Acaattggcagcagcagctcggatagtatcgacacactctggacgctggtcgtgtgatggactgttgccgccacacttgctgccttga cctgtgaatatccctgccgcttttatcaaacagcctcagtgtgtttgatcttgtgtgtacgcgcttttgcgagttgctagctgcttgtgctattt gcgaataccacccccagcatccccttccctcgtttcatatcgcttgcatcccaaccgcaacttatctacgctgtcctgctatccctcagcg ctgctcctgctcctgctcactgcccctcgcacagccttggtttgggctccgcctgtattctcctggtactgcaacctgtaaaccagcactg caatgctgatgcacgggaagtagtgggatgggaacacaaatggaggatccCGCGTCTCGAACAGAGCGCGCA

GAGGAACGCTGAAGGTCTCGCCTCTGTCGCACCTCAGCGCGGCATACACCACAA

TAACCACCTGACGAATGCGCTTGGTTCTTCGTCCATTAGCGAAGCGTCCGGTTCA

CACACGTGCCACGTTGGCGAGGTGGCAGGTGACAATGATCGGTGGAGCTGATGG

TCGAAACGTTCACAGCCTAGGGATATCgaattcggccgacaggacgcgcgtcaaaggtgctggtcgtgt atgccctggccggcaggtcgttgctgctgctggttagtgattccgccaaccctgattttggcgtcttattttggcgtggcaaacgctggc gcccgcgagccgggccggcggcgatgcggtgccccacggctgccggaatccaagggaggcaagagcgcccgggtcagttga agggctttacgcgcaaggtacagccgctcctgcaaggctgcgtggtggaattggacgtgcaggtcctgctgaagttcctccaccg cctcaccagcggacaaagcaccggtgtatcaggtccgtgtcatccactctaaagagctcgactacgacctactgatggccctaga ttcttcatcaaaaacgcctgagacacttgcccaggattgaaactccctgaagggaccaccaggggccctgagttgttccttccccc cgtggcgagctgccagccaggctgtacctgtgatcgaggctggcgggaaaataggcttcgtgtgctcaggtcatgggaggtgca ggacagctcatgaaacgccaacaatcgcacaattcatgtcaagctaatcagctatttcctcttcacgagctgtaattgtcccaaaat tctggtctaccgggggtgatccttcgtgtacgggcccttccctcaaccctaggtatgcgcgcatgcggtcgccgcgcaactcgcgc gagggccgagggtttgggacgggccgtcccgaaatgcagttgcacccggatgcgtggcacctttttttgcgataatttatgcaatgg actgctctgcaaaattctggctctgtcgccaaccctaggatcagcggcgtaggatttcgtaatcattcgtcctgatggggagctacc gactaccctaatatcagcccgactgcctgacgccagcgtccacttttgtgcacacattccattcgtgcccaagacatttcattgtggt gcgaagcgtccccagttacgctcacctgtttccgacctccttactgttctgtcgacagagcgggcccacaggccggtcgcagcca ctagtATGgccatcgcggcggccgcggtgatcgtgcccctgtccctgctgacttcgtgtccggcctgatcgtcaacctggtgcag gccgtctgcttcgtcctgatccgcccccctgtccaagaacacgtaccgccgcatcaaccgcgtggtcgcggagctgctgtggctgga gctggtgtggctgatcgactggtgggcgggcgtgaagatcaaggtcacacggaccacgagacgaccacctgatgggcaagga gcacgccctggtcatctgcaaccacaagtccgacatcgactggctggtcggctgggtcctgggccagcgctccggctgcctgggc tccaccctggcggtcatgaagaagtcctccaagacctgcccgtcctgggctggtccatgtggactccgagtacctgacctggagc gctcctgggccaaggacgagatcacgctgaagtccggcctgaaccgcctgaaggactaccccctgcccttctggctggcgctgtt cgtggagggcacgcgcttcacccgcgcgaagctgctggcggcgcagcagtacgccgcgtcctccggcctgcccgtgccccgca acgtgctgatcccccgcacgaagggcttcgtgtcctccgtgtcccacatgcgctccacgtgcccgcgatctacgacgtcaccgtgg ccatccccaagacgtcccccccccccacgctgatccgcatgacaagggccagtcctccgtgctgcacgtgcacctgaagcgcca cctgatgaaggacctgcccgagtccgacgacgccgtcgcgcagtggtgccgcgacatatcgtggagaaggacgcgctgctgg acaagcacaacgccgaggacaccactccggccaggagctgcaggagaccggccgccccatcaagtccctgctggtcgtcatct cctgggccgtcctggaggtgttcggcgccgtcaagttcctgcagtggtcctccctgctgtcctcctggaagggcctggcgttctccgg catcggcctgggcgtgatcaccctgctgatgcacatcctgatcctgactcccagtccgagcgctccacccccgccaaggtggccc ccgcgaagcccaagaacgagggcgagtcctccaagaccgagatggagaaggagaagTGAttaattaactcgaggcagcag cagctcggatagtatcgacacactctggacgctggtcgtgtgatggactgttgccgccacacttgctgccttgacctgtgaatatccctg ccgcattatcaaacagcctcagtgtgatgatcagtgtgtacgcgcattgcgagttgctagctgcttgtgctatttgcgaataccaccccc -continued agcatcccatccctcgatcatatcgcttgcatcccaaccgcaacttatctacgctgtcctgctatccctcagcgctgctcctgctcctgct cactgcccctcgcacagccttggtttgggctccgcctgtattctcctggtactgcaacctgtaaaccagcactgcaatgctgatgcacgg gaagtagtgggatgggaacacaaatggaaagcttgagctcagcggcgacggtcctgctaccgtacgacgttgggcacgcccatg aaagtttgtataccgagcttgttgagcgaactgcaagcgcggctcaaggatacttgaactcctggattgatatcggtccaataa tggatggaaaatccgaacctcgtgcaagaactgagcaaacctcgttacatggatgcacagtcgccagtccaatgaacattga agtgagcgaactgttcgcttcggtggcagtactactcaaagaatgagctgctgttaaaaatgcactetcgttctctcaagtgagt ggcagatgagtgetcacgcctgcacttcgctgcccgtgtcatgccctgcgccccaaaatttgaaaaaagggatgagattattgg gcaatggacgacgtcgtcgctccgggagtcaggaccggcggaaaataagaggcaacacactccgcttcttagctcttcg To determine the impact of the CuPSR23 LPAAT2 and LPAAT3 genes on mid-chain fatty acid accumulation, the above constructs containing the codon optimized CuPSR23 LPAAT2 or LPAAT3 genes driven by the UTEX 1453 AMT3 promoter were transformed into strain B.

Primary transformants were clonally purified and grown under standard lipid production conditions at pH7.0 (all the strains require growth at pH 7.0 to allow for maximal expression of the CuPSR23 LPAAT2 or LPAAT3 gene driven by the pH-regulated AMT3 promoter). The resulting profiles from a set of representative clones arising from these transformations are shown in Table 34, below. D1520 represents clones of Strain B with CuPSR23 LPAAT2 and D1521 represents clones of Strain B with CuPSR23 LPAAT3.

TABLE 34

Fatty acid profiles of Strain B and representative transgenic lines transformed with pSZ2299 and pSZ2300 DNA.

| Sample ID | C10:0 | C12:0 | C14:0 | C16:0 | C18:0 | C18:1 | C18:2 |
|---|---|---|---|---|---|---|---|
| Strain B | 4.83 | 28.54 | 15.64 | 12.64 | 1.3 | 27.99 | 7.75 |
| D1520-A | 8.59 | 35.09 | 16.55 | 11.96 | 1.69 | 19.49 | 5.59 |
| D1520-B | 8.13 | 33.93 | 16.46 | 12.44 | 1.57 | 20.66 | 5.96 |
| D1520-C | 7.6 | 33.1 | 16.21 | 12.65 | 1.5 | 21.41 | 6.48 |
| D1520-D | 7.35 | 32.54 | 16.03 | 12.79 | 1.67 | 22.16 | 6.41 |
| D1520-E | 7.28 | 32.21 | 16.2 | 12.99 | 1.73 | 22.39 | 6.28 |
| D1521-A | 6.14 | 31.5 | 15.98 | 12.96 | 1.96 | 22.52 | 8 |
| D1521-B | 6.17 | 31.38 | 15.98 | 12.87 | 2.08 | 22.54 | 7.92 |
| D1521-C | 5.99 | 31.31 | 15.75 | 12.79 | 2.23 | 22.45 | 8.36 |
| D1521-D | 5.95 | 31.05 | 15.71 | 12.84 | 2.48 | 22.69 | 8.32 |
| D1521-E | 5.91 | 30.58 | 15.85 | 13.22 | 1.97 | 23.55 | 7.84 |

The transgenic CuPSR23 LPAAT2 strains (D1520A-E) show a significant increase in the accumulation of C10:0, C12:0, and C14:0 fatty acids with a concomitant decrease in C18:1 and C18:2. The trans genic CuPSR23 LPAAT3 strains (D1521A-E) show a significant increase in the accumulation of C10:0, C12:0, and C14:0 fatty acids with a concomitant decrease in C18:1. The expression of the CuPSR23 LPAAT in these transgenic lines appears to be directly responsible for the increased accumulation of mid-chain fatty acids in general, and especially laurates. While the transgenic lines show a shift from longer chain fatty acids (C16:0 and above) to mid-chain fatty acids, the shift is targeted predominantly to C10:0 and C12:0 fatty acids with a slight effect on C14:0 fatty acids. The data presented also show that co-expression of the LPAAT2 and LPAAT3 genes from *Cuphea* PSR23 and the FATB2 from *C. wrightii* (expressed in the strain Strain B) have an additive effect on the accumulation of C12:0 fatty acids.

Our results suggest that the LPAAT enzymes from *Cuphea* PSR23 are active in the algal strains derived from UTEX 1435. These results also demonstrate that the enzyme functions in conjunction with the heterologous FatB2 acyl-ACP thioesterase enzyme expressed in Strain B, which is derived from *Cuphea wrightii.*

Example 44: Alteration of Fatty Acid Levels in Strain UTEX1435 by the Expression of *Cuphea* Psr23 LPAATX in Combination with *Cuphea Wrightii* FATB2

Here we demonstrate the effect of expression of a 1-acyl-sn-glycerol-3-phosphate acyltransferase (LPAAT) in a previously described *P. moriformis* (UTEX 1435) transgenic strain, Strain B. As described above, Strain B is a transgenic strain expressing the acyl ACP thioesterase (FATB2) from *Cuphea wrightii*, which accumulates C12:0 fatty acids between 40 to 49%. Further to Example 43, a third CuPSR23 LPAAT, LPAATx, was identified by analysis of a combination of CuPSR23 genomic sequences and transcriptomic sequences derived from seed RNAs. Expression of a mid-chain specific LPAAT should thus increase the percentage of TAGs that have a capric acid (C10:0 fatty acid), lauric acid (C12:0 fatty acid), or myristic acid (C14:0 fatty acid) at the sn-2 position, and should consequently elevate the overall levels of these fatty acids. In Example 43, LPAAT2 and LPAAT3 were shown to increase caprate, laurate, and myristate accumulation in strain B. LPAATx was introduced into strain B to determine its effect on fatty acid levels in this strain. The LPAATx gene was codon optimized to reflect UTEX 1435 codon usage. Transformations, cell culture, lipid production and fatty acid analysis were all carried out as previously described.

Decreased Caprate, Laurate, and Myristate Accumulation and Increased Palmitate and Stearate Accumulation in Strain Strain B by the Expression of the *Cuphea* PSR231-acyl-sn-glycerol-3-phosphate acyltransferase (LPAATx) [pSZ2575]:

In this example, transgenic strains were generated via transformation of strain B with the construct pSZ2575 encoding CuPSR23 LPAATx. The transgenic strains were selected for resistance to the antibiotic G418. Construct pSZ2575 can be written as pLOOP5'::CrTUB2:NeoR:CvNR::PmAMT3:CuPSR23 LPAATx:CvNR::pLOOP3'. The sequence of the transforming DNA is provided below (pSZ2575). The relevant restriction sites in the construct from 5'-3', BspQ1, KpnI, XbaI, MfeI, BamHI, EcoRI, SpeI, XhoI, SacI, BspQ1, respectively, are indicated in lowercase, bold, and underlined. BspQ1 sites delimit the 5' and 3' ends of the transforming DNA. Bold, lowercase sequences at the 5' and 3' end of the construct represent genomic DNA from UTEX 1435 that target integration to the pLoop locus via homologous recombination. Proceeding in the 5' to 3' direction, the selection cassette has the *C. reinhardtii* β-tubulin promoter driving expression of the NeoR gene (conferring resistance to G418) and the *Chlorella vulgaris* Nitrate Reductase (NR) gene 3' UTR. The promoter is indicated by lowercase, boxed text. The initiator ATG and terminator TGA for NeoR are indicated by uppercase italics, while the coding region is indicated with lowercase italics. The 3' UTR is indicated by lowercase underlined text. The spacer region between the two cassettes is indicated by upper case text. The second cassette containing the codon optimized LPAATx gene (pSZ2575) from *Cuphea* PSR23 is driven by the *Prototheca moriformis* endogenous AMT3 promoter, and has the same *Chlorella vulgaris* Nitrate Reductase (NR) gene 3' UTR. In this cassette, the AMT3 promoter is indicated by lowercase, boxed text. The initiator ATG and terminator TGA for the CuPSR23 LPAATx genes are indicated in uppercase italics, while the coding region is indicated by lowercase italics. The 3' UTR is indicated by lowercase underlined text. The final construct was sequenced to ensure correct reading frame and targeting sequences.

pSZ2575 Transforming Construct (SEQ ID NO: 92)

gctcttccgctaacggaggtctgtcaccaaatggaccccgtctattgcgggaaaccacggcgatggcacgtttcaaaacttgatg aaatacaatattcagtatgtcgcgggcggcgacggcggggagctgatgtcgcgctgggtattgcttaatcgccagcttcgccccc gtcttggcgcgaggcgtgaacaagccgaccgatgtgcacgagcaaatcctgacactagaagggctgactcgcccggcacggctga attacacaggcttgcaaaaataccagaatttgcacgcaccgtattcgcggtattttgttggacagtgaatagcgatgcggcaatg gcttgtggcgttagaaggtgcgacgaaggtggtgccaccactgtgccagccagtcctggcggctcccagggccccgatcaagagc caggacatccaaactacccacagcatcaacgccccggcctatactcgaaccccacttgcactctgcaatggtatgggaaccacgg ggcagtcttgtgtgggtcgcgcctatcgcggtcggcgaagaccgggaaggtaccctttcttgcgctatgacacttccagcaaaag gtagggcgggctgcgagacggcttcccggcgctgcatgcaacaccgatgatgcttcgacccccccgaagctccttcggggctgcat gggcgctccgatgccgctccagggcgagcgctgtttaaatagccaggcccccgattgcaaagacattatagcgagctaccaaagc catattcaaacacctagatcactaccacttctacacaggccactcgagcttgtgatcgcactccgctaagggggcgcctcttcct cttcgtttcagtcacaacccgcaaactctagaatatca*ATGatcgagcaggacggcctccacgccggctcccccgccgcctggg*

*tggagcgcctgttcggctacgactgggcccagcagaccatcggctgctccgacgccgccgtgttccgcctgtccgcccagggccg*

*ccccgtgctgttcgtgaagaccgacctgtccggcgccctgaacgagctgcaggacgaggccgcccgcctgtcctggctggccacc*

*accggcgtgccctgcgccgccgtgctggacgtggtgaccgaggccggccgcgactggctgctgctgggcgaggtgcccggccagg*

*acctgctgtcctcccacctggcccccgccgagaaggtgtccatcatggccgacgccatgcgccgcctgcacaccctggaccccgc*

*cacctgccccttcgaccaccaggccaagcaccgcatcgagcgcgcccgcacccgcatggaggccggcctggtggaccaggacgac*

*ctggacgaggagcaccagggcctggcccccgccgagctgttcgcccgcctgaaggcccgcatgcccgacggcgaggacctggtgg*

*tgacccacggcgacgcctgcctgcccaacatcatggtggagaacggccgcttctccggcttcatcgactgcggccgcctgggcgt*

*ggccgaccgctaccaggacatcgccctggccacccgcgacatcgccgaggagctgggcggcgagtgggccgaccgcttcctggtg*

*ctgtacggcatcgccgcccccgactcccagcgcatcgccttctaccgcctgctggacgagttcttcTGA*caattggcagcagcag ctcggatagtatcgacacactctggacgctggtcgtgtgatggactgttgccgccacacttgctgccttgacctgtgaatatccc tgccgcttttatcaaacagcctcagtgtgtttgatcttgtgtgtacgcgcttttgcgagttgctagctgcttgtgctatttgcga ataccacccccagcatccccttccctcgtttcatatcgcttgcatcccaaccgcaacttatctacgctgtcctgctatccctcag cgctgctcctgctcctgctcactgcccctcgcacagccttggtttgggctccgcctgtattctcctggtactgcaacctgtaaac cagcactgcaatgctgatgcacgggaagtagtgggatgggaacacaaatggaggatccCGCGTCTCGAACAGAGCGCGCAGAGGA ACGCTGAAGGTCTCGCCTCTGTCGCACCTCAGCGCGGCATACACCACAATAACCACCTGACGAATGCGCTTGGTTCTTCGTCCAT -continued TAGCGAAGCGTCCGGTTCACACACGTGCCACGTTGGCGAGGTGGCAGGTGACAATGATCGGTGGAGCTGATGGTCGAAACGTTCA CAGCCTAGGGATATCgaattcggccgacaggacgcgcgtcaaaggtgctggtcgtgtatgccctggccggcaggtcgttgctgct gctggttagtgattccgcaaccctgattttggcgtcttattttggcgtggcaaacgctggcgcccgcgagccgggccggcggcga tgcggtgccccacggctgccggaatccaagggaggcaagagcgcccgggtcagttgaagggctttacgcgcaaggtacagccgct cctgcaaggctgcgtggtggaattggacgtgcaggtcctgctgaagttcctccaccgcctcaccagcggacaaagcaccggtgta tcaggtccgtgtcatccactctaaagagctcgactacgacctactgatggccctagattcttcatcaaaaacgcctgagacactt gcccaggattgaaactccctgaagggaccaccaggggccctgagttgttccttccccccgtggcgagctgccagccaggctgtac ctgtgatcgaggctggcgggaaaataggcttcgtgtgctcaggtcatgggaggtgcaggacagctcatgaaacgccaacaatcgc acaattcatgtcaagctaatcagctatttcctcttcacgagctgtaattgtcccaaaattctggtctaccgggggtgatccttcg tgtacgggcccttccctcaaccctaggtatgcgcgcatgcggtcgccgcgcaactcgcgcgagggccgagggtttgggacgggcc gtcccgaaatgcagttgcacccggatgcgtggcaccttttttgcgataatttatgcaatggactgctctgcaaaattctggctct gtcgccaaccctaggatcagcggcgtaggatttcgtaatcattcgtcctgatggggagctaccgactaccctaatatcagcccga ctgcctgacgccagcgtccacttttgtgcacacattccattcgtgcccaagacatttcattgtggtgcgaagcgtccccagttac gctcacctgtttcccgacctccttactgttctgtcgacagagcgggcccacaggccggtcgcagccactagtATGgagatccccc cccactgcctgtgctcccccctcccccgcccccctcccagctgtactacaagaagaagaagcacgccatcctgcagacccagacccc ctaccgctaccgcgtgtcccccacctgcttcgcccccccccgcctgcgcaagcagcacccctacccccctgcccgtgctgtgctac cccaagctgctgcacttctcccagccccgctacccccctggtgcgctcccacctggccgaggccggcgtggcctaccgccccggct acgagctgctgggcaagatccgcggcgtgtgcttctacgccgtgaccgccgccgtggccctgctgctgttccagtgcatgctgct gctgcaccccttcgtgctgctgttcgaccccttcccccgcaaggcccaccacaccatcgccaagctgtggtccatctgctccgtg tccctgttctacaagatccacatcaagggcctggagaacctgcccccccccactcccccgccgtgtacgtgtccaaccaccagt ccttcctggacatctacaccctgctgaccctgggccgcaccttcaagttcatctccaagaccgagatcttcctgtaccccatcat cggctgggccatgtacatgctgggcaccatcccccctgaagcgcctggactcccgctcccagctggacaccctgaagcgctgcatg gacctgatcaagaagggcgcctccgtgttcttcttccccgagggcacccgctccaaggacggcaagctgggcgccttcaagaagg gcgccttctccatcgccgccaagtccaaggtgcccgtggtgcccatcaccctgatcggcaccggcaagatcatgccccccggctc cgagctgaccgtgaaccccggcaccgtgcaggtgatcatccacaagcccatcgagggctccgacgccgaggccatgtgcaacgag gcccgcgccaccatctcccactccctggacgacTGAttaattaactcgaggcagcagcagctcggatagtatcgacacactctgg acgctggtcgtgtgatggactgttgccgccacacttgctgccttgacctgtgaatatccctgccgcttttatcaaacagcctcag tgtgtttgatcttgtgtgtacgcgcttttgcgagttgctagctgcttgtgctatttgcgaataccacccccagcatccccttccc tcgtttcatatcgcttgcatcccaaccgcaacttatctacgctgtcctgctatccctcagcgctgctcctgctcctgctcactgc ccctcgcacagccttggtttgggctccgcctgtattctcctggtactgcaaacctgtaaaccagcactgcaatgctgatgcacgg gaagtagtgggatgggaacacaaatggaaagcttgagctcagcggcgacggtcctgctaccgtacgacgttgggcacgcccatga aagtttgtataccgagcttgttgagcgaactgcaagcgcggctcaaggatacttgaactcctggattgatatcggtccaataatg gatggaaaatccgaacctcgtgcaagaactgagcaaacctcgttacatggatgcacagtcgccagtccaatgaacattgaagtga gcgaaactgttcgcttcggtggcagtactactcaaagaatgagctgctgttaaaaatgcactctcgttctctcaagtgagtggca gatgagtgctcacgccttgcacttcgctgcccgtgtcatgccctgcgccccaaaatttgaaaaaagggatgagattattgggcaa tggacgacgtcgtcgctccgggagtcaggaccggcggaaaataagaggcaacacactccgcttcttagctcttcg

To determine the impact of the CuPSR23 LPAATx gene on fatty acid accumulation, the above construct containing the codon optimized CuPSR23 LPAATx gene driven by the UTEX 1453 AMT3 promoter was transformed into strain B.

Primary transformants were clonally purified and grown under low nitrogen conditions at pH7.0; the strains require growth at pH 7.0 to allow for maximal expression of the CuPSR23 LPAATx and CwFATB2 genes driven by the pH-regulated AMT3 promoter. The resulting profiles from a set of representative clones arising from these transformations are shown in Table 35, below. D1542 represents clones of Strain B with CuPSR23 LPAATx.

TABLE 35

Fatty acid profiles of Strain B and representative transgenic lines transformed with pSZ2575.

| Sample ID | C10:0 | C12:0 | C14:0 | C16:0 | C18:0 | C18:1 | C18:2 |
|---|---|---|---|---|---|---|---|
| Strain B | 4.77 | 28.63 | 15.48 | 12.65 | 1.28 | 28.20 | 7.57 |
| D1542-A | 1.19 | 13.25 | 10.48 | 21.34 | 4.49 | 32.07 | 14.78 |
| D1542-B | 1.15 | 14.01 | 10.62 | 20.61 | 3.99 | 32.12 | 15.24 |
| D1542-C | 1.21 | 13.69 | 10.83 | 20.40 | 3.59 | 33.54 | 15.05 |
| D1542-D | 1.56 | 16.83 | 11.51 | 18.44 | 2.94 | 33.97 | 12.74 |
| D1542-E | 2.15 | 18.58 | 11.94 | 18.22 | 3.17 | 32.63 | 11.62 |

The transgenic CuPSR23 LPAATx strains (D1542A-E) show a significant decrease in the accumulation of C10:0, C12:0, and C14:0 fatty acids relative to the parent, Strain B, with a concomitant increase in C16:0, C18:0, C18:1 and C18:2. The expression of the CuPSR23 LPAATx gene in these transgenic lines appears to be directly responsible for the decreased accumulation of mid-chain fatty acids (C10-C14) and the increased accumulation of C16:0 and C18 fatty acids, with the most pronounced increase observed in palmitates (C16:0). The data presented also show that despite the expression of the midchain specific FATB2 from *C. wrightii* (present in Strain B), the expression of CuPSR23 LPAATx appears to favor incorporation of longer chain fatty acids into TAGs.

Our results suggest that the LPAATx enzyme from *Cuphea* PSR23 is active in the algal strains derived from UTEX 1435. Contrary to *Cuphea* PSR23 LPAAT2 and LPAAT3, which increase mid-chain fatty acid levels, CuPSR23 LPAATx leads to increased C16:0 and C18:0 levels. These results demonstrate that the different LPAATs derived from CuPSR23 (LPAAT2, LPAAT3, and LPAATx) exhibit different fatty acid specificities in Strain B as judged by their effects on overall fatty acid levels.

Example 45: Reduction in Chain Length of Fatty Acid Profile as a Result of Overexpressing an Endogenous Microalgal FATA Acyl-ACP Thioesterase Here, we demonstrate that over expression of the *Prototheca moriformis* endogenous thioesterases FATA1 in UTEX1435 results in a clear diminution of cell triglyceride C18:0 and C18:1 acyl chains with an increase in C16:0, C14:0.

Constructs Used for the Over Expression of the *P. moriformis* FATA1 Gene (pSZ2422, pSZ2421):

To over express the PmFATA1 in *P. moriformis* STRAIN J, a codon optimized PmFATA1 gene was been transformed into STRAIN J. The *Saccharomyces cerevisiae* invertase gene was utilized as the selectable marker to confer the ability of growing on sucrose media. The construct pSZ2422 that have been expressed in STRAIN J can be written as: 6SA::CrTUB2-ScSUC2-CvNR3':PmAMT3-Pm FATA1 (opt)-CvNR3'::6SB, and the construct pSZ2421 can be written as 6SA:: CrTUB2-ScSUC2-CvNR3':PmAMT3-S106SAD TP-Pm FATA1 (opt)-CvNR3'::6SB.

The sequence of the transforming DNA is provided below. Relevant restriction sites in the construct pSZ2422 are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from STRAIN J that permit targeted integration at 6 s locus via homologous recombination. Proceeding in the 5' to 3' direction, the *C. reinhardtii* β-tubulin promoter driving the expression of the yeast sucrose invertase gene (conferring the ability of STRAIN J to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *P. moriformis*, indicated by boxed italics text. The Initiator ATG and terminator TGA codons of the PmFATA1 are indicated by uppercase, bold italics, while the remainder of the gene is indicated by bold italics. The *C. vulgaris* nitrate reductase 3' UTR is again indicated by lowercase underlined text followed by the STRAIN J 6S genomic region indicated by bold, lowercase text.

Relevant restriction sites in the construct pSZ2421 are the same as pSZ2422. In pSZ2421, the PmFATA1 is fused to the *Chlorella protothecoides* S106 stearoyl-ACP desaturase transit peptide and the transit peptide is located between initiator ATG of PmFATA1 and the Asc I site.

Nucleotide sequence of transforming DNA contained in pSZ2422

(SEQ ID NO: 93)

gctcttcgccgccgccactcctgctcgagcgcgcccgcgcgtgcgccgccagcgccttggccttttcgccgcgctcgtgcgcgtc gctgatgtccatcaccaggtccatgaggtctgccttgcgccggctgagccactgcttcgtccgggcggccaagaggagcatga gggaggactcctggtccagggtcctgacgtggtcgcggctctgggagcgggccagcatcatctggctctgccgcaccgaggc cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaacccccttgcgcgttagtgttgccatcctttgcagaccggtgag agccgacttgttgtgcgccacccccacaccacctcctcccagaccaattctgtcacctttttggcgaaggcatcggcctcggcc tgcagagaggacagcagtgcccagccgctggggttggcggatgcacgctcaggtaccctttcttgcgctatgacacttccagca aaaggtagggcgggctgcgagacggcttcccggcgctgcatgcaacaccgatgatgcttcgacccccgaagctccttcggggctg catgggcgctccgatgccgctccagggcgagcgctgtttaaatagccaggcccccgattgcaaagacattatagcgagctaccaaag ccatattcaaacacctagatcactaccacttctacacaggccactcgagcttgtgatcgcactccgctaagggggcgcctcttcctcttc gtttcagtcacaacccgcaaactctagaatatca*ATG**ctgctgcaggccttcctgttcctgctggccggcttcgccgccaagatcag*

*cgcctccatgacgaacgagacgtccgaccgccccctggtgcacttcacccccaacaagggctggatgaacgaccccaacggcc*

*tgtggtacgacgagaaggacgccaagtggcacctgtacttccagtacaacccgaacgacaccgtctgggggacgcccttgttctg*

*gggccacgccacgtccgacgacctgaccaactgggaggaccagcccatcgccatcgccccgaagcgcaacgactccggcgc*

*cttctccggctccatggtggtggactacaacaacacctccggcttcttcaacgacaccatcgacccgcgccagcgctgcgtggcca*

*tctggacctacaacaccccggagtccgaggagcagtacatctcctacagcctggacggcggctacaccttcaccgagtaccaga*

*agaaccccgtgctggccgccaactccacccagttccgcgacccgaaggtcttctggtacgagccctcccagaagtggatcatgac*

*cgcggccaagtcccaggactacaagatcgagatctactcctccgacgacctgaagtcctggaagctggagtccgcgttcgccaa*

*cgagggcttcctcggctaccagtacgagtgccccggcctgatcgaggtccccaccgagcaggaccccagcaagtcctactgggt*

*gatgttcatctccatcaaccccggcgccccggccggcggctccttcaaccagtacttcgtcggcagcttcaacggcacccacttcg*

*aggccttcgacaaccagtcccgcgtggtggacttcggcaaggactactacgccctgcagaccttcttcaacaccgacccgaccta*

*cgggagcgccctgggcatcgcgtgggcctccaactgggagtactccgccttcgtgcccaccaacccctggcgctcctccatgtccc*

*tcgtgcgcaagttctccctcaacaccgagtaccaggccaacccggagacggagctgatcaacctgaaggccgagccgatcctg*

*aacatcagcaacgccggcccctggagccggttcgccaccaacaccacgttgacgaaggccaacagctacaacgtcgacctgtc*

*caacagcaccggcaccctggagttcgagctggtgtacgccgtcaacaccacccagacgatctccaagtccgtgttcgcggacctc*

*tccctctggttcaagggcctggaggaccccgaggagtacctccgcatgggcttcgaggtgtccgcgtcctccttcttcctggaccgc*

*gggaacagcaaggtgaagttcgtgaaggagaacccctacttcaccaaccgcatgagcgtgaacaaccagcccttcaagagcg*

*agaacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcgac*

*aagttccaggtgcgcgaggtcaag**TGA*caattggcagcagcagctcggatagtatcgacacactctggacgctggtcgtgtgat ggactgttgccgccacacttgctgccttgacctgtgaatatccctgccgcttttatcaaacagcctcagtgtgtttgatcttgtgtgtacgcg cttttgcgagttgctagctgcttgtgctatttgcgaataccacccccagcatccccttccctcgtttcatatcgcttgcatcccaaccgcaac ttatctacgctgtcctgctatccctcagcgctgctcctgctcctgctcactgcccctcgcacagccttggtttgggctccgcctgtattctcc tggtactgcaacctgtaaaccagcactgcaatgctgatgcacgggaagtagtgggatgggaacacaaatggaggatcccgcgtctcg aacagagcgcgcagaggaacgctgaaggtctcgcctctgtcgcacctcagcgcggcatacaccacaataaccacctgacgaatgcg -continued cttggttcttcgtccattagcgaagcgtccggttcacacacgtgccacgttggcgaggtggcaggtgacaatgatcggtggagctgatg gtcgaaacgttcacagcctagggatatcgaattc*ggccgacaggacgcgcgtcaaaggtgctggtcgtgtatgccctggccggca*

*ggtcgttgctgctgctggttagtgattccgcaaccctgattttggcgtcttattttggcgtggcaaacgctggcgcccgcgagccggg*

*ccggcggcgatgcggtgccccacggctgccggaatccaagggaggcaagagcgcccgggtcagttgaagggctttacgcgca*

*aggtacagccgctcctgcaaggctgcgtggtggaattggacgtgcaggtcctgctgaagttcctccaccgcctcaccagcggaca*

*aagcaccggtgtatcaggtccgtgtcatccactctaaagaactcgactacgacctactgatggccctagattcttcatcaaaaacg*

*cctgagacacttgcccaggattgaaactccctgaagggaccaccaggggccctgagttgttccttccccccgtggcgagctgcca*

*gccaggctgtacctgtgatcgaggctggcgggaaaataggcttcgtgtgctcaggtcatgggaggtgcaggacagctcatgaaa*

*cgccaacaatcgcacaattcatgtcaagctaatcagctatttcctcttcacgagctgtaattgtcccaaaattctggtctaccggggg*

*tgatccttcgtgtacgggcccttccctcaaccctaggtatgcgcgcatgcggtcgccgcgcaactcgcgcgagggccgagggtttg*

*ggacgggccgtcccgaaatgcagttgcacccggatgcgtggcacctttttttgcgataatttatgcaatggactgctctgcaaaattct*

*ggctctgtcgccaaccctaggatcagcggcgtaggatttcgtaatcattcgtcctgatggggagctaccgactaccctaatatcagc*

*ccgactgcctgacgccagcgtccacttttgtgcacacattccattcgtgcccaagacatttcattgtggtgcgaagcgtccccagtta*

*cgctcacctgtttcccgacctccttactgttctgtcgacagagcgggcccacaggccggtcgcagcc*actagtATGgcccccac

*ctccctgctggcctccaccggcgtgtcctccgcctccctgtggtcctccgcccgctcctccgcctgcgccttccccgtggaccacgcc*

*gtgcgcggcgcccccagcgcccccctgcccatgcagcgccgctgcttccgcaccgtggccgtgcgcgggcgcgccgccgcccc*

*cgccgtggccgtgcgccccgagcccgcccaggagttctgggagcagctggagccctgcaagatggccgaggacaagcgcatc*

*ttcctggaggagcaccgcatccgcggcaacgaggtgggcccctcccagcgcctgaccatcaccgccgtggccaacatcctgca*

*ggaggccgccggcaaccacgccgtggccatgtggggccgctcctccgagggcttcgccaccgaccccgagctgcaggaggcc*

*ggcctgatcttcgtgatgacccgcatgcagatccagatgtaccgctacccccgctggggcgacctgatgcaggtggagacctggtt*

*ccagaccgccggcaagctgggcgcccagcgcgagtgggtgctgcgcgacaagctgaccggcgaggccctgggcgccgccac*

*ctcctcctgggtgatgatcaacatccgcacccgccgcccctgccgcatgcccgagctggtgcgcgtgaagtccgccttcttcgccc*

*gcgagcccccccgcctggccctgccccccgccgtgacccgcgccaagctgcccaacatcgccacccccgccccccctgcgcggc*

*caccgccaggtggcccgccgcaccgacatggacatgaacggccacgtgaacaacgtggcctacctggcctggtgcctggaggc*

*cgtgcccgagcacgtgttctccgactaccacctgtaccagatggagatcgacttcaaggccgagtgccacgccggcgacgtgatc*

*tcctcccaggccgagcagatcccccccaggaggccctgacccacaacggcgccggccgcaacccctcctgcttcgtgcactcc*

*atcctgcgcgccgagaccgagctggtgcgcgcccgcaccacctggtccgcccccatcgacgcccccgccgccaagcccccaa*

*ggcctcccacatggactacaaggaccacgacggcgactacaaggaccacgacatcgactacaaggacgacgacgacaagT*

*GAatcgatagatctcttaaggcagcagcagctcggatagtatcgacacactctggacgctggtcgtgtgatggactgttgccgccac acttgctgccttgacctgtgaatatccctgccgcttttatcaaacagcctcagtgtgtttgatcttgtgtgtacgcgcttttgcgagttgctag ctgcttgtgctatttgcgaataccacccccagcatccccttccctcgtttcatatcgcttgcatcccaaccgcaacttatctacgctgtcctg ctatccctcagcgctgctcctgctcctgctcactgcccctcgcacagccttggtttgggctccgcctgtattctcctggtactgcaacctgt -continued

```
aaaccagcactgcaatgctgatgcacgggaagtagtgggatgggaacacaaatggaaagcttaattaagagctcttgttttccagaa
ggagttgctccttgagcctttcattctcagcctcgataacctccaaagccgctctaattgtggaggggttcgaatttaaaagctt
ggaatgttggttcgtgcgtctggaacaagcccagacttgttgctcactgggaaaaggaccatcagctccaaaaaacttgccgc
tcaaaccgcgtacctctgetttcgcgcaatctgccctgttgaaatcgccaccacattcatattgtgacgcttgagcagtetgtaat
tgcctcagaatgtggaatcatctgcccctgtgcgagcccatgccaggcatgtcgcgggcgaggacacccgccactcgtacag
cagaccattatgctacctcacaatagttcataacagtgaccatatttctcgaagctccccaacgagcacctccatgctctgagtg
gccacccccggccctggtgcttgcggagggcaggtcaaccggcatggggctaccgaaatccccgaccggatcccaccacc
ccgcgatgggaagaatctctccccgggatgtgggcccaccaccagcacaacctgctggcccaggcgagcgtcaaaccatacc
acacaaatatccttggcatcggccctgaattccttctgccgctctgctacccggtgcttctgtccgaagcaggggttgctaggga
tcgctccgagtccgcaaacccttgtcgcgtggcggggcttgttcgagcttgaagagc
```

To determine the impact on fatty acid profiles when the endogenous FATA1 gene have been over expressed in STRAIN J, both the *P. moriformis* FATA1 with native transit peptide and PmFATA1 fused to a *Chlorella protothecoides* SAD transit peptide were driven by the amt03 promoter and the resulting plasmids were transformed independently into STRAIN J.

Primary transformants were clonally purified and grown under low-nitrogen lipid production conditions at pH7.0 (all the plasmids require growth at pH 7.0 to allow for maximal PmFATA1 gene expression when driven by the pH regulated amt03 promoter). The resulting profiles from representative clones arising from transformations with pSZ2422 and pSZ2421 into STRAIN J are shown in the tables below.

In Table 36, below, the impact of over expressing native PmFATA1 is a clear diminution of C18:1 chain lengths with an increase in C16:0, C14:0, and possibly in C18:0. Considering the protein localization of processing, we also tried the PmFATA1 fused to a *Chlorella protothecoides* stearoyl-ACP desaturase transit peptide. Similar to the results we observed in the amt03-native PmFATA1 construct, the C16:0 and C14:0 levels are significantly higher than the parental strain J.

TABLE 36

Fatty acid profiles in Strain J and derivative transgenic lines transformed with pSZ2422 DNA.

| Sample ID | C14:0 | C16:0 | C18:0 | C18:1 | C18:2 |
|---|---|---|---|---|---|
| pH 7; Strain J; T374; D1377-7 96well | 7.69 | 55.00 | 4.92 | 24.94 | 5.19 |
| pH 7; Strain J; T374; D1377-13 96well | 6.39 | 54.11 | 5.85 | 25.91 | 5.76 |
| pH 7; Strain J; T374; D1377-14 96well | 6.57 | 53.55 | 4.68 | 27.18 | 5.74 |
| pH 7; Strain J; T374; D1377-16 96well | 5.29 | 49.93 | 4.24 | 30.76 | 7.27 |
| pH 7; Strain J; T374; D1377-9 96well | 4.76 | 49.10 | 4.75 | 32.36 | 6.77 |
| pH 7; Strain J; T374; D1377-19 96well | 4.28 | 46.06 | 5.14 | 35.87 | 6.69 |
| Ctrl-pH 7; Strain J | 1.42 | 27.63 | 3.31 | 57.20 | 8.00 |

TABLE 37

Fatty acid profiles in STRAIN J and derivative transgenic lines transformed with pSZ2421 DNA.

| Sample ID | C14:0 | C16:0 | C18:0 | C18:1 | C18:2 |
|---|---|---|---|---|---|
| pH 7; STRAIN J; T374; D1376-21 96well | 6.76 | 57.06 | 4.12 | 23.66 | 6.07 |
| pH 7; STRAIN J; T374; D1376-22 96well | 6.56 | 54.62 | 5.44 | 25.69 | 5.64 |
| pH 7; STRAIN J; T374; D1376-23 96well | 4.54 | 48.38 | 4.27 | 33.23 | 7.24 |
| pH 7; STRAIN J; T374; D1376-19 96well | 4.48 | 47.66 | 4.60 | 34.28 | 6.91 |
| pH 7; STRAIN J; T374; D1376-20 96well | 4.53 | 47.30 | 4.67 | 34.51 | 6.80 |
| pH 7; STRAIN J; T374; D1376-17 96well | 3.56 | 42.70 | 4.03 | 39.85 | 7.52 |
| Ctrl-pH 7; STRAIN J | 1.42 | 27.63 | 3.31 | 57.20 | 8.00 |

Thus, we conclude that percent myristic and lauric acid levels in the fatty acid profile of a microalgal cell can be increased by overexpression of a C18-preferring acyl-ACP thioesterase.

Example 46: Cell Oils Suitable for Use as Roll-In Shortenings

The nutritional and functional properties of edible fats have been traditionally associated with specific chemical compositions and crystallization conditions. Switching from one oil source to another is usually a difficult task since both the melting behavior and structure of the fat changes dramatically, leading to adverse changes in functionality. In recent history, we can recall the painful period when partially hydrogenated fats were replaced with palm oil and palm oil fractions. We examined how the yield stress, elastic modulus, polymorphism, microstructure and melting profile of two fats with vastly different chemical compositions can be matched. Oil A was produced from *Prototheca moriformis* cells expressing an exogenous invertase and an *Ulmus americana* acyl-ACP thioesterase with a *Chlorella protothecoides* plastid targeting sequence. Oil B was produced from *Prototheca moriformis* cells expressing an exogenous invertase and a *Cuphea hookeriana* acyl-ACP thioesterase. Oil A contained greater than 62% (w/w) medium chain fatty acids, or MCT (C8:0-C14:0), 23% (C16:0+C18:0) and 9% C18:1, while Oil B contained less than 2% C8:0-C14:0, 54% (C16:0+C18:0) and 29% C18:1. Oil A was thus a medium chain triglyceride rich fat, while Oil B resembled palm oil. Both oils had a solid fat content of ~45% at 20° C., and very similar SFC versus temperature profiles. DSC (dynamic scanning calorimetry) melting profiles showed two major peaks centered around ~12-13° C. and ~28-35° C. Both fats were in the beta-prime polymorphic form (as determined by X-ray diffraction) and displayed asymmetric, elongated crystallite morphology with characteristic features. The yield stresses and storage moduli (G') of Oil A and Oil B were 520-550 Pa, and $7\times10^6$ Pa-$1.8\times10^7$ Pa, respectively. A yield stress in this region suggests a satisfactory plasticity, which combined with a high storage modulus makes for an ideal roll-in shortening. Thus, it is possible to alter the chemical composition of a food oil while retaining its lamination functionality.

Other suitable enzymes for use with the cells and methods of any of the above embodiments of the invention include those that have at least 70% amino acid identity with one of the proteins listed in the description above and that exhibit the corresponding desired enzymatic activity. In additional embodiments, the enzymatic activity is present in a sequence that has at least about 75%, at least about 80%, at least about 85%, at least about 90%, at least about 95%, or at least about 99% identity with one of the above described nucleic acid sequences, all of which are hereby incorporated by reference as if fully set forth.

Example 47: Fractionation to Remove Trisaturates from a Tailored Microbial Oil that is a Cocoa Butter Mimetic A refined bleached and deodorized oil was obtained from Strain K4 (see Example 35). The oil was heated to 70° C. and cooled at 0.5° C. per min to 36° C. and held at 36° C. for 1 hour. An approximately 2.5 ml sample was then centrifuged at 36° C. for 1 hour at 4300. A liquid supernatant was recovered and analyzed using lipase and mass spectrometry. The sample was found to be depleted in tristearin (SSS), SSP, and PPS. The triacylglycerols of the sample were found to be very similar to that of cocoa butter and the liquid supernatant was even closer to that of cocoa butter in terms of low amounts of trisaturates. Further fractionation experiments are described in Example 64.

TABLE 38

TAG profile of oil from the K4 strain before and after fractionation as compared to cocoa butter.

| TAG | K4 oil | fractionation upper layer (liquid) | cocoa butter |
|---|---|---|---|
| OOL (+?) | 0.12 | 0.12 | 0.00 |
| POL | 0.23 | 0.31 | 0.33 |
| PLP | 2.41 | 3.38 | 1.58 |
| MOP | 0.93 | 1.25 | 0.00 |
| PPM (+MMS) | 0.42 | 0.29 | 0.00 |
| OOO | 0.23 | 0.34 | 0.00 |
| SOL | 0.36 | 0.47 | 0.32 |
| OOP | 0.95 | 1.42 | 2.44 |
| PLS | 5.66 | 7.90 | 2.90 |
| POP (+MSO) | 11.80 | 15.20 | 17.93 |
| PPP + MPS | 2.22 | 1.07 | 0.36 |
| OOS | 1.19 | 1.68 | 3.02 |
| SLS (+PLA) | 3.96 | 5.11 | 1.77 |
| POS | 27.22 | 32.80 | 40.25 |
| PPS (+SSM) | 6.47 | 1.52 | 0.49 |
| MaOO | 0.00 | 0.00 | 0.36 |
| SLA | 0.31 | 0.34 | 0.00 |
| SOS (+POA) | 17.84 | 22.50 | 24.93 |

TABLE 38-continued

TAG profile of oil from the K4 strain before and after fractionation as compared to cocoa butter.

| TAG | K4 oil | fractionation upper layer (liquid) | cocoa butter |
|---|---|---|---|
| SSP (+PPA) | 9.24 | 0.96 | 0.63 |
| SOA (+POB) | 1.39 | 1.68 | 1.51 |
| SSS (+PSA) | 5.25 | 0.23 | 0.33 |
| SOB + LgOP | 0.38 | 0.44 | 0.27 |
| SSA | 0.41 | 0.00 | 0.00 |
| SOLg | 0.41 | 0.00 | 0.00 |
| PSLg + ASB | 0.26 | 0.00 | 0.00 |
| SOHx | 0.12 | 0.51 | 0.00 |
| SSLg | 0.21 | 0.14 | 0.15 |
| SUM area % | 100.00 | 99.67 | 99.57 |

Example 48: Production of High-Stearate Triglyceride Oil in an Oleaginous Cell by Overexpression of KASII, Knockout of One Sad Allele and Repression of a Second Sad Allele The oleaginous, non-photosynthetic alga, *Prototheca moriformis*, stores copious amounts of triacylglyceride oil under conditions where the nutritional carbon supply is in excess, but cell division is inhibited due to limitation of other essential nutrients. Bulk biosynthesis of fatty acids with carbon chain lengths up to C18 occurs in the plastids; fatty acids are then exported to the endoplasmic reticulum where elongation past C18 and incorporation into triacylglycerides (TAGs) is believed to occur. Lipids are stored in large cytoplasmic organelles called lipid bodies until environmental conditions change to favor growth, whereupon they are rapidly mobilized to provide energy and carbon molecules for anabolic metabolism. Wild-type *P. moriformis* storage lipid is mainly comprised of ~60% oleic (C18:1), ~25-30% palmitic (C16:0), and ~5-8% linoleic (C18:2) acids, with minor amounts of stearic (C18:0), myristic (C14:0), α-linolenic (C18:3 α), and palmitoleic (C16:1) acids. This fatty acid profile results from the relative activities and substrate affinities of the enzymes of the endogenous fatty acid biosynthetic pathway. *P. moriformis* is amenable to manipulation of fatty acid and lipid biosynthesis using molecular genetic tools, enabling the production of oils with fatty acid profiles that are very different to the wild-type composition. Herein we describe strains where we have modified the expression of stearoyl-ACP desaturase (SAD) and β-ketoacyl-ACP synthase II (KASII) genes in order to generate strains with up to 57% stearate and as little as 7% palmitate. We identify additional strains with up to 55% stearate and as low as 2.4% linoleate when we perform similar modifications in conjunction with down-regulating the expression of the FATA thioesterase and the FAD2 fatty acid desaturase genes.

Soluble SADs are plastid-localized, di-iron enzymes which catalyze the desaturation of acyl carrier protein (ACP)-bound stearate to oleate (C18:1 cis-$\Delta^9$). Previously, we have established that hairpin constructs targeting the SAD1 or SAD2 transcripts activate the cellular RNA interference (RNAi) machinery, down-regulating SAD activity and resulting in elevated levels of C18:0 in the storage lipid. SAD activity is also reduced in strains where we disrupt one of the two alleles of SAD2, encoding the major SADs that are expressed during storage lipid biosynthesis. The Fatty Acid Desaturase 2 (FAD2) gene encodes an endoplasmic reticulum membrane-associated desaturase that converts oleate to linoleate (C18:2 cis-$\Delta^9$, cis-$\Delta^{12}$). Hairpin RNAi constructs targeting FAD2 reduce linoleate levels to 1-2%. KASII is a fatty acid synthase which specifically catalyzes the condensation of malonyl-ACP with palmitoyl (C16:0)-ACP to form β-keto-stearoyl-ACP. We have shown that overexpression of KASII in *P. moriformis* causes C16:0 levels to decrease with a concomitant increase in C18:1 abundance. In the examples below we demonstrate that by down-regulating SAD gene expression using RNAi, disrupting an allele of the SAD2 gene, and overexpressing the KASII fatty acid synthase, we generate strains capable of accumulating stearate in excess of 50% of the total fatty acids, and with SOS as the major TAG species. SOS levels increase up to 47% in strains which combine SAD2 and FAD2 down-regulation with KASII overexpression.

Constructs Used for SAD2 Knockout/RNAi in S1920:

A DNA construct, pSZ2282, was made to simultaneously disrupt the SAD2-1 allele and express a SAD2 hairpin construct in Strain J. A *Saccharomyces cerevisiae* SUC2 gene, encoding sucrose invertase, which was codon-optimized for expression in *P. moriformis*, was utilized as a selectable marker for transformation. The sequence of the transforming DNA is provided immediately below. Relevant restriction sites are indicated in lowercase, bold, and are from 5'-3' BspQI, KpnI, AscI, MfeI, BamHI, AvrII, EcoRV, EcoRI, SpeI, BamHI, HinDIII, and SacI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlamydomonas reinhardtii* TUB2 promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The 3' UTR of the *Chlorella vulgaris* nitrate reductase (NR) gene is indicated by small capitals, followed by a spacer region indicated by lowercase text. A second *C. reinhardtii* TUB2 promoter sequence, indicated by lowercase boxed text, drives expression of the SAD2 hairpin *C* sequence. The sense and antisense strands are indicated with uppercase, bold italics, and are separated by the *P. moriformis* $\Delta^{12}$-fatty acid desaturase (FAD2) intron and the first 10 bases of the FAD2 second exon (uppercase italics). A second *C. vulgaris* NR 3' UTR is indicated by small capitals.

Nucleotide sequence of the transforming DNA from pSZ2282:

(SEQ ID NO: 94)

gctcttcgggtcgccgcgctgcctcgcgtcccctggtggtgcgcgcggtcgccagcgaggccccgctgggcgttccgccctcggtgca gcgcccctcccccgtggtctactccaagctggacaagcagcaccgcctgacgcccgagcgcctggagctggtgcagagcatggggc agtttgcggaggagagggtgctgcccgtgctgcaccccgtggacaagctgtggcagccgcaggacttttgcccgaccccgagtcgc ccgacttcgaggatcaggtggcggagctgcgcgcgcgcgccaaggacctgcccgacgagtactttgtggtgctggtgggggacatg atcacggaggaggcgctgccgacctacatggccatgctcaacacgctggacggcgtgcgcgacgacacgggcgcggccgaccacc cgtgggcgcgctggacgcggcagtgggtggccgaggagaaccggcacggcgacctgctgaacaagtactgctggctgacggggc gcgtcaacatgcgggccgtggaggtgaccatcaacaacctgatcaagagcggcatgaacccgcagacggacaacaacccttattt ggggttcgtctacacctccttccaggagcgcgccaccaagtaggtaccctttcttgcgctatgacacttccagcaaaaggtagggcg ggctgcgagacggcttcccggcgctgcatgcaacaccgatgatgcttcgacccccgaagctccttcggggctgcatgggcgctccg atgccgctccagggcgagcgctgtttaaatagccaggcccccgattgcaaagacattatagcgagctaccaaagccatattcaaac acctagatcactaccacttctacacaggccactcgagcttgtgatcgcactccgctaagggggcgcctcttcctcttcgtttcagtcac aacccgcaaacggcgcgcc*ATGctgctgcaggccttcctgttcctgctggccggcttcgccgccaagatcagcgcctccatgac*

*gaacgagacgtccgaccgccccctggtgcacttcacccccaacaagggctggatgaacgaccccaacggcctgtggtacgac*

*gagaaggacgccaagtggcacctgtacttccagtacaacccgaacgacaccgtctgggggacgcccttgttctggggccacg*

*ccacgtccgacgacctgaccaactgggaggaccagcccatcgccatcgccccgaagcgcaacgactccggcgccttctccggc*

*tccatggtggtggactacaacaacacctccggcttcttcaacgacaccatcgacccgcgccagcgctgcgtggccatctggacc*

*tacaacaccccggagtccgaggagcagtacatctcctacagcctggacggcggctacaccttcaccgagtaccagaagaacc*

*ccgtgctggccgccaactccacccagttccgcgacccgaaggtcttctggtacgagccctcccagaagtggatcatgaccgcgg*

*ccaagtcccaggactacaagatcgagatctactcctccgacgacctgaagtcctggaagctggagtccgcgttcgccaacgag*

*ggcttcctcggctaccagtacgagtgccccggcctgatcgaggtccccaccgagcaggaccccagcaagtcctactgggtgat*

*gttcatctccatcaaccccggcgccccggccggcggctccttcaaccagtacttcgtcggcagcttcaacggcacccacttcgag*

*gccttcgacaaccagtcccgcgtggtggacttcggcaaggactactacgccctgcagaccttcttcaacaccgacccgacctac*

-continued gggagcgccctgggcatcgcgtgggcctccaactgggagtactccgccttcgtgcccaccaaccccctggcgctcctccatgtccc tcgtgcgcaagttctccctcaacaccgagtaccaggccaacccggagacggagctgatcaacctgaaggccgagccgatcct gaacatcagcaacgccggccccctggagccggttcgccaccaacaccacgttgacgaaggccaacagctacaacgtcgacctg tccaacagcaccggcaccctggagttcgagctggtgtacgccgtcaacaccacccagacgatctccaagtccgtgttcgcgga cctctccctctggttcaagggcctggaggaccccgaggagtacctccgcatgggcttcgaggtgtccgcgtcctccttcttcctgg accgcgggaacagcaaggtgaagttcgtgaaggagaacccctacttcaccaaccgcatgagcgtgaacaaccagcccttca agagcgagaacgacctgtcctactacaaggtgtacggcttgctggaccagaacatcctggagctgtacttcaacgacggcga cgtcgtgtccaccaacacctacttcatgaccaccgggaacgccctgggctccgtgaacatgacgacgggggtggacaacctgt tctacatcgacaagttccaggtgcgcgaggtcaagTGAcaattgGCAGCAGCAGCTCGGATAGTATCGACACACTCTGGAC GCTGGTCGTGTGATGGACTGTTGCCGCCACACTTGCTGCCTTGACCTGTGAATATCCCTGCCGCTTTTATCAAACAGCCTCA GTGTGTTTGATCTTGTGTGTACGCGCTTTTGCGAGTTGCTAGCTGCTTGTGCTATTTGCGAATACCACCCCCAGCATCCCCT TCCCTCGTTTCATATCGCTTGCATCCCAACCGCAACTTATCTACGCTGTCCTGCTATCCCTCAGCGCTGCTCCTGCTCCTGCT CACTGCCCCTCGCACAGCCTTGGTTTGGGCTCCGCCTGTATTCTCCTGGTACTGCAACCTGTAAACCAGCACTGCAATGCT GATGCACGGGAAGTAGTGGGATGGGAACACAAATGGAggatcccgcgtctcgaacagagcgcgcagaggaacgctgaaggt ctcgcctctgtcgcacctcagcgcggcatacaccacaataaccacctgacgaatgcgcttggttcttcgtccattagcgaagcgtccg gttcacacacgtgccacgttggcgaggtggcaggtgacaatgatcggtggagctgatggtcgaaacgttcacagcctagggatatc gaattcctttcttgcgctatgacacttccagcaaaaggtagggcgggctgcgagacggcttcccggcgctgcatgcaacaccgatga tgcttcgacccccccgaagctccttcggggctgcatgggcgctccgatgccgctccagggcgagcgctgtttaaatagccaggcccccc gattgcaaagacattatagcgagctaccaaagccatattcaaacacctagatcactaccacttctacacaggccactcgagcttgtg atcgcactccgctaagggggcgcctcttcctcttcgtttcagtcacaacccgcaaacactagtGCGCTGGACGCGGCAGTG

GGTGGCCGAGGAGAACCGGCACGGCGACCTGCTGAACAAGTACTGTTGGCTGACGGGGCGCGTC

AACATGCGGGCCGTGGAGGTGACCATCAACAACCTGATCAAGAGCGGCATGAACCCGCAGACGG

ACAACAACCCTTACTTGGGCTTCGTCTACACCTCCTTCCAGGAGCGCGACCAAGTACAGCCACGG

CAACACCGCGCGCCTTGCGGCCGAGCAGTGTGTTTGAGGGTTTTGGTTGCCCGTATCGAGGTCCTGG

TGGCGCGCATGGGGGAGAGAAGGCGCCTGTCCCGCTGACCCCCCCGGCTACCCTCCCGGCACCTTCCAG

GGCGCGTACGggatccTGCTCGGCCGCAAGGCGCGCGGTGTTGCCGTGGCTGTACTTGGTCGCGCGC

TCCTGGAAGGAGGTGTAGACGAAGCCCAAGTAAGGGTTGTTGTCCGTCTGCGGGTTCATGCCGCT

CTTGATCAGGTTGTTGATGGTCACCTCCACGGCCCGCATGTTGACGCGCCCCGTCAGCCAACAGTAC

TTGTTCAGCAGGTCGCCGTGCCGGTTCTCCTCGGCCACCCACTGCCGCGTCCAGCGCaagcttGCAGCAG

CAGCTCGGATAGTATCGACACACTCTGGACGCTGGTCGTGTGATGGACTGTTGCCGCCACACTTGCTGCCTTGACCTGTGA

ATATCCCTGCCGCTTTTATCAAACAGCCTCAGTGTGTTTGATCTTGTGTGTACGCGCTTTTGCGAGTTGCTAGCTGCTTGTG

CTATTTGCGAATACCACCCCCAGCATCCCCTTCCCTCGTTTCATATCGCTTGCATCCCAACCGCAACTTATCTACGCTGTCCT

GCTATCCCTCAGCGCTGCTCCTGCTCCTGCTCACTGCCCCTCGCACAGCCTTGGTTTGGGCTCCGCCTGTATTCTCCTGGTA

CTGCAACCTGTAAACCAGCACTGCAATGCTGATGCACGGGAAGTAGTGGGATGGGAACACAAATGGAAAGCTGgagctc cagccacggcaacaccgcgcgccttgcggccgagcacggcgacaagaacctgagcaagatctgcgggctgatcgccagcgacga gggccggcacgagatcgcctacacgcgcatcgtggacgagttcttccgcctcgaccccgagggcgccgtcgccgcctacgccaaca tgatgcgcaagcagatcaccatgcccgcgcacctcatggacgacatgggccacggcgaggccaacccgggccgcaacctcttcgc cgacttctccgcggtcgccgagaagatcgacgtctacgacgccgaggactactgccgcatcctggagcacctcaacgcgcgctgga -continued aggtggacgagcgccaggtcagcggccaggccgccgcggaccaggagtacgtcctgggcctgcccagcgcttccggaaactcgc cgagaagaccgccgccaagcgcaagcgcgtcgcgcgcaggcccgtcgccttctcctggatctccgggcgcgagatcatggtctagg gagcgacgagtgtgcgtgcggggctggcgggagtgggacgccctcctcgctcctctctgttctgaacggaacaatcggccaccccg cgctacgcgccacgcatcgagcaacgaagaaaaccccccgatgataggttgcggtggctgccgggatatagatccggccgcacat caaagggccctccgccagagaagaagctcctttcccagcagactcctgaagagc

Identification and Analysis of SAD2 Knockout/Knockdown Strains:

Construct D1283, derived from pSZ2282, was transformed into Strain J. Primary transformants were clonally purified and grown under standard lipid production conditions at pH 5. The resulting fatty acid profiles from representative clones arising from transformation with pSZ2282 into Strain J are summarized in Table 39, below. D1283 transformants accumulated up to ~42% C18:0 at the expense of C18:1, indicating that SAD activity was significantly reduced in these strains.

TABLE 39

Fatty acid profiles of D1283 [pSZ2282] primary transformants, compared to the wild-type parental strain, Strain J.

| Strain | | J | D1283-4 | D1283-7 | D1283-19 | D1283-27 | D1283-40 | D1283-24 |
|---|---|---|---|---|---|---|---|---|
| Fatty | C12:0 | 0.04 | 0.05 | 0.06 | 0.07 | 0.06 | 0.04 | 0.05 |
| Acid | C14:0 | 1.31 | 0.92 | 1.07 | 1.01 | 1.08 | 1.03 | 0.96 |
| Area % | C16:0 | 26.68 | 28.23 | 29.21 | 27.24 | 27.67 | 27.02 | 27.07 |
| | C16:1 | 0.78 | 0.05 | 0.06 | 0.08 | 0.33 | 0.14 | 0.12 |
| | C17:0 | 0.11 | 0.12 | 0.15 | 0.10 | 0.10 | 0.12 | 0.13 |
| | C18:0 | 3.15 | **41.98** | **40.94** | **34.20** | **26.26** | **23.18** | **22.82** |
| | C18:1 | 59.30 | 19.37 | 18.17 | 26.87 | 34.77 | 38.74 | 39.38 |
| | C18:2 | 7.47 | 6.22 | 7.43 | 7.42 | 7.31 | 7.25 | 7.38 |
| | C18:3α | 0.57 | 0.93 | 1.03 | 0.75 | 0.71 | 0.72 | 0.51 |
| | C20:0 | 0.32 | 1.81 | 1.67 | 1.75 | 1.35 | 1.36 | 1.23 |
| | C20:1 | 0.00 | 0.10 | 0.00 | 0.12 | 0.00 | 0.12 | 0.11 |
| | C22:0 | 0.05 | 0.17 | 0.13 | 0.20 | 0.16 | 0.16 | 0.15 |
| | C24:0 | 0.00 | 0.00 | 0.00 | 0.10 | 0.00 | 0.00 | 0.00 |
| sum C18 | | 70.49 | 68.5 | 67.57 | 69.24 | 69.05 | 69.89 | 70.09 |
| saturates | | 31.66 | 73.28 | 73.23 | 64.67 | 56.68 | 52.91 | 52.41 |
| unsaturates | | 68.12 | 26.67 | 26.69 | 35.24 | 43.12 | 46.97 | 47.50 |

In Table 39, Stearate (C18:0) levels greater than the wild-type level are highlighted with bold text.

The fatty acid profiles of transformants D1283-4 and -7 were determined to be stable after more than 30 generations of growth in the absence of selection (growth on sucrose). The performance of selected strains in shake flask assays was then evaluated, and the fatty acid profiles and lipid titers are presented in Table 40, below. Strain X had the highest level of C18:0 (~44%) and the best lipid titer (~26%) relative to the Strain J parent, and so was selected for further fermentation development.

TABLE 40

Fatty acid profiles and lipid titers of SAD2 knockout/knockdown strains derived from D1283 primary transformants, compared to the wild-type parental strain, Strain J.

| | | | | Primary | | | |
|---|---|---|---|---|---|---|---|
| | | | T342; D1283-4 | | | T342; D1283-7 | |
| Strain | | J | S | T | U | V | W | X |

| | | J | S | T | U | V | W | X |
|---|---|---|---|---|---|---|---|---|
| Fatty | C14:0 | 1.59 | 1.61 | 1.58 | 1.55 | 1.81 | 1.84 | 1.34 |
| Acid | C16:0 | 30.47 | 29.41 | 28.58 | 29.24 | 28.77 | 29.09 | 28.47 |

TABLE 40-continued

Fatty acid profiles and lipid titers of SAD2 knockout/knockdown strains derived from D1283 primary transformants, compared to the wild-type parental strain, Strain J.

| | | | | Primary | | | |
|---|---|---|---|---|---|---|---|
| | | | T342; D1283-4 | | | T342; D1283-7 | |
| Strain | | J | S | T | U | V | W | X |
| Area % | C16:1 | 0.82 | 0.05 | 0.07 | 0.05 | 0.07 | 0.05 | 0.06 |
| | C17:0 | 0.10 | 0.30 | 0.29 | 0.28 | 0.46 | 0.37 | 0.19 |
| | C18:0 | 3.58 | **42.85** | **41.86** | **43.38** | **39.99** | **41.41** | **44.42** |
| | C18:1 | 56.96 | 13.52 | 15.55 | 13.49 | 13.57 | 12.98 | 15.64 |
| | C18:2 | 5.50 | 8.01 | 7.85 | 7.65 | 10.37 | 9.47 | 5.72 |
| | C18:3α | 0.37 | 0.78 | 0.73 | 0.82 | 0.95 | 0.91 | 0.64 |
| | C20:0 | 0.22 | 2.06 | 2.11 | 2.11 | 1.98 | 1.98 | 2.32 |
| | C22:0 | 0.05 | 0.32 | 0.34 | 0.33 | 0.33 | 0.32 | 0.35 |
| | C24:0 | 0.03 | 0.43 | 0.42 | 0.44 | 0.49 | 0.49 | 0.37 |
| lipid titer (% parent) | | 100 | 12.3 | 12.6 | 13.6 | 6.2 | 8.2 | 25.9 |

In Table 40, Stearate (C18:0) levels greater than the wild-type level are highlighted with bold text.

We optimized the performance of Strain X in 7-L fermentations, and found that we could match the ~44% C18:0 level obtained in shake flasks, with lipid productivities that were ~45% of the wild-type parent. The fatty acid profiles and lipid titers of representative strain K-4 fermentations are summarized in Table 41, below. Fermentation of Strain X under optimal conditions yielded nearly 44% C18:0, which was similar to the stearate level that accumulated in shake flask assays. Strain X produced high C18:0 levels at both flask and 7-L scale and had acceptable lipid productivity in 7-L fermentations; consequently this strain was selected as a base strain for additional modifications aimed at increasing C18:0 accumulation.

TABLE 41

Fatty acid profiles and lipid titers of Strain X, compared to a control transgenic Strain Y.

| | | Strain | | | |
|---|---|---|---|---|---|
| | | Y | K-4 | K-4 | K-4 |
| | | Fermentation | | | |
| | | 110088F14 | 120489F5 | 120531F8 | 120580F1 |
| Fatty Acid Area % | C14:0 | 1.47 | 1.18 | 1.15 | 1.27 |
| | C16:0 | 25.66 | 28.68 | 28.38 | 28.35 |
| | C16:1 | 0.71 | 0.11 | 0.09 | 0.06 |
| | C18:0 | 3.16 | **41.63** | **42.40** | **43.67** |
| | C18:1 | 62.24 | 20.78 | 19.38 | 17.63 |
| | C18:2 | 5.90 | 5.06 | 5.38 | 5.58 |
| | C18:3α | 0.16 | 0.24 | 0.25 | 0.25 |
| | C20:0 | 0.24 | 1.36 | 1.99 | 2.11 |
| | C22:0 | 0.05 | 0.19 | 0.28 | 0.31 |
| | C24:0 | 0.05 | 0.34 | 0.29 | 0.31 |
| | sum C18 | 71.46 | 67.71 | 67.41 | 67.13 |
| | saturates | 30.63 | 73.38 | 74.49 | 76.02 |
| | unsaturates | 69.01 | 26.19 | 25.10 | 23.52 |
| | total lipid (g/L) | 930 | 383 | 539 | 475 |

In Table 41, Stearate (C18:0) levels greater than the control are highlighted with bold text. Strain Y contains *S. cerevisiae* SUC2, encoding sucrose invertase, integrated at the 6S locus, and has a fatty acid profile that is indistinguishable from the Strain J wild-type parent.

Constructs Used for KASII Overexpression in Strain K-4:

DNA construct pSZ2734 was made to overexpress a codon-optimized *P. moriformis* KASII gene in Strain X. The neoR gene from transposon Tn5, conferring resistance to aminoglycoside antibiotics, was used as a selectable marker for transformation. The sequence of the transforming DNA is provided immediately below. Relevant restriction sites are indicated in lowercase, bold, and are from 5'-3' BspQI, KpnI, XbaI, MfeI, BamHI, AvrII, EcoRV, SpeI, AscI, ClaI, BglII, AflII, HinDIII and SacI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the 6S locus. Proceeding in the 5' to 3' direction, the *C. reinhardtii* TUB2 promoter driving the expression of neoR (encoding aminoglycoside phosphotransferase activity, thereby permitting the strain to grow on G418) is indicated by lowercase, boxed text. The initiator ATG and terminator TGA for neoR are indicated by uppercase italics, while the coding region is indicated with lowercase italics. The 3' UTR of the *C. vulgaris* NR gene is indicated by small capitals, followed by a spacer region indicated by lowercase text. The *P. moriformis* SAD2-2 promoter sequence, indicated by boxed text, drives expression of the codon-optimized *P. moriformis* KASII gene. The region encoding the KASII plastid targeting sequence is indicated by uppercase italics. The sequence that encodes the mature *P. moriformis* KASII polypeptide is indicated with bold, uppercase italics, while a 3× FLAG epitope encoding sequence is in bold, underlined, uppercase italics. A second *C. vulgaris* NR3' UTR is indicated by small capitals.

Nucleotide sequence of the transforming DNA from pSZ2734:

(SEQ ID NO: 95)

gctcttcgccgccgccactcctgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggagg actcctggtccagggtcctgacgtggtcgcggctctgggagcgggccagcatcatctggctctgccgcaccgaggccgcctccaact ggtcctccagcagccgcagtcgccgccgaccctggcagaggaagacaggtgaggggtgtatgaattgtacagaacaaccacgagc cttgtctaggcagaatccctaccagtcatggctttacctggatgacggcctgcgaacagctgtccagcgaccctcgctgccgccgctt ctcccgcacgcttctttccagcaccgtgatggcgcgagccagcgccgcacgctggcgctgcgcttcgccgatctgaggacagtcggg gaactctgatcagtctaaacccccttgcgcgttagtgttgccatcctttgcagaccggtgagagccgacttgttgtgcgccaccccca caccacctcctcccagaccaattctgtcacctttttggcgaaggcatcggcctcggcctgcagagaggacagcagtgcccagccgct gggggttggcggatgcacgctcaggtaccctttcttgcgctatgacacttccagcaaaaggtagggcgggctgcgagacggcttccc ggcgctgcatgcaacaccgatgatgcttcgacccccgaagctccttcggggctgcatgggcgctccgatgccgctccagggcgag cgctgtttaaatagccaggcccccgattgcaaagacattatagcgagctaccaaagccatattcaaacacctagatcactaccactt ctacacaggccactcgagcttgtgatcgcactccgctaagggggcgcctcttcctcttcgtttcagtcacaacccgcaaactctagaa tatca*ATGatcgagcaggacggcctccacgccggctcccccgccgcctgggtggagcgcctgttcggctacgactgggcccag*

*cagaccatcggctgctccgacgccgccgtgttccgcctgtccgcccagggccgccccgtgctgttcgtgaagaccgacctgtccg*

*gcgccctgaacgagctgcaggacgaggccgcccgcctgtcctggctggccaccaccggcgtgccctgcgccgccgtgctggac*

-continued

*gtggtgaccgaggccggccgcgactggctgctgctgggcgaggtgcccggccaggacctgctgtcctcccacctggcccccgc*

*cgagaaggtgtccatcatggccgacgccatgcgccgcctgcacaccctggaccccgccacctgccccttcgaccaccaggcca*

*agcaccgcatcgagcgcgcccgcacccgcatggaggccggcctggtggaccaggacgacctggacgaggagcaccagggc*

*ctggcccccgccgagctgttcgcccgcctgaaggcccgcatgcccgacggcgaggacctggtggtgacccacggcgacgcctg*

*cctgcccaacatcatggtggagaacggccgcttctccggcttcatcgactgcggccgcctgggcgtggccgaccgctaccagg*

*acatcgccctggccacccgcgacatcgccgaggagctgggcggcgagtgggccgaccgcttcctggtgctgtacggcatcgcc*

*gcccccgactcccagcgcatcgccttctaccgcctgctggacgagttcttcTGA*caattgGCAGCAGCAGCTCGGATAG

TATCGACACACTCTGGACGCTGGTCGTGTGATGGACTGTTGCCGCCACACTTGCTGCCTTGACCTGT

GAATATCCCTGCCGCTTTTATCAAACAGCCTCAGTGTGTTTGATCTTGTGTGTACGCGCTTTTGCGAG

TTGCTAGCTGCTTGTGCTATTTGCGAATACCACCCCCAGCATCCCCTTCCCTCGTTTCATATCGCTTGC

ATCCCAACCGCAACTTATCTACGCTGTCCTGCTATCCCTCAGCGCTGCTCCTGCTCCTGCTCACTGCCC

CTCGCACAGCCTTGGTTTGGGCTCCGCCTGTATTCTCCTGGTACTGCAACCTGTAAACCAGCACTGCA

ATGCTGATGCACGGGAAGTAGTGGGATGGGAACACAAATGGAggatcccgcgtctcgaacagagcgcgcaga ggaacgctgaaggtctcgcctctgtcgcacctcagcgcggcatacaccacaataaccacctgacgaatgcgcttggttcttcgtccat tagcgaagcgtccggttcacacacgtgccacgttggcgaggtggcaggtgacaatgatcggtggagctgatggtcgaaacgttcac agcctagggatatcCTGAAGAATGGGAGGCAGGTGTTGTTGATTATGAGTGTGTAAAAGAAAGGGGTA

GAGAGCCGTCCTCAGATCCGACTACTATGCAGGTAGCCGCTCGCCCATGCCCGCCTGGCTGAATATT

GATGCATGCCCATCAAGGCAGGCAGGCATTTCTGTGCACGCACCAAGCCCACAATCTTCCACAACAC

ACAGCATGTACCAACGCACGCGTAAAAGTTGGGGTGCTGCCAGTGCGTCATGCCAGGCATGATGTG

CTCCTGCACATCCGCCATGATCTCCTCCATCGTCTCGGGTGTTTCCGGCGCCTGGTCCGGGAGCCGTT

CCGCCAGATACCCAGACGCCACCTCCGACCTCACGGGGTACTTTTCGAGCGTCTGCCGGTAGTCGAC

GATCGCGTCCACCATGGAGTAGCCGAGGCGCCGGAACTGGCGTGACGGAGGAGGAGAGGGAGG

AGAGAGAGGGGGGGGGGGGGGGGGATGATTACACGCCAGTCTCACAACGCATGCAAGACCCGT

TTGATTATGAGTACAATCATGCACTACTAGATGGATGAGCGCCAGGCATAAGGCACACCGACGTTG

ATGGCATGAGCAACTCCCGCATCATATTTCCTATTGTCCTCACGCCAAGCCGGTCACCATCCGCATGC

TCATATTACAGCGCACGCACCGCTTCGTGATCCACCGGGTGAACGTAGTCCTCGACGGAAACATCTG

GCTCGGGCCTCGTGCTGGCACTCCCTCCCATGCCGACAACCTTTCTGCTGTCACCACGACCCACGATG

CAACGCGACACGACCCGGTGGGACTGATCGGTTCACTGCACCTGCATGCCAATTGTCACAAGCGCAT

ACTCCAATCGTATCCGTTTGATTTCTGTGAAAACTCGCTCGACCGCCCGCGTCCCGCAGGCAGCGAT

GACGTGTGCGTGACCTGGGTGTTTCGTCGAAAGGCCAGCAACCCCAAATCGCAGGCGATCCGGAGA

TTGGGATCTGATCCGAGCTTGGACCAGATCCCCCACGATGCGGCACGGGAACTGCATCGACTCGGC

GCGGAACCCAGCTTTCGTAAATGCCAGATTGGTGTCCGATACCTTGATTTGCCATCAGCGAAACAAG

ACTTCAGCAGCGAGCGTATTTGGCGGGCGTGCTACCAGGGTTGCATACATTGCCCATTTCTGTCTGG

ACCGCTTTACCGGCGCAGAGGGTGAGTTGATGGGGTTGGCAGGCATCGAAACGCGCGTGCATGGT

-continued

GTGTGTGTCTGTTTTCGGCTGCACAATTTCAATAGTCGGATGGGCGACGGTAGAATTGGGTGTTGC

GCTCGCGTGCATGCCTCGCCCCGTCGGGTGTCATGACCGGGACTGGAATCCCCCCTCGCGACCCTCC

TGCTAACGCTCCCGACTCTCCCGCCCGCGCGCAGGATAGACTCTAGTTCAACCAATCGACAactagtAT

GCAGACCGCCCACCAGCGCCCCCCCACCGAGGGCCACTGCTTCGGCGCCCGCCTGCCCACCGCCTCCC

GCCGCGCCGTGCGCCGCGCCTGGTCCCGCATCGCCCGCGggcgcgccGCCGCCGCCGCCGACGCCAAC

CCCGCCCGCCCCGAGCGCCGCGTGGTGATCACCGGCCAGGGCGTGGTGACCTCCCTGGGCCAGACC

ATCGAGCAGTTCTACTCCTCCCTGCTGGAGGGCGTGTCCGGCATCTCCCAGATCCAGAAGTTCGACA

CCACCGGCTACACCACCACCATCGCCGGCGAGATCAAGTCCCTGCAGCTGGACCCCTACGTGCCCAA

GCGCTGGGCCAAGCGCGTGGACGACGTGATCAAGTACGTGTACATCGCCGGCAAGCAGGCCCTGG

AGTCCGCCGGCCTGCCCATCGAGGCCGCCGGCCTGGCCGGCGCCGGCCTGGACCCCGCCCTGTGCG

GCGTGCTGATCGGCACCGCCATGGCCGGCATGACCTCCTTCGCCGCCGGCGTGGAGGCCCTGACCC

GCGGCGGCGTGCGCAAGATGAACCCCTTCTGCATCCCCTTCTCCATCTCCAACATGGGCGGCGCCAT

GCTGGCCATGGACATCGGCTTCATGGGCCCCAACTACTCCATCTCCACCGCCTGCGCCACCGGCAAC

TACTGCATCCTGGGCGCCGCCGACCACATCCGCCGCGGCGACGCCAACGTGATGCTGGCCGGCGGC

GCCGACGCCGCCATCATCCCCTCCGGCATCGGCGGCTTCATCGCCTGCAAGGCCCTGTCCAAGCGCA

ACGACGAGCCCGAGCGCGCCTCCCGCCCCTGGGACGCCGACCGCGACGGCTTCGTGATGGGCGAG

GGCGCCGGCGTGCTGGTGCTGGAGGAGCTGGAGCACGCCAAGCGCCGCGGCGCCACCATCCTGGC

CGAGCTGGTGGGCGGCGCCGCCACCTCCGACGCCCACCACATGACCGAGCCCGACCCCCAGGGCCG

CGGCGTGCGCCTGTGCCTGGAGCGCGCCCTGGAGCGCGCCCGCCTGGCCCCCGAGCGCGTGGGCTA

CGTGAACGCCCACGGCACCTCCACCCCCGCCGGCGACGTGGCCGAGTACCGCGCCATCCGCGCCGT

GATCCCCCAGGACTCCCTGCGCATCAACTCCACCAAGTCCATGATCGGCCACCTGCTGGGCGGCGCC

GGCGCCGTGGAGGCCGTGGCCGCCATCCAGGCCCTGCGCACCGGCTGGCTGCACCCCAACCTGAAC

CTGGAGAACCCCGCCCCCGGCGTGGACCCCGTGGTGCTGGTGGGCCCCCGCAAGGAGCGCGCCGA

GGACCTGGACGTGGTGCTGTCCAACTCCTTCGGCTTCGGCGGCCACAACTCCTGCGTGATCTTCCGC

AAGTACGACGAGATGGACTACAAGGACCACGACGGCGACTACAAGGACCACGACATCGACTACA

AGGACGACGACGACAAGTGAatcgatagatctcttaagGCAGCAGCAGCTCGGATAGTATCGACACACTC

TGGACGCTGGTCGTGTGATGGACTGTTGCCGCCACACTTGCTGCCTTGACCTGTGAATATCCCTGCC

GCTTTTATCAAACAGCCTCAGTGTGTTTGATCTTGTGTGTACGCGCTTTTGCGAGTTGCTAGCTGCTT

GTGCTATTTGCGAATACCACCCCCAGCATCCCCTTCCCTCGTTTCATATCGCTTGCATCCCAACCGCAA

CTTATCTACGCTGTCCTGCTATCCCTCAGCGCTGCTCCTGCTCCTGCTCACTGCCCCTCGCACAGCCTT

GGTTTGGGCTCCGCCTGTATTCTCCTGGTACTGCAACCTGTAAACCAGCACTGCAATGCTGATGCAC

GGGAAGTAGTGGGATGGGAACACAAATGGAaagcttaattaagagctcttgttttccagaaggagttgctccttgag cctttcattctcagcctcgataacctccaaagccgctctaattgtggagggggttcgaatttaaaagcttggaatgttggttcgtgcgt ctggaacaagcccagacttgttgctcactgggaaaaggaccatcagctccaaaaaacttgccgctcaaaccgcgtacctctgcttc gcgcaatctgccctgttgaaatcgccaccacattcatattgtgacgcttgagcagtctgtaattgcctcagaatgtggaatcatctgcc ccctgtgcgagcccatgccaggcatgtcgcgggcgaggacacccgccactcgtacagcagaccattatgctacctcacaatagttca -continued

```
taacagtgaccatatttctcgaagctccccaacgagcacctccatgctctgagtggccaccccccggccctggtgcttgcggagggc

aggtcaaccggcatggggctaccgaaatccccgaccggatcccaccacccccgcgatgggaagaatctctccccgggatgtgggcc

caccaccagcacaacctgctggcccaggcgagcgtcaaaccataccacacaaatatccttggcatcggccctgaattccttctgccg

ctctgctacccggtgcttctgtccgaagcaggggttgctagggatcgctccgagtccgcaaacccttgtcgcgtggcggggcttgttc

gagcttgaagagc
```

Overexpression of KASII in Strain X:

Construct D1653 derived from pSZ2734 was transformed into Strain X as described previously. Primary transformants were clonally purified and grown under standard lipid production conditions at pH 5. The resulting fatty acid profiles from representative clones arising from transformation of Strain X with D1653 are summarized in Table 42, below. Overexpression of KASII in the SAD2 knockout/knockdown Strain K-4 background resulted in multiple strains accumulating over 50% C18:0 and with substantially reduced levels of C16:0. We also observed that KASII overexpressing lines had lower overall ratios of saturated to unsaturated fatty acids compared to Strain X.

TABLE 42

Fatty acid profiles of D1653 [pSZ2734] primary transformants, compared to the Strain X base strain and the wild-type parental strain, Strain J.

| Fatty Acid Area %¤ | Strain¤ J¤ | K-4¤ | D1653-89¤ | D1653-10A¤ | D1653-2B¤ | D1653-5B¤ | D1653-7A¤ | D1653-75¤ | D1653-90¤ | D1653-9B¤ | D1653-72¤ | D1653-6B¤ | D1653-82¤ | D1653-66¤ |
|---|---|---|---|---|---|---|---|---|---|---|---|---|---|---|
| C12:0¤ | 0.04¤ | 0.06¤ | 0.27¤ | 0.13¤ | 0.20¤ | 0.19¤ | 0.24¤ | 0.13¤ | 0.12¤ | 0.27¤ | 0.16¤ | 0.18¤ | 0.25¤ | 0.22¤ |
| C14:0¤ | 1.44¤ | 1.06¤ | 1.65¤ | 1.65¤ | 1.79¤ | 1.67¤ | 1.70¤ | 1.53¤ | 1.50¤ | 1.74¤ | 1.57¤ | 1.64¤ | 1.48¤ | 1.56¤ |
| C16:0¤ | 29.23¤ | 29.83¤ | **8.16¤** | **11.45¤** | **10.68¤** | **10.11¤** | **9.27¤** | **11.14¤** | **11.08¤** | **9.40¤** | **9.78¤** | **9.95¤** | **8.12¤** | **8.65¤** |
| C16:1¤ | 0.88¤ | 0.10¤ | 0.04¤ | 0.00¤ | 0.00¤ | 0.00¤ | 0.00¤ | 0.04¤ | 0.04¤ | 0.00¤ | 0.04¤ | 0.00¤ | 0.05¤ | 0.06¤ |
| C18:0¤ | 2.97¤ | **40.17¤** | **54.25¤** | **53.87¤** | **53.61¤** | **53.46¤** | **53.32¤** | **53.32¤** | **53.15¤** | **52.43¤** | **52.20¤** | **51.23¤** | **50.52¤** | **50.02¤** |
| C18:1¤ | 58.07¤ | 20.19¤ | 23.92¤ | 22.12¤ | 22.20¤ | 23.48¤ | 24.02¤ | 22.73¤ | 23.45¤ | 23.94¤ | 25.21¤ | 26.07¤ | 28.00¤ | 28.29¤ |
| C18:2¤ | 6.25¤ | 5.25¤ | 6.75¤ | 6.05¤ | 6.42¤ | 6.25¤ | 6.56¤ | 6.19¤ | 5.96¤ | 6.88¤ | 6.28¤ | 6.31¤ | 6.59¤ | 6.31¤ |
| C18:3α¤ | 0.50¤ | 0.68¤ | 0.79¤ | 0.88¤ | 0.78¤ | 0.79¤ | 0.79¤ | 0.85¤ | 0.82¤ | 0.86¤ | 0.78¤ | 0.78¤ | 0.78¤ | 0.83¤ |
| C20:0¤ | 0.22¤ | 1.88¤ | 3.21¤ | 2.81¤ | 3.01¤ | 2.91¤ | 3.02¤ | 2.86¤ | 2.77¤ | 3.21¤ | 2.74¤ | 2.80¤ | 2.87¤ | 2.80¤ |
| C20:1¤ | 0.02¤ | 0.07¤ | 0.19¤ | 0.21¤ | 0.34¤ | 0.27¤ | 0.28¤ | 0.12¤ | 0.11¤ | 0.41¤ | 0.14¤ | 0.30¤ | 0.28¤ | 0.26¤ |
| C22:0¤ | 0.05¤ | 0.26¤ | 0.41¤ | 0.34¤ | 0.40¤ | 0.37¤ | 0.37¤ | 0.36¤ | 0.35¤ | 0.42¤ | 0.36¤ | 0.37¤ | 0.36¤ | 0.37¤ |
| C24:0¤ | 0.04¤ | 0.27¤ | 0.49¤ | 0.38¤ | 0.42¤ | 0.41¤ | 0.45¤ | 0.38¤ | 0.36¤ | 0.46¤ | 0.39¤ | 0.37¤ | 0.41¤ | 0.41¤ |
| sum C18¤ | 67.78¤ | 66.24¤ | 85.31¤ | 82.92¤ | 83.01¤ | 83.98¤ | 84.69¤ | 83.09¤ | 83.38¤ | 84.11¤ | 84.47¤ | 84.39¤ | 85.89¤ | 85.45¤ |
| saturates¤ | 33.97¤ | 73.52¤ | 68.34¤ | 70.63¤ | 70.11¤ | 69.12¤ | 68.37¤ | 69.72¤ | 69.33¤ | 67.93¤ | 67.20¤ | ***66.54¤*** | ***64.01¤*** | ***64.03¤*** |
| unsaturates¤ | 65.71¤ | 26.23¤ | 31.29¤ | 29.26¤ | 29.74¤ | 30.79¤ | 31.65¤ | 29.93¤ | 30.38¤ | 32.09¤ | 32.45¤ | ***33.46¤*** | ***35.70¤*** | ***35.75¤*** |

In Table 42, Stearate (C18:0) levels greater than the wild-type level are highlighted with bold text. Palmitate (C16:0) levels lower than Strain X or J are highlighted with bold. For three strains the ratio of saturated to unsaturated fatty acids is ≤2:1; these are highlighted with bold, italicized text.

Stable lines were isolated from the primary transformants shown in Table 42. The fatty acid profiles and lipid titers of shake flask cultures are presented in Table 43, below. The strains accumulated up to 55% C18:0, with as low as 7% C16:0, with comparable lipid titers to the Strain X parent. The saturates:unsaturates ratios were substantially reduced compared to Strain X. Strains AU and AV were selected for evaluation in 3-L high-density fermentations.

TABLE 43

Shake flask assays of strains derived from D1653, expressing KASII, driven by the PmSAD2-2 promoter, targeted to the 6S locus.

| | | | | Primary | | | | | | | | |
|---|---|---|---|---|---|---|---|---|---|---|---|---|
| | | | | D1653-6B | | D1653-9B | D1653-10A | | D1653-72 | | D1653-89 | |
| Strain | | | K-4 | 5664 | AU | BM | BN | BO | BP | BQ | BR | AV | BS |
| Fatty | 10:0 | .02 | .04 | .08 | .09 | .12 | .06 | .06 | .08 | .09 | .12 | .12 | .12 |
| Acid | 12:0 | .04 | .09 | .28 | .29 | .35 | .20 | .20 | .23 | .26 | .32 | .32 | .33 |
| Area % | 14:0 | .42 | .12 | .81 | .66 | .73 | .75 | .72 | .50 | .61 | .38 | .43 | .38 |
| | 16:0 | 5.59 | 8.56 | **.39** | **.61** | **.44** | **.98** | **0.11** | **.26** | **.95** | **.81** | **.21** | **.63** |
| | 16:1 | .03 | .10 | .06 | .05 | .06 | .06 | .06 | .04 | .04 | .03 | .03 | .03 |
| | 18:0 | .60 | **0.13** | **7.60** | **2.47** | **5.12** | **0.25** | **9.73** | **4.56** | **4.01** | **2.96** | **3.68** | **2.12** |
| | 18.1 | 2.08 | 0.74 | 7.78 | 3.93 | 1.31 | 5.37 | 5.70 | 2.86 | 2.87 | 4.37 | 3.99 | 5.17 |

TABLE 43-continued

Shake flask assays of strains derived from D1653, expressing KASII, driven by the PmSAD2-2 promoter, targeted to the 6S locus.

| | | | Primary | | | | | | | | | |
|---|---|---|---|---|---|---|---|---|---|---|---|---|
| | | | D1653-6B | | D1653-9B | D1653-10A | | D1653-72 | | D1653-89 | | |
| Strain | | K-4 | 5664 | AU | BM | BN | BO | BP | BQ | BR | AV | BS |
| 18.2 | .16 | .83 | .98 | .52 | .72 | .55 | .64 | .20 | .24 | .11 | .83 | .04 |
| 18:3α | .40 | .89 | .21 | .22 | .49 | .17 | .07 | .20 | .29 | .28 | .24 | .31 |
| 20:0 | .18 | .82 | .62 | .93 | .75 | .63 | .66 | .97 | .72 | .43 | .10 | .59 |
| 20:1 | .04 | .13 | .37 | .36 | .39 | .34 | .34 | .35 | .34 | .48 | .41 | .47 |
| 20:1 | .07 | .00 | .00 | .00 | .00 | .00 | .00 | .00 | .00 | .00 | .00 | .00 |
| 20:1 | .15 | .08 | .11 | .09 | .11 | .10 | .10 | .09 | .10 | .12 | .10 | .12 |
| 22:0 | .02 | .20 | .28 | .30 | .24 | .29 | .28 | .30 | .27 | .32 | .29 | .35 |
| 24:0 | .00 | .03 | .16 | .29 | .00 | .03 | .15 | .16 | .02 | .05 | .04 | .07 |
| Sum C18 | 1.23 | 7.58 | 4.57 | 5.13 | 5.63 | 4.34 | 4.13 | 5.81 | 5.40 | 6.71 | 6.73 | 6.63 |
| Saturates | 9.86 | 1.97 | ***2.22*** | ***6.63*** | 68.74 | ***5.20*** | ***4.90*** | 8.05 | 7.90 | ***5.37*** | ***6.17*** | ***4.57*** |
| Unsaturates | 9.91 | 7.76 | ***7.50*** | ***3.15*** | 31.07 | ***4.57*** | ***4.89*** | 1.73 | 3.87 | ***4.37*** | ***3.59*** | ***5.13*** |

In Table 43, Strain X is the parent strain; Strain J is the wild-type base strain. Stearate (C18:0) levels at least two-fold higher than in the wild-type strain are highlighted in bold. Palmitate levels that are less than in Strain J and Strain K-4 are highlighted bold. Bold italics indicate that the saturates:unsaturates ratio is ≤2:1.

The fatty acid profiles and performance metrics of strains AU and AV are detailed in Table 44, below. The fatty acid profile of the parent strain X, grown under the same fermentation conditions, is presented for comparison. The strains that over-express KASII accumulate about 11% more C18:0 than the strain K-4 parent. C16:0 is reduced to 7-9%, and levels of unsaturated fatty acids increase by 4-5%. The lipid titers of Strain AU and AV were comparable to K-4, indicating that KASII over-expression did not have deleterious effects on lipid production.

TABLE 44

End point fatty acid profiles of biomass from Strain X, AU and AV fermentations.

| | Strain | | |
|---|---|---|---|
| | K-4 | AU | AV |
| | Fermentation | | |
| | 120580F1 | 130097F3 | 130098F4 |
| | pH | | |
| | 5 | 5 | 5 |
| C14:0 | 1.27 | 1.50 | 1.35 |
| C16:0 | 28.35 | **8.88** | **7.33** |
| C16:1 | 0.06 | 0.02 | 0.03 |
| C18:0 | **43.67** | **56.88** | **57.24** |
| C18:1 | 17.63 | 21.57 | 21.66 |
| C18:2 | 5.58 | 6.06 | 6.94 |
| C18:3α | 0.25 | 0.29 | 0.22 |
| C20:0 | 2.11 | 3.28 | 3.46 |
| C22:0 | 0.31 | 0.40 | 0.40 |
| C24:0 | 0.31 | 0.37 | 0.40 |
| sum C18 | 67.13 | 84.80 | 86.06 |
| saturates | 76.02 | 71.31 | 70.18 |
| unsaturates | 23.52 | 27.94 | 28.85 |
| total lipid (g/L) | 475 | 529 | 418 |

The fermentations were cultured for 6 days using a fed-batch process. The Strain X fatty acid profile from fermentation 120580F1 was presented in Table 41, and is shown again in Table 44 for comparison with Strains AU and AV. All fermentations were carried out at 32° C., pH 5, 30% dissolved oxygen (DO), 300 mM nitrogen [N], and 557.5 μM iron. The sugar source was 70% sucrose (S70). Stearate (C18:0) levels higher than in the wild-type strain are indicated with bold. Palmitate (C16:0) levels that are less than in the wild-type are highlighted bold.

Lab scale oils were prepared from biomass derived from the shake flasks and fermentations described above. The TAG compositions of these oils were determined by LC/MS. SOS is the major TAG species in both Strain AU and AV, ranging from 33-35% in the biomass from shake flasks, and reaching 37% in the high-density fermentation biomass. The major palmitate-containing TAGs are substantially reduced, and trisaturate levels are less than half of those observed in Strain X oils. These results demonstrate that KASII over-expression in a high-stearate background significantly improves SOS accumulation, and reduces the accumulation of trisaturated TAGs.

Constructs Used for FATA-1 Disruption, KASII Over-Expression and FAD2 RNAi in Strain J:

A DNA construct, pSZ2419, was made to simultaneously disrupt the FATA-1 allele, over-express *P. moriformis* KASII and express a FAD2 hairpin construct in Strain J. A version of the *S. cerevisiae* SUC2 gene, encoding sucrose invertase, which was codon-optimized for expression in *P. moriformis*, was utilized as a selectable marker for transformation. The sequence of the transforming DNA is provided immediately below. Relevant restriction sites are indicated in lowercase, bold, and are from 5'-3' BspQI, KpnI, AscI, MfeI, BamHI, AvrII, EcoRV, EcoRI, SpeI, AscI, ClaI, BglII, AflII, HinDIII, SacI, SpeI, and XhoI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the FATA-1 locus. Proceeding in the 5' to 3' direction, the *C. reinhardtii* TUB2 promoter driving the expression of the *S. cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The 3' UTR of the *C. vulgaris* nitrate reductase (NR) gene is indicated by small capitals, followed by a spacer region indicated by lowercase text. The *P. moriformis* AMT3 promoter, indicated by lowercase boxed text, drives expression of the *P. moriformis* KASII gene. The region encoding the plastid targeting peptide from *Chlorella protothecoides* SAD1 is indicated by uppercase italics. The sequence that encodes the mature *P. moriformis* KASII polypeptide is indicated with bold, uppercase italics, while a 3×FLAG epitope encoding sequence is in bold, underlined, uppercase italics. A second *C. vulgaris* NR3' UTR is indicated by small capitals. A second *C. reinhardtii* TUB2 promoter sequence, indicated by lowercase boxed text, drives expression of the *P. moriformis* FAD2 hairpin A sequence. The sense and antisense strands are indicated with uppercase, bold italics, and are separated by the FAD2 intron and the first 10 bases of the FAD2 second exon (uppercase italics). A third *C. vulgaris* NR3' UTR is indicated by small capitals, followed by a second spacer region that is indicated by lowercase text.

Nucleotide sequence of the transforming DNA from pSZ2419:

(SEQ ID NO: 96)

gctcttcggagtcactgtgccactgagttcgactggtagctgaatggagtcgctgctccactaaacgaattgtcagcaccgccagcc ggccgaggacccgagtcatagcgagggtagtagcgcatggcaccgaccagcctgcttgccagtactggcgtctcttccgcttct ctgtggtcctctgcgcgctccagcgcgtgcgcttttccggtggatcatgcggtccgtggcgcaccgcagcggccgctgcccatgcagc gccgctgcttccgaacagtggcggtcagggccgcacccgcggtagccgtccgtccggaacccgcccaagagttttgggagcagctt gagccctgcaagatggcggaggacaagcgcatcttcctggaggagcaccggtgcgtggaggtccggggctgaccggccgtcgcat tcaacgtaatcaatcgcatgatgatcagaggacacgaagtcttggtggcggtggccagaaacactgtccattgcaagggcataggg atgcgttccttcacctctcatttctcatttctgaatccctccctgctcactctttctcctcctccttcccgttcacgcagcattcggggtacc ctttcttgcgctatgacacttccagcaaaaggtagggcgggctgcgagacggcttcccggcgctgcatgcaacaccgatgatgcttc gacccccccgaagctccttcggggctgcatgggcgctccgatgccgctccagggcgagcgctgtttaaatagccaggcccccgattgc aaagacattatagcgagctaccaaagccatattcaaacacctagatcactaccacttctacacaggccactcgagcttgtgatcgca ctccgctaagggggcgcctcttcctcttcgtttcagtcacaacccgcaaacggcgcgcc*ATGctgctgcaggccttcctgttcctgct*

*ggccggcttcgccgccaagatcagcgcctccatgacgaacgagacgtccgaccgccccctggtgcacttcacccccaacaagg*

*gctggatgaacgaccccaacggcctgtggtacgacgagaaggacgccaagtggcacctgtacttccagtacaacccgaacg*

*acaccgtctgggggacgcccttgttctggggccacgccacgtccgacgacctgaccaactgggaggaccagcccatcgccatc*

*gccccgaagcgcaacgactccggcgccttctccggctccatggtggtggactacaacaacacctccggcttcttcaacgacacc*

*atcgacccgcgccagcgctgcgtggccatctggacctacaacaccccggagtccgaggagcagtacatctcctacagcctgga*

*cggcggctacaccttcaccgagtaccagaagaaccccgtgctggccgccaactccacccagttccgcgacccgaaggtcttctg*

*gtacgagccctcccagaagtggatcatgaccgcggccaagtcccaggactacaagatcgagatctactcctccgacgacctga*

*agtcctggaagctggagtccgcgttcgccaacgagggcttcctcggctaccagtacgagtgccccggcctgatcgaggtcccc*

*accgagcaggaccccagcaagtcctactgggtgatgttcatctccatcaaccccggcgccccggccggcggctccttcaaccag*

*tacttcgtcggcagcttcaacggcacccacttcgaggccttcgacaaccagtcccgcgtggtggacttcggcaaggactactac*

*gccctgcagaccttcttcaacaccgacccgacctacgggagcgccctgggcatcgcgtgggcctccaactgggagtactccgcc*

*ttcgtgcccaccaaccccctggcgctcctccatgtccctcgtgcgcaagttctccctcaacaccgagtaccaggccaacccggaga*

*cggagctgatcaacctgaaggccgagccgatcctgaacatcagcaacgccggccccctggagccggttcgccaccaacaccac*

*gttgacgaaggccaacagctacaacgtcgacctgtccaacagcaccggcaccctggagttcgagctggtgtacgccgtcaac*

*accacccagacgatctccaagtccgtgttcgcggacctctccctctggttcaagggcctggaggaccccgaggagtacctccgc*

*atgggcttcgaggtgtccgcgtcctccttcttcctggaccgcgggaacagcaaggtgaagttcgtgaaggagaacccctacttc*

*accaaccgcatgagcgtgaacaaccagcccttcaagagcgagaacgacctgtcctactacaaggtgtacggcttgctggacc*

*agaacatcctggagctgtacttcaacgacggcgacgtcgtgtccaccaacacctacttcatgaccaccgggaacgccctgggc*

*tccgtgaacatgacgacgggggtggacaacctgttctacatcgacaagttccaggtgcgcgaggtcaagTGA*AcaattgGCA

GCAGCAGCTCGGATAGTATCGACACACTCTGGACGCTGGTCGTGTGATGGACTGTTGCCGCCACACT

TGCTGCCTTGACCTGTGAATATCCCTGCCGCTTTTATCAAACAGCCTCAGTGTGTTTGATCTTGTGTGT

ACGCGCTTTTGCGAGTTGCTAGCTGCTTGTGCTATTTGCGAATACCACCCCCAGCATCCCCTTCCCTC

-continued

GTTTCATATCGCTTGCATCCCAACCGCAACTTATCTACGCTGTCCTGCTATCCCTCAGCGCTGCTCCTG

CTCCTGCTCACTGCCCCTCGCACAGCCTTGGTTTGGGCTCCGCCTGTATTCTCCTGGTACTGCAACCT

GTAAACCAGCACTGCAATGCTGATGCACGGGAAGTAGTGGGATGGGAACACAAATGGAggatcccgc gtctcgaacagagcgcgcagaggaacgctgaaggtctcgcctctgtcgcacctcagcgcggcatacaccacaataaccacctgacg aatgcgcttggttcttcgtccattagcgaagcgtccggttcacacacgtgccacgttggcgaggtggcaggtgacaatgatcggtgg agctgatggtcgaaacgttcacagcctagggatatcgaattcggccgacaggacgcgcgtcaaaggtgctggtcgtgtatgccctg gccggcaggtcgttgctgctgctggttagtgattccgcaaccctgattttggcgtcttattttggcgtggcaaacgctggcgcccgcga gccgggccggcggcgatgcggtgccccacggctgccggaatccaagggaggcaagagcgcccgggtcagttgaagggctttacgc gcaaggtacagccgctcctgcaaggctgcgtggtggaattggacgtgcaggtcctgctgaagttcctccaccgcctcaccagcgga caaagcaccggtgtatcaggtccgtgtcatccactctaaagaactcgactacgacctactgatggccctagattcttcatcaaaaac gcctgagacacttgcccaggattgaaactccctgaagggaccaccaggggccctgagttgttccttcccccgtggcgagctgccag ccaggctgtacctgtgatcgaggctggcgggaaaataggcttcgtgtgctcaggtcatgggaggtgcaggacagctcatgaaacgc caacaatcgcacaattcatgtcaagctaatcagctatttcctcttcacgagctgtaattgtcccaaaattctggtctaccgggggtgat ccttcgtgtacgggcccttccctcaaccctaggtatgcgcgcatgcggtcgccgcgcaactcgcgcgagggccgagggtttgggacg ggccgtcccgaaatgcagttgcacccggatgcgtggcaccttttttgcgataatttatgcaatggactgctctgcaaaattctggctct gtcgccaaccctaggatcagcggcgtaggatttcgtaatcattcgtcctgatggggagctaccgactaccctaatatcagcccgact gcctgacgccagcgtccacttttgtgcacacattccattcgtgcccaagacatttcattgtggtgcgaagcgtccccagttacgctcac ctgtttcccgacctccttactgttctgtcgacagagcgggcccacaggccggtcgcagccactagt*ATGGCCACCGCATCCAC*

*TTTCTCGGCGTTCAATGCCCGCTGCGGCGACCTGCGTCGCTCGGCGGGCTCCGGGCCCCGGCGCCCA*

*GCGAGGCCCCTCCCCGTGCGCG**ggcgcgccGCCGCCGCCGCCGACGCCAACCCCGCCCGCCCCGAGCG*

*CCGCGTGGTGATCACCGGCCAGGGCGTGGTGACCTCCCTGGGCCAGACCATCGAGCAGTTCTACTC*

*CTCCCTGCTGGAGGGCGTGTCCGGCATCTCCCAGATCCAGAAGTTCGACACCACCGGCTACACCACC*

*ACCATCGCCGGCGAGATCAAGTCCCTGCAGCTGGACCCCTACGTGCCCAAGCGCTGGGCCAAGCGC*

*GTGGACGACGTGATCAAGTACGTGTACATCGCCGGCAAGCAGGCCCTGGAGTCCGCCGGCCTGCC*

*CATCGAGGCCGCCGGCCTGGCCGGCGCCGGCCTGGACCCCGCCCTGTGCGGCGTGCTGATCGGCAC*

*CGCCATGGCCGGCATGACCTCCTTCGCCGCCGGCGTGGAGGCCCTGACCCGCGGCGGCGTGCGCAA*

*GATGAACCCCTTCTGCATCCCCTTCTCCATCTCCAACATGGGCGGCGCCATGCTGGCCATGGACATC*

*GGCTTCATGGGCCCCAACTACTCCATCTCCACCGCCTGCGCCACCGGCAACTACTGCATCCTGGGCG*

*CCGCCGACCACATCCGCCGCGGCGACGCCAACGTGATGCTGGCCGGCGGCGCCGACGCCGCCATCA*

*TCCCCTCCGGCATCGGCGGCTTCATCGCCTGCAAGGCCCTGTCCAAGCGCAACGACGAGCCCGAGC*

*GCGCCTCCCGCCCCTGGGACGCCGACCGCGACGGCTTCGTGATGGGCGAGGGCGCCGGCGTGCTG*

*GTGCTGGAGGAGCTGGAGCACGCCAAGCGCCGCGGCGCCACCATCCTGGCCGAGCTGGTGGGCG*

*GCGCCGCCACCTCCGACGCCCACCACATGACCGAGCCCGACCCCCAGGGCCGCGGCGTGCGCCTGT*

*GCCTGGAGCGCGCCCTGGAGCGCGCCCGCCTGGCCCCCGAGCGCGTGGGCTACGTGAACGCCCAC*

*GGCACCTCCACCCCCGCCGGCGACGTGGCCGAGTACCGCGCCATCCGCGCCGTGATCCCCCAGGACT*

-continued

*CCCTGCGCATCAACTCCACCAAGTCCATGATCGGCCACCTGCTGGGCGGCGCCGGCGCCGTGGAGG*

*CCGTGGCCGCCATCCAGGCCCTGCGCACCGGCTGGCTGCACCCCAACCTGAACCTGGAGAACCCCG*

*CCCCCGGCGTGGACCCCGTGGTGCTGGTGGGCCCCCGCAAGGAGCGCGCCGAGGACCTGGACGTG*

*GTGCTGTCCAACTCCTTCGGCTTCGGCGGCCACAACTCCTGCGTGATCTTCCGCAAGTACGACGAGA*

*TGGACTACAAGGACCACGACGGCGACTACAAGGACCACGACATCGACTACAAGGACGACGACGAC*

*AAGTGA*atcgatagatctcttaagGCAGCAGCAGCTCGGATAGTATCGACACACTCTGGACGCTGGTCGT

GTGATGGACTGTTGCCGCCACACTTGCTGCCTTGACCTGTGAATATCCCTGCCGCTTTTATCAAACAG

CCTCAGTGTGTTTGATCTTGTGTGTACGCGCTTTTGCGAGTTGCTAGCTGCTTGTGCTATTTGCGAAT

ACCACCCCCAGCATCCCCTTCCCTCGTTTCATATCGCTTGCATCCCAACCGCAACTTATCTACGCTGTC

CTGCTATCCCTCAGCGCTGCTCCTGCTCCTGCTCACTGCCCCTCGCACAGCCTTGGTTTGGGCTCCGC

CTGTATTCTCCTGGTACTGCAACCTGTAAACCAGCACTGCAATGCTGATGCACGGGAAGTAGTGGGA

TGGGAACACAAATGGAaagcttaattaagagctcctttcttgcgctatgacacttccagcaaaaggtagggcgggctgcga gacggcttcccggcgctgcatgcaacaccgatgatgcttcgacccccccgaagctccttcggggctgcatgggcgctccgatgccgct ccagggcgagcgctgtttaaatagccaggcccccgattgcaaagacattatagcgagctaccaaagccatattcaaacacctagat cactaccacttctacacaggccactcgagcttgtgatcgcactccgctaagggggcgcctcttcctcttcgtttcagtcacaacccgc aaac*actagtATGGCTATCAAGACGAACAGGCAGCCTGTGGAGAAGCCTCCGTTCACGATCGGGACG*

*CTGCGCAAGGCCATCCCCGCGCACTGTTTCGAGCGCTCGGCGCTTCGTAGCAGCATGTACCTGGCCT*

*TTGACATCGCGGTCATGTCCCTGCTCTACGTCGCGTCGACGTACATCGACCCTGCACCGGTGCCTAC*

*GTGGGTCAAGTACGGCATCATGTGGCCGCTCTACTGGTTCTTCCAG*GTGTGTTTGAGGGTTTTGGTT*

*GCCCGTATTGAGGTCCTGGTGGCGCGCATGGAGGAGAAGGCGCCTGTCCCGCTGACCCCCCCGGCT*

*ACCCTCCCGGCACCTTCCAGGGCGCGTACG*___GGAAGAACCAGTAGAGCGGCCACATGATGCCGTACT___

*TGACCCACGTAGGCACCGGTGCAGGGTCGATGTACGTCGACGCGACGTAGAGCAGGGACATGACC*

*GCGATGTCAAAGGCCAGGTACATGCTGCTACGAAGCGCCGAGCGCTCGAAACAGTGCGCGGGGA*

*TGGCCTTGCGCAGCGTCCCGATCGTGAACGGAGGCTTCTCCACAGGCTGCCTGTTCGTCTTGATAGC*

*CATctcgag*GCAGCAGCAGCTCGGATAGTATCGACACACTCTGGACGCTGGICGTGTGATGGACTGTT

GCCGCCACACTTGCTGCCTTGACCTGTGAATATCCCTGCCGCTTTTATCAAACAGCCTCAGTGTGTTT

GATCTTGTGTGTACGCGCTTTTGCGAGTTGCTAGCTGCTTGTGCTATTTGCGAATACCACCCCCAGCA

TCCCCTTCCCTCGTTTCATATCGCTTGCATCCCAACCGCAACTTATCTACGCTGTCCTGCTATCCCTCAG

CGCTGCTCCTGCTCCTGCTCACTGCCCCTCGCACAGCCTTGGTTTGGGCTCCGCCTGTATTCTCCTGGT

ACTGCAACCTGTAAACCAGCACTGCAATGCTGATGCACGGGAAGTAGTGGGATGGGAACACAAATG

GAaagctgtattgttttccagaaggagttgctccttgagcctttcattctcagcctcgataacctccaaagccgctctaattgtggagg gggttcgaagacagggtggttggctggatggggaaacgctggtcgcgggattcgatcctgctgcttatatcctccctggaagcacac ccacgactctgaagaagaaaacgtgcacacacacaacccaaccggccgaatatttgcttccttatcccgggtccaagagagactgc gatgccccctcaatcagcatcctcctccctgccgcttcaatcttccctgcttgcctgcgcccgcggtgcgccgtctgcccgcccagtc agtcactcctgcacaggccccttgtgcgcagtgctcctgtaccctttaccgctccttccattctgcgaggcccccctattgaatgtattcg -continued ttgcctgtgtggccaagcgggctgctgggcgcgccgccgtcgggcagtgctcggcgactttggcggaagccgattgttcttctgtaag ccacgcgcttgctgctttgggaagagaagggggggggtactgaatggatgaggaggagaaggaggggtattggtattatctgagtt gggtgaagagc

Identification and Analysis of FATA-1 Knockout, KASII Over-Expression and FAD2 RNAi Strains:

Construct D1358, derived from pSZ2419, was transformed into Strain J as described previously. Primary transformants were clonally purified and grown under standard lipid production conditions at pH 5. The resulting fatty acid profiles from representative clones arising from transformation of Strain J with D1358 are summarized in Table 45, below. The *P. moriformis* AMT3 promoter is repressed at pH 5 so the observed phenotypes did not reflect over-expression of *P. moriformis* KASII. Nevertheless, we observed that multiple strains had substantially reduced levels of C16:0 and 10-15% increases in C18:1, suggesting that the construct had disrupted the FATA-1 target gene, increasing the amount of palmitoyl-ACP available for extension by endogenous KASII. One line, D1358-13, was selected for further analysis. D1358-13 accumulated ~17% C16:0, ~75% C18:1 and less than 2% C18:2, indicating that we had successfully integrated at FATA-1 and downregulated activity of the FAD2 $\Delta^{12}$-desaturase in this strain.

In Table 45, Oleate (C18:1) levels greater than the wild-type level are highlighted with bold text. Palmitate (C16:0) levels less than the wild-type are highlighted with bold text. Levels of linoleate (C18:2) reduced by 1% or more compared to the Strain J parent are highlighted with bold text.

The fatty acid profiles of strains derived from transformant D1358-13 were determined to be stable after more than 60 generations of growth in the absence of selection (growth on sucrose). The performance of selected strains in shake flask assays was then evaluated, and the fatty acid profiles and lipid titers are presented in Table 46, below. Flask experiments were performed at pH 7, enabling activation of the PmAMT3 promoter driving expression of the KASII transgene. The combination of KASII over-expression and FATA-1 knockout leads to further reductions in palmitate levels and enhanced oleate accumulation compared to the phenotypes observed at pH 5 (Table 45). With more than 82% C18:1, less than 11% C16:0, less than 2% C18:2 and ~83% of the wild-type lipid titer, Strain AA was determined to be the most appropriate strain from this set to serve as a host strain for subsequent modifications to elevate stearate levels. DNA blot analysis showed that S5003 has a simple insertion of construct D1358 [pSZ2419] at the FATA-1 locus.

TABLE 45

Fatty acid profiles of D1358 [pSZ2419] primary transformants, compared to the wild-type parental strain, Strain J.

| Fatty | Strain¤ | | | | | | | | | | |
|---|---|---|---|---|---|---|---|---|---|---|---|
| Area %¤ | J¤ | D1358-13¤ | D1358-19¤ | D1358-11¤ | D1358-9¤ | D1358-30¤ | D1358-28¤ | D1358-6¤ | D1358-8¤ | D1358-10¤ | D1358-3¤ |
| C12:0¤ | 0.05¤ | 0.08¤ | 0.06¤ | 0.08¤ | 0.06¤ | 0.07¤ | 0.07¤ | 0.09¤ | 0.07¤ | 0.08¤ | 0.10¤ |
| C14:0¤ | 1.32¤ | 0.79¤ | 0.83¤ | 0.85¤ | 0.87¤ | 0.84¤ | 0.91¤ | 0.86¤ | 0.89¤ | 0.92¤ | 0.60¤ |
| C16:0¤ | 26.66¤ | **17.43¤** | **18.84¤** | **20.03¤** | **16.27¤** | **18.4¤** | **19.1¤** | **18.18¤** | **15.6¤** | **16.42¤** | **11.24¤** |
| C16:1¤ | 0.84¤ | 0.74¤ | 0.79¤ | 0.97¤ | 0.60¤ | 0.77¤ | 1.17¤ | 0.75¤ | 0.56¤ | 0.61¤ | 0.57¤ |
| C18:0¤ | 3.10¤ | 2.87¤ | 2.97¤ | 2.36¤ | 3.20¤ | 2.67¤ | 2.10¤ | 2.82¤ | 3.22¤ | 3.19¤ | 2.30¤ |
| C18:1¤ | 59.07¤ | **74.78¤** | **69.54¤** | **68.78¤** | **71.48¤** | **69.55¤** | **69.02¤** | **68.93¤** | **70.44¤** | **69.64¤** | **75.27¤** |
| C18:2¤ | 7.39¤ | 1.97¤ | 5.47¤ | 5.61¤ | 6.22¤ | 6.31¤ | 6.42¤ | 6.8¤ | 7.68¤ | 7.78¤ | 8.51¤ |
| C18:3α¤ | 0.55¤ | 0.23¤ | 0.59¤ | 0.51¤ | 0.26¤ | 0.39¤ | 0.46¤ | 0.38¤ | 0.24¤ | 0.27¤ | 0.24¤ |
| C20:0¤ | 0.24¤ | 0.22¤ | 0.20¤ | 0.13¤ | 0.32¤ | 0.20¤ | 0.03¤ | 0.20¤ | 0.33¤ | 0.31¤ | 0.22¤ |
| C20:1¤ | 0.11¤ | 0.40¤ | 0.29¤ | 0.37¤ | 0.23¤ | 0.33¤ | 0.33¤ | 0.39¤ | 0.36¤ | 0.27¤ | 0.40¤ |
| C22:0¤ | 0.11¤ | 0.09¤ | 0.08¤ | 0.07¤ | 0.09¤ | 0.08¤ | 0.08¤ | 0.08¤ | 0.09¤ | 0.11¤ | 0.11¤ |
| sum-C18¤ | 70.11¤ | 79.85¤ | 78.57¤ | 77.26¤ | 81.16¤ | 78.92¤ | 78.00¤ | 78.93¤ | 81.58¤ | 80.88¤ | 86.32¤ |
| saturates¤ | 31.48¤ | 21.48¤ | 22.98¤ | 23.52¤ | 20.81¤ | 22.26¤ | 22.29¤ | 22.23¤ | 20.20¤ | 21.03¤ | 14.57¤ |
| unsaturates¤ | 67.96¤ | 78.12¤ | 76.68¤ | 76.24¤ | 78.79¤ | 77.35¤ | 77.4 ¤ | 77.25¤ | 79.28¤ | 78.57¤ | 84.99¤ |

TABLE 46

Fatty acid profiles and lipid titers of FATA-1 knockout, KASII over-expressing, FAD2 RNAi lines derived from D1358-13 primary transformants, compared to the wild-type parental strain, Strain J.

| Fatty Acid Area | Primary T389; D1358-13¤ Strain¤ | | | | | | | | | | | | | |
|---|---|---|---|---|---|---|---|---|---|---|---|---|---|---|
| %¤ | J¤ | AA¤ | AB¤ | AC¤ | AD¤ | AE¤ | AF¤ | AG¤ | AH¤ | AI¤ | AJ¤ | AK¤ | AL¤ | AM¤ |
| C12:0¤ | 0.05¤ | 0.08¤ | 0.09¤ | 0.11¤ | 0.19¤ | 0.11¤ | 0.14¤ | 0.10¤ | 0.12¤ | 0.06¤ | 0.11¤ | 0.09¤ | 0.20¤ | 0.20¤ |
| C14:0¤ | 1.34¤ | 0.96¤ | 0.98¤ | 1.03¤ | 1.04¤ | 0.96¤ | 1.02¤ | 0.98¤ | 1.03¤ | 0.98¤ | 1.01¤ | 1.00¤ | 1.03¤ | 1.02¤ |
| C16:0¤ | 29.69¤ | **10.72¤** | **10.47¤** | **8.90¤** | **6.99¤** | **9.53¤** | **9.27¤** | **10.13¤** | **8.99¤** | **10.76¤** | **9.58¤** | **10.00¤** | **6.64¤** | **6.38¤** |
| C16:1¤ | 0.88¤ | 0.42¤ | 0.39¤ | 0.31¤ | 0.29¤ | 0.33¤ | 0.37¤ | 0.41¤ | 0.32¤ | 0.40¤ | 0.35¤ | 0.35¤ | 0.27¤ | 0.27¤ |
| C18:0¤ | 2.78¤ | 2.92¤ | 3.00¤ | 3.16¤ | 2.71¤ | 2.88¤ | 2.85¤ | 2.91¤ | 3.21¤ | 3.03¤ | 3.10¤ | 3.20¤ | 2.77¤ | 2.71¤ |
| C18:1¤ | 58.45¤ | **82.08¤** | **82.24¤** | **83.66¤** | **85.49¤** | **83.28¤** | **83.38¤** | **82.57¤** | **83.51¤** | **82.12¤** | **83.10¤** | **82.63¤** | **85.88¤** | **86.13¤** |
| C18:2¤ | 5.83¤ | 1.89¤ | 1.88¤ | 1.80¤ | 2.01¤ | 1.83¤ | 1.89¤ | 1.89¤ | 1.77¤ | 1.73¤ | 1.75¤ | 1.76¤ | 1.94¤ | 1.96¤ |
| C18: 3α¤ | 0.42¤ | 0.23¤ | 0.23¤ | 0.25¤ | 0.35¤ | 0.27¤ | 0.29¤ | 0.27¤ | 0.25¤ | 0.22¤ | 0.24¤ | 0.23¤ | 0.34¤ | 0.36¤ |
| C20:0¤ | 0.17¤ | 0.15¤ | 0.16¤ | 0.17¤ | 0.15¤ | 0.15¤ | 0.16¤ | 0.16¤ | 0.17¤ | 0.14¤ | 0.16¤ | 0.16¤ | 0.15¤ | 0.15¤ |
| C20:1¤ | 0.05¤ | 0.23¤ | 0.24¤ | 0.27¤ | 0.36¤ | 0.28¤ | 0.29¤ | 0.26¤ | 0.27¤ | 0.21¤ | 0.25¤ | 0.24¤ | 0.38¤ | 0.39¤ |
| sum-C18¤ | 67.48¤ | 87.12¤ | 87.35¤ | 88.87¤ | 90.56¤ | 88.26¤ | 88.41¤ | 87.64¤ | 88.74¤ | 87.10¤ | 88.19¤ | 87.82¤ | 90.93¤ | 91.16¤ |
| saturates¤ | 34.03¤ | 14.83¤ | 14.70¤ | 13.37¤ | 11.08¤ | 13.63¤ | 13.44¤ | 14.28¤ | 13.52¤ | 14.99¤ | 13.96¤ | 14.45¤ | 10.79¤ | 10.46¤ |
| unsaturates¤ | 65.63¤ | 84.85¤ | 84.98¤ | 86.29¤ | 88.50¤ | 86.05¤ | 86.22¤ | 85.40¤ | 86.12¤ | 84.68¤ | 85.69¤ | 86.21¤ | 88.81¤ | 89.11¤ |
| lipid titer (% parent)¤ | 100.0¤ | 82.8¤ | 81.1¤ | 72.8¤ | 54.4¤ | 68.3¤ | 63.7¤ | 70.6¤ | 72.2¤ | 106.9¤ | 76.5¤ | 77.5¤ | 56.7¤ | 54.6¤ |

In Table 46, Stearate (C18:1) levels greater than the wild-type level are highlighted with bold text. Palmitate (C16:0) levels lower than the wild-type are highlighted with bold text. Linoleate (C18:2) levels that are lower than the wild-type are indicated with bold text.

Constructs Used for SAD2 Knockout/RNAi in S5003:

Two DNA constructs, pSZ2283 and pSZ2697, were made to simultaneously disrupt the SAD2-1 allele and express a SAD2 hairpin construct in Strain AA. In each construct, the neoR gene from transposon Tn5, conferring resistance to aminoglycoside antibiotics, was used as a selectable marker for transformation. The sequence of the transforming DNA derived from pSZ2283 is provided immediately below. Relevant restriction sites are indicated in lowercase, bold, and are from 5'-3' BspQI, KpnI, XbaI, MfeI, BamHI, AvrII, EcoRV, EcoRI, SpeI, BamHI, HinDIII, and SacI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlamydomonas reinhardtii* TUB2 promoter driving the expression of neoR (encoding aminoglycoside phosphotransferase activity, thereby permitting the strain to grow on G418) is indicated by lowercase, boxed text. The initiator ATG and terminator TGA for neoR are indicated by uppercase italics, while the coding region is indicated with lowercase italics. The 3' UTR of the *C. vulgaris* NR gene is indicated by small capitals, followed by a spacer region indicated by lowercase text. A second *C. reinhardtii* TUB2 promoter sequence, indicated by lowercase boxed text, drives expression of the SAD2 hairpin C sequence. The sense and antisense strands are indicated with uppercase, bold italics, and are separated by the *P. moriformis* FAD2 intron and the first 10 bases of the FAD2 second exon (uppercase italics). A second *C. vulgaris* NR3' UTR is indicated by small capitals.

Nucleotide sequence of the transforming DNA from pSZ2283:

(SEQ ID NO: 97)

gctcttcgggtcgccgcgctgcctcgcgtcccctggtggtgcgcgcggtcgccagcgaggccccgctgggcgttccgccctcggtgca gcgcccctcccccgtggtctactccaagctggacaagcagcaccgcctgacgcccgagcgcctggagctggtgcagagcatggggc agtttgcggaggagagggtgctgcccgtgctgcaccccgtggacaagctgtggcagccgcaggacttttgcccgaccccgagtcgc ccgacttcgaggatcaggtggcggagctgcgcgcgcgcgccaaggacctgcccgacgagtactttgtggtgctggtggggacatg atcacggaggaggcgctgccgacctacatggccatgctcaacacgctggacggcgtgcgcgacgacacgggcgcggccgaccacc cgtgggcgcgctggacgcggcagtgggtggccgaggagaaccggcacggcgacctgctgaacaagtactgctggctgacggggc gcgtcaacatgcgggccgtggaggtgaccatcaacaacctgatcaagagcggcatgaacccgcagacggacaacaacccttattt ggggttcgtctacacctccttccaggagcgcgccaccaagtaggtaccctttcttgcgctatgacacttccagcaaaaggtagggcg ggctgcgagacggcttcccggcgctgcatgcaacaccgatgatgcttcgacccccccgaagctccttcggggctgcatgggcgctccg -continued atgccgctccagggcgagcgctgtttaaatagccaggcccccgattgcaaagacattatagcgagctaccaaagccatattcaaac acctagatcactaccacttctacacaggccactcgagcttgtgatcgcactccgctaagggggcgcctcttcctcttcgtttcagtcac aacccgcaaactctagaatatca*ATGatcgagcaggacggcctccacgccggctcccccgccgcctgggtggagcgcctgttc*

*ggctacgactgggcccagcagaccatcggctgctccgacgccgccgtgttccgcctgtccgcccagggccgccccgtgctgttc*

*gtgaagaccgacctgtccggcgccctgaacgagctgcaggacgaggccgcccgcctgtcctggctggccaccaccggcgtgc*

*cctgcgccgccgtgctggacgtggtgaccgaggccggccgcgactggctgctgctgggcgaggtgcccggccaggacctgct*

*gtcctcccacctggcccccgccgagaaggtgtccatcatggccgacgccatgcgccgcctgcacaccctggaccccgccacctg*

*ccccttcgaccaccaggccaagcaccgcatcgagcgcgcccgcacccgcatggaggccggcctggtggaccaggacgacctg*

*gacgaggagcaccagggcctggcccccgccgagctgttcgcccgcctgaaggcccgcatgcccgacggcgaggacctggtg*

*gtgacccacggcgacgcctgcctgcccaacatcatggtggagaacggccgcttctccggcttcatcgactgcggccgcctgggc* gtggccgaccgctaccaggacatcgccctggccacccgcgacatcgccgaggagctgggcggcgagtgggccgaccgcttcc

*tggtgctgtacggcatcgccgcccccgactcccagcgcatcgccttctaccgcctgctggacgagttcttcTGA*caattgGCAG

CAGCAGCTCGGATAGTATCGACACACTCTGGACGCTGGTCGTGTGATGGACTGTTGCCGCCACACTT

GCTGCCTTGACCTGTGAATATCCCTGCCGCTTTTATCAAACAGCCTCAGTGTGTTTGATCTTGTGTGT

ACGCGCTTTTGCGAGTTGCTAGCTGCTTGTGCTATTTGCGAATACCACCCCCAGCATCCCCTTCCCTC

GTTTCATATCGCTTGCATCCCAACCGCAACTTATCTACGCTGTCCTGCTATCCCTCAGCGCTGCTCCTG

CTCCTGCTCACTGCCCCTCGCACAGCCTTGGTTTGGGCTCCGCCTGTATTCTCCTGGTACTGCAACCT

GTAAACCAGCACTGCAATGCTGATGCACGGGAAGTAGTGGGATGGGAACACAAATGGAggatcccgc gtctcgaacagagcgcgcagaggaacgctgaaggtctcgcctctgtcgcacctcagcgcggcatacaccacaataaccacctgacg aatgcgcttggttcttcgtccattagcgaagcgtccggttcacacacgtgccacgttggcgaggtggcaggtgacaatgatcggtgg agctgatggtcgaaacgttcacagcctagggatatcgaattcctttcttgcgctatgacacttccagcaaaaggtagggcgggctgc gagacggcttcccggcgctgcatgcaacaccgatgatgcttcgacccccgaagctccttcggggctgcatgggcgctccgatgccg ctccagggcgagcgctgtttaaatagccaggcccccgattgcaaagacattatagcgagctaccaaagccatattcaaacacctag atcactaccacttctacacaggccactcgagcttgtgatcgcactccgctaagggggcgcctcttcctcttcgtttcagtcacaacccg caaacactagt*GCGCTGGACGCGGCAGTGGGTGGCCGAGGAGAACCGGCACGGCGACCTGCTGAAC*

*AAGTACTGTTGGCTGACGGGGCGCGTCAACATGCGGGCCGTGGAGGTGACCATCAACAACCTGAT*

*CAAGAGCGGCATGAACCCGCAGACGGACAACAACCCTTACTTGGGCTTCGTCTACACCTCCTTCCAG*

*GAGCGCGCGACCAAGTACAGCCACGGCAACACCGCGCGCCTTGCGGCCGAGCA*_GTGTGTTTGAGG_

GTTTTGGTTGCCCGTATCGAGGTCCTGGTGGCGCGCATGGGGGAGAAGGCGCCTGTCCCGCTGACC

*CCCCCGGCTACCCTCCCGGCACCTTCCAGGGCGCGTACG*ggatcc*TGCTCGGCCGCAAGGCGCGCGGT*

*GTTGCCGTGGCTGTACTTGGTCGCGCGCTCCTGGAAGGAGGTGTAGACGAAGCCCAAGTAAGGGT*

*TGTTGTCCGTCTGCGGGTTCATGCCGCTCTTGATCAGGTTGTTGATGGTCACCTCCACGGCCCGCAT*

*GTTGACGCGCCCCGTCAGCCAACAGTACTTGTTCAGCAGGTCGCCGTGCCGGTTCTCCTCGGCCACC*

*CACTGCCGCGTCCAGCGC*aagcttGCAGCAGCAGCTCGGATAGTATCGACACACTCTGGACGCTGGTC

GTGTGATGGACTGTTGCCGCCACACTTGCTGCCTTGACCTGTGAATATCCCTGCCGCTTTTATCAAAC

AGCCTCAGTGTGTTTGATCTTGTGTGTACGCGCTTTTGCGAGTTGCTAGCTGCTTGTGCTATTTGCGA

ATACCACCCCCAGCATCCCCTTCCCTCGTTTCATATCGCTTGCATCCCAACCGCAACTTATCTACGCTG

-continued

TCCTGCTATCCCTCAGCGCTGCTCCTGCTCCTGCTCACTGCCCCTCGCACAGCCTTGGTTTGGGCTCCG

CCTGTATTCTCCTGGTACTGCAACCTGTAAACCAGCACTGCAATGCTGATGCACGGGAAGTAGTGGG

ATGGGAACACAAATGGAaagctggagctccagccacggcaacaccgcgcgccttgcggccgagcacggcgacaagaacc tgagcaagatctgcgggctgatcgccagcgacgagggccggcacgagatcgcctacacgcgcatcgtggacgagttcttccgcctc gaccccgagggcgccgtcgccgcctacgccaacatgatgcgcaagcagatcaccatgcccgcgcacctcatggacgacatgggcc acggcgaggccaacccgggccgcaacctcttcgccgacttctccgcggtcgccgagaagatcgacgtctacgacgccgaggactac tgccgcatcctggagcacctcaacgcgcgctggaaggtggacgagcgccaggtcagcggccaggccgccgcggaccaggagtac gtcctgggcctgccccagcgcttccggaaactcgccgagaagaccgccgccaagcgcaagcgcgtcgcgcgcaggcccgtcgcctt ctcctggatctccgggcgcgagatcatggtctaggggagcgacgagtgtgcgtgcggggctggcgggagtgggacgccctcctcgct cctctctgttctgaacggaacaatcggccaccccgcgctacgcgccacgcatcgagcaacgaagaaaaccccccgatgataggttg cggtggctgccgggatatagatccggccgcacatcaaagggcccctccgccagagaagaagctcctttcccagcagactcctgaag agc

The sequence of the transforming DNA derived from pSZ2697 is provided immediately below. Relevant restriction sites are indicated in lowercase, bold, and are from 5'-3' NsiI, SpeI, BamHI, HinDIII, SacII, EcoRV, KpnI, XbaI, MfeI, BamHI, AvrII, EcoRV, EcoRI and XbaI, respectively. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the SAD2 hairpin *C* sense and antisense strands are indicated with uppercase, bold italics, and are separated by the *P. moriformis* FAD2 intron and the first 10 bases of the FAD2 second exon (uppercase italics). The 3' UTR of the *C. vulgaris* NR gene is indicated by small capitals. The *Chlorella sorokiniana* Glutamate Dehydrogenase (GDH) promoter, driving the expression of neoR (encoding aminoglycoside phosphotransferase activity, thereby permitting the strain to grow on G418) is indicated by lowercase, boxed text. The initiator ATG and terminator TGA for neoR are indicated by uppercase italics, while the coding region is indicated with lowercase italics. A second *C. vulgaris* NR3' UTR is indicated by small capitals, followed by a spacer region indicated by lowercase text.

Nucleotide sequence of the transforming DNA from pSZ2697:

(SEQ ID NO: 98)

atgcatgccggtcaccacccgcatgctcgtactacagcgcacgcaccgcttcgtgatccaccgggtgaacgtagtcctcgacggaa acatctggttcgggcctcctgcttgcactcccgcccatgccgacaacctttctgctgttaccacgacccacaatgcaacgcgacacga ccgtgtgggactgatcggttcactgcacctgcatgcaattgtcacaagcgcttactccaattgtattcgtttgttttctgggagcagttg ctcgaccgcccgcgtcccgcaggcagcgatgacgtgtgcgtggcctgggtgtttcgtcgaaaggccagcaaccctaaatcgcaggc gatccggagattgggatctgatccgagtttggaccagatccgcccccgatgcggcacgggaactgcatcgactcggcgcggaaccca gctttcgtaaatgccagattggtgtccgatacctggatttgccatcagcgaaacaagacttcagcagcgagcgtatttggcgggcgt gctaccagggttgcatacattgcccatttctgtctggaccgctttactggcgcagagggtgagttgatggggttggcaggcatcgaaa cgcgcgtgcatggtgtgcgtgtctgttttcggctgcacgaattcaatagtcggatgggcgacggtagaattgggtgtggcgctcgcgt gcatgcctcgccccgtcgggtgtcatgaccgggactggaatcccccctcgcgaccatcttgctaacgctcccgactctcccgactagt

*GCGCTGGACGCGGCAGTGGGTGGCCGAGGAGAACCGGCACGGCGACCTGCTGAACAAGTACTGT*

*TGGCTGACGGGGCGCGTCAACATGCGGGCCGTGGAGGTGACCATCAACAACCTGATCAAGAGCG*

*GCATGAACCCGCAGACGGACAACAACCCTTACTTGGGCTTCGTCTACACCTCCTTCCAGGAGCGCGC*

*GACCAAGTACAGCCACGGCAACACCGCGCGCCTTGCGGCCGAGCA**GTGTGTTTGAGGGTTTTGGTT*

GCCCGTATCGAGGTCCTGGTGGCGCGCATGGGGGAGAAGGCGCCTGTCCCGCTGACCCCCCCGGCT

*ACCCTCCCGGCACCTTCCAGGGCGCGTACG*ggatcc*TGCTCGGCCGCAAGGCGCGCGGTGTTGCCGTG*

*GCTGTACTTGGTCGCGCGCTCCTGGAAGGAGGTGTAGACGAAGCCCAAGTAAGGGTTGTTGTCCG*

*TCTGCGGGTTCATGCCGCTCTTGATCAGGTTGTTGATGGTCACCTCCACGGCCCGCATGTTGACGCG*

-continued

*CCCCGTCAGCCAACAGTACTTGTTCAGCAGGTCGCCGTGCCGGTTCTCCTCGGCCACCCACTGCCGC*

*GTCCAGCGC*aagcttGCAGCAGCAGCTCGGATAGTATCGACACACTCTGGACGCTGGTCGTGTGATG

GACTGTTGCCGCCACACTTGCTGCCTTGACCTGTGAATATCCCTGCCGCTTTTATCAAACAGCCTCAG

TGTGTTTGATCTTGTGTGTACGCGCTTTTGCGAGTTGCTAGCTGCTTGTGCTATTTGCGAATACCACC

CCCAGCATCCCCTTCCCTCGTTTCATATCGCTTGCATCCCAACCGCAACTTATCTACGCTGTCCTGCTA

TCCCTCAGCGCTGCTCCTGCTCCTGCTCACTGCCCCTCGCACAGCCTTGGTTTGGGCTCCGCCTGTATT

CTCCTGGTACTGCAACCTGTAAACCAGCACTGCAATGCTGATGCACGGGAAGTAGTGGGATGGGAA

CACAAATGGAAAGCTGgagctcaaagatatcaacttaattaaccaaggtacccgcctgcaacgcaagggcagccacagcc gctcccacccgccgctgaaccgacacgtgcttgggcgcctgccgcctgcctgccgcatgcttgtgctggtgaggctgggcagtgctg ccatgctgattgaggcttggttcatcgggtggaagcttatgtgtgtgctgggcttgcatgccgggcaatgcgcatggtggcaagagg gcggcagcacttgctggagctgccgcggtgcctccaggtggttcaatcgcggcagccagagggatttcagatgatcgcgcgtacag gttgagcagcagtgtcagcaaaggtagcagtttgccagaatgatcggttcagctgttaatcaatgccagcaagagaaggggtcaag tgcaaacacgggcatgccacagcacgggcaccggggagtggaatggcaccaccaagtgtgtgcgagccagcatcgccgcctggct gtttcagctacaacggcaggagtcatccaacgtaaccatgagctgatcaacactgcaatcatcgggcgggcgtgatgcaagcatgc ctggcgaagacacatggtgtgcggatgctgccggctgctgcctgctgcgcacgccgttgagttggcagcaggctcagccatgcactg gatggcagctgggctgccactgcaatgtggtggataggatgcaagtggagcgaataccaaaccctctggctgcttgctgggttgcat ggcatcgcaccatcagcaggagcgcatgcgaagggactggccccatgcacgccatgccaaaccggagcgcaccgagtgtccaca ctgtcaccaggcccgcaagctttgcagaaccatgctcatggacgcatgtagcgctgacgtcccttgacggcgctcctctcgggtgtg ggaaacgcaatgcagcacaggcagcagaggcggcggcagcagagcggcggcagcagcggcgggggccacccttcttgcggggt cgcgccccagccagcggtgatgcgctgatcccaaacgagttcacattcatttgcatgcctggagaagcgaggctggggcctttgggc tggtgcagcccgcaatggaatgcgggaccgccaggctagcagcaaaggcgcctcccctactccgcatcgatgttccatagtgcatt ggactgcatttgggtggggcggccggctgtttctttcgtgttgcaaaacgcgccagctcagcaacctgtcccgtgggtcccccgtgcc gatgaaatcgtgtgcacgccgatcagctgattgcccggctcgcgaagtaggcgccctcctttctgctcgccctctctccgtcccgcctc taga*atatcaATGatcgagcaggacggcctccacgccggctcccccgccgcctgggtggagcgcctgttcggctacgactggg*

*cccagcagaccatcggctgctccgacgccgccgtgttccgcctgtccgcccagggccgccccgtgctgttcgtgaagaccgacct*

*gtccggcgccctgaacgagctgcaggacgaggccgcccgcctgtcctggctggccaccaccggcgtgccctgcgccgccgtgc*

*tggacgtggtgaccgaggccggccgcgactggctgctgctgggcgaggtgcccggccaggacctgctgtcctcccacctggcc*

*cccgccgagaaggtgtccatcatggccgacgccatgcgccgcctgcacaccctggaccccgccacctgccccttcgaccaccag*

*gccaagcaccgcatcgagcgcgcccgcacccgcatggaggccggcctggtggaccaggacgacctggacgaggagcacca*

*gggcctggcccccgccgagctgttcgcccgcctgaaggcccgcatgcccgacggcgaggacctggtggtgacccacggcgac*

*gcctgcctgcccaacatcatggtggagaacggccgcttctccggcttcatcgactgcggccgcctgggcgtggccgaccgctac*

*caggacatcgccctggccacccgcgacatcgccgaggagctgggcggcgagtgggccgaccgcttcctggtgctgtacggca*

*tcgccgcccccgactcccagcgcatcgccttctaccgcctgctggacgagttcttcTGA*caattgGCAGCAGCAGCTCGGA -continued

TAGTATCGACACACTCTGGACGCTGGTCGTGTGATGGACTGTTGCCGCCACACTTGCTGCCTTGACC

TGTGAATATCCCTGCCGCTTTTATCAAACAGCCTCAGTGTGTTTGATCTTGTGTGTACGCGCTTTTGC

GAGTTGCTAGCTGCTTGTGCTATTTGCGAATACCACCCCCAGCATCCCCTTCCCTCGTTTCATATCGCT

TGCATCCCAACCGCAACTTATCTACGCTGTCCTGCTATCCCTCAGCGCTGCTCCTGCTCCTGCTCACTG

CCCCTCGCACAGCCTTGGTTTGGGCTCCGCCTGTATTCTCCTGGTACTGCAACCTGTAAACCAGCACT

GCAATGCTGATGCACGGGAAGTAGTGGGATGGGAACACAAATGGAggatcccgcgtctcgaacagagcgcg cagaggaacgctgaaggtctcgcctctgtcgcacctcagcgcggcatacaccacaataaccacctgacgaatgcgcttggttcttcg tccattagcgaagcgtccggttcacacacgtgccacgttggcgaggtggcaggtgacaatgatcggtggagctgatggtcgaaacg ttcacagcctagggatatcgaattccgggtcgccgcgctgcctcgcgtcccctggtggtgcgcgcggtcgccagcgaggccccgctg ggcgttccgccctcggtgcagcccccctcccccgtggtctactccaagctggacaagcagcaccgcctgacgcccgagcgcctgg gctggtgcagagcatggggcagtttgcggaggagagggtgctgcccgtgctgcaccccgtggacaagctgtggcagccgcaggac tttttgcccgaccccgagtcgcccgacttcgaggatcaggtggcggagctgcgcgcgcgcgccaaggacctgcccgacgagtacttt gtggtgctggtgggggacatgatcacggaggaggcgctgccgacctacatggccatgctcaacacgctggacggcgtgcgcgacg acacgggcgcggccgaccacccgtgggcgcgctggacgcggcagtgggtggccgaggagaaccggcacggcgacctgctgaaca agtactgctggctgacggggcgcgtcaacatgcgggccgtggaggtgaccatcaacaacctgatcaagagcggcatgaacccgca gacggacaacaacccttatttggggttcgtctacacctccttccaggagcgcgccaccaagtatctaga

Identification and Analysis of SAD2 Knockout/Knockdown Strains in the S5003 Background:

Constructs D1639, derived from pSZ2697, and D1682, derived from pSZ2283, were transformed into Strain AA as described previously. Primary transformants were clonally purified and grown under standard lipid production conditions at pH 7. The resulting fatty acid profiles from representative clones arising from transformation are summarized in Table 47, below. D1639 transformants accumulated up to 56% C18:0, and D1682 transformants accumulated a maximum of about 35% C18:0. Most of the increases in stearate came at the expense of C18:1, indicating that SAD activity was significantly reduced by the SAD2 knockout/RNAi constructs in these strains. C16:0 levels varied from 6% to 14%; C18:2 ranged from 2-5%. Most strains maintained the low C16:0 and C18:2 phenotypes of the Strain AA parent. These fatty acid profiles demonstrate that down-regulating SAD2 expression using knockout/RNAi constructs, in a background with disrupted FATA-1, KASII over-expression and FAD2 RNAi, produces strains with high C18:0, low C16:0 and low C18:2 phenotypes. These strains will be useful for production of high stability, high stearate, high oleic oils, and oils which have high SOS content.

TABLE 47

Fatty acid profiles of D1639 [pSZ2697] and D1682 [pSZ2283] primary transformants, compared to the wild-type strain, Strain J, and the Strain AA parental base strain.

| Strain | | J | AA | D1682-4 | D1682-17 | D1682-7 | D1682-6 | D1639-2 | D1639-5 | D1639-10 | D1639-19 |
|---|---|---|---|---|---|---|---|---|---|---|---|
| Fatty | C12:0 | 0.04 | 0.11 | 0.14 | 0.10 | 0.32 | 0.31 | 0.00 | 0.19 | 0.17 | 0.00 |
| Acid | C14:0 | 1.29 | 0.98 | 1.03 | 0.94 | 1.11 | 1.15 | 1.64 | 1.39 | 1.61 | 1.02 |
| Area % | C16:0 | 27.50 | **7.75** | **8.68** | **10.41** | **5.70** | **5.96** | **7.54** | **9.90** | **14.39** | **12.02** |
| | C16:1 | 0.71 | 0.30 | 0.06 | 0.07 | 0.07 | 0.10 | 0.00 | 0.00 | 0.00 | 0.00 |
| | C18:0 | 3.28 | 3.60 | 35.46 | 29.92 | 24.66 | 22.30 | 55.96 | 53.38 | 43.46 | 37.30 |
| | C18:1 | 57.80 | **84.14** | 48.39 | 52.49 | 61.04 | 63.60 | 23.70 | 26.79 | 32.93 | 42.81 |
| | C18:2 | 7.90 | 2.09 | 2.37 | 2.36 | 3.03 | 2.88 | 5.09 | 3.5 | 3.22 | 2.79 |
| | C18:3α | 0.57 | 0.32 | 0.90 | 0.65 | 0.66 | 0.58 | 1.59 | 0.98 | 1.01 | 0.85 |
| | C20:0 | 0.28 | 0.23 | 2.07 | 1.87 | 1.75 | 1.51 | 3.04 | 2.73 | 2.29 | 2.22 |
| | C20:1 | 0.18 | 0.35 | 0.54 | 0.49 | 0.78 | 0.83 | 0.37 | 0.33 | 0.30 | 0.40 |
| | C22:0 | 0.06 | 0.02 | 0.27 | 0.27 | 0.23 | 0.20 | 0.43 | 0.36 | 0.29 | 0.29 |
| | C24:0 | 0.09 | 0.02 | 0.33 | 0.26 | 0.34 | 0.26 | 0.64 | 0.45 | 0.32 | 0.31 |
| sum C18 | | 69.55 | 90.14 | 86.72 | 85.42 | 89.39 | 89.36 | 86.34 | 84.65 | 80.62 | 83.75 |
| saturates | | 32.54 | 12.70 | 47.98 | 43.77 | 34.11 | 31.69 | 69.25 | 68.40 | 62.53 | 53.16 |
| unsaturates | | 67.16 | 87.21 | 51.86 | 66.06 | 65.58 | 67.99 | 30.75 | 31.60 | 37.46 | 46.85 |

In Table 47, Stearate (C18:0) levels greater than the wild-type level are highlighted with bold text. Oleate (C18:1) levels that are higher than in the wild-type are indicated with bold text. Palmitate (C16:0) levels less than the wild-type level are highlighted with bold. Reduced levels of linoleate (C18:2) compared to the wild-type are highlighted with bold text.

Stable lines were isolated from a number of D1639 and D1682 transformants. Shake flask assays were carried out to evaluate the performance of four lines derived from D1639-5. Fatty acid profiles and relative lipid titers from the biomass are shown in Table 48, below.

TABLE 48

Shake flask assays of strains derived from D1639-5, expressing SAD2hpC, driven by the CrTUB2 promoter, targeted to the SAD2-1 locus.

| | | | | Primary T530; D1639-5 | | | |
|---|---|---|---|---|---|---|---|
| Strain | | J | AA | AW | AX | AY | BL |
| Fatty Acid Area % | C10:0 | 0.01 | 0.00 | 0.07 | 0.08 | 0.05 | 0.04 |
| | C12:0 | 0.02 | 0.11 | 0.19 | 0.22 | 0.25 | 0.23 |
| | C14:0 | 1.52 | 1.10 | 1.35 | 1.32 | 1.30 | 1.43 |
| | C16:0 | 31.61 | **9.59** | **9.28** | **8.44** | **7.74** | **9.46** |
| | C16.1 | 1.04 | 0.34 | 0.03 | 0.02 | 0.01 | 0.01 |
| | C17:0 | 0.10 | 0.11 | 0.10 | 0.10 | 0.10 | 0.09 |
| | C18:0 | 2.98 | 4.36 | **53.01** | **53.52** | **55.32** | **52.09** |
| | C18:1 | 54.81 | **80.84** | 27.26 | 27.52 | 27.42 | 28.06 |
| | C18:2 | 6.88 | **2.42** | **3.55** | **3.52** | **2.38** | **3.45** |
| | C18:3α | 0.53 | 0.33 | 0.97 | 1.03 | 0.82 | 1.06 |
| | C20:0 | 0.26 | 0.31 | 2.88 | 2.94 | 3.15 | 2.72 |
| | C20:1 | 0.05 | 0.34 | 0.38 | 0.38 | 0.40 | 0.37 |
| | C22:0 | 0.03 | 0.06 | 0.36 | 0.37 | 0.39 | 0.35 |
| | C24:0 | 0.07 | 0.08 | 0.53 | 0.54 | 0.53 | 0.60 |
| sum C18 | | 65.19 | 87.95 | 84.79 | 85.58 | 85.94 | 84.66 |
| saturates | | 36.59 | 15.70 | 67.76 | 67.52 | 68.82 | 66.99 |
| unsaturates | | 63.30 | 84.26 | 32.19 | 32.46 | 31.02 | 32.95 |
| % wild-type lipid titer | | 100.0 | 70.3 | 34.8 | 33.7 | 31.4 | 35.3 |

In Table 48, Strain AA is the parent strain; Strain J is the wild-type base strain. Stearate (C18:0) levels higher than in the wild-type strain are indicated with bold. Bold text indicates the increased level of oleate (C18:1) in Strain AA compared to the wild-type. Palmitate (C16:0) levels that are less than in the wild-type are highlighted bold. Linoleate (C18:2) levels that are less than in the wild-type are indicated with bold.

Figure 21:
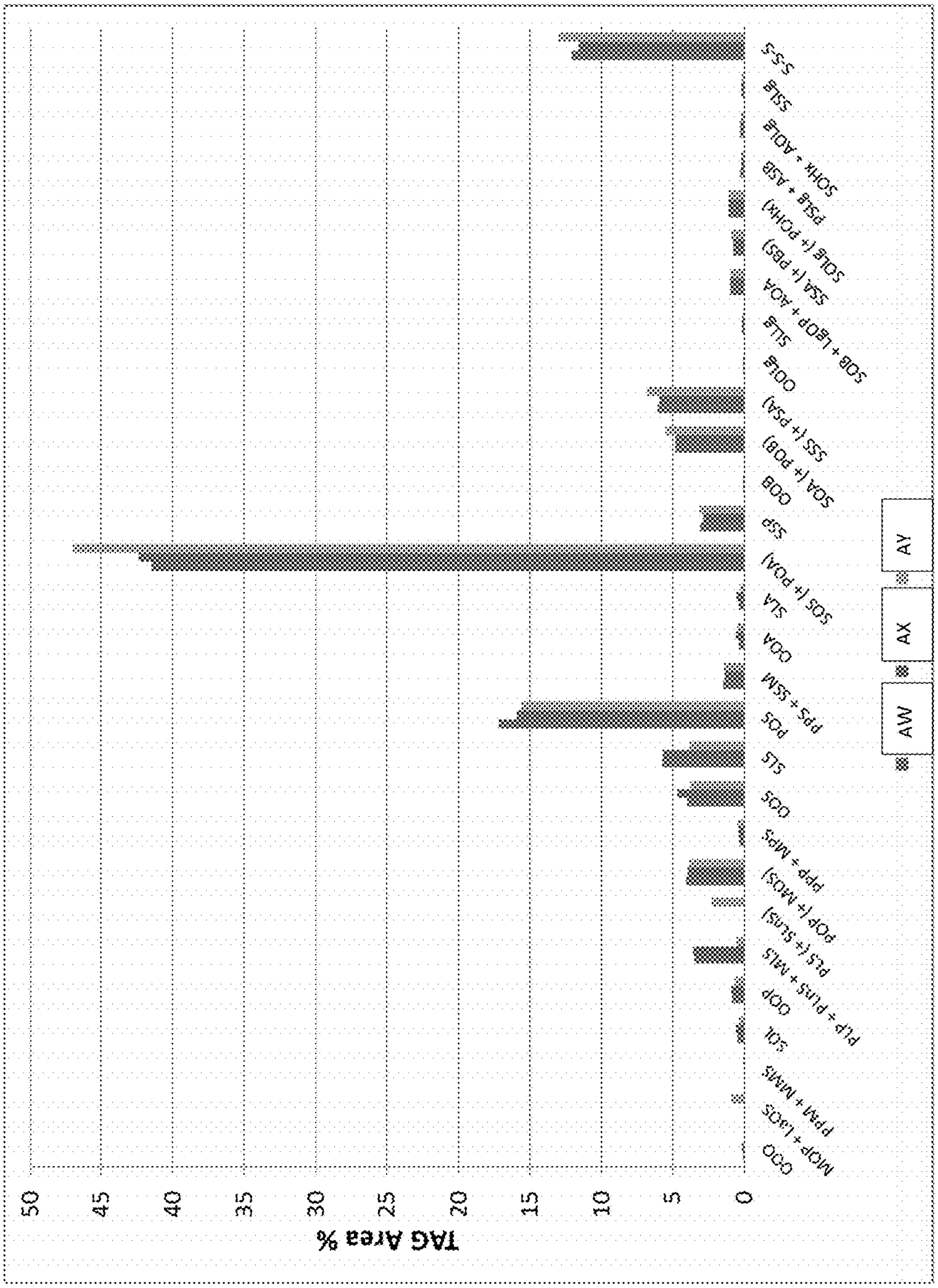
FIG. 21 shows TAG composition of Strain AW Strain AX and Strain AY oils from shake flask biomass. La=laurate (C12:0), M=myristate (C14:0), P=palmitate (C16:0), Po=palmitoleate (C16:1), S=stearate (C18:0), O=oleate (C18:1), L=linoleate (C18:2), Ln=α-linolenate (C18:3), A=arachidate (C20:0), B=behenate (C22:0), Lg=lignocerate (C24:0), Hx=hexacosanoate (C26:0). S—S—S refers to the sum of TAGs in which all three fatty acids are saturated. In each block of bars, the strains are shown in the order illustrated at the bottom of the figure.
Figure 22:
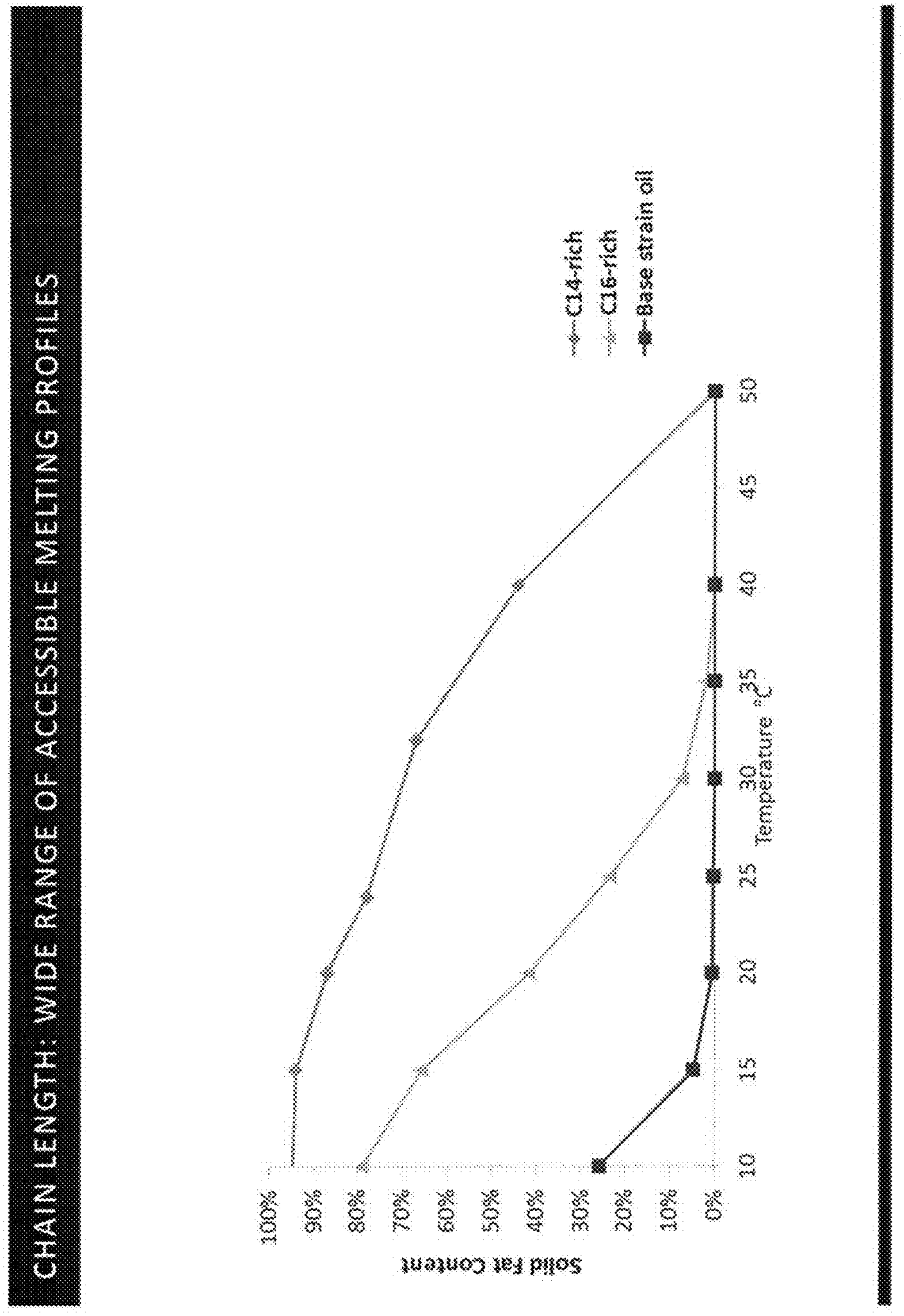
FIG. 22 shows the fatty acid profile and solid fat content of a refined, bleached and deodorized myristate rich oil from a genetically engineered *Prototheca moriformis* strain as discussed in Example 52.

Lab scale oils were prepared from biomass collected from the Strain AW, AX and AY shake flasks. The TAG compositions of these oils were determined by LC/MS, and are shown in FIG. 21. SOS accumulation ranged from 42-47% in these strains. POS was the next most abundant TAG, at 16-17%. Linoleate-containing TAGs were reduced by more than 50% compared to the Strain AU and AV oils, described above. Strain AW, AX, and AY oils contained 12-13% trisaturated TAGs (S—S—S), similar to the amounts that accumulated in the Strain AU and AX oils. Modulation of SAD activity during oil production to prevent overproduction of saturated fatty acids may help to reduce accumulation of trisaturates.

Example 49: Properties of Methyl Oleate from High Oleic Microalgal Oils

Esterified oils high in methyl oleate are useful in a variety of applications such as cleaning and lubrication of machinery. For some of these applications, high thermal stability is desired. Thermal stability testing was performed on methylated oil prepared from high-oleic and high-stability-high oleic triglyceride oils prepared from heterotrophically grown oleaginous microalgae as described above. The oils were bleached and deodorized prior to methylation. Commercially available soya methyl ester was used as a control.

High Oleic (HO) oil was prepared from a high oil-yielding strain of *Prototheca moriformis* transformed with a plasmid that can be described as FatA1_Btub:inv:nr::amt03-CwTE2:nr_FatA1. This plasmid was designed to homologously recombine in the FATA1 chromosomal site, thus ablating a FATA acyl-ACP thioesterase chromosomal allele, while expressing an exogenous acyl-ACP thioesterase from *Cuphea wrightii* (CwTE2, SEQ ID NO: 11) under control of the pH-regulatable amt3 promoter. The CwTE2 gene can be downregulated by cultivation at pH 5 during oil production to further elevate oleate production. Sucrose invertase was also expressed as a selection marker and to allow for cultivation of the strain on sucrose as a sole carbon source. The 3' UTR sequences are from the *Chlorella vulgaris* nitrate reductase gene. The resulting HO strain is denoted Stain Q. The fatty acid profile of the oil produced by Strain Q is listed below in Table 49.

TABLE 49

Fatty acid profile of high oleic oil from Strain Q.

| Fatty Acid | Area % |
|---|---|
| C10 | 0.01 |
| C12:0 | 0.03 |
| C14:0 | 0.43 |
| C15:0 | 0.03 |
| C16:0 | 7.27 |
| C16:1 iso | 0.81 |
| C16:1 | 0.689 |
| C17:0 | 0.06 |
| C18:0 | 1.198 |
| C18:1 | 80.15 |
| C18:1 iso | 0.08 |
| C18:2 | 8.38 |
| C18:3 ALPHA | 0.25 |
| C20:0 | 0.02 |
| C20:1 | 0.38 |
| C22:0 | 0.04 |
| C24:0 | 0.03 |

A high-stability-high-oleic oil (HSAO) was also prepared from a high oil-yielding strain of *Prototheca moriformis* transformed with a plasmid that can be described as FADc5'_Btub:inv:nr::btub-CpSAD_CtOTE:nr_FADc3'. The resulting strain (Strain R) expresses sucrose invertase as a selectable marker and to allow for cultivation on sucrose as a sole carbon source. In addition, a FAD allele (encoding fatty acid desaturase responsible for the conversion of oleate to linoleate) is disrupted and an oleate-specific acyl-ACP thioesterase (*Carthamus tinctorius* OTE, see example 5) fused to the transit peptide from the SAD gene of *Chlorella protothecoides* is expressed under control of the beta tubulin promoter. The 3' UTR sequences are from the *Chlorella vulgaris* nitrate reductase gene. The fatty acid profile of the oil produced by Strain R after heterotrophic cultivation is listed below in Table 50. The fatty acid profile has greater than 85% oleate yet almost none of the major polyunsaturates, linoleic and linolenic acids.

TABLE 50

Fatty acid profile of high oleic oil from Strain R.

| Fatty Acid | Area % |
|---|---|
| C10 | 0.02 |
| C12:0 | 0.07 |
| C14:0 | 0.09 |
| C15:0 | 0.05 |
| C16:0 | 7.28 |
| C16:1 | 0.70 |
| C17:0 | 0.08 |
| C18:0 | 2.15 |
| C18:1 | 86.32 |
| C20:0 | 0.30 |
| C20:1 | 0.46 |
| C22:0 | 0.08 |

TABLE 50-continued

| Fatty acid profile of high oleic oil from Strain R. | |
|---|---|
| Fatty Acid | Area % |
| C23:0 | 0.01 |
| C24:0 | 0.06 |

The HO and HSAO oils were methylated by known biodiesel production techniques to make methyl-HO and methyl-HSAO esters. These methyl esters where then subjection to thermal testing according to the following procedure:

1. Prepare equipment as shown in FIG. 1.
2. Add 1 liter of water to test vessel and bring to an active boil on the hotplate.
3. To each test product add 50 ppm Cobalt (0.083 g of 6% Cobalt Napthenate in 100.0 gram sample) and mix thoroughly.
4. Weigh out, in a watch glass, 7.0 g of 100% cotton gauze, (#50 Cheese Cloth).
5. Evenly distribute 14.0 g of test product, as prepared in step 3, onto the gauze.
6. Place thermocouple (thermometer) through the center of #15 stopper. Wrap cotton around the thermocouple.
7. Place wrapped cotton into 24 mesh wire frame cylinder so that it occupies the upper 4½ inches.
8. Position cylinder with wrapped gauze into the 1 L tall form beaker. Secure the beaker in the boiling water and begin recording the temperature increase with time.
9. Continue monitoring the temperature for 2 hours or until a 10 degree temperature drop in observed.
10. Plot temperature vs time on a graph.
11. Any sample which shows a temperature exceeding 100 degrees C. in 1 hour or 200 degrees C. in 2 hours should be regarded as a dangerous oxidation risk or one that is likely to spontaneously combust.

Figure 18:
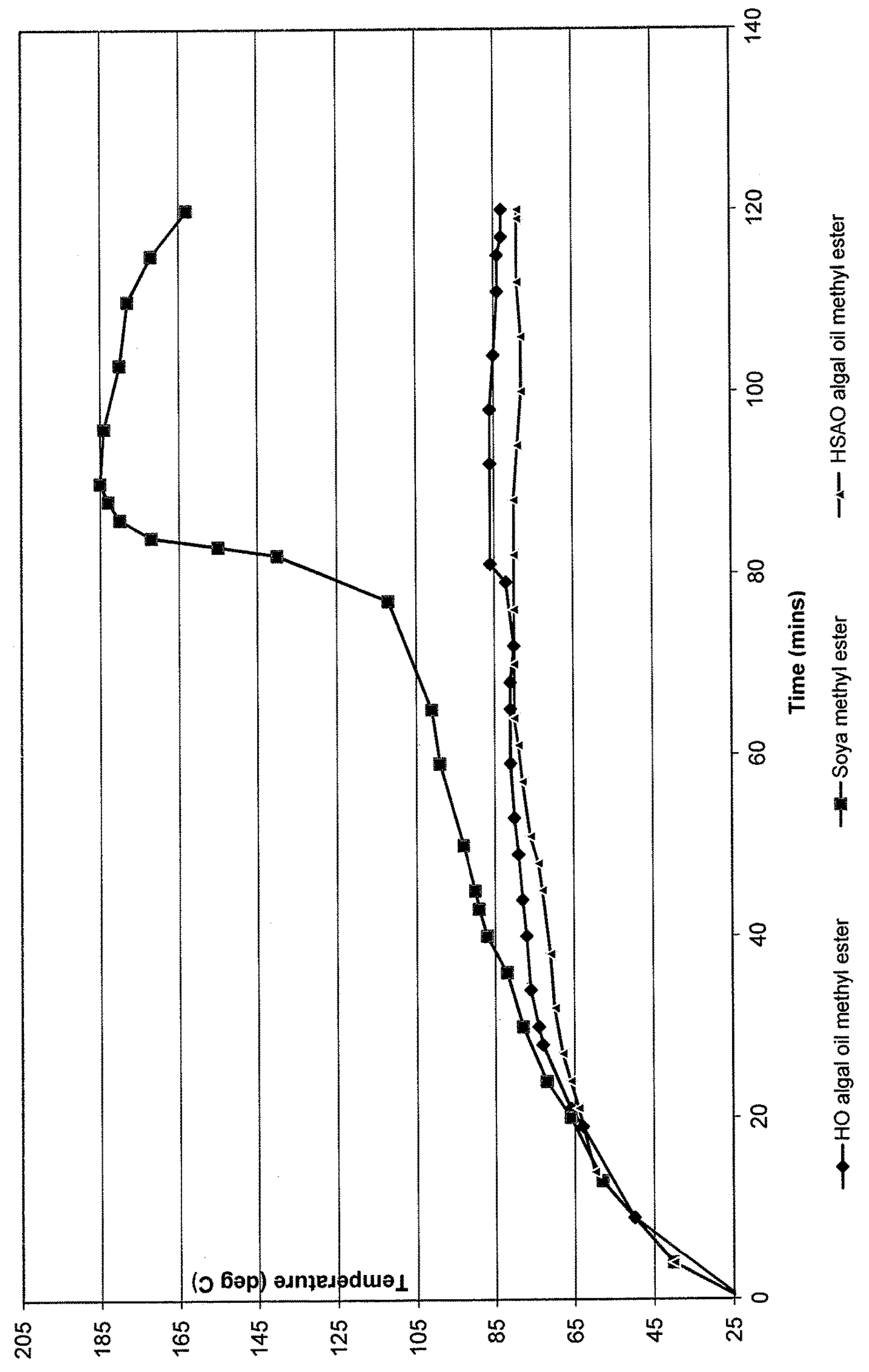
FIG. 18 shows the results of thermal stability testing performed on methylated oil prepared from high-oleic (HO) and high-stability high-oleic (HSAO) triglyceride oils prepared from heterotrophically grown oleaginous microalgae, in comparison to a soya methyl ester control sample.
Figure 20:
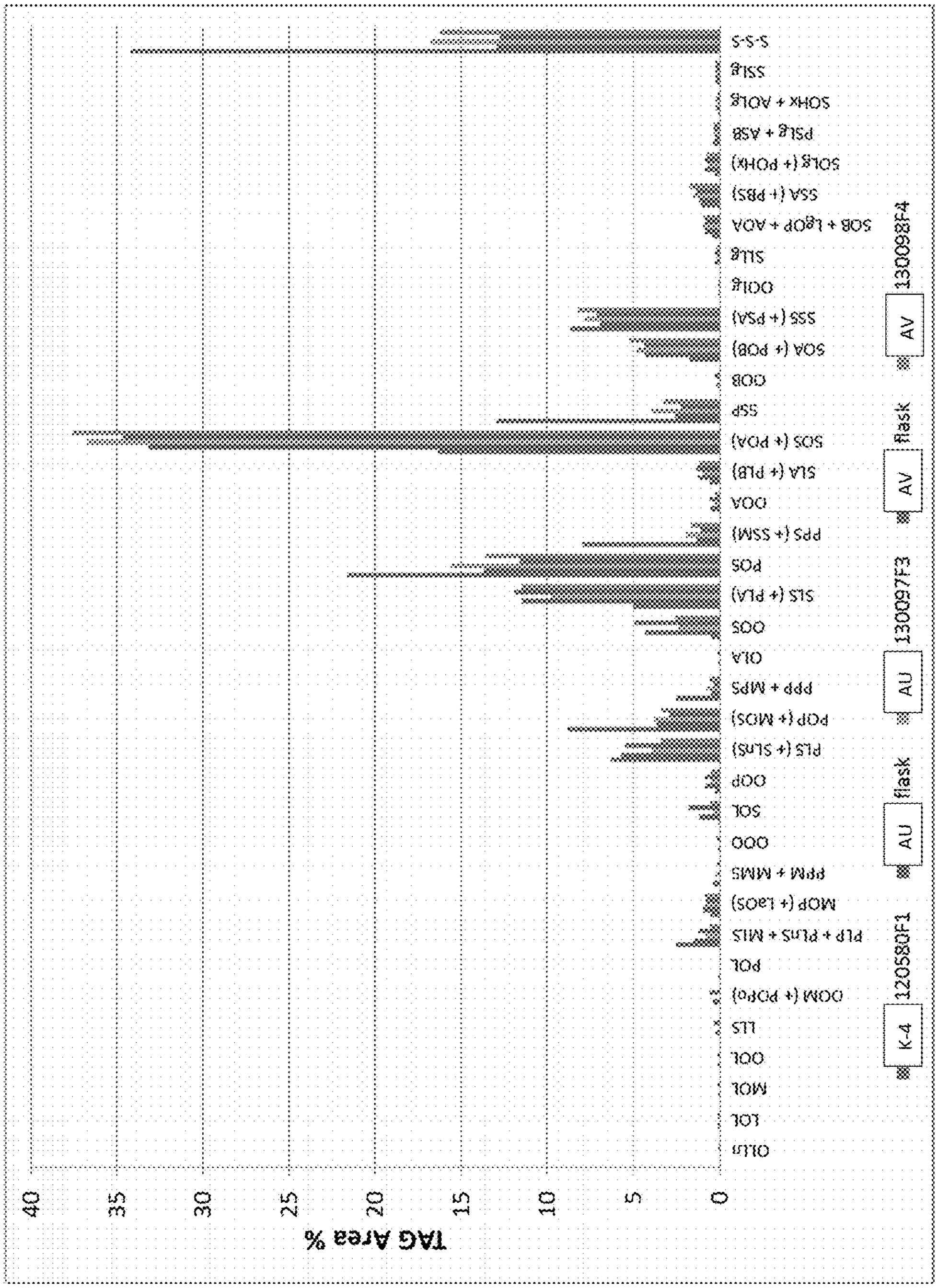
FIG. 20 shows TAG composition of Strain K-4, Strain AU and Strain AV oils from flask and fermenter biomass. La=laurate (C12:0), M=myristate (C14:0), P=palmitate (C16:0), Po=palmitoleate (C16:1), S=stearate (C18:0), O=oleate (C18:1), L=linoleate (C18:2), Ln=α-linolenate (C18:3), A=arachidate (C20:0), B=behenate (C22:0), Lg=lignocerate (C24:0), Hx=hexacosanoate (C26:0) S—S—S refers to the sum of TAGs in which all three fatty acids are saturated. In each block of bars, the strains are shown in the order illustrated at the bottom of the figure.

Results: The HO and HSAO methyl ester did not exhibit auto-oxidation as evidenced by a temperature rise. The control soya methyl ester sample did exhibit the potential for auto-oxidation. The time-temperature profiles are shown in FIG. 18.

In addition, methylated fatty acid from oil produced by Strain Q was found to have the following characteristics:

Flash Point (ASTM D93) of 182° C.

Non-VOC

Kauri Butanol value (ASTM D1133) of 53.5

Viscosity at 40° C. (ASTM D445) of 4.57 mm2/s

Acid Number (ASTM D664) of 0.17 mg KOH/g

Boiling range distribution (ASTM D2887) 325-362° C.

Example 50: Further Properties of High Oleic (HO) and High-Stability-High-Oleic (HSAO) Microalgal Oils The high oleic oil and the high-stability high-oleic algal oils can have the properties shown in FIG. 19 or these values±20% for the measured parameters.

In one experiment, HSAO microalgal oil showed 512 hour stability measured by OSI at 110° C. (estimated using 130° C. data) with antioxidants of 0.5% phenyl-alpha-naphthylamine (PANA) and 500 ppm ascorbyl palmitate (AP).

Example 51: Production of Low Saturate Oil by Conversion of Palmitic to Palmitoleate As described in the examples above, genetic manipulation of microalgae can decrease saturated fat levels, especially by increasing the production of oleic acid. However, in some cases, the acyl-ACP thioesterases expressed in the oleaginous cell liberate more than desirable amounts of palmitate. Here, we describe methods for converting palmitate (16:0) to palmitoleate (16:1) by overexpressing a palmitoyl-ACP desaturase (PAD) gene. The PAD gene can be obtained from natural sources such as *Macfadyena unguis* (Cat's claw), *Macadamia integrifolia* (*Macadamia* nut), *Hippophae rhamnoides* (sea buckthorn), or by creating a PAD via mutation of a stearoyl-ACP desaturase to have 16:1 activity. The *Macfadyena unguis* desaturase is denoted (MuPAD).

A high-oil-producing strain of *Prototheca moriformis* (Strain Z) is biolistically transformed with plasmid DNA constructs with a PAD gene. For example, one of the high oleic strains described in the Examples 6, 36, or 49 can further comprise an exogenous PAD gene. The constructs comprises sucrose invertase as a selectable marker and either the MuPAD or a SAD gene (e.g., *Olea europaea* stearoyl-ACP desaturase, GenBank Accession No. AAB67840.1) having the L118W mutation to shift substrate-specificity toward palmitate. See Cahoon, et al., Plant Physoil (1998) 117:593-598. Both the amt3 and beta tubulin (B tub) promoters are used. In addition, the native transit peptide of a plant PAD gene can be swapped with one known to be effective in microalgae (e.g., the transit peptide from the *Chlorella vularis* SAD gene).

The PAD gene can be expressed in a variety of strains including those with a FATA knockout or knockdown and/or a KASII knockin to produce high-oleic oil. Optionally, these strains can also produce high-stability (low polyunsaturate) oil by virtue of a FAD (delta 12 fatty acid desaturase) knockout, knockdown, or by placing FAD expression under control of a regulatable promoter and producing oil under conditions that downregulate FAD. In addition, useful base strains for the introduction of PAD gene activities might also include strains possessing KASII knockouts, and FATA Knockins, whereby levels of C16:0 palmitate are elevated.

As a result, lower levels of palmitic acid are found in the fatty acid profile of the microalgal oil as this is converted into cis-palmitoleic and cis-vaccenic acids. In some cases the total area percent of saturated fatty acids is less than equal to 3.5%, 3% or 2.5%.

Constructs for over expression of *Macfadyena unguis* C16:0 desaturase (MuPAD) follow:

1) pSZ3142: 6S::CrTUB2:ScSUC2:CvNR::PmAMT3:CpSADtp:MuPAD:CvNR::6S

Relevant restriction sites in the construct pSZ3142 6S::CrTUB2:ScSUC2:CvNR::PmAMT3:CpSADtp:MuPAD:CvNR::6S are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from that permit targeted integration at 6 s locus via homologous recombination. Proceeding in the 5' to 3' direction, the *C. reinhardtii* β-tubulin promoter driving the expression of the yeast sucrose invertase gene (conferring the ability of Strain Z to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *Prototheca moriformis*, indicated by boxed italics text. The Initiator ATG and terminator TGA codons of the MuPAD are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ3142:

(SEQ ID NO: 99)

gctcttcgccgccgccactcctgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaacccccttgcgcgttagtgttgccatcctttgcagaccggtgagagccgacttgttgtgcgccac cccccacaccacctcctcccagaccaattctgtcaccttttggcgaaggcatcggcctcggcctgcagagaggacagcagtgccc agccgctggggttggcggatgcacgctcaggtaccctttcttgcgctatgacacttccagcaaaaggtagggcgggctgcgagac ggcttcccggcgctgcatgcaacaccgatgatgcttcgacccccgaagctccttcggggctgcatgggcgctccgatgccgctcca gggcgagcgctgtttaaatagccaggcccccgattgcaaagacattatagcgagctaccaaagccatattcaaacacctagatcac taccacttctacacaggccactcgagcttgtgatcgcactccgctaagggggcgcctcttcctcttcgtttcagtcacaacccgcaaa ctctagaatatcaATG*ctgctgcaggccttcctgttcctgctggccggcttcgccgccaagatcagcgcctccatgacgaacga*

*gacgtccgaccgcccccctggtgcacttcacccccaacaagggctggatgaacgaccccaacggcctgtggtacgacgagaag*

*gacgccaagtggcacctgtacttccagtacaacccgaacgacaccgtctgggggacgcccttgttctggggccacgccacgtc*

*cgacgacctgaccaactgggaggaccagcccatcgccatcgccccgaagcgcaacgactccggcgccttctccggctccatgg*

*tggtggactacaacaacacctccggcttcttcaacgacaccatcgacccgcgccagcgctgcgtggccatctggacctacaaca*

*ccccggagtccgaggagcagtacatctcctacagcctggacggcggctacaccttcaccgagtaccagaagaaccccgtgctg*

*gccgccaactccacccagttccgcgacccgaaggtcttctggtacgagccctcccagaagtggatcatgaccgcggccaagtc*

*ccaggactacaagatcgagatctactcctccgacgacctgaagtcctggaagctggagtccgcgttcgccaacgagggcttcc*

*tcggctaccagtacgagtgccccggcctgatcgaggtccccaccgagcaggaccccagcaagtcctactgggtgatgttcatct*

*ccatcaaccccggcgccccggccggcggctccttcaaccagtacttcgtcggcagcttcaacggcacccacttcgaggccttcga*

*caaccagtcccgcgtggtggacttcggcaaggactactacgccctgcagaccttcttcaacaccgacccgacctacgggagcg*

*ccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatca*

*gcaacgccggcccctggagccggttcgccaccaacaccacgttgacgaaggccaacagctacaacgtcgacctgtccaacag*

*caccggcaccctggagttcgagctggtgtacgccgtcaacaccacccagacgatctccaagtccgtgttcgcggacctctccctc*

*tggttcaagggcctggaggaccccgaggagtacctccgcatgggcttcgaggtgtccgcgtcctccttcttcctggaccgcggg*

*aacagcaaggtgaagttcgtgaaggagaacccctacttcaccaaccgcatgagcgtgaacaaccagcccttcaagagcgag*

*aacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcga* caagttccaggtgcgcgaggtcaag*TGA*caattggcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtac gcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc -continued gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattc*ggccgacaggacgcgcgtcaaaggtgctggtcgtgtatgc*

*cctggccggcaggtcgttgctgctgctggttagtgattccgcaaccctgattttggcgtcttattttggcgtggcaaacgctggcg*

*cccgcgagccgggccggcggcgatgcggtgccccacggctgccggaatccaagggaggcaagagcgcccgggtcagttga*

*agggctttacgcgcaaggtacagccgctcctgcaaggctgcgtggtggaattggacgtgcaggtcctgctgaagttcctccac*

*cgcctcaccagcggacaaagcaccggtgtatcaggtccgtgtcatccactctaaagaactcgactacgacctactgatggccct*

*agattcttcatcaaaaacgcctgagacacttgcccaggattgaaactccctgaagggaccaccaggggccctgagttgttcctt*

*ccccccgtggcgagctgccagccaggctgtacctgtgatcgaggctggcgggaaaataggcttcgtgtgctcaggtcatggg*

*aggtgcaggacagctcatgaaacgccaacaatcgcacaattcatgtcaagctaatcagctatttcctcttcacgagctgtaatt*

*gtcccaaaattctggtctaccgggggtgatccttcgtgtacgggcccttccctcaaccctaggtatgcgcgcatgcggtcgccgc*

*gcaactcgcgcgagggccgagggtttgggacgggccgtcccgaaatgcagttgcacccggatgcgtggcaccttttttgcgat*

*aatttatgcaatggactgctctgcaaaattctggctctgtcgccaaccctaggatcagcggcgtaggatttcgtaatcattcgtc*

*ctgatggggagctaccgactaccctaatatcagcccgactgcctgacgccagcgtccacttttgtgcacacattccattcgtgcc*

*caagacatttcattgtggtgcgaagcgtccccagttacgctcacctgtttcccgacctccttactgttctgtcgacagagcgggcc* cacaggccggtcgcagccactagt*ATGgccaccgcatccactttctcggcgttcaatgcccgctgcggcgacctgcgtcgctc*

*ggcgggctccgggccccggcgcccagcgaggcccctccccgtgcgcgggcgcgccgccaccctgcgctccggcctgcgcgac*

*gtggagaccgtgaagaagaccttctcccccgcccgcgaggtgcacgtgcaggtgacccactccatggcccccagaagatc*

*gagatcttcaaggccatggaggactgggccgagaacaacatcctggtgcacctgaagaacgtggagaagtgcccccagc*

*cccaggacttcctgcccgaccccgcctccgacgagttccacgaccagatcaaggagctgcgcgagcgcgccaaggagatcc*

*ccgacgactacttcgtggtgctggtgggcgacatgatcaccgaggaggccctgcccacctaccagaccatgctgaacacctg*

*ggacggcgtgcgcgacgagaccggcgcctcccccacctcctgggccatctggacccgcgcctggaccgccgaggagaaccg*

*ccacggcgacccccctgaacaagtacctgtacctgtccggccgcgtggacatgaagcagatcgagaagaccatccagtacct*

*gatcggctccggcatggacccccgcaccgagaactcccccctacctgggcttcatctacacctccttccaggagcgcgccacctt*

*catctcccacggcaacaccgcccgcctggcccgcgaccacggcgacttcaagctggcccagatctgcggcaccatcgcctccg*

*acgagaagcgccacgagaccgcctacaccaagatcgtggagaagctgttcgagatcgaccccgacggcaccgtgctggcc*

*ttcggcgacatgatgaagaagaagatctccatgcccgaccacttcatgtacgacggccgcgacgacaacctgttcgaccact*

*tctcctccgtggcccagcgcctgggcgtgtacaccgccaaggactacgccgacatcctggagcacctggtgggccgctggaa*

*ggtggagaagctgaccggcctgtccgccgagggccagaaggcccaggactacgtgtgcggcctgcccccccgcatccgccg*

*cctggaggagcgcgcccagatccgcgccaagcaggcccccgcctgcccttctcctggatctacgaccgcgaggtgcagctg*

*atggactacaaggaccacgacggcgactacaaggaccacgacatcgactacaaggacgacgacgacaagTGA*atcgat agatctcttaaggcagcagcagctcggatagtatcgacacactctggacgctggtcgtgtgatggactgttgccgccacttgctgc -continued cttgacctgtgaatatccctgccgcttttatcaaacagcctcagtgtgtttgatcttgtgtgtacgcgcttttgcgagttgctagctgctt gtgctatttgcgaataccacccccagcatccccttccctcgtttcatatcgcttgcatcccaaccgcaacttatctacgctgtcctgcta tccctcagcgctgctcctgctcctgctcactgcccctcgcacagccttggtttgggctccgcctgtattctcctggtactgcaacctgta aaccagcactgcaatgctgatgcacgggaagtagtgggatgggaacacaaatggaaagcttaattaagagctcttgttttccagaa ggagttgctccttgagcctttcattctcagcctcgataacctccaaagccgctctaattgtggaggggttcgaatttaaaagcttgg aatgttggttcgtgcgtctggaacaagcccagacttgttgctcactgggaaaggaccatcagctccaaaaaacttgccgctcaaa ccgcgtacctctgctttcgcgcaatctgccctgttgaaatcgccaccacattcatattgtgacgcttgagcagtctgtaattgcctca gaatgtggaatcatctgcccccctgtgcgagcccatgccaggcatgtcgcgggcgaggacacccgccactcgtacagcagaccatt atgctacctcacaatagttcataacagtgaccatatttctcgaagctccccaacgagcacctccatgctctgagtggccaccccccg gccctggtgcttgcggagggcaggtcaaccggcatggggctaccgaaatccccgaccggatcccaccacccccgcgatgggaag aatctctccccgggatgtgggcccaccaccagcacaacctgctggcccaggcgagcgtcaaaccataccacacaaatatccttgg catcggccctgaattccttctgccgctctgctacccggtgcttctgtccgaagcaggggttgctagggatcgctccgagtccgcaaa cccttgtcgcgtggcggggcttgttcgagcttgaagagc

2) pSZ3145: 6S::CrTUB2:ScSUC2:CvNR::PmAMT3:MuPAD:CvNR::6S Relevant restriction sites in the construct pSZ3145 6S::CrTUB2:ScSUC2:CvNR::PmAMT3:MuPAD:CvNR::6S are indicated in lowercase, bold and underlining and are 5'-3' BspQ 1, Kpn I, Xba I, Mfe I, BamH I, EcoR I, Spe I, Cla I, Sac I, BspQ I, respectively. BspQI sites delimit the 5' and 3' ends of the transforming DNA. Bold, lowercase sequences represent genomic DNA from that permit targeted integration at 6 s locus via homologous recombination. Proceeding in the 5' to 3' direction, the *C. reinhardtii* β-tubulin promoter driving the expression of the yeast sucrose invertase gene (conferring the ability of Strain Z to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *Prototheca moriformis*, indicated by boxed italics text. The Initiator ATG and terminator TGA codons of the MuPAD are indicated by uppercase, bold italics, while the remainder of the coding region is indicated by bold italics. The *C. vulgaris* nitrate reductase 3' UTR is again indicated by lowercase underlined text followed by the 6S genomic region indicated by bold, lowercase text.

Nucleotide sequence of transforming DNA contained in pSZ3145:

(SEQ ID NO: 100)

gctcttcgccgccgccactcctgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaacccccttgcgcgttagtgttgccatcctttgcagaccggtgagagccgacttgttgtgcgccac cccccacaccacctcctcccagaccaattctgtcacctttttggcgaaggcatcggcctcggcctgcagagaggacagcagtgccc agccgctggggggttggcggatgcacgctcaggtaccctttcttgcgctatgacacttccagcaaaaggtagggcgggctgcgagac ggcttcccggcgctgcatgcaacaccgatgatgcttcgacccccccgaagctccttcggggctgcatgggcgctccgatgccgctcca gggcgagcgctgtttaaatagccaggcccccgattgcaaagacattatagcgagctaccaaagccatattcaaacacctagatcac taccacttctacacaggccactcgagcttgtgatcgcactccgctaagggggcgcctcttcctcttcgtttcagtcacaacccgcaaa ctctagaatatca*ATG**ctgctgcaggccttcctgttcctgctggccggcttcgccgccaagatcagcgcctccatgacgaacga*

*gacgtccgaccgccccctggtgcacttcacccccaacaagggctggatgaacgaccccaacggcctgtggtacgacgagaag*

*gacgccaagtggcacctgtacttccagtacaacccgaacgacaccgtctgggggacgcccttgttctggggccacgccacgtc*

-continued

*cgacgacctgaccaactgggaggaccagcccatcgccatcgccccgaagcgcaacgactccggcgccttctccggctccatgg*

*tggtggactacaacaacacctccggcttcttcaacgacaccatcgacccgcgccagcgctgcgtggccatctggacctacaaca*

*ccccggagtccgaggagcagtacatctcctacagcctggacggcggctacaccttcaccgagtaccagaagaaccccgtgctg*

*gccgccaactccacccagttccgcgacccgaaggtcttctggtacgagccctcccagaagtggatcatgaccgcggccaagtc*

*ccaggactacaagatcgagatctactcctccgacgacctgaagtcctggaagctggagtccgcgttcgccaacgagggcttcc*

*tcggctaccagtacgagtgccccggcctgatcgaggtccccaccgagcaggaccccagcaagtcctactgggtgatgttcatct*

*ccatcaaccccggcgccccggccggcggctccttcaaccagtacttcgtcggcagcttcaacggcacccacttcgaggccttcga*

*caaccagtcccgcgtggtggacttcggcaaggactactacgccctgcagaccttcttcaacaccgacccgacctacgggagcg*

*ccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatca*

*gcaacgccggcccctggagccggttcgccaccaacaccacgttgacgaaggccaacagctacaacgtcgacctgtccaacag*

*caccggcaccctggagttcgagctggtgtacgccgtcaacaccacccagacgatctccaagtccgtgttcgcggacctctccctc*

*tggttcaagggcctggaggaccccgaggagtacctccgcatgggcttcgaggtgtccgcgtcctccttcttcctggaccgcggg*

*aacagcaaggtgaagttcgtgaaggagaacccctacttcaccaaccgcatgagcgtgaacaaccagcccttcaagagcgag*

*aacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcga* caagttccaggtgcgcgaggtcaag*TGA*caattggcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtac gcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattc*ggccgacaggacgcgcgtcaaaggtgctggtcgtgtatgc*

*cctggccggcaggtcgttgctgctgctggttagtgattccgcaaccctgattttggcgtcttattttggcgtggcaaacgctggcg*

*cccgcgagccgggccggcggcgatgcggtgccccacggctgccggaatccaagggaggcaagagcgcccgggtcagttga*

*agggctttacgcgcaaggtacagccgctcctgcaaggctgcgtggtggaattggacgtgcaggtcctgctgaagttcctccac*

*cgcctcaccagcggacaaagcaccggtgtatcaggtccgtgtcatccactctaaagaactcgactacgacctactgatggccct*

*agattcttcatcaaaaacgcctgagacacttgcccaggattgaaactccctgaagggaccaccaggggccctgagttgttcctt*

*ccccccgtggcgagctgccagccaggctgtacctgtgatcgaggctggcgggaaaataggcttcgtgtgctcaggtcatggg*

*aggtgcaggacagctcatgaaacgccaacaatcgcacaattcatgtcaagctaatcagctatttcctcttcacgagctgtaatt*

*gtcccaaaattctggtctaccgggggtgatccttcgtgtacgggcccttccctcaaccctaggtatgcgcgcatgcggtcgccgc*

*gcaactcgcgcgagggccgagggtttgggacgggccgtcccgaaatgcagttgcacccggatgcgtggcaccttttttgcgat*

*aatttatgcaatggactgctctgcaaaattctggctctgtcgccaaccctaggatcagcggcgtaggatttcgtaatcattcgtc*

*ctgatggggagctaccgactaccctaatatcagcccgactgcctgacgccagcgtccacttttgtgcacacattccattcgtgcc*

-continued caagacatttcattgtggtgcgaagcgtccccagttacgctcacctgtttcccgacctccttactgttctgtcgacagagcgggcc cacaggccggtcgcagccactagtATGccctgaagctgaacgccatcaacttccagtcccccaagtgctcctccttcggcct gcccccgtggtgtccctgcgctcccccaagctgtccgtggccgccaccctgcgctccggcctgcgcgacgtggagaccgtga agaagaccttctcccccgcccgcgaggtgcacgtgcaggtgacccactccatggcccccagaagatcgagatcttcaaggc catggaggactgggccgagaacaacatcctggtgcacctgaagaacgtggagaagtgcccccagccccaggacttcctgc ccgaccccgcctccgacgagttccacgaccagatcaaggagctgcgcgagcgcgccaaggagatccccgacgactacttcg tggtgctggtgggcgacatgatcaccgaggaggccctgcccacctaccagaccatgctgaacacctgggacggcgtgcgcg acgagaccggcgcctcccccacctcctgggccatctggacccgcgcctggaccgccgaggagaaccgccacggcgacccccct gaacaagtacctgtacctgtccggccgcgtggacatgaagcagatcgagaagaccatccagtacctgatcggctccggcat ggacccccgcaccgagaactcccccctacctgggcttcatctacacctccttccaggagcgcgccaccttcatctcccacggcaa caccgcccgcctggcccgcgaccacggcgacttcaagctggcccagatctgcggcaccatcgcctccgacgagaagcgccac gagaccgcctacaccaagatcgtggagaagctgttcgagatcgaccccgacggcaccgtgctggccttcggcgacatgatg aagaagaagatctccatgcccgaccacttcatgtacgacggccgcgacgacaacctgttcgaccacttctcctccgtggccca gcgcctgggcgtgtacaccgccaaggactacgccgacatcctggagcacctggtgggccgctggaaggtggagaagctga ccggcctgtccgccgagggccagaaggcccaggactacgtgtgcggcctgccccccgcatccgccgcctggaggagcgcg cccagatccgcgccaagcaggcccccgcctgcccttctcctggatctacgaccgcgaggtgcagctgatggactacaagga ccacgacggcgactacaaggaccacgacatcgactacaaggacgacgacgacaagTGAatcgatagatctcttaaggcag cagcagctcggatagtatcgacacactctggacgctggtcgtgtgatggactgttgccgccacacttgctgccttgacctgtgaatat ccctgccgcttttatcaaacagcctcagtgtgtttgatcttgtgtgtacgcgcttttgcgagttgctagctgcttgtgctatttgcgaata ccacccccagcatccccttccctcgtttcatatcgcttgcatcccaaccgcaacttatctacgctgtcctgctatccctcagcgctgctc ctgctcctgctcactgcccctcgcacagccttggtttgggctccgcctgtattctcctggtactgcaacctgtaaaccagcactgcaat gctgatgcacgggaagtagtgggatgggaacacaaatggaaagcttaattaagagctcttgttttccagaaggagttgctccttga gcctttcattctcagcctcgataacctccaaagccgctctaattgtggaggggggttcgaatttaaaagcttggaatgttggttcgtgc gtctggaacaagcccagacttgttgctcactgggaaaaggaccatcagctccaaaaaacttgccgctcaaaccgcgtacctctgct ttcgcgcaatctgccctgttgaaatcgccaccacattcatattgtgacgcttgagcagtctgtaattgcctcagaatgtggaatcatc tgcccccctgtgcgagcccatgccaggcatgtcgcgggcgaggacacccgccactcgtacagcagaccattatgctacctcacaata gttcataacagtgaccatatttctcgaagctccccaacgagcacctccatgctctgagtggccaccccccggccctggtgcttgcgg agggcaggtcaaccggcatggggctaccgaaatccccgaccggatcccaccacccccgcgatgggaagaatctctccccgggat gtgggcccaccaccagcacaacctgctggcccaggcgagcgtcaaaccataccacacaaatatccttggcatcggccctgaattc cttctgccgctctgctacccggtgcttctgtccgaagcaggggttgctagggatcgctccgagtccgcaaacccttgtcgcgtggcg gggcttgttcgagcttgaagagc 3) pSZ3137: 6S::CrTUB2:ScSUC2:CvNR::CrTUB2:CpSADtp:MuPAD:CvNR::6S Relevant restriction sites in the construct pSZ3137 6S::CrTUB2:ScSUC2:CvNR::CrTUB2:CpSADtp:MuPAD:CvNR::6S are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from that permit targeted integration at 6 s locus via homologous recombination. Proceeding in the 5' to 3' direction, the *C. reinhardtii* β-tubulin promoter driving the expression of the yeast sucrose invertase gene (conferring the ability of Strain Z to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by *C. reinhardtii* β-tubulin promoter, indicated by boxed italics text. The Initiator ATG and terminator TGA codons of the MuPAD are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ3137:

(SEQ ID NO: 101)

gctcttcgccgccactcctgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaaccccttgcgcgttagtgttgccatcctttgcagaccggtgagagccgacttgttgtgcgccac cccccacaccacctcctcccagaccaattctgtcacctttttggcgaaggcatcggcctcggcctgcagagaggacagcagtgccc agccgctgggggttggcggatgcacgctcaggtaccctttcttgcgctatgacacttccagcaaaaggtagggcgggctgcgagac ggcttcccggcgctgcatgcaacaccgatgatgcttcgacccccgaagctccttcggggctgcatgggcgctccgatgccgctcca gggcgagcgctgtttaaatagccaggcccccgattgcaaagacattatagcgagctaccaaagccatattcaaacacctagatcac taccacttctacacaggccactcgagcttgtgatcgcactccgctaagggggcgcctcttcctcttcgtttcagtcacaacccgcaaa gtctagaatatca*ATG**ctgctgcaggccttcctgttcctgctggccggcttcgccgccaagatcagcgcctccatgacgaacga*

*gacgtccgaccgcccccctggtgcacttcacccccaacaagggctggatgaacgaccccaacggcctgtggtacgacgagaag*

*gacgccaagtggcacctgtacttccagtacaacccgaacgacaccgtctgggggacgcccttgttctggggccacgccacgtc*

*cgacgacctgaccaactgggaggaccagcccatcgccatcgccccgaagcgcaacgactccggcgccttctccggctccatgg*

*tggtggactacaacaacacctccggcttcttcaacgacaccatcgacccgcgccagcgctgcgtggccatctggacctacaaca*

*ccccggagtccgaggagcagtacatctcctacagcctggacggcggctacaccttcaccgagtaccagaagaaccccgtgctg*

*gccgccaactccacccagttccgcgacccgaaggtcttctggtacgagccctcccagaagtggatcatgaccgcggccaagtc*

*ccaggactacaagatcgagatctactcctccgacgacctgaagtcctggaagctggagtccgcgttcgccaacgagggcttcc*

*tcggctaccagtacgagtgccccggcctgatcgaggtccccaccgagcaggaccccagcaagtcctactgggtgatgttcatct*

*ccatcaaccccggcgccccggccggcggctccttcaaccagtacttcgtcggcagcttcaacggcacccacttcgaggccttcga*

*caaccagtcccgcgtggtggacttcggcaaggactactacgccctgcagaccttcttcaacaccgacccgacctacgggagcg*

*ccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatca*

*gcaacgccggcccctggagccggttcgccaccaacaccacgttgacgaaggccaacagctacaacgtcgacctgtccaacag*

*caccggcaccctggagttcgagctggtgtacgccgtcaacaccacccagacgatctccaagtccgtgttcgcggacctctccctc*

*tggttcaagggcctggaggaccccgaggagtacctccgcatgggcttcgaggtgtccgcgtcctccttcttcctggaccgcggg*

*aacagcaaggtgaagttcgtgaaggagaacccctacttcaccaaccgcatgagcgtgaacaaccagcccttcaagagcgag*

*aacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcga*

*caagttccaggtgcgcgaggtcaag**TGAcaattg*gcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtac gcgcttttgcgagttgctagctgcttgtgctatttgcgaataccacccccagcatccccttccctcgtttcatatcgcttgcatcccaacc -continued gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattcctttcttgcgctatgacacttccagcaaaaggtagggcggg ctgcgagacggcttcccggcgctgcatgcaacaccgatgatgcttcgacccccccgaagctccttcggggctgcatgggcgctcc gatgccgctccagggcgagcgctgtttaaatagccaggcccccgattgcaaagacattatagcgagctaccaaagccatattc aaacacctagatcactaccacttctacacaggccactcgagcttgtgatcgcactccgctaagggggcgcctcttcctcttcgttt cagtcacaacccgcaaacactagtATGgccaccgcatccactttctcggcgttcaatgcccgctgcggcgacctgcgtcgctc ggcgggctccgggccccggcgcccagcgaggcccctccccgtgcgcgggcgccgccaccctgcgctccggcctgcgcgac gtggagaccgtgaagaagaccttctcccccgcccgcgaggtgcacgtgcaggtgacccactccatggcccccagaagatc gagatcttcaaggccatggaggactgggccgagaacaacatcctggtgcacctgaagaacgtggagaagtgcccccagc cccaggacttcctgcccgaccccgcctccgacgagttccacgaccagatcaaggagctgcgcgagcgcgccaaggagatcc ccgacgactacttcgtggtgctggtgggcgacatgatcaccgaggaggccctgcccacctaccagaccatgctgaacacctg ggacggcgtgcgcgacgagaccggcgcctcccccacctcctgggccatctggacccgcgcctggaccgccgaggagaaccg ccacggcgacccccctgaacaagtacctgtacctgtccggccgcgtggacatgaagcagatcgagaagaccatccagtacct gatcggctccggcatggacccccgcaccgagaactcccccctacctgggcttcatctacacctccttccaggagcgcgccacctt catctcccacggcaacaccgcccgcctggcccgcgaccacggcgacttcaagctggcccagatctgcggcaccatcgcctccg acgagaagcgccacgagaccgcctacaccaagatcgtggagaagctgttcgagatcgaccccgacggcaccgtgctggcc ttcggcgacatgatgaagaagaagatctccatgcccgaccacttcatgtacgacggccgcgacgacaacctgttcgaccact tctcctccgtggcccagcgcctgggcgtgtacaccgccaaggactacgccgacatcctggagcacctggtgggccgctggaa ggtggagaagctgaccggcctgtccgccgagggccagaaggcccaggactacgtgtgcggcctgcccccccgcatccgccg cctggaggagcgcgcccagatccgcgccaagcaggcccccgcctgcccttctcctggatctacgaccgcgaggtgcagctg atggactacaaggaccacgacggcgactacaaggaccacgacatcgactacaaggacgacgacgacaagTGAatcgat agatctcttaaggcagcagcagctcggatagtatcgacacactctggacgctggtcgtgtgatggactgttgccgccacacttgctgc cttgacctgtgaatatccctgccgcttttatcaaacagcctcagtgtgtttgatcttgtgtgtacgcgcttttgcgagttgctagctgctt gtgctatttgcgaataccacccccagcatccccttccctcgtttcatatcgcttgcatcccaaccgcaacttatctacgctgtcctgcta tccctcagcgctgctcctgctcctgctcactgcccctcgcacagccttggtttgggctccgcctgtattctcctggtactgcaacctgta aaccagcactgcaatgctgatgcacgggaatagtgggatgggaacacaaatggaaagcttaattaagagctcttgttttccagaa ggagttgctccttgagcctttcattctcagcctcgataacctccaaagccgctctaattgtggagggggttcgaatttaaaagcttgg aatgttggttcgtgcgtctggaacaagcccagacttgttgctcactgggaaaaggaccatcagctccaaaaaacttgccgctcaaa ccgcgtacctctgctttcgcgcaatctgccctgttgaaatcgccaccacattcatattgtgacgcttgagcagtctgtaattgcctca gaatgtggaatcatctgccccctgtgcgagcccatgccaggcatgtcgcgggcgaggacacccgccactcgtacagcagaccatt atgctacctcacaatagttcataacagtgaccatatttctcgaagctccccaacgagcacctccatgctctgagtggccaccccccg gccctggtgcttgcggagggcaggtcaaccggcatggggctaccgaaatccccgaccggatcccaccacccccgcgatgggaag aatctctccccgggatgtgggcccaccaccagcacaacctgctggcccaggcgagcgtcaaaccataccacacaaatatccttgg

-continued catcggccctgaattccttctgccgctctgctacccggtgcttctgtccgaagcaggggttgctagggatcgctccgagtccgcaaa cccttgtcgcgtggcggggcttgttcgagcttgaagagc

Example 52: Myristate Rich Oil Produced by Overexpressing a *Cuphea Palustris* Thioesterase Here, we demonstrate that over expression of a *Cuphea palustris* thioesterase (Cpal FATB2, accession AAC49180) in UTEX1435 results in a large increase in C14:0 production (over 60% of the fatty acid profile).

Constructs used for the overexpression of the Cpal FATB2 gene were codon optimized for expression in *P. moriformis* as described herein. *Cuphea palustris* FATB2 is a C14 preferring thioesterase. Two constructs, both encoding the Cpal FATB2 gene, were prepared. The first construct, pSZ2479, can be written as 6SA::CrTUB2-ScSUC2-CvNR:PmAMT3-CpSAD1tpExt-CpalFATB2ExtA-CvNR::6SB. The FatB2 coding sequence is given as SEQ ID NO: 86 and the amino acid sequence is given as SEQ ID NO: 87. The second construct, pSZ2480 can be written as 6SA::CrTUB2-ScSUC2-CvNR:PmAMT3-CpSAD1tpExt_CpalFATB2FLAG_ExtA-CvNR::6SB. The nucleic acid sequence and amino acid sequence are given as SEQ ID NO: 88 and SEQ ID NO: 89.

*P. moriformis* transformed with pSZ2480 produced high levels of myristic acid. The myristate content was 65.70 percent. This is a very large increase when compared to the myristate content of the wild-type oil produced by the base strain, which has a myristate content of approximately 1%.

The fatty acid profile of the high myristate strain is shown in the Table 51 below.

TABLE 51

Fatty acid profile of high myristate strain.

| Fatty Acid | % |
|---|---|
| C10:0 | 0.04 |
| C12:0 | 1.19 |
| C14:0 | 65.7 |
| C16:0 | 13.55 |
| C18:0 | 0.57 |
| C18:1 | 12.2 |
| C18:2 | 5.13 |
| C20:0 | 0.05 |
| C22:0 | 0.01 |
| C24:0 | 0.01 |

Example 53: Production of Eicosenoic and Erucic Fatty Acids

In this example we demonstrate that expression of heterologous fatty acid elongase (FAE), also known as 3-ketoacyl-CoA synthase (KCS), genes from *Cramble abyssinica* (CaFAE, Accession No: AY793549), *Lunaria annua* (LaFAE, ACJ61777), and *Cardamine graeca* (CgFAE, ACJ61778) leads to production of very long chain monounsaturated fatty acids such as eicosenoic ($20:1^{\Delta 11}$) and erucic ($22:1^{\Delta 13}$) acids in classically mutagenized derivative of UTEX 1435, Strain Z. On the other hand a putative FAE gene from *Tropaeolum majus* (TmFAE, ABD77097) and two FAE genes from *Brassica napus* (BnFAE1, AAA96054 and BnFAE2, AAT65206), while resulting in modest increase in eicosenoic ($20:1^{\Delta 11}$), produced no detectable erucic acid in STRAIN Z. Interestingly the unsaturated fatty acid profile obtained with heterologous expression of BnFAE1 in STRAIN Z resulted in noticeable increase in Docosadienoic acid (22:2n6). All the genes were codon optimized to reflect UTEX 1435 codon usage. These results suggest that CaFAE, LaFAE or CgFAE genes encode condensing enzymes involved in the biosynthesis of very long-chain utilizing monounsaturated and saturated acyl substrates, with specific capability for improving the eicosenoic and erucic acid content.

Construct Used for the Expression of the *Cramble abyssinica* Fatty Acid Elongase (CaFAE) in *P. moriformis* (UTEX 1435 strain Z)-[pSZ3070]:

In this example STRAIN Z strains, transformed with the construct pSZ3070, were generated, which express sucrose invertase (allowing for their selection and growth on medium containing sucrose) and *C. abyssinica* FAE gene. Construct pSZ3070 introduced for expression in STRAIN Z can be written as 6S::CrTUB2-ScSUC2-Cvnr:PmAmt03-CaFAE-Cvnr::6S.

The sequence of the transforming DNA is provided below. Relevant restriction sites in the construct are indicated in lowercase, bold, and are from 5'-3' BspQI, KpnI, XbaI, MfeI, BamHI, EcoRI, SpeI, AflII, Sad, BspQI, respectively. BspQI sites delimit the 5' and 3' ends of the transforming DNA. Bold, lowercase sequences represent genomic DNA from STRAIN Z that permit targeted integration at the 6S locus via homologous recombination. Proceeding in the 5' to 3' direction, the *C. reinhardtii* β-tubulin promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The *Chlorella vulgaris* nitrate reductase (NR) gene 3' UTR is indicated by lowercase underlined text followed by an endogenous AMT3 promoter of *P. moriformis*, indicated by boxed italicized text. The Initiator ATG and terminator TGA codons of the CaFAE are indicated by uppercase, bold italics, while the remainder of the gene is indicated by bold italics. The *C. vulgaris* nitrate reductase 3' UTR is again indicated by lowercase underlined text followed by the STRAIN Z 6S genomic region indicated by bold, lowercase text. The final construct was sequenced to ensure correct reading frames and targeting sequences.

Nucleotide sequence of transforming DNA contained in plasmid pSZ3070:

(SEQ ID NO: 102)

gctcttcgccgccgccactcctgctcgagcgcgcccgcgcgtgcgccgccagcgccttggccttttcgccgcgctcgtgcgcgtcgctgatgt ccatcaccaggtccatgaggtctgccttgcgccggctgagccactgcttcgtccgggcggccaagaggagcatgagggaggactcctggt -continued ccagggtcctgacgtggtcgcggctctgggagcgggccagcatcatctggctctgccgcaccgaggccgcctccaactggtcctccagca gccgcagtcgccgccgaccctggcagaggaagacaggtgaggggggtatgaattgtacagaacaaccacgagccttgtctaggcagaa tccctaccagtcatggctttacctggatgacggcctgcgaacagctgtccagcgaccctcgctgccgccgcttctcccgcacgcttctttcca gcaccgtgatggcgcgagccagcgccgcacgctggcgctgcgcttcgccgatctgaggacagtcggggaactctgatcagtctaaacccc cttgcgcgttagtgttgccatcctttgcagaccggtgagagccgacttgttgtgcgccacccccacaccacctcctcccagaccaattctgt cacctttttggcgaaggcatcggcctcggcctgcagagaggacagcagtgcccagccgctgggggttggcggatgcacgctcaggtaccc tttcttgcgctatgacacttccagcaaaaggtagggcgggctgcgagacggcttcccggcgctgcatgcaacaccgatgatgcttcgaccccccg aagctccttcggggctgcatgggcgctccgatgccgctccagggcgagcgctgtttaaatagccaggcccccgattgcaaagacattatagcgag ctaccaaagccatattcaaacacctagatcactaccacttctacacaggccactcgagcttgtgatcgcactccgctaagggggcgcctcttcctctt cgtttcagtcacaacccgcaaactctagaatatca*ATG**ctgctgcaggccttcctgttcctgctggccggcttcgccgccaagatcagcgcctcc*

*atgacgaacgagacgtccgaccgccccctggtgcacttcacccccaacaagggctggatgaacgaccccaacggcctgtggtacgacgag*

*aaggacgccaagtggcacctgtacttccagtacaacccgaacgacaccgtctggggggacgcccttgttctggggccacgccacgtccgacg*

*acctgaccaactgggaggaccagcccatcgccatcgccccgaagcgcaacgactccggcgccttctccggctccatggtggtggactacaa*

*caacacctccggcttcttcaacgacaccatcgacccgcgccagcgctgcgtggccatctggacctacaacaccccggagtccgaggagcagt*

*acatctcctacagcctggacggcggctacaccttcaccgagtaccagaagaaccccgtgctggccgccaactccaccagttccgcgacccg*

*aaggtcttctggtacgagccctcccagaagtggatcatgaccgcggccaagtcccaggactacaagatcgagatctactcctccgacgacctg*

*aagtcctggaagctggagtccgcgttcgccaacgagggcttcctcggctaccagtacgagtgccccggcctgatcgaggtccccaccgagca*

*ggaccccagcaagtcctactgggtgatgttcatctccatcaaccccggcgccccggccggcggctccttcaaccagtacttcgtcggcagcttc*

*aacggcacccacttcgaggccttcgacaaccagtcccgcgtggtggacttcggcaaggactactacgccctgcagaccttcttcaacaccgac*

*ccgacctacgggagcgccctgggcatcgcgtgggcctccaactgggagtactccgccttcgtgcccaccaacccctggcgctcctccatgtcc*

*ctcgtgcgcaagttctccctcaacaccgagtaccaggccaacccggagacggagctgatcaacctgaaggccgagccgatcctgaacatca*

*gcaacgccggcccctggagccggttcgccaccaacaccacgttgacgaaggccaacagctacaactgcgacctgtccaacagcaccggca*

*ccctggagttcgagctggtgtacgccgtcaacaccacccagacgatctccaagtccgtgttcgcggacctctccctctggttcaagggcctgga*

*ggaccccgaggagtacctccgcatgggcttcgaggtgtccgcgtcctccttctggaccgcgggaacagcaaggtgaagttcgtgaagga*

*gaacccctacttcaccaaccgcatgagcgtgaacaaccagcccttcaagagcgagaacgacctgtcctactacaaggtgtacggcttgctgg*

*accagaacatcctggagctgtacttcaacgacggcgacgtcgtgtccaccaacacctacttcatgaccaccgggaacgccctgggctccgtg*

*aacatgacgacgggggtggacaacctgttctacatcgacaagttccaggtgcgcgaggtcaag**TGA*caattggcagcagcagctcggata gtatcgacacactctggacgctggtcgtgtgatugactgttgccgccacacttgctgccttgacctgtgaatatccctgccgcttttatcaaacagcctc agtgtgtttgatcttgtgtgtacgcgcttttgcgagttgctagctgcttgtgctatttgcgaataccacccccagcatccccttccctcgtttcatatcg cttgcatcccaaccgcaacttatctacgctgtcctgctatccctcagcgctgctcctgctcctgctcactgcccctcgcacagccttggtttgggctccg cctgtattctcctggtactgcaacctgtaaaccagcactgcaatgctgatgcacgggaagtagtgggatgggaacacaaatggaggatcccgcgtctc gaacagagcgcgcagaggaacgctgaaggtctcgcctctgtcgcacctcagcgcggcatacaccacaataaccacctgacgaatgcgcttggtt cttcgtccattagcgaagcgtccggttcacacacgtgccacgttggcgaggtggcaggtgacaatgatcggtggagctgatggtcgaaacgttcac agcctagggatatcgaattc*ggccgacaggacgcgcgtcaaaggtgctggtcgtgtatgccctggccggcaggtcgttgctgctgctggttagt*

*gattccgcaaccctgattttggcgtcttattttggcgtggcaaacgctggcgcccgcgagccgggccggcggcgatgcggtgccccacggctg*

*ccggaatccaagggaggcaagagcgcccgggtcagttgaagggctttacgcgcaaggtacagccgctcctgcaaggctgcgtggtggaatt*

*ggacgtgcaggtcctgctgaagttcctccaccgcctcaccagcggacaaagcaccggtgtatcaggtccgtgtcatccactctaaagaactcg*

-continued

*actacgacctactgatggccctagattcttcatcaaaaacgcctgagacacttgcccaggattgaaactccctgaagggaccaccaggggcc*

*ctgagttgttccttcccccgtggcgagctgccagccaggctgtacctgtgatcgaggctggcgggaaaataggctccgtgtgctcaggtcatgg*

*gaggtgcaggacagctcatgaaacgccaacaatcgcacaattcatgtcaagctaatcagctatttcctcttcacgagctgtaattgtccaaaa*

*ttctggtctaccgggggtgatccttcgtgtacgggcccttccctcaaccctaggtatgcgcgcatgcggtcgccgcgcaactcgcgcgagggcc*

*gagggtttgggacgggccgtcccgaaatgcagttgcacccggatgcgtggcaccttttttgcgataatttatgcaatggactgctctgcaaaatt*

*ctggctctgtcgccaaccctaggatcagcggcgtaggatttcgtaatcattcgtcctgatggggagctaccgactaccctaatatcagcccgact*

*gcctgacgccagcgtccacttttgtgcacacattccattcgtgcccaagacatttcattgtggtgcgaagcgtccccagttacgctcacctgtttcc*

*cgacctccttactgttctgtcgacagagcgggcccacaggccggtcgcagcca**ctagtATGacctccatcaacgtgaagctgctgtacc*

*actacgtgatcaccaacctgttcaacctgtgcttcttcccccctgaccgccatcgtggccggcaaggcctcccgcctgaccatcgacg*

*acctgcaccacctgtactactcctacctgcagcacaacgtgatcaccatcgccccccctgttcgccttcaccgtgttcggctccatcct*

*gtacatcgtgacccgccccaagcccgtgtacctggtggagtactcctgctacctgccccccacccagtgccgctcctccatctccaa*

*ggtgatggacatcttctaccaggtgcgcaaggccgaccccttccgcaacggcacctgcgacgactcctcctggctggacttcctgc*

*gcaagatccaggagcgctccggcctgggcgacgagacccacggccccgagggcctgctgcaggtgcccccccgcaagacctt*

*cgccgccgcccgcgaggagaccgagcaggtgatcgtgggcgccctgaagaacctgttcgagaacaccaaggtgaaccccaa*

*ggacatcggcatcctggtggtgaactcctccatgttcaaccccaccccctccctgtccgccatggtggtgaacaccttcaagctgcg*

*ctccaacgtgcgctccttcaacctgggcggcatgggctgctccgccggcgtgatcgccatcgacctggccaaggacctgctgcac*

*gtgcacaagaacacctacgccctggtggtgtccaccgagaacatcacctacaacatctacgccggcgacaaccgctccatgatg*

*gtgtccaactgcctgttccgcgtgggcggcgccgccatcctgctgtccaacaagccccgcgaccgccgccgctccaagtacgagc*

*tggtgcacaccgtgcgcacccacaccggcgccgacgacaagtccttccgctgcgtgcagcagggcgacgacgagaacggcaa*

*gaccggcgtgtccctgtccaaggacatcaccgaggtggccggccgcaccgtgaagaagaacatcgccaccctgggccccctga*

*tcctgcccctgtccgagaagctgctgttcttcgtgaccttcatggccaagaagctgttcaaggacaaggtgaagcactactacgtgc*

*ccgacttcaagctggccatcgaccacttctgcatccacgccggcggccgcgccgtgatcgacgtgctggagaagaacctgggcc*

*tggcccccatcgacgtggaggcctcccgctccaccctgcaccgcttcggcaacacctcctcctcctccatctggtacgagctggcct*

*acatcgaggccaagggccgcatgaagaagggcaacaaggtgtggcagatcgccctgggctccggcttcaagtgcaactccgc*

*cgtgtgggtggccctgtccaacgtgaaggcctccaccaactccccctgggagcactgcatcgaccgctaccccgtgaagatcgac*

*tccgactccgccaagtccgagacccgcgcccagaacggccgctccTGActtaag*gcagcagcagctcggatagtatcgacacactct ggacgctggtcgtgtgatggactgttgccgccacacttgctgccttgacctgtgaatatccctgccgcttttatcaaacagcctcagtgtgtttgatctt gtgtgtacgcgcttttgcgagttgctagctgcttgtgctatttgcgaataccacccccagcatccccttccctcgtttcatatcgcttgcatcccaaccg caacttatctacgctgtcctgctatccctcagcgctgctcctgctcctgctcactgcccctcgcacagccttggtttgggctccgcctgtattctcctgg tactgcaacctgtaaaccagcactgcaatgctgatgcacgggaagtagtgggatgggaacacaaatggaaagcttaattaagagctcttgttttccaga aggagttgctccttgagcctttcattctcagcctcgataacctccaaagccgctctaattgtggagggggttcgaatttaaaagcttggaatg ttggttcgtgcgtctggaacaagcccagacttgttgctcactgggaaaaggaccatcagctccaaaaaacttgccgctcaaaccgcgtacc tctgctttcgcgcaatctgccctgttgaaatcgccaccacattcatattgtgacgcttgagcagtctgtaattgcctcagaatgtggaatcatc tgccccctgtgcgagcccatgccaggcatgtcgcgggcgaggacacccgccactcgtacagcagaccattatgctacctcacaatagttca taacagtgaccatatttctcgaagctccccaacgagcacctccatgctctgagtggccacccccggccctggtgcttgcggagggcaggt

-continued caaccggcatggggctaccgaaatccccgaccggatcccaccacccccgcgatgggaagaatctctccccgggatgtgggcccaccacc agcacaacctgctggcccaggcgagcgtcaaaccataccacacaaatatccttggcatcggccctgaattccttctgccgctctgctacccg gtgcttctgtccgaagcaggggttgctagggatcgctccgagtccgcaaacccttgtcgcgtggcggggcttgttcgagcttgaagagc Constructs Used for the Expression of the FAE Genes from Higher Plants in STRAIN Z:

In addition to the CaFAE gene (pSZ3070), LaFAE (pSZ3071) from *Lunaria annua*, CgFAE (pSZ3072) from *Cardamine graeca*, TmFAE (pSZ3067) *Tropaeolum majus* and BnFAE1 (pSZ3068) and BnFAE2 (pSZ3069) genes from *Brassica napus* have been constructed for expression in STRAIN Z. These constructs can be described as:

pSZ3071—6S::CrTUB2-ScSUC2-Cvnr:PmAmt03-LaFAE-Cvnr::6S pSZ3072—6S::CrTUB2-ScSUC2-Cvnr:PmAmt03-CgFAE-Cvnr::6S pSZ3067—6S::CrTUB2-ScSUC2-Cvnr:PmAmt03-Tm-FAE-Cvnr::6S pSZ3068—6S::CrTUB2-ScSUC2-Cvnr:PmAmt03-Bn-FAE1-Cvnr::6S pSZ3069—6S::CrTUB2-ScSUC2-Cvnr:PmAmt03-Bn-FAE2-Cvnr::6S All these constructs have the same vector backbone; selectable marker, promoters, and 3' utr as pSZ3070, differing only in the respective FAE genes. Relevant restriction sites in these constructs are also the same as in pSZ3070. The sequences of LaFAE, CgFAE, TmFAE, BnFAE1 and BnFAE2 are shown below. Relevant restriction sites as bold text including SpeI and AflII are shown 5'-3' respectively.

Nucleotide sequence of LaFAE contained in pSZ3071:

(SEQ ID NO: 103)

actagtATGacctccatcaacgtgaagctgctgtaccactacgtgatcaccaacttcttcaactgtgcttcttcccctgaccgccat cctggccggcaaggcctcccgcctgaccaccaacgacctgcaccacttctactcctacctgcagcacaacctgatcaccctgacc ctgctgttcgccttcaccgtgttcggctccgtgctgtacttcgtgacccgccccaagcccgtgtacctggtggactactcctgctacctg cccccccagcacctgtccgccggcatctccaagaccatggagatcttctaccagatccgcaagtccgacccccctgcgcaacgtgg ccctggacgactcctcctccctggacttcctgcgcaagatccaggagcgctccggcctgggcgacgagacctacggccccgagg gcctgttcgagatcccccccgcaagaacctggcctccgcccgcgaggagaccgagcaggtgagcaggtgatcaacggcgccctgaagaa cctgttcgagaacaccaaggtgaaccccaaggagatcggcatcctggtggtgaactcctccatgttcaacccacccctccctgt ccgccatggtggtgaacaccttcaagctgcgctccaacatcaagtccttcaacctgggcggcatgggctgctccgccggcgtgatc gccatcgacctggccaaggacctgctgcacgtgcacaagaacacctacgccctggtggtgtccaccgagaacatcacccagaa catctacaccggcgacaaccgctccatgatggtgtccaactgcctgttccgcgtgggcggcgccgccatcctgctgtccaacaagc ccggcgaccgccgccgctccaagtaccgcctggcccacaccgtgcgcacccacaccggcgccgacgacaagtcctcggctgc gtgcgccaggaggaggacgactccggcaagaccggcgtgtccctgtccaaggacatcaccggcgtggccggcatcaccgtgc agaagaacatcaccaccctgggcccctggtgctgcccctgtccgagaagatcctgttcgtggtgaccttcgtggccaagaagct gctgaaggacaagatcaagcactactacgtgcccgacttcaagctggccgtggaccacttctgcatccacgccggcggccgcgc cgtgatcgacgtgctggagaagaacctgggcctgtcccccatcgacgtggaggcctcccgctccaccctgcaccgcttcggcaac acctcctcctcctccatctggtacgagctggcctacatgaggccaagggccgcatgaagaagggcaacaaggcctggcagatc gccgtgggctccggcttcaagtgcaactccgccgtgtgggtggccctgcgcaacgtgaaggcctccgccaactcccccctgggagc actgcatccacaagtaccccgtgcagatgtactccggctcctccaagtccgagacccgcgcccagaacggccgctccTGActta ag Nucleotide sequence of CgFAE contained in pSZ3072:

(SEQ ID NO: 104)

actagtATGacctccatcaacgtgaagctgctgtaccactacgtgctgaccaacttcttcaacctgtgcctgttcccccctgaccgcctt ccccgccggcaaggcctcccagctgaccaccaacgacctgcaccacctgtactcctacctgcaccacaacctgatcaccgtgac cctgctgttcgccttcaccgtgttcggctccatcctgtacatcgtgacccgccccaagcccgtgtacctggtggactactcctgctacc tgcccccccgccacctgtcctgcggcatctcccgcgtgatggagatcttctacgagatccgcaagtccgacccctcccgcgaggtg cccttcgacgacccctcctccctggagttcctgcgcaagatccaggagcgctccggcctgggcgacgagacctacggcccccag ggcctggtgcacgacatgcccctgcgcatgaacttcgccgccgcccgcgaggagaccgagcaggtgatcaacggcgccctgga -continued gaagctgttcgagaacaccaaggtgaacccccgcgagatcggcatcctggtggtgaactcctccatgttcaaccccacccccctcc ctgtccgccatggtggtgaacaccttcaagctgcgctccaacatcaagtccttctccctgggcggcatgggctgctccgccggcatc atcgccatcgacctggccaaggacctgctgcacgtgcacaagaacacctacgccctggtggtgtccaccgagaacatcacccac tccacctacaccggcgacaaccgctccatgatggtgtccaactgcctgttccgcatgggcggcgccgccatcctgctgtccaacaa ggccggcgaccgccgccgctccaagtacaagctggcccacaccgtgcgcacccacaccggcgccgacgaccagtccttccgct gcgtgcgccaggaggacgacgaccgcggcaagatcggcgtgtgcctgtccaaggacatcaccgccgtggccggcaagaccgt gaccaagaacatcgccaccctgggcccccctggtgctgcccctgtccgagaagttcctgtacgtggtgtccctgatggccaagaag ctgttcaagaacaagatcaagcacacctacgtgcccgacttcaagctggccatcgaccacttctgcatccacgccggcggccgcg ccgtgatcgacgtgctggagaagaacctggccctgtcccccgtggacgtggaggcctcccgctccaccctgcaccgcttcggcaa cacctcctcctcctccatctggtacgagctggcctacatcgaggccaagggccgcatgaagaagggcaacaaggtgtggcagat cgccatcggctccggcttcaagtgcaactccgccgtgtgggtggccctgtgcaacgtgaagccctccgtgaactcccccctgggag cactgcatcgaccgctaccccgtggagatcaactacggctcctccaagtccgagacccgcgcccagaacggccgctccTGActt aag Nucleotide sequence of TmFAE contained in pSZ3067:

(SEQ ID NO: 105)

actagtATGtccggcaccaaggccacctccgtgtccgtgcccctgcccgacttcaagcagtccgtgaacctgaagtacgtgaagc tgggctaccactactccatcacccacgccatgtacctgttcctgacccccctgctgctgatcatgtccgcccagatctccaccttctcc atccaggacttccaccacctgtacaaccacctgatcctgcacaacctgtcctccctgatcctgtgcatcgccctgctgttcgtgct gaccctgtacttcctgacccgccccacccccgtgtacctgctgaacttctcctgctacaagcccgacgccatccacaagtgcgacc gccgccgcttcatggacaccatccgcggcatgggcacctacaccgaggagaacatcgagttccagcgcaaggtgctggagcgc tccggcatcggcgagtcctcctacctgcccccaccgtgttcaagatcccccccgcgtgtacgacgccgaggagcgcgccgag gccgagatgctgatgttcggcgccgtggacggcctgttcgagaagatctccgtgaagcccaaccagatcggcgtgctggtggtga actgcggcctgttcaaccccatcccctccctgtcctccatgatcgtgaaccgctacaagatgcgcggcaacgtgttctcctacaacct gggcggcatgggctgctccgccggcgtgatctccatcgacctggccaaggacctgctgcaggtgcgccccaactcctacgccctg gtggtgtccctggagtgcatctccaagaacctgtacctgggcgagcagcgctccatgctggtgtccaactgcctgttccgcatgggc ggcgccgccatcctgctgtccaacaagatgtccgaccgctggcgctccaagtaccgcctggtgcacaccgtgcgcacccacaag ggcaccgaggacaactgcttctcctgcgtgacccgcaaggaggactccgacggcaagatcggcatctccctgtccaagaacctg atggccgtggccggcgacgccctgaagaccaacatcaccaccctgggccccctggtgctgcccatgtccgagcagctgctgttctt cgccaccctggtgggcaagaaggtgttcaagatgaagctgcagccctacatccccgacttcaagctggccttcgagcacttctgc atccacgccggcgccgcgccgtgctggacgagctggagaagaacctgaagctgtcctcctggagccctcccgcat gtccctgtaccgcttcggcaacacctcctcctcctccctgtggtacgagctggcctactccgaggccaagggccgcatcaagaagg gcgaccgcgtgtggcagatcgccttcggctccggcttcaagtgcaactccgccgtgtggaaggccctgcgcaacgtgaaccccg ccgaggagaagaacccctggatggacgagatccacctgttccccgtggaggtgcccctgaacTGActtaag Nucleotide sequence of BnFAE1 contained in pSZ3068:

(SEQ ID NO: 106)

actagtATGacctccatcaacgtgaagctgctgtaccactacgtgatcaccaacctgttcaacctgtgcttcttcccccctgaccgcc atcgtggccggcaaggcctacctgaccatcgacgacctgcaccacctgtactactcctacctgcagcacaacctgatcaccatcg ccccccctgctggccttcaccgtgttcggctccgtgctgtacatcgccacccgccccaagcccgtgtacctggtggagtactcctgcta cctgcccccccacccactgccgctcctccatctccaaggtgatggacatcttcttccaggtgcgcaaggccgacccctcccgcaacg -continued gcacctgcgacgactcctcctggctggacttcctgcgcaagatccaggagcgctccggcctgggcgacgagacccacggcccc gagggcctgctgcaggtgccccccgcaagaccttcgcccgcgcccgcgaggagaccgagcaggtgatcatcggcgccctgg agaacctgttcaagaacaccaacgtgaaccccaaggacatcggcatcctggtggtgaactcctccatgttcaaccccacccccctc cctgtccgccatggtggtgaacaccttcaagctgcgctccaacgtgcgctccttcaacctgggcggcatgggctgctccgccggcg tgatcgccatcgacctggccaaggacctgctgcacgtgcacaagaacacctacgccctggtggtgtccaccgagaacatcacct acaacatctacgccggcgacaaccgctccatgatggtgtccaactgcctgttccgcgtgggcggcgccgccatcctgctgtccaac aagccccgcgaccgccgccgctccaagtacgagctggtgcacaccgtgcgcacccacaccggcgccgacgacaagtccttcc gctgcgtgcagcagggcgacgacgagaacggccagaccggcgtgtccctgtccaaggacatcaccgacgtggccggccgcac cgtgaagaagaacatcgccaccctgggccccctgatcctgcccctgtccgagaagctgctgttcttcgtgaccttcatgggcaaga agctgttcaaggacgagatcaagcactactacgtgcccgacttcaagctggccatcgaccacttctgcatccacgccggcggcaa ggccgtgatcgacgtgctggagaagaacctgggcctggcccccatcgacgtggaggcctcccgctccaccctgcaccgcttcgg caacacctcctcctcctccatctggtacgagctggcctacatcgagcccaagggccgcatgaagaagggcaacaaggtgtggca gatcgccctgggctccggcttcaagtgcaactccgccgtgtgggtggccctgaacaacgtgaaggcctccaccaactcccccctgg gagcactgcatcgaccgctaccccgtgaagatcgactccgactccggcaagtccgagacccgcgtgcccaacggccgctccTG Acttaag Nucleotide sequence of BnFAE2 contained in pSZ3069:

(SEQ ID NO: 107)

actagtATGgagcgcaccaactccatcgagatggaccaggagcgcctgaccgccgagatggccttcaaggactcctcctccgc cgtgatccgcatccgccgccgcctgcccgacttcctgacctccgtgaagctgaagtacgtgaagctgggcctgcacaactccttca acttcaccaccttcctgttcctgctgatcatcctgcccctgaccggcaccgtgctggtgcagctgaccggcctgaccttcgagaccttc tccgagctgtggtacaaccacgccgcccagctggacggcgtgacccgcctggcctgcctggtggtgtccctgtgcttcgtgctgatcatc tacgtgaccaaccgctccaagcccgtgtacctggtggacttctcctgctacaagcccgaggacgagcgcaagatgtccgtggact ccttcctgaagatgaccgagcagaacggcgccttcaccgacgacaccgtgcagttccagcagcgcatctccaaccgcgccggc ctgggcgacgagacctacctgccccgcggcatcacctccacccccccccaagctgaacatgtccgaggcccgcgccgaggccga ggccgtgatgttcggcgccctggactccctgttcgagaagaccggcatcaagcccgccgaggtgggcatcctgatcgtgtcctgct ccctgttcaaccccacccccctccctgtccgccatgatcgtgaaccactacaagatgcgcgaggacatcaagtcctacaacctggg cggcatgggctgctccgccggcctgatctccatcgacctggccaacaacctgctgaaggccaaccccaactcctacgccgtggtg gtgtccaccgagaacatcaccctgaactggtacttcggcaacgaccgctccatgctgtgcaactgcatcttccgcatgggcgg cgccgccatcctgctgtccaaccgccgccaggaccgctccaagtccaagtacgagctggtgaacgtggtgcgcacccacaagg gctccgacgacaagaactacaactgcgtgtaccagaaggaggacgagcgcggcaccatcggcgtgtccctggcccgcgagct gatgtccgtggccggcgacgccctgaagaccaacatcaccaccctgggccccatggtgctgcccctgtccggccagctgatgttct ccgtgtccctggtgaagcgcaagctgctgaagctgaagtgaagccctacatccccgacttcaagctggccttcgagcacttctgc atccacgccggcggccgcgccgtgctggacgaggtgcagaagaacctggacctggaggactggcacatggagccctcccgca tgaccctgcaccgcttcggcaacacctcctcctcctccctgtggtacagatggcctacaccgaggccaagggccgcgtgaaggc cggcgaccgcctgtggcagatcgccttcggctccggcttcaagtgcaactccgccgtgtggaaggccctgcgcgtggtgtccacc gaggagctgaccggcaacgcctgggccggctccatcgagaactaccccgtgaagatcgtgcagTGActtaag To determine their impact on fatty acid profiles, the above constructs containing various heterologous FAE genes, driven by the PmAMT3 promoter, were transformed independently into STRAIN Z.

Primary transformants were clonally purified and grown under low-nitrogen lipid production conditions at pH7.0 (all the plasmids require growth at pH 7.0 to allow for maximal FAE gene expression when driven by the pH regulated PmAMT03 promoter). The resulting profiles from a set of representative clones arising from transformations with pSZ3070, pSZ3071, pSZ3072, pSZ3067, pSZ3068 and pSZ3069 into STRAIN Z are shown in Tables 52-57, respectively, below.

Figure 23:
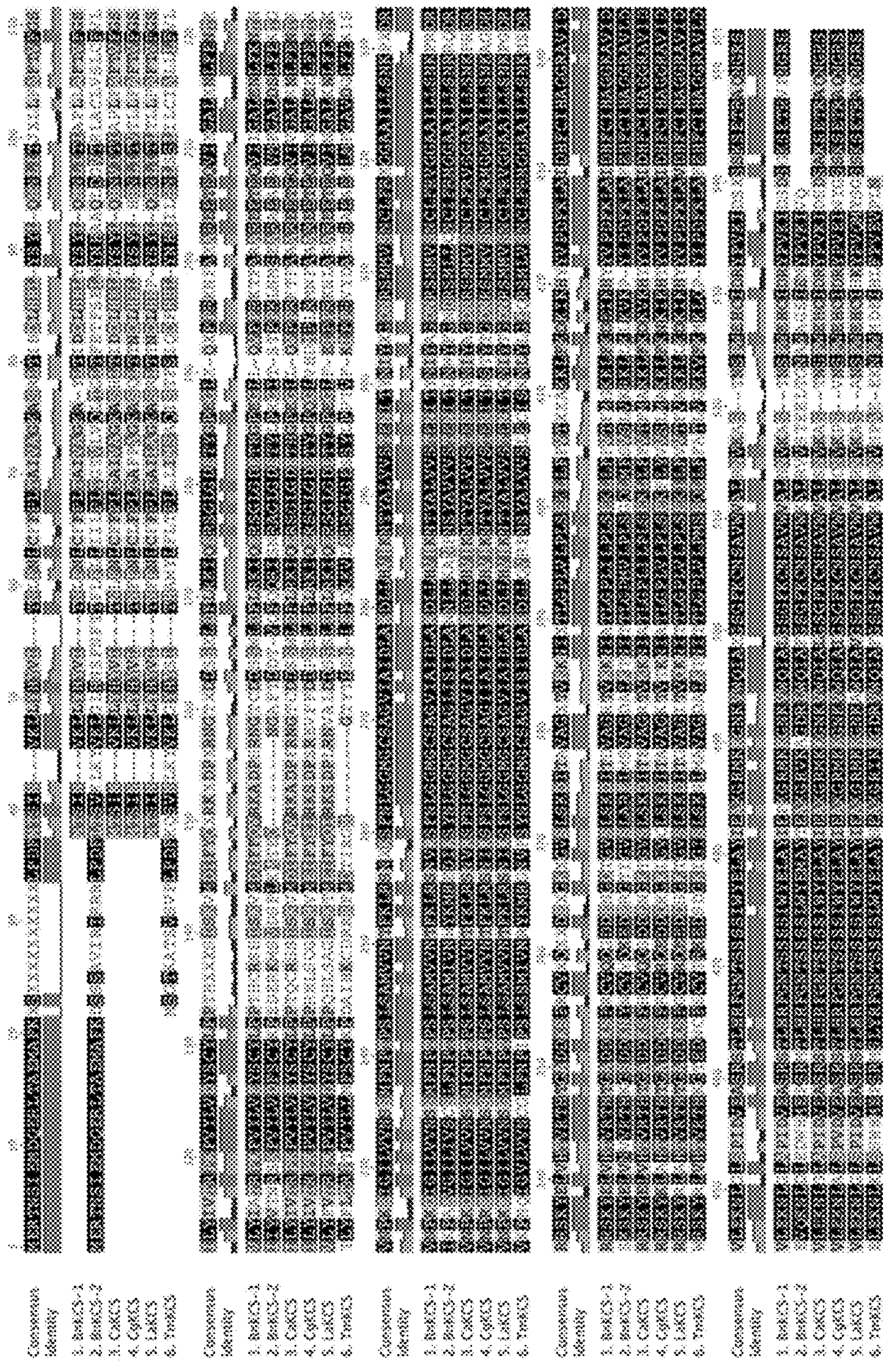
FIG. 23 shows the pairwise alignment of heterologous FAE proteins (SEQ ID NOS 165-171, respectively, in order of appearance) expressed in STRAIN Z.

All the transgenic STRAIN Z strains expressing heterologous FAE genes show an increased accumulation of C20:1 and C22:1 fatty acid (see Tables 52-57). The increase in eicosenoic ($20:1^{\Delta 11}$) and erucic ($22:1^{\Delta 13}$) acids levels over the wildtype is consistently higher than the wildtype levels. Additionally, the unsaturated fatty acid profile obtained with heterologous expression of BnFAE1 in STRAIN Z resulted in noticeable increase in Docosadienoic acid (C22:2n6). Protein alignment of aforementioned FAE expressed in STRAIN Z is shown in FIG. 23.

TABLE 52

Unsaturated fatty acid profile in STRAIN Z and representative derivative transgenic lines transformed with pSZ3070 (CaFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1828-20 | 51.49 | 9.13 | 0.65 | 4.35 | 1.24 | 0.11 | 0.00 |
| STRAIN Z; T588; D1828-23 | 55.59 | 7.65 | 0.50 | 3.78 | 0.85 | 0.00 | 0.13 |
| STRAIN Z; T588; D1828-43 | 54.70 | 7.64 | 0.50 | 3.44 | 0.85 | 0.09 | 0.00 |
| STRAIN Z; T588; D1828-12 | 52.43 | 7.89 | 0.59 | 2.72 | 0.73 | 0.00 | 0.00 |
| STRAIN Z; T588; D1828-19 | 56.02 | 7.12 | 0.52 | 3.04 | 0.63 | 0.10 | 0.11 |
| Cntrl STRAIN Z pH 7 | 57.99 | 6.62 | 0.56 | 0.19 | 0.00 | 0.06 | 0.05 |
| Cntrl STRAIN Z pH 5 | 57.70 | 7.08 | 0.54 | 0.11 | 0.00 | 0.05 | 0.05 |

TABLE 53

Unsaturated fatty acid profile in STRAIN Z and representative derivative transgenic lines transformed with pSZ3071 (LaFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1829-36 | 54.66 | 7.04 | 0.52 | 1.82 | 0.84 | 0.12 | 0.09 |
| STRAIN Z; T588; D1829-24 | 56.27 | 6.72 | 0.51 | 1.70 | 0.72 | 0.09 | 0.00 |
| STRAIN Z; T588; D1829-11 | 56.65 | 8.36 | 0.54 | 2.04 | 0.67 | 0.00 | 0.00 |
| STRAIN Z; T588; D1829-35 | 55.57 | 7.71 | 0.53 | 0.10 | 0.66 | 0.00 | 0.00 |
| STRAIN Z; T588; D1829-42 | 56.03 | 7.06 | 0.54 | 1.54 | 0.51 | 0.06 | 0.08 |
| Cntrl STRAIN Z pH 7 | 57.70 | 7.08 | 0.54 | 0.11 | 0.00 | 0.06 | 0.05 |
| Cntrl STRAIN Z pH 5 | 57.99 | 6.62 | 0.56 | 0.19 | 0.00 | 0.05 | 0.05 |

TABLE 54

Unsaturated fatty acid profile in STRAIN Z and representative derivative transgenic lines transformed with pSZ3072 (CgFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1830-47 | 57.74 | 7.79 | 0.52 | 1.61 | 0.25 | 0.11 | 0.05 |
| STRAIN Z; T588; D1830-16 | 58.06 | 7.39 | 0.55 | 1.64 | 0.22 | 0.07 | 0.06 |
| STRAIN Z; T588; D1830-12 | 57.77 | 6.86 | 0.51 | 1.34 | 0.19 | 0.09 | 0.00 |
| STRAIN Z; T588; D1830-37 | 58.45 | 7.54 | 0.49 | 1.65 | 0.19 | 0.06 | 0.00 |
| STRAIN Z; T588; D1830-44 | 57.10 | 7.28 | 0.56 | 1.43 | 0.19 | 0.07 | 0.00 |
| Cntrl STRAIN Z pH 7 | 57.70 | 7.08 | 0.54 | 0.11 | 0.00 | 0.06 | 0.05 |
| Cntrl STRAIN Z pH 5 | 57.99 | 6.62 | 0.56 | 0.19 | 0.00 | 0.05 | 0.05 |

TABLE 55

Unsaturated fatty acid profile in Strain AR and representative derivative transgenic lines transformed with pSZ3070 (TmFAE) DNA. No detectable Erucic (22:1) acid peaks were reported for these transgenic lines.

| Sample ID | C18:1 | C18:2 | C18:3a | C20:1 | C22:2n6 | C22:5 |
|---|---|---|---|---|---|---|
| STRAIN Z; T588; D1825-47 | 59.97 | 7.44 | 0.56 | 0.57 | 0.00 | 0.00 |
| STRAIN Z; T588; D1825-35 | 58.77 | 7.16 | 0.51 | 0.50 | 0.09 | 0.11 |
| STRAIN Z; T588; D1825-27 | 60.40 | 7.82 | 0.47 | 0.44 | 0.07 | 0.07 |
| STRAIN Z; T588; D1825-14 | 58.07 | 7.32 | 0.54 | 0.41 | 0.05 | 0.05 |
| STRAIN Z; T588; D1825-40 | 58.66 | 7.74 | 0.46 | 0.39 | 0.08 | 0.00 |
| Cntrl STRAIN Z pH 7 | 57.99 | 6.62 | 0.56 | 0.19 | 0.05 | 0.05 |
| Cntrl STRAIN Z pH 5 | 57.70 | 7.08 | 0.54 | 0.11 | 0.06 | 0.05 |

TABLE 56

Unsaturated fatty acid profile in STRAIN Z and representative derivative transgenic lines transformed with pSZ3068 (BnFAE1) DNA. No detectable Erucic (22:1) acid peaks were reported for these transgenic lines.

| Sample ID | C18:1 | C18:2 | C18:3a | C20:1 | C22:2n6 | C22:5 |
|---|---|---|---|---|---|---|
| STRAIN Z; T588; D1826-30 | 59.82 | 7.88 | 0.55 | 0.32 | 0.17 | 0.10 |
| STRAIN Z; T588; D1826-23 | 59.32 | 8.02 | 0.58 | 0.27 | 0.18 | 0.07 |
| STRAIN Z; T588; D1826-45 | 59.63 | 7.49 | 0.55 | 0.27 | 0.19 | 0.08 |
| STRAIN Z; T588; D1826-24 | 59.35 | 7.78 | 0.57 | 0.26 | 0.23 | 0.00 |
| STRAIN Z; T588; D1826-34 | 59.14 | 7.61 | 0.57 | 0.25 | 0.22 | 0.05 |
| Cntrl STRAIN Z pH 7 | 57.81 | 7.15 | 0.59 | 0.19 | 0.04 | 0.06 |
| Cntrl STRAIN Z pH 5 | 58.23 | 6.70 | 0.58 | 0.18 | 0.05 | 0.06 |

TABLE 57

Unsaturated fatty acid profile in STRAIN Z and representative derivative transgenic lines transformed with pSZ3069 (BnFAE2) DNA. No detectable Erucic (22:1) acid peaks were reported for these transgenic lines.

| Sample ID | C18:1 | C18:2 | C18:3a | C20:1 | C22:2n6 | C22:5 |
|---|---|---|---|---|---|---|
| STRAIN Z; T588; D1827-6 | 60.59 | 8.20 | 0.57 | 0.34 | 0.00 | 0.07 |
| STRAIN Z; T588; D1827-42 | 59.62 | 6.44 | 0.52 | 0.30 | 0.07 | 0.00 |
| STRAIN Z; T588; D1827-48 | 59.71 | 7.99 | 0.59 | 0.30 | 0.06 | 0.00 |
| STRAIN Z; T588; D1827-43 | 60.66 | 8.21 | 0.59 | 0.29 | 0.04 | 0.00 |
| STRAIN Z; T588; D1827-3 | 60.26 | 7.99 | 0.57 | 0.28 | 0.04 | 0.00 |
| Cntrl STRAIN Z pH 7 | 57.81 | 7.15 | 0.59 | 0.19 | 0.04 | 0.06 |
| Cntrl STRAIN Z pH 5 | 58.23 | 6.70 | 0.58 | 0.18 | 0.05 | 0.06 |

Example 54: Elevating Total Unsaturated Fatty Acids Level by Expressing Heterologous Desaturase Genes One of the approaches to generate a "zero SAT FAT" (e.g., total unsaturated fatty acids target at 97% or more/less than or equal to 3% saturated fat) strain is to express desaturase genes in a high oleic strain such as Strain N, which we found to produce about 85% C18:1 with total un-saturates around 93% in multiple fermentation runs. We investigated if the total saturates will be further diminished by expressing desaturase genes in Strain N.

In the examples below, we demonstrated the ability to reduce stearic and palmitic levels in wild type strain UTEX1435 by over expression of heterologous stearoyl-ACP desaturase genes, including desaturases from *Olea europaea, Ricinus communis*, and *Chlorella protothecoides*.

Construct Used for the Expression of the *Olea europaea* Stearoyl-ACP Desaturase:

To introduce the *O. europaea* stearoyl-ACP desaturase (Accession No: AAB67840.1) into UTEX1435, Strain A, the *Saccharomyces cerevisiae* invertase gene was utilized as the selectable marker to confer the ability of growing on sucrose media. The construct that has been expressed in UTEX1435, Strain A can be written as 6SA::CrTUB2:ScSUC2:CvNR::CrTUB2:CpSADtp:OeSAD:CvNR::6SB and is termed pSZ1377.

Relevant restriction sites in the construct pSZ1377 are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA that permit targeted integration at 6 s locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the second *C. reinhardtii* β-tubulin promoter driving the expression of the OeSAD, indicated by boxed italics text. The Initiator ATG and terminator TGA codons of the OeSAD are indicated by uppercase, bold italics, while the remainder of the stearoyl-ACP desaturase coding region is indicated by bold italics. The *Chlorella protothecoides* stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ 1377:

(SEQ ID NO: 108)

gctcttcgccgccgccactcctgctcgagcgcgcccgcgcgtgcgccgccagcgccttggccttttcgccgcgctcgtgcgcgtcgctgatgtcca tcaccaggtccatgaggtctgccttgcgccggctgagccactgcttgtccgggcggccaagaggagcatgagggaggactcctggtccaggg tcctgacgtggtcgcggctctgggagcgggccagcatcatctggctctgccgcaccgaggccgcctccaactggtcctccagcagccgcagtcg ccgccgaccctggcagaggaagacaggtgaggggggtatgaattgtacagaacaaccacgagccttgtctaggcagaatccctaccagtcat ggctttacctggatgacggcctgcgaacagctgtccagcgaccctcgctgccgccgcttctcccgcacgcttctttccagcaccgtgatggcgcg agccagcgccgcacgctggcgctgcgcttcgccgatctgaggacagtcggggaactctgatcagtctaaaccccttgcgcgttagtgttgcca tcctttgcagaccggtgagagccgacttgttgtgcgccacccccacaccacctcctcccagaccaattctgtcacctttttggcgaaggcatcgg cctcggcctgcagagaggacagcagtgcccagccgctggggggttggcggatgcacgctcaggtaccctttcttgcgctatgacacttccagcaa aaggtagggcgggctgcgagacggcttcccggcgctgcatgcaacaccgatgatgcttcgacccccccgaagctccttcggggctgcatgggcgc tccgatgccgctccagggcgagcgctgtttaaatagccaggcccccgattgcaaagacattatagcgagctaccaaagccatattcaaacacct agatcactaccacttctacacaggccactcgagcttgtgatcgcactccgctaagggggcgcctcttcctcttcgtttcagtcacaacccgcaaac tctagaatatca*ATG*ctgctgcaggccttcctgttcctgctggccggcttcgccgccaagatcagcgcctccatgacgaacgagacgtccga ccgccccctggtgcacttcacccccaacaagggctggatgaacgaccccaacggcctgtggtacgacgagaaggacgccaagtggcacc tgtacttccagtacaacccgaacgacaccgtctgggggacgcccttgttctggggccacgccacgtccgacgacctgaccaactgggaagg accagcccatcgccatcgcccgaagcgcaacgactccggcgccttctccggctccatggtggtggactacaacaacacctccggcttcttc aacgacaccatcgacccgcgccagcgctgcgtggccatctggacctacaacaccccggagtccgaggagcagtacatctcctacagcctg gacggcggctacaccttcaccgagtaccagaagaaccccgtgctggccgccaactccacccagttccgcgacccgaaggtcttctggtacg agccctcccagaagtggatcatgaccgcggccaagtcccaggactacaagatcgagatctactcctccgacgacctgaagtcctggaagc tggagtccgcgttcgccaacgagggcttcctcggctaccagtacgagtgccccggcctgatcgaggtccccaccgagcaggaccccagca agtcctactgggtgatgttcatctccatcaaccccggcgccccggccggcggctccttcaaccagtacttcgtcggcagcttcaacggcaccc acttcgaggccttcgacaaccagtcccgcgtggtggacttcggcaaggactactacgccctgcagaccttcttcaacaccgacccgactac gggagcgccctgggcatcgcgtgggcctccaactgggagtactccgccttcgtgcccaccaacccctggcgctcctccatgtccctcgtgcgc aagttctccctcaacaccgagtaccaggccaacccggagacggagctgatcaacctgaaggccgagccgatcctgaacatcagcaacgc cggccccctggagccggttcgccaccaacaccacgttgacgaaggccaacagctacaacgtcgacctgtccaacagcaccggcaccctgga gttcgagctggtgtacgccgtcaacaccacccagacgatctccaagtccgtgttcgcggacctctccctctggttcaagggcctggaggacc ccgaggagtacctccgcatgggcttcgaggtgtccgcgtcctccttcttcctggaacgcgggaacagcaaggtgaagttcgtgaaggaga acccctacttcaccaaccgcatgagcgtgaacaaccagcccttcaagagcgagaacgcctgtcctactacaaggtgtacggcttgctgga ccagaacatcctggagctgtacttcaacgacggcgacgtcgtgtccaccaacacctacttcatgaccaccgggaacgccctgggctccgtg aacatgacgacgggggtggacaacctgttctacatcgacaagttccaggtgcgcgaggtcaag*TGA*caattggcagcagcagctcggat agtatcgacacactctggacgctggtcgtgtgatggactgttgccgccacacttgctgccttgacctgtgaatatccctgccgcttttatcaaacag cctcagtgtgtttgatcttgtgtgtacgcgcttttgcgagttgctagctgcttgtgctatttgcgaataccacccccagcatccccttccctcgtttcat atcgcttgcatcccaaccgcaacttatctacgctgtcctgctatccctcagcgctgctcctgctcctgctcactgcccctcgacagccttggtttgg gctccgcctgtattctcctggtactgcaacctgtaaaccagcactgcaatgctgatgcacgggaagtagtgggatgggaacacaaatggaggat cccgcgtctcgaacagagcgcgcagaggaacgctgaaggtctcgcctctgtcgacctcagcgcggcatacaccacaataaccacctgacgaa tgcgcttggttcttcgtccattagcgaagcgtccggttcacacacgtgccacgttggcgaggtggcaggtgacaatgatcggtggagctgatggtc -continued gaaacgttcacagcctagggatatcgaattcctttcttgcgctatgacacttccagcaaaaggtagggcgggctgcgagacggcttcccggc gctgcatgcaacaccgatgatgcttcgacccccgaagctccttcggggctgcatgggcgctccgatgccgctccagggcgagcgctgttta aatagccaggcccccgattgcaaagacattatagcgagctaccaaagccatattcaaacacctagatcactaccacttctacacaggccc ctcgagcttgtgatcgcactccgctaagggggcgcctcttcctcttcgtttcagtcacaacccgcaaacactagtATGgccaccgcatccact ttctcggcgttcaatgcccgctgcggcgacctgcgtcgctcggcgggctccgggccccggcgcccagcgaggcccctccccgtgcgcgggc gcgccgaggtgcacgtgcaggtgacccactccctggccccgagaagcgcgagatcttcaactccctgaacaactgggcccaggagaa catcctggtgctgctgaaggacgtggacaagtgctggcagccctccgacttcctgcccgactccgcctccgagggcttcgacgagcaggt gatggagctgcgcaagcgctgcaaggagatccccgacgactacttcatcgtgctggtgggcgacatgatcaccgaggaggccctgccc acctaccagaccatgctgaacaccctggacggcgtgcgcgacgagaccggcgcctccctgacccctgggccatctggacccgcgcctg gaccgccgaggagaaccgccacggcgacctgctgaacaagtacctgtacctgtccggccgcgtggacatgaagcagatcgagaagac catccagtacctgatcggctccggcatggacccccgcaccgagaacaacccctacctgggcttcatctacacctccttccaggagcgcgcc accttcatctcccacggcaacaccgcccgcctggccaaggagcacggcgacctgaagctggcccagatctgcggcatcatcgccgccga cgagaagcgccacgagaccgcctacaccaagatcgtggagaagctgttcgagatcgaccccgacggcaccgtgctggccctggccgac atgatgcgcaagaaggtgtccatgcccgcccacctgatgtacgacggccaggacgacaacctgttcgagaacttctcctccgtggccca gcgcctgggcgtgtacaccgccaaggactacgccgacatcctggagttcctggtgggccgctgggacatcgagaagctgaccggcctgt ccggcgagggccgcaaggccaggactacgtgtgcaccctgcccccccgcatccgccgcctggaggagcgcgcccagtcccgcgtgaa gaaggcctccgccacccccttctcctggatcttcggccgcgagatcaacctgatggactacaaggaccacgacggcgactacaaggacc acgacatcgactacaaggacgacgacgacaagTGAatcgatagatctcttaaggcagcagcagctcggatagtatcgacacactctggac gctggtcgtgtgatggactgttgccgccacacttgctgccttgacctgtgaatatccctgccgcttttatcaaacagcctcagtgtgtttgatcttgtg tgtacgcgcttttgcgagttgctagctgcttgtgctatttgcgaataccacccccagcatccccttccctcgtttcatatcgcttgcatcccaaccgca acttatctacgctgtcctgctatccctcagcgctgctcctgctcctgctcactgcccctcgcacagccttggtttgggctccgcctgtattctcctggt actgcaacctgtaaaccagcactgcaatgctgatgcacgggaagtagtgggatgggaacacaaatggaaagcttaattaagagctcttgttttc cagaaggagttgctccttgagcctttcattctcagcctcgataacctccaaagccgctctaattgtggaggggttcgaatttaaaagcttggaa tgttggttcgtgcgtctggaacaagcccagacttgttgctcactgggaaaaggaccatcagctccaaaaaacttgccgctcaaaccgcgtacct ctgctttcgcgcaatctgccctgttgaaatcgccaccacattcatattgtgacgcttgagcagtctgtaattgcctcagaatgtggaatcatctgc cccctgtgcgagcccatgccaggcatgtcgcgggcgaggacacccgccactcgtacagcagaccattatgctacctcacaatagttcataaca gtgaccatatttctcgaagctccccaacgagcacctccatgctctgagtggccaccccccggccctggtgcttgcggagggcaggtcaaccggc atggggctaccgaaatccccgaccggatcccaccacccccgcgatgggaagaatctctccccgggatgtgggccaccaccagcacaacctgc tggcccaggcgagcgtcaaaccataccacacaaatatccttggcatcggccctgaattccttctgccgctctgctacccggtgcttctgtccgaa gcaggggttgctagggatcgctccgagtccgcaaacccttgtcgcgtggcggggcttgttcgagcttgaagagc Construct Used for the Expression of the *Ricinus communis* Stearoyl-ACP Desaturase:

To introduce the *Ricinus communis* stearoyl-ACP desaturase (Accession No: AAA74692.1) into UTEX1435, Strain A, the *Saccharomyces cerevisiae* invertase gene was utilized as the selectable marker to confer the ability of growing on sucrose media. The construct that has been expressed in UTEX1435, Strain A can be written as 6SA::CrTUB2:ScSUC2:CvNR::PmAMT03:CpSADtp:RcSAD:CvNR::6SB and is termed pSZ1454.

Relevant restriction sites in the construct pSZ1454 are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA that permit targeted integration at 6s nuclear chromosomal locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the endogenous AMT03 promoter driving the expression of the RcSAD, indicated by boxed italics text.

The Initiator ATG and terminator TGA codons of the RcSAD are indicated by uppercase, bold italics, while the remainder of the stearoyl-ACP desaturase coding region is indicated by bold italics. The *Chlorella protothecoides* stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ1454:

(SEQ ID NO: 109)

gctcttcgccgccgccactcctgctcgagcgcgcccgcgcgtgcgccgccagcgccttggccttttcgcgcgctcgtgcgcgtc gctgatgtccatcaccaggtccatgaggtctgccttgcgccggctgagccactgcttcgtccgggcggccaaagaggagcatga gggaggactcctggtccagggtcctgacgtggtcgcggctctgggagcgggccagcatcatctggctctgccgaccgaggc cgcctccaactggtcctccagcagccgcagtcgccgccgaccctggagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaacccccttgcgcgttagtgttgccatcctttgcagaccggtgag agccgacttgttgtgcgccacccccacaccacctcctcccagaccaattctgtcacctttttggcgaaggcatcggcctcggcc tgcagagaggacagcagtgcccagccgctggggttggcggatgcacgctcaggtaccctttcttgcgctatgacacttccagca aaaggtagggcgggctgcgagacggcttcccggcgctgcatgcaacaccgatgatgcttcgaccccccgaagctccttcggggctg catgggcgctccgatgccgctccagggcgagcgctgtttaaatagccaggcccccgattgcaaagacattatagcgagctaccaaag ccatattcaaacacctagatcactaccacttctacacaggccactcgagcttgtgatcgcactccgctaagggggcgcctcttcctcttc gtttcagtcacaacccgcaaactctagaatatca*ATG**ctgctgcaggccttcctgttcctgctggccggcttcgccgccaagatcag*

*cgcctccatgacgaacgagcgtccgaccgccccctggtgcacttcacccccaacaagggctggatgaacgaccccaacggcc*

*tgtggtacgacgagaaggacgccaagtggcacctgtacttccagtacaacccgaacgacaccgtctggggggacgcccttgttctg*

*gggccacgccacgtccgacgacctgaccaactgggaggaccagcccatcgccatcgccccgaagcgcaacgactccggcgc*

*cttctccggctccatggtggtggactacaacaacacctccggcttcttcaacgacaccatcgacccgcgccagcgctgcgtggcca*

*tctggacctacaacaccccggagtccgaggagcagtacatctcctacagcctggacggcggctacaccttcaccgagtaccaga*

*agaaccccgtgctggccgccaactccacccagttccgcgacccgaaggtcttctggtacgagccctcccagaagtggatcatgac*

*cgcggccaagtcccaggactacaagatcgagatctactcctccgacgacctgaagtcctggaagctggagtccgcgttcgccaa*

*cgagggcttcctcggctaccagtacgagtgccccggcctgatcgaggtccccacgagcaggaccccagcaagtcctactgggt*

*gatgttcatctccatcaaccccggcgccccggccggcggctccttcaaccagtacttcgtcggcagcttcaacggcacccacttcg*

*aggccttcgacaaccagtcccgcgtggtggacttcggcaaggactactacgccctgcagaccttcttcaacaccgacccgaccta*

*cgggagcgccctgggcatcgcgtgggcctccaactgggagtactccgccttcgtgcccaccaacccctggcgctcctccatgtccc*

*tcgtgcgaagttctccctcaacaccgagtaccaggccaacccggagacggagctgatcaacctgaaggccgagccgatcctg*

*aacatcagcaacgccggcccctggagccggttcgccaccaacaccacgttgacgaaggccaacagctacaacgtcgacctgtc*

*caacagcaccggcaccctggagttcgagctggtgtacgccgtcaacaccacccagacgatctccaagtccgtgttcgcggacctc*

*tccctctggttcaagggcctggaggaccccgaggagtacctccgcatgggcttcgaggtgtccgcgtcctccttcttcctggaccgc*

*gggaacagcaaggtgaagttcgtgaaggagaacccctacttcaccaaccgcatgagcgtgaacaaccagccttcaagagcg*

*agaacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcgac*

*aagttccaggtgcgcgaggtcaag**TGA*caattggcagcagcagctcggatagtatcgacacactctggacgctggtcgtgtgat ggactgttgccgccacacttgctgccttgacctgtgaatatccctgccgcttttatcaaacagcctcagtgtgtttgatcttgtgtgtacgcg cttttgcgagttgctagctgcttgtgctatttgcgaataccacccccagcatccccttccctcgtttcatatcgcttgcatccaaccgcaac ttatctacgctgtcctgctatccctcagcgctgctcctgctcctgctcactgcccctcgcacagccttggtttgggctccgcctgtattctcc -continued tggtactgcaacctgtaaaccagcactgcaatgctgatgcacgggaagtagtgggatgggaacacaaatggaggatcccgcgtctcg aacagagcgcgcagaggaacgctgaaggtctcgcctctgtcgcacctcagcgcggcatacaccacaataaccacctgacgaatgcg cttggttcttcgtccattagcgaagcgtccggttcacacacgtgccacgttggcgaggtggcaggtgacaatgatcggtggagctgatg gtcgaaacgttcacagcctagggatatcgaattc*ggccgacaggacgcgcgtcaaaggtgctggtcgtgtatgccctggccggca*

*ggtcgttgctgctgctggttagtgattccgcaaccctgattttggcgtcttattttggcgtggcaaacgctggcgcccgcgagccggg*

*ccggcggcgatgcggtgccccacggctgccggaatccaagggaggcaagagcgcccgggtcagttgaagggctttacgcgca*

*aggtacagccgctcctgcaaggctgcgtggtggaattggacgtgcaggtcctgctgaagttcctccaccgcctcaccagcggaca*

*aagcaccggtgtatcaggtccgtgtcatccactctaaagaactcgactacgacctactgatggccctagattcttcatcaaaaacg*

*cctgagacacttgcccaggattgaaactccctgaagggaccaccaggggccctgagttgttccttccccccgtggcgagctgcca*

*gccaggctgtacctgtgatcgaggctggcgggaaaataggcttcgtgtgctcaggtcatgggaggtgcaggacagctcatgaaa*

*cgccaacaatcgcacaattcatgtcaagctaatcagctatttcctcttcacgagctgtaattgtcccaaaattctggtctaccggggg*

*tgatccttcgtgtacgggcccttccctcaaccctaggtatgcgcgcatgcggtcgccgcgcaactcgcgcgagggccgagggtttg*

*ggacgggccgtcccgaaatgcagttgcacccggatgcgtggcaccttttttgcgataatttatgcaatggactgctctgcaaaattct*

*ggctctgtcgccaaccctaggatcagcggcgtaggatttcgtaatcattcgtcctgatggggagctaccgactaccctaatatcagc*

*ccgactgcctgacgccagcgtccacttttgtgcacacattccattcgtgcccaagacatttcattgtggtgcgaagcgtccccagtta*

*cgctcacctgtttcccgacctccttactgttctgtcgacagagcgggcccacaggccgtcgcagcc*~~~~actagtATGgccaccgc

*atccactttctcggcgttcaatgcccgctgcggcgacctgcgtcgctcggcgggctccgggccccggcgcccagcgaggcccctc*

*cccgtgcgcgggcgcgccgcctccaccctgaagtccggctccaaggaggtggagaacctgaagaagcccttcatgcccccccg*

*cgaggtgcacgtgcaggtgacccactccatgcccccccagaagatcgagatcttcaagtccctggacaactgggccgaggaga*

*acatcctggtgcacctgaagcccgtggagaagtgctggcagccccaggacttcctgcccgaccccgcctccgacggcttcgacg*

*agcaggtgcgcgagctgcgcgagcgcgccaaggagatccccgacgactacttcgtggtgctggtgggcgacatgatcaccgag*

*gaggccctgcccacctaccagaccatgctgaacaccctggacggcgtgcgcgacgagaccggcgcctcccccacctcctgggc*

*catctggacccgcgcctggaccgccgaggagaaccgccacggcgacctgctgaacaagtacctgtacctgtccggccgcgtgg*

*acatgcgccagatcgagaagaccatccagtacctgatcggctccggcatggacccccgcaccgagaactcccccctacctgggct*

*tcatctacacctccttccaggagcgcgccaccttcatctcccacggcaacaccgcccgccaggccaaggagcacggcgacatca*

*agctggcccagatctgcggcaccatcgccgccgacgagaagcgccacgagaccgcctacaccaagatcgtggagaagctgtt*

*cgagatcgaccccgacggcaccgtgctggccttcgccgacatgatgcgaagaagatctccatgcccgcccacctgatgtacga*

*cggccgcgacgacaacctgttcgaccacttctccgccgtggcccagcgcctgggcgtgtacaccgccaaggactacgccgacat*

*cctggagttcctggtgggccgctggaaggtggacaagctgaccggcctgtccgccgagggccagaaggcccaggactacgtgt*

*gccgcctgcccccccgcatccgccgcctggaggagcgcgcccagggccgcgccaaggaggcccccaccatgcccttctcctgg*

*atcttcgaccgccaggtgaagctgatggactacaaggaccacgacggcgactacaaggaccacgacatcgactacaaggacg* acgacgacaagTGAatcgatagatctcttaaggcagcagcagctcggatagtatcgacacactctggacgctggtcgtgtgatgg actgttgccgccacacttgctgccttgacctgtgaatatccctgccgcttttatcaaacagcctcagtgtgtttgatcttgtgtgtacgcgctt ttgcgagttgctagctgcttgtgctatttgcgaataccacccccagcatccccttccctcgtttcatatcgcttgcatcccaaccgcaactta tctacgctgtcctgctatccctcagcgctgctcctgctcctgctcactgcccctcgcacagccttggtttgggctccgcctgtatttctcctg -continued gtactgcaacctgtaaaccagcactgcaatgctgatgcacgggaagtagtgggatgggaacacaaatggaaagcttaattaagagct cttgttttccagaaggagttgctccttgagcctttcattctcagcctcgataacctccaaagccgctctaattgtggagggggttc gaatttaaaagcttggaatgttggttcgtgcgtctggaacaagccagacttgttgctcactgggaaaaggaccatcagctcca aaaaacttgccgctcaaaccgcgtacctctgctttcgcgcaatctgccctgttgaaatcgccaccacattcatattgtgacgcttg agcagtctgtaattgcctcagaatgtggaatcatctgccccctgtgcgagcccatgccaggcatgtcgcgggcgaggacaccc gccactcgtacagcagaccattatgctacctcacaatagttcataacagtgaccatatttctcgaagctccccaacgagcacct ccatgctctgagtggccaccccccggccctggtgcttgcggagggcaggtcaaccggcatggggctaccgaaatccccgacc ggatcccaccacccccgcgatgggaagaatctctccccgggatgtgggcccaccaccagcacaacctgctggcccaggcga gcgtcaaaccataccacacaaatatccttggcatcggccctgaattccttctgccgctctgctaccggtgcttctgtccgaagc aggggttgctagggtcgctccgagtccgaaacccttgtcgcgtggcggggcttgttcgagcttgaagagc Construct Used for the Expression of the *Chlorella protothecoides* Stearoyl-ACP Desaturase:

To introduce the *Chlorella protothecoides* stearoyl-ACP desaturase into UTEX1435, Strain Z, the *Saccharomyces cerevisiae* invertase gene was utilized as the selectable marker to confer the ability of growing on sucrose media. The construct that has been expressed in UTEX1435, Strain Z can be written as 6SA::CrTUB2:ScSUC2:CvNR::PmAMT03:CpSAD1:CvNR::6SB and is termed pSZ3144.

Relevant restriction sites in the construct pSZ3144 are indicated in lowercase, bold and underlining and are 5'-3' BspQ 1, Kpn I, Xba I, Mfe I, BamH I, EcoR I, Spe I, Cla I, Sac I, BspQ I, respectively. BspQI sites delimit the 5' and 3' ends of the transforming DNA. Bold, lowercase sequences represent genomic DNA that permit targeted integration at 6s locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the endogenous AMT03 promoter driving the expression of the CpSAD1, indicated by boxed italics text. The Initiator ATG and terminator TGA codons of the CpSAD1 are indicated by uppercase, bold italics, while the remainder of the stearoyl-ACP desaturase coding region is indicated by bold italics. The *C. vulgaris* nitrate reductase 3' UTR is again indicated by lowercase underlined text followed by the 6S genomic region indicated by bold, lowercase text.

Nucleotide sequence of transforming DNA contained in pSZ3144:

(SEQ ID NO: 110)

gctcttcgccgccgccactcctgctcgagcgcgcccgcgcgtgcgccgccagcgccttggcttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaaccccccttgcgcgttagtgttgccatcctttgcagaccggtgagagccgacttgttgtgcgccac cccccacaccacctcctcccagaccaattctgtcacctttttggcgaaggcatcggcctcggcctgcagagaggacagcagtgccc agccgctggggttggcggatgcacgctcaggtaccctttcttgcgctatgacacttccagcaaaaggtagggcgggctgcgagac ggcttcccggcgctgcatgcaacaccgatgatgcttcgacccccgaagctccttcggggctgcatgggcgctccgatgccgctcca gggcgagcgctgtttaaatagccaggcccccgattgcaaagacattatagcgagctaccaaagccatattcaaacacctagatcac taccacttctacacaggccactcgagcttgtgatcgcactccgctaagggggcgcctcttcctcttcgtttcagtcacaacccgcaaa ctctagaatatca*ATG*ctgctgcaggccttcctgttcctgctggccggcttcgccgccaagatcagcgcctccatgacgaacga gacgtccgaccgcccctggtgcacttcacccccaacaagggctggatgaacgaccccaacggcctgtggtacgacgagaag gacgccaagtggcacctgtacttccagtacaacccgaacgacaccgtctgggggacgcccttgttctggggccacgccacgtc cgacgacctgaccaactgggaggaccagcccatcgccatcgccccgaagcgcaacgactccggcgccttctccggctccatgg -continued tggtggactacaacaacacctccggcttcttcaacgacaccatcgacccgcgccagcgctgcgtggccatctggacctacaaca ccccggagtccgaggagcagtacatctcctacagcctggacggcggctacaccttcaccgagtaccagaagaaccccgtgctg gccgccaactccacccagttccgcgacccgaaggtcttctggtacgagccctcccagaagtggatcatgaccgcggccaagtc ccaggactacaagatcgagatctactcctccgacgacctgaagtcctggaagctggagtccgcgttcgccaacgagggcttcc tcggctaccagtacgagtgccccggcctgatcgaggtccccaccgagcaggaccccagcaagtcctactgggtgatgttcatct ccatcaaccccggcgccccggccggcggctccttcaaccagtacttcgtcggcagcttcaacggcacccacttcgaggccttcga caaccagtcccgcgtggtggacttcggcaaggactactacgccctgcagaccttcttcaacaccgacccgacctacgggagcg ccctgggcatcgcgtgggcctccaactgggagtactccgccttcgtgcccaccaacccctggcgctcctccatgtccctcgtgcgc aagttctccctcaacaccgagtaccaggccaacccggagacggagctgatcaacctgaaggccgagccgatcctgaacatca gcaacgccggcccctggagccggttcgccaccaacaccacgttgacgaaggccaacagctacaacgtcgacctgtccaacag caccggcaccctggagttcgagctggtgtacgccgtcaacaccacccagacgatctccaagtccgtgttcgcggacctctccctc tggttcaagggcctggaggaccccgaggagtacctccgcatgggcttcgaggtgtccgcgtcctcctcttcctggaccgcggg aacagcaaggtgaagttcgtgaaggagaacccctacttcaccaaccgcatgagcgtgaacaaccagcccttcaagagcgag aacgacctgtcctactacaaggtgtacggcttgctggaccagaacatcctggagctgtacttcaacgacggcgacgtcgtgtcc accaacacctacttcatgaccaccgggaacgccctgggctccgtgaacatgacgacgggggtggacaacctgttctacatcga caagttccaggtgcgcgaggtcaagTGAcaattggcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtc gcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattcggccgacaggacgcgcgtcaaaggtgctggtcgtgtatgc cctggccggcaggtcgttgctgctgctggttagtgattccgcaaccctgattttggcgtcttattttggcgtggcaaacgctggcg cccgcgagccgggccggcggcgatgcggtgccccacggctgccggaatccaagggaggcaagagcgcccgggtcagttga agggctttacgcgcaaggtacagccgctcctgcaaggctgcgtggtggaattggacgtgcaggtcctgctgaagttcctccac cgcctcaccagcggacaaagcaccggtgtatcaggtccgtgtcatccactctaaagaactcgactacgacctactgatggccct agattcttcatcaaaaacgcctgagacacttgcccaggattgaaactccctgaagggaccaccaggggccctgagttgttcctt cccccgtggcgagctgccagccaggctgtacctgtgatcgaggctggcgggaaaataggcttcgtgtgctcaggtcatggg aggtgcaggacagctcatgaaacgccaacaatcgcacaattcatgtcaagctaatcagctatttcctcttcacgagctgtaatt gtcccaaaattctggtctaccgggggtgatccttcgtgtacgggcccttccctcaaccctaggtatgcgcgcatgcggtcgccgc gcaactcgcgcgagggccgagggtttgggacgggccgtcccgaaatgcagttgcacccggatgcgtggcacctttttttgcgat aatttatgcaatggactgctctgcaaaattctggctctgtcgccaaccctaggatcagcggcgtaggatttcgtaatcattcgtc ctgatggggagctaccgactaccctaatatcagcccgactgcctgacgccagcgtccacttttgtgcacacattccattcgtgcc caagacatttcattgtggtgcgaagcgtccccagttacgctcacctgtttcccgacctccttactgttctgtcgacagagcgggcc -continued cacaggccggtcgcagccactagtATGgccaccgcctccaccttctccgccttcaacgcccgctgcggcgacctgcgccgctcc gccggctccggccccgccgccccgcccgcccccctgcccgtgcgcgccgccatcgcctccgaggtgcccgtggccaccacctccc cccgccccggccccaccgtgtactccaagctggacaaggcccacaccctgacccccgagcgcatggagctgatcaacggcat gtccgccttcgccgaggagcgcatcctgcccgtgctgcagcccgtggagaagctgtggcagccccaggacctgctgcccgac cccgagtccccgacttcctggaccaggtggccgagctgcgcgcccgcgccgccaacgtgcccgacgactacttcgtggtgct ggtgggcgacatgatcaccgaggaggccctgcccacctacatggccatgctgaacaccctggacggcgtgcgcgacgaga ccggcgccgccgaccacccctggggccgctggacccgccagtgggtggccgaggagaaccgccacggcgacctgctgaac aagtactgctggctgaccggccgcgtgaacatgaaggccatcgaggtgaccatccagaacctgatcggctccggcatgaac cccaagaccgagaacaacccctacctgggcttcgtgtacacctccttccaggagcgcgccaccaagtactcccacggcaaca ccgcccgcctggccgcccagtacggcgacgccaccctgtccaaggtgtgcggcgtgatcgccgccgacgagggccgccacg agatcgcctacacccgcatcgtggaggagttcttccgcctggaccccgagggcgccatgtccgcctacgccgacatgatgcg caagcagatcaccatgcccgcccacctgatggacgaccagcagcacggcacccgcaacaccggccgcaacctgttcgccga cttctccgccgtgaccgagaagctggacgtgtacgacgccgaggactactgcaagatcctggagcacctgaactcccgctgg aagatcgccgaccgcaccgtgtccggcgacgccggcgccgaccaggagtacgtgctgcgcctgccctcccgcttccgcaagc tggccgagaagtccgccgccaagcgcgccaagaccaagcccaagcccgtggccttctcctggctgtccggccgcgaggtga tggtgTGAatcgatagatctcttaaggcagcagcagctcggatagtatcgacacactctggacgctggtcgtgtgatggactgttg ccgccacacttgctgccttgacctgtgaatatccctgccgcttttatcaaacagcctcagtgtgtttgatcttgtgtgtacgcgcttttgc gagttgctagctgcttgtgctatttgcgaataccacccccagcatccccttccctcgtttcatatcgcttgcatcccaaccgcaacttat ctacgctgtcctgctatccctcagcgctgctcctgctcctgctcactgcccctcgcacagccttggtttgggctccgcctgtattctcctg gtactgcaacctgtaaaccagcactgcaatgctgatgcacgggaagtagtgggatgggaacacaaatggaaagcttaattaagag ctcttgttttccagaaggagttgctccttgagcctttcattctcagcctcgataacctccaaagccgctctaattgtggaggggttcg aatttaaaagcttggaatgttggttcgtgcgtctggaacaagcccagacttgttgctcactgggaaaaggaccatcagctccaaaa aacttgccgctcaaaccgcgtacctctgctttcgcgcaatctgccctgttgaaatcgccaccacattcatattgtgacgcttgagcag tctgtaattgcctcagaatgtggaatcatctgcccccctgtgcgagcccatgccaggcatgtcgcgggcgaggacacccgccactcg tacagcagaccattatgctacctcacaatagttcataacagtgaccatatttctcgaagctccccaacgagcacctccatgctctga gtggccacccccccggccctggtgcttgcggagggcaggtcaaccggcatggggctaccgaaatccccgaccggatcccaccaccc ccgcgatgggaagaatctctccccgggatgtgggcccaccaccagcacaacctgctggcccaggcgagcgtcaaaccataccac acaaatatccttggcatcggccctgaattccttctgccgctctgctacccggtgcttctgtccgaagcaggggttgctagggatcgct ccgagtccgcaaacccttgtcgcgtggcggggcttgttcgagcttgaagagc Primary transformants were clonally purified and grown under low-nitrogen lipid production conditions at either pH5.0 or pH7.0, depending on the promoters that drive the expression of the desaturase genes. Transgenic lines arising from the transformations with pSZ1377 (D583) were assayed in (low-nitrogen) lipid production media at pH5.0, because of the nature of the promoters and the fact that *P. moriformis* produces more lipid at pH5.0. Transgenic lines generated from the transformation of pSZ1454 (D648) and pSZ3144 (D1923) are assayed at pH 7.0 to allow for maximal desaturase gene expression when driven by the pH regulated PmAMT3 promoter. The resulting profiles from representative clones arising from transformations with D583, D648, and D1923 are shown in Tables 58, 59 and 60, respectively, below. The result of expression of OeSAD and CpSAD1 genes is a clear diminution of C18:0 chain lengths with an increase in C18:1. Also we noticed that there is a subtle increase in the level of C16:1, indicating these stearoyl-ACP desaturases may have broad specificity. The transformants resulted from the expression of RcSAD gene also diminishes in the level of C18:0, and elevation in C16:1. Notably, C16:1 could be increased from under 1% to over 1.5% or over 2%. However, there is also a drop in the level of C18:1 fatty acid and increase in C18:2, which may be caused by the growth defect of these transgenic lines.

TABLE 58

Lipid profile of representative clones arising from transformation with D583 (pSZ1377) DNA.

| Sample ID | C16:0 | C16:1 | C18:0 | C18:1 | C18:2 |
|---|---|---|---|---|---|
| D583-25 | 19.20 | 1.53 | 1.15 | 64.08 | 11.76 |
| D583-10 | 21.86 | 0.99 | 1.77 | 61.43 | 11.42 |
| D583-3 | 21.94 | 0.95 | 1.85 | 62.22 | 10.53 |
| D583-33 | 20.76 | 0.95 | 1.85 | 61.76 | 12.17 |
| D583-26 | 20.18 | 0.92 | 1.89 | 62.56 | 11.97 |
| D583-1 | 21.28 | 0.95 | 1.90 | 62.63 | 10.94 |
| S1331 | 25.48 | 0.71 | 3.23 | 59.70 | 8.25 |

TABLE 59

Lipid profile of representative clones arising from transformation with D648 (pSZ1454) DNA.

| Sample ID | C16:0 | C16:1 | C18:0 | C18:1 | C18:2 |
|---|---|---|---|---|---|
| D648-9 | 26.92 | 2.30 | 1.12 | 54.27 | 11.30 |
| D648-28 | 26.54 | 2.50 | 1.32 | 52.58 | 12.90 |
| D648-15 | 29.47 | 1.68 | 1.48 | 51.74 | 11.48 |
| D648-12 | 27.39 | 1.41 | 1.66 | 54.45 | 11.58 |
| D648-43 | 29.74 | 1.52 | 1.68 | 52.59 | 10.85 |
| D648-7 | 26.98 | 1.62 | 1.69 | 54.51 | 11.39 |
| S1331-pH7 | 25.86 | 0.96 | 2.84 | 58.33 | 9.16 |

TABLE 60

Lipid profile of representative clones arising from transformation with D1923 (pSZ3144) DNA.

| Sample ID | C14:0 | C14:1 | C16:0 | C16:1 | C18:0 | C18:1 | C18:2 |
|---|---|---|---|---|---|---|---|
| Block 2; E2; pH 7; STRAIN Z; T613; D1923-2 | 1.46 | 0.11 | 20.74 | 2.54 | 0.86 | 63.99 | 9.03 |
| Block 2; G12; pH 7; STRAIN Z; T613; D1923-36 | 1.52 | 0.10 | 25.20 | 1.97 | 1.67 | 61.10 | 7.38 |
| Block 2; E8; pH 7; STRAIN Z; T613; D1923-8 | 1.48 | 0.09 | 26.41 | 1.78 | 1.54 | 60.54 | 7.01 |
| Block 2; F3; pH 7 STRAIN Z; T613; D1923-15 | 1.50 | 0.07 | 25.87 | 1.75 | 1.62 | 61.25 | 6.94 |
| Block 2; F9; pH 7; STRAIN Z; T613; D1923-21 | 1.47 | 0.07 | 27.02 | 1.73 | 1.84 | 60.15 | 6.55 |
| Block 2; F4; pH 7; STRAIN Z; T613; D1923-16 | 1.44 | 0.07 | 24.30 | 1.71 | 1.41 | 62.79 | 7.29 |
| pH7 STRAIN Z | 1.47 | 0.00 | 28.25 | 0.82 | 3.16 | 58.27 | 6.72 |

Example 55: Generation of Palmitoleic Acid by Introducing Mutated (L118W) Stearoyl-ACP Desaturases To generate lower total saturates (Zero SAT FAT) strains, we have introduced both putative stearoyl-ACP desaturases (SAD) and palmitoyl-ACP desaturase (PAD) genes into *Prototheca moriformis*. We found that a single amino acid substitution (L118W) in *P. moriformis* SAD2-1 and *Olea europaea* SAD resulted in an increase in desaturation of palmitate moieties in the triglycerides produced by the cell. Oils with fatty acid profiles of over 5% palmitoleic acid were produced in the resulting transgenic lines. Therefore, the mutated SADs could be very useful to elevate palmitoleic as a route to lower total saturates, or to obtain palmitoleic acid containing oils. Oils with over 2, 3, 4, and 5 area % palmitoleic were obtained.

The *Saccharomyces cerevisiae* invertase gene (Accession no: NP 012104) was utilized as the selectable marker to introduce the *Prototheca moriformis* stearoyl-ACP desaturase PmSAD2-1 (L118W) and *Olea europaea* stearoyl-ACP desaturase OeSAD (L118W) into 6S nuclear chromosomal locus of *P. moriformis* strain Z by homologous recombination using previously described biolistic transformation methods.

The constructs that have we used to transform Strain Z can be written as:
1) 6SA::CrTUB2:ScSUC2:CvNR::PmUAPA1:PmSAD2-1 (L118W)-CvNR::6SB (pSZ3305, D2066)
2) 6SA::CrTUB2:ScSUC2:CvNR::CrTUB2: PmSAD2-1 (L118W)-CvNR::6SB (pSZ3299, D2060)
3) 6SA::CrTUB2:ScSUC2:CvNR::CrTUB2:CpSADtp-OeSAD (L118W)-CvNR::6SB (pSZ3298, D2059)

Construct pSZ3305: 6SA::CrTUB2:ScSUC2:CvNR:: PmUAPA1:PmSAD2-1(L118W)-CvNR::6SB

The sequence of the pSZ3305 transforming DNA is provided below. Relevant restriction sites in pSZ3305 6SA:: CrTUB2:ScSUC2:CvNR::PmUAPA1:PmSAD2-1 (L118W)-CvNR::6SB are indicated in lowercase, bold and underlining and are 5'-3' BspQ 1, Kpn I, Asc I, Mfe I, EcoRV, SpeI, AscI, ClaI, Sac I, BspQ I, respectively. BspQI sites delimit the 5' and 3' ends of the transforming DNA. Bold, lowercase sequences represent 6SA genomic DNA that permit targeted integration at 6S locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the *P. moriformis* UAPA1 promoter, indicated by boxed italics text. The initiator ATG and terminator TGA codons of the PmSAD2-1 (L118W) are indicated by uppercase, bold italics, while the remainder of the coding region is indicated by bold italics. The *C. vulgaris* nitrate reductase 3' UTR is again indicated by lowercase underlined text followed by the 6SB genomic region indicated by bold, lowercase text.

Nucleotide sequence of transforming DNA contained in pSZ3305:

(SEQ ID NO: 111)

gctcttcgccgccgccactcctgctcgagcgcgcccgcgcgtgcgccgccagcgccttggccttttcgccgcgctcgtgcgcgtc gctgatgtccatcaccaggtccatgaggtctgccttgcgccggctgagccactgcttcgtccgggcggccaagaggagcatga gggaggactcctggtccagggtcctgacgtggtcgcggctctgggagcgggccagcatcatctggctctgccgcaccgaggc cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaaccccttgcgcgttagtgttgccatcctttgcagaccggtgag agccgacttgttgtgcgccacccccacaccacctcctcccagaccaattctgtcacctttttggcgaaggcatcggcctcggcc tgcagagaggacagcagtgcccagccgctggggttggcggatgcacgctcaggtaccctttcttgcgctatgacacttccagca aaaggtagggcgggctgcgagacggcttcccggcgctgcatgcaacaccgatgatgcttcgacccccccgaagctccttcggggctg catgggcgctccgatgccgctccagggcgagcgctgtttaaatagccaggcccccgattgcaaagacattatagcgagctaccaaag ccatattcaaacacctagatcactaccacttctacacaggccactcgagcttgtgatcgcactccgctaagggggcgcctcttcctcttc gtttcagtcacaacccgcaaacggcgcgcc*ATG**ctgctgcaggccttcctgttcctgctggccggcttcgccgccaagatcagcg*

*cctccatgacgaacgagacgtccgaccgccccctggtgcacttcacccccaacaagggctggatgaacgaccccaacggcctg*

*tggtacgacgagaaggacgccaagtggcacctgtacttccagtacaacccgaacgacaccgtctgggggacgcccttgttctgg*

*ggccacgccacgtccgacgacctgaccaactgggaggaccagcccatcgccatcgccccgaagcgcaacgactccggcgcct*

*tctccggctccatggtggtggactacaacaacacctccggcttcttcaacgacaccatcgacccgcgccagcgctgcgtggccatc*

*tggacctacaacaccccggagtccgaggagcagtacatctcctacagcctggacggcggctacaccttcaccgagtaccagaa*

*gaaccccgtgctggccgccaactccacccagttccgcgacccgaaggtcttctggtacgagccctcccagaagtggatcatgacc*

*gcggccaagtcccaggactacaagatcgagatctactcctccgacgacctgaagtcctggaagctggagtccgcgttcgccaac*

*gagggcttcctcggctaccagtacgagtgccccggcctgatcgaggtccccaccgagcaggaccccagcaagtcctactgggtg*

*atgttcatctccatcaaccccggcgccccggccggcggctccttcaaccagtacttcgtcggcagcttcaacggcacccacttcga*

*ggccttcgacaaccagtcccgcgtggtggacttcggcaaggactactacgccctgcagaccttcttcaacaccgacccgacctac*

*gggagcgccctgggcatcgcgtgggcctccaactgggagtactccgccttcgtgcccaccaacccctggcgctcctccatgtcct*

*cgtgcgcaagttctccctcaacaccgagtaccaggccaacccggagacggagctgatcaacctgaaggccgagccgatcctga*

*acatcagcaacgccggcccctggagccggttcgccaccaacaccacgttgacgaaggccaacagctacaacgtcgacctgtcc*

*aacagcaccggcaccctggagttcgagctggtgtacgccgtcaacaccacccagacgatctccaagtccgtgttcgcggacctct*

*ccctctggttcaagggcctggaggaccccgaggagtacctccgcatgggcttcgaggtgtccgcgtcctccttcttcctggaccgcg*

*ggaacagcaaggtgaagttcgtgaaggagaacccctacttcaccaaccgcatgagcgtgaacaaccagcccttcaagagcga*

*gaacgacctgtcctactacaaggtgtacggcttgctggaccagaacatcctggagctgtacttcaacgacggcgacgtcgtgtcca*

*ccaacacctacttcatgaccaccgggaacgccctgggctccgtgaacatgacgacgggggtggacaacctgttctacatcgaca*

-continued agttccaggtgcgcgaggtcaagTGAcaattggcagcagcagctcggatagtatcgacacactctggacgctggtcgtgtgatg gactgttgccgccacacttgctgccttgacctgtgaatatccctgccgcttttatcaaacagcctcagtgtgtttgatcttgtgtgtacgcgc ttttgcgagttgctagctgcttgtgctatttgcgaataccacccccagcatccccttccctcgtttcatatcgcttgcatcccaaccgcaactt atctacgctgtcctgctatccctcagcgctgctcctgctcctgctcactgcccctcgcacagccttggtttgggctccgcctgtattctcct ggtactgcaacctgtaaaccagcactgcaatgctgatgcacgggaagtagtgggatgggaacacaaatggaggatcccgcgtctcg aacagagcgcgcagaggaacgctgaaggtctcgcctctgtcgcacctcagcgcggcatacaccacaataaccacctgacgaatgcg cttggttcttcgtccattagcgaagcgtccggttcacacacgtgccacgttggcgaggtggcaggtgacaatgatcggtggagctgatg gtcgaaacgttcacagcctagggatatcatagcgactgctacccccgaccatgtgccgaggcagaaattatatacaagaagcag atcgcaattaggcacatcgctttgcattatccacacactattcatcgctgctgcggcaaggctgcagagtgtatttttgtggcccagg agctgagtccgaagtcgacgcgacgagcggcgcaggatccgacccctagacgagctctgtcattttccaagcacgcagctaaat gcgctgagaccgggtctaaatcatccgaaaagtgtcaaaatggccgattgggttcgcctaggacaatgcgctgcggattcgctcg agtccgctgccggccaaaaggcggtggtacaggaaggcgcacggggccaaccctgcgaagccgggggcccgaacgccgac cgccggccttcgatctcgggtgtccccctcgtcaatttcctctctcgggtgcagccacgaaagtcgtgacgcaggtcacgaaatcc ggttacgaaaaacgcaggtcttcgcaaaaacgtgagggtttcgcgtctcgccctagctattcgtatcgccgggtcagacccacgtg cagaaaagcccttgaataacccgggaccgtggttaccgcgccgcctgcaccaggggggcttatataagcccacaccacacctgtc tcaccacgcatttctccaactcgcgacttttcggaagaaattgttatccacctagtatagactgccacctgcaggaccttgtgtcttgc agtttgtattggtcccggccgtcgagctcgacagatctgggctagggttggcctggccgctcggcactcccctttagccgcgcgcat ccgcgttccagaggtgcgattcggtgtgtggagcattgtcatgcgcttgtgggggtcgttccgtgcgcggcgggtccgccatgggc gccgacctgggccctagggtttgttttcgggccaagcgagcccctctcacctcgtcgcccccccgcattccctctctcttgcagccac tagtATGgcctccgctgtgaccttcgcctgcgctcctcctcgcaggcgcgccggtgccgtggccgctcctggccgacgcgctgcc tctcgtcctctggtggtgcacgccgtggcctccgaggctcctctgggcgtgcctccctccgtgcagcgcccttctcccgtggtgtactc caagctggacaagcagcaccgcctgacgcctgagcgcctggagctggtgcagtccatgggccagttcgccgaggagcgcgtgc tgcccgtgctgcaccccgtggacaagctgtggcagccccaggacttcctgcccgaccccgagtcccccgacttcgaggaccagg tggccgagctgcgcgcccgcgccaaggacctgcccgacgagtacttcgtggtgctggtgggcgacatgatcaccgaggaggcc ctgcccacctacatggccatgctgaacacctgggacggcgtgcgcgacgacaccggcgccgccgaccacccctgggcccgctg gacccgccagtgggtggccgaggagaaccgccacggcgacctgctgaacaagtactgctggctgaccggccgcgtgaacatg cgcgccgtggaggtgaccatcaacaacctgatcaagtccggcatgaacccccagaccgacaacaacccctacctgggcttcgtg tacacctccttccaggagcgcgccaccaagtactcccacggcaacaccgcccgcctggccgccgagcacggcgacaagggcc tgtccaagatctgcggcctgatcgcctccgacgagggccgccacgagatcgcctacacccgcatcgtggacgagttcttccgcct ggaccccgagggcgccgtggccgcctacgccaacatgatgcgcaagcagatcaccatgcccgcccacctgatggacgacatg -continued ggccacggcgaggccaacccggccgcaacctgttcgccgacttctccgccgtggccgagaagatcgacgtgtacgacgccga ggactactgccgcatcctggagcacctgaacgcccgctggaaggtggacgagcgccaggtgtccggccaggccgccgccgac caggagtacgtgctgggcctgccccagcgcttccgcaagctggccgagaagaccgccgccaagcgcaagcgcgtggcccgcc gccccgtggccttctcctggatctccggccgcgagatcatggtgTGAatcgatagatctcttaaggcagcagcagctcggatagta tcgacacactctggacgctggtcgtgtgatggactgttgccgccacacttgctgccttgacctgtgaatatccctgccgcttttatcaaac agcctcagtgtgtttgatcttgtgtgtacgcgcttttgcgagttgctagctgcttgtgctatttgcgaataccacccccagcatccccttccct cgtttcatatcgcttgcatcccaaccgcaacttatctacgctgtcctgctatccctcagcgctgctcctgctcctgctcactgcccctcgca cagccttggtttgggctccgcctgtattctcctggtactgcaacctgtaaaccagcactgcaatgctgatgcacgggaagtagtgggatg ggaacacaaatggaaagcttaattaagagctcttgttttccagaaggagttgctccttgagcctttcattctcagcctcgataacctc caaagccgctctaattgtggagggggttcgaatttaaaagcttggaatgttggttcgtgcgtctggaacaagcccagacttgtt gctcactgggaaaaggaccatcagctccaaaaaacttgccgctcaaaccgcgtacctctgctttcgcgcaatctgccctgttga aatcgccaccacattcatattgtgacgcttgagcagtctgtaattgcctcagaatgtggaatcatctgccccctgtgcgagccca tgccaggcatgtcgcgggcgaggacacccgccactcgtacagcagaccattatgctacctcacaatagttcataacagtgacc atatttctcgaagctccccaacgagcacctccatgctctgagtggccaccccccggccctggtgcttgcggagggcaggtcaac cggcatggggctaccgaaatccccgaccggatcccaccacccccgcgatgggaagaatctctccccgggatgtgggcccacc accagcacaacctgctggcccaggcgagcgtcaaaccataccacacaaatatccttggcatcggccctgaattccttctgccg ctctgctacccggtgcttctgtccgaagcaggggttgctagggatcgctccgagtccgcaaacccttgtcgcgtggcggggctt gttcgagcttgaagagc Construct pSZ3299: 6SA::CrTUB2:ScSUC2:CvNR::CrTUB2: PmSAD2-1(L118W)-CvNR::6SB The sequence of the pSZ3299 transforming DNA is provided in Sequence 56-2. Relevant restriction sites in pSZ3299 6SA::CrTUB2:ScSUC2:CvNR::CrTUB2:PmSAD2-1(L118W)-CvNR::6SB are indicated in lowercase, bold and underlining and are 5'-3' BspQ 1, Kpn I, XbaI, Mfe I, EcoRV, SpeI, AscI, ClaI, Sac I, BspQ I, respectively. BspQI sites delimit the 5' and 3' ends of the transforming DNA. Bold, lowercase sequences represent 6SA genomic DNA that permit targeted integration at 6S locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the *C. reinhardtii* β-tubulin promoter, indicated by boxed italics text. The Initiator ATG and terminator TGA codons of the PmSAD2-1 (L118W) are indicated by uppercase, bold italics, while the remainder of the coding region is indicated by bold italics. The *C. vulgaris* nitrate reductase 3' UTR is again indicated by lowercase underlined text followed by the 6SB genomic region indicated by bold, lowercase text.

Nucleotide sequence of transforming DNA contained in pSZ3299:

(SEQ ID NO: 112)

gctcttcgccgccgccactcctgctcgagcgcgcccgcgcgtgcgccgccagcgccttggccttttcgccgcgctcgtgcgcgtc gctgatgtccatcaccaggtccatgaggtctgccttgcgccggctgagccactgcttcgtccgggcggccaagaggagcatga gggaggactcctggtccagggtcctgacgtggtcgcggctctgggagcgggccagcatcatctggctctgccgcaccgaggc cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaaccccttgcgcgttagtgttgccatcctttgcagaccggtgag agccgacttgttgtgcgccacccccacaccacctcctcccagaccaattctgtcacctttttggcgaaggcatcggcctcggcc tgcagagaggacagcagtgcccagccgctggggttggcggatgcacgctcaggtaccctttcttgcgctatgacacttccagca -continued aaaggtagggcgggctgcgagacggcttcccggcgctgcatgcaacaccgatgatgcttcgaccccccgaagctccttcggggctg catgggcgctccgatgccgctccagggcgagcgctgtttaaatagccaggcccccgattgcaaagacattatagcgagctaccaaag ccatattcaaacacctagatcactaccacttctacacaggccactcgagcttgtgatcgcactccgctaagggggcgcctcttcctcttc gtttcagtcacaacccgcaaactctagaatatca*ATG**ctgctgcaggccttcctgttcctgctggccggcttcgccgccaagatcag*

*cgcctccatgacgaacgagacgtccgaccgcccctggtgcacttcacccccaacaagggctggatgaacgaccccaacggcc*

*tgtggtacgacgagaaggacgccaagtggcacctgtacttccagtacaacccgaacgacaccgtctgggggacgcccttgtgttctg*

*gggccacgccacgtccgacgacctgaccaactgggaggaccagcccatcgccatcgccccgaagcgcaacgactccggcgc*

*cttctccggctccatggtggtggactacaacaacacctccggcttcttcaacgacaccatcgacccgcgccagcgctgcgtggcca*

*tctggacctacaacaccccggagtccgaggagcagtacatctcctacagcctggacggcggctacaccttcaccgagtaccaga*

*agaaccccgtgctggccgccaactccacccagttccgcgacccgaaggtcttctggtacgagccctcccagaagtggatcatgac*

*cgcggccaagtcccaggactacaagatcgagatctactcctccgacgacctgaagtcctggaagctggagtccgcgttcgccaa*

*cgagggcttcctcggctaccagtacgagtgccccggcctgatcgaggtccccaccgagcaggaccccagcaagtcctactgggt*

*gatgttcatctccatcaaccccggcgccccggccggcggctccttcaaccagtacttcgtcggcagcttcaacggcacccacttcg*

*aggccttcgacaaccagtcccgcgtggtggacttcggcaaggactactacgccctgcagaccttcttcaacaccgacccgaccta*

*cgggagcgccctgggcatcgcgtgggcctccaactgggagtactccgccttcgtgcccaccaacccctggcgctcctccatgtccc*

*tcgtgcgcaagttctccctcaacaccgagtaccaggccaacccggagacggagctgatcaacctgaaggccgagccgatcctg*

*aacatcagcaacgccggcccctggagccggttcgccaccaacaccacgttgacgaaggccaacagctacaacgtcgacctgtc*

*caacagcaccggcaccctggagttcgagctggtgtacgccgtcaacaccacccagacgatctccaagtccgtgttcgcggacctc*

*tccctctggttcaagggcctggaggaccccgaggagtacctccgcatgggcttcgaggtgtccgcgtcctccttcttcctggaccgc*

*gggaacagcaaggtgaagttcgtgaaggagaacccctacttcaccaaccgcatgagcgtgaacaaccagcccttcaagagcg*

*agaacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcgac*

*aagttccaggtgcgcgaggtcaag**TGA*caattggcagcagcagctcggatagtatcgacacactctggacgctggtcgtgtgat ggactgttgccgccacacttgctgccttgacctgtgaatatccctgccgcttttatcaaacagcctcagtgtgtttgatcttgtgtgtacgcg cttttgcgagttgctagctgcttgtgctatttgcgaataccacccccagcatccccttccctcgtttcatatcgcttgcatcccaaccgcaac ttatctacgctgtcctgctatccctcagcgctgctcctgctcctgctcactgcccctcgcacagccttggtttgggctccgcctgtattctcc tggtactgcaacctgtaaaccagcactgcaatgctgatgcacgggaagtagtgggatgggaacacaaatggaggatcccgcgtctcg aacagagcgcgcagaggaacgctgaaggtctcgcctctgtcgcacctcagcgcggcatacaccacaataaccacctgacgaatgcg cttggttcttcgtccattagcgaagcgtccggttcacacacgtgccacgttggcgaggtggcaggtgacaatgatcggtggagctgatg gtcgaaacgttcacagcctagggatatcgaattc*ctttcttgcgctatgacacttccagcaaaaggtagggcgggctgcgagacgg*

*cttcccggcgctgcatgcaacaccgatgatgcttcgaccccccgaagctccttcggggctgcatgggcgctccgatgccgctccag*

*ggcgagcgctgtttaaatagccaggcccccgattgcaaagacattatagcgagctaccaaagccatattcaaacacctagatca*

*ctaccacttctacacaggccactcgagcttgtgatcgcactccgctaagggggcgcctcttcctcttcgtttcagtcacaacccgcaa*

*ac*actagt*ATGgcctccgctgtgaccttcgcctgcgctcctcctcgcaggcgcgccggtgccgtggccgctcctggccgacgcg*

*ctgcctctcgtcctctggtggtgcacgccgtggcctccgaggctcctctgggcgtgcctccctccgtgcagcgcccttctcccgtggtg*

-continued tactccaagctggacaagcagcaccgcctgacgcctgagcgcctggagctggtgcagtccatgggccagttcgccgaggagcg cgtgctgcccgtgctgcaccccgtggacaagctgtggcagccccaggacttcctgcccgaccccgagtccccgacttcgaggac caggtggccgagctgcgcgcccgcgccaaggacctgcccgacgagtacttcgtggtgctggtgggcgacatgatcaccgagga ggccctgcccacctacatggccatgctgaacacctgggacggcgtgcgcgacgacaccggcgccgccgaccacccctgggcc cgctggacccgccagtgggtggccgaggagaaccgccacggcgacctgctgaacaagtactgctggctgaccggccgcgtga acatgcgcgccgtggaggtgaccatcaacaacctgatcaagtccggcatgaacccccagaccgacaacaacccctacctgggc ttcgtgtacacctccttccaggagcgcgccaccaagtactcccacggcaacaccgcccgcctggccgccgagcacggcgacaa gggcctgtccaagatctgcggcctgatcgcctccgacgagggccgccacgagatcgcctacacccgcatcgtggacgagttcttc cgcctggaccccgagggcgccgtggccgcctacgccaacatgatgcgcaagcagatcaccatgcccgcccacctgatggacg acatgggccacggcgaggccaaccccggccgcaacctgttcgccgacttctccgccgtggccgagaagatcgacgtgtacgac gccgaggactactgccgcatcctggagcacctgaacgcccgctggaaggtggacgagcgccaggtgtccggccaggccgccg ccgaccaggagtacgtgctgggcctgccccagcgcttccgcaagctggccgagaagaccgccgccaagcgcaagcgcgtggc ccgccgccccgtggccttctcctggatctccggccgcgagatcatggtgTGAatcgatagatctcttaaggcagcagcagctcgg atagtatcgacacactctggacgctggtcgtgtgatggactgttgccgccacacttgctgccttgacctgtgaatatccctgccgcttttat caaacagcctcagtgtgtttgatcttgtgtgtacgcgcttttgcgagttgctagctgcttgtgctatttgcgaataccacccccagcatccc cttccctcgtttcatatcgcttgcatcccaaccgcaacttatctacgctgtcctgctatccctcagcgctgctcctgctcctgctcactgccc ctcgcacagccttggtttgggctccgcctgtattctcctggtactgcaacctgtaaaccagcactgcaatgctgatgatgcacgggaagtagt gggatgggaacacaaatggaaagcttaattaagagctcttgttttccagaaggagttgctccttgagcctttcattctcagcctcgat aacctccaaagccgctctaattgtggagggggttcgaatttaaaagcttggaatgttggttcgtgcgtctggaacaagcccaga cttgttgctcactgggaaaaggaccatcagctccaaaaaacttgccgctcaaaccgcgtacctctgctttcgcgcaatctgccct gttgaaatcgccaccacattcatattgtgacgcttgagcagtctgtaattgcctcagaatgtggaatcatctgccccctgtgcga gcccatgccaggcatgtcgcgggcgaggacacccgccactcgtacagcagaccattatgctacctcacaatagttcataacag tgaccatatttctcgaagctccccaacgagcacctccatgctctgagtggccacccccggccctggtgcttgcggagggcagg tcaaccggcatggggctaccgaaatccccgaccggatcccaccacccccgcgatgggaagaatctctccccgggatgtgggc ccaccaccagcacaacctgctggcccaggcgagcgtcaaaccataccacacaaatatccttggcatcggccctgaattccttc tgccgctctgctacccggtgcttctgtccgaagcaggggttgctagggatcgctccgagtccgcaaacccttgtcgcgtggcgg ggcttgttcgagcttgaagagc Construct pSZ3298: 6SA::CrTUB2:ScSUC2:CvNR::CrTUB2:CpSADtp-OeSAD(L118W)-CvNR::6SB The sequence of the pSZ3299 transforming DNA is provided below. Relevant restriction sites in the construct pSZ3298 6SA::CrTUB2:ScSUC2:CvNR::CrTUB2:CpSADtp-OeSAD(L118W)-CvNR::6SB are indicated in lowercase, bold and underlining and are 5'-3' BspQ 1, Kpn I, XbaI, Mfe I, EcoRV, SpeI, AscI, ClaI, Sac I, BspQ I, respectively. BspQI sites delimit the 5' and 3' ends of the transforming DNA. Bold, lowercase sequences represent 6SA genomic DNA that permit targeted integration at 6S locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the *C. reinhardtii* β-tubulin promoter, indicated by boxed italics text. The Initiator ATG and terminator TGA codons of the OeSAD (L118W) are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the 6SB genomic region indicated by bold, lowercase text.

Nucleotide sequence of transforming DNA contained in pSZ3298:

(SEQ ID NO: 113)

gctcttcgccgccgccactcctgctcgagcgcgcccgcgcgtgcgccgccagcgccttggccttttcgccgcgctcgtcgcgtc gctgatgtccatcaccaggtccatgaggtctgccttgcgccggctgagccactgcttcgtccgggcggccaagaggagcatga gggaggactcctggtccagggtcctgacgtggtcgcggctctgggagcgggccagcatcatctggctctgccgcaccgaggc cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaacccccttgcgcgttagtgttgccatcctttgcagaccggtgag agccgacttgttgtgcgccacccccacaccacctcctcccagaccaattctgtcacctttttggcgaaggcatcggcctcggcc tgcagagaggacagcagtgcccagccgctggggggttggcggatgcacgctcaggtaccctttcttgcgctatgacacttccagca aaaggtagggcgggctgcgagacggcttcccggcgctgcatgcaacaccgatgatgcttcgacccccccgaagctccttcggggctg catgggcgctccgatgccgctccagggcgagcgctgtttaaatagccaggcccccgattgcaaagacattatagcgagctaccaaag ccatattcaaacacctagatcactaccacttctacacaggccactcgagcttgtgatcgcactccgctaagggggcgcctcttcctcttc gtttcagtcacaacccgcaaactctagaatatca*ATG**ctgctgcaggccttcctgttcctgctggccggcttcgccgccaagatcag*

*cgcctccatgacgaacgagacgtccgaccgccccctggtgcacttcacccccaacaagggctggatgaacgaccccaacggcc*

*tgtggtacgacgagaaggacgccaagtggcacctgtacttccagtacaacccgaacgacaccgtctgggggacgcccttgttctg*

*gggccacgccacgtccgacgacctgaccaactgggaggaccagcccatcgccatcgccccgaagcgcaacgactccggcgc*

*cttctccggctccatggtggtggactacaacaacacctccggcttcttcaacgacaccatcgacccgcgccagcgctgcgtggcca*

*tctggacctacaacaccccggagtccgaggagcagtacatctcctacagcctggacggcggctacaccttcaccgagtaccaga*

*agaaccccgtgctggccgccaactccacccagttccgcgacccgaaggtcttctggtacgagccctcccagaagtggatcatgac*

*cgcggccaagtcccaggactacaagatcgagatctactcctccgacgacctgaagtcctggaagctggagtccgcgttcgccaa*

*cgagggcttcctcggctaccagtacgagtgccccggcctgatcgaggtccccaccgagcaggaccccagcaagtcctactgggt*

*gatgttcatctccatcaaccccggcgccccggccggcggctccttcaaccagtacttcgtcggcagcttcaacggcacccacttcg*

*aggccttcgacaaccagtcccgcgtggtggacttcggcaaggactactacgccctgcagaccttcttcaacaccgacccgaccta*

*cgggagcgccctgggcatcgcgtgggcctccaactgggagtactccgccttcgtgcccaccaacccctggcgctcctccatgtccc*

*tcgtgcgcaagttctccctcaacaccgagtaccaggccaacccggagacggagctgatcaacctgaaggccgagccgatcctg*

*aacatcagcaacgccggcccctggagccggttcgccaccaacaccacgttgacgaaggccaacagctacaacgtcgacctgtc*

*caacagcaccggcaccctggagttcgagctggtgtacgccgtcaacaccacccagacgatctccaagtccgtgttcgcggacctc*

*tccctctggttcaagggcctggaggaccccgaggagtacctccgcatgggcttcgaggtgtccgcgtcctccttcttcctggaccgc*

*gggaacagcaaggtgaagttcgtgaaggagaacccctacttcaccaaccgcatgagcgtgaacaaccagcccttcaagagcg*

*agaacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcgac*

-continued aagttccaggtgcgcgaggtcaagTGAcaattggcagcagcagctcggatagtatcgacacactctggacgctggtcgtgtgat ggactgttgccgccacacttgctgccttgacctgtgaatatccctgccgcttttatcaaacagcctcagtgtgtttgatcttgtgtgtacgcg cttttgcgagttgctagctgcttgtgctatttgcgaataccacccccagcatccccttccctcgtttcatatcgcttgcatcccaaccgcaac ttatctacgctgtcctgctatccctcagcgctgctcctgctcctgctcactgcccctcgcacagccttggtttgggctccgcctgtattctcc tggtactgcaacctgtaaaccagcactgcaatgctgatgcacgggaagtagtgggatgggaacacaaatggaggatccccgcgtctcg aacagagcgcgcagaggaacgctgaaggtctcgcctctgtcgcacctcagcgcggcatacaccacaataaccacctgacgaatgcg cttggttcttcgtccattagcgaagcgtccggttcacacacgtgccacgttggcgaggtggcaggtgacaatgatcggtggagctgatg gtcgaaacgttcacagcctagggatatcgaattcctttcttgcgctatgacacttccagcaaaaggtagggcgggctgcgagacgg cttcccggcgctgcatgcaacaccgatgatgcttcgacccccccgaagctccttcggggctgcatgggcgctccgatgccgctccag ggcgagcgctgtttaaatagccaggcccccgattgcaaagacattatagcgagctaccaaagccatattcaaacacctagatca ctaccacttctacacaggccactcgagcttgtgatcgcactccgctaagggggcgcctcttcctcttcgtttcagtcacaacccgcaa acactagtATGgccaccgcatccactttctcggcgttcaatgcccgctgcggcgacctgcgtcgctcggcgggctccgggcccc ggcgcccagcgaggcccctccccgtgcgcgggcgcgccgaggtgcacgtgcaggtgacccactccctggcccccgagaagcg cgagatcttcaactccctgaacaactgggcccaggagaacatcctggtgctgctgaaggacgtggacaagtgctggcagccctc cgacttcctgcccgactccgcctccgagggcttcgacgagcaggtgatggagctgcgcaagcgctgcaaggagatccccgacg actacttcatcgtgctggtgggcgacatgatcaccgaggaggccctgcccacctaccagaccatgctgaacacctgggacggcgt gcgcgacgagaccggcgcctccctgacccccctgggccatctggacccgcgcctggaccgccgaggagaaccgccacggcga cctgctgaacaagtacctgtacctgtccggccgcgtggacatgaagcagatcgagaagaccatccagtacctgatcggctccgg catggacccccgcaccgagaacaacccctacctgggcttcatctacacctccttccaggagcgcgccaccttcatctcccacggc aacaccgcccgcctggccaaggagcacggcgacctgaagctggcccagatctgcggcatcatcgccgccgacgagaagcgc cacgagaccgcctacaccaagatcgtggagaagctgttcgagatcgaccccgacggcaccgtgctggccctggccgacatgat gcgcaagaaggtgtccatgcccgcccacctgatgtacgacggccaggacgacaacctgttcgagaacttctcctccgtggccca gcgcctgggcgtgtacaccgccaaggactacgccgacatcctggagttcctggtgggccgctgggacatcgagaagctgaccg gcctgtccggcgagggccgcaaggcccaggactacgtgtgcaccctgcccccccgcatccgccgcctggaggagcgcgccca gtcccgcgtgaagaaggcctccgccacccccttctcctggatcttcggccgcgagatcaacctgatggactacaaggaccacgac ggcgactacaaggaccacgacatcgactacaaggacgacgacgacaagTGAatcgatagatctcttaaggcagcagcagct cggatagtatcgacacactctggacgctggtcgtgtgatggactgttgccgccacacttgctgccttgacctgtgaatatccctgccgctt ttatcaaacagcctcagtgtgtttgatcttgtgtgtacgcgcttttgcgagttgctagctgcttgtgctatttgcgaataccacccccagcatc cccttccctcgtttcatatcgcttgcatcccaaccgcaacttatctacgctgtcctgctatccctcagcgctgctcctgctcctgctcactgc ccctcgcacagccttggtttgggctccgcctgtattctcctggtactgcaacctgtaaaccagcactgcaatgctgatgcacgggaagta gtgggatgggaacacaaatggaaagcttaattaagagctcttgttttccagaaggagttgctccttgagcctttcattctcagcctcg ataacctccaaagccgctctaattgtggaggggttcgaatttaaaagcttggaatgttggttcgtgcgtctggaacaagccca -continued

```
gacttgttgctcactgggaaaaggaccatcagctccaaaaaacttgccgctcaaaccgcgtacctctgctttcgcgcaatctgc

cctgttgaaatcgccaccacattcatattgtgacgcttgagcagtctgtaattgcctcagaatgtggaatcatctgcccccctgtgc

gagcccatgccaggcatgtcgcgggcgaggacacccgccactcgtacagcagaccattatgctacctcacaatagttcataac

agtgaccatatttctcgaagctccccaacgagcacctccatgctctgagtggccaccccccggccctggtgcttgcggagggca

ggtcaaccggcatggggctaccgaaatccccgaccggatcccaccacccccgcgatgggaagaatctctccccgggatgtgg

gcccaccaccagcacaacctgctggcccaggcgagcgtcaaaccataccacacaaatatccttggcatcggccctgaattcct

tctgccgctctgctacccggtgcttctgtccgaagcaggggttgctagggatcgctccgagtccgcaaacccttgtcgcgtggcg

gggcttgttcgagcttgaagagc
```

Primary transformants were clonally purified and grown under low-nitrogen lipid production conditions at pH5.0. The resulting profiles from representative clones arising from transformations with pSZ3305, pSZ3299 and pSZ3298 into Strain Z are shown in Tables 61-63 respectively. Thus, introductions of such mutations or genes can increase levels pf palmitoleic acid and decrease levels of saturation in the fatty acid profiles of oils produced by recombinant microalgae. Oils were obtained with C16:1/C16:0 ratios of at least 0.1, 0.15, and 0.18.

TABLE 61

Fatty acid profiles in Strain Z and derivative transgenic lines transformed with pSZ3305 (D2066).

| Sample ID | C14:0 | C16:0 | C16:1 | C18:0 | C18:1 | C18:2 | C16:1:C16:0 ratio |
|---|---|---|---|---|---|---|---|
| pH5; T657; D2066-29 | 1.27 | 24.73 | 4.55 | 3.63 | 58.62 | 5.84 | 0.18 |
| pH5; T657; D2066-16 | 1.27 | 22.89 | 3.94 | 3.17 | 60.69 | 6.61 | 0.17 |
| pH5; T657; D2066-36 | 1.33 | 25.47 | 3.07 | 3.58 | 59.32 | 5.86 | 0.12 |
| pH5; T657; D2066-19 | 1.28 | 22.48 | 2.42 | 3.66 | 61.65 | 7.02 | 0.11 |
| pH5;; T657; D2066-12 | 1.29 | 26.25 | 2.26 | 3.99 | 59.27 | 5.50 | 0.09 |
| pH5; T657; D2066-21 | 1.33 | 24.49 | 2.26 | 3.24 | 61.42 | 6.01 | 0.09 |
| pH5; Strain Z (200:1) | 1.40 | 27.70 | 0.89 | 3.91 | 57.34 | 7.05 | 0.03 |

TABLE 62

Fatty acid profiles in Strain Z and derivative transgenic lines transformed with pSZ3299 (D2060).

| Sample ID | C14:0 | C16:0 | C16:1 | C18:0 | C18:1 | C18:2 | C16:1:C16:0 ratio |
|---|---|---|---|---|---|---|---|
| pH5; T655; D2060-9 | 1.35 | 24.67 | 2.73 | 3.21 | 60.34 | 6.22 | 0.11 |
| pH5; T655; D2060-23 | 1.52 | 30.05 | 2.64 | 1.65 | 55.38 | 7.03 | 0.09 |
| pH5; T655; D2060-21 | 1.29 | 23.54 | 2.43 | 2.94 | 62.25 | 6.18 | 0.10 |
| pH5; T655; D2060-2 | 1.29 | 24.30 | 2.22 | 2.57 | 62.09 | 6.28 | 0.09 |
| pH5; T655; D2060-12 | 1.37 | 27.67 | 1.90 | 2.84 | 59.69 | 5.41 | 0.07 |
| pH5; T655; D2060-14 | 1.41 | 25.01 | 1.62 | 2.47 | 61.30 | 6.96 | 0.06 |
| pH5 Strain Z | 1.40 | 27.89 | 0.87 | 3.25 | 57.84 | 7.19 | 0.03 |

TABLE 63

Fatty acid profiles in Strain Z and derivative transgenic lines transformed with pSZ3298 (D2059).

| Sample ID | C14:0 | C16:0 | C16:1 | C18:0 | C18:1 | C18:2 | C16:1:C16:0 ratio |
|---|---|---|---|---|---|---|---|
| pH5; T655; D2059-21 | 1.09 | 25.44 | 5.04 | 1.86 | 54.78 | 10.44 | 0.19 |
| pH5; T655; D2059-19 | 1.28 | 23.11 | 2.71 | 2.19 | 60.66 | 8.64 | 0.12 |
| pH5; T655; D2059-4 | 1.68 | 28.19 | 1.61 | 2.54 | 58.39 | 6.37 | 0.06 |
| pH5; T655; D2059-23 | 1.37 | 23.25 | 1.45 | 2.92 | 62.15 | 7.44 | 0.06 |
| pH5; T655; D2059-1 | 1.38 | 23.34 | 1.28 | 2.68 | 62.31 | 7.62 | 0.05 |
| pH5 Strain Z | 1.40 | 27.89 | 0.87 | 3.25 | 57.84 | 7.19 | 0.03 |

Example 56: Down Regulation of FATA and Over Expression of the *Prototheca Moriformis* Keto-Acyl-ACP Synthase II (PMKASII) Gene A transgenic *P. moriformis* line was created with down-regulation of an endogenous FATA1 gene combined with overexpression of an endogenous KASII gene. The resulting strain produced a triglyceride-rich oil that was enriched in oleate.

In the example below, we have followed up on previous work demonstrating that triacylglycerols in algae can be significantly enriched in levels of oleate (C18:1) utilizing molecular genetic approaches, such as down regulating endogenous FATA1 (a single FATA allele) and over-expression of endogenous KASII activity. In this example, we focus our efforts on combining these approaches into a single transgenic line. Constructs that disrupt a single copy of the FATA1 allele while simultaneously overexpressing the *P. moriformis* KASII gene (PmKASII). were introduced into a high oleic *Prototheca moriformis* Strain AO. Strain AO was derived from a high 18:1 producing mutant derived from UTEX 1435 using classical mutagenesis techniques. One of the resulting strains, termed Strain AP, produced an oil with a fatty acid profile having 85% C18:1 with total un-saturates around 93% in multiple fermentation runs. The strain AP also had high lipid productivity.

The *Saccharomyces cerevisiae* invertase gene (Accession no: NP 012104) was utilized as the selectable marker to introduce the PmKASII into the FATA1 nuclear chromosomal locus of *P. moriformis* strain AO by homologous recombination using biolistic transformation. To investigate the KASII activity when driven by different promoters, PmKASII was fused to several promoters: PmUAPA1, PmLDH1, and PmAMT3. Note that the integration constructs are all designed as reverse orientation to the FATA1 gene; this was found to give a greater likelihood of stable invertase expression. Therefore, the constructs that have been expressed in Strain AH can be written as:

1) FATA1 3'::CrTUB2:ScSUC2:CvNR::PmUAPA1:Pm-KASII-CvNR::FATA1 5' (pSZ2533)

2) FATA1 3'::CrTUB2:ScSUC2:CvNR::PmLDH1:Pm-KASII-CvNR::FATA1 5' (pSZ2532)

3) FATA1 3'::CrTUB2:ScSUC2:CvNR::PmAMT3:Pm-KASII-CvNR::FATA1 5' (pSZ2750)

Strain AP is one of the transformants generated from pSZ2533. Relevant restriction sites in the construct pSZ2533 FATA13'::CrTUB2:ScSUC2:CvNR::PmUAPA1:PmKASII-CvNR::FATA1 5' are indicated in lowercase, bold and underlining and are 5'-3' BspQ 1, Kpn I, Asc I, Mfe I, EcoRV, SpeI, AscI, ClaI, Sac I, BspQ I, respectively. BspQI sites delimit the 5' and 3' ends of the transforming DNA. Bold, lowercase sequences represent FATA1 3' genomic DNA that permit targeted integration at FATA1 locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics The *Chlorella vulgaris* nitrate reductase 3' UTR is indicated by lowercase underlined text followed by the *P. moriformis* UAPA1 promoter, indicated by boxed italics text. The Initiator ATG and terminator TGA codons of the PmKASII are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the FATA1 5' genomic region indicated by bold, lowercase text.

Nucleotide sequence of transforming DNA contained in pSZ2533:

(SEQ ID NO: 114)

gctcttcacccaactcagataataccaatacccctccttctcctcctcatccattcagtacccccccccttctcttcccaaagcagc aagcgcgtggcttacagaagaacaatcggcttccgccaaagtcgccgagcactgcccgacggcggcgcccagcagcccg cttggccacacaggcaacgaatacattcaatagggggcctcgcagaatggaaggagcggtaaagggtacaggagcactgc gcacaaggggcctgtgcaggagtgactgactgggcgggcagacggcgcaccgcgggcgcaggcaagcagggaagattga agcggcagggaggaggatgctgattgagggggcatcgcagtctctcttggacccgggataaggaagcaaatattcggccg gttgggttgtgtgtgtgcacgttttcttcttcagagtcgtgggtgtgcttccagggaggatataagcagcaggatcgaatcccgc gaccagcgtttccccatccagccaaccaccctgtcggtaccctttcttgcgctatgacacttccagcaaaaggtagggcgggctgc gagacggcttcccggcgctgcatgcaacaccgatgatgcttcgacccccgaagctccttcggggctgcatgggcgctccgatgcc gctccagggcgagcgctgtttaaatagccaggcccccgattgcaaagacattatagcgagctaccaaagccatattcaaacacctaga tcactaccacttctacacaggccactcgagcttgtgatcgcactccgctaagggggcgcctcttcctcttcgtttcagtcacaacccgca aac**ggcgcgcc*ATG***_ctgctgcaggccttcctgttcctgctggccggcttcgccgccaagatcagcgcctccatgacgaacgaga_

_cgtccgaccgcccctggtgcacttcacccccaacaagggctggatgaacgaccccaacggcctgtggtacgacgagaaggac_

_gccaagtggcacctgtacttccagtacaacccgaacgacaccgtctgggggacgcccttgttctggggccacgccacgtccgac_

_gacctgaccaactgggaggaccagcccatcgccatcgccccgaagcgcaacgactccggcgccttctccggctccatggtggtg_

_gactacaacaacacctccggcttcttcaacgacaccatcgacccgcgccagcgctgcgtggccatctggacctacaacaccccg_

-continued gagtccgaggagcagtacatctcctacagcctggacggcggctacaccttcaccgagtaccagaagaaccccgtgctggccgc caactccacccagttccgcgacccgaaggtcttctggtacgagccctcccagaagtggatcatgaccgcggccaagtcccagga ctacaagatcgagatctactcctccgacgacctgaagtcctggaagctggagtccgcgttcgccaacgagggcttcctcggctacc agtacgagtgccccggcctgatcgaggtccccaccgagcaggaccccagcaagtcctactgggtgatgttcatctccatcaaccc cggcgccccggccggcggctccttcaaccagtacttcgtcggcagcttcaacggcacccacttcgaggccttcgacaaccagtcc cgcgtggtggacttcggcaaggactactacgccctgcagaccttcttcaacaccgacccgacctacgggagcgccctgggcatc gcgtgggcctccaactgggagtactccgccttcgtgcccaccaacccctggcgctcctccatgtccctcgtgcgcaagttctccctc aacaccgagtaccaggccaacccggagacggagctgatcaacctgaaggccgagccgatcctgaaacatcagcaacgccggc ccctggagccggttcgccaccaacaccacgttgacgaaggccaacagctacaacgtcgacctgtccaacagcaccggcaccct ggagttcgagctggtgtacgccgtcaacaccacccagacgatctccaagtgttcgcggacctctccctctggttcaagggcct ggaggaccccgaggagtacctccgcatgggcttcgaggtgtccgcgtcctccttcttcctggaccgcgggaacagcaaggtgaa gttcgtgaaggagaacccctacttcaccaaccgcatgagcgtgaacaaccagcccttcaagagcgagaacgacctgtcctacta caaggtgtacggcttgctggaccagaacatcctggagctgtacttcaacgacggcgacgtcgtgtccaccaacacctacttcatga ccaccgggaacgccctgggctccgtgaacatgacgacgggggtggacaacctgttctacatcgacaagttccaggtgcgcgag gtcaagTGAcaattggcagcagcagctcggatagtatcgacacactctggacgctggtcgtgtgatggactgttgccgccacactt gctgccttgacctgtgaatatccctgccgcttttatcaaacagcctcagtgtgtttgatcttgtgtgtacgcgcttttgcgagttgctagctgc ttgtgctatttgcgaataccacccccagcatccccttccctcgtttcatatcgcttgcatcccaaccgcaacttatctacgctgtcctgctatc cctcagcgctgctcctgctcctgctcactgcccctcgcacagccttggtttgggctccgcctgtattctcctggtactgcaacctgtaaac cagcactgcaatgctgatgcacgggaagtagtgggatgggaacacaaatggaggatcccgcgtctcgaacagagcgcgcagagga acgctgaaggtctcgcctctgtcgcacctcagcgcggcatacaccacaataaccacctgacgaatgcgcttggttcttcgtccattagc gaagcgtccggttcacacacgtgccacgttggcgaggtggcaggtgacaatgatcggtggagctgatggtcgaaacgttcacagcct agggatatcatagcgactgctacccccgaccatgtgccgaggcagaaattatatacaagaagcagatcgcaattaggcacatc gctttgcattatccacacactattcatcgctgctgcggcaaggctgcagagtgtatttttgtggcccaggagctgagtccgaagtcga cgcgacgagcggcgcaggatccgacccctagacgagctctgtcattttccaagcacgcagctaaatgcgctgagaccgggtcta aatcatccgaaaagtgtcaaaatggccgattgggttcgcctaggacaatgcgctgcggattcgctcgagtccgctgccggccaaa aggcggtggtacaggaaggcgcacggggccaaccctgcgaagccgggggcccgaacgccgaccgccggccttcgatctcgg gtgtccccctcgtcaatttcctctctcgggtgcagccacgaaagtcgtgacgcaggtcacgaaatccggttacgaaaaacgcagg tcttcgcaaaaacgtgagggtttcgcgtctcgccctagctattcgtatcgccgggtcagacccacgtgcagaaaagcccttgaata acccgggaccgtggttaccgcgccgcctgcaccagggggcttatataagcccacaccacacctgtctcaccacgcatttctccaa ctcgcgacttttcggaagaaattgttatccacctagtatagactgccacctgcaggaccttgtgtcttgcagtttgtattggtcccggcc gtcgagctcgacagatctgggctagggttggcctggccgctcggcactccctttagccgcgcgcatccgcgttccagaggtgcg attcggtgtgtggagcattgtcatgcgcttgtgggggtcgttccgtgcgcggcgggtccgccatgggcgccgacctgggccctagg gtttgttttcgggccaagcgagcccctctcacctcgtcgcccccccgcattccctctctcttgcagccttgccactagtATGgccac cgcatccactttctcggcgttcaatgcccgctgcggcgacctgcgtcgctcggcgggctccgggccccggcgcccagcgaggccc

-continued ctccccgtgcgcgggcgcgccgccgccgccgacgccaaccccgcccgccccgagcgccgcgtggtgatcaccggccagg gcgtggtgacctccctgggccagaccatcgagcagttctactcctccctgctggagggcgtgtccggcatctcccagatccagaag ttcgacaccaccggctacaccaccaccatcgccggcgagatcaagtccctgcagctggacccctacgtgcccaagcgctgggcc aagcgcgtggacgacgtgatcaagtacgtgtacatcgccggcaagcaggccctggagtccgccggcctgcccatcgaggccgc cggcctggccggcgccggcctggaccccgccctgtgcggcgtgctgatcggcaccgccatggccggcatgacctccttcgccgc cggcgtggaggccctgacccgcggcggcgtgcgcaagatgaaccccttctgcatccccttctccatctccaacatgggcggcgcc atgctggccatggacatcggcttcatgggccccaactactccatctccaccgcctgcgccaccggcaactactgcatcctgggcgc cgccgaccacatccgccgcggcgacgccaacgtgatgctggccggcggcgccgacgccgccatcatcccctccggcatcggcg gcttcatcgcctgcaaggccctgtccaagcgcaacgacgagcccgagcgcgcctcccgcccctgggacgccgaccgcgacgg cttcgtgatgggcgagggcgccggcgtgctggtgctggaggagctggagcacgccaagcgccgcggcgccaccatcctggccg agctggtgggcggcgccgccacctccgacgcccaccacatgaccgagcccgacccccagggccgcggcgtgcgcctgtgcct ggagcgcgccctggagcgcgcccgcctggcccccgagcgcgtgggctacgtgaacgcccacggcacctccacccccgccggc gacgtggccgagtaccgcgccatccgcgccgtgatcccccaggactccctgcgcatcaactccaccaagtccatgatcggccac ctgctgggcggcgccggcgccgtggaggccgtggccgccatccaggccctgcgcaccggctggctgcaccccaacctgaacct ggagaaccccgcccccggcgtggaccccgtggtgctggtgggcccccgcaaggagcgcgccgaggacctggacgtggtgctg tccaactccttcggcttcggcggccacaactcctgcgtgatcttccgcaagtacgacgagatggactacaaggaccacgacggcg actacaaggaccacgacatcgactacaaggacgacgacgacaagTGAatcgatagatctcttaaggcagcagcagctcggat agtatcgacacactctggacgctggtcgtgtgatggactgttgccgccacacttgctgccttgacctgtgaatatccctgccgcttttatca aacagcctcagtgtgtttgatcttgtgtgtacgcgcttttgcgagttgctagctgcttgtgctatttgcgaataccacccccagcatcccctt ccctcgtttcatatcgcttgcatcccaaccgcaacttatctacgctgtcctgctatccctcagcgctgctcctgctcctgctcactgcccctc gcacagccttggtttgggctccgcctgtattctcctggtactgcaacctgtaaaccagcactgcaatgctgatgcacgggaagtagtgg gatgggaacacaaatggaaagcttaattaagagctcttgttttccagaaggagttgctccttgagcctttcattctcagcctcgataa cctccaaagccgctctaattgtggaggggttcgaaccgaatgctgcgtgaacgggaaggaggaggagaaagagtgagca gggagggattcagaaatgagaaatgagaggtgaaggaacgcatccctatgcccttgcaatggacagtgtttctggccaccgc caccaagacttcgtgtcctctgatcatcatgcgattgattacgttgaatgcgacggccggtcagccccggacctccacgcaccg gtgctcctccaggaagatgcgcttgtcctccgccatcttgcagggctcaagctgctcccaaaactcttgggcgggttccggacg gacggctaccgcgggtgcggccctgaccgccactgttcggaagcagcggcgctgcatgggcagcggccgctgcggtgcgcc acggaccgcatgatccaccggaaaagcgcacgcgctggagcgcgcagaggaccacagagaagcggaagagacgccagta ctggcaagcaggctggtcggtgccatggcgcgctactaccctcgctatgactcgggtcctcggccggctggcggtgctgacaa ttcgtttagtggagcagcgactccattcagctaccagtcgaactcagtggcacagtgactccgctcttc In addition to the construct pSZ2533, we also investigated the PmKASII activity when the KASII gene driven by other promoters, including PmLDH1, and PmAMT3. The plasmid pSZ2532 can be written as FATA1 3'::CrTUB2:ScSUC2:CvNR::PmLDH1:PmKASII-CvNR::FATA1 5', while the plasmid pSZ2750 can be written as FATA1 3'::CrTUB2:ScSUC2: CvNR::PmAMT3:PmKASII-CvNR::FATA1 5'. Since the sequences of these two plasmids are the same as pSZ2533 except for the promoter that drives the PmKASII, the following sequences only show the sequence of the PmLDH1 and PmAMT3 promoters.

Nucleotide sequence of PmLDH1 promoter that drive the expression of PmKASII in pSZ2532:

(SEQ ID NO: 115)

Gatatc*tccctccgtctctgcactctggcgcccctcctccgtctcgtggactgacggacgagagtctggggcgccgcttttctatccac*

*accgccctttccgcatcgaagacaccacccatcgtgccgccaggtcttccccaatcacccgccctgtggtcctctctcccagccgtg*

*tttggtcgctgcgtccacatttttccattcgtgccccacgatcctcgcccatcttggcgccttggataggcaccctttttcagcacgccc*

*tggtgtgtagcacaacctgacctctctctaccgcatcgcctccctcccacacctcagttgactccctcgtcgcacgttgcacccgcaa*

*gctccccatttcatcctattgacaatcgcacactgtacatgtatgctcattattttgcaaaaaaacagggggtcggttcactcctggca*

*gacgacgcggtgctgccgcgcgccgctgaggcggcgtcgcgacggcaacacccatcgcaccgcacgtcgacgagtcaaccc*

*accctgctcaacggtgatctccccatcgcgacacccccgtgaccgtactatgtgcgtccatacgcaacatgaaaaggaccttggt*

*ccccggaggcggcgagctcgtaatcccgaggttggccccgcttccgctggacacccatcgcatcttccggctcgcccgctgtcga*

*gcaagcgccctcgtgcgcgcaacccttgtggtgcctgcccgcagagccgggcataaaggcgagcaccacacccgaaccagtc*

*caatttgctttctgcattcactcaccaacttttacatccacacatcgtactaccacacctgcccagtcgggtttgatttctattgcaaagg*

*tgcggggggttggcgcactgcgtgggttgtgcagccggccgccgcggctgtacccagcgatcaggtagcttgggctgtatcttct*

*caagcattaccttgtcctgggcgtaggtttgcc*actagt

Nucleotide sequence of PmAMT3 promoter that drive the expression of PmKASII in pSZ2750:

(SEQ ID NO: 116)

Gatatcgaattcggccgacaggacgcgcgtcaaaggtgctggtcgtgtatgccctggccggcaggtcgttgctgctgctggttagtg attccgcaaccctgattttggcgtcttattttggcgtggcaaacgctggcgcccgcgagccgggccggcggcgatgcggtgccccac ggctgccggaatccaagggaggcaagagcgcccgggtcagttgaagggctttacgcgcaaggtacagccgctcctgcaaggctgc gtggtggaattggacgtgcaggtcctgctgaagttcctccaccgcctcaccagcggacaaagcaccggtgtatcaggtccgtgtcatc cactctaaagaactcgactacgacctactgatggccctagattcttcatcaaaaacgcctgagacacttgcccaggattgaaactccctg aagggaccaccaggggccctgagttgttccttccccccgtggcgagctgccagccaggctgtacctgtgatcgaggctggcgggaa aataggcttcgtgtgctcaggtcatgggaggtgcaggacagctcatgaaacgccaacaatcgcacaattcatgtcaagctaatcagct atttcctcttcacgagctgtaattgtcccaaaattctggtctaccgggggtgatccttcgtgtacgggcccttccctcaaccctaggtatgc gcgcatgcggtcgccgcgcaactcgcgcgagggccgagggtttgggacgggccgtcccgaaatgcagttgcacccggatgcgtg gcacctttttttgcgataatttatgcaatggactgctctgcaaaattctggctctgtcgccaaccctaggatcagcggcgtaggatttcgtaa tcattcgtcctgatggggagctaccgactaccctaatatcagcccgactgcctgacgccagcgtccacttttgtgcacacattccattcgt gcccaagacatttcattgtggtgcgaagcgtccccagttacgctcacctgtttcccgacctccttactgttctgtcgacagagcgggccc acaggccggtcgcagccactagt

Primary transformants were clonally purified and grown under low-nitrogen lipid production conditions at either pH5.0 or pH7.0, depend on the promoters that driven the expression of the PmKASII gene. Transgenic lines arising from the transformations with pSZ2533 (D1636) and pSZ2532 (D1637) were assayed in lipid production media at pH5.0, because of the nature of the promoters and the fact that *P. moriformis* produces more lipid at pH5.0. Transgenic lines generated from the transformation of pSZ2750 (D1684) were assayed at pH 7.0 to allow for maximal PmKASII gene expression when driven by the pH regulated PmAMT3 promoter. The resulting profiles from representative clones arising from transformations with D1636 (pSZ2533), D1637 (pSZ2532), and D1684 (pSZ2750) are shown in Tables 64-66, respectively.

The impact of FATA1 knock-out and simultaneously overexpressing the *P. moriformis* KASII gene is a clear diminution of C16:0 chain lengths with a significant increase in C18:1. At pH5.0, it appears that PmUAPA1 is stronger than PmLDH1, the palmitate level in D1636 transformants is close to 3%, while none of the transformants in D1637 go below 7% at the same condition.

TABLE 64

Lipid profile of representative clones arising from transformation with D1636 (pSZ2533) DNA.

| Sample ID | C14:0 | C16:0 | C18:0 | C18:1 | C18:2 |
|---|---|---|---|---|---|
| pH5; T523; D1636-3 | 0.53 | 3.31 | 6.15 | 79.89 | 7.19 |
| pH5; T523; D1636-4 | 0.48 | 3.54 | 5.34 | 80.78 | 6.92 |
| pH5; T523; D1636-5 | 0.48 | 3.59 | 5.41 | 81.37 | 6.55 |
| pH5; T523; D1636-12 | 0.61 | 3.59 | 3.67 | 80.52 | 8.93 |
| pH5; T523; D1636-13 | 0.55 | 3.80 | 4.88 | 81.83 | 6.61 |
| pH5; T523; D1636-21 | 0.54 | 4.18 | 2.82 | 82.26 | 8.17 |
| pH5; Strain AO | 0.89 | 17.28 | 2.69 | 70.53 | 6.86 |

TABLE 65

Lipid profile of representative clones arising from transformation with D1637 (pSZ2532) DNA.

| Sample ID | C14:0 | C16:0 | C18:0 | C18:1 | C18:2 |
|---|---|---|---|---|---|
| pH5; T523; D1637-6 | 0.46 | 7.64 | 3.43 | 80.08 | 6.33 |
| pH5; T523; D1637-12 | 0.66 | 8.49 | 1.90 | 77.06 | 9.59 |
| pH5; T523; D1637-13 | 0.47 | 8.59 | 3.18 | 79.39 | 6.54 |
| pH5; T523; D1637-15 | 0.60 | 9.60 | 2.51 | 76.41 | 8.85 |
| pH5; T523; D1637-7 | 0.61 | 11.16 | 2.21 | 75.82 | 8.04 |
| pH5; T523; D1637-8 | 0.93 | 11.29 | 3.61 | 74.84 | 6.61 |
| pH5; Strain AO | 0.89 | 17.28 | 2.69 | 70.53 | 6.86 |

TABLE 66

Lipid profile of representative clones arising from transformation with D1684 (pSZ2750) DNA.

| Sample ID | C14:0 | C16:0 | C18:0 | C18:1 | C18:2 |
|---|---|---|---|---|---|
| pH7; T532; D1684-14 | 0.55 | 5.04 | 4.90 | 78.88 | 8.19 |
| pH7; T532; D1684-23 | 0.58 | 5.80 | 4.98 | 77.51 | 8.69 |
| pH7; T532; D1684-1 | 0.59 | 6.37 | 4.99 | 77.47 | 8.03 |
| pH7; T532; D1684-24 | 0.55 | 6.37 | 4.83 | 77.98 | 7.73 |
| pH7; T532; D1684-11 | 0.61 | 6.61 | 4.88 | 76.14 | 8.96 |
| pH7; T532; D1684-16 | 0.57 | 6.61 | 5.01 | 77.74 | 7.83 |
| pH7; Strain AO | 0.84 | 20.12 | 3.52 | 66.86 | 6.77 |

Example 57: Generation of a High-Oleic High-Stability (HOHS) Oil-Producing Strain Strain AP of Example 56 produces oil with about 85% oleic acid with total un-saturates around 93%. Here we show that that the oxidative stability of the high-oleic oil can be improved by knock-down of a delta 12 fatty acid desaturase, thereby reducing linoleic acid production in the oleaginous cell.

We expressed a hairpin-RNA-producing construct in Strain AP targeting an endogenous FAD gene, PmFAD2. The resulting strains, including Strain AQ, produce >90% C18:1 and <1% C18:2 in fermenters. Most importantly, Strain AQ retains the same level of lipid productivity and sucrose hydrolyzing ability as its parental strain, Strain AP.

Generation of High Oleic High Stability Oil Producing Strain AQ: Construct Used for Down Regulating PmFAD2.

To generate a strain that produces oil with high oxidative stability, the hairpin PmFAD2 was introduced into AP for down regulating PmFAD2 expression. Strain AQ is a stable line generated from the transformation of pSZ3372 DNA (6SA::PmHXT1:ScarMEL1:CvNR::CrTUB2: Hairpin PmFAD2:CvNR::6SB) into Strain AP. In this construct, the *Saccharomyces carlbergensis* MEL1 gene was utilized as the selectable marker to introduce the Hairpin PmFAD2 into the 6S nuclear chromosomal locus of *P. moriformis* strain AQ by homologous recombination using previously described transformation methods (biolistics).

The sequence of the pSZ3372 transforming DNA is provided below. Relevant restriction sites in pSZ3372 are indicated in lowercase, bold and underlining and are 5'-3' BspQ 1, Kpn I, SpeI, Mfe I, BamHI, EcoRV, SpeI, XhoI, SacI, BspQ I, respectively. BspQI sites delimit the 5' and 3' ends of the transforming DNA. Bold, lowercase sequences represent 6SA genomic DNA that permits targeted integration at 6S locus via homologous recombination. Proceeding in the 5' to 3' direction, the *P. moriformis* HXT1 promoter driving the expression of the *S. carlbergensis* MEL1 gene is indicated by boxed text. The initiator ATG and terminator TGA for ScarMEL1 are indicated by uppercase, bold italics while the coding region is indicated in lowercase italics. The *Chlorella vulgaris* nitrate reductase 3' UTR is indicated by lowercase underlined text followed by the *C. reinhardtii* β-tubulin promoter, indicated by boxed italics text. The hairpin PmFAD2 cassette includes the *P. moriformis* FAD2 exon1 (indicated by italics underlined text), the intron of PmFAD2 (italics lowercase text), and followed by the inverted PmFAD2 exon1 (indicated by italics underlined text). The *C. vulgaris* nitrate reductase 3' UTR is again indicated by lowercase underlined text followed by the 6SB genomic region indicated by bold, lowercase text.

Nucleotide sequence of transforming DNA contained in pSZ3372:

(SEQ ID NO: 117)

<u>gctcttc</u>gccgccgccactcctgctcgagcgcgcccgcgcgtgcgccgccagcgccttggccttttcgccgcgctcgtgcgcgtc gctgatgtccatcaccaggtccatgaggtctgccttgcgccggctgagccactgcttcgtccgggcggccaagaggagcatga

-continued gggaggactcctggtccagggtcctgacgtggtcgcggctctgggagcgggccagcatcatctggctctgccgcaccgaggc cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaaccccccttgcgcgttagtgttgccatcctttgcagaccggtgag agccgacttgttgtgcgccacccccccacaccacctcctcccagaccaattctgtcaccttttttggcgaaggcatcggcctcggcc tgcagagaggacagcagtgcccagccgctggggggttggcggatgcacgctcaggtaccgcggtgagaatcgaaaatgcatcgt ttctaggttcggagacggtcaattccctgctccggcgaatctgtcggtcaagctggccagtggacaatgttgctatggcagcccgcgca catgggcctcccgacgcggccatcaggagcccaaacagcgtgtcagggtatgtgaaactcaagaggtccctgctgggcactccggc cccactccgggggcgggacgccaggcattcgcggtcggtcccgcgcgacgagcgaaatgatgattcggttacgagaccaggacgt cgtcgaggtcgagaggcagcctcggacacgtctcgctagggcaacgccccgagtccccgcgagggccgtaaacattgtttctgggt gtcggagtgggcatttttgggcccgatccaatcgcctcatgccgctctcgtctggtcctcacgttcgcgtacggcctggatcccggaaag ggcggatgcacgtggtgttgccccgccattggcgcccacgtttcaaagtccccggccagaaatgcacaggaccggcccggctcgca caggccatgctgaacgcccagatttcgacagcaacaccatctagaataatcgcaaccatccgcgttttgaacgaaacgaaacggcgc tgtttagcatgtttccgacatcgtgggggccgaagcatgctccgggggggaggaaagcgtggcacagcggtagcccattctgtgccac acgccgacgaggaccaatccccggcatcagccttcatcgacggctgcgccgcacatataaagccggacgcctaaccggtttcgtgg ttatgactagt*ATG**ttcgcgttctacttcctgacggcctgcatctccctgaagggcgtgttcggcgtgtccccctcctacaacggcct*

*gggcctgacgccccagatgggctgggacaactggaacacgttcgcctgcgacgtctccgagcagctgctgctggacacggccg*

*accgcatctccgacctgggcctgaaggacatgggctacaagtacatcatcctggacgactgctggtcctccggccgcgactccga*

*cggcttcctggtcgccgacgagcagaagttcccccaacggcatgggccacgtcgccgaccacctgcacaacaactccttcctgttc*

*ggcatgtactcctccgcgggcgagtacacgtgcgccggctaccccggctccctgggccgcgaggaggaggacgcccagttcttc*

*gcgaacaaccgcgtggactacctgaagtacgacaactgctacaacaagggccagttcggcacgcccgagatctcctaccaccg*

*ctacaaggccatgtccgacgccctgaacaagacgggccgccccatcttctactccctgtgcaactggggccaggacctgaccttct*

*actggggctccggcatcgcgaactcctggcgcatgtccggcgacgtcacggcggagttcacgcgccccgactcccgctgcccct*

*gcgacggcgacgagtacgactgcaagtacgccggcttccactgctccatcatgaacatcctgaacaaggccgcccccatgggcc*

*agaacgcgggcgtcggcggctggaacgacctggacaacctggaggtcggcgtcggcaacctgacggacgacgaggagaag*

*gcgcacttctccatgtgggccatggtgaagtccccccctgatcatcggcgcgaacgtgaacaacctgaaggcctcctcctactccat*

*ctactcccaggcgtccgtcatcgccatcaaccaggactccaacggcatccccgccacgcgcgtctggcgctactacgtgtccgac*

*acggacgagtacggccagggcgagatccagatgtggtccggccccctggacaacggcgaccaggtcgtggcgctgctgaacg*

*gcggctccgtgtcccgccccatgaacacgaccctggaggagatcttcttcgactccaacctgggctccaagaagctgacctccac*

*ctgggacatctacgacctgtgggcgaaccgcgtcgacaactccacggcgtccgccatcctgggccgcaacaagaccgccaccg*

*gcatcctgtacaacgccaccgagcagtcctacaaggacggcctgtccaagaacgacacccgcctgttcggccagaagatcggc*

-continued tccctgtcccccaacgcgatcctgaacacgaccgtccccgcccacggcatcgcgttctaccgcctgcgcccctcctccTGAcaat tggcagcagcagctcggatagtatcgacacactctggacgctggtcgtgtgatggactgttgccgccacacttgctgccttgacctgtg aatatccctgccgcttttatcaaacagcctcagtgtgtttgatcttgtgtgtacgcgcttttgcgagttgctagctgcttgtgctatttgcgaat accacccccagcatccccttccctcgtttcatatcgcttgcatcccaaccgcaacttatctacgctgtcctgctatccctcagcgctgctcc tgctcctgctcactgcccctcgcacagccttggtttgggctccgcctgtattctcctggtactgcaacctgtaaaccagcactgcaatgct gatgcacgggaagtagtgggatgggaacacaaatggaggatcccgcgtctcgaacagagcgcgcagaggaacgctgaaggtctc gcctctgtcgcacctcagcgcggcatacaccacaataaccacctgacgaatgcgcttggttcttcgtccattagcgaagcgtccggttc acacacgtgccacgttggcgaggtggcaggtgacaatgatcggtggagctgatggtcgaaacgttcacagcctagggatatcgaatt cctttcttgcgctatgacacttccagcaaaaggtagggcgggctgcgagacggcttcccggcgctgcatgcaacaccgatgatgc ttcgacccccccgaagctccttcggggctgcatgggcgctccgatgccgctccagggcgagcgctgtttaaatagccaggcccccg attgcaaagacattatagcgagctaccaaagccatattcaaacacctagatcactaccacttctacacaggccactcgagcttgtg atcgcactccgctaagggggcgcctcttcctcttcgtttcagtcacaacccgcaaacactagtATGgctatcaagacgaacagg cagcctgtggagaagcctccgttcacgatcgggacgctgcgcaaggccatccccgcgcactgtttcgagcgctcggcgcttcgta gcagcatgtacctggcctttgacatcgcggtcatgtccctgctctacgtcgcgtcgacgtacatcgaccctgcaccggtgcctacgtg ggtcaagtacggcatcatgtggccgctctactggttcttccaggtgtgtttgagggttttggttgcccgtattgaggtcctggtggcgcg catggaggagaaggcgcctgtcccgctgacccccccggctaccctcccggcaccttccagggcgcgtacgggaagaaccagta gagcggccacatgatgccgtacttgacccacgtaggcaccggtgcagggtcgatgtacgtcgacgcgacgtagagcagggaca tgaccgcgatgtcaaaggccaggtacatgctgctacgaagcgccgagcgctcgaaacagtgcgcggggatggccttgcgcagc gtcccgatcgtgaacggaggcttctccacaggctgcctgttcgtcttgatagccatctcgaggcagcagcagctcggatagtatcga cacactctggacgctggtcgtgtgatggactgttgccgccacacttgctgccttgacctgtgaatatccctgccgcttttatcaaacagcc tcagtgtgtttgatcttgtgtgtacgcgcttttgcgagttgctagctgcttgtgctatttgcgaataccacccccagcatccccttccctcgttt catatcgcttgcatcccaaccgcaacttatctacgctgtcctgctatccctcagcgctgctcctgctcctgctcactgcccctcgcacagc cttggtttgggctccgcctgtattctcctggtactgcaacctgtaaaccagcactgcaatgctgatgcacgggaagtagtgggatggga acacaaatggaaagctgtagagctcttgttttccagaaggagttgctccttgagcctttcagttctcagcctcgataacctccaaagc cgctctaattgtggagggggttcgaatttaaaagcttggaatgttggttcgtgcgtctggaacaagcccagacttgttgctcact gggaaaaggaccatcagctccaaaaaacttgccgctcaaaccgcgtacctctgctttcgcgcaatctgccctgttgaaatcgcc accacattcatattgtgacgcttgagcagtctgtaattgcctcagaatgtggaatcatctgccccctgtgcgagcccatgccagg catgtcgcgggcgaggacacccgccactcgtacagcagaccattatgctacctcacaatagttcataacagtgaccatatttct cgaagctccccaacgagcacctccatgctctgagtggccaccccccggccctggtgcttgcggagggcaggtcaaccggcat ggggctaccgaaatccccgaccggatcccaccacccccgcgatgggaagaatctctccccgggatgtgggcccaccaccagc acaacctgctggcccaggcgagcgtcaaaccataccacacaaatatccttggcatcggccctgaattccttctgccgctctgct acccggtgcttctgtccgaagcaggggttgctagggatcgctccgagtccgcaaacccttgtcgcgtggcggggcttgttcgag cttgaagagc We introduced the hairpin PmFAD2 construct into strain AP. Transgenic lines arising from the transformations with pSZ3372 (D2082) were assayed in lipid production media at pH5.0, the resulting profiles from representative clones are shown in Table 67. Among more than 400 transformants we had screened, the strain AQ was isolated from the transformant D2082.1, which produced <1% C18:2 during the initial profile screening. Thus, this strain can be used to produce a triglyceride oil that is both high in oleic acid and low in polyunsaturates. Due to the low polyunsaturate levels, the oil is expected to have a high oxidative stability when tested via the AOCS Cd 12b-92 method (see Section IV of this patent application and corresponding examples).

TABLE 67

Lipid profile of representative clones arising from transformation with D2082 (pSZ3372) DNA.

| Sample ID | C16:0 | C18:0 | C18:1 | C18:2 | C18:3 α |
|---|---|---|---|---|---|
| SAP_pH5.0_glucose_day5-T658; D2082-1 | 4.42 | 3.80 | 89.36 | 0.65 | 0.10 |
| StrainAP_pH5.0_glucose_day5-T658; D2082-87 | 3.77 | 4.01 | 88.70 | 1.52 | 0.19 |
| StrainAP_pH5.0_glucose_day5-T658; D2082-93 | 5.14 | 3.58 | 87.63 | 1.65 | 0.19 |
| StrainAP_pH5.0_glucose_day5-T658; D2082-78 | 3.74 | 2.40 | 89.69 | 1.97 | 0.23 |
| StrainAP_pH5.0_glucose_day5 | 4.10 | 3.77 | 83.55 | 6.41 | 0.40 |

Figure 24:
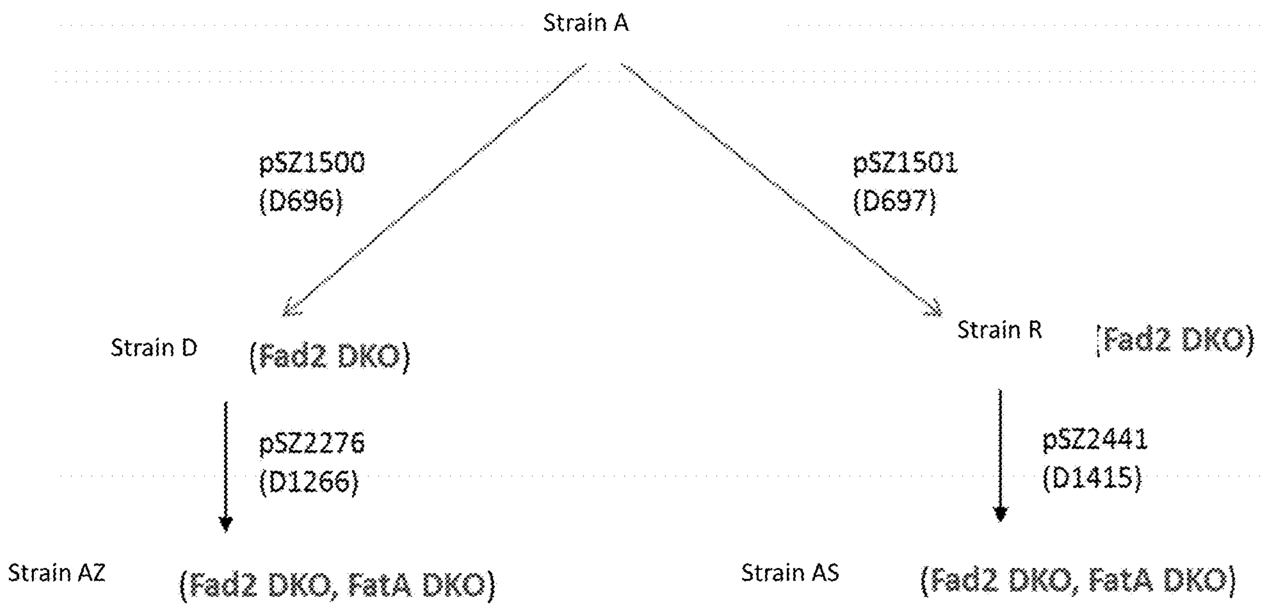
FIG. 24 shows genetic modification of a microalgal strain to produced double knockouts of FAD2/FADc and FATA.

Example 58: Generating High Oleic "Zero" Linoleic Strains by Knock-Out *Prototheca Morformis* (PM) FAD2 and FATA Genes and Over-Expression of PMKASII Gene Triacylglycerols in microalgae can be significantly enriched in levels of oleate (C18:1) utilizing molecular genetic approaches, such as down regulating endogenous FATA1 and FADc genes and over-expression of endogenous KASII activity. In this example, we focus our efforts on combining these approaches into a single transgenic line. Constructs that disrupt a single copy of the FATA1 allele while simultaneously overexpressing the *Prototheca moriformis* KASII gene were introduced into different Δfad2 lines, termed Strain R and Strain D (see genealogy in FIG. 24). The resulting strains, such as Strain AS and Strain AZ produces around 90% C18:1 with <0.05% C18:2.

Strain D and Strain R are Δfad2 lines that produce oils comprised of 0% C18:2, and between 76% to 87% C18:1, depending upon whether they are grown in shake flasks or high cell density fermentations, respectively. To further elevate oleate levels in Strain D and Strain R, constructs that disrupt a single copy of the FATA1 allele while simultaneously overexpressing the *P. moriformis* KAS II gene were introduced in StrainD/Strain R via particle bombardment.

Construct to Knock Out FATA Genes and Over Expression of PmKASII in S2530 Background.

Relevant restriction sites in the construct FATA1::CpACT-AtThic-nr:AMT03-5106SAD-PmKASII-nr::FATA1 (termed pSZ2276) are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from UTEX1435 that permit targeted integration at FATA1 gene via homologous recombination. Proceeding in the 5' to 3' direction, the actin gene promoter from UTEX 250 driving the expression of the *Arabidopsis thaliana* THIC gene is indicated by the boxed text. The initiator ATG and terminator TGA for AtTHIC are indicated by uppercase, bold italics while the coding region is indicated in lowercase italics. The *Chlorella vulgaris* nitrate reductase 3' UTR is indicated by lowercase underlined text followed by an endogenous AMT03 promoter of *Prototheca moriformis*, indicated by boxed italics text. The Initiator ATG and terminator TGA codons of the *P. moriformis* KASII gene are indicated by uppercase, bold italics, while the remainder of the PmKASII coding region is indicated by bold italics. The *Chlorella protothecoides* UTEX 250 stearoyl-ACP desaturase transit peptide is located between initiator ATG and the Asc I site. The *C. vulgaris* nitrate reductase 3' UTR is again indicated by lowercase underlined text followed by the UTEX1435 FATA1 genomic region indicated by bold, lowercase text.

Nucleotide sequence of transforming DNA contained in pSZ2276:

(SEQ ID NO: 118)

gctcttcggagtcactgtgccactgagttcgactggtagctgaatggagtcgctgctccactaaacgaattgtcagcaccgcca gccggccgaggacccgagtcatagcgagggtagtagcgcgccatggcaccgaccagcctgcttgccagtactggcgtctcttc cgcttctctgtggtcctctgcgcgctccagcgcgtgcgcttttccggtggatcatgcggtccgtggcgcaccgcagcggccgctg cccatgcagcgccgctgcttccgaacagtggcggtcagggccgcacccgcggtagccgtccgtccggaacccgcccaagagt tttgggagcagcttgagccctgcaagatggcggaggacaagcgcatcttcctggaggagcaccggtgcgtggaggtccgggg ctgaccggccgtcgcattcaacgtaatcaatcgcatgatgatcagaggacacgaagtcttggtggcggtggccagaaacact gtccattgcaagggcatagggatgcgttccttcacctctcatttctcatttctgaatccctccctgctcactctttctcctccttc ccgttcacgcagcattcggggtaccagtttaggtccagcgtccgtgggggggacgggctgggagcttgggccgggaagggcaa gacgatgcagtccctctggggagtcacagccgactgtgtgtgttgcactgtgcggcccgcagcactcacacgcaaaatgcctggccg acaggcaggccctgtccagtgcaacatccacggtccctctcatcaggctcaccttgctcattgacataacggaatgcgtaccgctctttc agatctgtccatccagagaggggagcaggctccccaccgacgctgtcaaacttgcttcctgcccaaccgaaaacattattgtttgagg gggggggggggggggcagattgcatggcgggatatctcgtgaggaacatcactgggacactgtggaacacagtgagtgcagtatg -continued cagagcatgtatgctaggggtcagcgcaggaagggggcctttcccagtctcccatgccactgcaccgtatccacgactcaccaggac cagcttcttgatcggcttccgctcccgtggacaccagtgtgtagcctctggactccaggtatgcgtgcaccgcaaaggccagccgatc gtgccgattcctggggtggaggatatgagtcagccaacttggggctcagagtgcacactggggcacgatacgaaacaacatctacac cgtgtcctccatgctgacacaccacagcttcgctccacctgaatgtgggcgcatgggcccgaatcacagccaatgtcgctgctgccat aatgtgatccagaccctctccgcccagatgccgagcggatcgtgggcgctgaatagattcctgtttcgatcactgtttgggtcctttccttt tcgtctcggatgcgcgtctcgaaacaggctgcgtcgggctttcggatcccttttgctccctccgtcaccatcctgcgcgcgggcaagtt gcttgaccctgggctgtaccagggttggagggtattaccgcgtcaggccattcccagcccggattcaattcaaagtctgggccaccac cctccgccgctctgtctgatcactccacattcgtgcatacactacgttcaagtcctgatccaggcgtgtctcgggacaaggtgtgcttga gtttgaatctcaaggacccactccagcacagctgctggttgaccccgccctcgcaatctagaATGgccgcgtccgtccactgcacc ctgatgtccgtggtctgcaacaacaagaaccactccgcccgccccaagctgcccaactcctccctgctgcccggcttcgacgtggt ggtccaggccgcggccacccgcttcaagaaggagacgacgaccacccgcgccacgctgacgttcgacccccccacgaccaac tccgagcgcgccaagcagcgcaagcacaccatcgacccctcctcccccgacttccagcccatcccctccttcgaggagtgcttcc ccaagtccacgaaggagcacaaggaggtggtgcacgaggagtccggccacgtcctgaaggtgcccttccgccgcgtgcacctg tccggcggcgagcccgccttcgacaactacgacacgtccggcccccagaacgtcaacgcccacatcggcctggcgaagctgcg caaggagtggatcgaccgccgcgagaagctgggcacgccccgctacacgcagatgtactacgcgaagcagggcatcatcacg gaggagatgctgtactgcgcgacgcgcgagaagctggaccccgagttcgtccgctccgaggtcgcgcggggccgcgccatcat cccctccaacaagaagcacctggagctggagcccatgatcgtgggccgcaagttcctggtgaaggtgaacgcgaacatcggca actccgccgtggcctcctccatcgaggaggaggtctacaaggtgcagtgggccaccatgtggggcgccgacaccatcatggacc tgtccacgggccgccacatccacgagacgcgcgagtggatcctgcgcaactccgcggtccccgtgggcaccgtccccatctacc aggcgctggagaaggtggacggcatcgcggagaacctgaactgggaggtgttccgcgagacgctgatcgagcaggccgagc agggcgtggactacttcacgatccacgcgggcgtgctgctgcgctacatcccccctgaccgccaagcgcctgacgggcatcgtgtc ccgcggcggctccatccacgcgaagtggtgcctggcctaccacaaggagaacttcgcctacgagcactgggacgacatcctgg acatctgcaaccagtacgacgtcgccctgtccatcggcgacggcctgcgccccggctccatctacgacgccaacgacacggccc agttcgccgagctgctgacccagggcgagctgacgcgccgcgcgtgggagaaggacgtgcaggtgatgaacgagggccccg gccacgtgcccatgcacaagatccccgagaacatgcagaagcagctggagtggtgcaacgaggcgcccttctacaccctgggc cccctgacgaccgacatcgcgcccggctacgaccacatcacctccgccatcggcgcggccaacatcggcgccctgggcaccgc cctgctgtgctacgtgacgcccaaggagcacctgggcctgcccaaccgcgacgac gtgaaggcgggcgtcatcgcctacaaga tcgccgcccacgcggccgacctggccaagcagcacccccacgcccaggcgtgggacgacgcgctgtccaaggcgcgcttcga gttccgctggatggaccagttcgcgctgtccctggaccccatgacggcgatgtccttccacgacgagacgctgcccgcggacggc gcgaaggtcgcccacttctgctccatgtgcggccccaagttctgctccatgaagatcacggaggacatccgcaagtacgccgagg agaacggctacggctccgccgaggaggccatccgccagggcatggacgccatgtccgaggagttcaacatcgccaagaagac gatctccggcgagcagcacggcgaggtcggcggcgagatctacctgcccgagtcctacgtcaaggccgcgcagaagTGAca attggcagcagcagctcggatagtatcgacacactctggacgctggtcgtgtgatggactgttgccgccacacttgctgccttgacctg tgaatatccctgccgcttttatcaaacagcctcagtgtgtttgatcttgtgtgtacgcgcttttgcgagttgctagctgcttgtgctatttgcga ataccacccccagcatccccttccctcgtttcatatcgcttgcatcccaaccgcaacttatctacgctgtcctgctatccctcagcgctgct cctgctcctgctcactgcccctcgcacagccttggtttgggctccgcctgtattctcctggtactgcaacctgtaaaccagcactgcaatg -continued ctgatgcacgggaagtagtgggatgggaacacaaatggaggatcccgcgtctcgaacagagcgcgcagaggaacgctgaaggtct cgcctctgtcgcacctcagcgcggcatacaccacaataaccacctgacgaatgcgcttggttcttcgtccattagcgaagcgtccggtt cacacacgtgccacgttggcgaggtggcaggtgacaatgatcggtggagctgatggtgaaacgttcacagcctagggatatcgaat tc*ggccgacaggacgcgcgtcaaaggtgctggtcgtgtatgccctggccggcaggtcgttgctgctgctggttagtgattccgcaa*

*ccctgattttggcgtcttattttggcgtggcaaacgctggcgcccgcgagccgggccggcggcgatgcggtgccccacggctgcc*

*ggaatccaagggaggcaagagcgcccgggtcagttgaagggctttacgcgcaaggtacagccgctcctgcaaggctgcgtggt*

*ggaattggacgtgcaggtcctgctgaagttcctccaccgcctcaccagcggacaaagcaccggtgtatcaggtccgtgtcatcca*

*ctctaaagaactcgactacgacctactgatggccctagattcttcatcaaaaacgcctgagacacttgcccaggattgaaactccc*

*tgaagggaccaccaggggccctgagttgttccttccccccgtggcgagctgccagccaggctgtacctgtgatcgaggctggcgg*

*gaaaataggcttcgtgtgctcaggtcatgggaggtgcaggacagctcatgaaacgccaacaatcgcacaattcatgtcaagcta*

*atcagctatttcctcttcacgagctgtaattgtcccaaaattctggtctaccggggggtgatccttcgtgtacgggcccttccctcaaccc*

*taggtatgcgcgcatgcggtcgcccgcgcaactcgcgcgagggccgagggtttgggacgggccgtcccgaaatgcagttgcacc*

*cggatgcgtggcacctttttttgcgataatttatgcaatggactgctctgcaaaattctggctctgtcgccaaccctaggatcagcggc*

*gtaggatttcgtaatcattcgtcctgatggggagctaccgactaccctaatatcagcccgactgcctgacgccagcgtccacttttgt*

*gcacacattccattcgtgcccaagacatttcattgtggtgcgaagcgtccccagttacgctcacctgtttcccgacctccttactgttct*

*gtcgacagagcgggcccacaggccggtcgcagcc***actagt*ATGcagaccgcccaccagcgcccccccaccgagggccact***

*gcttcggcgcccgcctgcccaccgcctcccgccgcgccgtgcgccgcgcctggtcccgcatcgcccgcgggcgcgccgccgcc*

*gccgccgacgccaaccccgcccgccccgagcgccgcgtggtgatcaccggccagggcgtggtgacctccctgggccagacca*

*tcgagcagttctactcctccctgctggagggcgtgtccggcatctcccagatccagaagttcgacaccaccggctacaccaccacc*

*atcgccggcgagatcaagtccctgcagctggacccctacgtgcccaagcgctgggccaagcgcgtggacgacgtgatcaagta*

*cgtgtacatcgccggcaagcaggccctggagtccgccggcctgcccatcgaggccgccggcctggccggcgccggcctggacc*

*ccgccctgtgcggcgtgctgatcggcaccgccatggccggcatgacctccttcgccgccggcgtggaggccctgacccgcggcg*

*gcgtgcgcaagatgaaccccttctgcatccccttctccatctccaacatgggcggcgccatgctggccatggacatcggcttcatgg*

*gccccaactactccatctccaccgcctgcgccaccggcaactactgcatcctgggcgccgccgaccacatccgccgcggcgacg*

*ccaacgtgatgctggccggcggcgccgacgccgccatcatcccctccggcatcggcggcttcatcgcctgcaaggccctgtccaa*

*gcgcaacgacgagcccgagcgcgcctcccgcccctgggacgccgaccgcgacggcttcgtgatgggcgagggcgccggcgt*

*gctggtgctggaggagctggagcacgccaagcgccgcggcgccaccatcctggccgagctggtgggcggcgccgccacctcc*

*gacgcccaccacatgaccgagcccgacccccagggccgcggcgtgcgcctgtgcctggagcgcgccctggagcgcgcccgcc*

*tggcccccgagcgcgtgggctacgtgaacgcccacggcacctccacccccgccggcgacgtggccgagtaccgcgccatccgc*

-continued

*gccgtgatcccccaggactccctgcgcatcaactccaccaagtccatgatcggccacctgctgggcggcgccggcgccgtggag*

*gccgtggccgccatccaggccctgcgcaccggctggctgcaccccaacctgaacctggagaaccccgcccccggcgtggaccc*

*cgtggtgctggtgggccccgcaaggagcgcgccgaggacctggacgtggtgctgtccaactccttcggcttcggcggccacaa*

*ctcctgcgtgatcttccgcaagtacgacgagatggactacaaggaccacgacggcgactacaaggaccacgacatcgactaca*

*aggacgacgacgacaagTGA*atcgatagatctcttaaggcagcagcagctcggatagtatcgacacactctggacgctggtcgt gtgatggactgttgccgccacacttgctgccttgacctgtgaatatccctgccgcttttatcaaacagcctcagtgtgtttgatcttgtgtgt acgcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgta ttctcctggtactgcaacctgtaaaccagcactgcaatgctgatgcacgggaagtagtgggatgggaacacaaatggaaagcttaatta agagctcttgttttccagaaggagttgctccttgagcctttcattctcagcctcgataacctccaaagccgctctaattgtggagggggttc gaagacagggtggttggctggatggggaaacgctggtcgcgggattcgatcctgctgcttatatcctccctggaagcacaccc acgactctgaagaagaaaacgtgcacacacacaacccaaccggccgaatatttgcttccttatcccgggtccaagagagact gcgatgccccctcaatcagcatcctcctccctgccgcttcaatcttccctgcttgcctgcgcccgcggtgcgccgtctgcccgcc cagtcagtcactcctgcacaggccccttgtgcgcagtgctcctgtaccctttaccgctccttccattctgcgaggcccccctattga atgtattcgttgcctgtgtggccaagcgggctgctgggcgcgccgccgtcgggcagtgctcggcgactttggcggaagccgatt gttcttctgtaagccacgcgcttgctgctttgggaagagaagggggggggtactgaatggatgaggaggagaaggaggggta ttggtattatctgagttgggtgaagagc

Construct to Knock Out FATA Genes and Over Expression of PmKASII in S2532 Background.

Relevant restriction sites in the construct FATA1::CpACT-AtThic-nr:PmUAPA1-S106SAD-PmKASII-nr::FATA1 (termed pSZ2441) are indicated in lowercase, bold and underlining and are 5'-3' BspQ 1, Kpn I, Xba I, Mfe I, BamH I, EcoR V, Spe I, Asc I, Cla I, Sac I, BspQ I, respectively. BspQI sites delimit the 5' and 3' ends of the transforming DNA. Bold, lowercase sequences represent genomic DNA from UTEX1435 that permit targeted integration at FATA1 gene via homologous recombination. Proceeding in the 5' to 3' direction, the actin gene promoter from UTEX 250 driving the expression of the *A. thaliana* THIC gene is indicated by the boxed text. The initiator ATG and terminator TGA for AtTHIC are indicated by uppercase, bold italics while the coding region is indicated in lowercase italics. The *Chlorella vulgaris* nitrate reductase 3' UTR is indicated by lowercase underlined text followed by an endogenous UAPA1 promoter of *Prototheca moriformis*, indicated by boxed italics text. The Initiator ATG and terminator TGA codons of the *P. moriformis* KASII gene are indicated by uppercase, bold italics, while the remainder of the PmKASII coding region is indicated by bold italics. The *Chlorella protothecoides* UTEX 250 stearoyl-ACP desaturase transit peptide is located between initiator ATG and the Asc I site. The *C. vulgaris* nitrate reductase 3' UTR is again indicated by lowercase underlined text followed by the UTEX1435 FATA1 genomic region indicated by bold, lowercase text.

Nucleotide sequence of transforming DNA contained in pSZ2441:

(SEQ ID NO: 119)

gctcttcggagtcactgtgccactgagttcgactggtagctgaatggagtcgctgctccactaaacgaattgtcagcaccgcca gccggccgaggacccgagtcatagcgagggtagtagcgcgccatggcaccgaccagcctgcttgccagtactggcgtctcttc cgcttctctgtggtcctctgcgcgctccagcgcgtgcgcttttccggtggatcatgcggtccgtggcgcaccgcagcggccgctg cccatgcagcgccgctgcttccgaacagtggcggtcagggccgcacccgcggtagccgtccgtccggaacccgcccaagagt tttgggagcagcttgagccctgcaagatggcggaggacaagcgcatctcctggaggagcaccggtgcgtggaggtccgggg ctgaccggccgtcgcattcaacgtaatcaatcgcatgatgatcagaggacacgaagtcttggtggcggtggccagaaacact gtccattgcaagggcatagggatgcgttccttcacctctcatttctcatttctgaatccctccctgctcactctttctcctcctccttc ccgttcacgcagcattcggggtaccagtttaggtccagcgtccgtgggggggacgggctgggagcttgggccgggaagggcaa gacgatgcagtccctctggggagtcacagccgactgtgtgtgttgcactgtgcggcccgcagcactcacacgcaaaatgcctggccg -continued acaggcaggccctgtccagtgcaacatccacggtccctctcatcaggctcaccttgctcattgacataacggaatgcgtaccgctctttc agatctgtccatccagagaggggagcaggctccccaccgacgctgtcaaacttgcttcctgcccaaccgaaaacattattgtttgagg gggggggggggggggcagattgcatggcgggatatctcgtgaggaacatcactgggacactgtggaacacagtgagtgcagtatg cagagcatgtatgctaggggtcagcgcaggaagggggcctttcccagtctcccatgccactgcaccgtatccacgactcaccaggac cagcttcttgatcggcttccgctcccgtggacaccagtgtgtagcctctggactccaggtatgcgtgcaccgcaaaggccagccgatc gtgccgattcctggggtggaggatatgagtcagccaacttggggctcagagtgcacactggggcacgatacgaaacaacatctacac cgtgtcctccatgctgacacaccacagcttcgctccacctgaatgtgggcgcatgggcccgaatcacagccaatgtcgctgctgccat aatgtgatccagaccctctccgcccagatgccgagcggatcgtgggcgctgaatagattcctgtttcgatcactgtttgggtcctttccttt tcgtctcggatgcgcgtctcgaaacaggctgcgtcgggctttcggatccctttttgctccctccgtcaccatcctgcgcgcgggcaagtt gcttgaccctgggctgtaccagggttggagggtattaccgcgtcaggccattcccagcccggattcaattcaaagtctgggccaccac cctccgccgctctgtctgatcactccacattcgtgcatacactacgttcaagtcctgatccaggcgtgtctcgggacaaggtgtgcttga gtttgaatctcaaggacccactccagcacagctgctggttgaccccgccctcgcaatctaga*ATG**gccgcgtccgtccactgcacc*

*ctgatgtccgtggtctgcaacaacaagaaccactccgcccgccccaagctgcccaactcctccctgctgcccggcttcgacgtggt*

*ggtccaggccgcggccacccgcttcaagaaggagacgacgaccacccgcgccacgctgacgttcgacccccccacgaccaac*

*tccgagcgcgccaagcagcgcaagcacaccatcgacccctcctcccccgacttccagcccatcccctccttcgaggagtgcttcc*

*ccaagtccacgaaggagcacaaggaggtggtgcacgaggagtccggccacgtcctgaaggtgcccttccgccgcgtgcacctg*

*tccggcggcgagcccgccttcgacaactacgacacgtccggcccccagaacgtcaacgcccacatcggcctggcgaagctgcg*

*caaggagtggatcgaccgccgcgagaagctgggcacgccccgctacacgcagatgtactacgcgaagcagggcatcatcacg*

*gaggagatgctgtactgcgcgacgcgcgagaagctggaccccgagttcgtccgctccgaggtcgcgcggggccgcgccatcat*

*cccctccaacaagaagcacctggagctggagcccatgatcgtgggccgcaagttcctggtgaaggtgaacgcgaacatcggca*

*actccgccgtggcctcctccatcgaggaggaggtctacaaggtgcagtgggccaccatgtggggcgccgacaccatcatggacc*

*tgtccacgggccgccacatccacgagacgcgcgagtggatcctgcgcaactccgcggtccccgtgggcaccgtccccatctacc*

*aggcgctggagaaggtggacggcatcgcggagaacctgaactgggaggtgttccgcgagacgctgatcgagcaggccgagc*

*agggcgtggactacttcacgatccacgcgggcgtgctgctgcgctacatcccccctgaccgccaagcgcctgacgggcatcgtgtc*

*ccgcggcggctccatccacgcgaagtggtgcctggcctaccacaaggagaacttcgcctacgagcactgggacgacatcctgg*

*acatctgcaaccagtacgacgtcgccctgtccatcggcgacggcctgcgccccggctccatctacgacgccaacgacacggccc*

*agttcgccgagctgctgacccagggcgagctgacgcgccgcgcgtgggagaaggacgtgcaggtgatgaacgagggccccg*

*gccacgtgcccatgcacaagatccccgagaacatgcagaagcagctggagtggtgcaacgaggcgcccttctacaccctgggc*

*cccctgacgaccgacatcgcgcccggctacgaccacatcacctccgccatcggcgcggccaacatcggcgccctgggcaccgc*

*cctgctgtgctacgtgacgcccaaggagcacctgggcctgcccaaccgcgacgacgtgaaggcgggcgtcatcgcctacaaga*

*tcgccgcccacgcggccgacctggccaagcagcacccccacgcccaggcgtgggacgacgcgctgtccaaggcgcgcttcga*

*gttccgctggatggaccagttcgcgctgtccctggaccccatgacggcgatgtccttccacgacgagacgctgcccgcggacggc*

*gcgaaggtcgcccacttctgctccatgtgcggccccaagttctgctccatgaagatcacggaggacatccgcaagtacgccgagg*

*agaacggctacggctccgccgaggaggccatccgccagggcatggacgccatgtccgaggagttcaacatcgccaagaagac*

*gatctccggcgagcagcacggcgaggtcggcggcgagatctacctgcccgagtcctacgtcaaggccgcgcagaag*TGAca -continued attggcagcagcagctcggatagtatcgacacactctggacgctggtcgtgtgatggactgttgccgccacacttgctgccttgacctg tgaatatccctgccgcttttatcaaacagcctcagtgtgtttgatcttgtgtgtacgcgcttttgcgagttgctagctgcttgtgctatttgcga ataccacccccagcatccccttccctcgtttcatatcgcttgcatcccaaccgcaacttatctacgctgtcctgctatccctcagcgctgct cctgctcctgctcactgcccctcgcacagccttggtttgggctccgcctgtattctcctggtactgcaacctgtaaaccagcactgcaatg ctgatgcacgggaagtagtgggatgggaacacaaatggaggatcccgcgtctcgaacagagcgcgcagaggaacgctgaaggtct cgcctctgtcgcacctcagcgcggcatacaccacaataaccacctgacgaatgcgcttggttcttcgtccattagcgaagcgtccggt cacacacgtgccacgttggcgaggtggcaggtgacaatgatcggtggagctgatggtcgaaacgttcacagcctagggatatc*ata*

*gcgactgctacccccccgaccatgtgccgaggcagaaattatatacaagaagcagatcgcaattaggcacatcgctttgcattatc*

*cacacactattcatcgctgctgcggcaaggctgcagagtgtatttttgtggcccaggagctgagtccgaagtcgacgcgacgagc*

*ggcgcaggatccgacccctagacgagctctgtcattttccaagcacgcagctaaatgcgctgagaccgggtctaaatcatccgaa*

*aagtgtcaaaatggccgattgggttcgcctaggacaatgcgctgcggattcgctcgagtccgctgccggccaaaaggcggtggt*

*acaggaaggcgcacggggccaaccctgcgaagccgggggcccgaacgccgaccgccggccttcgatctcgggtgtccccctc*

*gtcaattttcctctctcgggtgcagccacgaaagtcgtgacgcaggtcacgaaatccggttacgaaaaacgcaggtcttcgcaaaa*

*acgtgagggtttcgcgtctcgccctagctattcgtatcgccgggtcagacccacgtgcagaaaagcccttgaataacccgggacc*

*gtggttaccgcgccgcctgcaccaggggggcttatataagcccacaccacacctgtctcaccacgcatttctccaactcgcgactttt*

*cggaagaaattgttatccacctagtatagactgccacctgcaggaccttgtgtcttgcagtttgtattggtcccggccgtcgagctcg*

*acagatctgggctagggttggcctggccgctcggcactcccctttagccgcgcgcatccgcgttccagaggtgcgattcggtgtgt*

*ggagcattgtcatgcgcttgtgggggtcgttccgtgcgcggcgggtccgccatgggcgccgacctgggccctagggtttgttttcgg*

*gccaagcgagcccctctcacctcgtcgccccccgcattccctctctcttgcagcc*actagt*ATGgccaccgcatccactttctcg*

*gcgttcaatgcccgctgcggcgacctgcgtcgctcggcgggctccgggccccggcgcccagcgaggcccctccccgtgcgcgg*

*gcgcgccgccgccgccgccgacgccaaccccgcccgccccgagcgccgcgtggtgatcaccggccagggcgtggtgacctcc*

*ctgggccagaccatcgagcagttctactcctccctgctggagggcgtgtccggcatctcccagatccagaagttcgacaccaccg*

*gctacaccaccaccatcgccggcgagatcaagtccctgcagctggacccctacgtgcccaagcgctgggccaagcgcgtggac*

*gacgtgatcaagtacgtgtacatcgccggcaagcaggccctggagtccgccggcctgcccatcgaggccgccggcctggccgg*

*cgccggcctggaccccgccctgtgcggcgtgctgatcggcaccgccatggccggcatgacctccttcgccgccggcgtggaggc*

*cctgacccgcggcggcgtgcgcaagatgaaccccttctgcatccccttctccatctccaacatgggcggcgccatgctggccatgg*

*acatcggcttcatgggccccaactactccatctccaccgcctgcgccaccggcaactactgcatcctgggcgccgccgaccacat*

*ccgccgcggcgacgccaacgtgatgctggccggcggcgccgacgccgccatcatcccctccggcatcggcggcttcatcgcctg*

*caaggccctgtccaagcgcaacgacgagcccgagcgcgcctcccgcccctgggacgccgaccgcgacggcttcgtgatgggc*

*gagggcgccggcgtgctggtgctggaggagctggagcacgccaagcgccgcggcgccaccatcctggccgagctggtgggcg*

-continued gcgccgccacctccgacgcccaccacatgaccgagcccgacccccagggccgcggcgtgcgcctgtgcctggagcgcgccct ggagcgcgcccgcctggcccccgagcgcgtgggctacgtgaacgcccacggcacctccacccccgccggcgacgtggccgag taccgcgccatccgcgccgtgatcccccaggactccctgcgcatcaactccaccaagtccatgatcggccacctgctgggcggcg ccggcgccgtggaggccgtggccgccatccaggccctgcgcaccggctggctgcaccccaacctgaacctggagaaccccgc ccccggcgtggaccccgtggtgctggtgggcccccgcaaggcgcgcgccgaggacctggacgtggtgctgtccaactccttcgg cttcggcggccacaactcctgcgtgatcttccgcaagtacgacgagatggactacaaggaccacgacggcgactacaaggacc acgacatcgactacaaggacgacgacgacaagTAGatcgatagatctcttaaggcagcagcagctcggatagtatcgacacac tctggacgctggtcgtgtgatggactgttgccgccacacttgctgccttgacctgtgaatatccctgccgcttttatcaaacagcctcagt gtgtttgatcttgtgtgtacgcgcttttgcgagttgctagctgcttgtgctatttgcgaataccacccccagcatccccttccctcgtttcatat cgcttgcatcccaaccgcaacttatctacgctgtcctgctatccctcagcgctgctcctgctcctgctcactgcccctcgcacagccttgg tttgggctccgcctgtattctcctggtactgcaacctgtaaaccagcactgcaatgctgatgcacgggaagtagtgggatgggaacaca aatggaaagcttaattaagagctcttgttttccagaaggagttgctccttgagcctttcattctcagcctcgataacctccaaagccgctcta attgtggaggggggttcgaagacagggtggttggctggatggggaaacgctggtcgcgggattcgatcctgctgcttatatcctcc ctggaagcacacccacgactctgaagaagaaaacgtgcacacacacaacccaaccggccgaatatttgcttccttatcccgg gtccaagagagactgcgatgcccccctcaatcagcatcctcctccctgccgcttcaatcttccctgcttgcctgcgcccgcggtg cgccgtctgcccgcccagtcagtcactcctgcacaggccccttgtgcgcagtgctcctgtaccctttaccgctccttccattctgc gaggcccccctattgaatgtattcgttgcctgtgtggccaagcgggctgctgggcgcgccgccgtcgggcagtgctcggcgactt tggcggaagccgattgttcttctgtaagccacgcgcttgctgctttgggaagagaaggggggggggtactgaatggatgaggag gagaaggaggggtattggtattatctgagttgggtgaagagc Southern blot analysis of Strain AS and Strain AZ indicated that both are PmFATA double knock-out mutants. Since the PmFAD2 disruption cassettes contain a *Carthamus tinctorius* putative oleoyl-specific ACP-thioesterase (CtOTE), the absence of the endogenous FATA genes seems to be fully complemented by the expression of the CtOTE.

To determine the impact of FATA1 inactivation and over expression of PmKASII gene on lipid composition in Δfad2 lines Strain D/Strain R, the primary transformants of D1266/Strain D and D1415/Strain R were clonally purified and grown under standard lipid production conditions at both pH5.0 and pH7.0. The resulting profiles from the transgenic line arising from transformation with pSZ2276 into Strain D are shown in Table 68, and transgenic lines arising from transformation with pSZ2441 into Strain R are shown in Table 69.

As can be seen from Table 68, in Strain AZ at pH7.0, the combination of full activity of PmKASII driven by AMT03 and FATA1 knock results in very low levels of C16:0 (2%). Meanwhile, the *Carthamus tinctorius* thioesterase is also activated since it is also driven by AMT03 promoter. We observe 7.8% C18:0 when Strain AZ is cultivated at pH7. At pH5.0, decrease of the C16:0 level is largely contributed by the FATA1 inactivation, although PmKASII can be partially activated since we run the seed culture at pH6.8. The stearic level of Strain AZ is low at pH5.0 due to the low expression of the *C. tinctorius* TE. Overall, the oleic levels of Strain AZ exceed 85% (around 88%) at both pH7.0 and pH5.0.

TABLE 68

Fatty acid profiles in S1331, S2530 and S4266 at both pH 5.0 and pH 7.0

| Strains | C16:0 | C18:0 | C18:1 | C18:2 | C20:1 |
|---|---|---|---|---|---|
| Strain A_pH 5 | 26.6 | 3.3 | 60.5 | 6.7 | 0.07 |
| Strain A_pH 7 | 28.3 | 4.1 | 58 | 6.5 | 0.06 |
| Strain D_pH 5 | 17 | 3.6 | 77.1 | 0.01 | 0.14 |
| Strain D_pH 7 | 19.5 | 5.3 | 72.6 | 0.01 | 0.09 |
| Strain AZ_pH 5 | 4.1 | 2.36 | 88.5 | 0.04 | 3.1 |
| Strain AZ_pH 7 | 2.1 | 7.8 | 87.9 | 0.01 | 0.5 |

In the transgenic line Strain AS, both CrTUB2 and PmUAPA1 promoters are pH unbiased, hence, as reported in Table 69, the lipid profile at pH5.0 and pH7.0 are essentially same. Relative to Strain AZ, Strain AS produces much less stearic acid. Although the palmitic level in Strain AS is bit higher than that in Strain AZ, the oleic level in Strain AS is above 90%, which is the highest level we observed in the shake flask experiment.

TABLE 69

Fatty acid profiles in S1331, S2532 and S5204 at both pH 5.0 and pH 7.0

| Strains | C16:0 | C18:0 | C18:1 | C18:2 |
|---|---|---|---|---|
| Strain A_pH 5 | 26.6 | 3.3 | 60.5 | 6.7 |
| Strain A_pH 7 | 28.3 | 4.1 | 58 | 6.5 |

TABLE 69-continued

Fatty acid profiles in S1331, S2532
and S5204 at both pH 5.0 and pH 7.0

| Strains | C16:0 | C18:0 | C18:1 | C18:2 |
|---|---|---|---|---|
| Strain R_pH 5 | 23.3 | 2.1 | 72.1 | 0.01 |
| Strain R_pH 7 | 23.4 | 2.3 | 71.9 | 0.01 |
| Strain AS_pH 5 | 5.5 | 1.4 | 91.5 | 0.01 |
| Strain AS_pH 7 | 5.6 | 1.6 | 91.3 | 0.01 |

Example 59: Complementation of FAD2 and FATA Knockout and KASII Overexpression Generates a Unique Oil with High C18-2 and Low C18-3 Levels As described in Example 58, Strain AS was generated by knocking both copies of PmFATA1 in a *Prototheca moriformis* strain while simultaneously overexpressing PmKASII gene into a Δfad2 line (Strain R). Strain R is a FAD2 (also known as FADc) knockout strain generated by insertion of a oleate-specific *C. tinctorius* acyl-ACP thioesterase (GenBank Accession No: AAA33019.1) into a high-lipid producing strain derived from UTEX 1435, under the control of CrTUB2 promoter at the FAD2 locus. Strain AS and its parent, Strain R, have a disrupted endogenous PmFAD2-1 gene resulting in no Δ12 specific desaturase activity manifested as 0% C18:2 (linoleic acid) levels in both nitrogen-rich seed and nitrogen-poor lipid production conditions. Lack of C18:2 in Stain AS (and its parent Strain R) resulted in growth defects which could be partially mitigated by exogenous addition of linoleic acid in the seed stage. However, for industrial applications, exogenous addition of linoleic acid is expensive. Complementation of Strain R (and a second Δfad2 strain) with PmFAD2-1 restored C18:2 levels back to wild type levels and also resulted in rescued growth characteristics during seed and lipid production without any linoleic supplementation.

In the present example we demonstrate that:
In trans expression of fatty acid desaturase-2 gene from *Prototheca moriformis* (PmFad2-1) under the control of a pH inducible PmAMT3 promoter results in functional complementation of PmFAD2-1 with restored growth and C18:2 levels in Δfad2, Δfata1 strain AS;
Complementation of Strain AS is conditional/inducible and occurs at pH 7.0 when the AMT3 promoter is actively driving the expression of PmFAD2-1 as opposed to pH 5.0 when the AMT3 promoter is inactive; and
Over expression of PmFAD2-1 at pH 7.0 results in strains with >20% C18:2 levels. The fatty acid profile of these high C18:2 strains mimic canola oil closely except that the new oil has 5 fold less C18:3 than the canola oil (10%). The elevated C18:2 levels are seen only in strains derived from Strain AS overexpressing PmFAD2-1 since overexpression of the same gene in wild-type (i.e., non-engineered) control Strain Z does not result in higher C18:2 levels.

Construct Used for the Expression of the *Prototheca moriformis* Fatty Acid Desaturase 2 (PmFAD2-1) in Δfad2 Strains Strain AS and Strain Z-[pSZ2721].

Δfad2 Δfata1 Strain AS and Strain Z were transformed with the construct pSZ2721. The sequence of the transforming DNA is provided below. Relevant restriction sites in the construct pSZ2721 (6S::CpACT-ScMEL1-CvNR::PmAMT3-PmFAD2-1-CvNR::6S) are indicated in lowercase, underlined and bold, and are from 5'-3' BspQ 1, KpnI, Xba I, Mfe I, BamH I, EcoR I, Spe I, Cla I, Sac I, BspQ I, respectively. BspQI sites delimit the 5' and 3' ends of the transforming DNA. Bold, lowercase sequences represent genomic DNA from UTEX 1435 that permits targeted integration of PmFAD2-1 at the 6S locus via homologous recombination. Proceeding in the 5' to 3' direction, the actin (ACT) gene promoter from UTEX 250 driving the expression of the *Saccharomyces cerevisiae* MEL1 gene is indicated by the boxed text. The Initiator ATG and terminator TGA for ScMEL1 are indicated by uppercase, bold italics while the coding region is indicated in lowercase italics. The *Chlorella vulgaris* nitrate reductase 3' UTR is indicated by lowercase underlined text followed by an endogenous AMT03 promoter of *Prototheca moriformis*, indicated by boxed italics text. The Initiator ATG and terminator TGA codons of the PmFAD2-1 are indicated by uppercase, bold italics, while the remainder of the gene is indicated by bold italics. The *C. vulgaris* nitrate reductase 3' UTR is again indicated by lowercase underlined text followed by the UTEX 1435 6S genomic region indicated by bold, lowercase text. The final construct was sequenced to ensure correct reading frames and targeting sequences.

Nucleotide sequence of transforming DNA contained in plasmid pSZ2721:

(SEQ ID NO: 120)

```
gctcttcggagtcactgtgccactgagttcgactggtagctgaatggagtcgctgctccactaaacgaattgtcagcaccgcca

gccggccgaggacccgagtcatagcgagggtagtagcgcgccatggcaccgaccagcctgcttgccagtactggcgtctcttc

cgcttctctgtggtcctctgcgcgctccagcgcgtgcgcttttccggtggatcatgcggtccgtggcgcaccgcagcggccgctg

cccatgcagcgccgctgcttccgaacagtggcggtcagggccgcaccgcggtagccgtccgtccggaacccgcccaagagt

tttgggagcagcttgagccctgcaagatggcggaggacaagcgcatcttcctggaggagcaccggtgcgtggaggtccgggg

ctgaccggccgtcgcattcaacgtaatcaatcgcatgatgatcagaggacacgaagtcttggtggcggtggccagaaacact

gtccattgcaagggcatagggatgcgttccttcacctctcatttctcatttctgaatccctccctgctcactctttctcctcctccttc

ccgttcacgcagcattcggggtaccagtttaggtccagcgtccgtgggggggggacgggctgggagcttgggccgggaagggcaa

gacgatgcagtccctctggggagtcacagccgactgtgtgtgttgcactgtgcggcccgcagcactcacacgcaaaatgcctggccg

acaggcaggccctgtccagtgcaacatccacggtccctctcatcaggctcaccttgctcattgacataacggaatgcgtaccgctctttc
```

-continued agatctgtccatccagagaggggagcaggctccccaccgacgctctcaaacttgcttcctgcccaaccgaaaacattattgtttgagg gggggggggggggggcagattgcatggcgggatatctcgtgaggaacatcactgggacactgtggaacacagtgagtgcagtatg cagagcatgtatgctaggggtcagcgcaggaaggggggcctttcccagtctcccatgccactgcaccgtatccacgactcaccaggac cagcttcttgatcggcttccgctcccgtggacaccagtgtgtagcctctggactccaggtatgcgtgcaccgcaaaggccagccgatc gtgccgattcctggggtggaggatatgagtcagccaacttggggctcagagtgcacactggggcacgatacgaaacaacatctacac cgtgtcctccatgctgacacaccacagcttcgctccacctgaatgtgggcgcatgggcccgaatcacagccaatgtcgctgctgccat aatgtgatccagaccctctccgcccagatgccgagcggatcgtgggcgctgaatagattcctgtttcgatcactgtttgggtcctttccttt tcgtctcggatgcgcgtctcgaaacaggctgcgtcgggctttcggatcccttttgctccctccgtcaccatcctgcgcgcgggcaagtt gcttgaccctgggctgtaccagggttggagggtattaccgcgtcaggccattcccagcccggattcaattcaaagtctgggccaccac cctccgccgctctgtctgatcactccacattcgtgcatacactacgttcaagtcctgatccaggcgtgtctcgggacaaggtgtgcttga gtttgaatctcaaggacccactccagcacagctgctggttgaccccgccctcgcaatctaga*ATG**ttcgcgttctacttcctgacggc*

*ctgcatctccctgaagggcgtgttcggcgtctccccctcctacaacggcctgggcctgacgccccagatgggctgggacaactgg*

*aacacgttcgcctgcgacgtctccgagcagctgctgctggacacggccgaccgcatctccgacctgggcctgaaggacatgggc*

*tacaagtacatcatcctggacgactgctggtcctccggccgcgactccgacggcttcctggtcgccgacgagcagaagttcccca*

*acggcatgggccacgtcgccgaccacctgcacaacaactccttcctgttcggcatgtactcctccgcgggcgagtacacgtgcgc*

*cggctaccccggctccctgggccgcgaggaggaggacgcccagttcttcgcgaacaaccgcgtggactacctgaagtacgaca*

*actgctacaacaagggccagttcggcacgcccgagatctcctaccaccgctacaaggccatgtccgacgccctgaacaagacg*

*ggccgccccatcttctactccctgtgcaactggggccaggacctgaccttctactggggctccggcatcgcgaactcctggcgcat*

*gtccggcgacgtcacggcggagttcacgcgccccgactcccgctgcccctgcgacggcgacgagtacgactgcaagtacgccg*

*gcttccactgctccatcatgaacatcctgaacaaggccgcccccatgggccagaacgcgggcgtcggcggctggaacgacctg*

*gacaacctggaggtcggcgtcggcaacctgacggacgacgaggagaaggcgcacttctccatgtgggccatggtgaagtcccc*

*cctgatcatcggcgcgaacgtgaacaacctgaaggcctcctcctactccatctactcccaggcgtccgtcatcgccatcaaccagg*

*actccaacggcatccccgccacgcgcgtctggcgctactacgtgtccgacacggacgagtacggccagggcgagatccagatg*

*tggtccggcccccctggacaacggcgaccaggtcgtggcgctgctgaacggcggctccgtgtcccgccccatgaacacgaccctg*

*gaggagatcttcttcgactccaaccttgggctccaagaagctgacctccacctgggacatctacgacctgtgggcgaaccgcgtcg*

*acaactccacggcgtccgccatcctgggccgcaacaagaccgccaccggcatcctgtacaacgccaccgagcagtcctacaag*

*gacggcctgtccaagaacgacacccgcctgttcggccagaagatcggctccctgtcccccaacgcgatcctgaacacgaccgtc*

*cccgcccacggcatcgcgttctaccgcctgcgcccctcctcc**TGA*caattggcagcagcagctcggatagtatcgacacactctg gacgctggtcgtgtgatggactgttgccgccacacttgctgccttgacctgtgaatatccctgccgcttttatcaaacagcctcagtgtgtt tgatcttgtgtgtacgcgcttttgcgagttgctagctgcttgtgctatttgcgaataccacccccagcatccccttccctcgtttcatatcgctt gcatcccaaccgcaacttatctacgctgtcctgctatccctcagcgctgctcctgctcctgctcactgcccctcgcacagccttggtttgg gctccgcctgtattctcctggtactgcaacctgtaaaccagcactgcaatgctgatgcacgggaagtagtgggatgggaacacaaatg gaggatcccgcgtctcgaacagagcgcgcagaggaacgctgaaggtctcgcctctgtcgcacctcagcgcggcatacaccacaat aaccacctgacgaatgcgcttggttcttcgtccattagcgaagcgtccggttcacacacgtgccacgttggcgaggtggcaggtgaca atgatcggtggagctgatggtcgaaacgttcacagcctagggatatcgaattc*ggccgacaggacgcgcgtcaaaggtgctggtc*

*gtgtatgccctggccggcaggtcgttgctgctgctggttagtgattccgcaaccctgattttggcgtcttattttggcgtggcaaacgct*

*ggcgcccgcgagccgggccggcggcgatgcggtgccccacggctgccggaatccaagggaggcaagagcgcccgggtcag*

-continued ttgaagggctttacgcgcaaggtacagccgctcctgcaaggctgcgtggtggaattggacgtgcaggtcctgctgaagttcctcca ccgcctcaccagcggacaaagcaccggtgtatcaggtccgtgtcatccactctaaagaactcgactacgacctactgatggccct agattcttcatcaaaaacgcctgagacacttgcccaggattgaaactccctgaagggaccaccaggggccctgagttgttccttcc ccccgtggcgagctgccagccaggctgtacctgtgatcgaggctggcgggaaaataggcttcgtgtgctcaggtcatgggaggt gcaggacagctcatgaaacgccaacaatcgcacaattcatgtcaagctaatcagctatttcctcttcacgagctgtaattgtcccaa aattctggtctaccgggggtgatccttcgtgtacgggcccttccctcaaccctaggtatgcgcgcatgcggtcgccgcgcaactcgc gcgagggccgagggtttgggacgggccgtcccgaaatgcagttgcacccggatgcgtggcacctttttttgcgataatttatgcaat ggactgctctgcaaaattctggctctgtcgccaaccctaggatcagcggcgtaggatttcgtaatcattcgtcctgatggggagcta ccgactaccctaatatcagcccgactgcctgacgccagcgtccacttttgtgcacacattccattcgtgcccaagacatttcattgtg gtgcgaagcgtccccagttacgctcacctgtttcccgacctccttactgttctgtcgacagagcgggcccacaggccggtcgcagc cactagtATGgccatcaagaccaaccgccagcccgtggagaagcccccccttcaccatcggcaccctgcgcaaggccatccc cgcccactgcttcgagcgctccgccctgcgctcctccatgtacctggccttcgacatcgccgtgatgtccctgctgtacgtggcctcc acctacatcgaccccgcccccgtgcccacctgggtgaagtacggcgtgatgtggcccctgtactggttcttccagggcgccttcgg caccggcgtgtgggtgtgcgcccacgagtgcggccaccaggccttctcctcctcccaggccatcaacgacggcgtgggcctggtg ttccactccctgctgctggtgccctactactcctggaagcactcccaccgccgccaccactccaacaccggctgcctggacaagga cgaggtgttcgtgcccccccaccgcgccgtggcccacgagggcctggagtgggaggagtggctgcccatccgcatgggcaagg tgctggtgaccctgaccctgggctggcccctgtacctgatgttcaacgtggcctcccgcccctacccccgcttcgccaaccacttcg acccctggtcccccatcttctccaagcgcgagcgcatcgaggtggtgatctccgacctggccctggtggccgtgctgtccggcctgt ccgtgctgggccgcaccatgggctgggcctggctggtgaagacctacgtggtgccctacctgatcgtgaacatgtggctggtgctg atcaccctgctgcagcacacccaccccgccctgccccactacttcgagaaggactgggactggctgcgcggcgccatggccacc gtggaccgctccatgggcccccccttcatggacaacatcctgcaccacatctccgacacccacgtgctgcaccacctgttctccac catcccccactaccacgccgaggaggcctccgccgccatccgccccatcctgggcaagtactaccagtccgactcccgctgggt gggccgcgccctgtgggaggactggcgcgactgccgctacgtggtgcccgacgcccccgaggacgactccgccctgtggttcca caagTAGatcgatagatctcttaaggcagcagcagctcggatagtatcgacacactctggacgctggtcgtgtgatggactgttgc cgccacacttgctgccttgacctgtgaatatccctgccgcttttatcaaacagcctcagtgtgtttgatcttgtgtgtacgcgcttttgcgagt tgctagctgcttgtgctatttgcgaataccacccccagcatccccttccctcgtttcatatcgcttgcatcccaaccgcaacttatctacgct gtcctgctatccctcagcgctgctcctgctcctgctcactgcccctcgcacagccttggtttgggctccgcctgtattctcctggtactgca acctgtaaaccagcactgcaatgctgatgcacgggaagtagtgggatgggaacacaaatggaaagcttaattaagagctcttgttttcc agaaggagttgctccttgagcctttcattctcagcctcgataacctccaaagccgctctaattgtggaggggggttcgaagacagggtgg ttggctggatggggaaacgctggtcgcgggattcgatcctgctgcttatatcctccctggaagcacacccacgactctgaagaa gaaaacgtgcacacacacaacccaaccggccgaatatttgcttccttatcccgggtccaagagagactgcgatgccccccctca atcagcatcctcctccctgccgcttcaatcttccctgcttgcctgcgcccgcggtgcgccgtctgcccgcccagtcagtcactcct gcacaggccccttgtgcgcagtgctcctgtaccctttaccgctccttccattctgcgaggccccctattgaatgtattcgttgcctg tgtggccaagcgggctgctgggcgcgccgccgtcgggcagtgctcggcgactttggcggaagccgattgttcttctgtaagcc acgcgcttgctgctttgggaagagaaggggggggtactgaatggatgaggaggagaaggaggggtattggtattatctgag ttgggtgaagagc To determine its impact on growth and fatty acid profiles, the above construct was transformed independently into a Δfad2 Δfata1 Strain AS or wild type Strain Z. Primary transformants were clonally purified and grown under low-nitrogen lipid production conditions at pH7.0 (AMT3 promoter active) and pH5.0 (AMT3 promoter inactive) for Strain AS transformants or at pH7.0 for Strain Z transformants. The resulting profiles from a set of representative clones arising from transformations are shown in Tables 70-73 respectively.

Expression of endogenous PmFad2-1 driven by AMT3 promoter at pH 7.0, in Strain AS resulted in Δ12 specific desaturase activity with complete restoration of C18:2 fatty acid levels of the base strain A (Table 70). No such Δ12 specific desaturase activity and thus no significant C18:2 restoration is detected when the lipid production is run at pH 5.0 when the AMT3 promoter is inactive (Table 71).

Interestingly, lipid production in complemented Strain AS strains at pH 7.0 results in several strains with 2 fold or more increase in C18:2 levels. The resulting strains produce an oil profile that is similar to Canola oil except that the new oil has less C18:3 levels than the commercially available canola oil (Table 72). The increase in C18:2 is not seen in wild type (Strain Z) strains transformed with the same AMT3 driven PmFAD2-1.

While we have seen other strains with high C18:2 levels, all of them were associated with growth defects in seed as well as lipid production media. Here, however, we have been able to increase the C18:2 levels in a targeted manner without any detrimental effect on the growth of resulting strains. While Δfad2 strain R and Δfad2 Δfata1 strain AS grow very poorly and hardly reach an OD750 of 10-20 in 42 hours, complemented Strain AS (D1673) lines grow very rapidly in the same time span and reach OD750 between 50-80.

Thus, it can be seen that we were able to produce cell oils with fatty acid profiles of less than 10% linolenic acid yet >20% linoleic acid (indeed we achieved <2% linolenic acid and >20% linoleic acid). It is surprising that C18:2 levels are elevated only in Strain AS, which has almost 90% C18:1 levels as compared to Strain Z with only 57% C18:1 levels, suggests excess availability of substrate C18:1 in the ER is a key to boost C18:2 levels. Since *Prototheca* has evolved to utilize C18:1 onto TAGS very efficiently, in wild type situations most likely the substrate leaves the ER very rapidly before being further desaturated by FAD2 enzymes. This limitation may be overcome in strains like Strain AS with very high C18:1 levels that likely stays available for desaturation by PmFAD2-1.

TABLE 70

Fatty acid profile in representative complemented (D1673) and parent Strain AS lines at pH 7.0 transformed with pSZ2721 (PmFAD2-1) DNA.

| Sample ID | C14:0 | C16:0 | C18:0 | C18:1 | C18:2 | C18:3a |
|---|---|---|---|---|---|---|
| AS; T533; D1673-16; pH 7.0 | 0.49 | 6.33 | 2.44 | 66.53 | 21.36 | 1.38 |
| AS T533; D1673-17; pH 7.0 | 0.44 | 6.02 | 2.25 | 68.97 | 19.53 | 1.36 |
| AS; T533; D1673-02; pH 7.0 | 0.38 | 5.92 | 2.30 | 71.01 | 17.77 | 1.30 |
| AS; T533; D1673-03; pH 7.0 | 0.38 | 5.83 | 2.31 | 71.31 | 17.45 | 1.29 |
| AS; T533; D1673-10; pH 7.0 | 0.38 | 5.63 | 2.21 | 71.72 | 17.37 | 1.23 |
| AS; pH 7.0 | 0.30 | 5.59 | 1.63 | 90.88 | 0.10 | 0.00 |
| AT; pH 7.0 | 1.34 | 27.99 | 3.54 | 55.48 | 9.07 | 0.79 |

TABLE 71

Fatty acid profile in same representative complemented (D1673) and parent Strain AS lines at pH 5.0 transformed with pSZ2721 (PmFAD2-1) DNA.

| Sample ID | C14:0 | C16:0 | C18:0 | C18:1 | C18:2 | C18:3a |
|---|---|---|---|---|---|---|
| AS; T533; D1673-16; pH 5.0 | 0.47 | 5.16 | 1.76 | 90.94 | 0.06 | 0.18 |
| AS; T533; D1673-17; pH 5.0 | 0.45 | 4.97 | 1.72 | 91.32 | 0.05 | 0.00 |
| AS; T533; D1673-2; pH 5.0 | 0.46 | 5.20 | 1.75 | 90.94 | 0.05 | 0.18 |
| AS; T533; D1673-3; pH 5.0 | 0.41 | 4.93 | 1.65 | 89.92 | 1.56 | 0.16 |
| AS; T533; D1673-10; pH 5.0 | 0.45 | 4.97 | 1.69 | 89.96 | 1.35 | 0.16 |
| AS; pH 5.0 | 0.39 | 5.67 | 1.36 | 91.13 | 0.00 | 0.00 |
| AT; pH 5.0 | 1.03 | 24.69 | 3.30 | 63.47 | 5.80 | 0.38 |

TABLE 72

Fatty acid profile of a stable D1673 line along with base strain Z and Canola oil.

| Sample ID | C16:0 | C18:0 | C18:1 | C18:2 | C18:3α | C20:1 |
|---|---|---|---|---|---|---|
| pH5 Strain Z | 27.54 | 3.29 | 57.91 | 7.17 | 0.59 | 0.10 |
| pH7 Strain Z | 27.92 | 3.09 | 58.30 | 6.71 | 0.59 | 0.07 |
| pH7; AS; T533; D1673.5.2-1 | 4.43 | 1.31 | 70.32 | 20.30 | 1.72 | 0.75 |
| pH7; AS; T533; D1673.5.2-2 | 4.55 | 1.26 | 67.53 | 22.17 | 1.82 | 1.22 |
| pH7; AS; T533; D1673.5.2-3 | 4.34 | 1.29 | 69.51 | 20.78 | 1.65 | 1.01 |
| pH7; AS; T533; D1673.5.2-4 | 4.81 | 1.26 | 68.08 | 21.53 | 1.77 | 1.06 |
| pH7; AS; T533; D1673.5.2-5 | 4.61 | 1.30 | 68.02 | 21.57 | 1.74 | 1.17 |
| pH7; AS; T533; D1673.5.2-6 | 4.36 | 1.30 | 68.88 | 21.16 | 1.68 | 1.10 |
| pH7; AS; T533; D1673.5.2-7 | 4.38 | 1.28 | 69.30 | 21.08 | 1.70 | 0.97 |

TABLE 72-continued

Fatty acid profile of a stable D1673 line along with base strain Z and Canola oil.

| Sample ID | C16:0 | C18:0 | C18:1 | C18:2 | C18:3α | C20:1 |
|---|---|---|---|---|---|---|
| pH7; AS; T533; D1673.5.2-8 | 4.87 | 1.27 | 68.44 | 20.87 | 1.83 | 1.14 |
| Canola Oil | 4.00 | 2.00 | 62.00 | 22.00 | 10.00 | 1.00 |

TABLE 73

Fatty acid profile in Strain Z at pH 5.0 and pH 7.0 and representative derivative transgenic lines at pH 7.0 transformed with pSZ2721 (PmFAD2-1) DNA. The lines are sorted by C18:2 levels.

| Sample ID | C14:0 | C16:0 | C18:0 | C18:1 | C18:2 | C18:3a |
|---|---|---|---|---|---|---|
| Z; T573; D1791-23; pH 7.0 | 1.45 | 29.96 | 3.28 | 54.72 | 7.99 | 0.66 |
| Z; T573; D1791-6; pH 7.0 | 1.73 | 30.25 | 2.48 | 55.01 | 7.74 | 0.69 |
| Z; T573; D1791-17; pH 7.0 | 1.41 | 29.00 | 3.42 | 55.77 | 7.64 | 0.68 |
| Z; T573; D1791-14; pH 7.0 | 1.48 | 29.82 | 3.45 | 55.22 | 7.56 | 0.67 |
| Z; T573; D1791-8; pH 7.0 | 2.30 | 37.15 | 2.54 | 47.62 | 7.44 | 0.67 |
| Z; T573; D1791-2; pH 7.0 | 1.38 | 29.29 | 3.45 | 56.10 | 7.12 | 0.63 |
| Z; T573; D1791-10; pH 7.0 | 1.46 | 29.30 | 3.39 | 56.16 | 7.11 | 0.60 |
| Z; T573; D1791-5; pH 7.0 | 1.45 | 29.45 | 3.36 | 56.15 | 7.02 | 0.61 |
| Z; T573; D1791-11; pH 7.0 | 1.43 | 29.52 | 3.44 | 55.99 | 7.01 | 0.60 |
| Z; T573; D1791-13; pH 7.0 | 1.41 | 28.96 | 3.46 | 56.47 | 7.01 | 0.62 |
| Z; pH 7.0 | 1.41 | 27.76 | 3.45 | 57.71 | 7.17 | 0.58 |
| Z; pH 5.0 | 1.49 | 28.19 | 3.27 | 58.04 | 6.65 | 0.57 |

Example 60: Combinatorial Expression of Mid-Chain Thioesterases and Ketoacyl Synthases to Generate Oils with Highly Elevated and Balanced C10:0 and C12:0 Fatty Acid Levels In this example we describe two molecular approaches to generate oils with highly elevated and balanced C10:0 and C12:0 fatty acids in a classically mutagenized high-oil-yielding derivative of UTEX 1435, Strain BA. Resulting transgenic strains co-express two distinct mid-chain specific thioesterases, the broad specificity C10:0-C14:0 *Cuphea wrightii* FATB2 thioesterase (expressed in Stain BA), and predominantly C10:0-specific *Cuphea hookeriana* FATB2 thioesterase (part of incoming vectors). In addition, D1550 transformants express *C. wrightii* KASIV elongase gene integrated at a neutral genomic site, Thi4b, (vector pSZ2424), while D1681 transformants—*C. wrightii* KASAI elongase as a part of an endogenous KASI disruption cassette (vector pSZ2746). The use of different KASI activities of plant origin in combination with the exogenous thioesterases resulted in a significant increase in overall C10-C12 levels as well as improved C10:0 specificity of the *C. hookeriana* thioesterase. The best strain synthesized about 85% total C10:0-C12:0 fatty acids with balanced levels of about 42% C10:0 and ca. 44% C12:0 fatty acids, respectively, less than 4% C14:0, and less than 1.5% C8:0. The results show that selection of FATB and KAS genes can give rise to an oil with at least 50% total saturates with capric and lauric acids balanced to within 20% (or even to within 15%, or 10%).

Relevant restriction sites in pSZ2424 are indicated in lowercase, bold and underlining text and are 5'-3' Pme I, Kpn I, Xba I, Mfe I, Eco RI, Spe I, Xho I, Hind III, SnaBI, Spe I, Asc I, Xho I, Eco RI, Sac I, BspQI, respectively. Pme I and BspQI sites delimit the 5' and 3' ends of the transforming DNA. Bold, lowercase sequences represent genomic DNA from UTEX1435 that permit targeted integration at Thi4b locus via homologous recombination. Proceeding in the 5' to 3' direction, the *C. reinhardtii* B-tubulin promoter driving the expression of the neomycin phosphotransferase gene (NeoR, conferring the ability of cells to grow on G418) is indicated by boxed text. The initiator ATG and terminator TGA for NeoR are indicated by uppercase, bold italics while the coding region is indicated in lowercase italics. The *Chlorella vulgaris* nitrate reductase 3' UTR is indicated by lowercase underlined text. Next is the Amt03 promoter of *Prototheca moriformis* indicated by boxed lowercase text driving the expression of *Cuphea hookeriana* KASIV gene (ChKASIV) indicated in lowercase italics. The initiator ATG and terminator TGA for ChKASIV are indicated by uppercase, bold italics. The *Chlorella vulgaris* nitrate reductase 3' UTR is indicated by lowercase underlined text. Next is the Amt03 promoter of *Prototheca moriformis* indicated by boxed lowercase text driving the expression of *Cuphea hookeriana* FATB2 gene (ChFATB2) fused to plastid transit peptide sequence derived from *Prototheca moriformis* FAD gene indicated in lowercase italics. The initiator ATG and terminator TGA for ChFATB2 are indicated by uppercase, bold italics. The *C. vulgaris* nitrate reductase 3' UTR is again indicated by lowercase underlined text followed by the UTEX1435 Thi4b flanking sequence.

>pSZ2424 [Thi4b::CrTUB2-NeoR-CvNR:PmAmt03-ChKASIV-CvNR:PmAMT03-ChTE2-CvNR::Thi4b]. Nucleotide sequence of transforming DNA contained in pSZ2424:

(SEQ ID NO: 121)

<u>gtttaaac</u>ccctcaactgcgacgctgggaaccttctccgggcaggcgatgtgcgtgggtttgcctccttggcacggctctacacc ttcgagtacgccatgaggcggtgatggctgtggctgtgccccacttcgtccagggacggcaagtccatcatctgcatgcttggt

-continued gcgacgctacagcagtccctctgcagcagaggagcacgactttggccatttcacgcactcgagtgtacacaattcatttttctta aagtaaatgactgctgattgaccagatgctgtaacgctgatttcgctccagatcgcacagtcacagattgcgaccatgttgctg cgtctgaaaatctggattccgaattcgaccctggcgctccatccatgcaacagatggcgacacttgttacaattcctgtcgccca tcggcatggagcaggtccacttagatccccgatcacccacgcgcatctcgctaatagtcattcattcgtgtcttcgatcaaagtc aggtgagtatgcatggatcttggttgacgatgcggtatgggtttgcgccgctgactgcagggtctgtccaaggcaagccaaccc agctcctctcctcgacaatactctcgcagacaaagccagccacttgccatccagattgccaataaactcaatcatggcttctgtc atgccatccatgggtctgatgaatggtcacgctcgtgtcctgaccgttccccagcctctggcgtcccctgccccgcccaccagcc cacgccgcgcggcagtcgctgccaaggctgtctcggaggtaccctttcttgcgctatgacacttccagcaaaaggtagggcgggct gcgagacggcttcccggcgctgcatgcaacaccgatgatgcttcgacccccgaagctccttcggggctgcatgggcgctccgatg ccgctccagggcgagcgctgtttaaatagccaggcccccgattgcaaagacattatagcgagctaccaaagccatattcaaacaccta gatcactaccacttctacacaggccactcgagcttgtgatcgcactccgctaagggggcgcctcttcctcttcgtttcagtcacaacccg caaactctagaatatca*ATG**atcgagcaggacggcctccacgccggctcccccgccgcctgggtggagcgcctgttcggctac*

*gactgggcccagcagaccatcggctgctccgacgccgccgtgttccgcctgtccgcccagggccgccccgtgctgttcgtgaaga*

*ccgacctgtccggcgccctgaacgagctgcaggacgaggccgcccgcctgtcctggctggccaccaccggcgtgccctgcgcc*

*gccgtgctggacgtggtgaccgaggccggccgcgactggctgctgctgggcgaggtgcccggccaggacctgctgtcctcccac*

*ctggcccccgccgagaaggtgtccatcatggccgacgccatgcgccgcctgcacaccctggaccccgccacctgccccttcgac*

*caccaggccaagcaccgcatcgagcgcgcccgcacccgcatggaggccggcctggtggaccaggacgacctggacgagga*

*gcaccagggcctggcccccgccgagctgttcgcccgcctgaaggcccgcatgcccgacggcgaggacctggtggtgacccacg*

*gcgacgcctgcctgcccaacatcatggtggagaacggccgcttctccggcttcatcgactgcggccgcctgggcgttggccgaccg*

*ctaccaggacatcgcctggccacccgcgacatcgccgaggagctgggcggcgagtgggccgaccgcttcctggtgctgtacg*

*gcatcgccgcccccgactcccagcgcatcgccttctaccgcctgctggacgagttcttc**TGA*caattggcagcagcagctcggat agtatcgacacactctggacgctggtcgtgtgatggactgttgccgccacacttgctgccttgacctgtgaatatccctgccgcttttatca aacagcctcagtgtgtttgatcttgtgtgtacgcgcttttgcgagttgctagctgcttgtgctatttgcgaataccacccccagcatccccctt ccctcgtttcatatcgcttgcatcccaaccgcaacttatctacgctgtcctgctatccctcagcgctgctcctgctcctgctcactgcccctc gcacagccttggtttgggctccgcctgtattctcctggtactgcaacctgtaaaccagcactgcaatgctgatgcacgggaagtagtgg gatgggaacacaaatggaaagctgtatagggataagaattcggccgacaggacgcgcgtcaaaggtgctggtcgtgtatgccctgg ccggcaggtcgttgctgctgctggttagtgattccgcaaccctgattttggcgtcttattttggcgtggcaaacgctggcgcccgcgagc cgggccggcggcgatgcggtgccccacggctgccggaatccaagggaggcaagagcgcccgggtcagttgaagggctttacgc gcaaggtacagccgctcctgcaaggctgcgtggtggaattggacgtgcaggtcctgctgaagttcctccaccgcctcaccagcggac aaagcaccggtgtatcaggtccgtgtcatccactctaaagaactcgactacgacctactgatggccctagattcttcatcaaaaacgcct gagacacttgcccaggattgaaactccctgaagggaccaccaggggccctgagttgttccttcccccgtggcgagctgccagccag gctgtacctgtgatcgaggctggcgggaaaataggcttcgtgtgctcaggtcatgggaggtgcaggacagctcatgaaacgccaaca atcgcacaattcatgtcaagctaatcagctatttcctcttcacgagctgtaattgtcccaaaattctggtctaccgggggtgatccttcgtgt acgggcccttccctcaaccctaggtatgcgcgcatgcggtcgccgcgcaactcgcgcgagggccgagggtttgggacgggccgtc ccgaaatgcagttgcacccggatgcgtggcacctttttttgcgataatttatgcaatggactgctctgcaaaattctggctctgtcgccaac cctaggatcagcggcgtaggatttcgtaatcattcgtcctgatggggagctaccgactaccctaatatcagcccgactgcctgacgcca -continued gcgtccacttttgtgcacacattccattcgtgcccaagacatttcattgtggtgcgaagcgtccccagttacgctcacctgtttcccgacct ccttactgttctgtcgacagagcgggcccacaggccggtcgcagccactagtgcgaccgccagctgc*ATG**gtggcgtcgcccttc*

*tgcacctggctggtcgccgcgtgcatgcccacctccagcgacaacgacccccgctcgctgtcccacaagcgcctgcgcctgagc*

*cgccgccgccgcacctgagctcgcactgctccctgcgcggcagcaccttccagtgcctggacccctgcaaccagcagcgcttcc*

*tgggcgacaacggcttcgcgtcgctgttcggctccaagcccctgcgcagcaaccgcggccacctgcgcctgggccgcacctcgc*

*actccggcgaggtgatggccgtcgcgatggcagcccgcccaggaggtgagcaccaacaagaagcccgcgaccaagcagcgcc*

*gcgtggtcgtgaccggcatgggcgtcgtgacccccctgggccacgaccccgacgtgtattataacaacctgctggacggcatctc*

*gggcatctccgagatcgagaacttcgactgcagccagttccccacccgcatcgccggcgagatcaagtcgttctccaccgacggc*

*tgggtcgcgcccaagttcagcgagcgcatggacaagttcatgctgtatatgctgaccgccggcaagaaggcgctggccgacggc*

*ggcatcaccgaggacgcgatgaaggagctgaacaagcgcaagtgcggcgtgctgatcggctcgggcctgggcggcatgaag*

*gtcttctccgacagcatcgaggccctgcgcacctcgtataagaagatctccccettctgcgtgcccttcagcaccaccaacatgggc*

*tcggcgatcctggcgatggacctgggctggatgggccccaactattccatcagcaccgcgtgcgccacctcgaacttctgcatcct*

*gaacgcggccaaccacatcatcaagggcgaggcggacatgatgctgtgcggcggctccgacgccgcggtgctgcccgtcggc*

*ctgggcggcttcgtggcctgccgcgcgctgagccagcgcaacaacgaccccaccaaggcctcgcgcccctgggactccaaccg*

*cgacggcttcgtcatgggcgagggcgcgggcgtgctgctgctggaggagctggagcacgccaagaagcgcggcgcgaccatc*

*tatgccgagttcctgggcggcagcttcacctgcgacgcgtatcacatgaccgagccccaccccgagggcgccggcgtcatcctgt*

*gcatcgagaaggcgctggcccagtcgggcgtgtcccgcgaggacgtgaactatatcaacgcgcacgccaccagcacccccgc*

*gggcgacatcaaggagtatcaggccctggcgcactgcttcggccagaactcggagctgcgcgtcaactccaccaagagcatga*

*tcggccacctgctgggcggcgccggcggcgtggaggcggtcgccgtggtccaggcgatccgcaccggctggatccaccccaac*

*atcaacctggaggaccccgacgagggcgtggacgccaagctgctggtcggccccaagaaggagaagctgaaggtgaaggtc*

*ggcctgtcgaactccttcggcttcggcggccacaacagctcgatcctgttcgcgccctgcaac**TGA*ctcgaggcagcagcagct cggatagtatcgacacactctggacgctggtcgtgtgatggactgttgccgccacacttgctgccttgacctgtgaatatccctgccgctt ttatcaaacagcctcagtgtgtttgatcttgtgtgtacgcgcttttgcgagttgctagctgcttgtgctatttgcgaataccacccccagcatc cccttccctcgtttcatatcgcttgcatcccaaccgcaacttatctacgctgtcctgctatccctcagcgctgctcctgctcctgctcactgc ccctcgcacagccttggtttgggctccgcctgtattctcctggtactgcaacctgtaaaccagcactgcaatgctgatgcagggaagta gtgggatgggaacacaaatggaaagcttcacatacgtaggccgacaggacgcgcgtcaaaggtgctggtcgtgtatgccctggcc ggcaggtcgttgctgctgctggttagtgattccgcaaccctgattttggcgtcttattttggcgtggcaaacgctggcgcccgcgagccg ggccggcggcgatgcggtgccccacggctgccggaatccaagggaggcaagagcgcccgggtcagttgaagggctttacgcgca aggtacagccgctcctgcaaggctgcgtggtggaattggacgtgcaggtcctgctgaagttcctccaccgcctcaccagcggacaaa gcaccggtgtatcaggtccgtgtcatccactctaaagaactcgactacgacctactgatggccctagattcttcatcaaaaacgcctgag acacttgcccaggattgaaactccctgaagggaccaccaggggccctgagttgttccttcccccgtggcgagctgccagccaggct gtacctgtgatcgaggctggcgggaaaataggcttcgtgtgctcaggtcatgggaggtgcaggacagctcatgaaacgccaacaatc gcacaattcatgtcaagctaatcagctatttcctcttcacgagctgtaattgtcccaaaattctggtctaccgggggtgatccttcgtgtacg ggcccttccctcaaccctaggtatgcgcgcatgcggtcgccgcgcaactcgcgcgagggccgagggtttgggacgggccgtcccg aaatgcagttgcacccggatgcgtggcacctttttttgcgataatttatgcaatggactgctctgcaaaattctggctctgtcgccaaccta ggatcagcggcgtaggatttcgtaatcattcgtcctgatggggagctaccgactaccctaatatcagcccgactgcctgacgccagcgt ccacttttgtgcacacattccattcgtgcccaagacatttcattgtggtgcgaagcgtccccagttacgctcacctgtttcccgacctcctta -continued ctgttctgtcgacagagcgggcccacaggccggtcgcagccactagtATGgctatcaagacgaacaggcagcctgtggagaa gcctccgttcacgatcgggacgctgcgcaaggccatccccgcgcactgtttcgagcgctcggcgcttcgtgggcgcgcccagctg cccgactggagccgcctgctgaccgccatcaccaccgtgttcgtgaagtccaagcgccccgacatgcacgaccgcaagtccaa gcgccccgacatgctggtggacagcttcggcctggagtccaccgtgcaggacggcctggtgttccgccagtccttctccatccgct cctacgagatcggcaccgaccgcaccgccagcatcgagaccctgatgaaccacctgcaggagacctccctgaaccactgcaa gagcaccggcatcctgctggacggcttcggccgcaccctggagatgtgcaagcgcgacctgatctgggtggtgattaagatgca gatcaaggtgaaccgctaccccgcctggggcgacaccgtggagatcaacacccgcttcagccgcctgggcaagatcggcatgg gccgcgactggctgatctccgactgcaacaccggcgagatcctggtgcgcgccaccagcgcctacgccatgatgaaccagaag acccgccgcctgtccaagctgccctacgaggtgcaccaggagatcgtgcccctgttcgtggacagccccgtgatcgaggactccg acctgaaggtgcacaagttcaaggtgaagaccggcgacagcatccagaagggcctgacccccggctggaacgacctggacgt gaaccagcacgtgtccaacgtgaagtacatcggctggatcctggagagcatgcccaccgaggtgctggagacccaggagctgt gctccctggccctggagtaccgccgcgagtgcggccgcgactccgtgctggagagcgtgaccgccatggaccccagcaaggtg ggcgtgcgctcccagtaccagcacctgctgcgcctggaggacggcaccgccatcgtgaacggcgccaccgagtggcgcccca agaacgccggcgccaacggcgccatctccaccggcaagaccagcaacggcaatccgtgtccatggactacaaggaccacg acggcgactacaaggaccacgacatcgactacaaggacgacgacgacaagTGActcgaggcagcagcagctcggatagta tcgacacactctggacgctggtcgtgtgatggactgttgccgccacacttgctgccttgacctgtgaatatccctgccgcttttatcaaac agcctcagtgtgtttgatcttgtgtgtacgcgcttttgcgagttgctagctgcttgtgctatttgcgaataccacccccagcatccccttccct cgtttcatatcgcttgcatcccaaccgcaacttatctacgctgtcctgctatccctcagcgctgctcctgctcctgctcactgcccctcgca cagccttggtttgggctccgcctgtattctcctggtactgcaacctgtaaaccagcactgcaatgctgatgcacgggaagtagtgggatg ggaacacaaatggaaagctgtagaattctccagagctccagcgccatgccacgccttttgatggcttcaagtacgataacggtgt tggattgtgcgtttgttgcgtagtgtgcatggcttagaataatgcagttggatttcttgctcacggcaatgtcggcttgtccgcag gttcaaccccatttcggagtctcaggtcagccgcgcaatgaccagccgctacttcaaggacttgcacgacaacgccgaggtga gctatgtttaggccttgagtgaaaattgtcgtcgaagcatattcgcgctccgcgatagcatccaagcaaaatgtcaagtgcgttc cgatttgcgtccgcaggtcgatgttgtgatcgtcggtgccggatccgccggtctgtcctgcgcttacgagctgaccaagcacccc gacgtccgggtacgcgagctgagattcgattggacataaactgaaaatgaaatcttttggagaaatgtaagggtctcaagcgg tgctcgattgcaagaaattggtcgtcccccactccgcaggtcgccatcatcgagcagggcgttgcacctggtggcggcgcctg gctgggggacagctgttctcggccatgtgtgtacgtagaagggtggatttcggatggtttcgttgcacagctgtttgtcaatga tttgtcttagactattgccgatgtttctaaatgttttaggagctatgatatgtctgcaggcgactgaagagc Relevant restriction sites in pSZ2746 are indicated in lowercase, bold and underlining text and are 5'-3' BspQ 1, Kpn I, Xba I, Mfe I, Hind III, AscI, Spe I, Xho I, Eco RI, Nde I, Sna BI, Xho I, Hind III, Sac I, BspQ I, respectively. BspQI sites delimit the 5' and 3' ends of the transforming DNA. Bold, lowercase sequences represent genomic DNA from UTEX1435 that permit targeted integration (and knockout) at the KASI locus via homologous recombination. Proceeding in the 5' to 3' direction, the *C. reinhardtii* B-tubulin promoter driving the expression of the neomycin phosphotransferase gene (NeoR, conferring the ability of cells to grow on G418) is indicated by boxed text. The initiator ATG and terminator TGA for NeoR are indicated by uppercase, bold italics while the coding region is indicated in lowercase italics. The *Chlorella vulgaris* nitrate reductase 3' UTR is indicated by lowercase underlined text. Next is the UAPA1 promoter of *Prototheca moriformis* indicated by boxed lowercase text driving the expression of *Cuphea hookeriana* FATB2 gene (ChFATB2) fused to plastid transit peptide sequence derived from *Prototheca moriformis* FAD gene indicated in lowercase italics. The initiator ATG and terminator TGA for ChFATB2 are indicated by uppercase, bold italics. The *B. braunii* cd191 3'UTR is indicated by lowercase underlined text. Next is the Amt03 promoter of *Prototheca moriformis* indicated by boxed lowercase text driving the expression of *Cuphea wrightii* KASAI gene indicated by lowercase italics fused to *Prototheca moriformis* SAD1 plastid transit peptide sequence. The *C. wrightii* KASAI sequence is in lowercase italics and is delineated by initiator ATG and terminator TGA. The *C. vulgaris* nitrate reductase 3' UTR is again indicated by lowercase underlined text followed by the UTEX1435 KASI flanking sequence.

>pSZ2746 [KASI-1::CrTUB2-NeoR-CvNR:PmUAPA1-ChFATB2-Bbcd181:PmAmt03-PmSADtp-CwKASA1-CvNR::KasI-1]. Nucleotide sequence of transforming DNA contained in pSZ2746:

(SEQ ID NO: 122)

gctcttcgctcaccgcgtgaattgctgtcccaaacgtaagcatcatcgtggctcggtcacgcgatcctggatccggggatccta gaccgctggtggagagcgctgccgtcggattggtggcaagtaagattgcgcaggttggcgaagggagagaccaaaaccgga ggctggaagcgggcacaacatcgtattattgcgtatagtagagcagtggcagtcgcatttcgaggtccgcaacggatctcgca agctcgctacgctcacagtaggagaaaggggaccactgcccctgccagaatggtcgcgaccctctccctcgccggccccgcct gcaacacgcagtgcgtatccggcaagcgggctgtcgccttcaaccgcccccatgttggcgtccgggctcgatcaggtgcgctg aggggggtttggtgtgcccgcgcctctgggcccgtgtcggccgtgcggacgtggggccctgggcagtggatcagcagggtttg cgtgcaaatgcctataccggcgattgaatagcgatgaacgggatacggttgcgctcactccatgcccatgcgaccccgtttctg tccgccagccgtggtcgcccgggctgcgaagcgggaccccacccagcgcattgtgatcaccggaatgggcgtggggtaccct ttcttgcgctatgacacttccagcaaaaggtagggcgggctgcgagacggcttcccggcgctgcatgcaacaccgatgatgcttcgac cccccgaagctccttcggggctgcatgggcgctccgatgccgctccagggcgagcgctgtttaaatagccaggcccccgattgcaa agacattatagcgagctaccaaagccatattcaaacacctagatcactaccacttctacacaggccactcgagcttgtgatcgcactcc gctaagggggcgcctcttcctcttcgtttcagtcacaacccgcaaactctagaatatca*ATG**atcgagcaggacggcctccacgcc*

*ggctcccccgccgcctgggtggagcgcctgttcggctacgactgggcccagcagaccatcggctgctccgacgccgccgtgttcc*

*gcctgtccgcccagggccgccccgtgctgttcgtgaagaccgacctgtccggcgccctgaacgagctgcaggacgaggccgcc*

*cgcctgtcctggctggccaccaccggcgtgccctgcgccgccgtgctggacgtggtgaccgaggccggccgcgactggctgctg*

*ctgggcgaggtgcccggccaggacctgctgtcctcccacctggcccccgccgagaaggtgtccatcatggccgacgccatgcgc*

*cgcctgcacaccctggacccegccacctgccccttcgaccaccaggccaagcaccgcatcgagcgcgcccgcacccgcatgga*

*ggccggcctggtggaccaggacgacctggacgaggagcaccagggcctggcccccgccgagctgttcgcccgcctgaaggcc*

*cgcatgcccgacggcgaggacctggtggtgacccacggcgacgcctgcctgcccaacatcatggtggagaacggccgcttctcc*

*ggcttcatcgactgcggccgcctgggcgtggccgaccgctaccaggacatcgccctggccacccgcgacatcgccgaggagct*

*gggcggcgagtgggccgaccgcttcctggtgctgtacggcatcgccgcccccgactcccagcgcatcgccttctaccgcctgctg*

*gacgagttcttc**TGA*caattggcagcagcagctcggatagtatcggacacactctggacgctggtcgtgtgatggactgttgccgcc acacttgctgccttgacctgtgaatatccctgccgcttttatcaaacagcctcagtgtgtttgatcttgtgtgtacgcgcttttgcgagttgct agctgcttgtgctatttgcgaataccacccccagcatccccttccctcgtttcatatcgcttgcatcccaaccgcaacttatctacgctgtcc tgctatccctcagcgctgctcctgctcctgctcactgcccctcgcacagccttggtttgggctccgcctgtattctcctggtactgcaacct gtaaaccagcactgcaatgctgatgcacgggaagtagtgggatgggaacacaaatggaaagctgtatagggataaaagcttatagc gactgctacccccccgaccatgtgccgaggcagaaattatatacaagaagcagatcgcaattaggcacatcgctttgcattatccacaca ctattcatcgctgcggcaaggctgcagagtgtattttttgtggcccaggagctgagtccgaagtcgacgcgacgagcggcgcagg atccgacccctagacgagcactgtcattttccaagcacgcagctaaatgcgctgagaccgggtctaaatcatccgaaaagtgtcaaaat ggccgattgggttcgcctaggacaatgcgctgcggattcgctcgagtccgctgccggccaaaaggcggtggtacaggaaggcgca cggggccaaccctgcgaagccgggggcccgaacgccgaccgccggccttcgatctcgggtgtccccctcgtcaatttcctctctcg ggtgcagccacgaaagtcgtgacgcaggtcacgaaatccggttacgaaaaacgcaggtcttcgcaaaaacgtgagggtttcgcgtct cgccctagctattcgtatcgccgggtcagacccacgtgcagaaaagcccttgaataacccgggaccgtggttaccgcgccgcctgca ccaggggggcttatataagcccacaccacacctgtctcaccacgcatttctccaactcgcgacttttcggaagaaattgttatccacctagt atagactgccacctgcaggaccttgtgtcttgcagtttgtattggtcccggccgtcgagcacgacagatctgggctagggttggcctgg -continued ccgctcggcactcccctttagccgcgcgcatccgcgttccagaggtgcgattcggtgtgtggagcattgtcatgcgcttgtgggggtc gttccgtgcgcggcgggtccgccatgggcgccgacctgggccctagggtttgttttcgggccaagcgagcccctctcacctcgtcgc ccccccgcattccctctctcttgcagccactagtATGgctatcaagacgaacaggcagcctgtggagaagcctccgttcacgatc gggacgctgcgcaaggccatccccgcgcactgtttcgagcgctcggcgcttcgtgggcgcgcccagctgcccgactggagccgc ctgctgaccgccatcaccaccgtgttcgtgaagtccaagcgccccgacatgcacgaccgcaagtccaagcgccccgacatgctg gtggacagcttcggcctggagtccaccgtgcaggacggcctggtgttccgccagtccttctccatccgctcctacgagatcggcac cgaccgcaccgccagcatcgagaccctgatgaaccacctgcaggagacctccctgaaccactgcaagagcaccggcatcctgc tggacggcttcggccgcaccctggagatgtgcaagcgcgacctgatctgggtggtgattaagatgcagatcaaggtgaaccgcta ccccgcctggggcgacaccgtggagatcaacacccgcttcagccgcctgggcaagatcggcatgggccgcgactggctgatctc cgactgcaacaccggcgagatcctggtgcgcgccaccagcgcctacgccatgatgaaccagaagacccgccgcctgtccaag ctgccctacgaggtgcaccaggagatcgtgcccctgttcgtggacagccccgtgatcgaggactccgacctgaaggtgcacaag ttcaaggtgaagaccggcgacagcatccagaagggcctgacccccggctggaacgacctggacgtgaaccagcacgtgtcca acgtgaagtacatcggctggatcctggagagcatgcccaccgaggtgctggagacccaggagctgtgctccctggccctggagt accgccgcgagtgcggccgcgactccgtgctggagagcgtgaccgccatggaccccagcaaggtgggcgtgcgctcccagtac cagcacctgctgcgcctggaggacggcaccgccatcgtgaacggcgccaccgagtggcgccccaagaacgccggcgccaac ggcgccatctccaccggcaagaccagcaacggcaactccgtgtccatggactacaaggaccacgacggcgactacaaggacc acgacatcgactacaaggacgacgacgacaagTGActcgagagcgtccagcgtgtgggatgaagggtgcgatggaacggg gctgccgcccccctctgggcatctagctctgcaccgcacgccaggaagcccaagccaggccccgtcacactccctcgctgaagtg ttcccccctgccccacactcatccaggtatcaacgccatcatgttctacgtccccgtcatcttcaactccctggggagcgggcgccgc gcgtcgctgctgaacaccatcatcatcaacgccgtcaactttgttaattaagaattcggccgacaggacgcgcgtcaaaggtgctggt cgtgtatgccctggccggcaggtcgttgctgctgctggttagtgattccgcaaccctgattttggcgtcttattttggcgtggcaaacgct ggcgcccgcgagccgggccggcggcgatgcggtgccccacggctgccggaatccaagggaggcaagagcgcccgggtcagtt gaagggctttacgcgcaaggtacagccgctcctgcaaggctgcgtggtggaattggacgtgcaggtcctgctgaagttcctccaccg cctcaccagcggacaaagcaccggtgtatcaggtccgtgtcatccactctaaagaactcgactacgacctactgatggccctagattct tcatcaaaaacgcctgagacacttgcccaggattgaaactccctgaagggaccaccaggggccctgagttgttccttcccccgtggc gagctgccagccaggctgtacctgtgatcgaggctggcgggaaaataggcttcgtgtgctcaggtcatgggaggtgcaggacagct catgaaacgccaacaatcgcacaattcatgtcaagctaatcagctatttcctcttcacgagctgtaattgtcccaaaattctggtctaccgg gggtgatccttcgtgtacgggcccttccctcaaccctaggtatgcgcgcatgcggtcgccgcgcaactcgcgcgagggccgagggtt tgggacgggccgtcccgaaatgcagttgcacccggatgcgtggcacctttttttgcgataatttatgcaatggactgctctgcaaaattct ggctctgtcgccaaccctaggatcagcggcgtaggatttcgtaatcattcgtcctgatggggagctaccgactaccctaatatcagccc gactgcctgacgccagcgtccacttttgtgcacacattccattcgtgcccaagacatttcattgtggtgcgaagcgtccccagttacgctc acctgtttcccgacctccttactgttctgtcgacagagcgggcccacaggccggtcgcagcccatATGgcttccgcggcattcacc atgtcggcgtgccccgcgatgactggcagggcccctggggcacgtcgctccgacggccagtcgccacccgcctgaggtacgta ttccagtgcctggtggccagctgcatcgacccctgcgaccagtaccgcagcagcgccagcctgagcttcctgggcgacaacggct tcgccagcctgttcggcagcaagcccttcatgagcaaccgcggccaccgccgcctgcgccgcgccagccacagcggcgaggc catggccgtggccctgcagcccgcccaggaggccggcaccaagaagaagcccgtgatcaagcagcgccgcgtggtggtgacc -continued ggcatgggcgtggtgaccccctgggccacgagcccgacgtgttctacaacaacctgctggacggcgtgagcggcatcagcga gatcgagaccttcgactgcacccagttccccacccgcatcgccggcgagatcaagagcttcagcaccgacggctgggtggcccc caagctgagcaagcgcatggacaagttcatgctgtacctgctgaccgccggcaagaaggccctggccgacggcggcatcaccg acgaggtgatgaagagctggacaagcgcaagtgcggcgtgctgatcggcagcggcatgggcggcatgaaggtgttcaacga cgccatcgaggccctgcgcgtgagctacaagaagatgaaccccttctgcgtgcccttcgccaccaccaacatgggcagcgccat gctggccatggacctgggctggatgggccccaactacagcatcagcaccgcctgcgccaccagcaacttctgcatcctgaacgc cgccaaccacatcatccgcggcgaggccgacatgatgctgtgcggcggcagcgacgccgtgatcatccccatcggcctgggcg gcttcgtggcctgccgcgccctgagccagcgcaacagcgaccccaccaaggccagccgcccctgggacagcaaccgcgacg gcttcgtgatgggcgagggcgccggcgtgctgctgctggaggagctggagcacgccaagaagcgcggcgccaccatctacgcc gagttcctgggcggcagcttcacctgcgacgcctaccacatgaccgagccccaccccgagggcgccggcgtgatcctgtgcatc gagaaggccctggcccaggccggcgtgagcaaggaggacgtgaactacatcaacgcccacgccaccagcaccagcgccgg cgacatcaaggagtaccaggccctggcccgctcttcggccagaacagcgagctgcgcgtgaacagcaccaagagcatgatc ggccacctgctgggcgccgccggcggcgtggaggccgtgaccgtggtgcaggccatccgcaccggctggattcaccccaacct gaacctggaggaccccgacaaggccgtggacgccaagctgctggtgggccccaagaaggagcgcctgaacgtgaaggtggg
cctgagcaacagcttcggcttcggcggccacaacagcagcatcctgttcgcccccctgcaacgtgTGActcgaggcagcagcag ctcggatagtatcgacacactctggacgctggtcgtgtgatggactgttgccgccacacttgctgccttgacctgtgaatatccctgccg cttttatcaaacagcctcagtgtgtttgatcttgtgtgtacgcgcttttgcgagttgctagctgcttgtgctatttgcgaataccacccccagc atccccttccctcgtttcatatcgcttgcatcccaaccgcaacttatctacgctgtcctgctatccctcagcgctgctcctgctcctgctcact gcccctcgcacagccttggtttgggctccgcctgtattctcctggtactgcaacctgtaaaccagcactgcaatgctgatgcacgggaa gtagtgggatgggaacacaaatggaaagcttgagctccacctgcatccgcctggcgctcgaggacgccggcgtctcgcccgac gaggtcaactacgtcaacgcgcacgccacctccaccctggtgggcgacaaggccgaggtgcgcgcggtcaagtcggtctttg gcgacatgaagggcatcaagatgaacgccaccaagtccatgatcgggcactgcctgggcgccgccggcggcatggaggccg tcgccacgctcatggccatccgcaccggctgggtgcaccccaccatcaaccacgacaaccccatcgccgaggtcgacggcct ggacgtcgtcgccaacgccaaggcccagcacaaaatcaacgtcgccatctccaactccttcggcttcggcgggcacaactcc gtcgtcgcctttgcgcccttccgcgagtaggcggagcgagcgcgcttggctgaggagggaggcggggtgcgagccctttggct gcgcgcgatactctccccgcacgagcagactccacgcgcctgaatctacttgtcaacgagcaaccgtgtgttttgtccgtggcc attcttattatttctccgactgtggccgtactctgtttggctgtgcaagcaccgaagagcc Fatty acids profiles from representative shake flask cultures of stable lines derived from D1550 transformants are shown in Table 74. Two independent genetic lineages yielded strains with high and balanced levels of C10-C12:0 fatty acids.

TABLE 74

Fatty acid profiles in S5050 and derivative transgenic lines generated after transformation with pSZ2424 DNA.

| Strain | | Fatty Acid (area %) C8:0 | C10:0 | C12:0 | C14:0 | C16:0 | C18:0 | C18:1 | C18:2 | Total Saturates |
|---|---|---|---|---|---|---|---|---|---|---|
| Strain BA | | 0.32 | 14.96 | 43.84 | 16.60 | 10.49 | 0.54 | 9.64 | 2.49 | 86.75 |
| D1550-29.C4.A2 | | 4.02 | 32.82 | 40.98 | 7.37 | 5.06 | 0.40 | 5.61 | 2.37 | 90.65 |
| D1550-29.C4.A3 | | 4.50 | 33.93 | 40.23 | 7.09 | 4.91 | 0.36 | 5.38 | 2.30 | 91.02 |
| D1550-29.C4.A4 | | 3.57 | 34.31 | 41.04 | 6.86 | 4.90 | 0.36 | 4.98 | 2.56 | 91.04 |
| D1550-29.C4.A5 | | 4.66 | 34.23 | 39.68 | 6.96 | 4.90 | 0.36 | 5.55 | 2.32 | 90.79 |
| D1550-29.C6.E2 | | 3.59 | 35.44 | 40.49 | 6.32 | 4.74 | 0.34 | 4.94 | 2.63 | 90.92 |
| D1550-29.C6.E3 | | 3.60 | 35.55 | 40.90 | 6.33 | 4.67 | 0.34 | 4.66 | 2.52 | 91.39 |
| D1550-29.C6.E4 | BB | 3.97 | 35.85 | 40.23 | 6.26 | 4.65 | 0.34 | 4.83 | 2.51 | 91.30 |
| D1550-29.C6.E5 | | 4.02 | 35.19 | 39.89 | 6.59 | 4.79 | 0.34 | 5.12 | 2.60 | 90.82 |
| D1550-29-1.14 | | 3.30 | 39.62 | 40.04 | 5.16 | 4.04 | 0.30 | 3.49 | 2.67 | 92.46 |

TABLE 74-continued

Fatty acid profiles in S5050 and derivative transgenic lines generated after transformation with pSZ2424 DNA.

| Strain | | Fatty Acid (area %) C8:0 | C10:0 | C12:0 | C14:0 | C16:0 | C18:0 | C18:1 | C18:2 | Total Saturates |
|---|---|---|---|---|---|---|---|---|---|---|
| D1550-29-1.2 | | 3.12 | 39.50 | 40.22 | 5.13 | 3.86 | 0.29 | 3.42 | 2.82 | 92.12 |
| D1550-29-1.12 | | 3.26 | 39.36 | 39.91 | 5.13 | 4.15 | 0.30 | 3.73 | 2.77 | 92.11 |
| D1550-29-1.17 | | 3.25 | 39.21 | 40.21 | 5.22 | 4.11 | 0.30 | 3.70 | 2.67 | 92.30 |
| D1550-29-1.39 | | 4.12 | 38.44 | 39.23 | 5.83 | 4.25 | 0.30 | 3.96 | 2.46 | 92.17 |
| D1550-29-1.35 | BC | 3.60 | 38.06 | 39.79 | 5.89 | 4.35 | 0.29 | 3.98 | 2.58 | 91.98 |
| D1550-29-1.7 | | 3.15 | 39.18 | 40.04 | 5.24 | 4.05 | 0.32 | 3.68 | 2.88 | 91.98 |
| D1550-29-1.1 | | 2.87 | 38.29 | 40.76 | 5.20 | 4.20 | 0.31 | 3.79 | 2.86 | 91.63 |

Next, we analyzed the performance of D1681 strains that were constructed using the KASI replacement strategy. Interestingly, unlike D1550 transformants, the D1681 strains demonstrated greater variability in fatty acid profiles (Table 75). In addition, the D1681 derived lines had lower C8:0 levels than what we observed in the D1550 derived transgenic lines suggesting a direct role of *C. wrightii* KASAI in improving C10:0 specificity of *C. hookeriana* FATB2 thioesterase.

TABLE 75

Fatty acid profiles in Strain BA and derivative transgenic lines generated after transformation with pSZ2746 DNA.

| Strain | | Fatty Acid (area %) C8:0 | C10:0 | C12:0 | C14:0 | C16:0 | C18:0 | C18:1 | C18:2 | Total Saturates |
|---|---|---|---|---|---|---|---|---|---|---|
| Strain BA | | 0.89 | 13.17 | 40.52 | 17.53 | 11.60 | 0.59 | 11.38 | 2.95 | 84.30 |
| D1681.3.7-2 | BD | 1.44 | 31.83 | 44.97 | 6.52 | 4.83 | 0.30 | 6.53 | 2.45 | 89.89 |
| D1681.3.7-10 | | 1.84 | 31.41 | 43.64 | 6.90 | 5.15 | 0.31 | 7.08 | 2.46 | 89.25 |
| D1681.3.7-12 | BE | 1.85 | 31.64 | 43.50 | 6.76 | 5.08 | 0.31 | 7.16 | 2.49 | 89.14 |
| D1681.3.4-1 | | 1.29 | 31.61 | 45.92 | 6.65 | 4.49 | 0.29 | 6.20 | 2.46 | 90.25 |
| D1681.3.4-6 | BF | 1.48 | 32.26 | 45.11 | 6.55 | 4.56 | 0.29 | 6.23 | 2.41 | 90.25 |
| D1681.3.4-9 | | 1.42 | 31.22 | 45.40 | 6.93 | 4.69 | 0.30 | 6.49 | 2.47 | 89.96 |
| D1681.3.8-1 | | 1.35 | 27.72 | 44.72 | 8.78 | 5.97 | 0.37 | 7.36 | 2.51 | 88.91 |
| D1681.3.8-4 | | 1.44 | 27.51 | 44.34 | 8.72 | 6.05 | 0.36 | 7.84 | 2.51 | 88.42 |
| D1681-2.1-37 | | 0.64 | 34.80 | 47.17 | 4.84 | 3.81 | 0.31 | 4.37 | 2.43 | 91.57 |
| D1681-2.1-34 | | 0.62 | 35.26 | 47.07 | 4.77 | 3.77 | 0.30 | 4.22 | 2.36 | 91.79 |
| D1681-2.1-28 | BG | 0.64 | 35.99 | 46.80 | 4.65 | 3.68 | 0.29 | 4.02 | 2.34 | 92.05 |
| D1681-2.1-12 | | 0.67 | 34.78 | 47.21 | 4.94 | 3.79 | 0.34 | 4.30 | 2.35 | 91.73 |
| D1681.2.4-1.3 | BH | 0.57 | 35.95 | 47.73 | 4.93 | 3.39 | 0.03 | 0.24 | 3.96 | 92.60 |
| D1681.2.4-1.4 | | 0.56 | 36.71 | 47.55 | 4.86 | 3.26 | 0.03 | 0.24 | 3.61 | 92.97 |
| D1681.2.4-1.12 | BI | 1.89 | 34.72 | 44.70 | 6.32 | 4.03 | 0.02 | 0.27 | 5.18 | 91.68 |
| D1681.2.4-1.2 | | 1.73 | 36.43 | 44.25 | 5.57 | 4.09 | 0.03 | 0.32 | 4.55 | 92.10 |

Eight strains representing D1550 and D1681 families (from Tables 74-75) were subsequently evaluated in high cell density fermentations as shown in Table 76. Fermentations resulted in oils with a slightly improved mid-chain profile or the balance of C10-C12:0 fatty acid levels compared to the lab scale fermentation. Strain BE evaluated in two independent fermentations demonstrated superior profile reaching 85.2% C10-C12:0 fatty acid levels, 3.5% C14:0 levels, and ca. 1.2% C8:0 fatty acid levels, and accumulated over 92% total saturates.

TABLE 76

End-point fatty acid profiles in D1550 and D1681 derivative transgenic lines subjected to high cell density fermentation.

| | | Strain BB | BC | BG | BH | BI | BF | BE | |
|---|---|---|---|---|---|---|---|---|---|
| | Run | 130067 | 130196 | 130197 | 130291 | 130292 | 130253 | 130246 | PF13029 |
| Fatty Acid Profile | C8:0 | 5.3 | 4.62 | 4.62 | 0.54 | 1.53 | 1.59 | 2.1 | 1.19 |
| (Area %) | C10:0 | 36.19 | 36.16 | 36.16 | 33.24 | 40 | 40.46 | 40.94 | 41.59 |

TABLE 76-continued

End-point fatty acid profiles in D1550 and D1681 derivative transgenic lines subjected to high cell density fermentation.

| | Strain | | | | | | | |
|---|---|---|---|---|---|---|---|---|
| | BB | BC | BG | BH | BI | BF | BE | |
| C12:0 | 39.07 | 38.77 | 38.77 | 47.65 | 43.09 | 42.39 | 41.25 | 43.6 |
| C14:0 | 5.31 | 5.18 | 5.18 | 5 | 4.62 | 4.42 | 4.2 | 3.49 |
| C16:0 | 3.72 | 3.9 | 3.9 | 3.4 | 2.83 | 2.63 | 2.8 | 2.28 |
| C18:0 | 0.24 | 0.28 | 0.28 | 0.27 | 0.22 | 0.32 | 0.28 | 0.15 |
| C18:1 | 6.12 | 6.79 | 6.79 | 5.88 | 4.95 | 5.34 | 5.8 | 4.76 |
| C18:2 | 2.43 | 2.76 | 2.76 | 2.49 | 1.95 | 2.05 | 1.89 | 1.96 |
| C10-C14 | 80.57 | 80.11 | 80.11 | 85.89 | 87.71 | 87.27 | 86.39 | 88.68 |
| C10-C12 | 75.26 | 74.93 | 74.93 | 80.89 | 83.09 | 82.85 | 82.19 | 85.19 |
| Total Saturates | 89.83 | 88.91 | 88.91 | 90.1 | 92.29 | 91.81 | 91.57 | 92.3 |

Example 61: TAG Regiospecificity in UTEX1435 by Expression of *Cuphea* PSR23 LPAAT2 and LPAAT3 Genes In Example 43, we demonstrated that the expression of 2 different 1-acyl-sn-glycerol-3-phosphate acyltransferases (LPAATs), the LPAAT2 and LPAAT3 genes from *Cuphea* PSR23 (CuPSR23) in the UTEX1435 derivative strain 52014 resulted in elevation of C10:0, C12:0 and C14:0 fatty acids levels. In this example we provide evidence that *Cuphea* PSR23 LPAAT2 exhibits high specificity towards incorporating C10:0 fatty acids at sn-2 position in TAGs. The *Cuphea* PSR23 LPAAT3 specifically incorporates C18:2 fatty acids at sn-2 position in TAGs.

Composition and properties of *Prototheca moriformis* (UTEX 1435) transgenic strain B, transforming vectors pSZ2299 and pSZ2300 that express CuPSR23 LPAAT2 and LPAAT3 genes, respectively, and their sequences were described previously.

To determine the impact of *Cuphea* PSR23 LPAAT genes on the resulting fatty acid profiles we have taken advantage of Strain B which synthesizes both mid chain and long chain fatty acids at relatively high levels. As shown in Table 77, the expression of the LPAAT2 gene (D1520) in Strain B resulted in increased C10-C12:0 levels (up to 12% in the best strain, D1520.3-7) suggesting that this LPAAT is specific for mid chain fatty acids. Alternatively, expression of the LPAAT3 gene resulted in a relatively modest increase, (up to 5% in the best strain, D1521.28-7) indicating it has little or no impact on mid-chain levels.

TABLE 77

Fatty acid profiles of Strain B and representative transgenic lines transformed with pSZ2299 (D1520) and pSZ2300 (D1521) DNA.

| | Fatty Acid (area %) | | | | | | | | | |
|---|---|---|---|---|---|---|---|---|---|---|
| Strain | C8:0 | C10:0 | C12:0 | C14:0 | C16:0 | C18:0 | C18:1 | C18:2 | C10-C12 | Total Saturates |
| Strain B | 0.09 | 4.95 | 29.02 | 15.59 | 12.55 | 1.27 | 27.93 | 7.60 | 33.97 | 63.47 |
| D1520.8-6 | 0.00 | 6.71 | 31.15 | 15.80 | 13.04 | 1.42 | 24.32 | 6.56 | 37.86 | 68.12 |
| D1520.13-4 | 0.00 | 6.58 | 30.96 | 16.14 | 13.34 | 1.25 | 24.32 | 6.27 | 37.54 | 68.27 |
| D1520.19-4 | 0.00 | 7.53 | 32.94 | 16.64 | 12.63 | 1.17 | 21.96 | 6.11 | 40.47 | 70.91 |
| D1520.3-7 | 0.06 | 9.44 | 36.26 | 16.71 | 11.44 | 1.28 | 18.41 | 5.59 | 45.70 | 75.19 |
| D1521.13-8 | 0.00 | 6.21 | 33.13 | 16.70 | 12.30 | 1.18 | 20.84 | 8.70 | 39.34 | 69.52 |
| D1521.18-2 | 0.00 | 5.87 | 31.91 | 16.46 | 12.60 | 1.22 | 22.14 | 8.59 | 37.78 | 68.06 |
| D1521.24-8 | 0.00 | 5.75 | 31.47 | 16.13 | 12.60 | 1.42 | 23.31 | 8.22 | 37.22 | 67.37 |
| D1521.28-7 | 0.00 | 6.28 | 32.82 | 16.33 | 12.27 | 1.43 | 21.98 | 7.91 | 39.10 | 69.13 |

To determine if expression of the *Cuphea* PSR23 LPAAT genes affected regiospecificity of fatty acids at the sn-2 position, we analyzed TAGs from representative D1520 and D1521 strains utilizing the porcine pancreatic lipase method. See Example 2. As demonstrated in Table 78, the *Cuphea* PSR23 LPAAT2 gene shows remarkable specificity towards C10:0 fatty acids and appears to incorporate 50% more C10:0 fatty acids into the sn-2 position. The *Cuphea* PSR23 LPAAT3 gene appears to act exclusively on C18:2 fatty acids, resulting in redistribution of C18:2 fatty acids onto sn-2 position. Accordingly, microbial triglyceride oils with sn-2 profiles of greater than 15% or 20% C10:0 or C18:2 fatty acids are obtainable by introduction of an exogenous LPAAT gene having corresponding specificity.

TABLE 78

TAG and sn-2 fatty acid profiles in oils of parental S2014 strain and the progeny strains expressing Cuphea PSR23 LPAAT2 (BJ) and LPAAT3 (BK) genes.

| | | Strain Analysis | | | | | |
|---|---|---|---|---|---|---|---|
| | | Strain B | | Strain BJ (D1520.3-7) | | Strain BK (D1521.13-8) | |
| | | TAG Profile | sn-2 Profile | TAG Profile | sn-2 Profile | TAG Profile | sn-2 Profile |
| Fatty Acid (area %) | C8:0 | 0 | 0 | 0.1 | 0 | 0 | 0 |
| | C10:0 | 12 | 14.2 | 11 | 24.9 | 6.21 | 6.3 |
| | C12:0 | 42.8 | 25.1 | 40.5 | 24.3 | 33.13 | 19.5 |
| | C14:0 | 12.1 | 10.4 | 16.3 | 10 | 16.7 | 11.8 |
| | C16:0 | 7.3 | 1.3 | 10.2 | 1.4 | 12.3 | 3 |
| | C18:0 | 0.7 | 0.2 | 0.9 | 0.6 | 1.18 | 0.5 |
| | C18:1 | 18.5 | 36.8 | 15.4 | 29.2 | 20.84 | 36.3 |
| | C18:2 | 5.8 | 10.9 | 4.9 | 8.7 | 8.7 | 20.9 |
| | C18:3a | 0.6 | 0.8 | 0.4 | 0.8 | 0.48 | 1.2 |
| | C10-C14 | 66.9 | 49.7 | 67.8 | 59.2 | 56.0 | 37.6 |
| | C10-C12 | 54.8 | 39.3 | 51.5 | 49.2 | 39.3 | 25.8 |

Example 62: Introduction of Heterologous Thioesterases into a Heterologous KAS-Expressing *Prototheca Moriformis* Strain Here we demonstrate that heterologous fatty acyl-ACP thioesterases exhibit altered thioesterase specificity when combined with a heterologous plant KASI gene, *Cuphea wrightii* β-ketoacyl-ACP synthase (KAS), CwKASA1, in *P. moriformis* (UTEX 1435) transgenic strain, S5818. S5818 is a transgenic strain expressing a thioesterase chimera from *Cinnamomum camphora* and *Umbellularia californica*, CcFATB2-UcFATB2 chimera B, at the 6S locus and additionally expressing the *Cuphea wrightii* KAS, CwKASA1, at the pLOOP locus. The addition of the CcFATB2-UcFATB2 chimera B and CwKASA1 genes leads to an S5818 fatty acid profile with 45% C12:0 and 14% C14:0. Five different constructs encoding thioesterases that were previously shown to exhibit predominantly C14:0 thioesterase activity and with less pronounced C12:0 thioesterase activity in *P. moriformis* were introduced into S5818 in an effort to increase C14:0 and C12:0 levels in this background. However, introduction of the five different C14:0 thioesterases into S5818 led to unexpected but significant increases in C12:0 fatty acid levels (>50% overall) with only modest increases in C14:0 fatty acid levels (<20% overall). This result suggests that the KASI-FATB thioesterase combination exhibits a unique activity not displayed when either gene is introduced separately. The results demonstrate that combination of heterologous KAS genes with heterologous thioesterases in oleaginous cells can be used to produce fatty acid profiles not exhibited by introduction of either gene alone. Furthermore, introduction of heterologous KASs may be an important and fruitful approach for revealing novel specificities of additional heterologous thioesterases.

Strain S5818 Generation.

S5818 was created by two successive transformations. The UTEX1435 base strain, S3150 (Strain Z above), was transformed with pSZ2448 (6SA::CrTUB2-ScSUC2-CvNR:PmAMT3-CpSAD1tpExt-CcFATB2-UcFATB2-chimeraB-ExtA-CvNR::6SB), encoding the CcFATB2-UcFATB2 chimera B thioesterase targeting the 6S locus, to yield strain S4954. S4954 produces ~32% C12:0 and ~16% C14:0 fatty acid levels (Table 62-1). S4954 was subsequently transformed with pSZ2229 (pLOOP::CrTUB2-NeoR-CvNR:PmAMT3-PmSADtp_CwKASAI-CvNR::pLOOP), encoding the *C. wrightii* KASA1 gene targeting the pLOOP locus, to yield strain S5818. 55818 produces ~45% C12:0 and ~14% C14:0 fatty acid levels (Table 79).

TABLE 79

Fatty acid profiles of S3150, S4954, and S5818.

| Sample ID | C10:0 | C12:0 | C14:0 | C16:0 | C18:0 | C18:1 | C18:2 |
|---|---|---|---|---|---|---|---|
| Strain Z | 0 | 0.05 | 1.49 | 28.83 | 3.24 | 57.87 | 6.27 |
| S4954 | 0.17 | 31.52 | 16.39 | 9.81 | 1.19 | 32.14 | 7.19 |
| S5818 | 0.34 | 45.16 | 13.77 | 8.54 | 0.81 | 24.63 | 5.38 |

Identification of C14:0 thioesterases. In an effort to increase C14:0 fatty acid levels, and to a lesser degree C12:0 fatty acid levels, several thioesterases that were found to exhibit C14:0 and C12:0 thioesterase activity in *P. moriformis* were cloned into vectors for introduction into S5818. The *Cuphea hyssopifolia* thioesterase ChsFATB3 was discovered by us as part of efforts to identify novel thioesterases by sequencing the mature, plant oilseeds of *C.*

*hyssopifolia*. Although *C. hyssopifolia* seeds exhibit ~84% C12:0 and ~5% C14:0 fatty acid levels, the ChsFATB3 thioesterase we identified exhibits strong C14:0 thioesterase activity when expressed in S3150 (up to ~34% C14:0). A version of ChsFATB3 in which we optimized the putative plastid-targeting transit peptide, named pSAD1tp_trimmed: ChsFATB3, similarly exhibited strong C14:0 thioesterase activity (~33% C14:0; Table 80).

strains were selected for the ability to grow on melibiose. Cell culture, lipid production, and fatty acid analysis were all carried out as previously described. The transforming DNA for pSZ3390, pSZ3493, pSZ3494, pSZ3495, and pSZ3531 are provided below.

pSZ3390:

pSZ3390 can be written as DAO1b:: PmHXT1-Scar-Mel1-CvNR:PmUAPA1noSacI-CpSAD1tpExt-

TABLE 80

Fatty acid profiles of *Cuphea hyssopifolia* seeds and S3150 with introduction of ChsFATB3 or CpSAD1tp_trimmed:ChsFATB3.

| Sample ID | C8:0 | C10:0 | C12:0 | C14:0 | C16:0 | C18:0 | C18:1 | C18:2 |
|---|---|---|---|---|---|---|---|---|
| *Cuphea hyssopifolia* seeds | 0.24 | 6.53 | 83.69 | 5.13 | 1.10 | 0.12 | 0.00 | 1.74 |
| S3150 | 0.00 | 0.00 | 0.05 | 1.49 | 28.83 | 3.24 | 57.87 | 6.27 |
| S3150 + ChsFATB3 (T537; D1701-48) | 0.00 | 0.00 | 8.09 | 33.66 | 26.46 | 1.57 | 23.75 | 5.3 |
| S3150 + CpSAD1tp_trimmed:ChsFATB3 (T580; D1813-8) | 0.00 | 0.14 | 7.25 | 33.32 | 27.04 | 1.57 | 24.37 | 5.12 |

Similarly, we also identified the *Cuphea* heterophylla thioesterase ChtFATB1a as part of our efforts to identify novel thioesterases by sequencing the mature, plant oil seeds of *C. heterophylla*. Although *C. heterophylla* seeds exhibit ~44% C10:0, ~40% C12:0 fatty acid levels, and only ~4% C14:0, the transit peptide optimized version of the ChtFATB1a thioesterase we identified, CpSAD1tp_trimmed:ChtFATB1a, exhibits strong C14:0 thioesterase activity when expressed in S3150 (up to ~35% C14:0; Table 81).

Cpa1FATB2FLAGExtA-CvNR::DAO1b. The relevant restriction sites in the construct from 5'-3', BspQI, KpnI, SpeI, SnaBI, XhoI, EcoRI, SpeI, HindIII, SacI, BspQI, respectively, are indicated in lowercase, bold, and underlined. BspQI sites delimit the 5' and 3' ends of the transforming DNA. Bold, lowercase sequences at the 5' and 3' end of the construct represent genomic DNA from UTEX 1435 that target integration to the DAO1b locus via homologous recombination. Proceeding in the 5' to 3' direction, the selection cassette has the *P. moriformis* HXT1 promoter

TABLE 81

Fatty acid profiles of *Cuphea heterophylla* seeds and S3150 with introduction of CpSAD1tp_trimmed:ChtFATB1a.

| Sample ID | C8:0 | C10:0 | C12:0 | C14:0 | C16:0 | C18:0 | C18:1 | C18:2 |
|---|---|---|---|---|---|---|---|---|
| *Cuphea heterophylla* seeds | 3.50 | 44.27 | 40.04 | 4.26 | 1.22 | 0.25 | 2.21 | 3.56 |
| S3150 | 0.00 | 0.00 | 0.05 | 1.49 | 28.83 | 3.24 | 57.87 | 6.27 |
| S3150 + CpSAD1tp_trimmed:ChtFATB1a (T580; D1811-44) | 0.00 | 0.15 | 13.18 | 35.16 | 24.1 | 1.19 | 18.87 | 6.02 |

A published *Cuphea palustris* C14:0 thioesterase, Cpa1FATB2, was also introduced into S5818 (vide infra).

Introduction of C14:0 Thioesterases into S5818.

Five constructs were generated using C14:0 thioesterases for introduction into S5818 (Table 82).

driving the expression of the *S. carlbergensis* MEL1 gene (conferring the ability to grow on melibiose) and the *Chlorella vulgaris* Nitrate Reductase (NR) gene 3' UTR. The promoter is indicated by lowercase, boxed text. The initiator ATG and terminator TGA for ScarMEL1 are indicated by

TABLE 82

Constructs engineered for introduction into S5818.

| D# | pSZ# | Construct |
|---|---|---|
| D2104 | pSZ3390 | DAO1b::PmHXT1-ScarMel1-CvNR:PmUAPA1noSacI-CpSAD1tpExt-CpaIFATB2FLAGExtA-CvNR::DAO1b |
| D2202 | pSZ3493 | DAO1b5[1]::PmHXT1-ScarMEL1-CvNR:PmAMT3-ChsFATB3-CvNR::DAO1b3[1] |
| D2203 | pSZ3494 | DAO1b5[1]::PmHXT1-ScarMEL1-CvNR:PmAMT3-CpSAD1tp_trimmed:ChsFATB3-CvNR::DAO1b3[1] |
| D2204 | pSZ3495 | DAO1b5[1]::PmHXT1-ScarMEL1-CvNR:PmAMT3-CpSAD1tp_trimmed:ChtFATB1a-CvNR::DAO1b3[1] |
| D2235 | pSZ3531 | THI4A::PmHXT1-ScarMel1 - CpEF1a:PmUAPA1noSacI-CpSAD1tpExt-CpaIFATB2FLAGExtA-CvNR::THI4A |

pSZ3390 and pSZ3531 introduce the Cpa1FATB2 thioesterase gene into the DAO1b and THI4A loci, respectively, under the control of the pH5-responsive UAPA1 promoter. pSZ3493, pSZ3494, and pSZ3495 introduce ChsFATB3, CpSAD1tp_trimmed: ChsFATB3, and CpSAD1tp_trimmed: ChtFATB1a, respectively, into the DAO1b locus under the control of the pH7-responsive AMT3 promoter. Transgenic bold, uppercase italics, while the coding region is indicated with lowercase italics. The 3'UTR is indicated by lowercase, underlined text. The second cassette containing the CpSAD1tpExt-Cpa1FATB2FLAGExtA gene, fused to the heterologous *Chlorella protothecoides* SAD1 plastid-targeting transit peptide, is driven by the *P. moriformis* UAPA1 pH5-responsive promoter and has the *Chlorella vulgaris*

Nitrate Reductase (NR) gene 3' UTR. In this cassette, the UAPA1 promoter is indicated by lowercase, boxed text. The initiator ATG and terminator TGA for the CpSAD1tpExt-Cpa1FATB2FLAGExtA gene are indicated in bold, uppercase italics, while the coding region is indicated by lowercase italics. The 3' UTR is indicated by lowercase, underlined text.

pSZ3390 Transforming Construct:

(SEQ ID NO: 123)

gaagagcGCCCAATGTTTAAACagcccgcaccctcgttgatctgggagccctgcgcagccccttaaatcatctcag tcaggtttctgtgttcaactgagcctaaagggctttcgtcatgcgcacgagcacacgtatatcggccacgcagtttctcaaaagc ggtagaacagttcgcgagccctcgtaggtcgaaaacttgcgccagtactattaaattaaattaattgatcgaacgagacgcga aacttttgcagaatgccaccgagtttgcccagagaatgggagtggcgccattcaccatccgcctgtgcccggcttgattcgccg agacgatggacggcgagaccagggagcggcttgcgagccccgagccggtagcaggaacaatgatcgacaatcttcctgtcc aattactggcaaccattagaaagagccggagcgcgttgaaagtctgcaatcgagtaatttttcgatacgtcgggcctgctgaa ccctaaggctccggactttgtttaaggcgatccaagatgcacgcggccccaggcacgtatctcaagcacaaaccccagcctta gtttcgagactttgggagatagcgaccgatatctagtttggcattttgtatattaattacctcaagcaatggagcgctctgatgcg gtgcagcgtcggctgcagcacctggcagtggcgctagggtcgccctatcgctcggaacctggtcagctggctcccgcctcctgc tcagcctcttccggtaccgcggtgagaatcgaaaatgcatcgtttctaggttcggagacggtcaattccctgctccggcgaatctgtcg gtcaagctggccagtggacaatgttgctatggcagcccgcgcacatgggcctcccgacgcggccatcaggagcccaaacagcgtgt cagggtatgtgaaactcaagaggtccctgctgggcactccggccccactccgggggcgggacgccaggcattcgcggtcggtccc gcgcgacgagcgaaatgatgattcggttacgagaccaggacgtcgtcgaggtcgagaggcagcctcggacacgtctcgctagggc aacgccccgagtccccgcgagggccgtaaacattgtttctgggtgtcggagtgggcattttgggcccgatccaatcgcctcatgccgc tctcgtctggtcctcacgttcgcgtacggcctggatcccggaaagggcggatgcacgtggtgttgccccgccattggcgcccacgttt caaagtccccggccagaaatgcacaggaccggcccggctcgcacaggccatgctgaacgcccagatttcgacagcaacaccatct agaataatcgcaaccatccgcgttttgaacgaaacgaaacggcgctgtttagcatgtttccgacatcgtgggggccgaagcatgctcc gggggaggaaagcgtggcacagcggtagcccattctgtgccacacgccgacgaggaccaatccccggcatcagccttcatcgac ggctgcgccgcacatataaagccggacgcctaaccggtttcgtggttatg**actagt*ATG***
*ttcgcgttctacttcctgacggcctgcat*

*ctccctgaagggcgtgttcggcgtctcccccctcctacaacggcctgggcctgacgccccagatgggctgggacaactggaacac*

*gttcgcctgcgacgtctccgagcagctgctgctggacacggccgaccgcatctccgacctgggcctgaaggacatgggctacaa*

*gtacatcatcctggacgactgctggtcctccggccgcgactccgacggcttcctggtcgccgacgagcagaagttccccaacggc*

*atgggccacgtcgccgaccacctgcacaacaactccttcctgttcggcatgtactcctccgcgggcgagtacacgtgcgccggcta*

*ccccggctccctgggccgcgaggaggaggacgcccagttcttcgcgaacaaccgcgtggactacctgaagtacgacaactgct*

*acaacaagggccagttcggcacgcccgagatctcctaccaccgctacaaggccatgtccgacgccctgaacaagacgggccg*

*ccccatcttctactccctgtgcaactggggccaggacctgaccttctactggggctccggcatcgcgaactcctggcgcatgtccgg*

*cgacgtcacggcggagttcacgcgccccgactcccgctgcccctgcgacggcgacgagtacgactgcaagtacgccggcttcc*

*actgctccatcatgaacatcctgaacaaggccgcccccatgggccagaacgcgggcgtcggcggctggaacgacctggacaa*

*cctggaggtcggcgtcggcaacctgacggacgacgaggagaaggcgcacttctccatgtgggccatggtgaagtccccccctgat*

*catcggcgcgaacgtgaacaacctgaaggcctcctcctactccatctactcccaggcgtccgtcatcgccatcaaccaggactcc*

*aacggcatccccgccacgcgcgtctggcgctactacgtgtccgacacggacgagtacggccagggcgagatccagatgtggtc*

*cggcccccctggacaacggcgaccaggtcgtggcgctgctgaacggcggctccgtgtcccgccccatgaacacgaccctggagg*

*agatcttcttcgactccaacctgggctccaagaagctgacctccacctgggacatctacgacctgtgggcgaaccgcgtcgacaa*

*ctccacggcgtccgccatcctgggccgcaacaagaccgccaccggcatcctgtacaacgccaccgagcagtcctacaaggacg*

*gcctgtccaagaacgacacccgcctgttcggccagaagatcggctccctgtcccccaacgcgatcctgaacacgaccgtccccg*

-continued

*cccacggcatcgcgttctaccgcctgcgcccctcctcc**TGA*tacgtactcgaggcagcagcagctcggatagtatcgacacactc tggacgctggtcgtgtgatggactgttgccgccacacttgctgccttgacctgtgaatatccctgccgcttttatcaaacagcctcagtgt gtttgatcttgtgtgtacgcgcttttgcgagttgctagctgcttgtgctatttgcgaataccacccccagcatccccttccctcgtttcatatc gcttgcatcccaaccgcaacttatctacgctgtcctgctatccctcagcgctgctcctgctcctgctcactgcccctcgcacagccttggtt tgggctccgcctgtattctcctggtactgcaacctgtaaaccagcactgcaatgctgatgcacgggaagtagtgggatgggaacacaa atggaAAGCTGTAgaattcatagcgactgctacccccgaccatgtgccgaggcagaaattatatacaagaagcagatcgca attaggcacatcgctttgcattatccacacactattcatcgctgctgcggcaaggctgcagagtgtatttttgtggcccaggagctgagtc cgaagtcgacgcgacgagcggcgcaggatccgacccctagacgagcactgtcattttccaagcacgcagtaatgcgctgagacc gggtctaaatcatccgaaaagtgtcaaaatggccgattgggttcgcctaggacaatgcgctgcggattcgctcgagtccgctgccggc caaaaggcggtggtacaggaaggcgcacggggccaaccctgcgaagccgggggcccgaacgccgaccgccggccttcgatctc gggtgtccccctcgtcaatttcctctctcgggtgcagccacgaaagtcgtgacgcaggtcacgaaatccggttacgaaaaacgcaggt cttcgcaaaaacgtgagggtttcgcgtctcgccctagctattcgtatcgccgggtcagacccacgtgcagaaaagcccttgaataaccc gggaccgtggttaccgcgccgcctgcaccagggggcttatataagcccacaccacacctgtctcaccacgcatttctccaactcgcga cttttcggaagaaattgttatccacctagtatagactgccacctgcaggaccttgtgtcttgcagtttgtattggtcccggccgtcgagcac gacagatctgggctagggttggcctggccgctcggcactcccctttagccgcgcgcatccgcgttccagaggtgcgattcggtgtgtg gagcattgtcatgcgcttgtgggggtcgttccgtgcgcggcgggtccgccatgggcgccgacctgggccctagggtttgttttcgggc caagcgagcccctctcacctcgtcgcccccccgcattccctctctcttgcagcCactagtAACA*ATG**gccaccgcatccacttt*

*ctcggcgttcaatgcccgctgcggcgacctgcgtcgctcggcgggctccgggccccggcgcccagcgaggcccctccccgtgcg*

*cgctgccatcgccagcgaggtccccgtggccaccacctcccccgggcgcaccccaaggcgaaggcagcgcggtgtcgctg*

*aagtcgggctccctggagacccaggaggacaagacgagcagctcgtcccccccccccgcacgttcatcaaccagctgcccgt*

*gtggagcatgctgctgtcggcggtgaccacggtcttcggcgtggccgagaagcagtggcccatgctggaccgcaagtccaagcg*

*ccccgacatgctggtcgagcccctgggcgtggaccgcatcgtctacgacggcgtgagcttccgccagtcgttctccatccgcagct*

*acgagatcggcgccgaccgcaccgcctcgatcgagacgctgatgaacatgttccaggagacctccctgaaccactgcaagatc*

*atcggcctgctgaacgacggcttcggccgcacgcccgagatgtgcaagcgcgacctgatctgggtcgtgaccaagatgcagatc*

*gaggtgaaccgctaccccacgtggggcgacaccatcgaggtcaacacgtgggtgagcgcctcgggcaagcacggcatgggcc*

*gcgactggctgatctccgactgccacaccggcgagatcctgatccgcgcgacgagcgtctgggcgatgatgaaccagaagacc*

*cgccgcctgtcgaagatcccctacgaggtgcgccaggagatcgagccccagttcgtcgactccgcccccgtgatcgtggacgac*

*cgcaagttccacaagctggacctgaagacgggcgacagcatctgcaacggcctgacccccgctggacggacctggacgtga*

*accagcacgtcaacaacgtgaagtacatcggctggatcctgcagtcggtccccaccgaggtgttcgagacgcaggagctgtgcg*

*gcctgaccctggagtaccgccgcgagtgcggccgcgactccgtgctggagagcgtcacggccatggaccctcgaaggaggg*

*cgaccgctccctgtaccagcacctgctgcgcctggaggacggcgcggacatcgtgaagggccgcaccgagtggcgccccaag*

*aacgccggcgccaagggcgccatcctgacgggcaagaccagcaacggcaactcgatctccatggactacaaggaccacgac*

*ggcgactacaaggaccacgacatcgactacaaggacgacgacgacaag**TGA*aagcttgcagcagcagctcggatagtatcg acacactctggacgctggtcgtgtgatggactgttgccgccacacttgctgccttgacctgtgaatatccctgccgcttttatcaaacagc ctcagtgtgtttgatcttgtgtgtacgcgcttttgcgagttgctagctgcttgtgctatttgcgaataccacccccagcatccccttccctcgt ttcatatcgcttgcatcccaaccgcaacttatctacgctgtcctgctatccctcagcgctgctcctgctcctgctcactgcccctcgcacag ccttggtttgggctcccgcctgtattctcctggtactgcaacctgtaaaccagcactgcaatgctgatgcacgggaagtagtgggatgg gaacacaaatggaaagctggagctcagcgtctgcgtgttgggagctggagtcgtgggcttgacgacggcgctgcagctgttgca

-continued ggatgtgcctggcgtgcgcgttcacgtcgtggctgagaaatatggcgacgaaacgttgacggctggggccggcgggctgtgg atgccatacgcattgggtacgcggccattggatgggattgataggcttatggagggataatagagtttttgccggatccaacgc atgtggatgcggtatcccggtgggctgaaagtgtggaaggatagtgcattggctattcacatgcactgcccacccctttggca ggaaatgtgccggcatcgttggtgcaccgatggggaaaatcgacgttcgaccactacatgaagatttatacgtctgaagatgc agcgactgcgggtgcgaaacggatgacggtttggtcgtgtatgtcacagcatgtgctggatcttgcgggctaactcccctgcc acggcccattgcaggtgtcatgttgactggagggtacgacctttcgtccgtcaaattcccagaggaggacccgctctgggccg acattgtgcccactgaagagc pSZ3493, pSZ3494, and pSZ3495:

pSZ3493 can be written as DAO1b5'::PmHXT1-ScarMEL1-CvNR:PmAMT3-ChsFATB3-CvNR::DAO1b3'. pSZ3494 can be written as DAO1b5'::PmHXT1-ScarMEL1-CvNR:PmAMT3-CpSAD1tp_trimmed:ChsFATB3-CvNR::DAO1b3'. pSZ3495 can be written as DAO1b5'::PmHXT1-ScarMEL1-CvNR: PmAMT3-CpSAD1tp_trimmed:ChtFATB1a-CvNR::DAO1b3'. The sequences of the three constructs differ only in the sequence of the thioesterase gene. The full transforming sequence for pSZ3493 is displayed in SEQ ID NO:124. The sequences of the CpSAD1tp_trimmed:ChsFATB3 and CpSAD1tp_trimmed: ChtFATB1a genes alone, which take the place of ChsFATB3 from pSZ3493 in the pSZ3494 and pSZ3495 sequences, are displayed in SEQ ID NOs:125 and 126, respectively, along with flanking restriction sites.

The relevant restriction sites in the pSZ3493 construct from 5'-3', BspQI, KpnI, SpeI, SnaBI, XhoI, EcoRI, SpeI, XhoI, SacI, BspQI, respectively, are indicated in lowercase, bold, and underlined. BspQI sites delimit the 5' and 3' ends of the transforming DNA. Bold, lowercase sequences at the 5' and 3' end of the construct represent genomic DNA from UTEX 1435 that target integration to the DAO1b locus via homologous recombination. Proceeding in the 5' to 3' direction, the selection cassette has the *P. moriformis* HXT1 promoter driving the expression of the *S. carlbergensis* MEL1 gene (conferring the ability to grow on melibiose) and the *Chlorella vulgaris* Nitrate reductase (NR) gene 3' UTR. The promoter is indicated by lowercase, boxed text. The initiator ATG and terminator TGA for ScarMEL1 are indicated by bold, uppercase italics, while the coding region is indicated with lowercase italics. The 3'UTR is indicated by lowercase, underlined text. The second cassette is comprised of the ChsFATB3 gene driven by the *P. moriformis* AMT3 pH7-responsive promoter and with the *Chlorella vulgaris* Nitrate Reductase (NR) gene 3' UTR. In this cassette, the AMT3 promoter is indicated by lowercase, boxed text. The initiator ATG and terminator TGA for the ChsFATB3 gene are indicated in bold, uppercase italics, while the coding region is indicated by lowercase italics. The 3' UTR is indicated by lowercase, underlined text.

pSZ3493 Transforming Construct:

(SEQ ID NO: 124)

gaagagcGCCCAATGTTTAAACagcccgcaccctcgttgatctgggagccctgcgcagccccttaaatcatctcag tcaggtttctgtgttcaactgagcctaaagggctttcgtcatgcgcacgagcacacgtatatcggccacgcagtttctcaaaagc ggtagaacagttcgcgagccctcgtaggtcgaaaacttgcgccagtactattaaattaaattaattgatcgaacgagacgcga aacttttgcagaatgccaccgagtttgcccagagaatgggagtggcgccattcaccatccgcctgtgcccggcttgattcgccg agacgatggacggcgagaccagggagcggcttgcgagccccgagccggtagcaggaacaatgatcgacaatcttcctgtcc aattactggcaaccattagaaagagccggagcgcgttgaaagtctgcaatcgagtaatttttcgatacgtcgggcctgctgaa ccctaaggctccggactttgtttaaggcgatccaagatgcacgcggccccaggcacgtatctcaagcacaaaccccagcctta gtttcgagactttgggagatagcgaccgatatctagtttggcattttgtatattaattacctcaagcaatggagcgctctgatgcg gtgcagcgtcggctgcagcacctggcagtggcgctagggtcgccctatcgctcggaacctggtcagctggctcccgcctcctgc tcagcctcttccggtaccgcggtgagaatcgaaaatgcatcgtttctaggttcggagacggtcaattccctgctccggcgaatctgtcg gtcaagctggccagtggacaatgttgctatggcagcccgcgcacatgggcctcccgacgcggccatcaggagcccaaacagcgtgt cagggtatgtgaaactcaagaggtccctgctgggcactccggccccactccgggggcgggacgccaggcattcgcggtcggtccc gcgcgacgagcgaaatgatgattcggttacgagaccaggacgtcgtcgaggtcgagaggcagcctcggacacgtctcgctagggc aacgccccgagtccccgcgagggccgtaaacattgtttctgggtgtcggagtgggcattttgggcccgatccaatcgcctcatgccgc tctcgtctggtcctcacgttcgcgtacggcctggatcccggaaagggcggatgcacgtggtgttgccccgccattggcgcccacgttt caaagtccccggccagaaatgcacaggaccggcccggctcgcacaggccatgctgaacgcccagatttcgacagcaacaccatct agaataatcgcaaccatccgcgttttgaacgaaacgaaacggcgctgtttagcatgtttccgacatcgtgggggccgaagcatgctcc -continued gggggggaggaaagcgtggcacagcggtagcccattctgtgccacacgccgacgaggaccaatccccggcatcagccttcatcgac ggctgcgccgcacatataaagccggacgcctaaccggtttcgtggttatgactagtATG*ttcgcgttctacttcctgacggcctgcat*

*ctccctgaagggcgtgttcggcgtctcccccctcctacaacggcctgggcctgacgccccagatgggctgggacaactggaacac*

*gttcgcctgcgacgtctccgagcagctgctgctggacacggccgaccgcatctccgacctgggcctgaaggacatgggctacaa*

*gtacatcatcctggacgactgctggtcctccggccgcgactccgacggcttcctggtcgccgacgagcagaagttccccaacggc*

*atgggccacgtcgccgaccacctgcacaacaactccttcctgttcggcatgtactcctccgcgggcgagtacacgtgcgccggcta*

*ccccggctccctgggccgcgaggaggaggacgcccagttcttcgcgaacaaccgcgtggactacctgaagtacgacaactgct*

*acaacaagggccagttcggcacgcccgagatctcctaccaccgctacaaggccatgtccgacgccctgaacaagacgggccg*

*ccccatcttctactccctgtgcaactggggccaggacctgaccttctactggggctccggcatcgcgaactcctggcgcatgtccgg*

*cgacgtcacggcggagttcacgcgccccgactcccgctgcccctgcgacggcgacgagtacgactgcaagtacgccggcttcc*

*actgctccatcatgaacatcctgaacaaggccgcccccatgggccagaacgcgggcgtcggcggctggaacgacctggacaa*

*cctggaggtcggcgtcggcaacctgacggacgacgaggagaaggcgcacttctccatgtgggccatggtgaagtccccctgat*

*catcggcgcgaacgtgaacaacctgaaggcctcctcctactccatctactcccaggcgtccgtcatcgccatcaaccaggactcc*

*aacggcatccccgccacgcgcgtctggcgctactacgtgtccgacacggacgagtacggccagggcgagatccagatgtggtc*

*cggcccccctggacaacggcgaccaggtcgtggcgctgctgaacggcggctccgtgtcccgccccatgaacacgaccctggagg*

*agatcttcttcgactccaacctgggctccaagaagctgacctccacctgggacatctacgacctgtgggcgaaccgcgtcgacaa*

*ctccacggcgtccgccatcctgggccgcaacaagaccgccacggcatcctgtacaacgccaccgagcagtcctacaaggacg*

*gcctgtccaagaacgacacccgcctgttcggccagaagatcggctccctgtcccccaacgcgatcctgaacacgaccgtccccg*

*cccacggcatcgcgttctaccgcctgcgcccctcctcc*TGAtacgtactcgaggcagcagcagctcggatagtatcgacacactc tggacgctggtcgtgtgatggactgttgccgccacacttgctgccttgacctgtgaatatccctgccgcttttatcaaacagcctcagtgt gtttgatcttgtgtgtacgcgcttttgcgagttgctagctgcttgtgctatttgcgaataccacccccagcatccccttccctcgtttcatatc gcttgcatcccaaccgcaacttatctacgctgtcctgctatccctcagcgctgctcctgctcctgctcactgcccctcgcacagccttggtt tgggctccgcctgtattctcctggtactgcaacctgtaaaccagcactgcaatgctgatgcacgggaagtagtgggatgggaacacaa atggaAAGCTGTAgaattcggccgacaggacgcgcgtcaaaggtgctggtcgtgtatgccctggccggcaggtcgttgctg ctgctggttagtgattccgcaaccctgattttggcgtcttattttggcgtggcaaacgctggcgcccgcgagccgggccggcggcgat gcggtgccccacggctgccggaatccaagggaggcaagagcgcccgggtcagttgaagggctttacgcgcaaggtacagccgct ctgcaaggctgcgtggtggaattggacgtgcaggtcctgctgaagttcctccaccgcctcaccagcggacaaagcaccggtgtatc aggtccgtgtcatccactctaaagaactcgactacgacctactgatggccctagattcttcatcaaaaacgcctgagacacttgcccag gattgaaactccctgaagggaccaccaggggccctgagttgttccttccccccgtggcgagctgccagccaggctgtacctgtgatcg aggctggcgggaaaataggcttcgtgtgctcaggtcatgggaggtgcaggacagctcatgaaacgccaacaatcgcacaattcatgt caagctaatcagctatttcctcttcacgagctgtaattgtcccaaaattctggtctaccgggggtgatccttcgtgtacgggcccttccctc aaccctaggtatgcgcgcatgcggtcgccgcgcaactcgcgcgagggccgagggtttgggacgggccgtcccgaaatgcagttgc acccggatgcgtggcacctttttttgcgataatttatgcaatggactgctctgcaaaattctggctctgtcgccaaccctaggatcagcggc gtaggatttcgtaatcattcgtcctgatggggagctaccgactaccctaatatcagcccgactgcggacgccagcgtccacttttgtgc acacattccattcgtgcccaagacatttcattgtggtgcgaagcgtccccagttacgctcacctgtttcccgacctccttactgttctgtcg acagagcgggcccacaggccggtcgcagccactagtATG*gtggccgccgaggcctcctccgccctgttctccgtgcgcacccc*

*cggcacctcccccaagcccggcaagttcggcaactggcccacctccctgtccgtgcccttcaagtccaagtccaaccacaacgg*

*cggcttccaggtgaaggccaacgcctccgcccgccccaaggccaacggctccgccgtgtccctgaagtccggctccctggacac*

-continued ccaggaggacacctcctcctcctcctcccccccccgcaccttcatcaaccagctgcccgactggtccatgctgctgtccgccatcac caccgtgttcgtggccgccgagaagcagtggaccatgctggaccgcaagtccaagcgccccgacatgctgatggaccccttcgg cgtggaccgcgtggtgcaggacggcgccgtgttccgccagtccttctccatccgctcctacgagatcggcgccgaccgcaccgcc tccatcgagaccctgatgaacatcttccaggagacctccctgaaccactgcaagtccatcggcctgctgaacgacggcttcggcc gcacccccgagatgtgcaagcgcgacctgatctgggtggtgaccaagatgcacgtggaggtgaaccgctaccccacctggggc gacaccatcgaggtgaacacctgggtgtccgagtccggcaagaccggcatgggccgcgactggctgatctccgactgccacac cggcgagatcctgatccgcgccacctccatgtgcgccatgatgaaccagaagacccgccgcttctccaagttcccctacgaggtg cgccaggagctggcccccacttcgtggactccgcccccgtgatcgaggactaccagaagctgcacaagctggacgtgaagac cggcgactccatctgcaacggcctgacccccgctggaacgacctggacgtgaaccagcacgtgaacaagtgaagtacatcg gctggatcctggagtccgtgcccaccgaggtgttcgagacccaggagctgtgcggcctgaccctggagtaccgccgcgagtgcg gccgcgactccgtgctggagtccgtgaccgccatggacccctccaaggagggcgaccgctccctgtaccagcacctgctgcgcc tggaggacggcgccgacatcgccaagggccgcaccaagtggcgccccaagaacgccggcaccaacggcgccatctccaccg gcaagacctccaacggcaactccatctccatggactacaaggaccacgacggcgactacaaggaccacgacatcgactacaa ggacgacgacgacaagTAGctcgaggcagcagcagctcggatagtatcgacacactctggacgctggtcgtgtgatggactgtt gccgccacacttgctgccttgacctgtgaatatccctgccgcttttatcaaacagcctcagtgtgtttgatcttgtgtgtacgcgcttttgcg agttgctagctgcttgtgctatttgcgaataccacccccagcatccccttccctcgtttcatatcgcttgcatcccaaccgcaacttatctac gctgtcctgctatccctcagcgctgctcctgctcctgctcactgcccctcgcacagccttggtttgggctccgcctgtattctcctggtact gcaacctgtaaaccagcactgcaatgctgatgcacgggaagtagtgggatgggaacacaaatggaAAGCTGTATAGGG ATAACAGGGTAATgagctcagcgtctgcgtgttgggagctggagtcgtgggcttgacgacggcgctgcagctgttg caggatgtgcctggcgtgcgcgttcacgtcgtggctgagaaatatggcgacgaaacgttgacggctggggccggcgggctgt ggatgccatacgcattgggtacgcggccattggatgggattgataggcttatggagggataatagagtttttgccggatccaac gcatgtggatgcggtatcccggtgggctgaaagtgtggaaggatagtgcattggctattcacatgcactgcccacccctttgg caggaaatgtgccggcatcgttggtgcaccgatggggaaaatcgacgttcgaccactacatgaagatttatacgtctgaagat gcagcgactgcgggtgcgaaacggatgacggtttggtcgtgtatgtcacagcatgtgctggatcttgcgggctaactcccctg ccacggcccattgcaggtgtcatgttgactggagggtacgacctttcgtccgtcaaattcccagaggaggacccgctctgggcc gacattgtgcccactgaagagc CpSAD1tp_trimmed:ChsFATB3 (from pSZ3494):

(SEQ ID NO: 125)

actagtAACAATGgccaccgcctccaccuctccgcatcaacgcccgctgcggcgacctgcgccgctccgccggctccggcc cccgccgccccgcccgccccctgcccgtgcgcgccgccatcaacgcctccgcccgccccaaggccaacggctccgccgtgt ccctgaagtccggctccctggacacccaggaggacacctcctcctcctcctcccccccccgcaccacatcaaccagctgcc cgactggtccatgctgctgtccgccatcaccaccgtgacgtggccgccgagaagcagtggaccatgctggaccgcaagtcc aagcgccccgacatgctgatggaccccacggcgtggaccgcgtggtgcaggacggcgccgtgaccgccagtccactccatc cgctcctacgagatcggcgccgaccgcaccgcctccatcgagaccctgatgaacatcaccaggagacctccctgaaccact gcaagtccatcggcctgctgaacgacggcttcggccgcacccccgagatgtgcaagcgcgacctgatctgggtggtgacca agatgcacgtggaggtgaaccgctaccccacctggggcgacaccatcgaggtgaacacctgggtgtccgagtccggcaaga ccggcatgggccgcgactggctgatctccgactgccacaccggcgagatcctgatccgcgccacctccatgtgcgccatga tgaaccagaagacccgccgcttctccaagacccctacgaggtgcgccaggagctggcccccacttcgtggactccgcccc cgtgatcgaggactaccagaagctgcacaagctggacgtgaagaccggcgactccatctgcaacggcctgacccccgctg -continued gaacgacctggacgtgaaccagcacgtgaacaacgtgaagtacatcggctggatcctggagtccgtgcccaccgaggtgtt cgagacccaggagctgtgcggcctgaccctggagtaccgccgcgagtgcggccgcgactccgtgctggagtccgtgaccgc catggacccctccaaggagggcgaccgctccctgtaccagcacctgctgcgcctggaggacggcgccgacatcgccaaggg ccgcaccaagtggcgccccaagaacgccggcaccaacggcgccatctccaccggcaagacctccaacggcaactccatctc catggactacaaggaccacgacggcgactacaaggaccacgacatcgactacaaggacgacgacgacaag*TGA*<u>ctcgag</u>

CpSAD1tp_trimmed:ChtFATB1a (from pSZ3495):

(SEQ ID NO: 126)

<u>actagt</u>AACA*ATG*gccaccgcctccaccttctccgccttcaacgcccgctgcggcgacctgcgccgctccgccggctccgg cccccgccgccccgcccgcccccctgcccgtgcgcgccgccatcaacgcctccgcccaccccaaggccaacggctccgccgt gaacctgaagtccggctccctggagacccaggaggacacctcctcctcctcccccccccccgcaccacatcaagcagctg cccgactggggcatgctgctgtccaagatcaccaccgtgacggcgccgccgagcgccagtggaagcgccccggcatgctgg tggagcccacggcgtggaccgcatcaccaggacggcgtocaccgccagtccactccatccgctcctacgagatcggcgccg accgcaccgcctccatcgagaccctgatgaacatcaccaggagacctccctgaaccactgcaagtccatcggcctgctgaa cgacggcttcggccgcacccccgagatgtgcaagcgcgacctgatctgggtggtgaccaagatccaggtggaggtgaaccg ctaccccacctggggcgacaccatcgaggtgaacacctgggtgtccgagtccggcaagaacggcatgggccgcgactggct gatctccgactgccgcaccggcgagatcctgatccgcgccacctccgtgtgggccatgatgaaccgcaagacccgccgcct gtccaagacccctacgaggtgcgccaggagatcgcccccccacttcgtggactccgcccccgtgatcgaggacgacaagaag ctgcacaagctggacgtgaagaccggcgactccatccgcaagggcctgacccccgctggaacgacctggacgtgaaccag cacgtgaacaacgtgaagtacatcggctggatcctgaagtccgtgcccgccgaggtgacgagacccaggagctgtgcggcg tgaccctggagtaccgccgcgagtgcggccgcgactccgtgctggagtccgtgaccgccatggacaccgccaaggagggcg accgctccctgtaccagcacctgctgcgcctggaggacggcgccgacatcaccatcggccgcaccgagtggcgccccaaga acgccggcgccaacggcgccatctccaccggcaagacctccaacgagaactccgtgtccatggactacaaggaccacgacg gcgactacaaggaccacgacatcgactacaaggacgacgacgacaag*TGA*<u>ctcgag</u> pSZ3531:

pSZ3531 can be written as THI4A::PmHXT1-ScarMel1-CpEF1a:PmUAPA1noSacI-CpSAD1tpExt-Cpa1FATB2FLAGExtA-CvNR::THI4A. The relevant restriction sites in the construct from 5'-3', BspQI, KpnI, SpeI, SnaBI, EcoRV, EcoRI, SpeI, HindIII, SacI, BspQI, respectively, are indicated in lowercase, bold, and underlined. BspQI sites delimit the 5' and 3' ends of the transforming DNA. Bold, lowercase sequences at the 5' and 3' end of the construct represent genomic DNA from UTEX 1435 that target integration to the THI4A locus via homologous recombination. Proceeding in the 5' to 3' direction, the selection cassette has the *P. moriformis* HXT1 promoter driving the expression of the *S. carlbergensis* MEL1 gene (conferring the ability to grow on melibiose) and the *Chlorella protothecoides* EF1A gene 3' UTR. The promoter is indicated by lowercase, boxed text. The initiator ATG and terminator TGA for ScarMEL1 are indicated by bold, uppercase italics, while the coding region is indicated with lowercase italics. The 3'UTR is indicated by lowercase, underlined text. The second cassette containing the CpSAD1tpExt-Cpa1FATB2FLAGExtA gene, fused to the heterologous *Chlorella protothecoides* SAD1 plastid-targeting transit peptide, is driven by the *P. moriformis* UAPA1 pH5-responsive promoter and has the *Chlorella vulgaris* Nitrate Reductase (NR) gene 3' UTR. In this cassette, the UAPA1 promoter is indicated by lowercase, boxed text. The initiator ATG and terminator TGA for the CpSAD1tpExt-Cpa1FATB2FLAGExtA gene are indicated in bold, uppercase italics, while the coding region is indicated by lowercase italics. The 3' UTR is indicated by lowercase, underlined text.

pSZ3531 Transforming Construct:

(SEQ ID NO: 127)

<u>gaagagc</u>GCCCAATGTTTAAACCcctcaactgcgacgctgggaaccttctccgggcaggcgatgtgcgtgggttt gcctccttggcacggctctacaccgtcgagtacgccatgaggcggtgatggctgtgtcggttgccacttcgtccagagacggca agtcgtccatcctctgcgtgtgtggcgcgacgctgcagcagtccctctgcagcagatgagcgtgactttggccatttcacgcact cgagtgtacacaatccatttttcttaaagcaaatgactgctgattgaccagatactgtaacgctgatttcgctccagatcgcaca gatagcgaccatgttgctgcgtctgaaaatctggattccgaattcgaccctggcgctccatccatgcaacagatggcgacactt

-continued gttacaattcctgtcacccatcggcatggagcaggtccacttagattcccgatcacccacgcacatctcgctaatagtcattcgtt cgtgtcttcgatcaatctcaagtgagtgtgcatggatcttggttgacgatgcggtatgggtttgcgccgctggctgcagggtctg cccaaggcaagctaacccagctcctctccccgacaatactctcgcaggcaaagccggtcacttgccttccagattgccaataa actcaattatggcctctgtcatgccatccatgggtctgatgaatggtcacgctcgtgtcctgaccgttccccagcctctggcgtcc cctgccccgcccaccagcccacgccgcgcggcagtcgctgccaaggctgtctcggaggtaccgcggtgagaatcgaaaatgca tcgtttctaggttcggagacggtcaattccctgctccggcgaatctgtcggtcaagctggccagtggacaatgttgctatggcagcccg cgcacatgggcctcccgacgcggccatcaggagcccaaacagcgtgtcagggtatgtgaaactcaagaggtccctgctgggcactc cggccccactccgggggcgggacgccaggcattcgcggtcggtcccgcgcgacgagcgaaatgatgattcggttacgagaccag gacgtcgtcgaggtcgagaggcagcctcggacacgtctcgctagggcaacgccccgagtccccgcgagggccgtaaacattgtttc tgggtgtcggagtgggcattttgggcccgatccaatcgcctcatgccgctctcgtctggtcctcacgttcgcgtacggcctggatcccg gaaagggcggatgcacgtggtgttgccccgccattggcgcccacgtttcaaagtccccggccagaaatgcacaggaccggcccgg ctcgcacaggccatgctgaacgcccagatttcgacagcaacaccatctagaataatcgcaaccatccgcgttttgaacgaaacgaaac ggcgctgtttagcatgtttccgacatcgtgggggccgaagcatgctccgggggggaggaaagcgtggcacagcggtagcccattctgt gccacacgccgacgaggaccaatccccggcatcagccttcatcgacggctgcgccgcacatataaagccggacgcctaaccggttt cgtggttatg**actagt*ATG***_ttcgcgttctacttcctgacggcctgcatctccctgaagggcgtgttcggcgtctcccccctcctacaac_

_ggcctgggcctgacgccccagatgggctgggacaactggaacacgttcgcctgcgacgtctccgagcagctgctgctggacacg_

_gccgaccgcatctccgacctgggcctgaaggacatgggctacaagtacatcatcctggacgactgctggtcctccggccgcgact_

_ccgacggcttcctggtcgccgacgagcagaagttccccaacggcatgggccacgtcgccgaccacctgcacaacaactccttcc_

_tgttcggcatgtactcctccgcgggcgagtacacgtgcgccggctaccccggctccctgggccgcgaggaggaggacgcccagt_

_tcttcgcgaacaaccgcgtggactacctgaagtacgacaactgctacaacaagggccagttcggcacgcccgagatctcctacc_

_accgctacaaggccatgtccgacgccctgaacaagacgggccgccccatcttctactccctgtgcaactggggccaggacctga_

_ccttctactggggctccggcatcgcgaactcctggcgcatgtccggcgacgtcacggcggagttcacgcgccccgactcccgctg_

_cccctgcgacggcgacgagtacgactgcaagtacgccggcttccactgctccatcatgaacatcctgaacaaggccgcccccat_

_gggccagaacgcgggcgtcggcggctggaacgacctggacaacctggaggtcggcgtcggcaacctgacggacgacgagg_

_agaaggcgcacttctccatgtgggccatggtgaagtccccccctgatcatcggcggcgcgaacgtgaacaacctgaaggcctcctccta_

_ctccatctactcccaggcgtccgtcatcgccatcaaccaggactccaacggcatccccgccacgcgcgtctggcgctactacgtgt_

_ccgacacggacgagtacggccagggcgagatccagatgtggtccggccccctggacaacggcgaccaggtcgtggcgctgct_

_gaacggcggctccgtgtcccgccccatgaacacgaccctggaggagatcttcttcgactccaacctgggctccaagaagctgac_

_ctccacctgggacatctacgacctgtgggcgaaccgcgtcgacaactccacggcgtccgccatcctgggccgcaacaagaccg_

_ccaccggcatcctgtacaacgccaccgagcagtcctacaaggacggcctgtccaagaacgacacccgcctgttcggccagaag_

_atcggctccctgtcccccaacgcgatcctgaacacgaccgtccccgcccacggcatcgcgttctaccgcctgcgcccctcctcc_*T*

*GA*TACAACTTATtacgta_acggagcgtcgtgcgggagggagtgtgccgagcggggagtcccggtctgtgcgaggccc_

_ggcagctgacgctggcgagccgtacgccccgagggtcccccctcccctgcaccctcttccccttccctctgacggccgcgcctgttct_

_tgcatgttcagcgacgag_gatatcgaattcatagcgactgctacccccccgaccatgtgccgaggcagaaattatatacaagaagca gatcgcaattaggcacatcgctttgcattatccacacactattcatcgctgctgcggcaaggctgcagagtgtatttttgtggcccaggag ctgagtccgaagtcgacgcgacgagcggcgcaggatccgaccccctagacgagcactgtcattttccaagcacgcagctaaatgcgc -continued tgagaccgggtctaaatcatccgaaaaagtgtcaaaatggccgattgggttcgcctaggacaatgcgctgcggattcgctcgagtccgc tgccggccaaaaggcggtggtacaggaaggcgcacggggccaaccctgcgaagccgggggcccgaacgccgaccgccggcct tcgatctcgggtgtccccctcgtcaatttcctctctcgggtgcagccacgaaagtcgtgacgcaggtcacgaaatccggttacgaaaaa cgcaggtcttcgcaaaaacgtgagggtttcgcgtctcgccctagctattcgtatcgccgggtcagacccacgtgcagaaaagcccttg aataacccgggaccgtggttaccgcgccgcctgcaccagggggcttatataagcccacaccacacctgtctcaccacgcatttctcca actcgcgacttttcggaagaaattgttatccacctagtatagactgccacctgcaggaccttgtgtcttgcagtttgtattggtcccggccg tcgagcacgacagatctgggctagggttggcctggccgctcggcactcccctttagccgcgcgcatccgcgttccagaggtgcgatt cggtgtgtggagcattgtcatgcgcttgtgggggtcgttccgtgcgcggcgggtccgccatgggcgccgacctgggccctagggttt gttttcgggccaagcgagcccctctcacctcgtcgcccccccgcattccctctctcttgcagcCactagtAACA*ATG**gccaccg*

*catccactttctcggcgttcaatgcccgctgcggcgacctgcgtcgctcggcgggctccgggccccggcgcccagcgaggcccct*

*ccccgtgcgcgctgccatcgccagcgaggtccccgtggccaccacctcccccgggcgcaccccaaggcgaacggcagcgcg*

*gtgtcgctgaagtcgggctccctggagacccaggaggacaagacgagcagctcgtccccccccccccgcacgttcatcaacca*

*gctgcccgtgtggagcatgctgctgtcggcggtgaccacggtcttcggcgtggccgagaagcagtggcccatgctggaccgcaa*

*gtccaagcgccccgacatgctggtcgagcccctgggcgtggaccgcatcgtctacgacggcgtgagcttccgccagtcgttctcc*

*atccgcagctacgagatcggcgccgaccgcaccgcctcgatcgagacgctgatgaacatgttccaggagacctccctgaaccac*

*tgcaagatcatcggcctgctgaacgacggcttcggccgcacgcccgagatgtgcaagcgcgacctgatctgggtcgtgaccaag*

*atgcagatcgaggtgaaccgctaccccacgtggggcgacaccatcgaggtcaacacgtgggtgagcgcctcgggcaagcacg*

*gcatgggccgcgactggctgatctccgactgccacaccggcgagatcctgatccgcgcgacgagcgtctgggcgatgatgaacc*

*agaagacccgccgcctgtcgaagatcccctacgaggtgcgccaggagatcgagccccagttcgtcgactccgcccccgtgatcg*

*tggacgaccgcaagttccacaagctggacctgaagacgggcgacagcatctgcaacggcctgaccccccgctggacggacct*

*ggacgtgaaccagcacgtcaacaacgtgaagtacatcggctggatcctgcagtcggtccccaccgaggtgttcgagacgcagg*

*agctgtgcggcctgaccctggagtaccgccgcgagtgcggccgcgactccgtgctggagagcgtcacggccatggacccctcg*

*aaggagggcgaccgctccctgtaccagcacctgctgcgcctggaggacggcgcggacatcgtgaagggccgcaccgagtggc*

*gccccaagaacgccggcgccaagggcgccatcctgacgggcaagaccagcaacggcaactcgatctccatggactacaagg*

*accacgacggcgactacaaggaccacgacatcgactacaaggacgacgacgacaag**TGA*aagcttgcagcagcagctcg gatagtatcgacacactctggacgctggtcgtgtgatggactgttgccgccacacttgctgccttgacctgtgaatatccctgccgcttttt atcaaacagcctcagtgtgtttgatcttgtgtgtacgcgcttttgcgagttgctagcttgcttgtgctatttgcgaataccacccccagcatcc ccttccctcgtttcatatcgcttgcatcccaaccgcaacttatctacgctgtcctgctatccctcagcgctgctcctgctcctgctcactgcc cctcgcacagccttggtttgggctcccgcctgtattctcctggtactgcaacctgtaaaccagcactgcaatgctgatgcacgggaagta gtgggatgggaacacaaatggaaagctggagctccagcgccatgccacgccctttgatggcttcaagtacgattacggtgttgg attgtgtgtttgttgcgtagtgtgcatggtttagaataatacacttgatttcttgctcacggcaatctcggcttgtccgcaggttcaa ccccatttcggagtctcaggtcagccgcgcaatgaccagccgctacttcaaggacttgcacgacaacgccgaggtgagctatg tttaggacttgattggaaattgtcgtcgacgcatattcgcgctccgcgacagcacccaagcaaaatgtcaagtgcgttccgattt gcgtccgcaggtcgatgttgtgatcgtcggcgccggatccgccggtctgtcctgcgcttacgagctgaccaagcaccctgacgt ccgggtacgcgagctgagattcgattagacataaattgaagattaaacccgtagaaaaatttgatggtcgcgaaactgtgctc gattgcaagaaattgatcgtcctccactccgcaggtcgccatcatcgagcagggcgttgctcccggcggcggcgcctggctgg ggggacagctgttctcggccatgtgtgtacgtagaaggatgaatttcagctggttttcgttgcacagctgtttgtgcatgatttgtt tcagactattgttgaatgtttttagatttcttaggatgcatgatttgtctgcatgcgactgaagagc

Increased C12:0 Levels in Strain S5818 by the Expression of Heterologous "C14:0-Specific" Thioesterases.

In an effort to increase C14:0 fatty acid levels in S5818, several thioesterases that had previously displayed pronounced C14:0 thioesterase activity in *P. moriformis* were transformed into the S5818 background. Contrary to our expectations, we observed marked increases in C12:0 levels with decreases or only marginal increases in C14:0 levels. For example, introduction of the ChsFATB3 thioesterase (which leads to an increase in C14:0 levels of up to 34% in S3150) into S5818 causes C12:0 levels to rise to ~77% (Δ=+32% C12:0) and C14:0 levels to drop to ~7% (Δ=−7%). In addition, introduction of Cpa1FATB2 into S5818 at the DAO1b locus causes C12:0 levels to rise to ~64% (Δ=+19%) and C14:0 levels to drop to ~12% (Δ=−2%). The results for the top five transformants for each of the five constructs are displayed in Table 83.

TABLE 83

Fatty acid profiles for the top 5 transformants for each of the pSZ3493, pSZ3494, pSZ3495, pSZ3390, and pSZ3531 constructs upon introduction into S5818.

| | Sample ID | | | | | | | |
|---|---|---|---|---|---|---|---|---|
| pSZ#; construct | Strain # | C10:0 | C12:0 | C14:0 | C16:0 | C18:0 | C18:1 | C18:2 |
| N/A | S5818 | 0.34 | 45.16 | 13.77 | 8.54 | 0.81 | 24.63 | 5.38 |
| pSZ3493; ChsFATB3 | Block 6; C6; pH 7; S5818; T678; D2202-30 | 0.76 | 76.58 | 7.49 | 3.76 | 0.32 | 6.58 | 3.77 |
| | Block 6; D6; pH 7; S5818; T678; D2202-42 | 0.61 | 62.82 | 13.92 | 6.75 | 0.37 | 10.76 | 3.88 |
| | Block 6; D11; pH 7; S5818; T678; D2202-47 | 4.60 | 55.99 | 9.26 | 5.90 | 0.44 | 18.32 | 4.40 |
| | Block 6; A9; pH 7; S5818; T678; D2202-9 | 0.47 | 53.94 | 17.59 | 8.51 | 0.44 | 13.70 | 4.33 |
| | Block 6; D3; pH 7; S5818; T678; D2202-39 | 0.43 | 53.94 | 15.62 | 8.04 | 0.43 | 15.99 | 4.45 |
| pSZ3494; CpSAD1tp__trimmed:ChsFATB3 | Block 2; B8; pH 7; S5818; T678; D2203-20 | 0.43 | 56.76 | 14.15 | 7.60 | 0.56 | 14.23 | 5.09 |
| | Block 2; C1; pH 7; S5818; T678; D2203-25 | 0.46 | 54.82 | 17.03 | 7.81 | 0.46 | 13.67 | 4.85 |
| | Block 2; D1; pH 7; S5818; T678; D2203-37 | 0.43 | 54.47 | 11.51 | 8.14 | 0.95 | 18.58 | 4.99 |
| | Block 2; D7; pH 7; S5818; T678; D2203-43 | 0.43 | 52.86 | 18.70 | 8.91 | 0.58 | 13.18 | 4.45 |
| | Block 2; C11; pH 7; S5818; T678; D2203-35 | 0.44 | 52.81 | 19.54 | 8.87 | 0.54 | 12.57 | 4.29 |
| pSZ3495; CpSAD1tp__trimmed:ChtFATB1a | Block 2; G10; pH 7; S5818; T678; D2204-34 | 0.58 | 55.18 | 19.86 | 7.72 | 0.60 | 10.88 | 4.29 |
| | Block 2; H7; pH 7; S5818; T678; D2204-43 | 0.68 | 54.79 | 20.14 | 7.78 | 0.56 | 10.99 | 4.18 |
| | Block 2; H5; pH 7; S5818; T678; D2204-41 | 0.60 | 54.69 | 20.38 | 7.39 | 0.55 | 11.50 | 4.13 |
| | Block 2; G8; pH 7; S5818; T678; D2204-32 | 0.66 | 54.26 | 20.39 | 7.69 | 0.55 | 11.45 | 4.26 |
| | Block 2; F6; pH 7; S5818; T678; D2204-18 | 0.67 | 54.23 | 20.04 | 7.60 | 0.56 | 11.80 | 4.23 |
| pSZ3390; CpSAD1tpExt-CpalFATB2FLAGExtA (DAO1b) | Block 4; A5 pH 7; S5818; T674; D2104-5 | 0.58 | 63.83 | 12.10 | 5.89 | 0.55 | 10.46 | 5.44 |
| | Block 4; A12; pH 7; S5818; T674; D2104-12 | 0.48 | 61.92 | 16.15 | 5.87 | 0.50 | 9.86 | 4.41 |
| | Block 4; B9; pH 7; S5818; T674; D2104-21 | 0.41 | 54.31 | 18.41 | 7.26 | 0.51 | 13.80 | 4.49 |
| | Block 4; B5; pH 7; S5818; T674; D2104-17 | 0.37 | 53.56 | 16.54 | 7.25 | 0.58 | 16.34 | 4.42 |
| | Block 4; B11; pH 7; S5818; T674; D2104-23 | 0.41 | 52.44 | 17.99 | 7.60 | 0.54 | 15.38 | 4.66 |
| pSZ3531; CpSAD1tpExt-CpalFATB2FLAGExtA (THI4A) | Block 5B; A8; pH 7; S5818; T684; D2235-8 | 0.52 | 59.36 | 15.70 | 6.93 | 0.45 | 11.41 | 4.63 |
| | Block 5B; A12; pH 7; S5818; T684; D2235-12 | 0.44 | 55.60 | 16.98 | 6.98 | 0.53 | 14.21 | 4.59 |
| | Block 5B; B11; pH 7; S5818; T684; D2235-23 | 0.36 | 49.58 | 17.43 | 8.72 | 0.57 | 17.44 | 4.62 |
| | Block 5B; A4; pH 7; S5818; T684; D2235-4 | 0.35 | 49.43 | 18.63 | 8.22 | 0.62 | 17.29 | 4.54 |
| | Block 5B; A11; pH 7; S5818; T684; D2235-11 | 0.36 | 48.92 | 15.93 | 7.84 | 0.68 | 20.38 | 4.96 |

Of note, S5818 expresses the *C. wrightii* KASAI gene from the pLOOP locus. As *C. wrightii* produces seed oil with 62% C12:0, we believe it likely that the CwKASA1 gene has evolved to be specific for production of C12:0 fatty acids when combined with *C. wrightii* thioesterases. Indeed, *C. wrightii* FATB2 encodes a thioesterase that exhibits C12:0 activity when introduced into *P. moriformis*. Thus, it is possible that the "C14:0" thioesterase genes identified in our transcriptome sequencing, namely ChsFATB3 and ChtFATB1a, exhibit C14:0 activity only when in combination with the *P. moriformis* endogenous KASI gene. These results further extend to Cpa1FATB2, which has been repeatedly shown to increase C14:0 levels in *P. moriformis* (data not shown). However, when ChsFATB3, ChtFATB1a, and Cpa1FATB2 are combined with a KASI gene from a *Cuphea* species that produces high C12:0 fatty acids, such as CwKASA1 from *Cuphea wrightii*, then a C12:0 activity of these thioesterases is revealed/exhibited. It should be further noted that *C. hyssopifolia* and *C. heterophylla* produce only low levels of C14:0 in oilseeds (5% and 4%, respectively) while producing relatively high levels of C12:0 (84% and 40%, respectively). Since the ChsFATB3 and ChtFATB1a thioesterases were identified from RNAs expressed in mature oil seeds, it is possible that these thioesterases indeed exhibited C12:0 activity in *Cuphea* seeds, significantly contributing to the high levels of C12:0 found therein.

Our results indicate that the combination of thioesterase and KAS is likely to be extremely important in determining the specificity of the thioesterase-KAS machinery in generating midchain fatty acids. Furthermore, introduction of heterologous KASs may be an important and fruitful approach for revealing novel specificities of additional heterologous thioesterases.

Example 63: A Suite of Regulatable Promoters to Conditionally Control Gene Expression Levels in Oleaginous Cells in Synchrony with Lipid Production S5204 was generated by knocking out both copies of FATA1 in *Prototheca moriformis* (PmFATA1) while simultaneously overexpressing the endogenous PmKASII gene in a Δfad2 line, 52532. S2532 itself is a FAD2 (also known as FADc) double knockout strain that was previously generated by insertion of *C. tinctorius* ACP thioesterase (Accession No: AAA33019.1) into 51331, under the control of CrTUB2 promoter at the FAD2 locus. S5204 and its parent S2532 have a disrupted endogenous PmFAD2-1 gene resulting in no Δ12 specific desaturase activity manifested as 0% C18:2 (linoleic acid) levels in both seed and lipid production stages. Lack of any C18:2 in S5204 (and its parent S2532) results in growth defects which can be partially mitigated by exogenous addition of linoleic acid in the seed stage. For industrial applications of a zero linoleic oil however, exogenous addition of linoleic acid entails additional cost. We have previously shown that complementation of S5204 (and other Δfad2 strains S2530 and S2532) with pH inducible AMT03p driven PmFAD2-1 restores C18:2 to wild-type levels at pH 7.0 and also results in rescued growth characteristics during seed stage without any linoleic supplementation. Additionally when the seed from pH 7.0 grown complemented lines is subsequently transferred into low-nitrogen lipid production flasks with pH adjusted to 5.0 (to control AMT03p driven FAD2 protein levels), the resulting final oil profile matches the parent S5204 or S2532 profile with zero linoleic levels but with rescued growth and productivity metrics. Thus in essence with AMT03p driven FAD2-1 we have developed a pH regulatable strain that potentially could be used to generate oils with varying linoleic levels depending on the desired application.

*Prototheca moriformis* undergoes rapid cell division during the first 24-30 hrs in fermenters before nitrogen runs out in the media and the cells switch to storing lipids. This initial cell division and growth in fermenters is critical for the overall strain productivity and, as reported above, FAD2 protein is crucial for sustaining vigorous growth characteristic of a particular strain. However when first generation, single insertion, genetically clean, PmFAD2-1 complemented strains (S4694 and S4695) were run in 7 L fermenters at pH 5.0 (with seed grown at pH 7.0), they did not perform on par with the original parent base strain (S1331) in terms of productivity. Western data suggested that AMT03p promoter driving PmFAD2-1 (as measured by FAD2 protein levels) is severely down regulated between 0-30 hrs in fermenters irrespective of fermenter pH (5.0 or 7.0). Work on fermentation conditions (batched vs unbatched/limited initial N, pH shift from 7 to 5 at different time points during production phase) suggested that initial batching (and excess amounts) of nitrogen during early lipid production was the likely cause of AMT03p promoter down regulation in fermenters. Indeed, this initial repression in AMT03 can be directly seen in transcript time-course during fermentation. A significant depression of Amt03 expression was observed early in the run, which corresponds directly with $NH_4$ levels in the fermenter.

When the fermentations were performed with limited N, we were able to partially rescue the AMT03p promoter activity and while per cell productivity of S4694/S4695 was on par with the parent S1331, the overall productivity still lagged behind. These results suggest that a suboptimal or inactive AMT03p promoter and thus limitation of FAD2 protein in early fermentation stages inhibits any complemented strains from attaining their full growth potential and overall productivity. Here we identify new, improved promoter that allow differential gene activity during high-nitrogen growth and low-nitrogen lipid production phases.

In particular, we observed that:

In trans expression of the fatty acid desaturase-2 gene from *Prototheca moriformis* (PmFad2-1) under the control of down regulated promoter elements identified using a transcriptome based bioinformatics approach results in functional complementation of PmFAD2-1 with restored growth in Δfad2, Δfata1 strain S5204.

Complementation of S5204 manifested in a robust growth phenotype only occurs in seed and early fermentation stages when the new promoter elements are actively driving the expression of PmFAD2-1.

Once the cells enter the active lipid production phase (around the time when N runs out in the fermenter), the newly identified promoters are down regulated resulting in no additional FAD2 protein and the final oil profile of the complemented lines is same as the parent S5204 albeit with better growth characteristics.

These strains should potentially mitigate the problems that were encountered with AMT03p driven FAD2 in earlier complemented strains.

Importantly, we have identified down-regulatable promoters of varying strengths, some of which are relatively strong in the beginning with low-to-moderate levels provided during the remainder of the run. Thus depending on phenotype these promoters can be selected for fine-tuning the desired levels of transgenes.

Bioinformatics Methods:

RNA was prepared from cells taken from 8 time points during a typical fermenter run. RNA was polyA-selected for run on an Illumina HiSeq. Illumina paired-end data (100 bp reads×2, ~600 bp fragment size) was collected and processed for read quality using FastQC [www.bioinformatics.babraham.ac.uk/projects/fastqc/]. Reads were run through a custom read-processing pipeline that de-duplicates, quality-trims, and length-trims reads.

Transcripts were assembled from Illumina paired-end reads using Oases/velvet [Velvet: algorithms for de novo short read assembly using de Bruijn graphs. D. R. Zerbino and E. Birney. Genome Research 18:821-829] and assessed by N50 and other metrics. The transcripts from all 8 time points were further collapsed using CD-Hit. [Limin Fu, Beifang Niu, Zhengwei Zhu, Sitao Wu and Weizhong Li, CD-HIT: accelerated for clustering the next generation sequencing data. Bioinformatics, (2012), 28 (23): 3150-3152. doi: 10.1093/bioinformatics/bts565; Cd-hit: a fast program for clustering and comparing large sets of protein or nucleotide sequences", Weizhong Li & Adam Godzik Bioinformatics, (2006) 22:1658-9].

These transcripts were used as the base (reference assembly) for expression-level analysis. Reads from the 8 time points were analyzed using RSEM which provides raw read counts as well as a normalized value provided in Transcripts Per Million (TPM). [Li, Bo & Dewey, Colin N. (2011). RSEM: accurate transcript quantification from RNA-Seq data with or without a reference genome, BioMed Central: The Open Access Publisher. Retrieved at Oct. 10, 2012, from the website temoa: Open Educational Resources (OER) Portal at www.temoa.info/node/441614] The TPM was used to determine expression levels. Genes previously identified in screens for strong promoters were also used to gauge which levels should be considered as significantly high or low. This data was loaded into a Postgres database and visualized with Spotfire, along with integrated data that includes gene function and other characteristics such as categorization based on expression profile. This enabled rapid and targeted analysis of genes with significant changes in expression.

The promoters for genes, which we selected, were mapped onto a high-quality reference genome for S376 (our reference *Prototheca moriformis* strain). Briefly, PacBio long reads (~2 kb) were error-corrected by high-quality PacBio CCS reads (~600 bp) and assembled using the Allora assembler in SMRTPipe [pacbiodevnet.com]. This reference genome, in conjunction with transcriptome read mapping, was used to annotate the precise gene structures, promoter and UTR locations, and promoter elements within the region of interest, which then guided further sequencing and promoter element selection.

The criteria used for identifying new promoter elements were:

1. Reasonable expression (e.g., >500, <100, or <50 transcripts per million [TPM]) of a downstream gene in seed and early lipid production stages (T0-T30 hrs)
2. Severe down regulation of the gene above (e.g., >5-fold. 10-fold, or 15-fold) when the nitrogen gets depleted in the fermenters.
3. pH neutrality of the promoter elements (e.g., less than a 2-fold change in TPM on going from pH 5.0 top 7.0 in cultivation conditions), or at least effective operation under pH5 conditions.

Using the above described criteria we identified several potentially down regulated promoter elements that were eventually used to drive PmFAD2-1 expression in S5204. A range of promoters was chosen that included some that started as being weak promoters and went down to extremely low levels, through those that started quite high and dropped only to moderately low levels. This was done because it was unclear a priori how much expression would be needed for FAD2 early on to support robust growth, and how little FAD2 would be required during the lipid production phase in order to achieve the zero linoleic phenotype.

The promoter elements that were selected for screening and their allelic forms were named after their downstream gene and are as follows:

1. Carbamoyl phosphate synthase (PmCPS1p and PmCPS2p)
2. Dipthine synthase (PmDPS1p and PmDPS2p)
3. Inorganic pyrophosphatase (PmIPP1p)
4. Adenosylhomocysteinase (PmAHC1p and PmAHC2p)
5. Peptidyl-prolyl cis-trans isomerase (PmPPI1p and PmPPI2p)
6. GMP Synthetase (PmGMPS1p and PmGMPS2p)
7. Glutamate Synthase (PmGSp)
8. Citrate Synthase (PmCS1p and PmCS2p)
9. Gamma Glutamyl Hydrolase (PmGGH1p)
10. Acetohydroxyacid Isomerase (PmAHI1p and PmAHI2p)
11. Cysteine Endopeptidase (PmCEP1p)
12. Fatty acid desaturase 2 (PmFAD2-1p and PmFad2-2p) [CONTROL]

The transcript profile of two representative genes viz. PmIPP (Inorganic Pyrophosphatase) and PmAHC, (Adenosylhomocysteinase) start off very strong (4000-5000 TPM) but once the cells enter active lipid production their levels fall off very quickly. While the transcript levels of PmIPP drop off to nearly 0 TPM, the levels of PmAHC drop to around 250 TPM and then stay steady for the rest of the fermentation. All the other promoters (based on their downstream gene transcript levels) showed similar downward expression profiles.

The elements were PCR amplified and wherever possible promoters from allelic genes were identified, cloned and named accordingly e.g. the promoter elements for 2 genes of Carbamoyl phosphate synthase were named PmCPS1p and PmCPS2p. As a comparator promoter elements from PmFAD2-1 and PmFAD2-2 were also amplified and used to drive PmFAD2-1 gene. While, in the present example, we used FAD2-1 expression and hence C18:2 levels to interrogate the newly identified down regulated promoters, in principle these promoter elements can be used to down regulate any gene of interest.

Construct Used for the Expression of the *Prototheca moriformis* Fatty Acid Desaturase 2 (PmFAD2-1) Under the Expression of PmCPS1p in Δfad2 Strains S5204-[pSZ3377]:

The Δfad2 Δfata1 S5204 strain was transformed with the construct pSZ3377. The sequence of the transforming DNA is provided below. Relevant restriction sites in the construct pSZ3377 (6S::PmHXT1p-ScMEL1-CvNR::PmCPS1p-PmFAD2-1-CvNR::6S) are indicated in lowercase, underlined and bold, and are from 5'-3' BspQ 1, KpnI, SpeI, SnaBI, EcoRV, SpeI, AflII, Sad, BspQ I, respectively. BspQI sites delimit the 5' and 3' ends of the transforming DNA. Bold, lowercase sequences represent genomic DNA from UTEX 1435 that permits targeted integration of the transforming DNA at the 6S locus via homologous recombination. Proceeding in the 5' to 3' direction, the Hexose transporter (HXT1) gene promoter from UTEX 1435 driving the expression of the *Saccharomyces cerevisiae* Melibiase (ScMEL1) gene is indicated by the boxed text. The initiator ATG and terminator TGA for ScMEL1 are indicated by uppercase, bold italics while the coding region is indicated in lowercase italics. The *Chlorella vulgaris* nitrate reductase 3' UTR is indicated by lowercase underlined text followed by an UTEX 1435 CPS1p promoter of *Prototheca moriformis*, indicated by boxed italics text. The Initiator ATG and terminator TGA codons of the PmFAD2-1 are indicated by uppercase, bold italics, while the remainder of the gene is indicated by bold italics. The *C. vulgaris* nitrate reductase 3' UTR is again indicated by lowercase underlined text followed by the UTEX 1435 6S genomic region indicated by bold, lowercase text. The final construct was sequenced to ensure correct reading frames and targeting sequences.

Nucleotide sequence of transforming DNA contained in plasmid pSZ3377:

(SEQ ID NO: 128)

<u>gctcttc</u>ggagtcactgtgccactgagttcgactggtagctgaatggagtcgctgctccactaaacgaattgtcagcaccgcca gccggccgaggacccgagtcatagcgagggtagtagcgcgccatggcaccgaccagcctgcttgccagtactggcgtctcttc cgcttctctgtggtcctctgcgcgctccagcgcgtgcgcttttccggtggatcatgcggtccgtggcgcaccgcagcggccgctg cccatgcagcgccgctgcttccgaacagtggcggtcagggccgcacccgcggtagccgtccgtccggaacccgcccaagagt tttgggagcagcttgagccctgcaagatggcggaggacaagcgcatcttcctggaggagcaccggtgcgtggaggtccgggg ctgaccggccgtcgcattcaacgtaatcaatcgcatgatgatcagaggacacgaagtcttggtggcggtggccagaaacact gtccattgcaagggcatagggatgcgttccttcacctctcatttctcatttctgaatccctccctgctcactctttctcctccttc ccgttcacgcagcattcgg<u>ggtacc</u>gcggtgagaatcgaaaatgcatcgtttctaggttcggagacggtcaattccctgctccggcg aatctgtcggtcaagctggccagtggacaatgttgctatggcagcccgcgcacatgggcctcccgacgcggccatcaggagccaa -continued acagcgtgtcagggtatgtgaaactcaagaggtccctgctgggcactccggccccactccgggggcgggacgccaggcattcgcg gtcggtcccgcgcgacgagcgaaatgatgattcggttacgagaccaggacgtcgtcgaggtcgagaggcagcctcggacacgtctc gctagggcaacgccccgagtccccgcgagggccgtaaacattgtttctgggtgtcggagtgggcattttgggcccgatccaatcgcct catgccgctctcgtctggtcctcacgttcgcgtacggcctggatcccggaaagggcggatgcacgtggtgttgccccgccattggcgc ccacgtttcaaagtccccggccagaaatgcacaggaccggcccggctcgcacaggccatgctgaacgcccagatttcgacagcaac accatctagaataatcgcaaccatccgcgttttgaacgaaacgaaacggcgctgtttagcatgtttccgacatcgtgggggccgaagc atgctccgggggggaggaaagcgtggcacagcggtagcccattctgtgccacacgccgacgaggaccaatccccggcatcagcctt catcgacggctgcgccgcacatataaagccggacgcctaaccggtttcgtggttatgactagt*ATGttcgcgttctacttcctgacg*

*gcctgcatctccctgaagggcgtgttcggcgtctccccctcctacaacggcctgggcctgacgccccagatgggctgggacaact*

*ggaacacgttcgcctgcgacgtctccgagcagctgctgctggacacggccgaccgcatctccgacctgggcctgaaggacatgg*

*gctacaagtacatcatcctggacgactgctggtcctccggccgcgactccgacggcttcctggtcgccgacgagcagaagttccc*

*caacggcatgggccacgtcgccgaccacctgcacaacaactccttcctgttcggcatgtactcctccgcgggcgagtacacgtgc*

*gccggctacccggctccctgggccgcgaggaggaggacgcccagttcttcgcgaacaaccgcgtggactacctgaagtacga*

*caactgctacaacaagggccagttcggcacgcccgagatctcctaccaccgctacaaggccatgtccgacgccctgaacaaga*

*cgggccgccccatcttctactccctgtgcaactggggccaggacctgaccttctactggggctccggcatcgcgaactcctggcgc*

*atgtccggcgacgtcacggcggagttcacgcgccccgactcccgctgcccctgcgacggcgacgagtacgactgcaagtacgc*

*cggcttccactgctccatcatgaacatcctgaacaaggccgcccccatgggccagaacgcgggcgtcggcggctggaacgacct*

*ggacaacctggaggtcggcgtcggcaacctgacggacgacgaggagaaggcgcacttctccatgtgggccatggtgaagtccc*

*ccctgatcatcggcgcgaacgtgaacaacctgaaggcctcctcctactccatctactcccaggcgtccgtcatcgccatcaaccag*

*gactccaacggcatccccgccacgcgcgtctggcgctactacgtgtccgacacggacgagtacggccagggcgagatccagat*

*gtggtccggcccccctggacaacggcgaccaggtcgtggcgctgctgaacggcggctccgtgtcccgccccatgaacacgaccct*

*ggaggagatcttcttcgactccaacctgggctccaagaagctgacctccacctgggacatctacgacctgtgggcgaaccgcgtc*

*gacaactccacggcgtccgccatcctgggccgcaacaagaccgccaccggcatcctgtacaacgccaccgagcagtcctacaa*

*ggacggcctgtccaagaacgacacccgcctgttcggccagaagatcggctccctgtcccccaacgcgatcctgaacacgaccgt*

*ccccgcccacggcatcgcgttctaccgcctgcgcccctcctccTGA*tacgtagcagcagcagctcggatagtatcgacacactct ggacgctggtcgtgtgatggactgttgccgccacacttgctgccttgacctgtgaatatccctgccgcttttatcaaacagcctcagtgtg tttgatcttgtgtgtacgcgcttttgcgagttgctagctgcttgtgctatttgcgaataccacccccagcatccccttccctcgtttcatatcgc ttgcatcccaaccgcaacttatctacgctgtcctgctatccctcagcgctgctcctgctcctgctcactgcccctcgcacagccttggtttg ggctccgcctgtattctcctggtactgcaacctgtaaaccagcactgcaatgctgatgcacgggaagtagtgggatgggaacacaaat ggagatatc*gcgaggggtctgcctgggccagccgctccctctaaacacgggacgcgtggtccaattcgggcttcgggaccctttg*

*gcggtttgaacgccagggatggggcgcccgcgagcctggggaccccggcaacggcttccccagagcctgccttgcaatctcgc*

*gcgtcctctccctcagcacgtggcggttccacgtgtggtcgggcttcccggactagctcgcgtcgtgacctagcttaatgaacccag*

*ccgggcctgtagcaccgcctaagaggttttgattatttcattataccaatctattcgcc*actagt*ATGgccatcaagaccaaccgc*

*cagcccgtggagaagcccccttcaccatcggcaccctgcgcaaggccatccccgcccactgcttcgagcgctccgccctgcgct*

*cctccatgtacctggccttcgacatcgccgtgatgtccctgctgtacgtggcctccacctacatcgaccccgcccccgtgcccacctg*

-continued ggtgaagtacggcgtgatgtggcccctgtactggttcttccagggcgccttcggcaccggcgtgtgggtgtgcgcccacgagtgcg gccaccaggcctttctcctcctcccaggccatcaacgacggcgtgggcctggtgttccactccctgctgctggtgccctactactcctg gaagcactcccaccgccgccaccactccaacaccggctgcctggacaaggacgaggtgttcgtgcccccccaccgcgccgtgg cccacgagggcctggagtgggaggagtggctgcccatccgcatgggcaaggtgctggtgaccctgaccctgggctggcccctgt acctgatgttcaacgtggcctcccgcccctacccccgcttcgccaaccacttcgacccctggtcccccatcttctccaagcgcgagc gcatcgaggtggtgatctccgacctggccctggtggccgtgctgtccggcctgtccgtgctgggccgcaccatgggctgggcctgg ctggtgaagacctacgtggtgccctacctgatcgtgaacatgtggctggtgctgatcaccctgctgcagcacacccaccccgccct gccccactacttcgagaaggactgggactggctgcgcggcgccatggccaccgtggaccgctccatgggcccccccttcatgga caacatcctgcaccacatctccgacacccacgtgctgcaccacctgttctccaccatcccccactaccacgccgaggaggcctcc gccgccatccgccccatcctgggcaagtactaccagtccgactcccgctgggtgggccgcgccctgtgggaggactggcgcgac tgccgctacgtggtgcccgacgcccccgaggacgactccgccctgtggttccacaagTAGatcgatcttaaggcagcagcagct cggatagtatcgacacactctggacgctggtcgtgtgatggactgttgccgccacacttgctgccttgacctgtgaatatccctgccgctt ttatcaaacagcctcagtgtgtttgatcttgtgtgtacgcgcttttgcgagttgctagctgcttgtgctatttgcgaataccacccccagcatc cccttccctcgtttcatatcgcttgcatcccaaccgcaacttatctacgctgtcctgctatccctcagcgctgctcctgctcctgctcactgc ccctcgcacagccttggtttgggctccgcctgtattctcctggtactgcaacctgtaaaccagcactgcaatgctgatgcacgggaagta gtgggatgggaacacaaatggaaagcttaattaagagctcttgttttccagaaggagttgctccttgagcctttcattctcagcctcg ataacctccaaagccgctctaattgtggaggggggttcgaatttaaaagcttggaatgttggttcgtgcgtctggaacaagccca gacttgttgctcactgggaaaaggaccatcagctccaaaaaacttgccgctcaaaccgcgtacctctgctttcgcgcaatctgc cctgttgaaatcgccaccacattcatattgtgacgcttgagcagtctgtaattgcctcagaatgtggaatcatctgcccctgtgc gagcccatgccaggcatgtcgcgggcgaggacacccgccactcgtacagcagaccattatgctacctcacaatagttcataac agtgaccatatttctcgaagctccccaacgagcacctccatgctctgagtggccacccccggccctggtgcttgcggagggca ggtcaaccggcatggggctaccgaaatccccgaccggatcccaccacccccgcgatgggaagaatctctccccgggatgtgg gcccaccaccagcacaacctgctggcccaggcgagcgtcaaaccataccacacaaatatccttggcatcggccctgaattcct tctgccgctctgctacccggtgcttctgtccgaagcaggggttgctagggatcgctccgagtccgcaaacccttgtcgcgtggcg gggcttgttcgagcttgaagagc The recombination between *C. vulgaris* nitrate reductase 3' UTR's in the construct pSZ3377 results in multiple copies of PmFAD2-1 in transgenic lines which would then manifest most likely as higher C18:2 levels at the end of fermentation. Since the goal was to create a strain with 0% terminal C18:2, we took precautions to avoid this recombination. In another version of the above plasmid ScMEL1 gene was followed by *Chlorella protothecoides* (UTEX 250) elongation factor 1a (CpEF1a) 3' UTR instead of *C. vulgaris* 3' UTR. The sequence of *C. protothecoides* (UTEX 250) elongation factor 1a (CpEF1a) 3' UTR used in construct pSZ3384 and other constructs with this 3' UTR (described below) is shown below. Plasmid pSZ3384 could be written as 6S::PmHXT1p-ScMEL1-CpEF1a::PmCPS1p-PmFAD2-1-CvNR::6S.

Nucleotide sequence of *Chlorella protothecoides* (UTEX 250) elongation factor 1a (CpEF1a) 3' UTR in pSZ3384:

(SEQ ID NO: 129)

tacaacttattacgtaacggagcgtcgtgcgggagggagtgtgccgagc ggggagtcccggtctgtgcgaggcccggcagctgacgctggcgagccgt -continued acgccccgagggtcccctcccctgcaccctcttccccttccctctgac ggccgcgcctgttcttgcatgttcagcgacgaggatatc

The *C. protothecoides* (UTEX 250) elongation factor 1a 3' UTR sequence is flanked by restriction sites SnaBI on 5' and EcoRV on 3' ends shown in lowercase bold underlined text. Note that the plasmids containing CpEF1a 3' UTR (pSZ3384 and others described below) after ScMEL1 stop codon contains 10 extra nucleotides before the 5' SnaBI site. These nucleotides are not present in the plasmids that contain *C. vulgaris* nitrate reductase 3' UTR after the S. ScMEL1 stop codon.

In addition to plasmids pSZ3377 and pSZ3384 expressing either a recombinative CvNR-Promoter-PmFAD2-1-CvNR or non-recombinative CpEF1a-Promoter-PmFAD2-1-CvNR expression unit described above, plasmids using other promoter elements mentioned above were constructed for expression in S5204. These constructs along with their transformation identifiers (D #) can be described as:

| Plasmid ID | D # | Description |
|---|---|---|
| pSZ3378 | D2090 | 6SA::pPmHXT1-ScarIMEL1-CvNR:PmCPS2p-PmFad2-1-CvNR::6SB |
| pSZ3385 | D2097 | 6SA::pPmHXT1-ScarIMEL1-CpEF1a:PmCPS2p-PmFad2-1-CvNR::6SB |
| pSZ3379 | D2091 | 6SA::pPmHXT1-ScarIMEL1-CvNR:PmDPS1p-PmFad2-1-CvNR::6SB |
| pSZ3386 | D2098 | 6SA::pPmHXT1)-ScarIMEL1-CpEF1a:PmDPS1p-PmFad2-1-CvNR::6SB |
| pSZ3380 | D2092 | 6SA::pPmHXT1-ScarIMEL1-CvNR:PmDPS2p-PmFad2-1-CvNR::6SB |
| pSZ3387 | D2099 | 6SA::pPmHXT1-ScarIMEL1-CpEF1a:PmDPS2p-PmFad2-1-CvNR::6SB |
| pSZ3480 | D2259 | 6SA::pPmHXT1-ScarIMEL1-CvNR:PmIPP1p-PmFad2-1-CvNR::6SB |
| pSZ3481 | D2260 | 6SA::pPmHXT1-ScarIMEL1-CpEF1a:PmIPP1p-PmFad2-1-CvNR::6SB |
| pSZ3509 | D2434 | 6SA::pPmHXT1-ScarIMEL1-CvNR:PmAHC1p-PmFad2-1-CvNR::6SB |
| pSZ3516 | D2266 | 6SA::pPmHXT1-ScarIMEL1-CpEF1a:PmAHC1p-PmFad2-1-CvNR::6SB |
| pSZ3510 | D2435 | 6SA::pPmHXT1-ScarIMEL1-CvNR:PmAHC2p-PmFad2-1-CvNR::6SB |
| pSZ3513 | D2263 | 6SA::pPmHXT1-ScarIMEL1-CvNR:PmPPI1p-PmFad2-1-CvNR::6SB |
| pSZ3689 | D2440 | 6SA::pPmHXT1-ScarIMEL1-CpEF1a:PmPPI1p-PmFad2-1-CvNR::6SB |
| pSZ3514 | D2264 | 6SA::pPmHXT1-ScarIMEL1-CvNR:PmPPI2p-PmFad2-1-CvNR::6SB |
| pSZ3518 | D2268 | 6SA::pPmHXT1-ScarIMEL1-CpEF1a:PmPPI2p-PmFad2-1-CvNR::6SB |
| pSZ3515 | D2265 | 6SA::pPmHXT1-ScarIMEL1-CvNR:PmGMPS1p-PmFad2-1-CvNR::6SB |
| pSZ3519 | D2269 | 6SA::pPmHXT1-ScarIMEL1-CpEF1a:PmGMPS1p-PmFad2-1-CvNR::6SB |
| pSZ3520 | D2270 | 6SA::pPmHXT1-ScarIMEL1-CpEF1a:PmGMPS2p-PmFad2-1-CvNR::6SB |
| pSZ3684 | D2436 | 6SA::pPmHXT1-ScarIMEL1-CvNR:PmCS1p-PmFad2-1-CvNR::6SB |
| pSZ3686 | D2438 | 6SA::pPmHXT1-ScarIMEL1-CpEF1A:PmCS1p-PmFad2-1-CvNR::6SB |
| pSZ3685 | D2437 | 6SA::pPmHXT1-ScarIMEL1-CvNR:PmCS2p-PmFad2-1-CvNR::6SB |
| pSZ3688 | D2439 | 6SA::pPmHXT1-ScarIMEL1-CvNR:PmGGHp-PmFad2-1-CvNR::6SB |
| pSZ3511 | D2261 | 6SA::pPmHXT1-ScarIMEL1-CvNR:PmAHI2p-PmFad2-1-CvNR::6SB |
| pSZ3517 | D2267 | 6SA::pPmHXT1-ScarIMEL1-CpEF1a:PmAHI1p-PmFad2-1-CvNR::6SB |
| pSZ3512 | D2262 | 6SA::pPmHXT1-ScarIMEL1-CvNR:PmCEP1p-PmFad2-1-CvNR::6SB |
| pSZ3375 | D2087 | 6SA::pPmHXT1-ScarIMEL1-CvNR:PmFAD2-1p-PmFad2-1-CvNR::6SB |
| pSZ3382 | D2094 | 6SA::pPmHXT1-ScarIMEL1-CpEF1a:PmFAD2-1p-PmFad2-1-CvNR::6SB |
| pSZ3376 | D2088 | 6SA::pPmHXT1-ScarIMEL1-CvNR:PmFAD2-2p-PmFad2-1-CvNR::6SB |
| pSZ3383 | D2095 | 6SA::pPmHXT1-ScarIMEL1-CpEF1a:PmFAD2-2p-PmFad2-1-CvNR::6SB |

The above constructs are the same as pSZ3377 or pSZ3384 except for the promoter element that drives PmFAD2-1. The sequences of different promoter elements used in the above constructs are shown below.

Nucleotide sequence of Carbamoyl phosphate synthase allele 2 promoter contained in plasmid pSZ3378 and pSZ3385 (PmCPS2p promoter sequence):

(SEQ ID NO: 130)

*gcgaggggtctgcctgggccagccgctccctctgaacacgggacgcgtggtccaattcgggcttcgggaccctttggcggtttg*

*aacgcctgggagagggcgcccgcgagcctggggaccccggcaacggcttccccagagcctgccttgcaatctcgcgcgtcctc*

*tccctcagcacgtggcggttccacgtgtggtcgggcgtcccggactagctcacgtcgtgacctagcttaatgaacccagccggg*

*cctgcagcaccaccttagaggttttgatatttgattagaccaatctattcacc*

Nucleotide sequence of Dipthine synthase allele 1 promoter contained in plasmid pSZ3379 and pSZ3386 (PmDPS1p promoter sequence):

(SEQ ID NO: 131)

*ggcgaatagattggtataatgaaataatcaaaacctcttaggcggtgctacaggcccggctgggttcattaagctaggtcacg*

*acgcgagctagtccgggaagcccgaccacacgtggaaccgccacgtgctgagggagaggacgcgcgagattgcaaggca*

*ggctctggggaagccgttgccggggtccccaggctcgcgggcgccccatccctggcgttcaaaccgccaaaggtcccgaag*

*cccgaattggaccacgcgtcccgtgtttagagggagcggctggcccaggcagacccctcgc*

Nucleotide sequence of Dipthine synthase allele 2 promoter contained in plasmid pSZ3380 and pSZ3387 (PmDPS2p promoter sequence):

(SEQ ID NO: 132)

*ggtgaatagattggtctaatcaaataatcaaaacctctaaggtggtgctgcaggcccggctgggttcattaagctaggtcacg*

*acgtgagctagtccgggacgcccgaccacacgtggaaccgccacgtgctgagggagaggacgcgcgagattgcaaggcag*

*gctctggggaagccgttgccggggtccccaggctcgcgggcgccctctcccaggcgttcaaaccgccaaagggtcccgaagc*

*ccgaattggaccacgcgtcccgtgttcagagggagcggctggcccaggcagacccctcgc*

Nucleotide sequence of Inorganic pyrophosphatase allele 1 promoter contained in plasmid pSZ3480 and pSZ3481 (PmIPP1p promoter sequence):

(SEQ ID NO: 133)

*gtgatgggttctttagacgatccagcccaggatcatgtgttgcccacatggagcctatccacgctggcctagaaggcaagcac*

*atttcaaggtgaacccacgtccatggagcgatggcgccaatatctcgcctctagaccaagcggttctcaccccaactgcgtcat*

*ttgtatgtatggctgcaaagttgtcggtacgatagaggccgccaacctggcggcgagggcgaggagctggttgccgatctgt*

*gcccaagcatgtgtcggagctcggctgtctcggcagcgagctcctgtgcaaggggcttgcatcgagaatgtcaggcgataga*

*cactgcacgttggggacacggaggtgcccctgtggcgtgtcctggatgccctcgggtccgtcgcgagaagctctggcgaccag*

*cacccggccacaaccgcagcaggcgttcacccacaagaatcttccagatcgtgatgcgcatgtatcgtgacacgattggcgag*

*gtccgcaggacgcacacggactcgtccactcatcagaactggtcagggcacccatctgcgtcccttttcaggaaccacccaccg*

*ctgccaggcaccttcgccagcggcggactccacacagagaatgccttgctgtgagagaccatggccggcaagtgctgtcgga*

*tctgccgcatacggtcagtccccagcacaaggaagccaagagtacaggctgttggtgtcgatggaaggagtggccgttccca*

*caagtagtgagcggcagctgctcaacggcttcccccctgttcatcttggcaaagccagtgacttcctacaagtatgtgatgcaga*

*tcggcactgcaatctgtcggcatgcgtacagaacatcggctcgccagggcagcgttgctcgctctggatgagctgcttgggag*

*gaatcatcggcacacgccgtgccgtgccgcgccccgcgcccgtcgggaaaggcccccggttaggacactgccgcgtcagcc*

*agtcgtgggatcgatcggacgtggcgaatcctcgcccggacaccctcatcacaccccacatttccctgcaagcaatcttgccga*

*caaaatagtcaagatccattgggtttagggaacacgtgcgagactgggcagctgtatctgtccttgccccgcgtcaaattcctg*

*ggcgtgacgcagtcacaggagaatctattagaccctggacttgcagctcagtcatgggcgtgagtggctaaagcacctaggt*

*caggcgagtaccgccccttccccaggattcactcttctgcgattgacgttgagcctgcatcgggctgcttcgtcacc*

Nucleotide sequence of Adenosylhomocysteinase allele 1 promoter contained in plasmid pSZ3509 and pSZ3516 (PmAHC1p promoter sequence):

(SEQ ID NO: 134)

*tcggagctaaagcagagactggacaagacttgcgttcgcatactggtgacacagaatagctcccatctattcatacgcctttg*

*ggaaaaggaacgagccttgtggcctctgcattgctgcctgctttgaggccgaggacggtgcgggacgctcagatccatcagc*

*gatcgccccaccctcagagcacctccgatccaaggcaatactatcaggcaaagtttccaaattcaaacattccaaaatcacgc*

-continued cagggactggatcacacacgcagatcagcgccgttttgctctttgcctacgggcgactgtgccacttgtcgacccctggtgacg ggagggaccacgcctgcggttggcatccacttcgacggacccagggacggtttctcatgccaaacctgagatttgagcaccca gatgagcacattatgcgttttaggatgccgagcagcgggcgtgcaggaatctggtctcgccagattcaccgaagatgcgccc atcggagcgaggcgaggctttgtgaccacgcaaggcagtgtgaggcaaacacatagggacacctgcgtctttcaatgcac agacatctatggtgcccatgtatataaaatgggctacttctgagtcaaaccaacgcaaactgcgctatggcaaggccggcca aggttggaatcccggtctgtctggatttgagtttgtgggggctatcacgtgacaarccctgggattgggcggcagcagcgcac ggcctgggtggcaatggcgcactaatactgctgaaagcacggctctgcatccctttctcttgacctgcgattggtccttttcgcaa gcgtgatcatc Nucleotide sequence of Adenosylhomocysteinase allele 2 promoter contained in plasmid pSZ3510 (PmAHC2p promoter sequence):

(SEQ ID NO: 135)

tcggagctaaagcagaaactgaacaagacttgcgttcgcatacttgtgacactgaataggttcaatctattcatacgcctttgg gaaactgaacgagccttgtggcctctgcattgctgcctgctttgaggccgaggacggcgcggaacgcacagatccatcagcg atcgccccaccctcagagtacatccgatccaaggcaatactatcaggcaaagtttccaaattcaaacattccaaaattacgtca gggactggatcacacacgcagatcagcgccgttttgctctttgcctacgggcgactgtgccacttgtcgacgcctggtgacggg agggaccacgcctgcggttggcatccacttcgacggacccagggacggtctcacatgccaaacctgagatttgagcaccaag atgagcacattatgcgtttttggatgcctgagcagcgggcgtgcaggaatctggtctcgccagattcaccgaagatgcggcca tcggagcgaggcgagggctgtgtggccacgccaggcagtgtgaggcaaacacacagggacatctgcttctttcgatgcaca gacatctatgttgcccgtgcatataaaatgggctacttctgaatcaaaccaacgcaaacttcgctatggcaaggccggccaag gttggaatcccggtctgtctggatttgagtttgtgggggctatcacgtgacaatccctgggattgggcggcagcagcgcacgg cctggatggcaatggcgcactaatactgctgaaagcacggctctgcatccctttctcttgacctgcgattggtccttttcgcaagc gtgatcatc Nucleotide sequence of Peptidyl-prolyl cis-trans isomerase allele 1 promoter contained in plasmid pSZ3513 and pSZ3689 (PmPPI1p promoter sequence):

(SEQ ID NO: 136)

caccgatcactccgtcgccgcccaagagaaatcaacctcgatggagggcgaggtggatcagaggtattggttatcgttcgttc ttagtctcaatcaatcgtacaccttgcagttgcccgagtttctccacacatacagcacctcccgctcccagcccattcgagcgacc caatccgggcgatcccagcgatcgtcgtcgcttcagtgctgaccggtggaaagcaggagatctcgggcgagcaggaccacat ccagcccaggatcttcgactggctcagagctgaccctcacgcggcacagcaaaagtagcacgcacgcgttatgcaaactggtt acaacctgtccaacagtgttgcgacgttgactggctacattgtctgtctgtcgcgagtgcgcctgggcccttacggtgggacact ggaactccgccccgagtcgaacacctagggcgacgcccgcagcttggcatgacagctctccttgtgttctaaataccttgcgcg tgtgggaga Nucleotide sequence of Peptidyl-prolyl cis-trans isomerase allele 2 promoter contained in plasmid pSZ3514 and pSZ3518 (PmPPI2p promoter sequence):

(SEQ ID NO: 137)

*atccaccgatcactccgtcgccgcccaagagaattcaacctcgatggagggcaaggtggatcagaggtattggttatcgttcg*

*ctattagtctcaatcaatcgtgcaccttgcagttgctcgagtttctccacacatacagcacctcccgctcccagcccattcgagcg*

*acccaatccgggcgatcccagcgatcgtcgtcgcttcagtgctgaccggtggaaagcaggagatctcgggcgagcaggacc*

*acatccagcacaggatcttcgactggctcagagctgaccctcacgcggcacagcaaaagtagcccgcacgcgttatgcaaac*

*aggttacaacctgtccaacactgttgcgacgttgactggctacattgtctgtctgtcgcgagtacgcctggacccttacggtggg*

*acactggaactccgccccgagtcgaacacctagggcgacgcccgcagcttggcatgacagctctccttgtattctaaatacctc*

*gcgcgtgtgggagaa*

Nucleotide sequence of GMP Synthetase allele 1 promoter contained in plasmid pSZ3515 and pSZ3519 (PmGMPS1p promoter sequence):

(SEQ ID NO: 138)

*atgatgcgcgtgtacgactatcaaggaagaaagaggacttaatttcttaccttctaaccaccatattctttttgctggatgcttgc*

*tcgtctcgatgacaattgtgaacctcttgtgtgaccctgaccctgctgcaaggctctccgaccgcacgcaaggcgcagccggcg*

*cgtccggaggcgatcggatccaatccagtcgtcctcccgcagcccgggcacgtttgcccatgcaggcccttccacaccgctcaa*

*gagactcccgaacaccgcccactcggcactcgcttcggctgccgagtgcgcgtttgagtttgccctgccacagaagacacc*

Nucleotide sequence of GMP Synthetase allele 2 promoter contained in plasmid pSZ3520 (PmGMPS2p promoter sequence):

(SEQ ID NO: 139)

*atgatgcgcgtgtacgactatcaaggaagaaagaggacttaatttcttaccttctaaccaccatattctttttgctggatgcttgc*

*tcgtctcgatgacaattgtgaacctcttgtgtgaccctgaccctgctgcaaggctctccgaccgcacgcaaggcgcagccggcg*

*cgtccggaggcgatcggatccaatccagtcgtcctcccgcagcccgggcacgtttgcccatgcaggcccttccacaccgctcaa*

*gagactcccgaacaccgcccactcggcactcgcttcggctgccgagtgcgcgtttgagtttgccctgccacaggagacatc*

Nucleotide sequence of Citrate synthase allele 1 promoter contained in plasmid pSZ3684 and pSZ3686 (PmCS1p promoter sequence):

(SEQ ID NO: 140)

cccgggcgagctgtacgcctacggagcgaggcctggtgtgaccgttgcgatctcgccagcagacgtcgcggagcctcgtccca aaggccctttctgatcgagcttgtcgtccactggacgctttaagttgcgcgcgcgatgggataaccgagctgatctgcactcag attttggtttgttttcgcgcatggtgcagcgaggggaggtactacgctggggtacgagatcctccggattcccagaccgtgttg ccggcatttacccggtcatcgccagcgattcgggacgacaaggccttatcctgtgctgagacgctcgagcacgtttataaaatt gtgggtaccgcggtatgcacagcgttcaacacgcgccacgccgaaattggttggtggggagcacgtatgggactgacgtat ggccagcagcgaacactcaccgaacaagtgccaatgtataccttgcatcaatgatgctccggcagcttcgattgactgtctcga aaaagtgtgagcaagcagatcatgtggccgctctgtcgcgcagcacctgacgcattcgacacccacggcaatgcccaggcca gggaatagagagtaagacaactcccattgttcagcaaaacattgcatgcagtgccttcacaactatacaatgaatgggagg gaatatgggctctgcatgggacagcttagctgggacattcggctactgaacaagaaaaccccacgagaaccaattggcgaa acctgccgggaggaggtgatcgtttctgtaaatggcttacgcattccccccggcggctcacgaggggtgtggtgaaccctgcc agctgatcaagtgcttgctgacgtcggccagggaggtgtatgtgattgggccgtggggcgtgagttatcctaccgccggaccc gcgaagtcacatgacgaatggccgtgcgggatgacgagagcacgactcgctctttcttcgccggcccggcttcatggaggac aataataaagggtggccaccggcaacagcctccatacctgaaccgattccagacccaaacctcttgaattttgagggatcca gttcaccggtatagtcacg Nucleotide sequence of Citrate synthase allele 2 promoter contained in plasmid pSZ3685 (PmCS2p promoter sequence):

(SEQ ID NO: 141)

atccccgggcgagctgtacgcctacggagcgaggcctggtgtgaccgttgcgatctcgccagcagacgtcgcggagcctcgtc ccaaaggccctttctgatcgagcttgtcgtccactggacgctttaagttgcgcgcgcgatgggataaccgagctgatctgcactc agattttggtttgttttcgcgcatggtgcagcgaggggaggtactacgctggggtacgagatcctccggattcccagaccgtgt tgccggcatttacccggtcatcgccagcgattcgggacgacaaggccttatcctgtgctgagacgctcgagcacgtttataaaa ttgtggtcaccgtggtacgcacagcgtccaacacgcgccacgccgaaattcgttggtggggagcacgtatcggactgacgt atggccagcagcgaacactcaccaaacaggtgccaatgtatagcttgcatcaatgatgctctggcagcttcgattgactgtctc gaaaaagtgtgtgcaaacagattatgtggccgctctgtggccgcgcagcacctgacgcactcgacacccacggcaatgccca ggccaaggaacagagagtaagacaactcccattgttcagtaaaacattgcactgcagtgccttcacaaacatacaacgaatg ggagggaatatgggcttcgaatgggacagcttagctgggacattcggttactgaacaagaaaaccccacgagaaccaactg gcgaaacctgccgggaggaggtgatcgtttttgtaaatggcttacgcattccccccccggcggctcacggggggtgtggtgaa ccctgccagctgatcaagtgcttgctgacgtcggccagggaggtgtatgtgatttggccgtggggcgtgagttatcctaccgcc ggacccgcgaagtcacatgacgaatggccgtgcgggatgacgagagcagggctcgctctttcttcgccggcccggcttcatgg aggacaataataaagggtggccaccggcaacagccctccatacctgaaccgattccagacccaaacctcttgaattttgagg gatccagttcaccggtatagtcacga Nucleotide sequence of Gamma Glutamyl Hydrolase allele 1 promoter contained in plasmid pSZ3688 (PmGGH1p promoter sequence):

(SEQ ID NO: 142)

*gcgagtggttttgctgccgggaagggagtggggagcgtcgagcgagggacgcggcgctcgaggcgcacgtcgtctgtcaac*

*gcgcgcggccctcgcggcccgcggccccacccagctctaatcatcgaaaactaagaggctccacacgcctgtcgtagaatgca*

*tgggattcgccagtagaccacgatctgcgccgaagaagctggtctacccgacgtttttttgttgctcctttattctgaatgatatga*

*agatagtgtgcgcagtgccacgcataggcatcaggagcaagggaggacgggtcaacttgaaagaaccaaaccatccatcc*

*gagaaatgcgcatcatctttgtagtaccatcaaacgccttggccaatgtcttctgcatggacaacacaacctgctcctggccac*

*acggtcgacttggagcgccccatgcgcccaggtcgccacgacccgcggcccagcgcgcggcgattcgcctcacgagatcccg*

*gcggacccggcacgcccgcgggccgacggtgcgcttggcgatgctgctcattaacccacggccgtcacccgatccacatgctct*

*ttttcaacacatccacattggaatagagctctaccagggtgagtactgcattctttggggctgggaggaccccactcgacacct*

*ggtccttcatcggccgaaagcccgaacctgagcgcttccccgccccgttcctcatccccgactttccgatggcccattgcagtttc*

*aaac*

Nucleotide sequence of Acetohydroxyacid Isomerase allele 1 promoter contained in plasmid pSZ3517 (PmAHI1p promoter sequence):

(SEQ ID NO: 143)

*atctgggtggaggactgggagtaagatgtaaggatattaattaaacattctagtttgttgatggcacaacagtcaatgcattt*

*cagtcgtcttgctccttataacctatgcgtgtgccatcgccggccatgcacctgtggcgtggtaccgaccatcggggagaggcc*

*cgagattcggaggtacctcccgccctgggcgagcccttcacgtgacggcacaagtcccttgcatcggcccgcgagcacggaat*

*acagagccccgtgccccccacgggccctcacatcatccactccattgttcttgccacaccgatcagca*

Nucleotide sequence of Acetohydroxyacid Isomerase allele 2 promoter contained in plasmid pSZ3511 (PmAHI2p promoter sequence):

(SEQ ID NO: 144)

*tgggtggaggactgggaagaagatgtaaggatatcaatttaacattctagtttgttgatggcacaacagtcactgaataccg*

*ggcgtctggctgctaaaatagccggagcgtgtgccatcgccggccatgcatctgtggcgtggtaccgaccatcagggagagg*

*cccgagattcggaggtacctcccgccctgggcgagcccttcacgtgacggcacaagtcccttgcatcggcccgcgagcacgga*

*atacagagccccgtgctccccacgggccctcacatcatccactccattgttcttgccacaccgatcagc*

Nucleotide sequence of Cysteine Endopeptidase allele 1 promoter contained in plasmid pSZ3512 (PmCEP1 promoter sequence):

(SEQ ID NO: 145)

*ataacgaggcacaatgatcgatatttctatcgaacaactgtatttagccctgtacgtaccccgctcttgggccagcccgtccgtg*

*cttgccttcggaaaattgcatggcgcctcatgcaaactcgcgctctcacagcagatctcgcccagctcccgggagagcaatcgc*

*gggtggggcccggggcgaatccaggacgcgccccgcggggccgctccactcgccagggccaatgggcggcttatagtcctg*

-continued

```
gcatgggctctgcatgcacagtatcgcagtttgggcgaggtgttgcccccgcgatttcgaatacgcgacgcccggtactcgtgc

gagaacagggttcttg
```

Nucleotide sequence of Fatty acid desaturase 2 allele 1 promoter contained in plasmid pSZ3375 and 3382 (Pm-FAD2-1 promoter sequence):

(SEQ ID NO: 146)

```
atcgcgatggtgcgcactcgtgcgcaatgaatatggggtcacgcggtggacgaacgcggagggggcctggccgaatctagg

cttgcattcctcagatcactttctgccggcggtccggggtttgcgcgtcgcgcaacgctccgtctccctagccgctgcgcaccgcg

cgtgcgacgcgaaggtcattttccagaacaacgaccatggcttgtcttagcgatcgctcgaatgactgctagtgagtcgtacgc

tcgacccagtcgctcgcaggagaacgcggcaactgccgagcttcggcttgccagtcgtgactcgtatgtgatcaggaatcatt

ggcattggtagcattataattcggcttccgcgctgtttatgggcatggcaatgtctcatgcagtcgaccttagtcaaccaattctg

ggtggccagctccgggcgaccgggctccgtgtcgccgggcaccacctcctgccatgagtaacagggccgccctctcctcccgac

gttggcccactgaataccgtgtcttggggccctacatgatgggctgcctagtcgggcgggacgcgcaactgcccgcgcaatct

gggacgtggtctgaatcctccaggcgggtttccccgagaaagaaagggtgccgatttcaaagcagagccatgtgccgggccc

tgtggcctgtgttggcgcctatgtagtcaccccccctcacccaattgtcgccagtttgcgcaatccataaactcaaaactgcagct

tctgagctgcgctgttcaagaacacctctggggtttgctcacccgcgaggtcgacgcccagca
```

Nucleotide sequence of Fatty acid desaturase 2 allele 2 promoter contained in plasmid pSZ3376 and 3383 (Pm-FAD2-2 promoter sequence):

(SEQ ID NO: 147)

```
atcacgatggtgcgcattcgtgcaaagtgaatatggggtcacgcggtggacgaacgcggagggggcatgaccgaatctag

gctcgcattcctcagatcacttcatgccggcggtccggggtttgcgcgtcgcgcaaggctacgtctccctagccgctgcgcacca

cgcgtgcgacgcggaggccatcttccggagcaacgaccatggattgtcttagcgatcgcacgaatgagtgctagtgagtcgt

acgctcgacccagtcgctcgcaggagaaggcggcagctgccgagcttcggcttaccagtcgtgactcgtatgtgatcaggaat

cattggcattggtagcattataattcggcttccgcgctgcgtatgggcatggcaatgtctcatgcagtcgatcttagtcaaccaa

ttttgggtggccaggtccgggcgaccgggctccgtgtcgccgggcaccacctcctgccaggagtagcagggccgccctctcgtc

ccgacgttggcccactgaataccgtggcttcgagccctacatgatgggctgcctagtcgggcgggacgcgcaactgcccgcgc

gatctgggggctggtctgaatccttcaggcgggtgttacccgagaaagaaagggtgccgatttcaaagcagacccatgtgcc

gggccctgtggcctgtgttggcgcctatgtagtcaccccccctcacccaattgtcgccagtttgcgcactccataaactcaaaac

agcagcttctgagctgcgctgttcaagaacacctctggggtttgctcacccgcgaggtcgacgcccagca
```

To determine their impact on growth and fatty acid profiles, the above-described constructs were independently transformed into a Δfad2 Δfata1 strain S5204. Primary transformants were clonally purified and grown under standard lipid production conditions at pH5.0 or at pH7.0. The resulting profiles from a set of representative clones arising from transformations are shown in Tables 84-114.

TABLE 84

Fatty acid profile in some representative complemented (D2087) and parent S5204 lines transformed with pSZ3375 DNA containing PmFAD2-1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 7; S5204; T665; D2087-22 | 0.38 | 4.43 | 1.78 | 83.93 | 7.58 | 0.81 |
| pH 7; S5204; T665; D2087-16 | 0.41 | 4.92 | 1.94 | 83.21 | 7.55 | 0.84 |
| pH 7; S5204; T665; D2087-17 | 0.40 | 4.82 | 1.78 | 83.51 | 7.52 | 0.79 |
| pH 7; S5204; T665; D2087-26 | 1.30 | 8.06 | 2.54 | 79.03 | 7.30 | 0.82 |
| pH 7; S5204; T665; D2087-29 | 1.13 | 7.88 | 2.45 | 79.48 | 7.26 | 0.79 |

TABLE 85

Fatty acid profile in some representative complemented (D) and parent S5204 lines transformed with pSZ3382 DNA containing PmFAD2-1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 7; S5204; T672; D2094-5 | 0.49 | 5.76 | 2.95 | 83.39 | 5.08 | 0.84 |
| pH 7; S5204; T672; D2094-25 | 0.35 | 5.01 | 2.41 | 85.10 | 5.09 | 0.64 |
| pH 7; S5204; T672; D2094-13 | 0.33 | 5.07 | 2.30 | 84.89 | 5.30 | 0.69 |
| pH 7; S5204; T672; D2094-11 | 0.38 | 4.33 | 1.78 | 85.63 | 5.31 | 0.85 |
| pH 7; S5204; T672; D2094-8 | 0.35 | 5.29 | 2.32 | 84.59 | 5.34 | 0.66 |

TABLE 86

Fatty acid profile in some representative complemented (D2088) and parent S5204 lines transformed with pSZ3376 DNA containing PmFAD2-2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 7; S5204; T665; D2088-16 | 1.11 | 8.18 | 2.92 | 78.13 | 6.96 | 0.87 |
| pH 7; S5204; T665; D2088-20 | 1.06 | 7.78 | 2.95 | 78.65 | 6.95 | 0.84 |
| pH 7; S5204; T665; D2088-29 | 0.91 | 7.13 | 2.87 | 79.63 | 6.93 | 0.78 |

TABLE 86-continued

Fatty acid profile in some representative complemented (D2088) and parent S5204 lines transformed with pSZ3376 DNA containing PmFAD2-2p driving PmFAD2-1.

| Sample ID | C14:0 | C16:0 | C18:0 | C18:1 | C18:2 | C18:3 α |
|---|---|---|---|---|---|---|
| pH 7; S5204; T665; D2088-6 | 1.18 | 8.29 | 2.98 | 77.90 | 6.91 | 0.88 |
| pH 7; S5204; T665; D2088-18 | 1.10 | 7.98 | 3.09 | 78.42 | 6.78 | 0.81 |

TABLE 87

Fatty acid profile in some representative complemented (D) and parent S5204 lines transformed with pSZ3383 DNA containing PmFAD2-2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 7; S5204; T673; D2095-47 | 0.30 | 5.43 | 2.45 | 85.10 | 4.62 | 0.68 |
| pH 7; S5204; T673; D2095-14 | 0.38 | 5.16 | 2.48 | 84.46 | 5.41 | 0.68 |
| pH 7; S5204; T673; D2095-16 | 0.43 | 4.60 | 2.54 | 84.82 | 5.47 | 0.58 |
| pH 7; S5204; T673; D2095-6 | 0.34 | 5.41 | 2.57 | 84.21 | 5.49 | 0.66 |
| pH 7; S5204; T673; D2095-39 | 0.42 | 5.30 | 2.49 | 83.97 | 5.57 | 0.68 |

TABLE 88

Fatty acid profile in representative complemented (D2089) and parent S5204 lines transformed with pSZ3377 DNA containing PmCPS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T672; D2089-40 | 0.35 | 4.73 | 2.29 | 88.94 | 1.79 | 0.39 |
| pH 7; S5204; T672; D2089-2 | 0.51 | 4.85 | 2.96 | 87.55 | 2.05 | 0.41 |
| pH 7; S5204; T672; D2089-14 | 0.56 | 5.00 | 3.04 | 87.24 | 2.07 | 0.36 |
| pH 7; S5204; T672; D2089-7 | 0.38 | 5.04 | 2.39 | 88.02 | 2.39 | 0.44 |
| pH 7; S5204; T672; D2089-18 | 0.38 | 5.00 | 2.37 | 87.93 | 2.42 | 0.43 |

TABLE 89

Fatty acid profile in some representative complemented (D2096) and parent S5204 lines transformed with pSZ3384 DNA containing PmCPS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T673; D2096-6 | 0.33 | 4.18 | 1.10 | 92.91 | 0.00 | 0.00 |
| pH 7; S5204; T673; D2096-12 | 0.36 | 4.14 | 1.33 | 92.42 | 0.34 | 0.12 |
| pH 7; S5204; T673; D2096-14 | 0.32 | 4.35 | 1.64 | 92.12 | 0.35 | 0.14 |
| pH 7; S5204; T673; D2096-8 | 0.50 | 6.44 | 0.95 | 89.81 | 0.46 | 0.32 |
| pH 7; S5204; T673; D2096-1 | 0.29 | 3.93 | 1.79 | 91.19 | 1.34 | 0.37 |

TABLE 90

Fatty acid profile in some representative complemented (D2090) and parent S5204 lines transformed with pSZ3378 DNA containing PmCPS2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T672; D2090-5 | 0.33 | 4.73 | 1.84 | 91.24 | 0.00 | 0.00 |
| pH 7; S5204; T672; D2090-29 | 0.42 | 4.99 | 2.01 | 91.06 | 0.00 | 0.00 |
| pH 7; S5204; T672; D2090-22 | 0.43 | 4.31 | 1.87 | 90.44 | 0.78 | 0.16 |
| pH 7; S5204; T672; D2090-1 | 0.32 | 3.77 | 2.43 | 89.72 | 1.68 | 0.35 |
| pH 7; S5204; T672; D2090-32 | 0.49 | 5.01 | 1.97 | 88.48 | 1.84 | 0.38 |

TABLE 91

Fatty acid profile in some representative complemented (D2097) and parent S5204 lines transformed with pSZ3385 DNA containing PmCPS2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 5; S5204; T680; D2097-1 | 0.50 | 5.73 | 1.97 | 87.12 | 2.61 | 0.76 |
| pH 5; S5204; T680; D2097-2 | 0.75 | 8.20 | 2.46 | 85.73 | 0.89 | 0.53 |

TABLE 92

Fatty acid profile in some representative complemented (D2091) and parent S5204 lines transformed with pSZ3379 DNA containing PmDPS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T672; D2091-4 | 1.42 | 4.39 | 2.32 | 89.87 | 0.00 | 0.00 |
| pH 7; S5204; T672; D2091-14 | 0.27 | 4.79 | 2.24 | 90.94 | 0.00 | 0.00 |
| pH 7; S5204; T672; D2091-15 | 0.30 | 5.26 | 2.20 | 90.73 | 0.00 | 0.00 |
| pH 7; S5204; T672; D2091-19 | 0.31 | 4.51 | 1.77 | 91.65 | 0.00 | 0.00 |
| pH 7; S5204; T672; D2091-46 | 0.31 | 5.36 | 2.24 | 90.67 | 0.00 | 0.00 |

TABLE 93

Fatty acid profile in some representative complemented (D2098) and parent S5204 lines transformed with pSZ3386 DNA containing PmDPS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T680; D2098-39 | 0.34 | 4.89 | 1.56 | 92.08 | 0.00 | 0.00 |
| pH 7; S5204; T680; D2098-7 | 0.30 | 4.31 | 1.61 | 92.34 | 0.30 | 0.00 |
| pH 7; S5204; T680; D2098-3 | 0.33 | 3.89 | 1.58 | 92.65 | 0.36 | 0.00 |
| pH 7; S5204; T680; D2098-25 | 0.32 | 4.18 | 1.64 | 92.34 | 0.36 | 0.11 |
| pH 7; S5204; T680; D2098-13 | 0.32 | 4.36 | 1.50 | 92.10 | 0.37 | 0.12 |

TABLE 94

Fatty acid profile in some representative complemented (D2092) and parent S5204 lines transformed with pSZ3380 DNA containing PmDPS2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T672; D2092-35 | 0.29 | 5.13 | 1.59 | 92.16 | 0.00 | 0.00 |
| pH 7; S5204; T672; D2092-29 | 0.37 | 4.66 | 1.75 | 91.71 | 0.19 | 0.05 |
| pH 7; S5204; T672; D2092-15 | 0.24 | 3.47 | 1.84 | 93.19 | 0.43 | 0.11 |

TABLE 94-continued

Fatty acid profile in some representative complemented (D2092) and parent S5204 lines transformed with pSZ3380 DNA containing PmDPS2p driving PmFAD2-1.

| Sample ID | C14:0 | C16:0 | C18:0 | C18:1 | C18:2 | C18:3 α |
|---|---|---|---|---|---|---|
| pH 7; S5204; T672; D2092-21 | 0.25 | 3.50 | 1.82 | 93.16 | 0.44 | 0.09 |
| pH 7; S5204; T672; D2092-16 | 0.28 | 3.18 | 1.50 | 93.59 | 0.52 | 0.12 |

TABLE 95

Fatty acid profile in some representative complemented (D2099) and parent S5204 lines transformed with pSZ3387 DNA containing PmDPS2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 7; S5204; T680; D2099-20 | 0.31 | 4.02 | 1.46 | 93.07 | 0.00 | 0.00 |
| pH 7; S5204; T680; D2099-24 | 0.28 | 4.67 | 1.50 | 92.38 | 0.00 | 0.00 |
| pH 7; S5204; T680; D2099-27 | 0.40 | 4.07 | 1.22 | 93.26 | 0.00 | 0.00 |
| pH 7; S5204; T680; D2099-30 | 0.32 | 4.59 | 1.57 | 92.40 | 0.00 | 0.00 |
| pH 7; S5204; T680; D2099-35 | 0.30 | 4.56 | 1.54 | 92.49 | 0.00 | 0.00 |

TABLE 96

Fatty acid profile in some representative complemented (D2259) and parent S5204 lines transformed with pSZ3480 DNA containing PmIPP1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 5; S5204; T711; D2259-43 | 0.36 | 5.27 | 2.19 | 89.32 | 1.51 | 0.51 |
| pH 5; S5204; T711; D2259-22 | 0.35 | 4.88 | 2.17 | 86.34 | 4.41 | 0.70 |
| pH 5; S5204; T711; D2259-28 | 0.35 | 4.82 | 2.18 | 86.32 | 4.45 | 0.69 |
| pH 5; S5204; T711; D2259-21 | 0.33 | 4.90 | 2.08 | 86.33 | 4.49 | 0.74 |
| pH 5; S5204; T711; D2259-36 | 0.50 | 5.97 | 2.14 | 84.67 | 4.49 | 0.74 |

TABLE 97

Fatty acid profile in some representative complemented (D2260) and parent S5204 lines transformed with pSZ3481 DNA containing PmIPP1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.10 | 0.00 |
| pH 5; S5204 | 0.39 | 5.67 | 1.36 | 91.13 | 0.00 | 0.00 |
| pH 5; S5204; T711; D2260-32 | 0.36 | 4.96 | 2.10 | 89.46 | 1.55 | 0.49 |
| pH 5; S5204; T711; D2260-10 | 0.33 | 4.83 | 1.99 | 89.40 | 1.63 | 0.58 |
| pH 5; S5204; T711; D2260-2 | 0.34 | 4.83 | 2.16 | 89.39 | 1.64 | 0.49 |
| pH 5; S5204; T711; D2260-30 | 0.37 | 4.81 | 2.11 | 89.51 | 1.69 | 0.26 |
| pH 5; S5204; T711; D2260-41 | 0.33 | 4.91 | 2.17 | 89.73 | 1.72 | 0.16 |

TABLE 98

Fatty acid profile in some representative complemented (D2434) and parent S5204 lines transformed with pSZ3509 DNA containing PmAHC1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T768; D2434-32 | 0.33 | 4.45 | 1.55 | 81.55 | 8.51 | 1.38 |
| pH 5; S5204; T768; D2434-27 | 0.62 | 7.27 | 1.58 | 78.65 | 9.44 | 1.49 |
| pH 5; S5204; T768; D2434-4 | 0.38 | 5.81 | 1.79 | 79.63 | 10.01 | 1.18 |
| pH 5; S5204; T768; D2434-23 | 0.5 | 5.93 | 1.5 | 78.7 | 10.25 | 1.56 |
| pH 5; S5204; T768; D2434-43 | 0.51 | 6.08 | 1.6 | 78.79 | 10.25 | 1.36 |

TABLE 99

Fatty acid profile in some representative complemented (D2266) and parent S5204 lines transformed with pSZ3516 DNA containing PmAHC1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T718; D2266-46 | 0.32 | 5.41 | 1.94 | 91.26 | 0.11 | 0.00 |
| pH 5; S5204; T718; D2266-36 | 0.36 | 5.33 | 1.90 | 91.17 | 0.17 | 0.00 |
| pH 5; S5204; T718; D2266-35 | 0.37 | 4.96 | 2.13 | 90.82 | 0.41 | 0.00 |

TABLE 99-continued

Fatty acid profile in some representative complemented (D2266) and parent S5204 lines transformed with pSZ3516 DNA containing PmAHC1p driving PmFAD2-1.

| Sample ID | C14:0 | C16:0 | C18:0 | C18:1 | C18:2 | C18:3 α |
|---|---|---|---|---|---|---|
| pH 5; S5204; T718; D2266-41 | 0.38 | 5.33 | 2.10 | 90.31 | 0.44 | 0.31 |
| pH 5; S5204; T718; D2266-5 | 0.36 | 5.15 | 2.23 | 90.55 | 0.48 | 0.31 |

TABLE 100

Fatty acid profile in some representative complemented (D2435) and parent S5204 lines transformed with pSZ3510 DNA containing PmAHC2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T768; D2435-37 | 0.35 | 6.09 | 1.90 | 78.52 | 11.01 | 1.18 |
| pH 5; S5204; T768; D2435-3 | 0.43 | 5.90 | 1.97 | 78.74 | 10.97 | 1.20 |
| pH 5; S5204; T768; D2435-20 | 0.40 | 6.01 | 1.89 | 79.00 | 10.97 | 1.14 |
| pH 5; S5204; T768; D2435-13 | 0.39 | 6.11 | 1.89 | 78.26 | 10.84 | 1.24 |
| pH 5; S5204; T768; D2435-34 | 0.46 | 6.02 | 1.97 | 79.48 | 10.46 | 1.19 |

TABLE 101

Fatty acid profile in some representative complemented (D2263) and parent S5204 lines transformed with pSZ3513 DNA containing PmPPI1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T718; D2263-13 | 0.75 | 9.44 | 1.98 | 87.09 | 0.00 | 0.00 |
| pH 5; S5204; T718; D2263-14 | 0.58 | 7.72 | 1.64 | 89.26 | 0.00 | 0.00 |
| pH 5; S5204; T718; D2263-19 | 0.62 | 7.92 | 1.56 | 89.25 | 0.00 | 0.00 |
| pH 5; S5204; T718; D2263-26 | 0.42 | 7.39 | 1.70 | 89.28 | 0.00 | 0.00 |
| pH 5; S5204; T718; D2263-29 | 0.58 | 7.32 | 1.30 | 90.07 | 0.00 | 0.00 |

TABLE 102

Fatty acid profile in some representative complemented (D2440) and parent S5204 lines transformed with pSZ3689 DNA containing PmPPI1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T770; D2440-23 | 0.31 | 6.24 | 1.41 | 90.42 | 0.17 | 0.05 |
| pH 5; S5204; T770; D2440-32 | 0.23 | 4.69 | 1.41 | 91.72 | 0.17 | 0.00 |
| pH 5; S5204; T770; D2440-38 | 0.30 | 6.31 | 1.49 | 90.21 | 0.17 | 0.00 |
| pH 5; S5204; T770; D2440-7 | 0.30 | 6.33 | 1.38 | 90.29 | 0.18 | 0.05 |
| pH 5; S5204; T770; D2440-36 | 0.29 | 6.38 | 1.36 | 90.39 | 0.18 | 0.05 |
| pH 5; S5204; T770; D2440-8 | 0.34 | 5.63 | 1.15 | 91.15 | 0.19 | 0.05 |

TABLE 103

Fatty acid profile in some representative complemented (D2264) and parent S5204 lines transformed with pSZ3514 DNA containing PmPPI2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 7; S6207; T718; D2264-1 | 0.49 | 6.15 | 1.61 | 90.82 | 0.00 | 0.00 |
| pH 7; S6207; T718; D2264-6 | 0.38 | 5.36 | 1.51 | 91.58 | 0.00 | 0.00 |
| pH 7; S6207; T718; D2264-29 | 0.45 | 6.09 | 1.46 | 91.10 | 0.00 | 0.00 |
| pH 7; S6207; T718; D2264-4 | 0.40 | 5.42 | 2.28 | 89.86 | 0.90 | 0.00 |
| pH 7; S6207; T718; D2264-7 | 0.40 | 5.37 | 2.02 | 90.18 | 1.04 | 0.00 |

TABLE 104

Fatty acid profile in some representative complemented (D2268) and parent S5204 lines transformed with pSZ3518 DNA containing PmPPI2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T720; D2268-1 | 0.39 | 6.43 | 1.78 | 90.49 | 0.00 | 0.00 |
| pH 5; S5204; T720; D2268-2 | 0.38 | 6.49 | 1.74 | 90.38 | 0.00 | 0.00 |
| pH 5; S5204; T720; D2268-3 | 0.38 | 6.56 | 1.74 | 90.27 | 0.00 | 0.00 |
| pH 5; S5204; T720; D2268-4 | 0.45 | 5.73 | 1.52 | 91.75 | 0.00 | 0.00 |
| pH 5; S5204; T720; D2268-5 | 0.38 | 6.58 | 1.81 | 90.79 | 0.00 | 0.00 |

TABLE 105

Fatty acid profile in some representative complemented (D2265) and parent S5204 lines transformed with pSZ3515 DNA containing PmGMPS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T718; D2265-16 | 0.46 | 7.02 | 1.71 | 90.06 | 0.00 | 0.00 |
| pH 5; S5204; T718; D2265-43 | 0.00 | 7.90 | 1.90 | 89.27 | 0.00 | 0.00 |
| pH 5; S5204; T718; D2265-14 | 0.46 | 5.53 | 1.68 | 91.28 | 0.35 | 0.00 |
| pH 5; S5204; T718; D2265-4 | 0.39 | 6.17 | 1.75 | 90.44 | 0.42 | 0.00 |
| pH 5; S5204; T718; D2265-9 | 0.49 | 5.87 | 1.77 | 90.51 | 0.45 | 0.00 |

TABLE 106

Fatty acid profile in some representative complemented (D2269) and parent S5204 lines transformed with pSZ3519 DNA containing PmGMPS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T720; D2269-1 | 0.38 | 6.73 | 1.68 | 90.24 | 0.00 | 0.00 |
| pH 5; S5204; T720; D2269-3 | 0.36 | 6.76 | 1.71 | 90.17 | 0.00 | 0.00 |
| pH 5; S5204; T720; D2269-4 | 0.42 | 6.57 | 1.71 | 90.32 | 0.00 | 0.00 |
| pH 5; S5204 T720; D2269-5 | 0.59 | 8.81 | 1.93 | 87.97 | 0.00 | 0.00 |
| pH 5; S5204; T720; D2269-6 | 0.50 | 7.29 | 1.73 | 89.29 | 0.00 | 0.00 |

TABLE 107

Fatty acid profile in some representative complemented (D2270) and parent S5204 lines transformed with pSZ3520 DNA containing PmGMPS2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T720; D2270-1 | 0.37 | 6.80 | 1.74 | 90.18 | 0.00 | 0.00 |
| pH 5; S5204; T720; D2270-2 | 0.46 | 6.76 | 1.83 | 89.90 | 0.00 | 0.00 |
| pH 5; S5204; T720; D2270-3 | 0.41 | 6.69 | 1.70 | 90.22 | 0.00 | 0.00 |
| pH 5; S5204; T720; D2270-4 | 0.43 | 7.44 | 1.72 | 89.31 | 0.00 | 0.00 |
| pH 5; S5204; T720; D2270-5 | 0.44 | 6.98 | 1.78 | 89.79 | 0.00 | 0.00 |

TABLE 108

Fatty acid profile in some representative complemented (D2436) and parent S5204 lines transformed with pSZ3684 DNA containing PmCS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T768;D2436-48 | 7.59 | 1.57 | 88.88 | 0.18 | 0.00 | 0.00 |
| pH 5; S5204; T768;D2436-1 | 6.37 | 1.50 | 85.00 | 3.97 | 1.04 | 0.00 |
| pH 5; S5204; T768;D2436-16 | 9.40 | 1.86 | 81.13 | 4.11 | 1.21 | 0.00 |
| pH 5; S5204; T768;D2436-8 | 6.07 | 1.77 | 84.78 | 4.26 | 0.94 | 0.00 |
| pH 5; S5204; T768;D2436-32 | 5.97 | 1.62 | 85.28 | 4.50 | 0.98 | 0.00 |

TABLE 109

Fatty acid profile in some representative complemented (D2438) and parent S5204 lines transformed with pSZ3686 DNA containing PmCS1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T770; D2438-7 | 0.50 | 5.96 | 1.69 | 89.87 | 1.30 | 0.00 |
| pH 5; S5204; T770; D2438-11 | 0.41 | 6.05 | 1.86 | 87.88 | 2.46 | 0.00 |
| pH 5; S5204; T770; D2438-9 | 0.41 | 5.75 | 1.93 | 88.35 | 2.50 | 0.00 |
| pH 5; S5204; T770; D2438-15 | 0.45 | 6.18 | 1.85 | 87.86 | 2.59 | 0.00 |
| pH 5; S5204; T770; D2438-37 | 0.40 | 5.92 | 1.97 | 87.80 | 2.59 | 0.00 |

TABLE 110

Fatty acid profile in some representative complemented (D2437) and parent S5204 lines transformed with pSZ3685 DNA containing PmCSCp driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T768; D2437-15 | 0.00 | 4.83 | 1.98 | 90.43 | 1.17 | 0.53 |
| pH 5; S5204; T768; D2437-35 | 0.45 | 6.03 | 1.81 | 88.69 | 1.88 | 0.31 |
| pH 5; S5204; T768; D2437-17 | 0.39 | 4.96 | 2.00 | 88.58 | 3.24 | 0.00 |

TABLE 110-continued

Fatty acid profile in some representative complemented (D2437) and parent S5204 lines transformed with pSZ3685 DNA containing PmCSCp driving PmFAD2-1.

| Sample ID | C14:0 | C16:0 | C18:0 | C18:1 | C18:2 | C18:3 α |
|---|---|---|---|---|---|---|
| pH 5; S5204; T768; D2437-26 | 0.90 | 9.55 | 2.07 | 82.29 | 3.37 | 1.24 |
| pH 5; S5204; T768; D2437-8 | 0.53 | 10.76 | 1.55 | 79.62 | 4.46 | 1.12 |

TABLE 111

Fatty acid profile in some representative complemented (D2439) and parent S5204 lines transformed with pSZ3688 DNA containing PmGGHp driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T770; D2439-11 | 0.31 | 6.79 | 1.47 | 89.97 | 0.00 | 0.00 |
| pH 5; S5204; T770; D2439-22 | 0.27 | 4.19 | 0.94 | 92.91 | 0.08 | 0.00 |
| pH 5; S5204; T770; D2439-12 | 0.39 | 6.02 | 1.26 | 90.91 | 0.16 | 0.00 |
| pH 5; S5204; T770; D2439-34 | 0.64 | 6.50 | 1.10 | 89.53 | 0.20 | 0.00 |
| pH 5; S5204; T770; D2439-32 | 0.33 | 5.25 | 1.45 | 89.98 | 1.08 | 0.51 |

TABLE 112

Fatty acid profile in some representative complemented (D2261) and parent S5204 lines transformed with pSZ3511 DNA containing PmAHI2p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T711; D2261-35 | 0.45 | 5.06 | 2.02 | 89.35 | 1.73 | 0.63 |
| pH 5; S5204; T711; D2261-8 | 0.46 | 5.12 | 2.19 | 88.92 | 2.16 | 0.19 |
| pH 5; S5204; T711; D2261-43 | 0.37 | 5.12 | 2.15 | 88.62 | 2.30 | 0.45 |
| pH 5; S5204; T711; D2261-2 | 0.42 | 5.27 | 2.14 | 88.23 | 2.39 | 0.30 |
| pH 5; S5204; T711; D2261-24 | 0.41 | 5.14 | 2.23 | 88.44 | 2.39 | 0.45 |

TABLE 113

Fatty acid profile in some representative complemented (D2267) and parent S5204 lines transformed with pSZ3517 DNA containing PmAHI1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T720; D2267-3 | 0.34 | 4.87 | 2.11 | 90.00 | 1.20 | 0.39 |
| pH 5; S5204; T720; D2267-20 | 0.37 | 5.00 | 2.14 | 89.50 | 1.46 | 0.49 |
| pH 5; S5204; T720; D2267-36 | 0.34 | 4.90 | 2.08 | 89.75 | 1.67 | 0.36 |
| pH 5; S5204; T720; D2267-15 | 0.37 | 4.95 | 2.14 | 89.77 | 1.69 | 0.00 |
| pH 5; S5204; T720; D2267-2 | 0.35 | 4.85 | 2.12 | 89.71 | 1.72 | 0.32 |

TABLE 114

Fatty acid profile in some representative complemented (D2262) and parent S5204 lines transformed with pSZ3512 DNA containing PmCEP1p driving PmFAD2-1.

| Sample ID | C14:0 | C16:0 | C18:0 | C18:1 | C18:2 | C18:3 α |
|---|---|---|---|---|---|---|
| pH 7; S3150 | 1.71 | 29.58 | 3.13 | 56.53 | 6.43 | 0.68 |
| pH 5; S3150 | 1.56 | 27.70 | 2.98 | 59.49 | 5.95 | 0.53 |
| pH 7; S5204 | 0.30 | 5.59 | 1.63 | 90.88 | 0.1 | 0 |
| pH 5; S5204 | 0.39 | 5.67 | 1.36 | 91.13 | 0 | 0 |
| pH 5; S5204; T711; D2262-3 | 0.48 | 5.50 | 2.08 | 90.58 | 0.35 | 0.00 |
| pH 5; S5204; T711; D2262-33 | 0.39 | 5.20 | 2.17 | 89.90 | 1.08 | 0.37 |
| pH 5; S5204; T711; D2262-24 | 0.34 | 5.08 | 1.93 | 89.69 | 1.34 | 0.37 |
| pH 5; S5204; T711; D2262-32 | 0.40 | 4.89 | 2.19 | 89.88 | 1.45 | 0.27 |
| pH 5; S5204; T711; D2262-34 | 0.39 | 4.95 | 2.75 | 89.30 | 1.47 | 0.27 |

Combined baseline expression of endogenous PmFAD2-1 and PmFAD2-2 in wild type *Prototheca* strains (like S3150, S1920 or S1331) manifests as 5-7% C18:2. S5204 overexpresses PmKASII which results in the elongation of C16:0 to C18:0. This increased pool of C18:0 is eventually desaturated by PmSAD2 resulting in elevated C18:1 levels. Additionally disruption of the both copies of PmFAD2 (viz. PmFAD2-1 and PmFAD2-2) in S5204 prevents further desaturation of C18:1 into C18:2 and results in a unique high oleic oil (C18:1) with 0% linoleic acid (C18:2). However as mentioned above any strain with 0% C18:2 grows very poorly and requires exogenous addition of linoleic acid to sustain growth/productivity. Complementation of a strain like S5204 with inducible PmAMT03p driven PmFAD2-1 can rescue the growth phenotype while preserving the terminal high C18:1 with 0% C18:2 levels. However data suggests that PmAMT03 shuts off in the early stages of fermentation thus severely compromising the ability of any complemented strain to achieve its full growth and productivity potential. The goal of this work was to identify promoter elements that would allow the complemented strains to grow efficiently in early stages of fermentation (T0-T30 hrs; irrespective of excess batched N in the fermenters) and then effectively shut off once the cells enter active lipid production (when N in the media gets depleted) so that the complemented strains would still finish with very high C18:1 and 0% C18:2 levels. As a comparator we also complemented S5204 with PmFAD2-1 being driven by either PmFAd2-1p or PmFAD2-2p promoter elements.

Complementation of S5204 with PmFAD2-1 driven by either PmFAD2-1p or PmFAD2-2p promoter elements results in complete restoration of the C18:2 levels using vectors either designed to amplify PmFAD2-1 copy number (e.g. pSZ3375 or pSZ3376) or the ones where PmFAD2-1 copy number is restricted to one (pSZ3382 or pSZ3383). Copy number of the PmFAD2-1 in these strains seems to have very marginal effect on the terminal C18:2 levels.

On the other hand expression of PmFAD2-1 driven by any of new promoter elements results in marked decrease in terminal C18:2 levels. The representative profiles from various strains expressing new promoters driving FAD2-1 are shown in Tables 84-114. This reduction in C18:2 levels is even more pronounced in strains where the copy number of PmFAD2-1 is limited to one. Promoter elements like PmDPS1 (D2091 & D2098), PmDPS2 (D2092 & D2099), PmPPI1 (D2263 & D2440), PmPPI2 (D2264 & D2268), PmGMPS1 (D2265 & D2269), PmGMPS2 (D2270) resulted in strains with 0% or less than 0.5% terminal C18:2 levels in both single or multiple copy PmFAD2-1 versions. The rest of the promoters resulted in terminal C18:2 levels that ranged between 1-5%. One unexpected result was the data from PmAHC1p and PmAHC2p driving PmFAD2-1 in D2434 and D2435. Both these promoters resulted in very high levels of C18:2 (9-20%) in multiple copy FAD2-1 versions. The levels of terminal C18:2 in single copy version in D2266 was more in line with the transcriptomic data suggesting that PmAHC promoter activity and the corresponding PmAHC transcription is severely downregulated when cells are actively producing lipid in depleted nitrogen environment. A quick look at the transcriptome revealed that the initial transcription of PmAHC is very high (4000-5500 TPM) which then suddenly drops down to ~250 TPM. Thus it is conceivable that in strains with multiple copies on PmFAD2-1 (D2434 and D2435), the massive amount of PmFAD2-1 protein produced earlier in the fermentation lingers and results in high C18:2 levels. In single copy PmFAD2-1 strains this is not the case and thus we do not see elevated C18:2 levels in D2266.

In complemented strains with 0% terminal C18:2 levels, the key question was whether they were complemented in the first place. In order to ascertain that, representative strains along with parent S5204 and previously AMT03p driven PmFAD2-1 complemented S2532 (viz S4695) strains were grown in seed medium in 96 well blocks. The cultures were seeded at 0.1 OD units per ml and the OD750 was checked at different time points. Compared to S5204, which grew very poorly, only S4695 and newly complemented strains grew to any meaningful OD's at 20 and 44 hrs (Table 115) demonstrating that the promoters identified above are active early on and switch off once cells enter the active lipid production phase.

TABLE 115

Growth characteristics of Δfad2 Δfata1 strain S5204, S4695 and representative complemented S5204 lines in seed medium sorted by OD750 at 44 hrs. Note that in 1 ml 96 well blocks after initial rapid division and growth, cells stop growing efficiently because of lack of nutrients, aeration etc.

| Sample ID | C14:0 | C16:0 | C18:0 | C18:1 | C18:2 | C18:3 α | OD750 @20 hrs | OD750 @44 hrs | OD750 @58 hrs |
|---|---|---|---|---|---|---|---|---|---|
| S5204 | | | | | | | 0.162 | 7.914 | 10.93 |
| S5204 | | | | | | | 0.224 | 6.854 | 9.256 |
| S4695 | | | | | | | 1.456 | 29.032 | 32.766 |
| pH 7; S5204; T672; D2091-46 | 0.31 | 5.36 | 2.24 | 90.67 | 0.00 | 0.00 | 1.38 | 33.644 | 33.226 |
| pH 5; S5204; T720; D2268-1 | 0.39 | 6.43 | 1.78 | 90.49 | 0.00 | 0.00 | 0.75 | 32.782 | 31.624 |
| S5204; T720; D2270-47 | 0.39 | 6.69 | 1.81 | 90.05 | 0.00 | 0.00 | 1.204 | 32.752 | 31.602 |
| pH 5; S5204; T720; D2270-39 | 0.39 | 6.87 | 1.81 | 89.94 | 0.00 | 0.00 | 1.012 | 32.552 | 33.138 |
| pH 7; S5204; T680; D2099-35 | 0.30 | 4.56 | 1.54 | 92.49 | 0.00 | 0.00 | 0.48 | 32.088 | 31.92 |
| pH 5; S5204; T720; D2270-44 | 0.51 | 6.85 | 1.74 | 90.06 | 0.00 | 0.00 | 1.468 | 31.802 | 30.61 |
| pH 5; S5204; T720; D2270-41 | 0.00 | 7.85 | 1.65 | 89.18 | 0.00 | 0.00 | 1.576 | 31.35 | 30.69 |
| pH 5; S5204; T720; D2270-17 | 0.46 | 6.78 | 1.71 | 90.24 | 0.00 | 0.00 | 1.79 | 30.732 | 24.768 |
| pH 7; S5204; T680; D2099-30 | 0.32 | 4.59 | 1.57 | 92.40 | 0.00 | 0.00 | 0.59 | 30.166 | 34.64 |
| pH 5; S5204; T720; D2268-40 | 0.42 | 6.66 | 1.86 | 90.02 | 0.00 | 0.00 | 0.764 | 29.62 | 29 |
| pH 5; S5204; T720; D2270-23 | 0.39 | 6.52 | 1.72 | 90.35 | 0.00 | 0.00 | 1.334 | 29.604 | 27.518 |
| pH 5; S5204; T720; D2270-42 | 0.61 | 6.59 | 1.53 | 90.28 | 0.00 | 0.00 | 2.042 | 28.986 | 32.184 |
| pH 7; S5204; T672; D2090-5 | 0.33 | 4.73 | 1.84 | 91.24 | 0.00 | 0.00 | 1.326 | 28.976 | 35.508 |
| pH 7; S5204; T672; D2091-15 | 0.30 | 5.26 | 2.20 | 90.73 | 0.00 | 0.00 | 0.826 | 28.824 | 32.848 |
| pH 7; S5204; T680; D2099-20 | 0.31 | 4.02 | 1.46 | 93.07 | 0.00 | 0.00 | 1.31 | 28.732 | 26.61 |
| pH 5; S5204; T720; D2269-19 | 0.42 | 6.51 | 1.61 | 90.43 | 0.00 | 0.00 | 1.278 | 28.65 | 31.362 |
| pH 5; S5204; T720; D2269-29 | 0.43 | 7.36 | 1.72 | 89.35 | 0.00 | 0.00 | 1.342 | 28.376 | 28.66 |
| pH 5; S5204; T720; D2270-19 | 0.39 | 6.81 | 1.75 | 90.05 | 0.00 | 0.00 | 2.142 | 28.376 | 25.934 |
| pH 5; S5204; T720; D2270-43 | 0.80 | 7.64 | 1.66 | 88.93 | 0.00 | 0.00 | 1.896 | 28.174 | 32.376 |
| pH 5; S5204; T720; D2270-46 | 0.45 | 6.75 | 1.72 | 90.02 | 0.00 | 0.00 | 1.644 | 28.122 | 30.464 |
| pH 5; S5204; T720; D2268-3 | 0.38 | 6.56 | 1.74 | 90.27 | 0.00 | 0.00 | 0.926 | 28.114 | 31.552 |
| pH 5; S5204; T720; D2268-12 | 0.00 | 5.68 | 1.84 | 91.53 | 0.00 | 0.00 | 1.414 | 28.106 | 30.644 |
| pH 5; S5204; T720; D2269-37 | 0.54 | 7.12 | 1.75 | 89.80 | 0.00 | 0.00 | 1.268 | 28.078 | 30.014 |
| pH 5; S5204; T720; D2270-31 | 0.46 | 6.94 | 1.74 | 89.71 | 0.00 | 0.00 | 1.224 | 28.064 | 29.344 |
| pH 5; S5204; T720; D2270-48 | 0.00 | 7.21 | 1.87 | 90.16 | 0.00 | 0.00 | 1.352 | 28 | 28.21 |
| pH 5; S5204; T720; D2269-8 | 0.33 | 6.67 | 1.64 | 90.34 | 0.00 | 0.00 | 0.96 | 27.912 | 27.564 |
| pH 5; S5204; T720; D2268-32 | 0.44 | 6.59 | 1.85 | 90.11 | 0.00 | 0.00 | 0.78 | 27.834 | 31.952 |
| pH 5; S5204; T720; D2269-47 | 0.42 | 6.83 | 1.82 | 89.85 | 0.00 | 0.00 | 1.17 | 27.76 | 29.648 |
| pH 7; S5204; T672; D2091-19 | 0.31 | 4.51 | 1.77 | 91.65 | 0.00 | 0.00 | 1.568 | 27.682 | 25.828 |
| pH 5; S5204; T720; D2270-38 | 0.39 | 6.65 | 1.83 | 90.11 | 0.00 | 0.00 | 1.74 | 27.606 | 31.104 |
| pH 5; S5204; T720; D2268-2 | 0.38 | 6.49 | 1.74 | 90.38 | 0.00 | 0.00 | 0.95 | 27.564 | 32.254 |

TABLE 115-continued

Growth characteristics of Δfad2 Δfata1 strain S5204, S4695 and representative complemented S5204 lines in seed medium sorted by OD750 at 44 hrs. Note that in 1 ml 96 well blocks after initial rapid division and growth, cells stop growing efficiently because of lack of nutrients, aeration etc.

| Sample ID | C14:0 | C16:0 | C18:0 | C18:1 | C18:2 | C18:3 α | OD750 @20 hrs | OD750 @44 hrs | OD750 @58 hrs |
|---|---|---|---|---|---|---|---|---|---|
| pH 5; S5204; T720; D2269-35 | 0.38 | 7.04 | 1.68 | 89.82 | 0.00 | 0.00 | 1.19 | 27.482 | 29.186 |
| pH 5; S5204; T720; D2269-20 | 0.36 | 7.01 | 1.73 | 89.86 | 0.00 | 0.00 | 0.966 | 27.47 | 28.284 |
| pH 5; S5204; T720; D2269-13 | 0.39 | 6.76 | 1.89 | 89.98 | 0.00 | 0.00 | 0.936 | 27.39 | 33.464 |
| pH 7; S5204; T680; D2099-24 | 0.28 | 4.67 | 1.50 | 92.38 | 0.00 | 0.00 | 0.8 | 27.28 | 27.35 |
| pH 5; S5204; T720; D2268-11 | 0.38 | 6.56 | 1.85 | 90.56 | 0.00 | 0.00 | 1.136 | 27.254 | 32.508 |
| pH 5; S5204; T720; D2270-3 | 0.41 | 6.69 | 1.70 | 90.22 | 0.00 | 0.00 | 0.872 | 27.214 | 30.23 |
| pH 5; S5204; T720; D2269-33 | 0.39 | 6.36 | 1.67 | 90.59 | 0.00 | 0.00 | 0.956 | 27.194 | 30.568 |
| pH 5; S5204; T720; D2268-10 | 0.45 | 6.93 | 1.70 | 90.16 | 0.00 | 0.00 | 0.612 | 27.126 | 31.616 |
| pH 5; S5204; T720; D2269-43 | 0.36 | 6.55 | 1.84 | 90.25 | 0.00 | 0.00 | 0.998 | 27.086 | 29.618 |
| pH 5; S5204; T720; D2270-1 | 0.37 | 6.80 | 1.74 | 90.18 | 0.00 | 0.00 | 2.428 | 27.004 | 31.044 |
| pH 5; S5204; T720; D2268-4 | 0.45 | 5.73 | 1.52 | 91.75 | 0.00 | 0.00 | 0.736 | 26.948 | 28.796 |
| pH 5; S5204; T720; D2270-9 | 0.38 | 6.88 | 1.74 | 90.22 | 0.00 | 0.00 | 2.68 | 26.944 | 29.92 |
| pH 5; S5204; T720; D2269-26 | 0.41 | 6.85 | 1.68 | 90.03 | 0.00 | 0.00 | 0.896 | 26.794 | 31.31 |
| pH 5; S5204; T720; D2270-24 | 0.39 | 6.51 | 1.78 | 90.33 | 0.00 | 0.00 | 1.51 | 26.682 | 27.486 |
| pH 5; S5204; T720; D2269-18 | 0.41 | 7.04 | 1.71 | 89.83 | 0.00 | 0.00 | 1.024 | 26.58 | 29.794 |
| pH 5; S5204; T720; D2269-32 | 0.38 | 6.81 | 1.72 | 90.06 | 0.00 | 0.00 | 1.214 | 26.48 | 29.478 |
| pH 5; S5204; T720; D2268-31 | 0.33 | 6.68 | 1.76 | 90.20 | 0.00 | 0.00 | 0.808 | 26.432 | 31.294 |
| pH 5; S5204; T720; D2269-7 | 0.29 | 5.33 | 1.69 | 91.59 | 0.00 | 0.00 | 1.1 | 26.41 | 28.754 |
| pH 5; S5204; T720; D2268-6 | 0.39 | 6.62 | 1.70 | 90.28 | 0.00 | 0.00 | 0.626 | 26.372 | 30.822 |
| pH 7; S5204; T680; D2099-27 | 0.40 | 4.07 | 1.22 | 93.26 | 0.00 | 0.00 | 0.936 | 26.116 | 29.75 |
| pH 5; S5204; T720; D2269-39 | 0.48 | 6.88 | 1.82 | 89.67 | 0.00 | 0.00 | 2.218 | 26.106 | 30.8 |
| pH 5; S5204; T720; D2269-12 | 0.35 | 6.39 | 1.80 | 90.47 | 0.00 | 0.00 | 1.18 | 26.032 | 28.19 |
| pH 5; S5204; T720; D2269-42 | 0.39 | 6.99 | 1.67 | 89.91 | 0.00 | 0.00 | 2.132 | 25.924 | 27.854 |
| pH 5; S5204; T720; D2268-8 | 0.56 | 6.77 | 1.49 | 90.20 | 0.00 | 0.00 | 0.96 | 25.702 | 29.788 |
| pH 5; S5204; T720; D2270-37 | 0.44 | 7.33 | 1.71 | 89.69 | 0.00 | 0.00 | 0.916 | 25.612 | 34.034 |
| pH 5; S5204; T720; D2270-40 | 0.00 | 9.30 | 1.62 | 88.12 | 0.00 | 0.00 | 2.072 | 25.552 | 29.474 |
| pH 5; S5204; T720; D2270-14 | 0.43 | 7.40 | 1.71 | 89.73 | 0.00 | 0.00 | 1.916 | 25.526 | 27.908 |
| pH 5; S5204; T720; D2269-21 | 0.40 | 6.69 | 1.69 | 89.99 | 0.00 | 0.00 | 0.826 | 25.396 | 29 |
| pH 5; S5204; T718; D2265-16 | 0.46 | 7.02 | 1.71 | 90.06 | 0.00 | 0.00 | 0.9 | 25.332 | 32.018 |
| pH 5; S5204; T720; D2270-15 | 0.40 | 6.90 | 1.68 | 90.32 | 0.00 | 0.00 | 1.594 | 25.32 | 26.794 |
| pH 5; S5204; T720; D2269-40 | 0.00 | 7.00 | 1.66 | 90.15 | 0.00 | 0.00 | 1.804 | 25.286 | 29.468 |
| pH 5; S5204; T720; D2268-5 | 0.38 | 6.58 | 1.81 | 90.79 | 0.00 | 0.00 | 0.678 | 25.156 | 33.066 |
| pH 5; S5204; T720; D2270-18 | 0.45 | 6.20 | 1.45 | 91.09 | 0.00 | 0.00 | 2.646 | 25.126 | 27.536 |
| pH 5; S5204; T720; D2269-25 | 0.44 | 7.02 | 1.69 | 89.91 | 0.00 | 0.00 | 0.868 | 25.018 | 32.104 |
| pH 5; S5204; T720; D2269-30 | 0.45 | 6.77 | 1.78 | 90.00 | 0.00 | 0.00 | 0.718 | 24.978 | 29.868 |
| pH 5; S5204; T720; D2270-25 | 0.31 | 6.82 | 1.68 | 90.09 | 0.00 | 0.00 | 2.32 | 24.814 | 36.024 |
| pH 5; S5204; T720; D2270-21 | 0.52 | 7.23 | 1.70 | 89.99 | 0.00 | 0.00 | 1.92 | 24.58 | 25.398 |
| pH 5; S5204; T720; D2269-38 | 0.00 | 7.45 | 1.50 | 90.19 | 0.00 | 0.00 | 1.494 | 24.578 | 30.178 |
| pH 5; S5204; T720; D2268-9 | 0.48 | 5.94 | 1.51 | 90.83 | 0.00 | 0.00 | 0.73 | 24.344 | 30.83 |
| pH 5; S5204; T720; D2268-37 | 0.44 | 6.35 | 1.84 | 90.31 | 0.00 | 0.00 | 0.548 | 24.306 | 32.848 |
| pH 5; S5204; T720; D2269-28 | 0.41 | 7.12 | 1.66 | 89.73 | 0.00 | 0.00 | 0.808 | 24.288 | 31.27 |
| pH 5; S5204; T720; D2270-5 | 0.44 | 6.98 | 1.78 | 89.79 | 0.00 | 0.00 | 2.328 | 24.14 | 30.186 |
| pH 5; S5204; T720; D2269-23 | 0.44 | 6.99 | 1.71 | 89.43 | 0.00 | 0.00 | 0.876 | 24.076 | 29.494 |
| pH 5; S5204; T720; D2269-9 | 0.38 | 6.84 | 1.71 | 90.32 | 0.00 | 0.00 | 0.806 | 24 | 26.844 |
| pH 5; S5204; T720; D2269-24 | 0.55 | 7.31 | 1.71 | 89.68 | 0.00 | 0.00 | 1.09 | 23.97 | 29.642 |
| pH 5; S5204; T720; D2270-35 | 0.36 | 6.58 | 1.72 | 90.38 | 0.00 | 0.00 | 1.554 | 23.71 | 28.868 |
| pH 5; S5204; T720; D2269-15 | 0.00 | 5.69 | 1.36 | 91.86 | 0.00 | 0.00 | 1.246 | 23.584 | 28.196 |
| pH 5; S5204; T720; D2270-28 | 0.39 | 7.15 | 1.82 | 89.92 | 0.00 | 0.00 | 1.648 | 23.486 | 30.858 |
| pH 7; S5204; T680; D2098-39 | 0.34 | 4.89 | 1.56 | 92.08 | 0.00 | 0.00 | 1.08 | 23.46 | 31.888 |
| pH 5; S5204; T720; D2269-27 | 0.33 | 6.87 | 1.68 | 89.98 | 0.00 | 0.00 | 1.3 | 23.262 | 33.112 |
| pH 5; S5204; T718; D2265-43 | 0.00 | 7.90 | 1.90 | 89.27 | 0.00 | 0.00 | 0.832 | 23.23 | 30.052 |
| pH 5; S5204; T720; D2270-30 | 0.41 | 7.00 | 1.68 | 89.83 | 0.00 | 0.00 | 2.144 | 23.1 | 30.97 |
| pH 5; S5204; T720; D2268-25 | 0.00 | 7.05 | 1.94 | 90.20 | 0.00 | 0.00 | 0.716 | 23.088 | 29.922 |
| pH 5; S5204; T720; D2270-29 | 0.34 | 6.81 | 1.74 | 90.11 | 0.00 | 0.00 | 2.542 | 22.98 | 31.402 |
| pH 5; S5204; T720; D2269-45 | 0.00 | 7.64 | 1.56 | 89.90 | 0.00 | 0.00 | 0.806 | 22.892 | 29.022 |
| pH 5; S5204; T720; D2270-27 | 0.72 | 9.32 | 1.99 | 87.35 | 0.00 | 0.00 | 2.352 | 22.81 | 29.996 |
| pH 5; S5204; T720; D2269-11 | 0.65 | 6.41 | 1.69 | 90.22 | 0.00 | 0.00 | 1.056 | 22.768 | 26.056 |
| pH 5; S5204; T720; D2270-36 | 0.00 | 5.45 | 1.59 | 91.60 | 0.00 | 0.00 | 1.886 | 22.738 | 24.69 |
| pH 5; S5204; T720; D2269-22 | 0.39 | 7.12 | 1.72 | 89.63 | 0.00 | 0.00 | 1.08 | 22.634 | 27.532 |
| pH 5; S5204; T718; D2263-30 | 0.54 | 7.58 | 1.57 | 89.47 | 0.00 | 0.00 | 0.71 | 22.564 | 29.996 |
| pH 7; S5204; T672; D2091-47 | 0.32 | 5.22 | 2.23 | 90.45 | 0.00 | 0.00 | 0.938 | 22.486 | 32.046 |
| pH 5; S5204; T720; D2269-1 | 0.38 | 6.73 | 1.68 | 90.24 | 0.00 | 0.00 | 1.154 | 22.48 | 29.994 |
| pH 7; S5204; T673; D2096-6 | 0.33 | 4.18 | 1.10 | 92.91 | 0.00 | 0.00 | 0.91 | 22.446 | 28.714 |
| pH 5; S5204; T720; D2270-33 | 0.40 | 6.95 | 1.76 | 89.89 | 0.00 | 0.00 | 2.28 | 22.408 | 29.656 |
| pH 5; S5204; T718; D2263-14 | 0.58 | 7.72 | 1.64 | 89.26 | 0.00 | 0.00 | 0.306 | 22.35 | 32.294 |
| pH 5; S5204; T720; D2270-34 | 0.36 | 6.75 | 1.77 | 90.10 | 0.00 | 0.00 | 2.398 | 22.3 | 28.958 |
| pH 7; S5204; T672; D2090-29 | 0.42 | 4.99 | 2.01 | 91.06 | 0.00 | 0.00 | 1.16 | 22.112 | 30.376 |
| pH 5; S5204; T720; D2269-14 | 0.00 | 7.86 | 1.80 | 89.57 | 0.00 | 0.00 | 0.574 | 21.802 | 31.558 |
| pH 5; S5204; T718; D2263-29 | 0.58 | 7.32 | 1.30 | 90.07 | 0.00 | 0.00 | 0.418 | 21.746 | 30.426 |
| pH 5; S5204; T718; D2263-19 | 0.62 | 7.92 | 1.56 | 89.25 | 0.00 | 0.00 | 0.574 | 21.692 | 29.514 |
| pH 5; S5204; T720; D2269-10 | 0.39 | 6.82 | 1.70 | 90.05 | 0.00 | 0.00 | 1.104 | 21.622 | 25.264 |
| pH 5; S5204; T720; D2269-4 | 0.42 | 6.57 | 1.71 | 90.32 | 0.00 | 0.00 | 1.082 | 21.466 | 29.698 |

TABLE 115-continued

Growth characteristics of Δfad2 Δfata1 strain S5204, S4695 and representative complemented S5204 lines in seed medium sorted by OD750 at 44 hrs. Note that in 1 ml 96 well blocks after initial rapid division and growth, cells stop growing efficiently because of lack of nutrients, aeration etc.

| Sample ID | C14:0 | C16:0 | C18:0 | C18:1 | C18:2 | C18:3 α | OD750 @20 hrs | OD750 @44 hrs | OD750 @58 hrs |
|---|---|---|---|---|---|---|---|---|---|
| pH 5; S5204; T720; D2270-4 | 0.43 | 7.44 | 1.72 | 89.31 | 0.00 | 0.00 | 1.758 | 21.446 | 32.656 |
| pH 5; S5204; T720; D2269-34 | 0.00 | 6.69 | 1.78 | 90.64 | 0.00 | 0.00 | 0.946 | 21.438 | 28.538 |
| pH 5; S5204; T720; D2270-16 | 0.39 | 7.08 | 1.71 | 89.70 | 0.00 | 0.00 | 1.592 | 21.422 | 27.72 |
| pH 5; S5204; T718; D2263-26 | 0.42 | 7.39 | 1.70 | 89.28 | 0.00 | 0.00 | 0.514 | 21.328 | 29.746 |
| pH 5; S5204; T720; D2269-3 | 0.36 | 6.76 | 1.71 | 90.17 | 0.00 | 0.00 | 0.668 | 21.242 | 29.74 |
| pH 5; S5204; T720; D2270-22 | 0.35 | 6.77 | 1.67 | 90.15 | 0.00 | 0.00 | 1.194 | 21.026 | 25.084 |
| pH 5; S5204; T720; D2270-26 | 0.41 | 6.81 | 1.82 | 89.66 | 0.00 | 0.00 | 1.606 | 20.948 | 32.142 |
| pH 5; S5204; T720; D2270-10 | 0.46 | 6.98 | 1.80 | 90.03 | 0.00 | 0.00 | 0.792 | 20.728 | 28.264 |
| pH 5; S5204; T720; D2269-16 | 0.51 | 6.17 | 1.50 | 90.64 | 0.00 | 0.00 | 0.922 | 20.502 | 30.132 |
| pH 5; S5204; T720; D2270-8 | 0.50 | 6.95 | 1.42 | 90.34 | 0.00 | 0.00 | 2.252 | 20.486 | 28.34 |
| pH 5; S5204; T720; D2270-2 | 0.46 | 6.76 | 1.83 | 89.90 | 0.00 | 0.00 | 0.97 | 20.366 | 31.758 |
| pH 5; S5204; T720; D2269-36 | 0.00 | 7.43 | 1.66 | 89.88 | 0.00 | 0.00 | 0.754 | 20.006 | 29.648 |
| pH 5; S5204; T720; D2269-31 | 0.72 | 9.29 | 1.86 | 86.92 | 0.00 | 0.00 | 2.062 | 19.002 | 27.61 |
| pH 5; S5204; T720; D2269-44 | 0.00 | 9.45 | 1.58 | 88.16 | 0.00 | 0.00 | 1.378 | 18.576 | 22.52 |
| pH 7; S5204; T672; D2091-14 | 0.27 | 4.79 | 2.24 | 90.94 | 0.00 | 0.00 | 0.93 | 18.1 | 30.434 |
| pH 5; S5204; T720; D2270-32 | 0.40 | 7.14 | 1.74 | 89.63 | 0.00 | 0.00 | 1.668 | 17.966 | 27.06 |
| pH 5; S5204; T720; D2270-11 | 0.82 | 9.24 | 1.93 | 87.35 | 0.00 | 0.00 | 1.178 | 15.998 | 28.196 |
| pH 5; S5204; T720; D2269-48 | 0.72 | 9.05 | 2.14 | 88.08 | 0.00 | 0.00 | 1.172 | 14.694 | 25.384 |
| pH 5; S5204; T720; D2269-17 | 0.66 | 9.08 | 2.12 | 87.12 | 0.00 | 0.00 | 0.84 | 14.488 | 25.886 |
| pH 5; S5204; T720; D2270-20 | 0.62 | 8.35 | 1.97 | 88.43 | 0.00 | 0.00 | 1.37 | 14.168 | 23.794 |
| pH 5; S5204; T718; D2263-13 | 0.75 | 9.44 | 1.98 | 87.09 | 0.00 | 0.00 | 0.64 | 13.854 | 29.466 |
| pH 5; S5204; T720; D2269-46 | 0.43 | 6.87 | 1.71 | 89.81 | 0.00 | 0.00 | 0.646 | 10.452 | 31.464 |
| pH 5; S5204; T720; D2269-5 | 0.59 | 8.81 | 1.93 | 87.97 | 0.00 | 0.00 | 0.654 | 9.37 | 25.786 |
| pH 7; S5204; T672; D2091-4 | 1.42 | 4.39 | 2.32 | 89.87 | 0.00 | 0.00 | 0.686 | 8.182 | 16.454 |
| pH 5; S5204; T720; D2269-6 | 0.50 | 7.29 | 1.73 | 89.29 | 0.00 | 0.00 | 0.79 | 7.978 | 21.346 |
| pH 5; S5204; T720; D2270-45 | 0.00 | 9.16 | 1.65 | 88.19 | 0.00 | 0.00 | 0.464 | 3.448 | 16.796 |
| Blank | | | | | | | 0 | 0 | 0 |

It is comtemplated that these promoters, or variants thereof, discovered here can be used to regulate a fatty acid synthesis gene (e.g., any of the FATA, FATB, SAD, FAD2, KASI/IV, KASII, LPAAT or KCS genes disclosed herein) or other gene or gene-suppression element expressed in a cell including a microalgal cell. Variants can have for example 60, 65, 70, 75, 80, 85, 90, 95, 96, 97, 98, 99% or greater identity to the sequences disclosed here.

Example 64: Fractionation of a High SOS Oil to Increase SOS Concentration and Reduce Trisaturates Microalgal oil was fractionated using dry fractionation and solvent fractionation techniques. The starting material was an oil that was high in SOS triglycerides. The oil was produced from *Prototheca moriformis* strain S7566, in which a the endogenous KASII gene was inserted into (and thereby knocking out) a SADII locus; additionally, the C18-preferring FATA1 gene from *Garcinia mangostana* was inserted and a FADII hairpin RNA was produced; as described above. After cultivation and extracted, the oil was refined, bleached and deodorized. The fatty acid profile of the oil is given in Table 115. The SOS TAG area % was about 62%. During the RBD processing, the total trisaturates (i.e. triglycerides with three fully saturated acyl chains such as SSS, PSS, PPS, PPP, etc.) in the oil decreased from 5.1% to 1.2%.

TABLE 116

Fatty acid profile of clarified oil from strain 7566.

| | | Strain S7566 |
|---|---|---|
| Fatty Acid Area % | C14:0 | 0.49 |
| | C16:0 | 3.12 |
| | C18:0 | 54.77 |
| | C18:1 | 35.88 |
| | C18:2 | 2.16 |
| | C18:3 α | 0.23 |
| | C20:0 | 1.64 |
| | C22:0 | 0.19 |
| | C24:0 | 0.11 |
| | sum C18 | 93.05 |
| | saturates | 60.69 |
| | unsaturates | 38.55 |

The oil was fractionated using solvent (acetone or hexane) and dry fractionation. Acetone fractionation (1:1 oil-solvent, w/w; crystallization at 5° C.) gave excellent recovery of an SOS-enriched stearin fraction, with relatively little SOS in the olein fraction. SOS was at 77%, with total trisaturates<1% for the stearin fraction.

Hexane fractionation (1:1 oil-solvent, w/w; crystallization at 5° C.) gave a higher level (85%) of SOS, but also gave higher trisaturates (1.6%). Thus, using a single-step solvent fractionation, oils with over 75% SOS and less than 2% trisaturates were obtainable.

Dry fractionation was also successful in enriching SOS and decreasing trisaturates. The general approach was to remove trisaturates by crystallization at a higher temperature, then removing OOS at a lower temperature. The reverse order was also tried and yielded a superior result. It was also found that rinsing the SOS-enriched ("stearin") fraction with acetone helped in removing the olein fraction.

In one test, the oil was crystallized at 24° C. and the stearin fraction was rinsed with acetone. Analysis showed that OOS levels decreased. The stearin fraction was heated and allowed to cool and crystallize overnight at 29° C. The resulting liquid oil was separated from the crystallized trisaturates to afford a product with 84% SOS and <0.5% total trisaturates. Lipase-based sn-2 profile analysis of revealed that over 96% of that position was occupied by unsaturated fatty acids (93.3% oleate, 3.2% linolate, and 0.2% linolenate), while only 2.2% stearate was located there.

The DSC heating curve thermogram and DSC-derived solid fat content curve of the two step dry fractionated oil was compared to those of kokum butter. The two oils have essentially identical maximum heat-flow temperatures and the DSC-derived SFC curves are super-imposable. The oil could be expected to behave functionally similarly to kokum butter.

Example 65: Production of Microbial Oil with Over 60% SOS Content

Here, we demonstrate in the microalga *Prototheca moriformis*, that by disrupting an allele of the SAD2 gene, overexpressing KASII, knocking out endogenous FATA-1, overexpressing a more stearate-specific FATA (GarmFATA1 from *Garcinia mangostana*) relative to the endogenous FATA and activating FAD2 RNAi, we generate strains capable of accumulating over 60% SOS, useful as a structuring fat.

To reduce SAD activity, Strain S3150 was transformed with DNA constructs designed to recombine in the SAD2-1 and SAD2-2 alleles and express the selectable marker, *Arabidopsis thialiana* THIC (AtTHIC, codon-optimized for expression in *P. moriformis*). THIC encodes 4-amino-5-hydroxymethyl-2-methylpyrimidine synthase, thereby allowing growth in the absence of added thiamine. Transformants were selected in the absence of exogenous thiamine.

To make the SAD2-1 ablation construct pSZ2601, the *Arabidopsis thaliana* THIC gene (AtTHIC, codon-optimized for expression in *P. moriformis*), was utilized as a selectable marker for transformation. The sequence of the transforming DNA is shown in SEQ ID NO:148. Relevant restriction sites are indicated in lowercase, bold, and are from 5'-3' BspQI, PmeI, KpnI, XbaI, MfeI, SacI, BspQI and PmeI. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlorella protothecoides* ACT promoter (CpACT) driving the expression of the AtTHIC gene (encoding 4-amino-5-hydroxymethyl-2-methylpyrimidine synthase activity, thereby permitting the strain to grow in the absence of exogenous thiamine) is indicated by lowercase, boxed text. The initiator ATG and terminator TGA for AtTHIC are indicated by uppercase italics, while the coding region is indicated with lowercase italics. The 3' UTR of the *Chlorella vulgaris* nitrate reductase (CvNR) gene is indicated by small capitals.

Nucleotide sequence of the transforming DNA from pSZ2601:

(SEQ ID NO: 148)

gaagagcgcccaatgtttaaacGCCGGTCACCACCCGCATGCTCGTACTACAGCGCACGCACCGCTTCGTG

ATCCACCGGGTGAACGTAGTCCTCGACGGAAACATCTGGTTCGGGCCTCCTGCTTGCACTCCCGCCC

ATGCCGACAACCTTTCTGCTGTTACCACGACCCACAATGCAACGCGACACGACCGTGTGGGACTGAT

CGGTTCACTGCACCTGCATGCAATTGTCACAAGCGCTTACTCCAATTGTATTCGTTTGTTTTCTGGGA

GCAGTTGCTCGACCGCCCGCGTCCCGCAGGCAGCGATGACGTGTGCGTGGCCTGGGTGTTTCGTCG

AAAGGCCAGCAACCCTAAATCGCAGGCGATCCGGAGATTGGGATCTGATCCGAGTTTGGACCAGAT

CCGCCCCGATGCGGCACGGGAACTGCATCGACTCGGCGCGGAACCCAGCTTTCGTAAATGCCAGAT

TGGTGTCCGATACCTGGATTTGCCATCAGCGAAACAAGACTTCAGCAGCGAGCGTATTTGGCGGGC

GTGCTACCAGGGTTGCATACATTGCCCATTTCTGTCTGGACCGCTTTACTGGCGCAGAGGGTGAGTT

GATGGGGTTGGCAGGCATCGAAACGCGCGTGCATGGTGTGCGTGTCTGTTTTCGGCTGCACGAATT

CAATAGTCGGATGGGCGACGGTAGAATTGGGTGTGGCGCTCGCGTGCATGCCTCGCCCCGTCGGGT

GTCATGACCGGGACTGGAATCCCCCCTCGCGACCATCTTGCTAACGCTCCCGACTCTCCCGACCGCG

CGCAGGATAGACTCTTGTTCAACCAATCGACAaggtaccagtttaggtccagcgtccgtgggggggacgggctggga gcttgggccgggaagggcaagacgatgcagtccctctggggagtcacagccgactgtgtgtgttgcactgtgcggcccgcagcact cacacgcaaaatgcctggccgacaggcaggccctgtccagtgcaacatccacggtccctctcatcaggctcaccttgctcattgaca taacggaatgcgtaccgctctttcagatctgtccatccagagaggggagcaggctccccaccgacgctgtcaaacttgcttcctgcc caaccgaaaacattattgtttgagggggggggggggggggcagattgcatggcgggatatctcgtgaggaacatcactgggacac tgtggaacacagtgagtgcagtatgcagagcatgtatgctaggggtcagcgcaggaagggggcctttcccagtctcccatgccact -continued gcaccgtatccacgactcaccaggaccagcttcttgatcggcttccgctcccgtggacaccagtgtgtagcctctggactccaggtat gcgtgcaccgcaaaggccagccgatcgtgccgattcctgggtggaggatatgagtcagccaacttggggctcagagtgcacactgg ggcacgatacgaaacaacatctacaccgtgtcctccatgctgacacaccacagcttcgctccacctgaatgtgggcgcatgggccc gaatcacagccaatgtcgctgctgccataatgtgatccagaccctctccgcccagatgccgagcggatcgtgggcgctgaatagatt cctgtttcgatcactgtttgggtcctttccttttcgtctcggatgcgcgtctcgaaacaggctgcgtcgggctttcggatcccttttgctc cctccgtcaccatcctgcgcgcgggcaagttgcttgaccctgggctgataccagggttggagggtattaccgcgtcaggccattccc agcccggattcaattcaaagtctgggccaccaccctccgccgctctgtctgatcactccacattcgtgcatacactacgttcaagtcct gatccaggcgtgtctcgggacaaggtgtgcttgagtttgaatctcaaggacccactccagcacagctgctggttgaccccgccctcg caatctaga*ATGgccgcgtccgtccactgcaccctgatgtccgtggtctgcaacaacaagaaccactccgcccgccccaagct*

*gcccaactcctccctgctgcccggcttcgacgtggtggtccaggccgcggccacccgcttcaagaaggagacgacgaccaccc*

*gcgccacgctgacgttcgacccccccacgaccaactccgagcgcgccaagcagcgcaagcacaccatcgacccctcctccccc*

*gacttccagcccatcccctccttcgaggagtgcttccccaagtccacgaaggagcacaaggaggtggtgcacgaggagtccg*

*gccacgtcctgaaggtgcccttccgccgcgtgcacctgtccggcggcgagcccgccttcgacaactacgacacgtccggccccc*

*agaacgtcaacgcccacatcggcctggcgaagctgcgcaaggagtggatcgaccgccgcgagaagctgggcacgccccgct*

*acacgcagatgtactacgcgaagcagggcatcatcacggaggagatgctgtactgcgcgacgcgcgagaagctggaccccg*

*agttcgtccgctccgaggtcgcgcggggccgcgccatcatcccctccaacaagaagcacctggagctggagcccatgatcgtg*

*ggccgcaagttcctggtgaaggtgaacgcgaacatcggcaactccgccgtggcctcctccatcgaggaggaggtctacaagg*

*tgcagtgggccaccatgtggggcgccgacaccatcatggacctgtccacgggccgccacatccacgagacgcgcgagtggat*

*cctgcgcaactccgcggtccccgtgggcaccgtccccatctaccaggcgctggagaaggtggacggcatcgcggagaacctg*

*aactgggaggtgttccgcgagacgctgatcgagcaggccgagcagggcgtggactacttcacgatccacgcgggcgtgctgc*

*tgcgctacatcccccctgaccgccaagcgcctgacgggcatcgtgtcccgcggcggctccatccacgcgaagtggtgcctggcct*

*accacaaggagaacttcgcctacgagcactgggacgacatcctggacatctgcaaccagtacgacgtcgccctgtccatcggc*

*gacggcctgcgccccggctccatctacgacgccaacgacacggcccagttcgccgagctgctgacccagggcgagctgacgc*

*gccgcgcgtgggagaaggacgtgcaggtgatgaacgagggccccggccacgtgcccatgcacaagatccccgagaacatg*

*cagaagcagctggagtggtgcaacgaggcgcccttctacaccctgggcccccctgacgaccgacatcgcgcccggctacgacc*

*acatcacctccgccatcggcgcggccaacatcggcgccctgggcaccgccctgctgtgctacgtgacgcccaaggagcacctg*

*ggcctgcccaaccgcgacgacgtgaaggcgggcgtcatcgcctacaagatcgccgcccacgcggccgacctggccaagcag*

*cacccccacgcccaggcgtgggacgacgcgctgtccaaggcgcgcttcgagttccgctggatggaccagttcgcgctgtccctg*

*gaccccatgacggcgatgtccttccacgacgagacgctgcccgcggacggcgcgaaggtcgcccacttctgctccatgtgcgg*

*ccccaagttctgctccatgaagatcacggaggacatccgcaagtacgccgaggagaacggctacggctccgccgaggaggc*

*catccgccagggcatggacgccatgtccgaggagttcaacatcgccaagaagacgatctccggcgagcagcacggcgaggt*

*cggcggcgagatctacctgcccgagtcctacgtcaaggccgcgcagaagTGA*caattgGCAGCAGCAGCTCGGATAGTATC GACACACTCTGGACGCTGGTCGTGTGATGGACTGTTGCCGCCACACTTGCTGCCTTGACCTGTGAATATCCCTGCCGCTTT TATCAAACAGCCTCAGTGTGTTTGATCTTGTGTGTACGCGCTTTTGCGAGTTGCTAGCTGCTTGTGCTATTTGCGAATACCA CCCCCAGCATCCCCTTCCCTCGTTTCATATCGCTTGCATCCCAACCGCAACTTATCTACGCTGTCCTGCTATCCCTCAGCGCT GCTCCTGCTCCTGCTCACTGCCCCTCGCACAGCCTTGGTTTGGGCTCCGCCTGTATTCTCCTGGTACTGCAACCTGTAAACC AGCACTGCAATGCTGATGCACGGGAAGTAGTGGGATGGGAACACAAATGGAGGATCGTAgagctcTAGGGAGCGA

CGAGTGTGCGTGCGGGGCTGGCGGGAGTGGGACGCCCTCCTCGCTCCTCTCTGTTCTGAACGGAAC

AATCGGCCACCCCGCGCTACGCGCCACGCATCGAGCAACGAAGAAAACCCCCCGATGATAGGTTGC

-continued

GGTGGCTGCCGGGATATAGATCCGGCCGCACATCAAAGGGCCCCTCCGCCAGAGAAGAAGCTCCTT

TCCCAGCAGACTCCTTCTGCTGCCAAAACACTTCTCTGTCCACAGCAACACCAAAGGATGAACAGATC

AACTTGCGTCTCCGCGTAGCTTCCTCGGCTAGCGTGCTTGCAACAGGTCCCTGCACTATTATCTTCCT

GCTTTCCTCTGAATTATGCGGCAGGCGAGCGCTCGCTCTGGCGAGCGCTCCTTCGCGCCGCCCTCGC

TGATCGAGTGTACAGTCAATGAATGGTCCTGGGCGAAGAACGAGGGAATTTGTGGGTAAAACAAG

CATCGTCTCTCAGGCCCCGGCGCAGTGGCCGTTAAAGTCCAAGACCGTGACCAGGCAGCGCAGCGC

GTCCGTGTGCGGGCCCTGCCTGGCGGCTCGGCGTGCCAGGCTCGAGAGCAGCTCCCTCAGGTCGCC

TTGGACGGCCTCTGCGAGGCCGGTGAGGGCCTGCAGGAGCGCCTCGAGCGTGGCAGTGGCGGTCG

TATCCGGGTCGCCGGTCACCGCCTGCGACTCGCCATCCgaagagcgtttaaac

The sequence of the transforming DNA from the SAD2-1 disruption construct, pSZ2607, is shown below in SEQ ID NO:149. Relevant restriction sites are indicated in lowercase, bold, and are from 5'-3' PmeI, KpnI, XbaI, MfeI, SacI, BspQI and PmeI. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlorella protothecoides* ACT promoter (CpACT) driving the expression of the AtTHIC gene (encoding 4-amino-5-hydroxymethyl-2-methylpyrimidine synthase activity, thereby permitting the strain to grow in the absence of exogenous thiamine) is indicated by lowercase, boxed text. The initiator ATG and terminator TGA for AtTHIC are indicated by uppercase italics, while the coding region is indicated with lowercase italics. The 3' UTR of the *Chlorella vulgaris* nitrate reductase (CvNR) gene is indicated by small capitals.

Nucleotide sequence of the transforming DNA from pSZ2607:

(SEQ ID NO: 149)

gtttaaacGCCGGTCACCACCCGCATGCTCGTACTACAGCGCACGCACCGCTTCGTGATCCACCGGGTG

AACGTAGTCCTCGACGGAAACATCTGGTTCGGGCCTCCTGCTTGCACTCCCGCCCATGCCGACAACC

TTTCTGCTGTTACCACGACCCACAATGCAACGCGACACGACCGTGTGGGACTGATCGGTTCACTGCA

CCTGCATGCAATTGTCACAAGCGCTTACTCCAATTGTATTCGTTTGTTTTCTGGGAGCAGTTGCTCGA

CCGCCCGCGTCCCGCAGGCAGCGATGACGTGTGCGTGGCCTGGGTGTTTCGTCGAAAGGCCAGCAA

CCCTAAATCGCAGGCGATCCGGAGATTGGGATCTGATCCGAGTTTGGACCAGATCCGCCCCGATGC

GGCACGGGAACTGCATCGACTCGGCGCGGAACCCAGCTTTCGTAAATGCCAGATTGGTGTCCGATA

CCTGGATTTGCCATCAGCGAAACAAGACTTCAGCAGCGAGCGTATTTGGCGGGCGTGCTACCAGGG

TTGCATACATTGCCCATTTCTGTCTGGACCGCTTTACTGGCGCAGAGGGTGAGTTGATGGGGTTGGC

AGGCATCGAAACGCGCGTGCATGGTGTGCGTGTCTGTTTTCGGCTGCACGAATTCAATAGTCGGAT

GGGCGACGGTAGAATTGGGTGTGGCGCTCGCGTGCATGCCTCGCCCCGTCGGGTGTCATGACCGG

GACTGGAATCCCCCCTCGCGACCATCTTGCTAACGCTCCCGACTCTCCCGACCGCGCGCAGGATAGA

CTCTTGTTCAACCAATCGACAggtaccagtttaggtccagcgtccgtgggggggggacgggctgggagcttgggccgggaa gggcaagacgatgcagtccctctggggagtcacagccgactgtgtgtgttgcactgtgcggcccgcagcactcacacgcaaaatgc ctggccgacaggcaggccctgtccagtgcaacatccacggtccctctcatcaggctcaccttgctcattgacataacggaatgcgta ccgctctttcagatctgtccatccagagaggggagcaggctccccaccgacgctgtcaaacttgcttcctgcccaaccgaaaacatt attgtttgagggggggggggggggggggcagattgcatggcgggatatctcgtgaggaacatcactgggacactgtggaacacagtg agtgcagtatgcagagcatgtatgctaggggtcagcgcaggaagggggcctttcccagtctcccatgccactgcaccgtatccacg actcaccaggaccagcttcttgatcggcttccgctcccgtggacaccagtgtgtagcctctggactccaggtatgcgtgcaccgcaa aggccagccgatcgtgccgattcctgggtggaggatatgagtcagccaacttggggctcagagtgcacactggggcacgatacga aacaacatctacaccgtgtcctccatgctgacacaccacagcttcgctccacctgaatgtgggcgcatgggcccgaatcacagcca atgtcgctgctgccataatgtgatccagaccctctccgcccagatgccgagcggatcgtgggcgctgaatagattcctgtttcgatca -continued ctgtttgggtcctttccttttcgtctcggatgcgcgtctcgaaacaggctgcgtcgggctttcggatcccttttgctccctccgtcaccat cctgcgcgcgggcaagttgcttgaccctgggctgataccagggttggagggtattaccgcgtcaggccattcccagcccggattcaa ttcaaagtctgggccaccaccctccgccgctctgtctgatcactccacattcgtgcatacactacgttcaagtcctgatccaggcgtgt ctcgggacaaggtgtgcttgagtttgaatctcaaggacccactccagcacagctgctggttgaccccgccctcgcaatctaga*ATG*

*gccgcgtccgtccactgcaccctgatgtccgtggtctgcaacaacaagaaccactccgcccgccccaagctgcccaactcctccc*

*tgctgcccggcttcgacgtggtggtccaggccgcggccacccgcttcaagaaggagacgacgaccacccgcgccacgctgac*

*gttcgacccccccacgaccaactccgagcgcgccaagcagcgcaagcacaccatcgacccctcctcccccgacttccagcccat*

*cccctccttcgaggagtgcttccccaagtccacgaaggagcacaaggaggtggtgcacgaggagtccggccacgtcctgaag*

*gtgcccttccgccgcgtgcacctgtccggcggcgagcccgccttcgacaactacgacacgtccggcccccagaacgtcaacgcc*

*cacatcggcctggcgaagctgcgcaaggagtggatcgaccgccgcgagaagctgggcacgccccgctacacgcagatgtac*

*tacgcgaagcagggcatcatcacggaggagatgctgtactgcgcgacgcgcgagaagctggaccccgagttcgtccgctccg*

*aggtcgcgcggggccgcgccatcatcccctccaacaagaagcacctggagctggagcccatgatcgtgggccgcaagttcct*

*ggtgaaggtgaacgcgaacatcggcaactccgccgtggcctcctccatcgaggaggaggtctacaaggtgcagtgggccac*

*catgtggggcgccgacaccatcatggacctgtccacgggccgccacatccacgagacgcgcgagtggatcctgcgcaactcc*

*gcggtccccgtgggcaccgtccccatctaccaggcgctggagaaggtggacggcatcgcggagaacctgaactgggaggtg*

*ttccgcgagacgctgatcgagcaggccgagcagggcgtggactacttcacgatccacgcgggcgtgctgctgcgctacatccc*

*cctgaccgccaagcgcctgacgggcatcgtgtcccgcggcggctccatccacgcgaagtggtgcctggcctaccacaaggag*

*aacttcgcctacgagcactgggacgacatcctggacatctgcaaccagtacgacgtcgccctgtccatcggcgacggcctgcg*

*ccccggctccatctacgacgccaacgacacggcccagttcgccgagctgctgacccagggcgagctgacgcgccgcgcgtgg*

*gagaaggacgtgcaggtgatgaacgagggccccggccacgtgcccatgcacaagatccccgagaacatgcagaagcagct*

*ggagtggtgcaacgaggcgcccttctacaccctgggcccccctgacgaccgacatcgcgcccggctacgaccacatcacctccg*

*ccatcggcgcggccaacatcggcgccctgggcaccgccctgctgtgctacgtgacgcccaaggagcacctgggcctgcccaac*

*cgcgacgacgtgaaggcgggcgtcatcgcctacaagatcgccgcccacgcggccgacctggccaagcagcacccccacgccc*

*aggcgtgggacgacgcgctgtccaaggcgcgcttcgagttccgctggatggaccagttcgcgctgtccctggaccccatgacg*

*gcgatgtccttccacgacgagacgctgcccgcggacggcgcgaaggtcgcccacttctgctccatgtgcggccccaagttctgc*

*tccatgaagatcacggaggacatccgcaagtacgccgaggagaacggctacggctccgccgaggaggccatccgccaggg*

*catggacgccatgtccgaggagttcaacatcgccaagaagacgatctccggcgagcagcacggcgaggtcggcggcgagat*

*ctacctgcccgagtcctacgtcaaggccgcgcagaagTGA*caattgGCAGCAGCAGCTCGGATAGTATCGACACACTCTGG ACGCTGGTCGTGTGATGGACTGTTGCCGCCACACTTGCTGCCTTGACCTGTGAATATCCCTGCCGCTTTTATCAAACAGCCT CAGTGTGTTTGATCTTGTGTGTACGCGCTTTTGCGAGTTGCTAGCTGCTTGTGCTATTTGCGAATACCACCCCCAGCATCCC CTTCCCTCGTTTCATATCGCTTGCATCCCAACCGCAACTTATCTACGCTGTCCTGCTATCCCTCAGCGCTGCTCCTGCTCCTG CTCACTGCCCCTCGCACAGCCTTGGTTTGGGCTCCGCCTGTATTCTCCTGGTACTGCAACCTGTAAACCAGCACTGCAATGC TGATGCACGGGAAGTAGTGGGATGGGAACACAAATGGAGGATCGTAgagctcCAGCCACGGCAACACCGCGCG

CCTTGCGGCCGAGCACGGCGACAAGAACCTGAGCAAGATCTGCGGGCTGATCGCCAGCGACGAGG

GCCGGCACGAGATCGCCTACACGCGCATCGTGGACGAGTTCTTCCGCCTCGACCCCGAGGGCGCCG

TCGCCGCCTACGCCAACATGATGCGCAAGCAGATCACCATGCCCGCGCACCTCATGGACGACATGG

GCCACGGCGAGGCCAACCCGGGCCGCAACCTCTTCGCCGACTTCTCCGCGGTCGCCGAGAAGATCG

ACGTCTACGACGCCGAGGACTACTGCCGCATCCTGGAGCACCTCAACGCGCGCTGGAAGGTGGACG

AGCGCCAGGTCAGCGGCCAGGCCGCCGCGGACCAGGAGTACGTCCTGGGCCTGCCCCAGCGCTTCC

GGAAACTCGCCGAGAAGACCGCCGCCAAGCGCAAGCGCGTCGCGCGCAGGCCCGTCGCCTTCTCCT

GGATCTCCGGGCGCGAGATCATGGTCTAGGGAGCGACGAGTGTGCGTGCGGGGCTGGCGGGAGT

-continued

GGGACGCCCTCCTCGCTCCTCTCTGTTCTGAACGGAACAATCGGCCACCCCGCGCTACGCGCCACGC

ATCGAGCAACGAAGAAAACCCCCCGATGATAGGTTGCGGTGGCTGCCGGGATATAGATCCGGCCGC

ACATCAAAGGGCCCCTCCGCCAGAGAAGAAGCTCCTTTCCCAGCAGACTCCTgaagagcgtttaaac

The sequence of the transforming DNA from the SAD2-2 disruption construct, pSZ2622, is shown below in SEQ ID NO:150. Relevant restriction sites are indicated in lowercase, bold, and are from 5'-3' BspQI, PmeI, KpnI, XbaI, MfeI, SacI, BspQI and PmeI. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlorella protothecoides* ACT promoter (CpACT) driving the expression of the AtTHIC gene (encoding 4-amino-5-hydroxymethyl-2-methylpyrimidine synthase activity, thereby permitting the strain to grow in the absence of exogenous thiamine) is indicated by lowercase, boxed text. The initiator ATG and terminator TGA for AtTHIC are indicated by uppercase italics, while the coding region is indicated with lowercase italics. The 3' UTR of the *Chlorella vulgaris* nitrate reductase (CvNR) gene is indicated by small capitals.

Nucleotide sequence of the transforming DNA from pSZ2622:

(SEQ ID NO: 150)

gaagagcgcccaatgtttaaacGCCGGTCACCATCCGCATGCTCATATTACAGCGCACGCACCGCTTCGTGA

TCCACCGGGTGAACGTAGTCCTCGACGGAAACATCTGGCTCGGGCCTCGTGCTGGCACTCCCTCCCA

TGCCGACAACCTTTCTGCTGTCACCACGACCCACGATGCAACGCGACACGACCCGGTGGGACTGATC

GGTTCACTGCACCTGCATGCAATTGTCACAAGCGCATACTCCAATCGTATCCGTTTGATTTCTGTGAA

AACTCGCTCGACCGCCCGCGTCCCGCAGGCAGCGATGACGTGTGCGTGACCTGGGTGTTTCGTCGA

AAGGCCAGCAACCCCAAATCGCAGGCGATCCGGAGATTGGGATCTGATCCGAGCTTGGACCAGATC

CCCCACGATGCGGCACGGGAACTGCATCGACTCGGCGCGGAACCCAGCTTTCGTAAATGCCAGATT

GGTGTCCGATACCTTGATTTGCCATCAGCGAAACAAGACTTCAGCAGCGAGCGTATTTGGCGGGCG

TGCTACCAGGGTTGCATACATTGCCCATTTCTGTCTGGACCGCTTTACCGGCGCAGAGGGTGAGTTG

ATGGGGTTGGCAGGCATCGAAACGCGCGTGCATGGTGTGTGTGTCTGTTTTCGGCTGCACAATTTCA

ATAGTCGGATGGGCGACGGTAGAATTGGGTGTTGCGCTCGCGTGCATGCCTCGCCCCGTCGGGTGT

CATGACCGGGACTGGAATCCCCCCTCGCGACCCTCCTGCTAACGCTCCCGACTCTCCCGCCCGCGCG

CAGGATAGACTCTAGTTCAACCAATCGACAggtaccagtttaggtccagcgtccgtgggggggacgggctgggagc ttgggccgggaagggcaagacgatgcagtccctctggggagtcacagccgactgtgtgtgttgcactgtgcggcccgcagcactca cacgcaaaatgcctggccgacaggcaggccctgtccagtgcaacatccacggtccctctcatcaggctcaccttgctcattgacata acggaatgcgtaccgctctttcagatctgtccatccagagaggggagcaggctccccaccgacgctgtcaaacttgcttcctgccca accgaaaacattattgtttgagggggggggggggggggcagattgcatggcgggatatctcgtgaggaacatcactgggacactg tggaacacagtgagtgcagtatgcagagcatgtatgctaggggtcagcgcaggaagggggcctttcccagtctcccatgccactgc accgtatccacgactcaccaggaccagcttcttgatcggcttccgctcccgtggacaccagtgtgtagcctctggactccaggtatgc gtgcaccgcaaaggccagccgatcgtgccgattcctgggtggaggatatgagtcagccaacttggggctcagagtgcacactggg gcacgatacgaaacaacatctacaccgtgtcctccatgctgacacaccacagcttcgctccacctgaatgtgggcgcatgggcccg aatcacagccaatgtcgctgctgccataatgtgatccagaccctctccgcccagatgccgagcggatcgtgggcgctgaatagattc ctgtttcgatcactgtttgggtcctttccttttcgtctcggatgcgcgtctcgaaacaggctgcgtcgggctttcggatcccttttgctcc ctccgtcaccatcctgcgcgcgggcaagttgcttgaccctgggctgataccagggttggagggtattaccgcgtcaggccattccca gcccggattcaattcaaagtctgggccaccaccctccgccgctctgtctgatcactccacattcgtgcatacactacgttcaagtcctg atccaggcgtgtctcgggacaaggtgtgcttgagtttgaatctcaaggacccactccagcacagctgctggttgaccccgccctcgc -continued aatctaga*ATGgccgcgtccgtccactgcaccctgatgtccgtggtctgcaacaacaagaaccactccgcccgccccaagctg*

*cccaactcctccctgctgcccggcttcgacgtggtggtccaggccgcggccacccgcttcaagaaggagacgacgaccacccg*

*cgccacgctgacgttcgacccccccacgaccaactccgagcgcgccaagcagcgcaagcacaccatcgacccctcctcccccg*

*acttccagcccatcccctccttcgaggagtgcttccccaagtccacgaaggagcacaaggaggtggtgcacgaggagtccggc*

*cacgtcctgaaggtgcccttccgccgcgtgcacctgtccggcggcgagcccgccttcgacaactacgacacgtccggcccccag*

*aacgtcaacgcccacatcggcctggcgaagctgcgcaaggagtggatcgaccgccgcgagaagctgggcacgccccgctac*

*acgcagatgtactacgcgaagcagggcatcatcacggaggagatgctgtactgcgcgacgcgcgagaagctggaccccga*

*gttcgtccgctccgaggtcgcgcggggccgcgccatcatcccctccaacaagaagcacctggagctggagcccatgatcgtgg*

*gccgcaagttcctggtgaaggtgaacgcgaacatcggcaactccgccgtggcctcctccatcgaggaggaggtctacaaggt*

*gcagtgggccaccatgtggggcgccgacaccatcatggacctgtccacgggccgccacatccacgagacgcgcgagtggatc*

*ctgcgcaactccgcggtccccgtgggcaccgtccccatctaccaggcgctggagaaggtggacggcatcgcggagaacctga*

*actgggaggtgttccgcgagacgctgatcgagcaggccgagcagggcgtggactacttcacgatccacgcgggcgtgctgct*

*gcgctacatcccccctgaccgccaagcgcctgacgggcatcgtgtcccgcggcggctccatccacgcgaagtggtgcctggccta*

*ccacaaggagaacttcgcctacgagcactgggacgacatcctggacatctgcaaccagtacgacgtcgccctgtccatcggcg*

*acggcctgcgccccggctccatctacgacgccaacgacacggcccagttcgccgagctgctgacccagggcgagctgacgcg*

*ccgcgcgtgggagaaggacgtgcaggtgatgaacgagggccccggccacgtgcccatgcacaagatccccgagaacatgc*

*agaagcagctggagtggtgcaacgaggcgcccttctacaccctgggcccccctgacgaccgacatcgcgcccggctacgacca*

*catcacctccgccatcggcgcggccaacatcggcgccctgggcaccgccctgctgtgctacgtgacgcccaaggagcacctgg*

*gcctgcccaaccgcgacgacgtgaaggcgggcgtcatcgcctacaagatcgccgcccacgcggccgacctggccaagcagc*

*acccccacgcccaggcgtgggacgacgcgctgtccaaggcgcgcttcgagttccgctggatggaccagttcgcgctgtccctg*

*gaccccatgacggcgatgtccttccacgacgagacgctgcccgcggacggcgcgaaggtcgcccacttctgctccatgtgcgg*

*ccccaagttctgctccatgaagatcacggaggacatccgcaagtacgccgaggagaacggctacggctccgccgaggaggc*

*catccgccagggcatggacgccatgtccgaggagttcaacatcgccaagaagacgatctccggcgagcagcacggcgaggt*

*cggcggcgagatctacctgcccgagtcctacgtcaaggccgcgcagaagTGA*caattgGCAGCAGCAGCTCGGATAGTATC GACACACTCTGGACGCTGGTCGTGTGATGGACTGTTGCCGCCACACTTGCTGCCTTGACCTGTGAATATCCCTGCCGCTTT TATCAAACAGCCTCAGTGTGTTTGATCTTGTGTGTACGCGCTTTTGCGAGTTGCTAGCTGCTTGTGCTATTTGCGAATACCA CCCCCAGCATCCCCTTCCCTCGTTTCATATCGCTTGCATCCCAACCGCAACTTATCTACGCTGTCCTGCTATCCCTCAGCGCT GCTCCTGCTCCTGCTCACTGCCCCTCGCACAGCCTTGGTTTGGGCTCCGCCTGTATTCTCCTGGTACTGCAACCTGTAAACC AGCACTGCAATGCTGATGCACGGGAAGTAGTGGGATGGGAACACAAATGGAGGATCGTAgagctcCAGCCACGGC

AACACCGCGCGCCTGGCGGCCGAGCACGGCGACAAGGGCCTGAGCAAGATCTGCGGGCTGATCGC

CAGCGACGAGGGCCGGCACGAGATCGCCTACACGCGCATCGTGGACGAGTTCTTCCGCCTCGACCC

CGAGGGCGCCGTCGCCGCCTACGCCAACATGATGCGCAAGCAGATCACCATGCCCGCGCACCTCAT

GGACGACATGGGCCACGGCGAGGCCAACCCGGGCCGCAACCTCTTCGCCGACTTCTCCGCCGTCGC

CGAGAAGATCGACGTCTACGACGCCGAGGACTACTGCCGCATCCTGGAGCACCTCAACGCGCGCTG

GAAGGTGGACGAGCGCCAGGTCAGCGGCCAGGCCGCCGCGGACCAGGAGTACGTTCTGGGCCTGC

CCCAGCGCTTCCGGAAACTCGCCGAGAAGACCGCCGCCAAGCGCAAGCGCGTCGCGCGCAGGCCC

GTCGCCTTCTCCTGGATCTCCGGACGCGAGATTATGGTCTAGGGAGGTACGAGCGCGCGCGAGGGA

-continued

TTGGTGGGAGTGGGACGCGCTCGTCGCTCCTTTCTATTCTGAAGGGAAGATTGGCCACCCCGCTCCA

CGCGCCACGCATCGAGCAACGAAGAAAACCCCCCGATGATAGGTTGCAGTGGCTGCCGAGATATAG

ATCCGGCTGCACGTCAAAGGGCCCCTCGGCCAGAGAAGAAGCTCTTTTCCCAGCGACCGCAGACTCC

Tgaagagcgtttaaac

Constructs D1557, D1565 and D1566, derived from pSZ2601, pSZ2607 and pSZ2622, respectively, were transformed into S3150 as described previously. Primary transformants were clonally purified and grown under low-nitrogen lipid production conditions at pH 5. The resulting fatty acid profiles from representative clones are summarized in Table 117. SAD2-1 disruption strains derived from D1557 and D1565 transformants accumulated up to 13.4% C18:0 at the expense of C18:1, indicating that SAD activity was significantly reduced in these strains. C18:0 levels only increased to 8.5% in SAD2-2 disruption strains, suggesting that the expression or activity of SAD2-2 was lower than that of SAD2-1. We also observed that C20:0 levels increased up to 1.1% in strains with elevated C18:0, demonstrating that C18:0 was an effective primer for fatty acid elongation reactions in the endoplasmic reticulum (ER).

TABLE 117

Fatty acid profiles from representative clones.

| | | Strain | | | | | | | | |
|---|---|---|---|---|---|---|---|---|---|---|
| | | S3150 | D1557-2 | D1557-3 | D1565-10 | D1565-3 | D1565-8 | D1566-5 | D1566-6 | D1566-1 |
| Fatty | C14:0 | 1.30 | 1.14 | 1.20 | 1.08 | 1.12 | 1.11 | 1.18 | 1.12 | 1.21 |
| Acid | C16:0 | 28.71 | 29.32 | 29.74 | 28.84 | 29.34 | 29.11 | 29.21 | 29.13 | 28.46 |
| Area % | C16:1 | 0.76 | 0.21 | 0.23 | 0.21 | 0.21 | 0.21 | 0.32 | 0.31 | 0.31 |
| | C17:0 | 0.12 | 0.14 | 0.15 | 0.15 | 0.14 | 0.14 | 0.14 | 0.16 | 0.14 |
| | C18:0 | 2.93 | 13.42 | 11.92 | 14.29 | 14.14 | 14.04 | 8.47 | 8.47 | 7.68 |
| | C18:1 | 58.08 | 46.29 | 47.65 | 45.75 | 45.31 | 45.69 | 51.29 | 51.33 | 53.38 |
| | C18:2 | 6.81 | 7.15 | 6.96 | 7.09 | 7.18 | 7.19 | 7.25 | 7.34 | 6.92 |
| | C18:3 α | 0.59 | 0.69 | 0.63 | 0.72 | 0.72 | 0.73 | 0.71 | 0.73 | 0.62 |
| | C20:0 | 0.24 | 0.93 | 0.84 | 1.10 | 1.09 | 1.04 | 0.75 | 0.77 | 0.63 |
| | C22:0 | 0.05 | 0.16 | 0.15 | 0.19 | 0.19 | 0.18 | 0.14 | 0.14 | 0.11 |
| | C24:0 | 0.06 | 0.16 | 0.16 | 0.20 | 0.20 | 0.20 | 0.17 | 0.17 | 0.14 |
| | sum C18 | 68.40 | 67.55 | 67.16 | 67.85 | 67.35 | 67.65 | 67.72 | 67.87 | 68.60 |
| | saturates | 33.49 | 45.35 | 44.24 | 45.94 | 46.32 | 45.93 | 40.18 | 40.04 | 38.48 |
| | unsaturates | 66.52 | 54.62 | 55.76 | 54.04 | 53.68 | 54.07 | 59.83 | 59.97 | 61.50 |

In order to increase C18:0 accumulation at the expense of C16:0 we generated DNA constructs which simultaneously ablated SAD2-1 and over-expressed a codon-optimized version of the endogenous β-ketoacyl-ACP synthase II (PmKASII) gene. The sequence of the transforming DNA from the SAD2-1 ablation, PmKASII over-expression construct, pSZ2624, is shown below in SEQ ID NO:151. Relevant restriction sites are indicated in lowercase, bold, and are from 5'-3' PmeI, SpeI, AscI, ClaI, SacI, AvrII, EcoRV, AflII, KpnI, XbaI, MfeI, BamHI, BspQI and PmeI. Underlined sequences at the 5' and 3' flanks of the construct represent genomic DNA from *P. moriformis* that enable targeted integration of the transforming DNA via homologous recombination at the SAD2-1 locus. The SAD2-1 5' integration flank contained the endogeneous SAD2-1 promoter, enabling the in situ activation of the PmKASII gene. Proceeding in the 5' to 3' direction, the region encoding the PmKASII plastid targeting sequence is indicated by lowercase, underlined italics. The sequence that encodes the mature PmKASII polypeptide is indicated with lowercase italics, while a 3×FLAG epitope encoding sequence is in bold italics. The initiator ATG and terminator TGA for PmKASII-FLAG are indicated by uppercase italics. Two spacer regions are represented by lowercase text. The CpACT promoter driving the expression of the AtTHIC gene is indicated by lowercase, boxed text. The initiator ATG and terminator TGA for AtTHIC are indicated by uppercase italics, while the coding region is indicated with lowercase italics. The 3' UTR of the *Chlorella vulgaris* nitrate reductase (CvNR) gene is indicated by small capitals.

Nucleotide sequence of the transforming DNA from pSZ2624:

(SEQ ID NO: 151)

gtttaaacGCCGGTCACCACCCGCATGCTCGTACTACAGCGCACGCACCGCTTCGTGATCCACCGGGTG

AACGTAGTCCTCGACGGAAACATCTGGTTCGGGCCTCCTGCTTGCACTCCCGCCCATGCCGACAACC

TTTCTGCTGTTACCACGACCCACAATGCAACGCGACACGACCGTGTGGGACTGATCGGTTCACTGCA

CCTGCATGCAATTGTCACAAGCGCTTACTCCAATTGTATTCGTTTGTTTTCTGGGAGCAGTTGCTCGA

CCGCCCGCGTCCCGCAGGCAGCGATGACGTGTGCGTGGCCTGGGTGTTTCGTCGAAAGGCCAGCAA

CCCTAAATCGCAGGCGATCCGGAGATTGGGATCTGATCCGAGTTTGGACCAGATCCGCCCCGATGC

GGCACGGGAACTGCATCGACTCGGCGCGGAACCCAGCTTTCGTAAATGCCAGATTGGTGTCCGATA

CCTGGATTTGCCATCAGCGAAACAAGACTTCAGCAGCGAGCGTATTTGGCGGGCGTGCTACCAGGG

TTGCATACATTGCCCATTTCTGTCTGGACCGCTTTACTGGCGCAGAGGGTGAGTTGATGGGGTTGGC

AGGCATCGAAACGCGCGTGCATGGTGTGCGTGTCTGTTTTCGGCTGCACGAATTCAATAGTCGGAT

GGGCGACGGTAGAATTGGGTGTGGCGCTCGCGTGCATGCCTCGCCCCGTCGGGTGTCATGACCGG

GACTGGAATCCCCCCTCGCGACCATCTTGCTAACGCTCCCGACTCTCCCGACCGCGCGCAGGATAGA

CTCTTGTTCAACCAATCGACAactagt*ATGcacaccgcccaccagcgcccccccaccgagggccactgcttcggcgcc*

*cgcctgcccaccgcctcccgccgcgccgtgcgccgcgcctggtcccgcatcgcccgcg*ggcgcgcc*gccgccgccgccgacgcc*

*aaccccgcccgccccgagcgccgcgtggtgatcaccggccagggcgtggtgacctccctgggccagaccatcgagcagttcta*

*ctcctccctgctggagggcgtgtccggcatctcccagatccagaagttcgacaccaccggctacaccaccaccatcgccggcga*

*gatcaagtccctgcagctggacccctacgtgcccaagcgctgggccaagcgcgtggacgacgtgatcaagtacgtgtacatcg*

*ccggcaagcaggccctggagtccgccggcctgcccatcgaggccgccggcctggccggcgccggcctggaccccgccctgtgc*

*ggcgtgctgatcggcaccgccatggccggcatgacctccttcgccgccggcgtggaggccctgacccgcggcggcgtgcgcaa*

*gatgaaccccttctgcatccccttctccatctccaacatgggcggcgccatgctggccatggacatcggcttcatgggccccaact*

*actccatctccaccgcctgcgccaccggcaactactgcatcctgggcgccgccgaccacatccgccgcggcgacgccaacgtga*

*tgctggccggcggcgccgacgccgccatcatcccctccggcatcggcggcttcatcgcctgcaaggccctgtccaagcgcaacg*

*acgagcccgagcgcgcctcccgcccctgggacgccgaccgcgacggcttcgtgatgggcgagggcgccggcgtgctggtgct*

*ggaggagctggagcacgccaagcgccgcggcgccaccatcctggccgagctggtgggcggcgccgccacctccgacgccca*

*ccacatgaccgagcccgacccccagggccgcggcgtgcgcctgtgcctggagcgcgccctggagcgcgcccgcctggccccg*

*agcgcgtgggctacgtgaacgcccacggcacctccacccccgccggcgacgtggccgagtaccgcgccatccgcgccgtgatc*

*ccccaggactccctgcgcatcaactccaccaagtccatgatcggccacctgctgggcggcgccggcgccgtggaggccgtggc*

*cgccatccaggccctgcgcaccggctggctgcaccccaacctgaacctggagaaccccgcccccggcgtggaccccgtggtgc*

*tggtgggccccgcaaggagcgcgccgaggacctggacgtggtgctgtccaactccttcggcttcggcggccacaactcctgc*

*gtgatcttccgcaagtacgacgag*atggactacaaggaccacgacggcgactacaaggaccacgacatcgactacaagg*

*acgacgacgacaagTGA*atcgatAGATCTCTTAAGGCAGCAGCAGCTCGGATAGTATCGACACACTCTGGACGCTGGTC GTGTGATGGACTGTTGCCGCCACACTTGCTGCCTTGACCTGTGAATATCCCTGCCGCTTTTATCAAACAGCCTCAGTGTGTT TGATCTTGTGTGTACGCGCTTTTGCGAGTTGCTAGCTGCTTGTGCTATTTGCGAATACCACCCCCAGCATCCCCTTCCCTCG TTTCATATCGCTTGCATCCCAACCGCAACTTATCTACGCTGTCCTGCTATCCCTCAGCGCTGCTCCTGCTCCTGCTCACTGCC CCTCGCACAGCCTTGGTTTGGGCTCCGCCTGTATTCTCCTGGTACTGCAACCTGTAAACCAGCACTGCAATGCTGATGCAC GGGAAGTAGTGGGATGGGAACACAAATGGAAAGCTTAATTAAgagctccgcgtctcgaacagagcgcgcagaggaacgctg aaggtctcgcctctgtcgcacctcagcgcggcatacaccacaataaccacctgacgaatgcgcttggttcttcgtccattagcgaagc gtccggttcacacacgtgccacgttggcgaggtggcaggtgacaatgatcggtggagctgatggtcgaaacgttcacagcctagg**t -continued gatatccatcttaaggatctaagtaagattcgaagcgctcgaccgtgccggacggactgcagccccatgtcgtagtgaccgccaat gtaagtgggctggcgtttccctgtacgtgagtcaacgtcactgcacgcgcaccaccctctcgaccggcaggaccaggcatcgcgag atacagcgcgagccagacacggagtgccgagctatgcgcacgctccaactaggtaccagtttaggtccagcgtccgtgggggggg acgggctgggagcttgggccgggaagggcaagacgatgcagtccctctggggagtcacagccgactgtgtgtgttgcactgtgcgg cccgcagcactcacacgcaaaatgcctggccgacaggcaggccctgtccagtgcaacatccacggtccctctcatcaggctcacctt gctcattgacataacggaatgcgtaccgctctttcagatctgtccatccagagaggggagcaggctccccaccgacgctgtcaaact tgcttcctgcccaaccgaaaacattattgtttgagggggggggggggggggcagattgcatggcgggatatctcgtgaggaacatc actgggacactgtggaacacagtgagtgcagtatgcagagcatgtatgctaggggtcagcgcaggaagggggcattcccagtctc ccatgccactgcaccgtatccacgactcaccaggaccagcttcttgatcggcttccgctcccgtggacaccagtgtgtagcctctgga ctccaggtatgcgtgcaccgcaaaggccagccgatcgtgccgattcctgggtggaggatatgagtcagccaacttggggctcagag tgcacactggggcacgatacgaaacaacatctacaccgtgtcctccatgctgacacaccacagcttcgctccacctgaatgtgggcg catgggcccgaatcacagccaatgtcgctgctgccataatgtgatccagaccctctccgcccagatgccgagcggatcgtgggcgct gaatagattcctgtttcgatcactgtttgggtcattccttttcgtctcggatgcgcgtctcgaaacaggctgcgtcgggattcggatc ccttttgctccctccgtcaccatcctgcgcgcgggcaagttgcttgaccctgggctgataccagggttggagggtattaccgcgtcag gccattcccagcccggattcaattcaaagtctgggccaccaccctccgccgctctgtctgatcactccacattcgtgcatacactacgt tcaagtcctgatccaggcgtgtctcgggacaaggtgtgcttgagtttgaatctcaaggacccactccagcacagctgctggttgaccc cgccctcgcaatctaga*ATGgccgcgtccgtccactgcaccctgatgtccgtggtctgcaacaacaagaaccactccgcccgcc*

*ccaagctgcccaactcctccctgctgcccggcttcgacgtggtggtccaggccgcggccacccgcttcaagaaggagacgacg*

*accacccgcgccacgctgacgttcgacccccccacgaccaactccgagcgcgccaagcagcgcaagcacaccatcgacccctc*

*ctcccccgacttccagcccatcccctccttcgaggagtgcttccccaagtccacgaaggagcacaaggaggtggtgcacgagg*

*agtccggccacgtcctgaaggtgcccttccgccgcgtgcacctgtccggcggcgagcccgccttcgacaactacgacacgtccg*

*gcccccagaacgtcaacgcccacatcggcctggcgaagctgcgcaaggagtggatcgaccgccgcgagaagctgggcacgc*

*cccgctacacgcagatgtactacgcgaagcagggcatcatcacggaggagatgctgtactgcgcgacgcgcgagaagctgg*

*accccgagttcgtccgctccgaggtcgcgcggggccgcgccatcatcccctccaacaagaagcacctggagctggagcccatg*

*atcgtgggccgcaagttcctggtgaaggtgaacgcgaacatcggcaactccgccgtggcctcctccatcgaggaggaggtct*

*acaaggtgcagtgggccaccatgtggggcgccgacaccatcatggacctgtccacgggccgccacatccacgagacgcgcg*

*agtggatcctgcgcaactccgcggtccccgtgggcaccgtccccatctaccaggcgctggagaaggtggacggcatcgcgga*

*gaacctgaactgggaggtgttccgcgagacgctgatcgagcaggccgagcagggcgtggactacttcacgatccacgcggg*

*cgtgctgctgcgctacatcccccctgaccgccaagcgcctgacgggcatcgtgtcccgcggcggctccatccacgcgaagtggtg*

*cctggcctaccacaaggagaacttcgcctacgagcactgggacgacatcctggacatctgcaaccagtacgacgtcgccctgt*

*ccatcggcgacggcctgcgccccggctccatctacgacgccaacgacacggcccagttcgccgagctgctgacccagggcga*

*gctgacgcgccgcgcgtgggagaaggacgtgcaggtgatgaacgagggccccggccacgtgcccatgcacaagatccccg*

*agaacatgcagaagcagctggagtggtgcaacgaggcgcccttctacaccctgggccccctgacgaccgacatcgcgcccgg*

*ctacgaccacatcacctccgccatcggcgcggccaacatcggcgccctgggcaccgccctgctgtgctacgtgacgcccaagg*

*agcacctgggcctgcccaaccgcgacgacgtgaaggcgggcgtcatcgcctacaagatcgccgcccacgcggccgacctggc*

*caagcagcacccccacgcccaggcgtgggacgacgcgctgtccaaggcgcgcttcgagttccgctggatggaccagttcgcg*

*ctgtccctggaccccatgacggcgatgtccttccacgacgagacgctgcccgcggacggcgcgaaggtcgcccacttctgctcc*

*atgtgcggccccaagttctgctccatgaagatcacggaggacatccgcaagtacgccgaggagaacggctacggctccgccg*

*aggaggccatccgccagggcatggacgccatgtccgaggagttcaacatcgccaagaagacgatctccggcgagcagcacg*

*gcgaggtcggcggcgagatctacctgcccgagtcctacgtcaaggccgcgcagaagTGA*caattgACGGAGCGTCGTGCG -continued

GGAGGGAGTGTGCCGAGCGGGGAGTCCCGGTCTGTGCGAGGCCCGGCAGCTGACGCTGGCGAGCCGTACGCCCCGAG

GGTCCCCCTCCCCTGCACCCTCTTCCCCTTCCCTCTGACGGCCGCGCCTGTTCTTGCATGTTCAGCGACggatccTAGGGA

GCGACGAGTGTGCGTGCGGGGCTGGCGGGAGTGGGACGCCCTCCTCGCTCCTCTCTGTTCTGAACG

GAACAATCGGCCACCCCGCGCTACGCGCCACGCATCGAGCAACGAAGAAAACCCCCCGATGATAGG

TTGCGGTGGCTGCCGGGATATAGATCCGGCCGCACATCAAAGGGCCCCTCCGCCAGAGAAGAAGCT

CCTTTCCCAGCAGACTCCTTCTGCTGCCAAAACACTTCTCTGTCCACAGCAACACCAAAGGATGAACA

GATCAACTTGCGTCTCCGCGTAGCTTCCTCGGCTAGCGTGCTTGCAACAGGTCCCTGCACTATTATCT

TCCTGCTTTCCTCTGAATTATGCGGCAGGCGAGCGCTCGCTCTGGCGAGCGCTCCTTCGCGCCGCCCT

CGCTGATCGAGTGTACAGTCAATGAATGGTCCTGGGCGAAGAACGAGGGAATTTGTGGGTAAAACA

AGCATCGTCTCTCAGGCCCCGGCGCAGTGGCCGTTAAAGTCCAAGACCGTGACCAGGCAGCGCAGC

GCGTCCGTGTGCGGGCCCTGCCTGGCGGCTCGGCGTGCCAGGCTCGAGAGCAGCTCCCTCAGGTCG

CCTTGGACGGCCTCTGCGAGGCCGGTGAGGGCCTGCAGGAGCGCCTCGAGCGTGGCAGTGGCGGT

CGTATCCGGGTCGCCGGTCACCGCCTGCGACTCGCCATCcgaagagcgtttaaac

Using the methods of this example, by overexpressing KASII, and *Garcinia mangostana* FATA, and by reducing expression of endogenous SAD, FAD2, and FATA, we produced a strain of *P. moriformis* that produced and oil with greater than 55% SOS with Sat-O-Sat (where O is oleate and Sat is any saturated fatty acid) of about 70-75% and trisaturated TAGs of less than 6.5%.

Example 66: Combining KASII, FATA and LPAAT Transgenes to Produce an Oil High in SOS In *Prototheca moriformis*, we overexpressed the *P. moriformis* KASII, knocked out an endogenous SAD2 allele, knocked out the endogenous FATA allele, and overexpressed both a LPAAT from *Brassica napus* and a FATA gene from *Garcinia mangostana* ("GarmFAT1"). The resulting strain produced an oil with over 55% SOS, over 70% Sat-O-Sat, and less than 8% trisaturated TAGs.

A base strain was transformed with a linearized plasmid with flanking regions designed for homologous recombination at the SAD2 site. As in examples above, the construct ablated SAD2 and overexpressed *P. moriformis* KASII. A ThiC selection marker was used. This strain was further transformed with a construct designed to overexpress Garm-FATA1 with a *P. moriformis* SASD1 plastid targeting peptide via homologous recombination at the 6S chromosomal site using invertase as a selection marker. The resulting strain, produced oil with about 62% stearate, 6% palmitate, 5% linoleate, 45% SOS and 20% trisaturates.

The sequence of the transforming DNA from the Garm-FATA1 expression construct (pSZ3204) is shown below in SEQ ID NO:152. Relevant restriction sites are indicated in lowercase, bold, and are from 5'-3' BspQI, KpnI, XbaI, MfeI, BamHI, AvrII, EcoRV, SpeI, AscI, ClaI, AflII, Sad and BspQI. Underlined sequences at the 5' and 3' flanks of the construct represent genomic DNA from *P. moriformis* that enable targeted integration of the transforming DNA via homologous recombination at the 6S locus. Proceeding in the 5' to 3' direction, the CrTUB2 promoter driving the expression of *Saccharomyces cerevisiae* SUC2 (ScSUC2) gene, enabling strains to utilize exogenous sucrose, is indicated by lowercase, boxed text. The initiator ATG and terminator TGA of ScSUC2 are indicated by uppercase italics, while the coding region is represented by lowercase italics. The 3' UTR of the CvNR gene is indicated by small capitals. A spacer region is represented by lowercase text. The *P. moriformis* SAD2-2 (PmSAD2-2) promoter driving the expression of the chimeric CpSAD1tp_GarmFATA1_FLAG gene is indicated by lowercase, boxed text. The initiator ATG and terminator TGA are indicated by uppercase italics; the sequence encoding CpSAD1tp is represented by lowercase, underlined italics; the sequence encoding the GarmFATA1 mature polypeptide is indicated by lowercase italics; and the 3×FLAG epitope tag is represented by uppercase, bold italics. A second CvNR3' UTR is indicated by small capitals.

Nucleotide sequence of the transforming DNA from pSZ3204:

(SEQ ID NO: 152)

gctcttcGCCGCCGCCACTCCTGCTCGAGCGCGCCCGCGCGTGCGCCGCCAGCGCCTTGGCCTTTTCGC

CGCGCTCGTGCGCGTCGCTGATGTCCATCACCAGGTCCATGAGGTCTGCCTTGCGCCGGCTGAGCCA

CTGCTTCGTCCGGGCGGCCAAGAGGAGCATGAGGGAGGACTCCTGGTCCAGGGTCCTGACGTGGT

CGCGGCTCTGGGAGCGGGCCAGCATCATCTGGCTCTGCCGCACCGAGGCCGCCTCCAACTGGTCCT

CCAGCAGCCGCAGTCGCCGCCGACCCTGGCAGAGGAAGACAGGTGAGGGGGGTATGAATTGTACA

GAACAACCACGAGCCTTGTCTAGGCAGAATCCCTACCAGTCATGGCTTTACCTGGATGACGGCCTGC

GAACAGCTGTCCAGCGACCCTCGCTGCCGCCGCTTCTCCCGCACGCTTCTTTCCAGCACCGTGATGGC

-continued

GCGAGCCAGCGCCGCACGCTGGCGCTGCGCTTCGCCGATCTGAGGACAGTCGGGGAACTCTGATCA

GTCTAAACCCCCTTGCGCGTTAGTGTTGCCATCCTTTGCAGACCGGTGAGAGCCGACTTGTTGTGCG

CCACCCCCCACACCACCTCCTCCCAGACCAATTCTGTCACCTTTTTGGCGAAGGCATCGGCCTCGGCC

TGCAGAGAGGACAGCAGTGCCCAGCCGCTGGGGGTTGGCGGATGCACGCTCAggtaccctttcttgcgct atgacacttccagcaaaaggtagggcgggctgcgagacggcttcccggcgctgcatgcaacaccgatgatgcttcgacccccccga agctccttcggggctgcatgggcgctccgatgccgctccagggcgagcgctgtttaaatagccaggcccccgattgcaaagacatta tagcgagctaccaaagccatattcaaacacctagatcactaccacttctacacaggccactcgagcttgtgatcgcactccgctaag ggggcgcctcttcctcttcgtttcagtcacaacccgcaaactctagaatatca*ATGctgctgcaggccttcctgttcctgctggccg*

*gcttcgccgccaagatcagcgcctccatgacgaacgagacgtccgaccgccccctggtgcacttcacccccaacaagggctgg*

*atgaacgaccccaacggcctgtggtacgacgagaaggacgccaagtggcacctgtacttccagtacaacccgaacgacacc*

*gtctgggggacgcccttgttctggggccacgccacgtccgacgacctgaccaactgggaggaccagcccatcgccatcgcccc*

*gaagcgcaacgactccggcgccttctccggctccatggtggtggactacaacaacacctccggcttcttcaacgacaccatcga*

*cccgcgccagcgctgcgtggccatctggacctacaacaccccggagtccgaggagcagtacatctcctacagcctggacggcg*

*gctacaccttcaccgagtaccagaagaaccccgtgctggccgccaactccacccagttccgcgacccgaaggtcttctggtacg*

*agccctcccagaagtggatcatgaccgcggccaagtcccaggactacaagatcgagatctactcctccgacgacctgaagtcc*

*tggaagctggagtccgcgttcgccaacgagggcttcctcggctaccagtacgagtgccccggcctgatcgaggtccccaccga*

*gcaggaccccagcaagtcctactgggtgatgttcatctccatcaaccccggcgccccggccggcggctccttcaaccagtacttc*

*gtcggcagcttcaacggcacccacttcgaggccttcgacaaccagtcccgcgtggtggacttcggcaaggactactacgccctg*

*cagaccttcttcaacaccgacccgacctacgggagcgccctgggcatcgcgtgggcctccaactgggagtactccgccttcgtg*

*cccaccaacccctggcgctcctccatgtccctcgtgcgcaagttctccctcaacaccgagtaccaggccaacccggagacggag*

*ctgatcaacctgaaggccgagccgatcctgaacatcagcaacgccggcccctggagccggttcgccaccaacaccacgttgac*

*gaaggccaacagctacaacgtcgacctgtccaacagcaccggcaccctggagttcgagctggtgtacgccgtcaacaccacc*

*cagacgatctccaagtccgtgttcgcggacctctccctctggttcaagggcctggaggaccccgaggagtacctccgcatgggc*

*ttcgaggtgtccgcgtcctccttcttcctggaccgcgggaacagcaaggtgaagttcgtgaaggagaacccctacttcaccaac*

*cgcatgagcgtgaacaaccagcccttcaagagcgagaacgacctgtcctactacaaggtgtacggcttgctggaccagaaca*

*tcctggagctgtacttcaacgacggcgacgtcgtgtccaccaacacctacttcatgaccaccgggaacgccctgggctccgtga*

*acatgacgacgggggtggacaacctgttctacatcgacaagttccaggtgcgcgaggtcaagTGA*caattgGCAGCAGCAG CTCGGATAGTATCGACACACTCTGGACGCTGGTCGTGTGATGGACTGTTGCCGCCACACTTGCTGCCTTGACCTGTGAATA TCCCTGCCGCTTTTATCAAACAGCCTCAGTGTGTTTGATCTTGTGTGTACGCGCTTTTGCGAGTTGCTAGCTGCTTGTGCTA TTTGCGAATACCACCCCCAGCATCCCCTTCCCTCGTTTCATATCGCTTGCATCCCAACCGCAACTTATCTACGCTGTCCTGCT ATCCCTCAGCGCTGCTCCTGCTCCTGCTCACTGCCCCTCGCACAGCCTTGGTTTGGGCTCCGCCTGTATTCTCCTGGTACTG CAACCTGTAAACCAGCACTGCAATGCTGATGCACGGGAAGTAGTGGGATGGGAACACAAATGGAggatcccgcgtctcga acagagcgcgcagaggaacgctgaaggtctcgcctctgtcgcacctcagcgcggcatacaccacaataaccacctgacgaatgcg cttggttcttcgtccattagcgaagcgtccggttcacacacgtgccacgttggcgaggtggcaggtgacaatgatcggtggagctgat ggtcgaaacgttcacagcctagggatatcctgaagaatgggaggcaggtgttgttgattatgagtgtgtaaaagaaaggggtaga gagccgtcctcagatccgactactatgcaggtagccgctcgcccatgcccgcctggctgaatattgatgcatgcccatcaaggcagg caggcatttctgtgcacgcaccaagcccacaatcttccacaacacacagcatgtaccaacgcacgcgtaaaagttggggtgctgcc agtgcgtcatgccaggcatgatgtgctcctgcacatccgccatgatctcctccatcgtctcgggtgtttccggcgcctggtccgggag ccgttccgccagatacccagacgccacctccgacctcacggggtacttttcgagcgtctgccggtagtcgacgatcgcgtccaccat -continued ggagtagccgaggcgccggaactggcgtgacggagggaggagagggaggagagagaggggggggggggggggggatgattac acgccagtctcacaacgcatgcaagacccgtttgattatgagtacaatcatgcactactagatggatgagcgccaggcataaggca caccgacgttgatggcatgagcaactcccgcatcatatttcctattgtcctcacgccaagccggtcaccatccgcatgctcatattac agcgcacgcaccgcttcgtgatccaccgggtgaacgtagtcctcgacggaaacatctggctcgggcctcgtgctggcactccctccc atgccgacaacctttctgctgtcaccacgacccacgatgcaacgcgacacgacccggtgggactgatcggttcactgcacctgcatg caattgtcacaagcgcatactccaatcgtatccgtttgatttctgtgaaaactcgctcgaccgcccgcgtcccgcaggcagcgatgac gtgtgcgtgacctgggtgtttcgtcgaaaggccagcaaccccaaatcgcaggcgatccggagattgggatctgatccgagcttgga ccagatcccccacgatgcggcacgggaactgcatcgactcggcgcggaacccagattcgtaaatgccagattggtgtccgatacc ttgatttgccatcagcgaaacaagacttcagcagcgagcgtatttggcgggcgtgctaccagggttgcatacattgcccatttctgtc tggaccgctttaccggcgcagagggtgagttgatggggttggcaggcatcgaaacgcgcgtgcatggtgtgtgtgtctgttttcggct gcacaatttcaatagtcggatgggcgacggtagaattgggtgttgcgctcgcgtgcatgcctcgccccgtcgggtgtcatgaccggg actggaatccccctcgcgaccctcctgctaacgctcccgactctcccgcccgcgcgcaggatagactctagttcaaccaatcgaca actagt*ATGgccaccgcatccactttctcggcgttcaatgcccgctgcggcgacctgcgtcgctcggcgggctccgggccccgg*

*cgcccagcgaggcccctccccgtgcgcg*ggcgcgcc*atcccccccgcatcatcgtggtgtcctcctcctcctccaaggtgaaccc*

*cctgaagaccgaggccgtggtgtcctccggcctggccgaccgcctgcgcctgggctccctgaccgaggacggcctgtcctaca*

*aggagaagttcatcgtgcgctgctacgaggtgggcatcaacaagaccgccaccgtggagaccatcgccaacctgctgcagg*

*aggtgggctgcaaccacgcccagtccgtgggctactccaccggcggcttctccaccacccccaccatgcgcaagctgcgcctga*

*tctgggtgaccgcccgcatgcacatcgagatctacaagtaccccgcctggtccgacgtggtggagatcgagtcctggggccag*

*ggcgagggcaagatcggcacccgccgcgactggatcctgcgcgactacgccaccggccaggtgatcggccgcgccacctcca*

*agtgggtgatgatgaaccaggacacccgccgcctgcagaaggtggacgtggacgtgcgcgacgagtacctggtgcactgcc*

*cccgcgagctgcgcctggccttccccgaggagaacaactcctccctgaagaagatctccaagctggaggacccctcccagtac*

*tccaagctgggcctggtgccccgccgcgccgacctggacatgaaccagcacgtgaacaacgtgacctacatcggctgggtgct*

*ggagtccatgccccaggagatcatcgacacccacgagctgcagaccatcaccctggactaccgccgcgagtgccagcacgac*

*gacgtggtggactccctgacctcccccgagccctccgaggacgccgaggccgtgttcaaccacaacggcaccaacggctccgc*

*caacgtgtccgccaacgaccacggctgccgcaacttcctgcacctgctgcgcctgtccggcaacggcctggagatcaaccgcg*

*gccgcaccgagtggcgcaagaagcccacccgc**ATGGACTACAAGGACCACGACGGCGACTACAAGGACCAC*

*GACATCGACTACAAGGACGACGACGACAAGTGA*atcgatagatctcttaagGCAGCAGCAGCTCGGATAGTAT CGACACACTCTGGACGCTGGTCGTGTGATGGACTGTTGCCGCCACACTTGCTGCCTTGACCTGTGAATATCCCTGCCGCTT TTATCAAACAGCCTCAGTGTGTTTGATCTTGTGTGTACGCGCTTTTGCGAGTTGCTAGCTGCTTGTGCTATTTGCGAATACC ACCCCCAGCATCCCCTTCCCTCGTTTCATATCGCTTGCATCCCAACCGCAACTTATCTACGCTGTCCTGCTATCCCTCAGCGC TGCTCCTGCTCCTGCTCACTGCCCCTCGCACAGCCTTGGTTTGGGCTCCGCCTGTATTCTCCTGGTACTGCAACCTGTAAAC CAGCACTGCAATGCTGATGCACGGGAAGTAGTGGGATGGGAACACAAATGGAaagcttaattaagagctc**TTGTTTTCC

AGAAGGAGTTGCTCCTTGAGCCTTTCATTCTCAGCCTCGATAACCTCCAAAGCCGCTCTAATTGTGGA

GGGGGTTCGAATTTAAAAGCTTGGAATGTTGGTTCGTGCGTCTGGAACAAGCCCAGACTTGTTGCTC

ACTGGGAAAAGGACCATCAGCTCCAAAAAACTTGCCGCTCAAACCGCGTACCTCTGCTTTCGCGCAA

TCTGCCCTGTTGAAATCGCCACCACATTCATATTGTGACGCTTGAGCAGTCTGTAATTGCCTCAGAAT

GTGGAATCATCTGCCCCCTGTGCGAGCCCATGCCAGGCATGTCGCGGGCGAGGACACCCGCCACTC

GTACAGCAGACCATTATGCTACCTCACAATAGTTCATAACAGTGACCATATTTCTCGAAGCTCCCCAA

CGAGCACCTCCATGCTCTGAGTGGCCACCCCCCGGCCCTGGTGCTTGCGGAGGGCAGGTCAACCGG

-continued

CATGGGGCTACCGAAATCCCCGACCGGATCCCACCACCCCCGCGATGGGAAGAATCTCTCCCCGGG

ATGTGGGCCCACCACCAGCACAACCTGCTGGCCCAGGCGAGCGTCAAACCATACCACACAAATATCC

TTGGCATCGGCCCTGAATTCCTTCTGCCGCTCTGCTACCCGGTGCTTCTGTCCGAAGCAGGGGTTGCT

AGGGATCGCTCCGAGTCCGCAAACCCTTGTCGCGTGGCGGGGCTTGTTCGAGCTTgaagagc

The resulting strain was further transformed with a construct designed to recombine at (and thereby disrupt) the endogenous FATA and also express the LPAAT from *B. napus* under control of the UAPA1 promoter and using alpha galactosidase as a selectable marker with selection on melbiose. The resulting strain showed increased production of SOS (about 57-60%) and Sat-O-Sat (about 70-76%) and lower amounts of trisaturates (4.8 to 7.6%).

Strains were generated in the high-C18:0 56573 background in which we maximized SOS production and minimized the formation of trisaturated TAGs by targeting both the *Brassica napus* LPAT2(Bn1.13) gene and the PmFAD2hpA RNAi construct to the FATA-1 locus. The sequence of the transforming DNA from the PmFAD2hpA expression construct pSZ4164 is shown below in SEQ ID NO:153. Relevant restriction sites are indicated in lowercase, bold, and are from 5'-3' BspQI, KpnI, SpeI, SnaBI, BamHI, NdeI, NsiI, AflII, EcoRI, SpeI, BsiWI, XhoI, Sad and BspQI. Underlined sequences at the 5' and 3' flanks of the construct represent genomic DNA from *P. moriformis* that enable targeted integration of the transforming DNA via homologous recombination at the FATA-1 locus. Proceeding in the 5' to 3' direction, the PmHXT1 promoter driving the expression of *Saccharomyces carlbergensis* MEL1 (ScarMEL1) gene, enabling strains to utilize exogenous melibiose, is indicated by lowercase, boxed text. The initiator ATG and terminator TGA of ScarMEL1 are indicated by uppercase italics, while the coding region is represented by lowercase italics. The 3' UTR of the *P. moriformis* PGK gene is indicated by small capitals. A spacer region is represented by lowercase text. The *P. moriformis* UAPA1 promoter driving the expression of the BnLPAT2(Bn1.13) gene is indicated by lowercase, boxed text. The initiator ATG and terminator TGA are indicated by uppercase italics; the sequence encoding BnLPAT2(Bn1.13) is represented by lowercase, underlined italics. The 3' UTR of the CvNR gene is indicated by small capitals. A second spacer region is represented by lowercase text. The *C. reinhardtii* CrTUB2 promoter driving the expression of the PmFAD2hpA hairpin sequence is indicated by lowercase, boxed text. The FAD2 exon 1 sequence in the forward orientation is indicated with lowercase italics; the FAD2 intron 1 sequence is represented with lowercase, bold italics; a short linker region is indicated with lowercase text, and the FAD2 exon 1 sequence in the reverse orientation is indicated with lowercase, underlined italics. A second CvNR3' UTR is indicated by small capitals.

Nucleotide sequence of the transforming DNA from pSZ4164:

(SEQ ID NO: 153)

gctcttcCCAACTCAGATAATACCAATACCCCTCCTTCTCCTCCTCATCCATTCAGTACCCCCCCCCTTCTC

TTCCCAAAGCAGCAAGCGCGTGGCTTACAGAAGAACAATCGGCTTCCGCCAAAGTCGCCGAGCACT

GCCCGACGGCGGCGCGCCCAGCAGCCCGCTTGGCCACACAGGCAACGAATACATTCAATAGGGGG

CCTCGCAGAATGGAAGGAGCGGTAAAGGGTACAGGAGCACTGCGCACAAGGGGCCTGTGCAGGA

GTGACTGACTGGGCGGGCAGACGGCGCACCGCGGGCGCAGGCAAGCAGGGAAGATTGAAGCGGC

AGGGAGGAGGATGCTGATTGAGGGGGGCATCGCAGTCTCTCTTGGACCCGGGATAAGGAAGCAAA

TATTCGGCCGGTTGGGTTGTGTGTGTGCACGTTTTCTTCTTCAGAGTCGTGGGTGTGCTTCCAGGGA

GGATATAAGCAGCAGGATCGAATCCCGCGACCAGCGTTTCCCCATCCAGCCAACCACCCTGTcggtac cgcggtgagaatcgaaaatgcatcgtttctaggttcggagacggtcaattccctgctccggcgaatctgtcggtcaagctggccagt ggacaatgttgctatggcagcccgcgcacatgggcctcccgacgcggccatcaggagcccaaacagcgtgtcagggtatgtgaaa ctcaagaggtccctgctgggcactccggccccactccgggggcgggacgccaggcattcgcggtcggtcccgcgcgacgagcgaa atgatgattcggttacgagaccaggacgtcgtcgaggtcgagaggcagcctcggacacgtctcgctagggcaacgccccgagtccc cgcgagggccgtaaacattgtttctgggtgtcggagtgggcattttgggcccgatccaatcgcctcatgccgctctcgtctggtcctca cgttcgcgtacggcctggatcccggaaagggcggatgcacgtggtgttgccccgccattggcgcccacgtttcaaagtccccggcca gaaatgcacaggaccggcccggctcgcacaggccatgctgaacgcccagatttcgacagcaacaccatctagaataatcgcaacc atccgcgttttgaacgaaacgaaacggcgctgtttagcatgtttccgacatcgtgggggccgaagcatgctccgggggggaggaaag cgtggcacagcggtagcccattctgtgccacacgccgacgaggaccaatccccggcatcagccttcatcgacggctgcgccgcaca -continued tataaagccggacgcctaaccggtttcgtggttatgactagt*ATGttcgcgttctacttcctgacggcctgcatctccctgaagggc*

*gtgttcggcgtctcccctcctacaacggcctgggcctgacgccccagatgggctgggacaactggaacacgttcgcctgcgac*

*gtctccgagcagctgctgctggacacggccgaccgcatctccgacctgggcctgaaggacatgggctacaagtacatcatcct*

*ggacgactgctggtcctccggccgcgactccgacggcttcctggtcgccgacgagcagaagttccccaacggcatgggccacg*

*tcgccgaccacctgcacaacaactccttcctgttcggcatgtactcctccgcgggcgagtacacgtgcgccggctaccccggctc*

*cctgggccgcgaggaggaggacgcccagttcttcgcgaacaaccgcgtggactacctgaagtacgacaactgctacaacaa*

*gggccagttcggcacgcccgagatctcctaccaccgctacaaggccatgtccgacgccctgaacaagacgggccgccccatct*

*tctactccctgtgcaactggggccaggacctgaccttctactggggctccggcatcgcgaactcctggcgcatgtccggcgacgt*

*cacggcggagttcacgcgccccgactcccgctgcccctgcgacggcgacgagtacgactgcaagtacgccggcttccactgctc*

*catcatgaacatcctgaacaaggccgccccccatgggccagaacgcgggcgtcggcggctggaacgacctggacaacctgga*

*ggtcggcgtcggcaacctgacggacgacgaggagaaggcgcacttctccatgtgggccatggtgaagtccccccctgatcatc*

*ggcgcgaacgtgaacaacctgaaggcctcctcctactccatctactcccaggcgtccgtcatcgccatcaaccaggactccaac*

*ggcatccccgccacgcgcgtctggcgctactacgtgtccgacacggacgagtacggccagggcgagatccagatgtggtccg*

*gccccctggacaacggcgaccaggtcgtggcgctgctgaacggcggctccgtgtcccgccccatgaacacgaccctggagga*

*gatcttcttcgactccaacctgggctccaagaagctgacctccacctgggacatctacgacctgtgggcgaaccgcgtcgacaa*

*ctccacggcgtccgccatcctgggccgcaacaagaccgccaccggcatcctgtacaacgccaccgagcagtcctacaaggac*

*ggcctgtccaagaacgacacccgcctgttcggccagaagatcggctccctgtcccccaacgcgatcctgaacacgaccgtcccc*

*gcccacggcatcgcgttctaccgcctgcgcccctcctccTGA*tacaacttattacgtaTTCTGACCGGCGCTGATGTGGCGCGG ACGCCGTCGTACTCTTTCAGACTTTACTCTTGAGGAATTGAACCTTTCTCGCTTGCTGGCATGTAAACATTGGCGCAATTAA

TTGTGTGATGAAGAAAGGGTGGCACAAGATGGATCGCGAATGTACGAGATCGACAACGATGGTGATTGTTATGAGGGG

CCAAACCTGGCTCAATCTTGTCGCATGTCCGGCGCAATGTGATCCAGCGGCGTGACTCTCGCAACCTGGTAGTGTGTGCG

CACCGGGTCGCTTTGATTAAAACTGATCGCATTGCCATCCCGTCAACTCACAAGCCTACTCTAGCTCCCATTGCGCACTCGG

GCGCCCGGCTCGATCAATGTTCTGAGCGGAGGGCGAAGCGTCAGGAAATCGTCTCGGCAGCTGGAAGCGCATGGAATGC

GGAGCGGAGATCGAATCAggatcccgcgtctcgaacagagcgcgcagaggaacgctgaaggtctcgcctctgtcgcacctcagc gcggcatacaccacaataaccacctgacgaatgcgcttggttcttcgtccattagcgaagcgtccggttcacacacgtgccacgttg gcgaggtggcaggtgacaatgatcggtggagctgatggtcgaaacgttcacagcctagcatagcgactgctacccccgaccatgt gccgaggcagaaattatatacaagaagcagatcgcaattaggcacatcgctttgcattatccacacactattcatcgctgctgcggc aaggctgcagagtgtatttttgtggcccaggagctgagtccgaagtcgacgcgacgagcggcgcaggatccgacccctagacgag ctctgtcattttccaagcacgcagctaaatgcgctgagaccgggtctaaatcatccgaaaagtgtcaaaatggccgattgggttcgc ctaggacaatgcgctgcggattcgctcgagtccgctgccggccaaaaggcggtggtacaggaaggcgcacggggccaaccctgcg aagccgggggcccgaacgccgaccgccggccttcgatctcgggtgtccccctcgtcaatttcctctctcgggtgcagccacgaaagt cgtgacgcaggtcacgaaatccggttacgaaaaacgcaggtcttcgcaaaaacgtgagggtttcgcgtctcgccctagctattcgta tcgccgggtcagacccacgtgcagaaaagcccttgaataacccgggaccgtggttaccgcgccgcctgcaccaggggggcttatata agcccacaccacacctgtctcaccacgcatttctccaactcgcgacttttcggaagaaattgttatccacctagtatagactgccacc tgcaggaccttgtgtcttgcagtttgtattggtcccggccgtcgagctcgacagatctgggctagggttggcctggccgctcggcactc ccctttagccgcgcgcatccgcgttccagaggtgcgattcggtgtgtggagcattgtcatgcgcttgtgggggtcgttccgtgcgcgg cgggtccgccatgggcgccgacctgggccctagggtttgttttcgggccaagcgagcccctctcacctcgtcgcccccccgcattccc tctctcttgcagcc**cat*ATG***gccatggccgccgccgtgatcgtgcccctgggcatcctgttcttcatctccggcctggtggtgaac*

*ctgctgcaggccatctgctacgtgctgatccgcccccctgtccaagaacacctaccgcaagatcaaccgcgtggtggccgagacc*

-continued

*ctgtggctggagctggtgtggatcgtggactggtgggccggcgtgaagatccaggtgttcgccgacaacgagaccttcaacc*

*gcatgggcaaggagcacgccctggtggtgtgcaaccaccgctccgacatcgactggctggtgggctggatcctggcccagcg*

*ctccggctgcctgggctccgccctggccgtgatgaagaagtcctccaagttcctgcccgtgatcggctggtccatgtggttctccg*

*agtacctgttcctggagcgcaactgggccaaggacgagtccaccctgaagtccggcctgcagcgcctgaacgacttcccccgc*

*cccttctggctggccctgttcgtggagggcacccgcttcaccgaggccaagctgaaggccgcccaggagtacgccgcctcctcc*

*gagctgcccgtgccccgcaacgtgctgatcccccgcaccaagggcttcgtgtccgccgtgtccaacatgcgctccttcgtgcccg*

*ccatctacgacatgaccgtggccatccccaagacctcccccccccccaccatgctgcgcctgttcaagggccagccctccgtggt*

*gcacgtgcacatcaagtgccactccatgaaggacctgcccgagtccgacgacgccatcgcccagtggtgccgcgaccagttcg*

*tggccaaggacgccctgctggacaagcacatcgccgccgacaccttccccggccagcaggagcagaacatcggccgccccat*

*caagtccctggccgtggtgctgtcctggtcctgcctgctgatcctgggcgccatgaagttcctgcactggtccaacctgttctcctc*

*ctggaagggcatcgccttctccgccctgggcctgggcatcatcaccctgtgcatgcagatcctgatccgctcctcccagtccgag*

*cgctccacccccgccaaggtggtgcccgccaagcccaaggacaaccacaacgactccggctcctcctcccagaccgaggtgga*

*gaagcagaagTGA*atgcatGCAGCAGCAGCTCGGATAGTATCGACACACTCTGGACGCTGGTCGTGTGATGGACTGTTG CCGCCACACTTGCTGCCTTGACCTGTGAATATCCCTGCCGCTTTTATCAAACAGCCTCAGTGTGTTTGATCTTGTGTGTACG CGCTTTTGCGAGTTGCTAGCTGCTTGTGCTATTTGCGAATACCACCCCCAGCATCCCCTTCCCTCGTTTCATATCGCTTGCAT CCCAACCGCAACTTATCTACGCTGTCCTGCTATCCCTCAGCGCTGCTCCTGCTCCTGCTCACTGCCCCTCGCACAGCCTTGG

TTTGGGCTCCGCCTGTATTCTCCTGGTACTGCAACCTGTAAACCAGCACTGCAATGCTGATGCACGGGAAGTAGTGGGAT

GGGAACACAAATGGActtaaggatctaagtaagattcgaagcgctcgaccgtgccggacggactgcagccccatgtcgtagtga ccgccaatgtaagtgggctggcgtttccctgtacgtgagtcaacgtcactgcacgcgcaccaccctctcgaccggcaggaccaggca tcgcgagatacagcgcgagccagacacggagtgccgagctatgcgcacgctccaactagatatcatgtggatgatgagcatgaatt cctttcttgcgctatgacacttccagcaaaaggtagggcgggctgcgagacggcttcccggcgctgcatgcaacaccgatgatgctt cgacccccgaagctccttcggggctgcatgggcgctccgatgccgctccagggcgagcgctgtttaaatagccaggcccccgattg caaagacattatagcgagctaccaaagccatattcaaacacctagatcactaccacttctacacaggccactcgagcttgtgatcgc actccgctaagggggcgcctcttcctcttcgtttcagtcacaacccgcaaacactagt*ATGgctatcaagacgaacaggcagcct*

*gtggagaagcctccgttcacgatcgggacgctgcgcaaggccatccccgcgcactgtttcgagcgctcggcgcttcgtagcag*

*catgtacctggcctttgacatcgcggtcatgtccctgctctacgtcgcgtcgacgtacatcgaccctgcaccggtgcctacgtggg*

*tcaagtacggcatcatgtggccgctctactggttcttccag*gtgtgtttgagggttttggttgcccgtattgaggtcctggtggc

*gcgcatggaggagaaggcgcctgtcccgctgacccccccggctaccctcccggcaccttccag*ggcgcgtacg*ggaagaacc*

*agtagagcggccacatgatgccgtacttgacccacgtaggcaccggtgcagggtcgatgtacgtcgacgcgacgtagagca*

*gggacatgaccgcgatgtcaaaggccaggtacatgctgctacgaagcgccgagcgctcgaaacagtgcgcggggatggcct*

*tgcgcagcgtcccgatcgtgaacggaggcttctccacaggctgcctgttcgtcttgatagccat*ctcgagGCAGCAGCAGCTCG GATAGTATCGACACACTCTGGACGCTGGTCGTGTGATGGACTGTTGCCGCCACACTTGCTGCCTTGACCTGTGAATATCCC TGCCGCTTTTATCAAACAGCCTCAGTGTGTTTGATCTTGTGTGTACGCGCTTTTGCGAGTTGCTAGCTGCTTGTGCTATTTG CGAATACCACCCCCAGCATCCCCTTCCCTCGTTTCATATCGCTTGCATCCCAACCGCAACTTATCTACGCTGTCCTGCTATCC CTCAGCGCTGCTCCTGCTCCTGCTCACTGCCCCTCGCACAGCCTTGGTTTGGGCTCCGCCTGTATTCTCCTGGTACTGCAAC CTGTAAACCAGCACTGCAATGCTGATGCACGGGAAGTAGTGGGATGGGAACACAAATGGAAAGCTGTAgagctcttgtttt ccagaaggagttgctccttgagcctttcattctcagcctcgataacctccaaagccgctctaattgtggagggggttcgaaCCGAA

TGCTGCGTGAACGGGAAGGAGGAGGAGAAAGAGTGAGCAGGGAGGGATTCAGAAATGAGAAATG

AGAGGTGAAGGAACGCATCCCTATGCCCTTGCAATGGACAGTGTTTCTGGCCACCGCCACCAAGACT

-continued

TCGTGTCCTCTGATCATCATGCGATTGATTACGTTGAATGCGACGGCCGGTCAGCCCCGGACCTCCA

CGCACCGGTGCTCCTCCAGGAAGATGCGCTTGTCCTCCGCCATCTTGCAGGGCTCAAGCTGCTCCCA

AAACTCTTGGGCGGGTTCCGGACGGACGGCTACCGCGGGTGCGGCCCTGACCGCCACTGTTCGGAA

GCAGCGGCGCTGCATGGGCAGCGGCCGCTGCGGTGCGCCACGGACCGCATGATCCACCGGAAAAG

CGCACGCGCTGGAGCGCGCAGAGGACCACAGAGAAGCGGAAGAGACGCCAGTACTGGCAAGCAG

GCTGGTCGGTGCCATGGCGCGCTACTACCCTCGCTATGACTCGGGTCCTCGGCCGGCTGGCGGTGCT

GACAATTCGTTTAGTGGAGCAGCGACTCCATTCAGCTACCAGTCGAACTCAGTGGCACAGTGACTcc gctcttc

The described embodiments of the invention are intended to be merely exemplary and numerous variations and modifications will be apparent to those skilled in the art. All such variations and modifications are intended to be within the scope of the present invention. For example, the various triglyceride oils can be tailored in for a mixture of midchain and long chain fatty acids in order to adjust parameters such as polarity, solvency, and foam-height of the oils or chemicals made from the oils. In addition, where a knockout of a gene is called for, an equivalent result may be reached using knockdown techniques including mutation and expression of inhibitory substances such as RNAi or antisense.

SEQUENCE LISTING 6S 5' genomic donor sequence

SEQ ID NO: 1

GCTCTTCGCCGCCGCCACTCCTGCTCGAGCGCGCCCGCGCGTGCGCCGCCAGCGCCTTGGCCTTTTCG

CCGCGCTCGTGCGCGTCGCTGATGTCCATCACCAGGTCCATGAGGTCTGCCTTGCGCCGGCTGAGCCA

CTGCTTCGTCCGGGCGGCCAAGAGGAGCATGAGGGAGGACTCCTGGTCCAGGGTCCTGACGTGGTCGC

GGCTCTGGGAGCGGGCCAGCATCATCTGGCTCTGCCGCACCGAGGCCGCCTCCAACTGGTCCTCCAGC

AGCCGCAGTCGCCGCCGACCCTGGCAGAGGAAGACAGGTGAGGGGGGTATGAATTGTACAGAACAACC

ACGAGCCTTGTCTAGGCAGAATCCCTACCAGTCATGGCTTTACCTGGATGACGGCCTGCGAACAGCTG

TCCAGCGACCCTCGCTGCCGCCGCTTCTCCCGCACGCTTCTTTCCAGCACCGTGATGGCGCGAGCCAG

CGCCGCACGCTGGCGCTGCGCTTCGCCGATCTGAGGACAGTCGGGGAACTCTGATCAGTCTAAACCCC

CTTGCGCGTTAGTGTTGCCATCCTTTGCAGACCGGTGAGAGCCGACTTGTTGTGCGCCACCCCCCACA

CCACCTCCTCCCAGACCAATTCTGTCACCTTTTTGGCGAAGGCATCGGCCTCGGCCTGCAGAGAGGAC

AGCAGTGCCCAGCCGCTGGGGGTTGGCGGATGCACGCTCAGGTACC 6S 3' genomic donor sequence

SEQ ID NO: 2

GAGCTCCTTGTTTTCCAGAAGGAGTTGCTCCTTGAGCCTTTCATTCTCAGCCTCGATAACCTCCAAAG

CCGCTCTAATTGTGGAGGGGGTTCGAATTTAAAAGCTTGGAATGTTGGTTCGTGCGTCTGGAACAAGC

CCAGACTTGTTGCTCACTGGGAAAAGGACCATCAGCTCCAAAAAACTTGCCGCTCAAACCGCGTACCT

CTGCTTTCGCGCAATCTGCCCTGTTGAAATCGCCACCACATTCATATTGTGACGCTTGAGCAGTCTGT

AATTGCCTCAGAATGTGGAATCATCTGCCCCCTGTGCGAGCCCATGCCAGGCATGTCGCGGGCGAGGA

CACCCGCCACTCGTACAGCAGACCATTATGCTACCTCACAATAGTTCATAACAGTGACCATATTTCTC

GAAGCTCCCCAACGAGCACCTCCATGCTCTGAGTGGCCACCCCCCGGCCCTGGTGCTTGCGGAGGGCA

GGTCAACCGGCATGGGGCTACCGAAATCCCCGACCGGATCCCACCACCCCCGCGATGGGAAGAATCTC

TCCCCGGGATGTGGGCCCACCACCAGCACAACCTGCTGGCCCAGGCGAGCGTCAAACCATACCACACA

AATATCCTTGGCATCGGCCCTGAATTCCTTCTGCCGCTCTGCTACCCGGTGCTTCTGTCCGAAGCAGG

GGTTGCTAGGGATCGCTCCGAGTCCGCAAACCCTTGTCGCGTGGCGGGGCTTGTTCGAGCTTGAAGAG

C

-continued

*S. cereviseae* invertase protein sequence

SEQ ID NO: 3

MLLQAFLFLLAGFAAKISASMTNETSDRPLVHFTPNKGWMNDPNGLWYDEKDAKWHLYFQYNPNDTVW

GTPLFWGHATSDDLTNWEDQPIAIAPKRNDSGAFSGSMVVDYNNTSGFFNDTIDPRQRCVAIWTYNTP

ESEEQYISYSLDGGYTFTEYQKNPVLAANSTQFRDPKVFWYEPSQKWIMTAAKSQDYKIEIYSSDDLK

SWKLESAFANEGFLGYQYECPGLIEVPTEQDPSKSYWVMFISINPGAPAGGSFNQYFVGSFNGTHFEA

FDNQSRVVDFGKDYYALQTFFNTDPTYGSALGTAWASNWEYSAFVPTNPWRSSMSLVRKFSLNTEYQA

NPETELINLKAEPILNISNAGPWSRFATNTTLTKANSYNVDLSNSTGTLEFELVYAVNTTQTISKSVF

ADLSLWFKGLEDPEEYLRMGFEVSASSFFLDRGNSKVKFVKENPYFTNRMSVNNQPFKSENDLSYYKV

YGLLDQNILELYFNDGDVVSTNTYFMTTGNALGSVNMTTGVDNLFYIDKFQVREVK

*S. cereviseae* invertase protein coding sequence codon optimized for expression in *P. moriformis* (UTEX 1435)

SEQ ID NO: 4

ATGctgctgcaggccttcctgttcctgctggccggcttcgccgccaagatcagcgcctccatgacgaa cgagacgtccgaccgcccctggtgcacttcacccccaacaagggctggatgaacgaccccaacggcc tgtggtacgacgagaaggacgccaagtggcacctgtacttccagtacaacccgaacgacaccgtctgg gggacgcccttgttctggggccacgccacgtccgacgacctgaccaactgggaggaccagcccatcgc catcgccccgaagcgcaacgactccggcgccttctccggctccatggtggtggactacaacaacacct ccggcttcttcaacgacaccatcgacccgcgccagcgctgcgtggccatctggacctacaacaccccg gagtccgaggagcagtacatctcctacagcctggacggcggctacaccttcaccgagtaccagaagaa ccccgtgctggccgccaactccacccagttccgcgacccgaaggtcttctggtacgagccctcccaga agtggatcatgaccgcggccaagtcccaggactacaagatcgagatctactcctccgacgacctgaag tcctggaagctggagtccgcgttcgccaacgagggcttcctcggctaccagtacgagtgccccggcct gatcgaggtccccaccgagcaggaccccagcaagtcctactgggtgatgttcatctccatcaaccccg gcgccccggccggcggctccttcaaccagtacttcgtcggcagcttcaacggcacccacttcgaggcc ttcgacaaccagtcccgcgtggtggacttcggcaaggactactacgccctgcagaccttcttcaacac cgacccgacctacgggagcgccctgggcatcgcgtgggcctccaactgggagtactccgccttcgtgc ccaccaacccctggcgctcctccatgtccctcgtgcgcaagttctccctcaacaccgagtaccaggcc aacccggagacggagctgatcaacctgaaggccgagccgatcctgaacatcagcaacgccggcccctg gagccggttcgccaccaacaccacgttgacgaaggccaacagctacaacgtcgacctgtccaacagca ccggcaccctggagttcgagctggtgtacgccgtcaacaccacccagacgatctccaagtccgtgttc gcggacctctccctctggttcaagggcctggaggaccccgaggagtacctccgcatgggcttcgaggt gtccgcgtcctccttcttcctggaccgcgggaacagcaaggtgaagttcgtgaaggagaacccctact tcaccaaccgcatgagcgtgaacaaccagcccttcaagagcgagaacgacctgtcctactacaaggtg tacggcttgctggaccagaacatcctggagctgtacttcaacgacggcgacgtcgtgtccaccaacac ctacttcatgaccaccgggaacgccctgggctccgtgaacatgacgacgggggtggacaacctgttct acatcgacaagttccaggtgcgcgaggtcaagTGA

*Chlamydomonas reinhardtii* TUB2 (B-tub) promoter/5' UTR

SEQ ID NO: 5

CTTTCTTGCGCTATGACACTTCCAGCAAAAGGTAGGGCGGGCTGCGAGACGGCTTCCCGGCGCTGCAT

GCAACACCGATGATGCTTCGACCCCCCGAAGCTCCTTCGGGGCTGCATGGGCGCTCCGATGCCGCTCC

AGGGCGAGCGCTGTTTAAATAGCCAGGCCCCCGATTGCAAAGACATTATAGCGAGCTACCAAAGCCAT

ATTCAAACACCTAGATCACTACCACTTCTACACAGGCCACTCGAGCTTGTGATCGCACTCCGCTAAGG

GGGCGCCTCTTCCTCTTCGTTTCAGTCACAACCCGCAAAC

-continued

*Chlorella vulgaris* nitrate reductase 3'UTR

SEQ ID NO: 6

GCAGCAGCAGCTCGGATAGTATCGACACACTCTGGACGCTGGTCGTGTGATGGACTGTTGCCGCCACA

CTTGCTGCCTTGACCTGTGAATATCCCTGCCGCTTTTATCAAACAGCCTCAGTGTGTTTGATCTTGTG

TGTACGCGCTTTTGCGAGTTGCTAGCTGCTTGTGCTATTTGCGAATACCACCCCCAGCATCCCCTTCC

CTCGTTTCATATCGCTTGCATCCCAACCGCAACTTATCTACGCTGTCCTGCTATCCCTCAGCGCTGCT

CCTGCTCCTGCTCACTGCCCCTCGCACAGCCTTGGTTTGGGCTCCGCCTGTATTCTCCTGGTACTGCA

ACCTGTAAACCAGCACTGCAATGCTGATGCACGGGAAGTAGTGGGATGGGAACACAAATGGAAAGCTT

Nucleotide sequence of the codon-optimized expression cassette of *S. cerevisiae* suc2 gene with *C. reinhardtii* β-tubulin promoter/5'UTR and *C. vulgaris* nitrate reductase 3' UTR

SEQ ID NO: 7

CTTTCTTGCGCTATGACACTTCCAGCAAAAGGTAGGGCGGGCTGCGAGACGGCTTCCCGGCGCTGCAT

GCAACACCGATGATGCTTCGACCCCCCGAAGCTCCTTCGGGGCTGCATGGGCGCTCCGATGCCGCTCC

AGGGCGAGCGCTGTTTAAATAGCCAGGCCCCCGATTGCAAAGACATTATAGCGAGCTACCAAAGCCAT

ATTCAAACACCTAGATCACTACCACTTCTACACAGGCCACTCGAGCTTGTGATCGCACTCCGCTAAGG

GGGCGCCTCTTCCTCTTCGTTTCAGTCACAACCCGCAAACGGCGCGCCATGCTGCTGCAGGCCTTCCT

GTTCCTGCTGGCCGGCTTCGCCGCCAAGATCAGCGCCTCCATGACGAACGAGACGTCCGACCGCCCCC

TGGTGCACTTCACCCCCAACAAGGGCTGGATGAACGACCCCAACGGCCTGTGGTACGACGAGAAGGAC

GCCAAGTGGCACCTGTACTTCCAGTACAACCCGAACGACACCGTCTGGGGGACGCCCTTGTTCTGGGG

CCACGCCACGTCCGACGACCTGACCAACTGGGAGGACCAGCCCATCGCCATCGCCCCGAAGCGCAACG

ACTCCGGCGCCTTCTCCGGCTCCATGGTGGTGGACTACAACAACACCTCCGGCTTCTTCAACGACACC

ATCGACCCGCGCCAGCGCTGCGTGGCCATCTGGACCTACAACACCCCGGAGTCCGAGGAGCAGTACAT

CTCCTACAGCCTGGACGGCGGCTACACCTTCACCGAGTACCAGAAGAACCCCGTGCTGGCCGCCAACT

CCACCCAGTTCCGCGACCCGAAGGTCTTCTGGTACGAGCCCTCCCAGAAGTGGATCATGACCGCGGCC

AAGTCCCAGGACTACAAGATCGAGATCTACTCCTCCGACGACCTGAAGTCCTGGAAGCTGGAGTCCGC

GTTCGCCAACGAGGGCTTCCTCGGCTACCAGTACGAGTGCCCCGGCCTGATCGAGGTCCCCACCGAGC

AGGACCCCAGCAAGTCCTACTGGGTGATGTTCATCTCCATCAACCCCGGCGCCCCGGCCGGCGGCTCC

TTCAACCAGTACTTCGTCGGCAGCTTCAACGGCACCCACTTCGAGGCCTTCGACAACCAGTCCCGCGT

GGTGGACTTCGGCAAGGACTACTACGCCCTGCAGACCTTCTTCAACACCGACCCGACCTACGGGAGCG

CCCTGGGCATCGCGTGGGCCTCCAACTGGGAGTACTCCGCCTTCGTGCCCACCAACCCCTGGCGCTCC

TCCATGTCCCTCGTGCGCAAGTTCTCCCTCAACACCGAGTACCAGGCCAACCCGGAGACGGAGCTGAT

CAACCTGAAGGCCGAGCCGATCCTGAACATCAGCAACGCCGGCCCCTGGAGCCGGTTCGCCACCAACA

CCACGTTGACGAAGGCCAACAGCTACAACGTCGACCTGTCCAACAGCACCGGCACCCTGGAGTTCGAG

CTGGTGTACGCCGTCAACACCACCCAGACGATCTCCAAGTCCGTGTTCGCGGACCTCTCCCTCTGGTT

CAAGGGCCTGGAGGACCCCGAGGAGTACCTCCGCATGGGCTTCGAGGTGTCCGCGTCCTCCTTCTTCC

TGGACCGCGGGAACAGCAAGGTGAAGTTCGTGAAGGAGAACCCCTACTTCACCAACCGCATGAGCGTG

AACAACCAGCCCTTCAAGAGCGAGAACGACCTGTCCTACTACAAGGTGTACGGCTTGCTGGACCAGAA

CATCCTGGAGCTGTACTTCAACGACGGCGACGTCGTGTCCACCAACACCTACTTCATGACCACCGGGA

ACGCCCTGGGCTCCGTGAACATGACGACGGGGGTGGACAACCTGTTCTACATCGACAAGTTCCAGGTG

CGCGAGGTCAAGTGACAATTGGCAGCAGCAGCTCGGATAGTATCGACACACTCTGGACGCTGGTCGTG

TGATGGACTGTTGCCGCCACACTTGCTGCCTTGACCTGTGAATATCCCTGCCGCTTTTATCAAACAGC

CTCAGTGTGTTTGATCTTGTGTGTACGCGCTTTTGCGAGTTGCTAGCTGCTTGTGCTATTTGCGAATA

-continued

CCACCCCCAGCATCCCCTTCCCTCGTTTCATATCGCTTGCATCCCAACCGCAACTTATCTACGCTGTC

CTGCTATCCCTCAGCGCTGCTCCTGCTCCTGCTCACTGCCCCTCGCACAGCCTTGGTTTGGGCTCCGC

CTGTATTCTCCTGGTACTGCAACCTGTAAACCAGCACTGCAATGCTGATGCACGGGAAGTAGTGGGAT

GGGAACACAAATGGAGGATCC

*Prototheca moriformis* (UTEX 1435) Amt03 promoter

SEQ ID NO: 8

GGCCGACAGGACGCGCGTCAAAGGTGCTGGTCGTGTATGCCCTGGCCGGCAGGTCGTTGCTGCTGCTG

GTTAGTGATTCCGCAACCCTGATTTTGGCGTCTTATTTTGGCGTGGCAAACGCTGGCGCCCGCGAGCC

GGGCCGGCGGCGATGCGGTGCCCCACGGCTGCCGGAATCCAAGGGAGGCAAGAGCGCCCGGGTCAGTT

GAAGGGCTTTACGCGCAAGGTACAGCCGCTCCTGCAAGGCTGCGTGGTGGAATTGGACGTGCAGGTCC

TGCTGAAGTTCCTCCACCGCCTCACCAGCGGACAAAGCACCGGTGTATCAGGTCCGTGTCATCCACTC

TAAAGAGCTCGACTACGACCTACTGATGGCCCTAGATTCTTCATCAAAAACGCCTGAGACACTTGCCC

AGGATTGAAACTCCCTGAAGGGACCACCAGGGGCCCTGAGTTGTTCCTTCCCCCCGTGGCGAGCTGCC

AGCCAGGCTGTACCTGTGATCGAGGCTGGCGGGAAAATAGGCTTCGTGTGCTCAGGTCATGGGAGGTG

CAGGACAGCTCATGAAACGCCAACAATCGCACAATTCATGTCAAGCTAATCAGCTATTTCCTCTTCAC

GAGCTGTAATTGTCCCAAAATTCTGGTCTACCGGGGGTGATCCTTCGTGTACGGGCCCTTCCCTCAAC

CCTAGGTATGCGCGCATGCGGTCGCCGCGCAACTCGCGCGAGGGCCGAGGGTTTGGGACGGGCCGTCC

CGAAATGCAGTTGCACCCGGATGCGTGGCACCTTTTTTGCGATAATTTATGCAATGGACTGCTCTGCA

AAATTCTGGCTCTGTCGCCAACCCTAGGATCAGCGGCGTAGGATTTCGTAATCATTCGTCCTGATGGG

GAGCTACCGACTACCCTAATATCAGCCCGACTGCCTGACGCCAGCGTCCACTTTTGTGCACACATTCC

ATTCGTGCCCAAGACATTTCATTGTGGTGCGAAGCGTCCCCAGTTACGCTCACCTGTTTCCCGACCTC

CTTACTGTTCTGTCGACAGAGCGGGCCCACAGGCCGGTCGCAGCC

*Chlorella protothecoides* (UTEX 250) stearoyl ACP desaturase transit peptide cDNA sequence codon optimized for expression in *P. moriformis*.

SEQ ID NO: 9

ACTAGTATGGCCACCGCATCCACTTTCTCGGCGTTCAATGCCCGCTGCGGCGACCTGCGTCGCTCGGC

GGGCTCCGGGCCCCGGCGCCCAGCGAGGCCCCTCCCCGTGCGCGGGCGCGCC

*Cuphea wrightii* FatB2 thioesterase nucleic acid sequence; Gen Bank Accession No. U56104

SEQ ID NO: 10

ATGGTGGTGGCCGCCGCCGCCAGCAGCGCCTTCTTCCCCGTGCCCGCCCCCCGCCCCACCCCCAAGCC

CGGCAAGTTCGGCAACTGGCCCAGCAGCCTGAGCCAGCCCTTCAAGCCCAAGAGCAACCCCAACGGCC

GCTTCCAGGTGAAGGCCAACGTGAGCCCCCACGGGCGCGCCCCCAAGGCCAACGGCAGCGCCGTGAGC

CTGAAGTCCGGCAGCCTGAACACCCTGGAGGACCCCCCCAGCAGCCCCCCCCCCCGCACCTTCCTGAA

CCAGCTGCCCGACTGGAGCCGCCTGCGCACCGCCATCACCACCGTGTTCGTGGCCGCCGAGAAGCAGT

TCACCCGCCTGGACCGCAAGAGCAAGCGCCCCGACATGCTGGTGGACTGGTTCGGCAGCGAGACCATC

GTGCAGGACGGCCTGGTGTTCCGCGAGCGCTTCAGCATCCGCAGCTACGAGATCGGCGCCGACCGCAC

CGCCAGCATCGAGACCCTGATGAACCACCTGCAGGACACCAGCCTGAACCACTGCAAGAGCGTGGGCC

TGCTGAACGACGGCTTCGGCCGCACCCCCGAGATGTGCACCCGCGACCTGATCTGGGTGCTGACCAAG

ATGCAGATCGTGGTGAACCGCTACCCCACCTGGGGCGACACCGTGGAGATCAACAGCTGGTTCAGCCA

GAGCGGCAAGATCGGCATGGGCCGCGAGTGGCTGATCAGCGACTGCAACACCGGCGAGATCCTGGTGC

GCGCCACCAGCGCCTGGGCCATGATGAACCAGAAGACCCGCCGCTTCAGCAAGCTGCCCTGCGAGGTG

CGCCAGGAGATCGCCCCCCACTTCGTGGACGCCCCCCCCGTGATCGAGGACAACGACCGCAAGCTGCA

CAAGTTCGACGTGAAGACCGGCGACAGCATCTGCAAGGGCCTGACCCCCGGCTGGAACGACTTCGACG

-continued

TGAACCAGCACGTGAGCAACGTGAAGTACATCGGCTGGATTCTGGAGAGCATGCCCACCGAGGTGCTG

GAGACCCAGGAGCTGTGCAGCCTGACCCTGGAGTACCGCCGCGAGTGCGGCCGCGAGAGCGTGGTGGA

GAGCGTGACCAGCATGAACCCCAGCAAGGTGGGCGACCGCAGCCAGTACCAGCACCTGCTGCGCCTGG

AGGACGGCGCCGACATCATGAAGGGCCGCACCGAGTGGCGCCCCAAGAACGCCGGCACCAACCGCGCC

ATCAGCACCTGA

*Cuphea wrightii* FatB2 thioesterase amino acid sequence; Gen Bank Accession No. U56104

SEQ ID NO: 11

MVVAAAASSAFFPVPAPRPTPKPGKFGNWPSSLSQPFKPKSNPNGRFQVKANVSPHPKANGSAVSLKS

GSLNTLEDPPSSPPPRTFLNQLPDWSRLRTAITTVFVAAEKQFTRLDRKSKRPDMLVDWFGSETIVQD

GLVFRERFSIRSYEIGADRTASIETLMNHLQDTSLNHCKSVGLLNDGFGRTPEMCTRDLIWVLTKMQI

VVNRYPTWGDTVEINSWFSQSGKIGMGREWLISDCNTGEILVRATSAWAMMNQKTRRFSKLPCEVRQE

IAPHFVDAPPVIEDNDRKLHKFDVKTGDSICKGLTPGWNDFDVNQHVSNVKYIGWILESMPTEVLETQ

ELCSLTLEYRRECGRESVVESVTSMNPSKVGDRSQYQHLLRLEDGADIMKGRTEWRPKNAGTNRAIST

Codon-optimized coding region of *Cocus nucifera* C12:0-preferring LPAAT from pSZ2046

SEQ ID NO: 12

ATGGACGCCTCCGGCGCCTCCTCCTTCCTGCGCGGCCGCTGCCTGGAGTCCTGCTTCAAGGCCTCCTT

CGGCTACGTAATGTCCCAGCCCAAGGACGCCGCCGGCCAGCCCTCCCGCCGCCCCGCCGACGCCGACG

ACTTCGTGGACGACGACCGCTGGATCACCGTGATCCTGTCCGTGGTGCGCATCGCCGCCTGCTTCCTG

TCCATGATGGTGACCACCATCGTGTGGAACATGATCATGCTGATCCTGCTGCCCTGGCCCTACGCCCG

CATCCGCCAGGGCAACCTGTACGGCCACGTGACCGGCCGCATGCTGATGTGGATTCTGGGCAACCCCA

TCACCATCGAGGGCTCCGAGTTCTCCAACACCCGCGCCATCTACATCTGCAACCACGCCTCCCTGGTG

GACATCTTCCTGATCATGTGGCTGATCCCCAAGGGCACCGTGACCATCGCCAAGAAGGAGATCATCTG

GTATCCCCTGTTCGGCCAGCTGTACGTGCTGGCCAACCACCAGCGCATCGACCGCTCCAACCCCTCCG

CCGCCATCGAGTCCATCAAGGAGGTGGCCCGCGCCGTGGTGAAGAAGAACCTGTCCCTGATCATCTTC

CCCGAGGGCACCCGCTCCAAGACCGGCCGCCTGCTGCCCTTCAAGAAGGGCTTCATCCACATCGCCCT

CCAGACCCGCCTGCCCATCGTGCCGATGGTGCTGACCGGCACCCACCTGGCCTGGCGCAAGAACTCCC

TGCGCGTGCGCCCCGCCCCCATCACCGTGAAGTACTTCTCCCCCATCAAGACCGACGACTGGGAGGAG

GAGAAGATCAACCACTACGTGGAGATGATCCACGCCCTGTACGTGGACCACCTGCCCGAGTCCCAGAA

GCCCCTGGTGTCCAAGGGCCGCGACGCCTCCGGCCGCTCCAACTCCTGA pLoop 5' genomic donor sequence

SEQ ID NO: 13 gctcttcgctaacggaggtctgtcaccaaatggaccccgtctattgcgggaaaccacggcgatggcac gtttcaaaacttgatgaaatacaatattcagtatgtcgcgggcggcgacggcggggagctgatgtcgc gctgggtattgcttaatcgccagcttcgcccccgtcttggcgcgaggcgtgaacaagccgaccgatgt gcacgagcaaatcctgacactagaagggctgactcgcccggcacggctgaattacacaggcttgcaaa aataccagaatttgcacgcaccgtattcgcggtattttgttggacagtgaatagcgatgcggcaatgg cttgtggcgttagaaggtgcgacgaaggtggtgccaccactgtgccagccagtcctggcggctcccag ggccccgatcaagagccaggacatccaaactacccacagcatcaacgccccggcctatactcgaaccc cacttgcactctgcaatggtatgggaaccacggggcagtcttgtgtgggtcgcgcctatcgcggtcgg cgaagaccgggaaggtacc pLoop 3' genomic donor sequence

SEQ ID NO: 14 gagctcagcggcgacggtcctgctaccgtacgacgttgggcacgcccatgaaagtttgtataccgagc ttgttgagcgaactgcaagcgcggctcaaggatacttgaactcctggattgatatcggtccaataatg -continued gatggaaaatccgaacctcgtgcaagaactgagcaaacctcgttacatggatgcacagtcgccagtcc aatgaacattgaagtgagcgaactgttcgcttcggtggcagtactactcaaagaatgagctgctgtta aaaatgcactctcgttctctcaagtgagtggcagatgagtgctcacgccttgcacttcgctgcccgtg tcatgccctgcgccccaaaatttgaaaaaagggatgagattattgggcaatggacgacgtcgtcgctc cgggagtcaggaccggcggaaaataagaggcaacacactccgcttcttagctcttcc NeoR expression cassette including *C. reinhardtii* β-tubulin promoter/5'UTR and *C. vulgaris* nitrate reductase 3' UTR

SEQ ID NO: 15 ctttcttgcgctatgacacttccagcaaaaggtagggcgggctgcgagacggcttcccggcgctgcat gcaacaccgatgatgcttcgacccccgaagctccttcggggctgcatgggcgctccgatgccgctcc agggcgagcgctgtttaaatagccaggcccccgattgcaaagacattatagcgagctaccaaagccat attcaaacacctagatcactaccacttctacacaggccactcgagcttgtgatcgcactccgctaagg gggcgcctcttcctcttcgtttcagtcacaacccgcaaactctagaatatcaATGatcgagcaggacg gcctccacgccggctcccccgccgcctgggtggagcgcctgttcggctacgactgggcccagcagacc atcggctgctccgacgccgccgtgttccgcctgtccgcccagggccgccccgtgctgttcgtgaagac cgacctgtccggcgccctgaacgagctgcaggacgaggccgcccgcctgtcctggctggccaccaccg gcgtgccctgcgccgccgtgctggacgtggtgaccgaggccggccgcgactggctgctgctgggcgag gtgcccggccaggacctgctgtcctcccacctggcccccgccgagaaggtgtccatcatggccgacgc catgcgccgcctgcacaccctggaccccgccacctgccccttcgaccaccaggccaagcaccgcatcg agcgcgcccgcacccgcatggaggccggcctggtggaccaggacgacctggacgaggagcaccagggc ctggcccccgccgagctgttcgcccgcctgaaggcccgcatgcccgacggcgaggacctggtggtgac ccacggcgacgcctgcctgcccaacatcatggtggagaacggccgcttctccggcttcatcgactgcg gccgcctgggcgtggccgaccgctaccaggacatcgccctggccacccgcgacatcgccgaggagctg ggcggcgagtgggccgaccgcttcctggtgctgtacggcatcgccgcccccgactcccagcgcatcgc cttctaccgcctgctggacgagttcttcTGAcaattggcagcagcagctcggatagtatcgacacact ctggacgctggtcgtgtgatggactgttgccgccacacttgctgccttgacctgtgaatatccctgcc gcttttatcaaacagcctcagtgtgtttgatcttgtgtgtacgcgcttttgcgagttgctagctgctt gtgctatttgcgaataccacccccagcatccccttccctcgtttcatatcgcttgcatcccaaccgca acttatctacgctgtcctgctatccctcagcgctgctcctgctcctgctcactgcccctcgcacagcc ttggtttgggctccgcctgtattctcctggtactgcaacctgtaaaccagcactgcaatgctgatgca cgggaagtagtgggatgggaacacaaatggaggatcc

*Cocos nucifera* 1-acyl-sn-glycerol-3-phosphate acyltransferase (LPAAT)

SEQ ID NO: 16

MDASGASSFLRGRCLESCFKASFGYVMSQPKDAAGQPSRRPADADDFVDDDRWITVILSV

VRIAACFLSMMVITIVWNMIMLILLPWPYARIRQGNLYGHVTGRMLMWILGNPITIEGSE

FSNTRAIYICNHASLVDIFLIMWLIPKGTVTIAKKEIIWYPLFGQLYVLANHQRIDRSNP

SAAIESIKEVARAVVKKNLSLIIFPEGTRSKTGRLLPFKKGFIHIALQTRLPIVPMVLTG

THLAWRKNSLRVRPAPITVKYFSPIKTDDWEEEKINHYVEMIHALYVDHLPESQKPLVSK

GRDASGRSNS

-continued pSZ1500

SEQ ID NO: 17

GGGCTGGTCTGAATCCTTCAGGCGGGTGTTACCCGAGAAAGAAAGGGTGCCGATTTCAAAGCAGACCC

ATGTGCCGGGCCCTGTGGCCTGTGTTGGCGCCTATGTAGTCACCCCCCCTCACCCAATTGTCGCCAGT

TTGCGCACTCCATAAACTCAAAACAGCAGCTTCTGAGCTGCGCTGTTCAAGAACACCTCTGGGGTTTG

CTCACCCGCGAGGTCGACGCCCAGCATGGCTATCAAGACGAACAGGCAGCCTGTGGAGAAGCCTCCGT

TCACGATCGGGACGCTGCGCAAGGCCATCCCCGCGCACTGTTTCGAGCGCTCGGCGCTTCGTAGCAGC

ATGTACCTGGCCTTTGACATCGCGGTCATGTCCCTGCTCTACGTCGCGTCGACGTACATCGACCCTGC

ACCGGTGCCTACGTGGGTCAAGTACGGCATCATGTGGCCGCTCTACTGGTTCTTCCAGGTGTGTTTGA

GGGTTTTGGTTGCCCGTATTGAGGTCCTGGTGGCGCGCATGGAGGAGAAGGCGCCTGTCCCGCTGACC

CCCCCGGCTACCCTCCCGGCACCTTCCAGGGCGCCTTCGGCACGGGTGTCTGGGTGTGCGCGCACGAG

TGCGGCCACCAGGCCTTTTCCTCCAGCCAGGCCATCAACGACGGCGTGGGCCTGGTGTTCCACAGCCT

GCTGCTGGTGCCCTACTACTCCTGGAAGCACTCGCACCGGGTACCCTTTCTTGCGCTATGACACTTCC

AGCAAAAGGTAGGGCGGGCTGCGAGACGGCTTCCCGGCGCTGCATGCAACACCGATGATGCTTCGACC

CCCCGAAGCTCCTTCGGGGCTGCATGGGCGCTCCGATGCCGCTCCAGGGCGAGCGCTGTTTAAATAGC

CAGGCCCCCGATTGCAAAGACATTATAGCGAGCTACCAAAGCCATATTCAAACACCTAGATCACTACC

ACTTCTACACAGGCCACTCGAGCTTGTGATCGCACTCCGCTAAGGGGGCGCCTCTTCCTCTTCGTTTC

AGTCACAACCCGCAAACTCTAGAATATCAATGCTGCTGCAGGCCTTCCTGTTCCTGCTGGCCGGCTTC

GCCGCCAAGATCAGCGCCTCCATGACGAACGAGACGTCCGACCGCCCCCTGGTGCACTTCACCCCCAA

CAAGGGCTGGATGAACGACCCCAACGGCCTGTGGTACGACGAGAAGGACGCCAAGTGGCACCTGTACT

TCCAGTACAACCCGAACGACACCGTCTGGGGGACGCCCTTGTTCTGGGGCCACGCCACGTCCGACGAC

CTGACCAACTGGGAGGACCAGCCCATCGCCATCGCCCCGAAGCGCAACGACTCCGGCGCCTTCTCCGG

CTCCATGGTGGTGGACTACAACAACACCTCCGGCTTCTTCAACGACACCATCGACCCGCGCCAGCGCT

GCGTGGCCATCTGGACCTACAACACCCCGGAGTCCGAGGAGCAGTACATCTCCTACAGCCTGGACGGC

GGCTACACCTTCACCGAGTACCAGAAGAACCCCGTGCTGGCCGCCAACTCCACCCAGTTCCGCGACCC

GAAGGTCTTCTGGTACGAGCCCTCCCAGAAGTGGATCATGACCGCGGCCAAGTCCCAGGACTACAAGA

TCGAGATCTACTCCTCCGACGACCTGAAGTCCTGGAAGCTGGAGTCCGCGTTCGCCAACGAGGGCTTC

CTCGGCTACCAGTACGAGTGCCCCGGCCTGATCGAGGTCCCCACCGAGCAGGACCCCAGCAAGTCCTA

CTGGGTGATGTTCATCTCCATCAACCCCGGCGCCCCGGCCGGCGGCTCCTTCAACCAGTACTTCGTCG

GCAGCTTCAACGGCACCCACTTCGAGGCCTTCGACAACCAGTCCCGCGTGGTGGACTTCGGCAAGGAC

TACTACGCCCTGCAGACCTTCTTCAACACCGACCCGACCTACGGGAGCGCCCTGGGCATCGCGTGGGC

CTCCAACTGGGAGTACTCCGCCTTCGTGCCCACCAACCCCTGGCGCTCCTCCATGTCCCTCGTGCGCA

AGTTCTCCCTCAACACCGAGTACCAGGCCAACCCGGAGACGGAGCTGATCAACCTGAAGGCCGAGCCG

ATCCTGAACATCAGCAACGCCGGCCCCTGGAGCCGGTTCGCCACCAACACCACGTTGACGAAGGCCAA

CAGCTACAACGTCGACCTGTCCAACAGCACCGGCACCCTGGAGTTCGAGCTGGTGTACGCCGTCAACA

CCACCCAGACGATCTCCAAGTCCGTGTTCGCGGACCTCTCCCTCTGGTTCAAGGGCCTGGAGGACCCC

GAGGAGTACCTCCGCATGGGCTTCGAGGTGTCCGCGTCCTCCTTCTTCCTGGACCGCGGGAACAGCAA

GGTGAAGTTCGTGAAGGAGAACCCCTACTTCACCAACCGCATGAGCGTGAACAACCAGCCCTTCAAGA

GCGAGAACGACCTGTCCTACTACAAGGTGTACGGCTTGCTGGACCAGAACATCCTGGAGCTGTACTTC

AACGACGGCGACGTCGTGTCCACCAACACCTACTTCATGACCACCGGGAACGCCCTGGGCTCCGTGAA

CATGACGACGGGGGTGGACAACCTGTTCTACATCGACAAGTTCCAGGTGCGCGAGGTCAAGTGACAAT

-continued

TGGCAGCAGCAGCTCGGATAGTATCGACACACTCTGGACGCTGGTCGTGTGATGGACTGTTGCCGCCA

CACTTGCTGCCTTGACCTGTGAATATCCCTGCCGCTTTTATCAAACAGCCTCAGTGTGTTTGATCTTG

TGTGTACGCGCTTTTGCGAGTTGCTAGCTGCTTGTGCTATTTGCGAATACCACCCCCAGCATCCCCTT

CCCTCGTTTCATATCGCTTGCATCCCAACCGCAACTTATCTACGCTGTCCTGCTATCCCTCAGCGCTG

CTCCTGCTCCTGCTCACTGCCCCTCGCACAGCCTTGGTTTGGGCTCCGCCTGTATTCTCCTGGTACTG

CAACCTGTAAACCAGCACTGCAATGCTGATGCACGGGAAGTAGTGGGATGGGAACACAAATGGAGGAT

CCCGCGTCTCGAACAGAGCGCGCAGAGGAACGCTGAAGGTCTCGCCTCTGTCGCACCTCAGCGCGGCA

TACACCACAATAACCACCTGACGAATGCGCTTGGTTCTTCGTCCATTAGCGAAGCGTCCGGTTCACAC

ACGTGCCACGTTGGCGAGGTGGCAGGTGACAATGATCGGTGGAGCTGATGGTCGAAACGTTCACAGCC

TAGGGATATCGAATTCGGCCGACAGGACGCGCGTCAAAGGTGCTGGTCGTGTATGCCCTGGCCGGCAG

GTCGTTGCTGCTGCTGGTTAGTGATTCCGCAACCCTGATTTTGGCGTCTTATTTTGGCGTGGCAAACG

CTGGCGCCCGCGAGCCGGGCCGGCGGCGATGCGGTGCCCCACGGCTGCCGGAATCCAAGGGAGGCAAG

AGCGCCCGGGTCAGTTGAAGGGCTTTACGCGCAAGGTACAGCCGCTCCTGCAAGGCTGCGTGGTGGAA

TTGGACGTGCAGGTCCTGCTGAAGTTCCTCCACCGCCTCACCAGCGGACAAAGCACCGGTGTATCAGG

TCCGTGTCATCCACTCTAAAGAACTCGACTACGACCTACTGATGGCCCTAGATTCTTCATCAAAAACG

CCTGAGACACTTGCCCAGGATTGAAACTCCCTGAAGGGACCACCAGGGGCCCTGAGTTGTTCCTTCCC

CCCGTGGCGAGCTGCCAGCCAGGCTGTACCTGTGATCGAGGCTGGCGGGAAAATAGGCTTCGTGTGCT

CAGGTCATGGGAGGTGCAGGACAGCTCATGAAACGCCAACAATCGCACAATTCATGTCAAGCTAATCA

GCTATTTCCTCTTCACGAGCTGTAATTGTCCCAAAATTCTGGTCTACCGGGGGTGATCCTTCGTGTAC

GGGCCCTTCCCTCAACCCTAGGTATGCGCGCATGCGGTCGCCGCGCAACTCGCGCGAGGGCCGAGGGT

TTGGGACGGGCCGTCCCGAAATGCAGTTGCACCCGGATGCGTGGCACCTTTTTTGCGATAATTTATGC

AATGGACTGCTCTGCAAAATTCTGGCTCTGTCGCCAACCCTAGGATCAGCGGCGTAGGATTTCGTAAT

CATTCGTCCTGATGGGGAGCTACCGACTACCCTAATATCAGCCCGACTGCCTGACGCCAGCGTCCACT

TTTGTGCACACATTCCATTCGTGCCCAAGACATTTCATTGTGGTGCGAAGCGTCCCCAGTTACGCTCA

CCTGTTTCCCGACCTCCTTACTGTTCTGTCGACAGAGCGGGCCCACAGGCCGGTCGCAGCCACTAGTA

TGGCCACCGCATCCACTTTCTCGGCGTTCAATGCCCGCTGCGGCGACCTGCGTCGCTCGGCGGGCTCC

GGGCCCCGGCGCCCAGCGAGGCCCCTCCCCGTGCGCGGGCGCGCCGCCACCGGCGAGCAGCCCTCCGG

CGTGGCCTCCCTGCGCGAGGCCGACAAGGAGAAGTCCCTGGGCAACCGCCTGCGCCTGGGCTCCCTGA

CCGAGGACGGCCTGTCCTACAAGGAGAAGTTCGTGATCCGCTGCTACGAGGTGGGCATCAACAAGACC

GCCACCATCGAGACCATCGCCAACCTGCTGCAGGAGGTGGGCGGCAACCACGCCCAGGGCGTGGGCTT

CTCCACCGACGGCTTCGCCACCACCACCACCATGCGCAAGCTGCACCTGATCTGGGTGACCGCCCGCA

TGCACATCGAGATCTACCGCTACCCCGCCTGGTCCGACGTGATCGAGATCGAGACCTGGGTGCAGGGC

GAGGGCAAGGTGGGCACCCGCCGCGACTGGATCCTGAAGGACTACGCCAACGGCGAGGTGATCGGCCG

CGCCACCTCCAAGTGGGTGATGATGAACGAGGACACCCGCCGCCTGCAGAAGGTGTCCGACGACGTGC

GCGAGGAGTACCTGGTGTTCTGCCCCCGCACCCTGCGCCTGGCCTTCCCCGAGGAGAACAACAACTCC

ATGAAGAAGATCCCCAAGCTGGAGGACCCCGCCGAGTACTCCCGCCTGGGCCTGGTGCCCCGCCGCTC

CGACCTGGACATGAACAAGCACGTGAACAACGTGACCTACATCGGCTGGGCCCTGGAGTCCATCCCCC

CCGAGATCATCGACACCCACGAGCTGCAGGCCATCACCCTGGACTACCGCCGCGAGTGCCAGCGCGAC

GACATCGTGGACTCCCTGACCTCCCGCGAGCCCCTGGGCAACGCCGCCGGCGTGAAGTTCAAGGAGAT

CAACGGCTCCGTGTCCCCCAAGAAGGACGAGCAGGACCTGTCCCGCTTCATGCACCTGCTGCGCTCCG

CCGGCTCCGGCCTGGAGATCAACCGCTGCCGCACCGAGTGGCGCAAGAAGCCCGCCAAGCGCATGGAC

-continued

TACAAGGACCACGACGGCGACTACAAGGACCACGACATCGACTACAAGGACGACGACGACAAGTGAAT

CGATAGATCTCTTAAGGCAGCAGCAGCTCGGATAGTATCGACACACTCTGGACGCTGGTCGTGTGATG

GACTGTTGCCGCCACACTTGCTGCCTTGACCTGTGAATATCCCTGCCGCTTTTATCAAACAGCCTCAG

TGTGTTTGATCTTGTGTGTACGCGCTTTTGCGAGTTGCTAGCTGCTTGTGCTATTTGCGAATACCACC

CCCAGCATCCCCTTCCCTCGTTTCATATCGCTTGCATCCCAACCGCAACTTATCTACGCTGTCCTGCT

ATCCCTCAGCGCTGCTCCTGCTCCTGCTCACTGCCCCTCGCACAGCCTTGGTTTGGGCTCCGCCTGTA

TTCTCCTGGTACTGCAACCTGTAAACCAGCACTGCAATGCTGATGCACGGGAAGTAGTGGGATGGGAA

CACAAATGGAAAGCTTAATTAAGAGCTCCCGCCACCACTCCAACACGGGGTGCCTGGACAAGGACGAG

GTGTTTGTGCCGCCGCACCGCGCAGTGGCGCACGAGGGCCTGGAGTGGGAGGAGTGGCTGCCCATCCG

CATGGGCAAGGTGCTGGTCACCCTGACCCTGGGCTGGCCGCTGTACCTCATGTTCAACGTCGCCTCGC

GGCCGTACCCGCGCTTCGCCAACCACTTTGACCCGTGGTCGCCCATCTTCAGCAAGCGCGAGCGCATC

GAGGTGGTCATCTCCGACCTGGCGCTGGTGGCGGTGCTCAGCGGGCTCAGCGTGCTGGGCCGCACCAT

GGGCTGGGCCTGGCTGGTCAAGACCTACGTGGTGCCCTACCTGATCGTGAACATGTGGCTCGTGCTCA

TCACGCTGCTCCAGCACACGCACCCGGCGCTGCCGCACTACTTCGAGAAGGACTGGGACTGGCTGCGC

GGCGCCATGGCCACCGTGGACCGCTCCATGGGCCCGCCCTTCATGGACAACATCCTGCACCACATCTC

CGACACCCACGTGCTGCACCACCTCTTCAGCACCATCCCGCACTACCACGCCGAGGAGGCCTCCGCCG

CCATCAGGCCCATCCTGGGCAAGTACTACCAGTCCGACAGCCGCTGGGTCGGCCGCGCCCTGTGGGAG

GACTGGCGCGACTGCCGCTACGTCGTCCCGGACGCGCCCGAGGACGACTCCGCGCTCTGGTTCCACAA

GTGAGTGAGTGA

5' FADc genomic region donor DNA

SEQ ID NO: 18

GGGCTGGTCTGAATCCTTCAGGCGGGTGTTACCCGAGAAAGAAAGGGTGCCGATTTCAAAGCAGACCC

ATGTGCCGGGCCCTGTGGCCTGTGTTGGCGCCTATGTAGTCACCCCCCCTCACCCAATTGTCGCCAGT

TTGCGCACTCCATAAACTCAAAACAGCAGCTTCTGAGCTGCGCTGTTCAAGAACACCTCTGGGGTTTG

CTCACCCGCGAGGTCGACGCCCAGCATGGCTATCAAGACGAACAGGCAGCCTGTGGAGAAGCCTCCGT

TCACGATCGGGACGCTGCGCAAGGCCATCCCCGCGCACTGTTTCGAGCGCTCGGCGCTTCGTAGCAGC

ATGTACCTGGCCTTTGACATCGCGGTCATGTCCCTGCTCTACGTCGCGTCGACGTACATCGACCCTGC

ACCGGTGCCTACGTGGGTCAAGTACGGCATCATGTGGCCGCTCTACTGGTTCTTCCAGGTGTGTTTGA

GGGTTTTGGTTGCCCGTATTGAGGTCCTGGTGGCGCGCATGGAGGAGAAGGCGCCTGTCCCGCTGACC

CCCCCGGCTACCCTCCCGGCACCTTCCAGGGCGCCTTCGGCACGGGTGTCTGGGTGTGCGCGCACGAG

TGCGGCCACCAGGCCTTTTCCTCCAGCCAGGCCATCAACGACGGCGTGGGCCTGGTGTTCCACAGCCT

GCTGCTGGTGCCCTACTACTCCTGGAAGCACTCGCACCG

3' FADc genomic region donor DNA

SEQ ID NO: 19

CCGCCACCACTCCAACACGGGGTGCCTGGACAAGGACGAGGTGTTTGTGCCGCCGCACCGCGCAGTGG

CGCACGAGGGCCTGGAGTGGGAGGAGTGGCTGCCCATCCGCATGGGCAAGGTGCTGGTCACCCTGACC

CTGGGCTGGCCGCTGTACCTCATGTTCAACGTCGCCTCGCGGCCGTACCCGCGCTTCGCCAACCACTT

TGACCCGTGGTCGCCCATCTTCAGCAAGCGCGAGCGCATCGAGGTGGTCATCTCCGACCTGGCGCTGG

TGGCGGTGCTCAGCGGGCTCAGCGTGCTGGGCCGCACCATGGGCTGGGCCTGGCTGGTCAAGACCTAC

GTGGTGCCCTACCTGATCGTGAACATGTGGCTCGTGCTCATCACGCTGCTCCAGCACACGCACCCGGC

GCTGCCGCACTACTTCGAGAAGGACTGGGACTGGCTGCGCGGCGCCATGGCCACCGTGGACCGCTCCA

TGGGCCCGCCCTTCATGGACAACATCCTGCACCACATCTCCGACACCCACGTGCTGCACCACCTCTTC

-continued

AGCACCATCCCGCACTACCACGCCGAGGAGGCCTCCGCCGCCATCAGGCCCATCCTGGGCAAGTACTA

CCAGTCCGACAGCCGCTGGGTCGGCCGCGCCCTGTGGGAGGACTGGCGCGACTGCCGCTACGTCGTCC

CGGACGCGCCCGAGGACGACTCCGCGCTCTGGTTCCACAAGTGAGTGAGTGA

5' donor DNA sequence of *Prototheca moriformis* FATA1 knockout homologous recombination targeting construct

SEQ ID NO: 20

GCTCTTCGGAGTCACTGTGCCACTGAGTTCGACTGGTAGCTGAATGGAGTCGCTGCTCCACTAAACGA

ATTGTCAGCACCGCCAGCCGGCCGAGGACCCGAGTCATAGCGAGGGTAGTAGCGCGCCATGGCACCGA

CCAGCCTGCTTGCCAGTACTGGCGTCTCTTCCGCTTCTCTGTGGTCCTCTGCGCGCTCCAGCGCGTGC

GCTTTTCCGGTGGATCATGCGGTCCGTGGCGCACCGCAGCGGCCGCTGCCCATGCAGCGCCGCTGCTT

CCGAACAGTGGCGGTCAGGGCCGCACCCGCGGTAGCCGTCCGTCCGGAACCCGCCCAAGAGTTTTGGG

AGCAGCTTGAGCCCTGCAAGATGGCGGAGGACAAGCGCATCTTCCTGGAGGAGCACCGGTGCGTGGAG

GTCCGGGGCTGACCGGCCGTCGCATTCAACGTAATCAATCGCATGATGATCAGAGGACACGAAGTCTT

GGTGGCGGTGGCCAGAAACACTGTCCATTGCAAGGGCATAGGGATGCGTTCCTTCACCTCTCATTTCT

CATTTCTGAATCCCTCCCTGCTCACTCTTTCTCCTCCTCCTTCCCGTTCACGCAGCATTCGGGGTACC

3' donor DNA sequence of *Prototheca moriformis* FATA1 knockout homologous recombination targeting construct

SEQ ID NO: 21

GACAGGGTGGTTGGCTGGATGGGGAAACGCTGGTCGCGGGATTCGATCCTGCTGCTTATATCCTCCCT

GGAAGCACACCCACGACTCTGAAGAAGAAAACGTGCACACACACAACCCAACCGGCCGAATATTTGCT

TCCTTATCCCGGGTCCAAGAGAGACTGCGATGCCCCCCTCAATCAGCATCCTCCTCCCTGCCGCTTCA

ATCTTCCCTGCTTGCCTGCGCCCGCGGTGCGCCGTCTGCCCGCCCAGTCAGTCACTCCTGCACAGGCC

CCTTGTGCGCAGTGCTCCTGTACCCTTTACCGCTCCTTCCATTCTGCGAGGCCCCCTATTGAATGTAT

TCGTTGCCTGTGTGGCCAAGCGGGCTGCTGGGCGCGCCGCCGTCGGGCAGTGCTCGGCGACTTTGGCG

GAAGCCGATTGTTCTTCTGTAAGCCACGCGCTTGCTGCTTTGGGAAGAGAAGGGGGGGGGTACTGAAT

GGATGAGGAGGAGAAGGAGGGGTATTGGTATTATCTGAGTTGGGTGAAGAGC

*Chlorella protothecoides* actin promoter/5'UTR

SEQ ID NO: 22 agtttaggtccagcgtccgtggggggggacgggctgggagcttgggccgggaagggcaagacgatgca gtccctctggggagtcacagccgactgtgtgtgttgcactgtgcggcccgcagcactcacacgcaaaa tgcctggccgacaggcaggccctgtccagtgcaacatccacggtccctctcatcaggctcaccttgct cattgacataacggaatgcgtaccgctctttcagatctgtccatccagagaggggagcaggctcccca ccgacgctgtcaaacttgcttcctgcccaaccgaaaacattattgtttgagggggggggggggggggc agattgcatggcgggatatctcgtgaggaacatcactgggacactgtggaacacagtgagtgcagtat gcagagcatgtatgctaggggtcagcgcaggaagggggcctttcccagtctcccatgccactgcaccg tatccacgactcaccaggaccagcttcttgatcggcttccgctcccgtggacaccagtgtgtagcctc tggactccaggtatgcgtgcaccgcaaaggccagccgatcgtgccgattcctggggtggaggatatga gtcagccaacttggggctcagagtgcacactggggcacgatacgaaacaacatctacaccgtgtcctc catgctgacacaccacagcttcgctccacctgaatgtgggcgcatgggcccgaatcacagccaatgtc gctgctgccataatgtgatccagaccctctccgcccagatgccgagcggatcgtgggcgctgaataga ttcctgtttcgatcactgtttgggtcctttccttttcgtctcggatgcgcgtctcgaaacaggctgcg tcgggctttcggatcccttttgctccctccgtcaccatcctgcgcgcgggcaagttgcttgaccctgg gctgtaccagggttggagggtattaccgcgtcaggccattcccagcccggattcaattcaaagtctgg -continued gccaccaccctccgccgctctgtctgatcactccacattcgtgcatacactacgttcaagtcctgatc caggcgtgtctcgggacaaggtgtgcttgagtttgaatctcaaggacccactccagcacagctgctgg ttgaccccgccctcgcaa AtTHIC expression cassette comprising *Chlorella protothecoides* actin promoter/5'UTR, *Arabidopsis thaliana* THIC protein coding sequence codon-optimized for expression in *Prototheca moriformis*, and *Chlorella vulgaris* nitrate reductase 3' UTR

SEQ ID NO: 23 agtttaggtccagcgtccgtgggggggacgggctgggagcttgggccgggaagggcaagacgatgca gtccctctggggagtcacagccgactgtgtgtgttgcactgtgcggcccgcagcactcacacgcaaaa tgcctggccgacaggcaggccctgtccagtgcaacatccacggtccctctcatcaggctcaccttgct cattgacataacggaatgcgtaccgctctttcagatctgtccatccagagaggggagcaggctcccca ccgacgctgtcaaacttgcttcctgcccaaccgaaaacattattgtttgagggggggggggggggggc agattgcatggcgggatatctcgtgaggaacatcactgggacactgtggaacacagtgagtgcagtat gcagagcatgtatgctaggggtcagcgcaggaaggggggcctttcccagtctcccatgccactgcaccg tatccacgactcaccaggaccagcttcttgatcggcttccgctcccgtggacaccagtgtgtagcctc tggactccaggtatgcgtgcaccgcaaaggccagccgatcgtgccgattcctggggtggaggatatga gtcagccaacttggggctcagagtgcacactggggcacgatacgaaacaacatctacaccgtgtcctc catgctgacacaccacagcttcgctccacctgaatgtgggcgcatgggcccgaatcacagccaatgtc gctgctgccataatgtgatccagaccctctccgcccagatgccgagcggatcgtgggcgctgaataga ttcctgtttcgatcactgtttgggtcctttccttttcgtctcggatgcgcgtctcgaaacaggctgcg tcgggctttcggatcccttttgctccctccgtcaccatcctgcgcgcgggcaagttgcttgaccctgg gctgtaccagggttggagggtattaccgcgtcaggccattcccagcccggattcaattcaaagtctgg gccaccaccctccgccgctctgtctgatcactccacattcgtgcatacactacgttcaagtcctgatc caggcgtgtctcgggacaaggtgtgcttgagtttgaatctcaaggacccactccagcacagctgctgg ttgaccccgccctcgcaa<u>tctaga</u>*ATGgccgcgtccgtccactgcaccctgatgtccgtggtctgcaa*

*caacaagaaccactccgcccgccccaagctgcccaactcctccctgctgcccggcttcgacgtggtgg*

*tccaggccgcggccacccgcttcaagaaggagacgacgaccacccgcgccacgctgacgttcgacccc*

*cccacgaccaactccgagcgcgccaagcagcgcaagcacaccatcgacccctcctcccccgacttcca*

*gcccatcccctccttcgaggagtgcttccccaagtccacgaaggagcacaaggaggtggtgcacgagg*

*agtccggccacgtcctgaaggtgcccttccgccgcgtgcacctgtccggcggcgagcccgccttcgac*

*aactacgacacgtccggcccccagaacgtcaacgcccacatcggcctggcgaagctgcgcaaggagtg*

*gatcgaccgccgcgagaagctgggcacgccccgctacacgcagatgtactacgcgaagcagggcatca*

*tcacggaggagatgctgtactgcgcgacgcgcgagaagctggaccccgagttcgtccgctccgaggtc*

*gcgcggggccgcgccatcatcccctccaacaagaagcacctggagctggagcccatgatcgtgggccg*

*caagttcctggtgaaggtgaacgcgaacatcggcaactccgccgtggcctcctccatcgaggaggagg*

*tctacaaggtgcagtgggccaccatgtggggcgccgacaccatcatggacctgtccacgggccgccac*

*atccacgagacgcgcgagtggatcctgcgcaactccgcggtccccgtgggcaccgtccccatctacca*

*ggcgctggagaaggtggacggcatcgcggagaacctgaactgggaggtgttccgcgagacgctgatcg*

*agcaggccgagcagggcgtggactacttcacgatccacgcgggcgtgctgctgcgctacatcccccctg*

*accgccaagcgcctgacgggcatcgcgtcccgcggcggctccatccacgcgaagtggtgcctggccta*

*ccacaaggagaacttcgcctacgagcactgggacgacatcctggacatctgcaaccagtacgacgtcg*

*ccctgtccatcggcgacggcctgcgccccggctccatctacgacgccaacgacacggcccagttcgcc*

-continued

*gagctgctgacccagggcgagctgacgcgccgcgcgtgggagaaggacgtgcaggtgatgaacgaggg*

*ccccggccacgtgcccatgcacaagatccccgagaacatgcagaagcagctggagtggtgcaacgagg*

*cgcccttctacaccctgggcccccctgacgaccgacatcgcgcccggctacgaccacatcacctccgcc*

*atcggcgcggccaacatcggcgccctgggcaccgccctgctgtgctacgtgacgcccaaggagcacct*

*gggcctgcccaaccgcgacgacgtgaaggcgggcgtcatcgcctacaagatcgccgcccacgcggccg*

*acctggccaagcagcacccccacgcccaggcgtgggacgacgcgctgtccaaggcgcgcttcgagttc*

*cgctggatggaccagttcgcgctgtccctggaccccatgacggcgatgtccttccacgacgagacgct*

*gcccgcggacggcgcgaaggtcgcccacttctgctccatgtgcggccccaagttctgctccatgaaga*

*tcacggaggacatccgcaagtacgccgaggagaacggctacggctccgccgaggaggccatccgccag*

*ggcatggacgccatgtccgaggagttcaacatcgccaagaagacgatctccggcgagcagcacggcga*

*ggtcggcggcgagatctacctgcccgagtcctacgtcaaggccgcgcagaagTGA*caattggcagcag cagctcggatagtatcgacacactctggacgctggtcgtgtgatggactgttgccgccacacttgctg ccttgacctgtgaatatccctgccgcttttatcaaacagcctcagtgtgtttgatcttgtgtgtacgc gcttttgcgagttgctagctgcttgtgctatttgcgaataccacccccagcatccccttccctcgttt catatcgcttgcatcccaaccgcaacttatctacgctgtcctgctatccctcagcgctgctcctgctc ctgctcactgcccctcgcacagccttggtttgggctccgcctgtattctcctggtactgcaacctgta aaccagcactgcaatgctgatgcacgggaagtagtgggatgggaacacaaatggaggatcc PmKASII (*Prototheca moriformis* KASII) comprising a *C. protothecoides* S106 stearoyl-ACP desaturase transit peptide

SEQ ID NO: 24

ATGgccaccgcatccactttctcggcgttcaatgcccgctgcggcgacctgcgtcgctcggcgggctc cgggccccggcgcccagcgaggcccctccccgtgcgcggcgcgccgccgccgccgccgacgccaacc ccgcccgccccgagcgccgcgtggtgatcaccggccagggcgtggtgacctccctgggccagaccatc gagcagttctactcctccctgctggagggcgtgtccggcatctcccagatccagaagttcgacaccac cggctacaccaccaccatcgccggcgagatcaagtccctgcagctggacccctacgtgcccaagcgct gggccaagcgcgtggacgacgtgatcaagtacgtgtacatcgccggcaagcaggccctggagtccgcc ggcctgcccatcgaggccgccggcctggccggcgccggcctggaccccgccctgtgcggcgtgctgat cggcaccgccatggccggcatgacctccttcgccgccggcgtggaggccctgacccgcggcggcgtgc gcaagatgaaccccttctgcatccccttctccatctccaacatgggcggcgccatgctggccatggac atcggcttcatgggccccaactactccatctccaccgcctgcgccaccggcaactactgcatcctggg cgccgccgaccacatccgccgcggcgacgccaacgtgatgctggccggcggcgccgacgccgccatca tcccctccggcatcggcggcttcatcgcctgcaaggccctgtccaagcgcaacgacgagcccgagcgc gcctcccgcccctgggacgccgaccgcgacggcttcgtgatgggcgagggcgccggcgtgctggtgct ggaggagctggagcacgccaagcgccgcggcgccaccatcctggccgagctggtgggcggcgccgcca cctccgacgcccaccacatgaccgagcccgacccccagggccgcggcgtgcgcctgtgcctggagcgc gccctggagcgcgcccgcctggcccccgagcgcgtgggctacgtgaacgcccacggcacctccacccc cgccggcgacgtggccgagtaccgcgccatccgcgccgtgatcccccaggactccctgcgcatcaact ccaccaagtccatgatcggccacctgctgggcggcgccggcgccgtggaggccgtggccgccatccag gccctgcgcaccggctggctgcaccccaacctgaacctggagaaccccgcccccggcgtggaccccgt ggtgctggtgggccccgcaaggagcgcgccgaggacctggacgtggtgctgtccaactccttcggct tcggcggccacaactcctgcgtgatcttccgcaagtacgacgagatggactacaaggaccacgacggc gactacaaggaccacgacatcgactacaaggacgacgacgacaagTGA -continued PmKASII (*Prototheca moriformis* KASII) comprising a *C. protothecoides* S106 stearoylACP desaturase transit peptide

SEQ ID NO: 25

MATASTFSAFNARCGDLRRSAGSGPRRPARPLPVRGRAAAAADANPARPERRVVITGQGVVTSLGQTI

EQFYSSLLEGVSGISQIQKFDTTGYTTTIAGEIKSLQLDPYVPKRWAKRVDDVIKYVYIAGKQALESA

GLPIEAAGLAGAGLDPALCGVLIGTAMAGMTSFAAGVEALTRGGVRKMNPFCIPFSISNMGGAMLAMD

IGFMGPNYSISTACATGNYCILGAADHIRRGDANVMLAGGADAAIIPSGIGGFIACKALSKRNDEPER

ASRPWDADRDGFVMGEGAGVLVLEELEHAKRRGATILAELVGGAATSDAHHMTEPDPQGRGVRLCLER

ALERARLAPERVGYVNAHGTSTPAGDVAEYRAIRAVIPQDSLRINSTKSMIGHLLGGAGAVEAVAAIQ

ALRTGWLHPNLNLENPAPGVDPVVLVGPRKERAEDLDVVLSNSFGFGGHNSCVIFRKYDEMDYKDHDG

DYKDHDIDYKDDDDK

Codon-optimized *Prototheca moriformis* (UTEX 1435) FAD2 protein-coding sequence

SEQ ID NO: 26

ATGgccatcaagaccaaccgccagcccgtggagaagccccccttcaccatcggcaccctgcgcaaggc catccccgcccactgcttcgagcgctccgccctgcgctcctccatgtacctggccttcgacatcgccg tgatgtccctgctgtacgtggcctccacctacatcgaccccgcccccgtgcccacctgggtgaagtac ggcgtgatgtggcccctgtactggttcttccagggcgccttcggcaccggcgtgtgggtgtgcgccca cgagtgcggccaccaggccttctcctcctcccaggccatcaacgacggcgtgggcctggtgttccact ccctgctgctggtgccctactactcctggaagcactcccaccgccgccaccactccaacaccggctgc ctggacaaggacgaggtgttcgtgcccccccaccgcgccgtggcccacgagggcctggagtgggagga gtggctgcccatccgcatgggcaaggtgctggtgaccctgaccctgggctggcccctgtacctgatgt tcaacgtggcctcccgcccctacccccgcttcgccaaccacttcgacccctggtcccccatcttctcc aagcgcgagcgcatcgaggtggtgatctccgacctggccctggtggccgtgctgtccggcctgtccgt gctgggccgcaccatgggctgggcctggctggtgaagacctacgtggtgccctacctgatcgtgaaca tgtggctggtgctgatcaccctgctgcagcacacccaccccgccctgccccactacttcgagaaggac tgggactggctgcgcggcgccatggccaccgtggaccgctccatgggcccccccttcatggacaacat cctgcaccacatctccgacacccacgtgctgcaccacctgttctccaccatcccccactaccacgccg aggaggcctccgccgccatccgccccatcctgggcaagtactaccagtccgactcccgctgggtgggc cgcgccctgtgggaggactggcgcgactgccgctacgtggtgcccgacgcccccgaggacgactccgc cctgtggttccacaagTAG Amino acid sequence of *Prototheca moriformis* FAD2

SEQ ID NO: 27

MAIKTNRQPVEKPPFTIGTLRKAIPAHCFERSALRSSMYLAFDIAVMSLLYVASTYIDPAPVPTWVKY

GVMWPLYWFFQGAFGTGVWVCAHECGHQAFSSSQAINDGVGLVFHSLLLVPYYSWKHSHRRHHSNTGC

LDKDEVFVPPHRAVAHEGLEWEEWLPIRMGKVLVTLTLGWPLYLMFNVASRPYPRFANHFDPWSPIFS

KRERIEVVISDLALVAVLSGLSVLGRTMGWAWLVKTYVVPYLIVNMWLVLITLLQHTHPALPHYFEKD

WDWLRGAMATVDRSMGPPFMDNILHHISDTHVLHHLFSTIPHYHAEEASAAIRPILGKYYQSDSRWVG

RALWEDWRDCRYVVPDAPEDDSALWFHK

Codon-optimized coding region of *Brassica napus* C18:0-preferring thioesterase from pSZ1358

SEQ ID NO: 28

ACTAGTATGCTGAAGCTGTCCTGCAACGTGACCAACAACCTGCACACCTTCTCCTTCTTCTCCGACTC

CTCCCTGTTCATCCCCGTGAACCGCCGCACCATCGCCGTGTCCTCCGGGCGCGCCTCCCAGCTGCGCA

AGCCCGCCCTGGACCCCCTGCGCGCCGTGATCTCCGCCGACCAGGGCTCCATCTCCCCCGTGAACTCC

TGCACCCCCGCCGACCGCCTGCGCGCCGGCCGCCTGATGGAGGACGGCTACTCCTACAAGGAGAAGTT

-continued

CATCGTGCGCTCCTACGAGGTGGGCATCAACAAGACCGCCACCGTGGAGACCATCGCCAACCTGCTGC

AGGAGGTGGCCTGCAACCACGTGCAGAAGTGCGGCTTCTCCACCGACGGCTTCGCCACCACCCTGACC

ATGCGCAAGCTGCACCTGATCTGGGTGACCGCCCGCATGCACATCGAGATCTACAAGTACCCCGCCTG

GTCCGACGTGGTGGAGATCGAGACCTGGTGCCAGTCCGAGGGCCGCATCGGCACCCGCCGCGACTGGA

TCCTGCGCGACTCCGCCACCAACGAGGTGATCGGCCGCGCCACCTCCAAGTGGGTGATGATGAACCAG

GACACCCGCCGCCTGCAGCGCGTGACCGACGAGGTGCGCGACGAGTACCTGGTGTTCTGCCCCCGCGA

GCCCCGCCTGGCCTTCCCCGAGGAGAACAACTCCTCCCTGAAGAAGATCCCCAAGCTGGAGGACCCCG

CCCAGTACTCCATGCTGGAGCTGAAGCCCCGCCGCGCCGACCTGGACATGAACCAGCACGTGAACAAC

GTGACCTACATCGGCTGGGTGCTGGAGTCCATCCCCCAGGAGATCATCGACACCCACGAGCTGCAGGT

GATCACCCTGGACTACCGCCGCGAGTGCCAGCAGGACGACATCGTGGACTCCCTGACCACCTCCGAGA

TCCCCGACGACCCCATCTCCAAGTTCACCGGCACCAACGGCTCCGCCATGTCCTCCATCCAGGGCCAC

AACGAGTCCCAGTTCCTGCACATGCTGCGCCTGTCCGAGAACGGCCAGGAGATCAACCGCGGCCGCAC

CCAGTGGCGCAAGAAGTCCTCCCGCATGGACTACAAGGACCACGACGGCGACTACAAGGACCACGACA

TCGACTACAAGGACGACGACGACAAGTGAATCGAT

Amino acid sequence of *Brassica napus* C18:0-preferring thioesterase (Accession No. CAA52070.1)

SEQ ID NO: 29

MLKLSCNVTNNLHTFSFFSDSSLFIPVNRRTIAVSSSQLRKPALDPLRAVISADQGSISPVNSCTPAD

RLRAGRLMEDGYSYKEKFIVRSYEVGINKTATVETIANLLQEVACNHVQKCGFSTDGFATTLTMRKLH

LIWVTARMHIEIYKYPAWSDVVEIETWCQSEGRIGTRRDWILRDSATNEVIGRATSKWVMMNQDTRRL

QRVTDEVRDEYLVFCPREPRLAFPEENNSSLKKIPKLEDPAQYSMLELKPRRADLDMNQHVNNVTYIG

WVLESIPQEIIDTHELQVITLDYRRECQQDDIVDSLTTSEIPDDPISKFTGTNGSAMSSIQGHNESQF

LHMLRLSENGQEINRGRTQWRKKSSR

*Prototheca moriformis* FATA1 allele 1 5' homology donor region

SEQ ID NO: 30

GGAGTCACTGTGCCACTGAGTTCGACTGGTAGCTGAATGGAGTCGCTGCTCCACTAAACGAATTGTCA

GCACCGCCAGCCGGCCGAGGACCCGAGTCATAGCGAGGGTAGTAGCGCGCCATGGCACCGACCAGCCT

GCTTGCCAGTACTGGCGTCTCTTCCGCTTCTCTGTGGTCCTCTGCGCGCTCCAGCGCGTGCGCTTTTC

CGGTGGATCATGCGGTCCGTGGCGCACCGCAGCGGCCGCTGCCCATGCAGCGCCGCTGCTTCCGAACA

GTGGCGGTCAGGGCCGCACCCGCGGTAGCCGTCCGTCCGGAACCCGCCCAAGAGTTTTGGGAGCAGCT

TGAGCCCTGCAAGATGGCGGAGGACAAGCGCATCTTCCTGGAGGAGCACCGGTGCGTGGAGGTCCGGG

GCTGACCGGCCGTCGCATTCAACGTAATCAATCGCATGATGATCAGAGGACACGAAGTCTTGGTGGCG

GTGGCCAGAAACACTGTCCATTGCAAGGGCATAGGGATGCGTTCCTTCACCTCTCATTTCTCATTTCT

GAATCCCTCCCTGCTCACTCTTTCTCCTCCTCCTTCCCGTTCACGCAGCATTCGG

*Prototheca moriformis* FATA1 allele 1 3' homology donor region

SEQ ID NO: 31

GACAGGGTGGTTGGCTGGATGGGGAAACGCTGGTCGCGGGATTCGATCCTGCTGCTTATATCCTCCCT

GGAAGCACACCCACGACTCTGAAGAAGAAAACGTGCACACACACAACCCAACCGGCCGAATATTTGCT

TCCTTATCCCGGGTCCAAGAGAGACTGCGATGCCCCCCTCAATCAGCATCCTCCTCCCTGCCGCTTCA

ATCTTCCCTGCTTGCCTGCGCCCGCGGTGCGCCGTCTGCCCGCCCAGTCAGTCACTCCTGCACAGGCC

CCTTGTGCGCAGTGCTCCTGTACCCTTTACCGCTCCTTCCATTCTGCGAGGCCCCCTATTGAATGTAT

TCGTTGCCTGTGTGGCCAAGCGGGCTGCTGGGCGCGCCGCCGTCGGGCAGTGCTCGGCGACTTTGGCG

GAAGCCGATTGTTCTTCTGTAAGCCACGCGCTTGCTGCTTTGGGAAGAGAAGGGGGGGGGTACTGAAT

GGATGAGGAGGAGAAGGAGGGGTATTGGTATTATCTGAGTTGGGT

-continued

*Prototheca moriformis* FATA1 allele 2 5' homology donor region

SEQ ID NO: 32

AATGGAGTCGCTGCTCCACTAATCGAATTGTCAGCACCGCCAGCCGGCCGAGGACCCGAGTCATAGCG

AGGGTAGTAGCGCGCCATGGCACCGACCAGCCTGCTTGCCCGTACTGGCGTCTCTTCCGCTTCTCTGT

GCTCCTCTACGCGCTCCGGCGCGTGCGCTTTTCCGGTGGATCATGCGGTCCGTGGCGCACCGCAGCGG

CCGCTGCCCATGCAGCGCCGCTGCTTCCGAACAGTGGCTGTCAGGGCCGCACCCGCAGTAGCCGTCCG

TCCGGAACCCGCCCAAGAGTTTTGGGAGCAGCTTGAGCCCTGCAAGATGGCGGAGGACAAGCGCATCT

TCCTGGAGGAGCACCGGTGCGCGGAGGTCCGGGGCTGACCGGCCGTCGCATTCAACGTAATCAATCGC

ATGATGATCACAGGACGCGACGTCTTGGTGGCGGTGGCCAGGGACACTGCCCATTGCACAGGCATAGG

AATGCGTTCCTTCTCATTTCTCAGTTTTCTGAGCCCCTCCCTCTTCACTCTTTCTCCTCCTCCTCCCC

TCTCACGCAGCATTCGTGG

*Prototheca moriformis* FATA1 allele 2 3' homology donor region

SEQ ID NO: 33

CACTAGTATCGATTTCGAACAGAGGAGAGGGTGGCTGGTAGTTGCGGGATGGCTGGTCGCCCGTCGAT

CCTGCTGCTGCTATTGTCTCCTCCTGCACAAGCCCACCCACGACTCCGAAGAAGAAGAAGAAAACGCG

CACACACACAACCCAACCGGCCGAATATTTGCTTCCTTATCCCGGGTCCAAGAGAGACGGCGATGCCC

CCCTCAATCAGCCTCCTCCTCCCTGCCGCTCCAATCTTCCCTGCTTGCATGCGCCCGCGAGAGGCTGT

CTGCGCGCCCCGTCAGTCACTCCCCGTGCAGACGCCTCGTGCTCGGTGCTCCTGTATCCTTTACCGCT

CCTTTCATTCTGCGAGGCCCCCTGTTGAATGTATTCGTTGCCTGTGTGGCCAAGCGCGCTGCTGGGCG

CGCCGCCGTCGGGCGGTGCTCGGCGACTCTGGCGGAAGCCGGTTGTTCTTCTGTAAGCCACGCGCTTG

CTGCTTTTGGAAAAGAGGGGGGTTTACTGAATGGAGGAGGAGCAGGATAATTGGTAGTATCTGAGTTG

TTG

SAD2 hairpin C

SEQ ID NO: 34 actagtGCGCTGGACGCGGCAGTGGGTGGCCGAGGAGAACCGGCACGGCGACCTGCTGAACAAGTACT

GTTGGCTGACGGGGCGCGTCAACATGCGGGCCGTGGAGGTGACCATCAACAACCTGATCAAGAGCGGC

ATGAACCCGCAGACGGACAACAACCCTTACTTGGGCTTCGTCTACACCTCCTTCCAGGAGCGCGCGAC

CAAGTACAGCCACGGCAACACCGCGCGCCTTGCGGCCGAGCAGTGTGTTTGAGGGTTTTGGTTGCCCG

TATCGAGGTCCTGGTGGCGCGCATGGGGGAGAAGGCGCCTGTCCCGCTGACCCCCCCGGCTACCCTCC

CGGCACCTTCCAGGGCGCGTACGggatccTGCTCGGCCGCAAGGCGCGCGGTGTTGCCGTGGCTGTAC

TTGGTCGCGCGCTCCTGGAAGGAGGTGTAGACGAAGCCCAAGTAAGGGTTGTTGTCCGTCTGCGGGTT

CATGCCGCTCTTGATCAGGTTGTTGATGGTCACCTCCACGGCCCGCATGTTGACGCGCCCCGTCAGCC

AACAGTACTTGTTCAGCAGGTCGCCGTGCCGGTTCTCCTCGGCCACCCACTGCCGCGTCCAGCGCaag ctt

*Prototheca moriformis* FAD-D omega 3 desaturase

SEQ ID NO: 35

MSIQFALRAAYIKGTCQRLSGRGAALGLSRDWTPGWTLPRCWPASAAATAPPRARHQERAIHLTSGRR

RHSALASDADERALPSNAPGLVMASQANYFRVRLLPEQEEGELESWSPNVRHTTLLCKPRAMLSKLQM

RVMVGDRVIVTAIDPVNMTVHAPPFDPLPATRFLVAGEAADMDITVVLNKADLVPEEESAALAQEVAS

WGPVVLTSTLTGRGLQELERQLGSTTAVLAGPSGAGKSSIINALARAARERPSDASVSNVPEEQVVGE

DGRALANPPPFTLADIRNAIPKDCFRKSAAKSLAYLGDLSITGMAVLAYKINSPWLWPLYWFAQGTMF

WALFVVGHDCGHQSFSTSKRLNDALAWLGALAAGTWTWALGVLPMLNLYLAPYVWLLVTYLHHHGPSD

PREEMPWYRGREWSYMRGGLTTIDRDYGLFNKVHHDIGTHVVHH

-continued

SEQ ID NO: 36
MFWALFVVGHDCGHQSFSTSKRLNDAVGLFVHSIIGVPYHGWRISHRTHHNNHGHVENDESWYPPTES

GLKAMTDMGRQGRFHFPSMLFVYPFYLFWRSPGKTGSHFSPATDLFALWEAPLIRTSNACQLAWLGAL

AAGTWALGVLPMLNLYLAPYVISVAWLDLVTYLHHHGPSDPREEMPWYRGREWSYMRGGLTTIDRDYG

LFNKVHHDIGTHVVHHLFPQIPHYNLCRATKAAKKVLGPYYREPERCPLGLLPVHLLAPLLRSLGQDH

FVDDAGSVLFYRRAEGINPWIQKLLPWLGGARRGADAQRDAAQ

*Camelina sativa* omega-3 FAD7-2

SEQ ID NO: 37
MANLVLSECGIRPLPRIYTTPRSNFVSNNNKPIFKFRPFTSYKTSSSPLACSRDGFGKNWSLNVSVPL

TTTTPIVDESPLKEEEEEKQRFDPGAPPPFNLADIRAAIPKHCWVKNPWKSMSYVLRDVAIVFALAAG

ASYLNNWIVWPLYWLAQGTMFWALFVLGHDCGHGSFSNNPRLNNVVGHLLHSSILVPYHGWRISHRTH

HQNHGHVENDESWHPMSEKIYQSLDKPTRFFRFTLPLVMLAYPFYLWARSPGKKGSHYHPESDLFLPK

EKTDVLTSTACWTAMAALLICLNFVVGPVQMLKLYGIPYWINVMWLDFVTYLHHHGHEDKLPWYRGKE

WSYLRGGLTTLDRDYGVINNIHHDIGTHVIHHLFPQIPHYHLVEATEAVKPVLGKYYREPDKSGPLPL

HLLGILAKSIKEDHYVSDEGDVVYYKADPNMYGEIKVGAD

*Prototheca moriformis* delta 12 desaturase allele 2

SEQ ID NO: 38
MAIKTNRQPVEKPPFTIGTLRKAIPAHCFERSALRSSMYLAFDIAVMSLLYVASTYIDPAPVPTWVKY

GIMWPLYWFFQGAFGTGVWVCAHECGHQAFSSSQAINDGVGLVFHSLLLVPYYSWKHSHRRHHSNTGC

LDKDEVFVPPHRAVAHEGLEWEEWLPIRMGKVLVTLTLGWPLYLMFNVASRPYPRFANHFDPWSPIFS

KRERIEVVISDLALVAVLSGLSVLGRTMGWAWLVKTYVVPYMIVNMWLVLITLLQHTHPALPHYFEKD

WDWLRGAMATVDRSMGPPFMDSILHHISDTHVLHHLFSTIPHYHAEEASAAIRPILGKYYQSDSRWVG

RALWEDWRDCRYVVPDAPEDDSALWFHK

*Camelina sativa* omega-3 FAD7-1

SEQ ID NO: 39
MANLVLSECGIRPLPRIYTTPRSNFVSNNNKPIFKFRPLTSYKTSSPLFCSRDGFGRNWSLNVSVPLA

TTTPIVDESPLEEEEEEEKQRFDPGAPPPFNLADIRAAIPKHCWVKNPWKSMSYVLRDVAIVFALAAG

AAYLNNWIVWPLYWLAQGTMFWALFVLGHDCGHGSFSNNPRLNNVVGHLLHSSILVPYHGWRISHRTH

HQNHGHVENDESWHPMSEKIYQSLDKPTRFFRFTLPLVMLAYPFYLWARSPGKKGSHYHPESDLFLPK

EKTDVLTSTACWTAMAALLICLNFVVGPVQMLKLYGIPYWINVMWLDFVTYLHHHGHEDKLPWYRGKE

WSYLRGGLTTLDRDYGVINNIHHDIGTHVIHHLFPQIPHYHLVEATEAVKPVLGKYYREPDKSGPLPL

HLLGILAKSIKEDHYVSDEGDVVYYKADPNMYGEIKVGAD

PmFATA-hpB

SEQ ID NO: 40
actagtCATTCGGGGCAACGAGGTGGGCCCCTCGCAGCGGCTGACGATCACGGCGGTGGCCAACATCC

TGCAGGAGGCGGCGGGCAACCACGCGGTGGCCATGTGGGGCCGGAGCGTGTGTTTGAGGGTTTTGGTT

GCCCGTATTGAGGTCCTGGTGGCGCGCATGGGGGAGAAGGCGCCTGTCCCGCTGACCCCCCCGGCTAC

CCTCCCGGCACCTTCCAGGGCGCGTACGggatccGCTCCGGCCCCACATGGCCACCGCGTGGTTGCCC

GCCGCCTCCTGCAGGATGTTGGCCACCGCCGTGATCGTCAGCCGCTGCGAGGGGCCCACCTCGTTGCC

CCGAATGaagctt

PmFATA-hpC

SEQ ID NO: 41
actagtGGAGGGTTTCGCGACGGACCCGGAGCTGCAGGAGGCGGGTCTCATCTTTGTGATGACGCGCA

TGCAGATCCAGATGTACCGCTACCCGCGCTGGGGCGACCTGATGCAGGTGGAGACCTGGTTCCAGAGT

GTGTTTGAGGGTTTTGGTTGCCCGTATTGAGGTCCTGGTGGCGCGCATGGGGGAGAAGGCGCCTGTCC

CGCTGACCCCCCCGGCTACCCTCCCGGCACCTTCCAGGGCGCGTACGggatccTCTGGAACCAGGTCT

-continued

CCACCTGCATCAGGTCGCCCCAGCGCGGGTAGCGGTACATCTGGATCTGCATGCGCGTCATCACAAAG

ATGAGACCCGCCTCCTGCAGCTCCGGGTCCGTCGCGAAACCCTCCaagctt

PmFATA-hpD

SEQ ID NO: 42 actagtCGGCGGGCAAGCTGGGCGCGCAGCGCGAGTGGGTGCTGCGCGACAAGCTGACCGGCGAGGCG

CTGGGCGCGGCCACCTCGAGCTGGGTCATGATCAACATCCGCACGCGCCGGCCGTGCCGCATGCCGGG

TGTGTTTGAGGGTTTTGGTTGCCCGTATCGAGGTCCTGGTGGCGCGCATGGGGGAGAAGGCGCCTGTC

CCGCTGACCCCCCCGGCTACCCTCCCGGCACCTTCCAGGGCGCGTACGggatccCCGGCATGCGGCAC

GGCCGGCGCGTGCGGATGTTGATCATGACCCAGCTCGAGGTGGCCGCGCCCAGCGCCTCGCCGGTCAG

CTTGTCGCGCAGCACCCACTCGCGCTGCGCGCCCAGCTTGCCCGCCGaagctt

PmFATA-hpE

SEQ ID NO: 43 actagtGTCCGCGTCAAGTCGGCCTTCTTCGCGCGCGAGCCGCCGCGCCTGGCGCTGCCGCCCCGCGGT

CACGCGTGCCAAGCTGCCCAACATCGCGACGCCGGCGCCGCTGCGCGGGCACCGCCAGGTCGCGCGCC

GCACCGACATGGACATGAACGGGCACGTGAACAACGTGGCCTACCTGGCCTGGTGCCTGGAGTGTGTT

TGAGGGTTTTGGTTGCCCGTATTGAGGTCCTGGTGGCGCGCATGGGGGAGAAGGCGCCTGTCCCGCTG

ACCCCCCCGGCTACCCTCCCGGCACCTTCCAGGGCGCGTACGggatccTCCAGGCACCAGGCCAGGTA

GGCCACGTTGTTCACGTGCCCGTTCATGTCCATGTCGGTGCGGCGCGCGACCTGGCGGTGCCCGCGCA

GCGGCGCCGGCGTCGCGATGTTGGGCAGCTTGGCACGCGTGACCGCGGGCGGCAGCGCCAGGCGCGGC

GGCTCGCGCGCGAAGAAGGCCGACTTGACGCGGACaagctt

PmFATA-hpF

SEQ ID NO: 44 actagtCCGTGCCCGAGCACGTCTTCAGCGACTACCACCTCTACCAGATGGAGATCGACTTCAAGGCC

GAGTGCCACGCGGGCGACGTCATCTCCTCCCAGGCCGAGCAGATCCCGCCCCAGGAGGCGCTCACGCA

CAACGGCGCCGGCCGCAACCCCTCCTGCTTCGTCCATAGCATTCTGCGCGCCGAGACCGAGCGTGTGT

TTGAGGGTTTTGGTTGCCCGTATCGAGGTCCTGGTGGCGCGCATGGGGGAGAAGGCGCCTGTCCCGCT

GACCCCCCCGGCTACCCTCCCGGCACCTTCCAGGGCGCGTACGggatccGCTCGGTCTCGGCGCGCAG

AATGCTATGGACGAAGCAGGAGGGGTTGCGGCCGGCGCCGTTGTGCGTGAGCGCCTCCTGGGGCGGGA

TCTGCTCGGCCTGGGAGGAGATGACGTCGCCCGCGTGGCACTCGGCCTTGAAGTCGATCTCCATCTGG

TAGAGGTGGTAGTCGCTGAAGACGTGCTCGGGCACGGaagctt

PmFATA-hpG

SEQ ID NO: 45 actagtTCGTCCGCGCGCGAACCACATGGTCGGCCCCCATCGACGCGCCCGCCGCCAAGCCGCCCAAG

GCGAGCCACTGAGGACAGGGTGGTTGGCTGGATGGGGAAACGCTGGTCGCGGGATTCGATCCTGCTGC

TTATATCCTCGTGTGTTTGAGGGTTTTGGTTGCCCGTATTGAGGTCCTGGTGGCGCGCATGGGGGAGA

AGGCGCCTGTCCCGCTGACCCCCCCGGCTACCCTCCCGGCACCTTCCAGGGCGCGTACGggatccGAG

GATATAAGCAGCAGGATCGAATCCCGCGACCAGCGTTTCCCCATCCAGCCAACCACCCTGTCCTCAGT

GGCTCGCCTTGGGCGGCTTGGCGGCGGGCGCGTCGATGGGGGCCGACCATGTGGTTCGCGCGCGGACG

Aaagctt

Codon-optimized *Cuphea wrightii* KASAI

SEQ ID NO: 46

ATGGCCGCCGCCGCCAGCATGGTGGCCAGCCCCTTCTGCACCTGGCTGGTGGCCAGCTGCATGAGCAC

CAGCTTCGACAACGACCCCCGCAGCCCCAGCGTGAAGCGCTTCCCCCGCCGCAAGCGCGTGCTGAGCC

AGCGCGGCAGCACCTACGTATTCCAGTGCCTGGTGGCCAGCTGCATCGACCCCTGCGACCAGTACCGC

AGCAGCGCCAGCCTGAGCTTCCTGGGCGACAACGGCTTCGCCAGCCTGTTCGGCAGCAAGCCCTTCAT

-continued

GAGCAACCGCGGCCACCGCCGCCTGCGCCGCGCCAGCCACAGCGGCGAGGCCATGGCCGTGGCCCTGC

AGCCCGCCCAGGAGGCCGGCACCAAGAAGAAGCCCGTGATCAAGCAGCGCCGCGTGGTGGTGACCGGC

ATGGGCGTGGTGACCCCCCTGGGCCACGAGCCCGACGTGTTCTACAACAACCTGCTGGACGGCGTGAG

CGGCATCAGCGAGATCGAGACCTTCGACTGCACCCAGTTCCCCACCCGCATCGCCGGCGAGATCAAGA

GCTTCAGCACCGACGGCTGGGTGGCCCCCAAGCTGAGCAAGCGCATGGACAAGTTCATGCTGTACCTG

CTGACCGCCGGCAAGAAGGCCCTGGCCGACGGCGGCATCACCGACGAGGTGATGAAGGAGCTGGACAA

GCGCAAGTGCGGCGTGCTGATCGGCAGCGGCATGGGCGGCATGAAGGTGTTCAACGACGCCATCGAGG

CCCTGCGCGTGAGCTACAAGAAGATGAACCCCTTCTGCGTGCCCTTCGCCACCACCAACATGGGCAGC

GCCATGCTGGCCATGGACCTGGGCTGGATGGGCCCCAACTACAGCATCAGCACCGCCTGCGCCACCAG

CAACTTCTGCATCCTGAACGCCGCCAACCACATCATCCGCGGCGAGGCCGACATGATGCTGTGCGGCG

GCAGCGACGCCGTGATCATCCCCATCGGCCTGGGCGGCTTCGTGGCCTGCCGCGCCCTGAGCCAGCGC

AACAGCGACCCCACCAAGGCCAGCCGCCCCTGGGACAGCAACCGCGACGGCTTCGTGATGGGCGAGGG

CGCCGGCGTGCTGCTGCTGGAGGAGCTGGAGCACGCCAAGAAGCGCGGCGCCACCATCTACGCCGAGT

TCCTGGGCGGCAGCTTCACCTGCGACGCCTACCACATGACCGAGCCCCACCCCGAGGGCGCCGGCGTG

ATCCTGTGCATCGAGAAGGCCCTGGCCCAGGCCGGCGTGAGCAAGGAGGACGTGAACTACATCAACGC

CCACGCCACCAGCACCAGCGCCGGCGACATCAAGGAGTACCAGGCCCTGGCCCGCTGCTTCGGCCAGA

ACAGCGAGCTGCGCGTGAACAGCACCAAGAGCATGATCGGCCACCTGCTGGGCGCCGCCGGCGGCGTG

GAGGCCGTGACCGTGGTGCAGGCCATCCGCACCGGCTGGATTCACCCCAACCTGAACCTGGAGGACCC

CGACAAGGCCGTGGACGCCAAGCTGCTGGTGGGCCCCAAGAAGGAGCGCCTGAACGTGAAGGTGGGCC

TGAGCAACAGCTTCGGCTTCGGCGGCCACAACAGCAGCATCCTGTTCGCCCCCTGCAACGTGTGA

Codon-optimized *Cuphea wrightii* KASAI with *P.moriformis* SAD transit peptide

SEQ ID NO: 47

ATGGGCCGCGGTGTCTCCCTTCCCCGGCCCAGGGTCGCGGTGCGCGCCCAGTCGGCGAGTCAGGTTTT

GGAGAGCTGTATTCCAGTGCCTGGTGGCCAGCTGCATCGACCCCTGCGACCAGTACCGCAGCAGCGCC

AGCCTGAGCTTCCTGGGCGACAACGGCTTCGCCAGCCTGTTCGGCAGCAAGCCCTTCATGAGCAACCG

CGGCCACCGCCGCCTGCGCCGCGCCAGCCACAGCGGCGAGGCCATGGCCGTGGCCCTGCAGCCCGCCC

AGGAGGCCGGCACCAAGAAGAAGCCCGTGATCAAGCAGCGCCGCGTGGTGGTGACCGGCATGGGCGTG

GTGACCCCCCTGGGCCACGAGCCCGACGTGTTCTACAACAACCTGCTGGACGGCGTGAGCGGCATCAG

CGAGATCGAGACCTTCGACTGCACCCAGTTCCCCACCCGCATCGCCGGCGAGATCAAGAGCTTCAGCA

CCGACGGCTGGGTGGCCCCCAAGCTGAGCAAGCGCATGGACAAGTTCATGCTGTACCTGCTGACCGCC

GGCAAGAAGGCCCTGGCCGACGGCGGCATCACCGACGAGGTGATGAAGGAGCTGGACAAGCGCAAGTG

CGGCGTGCTGATCGGCAGCGGCATGGGCGGCATGAAGGTGTTCAACGACGCCATCGAGGCCCTGCGCG

TGAGCTACAAGAAGATGAACCCCTTCTGCGTGCCCTTCGCCACCACCAACATGGGCAGCGCCATGCTG

GCCATGGACCTGGGCTGGATGGGCCCCAACTACAGCATCAGCACCGCCTGCGCCACCAGCAACTTCTG

CATCCTGAACGCCGCCAACCACATCATCCGCGGCGAGGCCGACATGATGCTGTGCGGCGGCAGCGACG

CCGTGATCATCCCCATCGGCCTGGGCGGCTTCGTGGCCTGCCGCGCCCTGAGCCAGCGCAACAGCGAC

CCCACCAAGGCCAGCCGCCCCTGGGACAGCAACCGCGACGGCTTCGTGATGGGCGAGGGCGCCGGCGT

GCTGCTGCTGGAGGAGCTGGAGCACGCCAAGAAGCGCGGCGCCACCATCTACGCCGAGTTCCTGGGCG

GCAGCTTCACCTGCGACGCCTACCACATGACCGAGCCCCACCCCGAGGGCGCCGGCGTGATCCTGTGC

ATCGAGAAGGCCCTGGCCCAGGCCGGCGTGAGCAAGGAGGACGTGAACTACATCAACGCCCACGCCAC

CAGCACCAGCGCCGGCGACATCAAGGAGTACCAGGCCCTGGCCCGCTGCTTCGGCCAGAACAGCGAGC

-continued

TGCGCGTGAACAGCACCAAGAGCATGATCGGCCACCTGCTGGGCGCCGCCGGCGGCGTGGAGGCCGTG

ACCGTGGTGCAGGCCATCCGCACCGGCTGGATTCACCCCAACCTGAACCTGGAGGACCCCGACAAGGC

CGTGGACGCCAAGCTGCTGGTGGGCCCCAAGAAGGAGCGCCTGAACGTGAAGGTGGGCCTGAGCAACA

GCTTCGGCTTCGGCGGCCACAACAGCAGCATCCTGTTCGCCCCCTGCAACGTGTGA

Codon-optimized *Cuphea pulcherrima* KASIV

SEQ ID NO: 48

ATGCCCGCGGCCAGCTCGCTGCTGGCGTCCCCCCTGTGCACCTGGCTGCTGGCCGCGTGCATGAGCAC

CTCGTTCCACCCCTCCGACCCCCTGCCCCCCAGCATCTCGTCCCCCCGCCGCCGCCTGAGCCGCCGCC

GCATCCTGTCGCAGTGCGCCCCCCTGCCCTCCGCGAGCTCGGCCCTGCGCGGCTCCAGCTTCCACACC

CTGGTGACCTCGTATCTGGCGTGCTTCGAGCCCTGCCACGACTATTATACCAGCGCCTCCCTGTTCGG

CTCGCGCCCCATCCGCACCACCCGCCGCCACCGCCGCCTGAACCGCGCGAGCCCCTCGCGCGAGGCGA

TGGCGGTCGCCCTGCAGCCCGAGCAGGAGGTGACCACCAAGAAGAAGCCCTCCATCAAGCAGCGCCGC

GTCGTGGTCACCGGCATGGGCGTGGTCACCCCCCTGGGCCACGACCCCGACGTGTTCTATAACAACCT

GCTGGACGGCACCAGCGGCATCTCGGAGATCGAGACCTTCGACTGCGCGCAGTTCCCCACCCGCATCG

CCGGCGAGATCAAGTCCTTCAGCACCGACGGCTGGGTCGCGCCCAAGCTGTCGAAGCGCATGGACAAG

TTCATGCTGTATATGCTGACCGCCGGCAAGAAGGCGCTGACCGACGGCGGCATCACCGAGGACGTGAT

GAAGGAGCTGGACAAGCGCAAGTGCGGCGTCCTGATCGGCTCCGCGATGGGCGGCATGAAGGTGTTCA

ACGACGCGATCGAGGCCCTGCGCATCAGCTATAAGAAGATGAACCCCTTCTGCGTGCCCTTCGCGACC

ACCAACATGGGCTCGGCCATGCTGGCGATGGACCTGGGCTGGATGGGCCCCAACTATTCCATCAGCAC

CGCCTGCGCGACCTCGAACTTCTGCATCATGAACGCGGCCAACCACATCATCCGCGGCGAGGCGGACG

TCATGCTGTGCGGCGGCTCCGACGCCGTGATCATCCCCATCGGCATGGGCGGCTTCGTCGCGTGCCGC

GCCCTGAGCCAGCGCAACTCGGACCCCACCAAGGCGTCCCGCCCCTGGGACAGCAACCGCGACGGCTT

CGTGATGGGCGAGGGCGCCGGCGTCCTGCTGCTGGAGGAGCTGGAGCACGCGAAGAAGCGCGGCGCCA

CCATCTATGCGGAGTTCCTGGGCGGCTCGTTCACCTGCGACGCCTATCACATGACCGAGCCCCACCCC

GACGGCGCCGGCGTGATCCTGTGCATCGAGAAGGCGCTGGCCCAGTCCGGCGTCAGCCGCGAGGACGT

GAACTATATCAACGCGCACGCCACCTCGACCCCCGCGGGCGACATCAAGGAGTATCAGGCCCTGATCC

ACTGCTTCGGCCAGAACCGCGAGCTGAAGGTCAACTCCACCAAGAGCATGATCGGCCACCTGCTGGGC

GCGGCGGGCGGCGTGGAGGCGGTCTCGGTGGTCCAGGCCATCCGCACCGGCTGGATCCACCCCAACAT

CAACCTGGAGAACCCCGACGAGGGCGTGGACACCAAGCTGCTGGTGGGCCCCAAGAAGGAGCGCCTGA

ACGTCAAGGTGGGCCTGTCCAACAGCTTCGGCTTCGGCGGCCACAACTCGTCCATCCTGTTCGCGCCC

TATATCTGA

Codon-optimized *Cuphea hookeriana* KASIV

SEQ ID NO: 49

ATGGTGGCCGCCGCCGCCTCCAGCGCCTTCTTCCCCGTGCCCGCCCCCGGCGCCTCCCCCAAGCCCGG

CAAGTTCGGCAACTGGCCCTCCAGCCTGAGCCCCTCCTTCAAGCCCAAGTCCATCCCCAACGGCGGCT

TCCAGGTGAAGGCCAACGACAGCGCCCACCCCAAGGCCAACGGCTCCGCCGTGAGCCTGAAGAGCGGC

AGCCTGAACACCCAGGAGGACACCTCCTCCAGCCCCCCCCCCCGCACCTTCCTGCACCAGCTGCCCGA

CTGGAGCCGCCTGCTGACCGCCATCACCACCGTGTTCGTGAAGTCCAAGCGCCCCGACATGCACGACC

GCAAGTCCAAGCGCCCCGACATGCTGGTGGACAGCTTCGGCCTGGAGTCCACCGTGCAGGACGGCCTG

GTGTTCCGCCAGTCCTTCTCCATCCGCTCCTACGAGATCGGCACCGACCGCACCGCCAGCATCGAGAC

CCTGATGAACCACCTGCAGGAGACCTCCCTGAACCACTGCAAGAGCACCGGCATCCTGCTGGACGGCT

TCGGCCGCACCCTGGAGATGTGCAAGCGCGACCTGATCTGGGTGGTGATCAAGATGCAGATCAAGGTG

AACCGCTACCCCGCCTGGGGCGACACCGTGGAGATCAACACCCGCTTCAGCCGCCTGGGCAAGATCGG

-continued

CATGGGCCGCGACTGGCTGATCTCCGACTGCAACACCGGCGAGATCCTGGTGCGCGCCACCAGCGCCT

ACGCCATGATGAACCAGAAGACCCGCCGCCTGTCCAAGCTGCCCTACGAGGTGCACCAGGAGATCGTG

CCCCTGTTCGTGGACAGCCCCGTGATCGAGGACTCCGACCTGAAGGTGCACAAGTTCAAGGTGAAGAC

CGGCGACAGCATCCAGAAGGGCCTGACCCCCGGCTGGAACGACCTGGACGTGAACCAGCACGTGTCCA

ACGTGAAGTACATCGGCTGGATCCTGGAGAGCATGCCCACCGAGGTGCTGGAGACCCAGGAGCTGTGC

TCCCTGGCCCTGGAGTACCGCCGCGAGTGCGGCCGCGACTCCGTGCTGGAGAGCGTGACCGCCATGGA

CCCCAGCAAGGTGGGCGTGCGCTCCCAGTACCAGCACCTGCTGCGCCTGGAGGACGGCACCGCCATCG

TGAACGGCGCCACCGAGTGGCGCCCCAAGAACGCCGGCGCCAACGGCGCCATCTCCACCGGCAAGACC

AGCAACGGCAACTCCGTGTCCATGTGA

*Prototheca moriformis* (UTEX 1435) KAS1 allele 1 5' donor sequence
SEQ ID NO: 50 gctcttcctcaccgcgtgaattgctgtcccaaacgtaagcatcatcgtggctcggtcacgcgatcctg gatccggggatcctagaccgctggtggagagcgctgccgtcggattggtggcaagtaagattgcgcag gttggcgaagggagagaccaaaaccggaggctggaagcgggcacaacatcgtattattgcgtatagta gagcagtggcagtcgcatttcgaggtccgcaacggatctcgcaagctcgctacgctcacagtaggaga aaggggaccactgcccctgccagaatggtcgcgaccctctccctcgccggccccgcctgcaacacgca gtgcgtatccggcaagcgggctgtcgccttcaaccgcccccatgttggcgtccgggctcgatcaggtg cgctgaggggggtttggtgtgcccgcgcctctgggcccgtgtcggccgtgcggacgtggggccctggg cagtggatcagcagggtttgcgtgcaaatgcctataccggcgattgaatagcgatgaacgggatacgg ttgcgctcactccatgcccatgcgaccccgtttctgtccgccagccgtggtcgcccgggctgcgaagc gggaccccacccagcgcattgtgatcaccggaatgggcgtgggtacc

*Prototheca moriformis* (UTEX 1435) KAS1 allele 1 3' donor sequence
SEQ ID NO: 51 gagctccacctgcatccgcctggcgctcgaggacgccggcgtctcgcccgacgaggtcaactacgtca acgcgcacgccacctccaccctggtgggcgacaaggccgaggtgcgcgcggtcaagtcggtctttggc gacatgaagggcatcaagatgaacgccaccaagtccatgatcgggcactgcctgggcgccgccggcgg catggaggccgtcgccacgctcatggccatccgcaccggctgggtgcaccccaccatcaaccacgaca accccatcgccgaggtcgacggcctggacgtcgtcgccaacgccaaggcccagcacaaaatcaacgtc gccatctccaactccttcggcttcggcgggcacaactccgtcgtcgcctttgcgcccttccgcgagta ggcggagcgagcgcgcttggctgaggagggaggcggggtgcgagccctttggctgcgcgcgatactct ccccgcacgagcagactccacgcgcctgaatctacttgtcaacgagcaaccgtgtgttttgtccgtgg ccattcttattatttctccgactgtggccgtactctgtttggctgtgcaagcaccgaagagcc

*Prototheca moriformis* (UTEX 1435) KAS1 allele 2 5' donor sequence
SEQ ID NO: 52 gctcttcgcgcaagctcgctacgctcacagtaggagataggggaccactgcccctgccagaatggtcg cgaccctgtccctcgccggccccgcctgcaacacgcagtgcgtatccagcaagcgggttgtcgccttc aaccgcccccatgttggcgtccgggctcgatcaggtgcgctgaggggggtttggtgggcccgcgcctc tgggcccgtgtcggccgtgcggacgtggggcccggggtagtggatcagcaggggttgcatgcaaatgc ctataccggcgattgaatagcgatgaacgggatacggttgcgctcactccatgcccatgcgaccccgt ttctgtccgccagccgtggtcgcccgagctgcgaagcgggaccccacccagcgcattgtgatcaccgg aatgggcgtggcctccgtgtttggcaacgatgtcgagaccttttacgacaagcttctggaaggaacga -continued gcggcgtggacctgatttccaggtgcgtaggtccttggatgaatgcgtctaggttgcgaggtgactgg ccaggaagcagcaggcttggggtttggtgttctgatttctggtaatttgaggtttcattataagattc tgtacggtcttgtttcggggtacc

*Prototheca moriformis* (UTEX 1435) KAS1 allele 2 3' donor sequence

SEQ ID NO: 53 gagctccacctgcatccgcctggcgctcgaggacgccggcgtctcgcccgacgaggtcaactacgtca acgcgcacgccacctccaccctggtgggcgacaaggccgaggtgcgcgcggtcaagtcggtctttggc gacatgaagggcatcaagatgaacgccaccaagtccatgatcgggcactgcctgggcgccgccggcgg catggaggccgtcgccacgctcatggccatccgcaccggctgggtgcaccccaccatcaaccacgaca accccatcgccgaggtcgacggcctggacgtcgtcgccaacgccaaggcccagcacaaaatcaacgtc gccatctccaactccttcggcttcggcgggcacaactccgtcgtcgcctttgcgcccttccgcgagta ggcggagcgagcgcgcttggctgaggagggaggcggggtgcgagccctttggctgcgcgcgatactct ccccgcacgagcagactccacgcgcctgaatctacttgtcaacgagcaaccgtgtgttttgtccgtgg ccattcttattatttctccgactgtggccgtactctgtttggctgtgcaagcaccgaagagcc

*Prototheca moriformis* (UTEX 1435) KASI-hairpin B

SEQ ID NO: 54 actagtcaTGGTCGCCCGGGCTGCGAAGCGGACCCCACCCAGCGCATTGTGATCACCGGAATGGGCG

TGGCCTCCGTGTTTGGCAACGATGTCGAGACCTTTTACAgtgtgtttgagggttttggttgcccgtat tgaggtcctggtggcgcgcatggaggagaaggcgcctgtcccgctgacccccccggctaccctcccgg caccttccagggcgcgtacgggatccTGTAAAAGGTCTCGACATCGTTGCCAAACACGGAGGCCACGC CCATTCCGGTGATCACAATGCGCTGGGTGGGGTCCCGCTTCGCAGCCCGGGCGACCAaagctt

*Prototheca moriformis* (UTEX 1435) KASI-hairpin C

SEQ ID NO: 55 actagtcaTTGACATCTCCGAGTTCCCGACCAAGTTTGCGGCGCAGATCACCGGCTTCTCCGTGGAGG

ACTGCGTGGACAAGAAGAACGCGCGGCGGTACGACGACGCGCTGTCGTACGCGATGGTGGCCTCCAAG

AAGGCCCTGCGCCAGGCGGGACTGGAGAAGGACAAGTGCCCCGAGGGCTACGGAGgtgtgtttgaggg ttttggttgcccgtattgaggtcctggtggcgcgcatggaggagaaggcgcctgtcccgctgaccccc ccggctaccctcccggcaccttccagggcgcgtacgggatccCTCCGTAGCCCTCGGGGCACTTGTCC

TTCTCCAGTCCCGCCTGGCGCAGGGCCTTCTTGGAGGCCACCATCGCGTACGACAGCGCGTCGTCGTA

CCGCCGCGCGTTCTTCTTGTCCACGCAGTCCTCCACGGAGAAGCCGGTGATCTGCGCCGCAAACTTGG

TCGGGAACTCGGAGATGTCAAaagctt

*Prototheca moriformis* (UTEX 1435) KASI-hairpin D

SEQ ID NO: 56 actagtcaTGGGCGTGAGCACCTGCATCCGCCTGGCGCTCGAGGACGCCGGCGTCTCGCCCGACGAGG

TCAACTACGTCAACGCGCACGCCACCTCCACCCTGGTGGGCGACAAGGCCGAGGTGCGCGCGGTCAAG

TCGGTCTTTGGCGACATGAAGGGCATCAAGATgtgtgtttgagggttttggttgcccgtattgaggtc ctggtggcgcgcatggaggagaaggcgcctgtcccgctgacccccccggctaccctcccggcaccttc cagggcgcgtacgggatccATCTTGATGCCCTTCATGTCGCCAAAGACCGACTTGACCGCGCGCACCT

CGGCCTTGTCGCCCACCAGGGTGGAGGTGGCGTGCGCGTTGACGTAGTTGACCTCGTCGGGCGAGACG

CCGGCGTCCTCGAGCGCCAGGCGGATGCAGGTGCTCACGCCCAaagctt

*Prototheca moriformis* (UTEX 1435) KASI-hairpin E

SEQ ID NO: 57 actagtcaCAACCATCAACCACGACAACCCCATCGCCGAGGTCGACGGCCTGGACGTCGTCGCCAACG

CCAAGGCCCAGCACAAAATCAACGTCGCCATCTCCAACTCCTTCGgtgtgtttgagggttttggttgc ccgtattgaggtcctggtggcgcgcatggaggagaaggcgcctgtcccgctgacccccccggctaccc -continued tcccggcaccttccagggcgcgtacgggatccCGAAGGAGTTGGAGATGGCGACGTTGATTTTGTGCT GGGCCTTGGCGTTGGCGACGACGTCCAGGCCGTCGACCTCGGCGATGGGGTTGTCGTGGTTGATGGTa agctt Codon optimized *M. polymorpha* FAE3 (GenBank Accession No. AAP74370)

SEQ ID NO: 58

ATGgactcccgcgcccagaaccgcgacggcggcgaggacgtgaagcaggagctgctgtccgccggcga cgacggcaaggtgccctgccccaccgtggccatcggcatccgccagcgcctgcccgacttcctgcagt ccgtgaacatgaagtacgtgaagctgggctaccactacctgatcacccacgccatgttcctgctgacc ctgcccgccttcttcctggtggccgccgagatcggccgcctgggccacgagcgcatctaccgcgagct gtggacccacctgcacctgaacctggtgtccatcatggcctgctcctccgccctggtggccggcgcca ccctgtacttcatgtcccgccccccgccccgtgtacctggtggagttcgcctgctaccgccccgacgag cgcctgaaggtgtccaaggacttcttcctggacatgtcccgccgcaccggcctgttctcctcctcctc catggacttccagaccaagatcacccagcgctccggcctgggcgacgagacctacctgcccccgcca tcctggcctccccccccaacccctgcatgcgcgaggcccgcgaggaggccgccatggtgatgttcggc gccctggacgagctgttcgagcagaccggcgtgaagcccaaggagatcggcgtgctggtggtgaactg ctccctgttcaaccccacccccctccatgtccgccatgatcgtgaaccactaccacatgcgcggcaaca tcaagtccctgaacctgggcggcatgggctgctccgccggcctgatctccatcgacctggcccgcgac ctgctgcaggtgcacggcaacacctacgccgtggtggtgtccaccgagaacatcaccctgaactggta cttcggcgacgaccgctccaagctgatgtccaactgcatcttccgcatgggcggcgccgccgtgctgc tgtccaacaagcgccgcgagcgccgccgcgccaagtacgagctgctgcacaccgtgcgcacccacaag ggcgccgacgacaagtgcttccgctgcgtgtaccaggaggaggactccaccggctccctgggcgtgtc cctgtcccgcgagctgatggccgtggccggcaacgccctgaaggccaacatcaccaccctgggccccc tggtgctgcccctgtccgagcagatcctgttcttcgcctccctggtggcccgcaagttcctgaacatg aagatgaagccctacatccccgacttcaagctggccttcgagcacttctgcatccacgccggcggccg cgccgtgctggacgagctggagaagaacctggacctgaccgagtggcacatggagccctcccgcatga ccctgtaccgcttcggcaacacctcctcctcctccctgtggtacgagctggcctacaccgaggcccag ggccgcgtgaagcgcggcgaccgcctgtggcagatcgccttcggctccggcttcaagtgcaactccgc cgtgtggcgcgcgctgcgcaccgtgaagcccccccgtgaacaacgcctggtccgacgtgatcgaccgct tccccgtgaagctgccccagttcTGA

*M. polymorpha* FAE3 (GenBank Accession No. AAP74370)

SEQ ID NO: 59

MDSRAQNRDGGEDVKQELLSAGDDGKVPCPTVAIGIRQRLPDFLQSVNMKYVKLGYHYLITHAMFLLT

LPAFFLVAAEIGRLGHERIYRELWTHLHLNLVSIMACSSALVAGATLYFMSRPRPVYLVEFACYRPDE

RLKVSKDFFLDMSRRTGLFSSSSMDFQTKITQRSGLGDETYLPPAILASPPNPCMREAREEAAMVMFG

ALDELFEQTGVKPKEIGVLVVNCSLFNPIPSMSAMIVNHYHMRGNIKSLNLGGMGCSAGLISIDLARD

LLQVHGNIYAVVVSTENITLNWYFGDDRSKLMSNCIFRMGGAAVLLSNKRRERRRAKYELLHIVRTHK

GADDKCFRCVYQEEDSIGSLGVSLSRELMAVAGNALKANITTLGPLVLPLSEQILFFASLVARKFLNM

KMKPYIPDFKLAFEHFCIHAGGRAVLDELEKNLDLTEWHMEPSRMTLYRFGNISSSSLWYELAYTEAQ

GRVKRGDRLWQIAFGSGFKCNSAVWRALRIVKPPVNNAWSDVIDRFPVKLPQF

*Trypanosoma brucei* ELO3 (GenBank Accession No. AAX70673)

SEQ ID NO: 60

*ATG**ctgatgaacttcggcggctcctacgacgcctacatcaacaacttccagggcaccttcctggccga*

*gtggatgctggaccacccctccgtgccctacatcgccggcgtgatgtacctgatcctggtgctgtacg*

-continued

*tgcccaagtccatcatggcctcccagccccccctgaacctgcgcgccgccaacatcgtgtggaacctg*

*ttcctgaccctgttctccatgtgcggcgcctactacaccgtgccctacctggtgaaggccttcatgaa*

*ccccgagatcgtgatggccgcctccggcatcaagctggacgccaacacctcccccatcatcacccact*

*ccggcttctacaccaccacctgcgccctggccgactccttctacttcaacggcgacgtgggcttctgg*

*gtggccctgttcgccctgtccaagatccccgagatgatcgacaccgccttcctggtgttccagaagaa*

*gcccgtgatcttcctgcactggtaccaccacctgaccgtgatgctgttctgctggttcgcctacgtgc*

*agaagatctcctccggcctgtggttcgcctccatgaactactccgtgcactccatcatgtacctgtac*

*tacttcgtgtgcgcctgcggccaccgccgcctggtgcgccccttcgcccccatcatcaccttcgtgca*

*gatcttccagatggtggtgggcaccatcgtggtgtgctacacctacaccgtgaagcacgtgctgggcc*

*gctcctgcaccgtgaccgacttctccctgcacaccggcctggtgatgtacgtgtcctacctgctgctg*

*ttctcccagctgttctaccgctcctacctgtcccccgcgacaaggcctccatcccccacgtggccgc*

*cgagatcaagaagaaggagTGA*

*Trypanosoma brucei* ELO3 (GenBank Accession No. AAX70673)

SEQ ID NO: 61

MYPTHRDLILNNYSDIYRSPTCHYHTWHILIHTPINELLFPNLPRECDFGYDIPYFRGQIDVFDGWSM

IHFISSNWCIPITVCLCYIMMIAGLKKYMGPRDGGRAPIQAKNYIIAWNLFLSFFSFAGVYYTVPYHL

FDPENGLFAQGFYSTVCNNGAYYGNGNVGFFVWLFIYSKIFELVDIFFLLIRKNPVIFLHWYHHLTVL

LYCWHAYSVRIGTGIWFATMNYSVHSVMYLYFAMTQYGPSTKKFAKKFSKFITTIQILQMVVGIIVIF

AAMLYVTFDVPCYTSLANSVLGLMMYASYFVLFVQLYVSHYVSPKHVKQE

Codon optimized *Saccharomyces cerevisiae* ELO1 (GenBank Accession No. P39540)

SEQ ID NO: 62

*ATGgtgtccgactggaagaacttctgcctggagaaggcctcccgcttccgccccaccatcgaccgccc*

*cttcttcaacatctacctgtgggactacttcaaccgcgccgtgggctgggccaccgccggccgcttcc*

*agcccaaggacttcgagttcaccgtgggcaagcagcccctgtccgagccccgccccgtgctgctgttc*

*atcgccatgtactacgtggtgatcttcggcggccgctccctggtgaagtcctgcaagcccctgaagct*

*gcgcttcatctcccaggtgcacaacctgatgctgacctccgtgtccttcctgtggctgatcctgatgg*

*tggagcagatgctgcccatcgtgtaccgccacggcctgtacttcgccgtgtgcaacgtggagtcctgg*

*acccagcccatggagaccctgtactacctgaactacatgaccaagttcgtggagttcgccgacaccgt*

*gctgatggtgctgaagcaccgcaagctgaccttcctgcacacctaccaccacggcgccaccgccctgc*

*tgtgctacaaccagctggtgggctacaccgccgtgacctgggtgcccgtgaccctgaacctggccgtg*

*cacgtgctgatgtactggtactacttcctgtccgcctccggcatccgcgtgtggtggaaggcctgggt*

*gacccgcctgcagatcgtgcagttcatgctggacctgatcgtggtgtactacgtgctgtaccagaaga*

*tcgtggccgcctacttcaagaacgcctgcacccccagtgcgaggactgcctgggctccatgaccgcc*

*atcgccgccggcgccgccatcctgacctcctacctgttcctgttcatctccttctacatcgaggtgta*

*caagcgcggctccgcctccggcaagaagaagatcaacaagaacaacTGA*

*Saccharomyces cerevisiae* ELO1 (GenBank Accession No. P39540)

SEQ ID NO: 63

MVSDWKNFCLEKASRFRPTIDRPFFNIYLWDYFNRAVGWATAGRFQPKDFEFTVGKQPLSEPRPVLLF

IAMYYVVIFGGRSLVKSCKPLKLRFISQVHNLMLTSVSFLWLILMVEQMLPIVYRHGLYFAVCNVESW

TQPMETLYYLNYMTKFVEFADTVLMVLKHRKLTFLHTYHHGATALLCYNQLVGYTAVTWVPVTLNLAV

HVLMYWYYFLSASGIRVWWKAWVTRLQIVQFMLDLIVVYYVLYQKIVAAYFKNACTPQCEDCLGSMTA

IAAGAAILTSYLFLFISFYIEVYKRGSASGKKKINKNN

-continued

Codon optimized *Brassica napus* acyl-ACP thioesterase (GenBank Accession No. CAA52070) with 3X FLAG Tag

SEQ ID NO: 64

ATGctgaagctgtcctgcaacgtgaccaacaacctgcacaccttctccttcttctccgactcctccct gttcatccccgtgaaccgccgcaccatcgccgtgtcctccgggcgcgcctcccagctgcgcaagcccg ccctggacccccctgcgcgccgtgatctccgccgaccagggctccatctcccccgtgaactcctgcacc cccgccgaccgcctgcgcgccggccgcctgatggaggacggctactcctacaaggagaagttcatcgt gcgctcctacgaggtgggcatcaacaagaccgccaccgtggagaccatcgccaacctgctgcaggagg tggcctgcaaccacgtgcagaagtgcggcttctccaccgacggcttcgccaccaccctgaccatgcgc aagctgcacctgatctgggtgaccgcccgcatgcacatcgagatctacaagtaccccgcctggtccga cgtggtggagatcgagacctggtgccagtccgagggccgcatcggcacccgccgcgactggatcctgc gcgactccgccaccaacgaggtgatcggccgcgccacctccaagtgggtgatgatgaaccaggacacc cgccgcctgcagcgcgtgaccgacgaggtgcgcgacgagtacctggtgttctgcccccgcgagccccg cctggccttccccgaggagaacaactcctccctgaagaagatccccaagctggaggaccccgcccagt actccatgctggagctgaagccccgccgcgccgacctggacatgaaccagcacgtgaacaacgtgacc tacatcggctgggtgctggagtccatcccccaggagatcatcgacacccacgagctgcaggtgatcac cctggactaccgccgcgagtgccagcaggacgacatcgtggactccctgaccacctccgagatccccg acgaccccatctccaagttcaccggcaccaacggctccgccatgtcctccatccagggccacaacgag tcccagttcctgcacatgctgcgcctgtccgagaacggccaggagatcaaccgcggccgcacccagtg gcgcaagaagtcctcccgcATGGACTACAAGGACCACGACGGCGACTACAAGGACCACGACATCGACT

ACAAGGACGACGACGACAAGTGA

*Brassica napus* acyl-ACP thioesterase (Genbank Accession No. CAA52070) with 3X FLAG Tag (bold)

SEQ ID NO: 65

<u>MLKLSCNVTNNLHTFSFFSDSSLFIPVNRRTIAVSS</u>*GRA* SQLRKPALDPLRAVISADQGSISPVNSCT

PADRLRAGRLMEDGYSYKEKFIVRSYEVGINKTATVETIANLLQEVACNHVQKCGFSTSGFATTLTMR

KLHLIWVTARMHIEIYKYPAWSSVVEIETWCQSEGRIGTRRDWILRDSATNEVIGRATSKWVMMNQST

RRLQRVTDEVRSEYLVFCPREPRLAFFEENNSSLKKIPKLESPAQYSMLELKPRRADLUMNQHVNNVT

YIGWVLESIPQEIISTHELQVITLSYRRECQQSSIVSSLTTSEIPSDPISKFTGTNGSAMSSIQGHNE

SQFLHMLRLSENGQEINRGRTQWRKKSSRMDYKDHDGDYKDHDIDYKDDDDK

Codon optimized *Brassica napus* acyl-ACP thioesterase (GenBank Accession No. CAA52070), with UTEX 250 stearoyl-ACP desaturase (SAD) chloroplast transit peptide and 3X FLAG Tag

SEQ ID NO: 66

ATGgccaccgcatccactttctcggcgttcaatgcccgctgcggcgacctgcgtcgctcggcgggctc cgggccccggcgcccagcgaggcccctccccgtgcgcgggcgcgcctcccagctgcgcaagcccgccc tggacccccctgcgcgccgtgatctccgccgaccagggctccatctcccccgtgaactcctgcaccccc gccgaccgcctgcgcgccggccgcctgatggaggacggctactcctacaaggagaagttcatcgtgcg ctcctacgaggtgggcatcaacaagaccgccaccgtggagaccatcgccaacctgctgcaggaggtgg cctgcaaccacgtgcagaagtgcggcttctccaccgacggcttcgccaccaccctgaccatgcgcaag ctgcacctgatctgggtgaccgcccgcatgcacatcgagatctacaagtaccccgcctggtccgacgt ggtggagatcgagacctggtgccagtccgagggccgcatcggcacccgccgcgactggatcctgcgcg actccgccaccaacgaggtgatcggccgcgccacctccaagtgggtgatgatgaaccaggacacccgc cgcctgcagcgcgtgaccgacgaggtgcgcgacgagtacctggtgttctgcccccgcgagccccgcct ggccttccccgaggagaacaactcctccctgaagaagatccccaagctggaggaccccgcccagtact -continued ccatgctggagctgaagccccgccgcgccgacctggacatgaaccagcacgtgaacaacgtgacctac atcggctgggtgctggagtccatcccccaggagatcatcgacacccacgagctgcaggtgatcaccct ggactaccgccgcgagtgccagcaggacgacatcgtggactccctgaccacctccgagatccccgacg accccatctccaagttcaccggcaccaacggctccgccatgtcctccatccagggccacaacgagtcc cagttcctgcacatgctgcgcctgtccgagaacggccaggagatcaaccgcggccgcacccagtggcg caagaagtcctcccgcATGGACTACAAGGACCACGACGGCGACTACAAGGACCACGACATCGACTACA

AGGACGACGACGACAAGTGA

*Brassica napus* acyl-ACP thioesterase (GenBank Accession No. CAA52070) with UTEX 250 stearoyl-ACP desaturase (SAD) chloroplast transit peptide and 3X FLAG ® Tag

SEQ ID NO: 67

MATASTFSAFNARCGDLRRSAGSGPRRPARPLPVR*GRA* SQLRKPALDPLRAVISADQGSISPVNSCTP

ADRLRAGRLMEDGYSYKEKFIVRSYEVGINKTATVETIANLLQEVACNHVQKCGFSTDGFATTLTMRK

LHLIWVTARMHIEIYKYPAWSDVVEIETWCQSEGRIGTRRDWILRDSATNEVIGRATSKWVMMNQDTR

RLQRVTDEVRDEYLVFCPREPRLAFPEENNSSLKKIPKLEDPAQYSMLELKPRRADLDMNQHVNNVTY

IGWVLESIPQEIIDTHELQVITLDYRRECQQDDIVDSLTTSEIPDDPISKFTGTNGSAMSSIQGHNES

QFLHMLRLSENGQEINRGRTQWRKKSSRMDYKDHDGDYKDHDIDYKDDDDK

Codon optimized *C. tinctorius* FATA (GenBank Accession No. AAA33019) with UTEX 250 stearoyl-ACP desaturase (SAD) chloroplast transit peptide and 3X FLAG ® Tag

SEQ ID NO: 68

*ATG**gccaccgcatccactttctcggcgttcaatgcccgctgcggcgacctgcgtcgctcggcgggctc*

*cgggccccggcgcccagcgaggcccctccccgtgcgcg**ggcgcgcc**gccaccggcgagcagccctccg*

*gcgtggcctccctgcgcgaggccgacaaggagaagtccctgggcaaccgcctgcgcctgggctccctg*

*accgaggacggcctgtcctacaaggagaagttcgtgatccgctgctacgaggtgggcatcaacaagac*

*cgccaccatcgagaccatcgccaacctgctgcaggaggtgggcggcaaccacgcccagggcgtgggct*

*tctccaccgacggcttcgccaccaccaccaccatgcgcaagctgcacctgatctgggtgaccgcccgc*

*atgcacatcgagatctaccgctaccccgcctggtccgacgtgatcgagatcgagacctgggtgcaggg*

*cgagggcaaggtgggcacccgccgcgactggatcctgaaggactacgccaacggcgaggtgatcggcc*

*gcgccacctccaagtgggtgatgatgaacgaggacacccgccgcctgcagaaggtgtccgacgacgtg*

*cgcgaggagtacctggtgttctgcccccgcaccctgcgcctggccttccccgaggagaacaacaactc*

*catgaagaagatccccaagctggaggaccccgccgagtactcccgcctgggcctggtgccccgccgct*

*ccgacctggacatgaacaagcacgtgaacaacgtgacctacatcggctgggccctggagtccatcccc*

*cccgagatcatcgacacccacgagctgcaggccatcaccctggactaccgccgcgagtgccagcgcga*

*cgacatcgtggactccctgacctcccgcgagcccctgggcaacgccgccggcgtgaagttcaaggaga*

*tcaacggctccgtgtcccccaagaaggacgagcaggacctgtcccgcttcatgcacctgctgcgctcc*

*gccggctccggcctggagatcaaccgctgccgcaccgagtggcgcaagaagcccgccaagcgcATGGA*

*CTACAAGGACCACGACGGCGACTACAAGGACCACGACATCGACTACAAGGACGACGACGACAAG**TGA*

*C. tinctorius* FATA (GenBank Accession No. AAA33019) with UTEX 250 stearoyl-ACP desaturase (SAD) chloroplast transit peptide

SEQ ID NO: 69

MATASTFSAFNARCGDLRRSAGSGPRRPARPLPVR*GRA* ATGEQPSGVASLREADKEKSLGNRLRLGSL

TEDGLSYKEKFVIRCYEVGINKTATIETIANLLQEVGGNHAQGVGFSTDGFATTTTMRKLHLIWVTAR

MHIEIYRYPAWSDVIEIETWVQGEGKVGTRRDWILKDYANGEVIGRATSKWVMMNEDTRRLQKVSDDV

REEYLVFCPRTLRLAFPEENNNSMKKIPKLEDPAEYSRLGLVPRRSDLDMNKHVNNVTYIGWALESIP

-continued

PEIIDTHELQAITLDYRRECQRDDIVDSLTSREPLGNAAGVKFKEINGSVSPKKDEQDLSRFMHLLRS

AGSGLEINRCRTEWRKKPAKRMDYKDHDGDYKDHDIDYKDDDDK

Codon optimized *R. communis* FATA (Genbank Accession No. ABS30422) with a 3xFLAG epitope tag

SEQ ID NO: 70

*ATG**ctgaaggtgccctgctgcaacgccaccgaccccatccagtccctgtcctcccagtgccgcttcct*

*gacccacttcaacaaccgcccctacttcacccgccgcccctccatccccaccttcttctcctccaaga*

*actcctccgcctccctgcaggccgtggtgtccgacatctcctccgtggagtccgccgcctgcgactcc*

*ctggccaaccgcctgcgcctgggcaagctgaccgaggacggcttctcctacaaggagaagttcatcgt*

*ggggcgcgcccgctcctacgaggtgggcatcaacaagaccgccaccgtggagaccatcgccaacctgc*

*tgcaggaggtgggctgcaaccacgcccagtccgtgggcttctccaccgacggcttcgccaccaccacc*

*tccatgcgcaagatgcacctgatctgggtgaccgcccgcatgcacatcgagatctacaagtaccccgc*

*ctggtccgacgtggtggaggtggagacctggtgccagtccgagggccgcatcggcacccgccgcgact*

*ggatcctgaccgactacgccaccggccagatcatcggccgcgccacctccaagtgggtgatgatgaac*

*caggacacccgccgcctgcagaaggtgaccgacgacgtgcgcgaggagtacctggtgttctgccccg*

*cgagctgcgcctggccttccccgaggagaacaaccgctcctccaagaagatctccaagctggaggacc*

*ccgcccagtactccaagctgggcctggtgccccgccgcgccgacctggacatgaaccagcacgtgaac*

*aacgtgacctacatcggctgggtgctggagtccatcccccaggagatcatcgacacccacgagctgca*

*gaccatcaccctggactaccgccgcgagtgccagcacgacgacatcgtggactccctgacctccgtgg*

*agccctccgagaacctggaggccgtgtccgagctgcgcggcaccaacggctccgccaccaccaccgcc*

*ggcgacgaggactgccgcaacttcctgcacctgctgcgcctgtccggcgacggcctggagatcaaccg*

*cggccgcaccgagtggcgcaagaagtccgcccgcATGGACTACAAGGACCACGACGGCGACTACAAGG*

*ACCACGACATCGACTACAAGGACGACGACGACAAG**TGA*

*R. communis* FATA (Genbank Accession No. ABS30422) with a 3xFLAG ® epitope tag

SEQ ID NO: 71

MLKVPCCNATDPIQSLSSQCRFLTHFNNRPYFTRRPSIPTFFSSKNSSASLQAVVSDISSVESAACDS

LANRLRLGKLTEDGFSYKEKFIV*GRA* RSYEVGINKTATVETIANLLQEVGCNHAQSVGFSTDGFATTT

SMRKMHLIWVTARMHIEIYKYPAWSDVVEVETWCQSEGRIGTRRDWILTDYATGQIIGRATSKWVMMN

QDTRRLQKVTDDVREEYLVFCPRELRLAFPEENNRSSKKISKLEDPAQYSKLGLVPRRADLDMNQHVN

NVTYIGWVLESIPQEIIDTHELQTITLDYRRECQHDDIVDSLTSVEPSENLEAVSELRGTNGSATTTA

GDEDCRNFLHLLRLSGDGLEINRGRTEWRKKSARMDYKDHDGDYKDHDIDYKDDDDK

Codon optimized *G. mangostana* FATA1 (GenBank Accession No. AAB51523) with 3X FLAG ® epitope tag

SEQ ID NO: 72

*ATG**ctgaagctgtcctcctcccgctccccccctggcccgcatccccacccgcccccgccccaactccat*

*ccccccccgcatcatcgtggtgtcctcctcctcctccaaggtgaacccccctgaagaccgaggccgtgg*

*tgtcctccggcctggccgaccgcctgcgcctgggctccctgaccgaggacggcctgtcctacaaggag*

*aagttcatcgtgcgctgctacgaggtgggcatcaacaagaccgccaccgtggagaccatcgccaacct*

*gctgcaggaggtgggctgcaaccacgcccagtccgtgggctactccaccggcggcttctccaccaccc*

*ccaccatgcgcaagctgcgcctgatctgggtgaccgcccgcatgcacatcgagatctacaagtacccc*

*gcctggtccgacgtggtggagatcgagtcctggggccagggcgagggcaagatcggcacccgccgcga*

*ctggatcctgcgcgactacgccaccggccaggtgatcggccgcgccacctccaagtgggtgatgatga*

*accaggacacccgccgcctgcagaaggtggacgtggacgtgcgcgacgagtacctggtgcactgcccc*

-continued

*cgcgagctgcgcctggccttccccgaggagaacaactcctccctgaagaagatctccaagctggagga*

*cccctcccagtactccaagctgggcctggtgccccgccgcgccgacctggacatgaaccagcacgtga*

*acaacgtgacctacatcggctgggtgctggagtccatgccccaggagatcatcgacacccacgagctg*

*cagaccatcaccctggactaccgccgcgagtgccagcacgacgacgtggtggactccctgacctcccc*

*cgagccctccgaggacgccgaggccgtgttcaaccacaacggcaccaacggctccgccaacgtgtccg*

*ccaacgaccacggctgccgcaacttcctgcacctgctgcgcctgtccggcaacggcctggagatcaac*

*cgcggccgcaccgagtggcgcaagaagcccacccgcATGGACTACAAGGACCACGACGGCGACTACAA*

*GGACCACGACATCGACTACAAGGACGACGACGACAAGTGA*

*G. mangostana* FATA1 (GenBank Accession No. AAB51523) with 3X FLAG ® epitope tag

SEQ ID NO: 73

MLKLSSSRSPLARIPTRPRPNSIPPRIIVVSSSSSKVNPLKTEAVVSSGLADRLRLGSLTEDGLSYKE

KFIVRCYEVGINKTATVETIANLLQEVGCNHAQSVGYSTGGFSTTPTMRKLRLIWVTARMHIEIYKYP

AWSDVVEIESWGQGEGKIGTRRDWILRDYATGQVIGRATSKWVMMNQDTRRLQKVDVDVRDEYLVHCP

RELRLAFPEENNSSLKKISKLEDPSQYSKLGLVPRRADLDMNQHVNNVTYIGWVLESMPQEIIDTHEL

QTITLDYRRECQHDDVVDSLTSPEPSEDAEAVFNHNGTNGSANVSANDHGCRNFLHLLRLSGNGLEIN

RGRTEWRKKPTRMDYKDHDGDYKDHDIDYKDDDDK

Codon optimized *Theobroma cacao* FATA1 with 3X FLAG ® epitope tag

SEQ ID NO: 74

*ATG**ctgaagctgtcctcctgcaacgtgaccgaccagcgccaggccctggcccagtgccgcttcctggc*

*ccccccgccccccttctccttccgctggcgcaccccccgtggtggtgtcctgctccccctcctcccgcc*

*ccaacctgtcccccctgcaggtggtgctgtccggccagcagcaggccggcatggagctggtggagtcc*

*ggctccggctccctggccgaccgcctgcgcctgggctccctgaccgaggacggcctgtcctacaagga*

*gaagttcatcgtgcgctgctacgaggtgggcatcaacaagaccgccaccgtggagaccatcgccaacc*

*tgctgcaggaggtgggctgcaaccacgcccagtccgtgggctactccaccgacggcttcgccaccacc*

*cgcaccatgcgcaagctgcacctgatctgggtgaccgcccgcatgcacatcgagatctacaagtaccc*

*cgcctggtccgacgtgatcgagatcgagacctggtgccagtccgagggccgcatcggcacccgccgcg*

*actggatcctgaaggacttcggcaccggcgaggtgatcggccgcgccacctccaagtgggtgatgatg*

*aaccaggacacccgccgcctgcagaaggtgtccgacgacgtgcgcgaggagtacctggtgttctgccc*

*ccgcgagctgcgcctggccttccccgaggagaacaacaactccctgaagaagatcgccaagctggacg*

*actccttccagtactcccgcctgggcctgatgccccgccgcgccgacctggacatgaaccagcacgtg*

*aacaacgtgacctacatcggctgggtgctggagtccatgccccaggagatcatcgacacccacgagct*

*gcagaccatcaccctggactaccgccgcgagtgccagcaggacgacgtggtggactccctgacctccc*

*ccgagcaggtggagggcaccgagaaggtgtccgccatccacggcaccaacggctccgccgccgcccgc*

*gaggacaagcaggactgccgccagttcctgcacctgctgcgcctgtcctccgacggccaggagatcaa*

*ccgcggccgcaccgagtggcgcaagaagcccgcccgcATGGACTACAAGGACCACGACGGCGACTACA*

*AGGACCACGACATCGACTACAAGGACGACGACGACAAGTGA*

*Theobroma cacao* FATA1 with 3X FLAG ® epitope tag

SEQ ID NO: 75

MLKLSSCNVTDQRQALAQCRFLAPPAPFSFRWRTPVVVSCSPSSRPNLSPLQVVLSGQQQAGMELVES

GSGSLADRLRLGSLTEDGLSYKEKFIVRCYEVGINKTATVETIANLLQEVGCNHAQSVGYSTDGFATT

RTMRKLHLIWVTARMHIEIYKYPAWSDVIEIETWCQSEGRIGTRRDWILKDFGTGEVIGRATSKWVMM

NQDTRRLQKVSDDVREEYLVFCPRELRLAFPEENNNSLKKIAKLDDSFQYSRLGLMPRRADLDMNQHV

NNVTYIGWVLESMPQEIIDTHELQTITLDYRRECQQDDVVDSLTSPEQVEGTEKVSAIHGTNGSAAAR

EDKQDCRQFLHLLRLSSDGQEINKGRTEWRKKPARMDYKDHDGDYKDHDIDYKDDDDK

23S rRNA for UTEX 1439, UTEX 1441, UTEX 1435, UTEX 1437 *Prototheca moriformis*
SEQ ID NO: 76

TGTTGAAGAATGAGCCGGCGACTTAAAATAAATGGCAGGCTAAGAGAATTAATAACTCGAAACCTAAG

CGAAAGCAAGTCTTAATAGGGCGCTAATTTAACAAAACATTAAATAAAATCTAAAGTCATTTATTTTA

GACCCGAACCTGAGTGATCTAACCATGGTCAGGATGAAACTTGGGTGACACCAAGTGGAAGTCCGAAC

CGACCGATGTTGAAAAATCGGCGGATGAACTGTGGTTAGTGGTGAAATACCAGTCGAACTCAGAGCTA

GCTGGTTCTCCCCGAAATGCGTTGAGGCGCAGCAATATATCTCGTCTATCTAGGGGTAAAGCACTGTT

TCGGTGCGGGCTATGAAAATGGTACCAAATCGTGGCAAACTCTGAATACTAGAAATGACGATATATTA

GTGAGACTATGGGGGATAAGCTCCATAGTCGAGAGGGAAACAGCCCAGACCACCAGTTAAGGCCCCAA

AATGATAATGAAGTGGTAAAGGAGGTGAAAATGCAAATACAACCAGGAGGTTGGCTTAGAAGCAGCCA

TCCTTTAAAGAGTGCGTAATAGCTCACTG

Cu PSR23 LPAAT2-1
SEQ ID NO: 77

MAIAAAAVIFLFGLIFFASGLIINLFQALCFVLIRPLSKNAYRRINRVFAELLLSELLCLFDWWAGAK

LKLFTDPETFRLMGKEHALVIINHMTELDWMVGWVMGQHFGCLGSIISVAKKSTKFLPVLGWSMWFSE

YLYLERSWAKDKSTLKSHIERLIDYPLPFWLVIFVEGTRFTRTKLLAAQQYAVSSGLPVPRNVLIPRT

KGFVSCVSHMRSFVPAVYDVTVAFPKTSPPPTLLNLFEGQSIMLHVHIKRHAMKDLPESDDAVAEWCR

DKFVEKDALLDKHNAEDTFSGQEVCHSGSRQLKSLLVVISWVVVTTFGALKFLQWSSWKGKAFSAIGL

GIVTLLMHVLILSSQAERSNPAEVAQAKLKTGLSISKKVTDKEN

CuPSR23 LPAAT3-1
SEQ ID NO: 78

MAIAAAAVIVPLSLLFFVSGLIVNLVQAVCFVLIRPLSKNTYRRINRVVAELLWLELVWLIDWWAGVK

IKVFTDHETFHLMGKEHALVICNHKSDIDWLVGWVLGQRSGCLGSTLAVMKKSSKFLPVLGWSMWFSE

YLFLERSWAKDEITLKSGLNRLKDYPLPFWLALFVEGTRFTRAKLLAAQQYAASSGLPVPRNVLIPRT

KGFVSSVSHMRSFVPAIYDVTVAIPKTSPPPTLIRMFKGQSSVLHVHLKRHLMKDLPESDDAVAQWCR

DIFVEKDALLDKHNAEDTFSGQELQETGRPIKSLLVVISWAVLEVFGAVKFLQWSSLLSSWKGLAFSG

IGLGVITLLMHILILFSQSERSTPAKVAPAKPKNEGESSKTEMEKEK

Amino acid sequence for CuPSR23 LPPATx
SEQ ID NO: 79

MEIPPHCLCSPSPAPSQLYYKKKKHAILQTQTPYRYRVSPTCFAPPRLRKQHPYPLPVLCYPKLLHFS

QPRYPLVRSHLAEAGVAYRPGYELLGKIRGVCFYAVTAAVALLLFQCMLLLHPFVLLFDPFPRKAHHT

IAKLWSICSVSLFYKIHIKGLENLPPPHSPAVYVSNHQSFLDIYTLLTLGRTFKFISKTEIFLYPIIG

WAMYMLGTIPLKRLDSRSQLDTLKRCMDLIKKGASVFFFPEGTRSKDGKLGAFKKGAFSIAAKSKVPV

VPITLIGTGKIMPPGSELTVNPGTVQVIIHKPIEGSDAEAMCNEARATISHSLDD cDNA sequence for CuPSR23 LPAATx coding region
SEQ ID NO: 80

ATGGAGATCCCGCCTCACTGTCTCTGTTCGCCTTCGCCTGCGCCTTCGCAATTGTATTACAAGAAGAA

GAAGCATGCCATTCTCCAAACTCAAACTCCCTATAGATATAGAGTTTCCCCGACATGCTTTGCCCCCC

CCCGATTGAGGAAGCAGCATCCTTACCCTCTCCCTGTCCTCTGCTATCCAAAACTCCTCCACTTCAGC

CAGCCTAGGTACCCTCTGGTTAGATCTCATTTGGCTGAAGCTGGTGTTGCTTATCGTCCAGGATACGA

ATTATTAGGAAAAATAAGGGGAGTGTGTTTCTATGCTGTCACTGCTGCCGTTGCCTTGCTTCTATTTC

AGTGCATGCTCCTCCTCCATCCCTTTGTGCTCCTCTTCGATCCATTTCCAAGAAAGGCTCACCATACC

ATCGCCAAACTCTGGTCTATCTGCTCTGTTTCTCTTTTTTACAAGATTCACATCAAGGGTTTGGAAAA

-continued

TCTTCCCCCACCCCACTCTCCTGCCGTCTATGTCTCTAATCATCAGAGTTTTCTCGACATCTATACTC

TCCTCACTCTCGGTAGAACCTTCAAGTTCATCAGCAAGACTGAGATCTTTCTCTATCCAATTATCGGT

TGGGCCATGTATATGTTGGGTACCATTCCTCTCAAGCGGTTGGACAGCAGAAGCCAATTGGACACTCT

TAAGCGATGTATGGATCTCATCAAGAAGGGAGCATCCGTCTTTTTCTTCCCAGAGGGAACACGAAGTA

AAGATGGGAAACTGGGTGCTTTCAAGAAAGGTGCATTCAGCATCGCAGCAAAAAGCAAGGTTCCTGTT

GTGCCGATCACCCTTATTGGAACTGGCAAGATTATGCCACCTGGGAGCGAACTTACTGTCAATCCAGG

AACTGTGCAAGTAATCATACATAAACCTATCGAAGGAAGTGATGCAGAAGCAATGTGCAATGAAGCTA

GAGCCACGATTTCTCACTCACTTGATGATTAA cDNA sequence for CuPSR23 LPAAT 2-1 coding region

SEQ ID NO: 81

ATGGCGATTGCAGCGGCAGCTGTCATCTTCCTCTTCGGCCTTATCTTCTTCGCCTCCGGCCTCATAAT

CAATCTCTTCCAGGCGCTTTGCTTTGTCCTTATTCGGCCTCTTTCGAAAAACGCCTACMGGAGAATAA

ACAGAGTTTTTGCAGAATTGTTGTTGTCGGAGCTTTTATGCCTATTCGATTGGTGGGCTGGTGCTAAG

CTCAAATTATTTACCGACCCTGAAACCTTTCGCCTTATGGGCAAGGAACATGCTCTTGTCATAATTAA

TCACATGACTGAACTTGACTGGATGGTTGGATGGGTTATGGGTCAGCATTTTGGTTGCCTTGGGAGCA

TAATATCTGTTGCGAAGAAATCAACAAAATTTCTTCCGGTATTGGGGTGGTCAATGTGGTTTTCAGAG

TACCTATATCTTGAGAGAAGCTGGGCCAAGGATAAAAGTACATTAAAGTCACATATCGAGAGGCTGAT

AGACTACCCCCTGCCCTTCTGGTTGGTAATTTTTGTGGAAGGAACTCGGTTTACTCGGACAAAACTCT

TGGCAGCCCAGCAGTATGCTGTCTCATCTGGGCTACCAGTGCCGAGAAATGTTTTGATCCCACGTACT

AAGGGTTTTGTTTCATGTGTAAGTCACATGCGATCATTTGTTCCAGCAGTATATGATGTCACAGTGGC

ATTCCCTAAGACTTCACCTCCACCAACGTTGCTAAATCTTTTCGAGGGTCAGTCCATAATGCTTCACG

TTCACATCAAGCGACATGCAATGAAAGATTTACCAGAATCCGATGATGCAGTAGCAGAGTGGTGTAGA

GACAAATTTGTGGAAAAGGATGCTTTGTTGGACAAGCATAATGCTGAGGACACTTTCAGTGGTCAAGA

AGTTTGTCATAGCGGCAGCCGCCAGTTAAAGTCTCTTCTGGTGGTAATATCTTGGGTGGTTGTAACAA

CATTTGGGGCTCTAAAGTTCCTTCAGTGGTCATCATGGAAGGGGAAAGCATTTTCAGCTATCGGGCTG

GGCATCGTCACTCTACTTATGCACGTATTGATTCTATCCTCACAAGCAGAGCGGTCTAACCCTGCGGA

GGTGGCACAGGCAAAGCTAAAGACCGGGTTGTCGATCTCAAAGAAGGTAACGGACAAGGAAAACTAG cDNA sequence for CuPSR23 LPAAx 3-1 coding region

SEQ ID NO: 82

ATGGCGATTGCTGCGGCAGCTGTCATCGTCCCGCTCAGCCTCCTCTTCTTCGTCTCCGGCCTCATCGT

CAATCTCGTACAGGCAGTTTGCTTTGTACTGATTAGGCCTCTGTCGAAAAACACTTACAGAAGAATAA

ACAGAGTGGTTGCAGAATTGTTGTGGTTGGAGTTGGTATGGCTGATTGATTGGTGGGCTGGTGTCAAG

ATAAAAGTATTCACGGATCATGAAACCTTTCACCTTATGGGCAAAGAACATGCTCTTGTCATTTGTAA

TCACAAGAGTGACATAGACTGGCTGGTTGGGTGGGTTCTGGGACAGCGGTCAGGTTGCCTTGGAAGCA

CATTAGCTGTTATGAAGAAATCATCAAAGTTTCTCCCGGTATTAGGGTGGTCAATGTGGTTCTCAGAG

TATCTATTCCTTGAAAGAAGCTGGGCCAAGGATGAAATTACATTAAAGTCAGGTTTGAATAGGCTGAA

AGACTATCCCTTACCCTTCTGGTTGGCACTTTTTGTGGAAGGAACTCGGTTCACTCGAGCAAAACTCT

TGGCAGCCCAGCAGTATGCTGCCTCTTCGGGGCTACCTGTGCCGAGAAATGTTCTGATCCCGCGTACT

AAGGGTTTTGTTTCTTCTGTGAGTCACATGCGATCATTTGTTCCAGCCATATATGATGTTACAGTGGC

AATCCCAAAGACGTCACCTCCACCAACATTGATAAGAATGTTCAAGGGACAGTCCTCAGTGCTTCACG

TCCACCTCAAGCGACACCTAATGAAAGATTTACCTGAATCAGATGATGCTGTTGCTCAGTGGTGCAGA

GATATATTCGTCGAGAAGGATGCTTTGTTGGATAAGCATAATGCTGAGGACACTTTCAGTGGCCAAGA

ACTTCAAGAAACTGGCCGCCCAATAAAGTCTCTTCTGGTTGTAATCTCTTGGGCGGTGTTGGAGGTAT

-continued

TTGGAGCTGTGAAGTTTCTTCAATGGTCATCGCTGTTATCATCATGGAAGGGACTTGCATTTTCGGGA

ATAGGACTGGGTGTCATCACGCTACTCATGCACATACTGATTTTATTCTCACAATCCGAGCGGTCTAC

CCCTGCAAAAGTGGCACCAGCAAAGCCAAAGAATGAGGGAGAGTCCTCCAAGACGGAAATGGAAAAGG

AAAAGTAG cDNA sequence for CuPSR23 LPAATx coding region codon optimized for *Prototheca moriformis*

SEQ ID NO: 83

ATGgagatccccccccactgcctgtgctccccctcccccgccccctcccagctgtactacaagaagaa gaagcacgccatcctgcagacccagaccccctaccgctaccgcgtgtcccccacctgcttcgcccccc cccgcctgcgcaagcagcacccctacccccctgcccgtgctgtgctaccccaagctgctgcacttctcc cagccccgctaccccctggtgcgctcccacctggccgaggccggcgtggcctaccgccccggctacga gctgctgggcaagatccgcggcgtgtgcttctacgccgtgaccgccgccgtggccctgctgctgttcc agtgcatgctgctgctgcaccccttcgtgctgctgttcgaccccttcccccgcaaggcccaccacacc atcgccaagctgtggtccatctgctccgtgtccctgttctacaagatccacatcaagggcctggagaa cctgccccccccccactcccccgccgtgtacgtgtccaaccaccagtccttcctggacatctacaccc tgctgaccctgggccgcaccttcaagttcatctccaagaccgagatcttcctgtaccccatcatcggc tgggccatgtacatgctgggcaccatcccccctgaagcgcctggactcccgctcccagctggacaccct gaagcgctgcatggacctgatcaagaagggcgcctccgtgttcttcttccccgagggcacccgctcca aggacggcaagctgggcgccttcaagaagggcgccttctccatcgccgccaagtccaaggtgcccgtg gtgcccatcaccctgatcggcaccggcaagatcatgccccccggctccgagctgaccgtgaaccccgg caccgtgcaggtgatcatccacaagcccatcgagggctccgacgccgaggccatgtgcaacgaggccc gcgccaccatctcccactccctggacgacTGA cDNA sequence for CuPSR23 LPAAT 2-1 coding region codon optimized for *Prototheca moriformis*

SEQ ID NO: 84

ATGgcgatcgcggccgcggcggtgatcttcctgttcggcctgatcttcttcgcctccggcctgatcat caacctgttccaggcgctgtgcttcgtcctgatccgcccccctgtccaagaacgcctaccgccgcatca accgcgtgttcgcggagctgctgctgtccgagctgctgtgcctgttcgactggtgggcgggcgcgaag ctgaagctgttcaccgaccccgagacgttccgcctgatgggcaaggagcacgccctggtcatcatcaa ccacatgaccgagctggactggatggtgggctgggtgatgggccagcacttcggctgcctgggctcca tcatctccgtcgccaagaagtccacgaagttcctgcccgtgctgggctggtccatgtggttctccgag tacctgtacctggagcgctcctgggccaaggacaagtccaccctgaagtcccacatcgagcgcctgat cgactacccccctgcccttctggctggtcatcttcgtcgagggcacccgcttcacgcgcacgaagctgc tggcggcccagcagtacgcggtctcctccggcctgcccgtcccccgcaacgtcctgatcccccgcacg aagggcttcgtctcctgcgtgtcccacatgcgctccttcgtccccgcggtgtacgacgtcacggtggc gttccccaagacgtccccccccccccacgctgctgaacctgttcgagggccagtccatcatgctgcacg tgcacatcaagcgccacgccatgaaggacctgcccgagtccgacgacgccgtcgcggagtggtgccgc gacaagttcgtcgagaaggacgccctgctggacaagcacaacgcggaggacacgttctccggccagga ggtgtgccactccggctcccgccagctgaagtccctgctggtcgtgatctcctgggtcgtggtgacga cgttcggcgccctgaagttcctgcagtggtcctcctggaagggcaaggcgttctccgccatcggcctg ggcatcgtcaccctgctgatgcacgtgctgatcctgtcctcccaggccgagcgctccaaccccgccga ggtggcccaggccaagctgaagaccggcctgtccatctccaagaaggtgacggacaaggagaacTGA -continued cDNA sequence for CuPSR23 LPAAT 3-1 coding region codon optimized for *Prototheca moriformis*

SEQ ID NO: 85

ATGgccatcgcggcggccgcggtgatcgtgcccctgtccctgctgttcttcgtgtccggcctgatcgt caacctggtgcaggccgtctgcttcgtcctgatccgcccccctgtccaagaacacgtaccgccgcatca accgcgtggtcgcggagctgctgtggctggagctggtgtggctgatcgactggtgggcgggcgtgaag atcaaggtcttcacggaccacgagacgttccacctgatgggcaaggagcacgccctggtcatctgcaa ccacaagtccgacatcgactggctggtcggctgggtcctgggccagcgctccggctgcctgggctcca ccctggcggtcatgaagaagtcctccaagttcctgcccgtcctgggctggtccatgtggttctccgag tacctgttcctggagcgctcctgggccaaggacgagatcacgctgaagtccggcctgaaccgcctgaa ggactacccccctgcccttctggctggcgctgttcgtggagggcacgcgcttcacccgcgcgaagctgc tggcggcgcagcagtacgccgcgtcctccggcctgcccgtgccccgcaacgtgctgatcccccgcacg aagggcttcgtgtcctccgtgtcccacatgcgctccttcgtgcccgcgatctacgacgtcaccgtggc catccccaagacgtcccccccccccacgctgatccgcatgttcaagggccagtcctccgtgctgcacg tgcacctgaagcgccacctgatgaaggacctgcccgagtccgacgacgccgtcgcgcagtggtgccgc gacatcttcgtggagaaggacgcgctgctggacaagcacaacgccgaggacaccttctccggccagga gctgcaggagaccggccgccccatcaagtccctgctggtcgtcatctcctgggccgtcctggaggtgt tcggcgccgtcaagttcctgcagtggtcctccctgctgtcctcctggaagggcctggcgttctccggc atcggcctgggcgtgatcaccctgctgatgcacatcctgatcctgttctcccagtccgagcgctccac cccgccaaggtggcccccgcgaagcccaagaacgagggcgagtcctccaagaccgagatggagaagg agaagTGA Nucleic acid sequence encoding 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence in construct D1481 [pSZ2479]

SEQ ID NO: 86

GCGCACCCCAAGGCGAACGGCAGCGCGGTGTCGCTGAAGTCGGGCTCCCTGGAGACCCAGGAGGACAA

GACGAGCAGCTCGTCCCCCCCCCCCCGCACGTTCATCAACCAGCTGCCCGTGTGGAGCATGCTGCTGT

CGGCGGTGACCACGGTCTTCGGCGTGGCCGAGAAGCAGTGGCCCATGCTGGACCGCAAGTCCAAGCGC

CCCGACATGCTGGTCGAGCCCCTGGGCGTGGACCGCATCGTCTACGACGGCGTGAGCTTCCGCCAGTC

GTTCTCCATCCGCAGCTACGAGATCGGCGCCGACCGCACCGCCTCGATCGAGACGCTGATGAACATGT

TCCAGGAGACCTCCCTGAACCACTGCAAGATCATCGGCCTGCTGAACGACGGCTTCGGCCGCACGCCC

GAGATGTGCAAGCGCGACCTGATCTGGGTCGTGACCAAGATGCAGATCGAGGTGAACCGCTACCCCAC

GTGGGGCGACACCATCGAGGTCAACACGTGGGTGAGCGCCTCGGGCAAGCACGGCATGGGCCGCGACT

GGCTGATCTCCGACTGCCACACCGGCGAGATCCTGATCCGCGCGACGAGCGTCTGGGCGATGATGAAC

CAGAAGACCCGCCGCCTGTCGAAGATCCCCTACGAGGTGCGCCAGGAGATCGAGCCCCAGTTCGTCGA

CTCCGCCCCCGTGATCGTGGACGACCGCAAGTTCCACAAGCTGGACCTGAAGACGGGCGACAGCATCT

GCAACGGCCTGACCCCCCGCTGGACGGACCTGGACGTGAACCAGCACGTCAACAACGTGAAGTACATC

GGCTGGATCCTGCAGTCGGTCCCCACCGAGGTGTTCGAGACGCAGGAGCTGTGCGGCCTGACCCTGGA

GTACCGCCGCGAGTGCGGCCGCGACTCCGTGCTGGAGAGCGTCACGGCCATGGACCCCTCGAAGGAGG

GCGACCGCTCCCTGTACCAGCACCTGCTGCGCCTGGAGGACGGCGCGGACATCGTGAAGGGCCGCACC

GAGTGGCGCCCCAAGAACGCCGGCGCCAAGGGCGCCATCCTGACGGGCAAGACCAGCAACGGCAACTC

GATCTCCTGA

-continued

Amino acid sequence of 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence encoded by construct D1481 [pSZ2479]

SEQ ID NO: 87

AHPKANGSAVSLKSGSLETQEDKTSSSSPPPRTFINQLPVWSMLLSAVTTVFGVAEKQWP

MLDRKSKRPDMLVEPLGVDRIVYDGVSFRQSFSIRSYEIGADRTASIETLMNMFQETSLN

HCKIIGLLNDGFGRTPEMCKRDLIWVVTKMQIEVNRYPTWGDTIEVNTWVSASGKHGMGR

DWLISDCHTGEILIRATSVWAMMNQKTRRLSKIPYEVRQEIEPQFVDSAPVIVDDRKFHK

LDLKTGDSICNGLTPRWTDLDVNQHVNNVKYIGWILQSVPTEVFETQELCGLTLEYRREC

GRDSVLESVTAMDPSKEGDRSLYQHLLRLEDGADIVKGRTEWRPKNAGAKGAILTGKTSN

GNSIS

Nucleic acid sequence encoding 14:0-ACP thioesterase, *Cuphea palustris* (Cpal FATB2, accession AAC49180) containingan extended heterologous transit peptide from *C. protothecoides*, a 41 amino acid N-terminal extension derived from the native Cpal FATB2 sequence, and a C-terminal FLAG epitope tag in construct D1482 [pSZ2480]

SEQ ID No: 88

GCGCACCCCAAGGCGAACGGCAGCGCGGTGTCGCTGAAGTCGGGCTCCCTGGAGACCCAGGAGGACAA

GACGAGCAGCTCGTCCCCCCCCCCCCGCACGTTCATCAACCAGCTGCCCGTGTGGAGCATGCTGCTGT

CGGCGGTGACCACGGTCTTCGGCGTGGCCGAGAAGCAGTGGCCCATGCTGGACCGCAAGTCCAAGCGC

CCCGACATGCTGGTCGAGCCCCTGGGCGTGGACCGCATCGTCTACGACGGCGTGAGCTTCCGCCAGTC

GTTCTCCATCCGCAGCTACGAGATCGGCGCCGACCGCACCGCCTCGATCGAGACGCTGATGAACATGT

TCCAGGAGACCTCCCTGAACCACTGCAAGATCATCGGCCTGCTGAACGACGGCTTCGGCCGCACGCCC

GAGATGTGCAAGCGCGACCTGATCTGGGTCGTGACCAAGATGCAGATCGAGGTGAACCGCTACCCCAC

GTGGGGCGACACCATCGAGGTCAACACGTGGGTGAGCGCCTCGGGCAAGCACGGCATGGGCCGCGACT

GGCTGATCTCCGACTGCCACACCGGCGAGATCCTGATCCGCGCGACGAGCGTCTGGGCGATGATGAAC

CAGAAGACCCGCCGCCTGTCGAAGATCCCCTACGAGGTGCGCCAGGAGATCGAGCCCCAGTTCGTCGA

CTCCGCCCCCGTGATCGTGGACGACCGCAAGTTCCACAAGCTGGACCTGAAGACGGGCGACAGCATCT

GCAACGGCCTGACCCCCCGCTGGACGGACCTGGACGTGAACCAGCACGTCAACAACGTGAAGTACATC

GGCTGGATCCTGCAGTCGGTCCCCACCGAGGTGTTCGAGACGCAGGAGCTGTGCGGCCTGACCCTGGA

GTACCGCCGCGAGTGCGGCCGCGACTCCGTGCTGGAGAGCGTCACGGCCATGGACCCCTCGAAGGAGG

GCGACCGCTCCCTGTACCAGCACCTGCTGCGCCTGGAGGACGGCGCGGACATCGTGAAGGGCCGCACC

GAGTGGCGCCCCAAGAACGCCGGCGCCAAGGGCGCCATCCTGACGGGCAAGACCAGCAACGGCAACTC

GATCTCCatggactacaaggaccacgacggcgactacaaggaccacgacatcgactacaaggacgacg acgacaagtga Amino acid sequence of 14:0-ACP thioesterase, *Cuphea palustris* (Cpal FATB2, accession AAC49180) containingan extended heterologous transit peptide from *C. protothecoides*, a 41 amino acid N-terminal extension derived from the native Cpal FATB2 sequence, and a C-terminal FLAG epitope tag encoded by construct D1482 [pSZ2480]

SEQ ID NO: 89

AHPKANGSAVELKSGSLETQEDKTESSEPPPRTFINQLPVWSMLLSAVTTVFGVAEKQWP

MLDRKSKRPDMLVEPLGVDRIVYDGVSFRQSFSIRSYEIGADRTASIETLMNMFQETSLN

HCKIIGLLNDGFGRTPEMCKRDLIWVVTKMQIEVNRYPTWGDTIEVNTWVSASGKHGMGR

DWLISDCHTGEILIRATSVWAMMNQKTRRLSKIPYEVRQEIEPQFVDSAPVIVDDRKFHK

LDLKTGDSICNGLTPRWTDLDVNQHVNNVKYIGWILQSVPTEVFETQELCGLTLEYRREC

-continued

GRDSVLESVTAMDPSKEGDRSLYQHLLRLEDGADIVKGRTEWRPKNAGAKGAILTGKTSN

GNSISMDYKDHDGDYKDHDIDYKDDDDK

*Cuphea hyssopifolia* FATB3 coding region, codon optimized for *Prototheca moriformis*

SEQ ID NO: 154 gtggccgccgaggcctcctccgccctgttctccgtgcgcaccccggcacctcccccaagcccggcaa gttcggcaactggcccacctccctgtccgtgcccttcaagtccaagtccaaccacaacggcggcttcc aggtgaaggccaacgcctccgcccgccccaaggccaacggctccgccgtgtccctgaagtccggctcc ctggacacccaggaggacacctcctcctcctcctcccccccccgcaccttcatcaaccagctgcccga ctggtccatgctgctgtccgccatcaccaccgtgttcgtggccgccgagaagcagtggaccatgctgg accgcaagtccaagcgccccgacatgctgatggaccccttcggcgtggaccgcgtggtgcaggacggc gccgtgttccgccagtccttctccatccgctcctacgagatcggcgccgaccgcaccgcctccatcga gaccctgatgaacatcttccaggagacctccctgaaccactgcaagtccatcggcctgctgaacgacg gcttcggccgcacccccgagatgtgcaagcgcgacctgatctgggtggtgaccaagatgcacgtggag gtgaaccgctaccccacctggggcgacaccatcgaggtgaacacctgggtgtccgagtccggcaagac cggcatgggccgcgactggctgatctccgactgccacaccggcgagatcctgatccgcgccacctcca tgtgcgccatgatgaaccagaagacccgccgcttctccaagttcccctacgaggtgcgccaggagctg gcccccccacttcgtggactccgcccccgtgatcgaggactaccagaagctgcacaagctggacgtgaa gaccggcgactccatctgcaacggcctgacccccgctggaacgacctggacgtgaaccagcacgtga acaacgtgaagtacatcggctggatcctggagtccgtgcccaccgaggtgttcgagacccaggagctg tgcggcctgaccctggagtaccgccgcgagtgcggccgcgactccgtgctggagtccgtgaccgccat ggacccctccaaggagggcgaccgctccctgtaccagcacctgctgcgcctggaggacggcgccgaca tcgccaagggccgcaccaagtggcgccccaagaacgccggcaccaacggcgccatctccaccggcaag acctccaacggcaactccatctccatggactacaaggaccacgacggcgactacaaggaccacgacat cgactacaaggacgacgacgacaag

*Cuphea hyssopifolia* FATB1 coding region, codon optimized for *Prototheca moriformis*

SEQ ID NO: 155 gccaccgcctccaccttctccgccttcaacgcccgctgcggcgacctgcgccgctccgccggctccgg cccccgccgccccgcccgcccccctgcccgtgcgcgccgccatcaacgcctccgcccaccccaaggcca acggctccgccgtgaacctgaagtccggctccctggagacccaggaggacacctcctcctcctccccc ccccccgcaccttcatcaagcagctgcccgactggggcatgctgctgtccaagatcaccaccgtgtt cggcgccgccgagcgccagtggaagcgccccggcatgctggtggagcccttcggcgtggaccgcatct tccaggacggcgtgttcttccgccagtccttctccatccgctcctacgagatcggcgccgaccgcacc gcctccatcgagaccctgatgaacatcttccaggagacctccctgaaccactgcaagtccatcggcct gctgaacgacggcttcggccgcacccccgagatgtgcaagcgcgacctgatctgggtggtgaccaaga tccaggtggaggtgaaccgctaccccacctggggcgacaccatcgaggtgaacacctgggtgtccgag tccggcaagaacggcatgggccgcgactggctgatctccgactgccgcaccggcgagatcctgatccg cgccacctccgtgtgggccatgatgaaccgcaagacccgccgcctgtccaagttcccctacgaggtgc gccaggagatcgcccccccacttcgtggactccgcccccgtgatcgaggacgacaagaagctgcacaag ctggacgtgaagaccggcgactccatccgcaagggcctgaccccccgctggaacgacctggacgtgaa ccagcacgtgaacaacgtgaagtacatcggctggatcctgaagtccgtgcccgccgaggtgttcgaga cccaggagctgtgcggcgtgaccctggagtaccgccgcgagtgcggccgcgactccgtgctggagtcc -continued gtgaccgccatggacaccgccaaggagggcgaccgctccctgtaccagcacctgctgcgcctggagga cggcgccgacatcaccatcggccgcaccgagtggcgccccaagaacgccggcgccaacggcgccatct ccaccggcaagacctccaacgagaactccgtgtccatggactacaaggaccacgacggcgactacaag gaccacgacatcgactacaaggacgacgacgacaag

*Garcinia mangostana* FATA1 CDS

SEQ ID NO: 156

MLKLSSSRSPLARIPTRPRPNSIPPRIIVVSSSSSKVNPLKTEAVVSSGLADRLRLGSLTEDGLSYKEKF

IVRCYEVGINKTATVETIANLLQEVGCNHAQSVGYSTGGFSTTPTMRKLRLIWVTARMHIETYKYPAWSD

VVEIESWGQGEGKIGTRRDWILRDYATGQVIGRATSKWVMMNQDTRRLQKVDVDVRDEYLVHCPRELRLA

FPEENNSSLKKISKLEDPSQYSKLGLVPRRADLDMNQHVNNVTYIGWVLESMPQEIIDTHELQTITLDYR

RECQHDDVVDSLTSPEPSEDAEAVFNHNGTNGSANVSANDHGCRNFLHLLRLSGNGLEINRGRTEWRKKP

TR

*Brassic napus* LPAAT CDS

SEQ ID NO: 157

MAMAAAVIVPLGILFFISGLVVNLLQAVCYVLVRPMSKNTYRKINRVVAETLWLELVWIVDWWAGVKIQV

FADDETFNRMGKEHALVVCNHRSDIDWLVGWILAQRSGCLGSALAVMKKSSKFLPVIGNSMWFSEYLFLE

RNWAKDESTLQSGLQRLNDFPRPFWLALFVEGTRFTEAKLKAAQEYAASSELPVPRNVLIPRTKGFVSAV

SNMRSFVPAIYDMTVAIPKTSPPPTMLRLFKGQPSVVHVHIKCHSMKDLPEPEDEIAQWCRDQFVAKDAL

LDKHIAADTFPGQKEQNIGRPIKSLAVVVSWACLLTLGAMKFLHWSNLFSSWKGIALSAFGLGIITLCMQ

ILIRSSQSERSTPAKVAPAKPKDNHQSGPSSQTEVEEKQK

*Cuphea hookeriana* FATB2 CDS

SEQ ID NO: 158

MVAAAASSAFFPVPAPGASPKPGKFGNWPSSLSPSFKPKSIPNGGFQVKANDSAHPKANGSAVSLKSGSL

NTQEDTSSSPPPRTFLHQLPDWSRLLTAITTVFVKSKRPDMHDRKSKRPDMLVDSFGLESTVQDGLVFRQ

SFSIRSYEIGTDRTASIETLMNHLQETSLNHCKSTGILLDGFGRTLEMCKRDLIWVVIKMQIKVNRYPAW

GDTVEINTRFSRLGKIGMGRDWLISDCNTGEILVRATSAYAMMNQKTRRLSKLPYEVHQEIVPLFVDSPV

IEDSDLKVHKFKVKTGDSIQKGLTPGWNDLDVNQHVSNVKYIGWILESMPTEVLETQELCSLALEYRREC

GRDSVLESVTAMDPSKVGVRSQYQHLLRLEDGTAIVNGATEWRPKNAGANGAISTGKTSNGNSVS

*Cuphea wrightii* KASA1 CDS with *P moriformis* SAD transit peptide (underlined)

SEQ ID NO: 159

MASAAFTMSACPAMTGRAPGARRSGRPVATRLRYVFQCLVASCIDPCDQYRSSASLSFLGDNGFASLF

GSKPFMSNRGHRRLRRASHSGEAMAVALQPAQEAGTKKKPVIKQRRVVVTGMGVVTPLGHEPDVFYNN

LLDGVSGISEIETFDCTQFPTRIAGEIKSFSTDGWVAPKLSKRMDKFMLYLLTAGKKALADGGITDEV

MKELDKRKCGVLIGSGMGGMKVFNDATEALRVSYKKMNPFCVPFATTNMGSAMLAMDLGWMGPNYSIS

TACATSNFCILNAANHIIRGEADMMLCGGSDAVIIPIGLGGFVACRALSQRNSDPTKASRPWDSNRDG

FVMGEGAGVLLLEELEHAKKRGATIYAEFLGGSFTCDAYHMTEPHPEGAGVILCIEKALAQAGVSKED

VNYINAHATSTSAGDIKEYQALARCFGQNSELRVNSTKSMIGHLLGAAGGVEAVTVVQAIRTGWIHPN

LNLEDPDKAVDAKLLVGPKKERLNVKVGLSNSFGFGGHNSSILFAPCNV

Native *Protheca moriformis* KASII amino acid sequence (native transit peptide is underlined)

SEQ ID NO: 160

MQTAHQRPPTEGHCFGARLPTASRRAVRRAWSRIARAAAAADANPARPERRVVITGQGVVTSLGQTIE

QFYSSLLEGVSGISQIQKFDTTGYTTTIAGEIKSLQLDPYVPKRWAKRVDDVIKYVYIAGKQALESAG

LPIEAAGLAGAGLDPALCGVLIGTAMAGMTSFAAGVEALTRGGVRKMNPFCIPFSISNMGGAMLAMDI

GFMGPNYSISTACATGNYCILGAADHIRRGDANVMLAGGADAAIIPSGIGGFIACKALSKRNDEPERA

SRPWDADRDGFVMGEGAGVLVLEELEHAKRRGATILAELVGGAATSDAHHMTEPDPQGRGVRLCLERA

LERARLAPERVGYVNAHGTSTPAGDVAEYRAIRAVIPQDSLRINSTKSMIGHLLGGAGAVEAVAAIQA

LRTGWLHPNLNLENPAPGVDPVVLVGPRKERAEDLDVVLSNSFGFGGHNSCVIFRKYDE

Mature native *Protheca moriformis* KASII amino acid sequence (native transit peptide is underlined)

SEQ ID NO: 161

AAAAADANPARPERRVVITGQGVVTSLGQTIEQFYSSLLEGVSGISQIQKFDTTGYTTTIAGEIKSLQ

LDPYVPKRWAKRVDDVIKYVYIAGKQALESAGLPIEAAGLAGAGLDPALCGVLIGTAMAGMTSFAAGV

EALTRGGVRKMNPFCIPFSISNMGGAMLAMDIGFMGPNYSISTACATGNYCILGAADHIRRGDANVML

AGGADAAIIPSGIGGFIACKALSKRNDEPERASRPWDADRDGFVMGEGAGVLVLEELEHAKRRGATIL

AELVGGAATSDAHHMTEPDPQGRGVRLCLERALERARLAPERVGYVNAHGTSTPAGDVAEYRAIRAVI

PQDSLRINSTKSMIGHLLGGAGAVEAVAAIQALRTGWLHPNLNLENPAPGVDPVVLVGPRKERAEDLD

VVLSNSFGFGGHNSCVIFRKYDE

CcFATB2-UcFATB2 chimeric FATB

SEQ ID NO: 162

PDWSMLFAVITTIFSAAEKQWTNLEWKPKPNPPQLLDDHFGPHGLVFRRTFAIRSYEVGP

DRSTSIVAVMNHLQEAALNHAKSVGILGDGFGTTLEMSKRDLIWVVRRTHVAVERYPTWG

DTVEVECWIGASGNNGMRRDFLVRDCKTGEILTRCTSLSVLMNTRTRRLSTIPDEVRGEI

GPAFIDNVAVKDDEIKKLQKLNDSTADYIQGGLTPRWNDLDVNQHVNNLKYVAWVFETVP

DSIFESHHISSFTLEYRRECTRDSVLRSLTTVSGGSSEAGLVCDHLLQLEGGSEVLRART

EWRPKLTDSFRGISVIPAEPRV

*Cuphea hyssopifolia* FATB1

SEQ ID NO: 163

MVATNAAAFSAYTFFLTSPTHGYSSKRLADTQNGYPGTSLKSKSTPPPAAAAARNGALPLLASICKCP

KKADGSMQLDSSLVFGFQFYIRSYEVGADQTVSIQTVLNYLQEAAINHVQSAGYFGDSFGATPEMTKR

NLIWVITKMQVLVDRYPAWGDVVQVDTWTCSSGKNSMQRDWFVRDLKTGDIITRASSVWVLMNRLTRK

LSKIPEAVLEEAKLFVMNTAPTVDDNRKLPKLDGSSADYVLSGLTPRWSDLDMNQHVNNVKYIAWILE

SVPQSIPETHKLSAITVEYRRECGKNSVLQSLTNVSGDGITCGNSIIECHHLLQLETGPEILLARTEW

ISKEPGFRGAPIQAEKVYNNK*

*Cuphea hyssopifolia* FATB3

SEQ ID NO: 164

MVAAEASSALFSVRTPGTSPKPGKFGNWPTSLSVPFKSKSNHNGGFQVKANASARPKANGSAVSLKSG

SLDTQEDTSSSSSPPRTFINQLPDWSMLLSAITTVFVAAEKQWTMLDRKSKRPDMLMDPFGVDRVVQD

GAVFRQSFSIRSYEIGADRTASIETLMNIFQETSLNHCKSIGLLNDGFGRTPEMCKRDLIWVVTKMHV

EVNRYPTWGDTIEVNTWVSESGKTGMGRDWLISDCHTGEILIRATSMCAMMNQKTRRFSKFPYEVRQE

LAPHFVDSAPVIEDYQKLHKLDVKTGDSICNGLTPRWNDLDVNQHVNNVKYIGWILESVPTEVFETQE

LCGLTLEYRRECGRDSVLESVTAMDPSKEGDRSLYQHLLRLEDGADIAKGRTKWRPKNAGTNGAISTG

KTSNGNSIS*

---

What is claimed is:

1. A method of producing an oil comprising:

(a) cultivating a recombinant cell of the genus *Prototheca* or *Chlorella* under conditions to produce said oil, said recombinant cell having a knockout or knockdown of a FATA acyl-ACP thioesterase (FATA) gene, and expressing an oleoyl-preferring lysophosphatidic acid acyltransferase (LPAAT) gene; and (b) extracting said oil from said recombinant cell;

wherein said oil comprises at least 50% stearate-oleate-stearate (SOS) triglycerides.

2. The method of claim 1, wherein said oil comprises at least 60% SOS triglycerides.

3. The method of claim 2, wherein said oil has a viscosity of less than 30 cS and optionally of 25 cS±20% at 40° C. as measured by ASTM D445.

4. The method of claim 1, wherein said oil comprises at least 70% SOS triglycerides.

5. The method of claim 1, wherein said LPAAT gene encodes a protein with at least 90% amino acid sequence identity to the amino acid sequence of SEQ ID NO: 157.

6. The method of claim 1, wherein said recombinant cell is of the genus *Prototheca.*

7. The method of claim 6, wherein said recombinant cell is a *Prototheca moriformis* cell.

* * * * *